United States Patent
Cui et al.

(10) Patent No.: US 8,106,197 B2
(45) Date of Patent: *Jan. 31, 2012

(54) AMINOHETEROARYL COMPOUNDS AS PROTEIN KINASE INHIBITORS

(75) Inventors: Jingrong Jean Cui, San Diego, CA (US); Dilip Bhumralkar, San Diego, CA (US); Iriny Botrous, San Diego, CA (US); Ji Yu Chu, Fremont, CA (US); Lee A. Funk, Oceanside, CA (US); Cathleen Elizabeth Hanau, Chesterfield, MO (US); G. Davis Harris, Chesterfield, MO (US); Lei Jia, San Diego, CA (US); Joanne Johnson, Guilderland, NY (US); Stephen A. Kolodziej, Ballwin, MO (US); Pei-Pei Kung, San Diego, CA (US); Xiaoyuan (Sharon) Li, Los Altas, CA (US); Jason (Qishen) Lin, San Diego, CA (US); Jerry Jialun Meng, San Diego, CA (US); Mitchell David Nambu, San Diego, CA (US); Christopher G. Nelson, Fresno, CA (US); Mason Alan Pairish, San Diego, CA (US); Hong Shen, San Diego, CA (US); Michelle Tran-Dube, La Jolla, CA (US); Allison Walter, Rexford, NY (US); Fang-Jie Zhang, Sunnyvale, CA (US); Jennifer Zhang, Foster City, CA (US)

(73) Assignee: Pfizer Inc., New York, NY (US)

( * ) Notice: Subject to any disclaimer, the term of this patent is extended or adjusted under 35 U.S.C. 154(b) by 1376 days.

This patent is subject to a terminal disclaimer.

(21) Appl. No.: 11/598,765

(22) Filed: Nov. 14, 2006

(65) Prior Publication Data

US 2007/0072874 A1 Mar. 29, 2007

Related U.S. Application Data

(62) Division of application No. 10/786,610, filed on Feb. 26, 2004, now Pat. No. 7,230,098.

(60) Provisional application No. 60/449,588, filed on Feb. 26, 2003, provisional application No. 60/540,229, filed on Jan. 29, 2004.

(51) Int. Cl.
*C07D 241/02* (2006.01)

(52) U.S. Cl. .................................................. 544/408

(58) Field of Classification Search ........................ None
See application file for complete search history.

(56) References Cited

U.S. PATENT DOCUMENTS

| | | | |
|---|---|---|---|
| 6,242,435 B1* | 6/2001 | Achkar | 514/168 |
| 6,313,137 B1 | 11/2001 | Amin et al. | |
| 6,635,641 B2* | 10/2003 | Bender et al. | 514/247 |
| 7,230,098 B2* | 6/2007 | Cui et al. | 544/60 |
| 2006/0046991 A1 | 3/2006 | Cui et al. | |
| 2006/0128724 A1 | 6/2006 | Cui et al. | |

FOREIGN PATENT DOCUMENTS

| | | |
|---|---|---|
| EP | 0 204 285 B1 | 1/1992 |
| EP | 1 044 967 B1 | 8/2004 |
| JP | 07-109260 A | 4/1995 |
| WO | WO 93/15055 A1 | 8/1993 |
| WO | WO 98/37080 | 8/1998 |
| WO | WO 99/55706 A1 | 11/1999 |
| WO | WO 01/00213 A1 | 1/2001 |
| WO | WO 01/60806 A2 | 8/2001 |
| WO | WO 02/056882 A1 | 7/2002 |
| WO | WO 03/000666 A1 | 1/2003 |
| WO | WO03000666 * | 1/2003 |
| WO | WO 03/045924 A1 | 6/2003 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Foks et al. Acta Poloniae Pharmaceutica, 1999, 56(3), pp. 201-206.*
Banishashemi et al. Journal of Polymer Science, Part A-1, 1969, 7(8), pp. 2746-2748.*
Bradbury et al., "New Non-Peptide Endothelin-A Receptor Antagonists: Synthesis, Biological Properties, and Structure—Activity Relationships of 5-(Dimethylamino)-N-pyridyl-, -N-pyrimidinyl-, -N-pyridazinyl-, and -N-pyrazinyl-1-naphthalenesulfonamides," J. Med. Chem., 1997, pp. 996-1004, vol. 40, No. 6.
Bristol et al., "An Improved Synthesis of 2-Amino-3-alkyloxypyridines by a Phase-Transfer Catalyzed Ether Synthesis," Synthesis, Dec. 1981, pp. 971-973, vol. 12.
Dennin, et al., "Synthesis of Derivatives of Pyrazino[1,2-a]pyrimidin-4-ones," Journal of Heterocyclic Chemistry, Sep.-Oct. 1990, pp. 1639-1643, vol. 27.

(Continued)

*Primary Examiner* — Noble Jarrell
(74) *Attorney, Agent, or Firm* — Vincent P. Liptak; Stephen D. Prodnuk

(57) ABSTRACT

Aminopyridine and aminopyrazine compounds of formula (1), compositions including these compounds, and methods of their use are provided. Preferred compounds of formula 1 have activity as protein kinase inhibitors, including as inhibitors of c-MET.

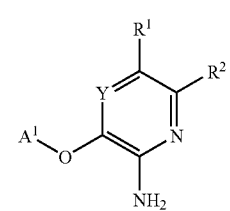

11 Claims, No Drawings

OTHER PUBLICATIONS

Foks et al., "Studies on Pyrazine Derivatives. XXX. Sythesis of Pyrazinylamino-1,3-Diazacycloalkanes of Potential Circulatory Activity," Acta Poloniae Pharmaceutica, Jan./Feb. 1997, pp. 55-62, vol. 54, No. 1.

Gavezzotti, "Are Crystal Structures Predictable?" Accounts of Chemical Research, vol. 27, pp. 309-314 (1994).

Jakubke et al.(editors), *Concise Encyclopedia Chemistry*, © 1993 by Walter de Gruyter & Co., p. 490.

Kaminski et al., "Antiulcer Agents. 2. Gastric Antisecretory, Cytoprotective, and Metabolic Properties of Substituted Imidazo[1,2-a]pyridines and Analogues," J. Med. Chem., 1987, pp. 2031-2046, vol. 30.

Lewis, *Hawley's Condensed Chemical Dictionary*, 12th ed., © 1993 by Van Nostrand Reinhold, p. 594.

Parker (editor), *McGraw-Hill Dictionary of Chemical Terms*, $3^{rd}$ ed., © 1994 McGraw-Hill, Inc. p. 200.

Shimomura et al., "Semi-synthetic aequorins with improved sensitivity to Ca2+ ions," Biochem. J., 1989, pp. 913-920, vol. 261.

Sollogoub et al., "First synthesis of 1-deazacytidine, the C-nucleoside analogue of cytidine," Tetrahedron Letters, 2001, pp. 3121-3123, vol. 43.

Vippagunta et al., :Crystalline Solids Advanced Drug Delivery Reviews, vol. 48, pp. 3-26 (2001).

Wisterowicz et al., Acta Poloniae Pharmaceutica, 1997, pp. 55-62, vol. 54, No. 1.

\* cited by examiner

AMINOHETEROARYL COMPOUNDS AS PROTEIN KINASE INHIBITORS

This application claims the benefit of U.S. Provisional Application Ser. Nos. 60/449,588, filed Feb. 26, 2003, and 60/540,229, filed Jan. 29, 2004, the disclosures of which are hereby incorporated by reference in their entireties.

FIELD OF THE INVENTION

The invention relates generally to novel chemical compounds and methods. More particularly, the invention provides novel aminoheteroaryl compounds, particularly aminopyridines and aminopyrazines, having protein tyrosine kinase activity, and methods of their synthesis and use.

BACKGROUND

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron* 9:303-391 (1992), which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made up of kinase insert domain-receptor fetal liver kinase-1 (KDR/FLK-1), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1-4, and seven ligands, FGF1-7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

Still another member of the tyrosine kinase growth factor receptor family is MET, often referred to as c-Met, also known as human hepatocyte growth factor receptor tyrosine kinase (hHGFR). c-Met is thought to play a role in primary tumor growth and metastasis.

A more complete listing of the known RTK subfamilies is described in Plowman et al., DN&P, 7(6):334-339 (1994), which is incorporated by reference.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr, AUR1, AUR2 and Yrk. For a more detailed discussion of CTKs, see Bolen, *Oncogene*, 8:2025-2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskeleton. The cytosol is the region within the cell where much of the cell's intermediary metabolic and biosynthetic activity occurs; e.g., it is in the cytosol that proteins are synthesized on ribosomes. The STKs include CDk2, Raf, the ZC family of kinases, the NEK family of kinases, and BUB1.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, trans-membrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. Pat. No. 4,966,849); soluble receptors and antibodies (Application No. WO 94/10202, Kendall and Thomas, *Proc. Nat'l Acad. Sci.*, 90:10705-10709 (1994), Kim, et al., *Nature*, 362:841-844 (1993)); RNA ligands (Jelinek, et al., *Biochemistry*, 33:10450-56); Takano, et al., *Mol. Bio. Cell*, 4:358A (1993); Kinsella, et al., *Exp. Cell Res.*, 199:56-62 (1992); Wright, et al., *J. Cellular Phys.*, 152:448-57) and tyrosine kinase inhibitors (WO 94/03427; WO 92/21660; WO 91/15495, WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY

In one embodiment, the invention provides a compound of formula 1

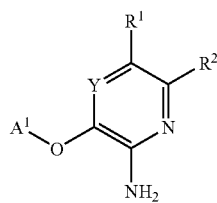

1 wherein:

Y is N or $CR^{12}$;

$R^1$ is selected from $C_{6-12}$ aryl, 5-12 membered heteroaryl, $C_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —NR$^4$C(O)R$^5$, —C(=NR$^6$)NR$^4$R$^5$, $C_{1-8}$ alkyl, $C_{2-8}$ alkenyl, and $C_{2-8}$ alkynyl; and each hydrogen in $R^1$ is optionally substituted by one or more $R^3$ groups;

$R^2$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$CR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, and each hydrogen in $R^2$ is optionally substituted by one or more $R^8$ groups;

$R^3$ is halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$CR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, each hydrogen in $R^3$ is optionally substituted by one or more $R^8$ groups, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by one or more $R^8$ groups;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —CN, —O—$C_{1-12}$ alkyl, —O—(CH$_2$)$_n$C$_{3-12}$ cycloalkyl, —O—(CH$_2$)$_n$C$_{6-12}$aryl, —O—(CH$_2$)$_n$(3-12 membered heteroalicyclic) or —O—(CH$_2$)$_n$(5-12 membered heteroaryl); and each hydrogen in $R^8$ is optionally substituted by one or more $R^{11}$ groups;

$A^1$ is —(CR$^9$R$^{10}$)$_n$-A$^2$ except that:
(i) when Y is N and $R^1$ is substituted or unsubstituted aryl or substituted or unsubstituted heteroaryl, $A^1$ is —CR$^9$R$^{10}$)$_n$-A$^2$ and n is not zero; and
(ii) when Y is N and $R^2$ is H and $A^1$ is m-chlorobenzyl, $R^1$ is not unsubstituted piperazine;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^5$R$^7$)$_n$OR$^4$, —CN, —C(O)R$^4$, —OC(O)R$^4$, —NR$^4$C(O)R$^5$, —(CR$^6$R$^7$)C(O)OR$^4$, —(CR$^6$R$^7$)$_n$CR$^4$R$^5$, —NR$^4$C(O)NR$^5$R$^6$, —NR$^4$S(O)$_p$R$^5$ or —C(O)NR$^4$R$^5$; $R^9$ and $R^{10}$ may combine to form a $C_{1-12}$ cycloalkyl, 3-12 membered heteroalicyclic, $C_{6-12}$ aryl or 5-12 membered heteroaryl ring; and each hydrogen in $R^9$ and $R^{10}$ is optionally substituted by one or more $R^3$ groups;

$A^2$ is $C_{6-12}$ aryl, 5-12 membered heteroaryl, $C_{3-12}$ cycloalkyl or 3-12 membered heteroalicyclic, and $A^2$ is optionally substituted by one or more $R^3$ groups;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic), —O—(CH$_2$)$_n$(5-12 membered heteroaryl) or —CN, and each hydrogen in R$^{11}$ is optionally substituted by one or more groups selected from halogen, —OH, —CN, —C$_{1-12}$ alkyl which may be partially or fully halogenated, —O—C$_{1-12}$ alkyl which may be partially or fully halogenated, —CO, —SO and —SO$_2$;

R$^{12}$ is hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, and each hydrogen in R$^{12}$ is optionally substituted by one or more R$^3$ groups;

R$^1$ and R$^2$ or R$^1$ and R$^{12}$ may be combined together to form a C$_{6-12}$ aryl, 5-12 membered heteroaryl, C$_{3-12}$ cycloalkyl or 3-12 membered heteroalicyclic group;

m is 0, 1 or 2;

n is 0, 1, 2, 3 or 4; and p is 1 or 2;

or a pharmaceutically acceptable salt, solvate or hydrate thereof.

In a particular aspect of this embodiment, Y is N. In a preferred aspect, R$^1$ is not piperazine. In another preferred aspect, R$^1$ is not heteroalicyclic.

In another particular aspect of this embodiment, Y is CR$^{12}$.

In particular aspects of this embodiment, and in combination with any other particular aspects of this embodiment, the compound has formula 1a

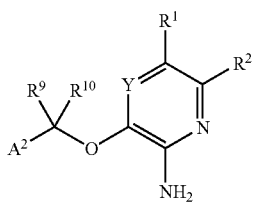

1a wherein A$^2$ is C$_{6-12}$ aryl or 5-12 membered heteroaryl optionally substituted by one or more R$^3$ groups.

In particular aspects of this embodiment, and in combination with any other particular aspects of this embodiment, R$^1$ is selected from C$_{6-12}$ aryl and 5-12 membered heteroaryl, and each hydrogen in R$^1$ is optionally substituted by one or more R$^3$ groups.

In particular aspects of this embodiment, and in combination with any other particular aspects of this embodiment not inconsistent with the following definition of R$^1$, R$^1$ is selected from C$_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —NR$^4$C(O)R$^5$, —C(=NR$^6$)NR$^4$R$^5$, C$_{1-8}$ alkyl, C$_{2-8}$ alkenyl, and C$_{2-8}$ alkynyl; and each hydrogen in R$^1$ is optionally substituted by one or more R$^3$ groups.

In particular aspects of this embodiment, and in combination with any other particular aspects of this embodiment, A$^2$ is substituted by at least one halogen atom.

In particular aspects of this embodiment, and in combination with any other particular aspects of this embodiment, R$^2$ is hydrogen, R$^9$ and R$^{10}$ are independently C$_{1-4}$ alkyl, and A$^2$ is phenyl substituted by at least one halogen atom.

In particular aspects of this embodiment, and in combination with any other particular aspects of this embodiment not inconsistent with the following definition of R$^1$, R$^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane or phenyl group, and each hydrogen in R$^1$ is optionally substituted by one or more R$^3$ groups.

In particular aspects of this embodiment, and in combination with any other particular aspects of this embodiment not inconsistent with the following definition of R$^1$, R$^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, triazine, trithiane or phenyl group, and each hydrogen in R$^1$ is optionally substituted by one or more R$^3$ groups. In a more particular aspect, R$^1$ is not heteroalicyclic.

In particular aspects of this embodiment, and in combination with any other particular aspects of this embodiment not inconsistent with the following definition of R$^1$, R$^1$ is a fused ring heteroaryl group, and each hydrogen in R$^1$ is optionally substituted by one or more R$^3$ groups.

In particular aspects of this embodiment, and in combination with any other particular aspects of this embodiment not inconsistent with the following definition of R$^1$, R$^1$ is a —SO$_2$NR$^4$R$^5$ group.

In another embodiment, the invention provides a compound of formula 2

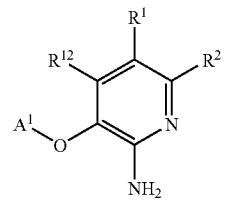

2 wherein:

R$^1$ is selected from C$_{6-12}$ aryl, 5-12 membered heteroaryl, C$_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —NR$^4$C(O)R$^5$, —C(=NR$^6$)NR$^4$R$^5$, C$_{1-8}$ alkyl, C$_{2-8}$ alkenyl, and C$_{2-8}$ alkynyl; and each hydrogen in R$^1$ is optionally substituted by one or more R$^3$ groups;

R$^2$ is hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, and each hydrogen in R$^2$ is optionally substituted by one or more R$^8$ groups;

R$^3$ is halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, each hydrogen in R$^3$ is optionally substituted by one or more R$^8$ groups, and R$^3$ groups on adjacent atoms may combine to form a C$_{6-12}$ aryl, 5-12 membered heteroaryl, C$_{3-12}$ cycloalkyl or 3-12 membered heteroalicyclic group;

each R$^4$, R$^5$, R$^6$ and R$^7$ is independently hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl; or any two of R$^4$, R$^5$, R$^6$ and R$^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of R$^4$, R$^5$, R$^6$ and R$^7$ bound to the same carbon atom may be combined to form a C$_{3-12}$ cycloalkyl, C$_{6-12}$ aryl, 3-12 membered heteroalicyclic or 5-12 membered heteroaryl group; and each hydrogen in R$^4$, R$^5$, R$^6$ and R$^7$ is optionally substituted by one or more R$^8$ groups;

each R$^8$ is independently halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —CN, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic) or —O—(CH$_2$)$_n$(5-12 membered heteroaryl); and each hydrogen in R$^8$ is optionally substituted by one or more R$^{11}$ groups;

A$^1$ is —(CR$^9$R$^{10}$)$_n$-A$^2$;

each R$^9$ and R$^{10}$ is independently hydrogen, halogen, C$_{1-12}$ alkyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —NR$^4$C(O)R$^5$, —(CR$^6$R$^7$)$_n$C(O)OR$^4$, —(CR$^6$R$^7$)$_n$NCR$^4$R$^5$, —NR$^4$C(O)NR$^5$R$^6$, —NR$^4$S(O)$_p$R$^5$ or —C(O)NR$^4$R$^5$; R$^9$ and R$^{10}$ may combine to form a C$_{3-12}$ cycloalkyl, 3-12 membered heteroalicyclic, C$_{6-12}$ aryl or 5-12 membered heteroaryl ring; and each hydrogen in R$^9$ and R$^{10}$ is optionally substituted by one or more R$^3$ groups;

A$^2$ is C$_{6-12}$ aryl, 5-12 membered heteroaryl, C$_{3-12}$ cycloalkyl or 3-12 membered heteroalicyclic, and A$^2$ is optionally substituted by one or more R$^3$ groups;

each R$^{11}$ is independently halogen, C$_{1-12}$ alkyl, C$_{1-12}$ alkoxy, C$_{3-12}$ cycloalkyl, C$_{6-12}$ aryl, 3-12 membered heteroalicyclic, 5-12 membered heteroaryl, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic), —O—(CH$_2$)$_n$(5-12 membered heteroaryl) or —CN, and each hydrogen in R$^{11}$ is optionally substituted by one or more groups selected from halogen, —OH, —CN, —C$_{1-12}$ alkyl which may be partially or fully halogenated, —O—C$_{1-12}$ alkyl which may be partially or fully halogenated, —CO, —SO and —SO$_2$;

R$^{12}$ is hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, and each hydrogen in R$^{12}$ is optionally substituted by one or more R$^3$ groups;

R$^1$ and R$^2$ or R$^1$ and R$^{12}$ may be combined together to form a C$_{6-12}$ aryl, 5-12 membered heteroaryl, C$_{3-12}$ cycloalkyl or 3-12 membered heteroalicyclic group;

m is 0, 1 or 2;

n is 0, 1, 2, 3 or 4; and p is 1 or 2;

or a pharmaceutically acceptable salt, solvate or hydrate thereof.

In a particular aspect of this embodiment, the compound has formula 2a

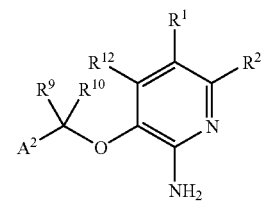

2a wherein A$^2$ is C$_{6-12}$ aryl or 5-12 membered heteroaryl optionally substituted by one or more R$^3$ groups.

In particular aspects of this embodiment, and in combination with any other particular aspects of this embodiment, R$^1$ is selected from C$_{6-12}$ aryl and 5-12 membered heteroaryl, and each hydrogen in R$^1$ is optionally substituted by one or more R$^3$ groups.

In particular aspects of this embodiment, and in combination with any other particular aspects of this embodiment not inconsistent with the following definition of R$^1$, R$^1$ is selected from C$_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —NR$^4$C(O)R$^5$, —C(=NR$^6$)NR$^4$R$^5$, C$_{1-8}$ alkyl, C$_{2-8}$ alkenyl, and C$_{2-8}$ alkynyl; and each hydrogen in R$^1$ is optionally substituted by one or more R$^3$ groups.

In particular aspects of this embodiment, and in combination with any other particular aspects of this embodiment, A$^2$ is substituted by at least one halogen atom.

In particular aspects of this embodiment, and in combination with any other particular aspects of this embodiment, R$^2$ is hydrogen, R$^9$ and R$^{10}$ are independently C$_{1-4}$ alkyl, and A$^2$ is phenyl substituted by at least one halogen atom.

In particular aspects of this embodiment, and in combination with any other particular aspects of this embodiment not inconsistent with the following definition of R$^1$, R$^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane or phenyl group, and each hydrogen in R$^1$ is optionally substituted by one or more R$^3$ groups.

In particular aspects of this embodiment, and in combination with any other particular aspects of this embodiment not inconsistent with the following definition of R$^1$, R$^1$ is a fused ring heteroaryl group, and each hydrogen in R$^1$ is optionally substituted by one or more R$^3$ groups.

In particular aspects of this embodiment, and in combination with any other particular aspects of this embodiment not inconsistent with the following definition of R$^1$, R$^1$ is a —SO$_2$NR$^4$R$^5$ group.

In another embodiment, the invention provides a compound of formula 3

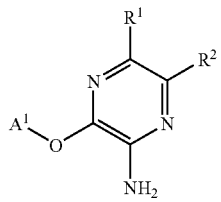

wherein:

R¹ is selected from $C_{6-12}$ aryl, 5-12 membered heteroaryl, $C_{3-12}$ cycloalkyl, 3-12 membered heteroalicyclic, $-O(CR^6R^7)_nR^4$, $-C(O)R^4$, $-C(O)OR^4$, $-CN$, $-NO_2$, $-S(O)_mR^4$, $-SO_2NR^4R^5$, $-C(O)NR^4R^5$, $-NR^4C(O)R^5$, $-C(=NR^6)NR^4R^5$, $C_{1-4}$ alkyl, $C_{2-8}$ alkenyl, and $C_{2-8}$ alkynyl; and each hydrogen in R¹ is optionally substituted by one or more R³ groups;

R² is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nNCR^4R^5$, $-C(=NR^6)NR^4R^5$, $-NR^4C(O)NR^5R^6$, $-NR^4S(O)_pR^5$ or $-C(O)NR^4R^5$, and each hydrogen in R² is optionally substituted by one or more R⁸ groups;

R³ is halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nNCR^4R^5$, $-C(=NR^6)NR^4R^5$, $-NR^4C(O)NR^5R^6$, $-NR^4S(O)_pR^5$ or $-C(O)NR^4R^5$, each hydrogen in R³ is optionally substituted by one or more R⁸ groups, and R³ groups on adjacent atoms may combine to form a $C_{6-12}$ aryl, 5-12 membered heteroaryl, $C_{3-12}$ cycloalkyl or 3-12 membered heteroalicyclic group;

each R⁴, R⁵, R⁶ and R⁷ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of R⁴, R⁵, R⁶ and R⁷ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of R⁴, R⁵, R⁶ and R⁷ bound to the same carbon atom may be combined to form a $C_{3-12}$ cycloalkyl, $C_{6-12}$ aryl, 3-12 membered heteroalicyclic or 5-12 membered heteroaryl group; and each hydrogen in R⁴, R⁵, R⁶ and R⁷ is optionally substituted by one or more R⁸ groups;

each R⁸ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-CN$, $-O-C_{1-12}$ alkyl, $-O-(CH_2)_nC_{3-12}$ cycloalkyl, $-O-(CH_2)_nC_{6-12}$ aryl, $-O-(CH_2)_n$(3-12 membered heteroalicyclic) or $-O-(CH_2)_n$(5-12 membered heteroaryl); and each hydrogen in R⁸ is optionally substituted by one or more R¹¹ groups;

A¹ is $-(CR^9R^{10})_n-A^2$ except that:
(i) when R¹ is substituted or unsubstituted aryl or substituted or unsubstituted heteroaryl, A¹ is $-(CR^9R^{10})_n-A^2$ and n is not zero; and
(ii) when R² is H and A¹ is m-chlorobenzyl, R¹ is not unsubstituted piperazine;

each R⁹ and R¹⁰ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-NR^4C(O)R^5$, $-(CR^6R^7)_nC(O)OR^4$, $-(CR^6R^7)_nNCR^4R^5$, $-NR^4C(O)NR^5R^6$, $-NR^4S(O)_pR^5$ or $-C(O)NR^4R^5$; R⁹ and R¹⁰ may combine to form a $C_{3-12}$ cycloalkyl, 3-12 membered heteroalicyclic, $C_{6-12}$ aryl or 5-12 membered heteroaryl ring; and each hydrogen in R⁹ and R¹⁰ is optionally substituted by one or more R³ groups;

A² is $C_{6-12}$ aryl, 5-12 membered heteroaryl, $C_{3-12}$ cycloalkyl or 3-12 membered heteroalicyclic, and A² is optionally substituted by one or more R³ groups;

each R¹¹ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, $-O-C_{1-12}$ alkyl, $-O-(CH_2)_nC_{3-12}$ cycloalkyl, $-O-(CH_2)_nC_{6-12}$ aryl, $-O-(CH_2)_n$(3-12 membered heteroalicyclic), $-O-(CH_2)_n$(5-12 membered heteroaryl) or $-CN$, and each hydrogen in R¹¹ is optionally substituted by one or more groups selected from halogen, $-OH$, $-CN$, $-C_{1-12}$ alkyl which may be partially or fully halogenated, $-O-C_{1-12}$ alkyl which may be partially or fully halogenated, $-CO$, $-SO$ and $-SO_2$;

R¹ and R² may be combined together to form a $C_{6-12}$ aryl, 5-12 membered heteroaryl, $C_{3-12}$ cycloalkyl or 3-12 membered heteroalicyclic group;

m is 0, 1 or 2;

n is 0, 1, 2, 3 or 4; and p is 1 or 2;

or a pharmaceutically acceptable salt, solvate or hydrate thereof.

In a particular aspect of this embodiment, the compound has formula 3a

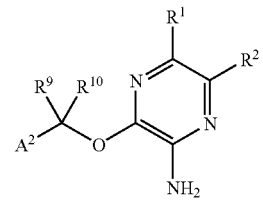

wherein A² is $C_{6-12}$ aryl or 5-12 membered heteroaryl optionally substituted by one or more R³ groups.

In particular aspects of this embodiment, and in combination with any other particular aspects of this embodiment, R¹ is selected from $C_{6-12}$ aryl and 5-12 membered heteroaryl, and each hydrogen in R¹ is optionally substituted by one or more R³ groups.

In particular aspects of this embodiment, and in combination with any other particular aspects of this embodiment not inconsistent with the following definition of R¹, R¹ is selected from $C_{3-12}$ cycloalkyl, 3-12 membered heteroalicyclic, $-O(CR^6R^7)_nR^4$, $-C(O)R^4$, $-C(O)OR^4$, $-CN$, $-NO_2$, $-S(O)_mR^4$, $-SO_2NR^4R^5$, $-C(O)NR^4R^5$, $-NR^4C(O)R^5$, $-C(=NR^6)NR^4R^5$, $C_{1-8}$ alkyl, $C_{2-8}$ alkenyl, and $C_{2-8}$ alkynyl; and each hydrogen in R¹ is optionally substituted by one or more R³ groups.

In particular aspects of this embodiment, and in combination with any other particular aspects of this embodiment, A² is substituted by at least one halogen atom.

In particular aspects of this embodiment, and in combination with any other particular aspects of this embodiment, $R^2$ is hydrogen, $R^9$ and $R^{10}$ are independently $C_{1-4}$ alkyl, and $A^2$ is phenyl substituted by at least one halogen atom.

In particular aspects of this embodiment, and in combination with any other particular aspects of this embodiment not inconsistent with the following definition of $R^1$, $R^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane or phenyl group, and each hydrogen in $R^1$ is optionally substituted by one or more $R^3$ groups.

In particular aspects of this embodiment, and in combination with any other particular aspects of this embodiment not inconsistent with the following definition of $R^1$, $R^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, triazine, trithiane or phenyl group, and each hydrogen in $R^1$ is optionally substituted by one or more $R^3$ groups. In still more particular aspects, $R^1$ is not heteroalicyclic.

In particular aspects of this embodiment, and in combination with any other particular aspects of this embodiment not inconsistent with the following definition of $R^1$, $R^1$ is a fused ring heteroaryl group, and each hydrogen in $R^1$ is optionally substituted by one or more $R^3$ groups.

In particular aspects of this embodiment, and in combination with any other particular aspects of this embodiment not inconsistent with the following definition of $R^1$, $R^1$ is a $-SO_2NR^4R^5$ group.

In another embodiment, the invention provides a compound of formula 4

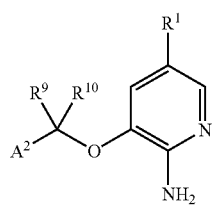

4 wherein:

$R^1$ is selected from $C_{6-12}$ aryl, 5-12 membered heteroaryl, $C_{3-12}$ cycloalkyl, 3-12 membered heteroalicyclic, $-O(CR^6R^7)_nR^4$, $-C(O)R^4$, $-C(O)OR^4$, $-CN$, $-NO_2$, $-S(O)_mR^4$, $-SO_2NR^4R^5$, $-C(O)NR^4R^5$, $-NR^4C(O)R^5$, $-C(=NR^6)NR^4R^5$, $C_{1-8}$ alkyl, $C_{2-8}$ alkenyl, and $C_{2-8}$ alkynyl; and each hydrogen in $R^1$ is optionally substituted by one or more $R^3$ groups;

$R^3$ is halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-O(CR^6R^7)R^4$, $-NR^4C(O)R^5$, $-(CR^6R^7)_nC(O)OR^4$, $-(CR^6R^7)_nNCR^4R^5$, $-C(=NR^6)NR^4R^5$, $-NR^4C(O)NR^5R^6$, $-NR^4S(O)_pR^5$ or $-C(O)NR^4R^5$, each hydrogen in $R^3$ is optionally substituted by one or more $R^8$ groups, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by one or more $R^5$ groups;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-CN$, $-O-C_{1-12}$ alkyl, $-O-(CH_2)_nC_{3-12}$ cycloalkyl, $-O-(CH_2)_nC_{6-12}$ aryl, $-O-(CH_2)_n(3\text{-}12\text{ membered heteroalicyclic})$ or $-O-(CH_2)_n(5\text{-}12\text{ membered heteroaryl})$; and each hydrogen in $R^8$ is optionally substituted by one or more $R^{11}$ groups;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-NR^4C(O)R^5$, $-(CR^6R^7)_nC(O)OR^4$, $-(CR^6R^7)_nNCR^4R^5$, $-NR^4C(O)NR^5R^6$, $-NR^4S(O)_pR^5$ or $-C(O)NR^4R^5$; $R^9$ and $R^{10}$ may combine to form a $C_{3-12}$ cycloalkyl, 3-12 membered heteroalicyclic, $C_{6-12}$ aryl or 5-12 membered heteroaryl ring; and each hydrogen in $R^9$ and $R^{10}$ is optionally substituted by one or more $R^3$ groups;

$A^2$ is $C_{6-12}$ aryl, 5-12 membered heteroaryl, $C_{3-12}$ cycloalkyl or 3-12 membered heteroalicylic, and $A^2$ is optionally substituted by one or more $R^3$ groups;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, $-O-C_{1-12}$ alkyl, $-O-(CH_2)_nC_{3-12}$ cycloalkyl, $-O-(CH_2)_nC_{6-12}$ aryl, $-O-(CH_2)_n(3\text{-}12\text{ membered heteroalicyclic})$, $-O-(CH_2)_n(5\text{-}12\text{ membered heteroaryl})$ or $-CN$, and each hydrogen in $R^{11}$ is optionally substituted by one or more groups selected from halogen, $-OH$, $-CN$, $-C_{1-12}$ alkyl which may be partially or fully halogenated, $-O-C_{1-12}$ alkyl which may be partially or fully halogenated, $-CO$, $-SO$ and $-SO_2$;

m is 0, 1 or 2;

n is 0, 1, 2, 3 or 4; and p is 1 or 2;

or a pharmaceutically acceptable salt, solvate or hydrate thereof.

In a particular aspect of this embodiment, $A^2$ is $C_{6-12}$ aryl or 5-12 membered heteroaryl optionally substituted by one or more $R^3$ groups.

In other particular aspects of this embodiment, preferred substituents and groups of substituents include those defined in particular aspects of the previous embodiments.

In another embodiment, the invention provides a compound of formula 5

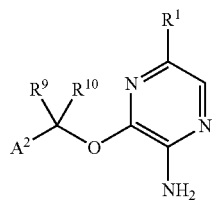

wherein:

$R^1$ is selected from $C_{6-12}$ aryl, 5-12 membered heteroaryl, $C_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —NR$^4$C(O)R$^5$, —C(=NR$^6$)NR$^4$R$^5$, $C_{1-8}$ alkyl, $C_{2-8}$ alkenyl, and $C_{2-8}$ alkynyl; and each hydrogen in $R^1$ is optionally substituted by one or more $R^3$ groups;

$R^3$ is halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, each hydrogen in $R^3$ is optionally substituted by one or more $R^8$ groups, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$; $R^5$, $R^6$ and $R^7$ is independently hydrogen, halogen, $C_{1-12}$ alkyl, $C_{2-12}$ alkenyl, $C_{2-12}$ alkynyl, $C_{1-2}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by one or more $R^8$ groups;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —CN, —O—$C_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic) or —O—(CH$_2$)$_n$(5-12 membered heteroaryl); and each hydrogen in $R^8$ is optionally substituted by one or more $R^{11}$ groups;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —NR$^4$C(O)R$^5$, —(CR$^6$R$^7$)$_n$C(O)OR$^4$, —(CR$^6$R$^7$)$_n$NCR$^4$R$^5$, —NR$^4$C(O)NR$^5$R$^6$, —NR$^4$S(O)$_p$R$^5$ or —C(O)NR$^4$R$^5$; $R^9$ and $R^{10}$ may combine to form a $C_{3-12}$ cycloalkyl, 3-12 membered heteroalicyclic, $C_{6-12}$ aryl or 5-12 membered heteroaryl ring; and each hydrogen in $R^9$ and $R^{10}$ is optionally substituted by one or more $R^3$ groups;

$A^2$ is $C_{6-12}$ aryl, 5-12 membered heteroaryl, $C_{3-12}$ cycloalkyl or 3-12 membered heteroalicyclic, and $A^2$ is optionally substituted by one or more $R^3$ groups; except that when $R^2$, $R^9$ and $R^{10}$ are all H and $A^2$ is m-chlorophenyl, $R^1$ is not unsubstituted piperazine;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic), —O—(CH$_2$)$_n$(5-12 membered heteroaryl) or —CN, and each hydrogen in $R^{11}$ is optionally substituted by one or more groups selected from halogen, —OH, —CN, —$C_{1-12}$ alkyl which may be partially or fully halogenated, —O—$C_{1-12}$ alkyl which may be partially or fully halogenated, —CO, —SO and —SO$_2$;

m is 0, 1 or 2;
n is 0, 1, 2, 3 or 4; and
p is 1 or 2;

or a pharmaceutically acceptable salt, solvate or hydrate thereof.

In a particular aspect of this embodiment, $A^2$ is $C_{6-12}$ aryl or 5-12 membered heteroaryl optionally substituted by one or more $R^3$ groups.

In other particular aspects of this embodiment, preferred substituents and groups of substituents include those defined in particular aspects of the previous embodiments.

In another embodiment, the invention provides a compound selected from the group consisting of: 4-[6-amino-5-(2,6-dichloro-benzyloxy)-pyridin-3-yl]-phenol; 3-(2,6-dichloro-benzyloxy)-5-[4-(2-morpholin-4-yl-ethoxy)-phenyl]-pyridin-2-ylamine; 3-(2,6-dichloro-benzyloxy)-5-[3-(2-morpholin-4-yl-ethoxy)-phenyl]-pyridin-2-ylamine; 3-(2,6-dichloro-benzyloxy)-5-(1H-indol-4-yl)-pyridin-2-ylamine; 3-[2-chloro-6-(1H-indol-4-yl)-benzyloxy]-5-(1H-indol-4-yl)-pyridin-2-ylamine; 2-[6-amino-5-2,6-dichloro-benzyloxy)-pyridin-3-yl]-pyrrole-1-carboxylic acid tert-butyl ester; 3-(2,6-dichloro-benzyloxy)-5-(1H-pyrrol-2-yl)-pyridin-2-ylamine; 3-(2,6-dichloro-benzyloxy)-5-(4-fluoro-phenyl)-pyridin-2-ylamine; 3-(2,6-dichloro-benzyloxy)-5-phenyl-pyridin-2-ylamine; 3-(2,6-dichloro-benzyloxy)-5-(2-fluoro-phenyl)-pyridin-2-ylamine; 3-(2,6-dichloro-benzyloxy)-5-(3-fluoro-phenyl)-pyridin-2-ylamine; 5-(4-amino-phenyl)-3-(2,6-dichloro-benzyloxy)-pyridin-2-ylamine; N-{4-[6-amino-5-(2,6-dichloro-benzyloxy)-pyridin-3-yl]-phenyl}-methanesulfonamide; N-{4-[6-amino-5-(2,6-dichloro-benzyloxy)-pyridin-3-yl]-phenyl}-acetamide; 3-[6-amino-5-(2,6-dichloro-benzyloxy)-pyridin-3-yl]-phenol; 3-(2,6-dichloro-benzyloxy)-5-(4-methoxy-phenyl)-pyridin-2-ylamine; 5-(3-amino-phenyl)-3-(2,6-dichloro-benzyloxy)-pyridin-2-ylamine; 3-(2,6-dichloro-benzyloxy)-5-(3-trifluoromethoxy-phenyl)-pyridin-2-ylamine; 2-[6-amino-5-(2,6-dichloro-benzyloxy)-pyridin-3-yl]-phenol; 3-(2,6-dichloro-benzyloxy)-5-(2-phenoxy-phenyl)-pyridin-2-ylamine; 3-(2,6-dichloro-benzyloxy)-5-(3,4-difluoro-phenyl)-pyridin-2-ylamine; 3-(2,6-dichloro-benzyloxy)-5-(3-isopropyl-phenyl)-pyridin-2-ylamine; 3-(2,6-dichloro-benzyloxy)-5-(2-trifluoromethyl-phenyl)-pyridin-2-ylamine; 3-(2,6-dichloro-benzyloxy)-5-(2-methoxy-phenyl)-pyridin-2-ylamine; 3-(2,6-dichloro-benzyloxy)-5-(4-trifluoromethyl-phenyl)-pyridin-2-ylamine; N-{2-[6-amino-5-(2,6-dichloro-benzyloxy)-pyridin-3-yl]-phenyl}-methanesulfonamide; {4-[6-amino-5-(2,6-dichloro-benzyloxy)-pyridin-3-yl]-phenyl}-methanol; 5-benzo[1,3]dioxol-5-yl-3-(2,6-dichloro-benzyloxy)-pyridin-2-ylamine; 3-(2,6-dichloro-benzyloxy)-5-(2-trifluoromethoxy-phenyl)-pyridin-2-ylamine; 3-(2,6-dichloro-benzyloxy)-5-(4-methyl-thiophen-2-yl)-pyridin-2-ylamine; 5-(2-benzyloxy-phenyl)-3-(2,6-dichloro-benzyloxy)-pyridin-2-ylamine; 3-(2,6-dichloro-benzyloxy)-5-(3-methoxy-phenyl)-pyridin-2-ylamine; 3-(2,6-dichloro-benzyloxy)-5-(1H-indol-2-yl)-pyridin-2-ylamine; 5-(4-benzyloxy-3- fluoro-phenyl)-3-(2,6-dichloro-benzyloxy)-pyridin-2-ylamine; 4-[6-amino-5-(2,6-dichloro-benzyloxy)-pyridin-3-yl]-benzoic acid; 4-[6-amino-5-(2,6-dichloro-benzyloxy)-pyridin-3-yl]-N-(2-diethylamino-ethyl)-benzamide; 4-[6-amino-5-(2,6-dichloro-benzyloxy)-pyridin-3-yl]-N-(3-diethylamino-propyl)-benzamide; {4-[6-amino-5-(2,6-dichloro-benzyloxy)-pyridin-3-yl]-phenyl}-(4-methyl-piperazin-1-yl)-methanone; {4-[6-amino-5-(2,6-dichloro-benzyloxy)-pyridin-3-yl]-phenyl}-[(2R)-2-pyrrolidin-1-ylmethyl-pyrrolidin-1-yl]-methanone; {4-[6-amino-5-(2,6-dichloro-benzyloxy)-pyridin-3-yl]-phenyl}-[(2S)-2-pyrrolidin-1-ylmethyl-pyrrolidin-1-yl]-methanone; {4-[6-amino-5-(2,6-dichloro-benzyloxy)-pyridin-3-yl]-phenyl}-(4-pyrrolidin-1-yl-piperidin-1-yl)-methanone; {4-[6-amino-5-(2,6-dichloro-benzyloxy)-pyridin-3-yl]-phenyl}[4-(2-hydroxy-ethyl)-piperidin-1-yl]-methanone; {4-[6-amino-5-(2,6-dichloro-benzyloxy)-pyridin-3-yl]-phenyl}-[(3S)-3-dimethylamino-pyrrolidin-1-yl]-methanone; {4-[6-amino-5-(2,6-dichloro-benzyloxy)-pyridin-3-yl]-phenyl}-[(3R)-3-dimethylamino-pyrrolidin-1-yl]-methanone; {4-[6-amino-5-(2,6-dichloro-benzyloxy)-pyridin-3-yl]-phenyl}-[(3S)-3-cyclopropylaminomethyl-piperidin-1-yl]-methanone; 4-[6-amino-5-(2,6-dichloro-benzyloxy)-pyridin-3-yl]-N-(2-hydroxy-3-pyrrolidin-1-yl-propyl)-benzamide; {4-[6-amino-5-(2,6-dichloro-benzyloxy)-pyridin-3-yl]-phenyl}-[(2S)-2-(3-fluoro-piperidin-1-ylmethyl)-pyrrolidin-1-yl]-methanone; {4-[6-amino-5-(2,6-dichloro-benzyloxy)-pyridin-3-yl]-phenyl}-(4-cyclopropyl-piperazin-1-yl)-methanone; {4-[6-amino-5-(2,6-dichloro-benzyloxy)-pyridin-3-yl]-phenyl}-{(2R)-2-[(cyclopropylmethyl-amino)-methyl]-pyrrolidin-1-yl}-methanone; 4-[6-amino-5-(2,6-dichloro-benzyloxy)-pyridin-3-yl]-N-cyclopropylmethyl-N-(2R)-pyrrolidin-2-ylmethyl-benzamide; 4-[6-amino-5-(2,6-dichloro-benzyloxy)-pyridin-3-yl]-N-(2-hydroxy-3-pyrrolidin-1-yl-propyl)-N-methyl-benzamide; {4-[6-amino-5-(2,6-dichloro-benzyloxy)-pyridin-3-yl]-phenyl}-{(2S)-2-[(3R)-3-hydroxy-pyrrolidin-1-ylmethyl]-pyrrolidin-1-yl}-methanone; 3-[6-amino-5-(2,6-dichloro-benzyloxy)-pyridin-3-yl]-benzoic acid; {3-[6-amino-5-(2,6-dichloro-benzyloxy)-pyridin-3-yl]-phenyl}-[(2R)-2-pyrrolidin-1-ylmethyl-pyrrolidin-1-yl]-methanone; {4-[6-amino-5-(2,6-dichloro-benzyloxy)-pyridin-3-yl]-phenoxy}-acetic acid; 2-{4-[6-amino-5-(2,6-dichloro-benzyloxy)-pyridin-3-yl]-phenoxy}-1-[(2R)-2-pyrrolidin-1-ylmethyl-pyrrolidin-1-yl]-ethanone; 2-{4-[6-amino-5-(2,6-dichloro-benzyloxy)-pyridin-3-yl]-phenoxy}-1-[(2S)-2-pyrrolidin-1-ylmethyl-pyrrolidin-1-yl]-ethanone; 3-(2,6-dichloro-benzyloxy)-5-(1H-indol-5-yl)-pyridin-2-ylamine; 3-(2,6-dichloro-benzyloxy)-5-[3-(1-methyl-1,2,3,6-tetrahydro-pyridin-4-yl)-1H-indol-5-yl]-pyridin-2-ylamine; 3-(2,6-dichloro-benzyloxy)-5-[3-(1-methyl-piperidin-4-yl)-1H-indol-5-yl]-pyridin-2-ylamine; 3-(2,6-dichloro-benzyloxy)-5-(3-morpholin-4-ylmethyl-1H-indol-5-yl)-pyridin-2-ylamine; 3-(2,6-dichloro-benzyloxy)-5-(3-piperidin-1-ylmethyl-1H-indol-5-yl)-pyridin-2-ylamine; 3-(2,6-dichloro-benzyloxy)-5-(3-pyrrolidin-1-ylmethyl-1H-indol-5-yl)-pyridin-2-ylamine; 3-(2,6-dichloro-benzyloxy)-5-(3-diethylaminomethyl-1H-indol-5-yl)-pyridin-2-ylamine; (1-{5-[6-amino-5-(2,6-dichloro-benzyloxy)-pyridin-3-yl]-1H-indol-3-ylmethyl}-(3R)-pyrrolidin-3-yl)-carbamic acid tert-butyl ester; 3-(2,6-dichloro-benzyloxy)-5-[3-(2,6-dimethyl-morpholin-4-ylmethyl)-1H-indol-5-yl]-pyridin-2-ylamine; N-(1-{5-[6-amino-5-(2,6-dichloro-benzyloxy)-pyridin-3-yl]-1H-indol-3-ylmethyl}-(3R)-pyrrolidin-3-yl)-acetamide; 1-(4-{5-[6-amino-5-(2,6-dichloro-benzyloxy)-pyridin-3-yl]-1H-indol-3-ylmethyl}-piperazin-1-yl)-ethanone; 3-(2-chloro-3,6-difluoro-benzyloxy)-5-(1H-indol-5-yl)-pyridin-2-ylamine; 1-(4-{5-[6-amino-5-(2-chloro-3,6-difluoro-benzyloxy)-pyridin-3-yl]-1H-indol-3-ylmethyl}-piperazin-1-yl)-ethanone; 3-(2-chloro-3,6-difluoro-benzyloxy)-5-[3-(2,6-dimethyl-morpholin-4-ylmethyl)-1H-indol-5-yl]-pyridin-2-ylamine; N-(1-{5-[6-amino-5-(2-chloro-3,6-difluoro-benzyloxy)-pyridin-3-yl]-1H-indol-3-ylmethyl}-(3S)-pyrrolidin-3-yl)-acetamide; 3-(2-chloro-3,6-difluoro-benzyloxy)-5-(3-piperidin-1-ylmethyl-1H-indol-5-yl)-pyridin-2-ylamine; 3-(2-chloro-3,6-difluoro-benzyloxy)-5-(3-morpholin-4-ylmethyl-1H-indol-5-yl)-pyridin-2-ylamine; 3-(2-chloro-3,6-difluoro-benzyloxy)-5-(3-pyrrolidin-1-ylmethyl-1H-indol-5-yl)-pyridin-2-ylamine; 5-[6-amino-5-(2,6-dichloro-benzyloxy)-pyridin-3-yl]-1H-indole-2-carboxylic acid ethyl ester; 5-[6-amino-5-(2,6-dichloro-benzyloxy)-pyridin-3-yl]-1H-indole-2-carboxylic acid; {5-[6-amino-5-(2,6-dichloro-benzyloxy)-pyridin-3-yl]-1H-indol-2-yl}-(4-methyl-piperazin-1-yl)-methanone; {5-[6-amino-5-(2,6-dichloro-benzyloxy)-pyridin-3-yl]-1H-indol-2-yl}-[(3R)-3-dimethylamino-pyrrolidin-1-yl]-methanone; {5-[6-amino-5-(2,6-dichloro-benzyloxy)-pyridin-3-yl]-1H-indol-2-yl}-[(2R)-2-pyrrolidin-1-ylmethyl-pyrrolidin-1-yl]-methanone; 5-[6-amino-5-(2,6-dichloro-benzyloxy)-pyridin-3-yl]-1H-indole-2-carboxylic acid (2-pyrrolidin-1-yl-ethyl)-amide; 5-[6-amino-5-(2,6-dichloro-benzyloxy)-pyridin-3-yl]-1H-indole-2-carboxylic acid (2-morpholin-4-yl-ethyl)-amide; (1-{5-[6-amino-5-(2,6-dichloro-benzyloxy)-pyridin-3-yl]-1H-indole-2-carbonyl}-(3S)-pyrrolidin-3-yl)-carbamic acid tert-butyl ester; {5-[6-amino-5-(2,6-dichloro-benzyloxy)-pyridin-3-yl]-1H-indol-2-yl}-[(3S)-3-amino-pyrrolidin-1-yl]-methanone; 5-[6-amino-5-(2,6-dichloro-benzyloxy)-pyridin-3-yl]-1H-indole-2-carboxylic acid (2-hydroxy-3-pyrrolidin-1-yl-propyl)-amide; 4-(6-amino-5-benzyloxy-pyridin-3-yl)-phenol; 3-benzyloxy-5-phenyl-pyridin-2-ylamine; 3-(3-methoxy-benzyloxy)-5-phenyl-pyridin-2-ylamine; 3-(2-chloro-4-fluoro-benzyloxy)-5-phenyl-pyridin-2-ylamine; 3-(2-chloro-benzyloxy)-5-phenyl-pyridin-2-ylamine; 3-(2,5-dichloro-benzyloxy)-5-phenyl-pyridin-2-ylamine; 3-(2-chloro-5-trifluoromethyl-benzyloxy)-5-phenyl-pyridin-2-ylamine; 3-(2,4-dichloro-5-fluoro-benzyloxy)-5-phenyl-pyridin-2-ylamine; 3-(2-chloro-3-trifluoromethyl-benzyloxy)-5-phenyl-pyridin-2-ylamine; 3-(2-chloro-3,6-difluoro-benzyloxy)-5-phenyl-pyridin-2-ylamine; 3-(3,4-dichloro-benzyloxy)-5-phenyl-pyridin-2-ylamine; 2-(2-amino-5-phenyl-pyridin-3-yloxymethyl)-benzonitrile; 3-(2-chloro-6-fluoro-3-methyl-benzyloxy)-5-phenyl-pyridin-2-ylamine; 5-Phenyl-3-(2,3,6-trifluoro-benzyloxy)-pyridin-2-ylamine; 3-(2,6-difluoro-benzyloxy)-5-phenyl-pyridin-2-ylamine; 3-(2,6-difluoro-3-methyl-benzyloxy)-5-phenyl-pyridin-2-ylamine; 3-(3-chloro-2,6-difluoro-benzyloxy)-5-phenyl-pyridin-2-ylamine; 3-(2-chloro-6-fluoro-benzyloxy)-5-phenyl-pyridin-2-ylamine; 3-(3-Fluoro-4-methoxy-benzyloxy)-5-phenyl-pyridin-2-ylamine; N-[3-(2-amino-5-phenyl-pyridin-3-yloxymethyl)-phenyl]-methanesulfonamide; 5-[4-(2-morpholin-4-yl-ethoxy)-phenyl]-3-(3-nitro-benzyloxy)-pyridin-2-ylamine; 5-[4-(2-morpholin-4-yl-ethoxy)-phenyl]-3-(naphthalen-1-ylmethoxy)-pyridin-2-ylamine; 3-(2-chloro-3,6-difluoro-benzyloxy)-5-[4-(2-morpholin-4-yl-ethoxy)-phenyl]-pyridin-2-ylamine; 2-{2-amino-5-[4-(2-morpholin-4-yl-ethoxy)-phenyl]-pyridin-3-yloxy}-N-(4-isopropyl-phenyl)-2-phenyl-acetamide; 3-(5-chloro-benzo[b]thiophen-3-ylmethoxy)-5-[4-(2-morpholin-4-yl-ethoxy)-phenyl]-pyridin-2-ylamine; {4-[6-amino-5-(4-fluoro-2-trifluoromethyl-benzyloxy)-pyridin-3-yl]-phenyl}-[(2R)-2-pyrrolidin-1-ylmethyl-pyrrolidin-1-yl]-methanone; {4-[6- amino-5-(2-fluoro-6-trifluoromethyl-benzyloxy)-pyridin-3-yl]-phenyl}-[(2R)-2-pyrrolidin-1-ylmethyl-pyrrolidin-1-yl]-methanone; {4-[6-amino-5-(5-fluoro-2-trifluoromethyl-benzyloxy)-pyridin-3-yl]-phenyl}-[(2R)-2-pyrrolidin-1-ylmethyl-pyrrolidin-1-yl]-methanone; (4-{6-amino-5-[1-(2-trifluoromethyl-phenyl)-ethoxy]-pyridin-3-yl}-phenyl)-[(2R)-2-pyrrolidin-1-ylmethyl-pyrrolidin-1-yl]-methanone; {4-[6-amino-5-(2-bromo-benzyloxy)-pyridin-3-yl]-phenyl}-[(2R)-2-pyrrolidin-1-ylmethyl-pyrrolidin-1-yl]-methanone; {4-[6-amino-5-(3-fluoro-2-trifluoromethyl-benzyloxy)-pyridin-3-yl]-phenyl}-[(2R)-2-pyrrolidin-1-ylmethyl-pyrrolidin-1-yl]-methanone; {4-[6-amino-5-(2-chloro-3,6-difluoro-benzyloxy)-pyridin-3-yl]-phenyl}-[(2R)-2-pyrrolidin-1-ylmethyl-pyrrolidin-1-yl]-methanone; 4-[6-amino-5-(2,6-difluoro-benzyloxy)-pyridin-3-yl]-phenol; 3-(2,6-difluoro-benzyloxy)-5-(1H-indol-4-yl)-pyridin-2-ylamine; 3-(2,6-difluoro-benzyloxy)-5-[4-(2-morpholin-4-yl-ethoxy)-phenyl]-pyridin-2-ylamine; 4-[6-amino-5-(2,6-difluoro-benzyloxy)-pyridin-3-yl]-benzoic acid; {4-[6-amino-5-(2,6-difluoro-benzyloxy)-pyridin-3-yl]-phenyl}-[(2R)-2-pyrrolidin-1-ylmethyl-pyrrolidin-1-yl]-methanone; {4-[6-amino-5-(2,6-difluoro-benzyloxy)-pyridin-3-yl]-phenyl}-[(2S)-2-pyrrolidin-1-ylmethyl-pyrrolidin-1-yl]-methanone; {4-[6-amino-5-(2,6-difluoro-benzyloxy)-pyridin-3-yl]-phenoxy}acetic acid ethyl ester; {4-[6-amino-5-(2,6-difluoro-benzyloxy)-pyridin-3-yl]-phenoxy}-acetic acid; 2-{4-[6-amino-5-(2,6-difluoro-benzyloxy)-pyridin-3-yl]-phenoxy}-1-[(2R)-2-pyrrolidin-1-ylmethyl-pyrrolidin-1-yl]-ethanone; 2-{4-[6-amino-5-(2,6-difluoro-benzyloxy)-pyridin-3-yl]-phenoxy}-1-[(2S)-2-pyrrolidin-1-ylmethyl-pyrrolidin-1-yl]-ethanone; 4-[6-amino-5-(2-chloro-6-fluoro-benzyloxy)-pyridin-3-yl]-phenol; 4-[6-amino-5-(2-chloro-4-fluoro-benzyloxy)-pyridin-3-yl]-phenol; 4-[6-amino-5-(2,4-dichloro-benzyloxy)-pyridin-3-yl]-phenol; 2-[2-amino-5-(4-hydroxy-phenyl)-pyridin-3-yloxymethyl]-benzonitrile; 4-[6-amino-5-(2-trifluoromethyl-benzyloxy)-pyridin-3-yl]-phenol; 4-[6-amino-5-(2-chloro-benzyloxy)-pyridin-3-yl]-phenol; 4-[6-amino-5-(4-tert-butyl-benzyloxy)-pyridin-3-yl]-phenol; N-{4-[6-amino-5-(2-cyano-benzyloxy)-pyridin-3-yl]-phenyl}-methanesulfonamide; 2-[2-amino-5-(4-methanesulfonylamino-phenyl)-pyridin-3-yloxymethyl]-benzamide; 2-[2-amino-5-(4-methanesulfonylamino-phenyl)-pyridin-3-yloxymethyl]-benzoic acid; N-(4-{6-amino-5-[2-(4-methyl-piperazine-1-carbonyl)-benzyloxy]-pyridin-3-yl}-phenyl)-methanesulfonamide; 2-[2-amino-5-(4-methanesulfonylamino-phenyl)-pyridin-3-yloxymethyl]-N-(2-hydroxy-ethyl)-benzamide; 2-[2-amino-5-(4-methanesulfonylamino-phenyl)-pyridin-3-yloxymethyl]-N-isobutyl-benzamide; 4-[6-amino-5-(2-chloro-6-fluoro-benzyloxy)-pyridin-3-yl]-benzoic acid; {4-[6-amino-5-(2-chloro-6-fluoro-benzyloxy)-pyridin-3-yl]-phenyl}-[(2R)-2-pyrrolidin-1-ylmethyl-pyrrolidin-1-yl]-methanone; {4-[6-amino-5-(2-chloro-6-fluoro-benzyloxy)-pyridin-3-yl]-phenyl}-[(2S)-2-pyrrolidin-1-ylmethyl-pyrrolidin-1-yl]-methanone; {4-[6-amino-5-(2-chloro-6-fluoro-benzyloxy)-pyridin-3-yl]-phenyl}-[(3S)-3-dimethylamino-pyrrolidin-1-yl]-methanone; {4-[6-amino-5-(2-chloro-6-fluoro-benzyloxy)-pyridin-3-yl]-phenyl}-[(3S)-3-amino-pyrrolidin-1-yl]-methanone; {4-[6-amino-5-(2-chloro-6-fluoro-benzyloxy)-pyridin-3-yl]-phenyl}-(4-methyl-piperazin-1-yl)-methanone; 1-(4-{4-[6-amino-5-(2-chloro-6-fluoro-benzyloxy)-pyridin-3-yl]-benzoyl}-piperazin-1-yl)-ethanone; 4-[6-amino-5-(2-chloro-6-fluoro-benzyloxy)-pyridin-3-yl]-N-(2-morpholin-4-yl-ethyl)-benzamide; 4-[6-amino-5-(2-chloro-6-fluoro-benzyloxy)-pyridin-3-yl]-N-(3-morpholin-4-yl-propyl)-benzamide; 4-[6-amino-5-(2-chloro-benzyloxy)-pyridin-3-yl]-benzoic acid; {4-[6-amino-5-(2-chloro-benzyloxy)-pyridin-3-yl]-phenyl}-[(2R)-2-pyrrolidin-1-ylmethyl-pyrrolidin-1-yl]-methanone; {4-[6-amino-5-(2-chloro-benzyloxy)-pyridin-3-yl]-phenyl}-[(2S)-2-pyrrolidin-1-ylmethyl-pyrrolidin-1-yl]-methanone; {4-[6-amino-5-(2-chloro-benzyloxy)-pyridin-3-yl]-phenyl}-[(3S)-3-dimethylamino-pyrrolidin-1-yl]-methanone; {4-[6-amino-5-(2-chloro-benzyloxy)-pyridin-3-yl]-phenyl}-[(3S)-3-amino-pyrrolidin-1-yl]-methanone; {4-[6-amino-5-(2-chloro-benzyloxy)-pyridin-3-yl]-phenyl}-(4-pyrrolidin-1-yl-piperidin-1-yl)-methanone; {4-[6-amino-5-(2-chloro-benzyloxy)-pyridin-3-yl]-phenyl}-(4-methyl-piperazin-1-yl)-methanone; 1-(4-{4-[6-amino-5-(2-chloro-benzyloxy)-pyridin-3-yl]-benzoyl}-piperazin-1-yl)-ethanone; 4-[6-amino-5-(2-chloro-benzyloxy)-pyridin-3-yl]-N-(2-morpholin-4-yl-ethyl)-benzamide; 4-[6-amino-5-(2-chloro-benzyloxy)-pyridin-3-yl]-N-(3-morpholin-4-yl-propyl)-benzamide; 4-[6-amino-5-(2-cyano-benzyloxy)-pyridin-3-yl]-benzoic acid; 2-{2-amino-5-[4-((2R)-2-pyrrolidin-1-ylmethyl-pyrrolidine-1-carbonyl)-phenyl]-pyridin-3-yloxymethyl}-benzonitrile; 2-{2-amino-5-[4-((2S)-2-pyrrolidin-1-ylmethyl-pyrrolidine-1-carbonyl)-phenyl]-pyridin-3-yloxymethyl}-benzonitrile; 2-{2-amino-5-[4-((3S)-3-dimethylamino-pyrrolidine-1-carbonyl)-phenyl]-pyridin-3-yloxymethyl}-benzonitrile; 2-{2-amino-5-[4-((3S)-3-amino-pyrrolidine-1-carbonyl)-phenyl]-pyridin-3-yloxymethyl}-benzonitrile; 2-{2-amino-5-[4-(4-pyrrolidin-1-yl-piperidine-1-carbonyl)-phenyl]-pyridin-3-yloxymethyl}-benzonitrile; 2-{2-amino-5-[4-(4-methyl-piperazine-1-carbonyl)-phenyl]-pyridin-3-yloxymethyl}-benzonitrile; 2-{5-[4-(4-acetyl-piperazine-1-carbonyl)-phenyl]-2-amino-pyridin-3-yloxymethyl}-benzonitrile; 4-[6-amino-5-(2-cyano-benzyloxy)-pyridin-3-yl]-N-(1-methyl-piperidin-4-yl)-benzamide; 4-[6-amino-5-(2-cyano-benzyloxy)-pyridin-3-yl]-N-(2-morpholin-4-yl-4-ethyl)-benzamide; 4-[6-amino-5-(2-cyano-benzyloxy)-pyridin-3-yl]-N-(3-morpholin-4-yl-propyl)-benzamide; 4-[6-amino-5-(2,4-dichloro-benzyloxy)-pyridin-3-yl]-benzoic acid; {4-[6-amino-5-(2,4-dichloro-benzyloxy)-pyridin-3-yl]-phenyl}-[(2R)-2-pyrrolidin-1-ylmethyl-pyrrolidin-1-yl]-methanone; {4-[6-amino-5-(2,4-dichloro-benzyloxy)-pyridin-3-yl]-phenyl}-[(2S)-2-pyrrolidin-1-ylmethyl-pyrrolidin-1-yl]-methanone; {4-[6-amino-5-(2,4-dichloro-benzyloxy)-pyridin-3-yl]-phenyl}-[(3S)-3-dimethylamino-pyrrolidin-1-yl]-methanone; {4-[6-amino-5-(2,4-dichloro-benzyloxy)-pyridin-3-yl]-phenyl}-[(3S)-3-amino-pyrrolidin-1-yl]-methanone; {4-[6-amino-5-(2,4-dichloro-benzyloxy)-pyridin-3-yl]-phenyl}-(4-pyrrolidin-1-yl-piperidin-1-yl)-methanone; {4-[6-amino-5-(2,4-dichloro-benzyloxy)-pyridin-3-yl]-phenyl}-(4-methyl-piperazin-1-yl)-methanone; 1-(4-{4-[6-amino-5-(2,4-dichloro-benzyloxy)-pyridin-3-yl]-benzoyl}-piperazin-1-yl)-ethanone; 4-[6-amino-5-(2,4-dichloro-benzyloxy)-pyridin-3-yl]-N-(1-methyl-piperidin-4-yl)-benzamide; 4-[6-amino-5-(2,4-dichloro-benzyloxy)-pyridin-3-yl]-N-(2-morpholin-4-yl-ethyl)-benzamide; 4-[6-amino-5-(2,4-dichloro-benzyloxy)-pyridin-3-yl]-N-(3-morpholin-4-yl-propyl)-benzamide; 4-[6-amino-5-(2-trifluoromethyl-benzyloxy)-pyridin-3-yl]-benzoic acid; {4-[6-amino-5-(2-trifluoromethyl-benzyloxy)-pyridin-3-yl]-phenyl}-[(2R)-2-pyrrolidin-1-ylmethyl-pyrrolidin-1-yl]-methanone; {4-[6-amino-5-(2-trifluoromethyl-benzyloxy)-pyridin-3-yl]-phenyl}-[(2S)-2-pyrrolidin-1-ylmethyl-pyrrolidin-1-yl]-methanone; {4-[6-amino-5-(2-trifluoromethyl-benzyloxy)-pyridin-3-yl]-phenyl}-[(3S)-3-dimethylamino-pyrrolidin-1-yl]-methanone; [(3S)-3-amino-pyrrolidin-1-yl]-{4-[6-amino-5-(2-trifluoromethyl-benzyloxy)-pyridin-3-yl]-phenyl}-methanone; {4-[6-amino-5-(2-trifluoromethyl-benzyloxy)-pyridin-3-yl]-phenyl}-(4- pyrrolidin-1-yl-piperidin-1-yl)-methanone; {4-[6-amino-5-(2-trifluoromethyl-benzyloxy)-pyridin-3-yl]-phenyl}-(4-methyl-piperazin-1-yl)-methanone; 1-(4-{4-[6-amino-5-(2-trifluoromethyl-benzyloxy)-pyridin-3-yl]-benzoyl}-piperazin-1-yl)-ethanone; 4-[6-amino-5-(2-trifluoromethyl-benzyloxy)-pyridin-3-yl]-N-(1-methyl-piperidin-4-yl)-benzamide; 4-[6-amino-5-(2-trifluoromethyl-benzyloxy)-pyridin-3-yl]-N-(2-morpholin-4-yl-ethyl)-benzamide; 4-[6-amino-5-(2-trifluoromethyl-benzyloxy)-pyridin-3-yl]-N-(3-morpholin-4-yl-propyl)-benzamide; 4-[6-amino-5-(4-#tert!-butyl-benzyloxy)-pyridin-3-yl]-benzoic acid; {4-[6-amino-5-(4-tert-butyl-benzyloxy)-pyridin-3-yl]-phenyl}-[(2R)-2-pyrrolidin-1-ylmethyl-pyrrolidin-1-yl]-methanone; {4-[6-amino-5-(4-tert-butyl-benzyloxy)-pyridin-3-yl]-phenyl}-[(2S)-2-pyrrolidin-1-ylmethyl-pyrrolidin-1-yl]-methanone; {4-[6-amino-5-(4-tert-butyl-benzyloxy)-pyridin-3-yl]-phenyl}-[(3R)-3-dimethylamino-pyrrolidin-1-yl]-methanone; {4-[6-amino-5-(4-tert-butyl-benzyloxy)-pyridin-3-yl]-phenyl}-(4-methyl-piperazin-1-yl)-methanone; 1-(4-{4-[6-amino-5-(4-tert-butyl-benzyloxy)-pyridin-3-yl]-benzoyl}-piperazin-1-yl)-ethanone; 4-[6-amino-5-(4-tert-butyl-benzyloxy)-pyridin-3-yl]-N-(1-methyl-piperidin-4-yl)-benzamide; 4-[6-amino-5-(4-tert-butyl-benzyloxy)-pyridin-3-yl]-N-(2-morpholin-4-yl-ethyl)-benzamide; 4-[6-amino-5-(4-tert-butyl-benzyloxy)-pyridin-3-yl]-N-(3-morpholin-4-yl-propyl)-benzamide; 4-[6-amino-5-(2-chloro-4-fluoro-benzyloxy)-pyridin-3-yl]-benzoic acid; {4-[6-amino-5-(2-chloro-4-fluoro-benzyloxy)-pyridin-3-yl]-phenyl}-[(2R)-2-pyrrolidin-1-ylmethyl-pyrrolidin-1-yl]-methanone; {4-[6-amino-5-(2-chloro-4-fluoro-benzyloxy)-pyridin-3-yl]-phenyl}-[(2S)-2-pyrrolidin-1-ylmethyl-pyrrolidin-1-yl]-methanone; {4-[6-amino-5-(2-chloro-4-fluoro-benzyloxy)-pyridin-3-yl]-phenyl}-[(3S)-3-dimethylamino-pyrrolidin-1-yl]-methanone; {4-[6-amino-5-(2-chloro-4-fluoro-benzyloxy)-pyridin-3-yl]-phenyl}-[(3S)-3-amino-pyrrolidin-1-yl]-methanone; {4-[6-amino-5-(2-chloro-4-fluoro-benzyloxy)-pyridin-3-yl]-phenyl}-(4-methyl-piperazin-1-yl)-methanone; 1-(4-{4-[6-amino-5-(2-chloro-4-fluoro-benzyloxy)-pyridin-3-yl]-benzoyl}-piperazin-1-yl)-ethanone; 4-[6-amino-5-(2-chloro-4-fluoro-benzyloxy)-pyridin-3-yl]-N-(2-morpholin-4-yl-ethyl)-benzamide; 4-[6-amino-5-(2-chloro-4-fluoro-benzyloxy)-pyridin-3-yl]-N-(3-morpholin-4-yl-propyl)-benzamide; 4-[6-amino-5-(2-chloro-3,6-difluoro-benzyloxy)-pyridin-3-yl]-benzoic acid; {4-[6-amino-5-(2-chloro-3,6-difluoro-benzyloxy)-pyridin-3-yl]-phenyl}-(4-methyl-piperazin-1-yl)-methanone; {4-[6-amino-5-(2-chloro-3,6-difluoro-benzyloxy)-pyridin-3-yl]-phenyl}-(4-pyrrolidin-1-yl-piperidin-1-yl)-methanone; {4-[6-amino-5-(2-chloro-3,6-difluoro-benzyloxy)-pyridin-3-yl]-phenyl}-(4-amino-piperidin-1-yl)-methanone; {4-[6-amino-5-(2-chloro-3,6-difluoro-benzyloxy)-pyridin-3-yl]-phenyl}-(3,5-dimethyl-piperazin-1-yl)-methanone; {4-[6-amino-5-(2-chloro-3,6-difluoro-benzyloxy)-pyridin-3-yl]-phenyl}-[(2S)-2-pyrrolidin-1-ylmethyl-pyrrolidin-1-yl]-methanone; {4-[6-amino-5-(2-chloro-3,6-difluoro-benzyloxy)-pyridin-3-yl]-phenyl}-[(3S)-3-dimethylamino-pyrrolidin-1-yl]-methanone; {4-[6-amino-5-(2-chloro-3,6-difluoro-benzyloxy)-pyridin-3-yl]-phenyl}-[(3R)-3-amino-pyrrolidin-1-yl]-methanone; {4-[6-amino-5-(2-chloro-3,6-difluoro-benzyloxy)-pyridin-3-yl]-phenyl}-[(3S)-3-amino-pyrrolidin-1-yl]-methanone; 4-[6-amino-5-(2-chloro-3,6-difluoro-benzyloxy)-pyridin-3-yl]-N-(1-methyl-piperidin-4-yl)-benzamide; 4-[6-amino-5-(2-chloro-3,6-difluoro-benzyloxy)-pyridin-3-yl]-N-(2-pyrrolidin-1-yl-ethyl)-benzamide; 4-[6-amino-5-(2-chloro-3,6-difluoro-benzyloxy)-pyridin-3-yl]-N-(3-pyrrolidin-1-yl-propyl)-benzamide; 4-[6-amino-5-(2-chloro-3,6-difluoro-benzyloxy)-pyridin-3-yl]-N-(2-morpholin-4-yl-ethyl)-benzamide; 4-[6-amino-5-(2-chloro-3,6-difluoro-benzyloxy)-pyridin-3-yl]-N-(3-morpholin-4-yl-propyl)-benzamide; 3-[6-amino-5-(2-chloro-3,6-difluoro-benzyloxy)-pyridin-3-yl]-benzoic acid; {3-[6-amino-5-(2-chloro-3,6-difluoro-benzyloxy)-pyridin-3-yl]-phenyl}-(4-methyl-piperazin-1-yl)-methanone; {3-[6-amino-5-(2-chloro-3,6-difluoro-benzyloxy)-pyridin-3-yl]-phenyl}-(4-pyrrolidin-1-yl-piperidin-1-yl)-methanone; {3-[6-amino-5-(2-chloro-3,6-difluoro-benzyloxy)-pyridin-3-yl]-phenyl}-(4-amino-piperidin-1-yl)-methanone; {3-[6-amino-5-(2-chloro-3,6-difluoro-benzyloxy)-pyridin-3-yl]-phenyl}-(3,5-dimethyl-piperazin-1-yl)-methanone; {3-[6-amino-5-(2-chloro-3,6-difluoro-benzyloxy)-pyridin-3-yl]-phenyl}-[(2S)-2-pyrrolidin-1-ylmethyl-pyrrolidin-1-yl]-methanone; {3-[6-amino-5-(2-chloro-3,6-difluoro-benzyloxy)-pyridin-3-yl]-phenyl}-[(3S)-3-dimethylamino-pyrrolidin-1-yl]-methanone; {3-[6-amino-5-(2-chloro-3,6-difluoro-benzyloxy)-pyridin-3-yl]-phenyl}-[(3R)-3-amino-pyrrolidin-1-yl]-methanone; {3-[6-amino-5-(2-chloro-3,6-difluoro-benzyloxy)-pyridin-3-yl]-phenyl}-[(3S)-amino-pyrrolidin-1-yl]-methanone; 3-[6-amino-5-(2-chloro-3,6-difluoro-benzyloxy)-pyridin-3-yl]-N-(1-methyl-piperidin-4-yl)-benzamide; 3-[6-amino-5-(2-chloro-3,6-difluoro-benzyloxy)-pyridin-3-yl]-N-(2-pyrrolidin-1-yl-ethyl)-benzamide; 3-[6-amino-5-(2-chloro-3,6-difluoro-benzyloxy)-pyridin-3-yl]-N-(3-pyrrolidin-1-yl-propyl)-benzamide; 3-[6-amino-5-(2-chloro-3,6-difluoro-benzyloxy)-pyridin-3-yl]-N-(2-morpholin-4-yl-ethyl)-benzamide; 3-[6-amino-5-(2-chloro-3,6-difluoro-benzyloxy)-pyridin-3-yl]-N-(3-morpholin-4-yl-propyl)-benzamide; N-[2-(4-acetyl-piperazin-1-yl)-ethyl]-3-[6-amino-5-(2-chloro-3,6-difluoro-benzyloxy)-pyridin-3-yl]-benzamide; 3-(2-chloro-3,6-difluoro-benzyloxy)-5-[4-(1,1-dioxo-1$\lambda^6$-isothiazolidin-2-yl)-phenyl]-pyridin-2-ylamine; 3-(2,6-dichloro-benzyloxy)-5-[4-(1,1-dioxo-1$\lambda^6$-isothiazolidin-2-yl)-phenyl]-pyridin-2-ylamine; 5-[4-(1,1-dioxo-1$\lambda^6$-isothiazolidin-2-yl)-phenyl]-3-(2-fluoro-6-trifluoromethyl-benzyloxy)-pyridin-2-ylamine; 2-diethylamino-ethanesulfonic acid {4-[6-amino-5-(2-chloro-3,6-difluoro-benzyloxy)-pyridin-3-yl]-phenyl}-amide; 2-cyclopropylamino-ethanesulfonic acid {4-[6-amino-5-(2-chloro-3,6-difluoro-benzyloxy)-pyridin-3-yl]-phenyl}-amide; 2-Pyrrolidin-1-yl-ethanesulfonic acid {4-[6-amino-5-(2-chloro-3,6-difluoro-benzyloxy)-pyridin-3-yl]-phenyl}-amide; 2-(4-hydroxy-piperidin-1-yl)-ethanesulfonic acid {4-[6-amino-5-(2-chloro-3,6-difluoro-benzyloxy)-pyridin-3-yl]-phenyl}-amide; 2-morpholin-4-yl-ethanesulfonic acid {4-[6-amino-5-(2-chloro-3,6-difluoro-benzyloxy)-pyridin-3-yl]-phenyl}-amide; 2-Piperidin-1-yl-ethanesulfonic acid {4-[6-amino-5-(2-chloro-3,6-difluoro-benzyloxy)-pyridin-3-yl]-phenyl}-amide; 2-dimethylamino-ethanesulfonic acid {4-[6-amino-5-(2-chloro-3,6-difluoro-benzyloxy)-pyridin-3-yl]-phenyl}-amide; 2-(4-acetyl-piperazin-1-yl)-ethanesulfonic acid {4-[6-amino-5-(2-chloro-3,6-difluoro-benzyloxy)-pyridin-3-yl]-phenyl}-amide; 2-(cyclopropylmethyl-amino)-ethanesulfonic acid {4-[6-amino-5-(2-chloro-3,6-difluoro-benzyloxy)-pyridin-3-yl]-phenyl}-amide; 2-[(3R)-3-hydroxy-pyrrolidin-1-yl]-ethanesulfonic acid {4-[6-amino-5-(2-chloro-3,6-difluoro-benzyloxy)-pyridin-3-yl]-phenyl}-amide; 2-[(2S)-2-hydroxymethyl-pyrrolidin-1-yl]-ethanesulfonic acid {4-[6-amino-5-(2-chloro-3,6-difluoro-benzyloxy)-pyridin-3-yl]-phenyl}-amide; 2-[4-(2-hydroxy-acetyl)-piperazin-1-yl]-ethanesulfonic acid {4-[6-amino-5-(2-chloro-3,6-difluoro-benzyloxy)-pyridin-3-yl]-phenyl}-amide; 2-(4-acetyl-piperazin-1-yl)-ethanesulfonic acid {3-[6-amino-5-(2-chloro-3,6-difluoro-benzyloxy)-pyridin-3- yl]-phenyl}-amide; 2-Pyrrolidin-1-yl-ethanesulfonic acid {3-[6-amino-5-(2-chloro-3,6-difluoro-benzyloxy)-pyridin-3-yl]-phenyl}-amide; 2-morpholin-4-yl-ethanesulfonic acid {3-[6-amino-5-(2-chloro-3,6-difluoro-benzyloxy)-pyridin-3-yl]-phenyl}-amide; 2-diethylamino-ethanesulfonic acid {3-[6-amino-5-(2-chloro-3,6-difluoro-benzyloxy)-pyridin-3-yl]-phenyl}-amide; 2-dimethylamino-ethanesulfonic acid {3-[6-amino-5-(2-chloro-3,6-difluoro-benzyloxy)-pyridin-3-yl]-phenyl}-amide; 2-Piperidin-1-yl-ethanesulfonic acid {3-[6-amino-5-(2-chloro-3,6-difluoro-benzyloxy)-pyridin-3-yl]-phenyl}-amide; 2-[(3R)-3-hydroxymethyl-pyrrolidin-1-yl]-ethanesulfonic acid {3-[6-amino-5-(2-chloro-3,6-difluoro-benzyloxy)-pyridin-3-yl]-phenyl}-amide; 2-(4-hydroxy-piperidin-1-yl)-ethanesulfonic acid {3-[6-amino-5-(2-chloro-3,6-difluoro-benzyloxy)-pyridin-3-yl]-phenyl}-amide; 2-[4-(2-hydroxy-acetyl)-piperazin-1-yl]-ethanesulfonic acid {3-[6-amino-5-(2-chloro-3,6-difluoro-benzyloxy)-pyridin-3-yl]-phenyl}-amide; 2-[(3R)-3-hydroxy-pyrrolidin-1-yl]-ethanesulfonic acid {3-[6-amino-5-(2-chloro-3,6-difluoro-benzyloxy)-pyridin-3-yl]-phenyl}-amide; 2-(cyclopropylmethyl-amino)-ethanesulfonic acid {3-[6-amino-5-(2-chloro-3,6-difluoro-benzyloxy)-pyridin-3-yl]-phenyl}-amide; 2-cyclopropylamino-ethanesulfonic acid {3-[6-amino-5-(2-chloro-3,6-difluoro-benzyloxy)-pyridin-3-yl]-phenyl}-amide; 3-(2-chloro-3,6-difluoro-benzyloxy)-5-(2-dimethylaminomethyl-phenyl)-pyridin-2-ylamine; compound with trifluoro-acetic acid; 3-(2-chloro-3,6-difluoro-benzyloxy)-5-(3-pyrrolidin-1-yl-phenyl)-pyridin-2-ylamine; compound with trifluoro-acetic acid; N-{4-[6-amino-5-(2-chloro-3,6-difluoro-benzyloxy)-pyridin-3-yl]-phenyl}-methanesulfonamide; compound with trifluoro-acetic acid; 5-[6-amino-5-(2-chloro-3,6-difluoro-benzyloxy)-pyridin-3-yl]-thiophene-2-carboxylic acid; {5-[6-amino-5-(2-chloro-3,6-difluoro-benzyloxy)-pyridin-3-yl]-thiophen-2-yl}-(4-methyl-piperazin-1-yl)-methanone; {5-[6-amino-5-(2-chloro-3,6-difluoro-benzyloxy)-pyridin-3-yl]-thiophen-2-yl}-[(2R)-2-pyrrolidin-1-ylmethyl-pyrrolidin-1-yl]-methanone; 5-[6-amino-5-(2-chloro-3,6-difluoro-benzyloxy)-pyridin-3-yl]-thiophene-2-carboxylic acid (1-methyl-piperidin-4-yl)-amide; {5-[6-amino-5-(2-chloro-3,6-difluoro-benzyloxy)-pyridin-3-yl]-thiophen-2-yl}-(3,5-dimethyl-piperazin-1-yl)-methanone; 5-[6-amino-5-(2-chloro-3,6-difluoro-benzyloxy)-pyridin-3-yl]-thiophene-2-carboxylic acid (2-pyrrolidin-1-yl-ethyl)-amide; {5-[6-amino-5-(2-chloro-3,6-difluoro-benzyloxy)-pyridin-3-yl]-thiophen-2-yl}-(4-pyrrolidin-1-yl-piperidin-1-yl)-methanone; 4-[6-amino-5-(3-fluoro-2-trifluoromethyl-benzyloxy)-pyridin-3-yl]-benzoic acid; {4-[6-amino-5-(3-fluoro-2-trifluoromethyl-benzyloxy)-pyridin-3-yl]-phenyl}-(4-pyrrolidin-1-yl-piperidin-1-yl)-methanone; 4-[6-amino-5-(3-fluoro-2-trifluoromethyl-benzyloxy)-pyridin-3-yl]-N-(1-methyl-piperidin-4-yl)-benzamide; {4-[6-amino-5-(3-fluoro-2-trifluoromethyl-benzyloxy)-pyridin-3-yl]-phenyl}-(3,5-dimethyl-piperazin-1-yl)-methanone; {4-[6-amino-5-(3-fluoro-2-trifluoromethyl-benzyloxy)-pyridin-3-yl]-phenyl}-(3-dimethylamino-pyrrolidin-1-yl)-methanone; {4-[6-amino-5-(3-fluoro-2-trifluoromethyl-benzyloxy)-pyridin-3-yl]-phenyl}-[(2S)-2-pyrrolidin-1-ylmethyl-pyrrolidin-1-yl]-methanone; 4-[6-amino-5-(3-fluoro-2-trifluoromethyl-benzyloxy)-pyridin-3-yl]-#N!-(2-morpholin-4-yl-ethyl)-benzamide; {4-[6-amino-5-(3-fluoro-2-trifluoromethyl-benzyloxy)-pyridin-3-yl]-phenyl}-(4-methyl-piperazin-1-yl)-methanone; N-[2-(4-acetyl-piperazin-1-yl)-ethyl]-4-[6-amino-5-(3-fluoro-2-trifluoromethyl-benzyloxy)-pyridin-3-yl]-benzamide; 2-Piperidin-1-yl-ethanesulfonic acid (4-{6-amino-5-[1-(2-chloro-3,6-difluoro-phenyl)-ethoxy]-pyridin-3-yl}-phenyl)-amide; 2-(4-hydroxy-piperidin-1-yl)-ethanesulfonic acid (4-{6-amino-5-[1-(2-chloro-3,6-difluoro-phenyl)-ethoxy]-pyridin-3-yl}-phenyl)-amide; 2-dimethylamino-ethanesulfonic acid (4-{6-amino-5-[1-(2-chloro-3,6-difluoro-phenyl)-ethoxy]-pyridin-3-yl}-phenyl)-amide; 2-cyclopropylamino-ethanesulfonic acid (4-{6-amino-5-[1-(2-chloro-3,6-difluoro-phenyl)-ethoxy]-pyridin-3-yl}-phenyl)-amide; 4-{6-amino-5-[1-(2,6-dichloro-3-fluoro-phenyl)-ethoxy]-pyridin-3-yl}-benzoic acid; (4-{6-amino-5-[1-(2,6-dichloro-3-fluoro-phenyl)-ethoxy]-pyridin-3-yl}-phenyl)-[(2R)-2-pyrrolidin-1-ylmethyl-pyrrolidin-1-yl]-methanone; 4-{6-amino-5-[1-(2,6-dichloro-3-fluoro-phenyl)-ethoxy]-pyridin-3-yl}-N-(1-methyl-piperidin-4-yl)-benzamide; (3-{6-amino-5-[1-(2,6-dichloro-3-fluoro-phenyl)-ethoxy]-pyridin-3-yl}-phenyl)-[(3R)-3-amino-pyrrolidin-1-yl)]-methanone; (4-{6-amino-5-[1-(2,6-dichloro-3-fluoro-phenyl)-ethoxy]-pyridin-3-yl}-phenyl)-(4-pyrrolidin-1-yl-piperidin-1-yl)-methanone; (4-{6-amino-5-[1-(2,6-dichloro-3-fluoro-phenyl)-ethoxy]-pyridin-3-yl}-phenyl)-(4-methyl-piperazin-1-yl)-methanone; (4-{6-amino-5-[1-(2,6-dichloro-3-fluoro-phenyl)-ethoxy]-pyridin-3-yl}-phenyl)-(3,5-dimethyl-piperazin-1-yl)-methanone; 2-cyclopropylamino-ethanesulfonic acid (4-{6-amino-5-[1-(2,6-dichloro-3-fluoro-phenyl)-ethoxy]-pyridin-3-yl}-phenyl)-amide; 2-dimethylamino-ethanesulfonic acid (4-{6-amino-5-[1-(2,6-dichloro-3-fluoro-phenyl)-ethoxy]-pyridin-3-yl}-phenyl)-amide; 2-[(3R)-3-hydroxy-pyrrolidin-1-yl)]-ethanesulfonic acid (4-{6-amino-5-[1-(2,6-dichloro-3-fluoro-phenyl)-ethoxy]-pyridin-3-yl}-phenyl)-amide; and pharmaceutically acceptable salts, hydrates and solvates thereof.

In another embodiment, the invention provides a compound selected from the group consisting of: 4-[5-amino-6-(2,6-dichloro-benzyloxy)-pyrazin-2-yl]-phenol; 3-(2,6-dichloro-benzyloxy)-5-[4-(1,1-dioxo-1$\lambda^6$-isothiazolidin-2-yl)-phenyl]-pyrazin-2-ylamine; 3-(2,6-dichloro-benzyloxy)-5-[3-(2-morpholin-4-yl-ethoxy)-phenyl]-pyrazin-2-ylamine; 3-(2,6-dichloro-benzyloxy)-5-[4-(2-morpholin-4-yl-ethoxy)-phenyl]-pyrazin-2-ylamine; 5-(4-amino-phenyl)-3-(2,6-dichloro-benzyloxy)-pyrazin-2-ylamine; 4-[5-amino-6-(2,6-dichloro-benzyloxy)-pyrazin-2-yl]-benzoic acid; {4-[5-amino-6-(2,6-dichloro-benzyloxy)-pyrazin-2-yl]-phenyl}-[(2R)-2-pyrrolidin-1-ylmethyl-pyrrolidin-1-yl]-methanone; {4-[5-amino-6-(2,6-dichloro-benzyloxy)-pyrazin-2-yl]-phenyl}-(4-pyrrolidin-1-yl-piperidin-1-yl)-methanone; 2-morpholin-4-yl-ethanesulfonic acid {4-[5-amino-6-(2-chloro-3,6-difluoro-benzyloxy)-pyrazin-2-yl]-phenyl}-amide; 2-piperidin-1-yl-ethanesulfonic acid {4-[5-amino-6-(2-chloro-3,6-difluoro-benzyloxy)-pyrazin-2-yl]-phenyl}-amide; 2-(4-Hydroxy-piperidin-1-yl)-ethanesulfonic acid {4-[5-amino-6-(2-chloro-3,6-difluoro-benzyloxy)-pyrazin-2-yl]-phenyl}-amide; 2-pyrrolidin-1-yl-ethanesulfonic acid {4-[5-amino-6-(2-chloro-3,6-difluoro-benzyloxy)-pyrazin-2-yl]-phenyl}-amide; 2-[(3R)-3-Hydroxy-pyrrolidin-1-yl]-ethanesulfonic acid {4-[5-amino-6-(2-chloro-3,6-difluoro-benzyloxy)-pyrazin-2-yl]-phenyl}-amide; 2-[(2S)-2-Hydroxymethyl-pyrrolidin-1-yl]-ethanesulfonic acid {4-[5-amino-6-(2-chloro-3,6-difluoro-benzyloxy)-pyrazin-2-yl]-phenyl}-amide; 2-(cyclopropylmethyl-amino)-ethanesulfonic acid {4-[5-amino-6-(2-chloro-3,6-difluoro-benzyloxy)-pyrazin-2-yl]-phenyl}-amide; 2-dimethylamino-ethanesulfonic acid {4-[5-amino-6-(2-chloro-3,6-difluoro-benzyloxy)-pyrazin-2-yl]-phenyl}-amide; 2-diethylamino-ethanesulfonic acid {4-[5-amino-6-(2-chloro-3,6-difluoro-benzyloxy)-pyrazin-2-yl]-phenyl}-amide; 2-(4-acetyl-piperazin-1-yl)-ethanesulfonic acid {4-[5-amino-6-(2-chloro-3,6-difluoro-benzyloxy)- pyrazin-2-yl]-phenyl}-amide; 2-[4-(2-Hydroxy-acetyl)-piperazin-1-yl]-ethanesulfonic acid {4-[5-amino-6-(2-chloro-3,6-difluoro-benzyloxy)-pyrazin-2-yl]-phenyl}-amide; 2-cyclopropylamino-ethanesulfonic acid {4-[5-amino-6-(2-chloro-3,6-difluoro-benzyloxy)-pyrazin-2-yl]-phenyl}-amide; 2-[(3R)-3-Hydroxymethyl-pyrrolidin-1-yl]-ethanesulfonic acid {3-[5-amino-6-(2-chloro-3,6-difluoro-benzyloxy)-pyrazin-2-yl]-phenyl}-amide; 2-(4-Hydroxy-piperidin-1-yl)-ethanesulfonic acid {3-[5-amino-6-(2-chloro-3,6-difluoro-benzyloxy)-pyrazin-2-yl]-phenyl}-amide; 2-(4-acetyl-piperazin-1-yl)-ethanesulfonic acid {3-[5-amino-6-(2-chloro-3,6-difluoro-benzyloxy)-pyrazin-2-yl]-phenyl}-amide; 2-piperidin-1-yl-ethanesulfonic acid {3-[5-amino-6-(2-chloro-3,6-difluoro-benzyloxy)-pyrazin-2-yl]-phenyl}-amide; 2-diethylamino-ethanesulfonic acid {3-[5-amino-6-(2-chloro-3,6-difluoro-benzyloxy)-pyrazin-2-yl]-phenyl}-amide; 2-morpholin-4-yl-ethanesulfonic acid {3-[5-amino-6-(2-chloro-3,6-difluoro-benzyloxy)-pyrazin-2-yl]-phenyl}-amide; 2-pyrrolidin-1-yl-ethanesulfonic acid {3-[5-amino-6-(2-chloro-3,6-difluoro-benzyloxy)-pyrazin-2-yl]-phenyl}-amide; 2-dimethylamino-ethanesulfonic acid {3-[5-amino-6-(2-chloro-3,6-difluoro-benzyloxy)-pyrazin-2-yl]-phenyl}-amide; 2-[4-(2-Hydroxy-acetyl)-piperazin-1-yl]-ethanesulfonic acid {3-[5-amino-6-(2-chloro-3,6-difluoro-benzyloxy)-pyrazin-2-yl]-phenyl}-amide; 2-(cyclopropylmethyl-amino)-ethanesulfonic acid {3-[5-amino-6-(2-chloro-3,6-difluoro-benzyloxy)-pyrazin-2-yl]-phenyl}-amide; 2-[(3R)-3-Hydroxy-pyrrolidin-1-yl]-ethanesulfonic acid {3-[5-amino-6-(2-chloro-3,6-difluoro-benzyloxy)-pyrazin-2-yl]-phenyl}-amide; 2-cyclopropylamino-ethanesulfonic acid {3-[5-amino-6-(2-chloro-3,6-difluoro-benzyloxy)-pyrazin-2-yl]-phenyl}-amide; 4-[5-amino-6-(2-chloro-3,6-difluoro-benzyloxy)-pyrazin-2-yl]-benzoic acid; {4-[5-amino-6-(2-chloro-3,6-difluoro-benzyloxy)-pyrazin-2-yl]-phenyl}-[(2R)-2-pyrrolidin-1-ylmethyl-pyrrolidin-1-yl]-methanone; 4-[5-amino-6-(2-chloro-3,6-difluoro-benzyloxy)-pyrazin-2-yl]-N-(2-pyrrolidin-1-yl-ethyl)-benzamide; {4-[5-amino-6-(2-chloro-3,6-difluoro-benzyloxy)-pyrazin-2-yl]-phenyl}-[(3S)-3-amino-pyrrolidin-1-yl]-methanone; N-[2-(4-acetyl-piperazin-1-yl)-ethyl]-4-[5-amino-6-(2-chloro-3,6-difluoro-benzyloxy)-pyrazin-2-yl]-benzamide; 4-[5-amino-6-(2-chloro-3,6-difluoro-benzyloxy)-pyrazin-2-yl]-N-(3-pyrrolidin-1-yl-propyl)-benzamide; {4-[5-amino-6-(2-chloro-3,6-difluoro-benzyloxy)-pyrazin-2-yl]-phenyl}-[(3S)-3-dimethylamino-pyrrolidin-1-yl]-methanone; {4-[5-amino-6-(2-chloro-3,6-difluoro-benzyloxy)-pyrazin-2-yl]-phenyl}-[(3R)-3-dimethylamino-pyrrolidin-1-yl]-methanone; {4-[5-amino-6-(2-chloro-3,6-difluoro-benzyloxy)-pyrazin-2-yl]-phenyl}-(3,5-dimethyl-piperazin-1-yl)-methanone; {4-[5-amino-6-(2-chloro-3,6-difluoro-benzyloxy)-pyrazin-2-yl]-phenyl}-(4-pyrrolidin-1-yl-piperidin-1-yl)-methanone; 4-[5-amino-6-(2-chloro-3,6-difluoro-benzyloxy)-pyrazin-2-yl]-N-(3-morpholin-4-yl-propyl)-benzamide; 4-[5-amino-6-(2-chloro-3,6-difluoro-benzyloxy)-pyrazin-2-yl]-N-(1-methyl-piperidin-4-yl)-benzamide; 4-[5-amino-6-(2-chloro-3,6-difluoro-benzyloxy)-pyrazin-2-yl]-N-(2-morpholin-4-yl-ethyl)-benzamide; {4-[5-amino-6-(2-chloro-3,6-difluoro-benzyloxy)-pyrazin-2-yl]-phenyl}-(4-methyl-piperazin-1-yl)-methanone; 3-[5-amino-6-(2-chloro-3,6-difluoro-benzyloxy)-pyrazin-2-yl]-benzoic acid; {3-[5-amino-6-(2-chloro-3,6-difluoro-benzyloxy)-pyrazin-2-yl]-phenyl}-(4-methyl-piperazin-1-yl)-methanone; {3-[5-amino-6-(2-chloro-3,6-difluoro-benzyloxy)-pyrazin-2-yl]-phenyl}-[(3R)-3-amino-pyrrolidin-1-yl]-methanone; {3-[5-amino-6-(2-chloro-3,6-difluoro-benzyloxy)-pyrazin-2-yl]-phenyl}-[(3S)-3-amino-pyrrolidin-1-yl]-methanone; {3-[5-amino-6-(2-chloro-3,6-difluoro-benzyloxy)-pyrazin-2-yl]-phenyl}-(3,5-dimethyl-piperazin-1-yl)-methanone; 3-[5-amino-6-(2-chloro-3,6-difluoro-benzyloxy)-pyrazin-2-yl]-N-(3-morpholin-4-yl-propyl)-benzamide; {3-[5-amino-6-(2-chloro-3,6-difluoro-benzyloxy)-pyrazin-2-yl]-phenyl}-(4-pyrrolidin-1-yl-piperidin-1-yl)-methanone; {3-[5-amino-6-(2-chloro-3,6-difluoro-benzyloxy)-pyrazin-2-yl]-phenyl}-[(3S)-3-dimethylamino-pyrrolidin-1-yl]-methanone; 3-[5-amino-6-(2-chloro-3,6-difluoro-benzyloxy)-pyrazin-2-yl]-N-(2-pyrrolidin-1-yl-ethyl)-benzamide; 3-[5-amino-6-(2-chloro-3,6-difluoro-benzyloxy)-pyrazin-2-yl]-N-(1-methyl-piperidin-4-yl)-benzamide; {3-[5-amino-6-(2-chloro-3,6-difluoro-benzyloxy)-pyrazin-2-yl]-phenyl}-[(2S)-pyrrolidin-1-ylmethyl-pyrrolidin-1-yl]-methanone; 3-[5-amino-6-(2-chloro-3,6-difluoro-benzyloxy)-pyrazin-2-yl]-N-(2-morpholin-4-yl-ethyl)-benzamide; N-[2-(4-acetyl-piperazin-1-yl)-ethyl]-3-[5-amino-6-(2-chloro-3,6-difluoro-benzyloxy)-pyrazin-2-yl]-benzamide; 3-[5-amino-6-(2-chloro-3,6-difluoro-benzyloxy)-pyrazin-2-yl]-N-(3-pyrrolidin-1-yl-propyl)-benzamide; 3-(2-chloro-3,6-difluoro-benzyloxy)-5-(1H-indol-5-yl)-pyrazin-2-ylamine; 3-(2-chloro-3,6-difluoro-benzyloxy)-5-(3-pyrrolidin-1-ylmethyl-1H-indol-5-yl)-pyrazin-2-ylamine; 3-(2-chloro-3,6-difluoro-benzyloxy)-5-(3-diethylaminomethyl-1H-indol-5-yl)-pyrazin-2-ylamine; 1-(4-{5-[5-amino-6-(2-chloro-3,6-difluoro-benzyloxy)-pyrazin-2-yl]-1H-indol-3-ylmethyl}-piperazin-1-yl)-ethanone; 3-(2-chloro-3,6-difluoro-benzyloxy)-5-[3-(2,6-dimethyl-morpholin-4-ylmethyl)-1H-indol-5-yl]-pyrazin-2-ylamine; N-(1-{5-[5-amino-6-(2-chloro-3,6-difluoro-benzyloxy)-pyrazin-2-yl]-1H-indol-3-ylmethyl}-(3S)-pyrrolidin-3-yl)-acetamide; 3-(2-chloro-3,6-difluoro-benzyloxy)-5-(3-piperidin-1-ylmethyl-1H-indol-5-yl)-pyrazin-2-ylamine; 3-(2-chloro-3,6-difluoro-benzyloxy)-5-(3-morpholin-4-ylmethyl-1H-indol-5-yl)-pyrazin-2-ylamine; 3-[1-(2-chloro-3,6-difluoro-phenyl)-2-methyl-propoxy]-5-[4-(2-morpholin-4-yl-ethoxy)-phenyl]-pyrazin-2-ylamine; 3-[1-(2-chloro-3,6-difluoro-phenyl)-ethoxy]-5-[4-(2-morpholin-4-yl-ethoxy)-phenyl]-pyrazin-2-ylamine; compound with trifluoro-acetic acid; 3-[1-(2,6-dichloro-3-fluoro-phenyl)-ethoxy]-5-[4-(2-morpholin-4-yl-ethoxy)-phenyl]-pyrazin-2-ylamine; compound with trifluoro-acetic acid; N-(4-{5-amino-6-[1-(2-chloro-3,6-difluoro-phenyl)-ethoxy]-pyrazin-2-yl}-phenyl)-methane-sulfonamide; 2-pyrrolidin-1-yl-ethanesulfonic acid (4-{5-amino-6-[1-(2-chloro-3,6-difluoro-phenyl)-ethoxy]-pyrazin-2-yl}-phenyl)-amide; 2-(4-Hydroxy-piperidin-1-yl)-ethanesulfonic acid (4-{5-amino-6-[1-(2-chloro-3,6-difluoro-phenyl)-ethoxy]-pyrazin-2-yl}-phenyl)-amide; 2-piperidin-1-yl-ethanesulfonic acid (4-{5-amino-6-[1-(2-chloro-3,6-difluoro-phenyl)-ethoxy]-pyrazin-2-yl}-phenyl)-amide; 2-(cyclopropylmethyl-amino)-ethanesulfonic acid (4-{5-amino-6-[1-(2-chloro-3,6-difluoro-phenyl)-ethoxy]-pyrazin-2-yl}-phenyl)-amide; 2-[(3R)-3-Hydroxy-pyrrolidin-1-yl]-ethanesulfonic acid (4-{5-amino-6-[1-(2-chloro-3,6-difluoro-phenyl)-ethoxy]-pyrazin-2-yl}-phenyl)-amide; 2-[(2S)-2-Hydroxymethyl-pyrrolidin-1-yl]-ethanesulfonic acid (4-{5-amino-6-[1-(2-chloro-3,6-difluoro-phenyl)-ethoxy]-pyrazin-2-yl}-phenyl)-amide; 2-dimethylamino-ethanesulfonic acid (4-{5-amino-6-[1-(2-chloro-3,6-difluoro-phenyl)-ethoxy]-pyrazin-2-yl}-phenyl)-amide; 2-morpholin-4-yl-ethanesulfonic acid (4-{5-amino-6-[1-(2-chloro-3,6-difluoro-phenyl)-ethoxy]-pyrazin-2-yl}-phenyl)-amide; 2-diethylamino-ethanesulfonic acid (4-{5-amino-6-[1-(2-chloro-3,6-difluoro-phenyl)-ethoxy]-pyrazin-2-yl}-phenyl)-amide; 2-cyclopropylamino-ethanesulfonic acid (4-{5-amino-6-[1-(2-chloro-3,6-difluoro-phenyl)-ethoxy]- pyrazin-2-yl}-phenyl)-amide; 3-{5-amino-6-[1-(2,6-dichloro-3-fluoro-phenyl)-ethoxy]-pyrazin-2-yl}benzoic acid; (3-{5-amino-6-[1-(2,6-dichloro-3-fluoro-phenyl)-ethoxy]-pyrazin-2-yl}-phenyl)-[(3S)-3-amino-pyrrolidin-1-yl)-m-ethanone; (3-{5-amino-6-[1-(2,6-dichloro-3-fluoro-phenyl)-ethoxy]-pyrazin-2-yl}-phenyl)-[(3R)-3-amino-pyrrolidin-1-yl)-m-ethanone; (3-{5-amino-6-[1-(2,6-dichloro-3-fluoro-phenyl)-ethoxy]-pyrazin-2-yl}-phenyl)-[(2R)-2-pyrrolidin-1-ylmethyl-pyrrolidin-1-yl)-methanone; N-[2-(4-acetyl-piperazin-1-yl)-ethyl]-3-{5-amino-6-[1-(2,6-dichloro-3-fluoro-phenyl)-ethoxy]-pyrazin-2-yl}-benzamide; (3-{5-amino-6-[1-(2,6-dichloro-3-fluoro-phenyl)-ethoxy]-pyrazin-2-yl}-phenyl)-[(2S)-2-pyrrolidin-1-ylmethyl-pyrrolidin-1-yl)-methanone; 3-{5-amino-6-[1-(2-chloro-3,6-difluoro-phenyl)-ethoxy]-pyrazin-2-yl}-benzoic acid; 3-{5-amino-6-[1-(2,6-dichloro-3-fluoro-phenyl)-ethoxy]-pyrazin-2-yl}-N-(1-methyl-piperidin-4-yl)-benzamide; 3-{5-amino-6-[1-(2,6-dichloro-3-fluoro-phenyl)-ethoxy]-pyrazin-2-yl}-N-(3-pyrrolidin-1-yl-propyl)-benzamide; (3-{5-amino-6-[1-(2,6-dichloro-3-fluoro-phenyl)-ethoxy]-pyrazin-2-yl}-phenyl)-(4-pyrrolidin-1-yl-piperidin-1-yl)-methanone; 4-[5-amino-6-(3-fluoro-2-trifluoromethyl-benzyloxy)-pyrazin-2-yl]-benzoic acid; 4-[5-amino-6-(3-fluoro-2-trifluoromethyl-benzyloxy)-pyrazin-2-yl]-N-(2-morpholin-4-yl-ethyl)-benzamide; 4-[5-amino-6-(3-fluoro-2-trifluoromethyl-benzyloxy)-pyrazin-2-yl]-N-(1-methyl-piperidin-4-yl)-benzamide; and pharmaceutically acceptable salts, hydrates and solvates thereof.

In another embodiment, the invention provides a compound selected from the group consisting of: (4-{6-amino-5-[1-(2,6-dichloro-3-fluoro-phenyl)-ethoxy]-pyridin-3-yl}-phenyl)-(4-methyl-piperazin-1-yl)-methanone; N-[2-(4-acetyl-piperazin-1-yl)-ethyl]-4-{6-amino-5-[1-(2,6-dichloro-3-fluoro-phenyl)-ethoxy]-pyridin-3-yl}-benzamide; 4-{6-amino-5-[1-(2,6-dichloro-3-fluoro-phenyl)-ethoxy]-pyridin-3-yl}-N-(3-pyrrolidin-1-yl-propyl)-benzamide; 4-{6-amino-5-[1-(2,6-dichloro-3-fluoro-phenyl)-ethoxy]-pyridin-3-yl}-N-(2-morpholin-4-yl-ethyl)-benzamide; (4-{6-amino-5-[1-(2,6-dichloro-3-fluoro-phenyl)-ethoxy]-pyridin-3-yl}-phenyl)-((S)-3-amino-pyrrolidin-1-yl)-methanone; (4-{6-amino-5-[1-(2,6-dichloro-3-fluoro-phenyl)-ethoxy]-pyridin-3-yl}-phenyl)-((R)-3-amino-pyrrolidin-1-yl)-methanone; (4-{6-amino-5-[1-(2,6-dichloro-3-fluoro-phenyl)-ethoxy]-pyridin-3-yl}-phenyl)-(4-amino-piperidin-1-yl)-methanone; (4-{6-amino-5-[1-(2,6-dichloro-3-fluoro-phenyl)-ethoxy]-pyridin-3-yl}-phenyl)-((S)-3-hydroxy-pyrrolidin-1-yl)-methanone; (4-{6-amino-5-[1-(2,6-dichloro-3-fluoro-phenyl)-ethoxy]-pyridin-3-yl}-phenyl)-((R)-3-hydroxy-pyrrolidin-1-yl)-methanone; (4-{6-amino-5-[1-(2,6-dichloro-3-fluoro-phenyl)-ethoxy]-pyridin-3-yl}-phenyl)-((R)-2-hydroxymethyl-pyrrolidin-1-yl)-methanone; 4-{6-amino-5-[1-(2,6-dichloro-3-fluoro-phenyl)-ethoxy]-pyridin-3-yl}-N-(2-diethylamino-ethyl)-benzamide; 4-{6-amino-5-[1-(2,6-dichloro-3-fluoro-phenyl)-ethoxy]-pyridin-3-yl}-N-(2-pyrrolidin-1-yl-ethyl)-benzamide; 3-{6-amino-5-[1-(2,6-dichloro-3-fluoro-phenyl)-ethoxy]-pyridin-3-yl}-benzoic acid; (3-{6-amino-5-[1-(2,6-dichloro-3-fluoro-phenyl)-ethoxy]-pyridin-3-yl}-phenyl)-(4-methyl-piperazin-1-yl)-methanone; 3-{6-amino-5-[1-(2,6-dichloro-3-fluoro-phenyl)-ethoxy]-pyridin-3-yl}-N-(1-methyl-piperidin-4-yl)-benzamide; (3-{6-amino-5-[1-(2,6-dichloro-3-fluoro-phenyl)-ethoxy]-pyridin-3-yl}-phenyl)-((S)-2-pyrrolidin-1-ylmethyl-pyrrolidin-1-yl)-methanone; N-[2-(4-acetyl-piperazin-1-yl)-ethyl]-3-{6-amino-5-[1-(2,6-dichloro-3-fluoro-phenyl)-ethoxy]-pyridin-3-yl}-benzamide; (3-{6-amino-5-[1-(2,6-dichloro-3-fluoro-phenyl)-ethoxy]-pyridin-3-yl}-phenyl)-((S)-3-amino-pyrrolidin-1-yl)-methanone; 3-{6-amino-5-[1-(2,6-dichloro-3-fluoro-phenyl)-ethoxy]-pyridin-3-yl}-N-(3-morpholin-4-yl-propyl)-benzamide; (3-{6-amino-5-[1-(2,6-dichloro-3-fluoro-phenyl)-ethoxy]-pyridin-3-yl}-phenyl)-((R)-2-pyrrolidin-1-ylmethyl-pyrrolidin-1-yl)-methanone; 3-{6-amino-5-[1-(2,6-dichloro-3-fluoro-phenyl)-ethoxy]-pyridin-3-yl}-N-(2-pyrrolidin-1-yl-ethyl)-benzamide; 3-{6-amino-5-[1-(2,6-dichloro-3-fluoro-phenyl)-ethoxy]-pyridin-3-yl}-N-(3-pyrrolidin-1-yl-propyl)-benzamide; 3-{6-amino-5-[1-(2,6-dichloro-3-fluoro-phenyl)-ethoxy]-pyridin-3-yl}-N-(2-morpholin-4-yl-ethyl)-benzamide; (3-{6-amino-5-[1-(2,6-dichloro-3-fluoro-phenyl)-ethoxy]-pyridin-3-yl}-phenyl)-(4-pyrrolidin-1-yl-piperidin-1-yl)-methanone; 2-diethylamino-ethanesulfonic acid (4-{6-amino-5-[1-(2,6-dichloro-3-fluoro-phenyl)-ethoxy]-pyridin-3-yl}-phenyl)-amide; 2-(4-Hydroxy-piperidin-1-yl)-ethanesulfonic acid (4-{6-amino-5-[1-(2,6-dichloro-3-fluoro-phenyl)-ethoxy]-pyridin-3-yl}-phenyl)-amide; 2-piperidin-1-yl-ethanesulfonic acid (4-{6-amino-5-[1-(2,6-dichloro-3-fluoro-phenyl)-ethoxy]-pyridin-3-yl}-phenyl)-amide; 2-(cyclopropylmethyl-amino)-ethanesulfonic acid (4-{6-amino-5-[1-(2,6-dichloro-3-fluoro-phenyl)-ethoxy]-pyridin-3-yl}-phenyl)-amide; 2-((R)-3-Hydroxy-pyrrolidin-1-yl)-ethanesulfonic acid (4-{6-amino-5-[1-(2-chloro-3,6-difluoro-phenyl)-ethoxy]-pyridin-3-yl}-phenyl)-amide; 2-cyclopropylamino-ethanesulfonic acid (4-{6-amino-5-[1-(2-chloro-3,6-difluoro-phenyl)-ethoxy]-pyridin-3-yl}-phenyl)-amide; 2-diethylamino-ethanesulfonic acid (4-{6-amino-5-[1-(2-chloro-3,6-difluoro-phenyl)-ethoxy]-pyridin-3-yl}-phenyl)-amide; 4-{6-amino-5-[1-(2-chloro-3,6-difluoro-phenyl)-ethoxy]-pyridin-3-yl}-benzoic acid; 4-{6-amino-5-[1-(2-chloro-3,6-difluoro-phenyl)-ethoxy]-pyridin-3-yl}-N-(2-morpholin-4-yl-ethyl)-benzamide; 4-{6-amino-5-[1-(2-chloro-3,6-difluoro-phenyl)-ethoxy]-pyridin-3-yl}-N-(1-methyl-piperidin-4-yl)-benzamide; (4-{6-amino-5-[1-(2-chloro-3,6-difluoro-phenyl)-ethoxy]-pyridin-3-yl}-phenyl)-((R)-2-pyrrolidin-1-ylmethyl-pyrrolidin-1-yl)-methanone; (4-{6-amino-5-[1-(2-chloro-3,6-difluoro-phenyl)-ethoxy]-pyridin-3-yl}-phenyl)-((R)-3-amino-pyrrolidin-1-yl)-methanone; (4-{6-amino-5-[1-(2-chloro-3,6-difluoro-phenyl)-ethoxy]-pyridin-3-yl}-phenyl)-((3R,5S)-3,5-dimethyl-piperazin-1-yl)-methanone; 4-{6-amino-5-[1-(2-chloro-3,6-difluoro-phenyl)-ethoxy]-pyridin-3-yl}-N-(3-pyrrolidin-1-yl-propyl)-benzamide; (4-{6-amino-5-[1-(2-chloro-3,6-difluoro-phenyl)-ethoxy]-pyridin-3-yl}-phenyl)-((S)-2-pyrrolidin-1-ylmethyl-pyrrolidin-1-yl)-methanone; (4-{6-amino-5-[1-(2-chloro-3,6-difluoro-phenyl)-ethoxy]-pyridin-3-yl}-phenyl)-(4-methyl-piperazin-1-yl)-methanone; (4-{6-amino-5-[1-(2-chloro-3,6-difluoro-phenyl)-ethoxy]-pyridin-3-yl}-phenyl)-(4-pyrrolidin-1-yl-piperidin-1-yl)-methanone; 4-{6-amino-5-[1-(2-chloro-3,6-difluoro-phenyl)-ethoxy]-pyridin-3-yl}-N-(2-pyrrolidin-1-yl-ethyl)-benzamide; (4-{6-amino-5-[1-(2-chloro-3,6-difluoro-phenyl)-ethoxy]-pyridin-3-yl}-phenyl)-((S)-3-amino-pyrrolidin-1-yl)-methanone; 3-{6-amino-5-[1-(2-chloro-3,6-difluoro-phenyl)-ethoxy]-pyridin-3-yl}-benzoic acid; (3-{6-amino-5-[1-(2-chloro-3,6-difluoro-phenyl)-ethoxy]-pyridin-3-yl}-phenyl)-((3R,5S)-3,5-dimethyl-piperazin-1-yl)-methanone; (3-{6-amino-5-[1-(2-chloro-3,6-difluoro-phenyl)-ethoxy]-pyridin-3-yl}-phenyl)-((R)-3-amino-pyrrolidin-1-yl)-methanone; 3-{6-amino-5-[1-(2-chloro-3,6-difluoro-phenyl)-ethoxy]-pyridin-3-yl}-N-(1-methyl-piperidin-4-yl)-benzamide; (3-{6-amino-5-[1-(2-chloro-3,6-difluoro-phenyl)-ethoxy]-pyridin-3-yl}-phenyl)-(4-methyl-piperazin-1-yl)-methanone; 3-{6-amino-5-[1-(2-chloro-3,6-difluoro-phenyl)-ethoxy]-pyridin-3-yl}-N-(3-pyrrolidin-1- yl-propyl)-benzamide; 3-{6-amino-5-[1-(2-chloro-3,6-difluoro-phenyl)-ethoxy]-pyridin-3-yl}-N-(2-pyrrolidin-1-yl-ethyl)-benzamide; (3-{6-amino-5-[1-(2-chloro-3,6-difluoro-phenyl)-ethoxy]-pyridin-3-yl}-phenyl)-((S)-3-amino-pyrrolidin-1-yl)-methanone; 3-{6-amino-5-[1-(2-chloro-3,6-difluoro-phenyl)-ethoxy]-pyridin-3-yl}-N-(2-morpholin-4-yl-ethyl)-benzamide; (3-{6-amino-5-[1-(2-chloro-3,6-difluoro-phenyl)-ethoxy]-pyridin-3-yl}-phenyl)-((R)-2-pyrrolidin-1-ylmethyl-pyrrolidin-1-yl)-methanone; (3-{6-amino-5-[1-(2-chloro-3,6-difluoro-phenyl)-ethoxy]-pyridin-3-yl}-phenyl)-((S)-2-pyrrolidin-1-ylmethyl-pyrrolidin-1-yl)-methanone; 3-[1-(2-chloro-3,6-difluoro-phenyl)-ethoxy]-5-[4-(2-morpholin-4-yl-ethoxy)-phenyl]-pyridin-2-ylamine; 3-[1-(2-chloro-3,6-difluoro-phenyl)-ethoxy]-5-[3-(2-morpholin-4-yl-ethoxy)-phenyl]-pyridin-2-ylamine; 3-[1-(2,6-dichloro-3-fluoro-phenyl)-ethoxy]-5-[4-(2-pyrrolidin-1-yl-ethoxy)-phenyl]-pyridin-2-ylamine; 3-[1-(2,6-dichloro-3-fluoro-phenyl)-ethoxy]-5-{4-[2-(1-methyl-pyrrolidin-2-yl)-ethoxy]-phenyl}-pyridin-2-ylamine; 3-[1-(2,6-dichloro-3-fluoro-phenyl)-ethoxy]-5-[4-(2-morpholin-4-yl-ethoxy)-phenyl]-pyridin-2-ylamine; 3-[1-(2,6-dichloro-3-fluoro-phenyl)-ethoxy]-5-[3-(2-morpholin-4-yl-ethoxy)-phenyl]-pyridin-2-ylamine; 1-(4-{6-amino-5-[1-(2,6-dichloro-3-fluoro-phenyl)-ethoxy]-pyridin-3-yl}-phenoxy)-3-morpholin-4-yl-propan-2-ol; 3-[1-(2,6-dichloro-3-fluoro-phenyl)-ethoxy]-5-[4-(2-diethylamino-ethoxy)-phenyl]-pyridin-2-ylamine; 3-[1-(2,6-dichloro-3-fluoro-phenyl)-ethoxy]-5-[4-(1-methyl-piperidin-3-ylmethoxy)-phenyl]-pyridin-2-ylamine; 3-[1-(2,6-dichloro-3-fluoro-phenyl)-ethoxy]-5-[4-(2-diisopropylamino-ethoxy)-phenyl]-pyridin-2-ylamine; 3-[1-(2,6-dichloro-3-fluoro-phenyl)-ethoxy]-5-[4-(1-methyl-piperidin-4-yloxy)-phenyl]-pyridin-2-ylamine; N-(4-{6-amino-5-[1-(2-chloro-3,6-difluoro-phenyl)-ethoxy]-pyridin-3-yl}-phenyl)-methanesulfonamide; 3-[1-(2-chloro-3,6-difluoro-phenyl)-ethoxy]-5-[4-(1,1-dioxo-1lambda*6*-isothiazolidin-2-yl)-phenyl]-pyridin-2-ylamine; N-(4-{6-amino-5-[1-(2,6-dichloro-3-fluoro-phenyl)-ethoxy]-pyridin-3-yl}-phenyl)-methanesulfonamide; 3-[1-(2,6-dichloro-3-fluoro-phenyl)-ethoxy]-5-phenyl-pyridin-2-ylamine; N-(4-{6-amino-5-[(R)-1-(2-chloro-3,6-difluoro-phenyl)-ethoxy]-pyridin-3-yl}-phenyl)-methanesulfonamide; 3-[1-(2,6-dichloro-3-fluoro-phenyl)-ethoxy]-5-thiophen-3-yl-pyridin-2-ylamine; 5-benzo[b]thiophen-2-yl-3-[1-(2,6-dichloro-3-fluoro-phenyl)-ethoxy]-pyridin-2-ylamine; 4-methyl-piperazine-1-carboxylic acid (4-{6-amino-5-[1-(2,6-dichloro-3-fluoro-phenyl)-ethoxy]-pyridin-3-yl}-phenyl)-amide; 1-(4-{6-amino-5-[1-(2,6-dichloro-3-fluoro-phenyl)-ethoxy]-pyridin-3-yl}-phenyl)-3-(2-pyrrolidin-1-yl-ethyl)-urea; 1-(4-{6-amino-5-[1-(2,6-dichloro-3-fluoro-phenyl)-ethoxy]-pyridin-3-yl}-phenyl)-3-(2-hydroxy-ethyl)-urea; 1-(4-{6-amino-5-[1-(2,6-dichloro-3-fluoro-phenyl)-ethoxy]-pyridin-3-yl}-phenyl)-3-(2-morpholin-4-yl-ethyl)-urea; (R)-3-amino-pyrrolidine-1-carboxylic acid (4-{6-amino-5-[1-(2,6-dichloro-3-fluoro-phenyl)-ethoxy]-pyridin-3-yl}-phenyl)-amide; (S)-3-amino-pyrrolidine-1-carboxylic acid (4-{6-amino-5-[1-(2,6-dichloro-3-fluoro-phenyl)-ethoxy]-pyridin-3-yl}-phenyl)-amide; 1-(4-{6-amino-5-[1-(2,6-dichloro-3-fluoro-phenyl)-ethoxy]-pyridin-3-yl}-phenyl)-3-(1-methyl-piperidin-4-yl)-urea; 1-(4-{6-amino-5-[1-(2-chloro-3,6-difluoro-phenyl)-ethoxy]-pyridin-3-yl}-phenyl)-3-(1-methyl-piperidin-4-yl)-urea; (R)-3-amino-pyrrolidine-1-carboxylic acid (4-{6-amino-5-[1-(2-chloro-3,6-difluoro-phenyl)-ethoxy]-pyridin-3-yl}-phenyl)-amide; (S)-3-amino-pyrrolidine-1-carboxylic acid (4-{6-amino-5-[1-(2-chloro-3,6-difluoro-phenyl)-ethoxy]-pyridin-3-yl}-phenyl)-amide; 1-(4-{6-amino-5-[1-(2-chloro-3,6-difluoro-phenyl)-ethoxy]-pyridin-3-yl}-phenyl)-3-(2-hydroxy-ethyl)-urea; 4-methyl-piperazine-1-carboxylic acid (4-{6-amino-5-[1-(2-chloro-3,6-difluoro-phenyl)-ethoxy]-pyridin-3-yl}-phenyl)-amide; 1-(4-{6-amino-5-[1-(2-chloro-3,6-difluoro-phenyl)-ethoxy]-pyridin-3-yl}-phenyl)-3-(2-pyrrolidin-1-yl-ethyl)-urea; 1-(4-{6-amino-5-[1-(2-chloro-3,6-difluoro-phenyl)-ethoxy]-pyridin-3-yl}-phenyl)-3-(2-morpholin-4-yl-ethyl)-urea; (R)-2-pyrrolidin-1-ylmethyl-pyrrolidine-1-carboxylic acid (4-{6-amino-5-[1-(2-chloro-3,6-difluoro-phenyl)-ethoxy]-pyridin-3-yl}-phenyl)-amide; 3-{6-amino-5-[1-(2,6-dichloro-phenyl)-ethoxy]-pyridin-3-yl}-benzoic acid; (3-{6-amino-5-[1-(2,6-dichloro-phenyl)-ethoxy]-pyridin-3-yl}-phenyl)-((3R,5S)-3,5-dimethyl-piperazin-1-yl)-methanone; (3-{6-amino-5-[1-(2,6-dichloro-phenyl)-ethoxy]-pyridin-3-yl}-phenyl)-(4-pyrrolidin-1-yl-piperidin-1-yl)-methanone; 3-{6-amino-5-[1-(2,6-dichloro-phenyl)-ethoxy]-pyridin-3-yl}-N-(2-pyrrolidin-1-yl-ethyl)-benzamide; 3-{6-amino-5-[1-(2,6-dichloro-phenyl)-ethoxy]-pyridin-3-yl}-N-(2-morpholin-4-yl-ethyl)-benzamide; (3-{6-amino-5-[1-(2,6-dichloro-phenyl)-ethoxy]-pyridin-3-yl}-phenyl)-((S)-2-pyrrolidin-1-ylmethyl-pyrrolidin-1-yl)-methanone; 3-{6-amino-5-[1-(2,6-dichloro-phenyl)-ethoxy]-pyridin-3-yl}-N-(3-pyrrolidin-1-yl-propyl)-benzamide; N-[2-(4-acetyl-piperazin-1-yl)-ethyl]-3-{6-amino-5-[1-(2,6-dichloro-phenyl)-ethoxy]-pyridin-3-yl}benzamide; 3-{6-amino-5-[1-(2,6-dichloro-phenyl)-ethoxy]-pyridin-3-yl}-N-(1-methyl-piperidin-4-yl)-benzamide; (3-{6-amino-5-[1-(2,6-dichloro-phenyl)-ethoxy]-pyridin-3-yl}-phenyl)-(4-methyl-piperazin-1-yl)-methanone; (3-{6-amino-5-[1-(2,6-dichloro-phenyl)-ethoxy]-pyridin-3-yl}-phenyl)-((R)-2-pyrrolidin-1-ylmethyl-pyrrolidin-1-yl)-methanone; (3-{6-amino-5-[1-(2,6-dichloro-phenyl)-ethoxy]-pyridin-3-yl}-phenyl)-((S)-3-amino-pyrrolidin-1-yl)-methanone; (3-{6-amino-5-[1-(2,6-dichloro-phenyl)-ethoxy]-pyridin-3-yl}-phenyl)-((R)-3-amino-pyrrolidin-1-yl)-methanone; 4-{6-amino-5-[1-(2,6-dichloro-phenyl)-ethoxy]-pyridin-3-yl}-benzoic acid; 4-{6-amino-5-[1-(2,6-dichloro-phenyl)-ethoxy]-pyridin-3-yl}-N-(2-pyrrolidin-1-yl-ethyl)-benzamide; 4-{6-amino-5-[1-(2,6-dichloro-phenyl)-ethoxy]-pyridin-3-yl}-N-(2-morpholin-4-yl-ethyl)-benzamide; (4-{6-amino-5-[1-(2,6-dichloro-phenyl)-ethoxy]-pyridin-3-yl}-phenyl)-((S)-2-pyrrolidin-1-ylmethyl-pyrrolidin-1-yl)-methanone; 4-{6-amino-5-[1-(2,6-dichloro-phenyl)-ethoxy]-pyridin-3-yl}-N-(1-methyl-piperidin-4-yl)-benzamide; (4-{6-amino-5-[1-(2,6-dichloro-phenyl)-ethoxy]-pyridin-3-yl}-phenyl)-((3R,5S)-3,5-dimethyl-piperazin-1-yl)-methanone; N-[2-(4-acetyl-piperazin-1-yl)-ethyl]-4-{6-amino-5-[1-(2,6-dichloro-phenyl)-ethoxy]-pyridin-3-yl}-benzamide; 4-{6-amino-5-[1-(2,6-dichloro-phenyl)-ethoxy]-pyridin-3-yl}-N-(3-pyrrolidin-1-yl-propyl)-benzamide; (4-{6-amino-5-[1-(2,6-dichloro-phenyl)-ethoxy]-pyridin-3-yl}-phenyl)-((S)-3-aminopyrrolidin-1-yl)-methanone; (4-{6-amino-5-[1-(2,6-dichloro-phenyl)-ethoxy]-pyridin-3-yl}-phenyl)-((R)-3-amino-pyrrolidin-1-yl)-methanone; (4-{6-amino-5-[1-(2,6-dichloro-phenyl)-ethoxy]-pyridin-3-yl}-phenyl)-((R)-2-pyrrolidin-1-ylmethyl-pyrrolidin-1-yl)-methanone; (4-{6-amino-5-[1-(2,6-dichloro-phenyl)-ethoxy]-pyridin-3-yl}-phenyl)-(4-pyrrolidin-1-yl-piperidin-1-yl)-methanone; (4-{6-amino-5-[1-(2,6-dichloro-phenyl)-ethoxy]-pyridin-3-yl}-phenyl)-(4-methyl-piperazin-1-yl)-methanone; (S)-2-pyrrolidin-1-ylmethyl-pyrrolidine-1-carboxylic acid (3-{6-amino-5-[1-(2,6-dichloro-3-fluoro-phenyl)-ethoxy]-pyridin-3-yl}-prop-2-ynyl)-amide; 4-methyl-piperazine-1-carboxylic acid (3-{6-amino-5-[1-(2,6-dichloro-3-fluoro-phenyl)-ethoxy]-pyridin-3-yl}-prop-2-ynyl)-amide; 4-pyrrolidin-1-yl-piperidine-1-carboxylic acid (3-{6-amino-5-[1-(2,6-dichloro-3-fluoro-phenyl)-ethoxy]-pyridin-3-yl}- prop-2-ynyl)-amide; (3R,5S)-3,5-dimethyl-piperazine-1-carboxylic acid (3-{6-amino-5-[1-(2,6-dichloro-3-fluoro-phenyl)-ethoxy]-pyridin-3-yl}-prop-2-ynyl)-amide; 1-(3-{6-amino-5-[1-(2,6-dichloro-3-fluoro-phenyl)-ethoxy]-pyridin-3-yl}-prop-2-ynyl)-3-(1-methyl-piperidin-4-yl)-urea; 1-(3-{6-amino-5-[1-(2,6-dichloro-3-fluoro-phenyl)-ethoxy]-pyridin-3-yl}-prop-2-ynyl)-3-(3-pyrrolidin-1-yl-propyl)-urea; 1-(3-{6-amino-5-[1-(2,6-dichloro-3-fluoro-phenyl)-ethoxy]-pyridin-3-yl}prop-2-ynyl)-3-(2-pyrrolidin-1-yl-ethyl)-urea; 1-(3-{6-amino-5-[1-(2,6-dichloro-3-fluoro-phenyl)-ethoxy]-pyridin-3-yl}-prop-2-ynyl)-3-(2-morpholin-4-yl-ethyl)-urea; 1-(3-{6-amino-5-[1-(2,6-dichloro-3-fluoro-phenyl)-ethoxy]-pyridin-3-yl}-prop-2-ynyl)-3-(3-morpholin-4-yl-propyl)-urea; (R)-2-pyrrolidin-1-ylmethyl-pyrrolidine-1-carboxylic acid (3-{6-amino-5-[1-(2,6-dichloro-3-fluoro-phenyl)-ethoxy]-pyridin-3-yl}prop-2-ynyl)-amide; 3-[1-(2,6-dichloro-3-fluoro-phenyl)-ethoxy]-5-(3-dimethylamino-prop-1-ynyl)-pyridin-2-ylamine; (3-{6-amino-5-[1-(2,6-dichloro-3-fluoro-phenyl)-ethoxy]-pyridin-3-yl}-prop-2-ynyl)-urea; N-(3-{6-amino-5-[1-(2,6-dichloro-3-fluoro-phenyl)-ethoxy]-pyridin-3-yl}-prop-2-ynyl)-2-piperidin-1-yl-acetamide; N-(3-{6-amino-5-[1-(2,6-dichloro-3-fluoro-phenyl)-ethoxy]-pyridin-3-yl}-prop-2-ynyl)-2-morpholin-4-yl-acetamide; N-(3-{6-amino-5-[1-(2,6-dichloro-3-fluoro-phenyl)-ethoxy]-pyridin-3-yl}-prop-2-ynyl)-2-pyrrolidin-1-yl-acetamide; N-(3-{6-amino-5-[1-(2,6-dichloro-3-fluoro-phenyl)-ethoxy]-pyridin-3-yl}-prop-2-ynyl)-2-((R)-3-hydroxy-pyrrolidin-1-yl)-acetamide; N-(3-{6-amino-5-[1-(2,6-dichloro-3-fluoro-phenyl)-ethoxy]-pyridin-3-yl}-prop-2-ynyl)-2-(4-hydroxy-piperidin-1-yl)-acetamide; N-(3-{6-amino-5-[1-(2,6-dichloro-3-fluoro-phenyl)-ethoxy]-pyridin-3-yl}-prop-2-ynyl)-2-dimethylamino-acetamide; N-(3-{6-amino-5-[1-(2,6-dichloro-3-fluoro-phenyl)-ethoxy]-pyridin-3-yl}-prop-2-ynyl)-2-diethylamino-acetamide; 2-(4-acetyl-piperazin-1-yl)-N-(3-{6-amino-5-[1-(2,6-dichloro-3-fluoro-phenyl)-ethoxy]-pyridin-3-yl}-prop-2-ynyl)-acetamide; 4-methyl-piperazine-1-carboxylic acid (3-{6-amino-5-[1-(2,6-dichloro-3-fluoro-phenyl)-ethoxy]-pyridin-3-yl}-1,1-dimethyl-prop-2-ynyl)-amide; (3R,5S)-3,5-dimethyl-piperazine-1-carboxylic acid (3-{6-amino-5-[1-(2,6-dichloro-3-fluoro-phenyl)-ethoxy]-pyridin-3-yl}-1,1-dimethyl-prop-2-ynyl)-amide; (R)-2-pyrrolidin-1-ylmethyl-pyrrolidine-1-carboxylic acid (3-{6-amino-5-[1-(2,6-dichloro-3-fluoro-phenyl)-ethoxy]-pyridin-3-yl}-1,1-dimethyl-prop-2-ynyl)-amide; (S)-2-pyrrolidin-1-ylmethyl-pyrrolidine-1-carboxylic acid (3-{6-amino-5-[1-(2,6-dichloro-3-fluoro-phenyl)-ethoxy]-pyridin-3-yl}-1,1-dimethyl-prop-2-ynyl)-amide; 1-(3-{6-amino-5-[1-(2,6-dichloro-3-fluoro-phenyl)-ethoxy]-pyridin-3-yl}-1,1-dimethyl-prop-2-ynyl)-3-(2-morpholin-4-yl-ethyl)-urea; 1-(3-{6-amino-5-[1-(2,6-dichloro-3-fluoro-phenyl)-ethoxy]-pyridin-3-yl}-1,1-dimethyl-prop-2-ynyl)-3-(2-pyrrolidin-1-yl-ethyl)-urea; 4-pyrrolidin-1-yl-piperidine-1-carboxylic acid (3-{6-amino-5-[1-(2,6-dichloro-3-fluoro-phenyl)-ethoxy]-pyridin-3-yl}-1,1-dimethyl-prop-2-ynyl)-amide; 3-{6-amino-5-[1-(2,6-dichloro-3-fluoro-phenyl)-ethoxy]-pyridin-3-yl}-propynoic acid cyclohexylamide; 3-{6-amino-5-[1-(2,6-dichloro-3-fluoro-phenyl)-ethoxy]-pyridin-3-yl}-propynoic acid isopropylamide; 4-(3-amino-3-methyl-but-1-ynyl)-2-[1-(2,6-dichloro-3-fluoro-phenyl)-ethoxy]-phenylamine; (4-{6-amino-5-[1-(3-fluoro-2-trifluoromethyl-phenyl)-ethoxy]-pyridin-3-yl}-phenyl)-(4-methyl-piperazin-1yl)-methanone; (4-{6-amino-5-[1-(3-fluoro-2-trifluoromethyl-phenyl)-ethoxy]-pyridin-3-yl}-phenyl)-(4-pyrrolidin-1-yl-piperidin-1-yl)-methanone; (4-{6-amino-5-[1-(3-fluoro-2-trifluoromethyl-phenyl)-ethoxy]-pyridin-3-yl}-phenyl)-((3R,5S)-3,5-dimethyl-piperazin-1-yl)-methanone; (4-{6-amino-5-[1-(3-fluoro-2-trifluoromethyl-phenyl)-ethoxy]-pyridin-3-yl}-phenyl)-((S)-2-pyrrolidin-1-ylmethyl-pyrrolidin-1-yl)-methanone; (4-{6-amino-5-[1-(3-fluoro-2-trifluoromethyl-phenyl)-ethoxy]-pyridin-3-yl}-phenyl)-((R)-2-pyrrolidin-1-ylmethyl-pyrrolidin-1-yl)-methanone; 4-{6-amino-5-[1-(3-fluoro-2-trifluoromethyl-phenyl)-ethoxy]-pyridin-3-yl}-N-(1-methyl-piperidin-4-yl)-benzamide; 4-{6-amino-5-[1-(3-fluoro-2-trifluoromethyl-phenyl)-ethoxy]-pyridin-3-yl}-N-(2-pyrrolidin-1-yl-ethyl)-benzamide; 4-{6-amino-5-[1-(3-fluoro-2-trifluoromethyl-phenyl)-ethoxy]-pyridin-3-yl}-N-(2-morpholin-4-yl-ethyl)-benzamide; 4-{6-amino-5-[1-(3-fluoro-2-trifluoromethyl-phenyl)-ethoxy]-pyridin-3-yl}-N-(3-pyrrolidin-1-yl-propyl)-benzamide; 4-{6-amino-5-[1-(3-fluoro-2-trifluoromethyl-phenyl)-ethoxy]-pyridin-3-yl}-N-(3-morpholin-4-yl-propyl)-benzamide; 6-amino-5-[1-(2,6-dichloro-3-fluoro-phenyl)-ethoxy]-nicotinonitrile; 6-amino-5-[1-(2,6-dichloro-3-cyano-phenyl)-ethoxy]-nicotinonitrile; 5-aminomethyl-3-[1-(2,6-dichloro-3-fluoro-phenyl)-ethoxy]-pyridin-2-ylamine; (R)-2-pyrrolidin-1-ylmethyl-pyrrolidine-1-carboxylic acid {6-amino-5-[1-(2,6-dichloro-3-fluoro-phenyl)-ethoxy]-pyridin-3-ylmethyl}-amide; N-{6-amino-5-[1-(2,6-dichloro-3-fluoro-phenyl)-ethoxy]-pyridin-3-ylmethyl}-methanesulfonamide; N-{6-amino-5-[1-(2,6-dichloro-3-fluoro-phenyl)-ethoxy]-pyridin-3-ylmethyl}-acetamide; N-{6-amino-5-[1-(2,6-dichloro-3-fluoro-phenyl)-ethoxy]-pyridin-3-ylmethyl}-4-methyl-benzenesulfonamide; 3-[1-(2,6-dichloro-3-fluoro-phenyl)-ethoxy]-5-vinyl-pyridin-2-ylamine; (S)-1-{6-amino-5-[1-(2,6-dichloro-3-fluoro-phenyl)-ethoxy]-pyridin-3-yl}-ethane-1,2-diol; (R)-1-{6-amino-5-[1-(2,6-dichloro-3-fluoro-phenyl)-ethoxy]-pyridin-3-yl}-ethane-1,2-diol; 3-[1-(2,6-dichloro-3-fluoro-phenyl)-ethoxy]-5-(1H-pyrazol-4-yl)-pyridin-2-ylamine; 3-[1-(2,6-dichloro-3-fluoro-phenyl)-ethoxy]-5-[1-(2-pyrrolidin-1-yl-ethyl)-1H-pyrazol-4-yl]-pyridin-2-ylamine; 3-[1-(2,6-dichloro-3-fluoro-phenyl)-ethoxy]-5-[1-(2-diisopropylamino-ethyl)-1H-pyrazol-4-yl]-pyridin-2-ylamine; 3-[1-(2,6-dichloro-3-fluoro-phenyl)-ethoxy]-5-[1-(2-morpholin-4-yl-ethyl)-1H-pyrazol-4-yl]-pyridin-2-ylamine; 5-bromo-3-(3-fluoro-2-methoxy-benzyloxy)-pyridin-2-ylamine; 5-bromo-3-[1-(3-fluoro-2-methoxy-phenyl)-ethoxy]-pyridin-2-ylamine; {4-[6-amino-5-(3-fluoro-2-methoxy-benzyloxy)-pyridin-3-yl]-phenyl}-((3R,5S)-3,5-dimethyl-piperazin-1-yl)-methanone; (4-{6-amino-5-[1-(3-fluoro-2-methoxy-phenyl)-ethoxy]-pyridin-3-yl}-phenyl)-((3R,5S)-3,5-dimethyl-piperazin-1-yl)-methanone; 5-bromo-3-(3-fluoro-2-isopropoxy-benzyloxy)-pyridin-2-ylamine; {4-[6-amino-5-(3-fluoro-2-isopropoxy-benzyloxy)-pyridin-3-yl]-phenyl}-((3R,5S)-3,5-dimethyl-piperazin-1-yl)-methanone; 5-(4-amino-phenyl)-3-[1-(2,6-dichloro-3-fluoro-phenyl)-ethoxy]-pyridin-2-ylamine; (4-{6-amino-5-[1-(2,6-dichloro-3-fluoro-phenyl)-ethoxy]-pyridin-3-yl}-phenoxy)-acetic acid methyl ester; (4-{6-amino-5-[1-(2,6-dichloro-3-fluoro-phenyl)-ethoxy]-pyridin-3-yl}-phenoxy)-acetic acid; 2-(4-{6-amino-5-[1-(2,6-dichloro-3-fluoro-phenyl)-ethoxy]-pyridin-3-yl}-phenoxy)-1-((3R,5S)-3,5-dimethyl-piperazin-1-yl)-ethanone; 2-(4-{6-amino-5-[1-(2,6-dichloro-3-fluoro-phenyl)-ethoxy]-pyridin-3-yl}-phenoxy)-1-((R)-3-hydroxy-pyrrolidin-1-yl)-ethanone; 4-[2-(4-{6-amino-5-[1-(2,6-dichloro-3-fluoro-phenyl)-ethoxy]-pyridin-3-yl}-phenoxy)-acetyl]-piperazine-1-carboxylic acid tert-butyl ester; 2-(4-{6-amino-5-[1-(2,6-dichloro-3-fluoro-phenyl)-ethoxy]-pyridin-3-yl}-phenoxy)-1-((R)-2-pyrrolidin-1-ylmethyl-pyrrolidin-1-yl)-ethanone; 5-bromo-3-(3-fluoro-6,7,8,9-tetrahydro-5H-benzocyclohepten-5-yloxy)-pyridin-2-ylamine; {4-[6- amino-5-(3-fluoro-6,7,8,9-tetrahydro-5H-benzocyclohepten-5-yloxy)-pyridin-3-yl]-phenyl}-((3R,5S)-3,5-dimethyl-piperazin-1-yl)-methanone; 3-(3-fluoro-6,7,8,9-tetrahydro-5H-benzocyclohepten-5-yloxy)-5-[4-(2-pyrrolidin-1-yl-ethoxy)-phenyl]-pyridin-2-ylamine; N-{4-[6-amino-5-(3-fluoro-6,7,8,9-tetrahydro-5H-benzocyclohepten-5-yloxy)-pyridin-3-yl]-phenyl}-methanesulfonamide; 3-(3-fluoro-6,7,8,9-tetrahydro-5H-benzocyclohepten-5-yloxy)-5-(1H-pyrazol-4-yl)-pyridin-2-ylamine; 5-bromo-3-[1-(2-chloro-3-fluoro-phenyl)-ethoxy]-pyridin-2-ylamine; 3-[1-(2-chloro-3-fluoro-phenyl)-ethoxy]-5-[4-(2-pyrrolidin-1-yl-ethoxy)-phenyl]-pyridin-2-ylamine; 5'-benzyloxy-[2,3']bipyridinyl-6'-ylamine; 5-benzyloxy-[3,3']bipyridinyl-6-ylamine; 3-benzyloxy-5-pyrimidin-5-yl-pyridin-2-ylamine; 5-benzyloxy-[3,3']bipyridinyl-6,6'-diamine; 5'-(2-chloro-benzyloxy)-[2,3']bipyridinyl-6'-ylamine; 5-(2-chloro-benzyloxy)-[3,3']bipyridinyl-6-ylamine; 3-(2-chloro-benzyloxy)-5-pyrimidin-5-yl-pyridin-2-ylamine; 5-(2-chloro-benzyloxy)-[3,3']bipyridinyl-6,6'-diamine; 5'-(4-chloro-benzyloxy)-[2,3']bipyridinyl-6'-ylamine; 5-(4-chloro-benzyloxy)-[3,3']bipyridinyl-6-ylamine; 3-(4-chloro-benzyloxy)-5-pyrimidin-5-yl-pyridin-2-ylamine; 5-(4-chloro-benzyloxy)-[3,3']bipyridinyl-6,6'-diamine; 5'-(2-chloro-3,6-difluoro-benzyloxy)-[2,3']bipyridinyl-6'-ylamine; 5-(2-chloro-3,6-difluoro-benzyloxy)-[3,3']bipyridinyl-6-ylamine; 5-(2-chloro-3,6-difluoro-benzyloxy)-[3,4']bipyridinyl-6-ylamine; 3-(2-chloro-3,6-difluoro-benzyloxy)-5-pyrimidin-5-yl-pyridin-2-ylamine; 5-(2-chloro-3,6-difluoro-benzyloxy)-[3,3']bipyridinyl-6,6'-diamine; 5'-(2,6-dichloro-benzyloxy)-[2,3']bipyridinyl-6'-ylamine; 5-(2,6-dichloro-benzyloxy)-[3,3']bipyridinyl-6-ylamine; 5-(2,6-dichloro-benzyloxy)-[3,4']bipyridinyl-6-ylamine; 3-(2,6-dichloro-benzyloxy)-5-pyrimidin-5-yl-pyridin-2-ylamine; 5-(2,6-dichloro-benzyloxy)-[3,3']bipyridinyl-6,6'-diamine; 5-[1-(2,6-dichloro-3-fluoro-phenyl)-ethoxy]-[3,3']bipyridinyl-6,6'-diamine; {6'-amino-5'-[1-(2,6-dichloro-3-fluoro-phenyl)-ethoxy]-[2,3']bipyridinyl-4-yl}-(4-methyl-piperazin-1-yl)-methanone; {6'-amino-5'-[1-(2,6-dichloro-3-fluoro-phenyl)-ethoxy]-[2,3']bipyridinyl-6-yl}-(4-methyl-piperazin-1-yl)-methanone; {6'-amino-5'-[1-(2,6-dichloro-3-fluoro-phenyl)-ethoxy]-[3,3']bipyridinyl-5-yl}-(4-methyl-piperazin-1-yl)-methanone; {6'-amino-5'-[1-(2,6-dichloro-3-fluoro-phenyl)-ethoxy]-[3,3']bipyridinyl-6-yl}-(4-methyl-piperazin-1-yl)-methanone; {6-amino-5-[1-(2,6-dichloro-3-fluoro-phenyl)-ethoxy]-[3,4']bipyridinyl-2'-yl}-(4-methyl-piperazin-1-yl)-methanone; 5-[1-(2-chloro-3,6-difluoro-phenyl)-ethoxy]-[3,3']bipyridinyl-6,6'-diamine; {6'-amino-5'-[1-(2-chloro-3,6-difluoro-phenyl)-ethoxy]-[2,3']bipyridinyl-5-yl}-(4-methyl-piperazin-1-yl)-methanone; {6'-amino-5'-[1-(2-chloro-3,6-difluoro-phenyl)-ethoxy]-[2,3']bipyridinyl-4-yl}-(4-methyl-piperazin-1-yl)-methanone; {6'-amino-5'-[1-(2-chloro-3,6-difluoro-phenyl)-ethoxy]-[2,3']bipyridinyl-6-yl}-(4-methyl-piperazin-1-yl)-methanone; {6'-amino-5'-[1-(2-chloro-3,6-difluoro-phenyl)-ethoxy]-[3,3']bipyridinyl-5-yl}(4-methyl-piperazin-1-yl)-methanone; {6'-amino-5'-[1-(2-chloro-3,6-difluoro-phenyl)-ethoxy]-[3,3']bipyridinyl-6-yl}-(4-methyl-piperazin-1-yl)-methanone; {6-amino-5-[1-(2-chloro-3,6-difluoro-phenyl)-ethoxy]-[3,4']bipyridinyl-2'-yl}-(4-methyl-piperazin-1-yl)-methanone; 5'-[1-(2,6-dichloro-3-fluoro-phenyl)-ethoxy]-[2,3']bipyridinyl-6'-ylamine; 5'-[1-(2-chloro-3,6-difluoro-phenyl)-ethoxy]-[2,3']bipyridinyl-6'-ylamine; 5-[1-(2-chloro-3,6-difluoro-phenyl)-ethoxy]-[3,3']bipyridinyl-6-ylamine; 3-[1-(2-chloro-3,6-difluoro-phenyl)-ethoxy]-5-pyrimidin-5-yl-pyridin-2-ylamine; {6'-amino-5'-[1-(2,6-dichloro-3-fluoro-phenyl)-ethoxy]-[2,3']bipyridinyl-5-yl}-(4-methyl-piperazin-1-yl)-methanone; 5-[1-(2-chloro-3,6-difluoro-phenyl)-ethoxy]-[3,4']bipyridinyl-6-ylamine; 5-benzyloxy-3-[1-(2-chloro-3,6-difluoro-phenyl)-ethoxy]-pyridin-2-ylamine; 3-[1-(2-chloro-3,6-difluoro-phenyl)-ethoxy]-5-(2-ethyl-butoxy)-pyridin-2-ylamine; 3-[1-(2-chloro-3,6-difluoro-phenyl)-ethoxy]-5-(3-methyl-butoxy)-pyridin-2-ylamine; 3-[1-(2-chloro-3,6-difluoro-phenyl)-ethoxy]-5-butoxy-pyridin-2-ylamine; 3-[1-(2-chloro-3,6-difluoro-phenyl)-ethoxy]-5-propoxy-pyridin-2-ylamine; 3-[1-(2-chloro-3,6-difluoro-phenyl)-ethoxy]-5-cyclohexylmethoxy-pyridin-2-ylamine; 6-amino-5-[1-(2-chloro-3,6-difluoro-phenyl)-ethoxy]-pyridin-3-ol; 3-[1-(2-chloro-3,6-difluoro-phenyl)-ethoxy]-5-(2-cyclohexyl-ethoxy)-pyridin-2-ylamine; 3-[1-(2-chloro-3,6-difluoro-phenyl)-ethoxy]-5-isobutoxy-pyridin-2-ylamine; 3-[1-(2-chloro-3,6-difluoro-phenyl)-ethoxy]-5-phenethyloxy-pyridin-2-ylamine; 3-[1-(2-chloro-3,6-difluoro-phenyl)-ethoxy]-5-(pyridin-2-ylmethoxy)-pyridin-2-ylamine; 3-[1-(2-chloro-3,6-difluoro-phenyl)-ethoxy]-5-(pyridin-4-ylmethoxy)-pyridin-2-ylamine; (4-{6-amino-5-[1-(2,6-dichloro-3-fluoro-phenyl)-ethoxy]-pyridin-3-yl}-phenyl)-((3R,5S)-3,5-dimethyl-piperazin-1-yl)-methanone; (4-{6-amino-5-[1-(2,6-dichloro-3-fluoro-phenyl)-ethoxy]-pyridin-3-yl}-phenyl)-((3R,5S)-3,5-dimethyl-piperazin-1-yl)-methanone; 5-{6-amino-5-[1-(2,6-dichloro-3-fluoro-phenyl)-ethoxy]-pyridin-3-yl}-2-fluoro-benzonitrile; 4-(4-{6-amino-5-[1-(2,6-dichloro-3-fluoro-phenyl)-ethoxy]-pyridin-3-yl}-phenyl)-piperidin-4-ol; (4-{6-amino-5-[1-(2,6-dichloro-3-fluoro-phenyl)-ethoxy]-pyridin-3-yl}-phenyl)-piperidin-1-yl-methanone; (4-{6-amino-5-[1-(2,6-dichloro-3-fluoro-phenyl)-ethoxy]-pyridin-3-yl}-phenyl)-pyrrolidin-1-yl-methanone; 4-{6-amino-5-[1-(2,6-dichloro-3-fluoro-phenyl)-ethoxy]-pyridin-3-yl}-3-methyl-benzoic acid methyl ester; 3-[1-(2,6-dichloro-3-fluoro-phenyl)-ethoxy]-5-[4-(dimethyl-piperazin-1-ylmethyl)-phenyl]-pyridin-2-ylamine; (4-{6-amino-5-[1-(2,6-dichloro-3-fluoro-phenyl)-ethoxy]-pyridin-3-yl}-3,5-dimethoxy-phenyl)-(dimethyl-piperazin-1-yl)-methanone; (4-{6-amino-5-[1-(2,6-dichloro-3-fluoro-phenyl)-ethoxy]-pyridin-3-yl}-2-fluoro-phenyl)-(dimethyl-piperazin-1-yl)-methanone; (4-{6-amino-5-[1-(2,6-dichloro-3-fluoro-phenyl)-ethoxy]-pyridin-3-yl}-3-fluoro-phenyl)-(dimethyl-piperazin-1-yl)-methanone; (4-{6-amino-5-[1-(2,6-dichloro-3-fluoro-phenyl)-ethoxy]-pyridin-3-yl}-3-methyl-phenyl)-(dimethyl-piperazin-1-yl)-methanone; (4-{6-amino-5-[1-(2,6-dichloro-3-fluoro-phenyl)-ethoxy]-pyridin-3-yl}-phenyl)-(4-methyl-[1,4]diazepan-1-yl)-methanone; (4-{6-amino-5-[1-(2,6-dichloro-3-fluoro-phenyl)-ethoxy]-pyridin-3-yl}-phenyl)-[1,4]diazepan-1-yl-methanone; (4-{6-amino-5-[1-(2,6-dichloro-3-fluoro-phenyl)-ethoxy]-pyridin-3-yl}-phenyl)-piperazin-1-yl-methanone; 3-[1-(2,6-dichloro-3-fluoro-phenyl)-ethoxy]-5-vinyl-pyridin-2-ylamine; (4-{6-amino-5-[1-(2,6-dichloro-3-fluoro-phenyl)-ethoxy]-pyridin-3-yl}-phenyl)-((3R,4S)-3,4-dihydroxy-pyrrolidin-1-yl)-methanone; 5-[(1-benzyl-pyrrolidin-3-ylamino)-methyl]-3-[1-(2,6-dichloro-3-fluoro-phenyl)-ethoxy]-pyridin-2-ylamine; 4-{6-amino-5-[1-(2,6-dichloro-3-fluoro-phenyl)-ethoxy]-pyridin-3-yl}-N-azetidin-3-yl-benzamide; 4-{6-amino-5-[1-(2,6-dichloro-3-fluoro-phenyl)-ethoxy]-pyridin-3-yl}-N,N-dimethyl-benzenesulfonamide; 3-[1-(2,6-dichloro-3-fluoro-phenyl)-ethoxy]-5-(6-methoxy-1H-benzoimidazol-2-yl)-pyridin-2-ylamine; 3-[1-(2,6-dichloro-3-fluoro-phenyl)-ethoxy]-5-(6-methoxy-1-methyl-1H-benzoimidazol-2-yl)-pyridin-2-ylamine; 3-[1-(2,6-dichloro-3-fluoro-phenyl)-ethoxy]-5-[4-(4-methyl-[1,4]diazepane-1-sulfonyl)-phenyl]-pyridin-2-ylamine; 6-{6-amino-5-[1-(2,6-dichloro-3-fluoro-phenyl)-ethoxy]-pyridin-3-yl}1-methyl-1H-indazole-3-carboxylic acid amide; 3-[1-(2,6-dichloro-3- fluoro-phenyl)-ethoxy]-5-(1-methyl-1H-pyrazol-4-yl)-pyridin-2-ylamine; 5-(3-chloro-phenyl)-3-[1-(2,6-dichloro-3-fluoro-phenyl)-ethoxy]-pyridin-2-ylamine; 3-[1-(2,6-dichloro-3-fluoro-phenyl)-ethoxy]-5-(4-fluoro-3-methyl-phenyl)-pyridin-2-ylamine; 3-[1-(2,6-dichloro-3-fluoro-phenyl)-ethoxy]-5-(3-trifluoromethyl-phenyl)-pyridin-2-ylamine; 3-[1-(2,6-dichloro-3-fluoro-phenyl)-ethoxy]-5-(3-fluoro-phenyl)-pyridin-2-ylamine; 3-[1-(2,6-dichloro-3-fluoro-phenyl)-ethoxy]-5-(3-trifluoromethoxy-phenyl)-pyridin-2-ylamine; 5-benzo[1,3]dioxol-5-yl-3-[1-(2,6-dichloro-3-fluoro-phenyl)-ethoxy]-pyridin-2-ylamine; 3-{6-amino-5-[1-(2,6-dichloro-3-fluoro-phenyl)-ethoxy]-pyridin-3-yl}-phenol; (3-{6-amino-5-[1-(2,6-dichloro-3-fluoro-phenyl)-ethoxy]-pyridin-3-yl}-phenyl)-methanol; 3-{6-amino-5-[1-(2,6-dichloro-3-fluoro-phenyl)-ethoxy]-pyridin-3-yl}-benzonitrile; 3-[1-(2,6-dichloro-3-fluoro-phenyl)-ethoxy]-5-(3-methoxy-phenyl)-pyridin-2-ylamine; 3-[1-(2,6-dichloro-3-fluoro-phenyl)-ethoxy]-5-(3,5-dichloro-phenyl)-pyridin-2-ylamine; 3-[1-(2,6-dichloro-3-fluoro-phenyl)-ethoxy]-5-(2,5-dimethyl-phenyl)-pyridin-2-ylamine; 5-(5-chloro-2-methoxy-phenyl)-3-[1-(2,6-dichloro-3-fluoro-phenyl)-ethoxy]-pyridin-2-ylamine; 5-(3-chloro-4-fluoro-phenyl)-3-[1-(2,6-dichloro-3-fluoro-phenyl)-ethoxy]-pyridin-2-ylamine; 3-[1-(2,6-dichloro-3-fluoro-phenyl)-ethoxy]-5-(5-fluoro-2-methoxy-phenyl)-pyridin-2-ylamine; 3-[1-(2,6-dichloro-3-fluoro-phenyl)-ethoxy]-5-(3-isopropyl-phenyl)-pyridin-2-ylamine; 3-[1-(2,6-dichloro-3-fluoro-phenyl)-ethoxy]-5-(3,4-dichloro-phenyl)-pyridin-2-ylamine; 4-{6-amino-5-[1-(2,6-dichloro-3-fluoro-phenyl)-ethoxy]-pyridin-3-yl}-benzonitrile; 3-[1-(2,6-dichloro-3-fluoro-phenyl)-ethoxy]-5-(3,4-difluoro-phenyl)-pyridin-2-ylamine; (4-{6-amino-5-[1-(2,6-dichloro-3-fluoro-phenyl)-ethoxy]-pyridin-3-yl}-phenyl)-((2R,6S)-2,6-dimethyl-morpholin-4-yl)-methanone; 3-[1-(2,6-dichloro-3-fluoro-phenyl)-ethoxy]-5-(2-ethoxy-phenyl)-pyridin-2-ylamine; 3-[1-(2,6-dichloro-3-fluoro-phenyl)-ethoxy]-5-(2,5-dimethoxy-phenyl)-pyridin-2-ylamine; 3-[1-(2,6-dichloro-3-fluoro-phenyl)-ethoxy]-5-(2,4-dimethoxy-phenyl)-pyridin-2-ylamine; 3-[1-(2,6-dichloro-3-fluoro-phenyl)-ethoxy]-5-(2,6-dimethoxy-phenyl)-pyridin-2-ylamine; 3-[1-(2,6-dichloro-3-fluoro-phenyl)-ethoxy]-5-(2-trifluoromethyl-phenyl)-pyridin-2-ylamine; 5-(2-chloro-phenyl)-3-[1-(2,6-dichloro-3-fluoro-phenyl)-ethoxy]-pyridin-2-ylamine; 3-[1-(2,6-dichloro-3-fluoro-phenyl)-ethoxy]-5-(2-trifluoromethoxy-phenyl)-pyridin-2-ylamine; 1-(2-{6-amino-5-[1-(2,6-dichloro-3-fluoro-phenyl)-ethoxy]-pyridin-3-yl}-phenyl)-ethanone; 3-[1-(2,6-dichloro-3-fluoro-phenyl)-ethoxy]-5-(2-fluoro-phenyl)-pyridin-2-ylamine; (2-{6-amino-5-[1-(2,6-dichloro-3-fluoro-phenyl)-ethoxy]-pyridin-3-yl}-phenyl)-methanol; 3-[1-(2,6-dichloro-3-fluoro-phenyl)-ethoxy]-5-o-tolyl-pyridin-2-ylamine; 3-[1-(2,6-dichloro-3-fluoro-phenyl)-ethoxy]-5-(2-methoxy-phenyl)-pyridin-2-ylamine; 3-[1-(2,6-dichloro-3-fluoro-phenyl)-ethoxy]-5-(2,6-dimethyl-phenyl)-pyridin-2-ylamine; (4-{6-amino-5-[1-(2,6-dichloro-3-fluoro-phenyl)-ethoxy]-pyridin-3-yl}-phenyl)-morpholin-4-yl-methanone; (4-{6-amino-5-[1-(2,6-dichloro-3-fluoro-phenyl)-ethoxy]-pyridin-3-yl}-2-chloro-phenyl)-((3R,5S)-dimethyl-piperazin-1-yl)-methanone; 4-{6-amino-5-[1-(2,6-dichloro-3-fluoro-phenyl)-ethoxy]-pyridin-3-yl}-2-methyl-phenyl)-((3R,5S)-dimethyl-piperazin-1-yl)-methanone; 3-[1-(2,6-dichloro-3-fluoro-phenyl)-ethoxy]-5-[4-((2R,6S)-2,6-dimethyl-morpholin-4-ylmethyl)-phenyl]-pyridin-2-ylamine; 3-[1-(2,6-dichloro-3-fluoro-phenyl)-ethoxy]-5-(4-morpholin-4-ylmethyl-phenyl)-pyridin-2-ylamine; 3-[1-(2,6-dichloro-3-fluoro-phenyl)-ethoxy]-5-(3,5-dimethyl-phenyl)-pyridin-2-ylamine; 3-[1-(2,6-dichloro-3-fluoro-phenyl)-ethoxy]-5-m-tolyl-pyridin-2-ylamine; 3-[1-(2,6-dichloro-3-fluoro-phenyl)-ethoxy]-5-(3,4-dimethoxy-phenyl)-pyridin-2-ylamine; 5-biphenyl-3-yl-3-[1-(2,6-dichloro-3-fluoro-phenyl)-ethoxy]-pyridin-2-ylamine; 5-(3,5-bis-trifluoromethyl-phenyl)-3-[1-(2,6-dichloro-3-fluoro-phenyl)-ethoxy]-pyridin-2-ylamine; 3-[1-(2,6-dichloro-3-fluoro-phenyl)-ethoxy]-5-(3,4-dichloro-phenyl)-pyridin-2-ylamine; 1-(3-{6-amino-5-[1-(2,6-dichloro-3-fluoro-phenyl)-ethoxy]-pyridin-3-yl}-phenyl)-ethanone; 3-[1-(2,6-dichloro-3-fluoro-phenyl)-ethoxy]-5-(3,5-difluoro-phenyl)-pyridin-2-ylamine; 3-[1-(2,6-dichloro-3-fluoro-phenyl)-ethoxy]-5-(2,5-dichloro-phenyl)-pyridin-2-ylamine; (4-{6-amino-5-[1-(2,6-dichloro-4-trifluoromethyl-phenyl)-ethoxy]-pyridin-3-yl}-phenyl)-((3R,5S)-3,5-dimethyl-piperazin-1-yl)-methanone; 3-[1-(2,6-dichloro-3-fluoro-phenyl)ethoxy]-5-(3-ethoxy-phenyl)-pyridin-2-ylamine; (4-{6-amino-5-[1-(2-trifluoromethyl-phenyl)-ethoxy]-pyridin-3-yl}-phenyl)-(3,5-dimethyl-piperazin-1-yl)-methanone; (4-{6-amino-5-[1-(3-trifluoromethyl-phenyl)-ethoxy]-pyridin-3-yl}-phenyl)-(3,5-dimethyl-piperazin-1-yl)-methanone; 7-[4-(3,5-dimethyl-piperazine-1-carbonyl)-phenyl]-2-phenyl-4H-pyrido[3,2-b][1,4]oxazin-3-one; {4-[6-amino-5-(3-fluoro-2-trifluoromethyl-benzyloxy)-pyridin-3-yl]-phenyl}-(3,5-dimethyl-piperazin-1-yl)-methanone; {4-[6-amino-5-(2,6-difluoro-benzyloxy)-pyridin-3-yl]-phenyl}-(3,5-dimethyl-piperazin-1-yl)-methanone; [4-(6-amino-5-benzyloxy-pyridin-3-yl)-phenyl]-(3,5-dimethyl-piperazin-1-yl)-methanone; (4-{6-amino-5-[1-(2-chloro-3,6-difluoro-phenyl)-ethoxy]-pyridin-3-yl}-phenyl)-(4-ethyl-piperazin-1-yl)-methanone; [4-(6-amino-5-benzyloxy-pyridin-3-yl)-phenyl]-(4-ethyl-piperazin-1-yl)-methanone; {4-[6-amino-5-(2-methyl-benzyloxy)-pyridin-3-yl]-phenyl}-(3,5-dimethyl-piperazin-1-yl)-methanone; 3-{2-amino-5-[4-(4-pyrrolidin-1-yl-piperidine-1-carbonyl)-phenyl]-pyridin-3-yloxymethyl}-benzoic acid methyl ester; 3-{2-amino-5-[4-(3,5-dimethyl-piperazine-1-carbonyl)-phenyl]-pyridin-3-yloxymethyl}-benzoic acid methyl ester; {4-[6-amino-5-(2-methyl-benzyloxy)-pyridin-3-yl]-phenyl}-(4-pyrrolidin-1-yl-piperidin-1-yl)-methanone; [4-(6-amino-5-cyclohexylmethoxy-pyridin-3-yl)-phenyl]-(4-pyrrolidin-1-yl-piperidin-1-yl)-methanone; 4-(1-{2-amino-5-[4-(4-pyrrolidin-1-yl-piperidine-1-carbonyl)-phenyl]-pyridin-3-yloxy}-ethyl)-[2-(3-hydroxy-phenyl)-ethyl]-benzamide; 4-(1-{2-amino-5-[4-(4-pyrrolidin-1-yl-piperidine-1-carbonyl)-phenyl]-pyridin-3-yloxy}-ethyl)-[2-(2,6-dichloro-phenyl)-ethyl]-benzamide; 4-(1-{2-amino-5-[4-(4-pyrrolidin-1-yl-piperidine-1-carbonyl)-phenyl]-pyridin-3-yloxy}-ethyl)-(1-benzyl-piperidin-4-yl)-benzamide; 4-(1-{2-amino-5-[4-(4-pyrrolidin-1-yl-piperidine-1-carbonyl)-phenyl]-pyridin-3-yloxy}-ethyl)-[3-(2-oxo-pyrrolidin-1-yl)-propyl]-benzamide; (4-{6-amino-5-[1-(2,6-dichloro-3-fluoro-phenyl)-ethoxy]-pyridin-3-yl}-phenyl)-(4-ethyl-piperazin-1-yl)-methanone; {4-[6-amino-5-(2,6-dichloro-benzyloxy)-pyridin-3-yl]-phenyl}-(3,5-dimethyl-piperazin-1-yl)-methanone; (6-amino-3-aza-bicyclo[3.1.0]hex-3-yl)-(4-{6-amino-5-[1-(2,6-dichloro-3-fluoro-phenyl)-ethoxy]-pyridin-3-yl}-phenyl)-methanone; 5-[1-(2,6-dichloro-3-fluoro-phenyl)-ethoxy]-6'-(2-morpholin-4-yl-ethoxy)-[3,3']bipyridinyl-6-ylamine; 6'-amino-5'-[1-(2,6-dichloro-3-fluoro-phenyl)-ethoxy]-1-(2-pyrrolidin-1-yl-ethyl)-1H-[3,3']bipyridinyl-6-one; 5-[1-(2,6-dichloro-3-fluoro-phenyl)-ethoxy]-6'-(2-pyrrolidin-1-yl-ethoxy)-[3,3']bipyridinyl-6-ylamine; 6'-amino-5'-[1-(2,6-dichloro-3-fluoro-phenyl)-ethoxy]-1-[2-(1-methyl-pyrrolidin-2-yl)-ethyl]-1H-[3,3']bipyridinyl-6-one; (4-{6-amino-5-[1-(2,4,6-trimethyl-phenyl)-ethoxy]-pyridin-3-yl}-phenyl)-(4-pyrrolidin-1-ylpiperidin-1-yl)-methanone; (4-{6-amino-5-[1-(2-chloro-6-fluoro-phenyl)-ethoxy]-pyridin-3-yl}-phenyl)-(4-pyrrolidin-1-yl-piperidin-1-yl)-methanone; 3-[1-(2,6-dichloro-3-fluoro-phenyl)-ethoxy]-5-(4-fluoro-phenyl)-pyridin-2-ylamine; 6'-amino-5'-[1-(2,6-dichloro-3-fluoro-phenyl)-ethoxy]-1H-[3,3']bipyridinyl-6-one; 5'-bromo-5-[1-(2,6-dichloro-3-fluoro-phenyl)-ethoxy]-[3,3']bipyridinyl-6-ylamine; 3-[1-(2,6-dichloro-3-fluoro-phenyl)-ethoxy]-5-(4-dimethylamino-phenyl)-pyridin-2-ylamine; 5-[1-(2,6-dichloro-3-fluoro-phenyl)-ethoxy]-2'-methoxy-[3,3']bipyridinyl-6-ylamine; 3-[1-(2,6-dichloro-3-fluoro-phenyl)-ethoxy]-5-(1H-indol-5-yl)-pyridin-2-ylamine; (4-{6-amino-5-[1-(2,6-dichloro-phenyl)-propoxy]-pyridin-3-yl}-phenyl)-(3,5-dimethyl-piperazin-1-yl)-methanone; [4-(6-amino-5-benzyloxy-pyridin-3-yl)-phenyl]-(4-pyrrolidin-1-yl-piperidin-1-yl)-methanone; 3-(2,6-dichloro-3-fluoro-benzyloxy)-5-thiazol-2-yl-pyridin-2-ylamine; (4-{6-amino-5-[1-(2-fluoro-6-trifluoromethyl-phenyl)-ethoxy]-pyridin-3-yl}-phenyl)-(4-pyrrolidin-1-yl-piperidin-1-yl)-methanone; 3-(2,6-dichloro-3-fluoro-benzyloxy)-5-(1-methyl-1H-imidazol-2-yl)-pyridin-2-ylamine; {4-[6-amino-5-(2,4,6-trimethyl-benzyloxy)-pyridin-3-yl]-phenyl}-(4-pyrrolidin-1-yl-piperidin-1-yl)-methanone; {4-[6-amino-5-(2,3,5,6-tetramethyl-benzyloxy)-pyridin-3-yl]-phenyl}-(4-pyrrolidin-1-yl-piperidin-1-yl)-methanone; {4-[6-amino-5-(2,4,6-trifluoro-benzyloxy)-pyridin-3-yl]-phenyl}-(4-pyrrolidin-1-yl-piperidin-1-yl)-methanone; (4-{6-amino-5-[1-(2-fluoro-6-trifluoromethyl-phenyl)-ethoxy]-pyridin-3-yl}-phenyl)-(4-pyrrolidin-1-yl-piperidin-1-yl)-methanone; 6-amino-5-[1-(2,6-dichloro-3-fluoro-phenyl)-ethoxy]-N-methyl-nicotinamidine; 6-amino-5-[1-(2,6-dichloro-3-fluoro-phenyl)-ethoxy]-N-(2-morpholin-4-yl-ethyl)-nicotinamidine; (4-{6-amino-5-[1-(2,4,5-trifluoro-phenyl)-propoxy]-pyridin-3-yl}-phenyl)-(4-pyrrolidin-1-yl-piperidin-1-yl)-methanone; (4-{6-amino-5-[1-(6-chloro-2-fluoro-3-methyl-phenyl)-ethoxy]-pyridin-3-yl}-phenyl)-(4-pyrrolidin-1-yl-piperidin-1-yl)-methanone; 3-(1-{2-amino-5-[4-(4-pyrrolidin-1-yl-piperidine-1-carbonyl)-phenyl]-pyridin-3-yloxy}-ethyl)-benzoic acid; and pharmaceutically acceptable salts, hydrates and solvates thereof.

In another embodiment, the invention provides a compound selected from the group consisting of: 3-{5-amino-6-[1-(2,6-dichloro-3-fluoro-phenyl)-ethoxy]-pyrazin-2-yl}-N-(3-pyrrolidin-1-yl-propyl)-benzamide; 3-{5-amino-6-[1-(2-chloro-3,6-difluoro-phenyl)-ethoxy]-pyrazin-2-yl}-N-(3-pyrrolidin-1-yl-propyl)-benzamide; 3-{5-amino-6-[1-(2-chloro-3,6-difluoro-phenyl)-ethoxy]-pyrazin-2-yl}-N-(1-methyl-piperidin-4-yl)-benzamide; 3-{5-amino-6-[1-(2-chloro-3,6-difluoro-phenyl)-ethoxy]-pyrazin-2-yl}-N-(2-pyrrolidin-1-yl-ethyl)-benzamide; 3-{5-amino-6-[1-(2-chloro-3,6-difluoro-phenyl)-ethoxy]-pyrazin-2-yl}-N-(2-morpholin-4-yl-ethyl)-benzamide; N-[2-(4-acetyl-piperazin-1-yl)-ethyl]-3-{5-amino-6-[1-(2-chloro-3,6-difluoro-phenyl)-ethoxy]-pyrazin-2-yl}-benzamide; (3-{5-amino-6-[1-(2-chloro-3,6-difluoro-phenyl)-ethoxy]-pyrazin-2-yl}-phenyl)-(4-methyl-piperazin-1-yl)-methanone; (3-{5-amino-6-[1-(2-chloro-3,6-difluoro-phenyl)-ethoxy]-pyrazin-2-yl}-phenyl)-(4-pyrrolidin-1-yl-piperidin-1-yl)-methanone; (3-{5-amino-6-[1-(2-chloro-3,6-difluoro-phenyl)-ethoxy]-pyrazin-2-yl}-phenyl)-((3R,5S)-3,5-dimethyl-piperazin-1-yl)-methanone; (3-{5-amino-6-[1-(2-chloro-3,6-difluoro-phenyl)-ethoxy]-pyrazin-2-yl}-phenyl)-((S)-2-pyrrolidin-1-ylmethyl-pyrrolidin-1-yl)-methanone; (3-{5-amino-6-[1-(2-chloro-3,6-difluoro-phenyl)-ethoxy]-pyrazin-2-yl}-phenyl)-((R)-3-amino-pyrrolidin-1-yl)-methanone; (3-{5-amino-6-[1-(2-chloro-3,6-difluoro-phenyl)-ethoxy]-pyrazin-2-yl}-phenyl)-((S)-3-amino-pyrrolidin-1-yl)-methanone; 4-{5-amino-6-[1-(2-chloro-3,6-difluoro-phenyl)-ethoxy]-pyrazin-2-yl}benzoic acid; 4-{5-amino-6-[1-(2-chloro-3,6-difluoro-phenyl)-ethoxy]-pyrazin-2-yl}-N-(3-pyrrolidin-1-yl-propyl)-benzamide; (4-{5-amino-6-[1-(2-chloro-3,6-difluoro-phenyl)-ethoxy]-pyrazin-2-yl}-phenyl)-(4-methyl-piperazin-1-yl)-methanone; (4-{5-amino-6-[1-(2-chloro-3,6-difluoro-phenyl)-ethoxy]-pyrazin-2-yl}-phenyl)-(4-pyrrolidin-1-yl-piperidin-1-yl)-methanone; 4-{5-amino-6-[1-(2-chloro-3,6-difluoro-phenyl)-ethoxy]-pyrazin-2-yl}-phenyl)-((3R,5S)-3,5-dimethyl-piperazin-1-yl)-methanone; (4-{5-amino-6-[1-(2-chloro-3,6-difluoro-phenyl)-ethoxy]-pyrazin-2-yl}-phenyl)-((S)-2-pyrrolidin-1-ylmethyl-pyrrolidin-1-yl)-methanone; (4-{5-amino-6-[1-(2-chloro-3,6-difluoro-phenyl)-ethoxy]-pyrazin-2-yl}-phenyl)-((R)-2-pyrrolidin-1-ylmethyl-pyrrolidin-1-yl)-methanone; (4-{5-amino-6-[1-(2-chloro-3,6-difluoro-phenyl)-ethoxy]-pyrazin-2-yl}-phenyl)-((R)-3-amino-pyrrolidin-1-yl)-methanone; 4-{5-amino-6-[1-(2-chloro-3,6-difluoro-phenyl)-ethoxy]-pyrazin-2-yl}-N-(1-methyl-piperidin-4-yl)-benzamide; 4-{5-amino-6-[1-(2-chloro-3,6-difluoro-phenyl)-ethoxy]-pyrazin-2-yl}-N-(2-pyrrolidin-1-yl-ethyl)-benzamide; 4-{5-amino-6-[1-(2-chloro-3,6-difluoro-phenyl)-ethoxy]-pyrazin-2-yl}-N-(2-morpholin-4-yl-ethyl)-benzamide; N-[2-(4-acetyl-piperazin-1-yl)-ethyl]-4-{5-amino-6-[1-(2-chloro-3,6-difluoro-phenyl)-ethoxy]-pyrazin-2-yl}benzamide; 2-[4-(2-Hydroxy-acetyl)-piperazin-1-yl]-ethanesulfonic acid (4-{5-amino-6-[1-(2-chloro-3,6-difluoro-phenyl)-ethoxy]-pyrazin-2-yl}-phenyl)-amide; 3-[5-amino-6-(3-fluoro-2-trifluoromethyl-benzyloxy)-pyrazin-2-yl]-benzoic acid; {3-[5-amino-6-(3-fluoro-2-trifluoromethyl-benzyloxy)-pyrazin-2-yl]-phenyl}-(4-pyrrolidin-1-yl-piperidin-1-yl)-methanone; 3-[5-amino-6-(3-fluoro-2-trifluoromethyl-benzyloxy)-pyrazin-2-yl]-N-{2-[ethyl-(2-methoxy-ethyl)-amino]-ethyl}-benzamide; {3-[5-amino-6-(3-fluoro-2-trifluoromethyl-benzyloxy)-pyrazin-2-yl]-phenyl}-(4-methyl-piperazin-1-yl)-methanone; 3-[5-amino-6-(3-fluoro-2-trifluoromethyl-benzyloxy)-pyrazin-2-yl]-N-(3-pyrrolidin-1-yl-propyl)-benzamide; N-[2-(4-acetyl-piperazin-1-yl)-ethyl]-3-[5-amino-6-(3-fluoro-2-trifluoromethyl-benzyloxy)-pyrazin-2-yl]-benzamide; {4-[5-amino-6-(3-fluoro-2-trifluoromethyl-benzyloxy)-pyrazin-2-yl]-phenyl}-(4-pyrrolidin-1-yl-piperidin-1-yl)-methanone; {4-[5-amino-6-(3-fluoro-2-trifluoromethyl-benzyloxy)-pyrazin-2-yl]-phenyl}-(4-methyl-piperazin-1-yl)-methanone; {4-[5-amino-6-(3-fluoro-2-trifluoromethyl-benzyloxy)-pyrazin-2-yl]-phenyl}-((S)-2-pyrrolidin-1-ylmethyl-pyrrolidin-1-yl)-methanone; (3-{5-amino-6-[1-(2,6-dichloro-3-fluoro-phenyl)-ethoxy)-pyrazin-2-yl}-phenyl)-(4-methyl-piperazin-1-yl)-methanone; (3-{5-amino-6-[1-(2,6-dichloro-3-fluoro-phenyl)-ethoxy]-pyrazin-2-yl}-phenyl)-((3R,5S)-3,5-dimethyl-piperazin-1-yl)-methanone; 3-{5-amino-6-[1-(2,6-dichloro-3-fluoro-phenyl)-ethoxy]-pyrazin-2-yl}-N-(1-methyl-piperidin-4-yl)-benzamide; 3-{5-amino-6-[1-(2,6-dichloro-3-fluoro-phenyl)-ethoxy]-pyrazin-2-yl}-N-(2-pyrrolidin-1-yl-ethyl)-benzamide; 3-{5-amino-6-[1-(2,6-dichloro-3-fluoro-phenyl)-ethoxy]-pyrazin-2-yl}-N-(2-morpholin-4-yl-ethyl)-benzamide; 3-{5-amino-6-[1-(2,6-dichloro-3-fluoro-phenyl)-ethoxy]-pyrazin-2-yl}-N-(3-morpholin-4-yl-propyl)-benzamide; (3-{5-amino-6-[1-(2,6-dichloro-3-fluoro-phenyl)-ethoxy]-pyrazin-2-yl}-phenyl)-(4-cyclopropylamino-piperidin-1-yl)-methanone; 3-{5-amino-6-[1-(2,6-dichloro-3-fluoro-phenyl)-ethoxy]-pyrazin-2-yl}-N-((S)-2-hydroxy-3-morpholin-4-yl-propyl)-benzamide; 3-{5-amino-6-[1-(2,6-dichloro-3-fluoro-phenyl)-ethoxy]-pyrazin-2-yl}-N-((R)-2-hydroxy-3-pyrrolidin-1-yl-propyl)-benzamide; (3-{6- amino-5-[1-(2,6-dichloro-3-fluoro-phenyl)-ethoxy]-pyridin-3-yl}-phenyl)-(4-pyrrolidin-1-yl-piperidin-1-yl)-methanone; 2-diethylamino-ethanesulfonic acid (4-{5-amino-6-[1-(2,6-dichloro-3-fluoro-phenyl)-ethoxy]-pyrazin-2-yl}-phenyl)-amide; 2-(4-Hydroxy-piperidin-1-yl)-ethanesulfonic acid (4-{5-amino-6-[1-(2,6-dichloro-3-fluoro-phenyl)-ethoxy]-pyrazin-2-yl}-phenyl)-amide; 2-dimethylamino-ethanesulfonic acid (4-{5-amino-6-[1-(2,6-dichloro-3-fluoro-phenyl)-ethoxy]-pyrazin-2-yl}-phenyl)-amide; 2-((R)-3-Hydroxy-pyrrolidin-1-yl)-ethanesulfonic acid (4-{5-amino-6-[1-(2,6-dichloro-3-fluoro-phenyl)-ethoxy]-pyrazin-2-yl}-phenyl)-amide; 2-pyrrolidin-1-yl-ethanesulfonic acid (4-{5-amino-6-[1-(2,6-dichloro-3-fluoro-phenyl)-ethoxy]-pyrazin-2-yl}-phenyl)-amide; 4-{5-amino-6-[1-(2,6-dichloro-3-fluoro-phenyl)-ethoxy]-pyrazin-2-yl}-benzoic acid; 4-{5-amino-6-[1-(2,6-dichloro-3-fluoro-phenyl)-ethoxy]-pyrazin-2-yl}-N-((R)-2-hydroxy-3-pyrrolidin-1-yl-propyl)-benzamide; (4-{5-amino-6-[1-(2,6-dichloro-3-fluoro-phenyl)-ethoxy]-pyrazin-2-yl}-phenyl)-(4-cyclopropylamino-piperidin-1-yl)-methanone; 4-{5-amino-6-[1-(2,6-dichloro-3-fluoro-phenyl)-ethoxy]-pyrazin-2-yl}-N-((S)-2-hydroxy-3-pyrrolidin-1-yl-propyl)-benzamide; 4-{5-amino-6-[1-(2,6-dichloro-3-fluoro-phenyl)-ethoxy]-pyrazin-2-yl}-N-((R)-2-hydroxy-3-morpholin-4-yl-propyl)-benzamide; 4-{5-amino-6-[1-(2,6-dichloro-3-fluoro-phenyl)-ethoxy]-pyrazin-2-yl}-N-(1-methyl-piperidin-4-yl)-benzamide; (4-{5-amino-6-[1-(2,6-dichloro-3-fluoro-phenyl)-ethoxy]-pyrazin-2-yl}-phenyl)-((S)-2-pyrrolidin-1-ylmethyl-pyrrolidin-1-yl)-methanone; (4-{5-amino-6-[1-(2,6-dichloro-3-fluoro-phenyl)-ethoxy]-pyrazin-2-yl}-phenyl)-(4-pyrrolidin-1-yl-piperidin-1-yl)-methanone; 4-{5-amino-6-[1-(2,6-dichloro-3-fluoro-phenyl)-ethoxy]-pyrazin-2-yl}-N-(2-morpholin-4-yl-ethyl)-benzamide; (4-{5-amino-6-[1-(2,6-dichloro-3-fluoro-phenyl)-ethoxy]-pyrazin-2-yl}-phenyl)-(4-methyl)-methanone; (4-{5-amino-6-[1-(2,6-dichloro-3-fluoro-phenyl)-ethoxy]-pyrazin-2-yl}-phenyl)-((3R,5S)-3,5-dimethyl-piperazin-1-yl)-methanone; 4-{5-amino-6-[1-(2,6-dichloro-phenyl)-ethoxy]-pyrazin-2-yl}-benzoic acid; (4-{5-amino-6-[1-(2,6-dichloro-phenyl)-ethoxy]-pyrazin-2-yl}-phenyl)-(4-pyrrolidin-1-yl-piperidin-1-yl)-methanone; 4-{5-amino-6-[1-(2,6-dichloro-phenyl)-ethoxy]-pyrazin-2-yl}-N-(2-morpholin-4-yl-ethyl)-benzamide; (4-{5-amino-6-[1-(2,6-dichloro-phenyl)-ethoxy]-pyrazin-2-yl}-phenyl)-((3R,5S)-3,5-dimethyl-piperazin-1-yl)-methanone; 4-{5-amino-6-[1-(2,6-dichloro-phenyl)-ethoxy]-pyrazin-2-yl}-N-(1-methyl-piperidin-4-yl)-benzamide; (4-{5-amino-6-[1-(2,6-dichloro-phenyl)-ethoxy]-pyrazin-2-yl}-phenyl)-((R)-2-pyrrolidin-1-ylmethyl-pyrrolidin-1-yl)-methanone; (4-{5-amino-6-[1-(2,6-dichloro-phenyl)-ethoxy]-pyrazin-2-yl}-phenyl)-((S)-2-pyrrolidin-1-ylmethyl-pyrrolidin-1-yl)-methanone; (4-{5-amino-6-[1-(2,6-dichloro-phenyl)-ethoxy]-pyrazin-2-yl}-phenyl)-(4-methyl-piperazin-1-yl)-methanone; (4-{5-amino-6-[1-(2,6-dichloro-phenyl)-ethoxy]-pyrazin-2-yl}-phenyl)-((R)-3-aminopyrrolidin-1-yl)-methanone; (4-{5-amino-6-[1-(2,6-dichloro-phenyl)-ethoxy]-pyrazin-2-yl}-phenyl)-((S)-3-aminopyrrolidin-1-yl)-methanone hydrogen chloride; 4-{5-amino-6-[1-(2,6-dichloro-phenyl)-ethoxy]-pyrazin-2-yl}-N-(2-pyrrolidin-1-yl-ethyl)-benzamide; 4-{5-amino-6-[1-(2,6-dichloro-phenyl)-ethoxy]-pyrazin-2-yl}-N-(3-pyrrolidin-1-yl-propyl)-benzamide; 3-{5-amino-6-[1-(2,6-dichloro-phenyl)-ethoxy]-pyrazin-2-yl}-benzoic acid; 3-{5-amino-6-[1-(2,6-dichloro-phenyl)-ethoxy]-pyrazin-2-yl}-N-(1-methyl-piperidin-4-yl)-benzamide; 3-{5-amino-6-[1-(2,6-dichloro-phenyl)-ethoxy]-pyrazin-2-yl}-N-(2-pyrrolidin-1-yl-ethyl)-benzamide; (3-{5-amino-6-[1-(2,6-dichloro-phenyl)-ethoxy]-pyrazin-2-yl}-phenyl)-((3R,5S)-3,5-dimethyl-piperazin-1-yl)-methanone; 3-{5-amino-6-[1-(2,6-dichloro-phenyl)-ethoxy]-pyrazin-2-yl}-N-(2-morpholin-4-yl-ethyl)-benzamide; (3-{5-amino-6-[1-(2,6-dichloro-phenyl)-ethoxy]-pyrazin-2-yl}-phenyl)-((S)-2-pyrrolidin-1-ylmethyl-pyrrolidin-1-yl)-methanone; (3-{5-amino-6-[1-(2,6-dichloro-phenyl)-ethoxy]-pyrazin-2-yl}-phenyl)-(4-pyrrolidin-1-yl-piperidin-1-yl)-methanone; N-[2-(4-acetyl-piperazin-1-yl)-ethyl]-4-{5-amino-6-[1-(2,6-dichloro-phenyl)-ethoxy]-pyrazin-2-yl}-benzamide; N-[2-(4-acetyl-piperazin-1-yl)-ethyl]-3-{5-amino-6-[1-(2,6-dichloro-phenyl)-ethoxy]-pyrazin-2-yl}-benzamide; (3-{5-amino-6-[1-(2,6-dichloro-phenyl)-ethoxy]-pyrazin-2-yl}-phenyl)-((R)-2-pyrrolidin-1-ylmethyl-pyrrolidin-1-yl)-methanone; 3-{5-amino-6-[1-(2,6-dichloro-phenyl)-ethoxy]-pyrazin-2-yl}-N-(3-pyrrolidin-1-yl-propyl)-benzamide; (3-{5-amino-6-[1-(2,6-dichloro-phenyl)-ethoxy]-pyrazin-2-yl}-phenyl)-((S)-3-amino-pyrrolidin-1-yl)-methanone; (3-{5-amino-6-[1-(2,6-dichloro-phenyl)-ethoxy]-pyrazin-2-yl}-phenyl)-((R)-3-amino-pyrrolidin-1-yl)-methanone hydrochloride salt; (3-{5-amino-6-[1-(2,6-dichloro-phenyl)-ethoxy]-pyrazin-2-yl}-phenyl)-methanone; 1-(4-{5-amino-6-[1-(2-chloro-3,6-difluoro-phenyl)-ethoxy]-pyrazin-2-yl}-phenyl)-3-(2-morpholin-4-yl-ethyl)-urea; (R)-2-pyrrolidin-1-ylmethyl-pyrrolidine-1-carboxylic acid (4-{5-amino-6-[1-(2-chloro-3,6-difluoro-phenyl)-ethoxy]-pyrazin-2-yl}-phenyl)-amide; 1-(4-{5-amino-6-[1-(2-chloro-3,6-difluoro-phenyl)-ethoxy]-pyrazin-2-yl}-phenyl)-3-(2-pyrrolidin-1-yl-ethyl)-urea; 4-methyl-piperazine-1-carboxylic acid (4-{5-amino-6-[1-(2-chloro-3,6-difluoro-phenyl)-ethoxy]-pyrazin-2-yl}-phenyl)-amide; 1-(4-{5-amino-[1-(2-chloro-3,6-difluoro-phenyl)-ethoxy]-pyrazin-2-yl}-phenyl)-3-(2-hydroxy-ethyl)-urea; (S)-3-amino-pyrrolidine-1-carboxylic acid (4-{5-amino-6-[1-(2-chloro-3,6-difluoro-phenyl)-ethoxy]-pyrazin-2-yl}-phenyl)-amide; 1-(4-{5-amino-6-[1-(2-chloro-3,6-difluoro-phenyl)-ethoxy]-pyrazin-2-yl}-phenyl)-3-(1-methyl-piperidin-4-yl)-urea; 4-methyl-piperazine-1-carboxylic acid (4-{5-amino-6-[1-(2,6-dichloro-3-fluoro-phenyl)-ethoxy]-pyrazin-2-yl}-phenyl)-amide; 1-(4-{5-amino-6-[1-(2,6-dichloro-3-fluoro-phenyl)-ethoxy]-pyrazin-2-yl}-phenyl)-3-(2-hydroxy-ethyl)-urea; (S)-3-amino-pyrrolidine-1-carboxylic acid (4-{5-amino-6-[1-(2,6-dichloro-3-fluoro-phenyl)-ethoxy]-pyrazin-2-yl}-phenyl)-amide; 1-(4-{5-amino-6-[1-(2,6-dichloro-3-fluoro-phenyl)-ethoxy]-pyrazin-2-yl}-phenyl)-3-(1-methyl-piperidin-4-yl)-urea; 5-[5-amino-6-(2-chloro-3,6-difluoro-benzyloxy)-pyrazin-2-yl]-thiophene-2-carboxylic acid; {5-[5-amino-6-(2-chloro-3,6-difluoro-benzyloxy)-pyrazin-2-yl]-thiophen-2-yl}-(4-methyl-piperazin-1-yl)-methanone; {5-[5-amino-6-(2-chloro-3,6-difluoro-benzyloxy)-pyrazin-2-yl]-thiophen-2-yl}-(4-pyrrolidin-1-yl-piperidin-1-yl)-methanone; {5-[5-amino-6-(2-chloro-3,6-difluoro-benzyloxy)-pyrazin-2-yl]-thiophen-2-yl}-((3R,5S)-3,5-dimethyl-piperazin-1-yl)-methanone; {5-[5-amino-6-(2-chloro-3,6-difluoro-benzyloxy)-pyrazin-2-yl]-thiophen-2-yl}-((R)-2-pyrrolidin-1-ylmethyl-pyrrolidin-1-yl)-methanone; 5-[5-amino-6-(2-chloro-3,6-difluoro-benzyloxy)-pyrazin-2-yl]-thiophene-2-carboxylic acid (2-morpholin-4-yl-ethyl)-amide; 3-[1-(2,6-dichloro-3-fluorophenyl)ethoxy]-5-{5-[(4-methylpiperazin-1-yl)carbonyl]-pyridin-2-yl}pyrazin-2-amine trifluoroacetate; 3-[1-(2,6-dichloro-3-fluoro-phenyl)-ethoxy]-5-pyridin-4-yl-pyrazin-2-ylamine; 3-[1-(2,6-dichloro-3-fluoro-phenyl)-ethoxy]-5-(1H-pyrrol-2-yl)-pyrazin-2-ylamine; (6-{5-amino-6-[1-(2,6-dichloro-3-fluoro-phenyl)-ethoxy]-pyrazin-2-yl}-pyridin-3-yl)-(4-methyl-piperazin-1-yl)-methanone; (2-{5-amino-6-[1-(2,6-dichloro-3-fluoro-phenyl)-ethoxy]-pyrazin-2-yl}-pyridin-4- yl)-(4-methyl-piperazin-1-yl)-methanone; (6-{5-amino-6-[1-(2,6-dichloro-3-fluoro-phenyl)-ethoxy]-pyrazin-2-yl}-pyridin-2-yl)-(4-methyl-piperazin-1-yl)-methanone; (5-{5-amino-6-[1-(2,6-dichloro-3-fluoro-phenyl)-ethoxy]-pyrazin-2-yl}-pyridin-3-yl)-(4-methyl-piperazin-1-yl)-methanone; (4-{5-amino-6-[1-(2,6-dichloro-3-fluoro-phenyl)-ethoxy]-pyrazin-2-yl}-pyridin-2-yl)-(4-methyl-piperazin-1-yl)-methanone; 6-{5-amino-6-[1-(2,6-dichloro-3-fluoro-phenyl)-ethoxy]-pyrazin-2-yl}-N-(2-morpholin-4-yl-ethyl)-nicotinamide; 5-{5-amino-6-[1-(2,6-dichloro-3-fluoro-phenyl)-ethoxy]-pyrazin-2-yl}-N-(2-morpholin-4-yl-ethyl)-nicotinamide; 6-{5-amino-6-[1-(2,6-dichloro-3-fluoro-phenyl)-ethoxy]-pyrazin-2-yl}-N-(3-morpholin-4-yl-propyl)-nicotinamide; 5-{5-amino-6-[1-(2,6-dichloro-3-fluoro-phenyl)-ethoxy]-pyrazin-2-yl}-N-(3-morpholin-4-yl-propyl)-nicotinamide; (6-{5-amino-6-[1-(2,6-dichloro-3-fluoro-phenyl)-ethoxy]-pyrazin-2-yl}-pyridin-3-yl)-(4-isopropyl-piperazin-1-yl)-methanone; and pharmaceutically acceptable salts, hydrates and solvates thereof.

In another aspect, the invention provides a compound selected from the group consisting of the compounds shown in Table 1 and pharmaceutically acceptable salts, hydrates and solvates thereof.

In another aspect, the invention provides a compound selected from the group consisting of the compounds shown in Table 2 and pharmaceutically acceptable salts, hydrates and solvates thereof.

In another aspect, the invention provides a compound selected from the group consisting of the compounds shown in Table 3 and pharmaceutically acceptable salts, hydrates and solvates thereof.

In another aspect, the invention provides a compound selected from the group consisting of the compounds shown in Table 4 and pharmaceutically acceptable salts, hydrates and solvates thereof.

In another aspect, the invention provides a compound selected from the group consisting of the compounds shown in Table 5 and pharmaceutically acceptable salts, hydrates and solvates thereof.

In another aspect, the invention provides a compound selected from the group consisting of the compounds shown in Table 6 and pharmaceutically acceptable salts, hydrates and solvates thereof.

In another aspect, the invention provides a compound selected from the group consisting of the compounds shown in Table 7 and pharmaceutically acceptable salts, hydrates and solvates thereof.

In another aspect, the invention provides a compound selected from the group consisting of the compounds shown in Table 8 and pharmaceutically acceptable salts, hydrates and solvates thereof.

In another embodiment, the invention provides compounds having the following chemical structure (Formula 6:

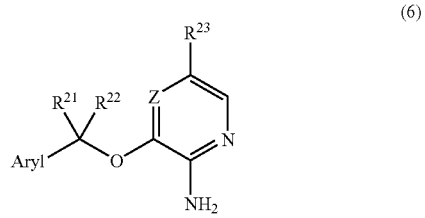

(6)

wherein,

Z is CH or N;

Aryl is an optionally fused aryl or an optionally fused heteroaryl group which is optionally substituted by one or more substituents selected from the group consisting of a halogen, $-OR^{24}$, $-COR^{24}$, $-COOR^{24}$, $-CONR^{24}R^{25}$, $-CN$, $-NO_2$, $-S(O)_mR^{24}$, $-SO_2NR^{24}R^{25}$, perfluoroalkyl, lower alkyl, cycloalkyl, heterocycle, alkenyl, alkynyl, aryl, $-NR^{24}R^{25}$, $-NR^{24}C(O)R^{25}$ and $-NR^{24}S(O)_pR^{25}$;

$R^{21}$ and $R^{22}$ are independently selected from the group consisting of hydrogen, halogen, $-COR^{24}$, $-COOR^{24}$, $-CONR^{24}R^{25}$, $-CN$, perfluoroalkyl, lower alkyl, cycloalkyl, heterocycle, alkenyl, alkynyl, and aryl;

$R^{23}$ is selected from the group consisting of:

an optionally fused aryl, heteroaryl, alicyclic or heterocyclic group, optionally substituted by one or more substituents selected from the group consisting of a halogen, $-(CH_2)_n-OR^{24}$, $-COR^{24}$, $-COOR^{24}$, $-CONR^{24}R^{25}$, $-CN$, $-NO_2$, $-S(O)_mR^{24}$, $-SO_2NR^{24}R^{25}$, perfluoroalkyl, $-O$-perfluoroalkyl, lower alkyl, cycloalkyl, heterocycle, heteroaryl, alkenyl, alkynyl, aryl, $-(CH_2)_n-NR^{24}R^{25}$, $-NR^{24}C(O)R^{25}$ and $-NR^{24}S(O)_pR^{25}$, wherein said heterocycle, heteroaryl and aryl substituents may be optionally substituted by a group selected from the group consisting of lower alkyl, halogen, $-C(O)NR^{24}R^{25}$, $NR^{24}R^{25}$, $NR^{24}C(O)R^{25}$ and $NR^{24}S(O)_pR^{25}$;

$-OR^{24}$, $-COR^{24}$, $-COOR^{24}$, $-CN$, $-NO_2$, $-S(O)_mR^{24}$, $-SO_2NR^{24}R^{25}$, perfluoroalkyl, cycloalkyl, heterocycle, alkenyl, and alkynyl;

$R^{24}$ and $R^{25}$ are independently selected from the group consisting of hydrogen, lower alkyl, cycloalkyl, alkenyl, alkynyl, aryl, aminoalkyl, alkylaminoalkyl, alkylaminocycloalkyl, dialkylaminoalkyl and $-(CH_2)_n$-heterocycle, wherein said $-(CH_2)_n$-heterocycle may be further substituted by one or more of lower alkyl, $-(CH_2)_n$-hydroxy, heterocycle and $-C(O)R^{26}$, or $R^{24}$ and $R^{25}$ can combine to form a 5- to 6-membered heterocyclic ring having one or more heteroatoms selected from the group consisting of N, O, S, S(O) and $SO_2$, said 5- to 6-membered heterocyclic ring may be optionally substituted by lower alkyl, $-(CH_2)_n$-heterocycle, cycloalkyl, halo, $-(CH_2)_n-NR^{26}R^{27}$, amino, $-C(O)R^{26}$, $-NR^{26}-C(O)OR^{27}$ and $-NR^{26}-C(O)R^{27}$;

wherein $R^{26}$ and $R^{27}$ are independently selected from the group consisting of hydrogen, lower alkyl, $-(CH_2)_n$-cycloalkyl and $-C(O)-(CH_2)_n-OH$;

except that when Z is N and $R^{21}$ and $R^{22}$ are H and Aryl is m-chlorophenyl, $R^{23}$ is not piperazine;

m is 0, 1 or 2;

n is 0, 1, 2 or 3;

p is 1 or 2;

or a pharmaceutically acceptable salt thereof.

In preferred aspect of this embodiment, in the compound of Formula (6), $R^{23}$ is aryl or heteroaryl.

In another preferred aspect of this embodiment, when Z is N, $R^{23}$ is not heteroalicyclic.

In another embodiment, the invention provides a pharmaceutical composition comprising any of the inventive compounds described herein. In particular aspects of this embodiment, the pharmaceutical composition comprises a compound of formula 1, a compound of formula 2, a compound of formula 3, a compound of formula 4, a compound of formula 5, a compound of formula 6, or a pharmaceutically acceptable salt, hydrate or solvate thereof, including particular aspects thereof as described above. In other particular aspects of this embodiment, the pharmaceutical composition comprises a compound selected from the compounds shown in Table 1, a compound selected from the compounds shown in Table 2, a compound selected from the compounds shown in Table 3, a compound selected from the compounds shown in Table 4, a compound selected from the compounds shown in Table 5, a compound selected from the compounds shown in Table 6, a compound selected from the compounds shown in Table 7, a compound selected from the compounds shown in Table 8, or a pharmaceutically acceptable salt, hydrate or solvate thereof.

Preferred compounds of the invention include those having c-MET inhibitory activity as defined by any one or more of $IC_{50}$, Ki, or percent inhibition. One skilled in the art can readily determine if a compound has such activity by carrying out the appropriate assay. In one embodiment, particularly preferred compounds have a c-MET $IC_{50}$ of less than 5 µM, or less than 2 µM, or less than 1 µM, or less than 500 nM, or less than 400 nM, or less than 300 nM, or less than 200 nM, or less than 100 nM, or less than 50 nM. In another embodiment, particularly preferred compounds have a c-MET Ki of less than 5 µM or less than 2 µM, or less than 1 µM, or less than 500 nM, or less than 400 nM, or less than 300 nM, or less than 200 nM, or less than 100 nM, or less than 50 nM. In another embodiment, particularly preferred compounds have a c-MET inhibition at 1 µM of at least 10% or at least 20% or at least 30% or at least 40% or at least 50% or at least 60% or at least 70% or at least 80% or at least 90%.

In another embodiment, the invention provides a process of preparing the compound of Formula (6), comprising
(i) brominating a compound of the formula (a):

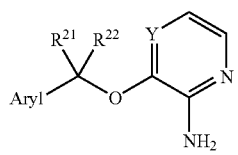

to give a compound of formula (b):
and

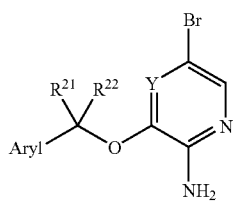

ii. reacting (b) with a boronic acid or ester derivative of the formula $R^{23}B(OR)_2$ in the presence of a palladium catalyst;
wherein R is hydrogen or an alcohol protecting group and Aryl, $R^{21}$, $R^{22}$, and $R^{23}$ are as defined defined above.

In another embodiment, $R^{23}$ is aryl or heteroaryl.

In another embodiment the invention provides a method of treating a subject suffering from a condition for which inhibition of Met receptor tyrosine kinase is indicated, comprising administering to the subject a therapeutically effective amount of any of the inventive compounds described herein.

The chemical formulae referred to herein may exhibit the phenomena of tautomerism and structural isomerism. This invention encompasses any tautomeric or structural isomeric form and mixtures thereof which possess the ability to modulate RTK, CTK and/or STK activity and is not limited to any one tautomeric or structural isomeric form.

In addition, the formulae referred to herein may also exhibit stereoisomerism, in which such compounds may adopt an R or S configuration at chiral centers. Thus, this invention also encompasses any stereoisomeric form, their corresponding enantiomers (d- and l- or (+) and (−) isomers) and diastereomers thereof, and mixtures thereof, which possess the ability to modulate RTK, CTK and/or STK activity and is not limited to any one stereoisomeric form.

In particular embodiments, the compound is chosen from the compounds in Tables 1-8.

Another embodiment of the invention relates to a method of treating a subject suffering from a condition for which inhibition of protein kinase is indicated, comprising administering to the subject a therapeutically effective amount of any of the inventive compounds described herein.

Another aspect of this invention relates to a method for the modulation of the catalytic activity of a PK by contacting a PK with a compound of this invention or a physiologically acceptable salt thereof.

A further aspect of this invention is that the modulation of the catalytic activity of PKs using a compound of this invention may be carried out in vitro or in vivo.

A still further aspect of this invention is that the protein kinase whose catalytic activity is being modulated by a compound of this invention is selected from the group consisting of receptor protein tyrosine kinases, cellular tyrosine kinases and serine-threonine kinases.

It is an aspect of this invention that the receptor tyrosine protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R, FGFR-4R, MET, DDR-1 and DDR-2.

In addition, it is an aspect of this invention that the cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk.

Another aspect of this invention is that the serine-threonine protein kinase whose catalytic activity is modulated by a compound of this invention is selected from the group consisting of CDK2, Raf, NEK and BUB1.

Another aspect of this invention relates to a method for treating or preventing a protein kinase related disorder in an organism comprising administering a therapeutically effective amount of any of the inventive compounds described herein to an organism, such as a mammal, particularly a human.

It is an aspect of this invention that the above-referenced protein kinase related disorder is selected from the group consisting of a receptor protein tyrosine kinase related disorder, a cellular tyrosine kinase disorder and a serine-threonine kinase related disorder.

In yet another aspect of this invention, the above referenced protein kinase related disorder is selected from the group consisting of a Met related disorder, an AUR2 related disorder, a ZC1 related disorder, a PDGFR related disorder, an IGFR related disorder and a flk related disorder.

The above referenced protein kinase related disorders include by way of example and not limitation, cancers such as lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lynphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem glioma or pituitary adenomas), cancers of the blood such as acute myeloid leukemia, chronic mueloid leukemia, etc, Barrett's esophagus (pre-malignant syndrome), neoplastic cutaneous disease, psoriasis, mycoses fungoides and benign prostatic hypertrophy, diabetes related diseases such as diabetic retinopathy, retinal ischemia and retinal neovascularization, hepatic cirrhosis, cardiovascular disease such as atherosclerosis, immunological disease such as autoimmune disease and renal disease. Preferably, the disease is cancer such as acute myeloid leukemia and colorectal cancer.

The above referenced protein kinase related disorder also includes disorders selected from the group consisting of diabetes, a hyper-proliferation disorder, hyperproliferative disorders of the kidney, von Hippel-Lindau disease, restenosis, fibrosis, psoriasis, osteoarthritis, rheumatoid arthritis, an inflammatory disorder and angiogenesis in yet another aspect of this invention.

Additional disorders which may be treated or prevented using the compounds of this invention are immunological disorders such as autoimmune diseases (e.g., AIDS, lupus, etc.) and cardiovascular disorders such as atherosclerosis.

It is an aspect of this invention that the protein kinase related disorder being treated or prevented by administration of a compound of this invention is a met kinase related disorder.

The organism in which the protein kinase related disorder is being treated or prevented is a human being in yet another aspect of this invention.

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteroids (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole.

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

The above method can be carried out in combination with a chemotherapeutic agent selected from the group consisting of mitotic inhibitors, alkylating agents, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include VIOXX™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1

(filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxy-carbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R)1-[4-(2-chloro-4-fluoro-benzyloxy)-benzenesulfonyl]-3-hydroxy-3-methyl-pip eridine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R)3-[4-(4-chloro-phenoxy)-benzenesulfonylamino]-tetrahydro-pyran-3-carboxylic acid hydroxyamide; (2R,3R)1-[4-(4-fluoro-2-methyl-benzyloxy)-benzenesulfonyl]-3-hydroxy-3-methyl-pip eridine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1] octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R)3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-11 inhibitors and other MMP inhibitors, can also be used in the present invention.

A compound of the invention can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTINΘ (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention.

VEGF inhibitors, for example 3-(2,4-Dimethylpyrrol-5-yl)methylene-2-indolinone, 5-(5-Fluoro-2-oxo-1,2-dihydro-indol-3-ylidenemethyl)-2,4-dimethyl-1H-pyrrole-3-carboxylic acid (2-diethylamino-ethyl)-amide, 3-[2,4-dimethyl-5-oxo-1,2-dihydroindole-3-ylidenemethyl)-1H-pyrrol-3-yl-propionic acid (Sugen Inc. of South San Francisco, Calif., USA), can also be combined with an inventive compound described herein. VEGF inhibitors are described in, for example in WO 99/24440, PCT International Application PCT/IB99/00797 (filed May 3, 1999), in WO 95/21613, WO 99/61422 (published Dec. 2, 1999), U.S. Pat. No. 5,834,504 (issued Nov. 10, 1998), WO 01/60814, WO 02/04407, WO 98/50356, U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of TheWoodlands, Tex., USA) and 2B-1 (Chiron), can furthermore be combined with a compound any of the inventive compounds described herein, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the inventive compounds described herein.

The inventive compounds described herein can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The above method can be also be carried out in combination with radiation therapy, wherein the amount of the inventive compound in combination with the radiation therapy is effective in treating the above diseases. Techniques for administering radiation therapy are known in the art, and these techniques can be used in the combination therapy described herein. The administration of the compound of the invention in this combination therapy can be determined as described herein.

Another aspect of the invention is directed to the use of any of the inventive compounds described herein in the preparation of a medicament, which is useful in the treatment of a disease mediated by abnormal Met kinase activity, such as cancer.

DETAILED DESCRIPTION

Definitions

The terms pyridine and pyrazine refer to the following structures respectively:

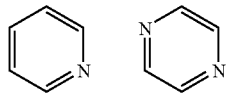

"Pharmaceutically acceptable salt" or "pharmaceutically acceptable salt thereof" refer to those salts which retain the biological effectiveness and properties of the free bases and which are obtained by reaction with inorganic or organic acids, such as hydrochloric acid, hydrobromic acid, hydroiodic acid, sulfuric acid, nitric acid, phosphoric acid, methanesulfonic acid, ethanesulfonic acid, p-toluenesulfonic acid, salicylic acid, acetic acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, and the like.

A "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

Compounds that have the same molecular formula but differ in the nature or sequence of bonding of their atoms or arrangements of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The inventive compounds herein may exhibit the phenomena of tautomerism and structural isomerism. This invention encompasses any tautomeric or structural isomeric form and mixtures thereof which possess the ability to modulate RTK, CTK and/or STK activity and is not limited to any one tautomeric or structural isomeric form.

It is contemplated that an inventive compound as described herein would be metabolized by enzymes in the body of the organism such as human being to generate a metabolite that can modulate the activity of the protein kinases. Such metabolites are within the scope of the present invention.

As used herein, "PK" refers to receptor protein tyrosine kinase (RTKs), non-receptor or "cellular" tyrosine kinase (CTKs) and serine-threonine kinases (STKs).

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

The term "catalytic activity" as used herein refers to the rate of phosphorylation of tyrosine under the influence, direct or indirect, of RTKs and/or CTKs or the phosphorylation of serine and threonine under the influence, direct or indirect, of STKs.

The term "contacting" as used herein refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished in vitro, i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium. The skilled artisan will understand that, for example, an isolated PK may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK, expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

As used herein, the terms "prevent", "preventing" and "prevention" refer to a method for barring an organism from acquiring a PK related disorder in the first place.

As used herein, the terms "treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal. In a preferred aspect, the organism is a mammal. In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

By "monitoring" is meant observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. For example, the catalytic activity of a PK may be observed by determining the rate or amount of phosphorylation of a target molecule.

Reference to compounds of the invention includes pharmaceutically acceptable salts, solvates and hydrates thereof.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

As used herein, "administer" or "administration" refers to the delivery of a compound or salt of the present invention or of a pharmaceutical composition containing a compound or salt of this invention to an organism for the purpose of prevention or treatment of a PK-related disorder.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; and (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The inventive compounds described herein may also act as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug.

Indications

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction, is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, *Neuron*, 9:303-391 (1992).

It has been shown that tyrosine phosphorylation sites on growth factor receptors function as high-affinity binding sites for SH2 (src homology) domains of signaling molecules. Fantl et al., *Cell*, 69:413-423 (1992), Songyang et al., *Mol. Cell. Biol.*, 14:2777-2785 (1994), Songyang et al., *Cell*, 72:767-778 (1993), and Koch et al., *Science*, 252:668-678 (1991). Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., *Cell*, 72:767-778 (1993). The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., *Cell*, 72:767-778 (1993). These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK-signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of the invention, in particular, the compounds generated in vivo from the compounds of the invention, inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the compounds of this invention binds in the general space normally occupied by the adenine ring of ATP.

In another aspect, the protein kinase, the catalytic activity of which is modulated by contact with a compound of this invention, is a protein tyrosine kinase, more particularly, a receptor protein tyrosine kinase. Among the receptor protein tyrosine kinases whose catalytic activity can be modulated with a compound of this invention, or salt thereof, are, without limitation, selected from the group consisting of Met, Flk, FGFR, PDGFR, HER, IR, IGF, IRR, CSFIR, C-Kit, C-fms, flt. In a preferred aspect, the receptor protein tyrosine kinase whose catalytic activity can be modulated with a compound of this invention, or salt thereof.

The protein tyrosine kinase whose catalytic activity is modulated by contact with a compound of this invention, or a salt thereof, can also be a non-receptor or cellular protein tyrosine kinase (CTK). Thus, the catalytic activity of CTKs such as, without limitation, Src, Frk, Btk, Csk, Abl, ZAP70, Fes, Fps, Fak, Jak, Ack, Yes, Fyn, Lyn, Lck, Blk, Hck, Fgr, Aur2 and Yrk may be modulated by contact with a compound or salt of this invention.

Still another group of PKs which may have their catalytic activity modulated by contact with a compound of this invention are the serine-threonine protein kinases such as, without limitation, CDK2, Raf, NEK (including NEK 4a, NEK 4b, NEK 5 and NEK 6) and BUB1.

In another aspect, this invention relates to a method for treating or preventing a PK related disorder by administering a therapeutically effective amount of a compound of this invention, or a salt thereof, to an organism.

It is also an aspect of this invention that a pharmaceutical composition containing a compound of this invention, or a salt thereof, is administered to an organism for the purpose of preventing or treating a PK related disorder.

This invention is therefore directed to compounds that modulate PK signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of solid tumors, including but not limited to carcinomas, sarcomas including Kaposi's sarcoma, erythroblastoma, glioblastoma, meningioma, astrocytoma, melanoma and myoblastoma. cancers such as lung cancer, NSCLC (non small celling cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lynphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem glioma or pituitary adenomas), cancers of the blood such as acute myeloid leukemia, chronic mueloid leukemia, etc, Barrett's esophagus (pre-malignant syndrome), neoplastic cutaneous disease, psoriasis, mycoses fungoides and benign prostatic hypertrophy, diabetes related diseases such as diabetic retinopathy, retinal ischemia and retinal neovascularization, hepatic cirrhosis, cardiovascular disease such as atherosclerosis, immunological disease such as autoimmune disease and renal disease. Preferably, the disease is cancer such as acute myeloid leukemia and colorectal cancer.

Further examples, without limitation, of the types of disorders related to inappropriate PK activity that the compounds described herein may be useful in preventing, treating and studying, are cell proliferative disorders, fibrotic disorders, metabolic disorders and infectious diseases.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, *J. Biological Chem.*, 267 (16):10931-10934 (1992). Uncontrolled vasculogenesis and/or angiogenesis has been associated with diseases such as diabetes as well as with malignant solid tumors that rely on vascularization for growth. Klagsburn & Soker, *Current Biology*, 3(10):699-702 (1993); Folkham, *J. Natl. Cancer Inst.*, 82:4-6 (1991); Weidner, et al., *New Engl. J. Med.*, 324:1-5 (1991).

As presently understood, the role of VEGF in endothelial cell proliferation and migration during angiogenesis and vasculogenesis indicates an important role for the KDR/FLK-1 receptor in these processes. Diseases such as diabetes mellitus (Folkman, 198, in XIth Congress of Thrombosis and Haemostasis (Verstraeta, et al., eds.), pp. 583-596, Leuven University Press, Leuven) and arthritis, as well as malignant tumor growth may result from uncontrolled angiogenesis. See e.g., Folkman, *N. Engl. J. Med.*, 285:1182-1186 (1971). The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., *DN&P*, 7(6):334-339 (1994). More particularly, the KDR/FLK-1 receptors highly specific role in neovascularization make it a choice target for therapeutic approaches to the treatment of cancer and other diseases which involve the uncontrolled formation of blood vessels.

Thus, one aspect of the present invention relates to compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Thus, in one aspect, this invention is directed to compounds that regulate, modulate and/or inhibit vasculogenesis and/or angiogenesis by affecting the enzymatic activity of the KDR/FLK-1 receptor and interfering with the signal transduced by KDR/FLK-1. In another aspect, the present invention is directed to compounds which regulate, modulate and/or inhibit the KDR/FLK-1 mediated signal transduction pathway as a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggest the administration of compounds which inhibit the KDR/Flk-1 mediated signal transduction pathway may also be used in the treatment of hemangioma, restenois and diabetic retinopathy.

A further aspect of this invention relates to the inhibition of vasculogenesis and angiogenesis by other receptor-mediated pathways, including the pathway comprising the flt-I receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signaling molecules that facilitate the appropriate cellular response, e.g., cell division and metabolic effects to the extracellular microenvironment. See, Schlessinger and Ullrich, *Neuron*, 9:1-20 (1992).

The close homology of the intracellular regions of KDR/FLK-1 with that of the PDGF-β receptor (50.3% homology) and/or the related flt-I receptor indicates the induction of overlapping signal transduction pathways. For example, for the PDGF-β receptor, members of the src family (Twamley et al., *Proc. Natl. Acad. Sci. USA*, 90:7696-7700 (1993)), phosphatidylinositol-3'-kinase (Hu et al., *Mol. Cell. Biol.*, 12:981-990 (1992), phospholipase cγ (Kashishian & Cooper, *Mol. Cell. Biol.*, 4:49-51 (1993)), ras-GTPase-activating protein, (Kashishian et al., *EMBO J.*, 11:1373-1382 (1992), PTP-ID/syp (Kazlauskas et al., *Proc. Natl. Acad. Sci. USA*, 90:6939-6943 (1993)), Grb2 (Arvidsson et al., *Mol Cell. Biol.*, 14:6715-6726 (1994)), and the adapter molecules Shc and Nck (Nishimura et al., *Mol Cell. Biol.*, 13:6889-6896 (1993)), have been shown to bind to regions involving different autophosphorylation sites. See generally, Claesson-Welsh, *Prog. Growth Factor Res.*, 5:37-54 (1994). Thus, it is likely that signal transduction pathways activated by KDR/FLK-1 include the ras pathway (Rozakis et al., *Nature*, 360:689-692 (1992)), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., *Kidney International,* 43:47S-54S (1993).

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., *Br. J. Cancer,* 63:227-233 (1991), Torp et al., *APMIS,* 100:713-719 (1992)) HER2/neu (Slamon et al., *Science,* 244:707-712 (1989)) and PDGF-R (Kumabe et al., *Oncogene,* 7:627-633 (1992)) are over-expressed in many tumors and/or persistently activated by autocrine loops. In fact, in the most common and severe cancers these receptor over-expressions (Akbasak and Suner-Akbasak et al., *J. Neurol. Sci.,* 111:119-133 (1992), Dickson et al., *Cancer Treatment Res.,* 61:249-273 (1992), Korc et al., *J. Clin. Invest.,* 90:1352-1360 (1992)) and autocrine loops (Lee and Donoghue, *J. Cell. Biol.,* 118:1057-1070 (1992), Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., *J. Clin. Invest.,* 84:1418-1423 (1989)) and small lung tumor cells (Macauley et al., *Cancer Res.,* 50:2511-2517 (1990)). In addition, IGF-1, while integrally involved in the normal growth and differentiation of the nervous system, also appears to be an autocrine stimulator of human gliomas. Sandberg-Nordqvist et al., *Cancer Res.,* 53:2475-2478 (1993). The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, *Eukaryotic Gene Expression,* 1:301-326 (1991). In a series of recent publications, Baserga suggests that IGF-IR plays a central role in the mechanism of transformation and, as such, could be a preferred target for therapeutic interventions for a broad spectrum of human malignancies. Baserga, *Cancer Res.,* 55:249-252 (1995), Baserga, *Cell,* 79:927-930 (1994), Coppola et al., *Mol. Cell. Biol.,* 14:4588-4595 (1994).

STKs have been implicated in many types of cancer including, notably, breast cancer (Cance, et al., *Int. J. Cancer,* 54:571-77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., *DN&P,* 7:334-339 (1994).

As noted previously, not only RTKs but CTKs including, but not limited to, src, abl, fps, yes, fyn, lyn, lck, blk, hck, fgr, AUR1, AUR2 and yrk (reviewed by Bolen et al., *FASEB J.,* 6:3403-3409 (1992)) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v-src}$) in chicken. Moreover, its cellular homolog, the proto-oncogene $pp60^{c-src}$ transmits oncogenic signals of many receptors. Over-expression of EGFR or HER2/neu in tumors leads to the constitutive activation of $pp60^{c\,src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents.

In yet another aspect, the compounds of the instant invention can also be used as anti-infective agents.

Finally, both RTKs and CTKs are currently suspected as being involved in hyperimmune disorders.

Pharmaceutical Compositions and Use

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable-liquids, such as fatty oils, liquid paraffin, liquid polyethylene glycols, cremophor, capmul, medium or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, malate, carbonate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%. At present, the therapeutically effective amounts of the inventive compounds described herein may range from approximately 25 $mg/m^2$ to 1000-$mg/m^2$ per day. Even more preferably 25 $mg/m^2$ to 150 $mg/m^2$.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

EXAMPLES

The following examples are given to illustrate the present invention. It should be understood, however, that the invention is not to be limited to the specific conditions or details described in these examples.

The numbering in the examples corresponds to the numbering in the Tables herein. Reaction schemes and example numbers beginning with a letter (I) relate to pyridine compounds, whereas those beginning with a letter (II) relate to pyrazine compounds. Example numbers beginning with L are library syntheses. Example numbers having a letter notation (a, b, c, etc.) illustrate the synthesis of reagents subsequently used in the synthesis of the inventive compounds, which have a number notation (1, 2, 3, etc.). Reagents can be synthesized as shown herein, or are available from commercial sources (e.g., Aldrich, Milwaukee, Wis.; Acros, Morris Plains, N.J.; Biosynth International, Naperville, Ill.; Frontier Scientific, Logan, Utah; TCI America, Portland, Oreg.; Combi-Blocks, San Diego, Calif.; Matrix Scientific, Columbia, S.C.; Acros, Morris Plains, N.J.; Alfa Aesar, Ward Hill, Mass.; Apollo Scientific, UK; etc.) or can be synthesized by procedures known in the art. When a general or exemplary synthetic procedure is referred to, one skilled in the art can readily determine the appropriate reagents, if not indicated, extrapolating from the general or exemplary procedures.

In the general procedures 1-43 described herein, although some of the procedures are generalized and exemplary, past tense is used to indicate that these general procedures were the procedures used to synthesize the compounds. Some of the general procedures are given as examples for preparing specific compounds. One skilled in the art can readily adapt such procedures to the synthesis of other compounds. It should be understood that R groups shown in the general procedures are meant to be generic and non-limiting, and do not correspond to definitions of R groups elsewhere in this document. Each such R group represents one or multiple chemical moieties that can be the same or different from other chemical moieties also represented by the same R symbol. Moreover, representation of an unsubstituted position in structures shown or referred to in the general procedures is for convenience and does not preclude substitution as described elsewhere herein. For specific groups that can be present, either as R groups in the general procedures or as optional substitutents not shown, refer to the descriptions in the remainder of this document, including the claims, summary and detailed description. It should be further understood that compound numbers shown in the general schemes and general procedures in the Examples are for convenient reference only, and do not correspond to the numbers used elsewhere throughout this document. For example, the nitropyridine compound (1) in general scheme I is different from the compound of formula 1

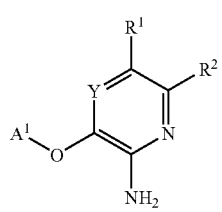

1 described herein.

General Scheme I for the Synthesis of 5-Aryl-3-(Substituted-Benzyloxy)-Pyridin-2-ylamine (6):

General Scheme II for the Synthesis of 5-Aryl-3-(Substituted-Benzyloxy)-Pyrazin-2-ylamine

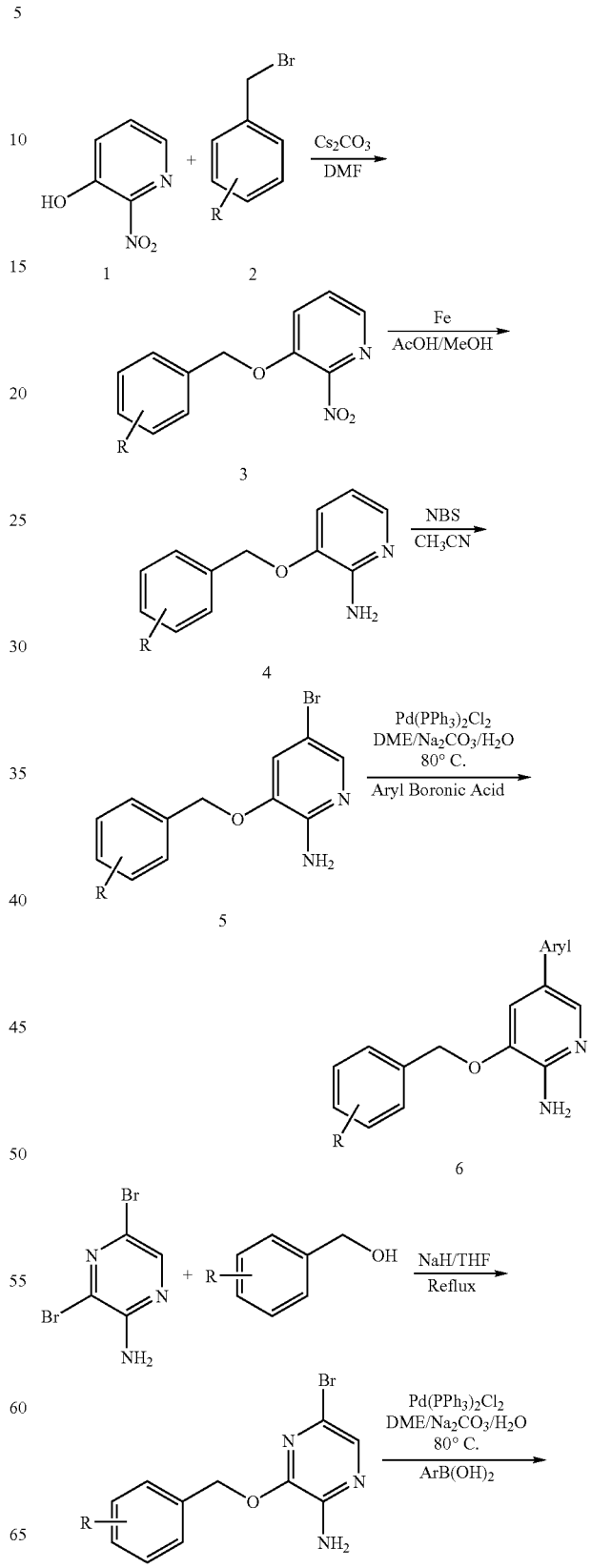

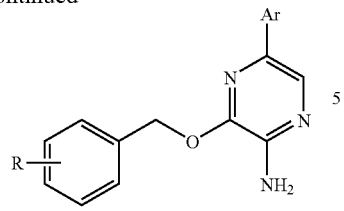

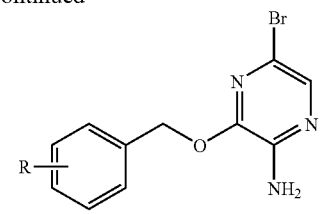

General Procedure 1 for the Synthesis of 5-Bromo-3-(Substituted-Benzyloxy)-Pyridin-2-ylamine (5):

1. Preparation of 3-(substituted-benzyloxy)-2-nitro-pyridine (3): To a stirred solution of $Cs_2CO_3$ (1.0 molar equivalent)) in DMF (0.2 M) under a $N_2$ atmosphere containing 3-hydroxy-4-nitro-pyridine (Aldrich, 1.0 molar equivalent) was added substituted benzyl bromide (1.0 molar equivalent). The mixture was stirred for 6 h at ambient temperature. The reaction was then diluted with EtOAc, and partitioned with $H_2O$. The aqueous layer was extracted with EtOAc twice. The organic layers were then combined, washed with $H_2O$ and brine, dried over $Na_2SO_4$, filtered, and concentrated to dryness under vacuum to yield 3-(substituted-benzyloxy)-2-nitro-pyridine (3) as a solid.

2. Preparation of 3-(substituted-benzyloxy)-pyridin-2-ylamine (4): To a stirred mixture of AcOH and EtOH (1.3:1) was suspended 3-(substituted-benzyloxy-2-nitro-pyridine (1.0 molar equivalent, 1 M) and iron chips (1.0 molar equivalent). The reaction was heated slowly to reflux and allowed to stir for 1 hr. The reaction was cooled to room temperature then filtered through a pad of celite. The resulting filtrate was neutralized with conc. $NH_4OH$, and then extracted with EtOAc for three times. The combined organic extracts were washed with saturated $NaHCO_3$, $H_2O$, and brine, dried over $Na_2SO_4$, filtered and concentrated to dryness under vacuum to yield 3-(substituted-benzyloxy)-pyridin-2-ylamine (4) as a solid.

3. Preparation of 5-bromo-3-(substituted benzyloxy)-pyridin-2-ylamine (5): A stirring solution of 3-(substituted-benzyloxy)-pyridin-2-ylamine (4) (1.0 molar equivalent) in acetonitrile was cooled to 0° C. using an ice bath. To this solution was added N-bromosuccinimide (Aldrich, 1.0 molar equivalent) portionwise. The reaction was stirred at 0° C. for 15 min. The reaction was concentrated to dryness under vacuum. The resulting dark oil was dissolved in EtOAc and partitioned with $H_2O$. The organic was then washed with saturated $NaHCO_3$ twice and brine once. Activated charcoal was added to the organic layer and warmed to reflux. The solution was then cooled to room temperature and filtered through a pad of celite. The organic was then concentrated to dryness under vacuum to one third the original volume. The solids were then filtered off to yield 5-bromo-3-(substituted benzyloxy)-pyridin-2-ylamine (5) as a solid.

General Procedure 2 for the Synthesis of 5-Bromo-3-(Substituted-Benzyloxy)-Pyrazin-2-ylamine.

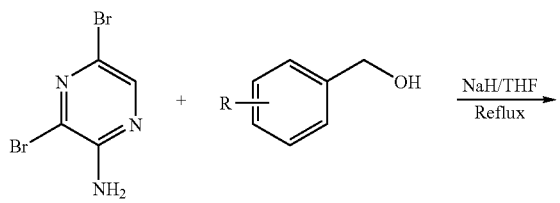

To an ice cooled solution of substituted benzyl alcohol (1.0 molar equivalent) and anhydrous tetrahydrofuran (0.14 M) was added sodium hydride (1.0 molar equivalent) slowly under nitrogen atmosphere. After stirring for 30 minutes, 3,5-dibromopyrazin-2-ylamine (1.0 molar equivalent) in tetrahydrofuran (0.56 M) was added via an addition funnel at a fast dropwise rate. Once the addition was complete the ice bath was removed and the reaction was refluxed under nitrogen and monitored by reversed phase HPLC. After 18 hr HPLC showed that the majority of the starting 3,5-dibromopyrazin-2-ylamine had been consumed and the reaction was allowed to cool to room temperature. The reaction mixture was concentrated, diluted with ethyl-acetate, and washed with brine. The organic layer was dried over anhydrous magnesium sulfate and concentrated in vacuum. The crude product was purified using a silica gel eluting with 1:1 ethyl acetate/dichloromethane to yield the 5-bromo-3-(substituted-benzyloxy)-pyrazin-2-ylamine as a white solid in 60-90% yield.

General Procedure 3 for the Synthesis of 5-Aryl-3-(Substituted-Benzyloxy)-Pyridin-2-ylamine and 5-Aryl-3-(Substituted-Benzyloxy)-Pyrazin-2-ylamine.

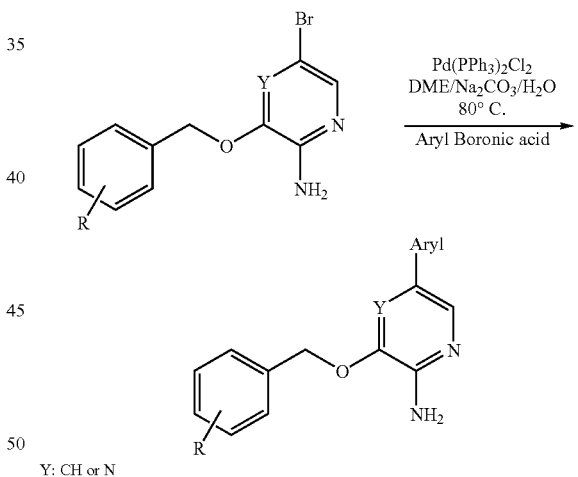

Y: CH or N

A mixture of 5-bromo-3-(substituted-benzyloxy)-pyridin-2-ylamine or 5-bromo-3-(substituted-benzyloxy)-pyrazin-2-ylamine (1 molar equivalent), aryl boronic acid or ester (1.2 molar equivalent), bis(triphenylphosphine) palladium II chloride (0.03 molar equivalent) and sodium carbonate (3.0 molar equivalent.) in ethylene glycol dimethyl ether and water (10:0.5, 0.03 M) was de-gassed and charged with nitrogen for three times, and then heated to reflux under nitrogen for overnight. The reaction was cooled to ambient temperature and diluted with ethyl acetate. The mixture was washed with water, brine, dried over $Na_2SO_4$, and purified on a silica gel column to afford 5-aryl-3-(substituted-benzyloxy)-pyridin-2-ylamine, or 5-aryl-3-(substituted-benzyloxy)-pyrazin-2-ylamine.

General Procedure 4 for Amidation Reaction of 6-amino-5-(substituted-benzyloxy)-pyridin-3-yl]-benzoic acid:

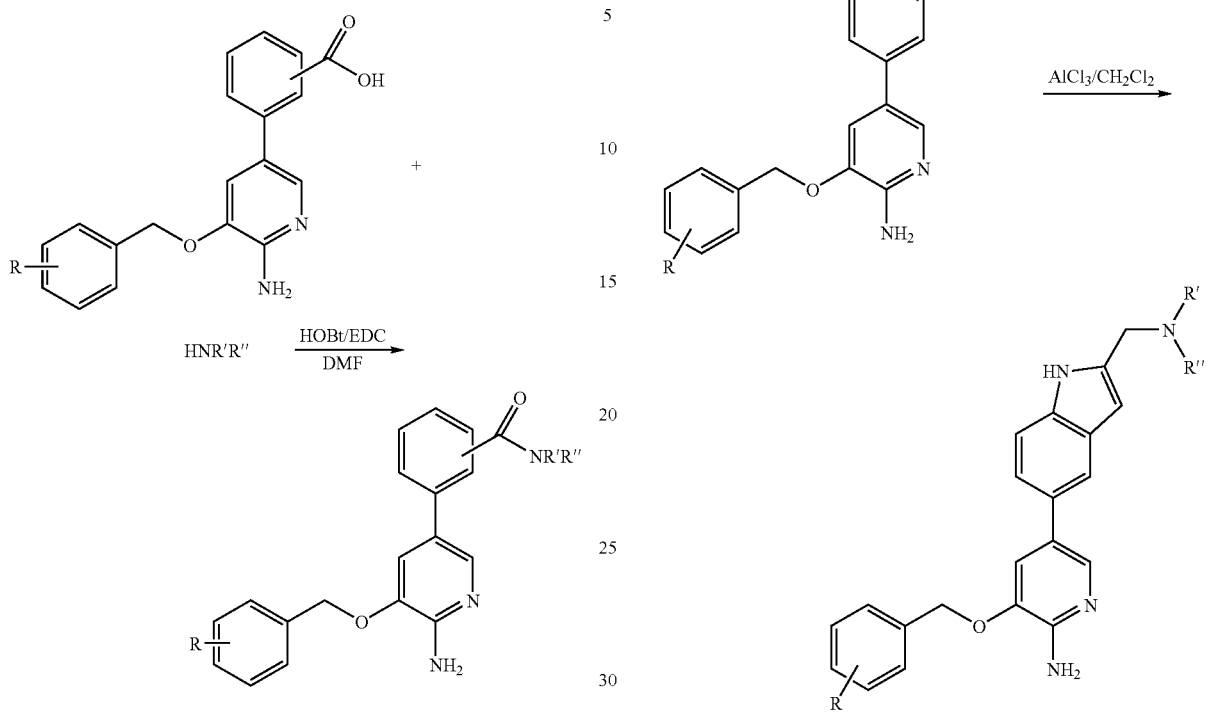

To a solution of 6-amino-5-(substituted-benzyloxy)-pyridin-3-yl]-benzoic acid (1 molar equivalent), 1-hydroxybenzotriazole hydrate (HOBT, 1.2 molar equivalent), and 1-(3-dimethylaminopropyl)-3-ethylcarbodiimide hydrochloride (EDC, 1.2 molar equivalent) in DMF (0.2 M) was added amine (1.2 molar equivalent). The reaction solution was stirred at room temperature for overnight, then diluted with EtOAc, and partitioned with $H_2O$. The organic was separated and the aqueous was extracted with EtOAc. The organic layers were combined, washed with saturated $NaHCO_3$, and concentrated to dryness under vacuum. The material was purified using column chromatography (silica gel, 99:1 to 95:5 $CH_2Cl_2$/MeOH). The fractions containing product were concentrated under vacuum to yield the amide product.

General procedure 5 for the preparation of 3-(substituted-benzyloxy)-5-(3-dialkylaminomethyl-1H-indol-5-yl)-pyridin-2-ylamine:

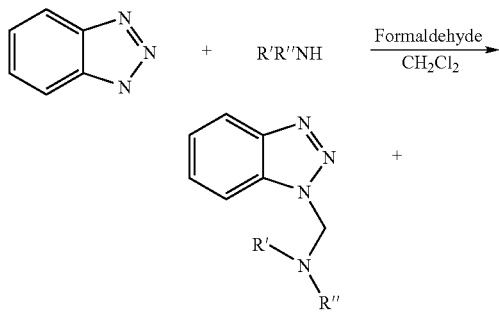

To a solution of benzotriazole (1.0 molar equivalent) in dichloromethane (0.2 M) was added amine (1.0 molar equilvalent). The reaction was stirred for 5 minutes at room temperature after which formaldehyde (37% by wt, 1.0 molar equivalent) was added and the reaction was capped and stirred at room temperature for 3 hr. Once TLC (10% ethyl acetate: dichloromethane) showed the consumption of starting benzotriaziole the reaction was dried with anhydrous magnesium sulfate (10 g), filtered and concentrated in vacuo. The crude product was purified with a silica gel column eluting with 1:1 ethyl acetate:dichloromethane to yield the desired product as a white solid.

To a solution of the aminomethylbenzotriazole intermediate (1.0 molar equivalent) in dichloromethane (0.43 M) was added aluminum chloride (2.0 molar equivalent), and then followed by 3-(2,6-Dichloro-benzyloxy)-5-(1H-indol-5-yl)-pyridine-2-ylamin (1.1 molar equivalent). The reaction was capped and heated with stirring to 40° C. for 3-4 hr. The reaction was then removed from the heat and allowed to cool to room temperature. The reaction mixture was diluted with sodium hydroxide (0.2 M) and chloroform, recapped and vigorously stirred at room temperature to dissolve the residue in the vial. The chloroform was extracted away from the aqueous, dried over anhydrous sodium sulfate and concentrated in vacuo. The crude product was purified with a silica gel column, first eluting with 1:1, ethyl acetate:dichloromethane, to elute the less polar impurities and then eluting the product with 90:9:1, chloroform:methanol:ammonium hydroxide. (Yields 10-67%.)

General Procedure 6 for the synthesis of 3-(Substituted-benzyloxy)-5-phenyl-pyridin-2-ylamine using example I-88:

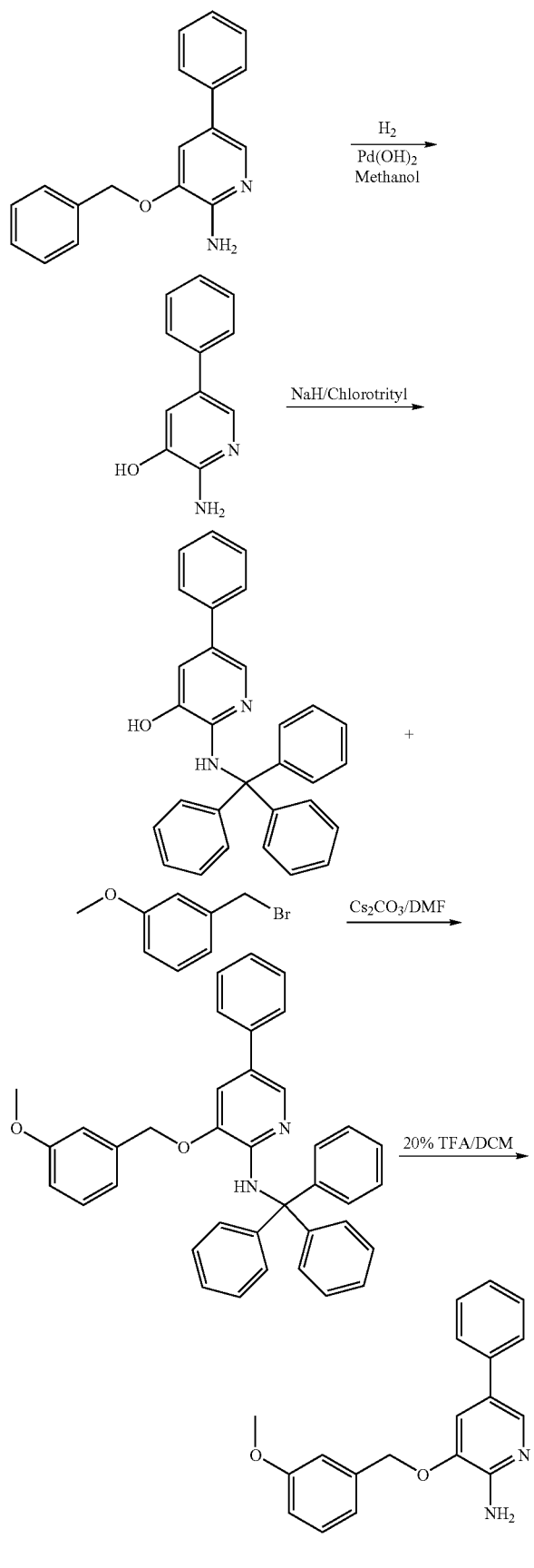

To a solution of 3-benzyloxy-5-phenyl-pyridin-2-ylamine (Example I-87, 3.27 g, 11.8 mmol) in methanol (30 mL) was added Pd(OH)$_2$ (2.5 g, 2.37 mmol). The mixture was degassed and charged with hydrogen three times, and then stirred under hydrogen balloon for 5 hr. The reaction was filtered through a celite pad, washed with methanol, and condensed. After high vacuum dry, 2-amino-5-phenyl-pyridin-3-ol was obtained (2.04 g, 93% yield). MS m/z 187 [M+1].

To a solution of 2-amino-5-phenyl-pyridin-3-ol (2.04 g, 10.95 mmol) in THF (anhydrous, 30 mL) was added NaH (1.31 g, 32.85 mmol) slowly. The mixture was stirred under nitrogen for 20 minutes, and then trityl chloride (3.66 g, 13.14 mmol) was added. The reaction was stirred at room temperature for over night under nitrogen. The solvent was evaporated, and the residue was dissolved in dichloromethane, washed with water, and dried over Na$_2$SO$_4$. After filtration and condensation, the crude product was purified on a silica gel column eluting with EtOAc-Hexane (1:10) to provide 5-phenyl-2-(trityl-amino)-pyridin-3-ol (1.09 g, 23% yield). MS m/z 427 [M+1].

To a solution of 5-phenyl-2-(trityl-amino)-pyridin-3-ol (100 mg, 0.24 mmol) in THF (3 mL) was added Cs$_2$CO$_3$ (79 mg, 0.24 mmol). The mixture was stirred at room temperature for 20 minutes, and then 3-methoxybenzylbromide (0.037 mL, 0.26 mmol) was added. The reaction was stirred at room temperature overnight, diluted with dichloromethane (5 mL), and filtered to remove the salts. The solvents were evaporated, and the residue was dissolved in 10% trifluoroacetic acid in dichloromethane (2 mL). The reaction was stirred for 2 hr, and evaporated. The residue was dissolved in dichloromethane, washed by sat. NaHCO$_3$, and dried over Na$_2$SO$_4$. After filtration and concentration, the crude product was purified on a silica gel column eluting with methanol-dichloromethane (from 3% to 15% gradient) to provide 3-(3-methoxy-benzyloxy)-5-phenyl-pyridin-2-ylamine as a white solid (43.5 mg, 60% yield).

General Procedure 7 for the Synthesis of 3-(Substituted-benzyloxy)-5-Aryl-pyridin-2-ylamine using Example I-106:

-continued

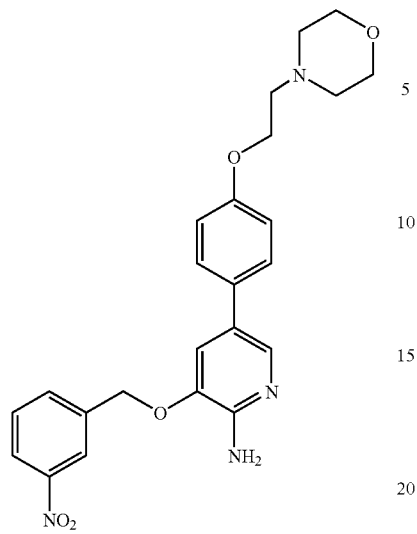

To a solution of 2-amino-5-[4-(2-morpholin-4-yl-ethoxy)-phenyl]-pyridin-3-ol (prepared according to the procedures for 2-amino-5-phenyl-pyridin-3-ol in Example I-88) (45.5 mg, 0.14 mmol) in DMF (3 mL) at 0° C. was added NaH (60% in oil) (5.6 mg, 0.14 mmol) and the mixture was stirred at 0° C. for 20 min. Then 1-Bromomethyl-3-nitro-benzene was added and the mixture was stirred at 0° C. for 1 hr and at room temperature for 2 hr. Cold 1 N aqueous HCl (0.1 mL) was added and the solvent was removed under reduced pressure. The residue was purified with silica gel chromatography (CH$_2$Cl$_2$:MeOH:NH$_4$OH 100:3:0.3) to give 5-[4-(2-morpholin-4-yl-ethoxy)-phenyl]-3-(3-nitro-benzyloxy)-pyridin-2-ylamine as yellow solid (44 mg, 68%).

General Procedure 8 for the Synthesis of {4-[6-Amino-5-(substituted-benzyloxy)-pyridin-3-yl]-phenyl}-[(2R)-2-pyrrolidin-1-ylmethyl-pyrrolidin-1-yl]-methanone using Example I-111:

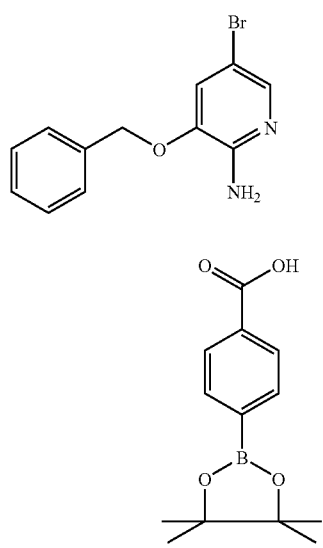

-continued

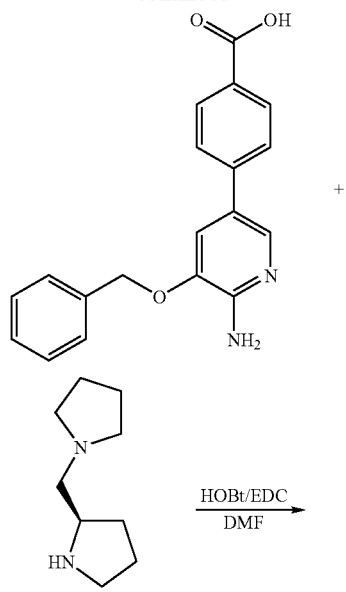

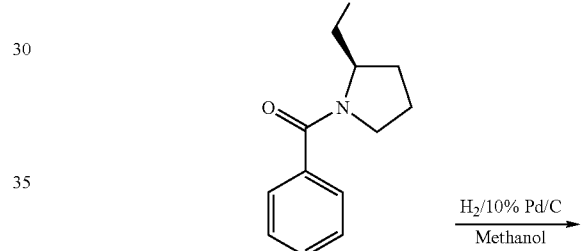

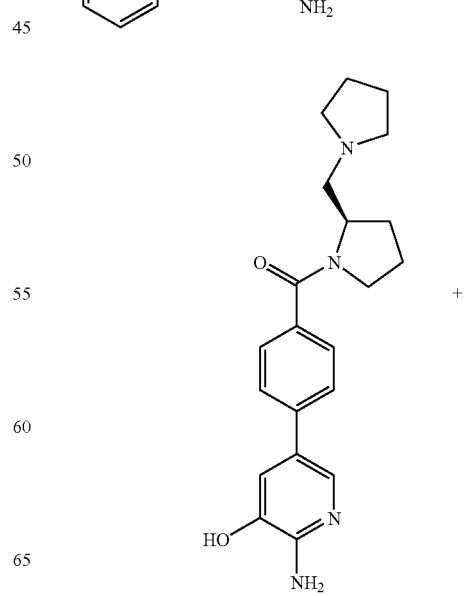

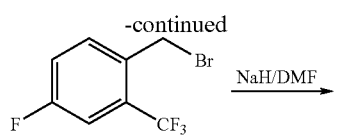

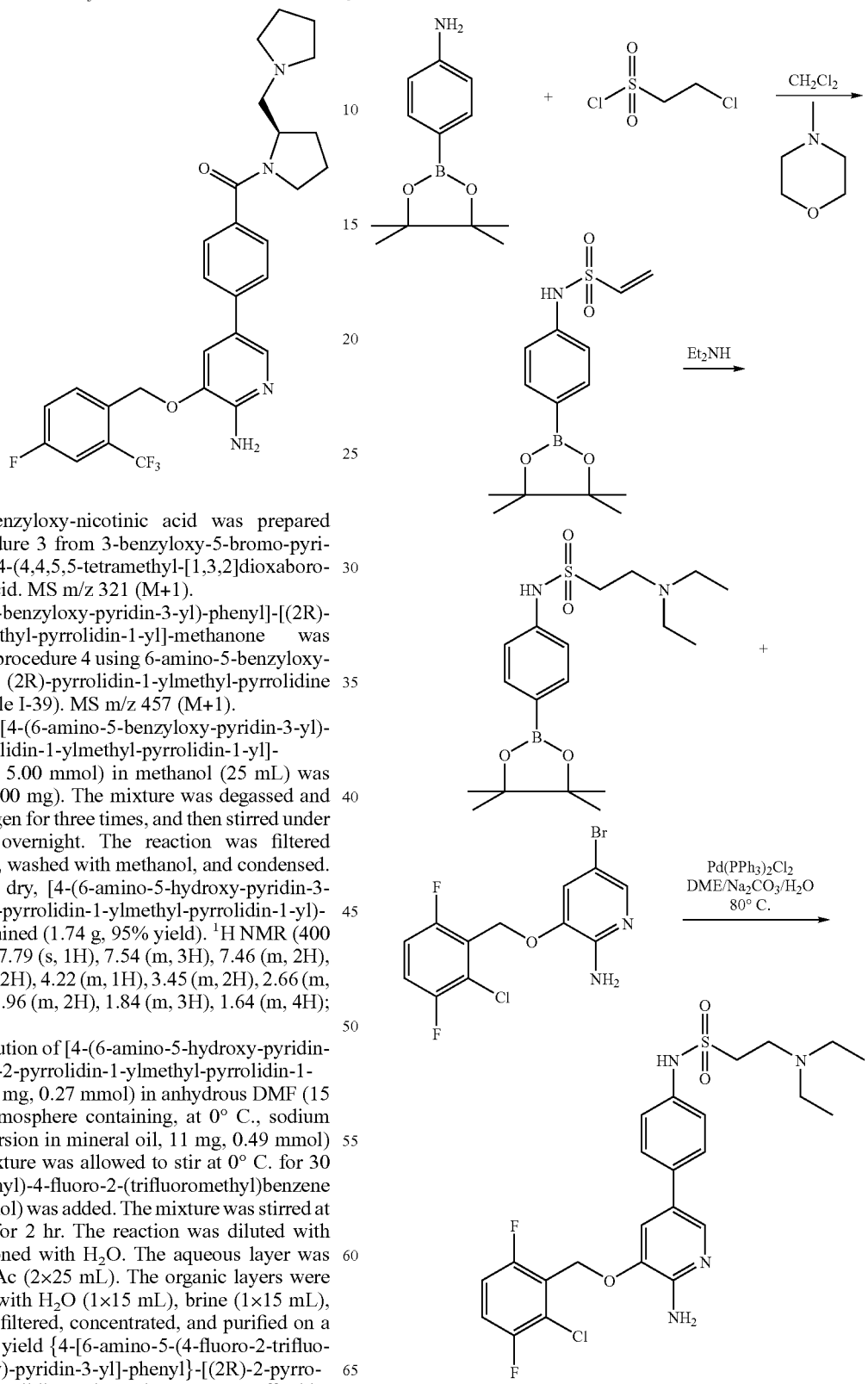

1. 6-Amino-5-benzyloxy-nicotinic acid was prepared according to procedure 3 from 3-benzyloxy-5-bromo-pyridin-2-ylamine and 4-(4,4,5,5-tetramethyl-[1,3,2]dioxaborolan-2-yl)-benzoic acid. MS m/z 321 (M+1).

2. [4-(6-amino-5-benzyloxy-pyridin-3-yl)-phenyl]-[(2R)-2-pyrrolidin-1-ylmethyl-pyrrolidin-1-yl]-methanone was prepared following procedure 4 using 6-amino-5-benzyloxy-nicotinic acid and (2R)-pyrrolidin-1-ylmethyl-pyrrolidine (prepared in Example I-39). MS m/z 457 (M+1).

3. To a solution of [4-(6-amino-5-benzyloxy-pyridin-3-yl)-phenyl]-[(2R)-pyrrolidin-1-ylmethyl-pyrrolidin-1-yl]-methanone (2.28 g, 5.00 mmol) in methanol (25 mL) was added 10% Pd/C (100 mg). The mixture was degassed and charged with hydrogen for three times, and then stirred under hydrogen balloon overnight. The reaction was filtered through a celite pad, washed with methanol, and condensed. After high vacuum dry, [4-(6-amino-5-hydroxy-pyridin-3-yl)-phenyl]-[(2R)-2-pyrrolidin-1-ylmethyl-pyrrolidin-1-yl]-methanone was obtained (1.74 g, 95% yield). $^1$H NMR (400 MHz, DMSO-$d_6$) δ 7.79 (s, 1H), 7.54 (m, 3H), 7.46 (m, 2H), 7.14 (s, 1H), 5.68 (s, 2H), 4.22 (m, 1H), 3.45 (m, 2H), 2.66 (m, 1H), 2.52 (m, 4H), 1.96 (m, 2H), 1.84 (m, 3H), 1.64 (m, 4H); MS m/z 367 (M+1).

4. To a stirred solution of [4-(6-amino-5-hydroxy-pyridin-3-yl)-phenyl]-[(2R)-2-pyrrolidin-1-ylmethyl-pyrrolidin-1-yl]-methanone (100 mg, 0.27 mmol) in anhydrous DMF (15 mL) under a $N_2$ atmosphere containing, at 0° C., sodium hydride (60% dispersion in mineral oil, 11 mg, 0.49 mmol) was added. The mixture was allowed to stir at 0° C. for 30 min. 1-(Bromomethyl)-4-fluoro-2-(trifluoromethyl)benzene (0.046 mL, 0.27 mmol) was added. The mixture was stirred at room temperature for 2 hr. The reaction was diluted with EtOAc, and partitioned with $H_2O$. The aqueous layer was extracted with EtOAc (2×25 mL). The organic layers were combined, washed with $H_2O$ (1×15 mL), brine (1×15 mL), dried over $MgSO_4$, filtered, concentrated, and purified on a silica gel column to yield {4-[6-amino-5-(4-fluoro-2-trifluoromethyl-benzyloxy)-pyridin-3-yl]-phenyl}-[(2R)-2-pyrrolidin-1-ylmethyl-pyrrolidin-1-yl]-methanone as off-white crystals.

General Procedure 9 for the Synthesis 2-Dialkylaminoethanesulfonic acid [6-amino-5-(substituted-benzyloxy)-pyridin-3-yl]-phenyl-amide using Example I-243.

1. To a solution of 4-(4,4,5,5-Tetramethyl-[1,3,2]dioxaborolan-2-yl)-phenylamine (5 g, 22.8 mmol) in dichloromethane (120 mL) was added N-methyl morpholine (7.5 mL, 68.4 mmol). This mixture was cooled to 0° C. under nitrogen atmosphere. 2-Chloroethanesulfonyl chloride (2.5 mL, 23.9 mmol) in dichloromethane (60 mL) was then added drop wise with stirring. Once the addition was complete the flask was stirred at 0° C. for 1 hr and then at room temperature while monitoring by TLC (1:1 ethyl acetate:hexanes) and staining with ninhydrin. After 4 h stirring some starting boronic ester still remained and an additional 0.2 equivalents (0.5 mL) of 2-chloroethanesulfonyl chloride in dichloromethane (25 mL) was added drop wise at room temperature. After 1 hr the boronic ester had been consumed as shown by TLC and the total reaction volume was reduced by one-half via rotary evaporation. The contents were diluted with ethyl acetate (200 mL), washed with 50% brine (2×100 mL), dried over anhydrous sodium sulfate and concentrated in vacuum. The crude product was purified using silica gel (120 g) and eluting with 10% ethyl acetate, dichloromethane to yield ethenesulfonic acid [4-(4,4,5,5-tetramethyl-[1,3,2]dioxaborolan-2-yl)-phenyl]-amidea as a white solid (6.2 g, 20.2 mmol, 89% yield). $^1$H NMR (CDCl$_3$, 300 MHz), δ 7.76 (d, J=8.4, 2H), 7.12 (d, J=8.45, 2H) 6.65 (s, 1H), 6.55 (dd, J=9.77, 6.7, 1H), 6.31 (d, J=16.54, 1H), 5.96 (d, J=9.8, 1H), 1.33 (s, 12H).

2. To a solution of ethenesulfonic acid [4-(4,4,5,5-tetramethyl-[1,3,2]dioxaborolan-2-yl)-phenyl]-amide (0.500 g, 1.6 mmol) in methanol (5 mL) was added diethylamine (0.707 g, 4.0 mmol) in methanol (5 mL), and the reaction was stirred at room temperature and monitored by TLC (1:1 Ethyl acetate:hexanes). After 2 hr the reaction was concentrated in vacuum and the residue partitioned between ethyl acetate (50 mL) and water (50 mL). The ethyl acetate was then washed with 50% brine (1×50 mL), dried over anhydrous sodium sulfate, filtered and concentrated in vacuum. Crude product was purified using a 10 g prepacked silica gel column, eluting with 1:1 ethyl acetate:dichloromethane to provide 2-diethylamino-ethanesulfonic acid [4-(4,4,5,5-tetramethyl-[1,3,2]dioxaborolan-2-yl)-phenyl]-amide as a white solid (0.346 g, 0.90 mmol, 56%). $^1$H NMR (CDCl$_3$, 300 MHz) δ 7.78 (d, J=6.65, 2H) 7.15 (d, J=6.66, 2H), 3.20 (m, 2H), 3.0 (m, 2H), 2.55 (q, J=7.15, 7.16 4H), 1.34 (s, 12H), 1.05 (t, J=7.19, 6H).

3. 2-diethylamino-ethanesulfonic acid {4-[6-amino-5-(2-chloro-3,6-difluoro-benzyloxy)-pyridin-3-yl]-phenyl}-amide was prepared following the general Suzuki coupling procedure 3 from 5-bromo-3-(2-chloro-3,6-difluoro-benzyloxy)-pyridin-2-ylamine and 2-diethylamino-ethanesulfonic acid [4-(4,4,5,5-tetramethyl-[1,3,2]dioxaborolan-2-yl)-phenyl]-amide prepared in part 2 as a white solid in 60% yield.

General Procedure 10:

1: 4-(4,4,5,5-tetramethyl 1,3,2 dioxaboralan-2-yl) aniline (3 g, 0.013 mol) was dissolved in dichloromethane (350 mL) to which pyridine (1.02 g, 0.013 mol) and 4-nitrophenyl chloroformate was added. The reaction was stirred for 13 hr where TLC analysis showed consumption of all starting materials. The solution was washed with saturated NaHCO$_3$ (3×50 mL), water (3×50 mL) and brine (3×50 mL). The organic layer was dried over Na$_2$SO$_4$ and solvent removed to yield a white crystalline solid [4-(4,4,5,5-Tetramethyl-[1,3,2]dioxaborolan-2-yl)-phenyl]-carbamic acid phenyl ester, 4.45 g, 91%. $^1$H NMR (CDCl$_3$ 300 MHz) δ 1.4 (s, 12H), 7.1 (brs, 1H), 7.3 (d, 2H), 7.5 (d, 2H), 7.8 (d, 2H), 8.3 (d, 2H).

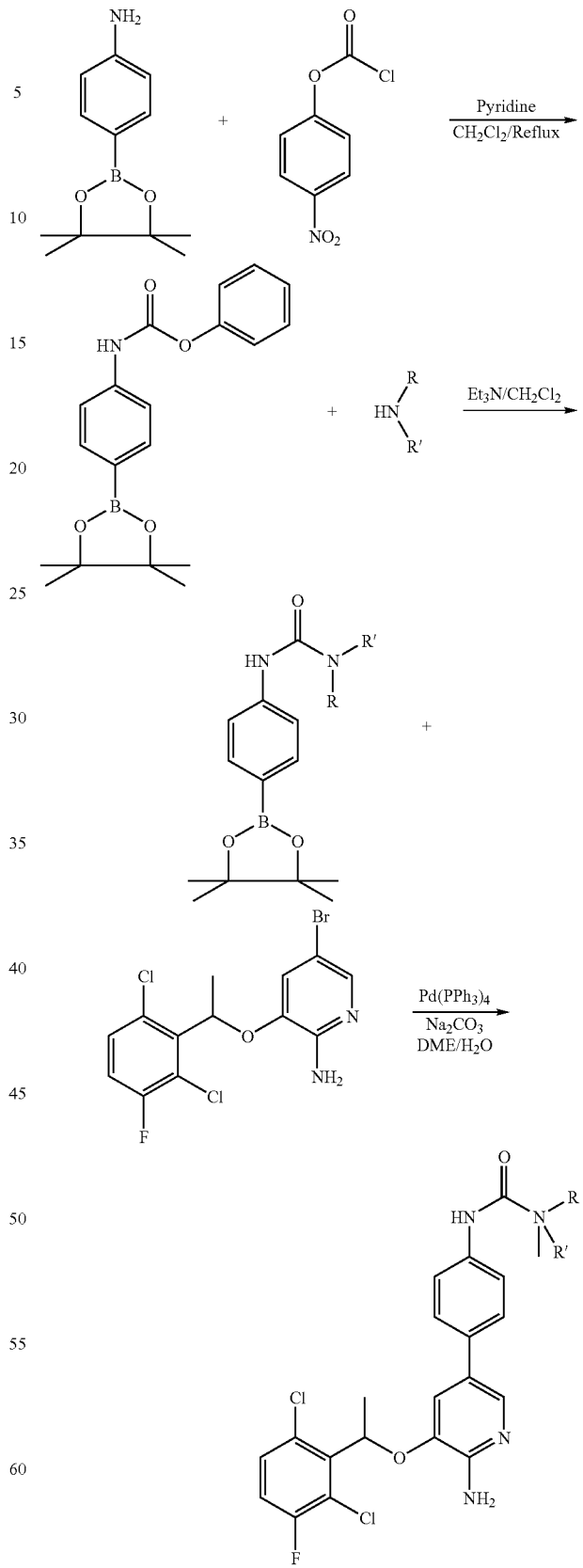

2: [4-(4,4,5,5-Tetramethyl-[1,3,2]dioxaborolan-2-yl)-phenyl]-carbamic acid phenyl ester (500 mg, 1.3 mmol) was dissolved in anhydrous dichloromethane (0.5 mL) and triethylamine (0.187 mL, 1.3 mmol). To this stirred solution was added 1-methyl piperazine (or any other amine) (0.144 mL, 1.3 mmol). The solution turned yellow instantly, and tlc analysis showed consumption of all starting material. The reaction was washed with water (3×500 mL), saturated sodium bicarbonate (2×200 mL) and dried prior to removal of solvents in vacuo. The boronic esters were used without purification.

3: To a mixture of 2.1 mL of DME and 2.8 mL of 2N $Na_2CO_3$ was added 100 mg of the bromide scaffold, 1 equivalent of the boronic acid, and 5 mol of $Pd(PPh_3)_4$. The reaction was stirred and heated at 80° C. overnight in a two dram vial. The crude mixture was filtered through ceolite and extracted with EtOAc (2×100 mL). The combined extracts were washed with $NaHCO_3$ (1×100 mL), followed by water (1×100 mL), and then saturated brine (1×100 mL). The resulting mixture was concentrated in vacuum. The residue was dissolved in hexane and purified via column chromatography.

General Procedure 11:

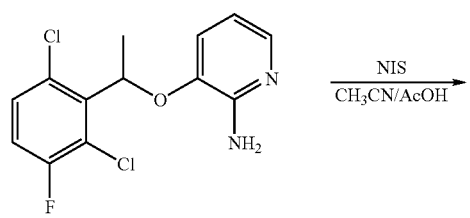

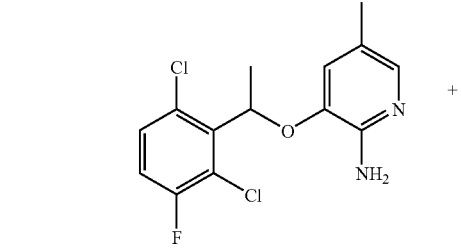

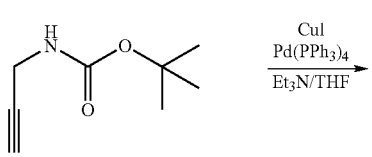

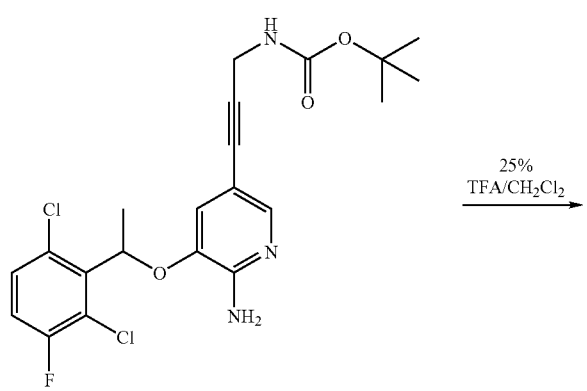

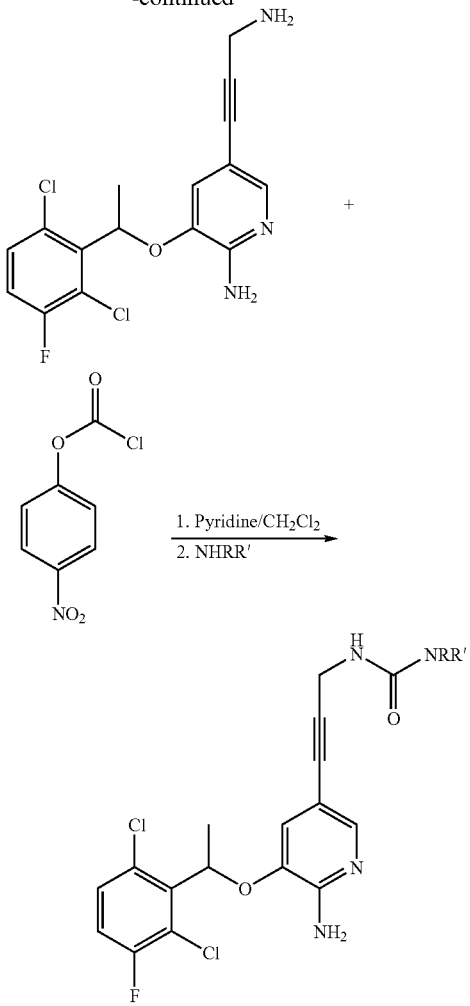

1: To a solution of 3-[1-(2,6-Dichloro-3-fluoro-phenyl)-ethoxy]-pyridin-2-ylamine (10.0 g, 33.2 mmol) in acetonitrile (600 mL) and acetic acid (120 mL) was added N-iodosuccinimide (11.2 g, 49.8 mmol). The mixture was stirred at room temperature for 4 hr and the reaction was quenched with $Na_2S_2O_5$ solution. After evaporation, the residue was partitioned between ethyl acetate and water. The organic layer was washed with 2N NaOH solution, brine, and dried over $Na_2SO_4$. The crude product was purified on a silica gel column to provide 3-[1-(2,6-dichloro-3-fluoro-phenyl)-ethoxy]-5-iodo-pyridin-2-ylamine (7.1 g, 50% yield). MS m/z 427 [M+1]

2: To a solution of 3-[1-(2,6-Dichloro-3-fluoro-phenyl)-ethoxy]-5-iodo-pyridin-2-ylamine (7.1 g, 16.6 mmol) and prop-2-ynyl-carbamic acid tert-butyl ester (3.1 g, 20.0 mmol) in THF (60 mL) and $Et_3N$ (60 mL) was added CuI (63 mg, 0.3 mmol) and $Pd(PPh_3)_4$ (384 mg, 0.3 mmol). The mixture was stirred under nitrogen and monitored by TLC until the reaction was complete. The mixture was extracted with EtOAc and washed by water. The crude product was purified on a silica gel column eluting with 20-40% EtOAc in hexanes to provide (3-{6-Amino-5-[1-(2,6-dichloro-3-fluoro-phenyl)-ethoxy]-pyridin-3-yl}-prop-2-ynyl)-carbamic acid tert-butyl ester (2.2 g, 29% yield).

3: The solution of (3-{6-Amino-5-[1-(2,6-dichloro-3-fluoro-phenyl)-ethoxy]-pyridin-3-yl}-prop-2-ynyl)-carbamic acid tert-butyl ester in 25% TFA in dichloromethane was stirred for 2 hr, then washed by 2N NaOH, water twice, brine, dried over Na₂SO₄. After filtration and evaporation, 5-(3-amino-pro-1-ynyl)-3-[1-(2,6-dichloro-3-fluoro-phenyl)-ethoxy]-pyridin-2-ylamine was obtained in 93% yield.

4: To a solution of 5-(3-amino-prop-1-ynyl)-3-[1-(2,6-dichloro-3-fluoro-phenyl)-ethoxy]-pyridin-2-ylamine (0.282 mmol, 1 eq) and 4-nitrophenyl chloroformate (1 eq) in anhydrous dichloromethane (10 mL) was added pyridine (1 eq). The reaction was stirred for 4 hr under nitrogen, and then the selected amine (1 eq) and triethylamine (1 eq) were added. The mixture was refluxed for 5 minutes and cooled to room temperature. The reaction mixture was washed with water. The organic layer was evaporated and purified on a silica gel column eluting with 0-20% methanol in dichloromethane on prepacked silica columns. Final yields varied between 24% and 71%.

General Procedure 12:

pared in procedure 11) (400 mg, 1.1 mmol) in dichloromethane (17 mL) was added chloroacetyl chloride (153 mg, 1.4 mmol). The reaction was stirred at room temperature with TLC monitor of the completion of the reaction. After the completion, the solvent was evaporated to get the crude product.

2: To a solution of N-(3-{6-Amino-5-[1-(2,6-dichloro-3-fluoro-phenyl)-ethoxy]-pyridin-3-yl}-prop-2-ynyl)-2-chloro-acetamide (1 eq) in acetonitrile (5 eq) was added the individual amine (5 eq). The mixture was refluxing under nitrogen overnight. After evaporation of solvent, the residue was purified on a silica gel column eluting with 1-10% methanol in dichloromethane to provide the product with yields varied between 47% to 97%.

General Procedure 13:

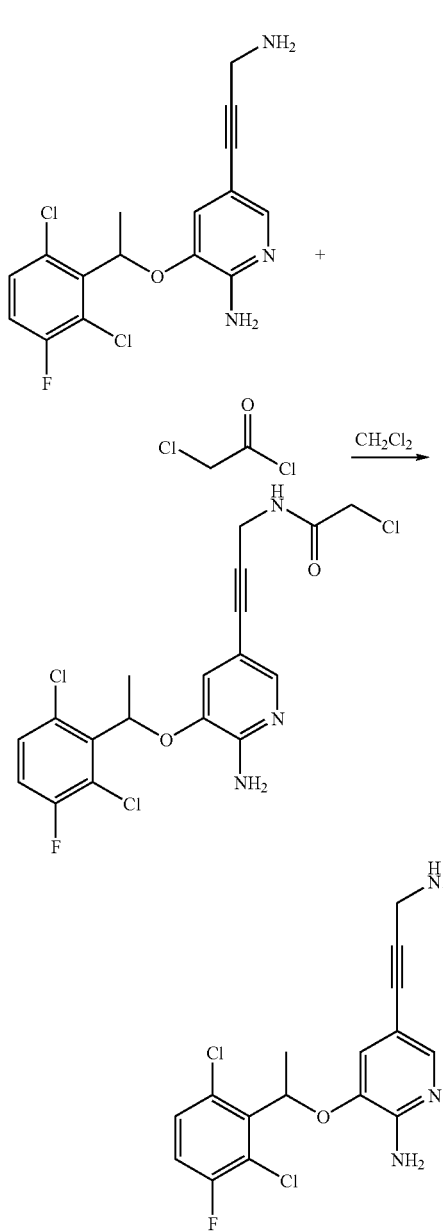

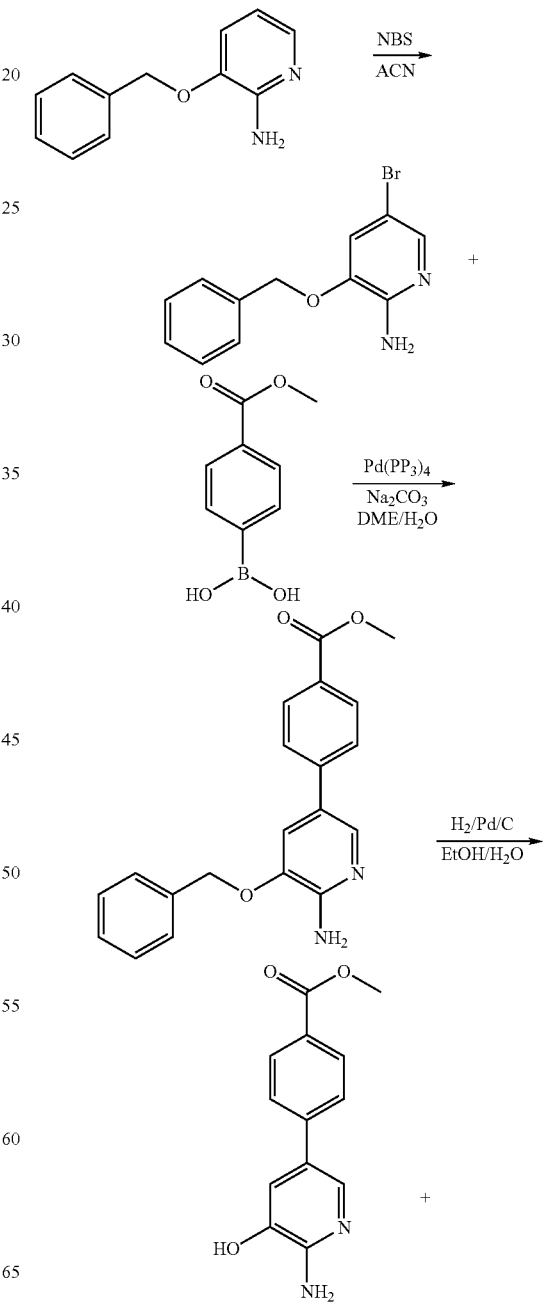

1: To a solution of 5-(3-amino-prop-1-ynyl)-3-[1-(2,6-dichloro-3-fluoro-phenyl)-ethoxy]-pyridin-2-ylamine (pre-

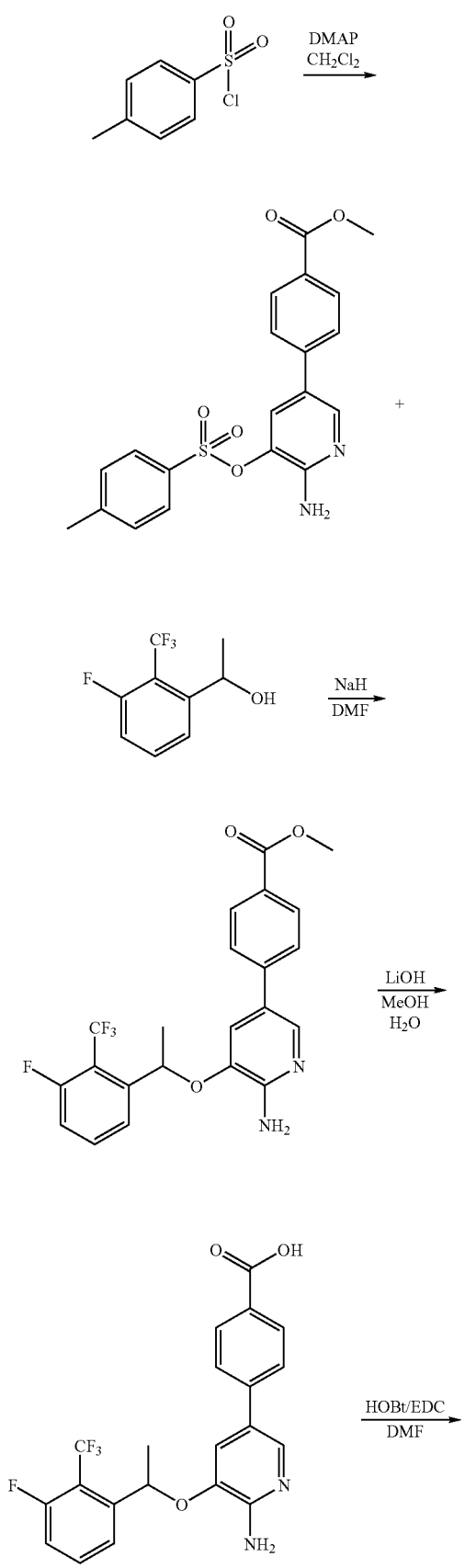

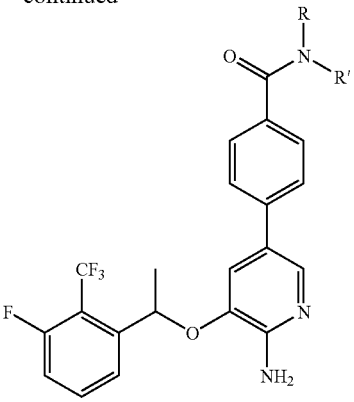

1. To a stirred solution of 2-amino-3-benzyloxypyridine (42.0 g, 0.21 mol) in CH$_3$CN (600 mL) at 0° C. was added N-bromosuccinimide (37.1 g, 0.21 mol) over 30 minutes. The mixture was stirred for 0.5 hr, after which the reaction was then diluted with EtOAc (900 mL) and partitioned with H$_2$O (900 mL). The organic layer was, washed with brine and dried (Na$_2$SO$_4$), filtered and concentrated to dryness under vacuum to yield 3-benzyloxy-5-bromo-pyridin-2-ylamine (31.0 g, 0.11 mol, 53%). $^1$H NMR (CDCl$_3$, 300 MHz) δ 4.63-4.78 (brs, 2H), 5.04 (s, 2H), 7.07 (d, 1H, J, 1.8 Hz), 7.33-7.42 (m, 5H), 7.73 (d, 1H, J, 1.8 Hz).

2. To a stirred mixture of 3-benzyloxy-5-bromo-pyridin-2-ylamine (31.0 g, 0.11 mol) in a mixture of DME (600 mL) and H$_2$O (600 mL) was added 4-carboxymethylboronic acid (29.9 g, 0.11 mol), Pd(PPh$_3$)$_4$ (6.4 g, 5.55 mmol), and Na$_2$CO$_3$ (82.0 g, 0.78 mol). The reaction was heated slowly to reflux and allowed to stir for 3 hr. The reaction was cooled to room temperature, then diluted with CH$_2$Cl$_2$ (1.5 L) and partitioned with H$_2$O (700 mL). The organic layer was washed with saturated NaHCO$_3$ (700 mL), dried (Na$_2$SO$_4$), filtered, and concentrated in vacuo. The crude material was purified by column chromatography (silica gel, 1:1 to 4:1 EtOAc:hexanes) and the fractions containing product were combined and concentrated in vacuo to yield 4-(6-amino-5-benzyloxy-pyridin-3-yl)-benzoic acid methyl ester (29.4 g, 0.086 mol, 79%). $^1$H NMR (CDCl$_3$, 300 MHz) δ 3.92 (s, 3H), 4.82-4.94 (brs, 2H), 5.15 (s, 2H), 7.22 (d, 1H, J, 1.8 Hz), 7.33-7.42 (m, 5H), 7.54 (d, 2H, J, 8.6), 7.98 (d, 1H, J, 1.8 Hz), 8.06(d, 2H, J, 8.6 Hz).

3. To a stirring solution of 4-(6-amino-5-benzyloxy-pyridin-3-yl)-benzoic acid methyl ester (10.0 g, 0.03 mol) in EtOH:H$_2$O (95:5, 600 mL) was added Pd/C (15.9 g, 0.015 mol) (the reaction was de-gassed under vacuum). The solution was allowed to stir under an H$_2$ atmosphere for 22 hr. The solution was filtered through wet celite and the celite washed with EtOH. The filtrate was concentrated under vacuum to yield 4-(6-Amino-5-hydroxy-pyridin-3-yl)-benzoic acid methyl ester (2.3 g, 9.3 mmol, 31%). $^1$H NMR (MeOD, 300 MHz) δ 3.90 (s, 3H), 7.21 (d, 1H, J, 1.9 Hz), 7.62 (d, 2H, J, 8.5 Hz), 7.76 (d, 1H, J, 1.9 Hz), 8.04(d, 2H, J, 8.5 Hz).

4. To a stirring solution of 4-(6-amino-5-hydroxy-pyridin-3-yl)-benzoic acid methyl ester (2.3 g, 9.3 mmol) in CH$_2$Cl$_2$ (180 mL) was added N,N-diisopropylethylamine (3.2 mL, 0.019 mol), 4-methyl-benzenesulfonyl chloride (2.66 g, 0.014 mol), and PS-DMAP (catalytic amount). The reaction was stirred at ambient temperature for 6 hr then filtered to remove the resin. The resin was washed with CH$_2$Cl$_2$ (3×20 mL), and the combined fractions were washed with 10% citric acid (100 mL), saturated NaCl (100 mL), dried (Na₂SO₄) and filtered and concentrated in vacuo. The resulting crude material was purified by column chromatography (silica gel, 100% CH₂Cl₂ to 95:5 CH₂Cl₂:MeOH) and the fractions containing the desired product were combined and concentrated in vacuo to yield 4-[6-Amino-5-(toluene-4-sulfonyloxy)-pyridin-3-yl]-benzoic acid methyl ester (3.3 g, 8.2 mmol, 88%). ¹H NMR (CDCl₃, 300 MHz) δ 2.47 (s, 3H), 3.93 (s, 3H), 4.81-4.88 (brs, 2H), 7.36-7.44 (m, 5H), 7.81 (d, 2H, J, 8.3 Hz), 8.05 (d, 2H, J, 8.4 Hz), 8.19-8.27 (brs, 1H).

5. To a stirred solution of 1-(3-fluoro-2-trifluoromethyl-phenyl)-ethanol (2.0 g, 9.6 mmol) in anhydrous DMF (500 mL) at 0° C. under a N₂ atmosphere was added NaH (0.38 g, 9.6 mmol). The reaction was allowed to stir for 0.5 hr. A solution of 4-[6-Amino-5-(toluene-4-sulfonyloxy)-pyridin-3-yl]-benzoic acid methyl ester (3.8 g, 9.6 mmol) in anhydrous DMF (30 mL) was added to the reaction mixture which was allowed to come to ambient temperature slowly and stirred for 21 hr at this temperature. The reaction was diluted with EtOAc (500 mL) and H₂O (100 mL). The organic layer was separated off and the aqueous was further extracted with EtOAc (1×200 mL). The organic layers were combined and washed with brine (1×100 mL), dried with Na₂SO₄ and concentrated to dryness under vacuum. The crude mixture was purified by column chromatography (silica gel, 40:60 to 70:30 EtOAc:hexanes) and the fractions containing product were combined and concentrated in vacuo to yield 4-{6-amino-5-[1-(3-fluoro-2-trifluoromethyl-phenyl)-ethoxy]-pyridin-3-yl}-benzoic acid methyl ester (1.4 g, 3.2 mmol, 34%). ¹H NMR (CDCl₃, 300 MHz) δ 1.73 (d, 3H, J, 6.2 Hz), 3.91 (s, 3H), 4.87-4.64 (brs, 2H), 5.81 (q, 1H, J, 6.1; 6.3 Hz), 6.92 (d, 1H, J, 1.8 Hz), 7.38 (d, 2H, J, 8.5 Hz), 7.46-7.66 (m, 3H), 7.93 (d, 1H, J, 1.8 Hz), 8.02 (d, 2H, J, 8.5 Hz).

6. To a stirred solution of 4-{6-amino-5-[1-(3-fluoro-2-trifluoromethyl-phenyl)-ethoxy]-pyridin-3-yl}-benzoic acid methyl ester (1.4 g, 3.2 mmol) in warm IPA (72 mL) was added H₂O (38 mL) containing LiOH (0.68 g, 16.2 mmol). The reaction was heated to reflux for 3.5 hr. The reaction was neutralized and diluted with EtOAc (200 mL) and extracted upon cooling. The organic layer was washed with brine (50 mL), dried over Na₂SO₄ and concentrated under vacuum to yield 4-{6-Amino-5-[1-(3-fluoro-2-trifluoromethyl-phenyl)-ethoxy]-pyridin-3-yl}-benzoic acid (1.2 g, 2.8 mmol, 88%). ¹H NMR (MeOD, 300 MHz) δ 1.75 (d, 3H, J, 6.2 Hz), 4.88-4.93 (m, 1H), 7.01 (d, 1H, J, 1.8 Hz), 7.39 (d, 2H, J, 8.3 Hz), 7.52-7.67 (m, 3H), 7.80 (d, 1H, J, 1.8 Hz), 7.97 (d, 2H, J, 8.3 Hz).

7. Preparation of amide compounds: A stirring solution of 4-{6-Amino-5-[1-(3-fluoro-2-trifluoromethyl-phenyl)-ethoxy]-pyridin-3-yl}-benzoic acid (50 mg, 0.12 mmol), EDC (27.0 mg, 0.13 mmol) and HOBt (18.0 mg, 0.13 mmol) in DMF (2 mL) was added to a two dram vial containing NHR₁R₂ (0.12 mmol). The reaction was stirred at room temperature for 18 hr. The reaction was then diluted with CH₂Cl₂ (3 mL) and partitioned with H₂O. The organic was separated washed with saturated NaCl (1×2 mL) and saturated NaHCO₃ (1×2 mL). The organic was concentrated to dryness under vacuum. The material was purified using column chromatography (silica gel, 99:1 to 95:5 CH₂Cl₂/MeOH). The fractions containing product were concentrated under vacuum to yield amide compounds.

General Procedure 14:

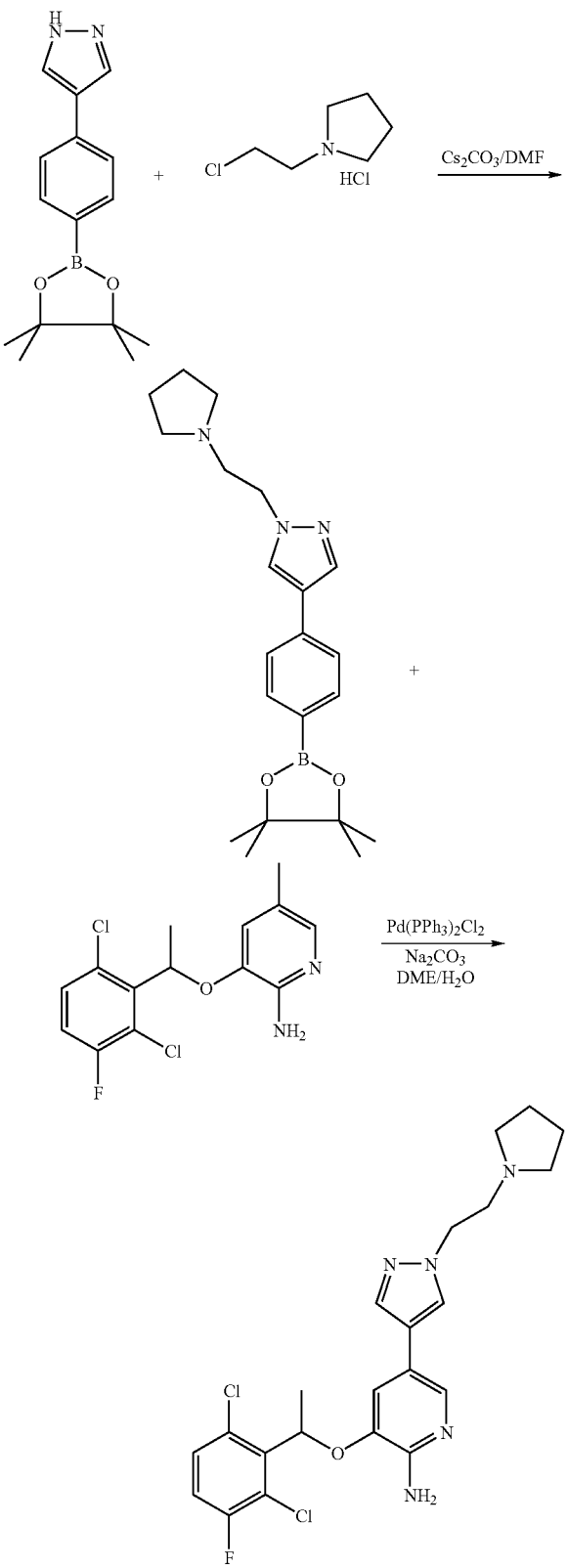

1: To a mixture of 1-(2-chloroethyl)pyrrolidine hydrochloride (200 mg, 1.18 mmol) and 4-[4-(4,4,5,5-Tetramethyl-[1, 3,2]dioxaborolan-2-yl)-phenyl]-1H-pyrazole (229 mg, 1.19 mmol) in DMF (6 mL) was added Cs$_2$CO$_3$. The mixture was stirred at room temperature overnight. Water (10 mL) was then added to the mixture. The product was extracted with EtOAc (3×10 mL). The combined extracts were then washed with brine (5×10 mL) to remove the DMF, then dried over Na$_2$SO$_4$, and concentrated (142 mg, 41% yield).

2: To a mixture of 3-[1-(2,6-Dichloro-3-fluoro-phenyl)-ethoxy]-5-iodo-pyridin-2-ylamine (200 mg, 0.468 mmol), pinacol boronic ester (1.2 eq), Na$_2$CO$_3$ (149 mg, 1.41 mmol) in water (1.25 mL), and dimethyl ethyl glycol (3.75 mL, 0.1M) was added Pd(PPh$_3$)$_2$Cl$_2$ (16 mg, 0.020 mmol) in a microwave reaction vessel. The system was degassed and charged with nitrogen. The mixture was stirred at 160° C. in a microwave apparatus for 15 minutes. The mixture was cooled to room temperature followed by the addition of water (10 mL). The product was extracted with EtOAc (3×20 mL), dried over Na$_2$SO$_4$, and concentrated. The crude product was purified by reverse phase HPLC with 0.1% TFA in water and acetonitrile.

General Procedure 15:

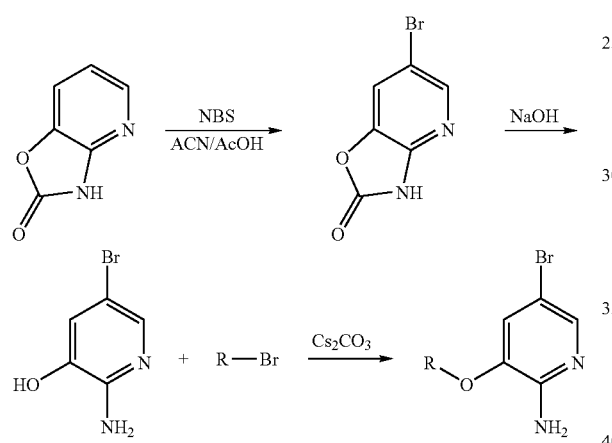

1: To a solution of 3H-oxazolo[4,5-b]pyridin-2-one (13.6 g, 100 mmol) in acetonitrile (600 mL) and acetic acid (120 mL) was added N-bromosuccinimide (21.4 g, 120 mmol). The mixture was stirred at room temperature for 4 hr and the reaction was quenched with Na$_2$S$_2$O$_5$ solution. After evaporation, the residue was partitioned between ethyl acetate and water. The organic layer was washed with 2N NaOH solution, brine, and dried over Na$_2$SO$_4$. The crude product was purified on a silica gel column to provide 6-bromo-3H-oxazolo[4,5-b]pyridin-2-one (11.5 g, 55% yield).

2: 6-Bromo-3H-oxazolo[4,5-b]pyridin-2-one (21.5 g, 100 mmol) was suspended in NaOH solution (2N, 250 mL, 500 mmol). The mixture was refluxed overnight and a clear solution was obtained. After cooling to room temperature, the reaction solution was neutralized to pH ~7. A lot of CO$_2$ was released and also precipitate was observed. The product was filtered, washed with water, and dried under high vacuum to provide 2-amino-5-bromo-pyridin-3-ol as an off-white solid (17.8 g, 98% yield).

3: To a solution of 2-amino-5-bromo-pyridin-3-ol (358 mg, 1.89 mmol) in DMF (8 mL) was added Cs$_2$CO$_3$ (620 mg, 1.89 mmol). The mixture was stirred at room temperature under nitrogen for 1 hr. To the reaction mixture was added bromo-compound (0.9 eq) in DMF (5 mL) slowly. The reaction solution was stirred under nitrogen for five hr, and then partitioned between water and ethyl acetate. The organic layer was washed with brine for three times, dried over MgSO$_4$. The crude product was purified on a silica gel column eluting with hexane-ethyl acetate (4:1) to provide the product with 70%-80% yield.

General Procedure 16 using Example I-488:

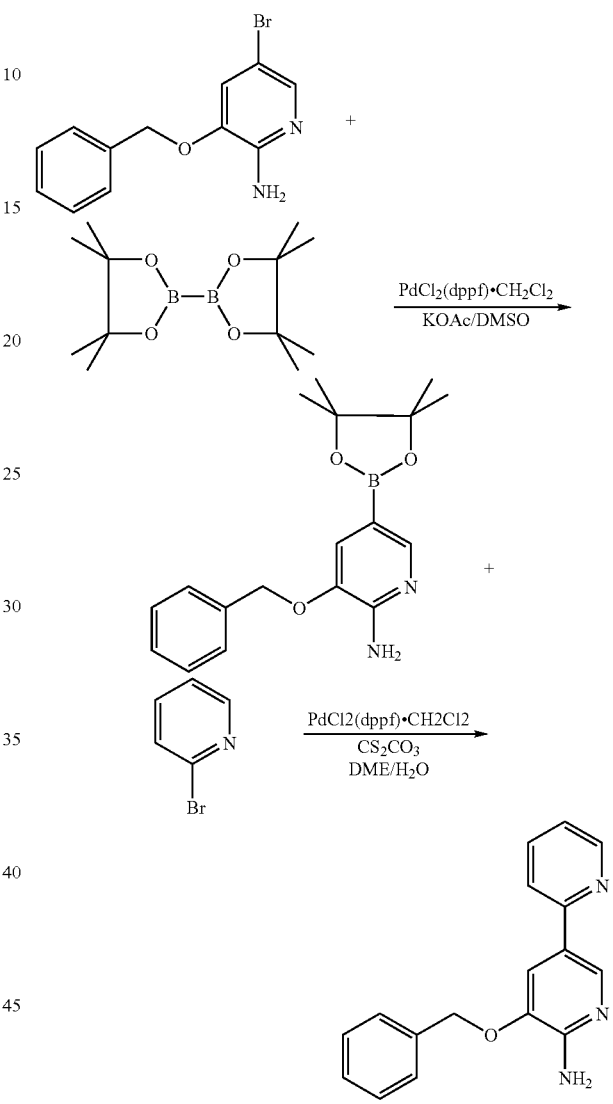

1. To a solution of 3-benzyloxy-5-bromo-pyridin-2-ylamine (1 g, 3.58 mmol) in dimethylsulfoxide (7 mL) was added sequentially bis(pinacolato)diborane (1.0 g, 3.94 mmol), potassium acetate (1.05 g, 10.7 mmol) [1,1'-bis (diphenylphosphino)ferrocine]dichloropalladium (II), complex with dichloromethane (1:1) (146 mg, 0.18 mmol). The mixture was heated to 80° C. for 16 hr and then cooled to room temperature. The reaction mixture was diluted with ethyl acetate (50 mL) and filtered. The filtrate was washed with water (2×50 mL) and dried over magnesium sulfate. Concentration in vacuo yielded the crude boronate as a brown solid (1.13 g, 97%). $^1$H NMR (CDCl$_3$) δ 1.32 (s, 12H), 5.08 (s, 2H), 5.44 (br s, 2H), 7.33-7.42 (m, 6H), 8.03 (s, 1H).

2. An 18 mL reaction vessel was charged with the crude 3-benzyloxy-5-(4,4,5,5-tetramethyl-[1,3,2]dioxaborolan-2-yl)-pyridin-2-ylamine (161 mg, 0.49 mmol), dimethoxyethane (3 mL) and 2-bromopyridine (117 mg, 0.74 mmol). To this solution was added [1,1'-bis(diphenylphosphino)ferrocine]dichloropalladium (II), complex with dichloromethane (1:1) (20 mg, 0.05 mmol) and a 2 M solution of cesium carbonate in water (0.75 mL, 1.5 mmol). The reactor was warmed to 80° C. for 66 hr under a nitrogen atmosphere, then cooled to room temperature. The reaction mixture was partitioned between ethyl acetate (5 mL) and water (5 mL). The organic layer was washed with additional water (5 mL) and diluted with dimethylformamide (5 mL). Polymer-bound sulfonic acid (0.5 g, 2.1 mmol) was added to the organic solution, and the resulting mixture was gently agitated for 2 hr. The resin was filtered and washed with dimethylformamide, methanol and methylene chloride (3×5 mL each solvent). Then the polymer was reacted with 2 M ammonia in methanol for 1 hr. The resin was filtered and washed with additional 2 M ammonia in methanol (2×5 mL), and the combined filtrates were concentrated in vacuo. Purification of the crude product by flash column chromatography yielded 52.2 mg of product as a tan solid (38% yield).

General Procedure 17:

(s, 9H), 1.74 (d, 3H), 5.75 (q, 1H), 6.61 (d, 1H), 76.89 (dt, 1H), 6.94-7.04 (m, 2H), 7.26(d, 1H), 8.19 (bs, 1H). MS m/z 401 (M+H)+.

3. To cesium carbonate in a 2 dram vial was added [3-(2-Chloro-3,6-difluoro-benzyloxy)-5-hydroxy-pyridin-2-yl]-carbamic acid tert-butyl ester (100 mg, 0.25 mmol) in anhydrous DMF (1 mL) followed by benzyl bromide (89.2 μL, 0.75 mmol). The vial was capped and stirred at 90° C. overnight. Reaction was filtered through a 5 mL Chem-Elut tube pre-wetted with water (3.5 mL) and eluted with 1:1 ethyl acetate:methylene chloride. After partial concentration, 4N HCl in dioxane (1-2 mL) was added and solution concentrated. Reverse phase chromatography (water:acetonitrile, 0.05% TFA) followed by lyophilization, gave the desired product as an off white amorphous solid (25.3 mg, 20.0%) and the bis-addition product as a tan amorphous solid (35.2 mg, 23.7%).

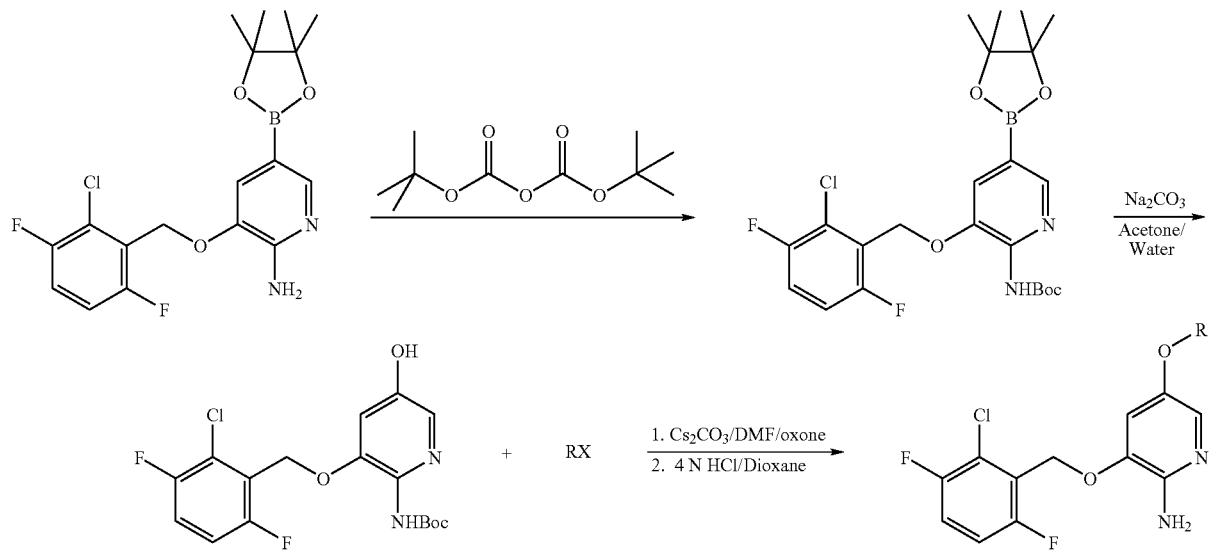

1. To the solution of 3-(2-Chloro-3,6-difluoro-benzyloxy)-5-(4,4,5,5-tetramethyl-[1,3,2]dioxaborolan-2-yl)-pyridin-2-ylamine (procedure 16) (10.0 g, 24.3 mmol) in t-butyl alcohol (50 mL) was added boc anhydride (5.83 g, 26.7 mmol) and reaction stirred at room temperature overnight. Additional boc anhydride (2.25 g, 10.3 mmol) was added and reaction stirred overnight again. Material was concentrated to a viscous black oil and used as-is.

2. The crude boronic ester (24.3 mmol theoretical) in THF (150 mL) was added to a solution of sodium bicarbonate (16.3 g, 194 mmol) in water (150 mL) and acetone (23 mL). The mixture was cooled to 2° C. and oxone (13.5 g, 21.9 mmol) added slowly, keeping temperature below 8° C. Upon completion of addition, reaction was stirred for 5 minutes then quenched with sodium bisulfite (14.2 g) in water (28 mL). Ethyl acetate was added (200 mL) and layers separated. Aqueous layer was neutralized with 6N HCl and extracted with ethyl acetate (2×200 mL). Combined organics were washed with water (250 mL) and brine (250 mL), dried (Na$_2$SO$_4$) and concentrated to a crude black oil. Silica gel chromatography (ethyl acetate/hexane) gave the product as a light brown foam (4.78 g, 49.0%). $^1$H NMR (CDCl$_3$) δ 1.48

General Procedure 18:

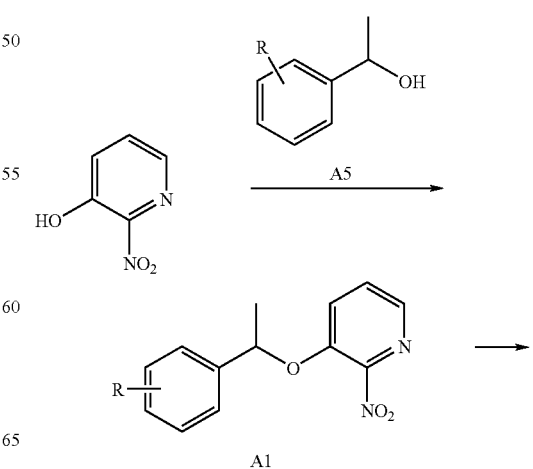

87
-continued

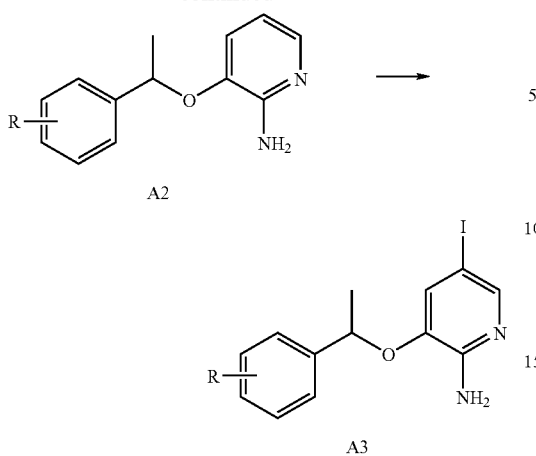

Sodium borohydride (1.5 molar equivalent) was added to solution of ketone (3.89 mmol) in 10 mL of ethanol under a nitrogen atmosphere. The resulting mixture was stirred at room temperature for 12 hr. The mixture was then put in an ice bath and quenched with dilute aqueous HCl. The ethanol was evaporated and EtOAc was added to extract the aqueous solution. The EtOAc layer was dried over $Na_2SO_4$. The $Na_2SO_4$ was filtered off and the filtrated was evaporated to give a oil residue, compound A5. The residue was used without further purification.

3-Hydroxy-2-nitropyridine (1.1 molar equivalent) and triphenylphosphine (1.5 molar equivalent) were added to a solution of compound A5 (1.1 mmol) in 10 mL of THF. The reaction mixture was then put in an ice bath and diisopropyl azodicarboxylate (1.5 molar equivalent) was added. The ice bath was removed and the mixture was stirred at room temperature for 12 hr. The solvent was evaporated to give a yellow oil residue. The residue was purified by silica gel chromatography (eluting EtOAc in hexanes) to give compound A1.

2 M HCl (0.2 mL) was added to solution of compound A1 (0.97 mmol) in 2 mL of ethanol. The mixture was then put in an ice bath and Fe powder (365 mg) was added slowly. The reaction was heated to 85° C. for 1 hr and cooled to room temperature. Celite (0.5 g) was added to stir and the resulting mixture was filtered through a bed of celite and rinsed with ethanol. The filtrated was evaporated to give a brown oil residue, compound A2. The residue was used without further purification.

Periodic acid (0.25 molar equivalent), iodine (0.5 molar equivalent), $H_2O$ (0.5 mL), and concentrate sulfuric acid (0.03 mL) were added to a solution of compound A2 in 3 mL of acetic acid. The reaction mixture was heated to 85° C. for 5 hr. The reaction mixture was then cooled in an ice bath and basified with sat. aq. $Na_2CO_3$ to a pH of 3-4. Ethyl acetate was added to extract the aqueous solution. Dry EtOAc layer over $Na_2SO_4$. The $Na_2SO_4$ was filtered off and the filtrated was evaporated to give a brown oil residue. The residue was purified by silica gel chromatography (eluting with EtOAc and hexanes) to give desired product, compound A3.

88

General Procedure 19:

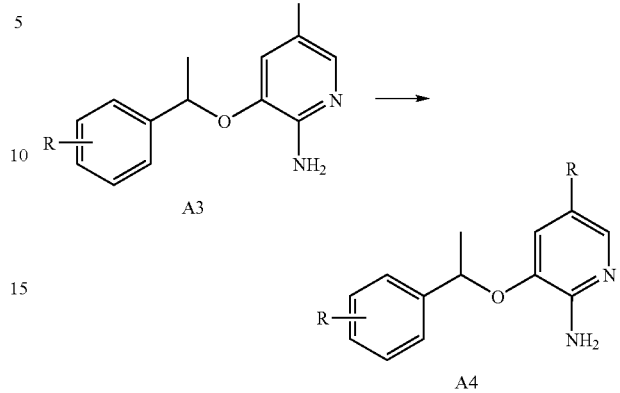

Boronic ester or boronic acid (1.3 molar equivalent) was added to a solution of compound A3 (0.47 mmol) in 5 mL of DME. The mixture was perged with nitrogen several times and then dichlorobis(triphenylphsophino) palladium (II) (0.05 molar equivalent) was added. Sodium carbonate (3 molar equivalent) in 1 mL of $H_2O$ was added to the reaction mixture and the resulting solution was heated to 85° C. for 12 hr. Water was added to the reaction mixture to quench the reaction. EtOAc was then added to extract the aqueous solution. Dry EtOAc layer over $Na_2SO_4$. The $Na_2SO_4$ was filtered off and the filtrated was evaporated to give a dark brown oil residue. The residue was purified by silica gel chromatography (eluting with $CH_3OH$, $CH_2Cl_2$, EtOAc, and hexanes) to give desired product, compound A4.

General Procedure 20:

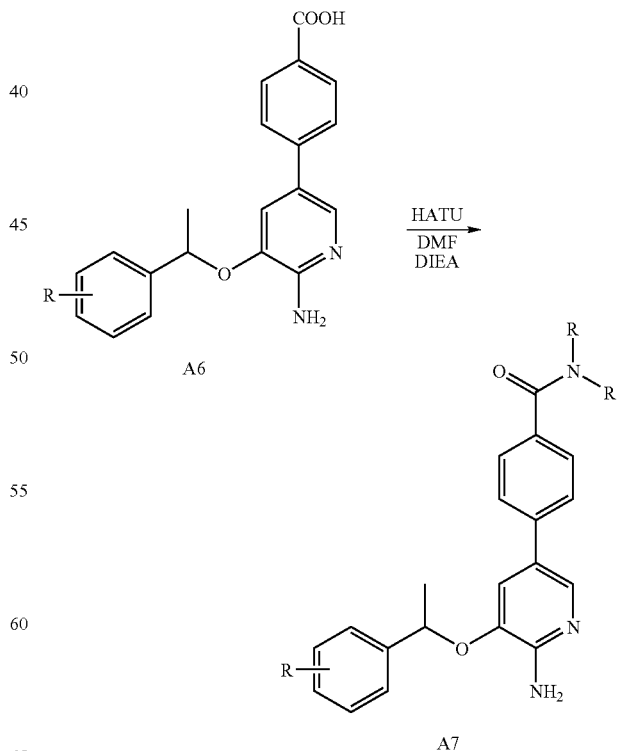

Compound A6 was prepared using general procedure 19. O-(7-azabenzotriazol-1-yl)-N,N,N',N'-tetramethyluronium phosphorus pentafloride (HATU) (1.1 molar equivalent), diisopropylethyl amine (5 molar equivalent) and amine (1.3 molar equivalent) were added to a solution of compound A6 (0.17 mmol) in 3 mL of DMF under a nitrogen atmosphere. The reaction was allowed to stir at room temperature for 12 hr. Saturated NaHCO$_3$ was added to the reaction mixture to quench the reaction. EtOAc was then added to extract the aqueous solution. Dry EtOAc layer over Na$_2$SO$_4$. The Na$_2$SO$_4$ was filtered off and the filtrate was evaporated to give a brown oil residue. The residue was purified by silica gel chromatography (eluting with EtOAc and hexanes) to give desired amide product, compound A7, as a yellow oil.

General Procedure 21:

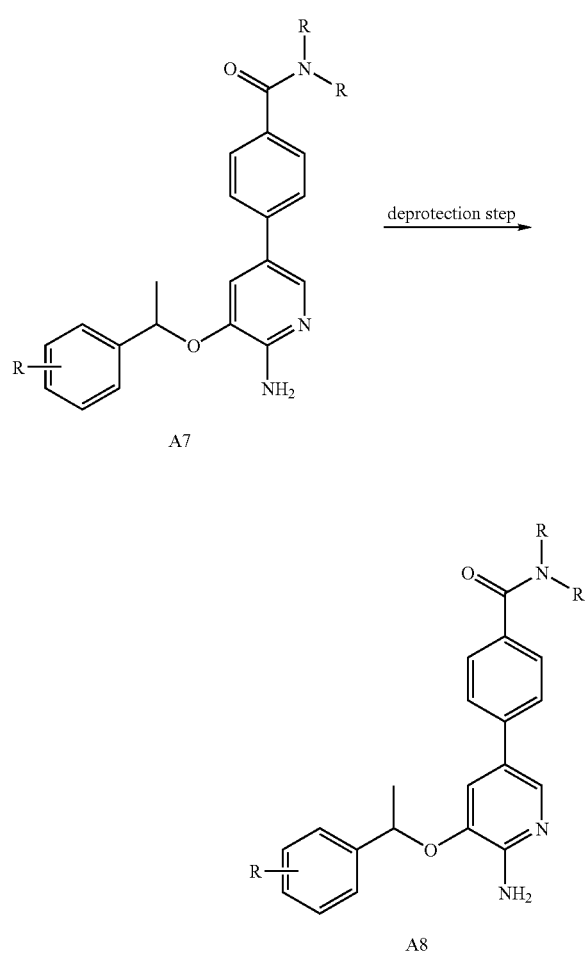

Acid (16 molar equivalent or less) was added to compound A7 (0.13 mmol) at room temperature. The resulting solution was stirred at room temperature or heated to 60° C. for 12 hr. The reaction mixture was evaporated and the residue was purified by silica gel chromatography (eluting with CH$_3$OH, EtOAc and CH$_2$Cl$_2$) to give desired amide product, compound A8, as a yellowish to white solid.

General Procedure 22:

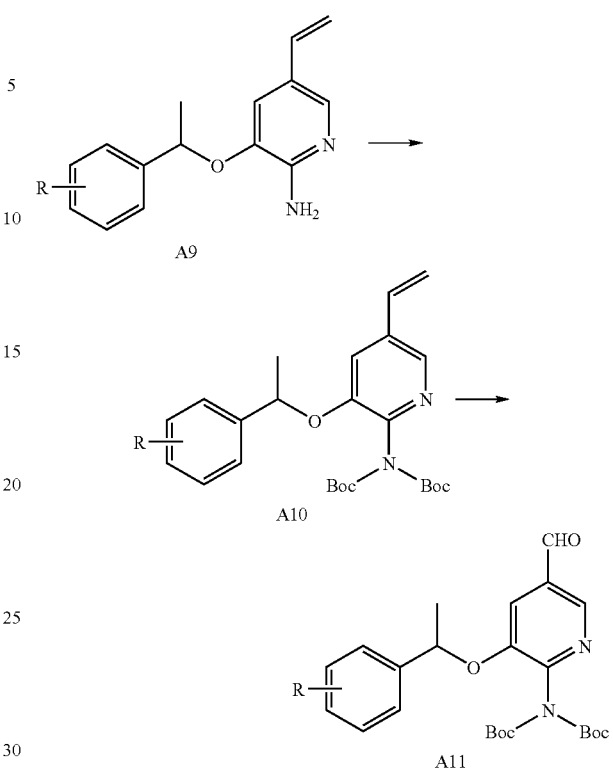

Compound A9 was prepared using general procedure 19. Di-tert-butyl dicarbonate (3 molar equivalent) and 4-(dimethylamino)pyridine (0.14 molar equivalent) were added to a solution of compound A9 (3 mmol) in 20 mL of DMF. The reaction mixture was stirred at room temperature for 12 hr. Water was added to the reaction mixture to quench the reaction. EtOAc was then added to extract the aqueous solution. Dry EtOAc layer over Na$_2$SO$_4$. The Na$_2$SO$_4$ was filtered off and the filtrated was evaporated to give a brown yellow oil residue. The residue was purified by silica gel chromatography (eluting with 25-30% EtOAc in hexanes) to give desired product, compound A10 as a yellowish oil (87.8% yield). Ozone was bubbled through a solution of compound A10 in 50 mL of CH$_2$Cl$_2$ at −78° C. and dimethyl sulfide was added to quench the reaction. Saturated sodium chloride was added to the reaction mixture and EtOAc was added to extract the aqueous solution. Combined EtOAc layer was dried over Na$_2$SO$_4$. The Na$_2$SO$_4$ was filtered off and the filtrated was evaporated to give a yellow oil residue. The residue was purified by silica gel chromatography (eluting with 35→40% EtOAc in hexanes) to give desired product, compound A11 as a yellowish oil (58.4% yield).

General Procedure 23: Reductive Amination

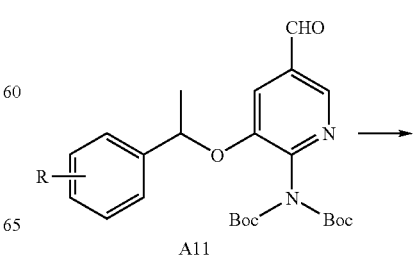

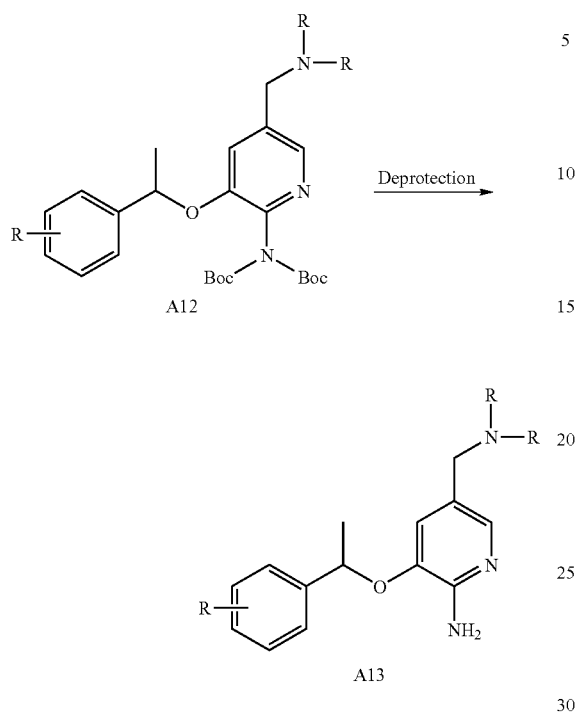

Amine hydrochloride salt (1.2 molar equivalent), sodium acetate (2 molar equivalent to the amine hydrochloride salt) were added to a solution of compound A11 (0.45 mmol) in 4 mL of CH$_3$OH under a nitrogen atmosphere. Molecular sieve (0.5 g) was added to the reaction mixture and then sodium cyanoborohydride (2 molar equivalent) was added. The resulting mixture was stirred at room temperature for 12 hr under a nitrogen atmosphere. The reaction mixture was filtered through a bed of celite and the filtrate was evaporated and purified by silica gel chromatography (eluting CH$_3$OH, EtOAc, and CH$_2$CL$_2$) to give desired product, compound A12 as an oil (52.6% yield). Acid (16 molar equivalent or less) was added to compound A12 (0.17 mmol) at room temperature. The resulting solution was stirred at room temperature or heated to 60° C. for 12 hr. The reaction mixture was evaporated and the residue was purified by silica gel chromatography (eluting with CH$_3$OH, EtOAc and CH$_2$Cl$_2$) to give desired product, compound A13.

General Procedure 24:

O-phenyldiamines (1.2 molar equivalent) and sodium bisulfite (2.1 molar equivalent) were added to a solution of compound A11 (0.41 mmol) in 5 mL of DMA. The resulting solution was heated to 110° C. for 12 hr. Water was added to the reaction mixture to quench the reaction. EtOAc was then added to extract the aqueous solution. Dry EtOAc layer over Na$_2$SO$_4$. The Na$_2$SO$_4$ was filtered off and the filtrated was evaporated to give a brown yellow oil residue. The residue was purified by silica gel chromatography (eluting with EtOAc in hexanes) to give desired product, compound A14. Acid (16 molar equivalent or less) was added to compound A14 (0.16 mmol) at room temperature. The resulting solution was stirred at room temperature or heated to 60° C. for 12 hr. The reaction mixture was evaporated and the residue was purified by silica gel chromatography (eluting with CH$_3$OH, EtOAc and CH$_2$Cl$_2$) to give desired amide product, compound A15.

General Procedure 25:

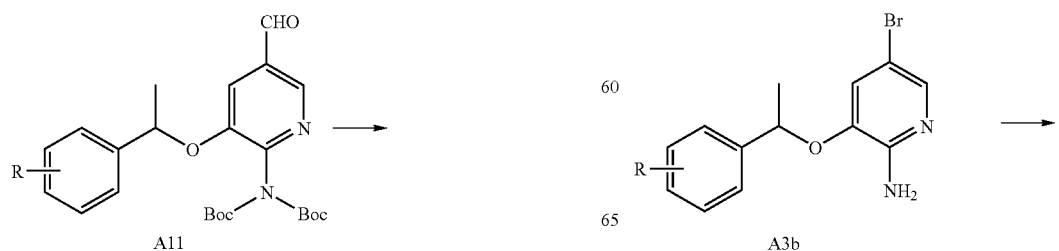

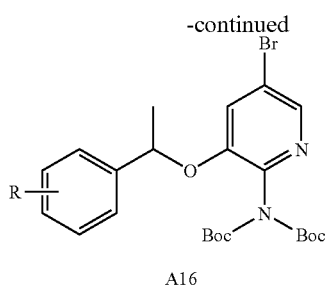

A16

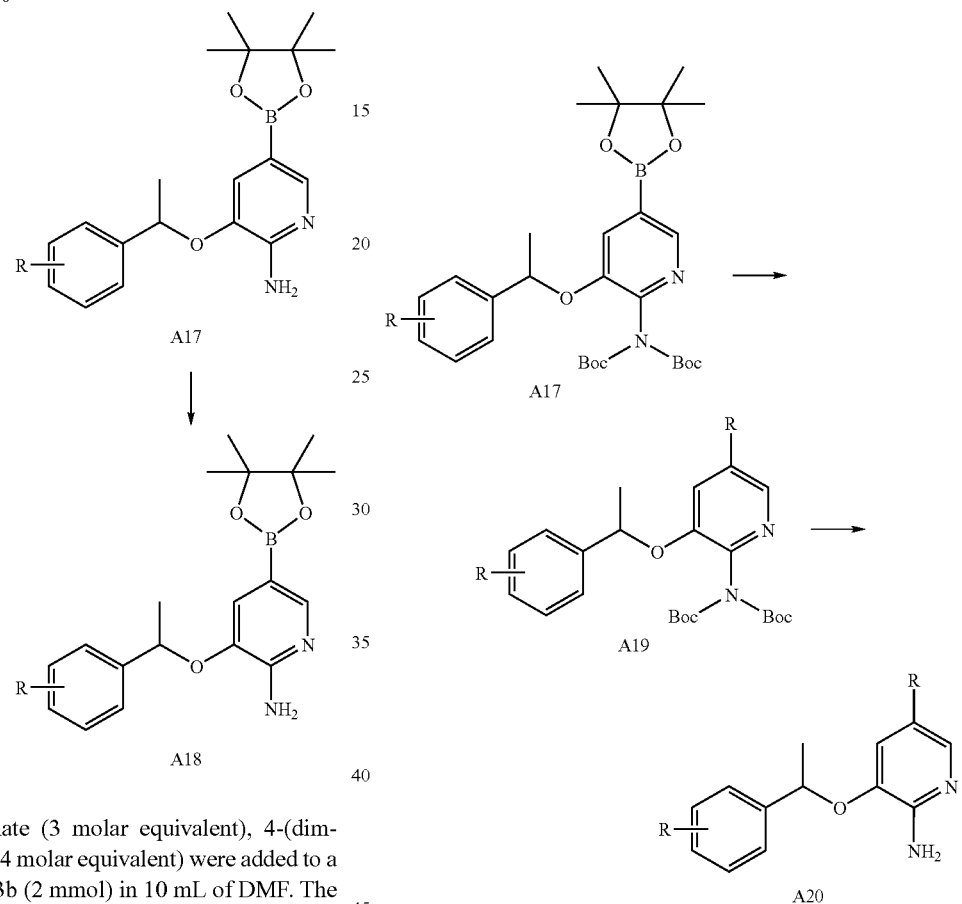

Di-tert-butyl dicarbonate (3 molar equivalent), 4-(dimethylamino)pyridine (0.14 molar equivalent) were added to a solution of compound A3b (2 mmol) in 10 mL of DMF. The reaction mixture was stirred at room temperature for 12 hr. Water was added to the reaction mixture to quench the reaction. EtOAc was then added to extract the aqueous solution. Dry EtOAc layer over $Na_2SO_4$. The $Na_2SO_4$ was filtered off and the filtrated was evaporated to give a brown yellow oil residue (compound a16). The residue was used without further purification.

Bis(pinacolato)diboron (1.2 molar equivalent) and potassium acetate (3.4 molar equivalent) were added to a solution of compound a16 in 4 mL of DMSO. The mixture was perged with nitrogen several times and then dichlorobis(triphenylphsophino) palladium (II) (0.05 molar equivalent) was added. The resulting solution was heated to 80° C. for 12 hr. Water was added to the reaction mixture to quench the reaction. EtOAc was then added to extract the aqueous solution. Dry EtOAc layer over $Na_2SO_4$. The $Na_2SO_4$ was filtered off and the filtrated was evaporated to give a dark brown oil residue. The residue was purified by silica gel chromatography (eluting with 30% EtOAc in hexanes) to give desired product, compound A17 (76% yield). HCl (5 molar equivalent) was added to a solution of compound A17 (0.43 mmol) in 4 mL of $CH_2Cl_2$. The resulting mixture was heated to 50° C. for 12 hr. Saturated $NaHCO_3$ was added to the reaction mixture to neutralize the reaction. EtOAc was then added to extract the aqueous solution. Dry EtOAc layer over $Na_2SO_4$. The $Na_2SO_4$ was filtered off and the filtrated was evaporated to give the desired product (compound A18) as a yellow solid (75% yield).

General Procedure 26:

Compound A17 (1.3 molar equivalent) was added to a solution of aryl halide (0.36 mmol) in 3 mL of DME. The mixture was perged with nitrogen several times and then dichlorobis(triphenylphsophino) palladium (II) (0.05 molar equivalent) was added. Sodium carbonate (3 molar equivalent) in 0.8 mL of $H_2O$ was added to the reaction mixture and the resulting solution was heated to 85° C. for 12 hr. Water was added to the reaction mixture to quench the reaction. EtOAc was then added to extract the aqueous solution. Dry EtOAc layer over $Na_2SO_4$. The $Na_2SO_4$ was filtered off and the filtrated was evaporated to give a dark brown oil residue. The residue was purified by silica gel chromatography (eluting with EtOAc in hexanes) to give desired product, compound A19 (74.4% yield). HCl (5 molar equivalent) was added to a solution of compound A19 (0.26 mmol) in 10 mL of isopropyl alcohol. The resulting mixture was heated to 50° C. for 12 hr. The solvent was evaporated to give the desired product, compound A20.

General Procedure 27:

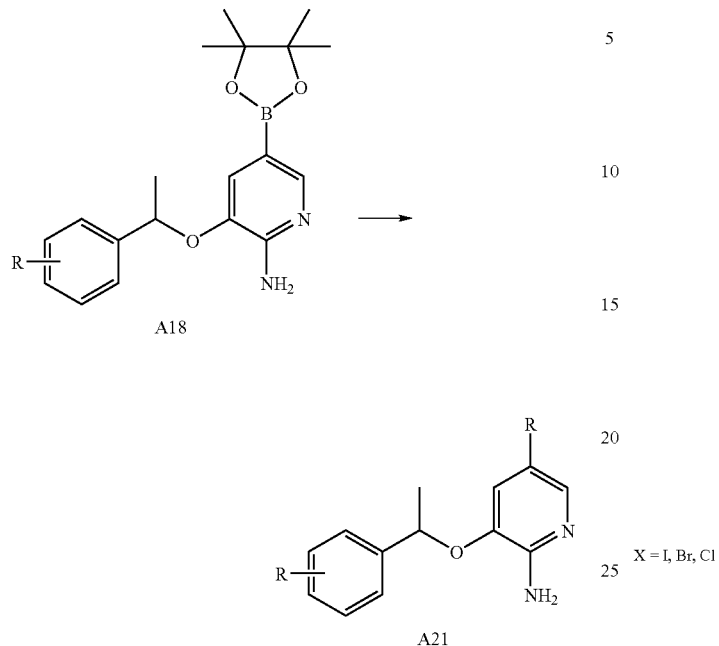

Compound A18 (1.3 molar equivalent) was added to a solution of aryl halide (0.21 mmol) in 3 mL of DME. The mixture was perged with nitrogen several times and then dichlorobis(triphenylphsophino) palladium (II) (0.05 molar equivalent) was added. Sodium carbonate (3 molar equivalent) in 0.6 mL of $H_2O$ was added to the reaction mixture and the resulting solution was heated to 85° C. for 12 hr. Water was added to the reaction mixture to quench the reaction. EtOAc was then added to extract the aqueous solution. Dry EtOAc layer over $Na_2SO_4$. The $Na_2SO_4$ was filtered off and the filtrated was evaporated to give a dark brown oil residue. The residue was purified by silica gel chromatography (eluting with $CH_3OH$, $CH_2Cl_2$, EtOAc, and hexanes) to give desired product, compound A21.

General Procedure 28:

Amine (1.5 molar equivalent) and $K_2CO_3$ (1.5 molar equivalent) were added to a solution of 4-halobenzyl halide (1.0 molar equivalent) in 2 mL of toluene. The resulting mixture was microwaved using Smithsynthesizer (150° C., 1 hr). Water was added to the reaction mixture to quench the reaction. EtOAc was then added to extract the aqueous solution. Dry EtOAc layer over $Na_2SO_4$. The $Na_2SO_4$ was filtered off and the filtrated was evaporated to give the desired product, compound A23. The residue was used in procedure 11 without further purification to synthesize compound A22.

General Procedure 29:

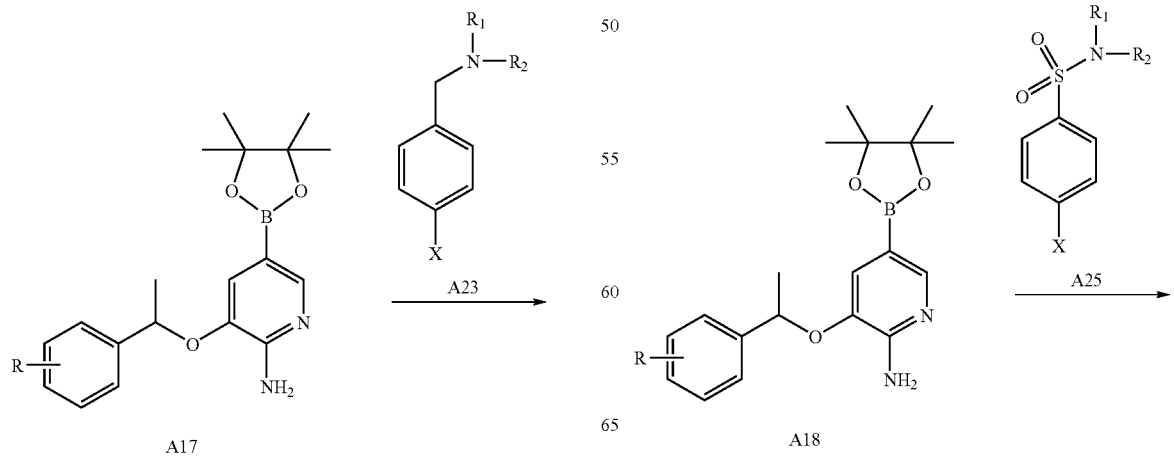

-continued

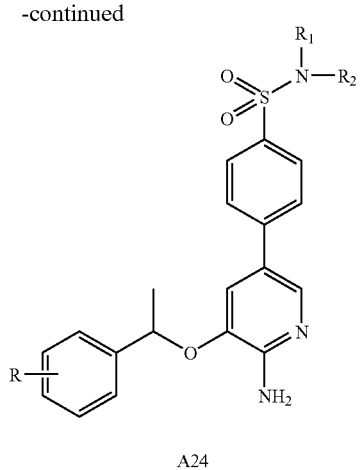

A24

X = I, Br, Cl,

Amine (1.2 molar equivalent) and diisopropylamine (5 molar equivalent) were added to a solution of 4-bromobenzenesulfonyl chloride (0.77 mmol) in 5 mL of CHCl₃ under a nitrogen atmosphere. The resulting mixture was stirred at room temperature for 4 hr. Water was added to the reaction mixture to quench the reaction. EtOAc was then added to extract the aqueous solution. Dry EtOAc layer over Na₂SO₄. The Na₂SO₄ was filtered off and the filtrated was evaporated to give the desired product, compound A25. The residue was used in procedure 11 without further purification to synthesize compound A24.

General Procedure 30:

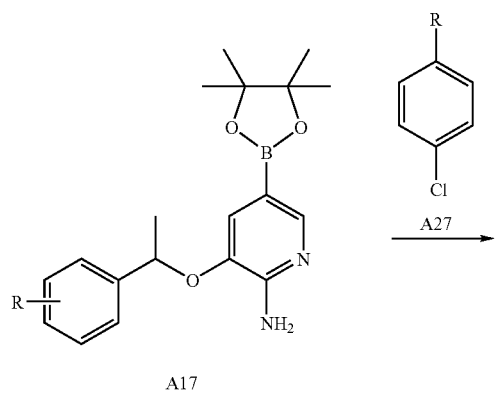

A17

Boronic ester or boronic acid (1.2 molar equivalent) was added to a solution of 1-chloro-4-iodobenzene (0.84 mmol) in 10 mL of ethylene glycol diemthylether (DME) under a nitrogen atmosphere. The mixture was perged with nitrogen several times and then dichlorobis(triphenylphsophino) palladium (II) (0.05 molar equivalent) was added. Sodium carbonate (3 molar equivalent) in 1.8 mL of H₂O was added to the reaction mixture and the resulting solution was heated to 85° C. for 12 hr. Water was added to the reaction mixture to quench the reaction. EtOAc was then added to extract the aqueous solution. Dry EtOAc layer over Na₂SO₄. The Na₂SO₄ was filtered off and the filtrated was evaporated to give a dark brown oil residue. The residue was purified by silica gel chromatography (eluting with CH₃OH, CH₂Cl₂, EtOAc, and hexanes) to give desired product, compound A27. Compound A27 was used in procedure 11 to synthesize compound A26.

General Procedure 31 for Chiral Separation of Racemates:

The racemic sample was purified using preparative supercritical fluid chromatography SFC-MS. The purification conditions were: column-Chiralpak AD-H, 250×21 mm, 5 micron, 100 A column (Column #:ADH0CJ-C1003); column temperature 35° C.; mobile phase 35% methanol (with 0.1% isopropylamine)-modified CO₂; preparative flow rate 52 mL/min; isobaric pressure at 120 bar. The specific chirality of the isomers was not definitively determined.

General Procedure 32: using Example I-617

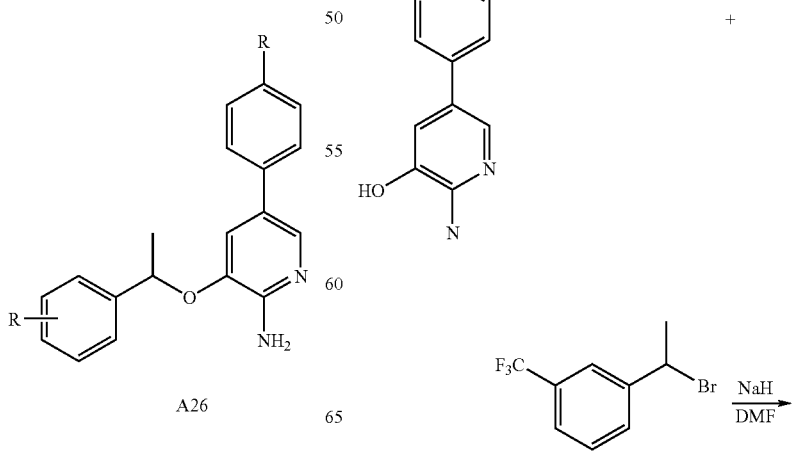

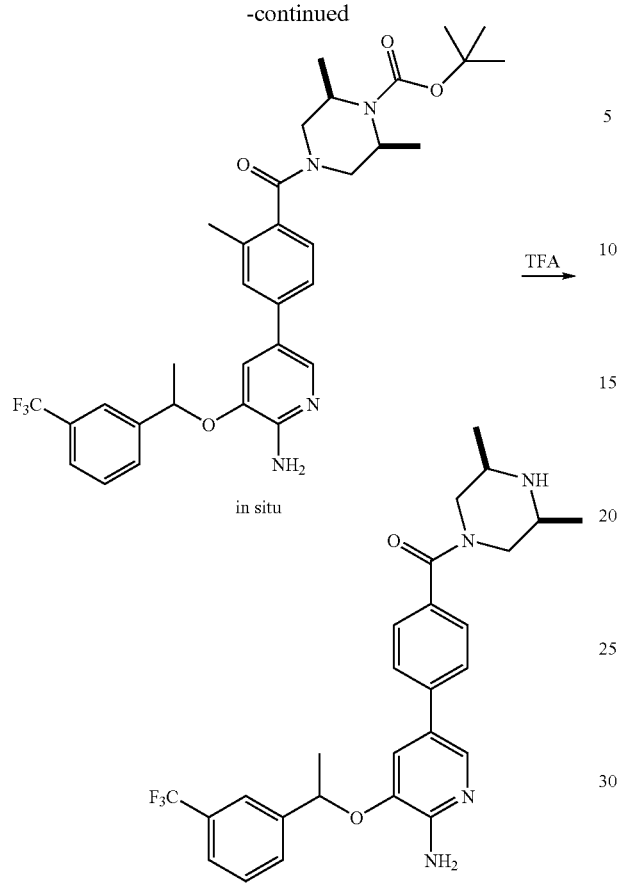

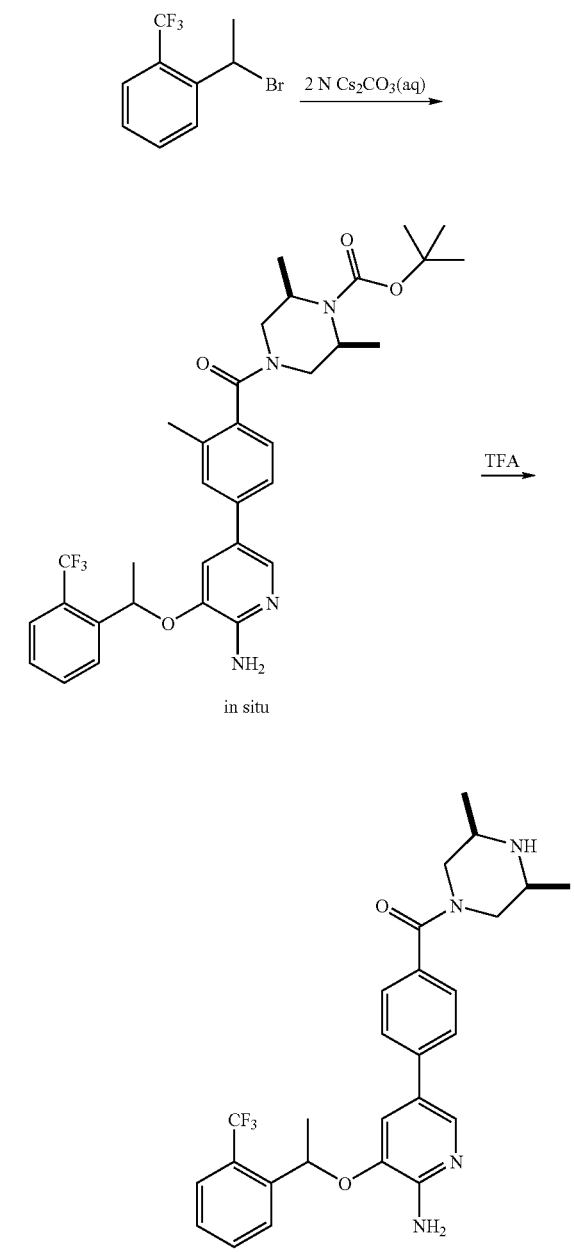

To a mixture of 4-[4-(6-Amino-5-hydroxy-pyridin-3-yl)-benzoyl]-2,6-dimethyl-piperazine-1-carboxylic acid tert-butyl ester (100 mg, 0.23 mmol) and 1-(1-bromo-ethyl)-3-trifluoromethyl-benzene (64 mg, 0.25 mmol) in DMF (2 ml) was added NaH (12 mg, 0.47 mmol) at 0° C. The mixture was stirred overnight. LCMS showed that the reaction was completed, DMF and water were removed. TFA (2 mL) was added to the residue and stirred at room temperature for 3 hr. TFA was removed followed by addition of methanol. The residue was purified by prep-HPLC to afford (4-{6-Amino-5-[1-(3-trifluoromethyl-phenyl)-ethoxy]-pyridin-3-yl}-phenyl)-(3,5-dimethyl-piperazin-1-yl)-methanone (30 mg, yield 25.7%).

General Procedure 33: using Example I-616

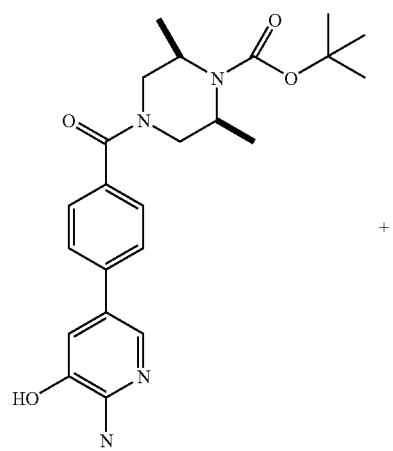

+

To a mixture of 4-[4-(6-Amino-5-hydroxy-pyridin-3-yl)-benzoyl]-2,6-dimethyl-piperazine-1-carboxylic acid tert-butyl ester (50 mg, 0.12 mmol) and 1-(1-bromo-ethyl)-2-trifluoromethyl-benzene (32 mg, 0.12 mmol) in DMF (2 ml) was added 2 M $Cs_2CO_3$ (0.18 mL, 0.35 mmol), followed by water (0.5 mL), the mixture was stirred overnight then heated at 70° C. for 8 hr, LCMS showed that the reaction was completed. The DMF and water were removed. TFA (2 mL was added to the residue and stirred at room temperature for 3 hr. The TFA was removed, followed by addition of methanol. The residue was purified by prep-HPLC to afford (4-{6-amino-5-[1-(2-trifluoromethyl-phenyl)-ethoxy]-pyridin-3-yl}-phenyl)-(3,5-dimethyl-piperazin-1-yl)-methanone (20 mg, yield 34.2%).

101

Procedure 34: using Example I-624

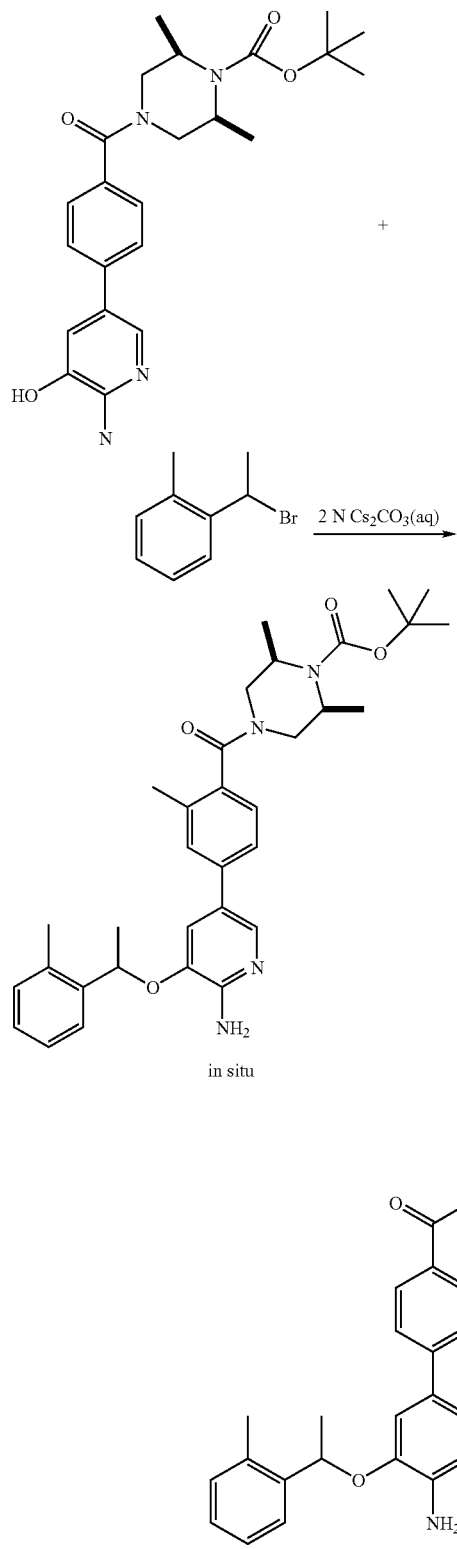

To a mixture of (2R,6S)-4-[4-(6-Amino-5-hydroxy-pyridin-3-yl)-benzoyl]-2,6-dimethyl-piperazine-1-carboxylic acid tert-butyl ester (100 mg, 0.23 mmol) and 1-bromomethyl-2-methyl-benzene (47 mg, 0.25 mmol) in DMF (2 mL) was added 2 M Cs₂CO₃ (0.35 mL, 0.7 mmol) followed by water (0.5 mL). The mixture was stirred at room temperature overnight. LCMS showed the reaction was completed, DMF was removed, followed by addition of 4 N HCl in dioxane (2 mL) and the reaction was stirred at room temperature for 3 hr. The volatiles were removed followed by addition of methanol. This solution was purified by prep-HPLC to afford {4-[6-Amino-5-(2-methyl-benzyloxy)-pyridin-3-yl]-phenyl}-(3,5-dimethyl-piperazin-1-yl)-methanone (47 mg, yield 46.6%).

Procedure 35: using Example I-635

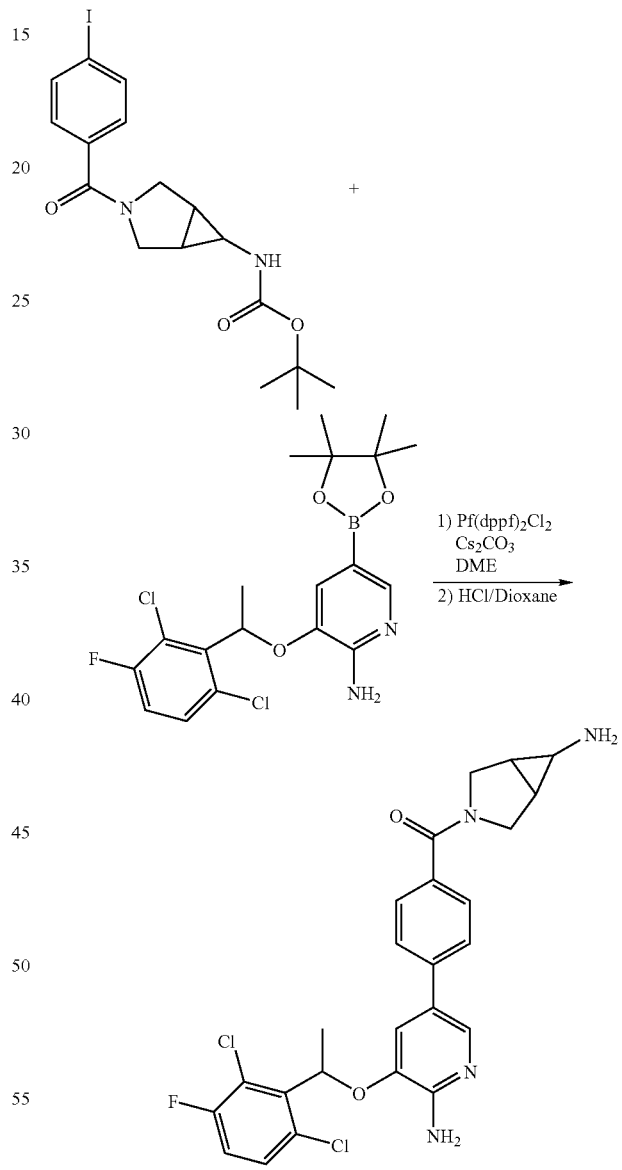

To a mixture of [3-(4-iodo-benzoyl)-3-aza-bicyclo[3.1.0]hex-6-yl]-carbamic acid tert-butyl ester (100 mg, 0.234 mmol) and 3-[1-(2,6-dichloro-3-fluoro-phenyl)-ethoxy]-5-(4,4,5,5-tetramethyl-[1,3,2]dioxaborolan-2-yl)-pyridin-2-ylamine (100 mg, 0.234 mmol) in DME (2 mL) was added Pd(dppf)₂Cl₂·CH₂Cl₂ (10 mg, 0.012 mmol) and Cs₂CO₃ (351 mg, 0.702 mmol). The mixture was bubbled with nitrogen for 10 min then microwaved at 150° C. for 30 min. LCMS checked that the reaction was completed. The crude reaction mixture was diluted with ethyl acetate followed by washings with water and brine. The solution was dried over MgSO$_4$. Purification by prep-HPLC afforded a solid. The solid was stirred with 4 N HCl/dioxane (3 mL) for 3 hr at room temperature. Removal of the volatiles led to a residue that was purified by prep-HPLC to afford (6-amino-3-aza-bicyclo[3.1.0]hex-3-yl)-(4-{6-amino-5-[1-(2,6-dichloro-3-fluoro-phenyl)-ethoxy]-pyridin-3-yl}-phenyl)-methanone (30 mg, yield 26%).

Procedure 36: using Example I-636

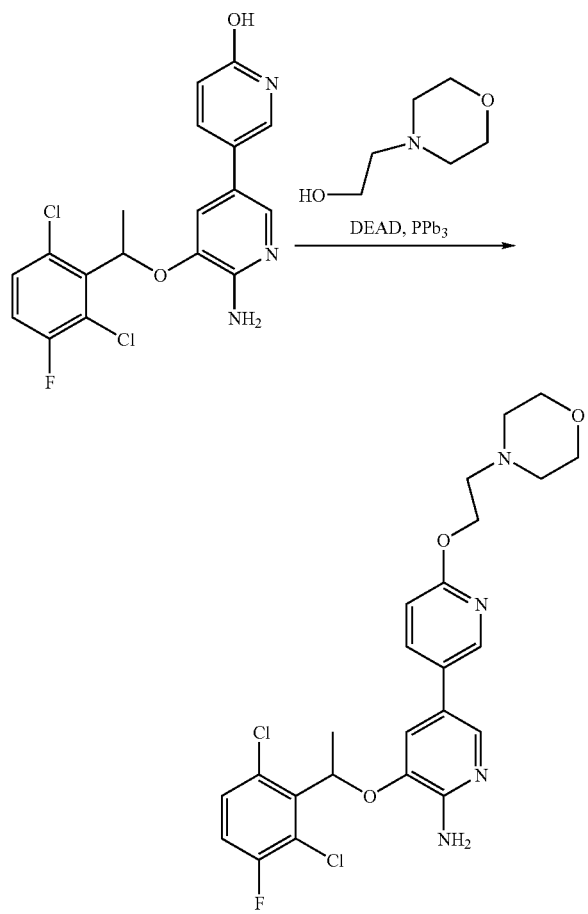

To a mixture of 6'-amino-5'-[1-(2,6-dichloro-3-fluoro-phenyl)-ethoxy]-[3,3']bipyridinyl-6-ol (78 mg, 0.20 mmol), triphenyphosphine (63 mg, 0.24 mmol) and 2-morpholin-4-yl-ethanol (0.026 mL, 0.22 mmol) was added DEAD (0.034 mL, 0.22 mmol). After stirring overnight more PPh$_3$ (63 mg, 0.24 mmol) and more DEAD (0.034 mL, 0.22 mmol) were added. After several hours, more alcohol (0.026 mL, 0.22 mmol) was added. After several more hours, more PPh$_3$ (63 mg, 0.24 mmol) and more DEAD (0.034 mL, 0.22 mmol) were added. After stirring overnight, the mixture was partitioned between dichloromethane and half-saturated brine. The phases were separated and the aqueous phase was extracted with dichloromethane. The combined organic phases were dried over Na$_2$SO$_4$ and concentrated by rotary evaporation. The residue was purified by silica gel chromatography using gradient elution of dichloromethane, methanol to afford 5-[1-(2,6-Dichloro-3-fluoro-phenyl)-ethoxy]-6'-(2-morpholin-4-yl-ethoxy)-[3,3']bipyridinyl-6-ylamine (53 mg, 53%).

Procedure 37: using Example I-650

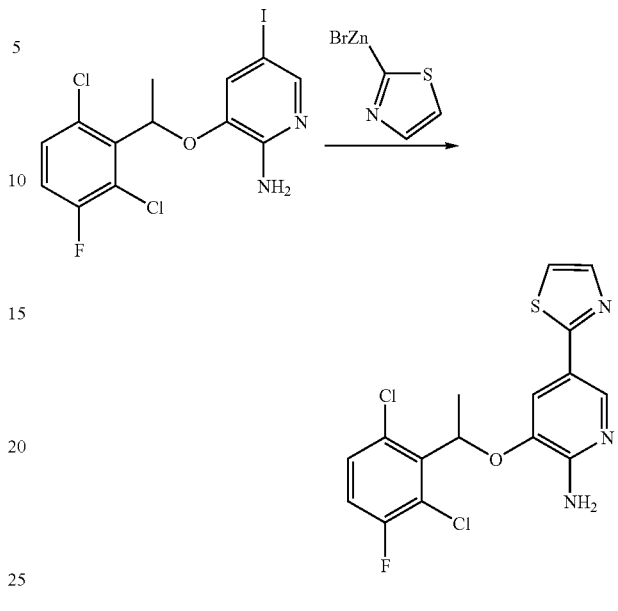

3-(2,6-Dichloro-3-fluoro-benzyloxy)-5-thiazol-2-yl-pyridin-2-ylamine: To a microwave tube equipped with a stir bar was added the iodo-pyridyl starting material (300 mg, 0.702 mmol), tetrakis(triphenylphosphine) palladium (0) (40 mg, 5 mol %) and tetrahydrofuran (anhydrous, 6 mL). The vial was capped and purged with nitrogen for 5 minutes. 2-Thiazolylzinc bromide (0.5 M in THF, 1.4 mmol, 2.8 mL) was then added via syringe. The vial was heated to 120° C. in the microwave for 10 minutes. TLC (1:1 ethyl actetate:methylene chloride) showed a large amount of starting material remaining. Additional 2-thiazolylzinc bromide (0.5 M in THF, 500 µL) was added and the vial was heated to 120° C. in the microwave for 20 minutes. TLC (1:1 ethyl actetate:methylene chloride) showed a large amount of starting material still remaining. Additional 2-thiazolylzinc bromide (0.5 M in THF, 500 µL) was added and the vial was heated to 120° C. in the microwave for 60 minutes. TLC (1:1 ethyl actetate:methylene chloride) still showed a large amount of starting material still remaining but also had become very messy. The vial contents were poured into a sat. NH$_4$Cl solution (10 mL) and this solution extracted with ethyl acetate (2×30 mL). The combined ethyl acetate layers were dried over Na$_2$SO$_4$, filtered and concentrated in vacuo. The crude product was loaded onto a 10 g prepacked silica gel column and 1:1 ethyl acetate:methylene chloride used to elute the desired product. (40 mg, 15%).

Procedure 38: using Example I-652

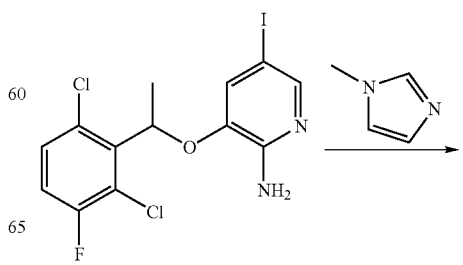

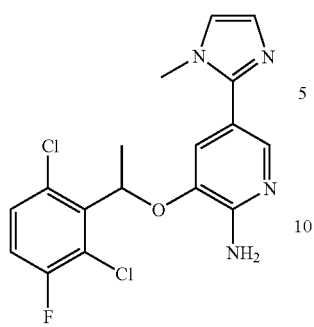

3-[1-(2,6-Dichloro-3-fluoro-phenyl)-ethoxy]-5-(1-methyl-1H-imidazol-2-yl)-pyridin-2-ylamine: N-methyl imidazole (92 mg, 1.1 mmol) was dissolved in tetrahydrofuran (anhydrous, 4 mL) in a 50 mL round bottom flask. The flask was cooled with a dry-ice/acetone bath under nitrogen atmosphere. N-butyl lithium (2.5 M, 562 µL, 1.4 mmol) was added via syringe in 100 µL portions over 5 minutes. The reaction was stirred at −70° C. for 30 minutes. Solid zinc chloride (anhydrous, 383 mg, 2.8 mmol) was added and the reaction stirred for 15 minutes. The ice bath was then removed and the reaction allowed to warm to room temperature. Once all of the zinc chloride was in solution and the reaction at room temperature, iodo scaffold (400 mg, 0.936 mmol) was added in tetrahydrofuran (anhydrous, 4 mL), followed by tetrakis (triphenylphosphine) palladium (0) (108 mg, 10 mol %) and the reaction heated to reflux. The reaction was monitored by LC/MS until all of the starting iodo scaffold was consumed. The reaction was allowed to cool and then diluted with a sat. NH₄Cl solution (20 mL). This solution was extracted with ethyl acetate (2×50 mL). The combined ethyl acetate layers were dried over Na₂SO₄, filtered and concentrated in vacuo. The crude product was loaded onto a 10 g prepacked silica gel column and 10% methanol:ethyl acetate was used to elute the desired product (25 mg, 7%).

General Procedure 39: using Example I-657

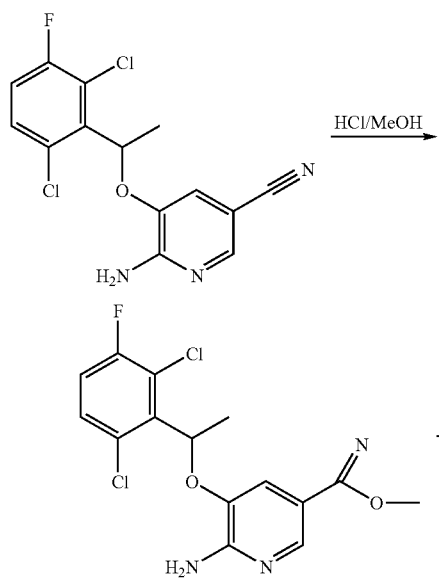

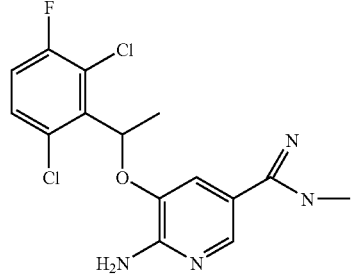

To 6-Amino-5-[1-(2,6-dichloro-3-fluoro-phenyl)-ethoxy]-nicotinonitrile (400 mg, 1.23 mmol) in 70 mL dry methanol at 0° C. was bubbled HCl gas for 3 minutes. Stirred overnight at 3° C. Removed volatiles and washed the solids with diethyl ether to yield quantitatively the imidate. To 200 mg of the imidate in 4 mL methanol at 0° C. was added 2N methylamine in THF (837 µL). Let stir at 0° C. for about 1 hr then let warm to rt overnight. The volatiles were removed and the residue was chromatographed with 10-20% methanol/dichloromethane to yield 70 mg of product.

General Procedure 40:

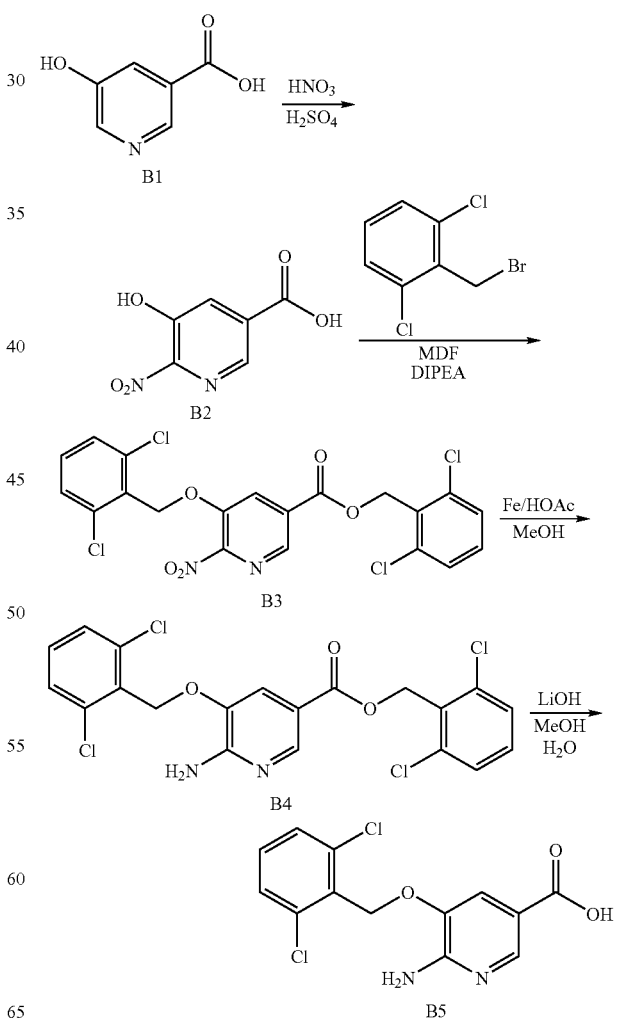

1. 6-Nitro-5-hydroxynicotinic acid (B2): To a solution of 5-hydroxynicotinic acid (B1) (7.0 g, 50 mmol) in concentrated $H_2SO_4$ was added 9 mL of fuming $HNO_3$ (90%) (9 mL). The reaction mixture was stirred at 55-60° C. in a sealed tube for four days. The mixture was then poured into ice and the pH was adjusted to 3 with 50% NaOH. $MgSO_4$ was added to saturate the aqueous mixture, which was then extracted with isopropyl alcohol (4×45 mL). After the removal of isopropyl alcohol under reduced pressure, 5.93 g (64% yield) of B2 was obtained as a yellow solid. MS (APCI), (M+H)+ 185. $^1$HNMR (DMSO-d6) δ 8.01 (d, 1H, Ar—H), 8.41(d, 1H, Ar—H).

2. 2,6-Dichlorobenzyl-6-nitro-5-[(2,6-dichlorobenzyl)oxy]nicotinate (B3): 6-nitro-5-hydroxynicotinic acid (B2) (3.4 g, 18.5 mmol), 2,6-dichlorobenzyl bromide (8.88 g, 37 mmol), DIPEA (5.5 g, 42.5 mmol) were dissolved in DMF (25 mL) in a 250 mL round bottomed flask and the reaction was stirred at room temperature for 4.5 hr and then concentrated under reduced pressure. The resulting mixture was poured into ice and the filtered. The solid collected was dried under reduced pressure to give 4.25 g (46% yield) of B3. MS (APCI) (M+H)+ 503. $^1$HNMR (DMSO-d6) δ 5.47 (s, 2H, $ArCH_2O$), 5.71 (s, 2H, $ArCH_2O$), 7.24-7.43 (m, 6H, Ar—H), 8.26(d, 1H, Ar—H), 8.66(d, 1H, Ar—H).

3. 2,6-Dichlorobenzyl-6-amino-5-[(2,6-dichlorobenzyl)oxy]nicotinate (B4): A mixture of 2,6-dichlorobenzyl-6-nitro-5-[(2,6-dichlorobenzyl)oxy]nicotinate (B3) (5.5 g, 10.96 mmol), iron powder (0.92 g, 16.43 mmol), glacial acetic acid (20 mL) and methanol (17 mL) was stirred at 85° C. for three hr. The reaction mixture was concentrated to near dryness, and ammonium hydroxide (30%) was added to neutralize the mixture. Minimum amount of DMF was added to dissolve the reaction mixture, which was purified by flash column chromatograph (eluent:EtOAc-EtOH, 9:1) to give 4.5 g (87%) of B4 as a pale yellow solid. MS (APCI) (M+H)+ 473.

4. 6-Amino-5-[(2,6-dichlorobenzyl)oxy]nicotinic acid (B5): A mixture of 2,6-dichlorobenzyl-6-amino-5-[(2,6-dichlorobenzyl)oxy]nicotinate (B4) (3.5 g, 7.4 mmol), lithium hydroxide (0.41 g, 17 mmol), water (22 mL) and methanol (30 mL) was stirred and reflux at 85° C. for 5 hr. The mixture was concentrated to dryness under reduced pressure. The resulting residue was dissolved in water, extracted with a mixture of $Et_2O$/hexane (1:1, 4×25 mL), neutralized with 1N HCl to form white precipitation, which was filtered and dried under reduced pressure to provide 1.83 grams (79%) of B5 as a white solid. MS (APCI) (M+H)+ 313. $^1$HNMR (DMSO-d6) δ 5.26 (s, 2H, $ArCH_2O$), 6.37 (s, 2H, $NH_2$), 7.43-7.48 (t, 1H, Ar—H), 7.54 (s, 2H, Ar—H), 7.56 (s, 1H, Ar—H), 8.18 (s, 1H, Ar—H).

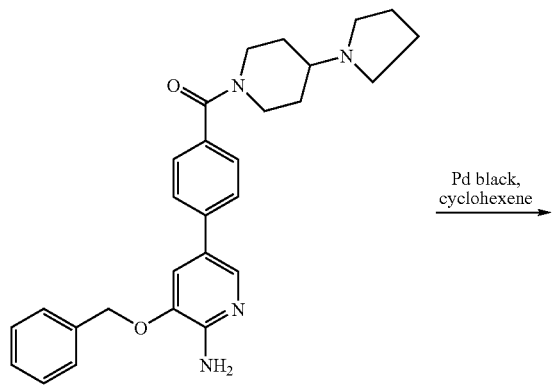

→ Pd black, cyclohexene

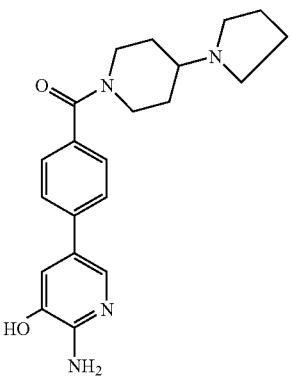

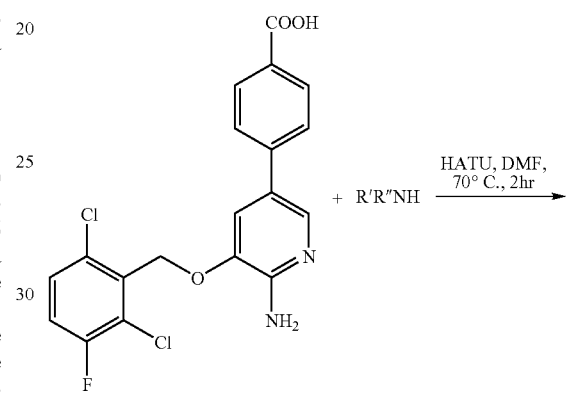

+ R'R"NH → HATU, DMF, 70° C., 2hr

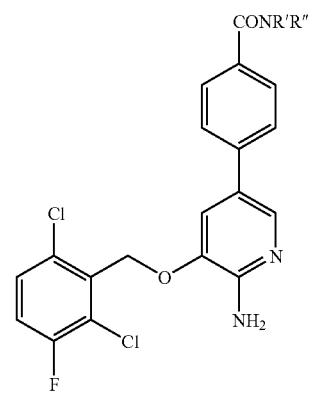

To an array of 400 μL of 0.2 M solution of different amines in DMF in a 96-well plate was added 400 μL (0.2 M in DMF) of 4-[6-amino-5-(2,6-dichloro-3-fluoro-benzyloxy)-pyridin-3-yl]-benzoic acid, 80 μL of triethylamine (1M in DMF) and 160 μL of HATU (0.5 M in DMF) and the reactions were stirred at 70° C. for 2 hr. The solvent was removed using the SpeedVac apparatus and the crude reaction mixtures were redissolved in DMSO and transferred using a liquid handler to a 1 mL 96-well plate to give a final theoretical concentration of ~10 mM. The reactions were analyzed and positive product identification was made using LC/MS. The mother stock solution was diluted to 50 nM and assayed for percent inhibition of c-MET at 50 nM.

General Procedure 41:

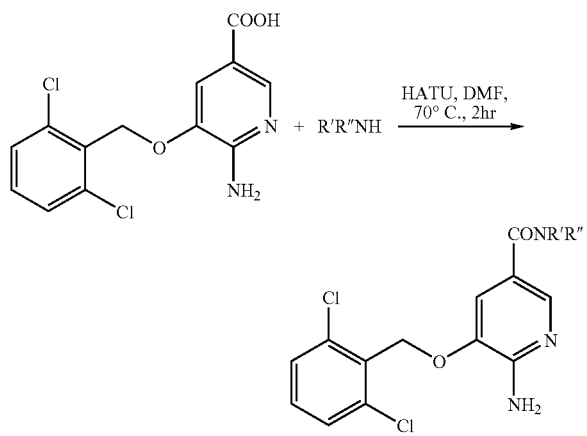

To an array of 400 μL of 0.2 M solution of different amines in DMF in a 96-well plate was added 400 μL (0.2 M in DMF) of 6-Amino-5-[(2,6-dichlorobenzyl)oxy]nicotinic acid, 80 μL of triethylamine (1M in DMF) and 160 μL of HATU (0.5 M in DMF) and the reactions were stirred at 70° C. for 2 hr. The solvent was removed using the SpeedVac apparatus and the crude reaction mixtures were redissolved in DMSO and transferred using a liquid handler to a 1 mL 96-well plate to give a final theoretical concentration of ~10 mM. The reactions were analyzed and positive product identification was made using LC/MS. The mother stock solution was diluted to 1 μM and assayed General Procedure 42:

[4-(6-Amino-5-hydroxy-pyridin-3-yl)-phenyl]-(4-pyrrolidin-1-yl-piperidin-1-yl)-methanone: To a solution of [4-(6-Amino-5-benzyloxy-pyridin-3-yl)-phenyl]-(4-pyrrolidin-1-yl-piperidin-1-yl)-methanone (3.67 g, 8.1 mmol) in 100 ml ethanol was added 25 ml cyclohexne and 367 mg palladium black. Reluxed overnight. The solution was filtered and the volatiles were removed. To the residue was added 60 mL of MeOH, 20 mL cyclohexene and 350 mg Pd black. Refluxed overnight. Filtered and removed volatiles, resuspended in methanol, added 350 mg Pd black and hydrogenated at 1 atm overnight (pressure reactors all busy). Filtered and isolated 3.0 grams of a solid foam. $^1$H NMR (400 MHz, DMSO-D6) δ ppm 7.82 (d, J=2.02 Hz, 1H) 7.58 (d, J=8.34 Hz, 2H) 7.41 (d, J=8.34 Hz, 2H) 7.12 (d, J=2.02 Hz, 1H) 5.74 (s, 2H) 3.33 (s, 5H) 3.08 (s, 2H) 1.95 (m, 8H) 1.49 (s, 2H). LC/MS(APCI) 367 m/e (M+1).

To an array of 10×75 mm test tubes were added [4-(6-Amino-5-hydroxy-pyridin-3-yl)-phenyl]-(4-pyrrolidin-1-yl-piperidin-1-yl)-methanone (0.2 M in DMF, 80 mmol, 1.0 eq.), Cs$_2$CO$_3$ (2 M, 160 μmol, 2.0 equiv) and different alkyl halides (0.2 M in DMF, 88 μmol, 1.1 eq.). The reactions were stirred at room temperature overnight. In order to separate the inorganic salts, the resulting suspension was evaporated and DMF (625 μL) was added. After agitation, the mixture was centrifuged to settle the solid residue, and the supernatant was transferred to a new 10×75 mm test tube. The reactions were analyzed and positive product identification was made using LC/MS. The mother stock solution was diluted to 1 μM and assayed.

General Procedure 43:

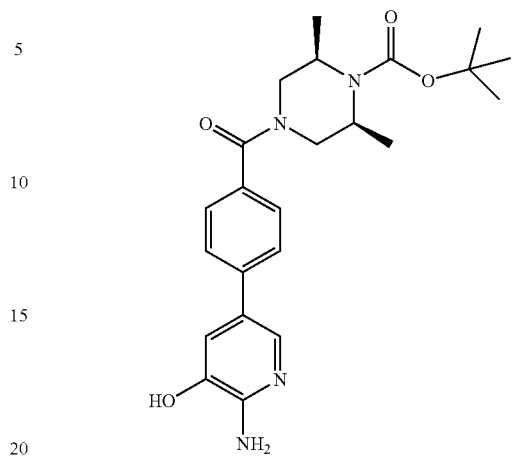

(2R,6S)-4-[4-(6-Amino-5-hydroxy-pyridin-3-yl)-benzoyl]-2,6-dimethyl-piperazine-1-carboxylic acid tert-butyl ester: See general procedure IG. Yield 83.5%. $^1$H NMR (400 MHz, DMSO-D6) δppm 7.81 (d, J=2.27 Hz, 1H) 7.57 (d, J=8.34 Hz, 2H) 7.41 (d, J=8.34 Hz, 2H) 7.12 (d, J=2.02 Hz, 1H) 5.70

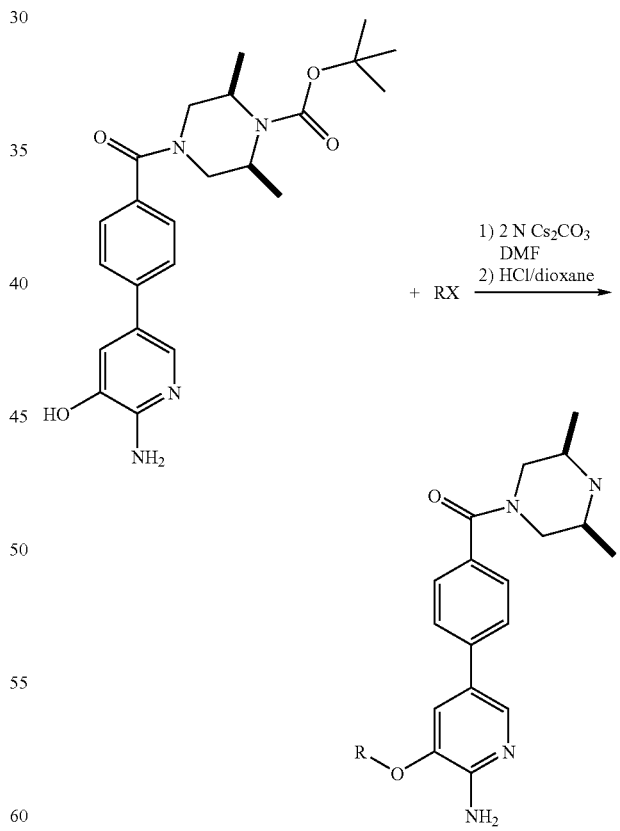

(s, 2H) 4.07 (s, 2H) 3.31 (s, 3H) 1.39 (s, 10H) 1.03-1.14 (m, 7H)

To an array of 10×75 mm test tubes were added (4-(6-Amino-5-hydroxy-pyridin-3-yl)-phenyl]-(4-pyrrolidin-1-yl-piperidin-1-yl)-methanone (0.2 M in DMF, 80 μmol, 1.0 eq.), Cs$_2$CO$_3$ (2 M, 160 µmol, 2.0 equiv) and different alkyl halides (0.2 M in DMF, 88 µmol, 1.1 eq.). The reactions were stirred at room temperature overnight. In order to separate the inorganic salts, the resulting suspension was evaporated and DMF (625 µL) was added. After stirring, the mixture was centrifuged to settle the solid residue, and the supernatant was transferred to a new 10×75 mm test tube. The solid residues were extracted with more DMF (400 µL) and the extracts were combined with the first organic layer. The DMF was evaporated, and HCl (4 M in dioxane, 2.5 mmol, 31 eq.) was added to the reaction mixture in the receiving test tube. The reaction mixture was stirred at room temperature for 3 hr. The reactions were analyzed and positive product identification was made using LC/MS. The mother stock solution was diluted to 1 µM and assayed.

Example I(a)

1. To a stirred solution of Cs$_2$CO$_3$ (11.63 g, 35.69 mmol) in DMF (180 mL) under a N$_2$ atmosphere containing 3-hydroxy-4-nitro-pyridine (5 g, 35.69 mmol) was added 2,6-dichlorobenzyl bromide (8.56 g, 35.69 mmol). The mixture was stirred for 6 h at ambient temperature. The reaction was then diluted with EtOAc (400 mL) and partitioned with H$_2$O (100 mL). The aqueous layer was extracted with EtOAc (2×50 mL). The organic layers were then combined and washed with H$_2$O (2×50 mL) and brine (1×50 mL). The organics were dried over Na$_2$SO$_4$, filtered and concentrated to dryness under vacuum to yield 3-(2,6-dichloro-benzyloxy)-2-nitro-pyridine (10.5 g, 98.4%) as a white solid.

2. To a stirred mixture of AcOH (650 mL) and EtOH (500 mL) was suspended 3-(2,6-dichloro-benzyloxy)-2-nitro-pyridine (37.4 g, 0.11 mol) and iron chips (69.4 g, 0.11 mol). The reaction was heated slowly to reflux and allowed to stir for 1 hr. The reaction was cooled to room temperature then filtered through a pad of celite. The resulting filtrate was neutralized with conc. NH$_4$OH (600 mL) and then extracted with EtOAc (3×500 mL). The combined organic extracts were washed with saturated NaHCO$_3$ (2×100 mL), H$_2$O (2×100 mL) and brine (1×100 mL) then dried (Na$_2$SO$_4$), filtered and concentrated to dryness under vacuum to yield 3-(2,6-dichloro-benzyloxy)-pyridin-2-ylamine (32.4 g, 0.11 mol, 99%) as a light yellow solid. $^1$H NMR (400 MHz, DMSO-d$_6$) δ 7.56 (m, 3H), 7.46 (dd, 2H), 7.36 (d, 1H), 6.62 (dd, 1H), 6.18 (br s, 2H, NH$_2$), 5.24 (s, 2H); MS m/z 270 [M+1].

3. A stirring solution of 3-(2,6-dichloro-benzyloxy)-pyridin-2-ylamine (32.4 g, 0.11 mol) in acetonitrile was cooled to 0° C. using an ice bath. To this solution was added N-bromosuccinimide (19.5 g, 0.11 mol) portionwise. The reaction was stirred at 0° C. for 15 min. The reaction was concentrated to dryness under vacuum. The resulting dark oil was dissolved in EtOAc (500 mL) and partitioned with H$_2$O (250 mL). The organic was then washed with sat'd NaHCO$_3$ (2×200 mL) and brine (1×200 mL). Activated charcoal was added to the organic layer and warmed to reflux. The solution was then cooled to room temperature and filtered through a pad of celite. The organic was then concentrated to dryness under vacuum to one third the original volume. The solids were then filtered off to yield 5-bromo-3-(2,6-dichloro-benzyloxy)-pyridin-2-ylamine (22.0 g, 0.07 mol, 64%) as a tan solid. The remaining filtrate was concentrated under vacuum to yield crude 5-bromo-3-(2,6-dichloro-benzyloxy)-pyridin-2-ylamine (12.19, 0.04 mol, 35%) as a brown solid.

Example I(b)

3-Benzyloxy-5-bromo-pyridin-2-ylamine was prepared following procedure 1 from 3-benzyloxy-pyridin-2-ylamine as a tan solid in 65% yield.

Example I(c)

5-Bromo-3-(2,6-difluoro-benzyloxy)-pyridin-2-ylamine was prepared following procedure 1. 3-(2,6-difluoro-benzyloxy)-2-nitro-pyridine was prepared in 99% yield. $^1$H NMR (400 MHz, DMSO-d$_6$) δ 8.14 (m, 2H), 7.79 (dd, 1H), 7.52 (m, 1H), 7.16 (m, 2H), 5.37 (s, 2H); MS m/z 266 [M+]. 3-(2,6-Difluoro-benzyloxy)-pyridin-2-ylamine was prepared in 100% yield. $^1$H NMR (400 MHz, DMSO-d$_6$) δ 7.88 (s, 2H), 7.64 (dd, 1H), 7.57 (m, 2H), 6.84 (dd, 1H), 5.24 (s, 2H); MS m/z 237 [M+1]. 5-Bromo-3-(2,6-difluoro-benzyloxy)-pyridin-2-ylamine was prepared in 91% yield.

Example I(d)

5-Bromo-3-(2-bromo-benzyloxy)-pyridin-2-ylamine was prepared following procedure 1. 3-(2-bromo-benzyloxy)-2-nitro-pyridine intermediate was prepared in 99% yield as a white solid. 3-(2-bromo-benzyloxy)-pyridin-2-ylamine was prepared in 100% yield as a solid. 5-Bromo-3-(2-bromo-benzyloxy)-pyridin-2-ylamine was obtained in 37% yield as a tan solid.

Example I(e)

5-Bromo-3-(2-chloro-6-fluoro-benzyloxy)-pyridin-2-ylamine was prepared following procedure 1. 3-(2-chloro-6-fluoro-benzyloxy)-2-nitro-pyridine was prepared in 90% yield as an off-white solid. $^1$H NMR (400 MHz, DMSO-d$_6$) δ 8.15 (m, 2H), 7.80 (m, 1H), 7.50 (m, 1H), 7.40 (m, 1H), 7.30 (m, 1H), 5.39 (s, 2H). 3-(2-chloro-6-fluoro-benzyloxy)-pyridin-2-ylamine was prepared in 88% yield as a tan solid. $^1$H NMR (400 MHz, DMSO-d$_6$) δ 7.70-7.15 (m, 5H), 6.45 (m, 1H), 5.45 (br s, 2H), 5.06 (s, 2H). 5-Bromo-3-(2-chloro-6-fluoro-benzyloxy)-pyridin-2-ylamine was prepared in 81% yield.

Example I(f)

5-Bromo-3-(2-chloro-4-fluoro-benzyloxy)-pyridin-2-ylamine was prepared following procedure 1. 3-(2-chloro-4-fluoro-benzyloxy)-2-nitro-pyridine was prepared in 91% yield as an off-white solid. $^1$H NMR (400 MHz, DMSO-d$_6$) δ 8.08 (m, 2H), 7.75 (m, 1H), 7.63 (m, 1H), 7.55 (m, 1H), 7.25 (m, 1H), 5.45 (s, 2H). 3-(2-chloro-4-fluoro-benzyloxy)-pyridin-2-ylamine was prepared in 100% yield as a tan solid. $^1$H NMR (400 MHz, DMSO-d$_6$) δ 7.70 (m, 2H), 7.47 (m, 1H), 7.20 (m, 1H), 7.08 (m, 1H), 6.45 (m, 1H), 5.62 (br s, 2H), 5.08 (s, 2H). 5-Bromo-3-(2-chloro-4-fluoro-benzyloxy)-pyridin-2-ylamine was prepared in 63% yield.

Example I(g)

5-Bromo-3-(2,4-dichloro-benzyloxy)-pyridin-2-ylamine was prepared following procedure 1. 3-(2,4-Dichloro-benzyloxy)-2-nitro-pyridine was prepared in 96% yield as an off-white solid. $^1$H NMR (400 MHz, DMSO-d$_6$) δ 8.05-7.50 (m, 6H), 5.39 (s, 2H); MS (m/z) 299 (M+1). 3-(2,4-Dichloro-benzyloxy)-pyridin-2-ylamine was prepared in 98% yield as a tan solid. $^1$H NMR (400 MHz, DMSO-d$_6$) δ 7.65-6.25 (m, 6H), 5.85 (br s, 2H), 5.06 (s, 2H). 5-Bromo-3-(2,4-dichloro-benzyloxy)-pyridin-2-ylamine was prepared in 65% yield.

Example I(h)

2-(2-Amino-5-bromo-pyridin-3-yloxymethyl)-benzonitrile was prepared following procedure 1. 2-(2-Nitro-pyridin-3-yloxymethyl)-benzonitrile was prepared in 91% yield as an off-white solid. $^1$H NMR (400 MHz, DMSO-$d_6$) δ 8.15-7.55 (m, 1H), 5.50 (s, 2H).2-(2-Amino-pyridin-3-yloxymethyl)-benzonitrile was prepared in 86% yield as a tan solid. $^1$H NMR (400 MHz, DMSO-$d_6$) δ 7.95-6.45 (m, 7H), 5.65 (br s, 2H), 5.20 (s, 2H). 2-(2-Amino-5-bromo-pyridin-3-yloxymethyl)-benzonitrile was prepared in 77% yield.

Example I(i)

5-Bromo-3-(2-trifluoromethyl-benzyloxy)-pyridin-2-ylamine was prepared following procedure 1. 3-(2-trifluoromethyl-benzyloxy)-2-nitro-pyridine was prepared in 92% yield as an off-white solid. $^1$H NMR (400 MHz, DMSO-$d_6$) δ 8.05-7.58 (m, 7H), 5.45 (s, 2H). 3-(2-trifluoromethyl-benzyloxy)-pyridin-2-ylamine was prepared in 80% yield as a tan solid. 5-Bromo-3-(2-chloro-4-fluoro-benzyloxy)-pyridin-2-ylamine was prepared in 43% yield as a solid.

Example I(j)

5-Bromo-3-(4-tert-butyl-benzyloxy)-pyridin-2-ylamine was prepared following procedure 1. 3-(4-tert-butyl-benzyloxy)-2-nitro-pyridine was prepared in 80% yield as an oil. $^1$H NMR (400 MHz, DMSO-$d_6$) δ 8.10-7.30 (m, 7H), 5.30 (s, 2H), 1.25 (s, 9H). 3-(4-tert-Butyl-benzyloxy)-pyridin-2-ylamine was prepared in 100% yield as a tan solid. $^1$H NMR (400 MHz, DMSO-$d_6$) δ 7.45-6.25 (m, 7H), 5.58 (br s, 2H), 5.05(s, 2H), 1.25 (s, 9H). 5-Bromo-3-(4-tert-butyl-benzyloxy)-pyridin-2-ylamine was prepared in 55% yield as a solid.

Example I(k)

5-Bromo-3-(2-chloro-benzyloxy)-pyridin-2-ylamine was prepared following procedure 1. 3-(2-Chloro-benzyloxy)-2-nitro-pyridine was prepared in 89% yield as an off-white solid. $^1$H NMR (400 MHz, DMSO-$d_6$) δ 8.10-7.40 (m, 7H), 5.40 (s, 2H). 3-(2-Chloro-benzyloxy)-pyridin-2-ylamine was prepared in 100% yield as a tan solid. $^1$H NMR (400 MHz, DMSO-$d_6$) δ 8.65-6.45 (m, 7H), 5.62 (br s, 2H), 5.10(s, 2H). 5-Bromo-3-(2-chloro-benzyloxy)-pyridin-2-ylamine was prepared in 22% yield as a solid.

Example I(l)

5-Bromo-3-(2-chloro-3,6-difluoro-benzyloxy)-pyridin-2-ylamine was prepared following procedure 1. 3-(2-chloro-3,6-difluoro-benzyloxy)-2-nitro-pyridine intermediate was prepared in 99% yield as an off white solid. $^1$H NMR (CDCl$_3$, 300 MHz) δ5.31 (s, 2H), 7.02-7.09 (dt, 1H, J, 4, 8), 7.17-7.23 (dt, 1H, J, 4.5, 8.4), 7.54-7.58 (dd, 1H, J, 4.5, 8.4), 7.71-7.68 (dd, 1H, J, 1.21, 8.4), 8.14-8.16 (dd, 1H, J, 1.23, 4.5). 3-(2-chloro-3,6-difluoro-benzyloxy)-pyridin-2-ylamine was prepared in 100% yield as a light yellow solid. $^1$H NMR (CDCl$_3$, 300 MHz) δ 4.6-4.8 (brs, 2H), 5.2 (s, 2H), 7.0-7.08 (dt, 1H, J, 4.1, 9.0), 7.09-7.12 (dd, 1H, J, 1.0, 7.8), 7.15-7.22 (dt, 1H, J, 4.8, 8.0), 7.69-7.71 (dd, 1H, J, 1.2, 5.1). 5-Bromo-3-(2-chloro3,6-difluoro-benzyloxy)-pyridin-2-ylamine was obtained in 64% yield as a tan solid.

Example I(m)

5-Bromo-3-(3-fluoro-2-trifluoromethyl-benzyloxy)-pyridin-2-ylamine was prepared following procedure 1 starting from 3-hydroxy-4-nitro-pyridine and 1-bromomethyl-3-fluoro-2-trifluoromethyl-benzene.

Example I(n)

1. 2,6-Dichloro-3-fluoroacetophenone (15 g, 0.072 mol) was stirred in THF (150 mL, 0.5M) at 0° C. using an ice bath for 10 min. Lithium aluminum hydride (2.75 g, 0.072 mol) was slowly added. The reaction was stirred at ambient temperature for 3 hr. The reaction was cooled in ice bath, and water (3 mL) was added drop wisely followed by adding 15% NaOH (3 mL) slowly. The mixture was stirred at ambient temperature for 30 min. 15% NaOH (9 mL), MgSO$_4$ were added and the mixture filtered to remove solids. The solids were washed with THF (50 mL) and the filtrate was concentrated to give 1-(2,6-Dichloro-3-fluoro-phenyl)-ethanol (14.8 gm, 95% yield) as a yellow oil. $^1$H-NMR (400 MHz, DMSO-$d_6$) δ 1.45 (d, 3H), 5.42 (m, 2H), 7.32 (m, 1H), 7.42 (m, 1H).

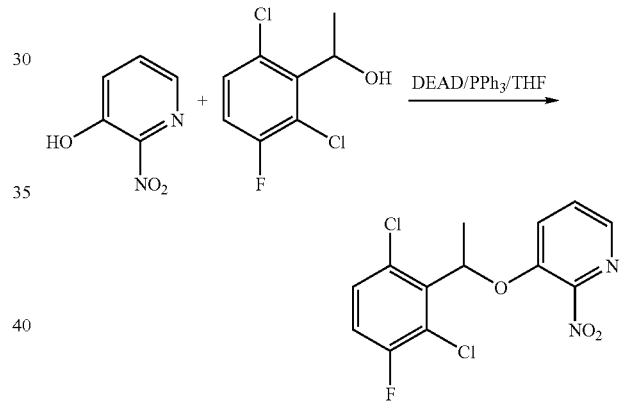

2. To a stirred solution of triphenyl phosphine (8.2 g, 0.03 mol) and DEAD (13.65 mL of a 40% solution in toluene) in THF (200 mL) at 0° C. was added a solution of 1-(2,6-dichloro-3-fluoro-phenyl)-ethanol (4.55 g, 0.021 mol) and 3-hydroxy-nitropyridine (3.35 g, 0.023 mol) in THF (200 mL). The resulting bright orange solution was stirred under a nitrogen atmosphere at ambient temperature for 4 hours at which point all starting materials had been consumed. The solvent was removed, and the crude material was dry loaded onto silica gel, and eluted with ethyl acetate-hexanes (20:80) to yield 3-(2,6-dichloro-3-fluoro-benzyloxy)-2-nitro-pyridine (6.21 g, 0.021 mol, 98%) as a pink solid. $^1$H NMR (CDCl$_3$, 300 MHz) δ1.8-1.85 (d, 3H), 6.0-6.15 (q, 1H), 7.0-7.1 (t, 1H), 7.2-7.21 (d, 1H), 7.25-7.5 (m, 2H), 8.0-8.05 (d, 1H).

3. 3-(2,6-dichloro-3-fluoro-benzyloxy)-pyridin-2-ylamine was prepared following procedure 1. To a stirred mixture of AcOH (650 mL) and EtOH (500 mL) was suspended 3-(2,6-dichloro-3-fluoro-benzyloxy)-2-nitro-pyridine (9.43 g, 0.028 mol) and iron chips (15.7 g, 0.28 mol). The reaction was heated slowly to reflux and allowed to stir for 1 hr. The reaction was cooled to room temperature then diethyl ether (500 mL) and water (500 mL) was added. The solution was carefully neutralized by the addition of sodium carbonate. The combined organic extracts were washed with sat'd NaHCO₃ (2×100 mL), H₂O (2×100 mL) and brine (1×100 mL) then dried (Na₂SO₄), filtered and concentrated to dryness under vacuum to yield 3-(2,6-dichloro-3-fluoro-benzyloxy)-pyridin-2-ylamine (9.04 g, 0.027 mol, 99%) as a light pink solid. $^1$H NMR (CDCl₃, 300 MHz) δ 1.8-1.85 (d, 3H), 4.9-5.2 (brs, 2H), 6.7-6.84 (q, 1H), 7.0-7.1 (m, 1H), 7.2-7.3 (m, 1H), 7.6-7.7 (m, 1H).

4. 5-bromo-3-(2,6-dichloro-3-fluoro-benzyloxy)-pyridin-2-ylamine was prepared following procedure 1. A stirring solution of 3-(2,6-dichloro-3-fluoro-benzyloxy)-pyridin-2-ylamine (9.07 g, 0.03 mol) in acetonitrile was cooled to 0° C. using an ice bath. To this solution was added NBS (5.33 g, 0.03 mol) portionwise. The reaction was stirred at 0° C. for 15 min. The reaction was concentrated to dryness under vacuum. The resulting dark oil was dissolved in EtOAc (500 mL), and purified via silica gel chromatography. The solvents were then removed in vacuo to yield 5-bromo-3-(2,6-dichloro-3-fluoro-benzyloxy)-pyridin-2-ylamine (5.8 g, 0.015 mol, 51%) as a white crystalline solid.

Example I(o)

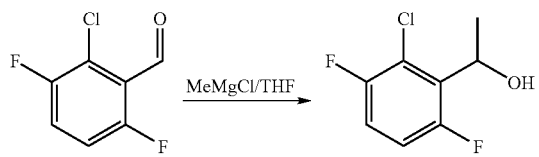

1. 2-Chloro-3,6-difluorobenzaldehyde (1.0 molar equivalent) was dissolved in THF (0.2M) and stirred at 0° C. for 5 min. The corresponding methylmagnesium chloride solution (1.1 molar equivalent) was added The reaction was warmed up gradually to ambient temperature and stirred for 2 hr. Methanol, and 1N HCl was added to the mixture and diluted with ethyl acetate. The mixture was washed with water, brine, dried over MgSO₄, filtered, and concentrated to give 1-(2-chloro-3,6-difluoro-phenyl)-ethanol as oil. $^1$H NMR (400 MHz, DMSO-d6) δ 1.42 (d, 3H), 5.21 (m, 1H), 5.42 (m, 1H), 7.09 (m, 1H), 7.18 (m, 1H).

2. 5-bromo-3-[1-(2-chloro-3,6-difluoro-phenyl)-ethoxy]-pyrazin-2-ylamine was prepared following the same procedure as Example I(n) starting from 1-(2-chloro-3,6-difluoro-phenyl)-ethanol and 3-hydroxy-nitropyridine.

Example II(a)

To an ice cooled solution of (2,6-dichloro-phenyl)-methanol (5 g, 28.2 mmol) in anhydrous tetrahydrofuran (200 mL) was added sodium hydride (1.13 g, 28.2 mmol, 60% disp.) slowly under nitrogen atmosphere. After stirring for 30 minutes, 3,5-dibromo-pyrazin-2-ylamine (7.08 g, 28.2 mmol) in anhydrous tetrahydrofuran (50 mL) was added via an addition funnel. Once the addition was complete the ice bath was removed and the reaction was refluxed under nitrogen and monitored by reversed phase HPLC. After 18 hr HPLC showed that the majority of the starting 3,5-dibromo-pyrazin-2-ylamine had been consumed and the reaction was allowed to cool to room temperature. The reaction mixture was concentrated in vacuum until 50 mL remained. The mixture was diluted with ethyl acetate (200 mL) and extracted with 50% brine (2×200 mL). The organic layer was dried over anhydrous magnesium sulfate and concentrated in vacuum. The crude product was purified using a silica gel column eluting with 1:1 ethyl acetate/dichloromethane to yield 5-bromo-3-(2,6-dichloro-benzyloxy)-pyrazin-2-ylamine as a white solid (8.17 g, 83% yield).

Example II(b)

5-Bromo-3-(2-chloro-3,6-difluoro-benzyloxy)-pyrazin-2-ylamine was prepared following procedure 2 from (2-chloro-3,6-difluoro-phenyl)-methanol and 3,5-dibromo-pyrazin-2-ylamine.

Example II(c)

1. 2-Chloro-3,6-difluorobenzaldehyde (1.0 molar equivalent) was dissolved in THF (0.2M) and stirred at 0° C. for 5 min. The corresponding methylmagnesium chloride solution (1.1 molar equivalent) was added. The reaction was warmed up gradually to ambient temperature and stirred for 2 hr. Methanol and 1N HCl were added to the mixture and diluted with ethyl acetate. The mixture was washed with water, brine, dried over MgSO₄, filtered, and concentrated to give 1-(2-chloro-3,6-difluoro-phenyl)-ethanol as oil. $^1$H NMR (400 MHz, DMSO-d₆) δ 1.42 (d, 3H), 5.21 (m, 1H), 5.42 (m, 1H), 7.09 (m, 1H), 7.18 (m, 1H).

2. 5-bromo-3-[1-(2-chloro-3,6-difluoro-phenyl)-ethoxy]-pyrazin-2-ylamine was prepared following procedure 2 from 1-(2-chloro-3,6-difluoro-phenyl)-ethanol and 3,5-dibromo-pyrazin-2-ylamine.

Example II(d)

1. 1-(2-Chloro-3,6-difluoro-phenyl)-2-methyl-propan-1-ol was prepared following the procedure of Example II(c) using isopropylmagnesium chloride. $^1$H NMR (400 MHz, DMSO-d₆) δ 0.63 (d, 3H), 1.06 (d, 3H), 2.19 (m, 1H), 4.59 (m, 1H), 5.54 (d, 1H), 7.21 (m, 1H), 7.36 (m, 1H).

2. 5-bromo-3-[1-(2-chloro-3,6-difluoro-phenyl)-2-methyl-propoxy]-pyrazin-2-ylamine was prepared following procedure 2 from 1-(2-chloro-3,6-difluoro-phenyl)-2-methyl-propan-1-ol and 3,5-dibromo-pyrazin-2-ylamine.

Example II(e)

1. 2,6-Dichloro-3-fluoroacetophenone (15 g, 0.072 mol) was stirred in THF (150 mL, 0.5M) at 0° C. using an ice bath for 10 min. Lithium aluminum hydride (from Aldrich, 2.75 g, 0.072 mol) was slowly added. The reaction was stirred at ambient temperature for 3 h. The reaction was cooled in ice bath, and water (3 mL) was added drop wisely followed by adding 15% NaOH (3 mL) slowly. The mixture was stirred at ambient temperature for 30 min. 15% NaOH (9 mL), MgSO₄ were added and the mixture filtered to remove solids. The solids were washed with THF (50 mL) and the filtrate was concentrated to give 1-(2,6-Dichloro-3-fluoro-phenyl)-ethanol (14.8 gm, 95% yield) as a yellow oil. $^1$H NMR (400 MHz, DMSO-d₆) δ 1.45 (d, 3H), 5.42 (m, 2H), 7.32 (m, 1H), 7.42 (m, 1H).

2. 5-Bromo-3-[1-(2,6-dichloro-3-fluoro-phenyl)-ethoxy]-pyrazin-2-ylamine was prepared following procedure 2 from 1-(2,6-dichloro-3-fluoro-phenyl)-ethanol and 3,5-dibromo-pyrazin-2-ylamine.

Example II(f)

5-Bromo-3-(3-fluoro-2-trifluoromethyl-benzyloxy)-pyrazin-2-ylamine was prepared following procedure 2 from (3-fluoro-2-trifluoromethyl-phenyl)-methanol and 3,5-di-bromo-pyrazin-2-ylamine.

Example I-1

A mixture of 5-bromo-3-(2,6-dichloro-benzyloxy)-pyridin-2-ylamine (example [(a), 100 mg, 0.29 mmol), 4-(4,4,5,5-tetramethyl-1,3-(2-dioxabordan-2-yl) phenol (86 mg, 0.35 mmol), bis(triphenylphosphine) palladium(II) chloride (8 mg, 0.009 mmol) and sodium carbonate (91 mg, 0.87 mmol) in ethylene glycol dimethyl ether (10 mL) and water (0.5 mL) was heated to reflux under nitrogen for 18 hours. The reaction was cooled to ambient temperature and diluted with ethyl acetate. The mixture was washed with water, brine, dried over $Na_2SO_4$, and purified on silica column to afford 4-[6-amino-5-(2,6-dichloro-benzyloxy)-pyridin-3-yl]-phenol as light pine crystals (89 mg, 85% yield).

Example I-2

1. To a mixture of 4-(4,4,5,5-tetramethyl-1,3-2-dioxabordan-2-yl)phenol (5.00 g, 22.72 mmol) and $Cs_2CO_3$ (16.29 g, 49.98 mmol) in DMF (100 mL) were added 4-(2-chloroethyl)-morpholine hydrochloride (4.65 g, 24.99 mmol) and KI (0.2 g, 0.6 mmol). The mixture was stirred at 65° C. oil bath

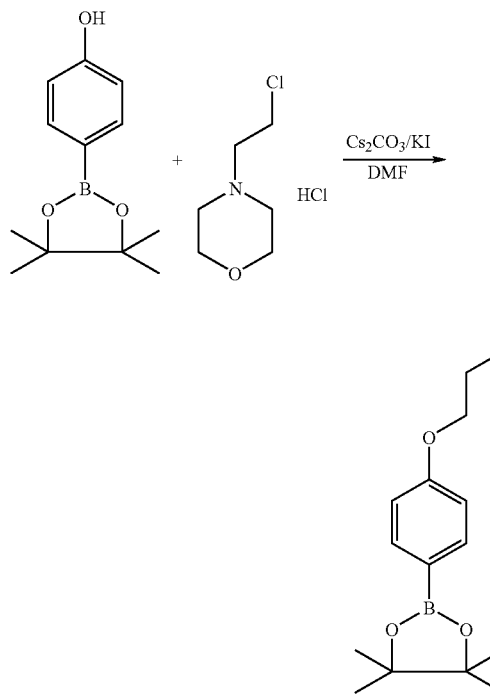

for overnight and then cooled to ambient temperature. The reaction mixture was diluted with ethyl acetate (600 mL), and partitioned with water. The water layer was extracted with ethyl acetate (2×50 mL). The combined ethyl acetate solution was washed with brine (5×100 mL), dried over $Na_2SO_4$, filtered, condensed, and dried in high vacuum to provide 4-{2-[4-(4,4,5,5-tetramethyl-[1,3,2]dioxaborolan-2-yl)-phenoxy]-ethyl}-morpholine (6.8 g, 90% yield) as an off-white solid. $^1$H NMR (400 MHz, DMSO-$d_6$) δ 7.55 (d, 2H), 6.90 (d, 2H), 4.07 (t, 2H), 3.54 (m, 4H), 2.65 (t, 2H), 2.43 (m, 4H).

2. 3-(2,6-Dichloro-benzyloxy)-5-[4-(2-morpholin-4-yl-ethoxy)-phenyl]-pyridin-2-ylamine was prepared from 5-bromo-3-(2,6-dichloro-benzyloxy)-pyridin-2-ylamine (example I(a)) and 4-{2-[4-(4,4,5,5-tetramethyl-[1,3,2]dioxaborolan-2-yl)-phenoxy]-ethyl}-morpholine (prepared in part 1) following procedure 3 as a white solid.

Example I-3

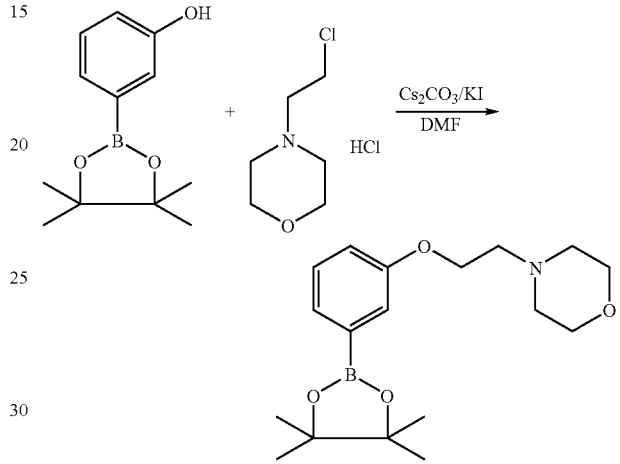

1. 3-{2-[4-(4,4,5,5-tetramethyl-[1,3,2]dioxaborolan-2-yl)-phenoxy]-ethyl}-morpholine was prepared following the same procedure as 4-{2-[4-(4,4,5,5-tetramethyl-[1,3,2]dioxaborolan-2-yl)-phenoxy]-ethyl}-morpholine in Example I-2 using 3-(4,4,5,5-tetramethyl-1,3-2-dioxabordan-2-yl) phenol in 92% yield as a white wax solid. $^1$H NMR (400 MHz, DMSO-$d_6$) δ 7.28 (t, 1H), 7.22 (dt, 1H), 7.14 (d, 1H), 7.04 (ddd, 1H), 4.06 (t, 2H), 3.56 (m, 4H), 2.49 (t, 2H), 2.45 (m, 4H).

2. 3-(2,6-Dichloro-benzyloxy)-5-[3-(2-morpholin-4-yl-ethoxy)-phenyl]-pyridin-2-ylamine was prepared from 5-bromo-3-(2,6-dichloro-benzyloxy)-pyridin-2-ylamine (example I(a)) and 3-{2-[4-(4,4,5,5-tetramethyl-[1,3,2]dioxaborolan-2-yl)-phenoxy]-ethyl}morpholine prepared in part 1 following procedure 3 as a light yellow solid.

Example I-4

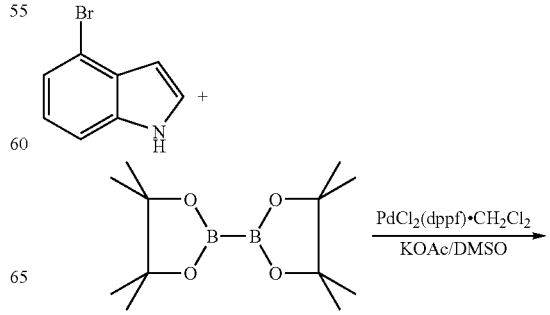

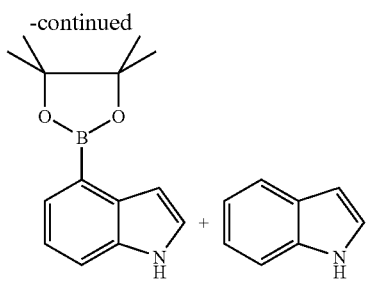

1. To a mixture of 4-bromoindole (9.80 g, 50 mmol), pinacole diborate (13.97 g, 55 mmol), and KOAc (14.72 g, 150 mmol) in DMSO (200 mL) was added palladium catalyst PdCl$_2$(dppf)CH$_2$Cl$_2$ (1.22 g, 1.5 mmol). The system was degassed, and then charged with nitrogen for three times. The mixture was stirred at 80° C. oil bath under nitrogen for 22 hours. TLC showed the complete disappearance of the starting material 4-bromoindole. The mixture was cooled to room temperature, and then poured to water (1 L). The product was extracted with ethyl acetate for three times. The combined extracts were washed by brine for five times to remove DMSO solvent, and then dried over Na$_2$SO$_4$. During the washing step, the catalyst may precipitate out, which was removed by filtration. The ethyl acetate solution was filtered and condensed. The residue was purified on a silica gel column eluting with EtOAc-hexane (9:1). The first fraction provided the side product indole (1.25 g, 21% yield), R$_f$ 0.55 (EtOAc-Hexane 5:1). The second fraction provided 4-(4,4,5,5-Tetramethyl-[1,3,2]dioxaborolan-2-yl)-1H-indole as a white solid (8.01 g, 66%), R$_f$ 0.46 (EtOAc-Hexane 5:1). $^1$H NMR (300 MHz, DMSO-d$_6$): δ11.03 (bs, 1H, N—H)), 7.49 (d, J=7.7 Hz, 1H, H-5), 7.38 (dd, J=0.9 Hz, J=7.0 Hz, 1H, H-7), 7.38 (t, J=2.6 Hz, 1H, H-2), 7.06 (dd, J=7.7 Hz, J=7.0 Hz, 1H, H-6), 6.73 (bd, J 2.2 Hz; 1H, H-3), 1.32 (s, 12H, 4CH$_3$); MS (m/e): 244 (M+H)$^+$.

2. 3-(2,6-dichloro-benzyloxy)-5-(1H-indol-4-yl)-pyridin-2-ylamine was prepared from 5-bromo-3-(2,6-dichloro-benzyloxy)-pyridin-2-ylamine (Example I(a)) and 4-(4,4,5,5-Tetramethyl-[1,3,2]dioxaborolan-2-yl)-1H-indole following procedure 3. The first fraction was identified to be 3-(2,6-dichloro-benzyloxy)-5-(1H-indol-4-yl)-pyridin-2-ylamine.

Example I-5

The same experiment was performed as Example 4, and the second fraction was identified as 3-[2-chloro-6-(1H-indol-4-yl)-benzyloxy]-5-(1H-indol-4-yl)-pyridin-2-ylamine.

Example I-6

2-[6-Amino-5-(2,6-dichloro-benzyloxy)-pyridin-3-yl]-pyrrole-1-carboxylic acid tert-butyl ester was prepared from 5-bromo-3-(2,6-dichloro-benzyloxy)-pyridin-2-ylamine (Example I(a)) and N-Boc pyrrole-2-boronic acid following procedure 3.

Example I-7

To a mixture of 2-[6-amino-5-(2,6-dichloro-benzyloxy)-pyridin-3-yl]-pyrrole-1-carboxylic acid tert-butyl ester (Example 6, 30 mg, 0.069 mmol) in ethanol/water (2:1, 10 mL) was added sodium carbonate (100 mg, 0.95 mmol). The mixture was refluxed overnight. The reaction was cooled to ambient temperature and extracted with ethyl acetate. The mixture was washed with water, brine, dried over Na$_2$SO$_4$, and purified on a silica gel column to afford 3-(2,6-dichloro-benzyloxy)-5-(1H-pyrrol-2-yl)-pyridin-2-ylamine.

Examples I-8 to I-12

The compounds of Examples I-8 to I-12 were prepared according to procedure 3 using 5-bromo-3-(2,6-dichloro-benzyloxy)-pyridin-2-ylamine and: 4-fluorophenyl boronic acid (Example I-8); phenyl boronic acid (Example I-9); 2-fluorophenyl boronic acid (Example I-10); 3-fluorophenyl boronic acid (Example I-11); and 4-(4,4,5,5-tetramethyl-[1,3,2]dioxaborolan-2-yl)-phenylamine (Example I-12).

Example I-13

To a solution of 5-(4-amino-phenyl)-3-(2,6-dichloro-benzyloxy)-pyridin-2-ylamine (100 mg, 0.28 mmol) in methylene chloride (5 mL) at 0° C., was added methanesulfonyl chloride (0.021 mL, 0.28 mmol) and 4-methylmorpholine (0.16 mL). The mixture was stirred at room temperature for 2 hr, and diluted with ethyl acetate. The organic layers were washed with brine, dried over sodium sulfate and concentrated. The residue was purified with a silica gel column eluting with hexane-ethyl acetate (5:1) to give N-{4-[6-amino-5-(2,6-dichloro-benzyloxy)-pyridin-3-yl]-phenyl}-methanesulfonamide.

Example I-14

To a solution of 5-(4-amino-phenyl)-3-(2,6-dichloro-benzyloxy)-pyridin-2-ylamine (100 mg, 0.28 mmol) in acetonitrite (3 mL) at 0° C., was added pyridine (0.035 mL, 1.5 eq.) and acetic anhydride (0.03 mL, 0.28 mmol). The mixture was stirred at room temperature over night, and the precipitate was filtered to provide N-{4-[6-amino-5-(2,6-dichloro-benzyloxy)-pyridin-3-yl]-phenyl}-acetamide as a white solid.

Examples I-15 to I-35

The compounds of Examples I-15 to I-35 were prepared according to procedure 3 from 5-bromo-3-(2,6-dichloro-benzyloxy)-pyridin-2-ylamine and: 3-(4,4,5,5-tetramethyl-[1,3,2]dioxaborolan-2-yl)-phenol (Example I-15); 4-methoxyphenyl boronic acid (Example I-16); 3-aminobenzeneboronic acid (Example I-17); 4-trifluoromethoxybenzeneboronic acid (Example I-18); 2-hydroxybenzene boronic acid (Example I-19); 2-phenoxyphenylboronic acid (Example I-20); 3,4-difluorophenylboronic acid (Example I-21); (3-isopropyl)-phenylboronic acid (Example I-22); (2-trifluoromethylphenyl)boronic acid (Example I-23); (2-methoxyphenyl)boronic acid (Example I-24); (4-trifluoromethylphenyl)boronic acid (Example I-25); [(2-methylsulfonylamino)phenyl]boronic acid (Example I-26); 4-hydroxymethylphenylboronic acid (Example I-27); 3,4-methylenedioxyphenylboronic acid (Example I-28); 2-trifluoromethoxyphenylboronic acid (Example I-29); 4-methylthiophene-2-boronic acid (Example I-30); 2-benzyloxyphenylboronic acid (Example I-31); 3-methoxyphenylboronic acid (Example I-32); 1-(tert-butoxycarbonyl)indole-2-boronic acid, and the tert-butoxycarbonyl group was removed using 20% trifluoroacetic acid in dichloromethane (Example I-33); (3-fluoro-4-benzyloxyphenyl)boronic acid (Example I-34); and 4-(4,4,5,5-tetramethyl-[1,3,2]dioxaborolan-2-yl)-benzoic acid (Example I-35).

Example I-36

To a solution of 4-[6-amino-5-(2,6-dichloro-benzyloxy)-pyridin-3-yl]-benzoic acid (50 mg, 0.13 mmol), HOBT (21 mg, 0.156 mmol), and EDC (30 mg, 0.156 mmol) in DMF (2 mL) was added N,N-diethylethylenediamine (0.022 mL, 0.156 mmol). The reaction was stirred at room temperature for 24 hr, then diluted with EtOAc, and partitioned with $H_2O$. The organic was separated and the aqueous was extracted with EtOAc. The organic layers were combined, washed with saturated $NaHCO_3$, and concentrated to dryness under vacuum. The material was purified using column chromatography (silica gel, 99:1 to 95:5 $CH_2Cl_2$/MeOH) to give 4-[6-amino-5-(2,6-dichloro-benzyloxy)-pyridin-3-yl]-N-(2-diethylamino-ethyl)-benzamide (45 mg, 72% yield) as a white solid.

Examples I-37 and I-38

The compounds of Examples I-37 and I-38 were prepared from 4-[6-amino-5-(2,6-dichloro-benzyloxy)-pyridin-3-yl]-benzoic acid and N,N-diethyl-1,3-propanediamine (Example I-37) and 1-methylpiperazine (Example I-38), following procedure 4.

Example I-39

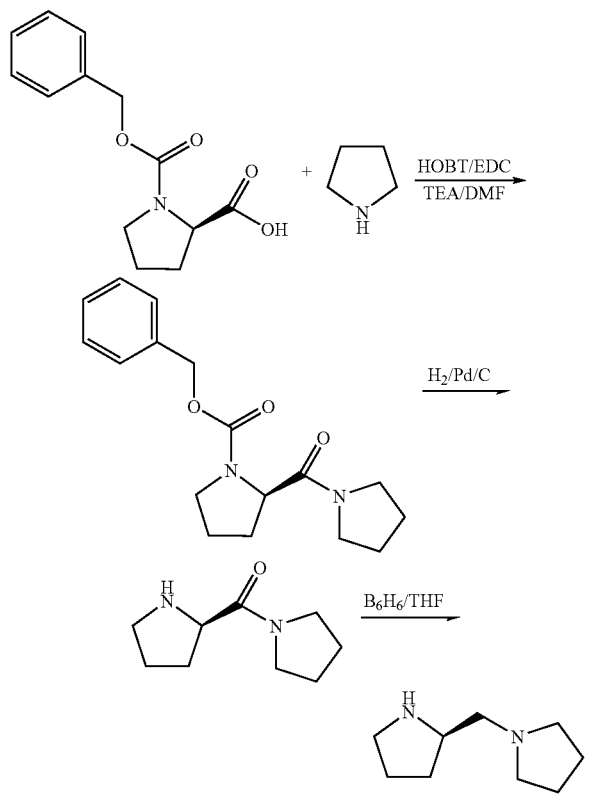

1. A mixture of (+)-carbobenzyloxy-D-proline (1.5 g, 6 mmol), EDC (2.3 g, 12 mmol), HOBt (800 mg, 6 mmol), TEA (1.5 mL) and pyrrolidine (853 mg, 12 mmol) in DMF (20 mL) was stirred at rt for 18 hr. The reaction was diluted with water and sodium bicarbonate, extracted with dichloromethane (3×). The combined DCM was concentrated and purified on a silica gel column to give (R)-2-(pyrrolidine-1-carbonyl)-pyrrolidine-1-carboxylic acid benzyl ester. (R)-2-(pyrrolidine-1-carbonyl)-pyrrolidine-1-carboxylic acid benzyl ester was hydrogenated using Pd/C in methanol at ambient temperature for 20 hr to provide pyrrolidin-1-yl-(R)-pyrrolidin-2-yl-methanone. To a solution of pyrrolidin-1-yl-(R)-pyrrolidin-2-yl-methanone (1.2 g, 7.1 mmol) in THF (10 mL) at 0° C. was added $B_2H_6$ (10 mL, 10 mmol). The mixture was heated to reflux for 16 hr. The reaction was acidified with HCl and concentrated. The residue was basified to pH 10 with 2N NaOH and extracted with 5% methanol in DCM. The organic layer was concentrated and purified on a silica gel column to give 800 mg (73%) of (R)-2-pyrrolidin-1-ylmethyl-pyrrolidine.

2. {4-[6-Amino-5-(2,6-dichloro-benzyloxy)-pyridin-3-yl]-phenyl}-(2R)-2-pyrrolidin-1-ylmethyl-pyrrolidin-1-yl]-methanone was prepared from 4-[6-amino-5-(2,6-dichloro-benzyloxy)-pyridin-3-yl]-benzoic acid and (2R)-2-pyrrolidin-1-ylmethyl-pyrrolidine following procedure 4.

Examples I-40 to I-45

The compounds of Examples I-40 to I-45 were prepared according to procedure 4 from 4-[6-amino-5-(2,6-dichloro-benzyloxy)-pyridin-3-yl]-benzoic acid and: (2S)-2-pyrrolidin-1-ylmethyl-pyrrolidine (Example I-40); 4-pyrrolidin-1-yl-piperidine (Example I-41); 4-piperidine ethanol (Example I-42); (3S)-(3-dimethylamino-pyrrolidine (Example I-43); (3R)-(3-dimethylamino-pyrrolidine (Example I-44); and (S)-3-cyclopropylaminomethyl-piperidine (prepared according to the procedures for (R)-2-pyrrolidin-1-ylmethyl-pyrrolidine in example I-39) (Example I-45).

Example I-46

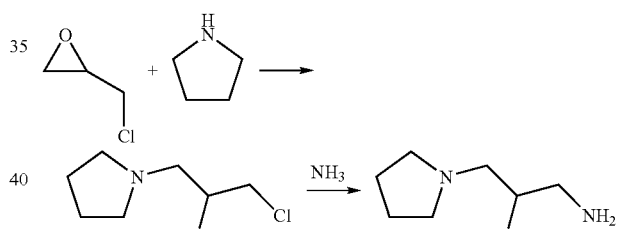

1. To a solution of epichlorohydrin (from Aldrich, Milwaukee, 3.91 mL, 50.0 mmol) in EtOH (100 mL) was added pyrrolidine (4.18 mL, 50.0 mmol) at room temperature. The mixture was stirred at 55-60° C. for 20 hr, then refluxed for 3 hr. The solvent was removed under reduced pressure and crude 1-chloro-3-pyrrolidin-1-yl-propan-2-ol was obtained as an oil (10 g). This oily product was dissolved in 7 M ammonia in MeOH (40 mL) and stirred at room temperature overnight. Then another 30 mL of 7M ammonia in MeOH was added and the mixture was stirred at 40° C. overnight. NMR showed that the starting material disappeared completely. The solvent was removed and the residue was dissolved in 2 N HCl and then lyophilized to give 10.8 g of oil salt product, which was dissolved in MeOH—$H_2O$ at 0° C. and the resin (AG1-X8, hydroxide form) was added in portions with stirring until the pH of the solution is above 9.0. After filtration, the filtrate was evaporated under reduced pressure to give the free amine 1-amino-3-pyrrolidin-1-yl-propan-2-ol as yellowish oil (8.6 g). This crude product was used for the reaction without further purification.

2. 4-[6-Amino-5-(2,6-dichloro-benzyloxy)-pyridin-3-yl]-N-(2-hydroxy-3-pyrrolidin-1-yl-propyl)-benzamide was prepared from 4-[6-amino-5-(2,6-dichloro-benzyloxy)-pyridin-3-yl]-benzoic acid and 1-amino-3-pyrrolidin-1-yl-propan-2-ol following procedure 4.

Examples I-47 to I-52

The compounds of Examples I-47 to I-52 were prepared according to procedure 4 from 4-[6-amino-5-(2,6-dichloro-benzyloxy)-pyridin-3-yl]-benzoic acid and: 3-fluoro-1 (2S)-pyrrolidin-2-ylmethyl-piperidine (prepared according to the procedures for (R)-2-pyrrolidin-1-ylmethyl-pyrrolidine) (Example I-47); 1-cyclopropyl-piperazine (Example I-48); (R)-2-[(cyclopropylmethyl-amino)-methyl]-pyrrolidine (prepared according to the procedures for (R)-2-pyrrolidin-1-ylmethyl-pyrrolidine) (first fraction, Example I-49; second fraction, Example I-50); N-(2-hydroxy-3-pyrrolidin-1-yl-propyl)-N-methyl amine (prepared according to the same procedure as 1-amino-3-pyrrolidin-1-yl-propan-2-ol (Example I-51); and (2S)-2-[(3R)-3-hydroxy-pyrrolidin-1-ylmethyl]-pyrrolidine (prepared according to the procedure for (R)-2-pyrrolidin-1-ylmethyl-pyrrolidine) (Example I-52).

Example I-53

3-[6-Amino-5-(2,6-dichloro-benzyloxy)-pyridin-3-yl]-benzoic acid was prepared from 5-bromo-3-(2,6-dichlorobenzyloxy)-pyridin-2-ylamine and 3-(4,4,5,5-tetramethyl-[1,3,2]dioxaborolan-2-yl)-benzoic acid following procedure 3.

Example I-54

{3-[6-Amino-5-(2,6-dichloro-benzyloxy)-pyridin-3-yl]-phenyl}-[(2R)-2-pyrrolidin-1-ylmethyl-pyrrolidin-1-yl]-methanone was prepared from 3-[6-amino-5-(2,6-dichloro-benzyloxy)-pyridin-3-yl]-benzoic acid and (R)-2-pyrrolidin-1-ylmethyl-pyrrolidine following procedure 4.

Example I-55

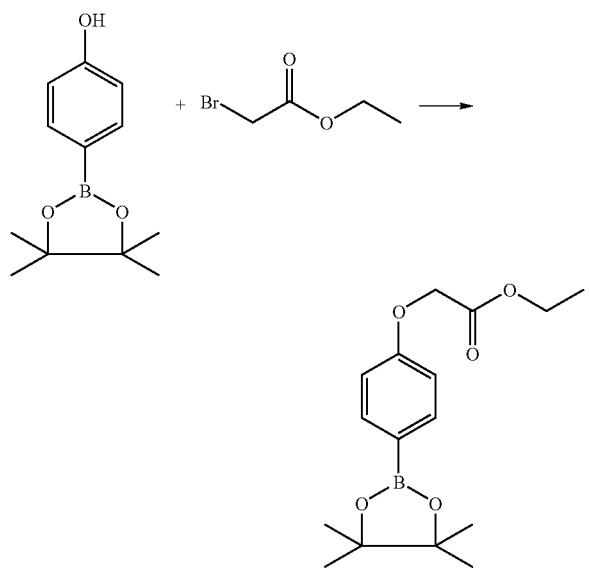

1. To a solution of 4-(4,4,5,5-tetramethyl-[1,3]dioxolan-2-yl)-phenol (10.0 g, 45.5 mmol) and $Cs_2CO_3$ (23.5 g, 68.25 mmol) in DMF (60 mL) was added ethyl α-bromoacetate (11.6 g, 68.25 mmol). The mixture was stirred at room temperature for 24 hours, then diluted with ethyl acetate, washed with water, dried over $Na_2SO_4$. After filtration and evaporation, the residue was dried under high vacuum to provide [4-(4,4,5,5-tetramethyl-[1,3]dioxolan-2-yl)-phenoxy]-acetic acid ethyl ester (12.52 g, 90% yield) as an oil.

2. A mixture of 5-bromo-3-(2,6-dichloro-benzyloxy)-pyridin-2-ylamine (Example I(a)) (2.2 g, 6.3 mmol), [4-(4,4,5,5-tetramethyl-[1,3]dioxolan-2-yl)-phenoxy]-acetic acid ethyl ester (2.9 g, 1.5 eq.), bis(triphenylphosphine)palladium (II) chloride (136 mg) and sodium carbonate (1.93 g, 3.0 eq.) in ethylene glycol dimethyl ether (30 mL), DMF (5 mL) and water (8 mL) was heated to 90-100° C. under nitrogen for 7 hr. The reaction was cooled to rt and diluted with ethyl acetate. The mixture was washed with water, brine, dried and purified on silica column to afford {4-[6-amino-5-(2,6-dichloro-benzyloxy)-pyridin-3-yl]-phenoxy}-acetic acid ethyl ester. This ester was treated with sodium carbonate and water at rt overnight. The reaction was diluted with ethyl acetate. The mixture was washed with water, brine, dried and purified on silica column to afford 4-[6-amino-5-(2,6-dichloro-benzyloxy)-pyridin-3-yl]-phenoxy}-acetic acid.

Example I-56

2-{4-[6-Amino-5-(2,6-dichloro-benzyloxy)-pyridin-3-yl]-phenoxy}-1-[(2R)-2-pyrrolidin-1-ylmethyl-pyrrolidin-1-yl]-ethanone was prepared from 4-[6-amino-5-(2,6-dichloro-benzyloxy)-pyridin-3-yl]-phenoxy)acetic acid and (R)-2-pyrrolidin-1-ylmethyl-pyrrolidine following procedure 4.

Example I-57

2-{4-[6-Amino-5-(2,6-dichloro-benzyloxy)-pyridin-3-yl]-phenoxy}-1-[(2S)-2-pyrrolidin-1-ylmethyl-pyrrolidin-1-yl]-ethanone was prepared from 4-[6-amino-5-(2,6-dichloro-benzyloxy)-pyridin-3-yl]-phenoxy)acetic acid and (S)-2-pyrrolidin-1-ylmethyl-pyrrolidine following procedure 4.

Example I-58

3-(2,6-Dichloro-benzyloxy)-5-(1H-indol-5-yl)-pyridin-2-ylamine was prepared from 5-bromo-3-(2,6-dichloro-benzyloxy)-pyridin-2-ylamine and indole-5-boronic acid following procedure 3.

Example I-59

To a solution of 3-(2,6-Dichloro-benzyloxy)-5-(1H-indol-5-yl)-pyridin-2-ylamine (example I-58, 200 mg, 0.52 mmol) in acetic acid (4 mL) and trifluoroacetic-acid (1 mL) was added 1-methyl-4-piperidone (0.32 mL, 2.6 mmol). The solution was refluxing for over night, and evaporated. The residue was dissolved in ethyl acetate, washed with saturated $NaHCO_3$ and brine, dried over $Na_2SO_4$, and condensed. The crude product was purified on a silica gel column eluting with dichloromethane-methanol-triethyl amine (95:5:0.1) to provide 3-(2,6-dichloro-benzyloxy)-5-[3-(1-methyl-1,2,3,6-tetrahydro-pyridin-4-yl)-1H-indol-5-yl]-pyridin-2-ylamine (103.5 mg, 41% yield) as an orange crystalline solid.

Example I-60

To a de-gassed solution of 3-(2,6-dichloro-benzyloxy)-5-[3-(1-methyl-1,2,3,6-tetrahydro-pyridin-4-yl)-1H-indol-5-yl]-pyridin-2-ylamine (example I-61, 130 mg, 0.27 mmol) in methanol (50 mL) and acetic acid (5 mL) was added 10% Pd/C (50 mg). The solution was degassed and charged with hydrogen for three times, and then was stirred under hydrogen balloon for over night. The mixture was filtered through a celite pad, washed with methanol, and then condensed. The residue was dissolved in ethyl acetate, washed with sat. NaHCO3 and brine, dried over $Na_2SO_4$, and condensed. The crude product was purified on a silica gel column eluting with dichloromethane-methanol-triethyl amine (95:5:0.1) to provide 3-(2,6-dichloro-benzyloxy)-5-[3-(1-methyl-piperidin-4-yl)-1H-indol-5-yl]-pyridin-2-ylamine as a white solid.

Examples I-61-I-68

The compounds of Examples I-61 to I-68 were prepared according to procedure 5 from 3-(2,6-Dichloro-benzyloxy)-5-(1H-indol-5-yl)-pyridin-2-ylamine and: morpholine (Example I-61); piperidine (Example I-62); pyrrolidine (Example I-63); diethylamine (Example I-64); pyrrolidin-3-yl-carbamic acid tert-butyl ester (Example I-65); 2,6-dimethyl-morpholine following (Example I-66); (R)-pyrrolidin-3-yl-acetamide (Example I-67); and piperazin-1-yl-ethanone (Example I-68).

Example I-69

3-(2-Chloro-3,6-difluoro-benzyloxy)-5-(1H-indol-5-yl)-pyridin-2-ylamine was prepared from 5-bromo-3-(2-chloro-3,6-difluoro-benzyloxy)-pyridin-2-ylamine and indole-5-boronic acid following procedure 3.

Examples I-70 to I-75

The compounds of Examples I-70 to I-75 were prepared according to procedure 5 from 3-(2-chloro-3,6-difluoro-benzyloxy)-5-(1H-indol-5-yl)-pyridin-2-ylamine and: piperazin-1-yl-ethanone (Example I-70); 2,6-dimethyl-morpholine (Example I-71); (3S)-pyrrolidin-3-yl-acetamide (Example I-72); piperidine (Example I-73); morpholine (Example I-74); and pyrrolidine (Example I-75).

Example I-76

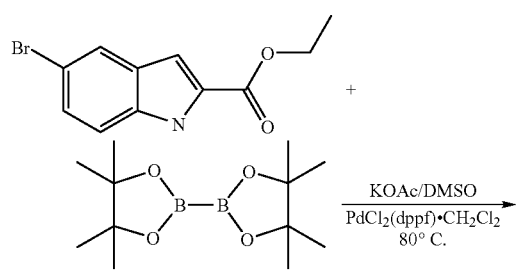

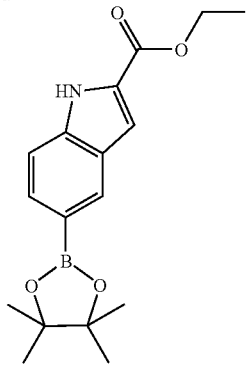

1. To a stirred solution of ethyl 5-bromo-1H-indole-2-carboxylate (5 g, 18.6 mmol) in DMSO (75 mL, 0.25 M), 4,4,4',4',5,5,5',5'-octamethyl-2,2'-bi-1,3,2-dioxaborolane (11.2 g, 44.3 mmol), potassium acetate (5.5 g, 56.0 mmol), and [bis(diphenylphosphino)ferrocene]dichloropalladium II (1.23 mmol) were added. The mixture was de-gassed and charged with nitrogen for three times, and then heated at 80° C. under nitrogen for overnight. The reaction was cooled to ambient temperature and diluted with ethyl acetate (2×100 mL). The mixture was washed with water (1×50 mL), brine (1×50 mL), dried over $MgSO_4$, and purified on a silica gel column to afford ethyl 5-(4,4,5,5-tetramethyl-1,3,2-dioxaborolan-2-yl)-1H-indole-2-carboxylate as an off-white solid; $^1$H NMR (400 MHz, DMSO-$d_6$) δ 1.31 (t, 3H), 4.32 (m, 2H), 7.18 (s, 1H), 7.42 (d, 1H), 7.54 (d, 1H), 8.05 (s, 1H), 11.96 (s, 1H); MS m/z 315 (M+1).

2. 5-[6-Amino-5-(2,6-dichloro-benzyloxy)-pyridin-3-yl]-1H-indole-2-carboxylic acid ethyl ester was prepared from 5-bromo-3-(2,6-dichloro-benzyloxy)-pyridin-2-ylamine and 5-(4,4,5,5-Tetramethyl-[1,3,2]dioxaborolan-2-yl)-1H-indole-2-carboxylic acid ethyl ester following procedure 3.

Example I-77

To a mixture of ethyl 5-{6-amino-5-[(2,6-dichlorobenzyl)oxy]pyridin-3-yl}-1H-indole-2-carboxylate (2.5 g, 5.5 mmol) in methanol:water (60 mL:20 mL), lithium hydroxide (0.65 g, 27.1 mmol) was added. The reaction was heated to reflux for overnight. Most of the solvent was evaporated and the mixture was acidified, and stirred for 10 min. The precipitate was filtered out and washed with water to yield 5-{6-amino-5-[(2,6-dichlorobenzyl)oxy]pyridin-3-yl}-1H-indole-2-carboxylic acid as tan solid.

Examples I-78 to I-85

The compounds of Examples I-78 to I-85 were prepared according to procedure 4 from 5-[6-Amino-5-(2,6-dichloro-benzyloxy)-pyridin-3-yl]-1H-indole-2-carboxylic acid and: N-methylpiperazine (Example I-78); (3R)-3-dimethylamino-pyrrolidine (Example I-79); (2R)-2-pyrrolidin-1-ylmethyl-pyrrolidine (prepared as in example I-39) (Example I-80); 2-pyrrolidin-1-yl-ethylamine (Example 1-81); 2-morpholin-4-yl-ethylamine (Example I-82); (S)-pyrrolidin-3-yl-carbamic acid tert-butyl ester (Example I-83), followed by deprotection of the Boc-group in 20% trifluoroacetic acid in dichloromethane (Example I-84); 2-hydroxy-3-pyrrolidin-1-yl-propylamine (Example I-85).

Example I-86

4-(6-Amino-5-benzyloxy-pyridin-3-yl)-phenol was prepared from 3-benzyloxy-5-bromo-pyridin-2-ylamine and 4-(4,4,5,5-tetramethyl-1,3-2-dioxabordan-2-yl) phenol following procedure 3.

Example I-87

3-Benzyloxy-5-phenyl-pyridin-2-ylamine was prepared from 3-benzyloxy-5-bromo-pyridin-2-ylamine and phenylboronic acid following procedure 3.

Example I-88

3-(3-Methoxy-benzyloxy)-5-phenyl-pyridin-2-ylamine was prepared according to procedure 6.

Examples I-89 to I-105

The compounds of Examples I-89 to I-105 were prepared according to procedure 6 from: 2-chloro-4-fluoro-benzylbromide (Example I-89); 2-chlorobenzylbromide (Example I-90); 2,5-dichlorobenzylbromide (Example I-91); 2-chloro-5-trifluoromethyl benzylbromide (Example I-92); 2,4-Dichloro-5-fluoro-benzylbromide (Example I-93); 2-chloro-3-trifluoromethyl-benzylbromide (Example 1-94); 2-chloro-3,6-difluoro-benzylbromide (Example I-95); 3,4-dichlorobenzylbromide (Example I-96); 2-bromomethyl-benzonitrile (Example I-97); 2-chloro-6-fluoro-3-methyl-benzylbromide (Example I-98); 2-bromomethyl-1,3,4-trifluoro-benzene (Example I-99); 2-bromomethyl-1,3-difluoro-benzene (Example I-100); 2-bromomethyl-1,3-difluoro-4-methyl-benzene (Example I-101); 2-bromomethyl-4-chloro-1,3-difluoro-benzene (Example I-102); 2-bromomethyl-1-chloro-3-fluoro-benzene (Example I-103); 4-bromomethyl-2-fluoro-1-methoxy-benzene (Example I-104); and 1-bromomethyl-3-nitro-benzene, followed by reduction of the nitro group to amino and reaction with methanesulfonyl chloride (Example I-105).

Example I-106

5-[4-(2-Morpholin-4-yl-ethoxy)-phenyl]-3-(3-nitro-benzyloxy)-pyridin-2-ylamine was synthesized according to procedure 7.

Examples I-107 to I-110

The compounds of Examples I-107 to I-110 were prepared according to procedure 7 from: 1-bromomethyl-naphthalene (Example I-107); 2-bromomethyl-3-chloro-1,4-difluoro-benzene (Example I-108); 2-bromo-N-(4-isopropyl-phenyl)-2-phenyl-acetamide (Example I-109); and 3-bromomethyl-5-chloro-benzo[b]thiophene (Example I-110).

Example I-111

{4-[6-Amino-5-(4-fluoro-2-trifluoromethyl-benzyloxy)-pyridin-3-yl]-phenyl}-[(2R)-2-pyrrolidin-1-ylmethyl-pyrrolidin-1-yl]-methanone was synthesized according to procedure 8.

Examples I-112 to I-117

The compounds of Examples I-112 to I-117 were prepared according to procedure 8 from: 2-bromomethyl-1-fluoro-3-trifluoromethyl-benzene (Example I-112); 2-bromomethyl-4-fluoro-1-trifluoromethyl-benzene (Example I-113); 1-(1-bromo-ethyl)-2-trifluoromethyl-benzene (Example I-114); 1-bromo-2-bromomethyl-benzene (Example I-115); 1-bromomethyl-3-fluoro-2-trifluoromethyl-benzene (Example I-116); and 2-bromomethyl-3-chloro-1,4-difluoro-benzene (Example 1-117).

Examples I-118 to I-121

The compounds of Examples I-118 to I-121 were prepared according to procedure 3 from 5-bromo-3-(2,6-difluoro-benzyloxy)-pyridin-2-ylamine and: 4-(4,4,5,5-tetramethyl-[1,3]dioxolan-2-yl)-phenol (Example I-118); 4-{2-[4-(4,4,5,5-tetramethyl-[1,3,2]dioxaborolan-2-yl)-phenoxy]-ethyl}-morpholine (Example I-119); 4-(4,4,5,5-tetramethyl-[1,3]dioxolan-2-yl)-1H-indole (Example I-120); and 4-(4,4,5,5-tetramethyl-[1,3]dioxolan-2-yl)-benzoic acid (Example I-121).

Example I-122

{4-[6-Amino-5-(2,6-difluoro-benzyloxy)-pyridin-3-yl]-phenyl}-[(2R)-2-pyrrolidin-1-ylmethyl-pyrrolidin-1-yl]-methanone was prepared from 4-[6-amino-5-(2,6-difluoro-benzyloxy)-pyridin-3-yl]-benzoic acid and (2R)-2-pyrrolidin-1-ylmethyl-pyrrolidine following procedure 4.

Example I-123

{4-[6-Amino-5-(2,6-difluoro-benzyloxy)-pyridin-3-yl]-phenyl}-[(2S)-2-pyrrolidin-1-ylmethyl-pyrrolidin-1-yl]-methanone was prepared from 4-[6-amino-5-(2,6-difluoro-benzyloxy)-pyridin-3-yl]-benzoic acid and (2S)-2-pyrrolidin-1-ylmethyl-pyrrolidine following procedure 4.

Example I-124

{4-[6-Amino-5-(2,6-difluoro-benzyloxy)-pyridin-3-yl]-phenoxy}-acetic acid ethyl ester was prepared from 5-bromo-3-(2,6-difluoro-benzyloxy)-pyridin-2-ylamine and of [4-(4,4,5,5-tetramethyl-[1,3]dioxolan-2-yl)-phenoxy]-acetic acid ethyl ester following procedure 3.

Example I-125

{4-[6-Amino-5-(2,6-difluoro-benzyloxy)-pyridin-3-yl]-phenoxy}-acetic acid ethyl ester (1.0 g, 2.41 mmol) was treated with sodium carbonate (1.28 g, 12.05 mmol) and water (10 mL) at 90-100° C. overnight. The reaction was cooled to rt and diluted with ethyl acetate. The mixture was washed with water, brine, dried and purified on silica column to afford 4-[6-amino-5-(2,6-difluoro-benzyloxy)-pyridin-3-yl]-phenoxy}-acetic acid.

Example I-126

2-{4-[6-Amino-5-(2,6-difluoro-benzyloxy)-pyridin-3-yl]-phenoxy}-1-[(2R)-2-pyrrolidin-1-ylmethyl-pyrrolidin-1-yl]-ethanone was prepared from 4-[6-Amino-5-(2,6-difluoro-benzyloxy)-pyridin-3-yl]-phenoxy}-acetic acid and (2R)-2-pyrrolidin-1-ylmethyl-pyrrolidine following procedure 4.

Example I-127

2-{4-[6-Amino-5-(2,6-difluoro-benzyloxy)-pyridin-3-yl]-phenoxy}-1-[(2S)-2-pyrrolidin-1-ylmethyl-pyrrolidin-1- yl]-ethanone was prepared from 4-[6-Amino-5-(2,6-difluoro-benzyloxy)-pyridin-3-yl]-phenoxy}-acetic acid and (2S)-2-pyrrolidin-1-ylmethyl-pyrrolidine following procedure 4.

Examples I-128 to I-134

The compounds of Examples I-128 to I-134 were prepared according to procedure 3 from 4-(4,4,5,5-tetramethyl-[1,3] dioxolan-2-yl)-phenol and: 5-bromo-3-(2-chloro-6-fluoro-benzyloxy)-pyridin-2-ylamine (Example I-128); 5-bromo-3-(2-chloro-4-fluoro-benzyloxy)-pyridin-2-ylamine (Example I-129); 5-bromo-3-(2,4-dichloro-benzyloxy)-pyridin-2-ylamine (Example I-130); 2-(2-amino-5-bromo-pyridin-3-yloxymethyl)-benzonitrile (Example I-131); 5-bromo-3-(2-trifluoromethyl-benzyloxy)-pyridin-2-ylamine (Example I-132); 5-bromo-3-(2-chloro-benzyloxy)-pyridin-2-ylamine (Example I-133); and 5-bromo-3-(4-tert-butyl-benzyloxy)-pyridin-2-ylamine (Example I-134).

Example I-135

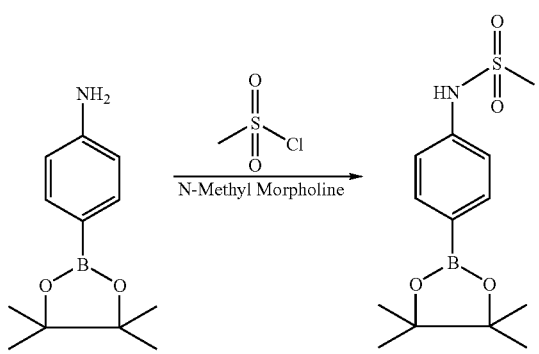

1. To a solution of 4-(4,4,5,5-tetramethyl-[1,3,2]dioxaborolan-2-yl)-phenylamine (5.00 g, 22.8 mmol) in methylene chloride (100 mL) and 4-methylmorpholine (16 mL) at 0° C. was added methanesulfonyl chloride (2.1 mL, 28 mmol). The mixture was stirred at room temperature for 2 hr, and diluted with ethyl acetate. The organic layer was washed with brine, dried over sodium sulfate and concentrated to provide N-[4-(4,4,5,5-tetramethyl-[1,3,2]dioxaborolan-2-yl)-phenyl]-methanesulfonamide as a white solid (6.32 g, 93% yield). MS m/z 298 (M+1).

2. N-{4-[6-Amino-5-(2-cyano-benzyloxy)-pyridin-3-yl]-phenyl}-methanesulfonamide was prepared following procedure 3 from 2-(2-Amino-5-bromo-pyridin-3-yloxymethyl)-benzonitrile and N-[4-(4,4,5,5-tetramethyl-[1,3,2] dioxaborolan-2-yl)-phenyl]-methanesulfonamide.

Example I-136

10% NaOH solution (25 mL) was added to N-{4-[6-amino-5-(2-cyano-benzyloxy)-pyridin-3-yl]-phenyl)methanesulfonamide (Example I-135, 650 mg, 1.65 mmol) in ethylene glycol (55 mL). The mixture was heated to reflux and allowed to stir for 24 hr. The reaction was cooled to room temperature. Most of the solvent was evaporated and the mixture was acidified. The precipitated solid was filtered out to afford 2-[2-Amino-5-(4-methanesulfonylamino-phenyl)-pyridin-3-yloxymethyl]-benzoic acid as light brown solid. The filtrate was neutralized and extracted with EtOAc (5×20 mL). The organic layer was combined, dried over MgSO$_4$, and concentrated to yield 2-[2-Amino-5-(4-methanesulfonylamino-phenyl)-pyridin-3-yloxymethyl]-benzamide as an off-white solid.

Example I-137

2-[2-Amino-5-(4-methanesulfonylamino-phenyl)-pyridin-3-yloxymethyl)-benzoic acid was prepared as in Example I-136.

Example I-138 to I-140

The compounds of Examples I-138 to I-140 were prepared according to procedure 4 from 2-[2-amino-5-(4-methanesulfonylamino-phenyl)-pyridin-3-yloxymethyl]-benzoic acid and: N-methyl-piperazine (Example I-138); 2-hydroxyethylamine (Example I-139); and isobutylamine (Example I-140).

Example I-141

5-Bromo-3-(2-chloro-6-fluoro-benzyloxy)-pyridin-2-ylamine (Example I(e), 9.00 g, 27.0 mmol), 4-carboxybenzeneboronic acid (4.41 g, 27.0 mmol), tetrakis(triphenylphosphine)palladium(0) (0.99 g, 0.9 mmol), potassium carbonate (13.1 g, 95.0 mmol), dimethylformamide (72 mL) and water (36 mL) were charged to a 250 mL three neck round bottom flask equipped with a thermometer, a reflux condenser and magnetic stirring. The mixture was purged with nitrogen and gradually heated from 81° C. to 98° C. over a period of 4 hr. Thin layer chromatography (ethyl acetate:hexane:acetic acid 4:6:0.5) showed a trace of starting material at Rf 0.7, product at Rf 0.4 and many small impurities. The mixture was cooled to 45° C. The solids were collected by vacuum filtration, washed with 30 mL of ethanol:water 1:1 and discarded. The filtrate was diluted with 432 mL of water and 8 mL of 9 N potassium hydroxide solution (to pH 12-13), cooled in an ice bath and stirred for 30 minutes. The solids were collected by vacuum filtration and washed with 5 mL of water. The filtrate was cooled in an ice bath and acidified to pH 7.5 with acetic acid using a pH meter. The solids were collected by vacuum filtration, washed with 10 mL of ethanol:water 1:1 and dried under vacuum to give 2.5 g of 4-[6-amino-5-(2-chloro-6-fluoro-benzyloxy)-pyridin-3-yl]-benzoic acid and a second compound as a brown solid in a ratio of about 1:1 by $^1$H-NMR. This material was discarded. The filtrate was acidified to pH 6.5 with acetic acid using a pH meter. The solids were collected by vacuum filtration, washed with 10 mL of ethanol:water 1:1 and dried under vacuum to give 3.6 g (36% yield) of 4-[6-amino-5-(2-chloro-6-fluoro-benzyloxy)-pyridin-3-yl]-benzoic acid as a brown solid containing a 5-10% impurity by $^1$H-NMR.

Examples I-142 to I-149

The compounds of Examples I-142 to I-149 were prepared according to procedure 4 from 4-[6-amino-5-(2-chloro-6-fluoro-benzyloxy)-pyridin-3-yl]-benzoic acid and: (2R)-2-pyrrolidin-1-ylmethyl-pyrrolidine (Example I-142); (2S)-2-pyrrolidin-1-ylmethyl-pyrrolidine (Example I-143); (3S)-3-dimethylamino-pyrrolidine (Example I-144); (S)-pyrrolidin-3-yl-carbamic acid tert-butyl ester, followed by de-protection of Boc-group with trifluoroacetic acid in dichloromethane (Example I-145); N-methylpiperazine (Example I-146); 1-piperazin-1-yl-ethanone (Example I-147); 2-morpholin-4-yl-ethylamine (Example I-148); 3-morpholin-4-yl-propylamine (Example I-149).

Example I-150

5-Bromo-3-(2-chloro-benzyloxy)-pyridin-2-ylamine (4.50 g, 14.3 mmol), 4-carboxybenzeneboronic acid (2.62 g, 15.8 mmol), tetrakis(triphenylphosphine)palladium(0) (0.56 g, 0.5 mmol), potassium carbonate (6.90 g, 50 mmol), dimethylformamide (36 mL), and water (18 mL) were charged to a 250 mL three neck round bottom flask equipped with a thermometer, a reflux condenser and magnetic stirring. The mixture was purged with nitrogen and gradually heated from 82 to 93° C. over a period of 4 hr. Thin layer chromatography (ethyl acetate:hexane:acetic acid 4:6:0.5) showed product at Rf 0.3 and a few small impurities. The mixture was cooled to 45° C. The solids were collected by vacuum filtration, washed with 10 mL of ethanol:water 1:1 and discarded. The combined filtrate was diluted with 216 mL of water and 4 mL of 9 N potassium hydroxide solution (to pH 12-13), cooled in an ice bath and stirred for 30 minutes with 3 g of Celite and 3 g of Norit. The solids were collected by vacuum filtration through a pad of Celite and washed with 10 mL of water. The solids were discarded. The combined filtrate was cooled in an ice bath and acidified to pH 7 with acetic acid using a pH meter. The solids were collected by vacuum filtration, washed with 20 mL of ethanol-water 1:1 and dried under vacuum to give 2.7 g (53% yield) of 4-[6-amino-5-(2-chloro-benzyloxy)-pyridin-3-yl]-benzoic acid.

Examples I-151 to I-159

The compounds of Examples I-151 to I-159 were prepared according to procedure 4 from 4-[6-amino-5-(2-chloro-benzyloxy)-pyridin-3-yl]-benzoic acid and: (2R)-2-pyrrolidin-1-ylmethyl-pyrrolidine (Example I-151); (2S)-2-pyrrolidin-1-ylmethyl-pyrrolidine (Example I-152); (3S)-3-dimethylamino-pyrrolidine (Example I-153); pyrrolidin-3-yl-carbamic acid tert-butyl ester, followed by de-protection of Boc-group with trifluoroacetic acid in dichloromethane (Example I-154); 4-pyrrolidin-1-yl-piperidine (Example I-155); N-methylpiperazine (Example I-156); 1-piperazin-1-yl-ethanone (Example I-157); 2-morpholin-4-yl-ethylamine (Example I-158); and 3-morpholin-4-yl-propylamine (Example I-159).

Example I-160

2-(2-Amino-5-bromo-pyridin-3-yloxymethyl)-benzonitrile (9.0 g, 29.6 mmol), 4-carboxybenzeneboronic acid (5.4 g, 32.5 mmol), tetrakis(triphenylphosphine)palladium(0) (1.1 g, 1.0 mmol), anhydrous potassium carbonate (13.8 g, 70.0 mmol), dimethylformamide (72 mL) and water (36 mL) were charged to a 250 mL three neck round bottom flask equipped with a thermometer, a reflux condenser and magnetic stirring. The mixture was purged with nitrogen and gradually heated from 81 to 90° C. over a period of 2 hr. Thin layer chromatography (ethyl acetate:hexane:acetic acid 4:6:0.5) showed a trace of starting material at Rf 0.7, product at Rf 0.4 and an impurity at Rf 0.5. The mixture was cooled to 45° C. The sticky solids were collected by vacuum filtration, washed with 30 mL of ethanol:water 1:1 and discarded. The filtrate was diluted with 432 mL of water and 8 mL of 9 N potassium hydroxide solution (to pH 12-13), cooled in an ice bath and stirred for 30 minutes. The solids were collected by vacuum filtration and washed with 20 mL of water. The solids were discarded. The filtrate was cooled in an ice bath acidified with acetic acid to pH 7.5 using a pH meter. The solids were collected by vacuum filtration, washed with 20 mL water and dried under vacuum to give 8.5 g (83% yield) of 4-[6-amino-5-(2-cyano-benzyloxy)-pyridin-3-yl]-benzoic acid as a very dark solid.

Examples I-161 to I-170

The compounds of Examples I-161 to I-170 were prepared according to procedure 4 from 4-[6-amino-5-(2-cyano-benzyloxy)-pyridin-3-yl]-benzoic acid and: (2R)-2-pyrrolidin-1-ylmethyl-pyrrolidine (Example I-161); (2R)-2-pyrrolidin-1-ylmethyl-pyrrolidine (Example I-162); (3S)-3-dimethylamino-pyrrolidine (Example I-163); (S)-pyrrolidin-3-yl-carbamic acid tert-butyl ester, followed by de-protection of Boc-group with trifluoroacetic acid in dichloromethane (Example I-164); 4-pyrrolidin-1-yl-piperidine (Example I-165); N-methylpiperazine (Example I-166); 1-piperazin-1-yl-ethanone (Example I-167); 1-methyl-piperidin-4-ylamine (Example I-168); 2-Morpholin-4-yl-ethylamine (Example I-169); and 3-morpholin-4-yl-propylamine (Example I-170).

Example I-171

5-Bromo-3-(2,4-dichloro-benzyloxy)-pyridin-2-ylamine (6.96 g, 20.0 mmol), 4-carboxybenzeneboronic acid (3.98 g, 24.0 mmol), tetrakis(triphenylphosphine)-palladium(0) (0.74 g, 0.66 mmol), potassium carbonate (9.7 g, 70 mmol), dimethylformamide (35 mL) and water (17 mL) were charged to a 250 mL three neck round bottom flask equipped with a thermometer, a reflux condenser and magnetic stirring. The mixture was purged with nitrogen and gradually heated from 81 to 95° C. over a period of 9 hr. Thin layer chromatography (ethyl acetate:hexane:acetic acid 4:6:0.5) showed a trace of starting material at Rf 0.7, product at Rf 0.4 and impurities at Rf 0.5 and 0.3. The mixture was cooled to room temperature and allowed to stand over for about 48 hr. The solids were collected by vacuum filtration, washed with 30 mL of ethanol:water 1:1 and saved. The filtrate was diluted with 210 mL of water and 8 mL of 9 N potassium hydroxide solution (to pH 12-13), cooled in an ice bath and stirred for 30 minutes. The solids were collected by vacuum filtration and washed with 5 mL of water to give about 1 g of a mixture of product and a spot running with starting material. This mixture was discarded. The filtrate was cooled in an ice bath and acidified to pH 5-6 with about 10 mL of acetic acid. The solids were collected by vacuum filtration, washed with 10 mL of ethanol:water 1:1 and dried under vacuum to give 2.9 g (37% yield) of 4-[6-amino-5-(2,4-dichloro-benzyloxy)-pyridin-3-yl]-benzoic acid as a brown solid.

Examples I-172 to I-181

The compounds of Examples I-172 to I-181 were prepared according to procedure 4 from 4-[6-amino-5-(2,4-dichloro-benzyloxy)-pyridin-3-yl]-benzoic acid and: (2R)-2-pyrrolidin-1-ylmethyl-pyrrolidine (Example I-172); (2S)-2-pyrrolidin-1-ylmethyl-pyrrolidine (Example I-173); (3S)-3-dimethylamino-pyrrolidine (Example I-174); (S)-pyrrolidin-3-yl-carbamic acid tert-butyl ester, followed by de-protection of Boc-group with trifluoroacetic acid in dichloromethane (Example I-175); 4-pyrrolidin-1-yl-piperidine (Example I-176); N-methylpiperazine (Example I-177); 1-piperazin-1-yl-ethanone (Example I-178); 1-methyl-piperidin-4-ylamine (Example I-179); 2-morpholin-4-yl-ethylamine (Example I-180); and 3-morpholin-4-yl-propylamine (Example I-181).

Example I-182

5-Bromo-3-(2-trifluoromethyl-benzyloxy)-pyridin-2-ylamine (5.80 g, 16.7 mmol), 4-carboxybenzeneboronic acid (3.05 g, 18.4 mmol), tetrakis(triphenylphosphine)-palladium (0) (0.62 g, 0.6 mmol), potassium carbonate (8.10 g, 58 mmol), dimethylformamide (47 mL) and water (23 mL) were charged to a 250 mL three neck round bottom flask equipped with a thermometer, a reflux condenser and magnetic stirring. The mixture was purged with nitrogen and gradually heated from 81 to 93° C. over a period of 4 hr. Thin layer chromatography (ethyl acetate:hexane:acetic acid 4:6:0.5) showed product at Rf 0.6 and a few small impurities. The mixture was cooled to 45° C. The solids were collected by vacuum filtration, washed with 10 mL of ethanol:water 1:1 and discarded. The filtrate was diluted with 300 mL of water and 4 mL of 9 N potassium hydroxide solution (to pH 12-13), cooled in an ice bath and stirred for 30 minutes with 3 g of Celite and 3 g of Norit. The solids were collected by vacuum filtration through a pad of Celite and washed with 10 mL of water. The solids were discarded. The filtrate was cooled in an ice bath and acidified to pH 7.3 with acetic acid using a pH meter. The solids were collected by vacuum filtration, washed with 20 mL of ethanol:water 1:1 and dried under vacuum to give 4.5 g (69% yield) of 4-[6-amino-5-(2-trifluoromethyl-benzyloxy)-pyridin-3-yl]-benzoic acid as a brown solid.

Examples I-183 to I-192

The compounds of Examples I-183 to I-192 were prepared according to procedure 4 from 4-[6-amino-5-(2-trifluoromethyl-benzyloxy)-pyridin-3-yl]-benzoic acid and: (2R)-2-pyrrolidin-1-ylmethyl-pyrrolidine (Example I-183); (2S)-2-pyrrolidin-1-ylmethyl-pyrrolidine (Example I-184); (3S)-3-dimethylamino-pyrrolidine (Example I-185); pyrrolidin-3-yl-carbamic acid tert-butyl ester, followed by de-protection of Boc-group with trifluoroacetic acid in dichloromethane (Example I-186); 4-pyrrolidin-1-yl-piperidine (Example I-187); N-methylpiperazine (Example I-188); 1-piperazin-1-yl-ethanone (Example I-189); 1-methyl-piperidin-4-ylamine (Example I-190); 2-morpholin-4-yl-ethylamine (Example I-191); and 3-morpholin-4-yl-propylamine (Example I-192).

Example I-193

2-(2-Amino-5-bromo-pyridin-3-yloxymethyl)-benzonitrile (9.0 g, 26.8 mmol), 4-carboxybenzeneboronic acid (4.9 g, 30.0 mmol), tetrakis(triphenylphosphine)-palladium(0) (1.1 g, 1.0 mmol), anhydrous potassium carbonate (13.1 g, 95 mmol), dimethylformamide (72 mL), and water (36 mL) were charged to a 250 mL three neck round bottom flask equipped with a thermometer, a reflux condenser and magnetic stirring. The mixture was purged with nitrogen and gradually heated from 81 to 96° C. over a period of 2 hr. Thin layer chromatography (ethyl acetate:hexane:acetic acid 4:6:0.5) showed a trace of starting material at Rf 0.8, product at Rf 0.5 and an impurity at Rf 0.4. The mixture was cooled to 45° C. and filtered to remove the solids. The filtrate was diluted with 432 mL of water and 8 mL of 9 N potassium hydroxide solution (to pH 12-13), cooled in an ice bath and 4 g of Celite and 2 g of Norit were added. The solids were collected by vacuum filtration through 4 g of Celite, washed with 30 mL of ethanol:water 1:1 and discarded The filtrate was cooled in an ice bath and acidified with acetic acid to pH 7.5 using a pH meter. The solids were collected by vacuum filtration, washed with 20 mL water and dried under vacuum to give 8.1 g (80% yield) 4-[6-amino-5-(4-tert-butyl-benzyloxy)-pyridin-3-yl]-benzoic acid as a dark solid.

Examples I-194 to I-201

The compounds of Examples I-194 to I-201 were prepared according to procedure 4 from 4-[6-Amino-5-(4-tert-butyl-benzyloxy)-pyridin-3-yl]-benzoic acid and: (2R)-2-pyrrolidin-1-ylmethyl-pyrrolidine (Example I-194); (2S)-2-pyrrolidin-1-ylmethyl-pyrrolidine (Example I-195); (3S)-3-dimethylamino-pyrrolidine (Example I-196); N-methylpiperazine (Example I-197); 1-piperazin-1-yl-ethanone (Example I-198); 1-methyl-piperidin-4-ylamine (Example I-199); 2-morpholin-4-yl-ethylamine (Example I-200); and 3-morpholin-4-yl-propylamine (Example I-201).

Example I-202

5-Bromo-3-(2-chloro-4-fluoro-benzyloxy)-pyridin-2-ylamine (9.00 g, 27.0 mmol), 4-carboxybenzeneboronic acid (4.41 g, 27.0 mmol), tetrakis(triphenylphosphine)-palladium (0) (0.99 g, 0.9 mmol), potassium carbonate (13.1 g, 95 mmol), dimethylformamide (72 mL), and water (36 mL) were charged to a 250 mL three neck round bottom flask equipped with a thermometer, a reflux condenser and magnetic stirring. The mixture was purged with nitrogen and gradually heated from 81 to 98° C. over a period of 4 hr. Thin layer chromatography (ethyl acetate:hexane:acetic acid 4:6:0.5) showed a trace of starting material at Rf 0.7, product at Rf 0.4 and a few small impurities. The mixture was cooled to 45° C. The solids were collected by vacuum filtration, washed with 20 mL of ethanol:water 1:1 and discarded. The filtrate was diluted with 432 mL of water and 8 mL of 9 N potassium hydroxide solution (to pH 12-13), cooled in an ice bath and stirred for 30 minutes. The solids were collected by vacuum filtration and washed with 5 mL of water to give about 1 g of a mixture which was discarded. The filtrate was cooled in an ice bath and acidified to pH 6.5 with acetic acid using a pH meter. The solids were collected by vacuum filtration, washed with 10 mL of ethanol:water 1:1 and dried under vacuum to give 3.6 g (36% yield) 4-[6-amino-5-(2-chloro-4-fluoro-benzyloxy)-pyridin-3-yl]-benzoic acid as a brown solid.

Examples I-203 to I-210

The compounds of Examples I-203 to I-210 were prepared according to procedure 4 from 4-[6-Amino-5-(2-chloro-4-fluoro-benzyloxy)-pyridin-3-yl]-benzoic acid and: (2R)-2-pyrrolidin-1-ylmethyl-pyrrolidine (Example I-203); (2S)-2-pyrrolidin-1-ylmethyl-pyrrolidine (Example I-204); (3S)-3-dimethylamino-pyrrolidine (Example I-205); (S)-pyrrolidin-3-yl-carbamic acid tert-butyl ester, followed by de-protection of Boc-group with trifluoroacetic acid in dichloromethane (Example I-206); N-methylpiperazine (Example I-207); 1-piperazin-1-yl)-ethanone (Example I-208); 2-morpholin-4-yl-ethylamine (Example I-209); and 3-morpholin-4-yl-propylamine (Example I-210).

Example I-211

4-[6-Amino-5-(2-chloro-3,6-difluoro-benzyloxy)-pyridin-3-yl]-benzoic acid methyl ester was prepared following procedure 3 from 5-bromo-3-(2-chloro-3,6-difluoro-benzyloxy)-pyridin-2-ylamine and 4-methoxycarbonylbenzeneboronic acid as an off-white solid in 55% yield. $^1$H NMR (CDCl$_3$, 300 MHz) δ3.94 (s, 3H), 4.79 (brs, 2H), 5.29-5.30 (d, 2H, J, 1.6), 7.06-7.19 (dt, 1H, J, 4.1, 9.0), 7.2-7.26 (m, 1H), 7.37-7.38 (d, 1H, 1.8), 7.58-7.61 (m, 2H), 8.01-8.02 (d, 2H, J, 1.8), 8.08-8.11 (m, 2H).

To a stirred solution of 4-[6-amino-5-(2-chloro-3,6-difluoro-benzyloxy)-pyridin-3-yl]-benzoic acid methyl ester (2.5 g, 6 mmol) in warm isopropanol (300 mL) was added H$_2$O (100 mL) containing LiOH (0.74 g, 31 mol). The reaction immediately turned orange and was left to stir at room temperature for 18 hr. The reaction was diluted with EtOAc (200 mL) and brine (50 mL). The organic was separated off and the aqueous was extracted with EtOAc (2×50 mL). The organic layers were combined and washed with brine (2×25 mL), dried with Na$_2$SO$_4$ and concentrated to dryness under vacuum to yield 4-[6-amino-5-(2-chloro-3,6-difluoro-benzyloxy)-pyridin-3-yl]-benzoic acid (2.4 g, 6 mmol, 99%) as an off-white solid.

Examples I-212 to I-224

The compounds of Examples I-212 to I-224 were prepared according to procedure 4 from 4-[6-amino-5-(2-chloro-3,6-difluoro-benzyloxy)-pyridin-3-yl]-benzoic acid and: N-methylpiperazine (Example I-212); 4-pyrrolidin-1-yl-piperidine (Example I-213); piperidin-4-yl-carbamic acid tert-butyl ester, followed by de-protection of Boc-group with trifluoroacetic acid in dichloromethane (Example I-214); 3,5-dimethyl-piperazine (Example I-215); (2S)-2-pyrrolidin-1-ylmethyl-pyrrolidine (Example I-216); (3S)-3-dimethylaminopyrrolidine (Example I-217); (R)-pyrrolidin-3-yl-carbamic acid tert-butyl ester, followed by de-protection of Boc-group with trifluoroacetic acid in dichloromethane (Example I-218); (S)-pyrrolidin-3-yl-carbamic acid tert-butyl ester, followed by de-protection of Boc-group with trifluoroacetic acid in dichloromethane (Example I-219); t-ethyl-piperidin-4-ylamine (Example I-220); 2-pyrrolidin-1-yl-ethylamine (Example I-221); 3-pyrrolidin-1-yl-propylamine (Example I-222); 2-morpholin-4-yl-ethylamine (Example I-223); and 3-morpholin-4-yl-propylamine (Example I-224).

Example I-225

3-[6-Amino-5-(2-chloro-3,6-difluoro-benzyloxy)-pyridin-3-yl]-benzoic acid was prepared using the same procedure as 4-[6-amino-5-(2-chloro-3,6-difluoro-benzyloxy)-pyridin-3-yl]-benzoic acid from 5-bromo-3-(2-chloro-3,6-difluoro-benzyloxy)-pyridin-2-ylamine and 3-methoxycarbonylbenzeneboronic acid.

Examples I-226 to I-239

The compounds of Examples I-226 to I-239 were prepared according to procedure 4 from 3-[6-amino-5-(2-chloro-3,6-difluoro-benzyloxy)-pyridin-3-yl]-benzoic acid and: N-methylpiperazine (Example I-226); 4-pyrrolidin-1-yl-piperidine (Example I-227); piperidin-4-yl-carbamic acid tert-butyl ester, and then followed by de-protection of Boc-group with trifluoroacetic acid in dichloromethane (Example I-228); 3,5-dimethyl-piperazine (Example I-229); (2S)-2-pyrrolidin-1-ylmethyl-pyrrolidine (Example I-230); (3S)-3-dimethylamino-pyrrolidine (Example I-231); (R)-pyrrolidin-3-yl-carbamic acid tert-butyl ester, followed by de-protection of Boc-group with trifluoroacetic acid in dichloromethane (Example I-232); (S)-pyrrolidin-3-yl-carbamic acid tert-butyl ester, followed by de-protection of Boc-group with trifluoroacetic acid in dichloromethane (Example I-233); 1-methyl-piperidin-4-ylamine (Example I-234); 2-pyrrolidin-1-yl-ethylamine (Example I-235); 3-pyrrolidin-1-yl-propylamine (Example I-236); 2-morpholin-4-yl-ethylamine (Example I-237); 3-morpholin-4-yl-propylamine (Example I-238); and I-[4-(2-amino-ethyl)-piperazin-1-yl]-ethanone (Example I-239).

Example I-240

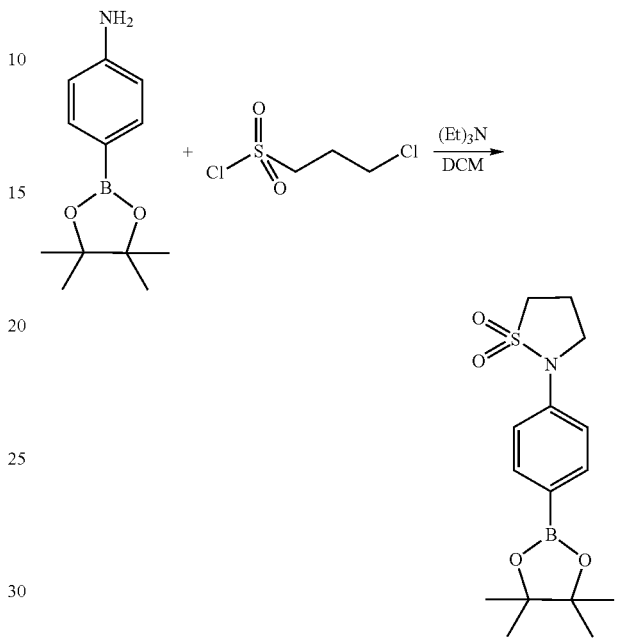

1. 4-(4,4,5,5-Tetramethyl-1,3,2-dioxaborolan-2-yl)aniline (5 g, 22.8 mmol) was dissolved in DCM (100 mL, 0.2M), triethylamine (15 mL, 5.0 molar equivalent) was added to the mixture. The reaction was stirred at 0° C. for 5 min. 3-chloropropane-1-sulfonyl chloride (4.2 g, 23.0 mmol) was added portion wise. The reaction was stirred at 0° C. for 1 hr and brought gradually to room temperature, heated to reflux at 70° C. for 2 hr. The mixture was cooled to room temperature, diluted with EtOAc and water. The organic layer was washed with brine, dried over MgSO$_4$, filtered, and concentrated. The residue was purified through a silica column to afford 2-[4-(4,4,5,5-tetramethyl-1,3,2-dioxaborolan-2-yl)phenyl] isothiazolidine 1,1-dioxide as off-white solid (5.2 g, 70% yield). $^1$H NMR (400 MHz, DMSO-d$_6$) δ 7.62 (d, 2H), 7.18 (d, 2H), 3.76 (t, 2H), 3.53 (t, 2H), 2.41 (t, 2H), 1.28 (s, 12H).

2. 3-(2-Chloro-3,6-difluoro-benzyloxy)-5-[4-(1,1-dioxo-1λ$^6$-isothiazolidin-2-yl)-phenyl]-pyridin-2-ylamine was prepared following procedure 3 from 5-bromo-3-(2-chloro-3,6-difluoro-benzyloxy)-pyridin-2-ylamine and 2-[4-(4,4,5,5-tetramethyl-1,3,2-dioxaborolan-2-yl)-phenyl] isothiazolidine 1,1-dioxide.

Example I-241

3-(2,6-Dichloro-benzyloxy)-5-[4-(1,1-dioxo-1λ$^6$-isothiazolidin-2-yl)-phenyl]-pyridin-2-ylamine was prepared following procedure 3 from 5-bromo-3-(2,6-dichloro-benzyloxy)-pyridin-2-ylamine and 2-[4-(4,4,5,5-tetramethyl-1,3,2-dioxaborolan-2-yl)-phenyl]iso-thiazolidine 1,1-dioxide.

Example I-242

5-[4-(1,1-dioxo-1λ$^6$-isothiazolidin-2-yl)-phenyl]-3-(2-fluoro-6-trifluoromethyl-benzyloxy)-pyridin-2-ylamine was prepared according to procedure 8.

Example I-243

2-Diethylamino-ethanesulfonic acid {4-[6-amino-5-(2-chloro-3,6-difluoro-benzyloxy)-pyridin-3-yl]-phenyl}-amide was synthesized according to procedure 9.

Examples I-244 to I-266

The compounds of Examples I-244 to I-266 were prepared following procedure 9.

Examples I-267 to I-269

The compounds of Examples I-267 to I-269 were prepared according to procedure 3, with purification by reversed phase preparative HPLC eluting with acetonitrile-water-trifluoroacetic acid system and obtained as trifluoroacetic acid salts, from 5-bromo-3-(2-chloro-3,6-difluoro-benzyloxy)-pyridin-2-ylamine and: 2-(dimethylaminomethyl)-phenylboronic acid (Example I-267); 3-(pyrrolidin-1-yl)-phenylboronic acid (Example I-268) and N-[4-(4,4,5,5-tetramethyl-[1,3,2]dioxaborolan-2-yl)-phenyl]-methanesulfonamide (Example I-269).

Example I-270

5-[6-Amino-5-(2-chloro-3,6-difluoro-benzyloxy)-pyridin-3-yl]-thiophene-2-carboxylic acid was prepared following procedure 3 starting from 5-bromo-3-(2-chloro-3,6-difluoro-benzyloxy)-pyridin-2-ylamine and 5-carboxythiophene-2-boronic acid.

Examples I-271 to I-276

Examples I-271 to I-276 were prepared according to procedure 4 from 5-[6-amino-5-(2-chloro-3,6-difluoro-benzyloxy)-pyridin-3-yl]-thiophene-2-carboxylic acid and: N-methylpiperazine (Example I-271); (2R)-2-pyrrolidin-1-ylmethyl-pyrrolidine (Example I-272); 1-methyl-piperidin-4-yl)-amine (Example I-273); 3,5-dimethyl-piperazine (Example I-274); 2-pyrrolidin-1-yl-ethylamine (Example I-275); and 4-pyrrolidin-1-yl-piperidine (Example I-276).

Example I-277

4-[6-Amino-5-(3-fluoro-2-trifluoromethyl-benzyloxy)-pyridin-3-yl]-benzoic acid was prepared using the same procedure as 4-[6-amino-5-(2-chloro-3,6-difluoro-benzyloxy)-pyridin-3-yl]-benzoic acid from 5-bromo-3-(3-fluoro-2-trifluoromethyl-benzyloxy)-pyridin-2-ylamine and 4-methoxycarbonylbenzeneboronic acid.

Examples I-278 to I-285

Examples I-278 to I-285 were prepared according to procedure 4 from 4-[6-amino-5-(3-fluoro-2-trifluoromethyl-benzyloxy)-pyridin-3-yl]-benzoic acid and: 4-pyrrolidin-1-yl-piperidine (Example I-278); 1-methyl-piperidin-4-ylamine (Example I-279); 3,5-dimethyl-piperazine (Example I-280); 3-dimethylamino-pyrrolidine (Example I-281); (2S)-2-pyrrolidin-1-ylmethyl-pyrrolidine (Example I-282); 2-morpholin-4-yl-ethylamine (Example I-283); N-methylpiperazine (Example I-284); and 4-acetyl-piperazin-1-yl)-ethylamine (Example I-285).

Examples I-286 to I-289

The compounds of Examples I-286 to I-289 were prepared following procedure 9.

Example I-290

4-{6-Amino-5-[1-(2,6-dichloro-3-fluoro-phenyl)-ethoxy]-pyridin-3-yl}-benzoic acid was prepared using the same procedure as 4-[6-amino-5-(2-chloro-3,6-difluoro-benzyloxy)-pyridin-3-yl]-benzoic acid from 5-bromo-3-[1-(2,6-dichloro-3-fluoro-phenyl)-ethoxy]-pyridin-2-ylamine and 4-methoxycarbonylbenzeneboronic acid.

Examples I-291 to I-296

The compounds of Examples I-291 to I-296 were prepared according to procedure 4 from 4-{6-amino-5-[1-(2,6-dichloro-3-fluoro-phenyl)-ethoxy]-pyridin-3-yl}-benzoic acid and: (2R)-2-pyrrolidin-1-ylmethyl-pyrrolidine (Example I-291); 1-methyl-piperidin-4-ylamine (Example I-292); (R)-pyrrolidin-3-yl-carbamic acid tert-butyl ester, followed by de-protection of Boc-group with trifluoroacetic acid in dichloromethane (Example I-293); 4-pyrrolidin-1-yl-piperidine (Example I-294); N-methyl-piperazine (Example I-295); and 3,5-dimethyl-piperazine (Example I-296).

Examples I-297 to I-299

The compounds of Examples I-297 to I-299 were prepared following procedure 9.

Examples I-300 to I-661 were prepared according to the procedures referenced in the Tables herein, except as specifically described in the following paragraphs. When multiple procedures are referenced in the Tables separated by "/", the indicated procedures were performed sequentially.

Example I-311

3-{6-Amino-5-[1-(2,6-dichloro-3-fluoro-phenyl)-ethoxy]-pyridin-3-yl}-benzoic acid was prepared using the same procedure as 4-[6-amino-5-(2-chloro-3,6-difluoro-benzyloxy)-pyridin-3-yl]-benzoic acid from 5-bromo-3-[1-(2,6-dichloro-3-fluoro-phenyl)-ethoxy]-pyridin-2-ylamine and 3-methoxycarbonylbenzeneboronic acid.

Example I-312

3-{6-Amino-5-[1-(2,6-dichloro-3-fluoro-phenyl)-ethoxy]-pyridin-3-yl}-phenyl)-(4-methyl-piperazin-1-yl)-methanone was prepared following procedure 4 starting from 3-{6-amino-5-[1-(2,6-dichloro-3-fluoro-phenyl)-ethoxy]-pyridin-3-yl}-benzoic acid and 1-methyl-piperidin-4-ylamine.

Example I-330

4-{6-Amino-5-[1-(2-chloro-3,6-difluoro-phenyl)-ethoxy]-pyridin-3-yl}-benzoic acid was prepared using the same procedure as 4-[6-amino-5-(2-chloro-3,6-difluoro-benzyloxy)-pyridin-3-yl]-benzoic acid from 5-bromo-3-[1-(2-chloro-3,6-difluoro-phenyl)-ethoxy]-pyridin-2-ylamine and 4-methoxycarbonylbenzeneboronic acid.

Example I-331

4-{6-Amino-5-[1-(2-chloro-3,6-difluoro-phenyl)-ethoxy]-pyridin-3-yl}-N-(2-morpholin-4-yl-ethyl)-benzamide was prepared following procedure 4 starting from 4-{6-amino-5-[1-(2-chloro-3,6-difluoro-phenyl)-ethoxy]-pyridin-3-yl}-benzoic acid and the corresponding amine.

Example I-342

3-{6-Amino-5-[1-(2-chloro-3,6-difluoro-phenyl)-ethoxy]-pyridin-3-yl}-benzoic acid was prepared using the same procedure as 4-[6-amino-5-(2-chloro-3,6-difluoro-benzyloxy)-pyridin-3-yl]-benzoic acid from 5-bromo-3-[1-(2-chloro-3,6-difluoro-phenyl)-ethoxy]-pyridin-2-ylamine and 3-methoxycarbonylbenzeneboronic acid.

Example I-343

(3-{6-Amino-5-[1-(2-chloro-3,6-difluoro-phenyl)-ethoxy]-pyridin-3-yl}-phenyl)-((3R,5S)-3,5-dimethyl-piperazin-1-yl)-methanone was prepared following procedure 4 starting from 3-{6-amino-5-[1-(2-chloro-3,6-difluoro-phenyl)-ethoxy]-pyridin-3-yl}-benzoic acid and the corresponding amine.

Example I-359

1. Preparation of 2-hydroxy-7-oxa-4-azonia-spiro[3.5]nonane: To a solution of morpholine (17.4 mL, 0.2 mol, 1.0 eq.) in ethanol (20 mL) was added epichlorohydrin (16.1 ml, 1.03 eq.) from the addition funnel. The reaction was cooled with an ice water bath and gradually raised-to-room temperature. After 24 hr, the reaction was concentrated at 50° C. until no more distillate could be condensed. The resulting oil was stored at room temperature for 24-48 hr or until a significant mass of crystals was observed. The slurry was diluted with acetone and filtered. The solids were dried under high vacuum. This provided 20 g of crystalline product. The mother liquors could be concentrated and the crystallization process repeated in increase recovery.

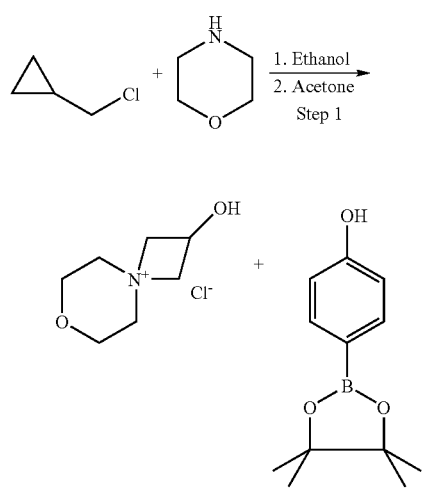

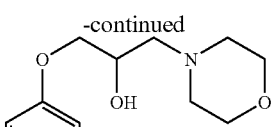

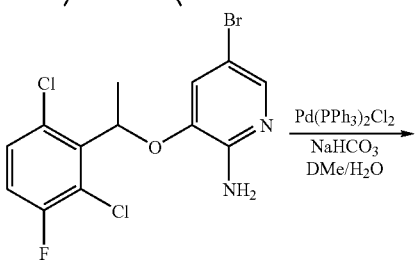

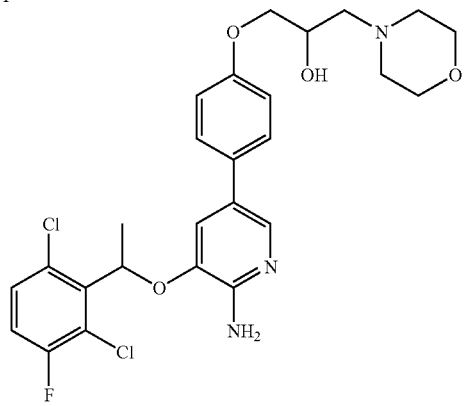

2. Preparation of 1-Morpholin-4-yl-3-[4-(4,4,5,5-tetramethyl-[1,3,2]dioxaborolan-2-yl)-phenoxy]-propan-2-ol: 4-(4,4,5,5-Tetramethyl-[1,3,2]dioxaborolan-2-yl)-phenol (440 mg, 2 mmol) was added to a stirred suspension of NaH (96 mg, 2 eq) in DMF (10 mL) at 0° C. After 1 hr, 2-hydroxy-7-oxa-4-azonia-spiro[3.5]nonane (714 mg, 2 eq.) was added. The mixture was stirred at room temperature overnight. The reaction mixture was poured into sat'd $NH_4Cl$ solution, and extracted with ethyl acetate. The extracts were washed with brine, dried over $Na_2SO_4$ and condensed to dryness. The crude product was purified with a silica gel column eluting with 2% methanol in methylene chloride to afford 220 mg of product as a pink solid (30%). $^1$H NMR (400 MHz, DMSO-$d_6$): δ 7.58 (d, J=8.2 Hz, 2H), 6.915 (d, J=7.8 Hz, 2H), 4.89 (d, J=2.0 Hz, 1H), 3.98 (m, 3H), 3.55 (m, 4H), 2.40 (m, 6H), 1.27 (s, 12H), MS (m/e): 364 $[M+H]^+$ (100%).

3. 1-(4-{6-Amino-5-[1-(2,6-dichloro-3-fluoro-phenyl)-ethoxy]-pyridin-3-yl}-phenoxy)-3-morpholin-4-yl-propan-2-ol was prepared following procedure 3 starting from 5-bromo-3-[1-(2,6-dichloro-3-fluoro-phenyl)-ethoxy]-pyridin-2-ylamine and 1-morpholin-4-yl-3-[4-(4,4,5,5-tetramethyl-[1,3,2]dioxaborolan-2-yl)-phenoxy]-propan-2-ol.

Example I-371

4-Methyl-piperazine-1-carboxylic acid (4-{6-amino-5-[1-(2,6-dichloro-3-fluoro-phenyl)-ethoxy]-pyridin-3-yl}-phenyl)-amide was prepared according to procedure 10.

Example I-386

3-{6-Amino-5-[1-(2,6-dichloro-phenyl)-ethoxy]-pyridin-3-yl}-benzoic acid was prepared using the same procedure as 4-[6-amino-5-(2-chloro-3,6-difluoro-benzyloxy)-pyridin-3-yl]-benzoic acid from 5-bromo-3-[1-(2,6-dichloro-phenyl)-ethoxy]-pyridin-2-ylamine and 3-methoxycarbonylbenzeneboronic acid.

Example I-387

(3-{6-Amino-5-[1-(2,6-dichloro-phenyl)-ethoxy]-pyridin-3-yl}-phenyl)-((3R,5S)-3,5-dimethyl-piperazin-1-yl)-methanone was prepared following procedure 4 starting from 3-{6-amino-5-(1-(2,6-dichloro-phenyl)-ethoxy]-pyridin-3-yl}-benzoic acid and 3,5-dimethyl-piperazine.

Example 399

4-{6-Amino-5-[1-(2,6-dichloro-phenyl)-ethoxy]-pyridin-3-yl}-benzoic acid was prepared using the same procedure as 4-[6-amino-5-(2-chloro-3,6-difluoro-benzyloxy)-pyridin-3-yl]-benzoic acid from 5-bromo-3-[1-(2,6-dichloro-phenyl)-ethoxy]-pyridin-2-ylamine and 4-methoxycarbonylbenzeneboronic acid

Example 400

4-{6-Amino-5-[1-(2,6-dichloro-phenyl)-ethoxy]-pyridin-3-yl}-N-(2-pyrrolidin-1-yl-ethyl)-benzamide was prepared following procedure 4 starting from 4-{6-amino-5-[1-(2,6-dichloro-phenyl)-ethoxy]-pyridin-3-yl}-benzoic acid and 2-pyrrolidin-1-yl-ethylamine.

Example I-454

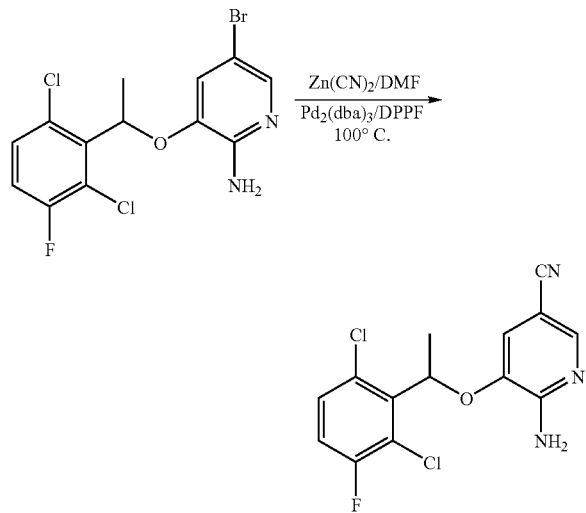

To a solution of 5-bromo-3-[1-(2,6-dichloro-3-fluoro-phenyl)-ethoxy]-pyridin-2-ylamine (5.00 g, 13.15 mmol) in DMF (73 mL) and water (1 mL) was added Zn(CN)$_2$ (4.50 g, 26.3 mmol), Pd$_2$(dba)$_3$ (0.602 g, 0.65 mmol), and DPPF (0.86 g, 1.55 mmol). The mixture was degassed and charged with nitrogen for three time, and then stirred under nitrogen at 100° C. for 3 hr. The reaction solution was partitioned between ethyl acetate and water. The organic layer was washed with a solution of sat. NH$_4$Cl-conc. NH$_4$OH-water (4:1:4), then dried over MgSO$_4$. The crude product was purified on a silica gel column eluting with ethyl acetate-hexanes (1:4) to provide 6-Amino-5-[1-(2,6-dichloro-3-fluoro-phenyl)-ethoxy]-nicotinonitrile as a white solid (4.15 g, 97% yield).

Example I-455

6-Amino-5-[1-(2,6-dichloro-3-cyano-phenyl)-ethoxy]-nicotinonitrile was obtained as a side product from the preparation of 6-Amino-5-[1-(2,6-dichloro-3-fluoro-phenyl)-ethoxy]-nicotinonitrile.

Example I-456

5-Aminomethyl-3-[1-(2,6-dichloro-3-fluoro-phenyl)-ethoxy]-pyridin-2-ylamine was prepared with the reduction of 6-amino-5-[1-(2,6-dichloro-3-fluoro-phenyl)-ethoxy]-nicotinonitrile. To a solution of borane in THF (1.0 M, 16.8 mL, 16.8 mmol) was added 6-amino-5-[1-(2,6-dichloro-3-fluoro-phenyl)-ethoxy]-nicotinonitrile (785 mg, 2.41 mmol) in anhydrous THF (8 mL) at 0° C. under nitrogen. The reaction solution was stirred under nitrogen at 0° C. for 5 hr, and then HCl solution (6N, 12 mL) was added slowly followed with the addition of water (12 mL) and methanol (80 mL). The mixture was stirred for overnight. After evaporation of solvents, the residue was partitioned between dichloromethane and NaOH solution (1 N). The water layer was extracted for three times, and the combined extracts were dried over MgSO$_4$. After filtration, evaporation and high vacuum dry, a white solid product was obtained (750 mg, 94% yield).

Example I-457

(R)-2-Pyrrolidin-1-ylmethyl-pyrrolidine-1-carboxylic acid {6-amino-5-[1-(2,6-dichloro-3-fluoro-phenyl)-ethoxy]-pyridin-3-ylmethyl}-amide was prepared with the same procedure as Step 4 in procedure 11.

Example I-462

(S)-1-{6-Amino-5-[1-(2,6-dichloro-3-fluoro-phenyl)-ethoxy]-pyridin-3-yl}-ethane-1,2-diol was prepared as follow: To a solution of asymmetric dihydroxylation-mix α (2.33 g) in a 1:1 mixture of t-BuOH and water (8 mL each) cooled to 0° C. was added 3-[1-(2,6-dichloro-3-fluoro-phenyl)-ethoxy]-5-vinyl-pyridin-2-ylamine (500 mg, 1.67 mmol). The reaction mixture was stirred at 0° C. until consumption of the starting material. Three more loadings of AD-mix α was added periodically to increase the reaction rate. Water was added (5 mL) and the mixture was extracted with EtOAc (3×20 mL). The combined organic layer was dried over Na$_2$SO$_4$, and concentrated. The crude product was purified by reverse phase HPLC to provide (S)-1-{6-amino-5-[1-(2,6-dichloro-3-fluoro-phenyl)-ethoxy]-pyridin-3-yl}ethane-1,2-diol (320 mg, 53% yield).

Example I-463

(R)-1-{6-Amino-5-[1-(2,6-dichloro-3-fluoro-phenyl)-ethoxy]-pyridin-3-yl}-ethane-1,2-diol was prepared with the same procedure as Example I-462 with AD-mix α.

Examples II-1 to II-6

The compounds of Examples II-1 to II-6 were prepared according to the Suzuki coupling procedure 3 from 5-bromo- 3-(2,6-dichloro-benzyloxy)-pyrazin-2-ylamine and: 4-(4,4,5,5-tetramethyl-[1,3,2]dioxaborolan-2-yl)-phenol (Example II-1); 2-[4-(4,4,5,5-tetramethyl-1,3,2-dioxaborolan-2-yl)-phenyl]isothiazolidine 1,1-dioxide (Example II-2); 3-{2-[4-(4,4,5,5-tetramethyl-[1,3,2]dioxaborolan-2-yl)-phenoxy]-ethyl}-morpholine (Example II-3); 4-{2-[4-(4,4,5,5-tetramethyl-[1,3,2]dioxaborolan-2-yl)-phenoxy]-ethyl}-morpholine (Example II-4); 4-(4,4,5,5-Tetramethyl-[1,3,2]dioxaborolan-2-yl)-phenylamine (Example II-5); and 4-(4,4,5,5-tetramethyl-[1,3,2]dioxaborolan-2-yl)-benzoic acid (Example II-6).

Example II-7

{4-[5-Amino-6-(2,6-dichloro-benzyloxy)-pyrazin-2-yl]-phenyl}-[(2R)-2-pyrrolidin-1-ylmethyl-pyrrolidin-1-yl]-methanone was prepared following the amidation procedure 4 from 4-[5-amino-6-(2,6-dichloro-benzyloxy)-pyrazin-2-yl]-benzoic acid and (2R)-2-pyrrolidin-1-ylmethyl-pyrrolidine.

Example II-8

{4-[5-Amino-6-(2,6-dichloro-benzyloxy)-pyrazin-2-yl]-phenyl}-(4-pyrrolidin-1-yl-piperidin-1-yl)-methanone was prepared following the amidation procedure 4 from 4-[5-amino-6-(2,6-dichloro-benzyloxy)-pyrazin-2-yl]-benzoic acid and 4-pyrrolidin-1-yl-piperidine.

Examples II-9 to II-32

The compounds of Examples II-9 to II-32 were prepared following the Suzuki coupling procedure 3 from 5-bromo-3-(2-chloro-3,6-difluoro-benzyloxy)-pyrazin-2-ylamine and the following compounds prepared according to the procedure in Example I-243: 2-morpholin-4-yl-ethanesulfonic acid [4-(4,4,5,5-tetramethyl-[1,3,2]dioxaborolan-2-yl)-phenyl]-amide (Example II-9); 2-piperidin-1-yl-ethanesulfonic acid [4-(4,4,5,5-tetramethyl-[1,3,2]dioxaborolan-2-yl)-phenyl]-amide (Example II-10); 2-(4-hydroxy-piperidin-1-yl)-ethanesulfonic acid [4-(4,4,5,5-tetramethyl-[1,3,2]dioxaborolan-2-yl)-phenyl]-amide (Example II-11); 2-pyrrolidin-1-yl-ethanesulfonic acid [4-(4,4,5,5-tetramethyl-[1,3,2]dioxaborolan-2-yl)-phenyl]-amide (Example II-12); 2-[(3R)-3-Hydroxy-pyrrolidin-1-yl]-ethanesulfonic acid [4-(4,4,5,5-tetramethyl-[1,3,2]dioxaborolan-2-yl)-phenyl]-amide (Example II-13); 2-[(2S)-2-Hydroxymethyl-pyrrolidin-1-yl]-ethanesulfonic acid [4-(4,4,5,5-tetramethyl-[1,3,2]dioxaborolan-2-yl)-phenyl]-amide (Example II-14); 2-(cyclopropylmethyl-amino)-ethanesulfonic acid [4-(4,4,5,5-tetramethyl-[1,3,2]dioxaborolan-2-yl)-phenyl]-amide (Example II-15); 2-dimethylamino-ethanesulfonic acid [4-(4,4,5,5-tetramethyl-[1,3,2]dioxaborolan-2-yl)-phenyl]-amide (Example II-16); 2-diethylamino-ethanesulfonic acid [4-(4,4,5,5-tetramethyl-[1,3,2]dioxaborolan-2-yl)-phenyl]-amide (Example II-17); 2-(4-acetyl-piperazin-1-yl)-ethanesulfonic acid [4-(4,4,5,5-tetramethyl-[1,3,2]dioxaborolan-2-yl)-phenyl]-amide (Example II-18); 2-[4-(2-hydroxy-acetyl)-piperazin-1-yl]-ethanesulfonic acid [4-(4,4,5,5-tetramethyl-[1,3,2]dioxaborolan-2-yl)-phenyl]-amide (Example II-19); 2-cyclopropylamino-ethanesulfonic acid [4-(4,4,5,5-tetramethyl-[1,3,2]dioxaborolan-2-yl)-phenyl]-amide (Example II-20); 2-[(3R)-2-Hydroxymethyl-pyrrolidin-1-yl]-ethanesulfonic acid [3-(4,4,5,5-tetramethyl-[1,3,2]dioxaborolan-2-yl)-phenyl]-amide (Example II-21); 2-(4-Hydroxy-piperidin-1-yl)-ethanesulfonic acid [3-(4,4,5,5-tetramethyl-[1,3,2]dioxaborolan-2-yl)-phenyl]-amide (Example II-22); 2-(4-acetyl-piperazin-1-yl)-ethanesulfonic acid [3-(4,4,5,5-tetramethyl-[1,3,2]dioxaborolan-2-yl)-phenyl]-amide (Example II-23); 2-piperidin-1-yl-ethanesulfonic acid [3-(4,4,5,5-tetramethyl-[1,3,2]dioxaborolan-2-yl)-phenyl]-amide (Example II-24); 2-diethylamino-ethanesulfonic acid [3-(4,4,5,5-tetramethyl-[1,3,2]dioxaborolan-2-yl)-phenyl]-amide (Example II-25); 2-morpholin-4-yl-ethanesulfonic acid [3-(4,4,5,5-tetramethyl-[1,3,2]dioxaborolan-2-yl)-phenyl]-amide (Example II-26); 2-pyrrolidin-1-yl-ethanesulfonic acid [3-(4,4,5,5-tetramethyl-[1,3,2]dioxaborolan-2-yl)-phenyl]-amide (Example II-27); 2-dimethylamino-ethanesulfonic acid [3-(4,4,5,5-tetramethyl-[1,3,2]dioxaborolan-2-yl)-phenyl]-amide (Example II-28); 2-[4-(2-hydroxy-acetyl)-piperazin-1-yl]-ethanesulfonic acid [3-(4,4,5,5-tetramethyl-[1,3,2]dioxaborolan-2-yl)-phenyl]-amide (Example II-29); 2-(cyclopropylmethyl-amino)-ethanesulfonic acid [3-(4,4,5,5-tetramethyl-[1,3,2]dioxaborolan-2-yl)-phenyl]-amide (Example II-30); 2-[(3R)-3-hydroxy-pyrrolidin-1-yl]-ethanesulfonic acid [3-(4,4,5,5-tetramethyl-[1,3,2]dioxaborolan-2-yl)-phenyl]-amide (Example II-31); and 2-cyclopropylamino-ethanesulfonic acid [3-(4,4,5,5-tetramethyl-[1,3,2]dioxaborolan-2-yl)-phenyl]-amide (Example II-32).

Example II-33

4-[5-Amino-6-(2-chloro-3,6-difluoro-benzyloxy)-pyrazin-2-yl]-benzoic acid was prepared following the Suzuki coupling procedure 3 from 5-bromo-3-(2-chloro-3,6-difluoro-benzyloxy)-pyrazin-2-ylamine and 4-(4,4,5,5-tetramethyl-[1,3,2]dioxa-borolan-2-yl)-benzoic acid.

Example II-34

{4-[5-Amino-6-(2-chloro-3,6-difluoro-benzyloxy)-pyrazin-2-yl]-phenyl}-[(2R)-2-pyrrolidin-1-ylmethyl-pyrrolidin-1-yl]-methanone was prepared following the amidation procedure 4 from 4-[5-amino-6-(2-chloro-3,6-difluoro-benzyloxy)-pyrazin-2-yl]-benzoic acid and (2R)-2-pyrrolidin-1-ylmethyl-pyrrolidine.

Examples II-35 to II-46

The compounds of Examples II-35 to II-46 were prepared according to the amidation procedure 4 from 4-[5-amino-6-(2-chloro-3,6-difluoro-benzyloxy)-pyrazin-2-yl]-benzoic acid and: 2-pyrrolidin-1-yl-ethylamine (Example II-35); (S)-pyrrolidin-3-yl-carbamic acid tert-butyl ester, followed by de-protection of Boc-group with trifluoroacetic acid in dichloromethane (Example II-36); 1-[4-(2-amino-ethyl)-piperazin-1-yl]-ethanone (Example II-37); 3-pyrrolidin-1-yl-propylamine (Example II-38); (3S)-3-dimethylamino-pyrrolidine (Example II-39); (R)-pyrrolidin-3-yl-carbamic acid tert-butyl ester, followed by de-protection of Boc-group with trifluoroacetic acid in dichloromethane (Example II-40); 3,5-dimethyl-piperazine (Example II-41); 4-pyrrolidin-1-yl-piperidine (Example II-42); 3-morpholin-4-yl-propylamine (Example II-43); 1-methyl-piperidin-4-ylamine (Example II-44); 2-morpholin-4-yl-ethylamine (Example II-45); and N-methylpiperazine (Example II-46).

Example II-47

3-[5-Amino-6-(2-chloro-3,6-difluoro-benzyloxy)-pyrazin-2-yl]-benzoic acid was prepared following the Suzuki coupling procedure 3 from 5-bromo-3-(2-chloro-3,6- difluoro-benzyloxy)-pyrazin-2-ylamine (Example II(b)) and 3-(4,4,5,5-tetramethyl-[1,3,2]dioxaborolan-2-yl)-benzoic acid (Aldrich, Milwaukee).

Examples II-48 to II-60

The compounds of Examples II-48 to II-60 were prepared according to the amidation procedure 4 from 3-[5-amino-6-(2-chloro-3,6-difluoro-benzyloxy)-pyrazin-2-yl]-benzoic acid and: N-methylpiperazine (Example II-48); (R)-pyrrolidin-3-yl-carbamic acid tert-butyl ester, followed by de-protection of Boc-group with trifluoroacetic acid in dichloromethane (Example II-49); (S)-pyrrolidin-3-yl-carbamic acid tert-butyl ester, followed by de-protection of Boc-group with trifluoroacetic acid in dichloromethane (Example II-50); 3,5-dimethyl-piperazine (Example II-51); 3-morpholin-4-yl-propylamine (Example II-52); 4-pyrrolidin-1-yl-piperidine (Example II-53); (3S)-3-dimethylamino-pyrrolidine (Example II-54); 2-pyrrolidin-1-yl-ethyl amine (Example II-55); 1-methyl-piperidin-4-ylamine (Example II-56); (2S)-pyrrolidin-1-ylmethyl-pyrrolidine (Example II-57); 2-morpholin-4-yl-ethylamine (Example II-58); 2-(4-Acetyl-piperazin-1-yl)-ethylamine (Example II-59); and 3-pyrrolidin-1-yl-propylamine (Example II-60).

Example II-61

3-(2-Chloro-3,6-difluoro-benzyloxy)-5-(1H-indol-5-yl)-pyrazin-2-ylamine was prepared from 5-bromo-3-(2-chloro-3,6-difluoro-benzyloxy)-pyrazin-2-ylamine and indole-5-boronic acid following procedure 3.

Examples II-62 to II-68

The compounds of Examples II-62 to II-68 were prepared according to procedure 5 from 3-(2-Chloro-3,6-difluoro-benzyloxy)-5-(1H-indol-5-yl)-pyrazin-2-ylamine and: pyrrolidine (Example II-62); diethylamine (Example II-63); 1-piperazin-1-yl-ethanone (Example II-64); 2,6-dimethyl-morpholine (Example II-65); N—(S)-pyrrolidin-3-yl-acetamide (Example II-66); piperidine (Example II-67); and morpholine (Example II-68).

Example II-69

3-[1-(2-Chloro-3,6-difluoro-phenyl)-2-methyl-propoxy]-5-[4-(2-morpholin-4-yl-ethoxy)-phenyl]-pyrazin-2-ylamine was prepared following the Suzuki coupling procedure 3 from 5-bromo-3-[1-(2-chloro-3,6-difluoro-phenyl)-2-methyl-propoxy]-pyrazin-2-ylamine and 4-{2-[4-(4,4,5,5-tetramethyl-[1,3,2]dioxaborolan-2-yl)-phenoxy]-ethyl}-morpholine.

Example II-70

(3-[1-(2-Chloro-3,6-difluoro-phenyl)-ethoxy]-5-[4-(2-morpholin-4-yl-ethoxy)-phenyl]-pyrazin-2-ylamine, compound with trifluoro-acetic acid, was prepared following the Suzuki coupling procedure 3 from 5-bromo-3-[1-(2-chloro-3,6-difluoro-phenyl)-2-methyl-propoxy]-pyrazin-2-ylamine and 4-{2-[4-(4,4,5,5-tetramethyl-[1,3,2]dioxaborolan-2-yl)-phenoxy]-ethyl}-morpholine. The product was purified with a reversed phase C-18 preparative HPLC eluting with acetonitrile-water-trifluoroacetic acid and obtained as a trifluoroacetic acid salt.

Examples II-71 to II-83

The compounds of Examples II-71 to II-83 were prepared according to the Suzuki coupling procedure 3 from 5-bromo-3-[1-(2,6-dichloro-3-fluoro-phenyl)-ethoxy]-pyrazin-2-ylamine and: 4-{2-[4-(4,4,5,5-tetramethyl-[1,3,2]dioxaborolan-2-yl)-phenoxy]-ethyl}-morpholine, followed by purification with a reversed phase C-18 preparative HPLC eluting with acetonitrile-water-trifluoroacetic acid and obtained as a trifluoroacetic acid salt (Example II-71); N-[4-(4,4,5,5-tetramethyl-[1,3,2]dioxaborolan-2-yl)-phenyl]-methane-sulfonamide (Example II-72); 2-pyrrolidin-1-yl-ethanesulfonic acid [4-(4,4,5,5-tetramethyl-[1,3,2] dioxaborolan-2-yl)-phenyl]-amide (prepared as in Example I-243) (Example II-73); 2-(4-hydroxy-piperidin-1-yl)-ethanesulfonic acid [4-(4,4,5,5-tetramethyl-[1,3,2]dioxaborolan-2-yl)-phenyl]-amide (prepared as in Example I-243) (Example II-74); 2-piperidin-1-yl-ethanesulfonic acid [4-(4,4,5,5-tetramethyl-[1,3,2]dioxaborolan-2-yl)-phenyl]-amide (prepared according to the procedure in Example I-243) (Example II-75); 2-(cyclopropylmethyl-amino)-ethanesulfonic acid [4-(4,4,5,5-tetramethyl-[1,3,2]dioxaborolan-2-yl)-phenyl]-amide (prepared as in Example I-243) (Example II-76); 2-[(3R)-3-Hydroxy-pyrrolidin-1-yl]-ethanesulfonic acid [4-(4,4,5,5-tetramethyl-[1,3,2]dioxaborolan-2-yl)-phenyl]-amide (prepared as in Example I-243) (Example II-77); 2-[(2S)-2-Hydroxymethyl-pyrrolidin-1-yl]-ethanesulfonic acid [4-(4,4,5,5-tetramethyl-[1,3,2] dioxaborolan-2-yl)-phenyl]-amide (prepared as in Example I-243) (Example II-78); 2-dimethylamino-ethanesulfonic acid [4-(4,4,5,5-tetramethyl-[1,3,2]dioxaborolan-2-yl)-phenyl]-amide (prepared as in Example I-243) (Example II-79); 2-morpholin-4-yl-ethanesulfonic acid [4-(4,4,5,5-tetramethyl-[1,3,2]dioxaborolan-2-yl)-phenyl]-amide (prepared as in Example I-243) (Example II-80); 2-diethylamino-ethanesulfonic acid [4-(4,4,5,5-tetramethyl-[1,3,2]dioxaborolan-2-yl)-phenyl]-amide (prepared as in Example I-243) (Example II-81); 2-cyclopropylamino-ethanesulfonic acid [4-(4,4,5,5-tetramethyl-[1,3,2]dioxaborolan-2-yl)-phenyl]-amide (prepared as in Example I-243); and 3-(4,4,5,5-tetramethyl-[1,3,2]dioxaborolan-2-yl)-benzoic acid (Example II-83).

Examples II-84 to II-88

The compounds of Examples II-84 to II-88 were prepared according to the amidation procedure 4 from 3-{5-amino-6-[1-(2,6-dichloro-3-fluoro-phenyl)-ethoxy]-pyrazin-2-yl}-benzoic acid and: (S)-pyrrolidin-3-yl-carbamic acid tert-butyl ester, followed by de-protection of Boc-group with trifluoroacetic acid in dichloromethane (Example II-84); (R)-pyrrolidin-3-yl-carbamic acid tert-butyl ester, followed by de-protection of Boc-group with trifluoroacetic acid in dichloromethane (Example II-85); (2R)-2-pyrrolidin-1-ylmethyl-pyrrolidine (Example II-86); 2-(4-acetyl-piperazin-1-yl)-ethylamine (Example II-87); and (2S)-pyrrolidin-1-ylmethyl-pyrrolidine (Example II-88).

Example II-89

3-{5-Amino-6-[1-(2-chloro-3,6-difluoro-phenyl)-ethoxy]-pyrazin-2-yl}-benzoic acid was prepared following the Suzuki coupling procedure 3 from 5-bromo-3-[1-(2-chloro-3,6-difluoro-phenyl)-ethoxy]-pyrazin-2-ylamine and 3-(4,4,5,5-tetramethyl-[1,3,2]dioxaborolan-2-yl)-benzoic acid.

Example II-90

3-{5-Amino-6-[1-(2,6-dichloro-3-fluoro-phenyl)-ethoxy]-pyrazin-2-yl}-N-(1-methyl-piperidin-4-yl)-benzamide was prepared following the amidation procedure 4 from 3-{5-amino-6-[1-(2-chloro-3,6-difluoro-phenyl)-ethoxy]-pyrazin-2-yl}-benzoic acid and 1-methyl-piperidin-4-ylamine.

Example II-91

3-{5-Amino-6-[1-(2,6-dichloro-3-fluoro-phenyl)-ethoxy]-pyrazin-2-yl}-N-(3-pyrrolidin-1-yl-propyl)-benzamide was prepared following the amidation procedure 4 from 3-{5-amino-6-[1-(2,6-dichloro-3-fluoro-phenyl)-ethoxy]-pyrazin-2-yl}-benzoic acid and 3-pyrrolidin-1-yl-propylamine.

Example II-92

(3-{5-Amino-6-[1-(2,6-dichloro-3-fluoro-phenyl)-ethoxy]-pyrazin-2-yl}-phenyl)-(4-pyrrolidin-1-yl-piperidin-1-yl)-methanone was prepared following the amidation procedure 4 from 3-{5-amino-6-[1-(2,6-dichloro-3-fluoro-phenyl)-ethoxy]-pyrazin-2-yl}-benzoic acid and 4-pyrrolidin-1-yl-piperidin-1-ylamine.

Example II-93

4-[5-Amino-6-(3-fluoro-2-trifluoromethyl-benzyloxy)-pyrazin-2-yl]-benzoic acid was prepared following the Suzuki coupling procedure 3 from 5-bromo-3-(3-fluoro-2-trifluoromethyl-benzyloxy)-pyrazin-2-ylamine and 3-(4,4,5,5-tetramethyl-[1,3,2]dioxaborolan-2-yl)-benzoic acid.

Example II-94

4-[5-Amino-6-(3-fluoro-2-trifluoromethyl-benzyloxy)-pyrazin-2-yl]-N-(2-morpholin-4-yl-ethyl)-benzamide was prepared following the amidation procedure 4 from 4-[5-amino-6-(3-fluoro-2-trifluoromethyl-benzyloxy)-pyrazin-2-yl]-benzoic acid and 2-morpholin-4-yl-ethylamine.

Example II-95

4-[5-Amino-6-(3-fluoro-2-trifluoromethyl-benzyloxy)-pyrazin-2-yl]-N-(1-methyl-piperidin-4-yl)-benzamide was prepared following the amidation procedure 4 from 4-[5-amino-6-(3-fluoro-2-trifluoromethyl-benzyloxy)-pyrazin-2-yl]-benzoic acid and 1-methyl-piperidin-4-ylamine.

Examples II-96 to II-211 were prepared according to the procedures referenced in the Tables herein, except as specifically described in the following paragraphs.

Example II-108

4-{5-Amino-6-[1-(2-chloro-3,6-difluoro-phenyl)-ethoxy]-pyrazin-2-yl}-benzoic acid was prepared using the same procedure as 4-[6-amino-5-(2-chloro-3,6-difluoro-benzyloxy)-pyridin-3-yl]-benzoic acid from 5-bromo-3-[1-(2-chloro-3,6-difluoro-phenyl)-ethoxy)-pyrazin-2-ylamine and 4-methoxycarbonylbenzeneboronic acid.

Example II-109

4-{5-Amino-6-[1-(2-chloro-3,6-difluoro-phenyl)-ethoxy]-pyrazin-2-yl}-N-(3-pyrrolidin-1-yl-propyl)-benzamide was prepared following procedure 4 starting from 4-{5-amino-6-[1-(2-chloro-3,6-difluoro-phenyl)-ethoxy]-pyrazin-2-yl}-benzoic acid and 3-pyrrolidin-1-yl-propylamine.

Example II-121

3-[5-Amino-6-(3-fluoro-2-trifluoromethyl-benzyloxy)-pyrazin-2-yl]-benzoic acid using the same procedures a 4-[6-amino-5-(2-chloro-3,6-difluoro-benzyloxy)-pyridin-3-yl]-benzoic acid from 5-bromo-3-(3-fluoro-2-trifluoromethyl-benzyloxy)-pyrazin-2-ylamine and 3-methoxycarbonylbenzeneboronic acid.

Example II-122

{3-[5-Amino-6-(3-fluoro-2-trifluoromethyl-benzyloxy)-pyrazin-2-yl]-phenyl}-(4-pyrrolidin-1-yl-piperidin-1-yl)-methanone was prepared following procedure 4 starting from 3-[5-Amino-6-(3-fluoro-2-trifluoromethyl-benzyloxy)-pyrazin-2-yl]-benzoic acid and 4-pyrrolidin-1-yl-piperidin-1-ylamine.

Example II-145

4-{5-Amino-6-[1-(2,6-dichloro-3-fluoro-phenyl)-ethoxy]-pyrazin-2-yl}-benzoic acid was prepared using the same procedure as 4-[6-amino-5-(2-chloro-3,6-difluoro-benzyloxy)-pyridin-3-yl]-benzoic acid from 5-bromo-3-[1-(2,6-dichloro-3-fluoro-phenyl)-ethoxy]-pyrazin-2-ylamine and 4-methoxycarbonylbenzeneboronic acid.

Example II-148

4-{5-Amino-6-[1-(2,6-dichloro-3-fluoro-phenyl)-ethoxy]-pyrazin-2-yl}-N-((R)-2-hydroxy-3-pyrrolidin-1-yl-propyl)-benzamide was prepared following procedure 4 starting from 4-{5-Amino-6-[1-(2,6-dichloro-3-fluoro-phenyl)-ethoxy]-pyrazin-2-yl}-benzoic acid and (R)-2-hydroxy-3-pyrrolidin-1-yl-propylamine.

Example II-156

4-{5-Amino-6-[1-(2,6-dichloro-phenyl)-ethoxy]-pyrazin-2-yl}-benzoic acid was prepared using the same procedure as 4-[6-amino-5-(2-chloro-3,6-difluoro-benzyloxy)-pyridin-3-yl]-benzoic acid from 5-bromo-3-[1-(2,6-dichloro-phenyl)-ethoxy]-pyrazin-2-ylamine and 4-methoxycarbonylbenzeneboronic acid.

Example II-157

(4-{5-Amino-6-[1-(2,6-dichloro-phenyl)-ethoxy]-pyrazin-2-yl}-phenyl)-(4-pyrrolidin-1-yl-piperidin-1-yl)-methanone was prepared following procedure 4 starting from 4-{5-Amino-6-[1-(2,6-dichloro-phenyl)-ethoxy]-pyrazin-2-yl}-benzoic acid and 4-pyrrolidin-1-yl-piperidin-1-ylamine.

Example II-168

3-{5-Amino-6-[1-(2,6-dichloro-phenyl)-ethoxy]-pyrazin-2-yl}-benzoic acid was prepared using the same procedure as 4-[6-amino-5-(2-chloro-3,6-difluoro-benzyloxy)-pyridin-3-yl]-benzoic acid from 5-bromo-3-[1-(2,6-dichloro-phenyl)-ethoxy]-pyrazin-2-ylamine and 3-methoxycarbonylbenzeneboronic acid.

Example II-169

3-{5-Amino-6-[1-(2,6-dichloro-phenyl)-ethoxy]-pyrazin-2-yl}-N-(1-methyl-piperidin-4-yl)-benzamide was prepared following procedure 4 starting from 3-{5-amino-6-[1-(2,6- dichloro-phenyl)-ethoxy]-pyrazin-2-yl}-benzoic acid and 1-methyl-piperidin-4-ylamine.

Example II-193

5-[5-Amino-6-(2-chloro-3,6-difluoro-benzyloxy)-pyrazin-2-yl]-thiophene-2-carboxylic acid was prepared following procedure 3 starting from 5-bromo-3-(2-chloro-3,6-difluoro-benzyloxy)-pyrazin-2-ylamine and 5-carboxythiophene-2-boronic acid.

Example II-194

{5-[5-Amino-6-(2-chloro-3,6-difluoro-benzyloxy)-pyrazin-2-yl]-thiophen-2-yl}-(4-methyl-piperazin-1-yl)-methanone was prepared following procedure 4 starting from 5-[5-Amino-6-(2-chloro-3,6-difluoro-benzyloxy)-pyrazin-2-yl]-thiophene-2-carboxylic acid and 4-methyl-piperazin-1-ylamine.

Examples L-1 to L-176 were prepared according to procedure 40. In Table 5, the compounds are grouped into sections, with each section having a letter designation. Example numbers are assigned left to right by rows. For example, in Section A, the compounds in the top row, from left to right, are Examples L-1 to L-4, and the compounds in the second row are, from left to right, Examples L-5-L-8. % Inhibition is the percent c-MET inhibition at 50 nM.

Examples L-177 to L-352 were prepared according to procedure 41. In Table 6, the compounds are grouped into sections, with each section having a letter designation. Example numbers are assigned left to right by rows. % Inhibition is the percent c-MET inhibition at 1 µM.

Examples L-353 to L-548 were prepared according to procedure 42. In Table 7, the compounds are grouped into sections, with each section having a letter designation. Example numbers are assigned left to right by rows. % Inhibition is the percent c-MET inhibition at 1 µM.

Examples L-549 to L-636 were prepared according to procedure 43. In Table 8, the compounds are grouped into sections, with each section having a letter designation. Example numbers are assigned left to right by rows. % Inhibition is the percent c-MET inhibition at 1 µM.

BIOLOGICAL EXAMPLES

It will be appreciated that, in any given series of compounds, a range of biological activities will be observed. In its presently preferred aspects, this invention relates to novel compounds capable of modulating, regulating and/or inhibiting protein kinase activity. The following assays may be employed to select those compounds demonstrating the optimal degree of the desired activity.

Assay Procedures

The following in vitro assay may be used to determine the level of activity and effect of the different compounds of the present invention on one or more of the PKs. Similar assays can be designed along the same lines for any PK using techniques well known in the art. A literature reference is provided (Technikova-Dobrova Z, Sardanelli A M, Papa S FEBS Lett. 1991 Nov. 4; 292: 69-72).

The general procedure is as follows: compounds and kinase assay reagents are introduced into test wells. The assay is initiated by addition of the kinase enzyme. Enzyme inhibitors reduce the measured activity of the enzyme.

In the continuous-coupled spectrophotometric assay the time-dependent production of ADP by the kinase is determined by analysis of the rate of consumption of NADH by measurement of the decrease in absorbance at 340 nm. As the PK produces ADP it is re-converted to ATP by reaction with phosphoenol pyruvate and pyruvate kinase. Pyruvate is also produced in this reaction. Pyruvate is subsequently converted to lactate by reaction with lactate dehydrogenase, which simultaneously converts NADH to NAD. NADH has a measurable absorbance at 340 nm whereas NAD does not.

The presently preferred protocol for conducting the continuous-coupled spectrophotometric experiments for specific PKs is provided below. However, adaptation of this protocol for determining the activity of compounds against other RTKs, as well as for CTKs and STKs, is well within the scope of knowledge of those skilled in the art.

HGFR Continuous-Coupled Spectrophotometric Assay

This assay analyzes the tyrosine kinase activity of HGFR on the Met-2 substrate peptide, a peptide derived from the activation loop of the HGFR.

Materials and Reagents:
1. HGFR enzyme from Upstate (Met, active) Cat. # 14-526
2. Met-2 Peptide (HGFR Activation Loop) Ac-ARDMY-DKEYYSVHNK (MW=1960). Dissolve up in 200 mM HEPES, pH 7.5 at 10 mM stock.
3. 1 M PEP (phospho-enol-pyruvate) in 200 mM HEPES, pH 7.5
4. 100 mM NADH (B-Nicotinamide Adenine Dinucleotide, Reduced Form) in 200 mM HEPES, pH 7.5
5. 4 M $MgCl_2$ (Magnesium Chloride) in $ddH_2O$
6. 1 M DTT (Dithiothreitol) in 200 mM HEPES, pH 7.5
7. 15 Units/mL LDH (Lactic Dehydrogenase)
8. 15 Units/mL PK (Pyruvate Kinase)
9. 5M NaCl dissolved in $ddH_2O$
10. Tween-20 (Protein Grade) 10% Solution
11. 1 M HEPES buffer: (N-[2-Hydroxyethyl]piperazine-N-[2-ethanesulfonic acid]) Sodium Salt. Dissolve in ddH2O, adjust pH to 7.5, bring volume to 1 L. Filter at 0.1 µm.
12. HPLC Grade Water; Burdick and Jackson #365-4, 1×4 liters (or equivalent)
13. 100% DMSO (SIGMA)
14. Costar # 3880—black clear flat bottom half area plates for $K_i$ determination and % inhibition
15. Costar # 3359—96 well polypropylene plates, round bottom for serial dilutions
16. Costar # 3635—UV-plate clear flat bottom plates for % inhibition
17. Beckman DU-650 w/micro cell holders
18. Beckman 4-position micro cell cuvette Procedure:

Prep Dilution Buffer (DB) for Enzyme (For 30 mL prep)
1. DB final concentration is 2 mM DTT, 25 mM $NaCl_2$, 5 mM $MgCl_2$, 0.01% Tween-20, and 50 mM HEPES buffer, pH 7.5.
2. Make up 50 mM HEPES by adding 1.5 mL 1 M HEPES into 28.1 mL of ddH2O. Add rest of the reagents. Into 50 mL conical vial, add 60 uL of 1M DTT, 150 uL 5M $NaCl_2$, 150 uL 1M $MgCl_2$, and 30 uL of 10% Tween-20 to give total volume of 30 mL.
3. Vortex for 5-10 seconds
4. Aliquot out DB at 1 mL/tube and label tubes as "DB HGFR"
5. Note: This can be prepared and stored ahead of time.
6. Freeze un-used aliquots in microcentrifuge tubes at −20° C. freezer.

Prep Compounds
1. For compound dilution plate, add 4 uL of 10 mM stock into column 1 of plate, and bring volume to 100 uL with 100% DMSO.

2. Set up the Precision 2000 dilution method. A final concentration of 200 uM compound in 50% DMSO, 100 mM HEPES (1:2 serial dilution).

Prep Coupled Enzymatic Buffer:

1. Final concentration in assay:

|   | Reagent (Stock Conc.) | Final Conc. In Assay |
|---|---|---|
| a. | PEP (1 M) | 1 mM |
| b. | NADH (100 mM) | 300 uM |
| c. | MgCl$_2$ (4 M) | 20 mM |
| d. | DTT (1 M) | 2 mM |
| e. | ATP (500 mM) | 300 uM |
| f. | HEPES 200 mM (pH 7.5) | 100 mM |
| g. | Pyruvate Kinase (PK) | 15 units/mL |
| h. | Lactic Dehydrogenase (LDH) | 15 units/mL |
| i. | Met-2 peptide (10 mM) | 0.500 mM |
| j. | HGFR | 50 nM |

2. For a 10 mL reaction buffer add 10 uL of 1M PEP, 33 uL of 100 mM NADH, 50 uL of 4M MgCl$_2$, 20 uL of 1M DTT, 6 uL of 500 mM ATP, and 500 uL of 10 mM Met-2 peptide into 100 mM HEPES buffer pH 7.5 and vortex/mix.
3. Add coupling enzymes, LDH and PK, into reaction mix. Mix by gentle inversion.

Running Samples

1. Spectrophotometer settings:

|   |   |   |
|---|---|---|
| i. | Absorbance wavelength (λ): | 340 nm |
| ii. | Incubation time: | 10 min |
| iii. | Run time: | 10 min |
| iv. | Temperature: | 37° C. |

2. Add 85 μL of CE reaction mix into each well of assay plate.
3. Add 5 μL of diluted compound into a well of the assay plate.
4. Add 5 μL of 50% DMSO for negative control into last column of assay plate.
5. Mix with multi-channel pipettor or orbital shaker.
6. Pre-incubate for 10 minutes at 37° C.
7. Add 10 μL of 500 nM HGFR to each well of assay plate; the final HGFR concentration is 50 nM in a total final volume of 100 μL.
8. Measure activity for 10 minutes at λ=340 nm and 37° C.

The following in vitro assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359-371). General procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art.

Other assays described herein measure the amount of DNA made in response to activation of a test kinase, which is a general measure of a proliferative response. General procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or H$^3$-thymidine is added. The amount of labeled DNA is detected with either an anti-BrdU antibody or by measuring radioactivity and is compared to control cells not contacted with a test compound.

MET Transphosphorylation Assay

This assay is used to measure phosphotyrosine levels on a poly(glutamic acid:tyrosine, 4:1) substrate as a means for identifying agonists/antagonists of met transphosphorylation of the substrate.

Materials and Reagents:

1. Corning 96-well ELISA plates, Corning Catalog # 25805-96.
2. Poly(glu-tyr), 4:1, Sigma, Cat. No; P 0275.
3. PBS, Gibco Catalog # 450-1300EB
4. 50 mM HEPES
5. Blocking Buffer: Dissolve 25 g Bovine Serum Albumin, Sigma Cat. No A-7888, in 500 mL PBS, filter through a 4 μm filter.
6. Purified GST fusion protein containing the Met kinase domain, SUGEN, Inc.
7. TBST Buffer.
8. 10% aqueous (MilliQue H$_2$O) DMSO.
9. 10 mM aqueous (dH$_2$O) Adenosine-5'-triphosphate, Sigma Cat. No. A-5394.
10. 2× Kinase Dilution Buffer: for 100 mL, mix 10 mL 1M HEPES at pH 7.5 with 0.4 mL 5% BSA/PBS, 0.2 mL 0.1 M sodium orthovanadate and 1 mL 5M sodium chloride in 88.4 mL dH$_2$O.
11. 4× ATP Reaction Mixture: for 10 mL, mix 0.4 mL 1 M manganese chloride and 0.02 mL 0.1 M ATP in 9.56 mL dH$_2$O.
12. 4× Negative Controls Mixture: for 10 mL, mix 0.4 mL 1 M manganese chloride in 9.6 mL dH$_2$O.
13. NUNC 96-well V bottom polypropylene plates, Applied Scientific Catalog # S-72092
14. 500 mM EDTA.
15. Antibody Dilution Buffer: for 100 mL, mix 10 mL 5% BSA/PBS, 0.5 mL 5% Carnation® Instant Milk in PBS and 0.1 mL 0.1 M sodium orthovanadate in 88.4 mL TBST.
16. Rabbit polyclonal antophosphotyrosine antibody, SUGEN, Inc.
17. Goat anti-rabbit horseradish peroxidase conjugated antibody, Biosource, Inc.
18. ABTS Solution: for 1 L, mix 19.21 g citric acid, 35.49 g Na$_2$HPO$_4$ and 500 mg ABTS with sufficient dH$_2$O to make 1 L.
19. ABTS/H$_2$O$_2$: mix 15 mL ABST solution with 2 μL H$_2$O$_2$ five minutes before use.
20. 0.2 M HCl Procedure:
1. Coat ELISA plates with 2 μg Poly(Glu-Tyr) in 100 μL PBS, hold-overnight at 4° C.
2. Block plate with 150 μL of 5% BSA/PBS for 60 min.
3. Wash plate twice with PBS then once with 50 mM Hepes buffer pH 7.4.
4. Add 50 μl of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in $dH_2O$) for controls to plate.
6. Incubate the kinase/compound mixture for 15 minutes.
7. Add 25 μL of 40 mM $MnCl_2$ to the negative control wells.
8. Add 25 μL ATP/$MnCl_2$ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of ABTS/$H_2O_2$ solution to each well.
16. If necessary, stop the development reaction with the addition of 100 μl of 0.2M HCl per well.
17. Read plate on Dynatech MR7000 ELISA reader with the test filter at 410 nM and the reference filter at 630 nM.

BrdU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

General Materials and Reagents:
1. The appropriate ligand.
2. The appropriate engineered cells.
3. BrdU Labeling Reagent: 10 mM, in PBS, pH 7.4 (Roche Molecular Biochemicals, Indianapolis, Ind.).
4. FixDenat: fixation solution (Roche Molecular Biochemicals, Indianapolis, Ind.).
5. Anti-BrdU-POD: mouse monoclonal antibody conjugated with peroxidase (Chemicon, Temecula, Calif.).
6. TMB Substrate Solution: tetramethylbenzidine (TMB, ready to use, Roche Molecular Biochemicals, Indianapolis, Ind.).
7. PBS Washing Solution: 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0% CS DMEM with 0.1% BSA) for 24 hours.
3. On day 3, the appropriate ligand and the test compound are added to the cells simultaneously. The negative control wells receive serum free DMEM with 0.4% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration is 10 μM) for 1.5 hours.
5. After incubation with labeling reagent, the medium is removed by decanting and tapping the inverted plate on a paper towel. FixDenat solution is added (50 μl/well) and the plates are incubated at room temperature for 45 minutes on a plate shaker.
6. The FixDenat solution is removed by decanting and tapping the inverted plate on a paper towel. Milk is added (5% dehydrated milk in PBS, 200 μl/well) as a blocking solution and the plate is incubated for 30 minutes at room temperature on a plate shaker.
7. The blocking solution is removed by decanting and the wells are washed once with PBS. Anti-BrdU-POD solution is added (1:200 dilution in PBS, 1% BSA, 50 μl/well) and the plate is incubated for 90 minutes at room temperature on a plate shaker.
8. The antibody conjugate is removed by decanting and rinsing the wells 5 times with PBS, and the plate is dried by inverting and tapping on a paper towel.
9. TMB substrate solution is added (100 μl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

HGF-Induced BrdU Incorporation Assay

Materials and Reagents:
1. Recombinant human HGF (Cat. No. 249-HG, R&D Systems, Inc. USA).
2. BxPC-3 cells (ATCC CRL-1687).
Remaining Materials and Reagents, as above.

Procedure:
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 μL serum-free medium (RPMI with 0.1% BSA) for 24 hours.
3. On day 3, 25 μL containing ligand (prepared at 1 μg/mL in RPMI with 0.1% BSA; final HGF conc. is 200 ng/mL) and test compounds are added to the cells. The negative control wells receive 25 μL serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 μM, and 1:3 dilutions are used (i.e. final test compound concentration range is 0.137-100 μM).
4. After 18 hours of ligand activation, 12.5 μL of diluted BrdU labeling reagent (1:100 in RPMI, 0.1% BSA) is added to each well and the cells are incubated with BrdU (final concentration is 10 μM) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 μL/well) and the plate is incubated for 90 minutes at room temperature on a plate shaker.

8. Same as General Procedure.
9. Same as General Procedure.
10. Same as General Procedure.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, Acta Pathol. Microbial. Scand. 77:758-760), many different human tumor cell lines (e.g., mammary, lung, genitourinary, gastrointestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid-carcinoma, ATCC # CRL 1555), Calu 6 cells (lung, ATCC # HTB 56), PC3 cells (prostate, ATCC # CRL-1435), SKOV3TP5 cells, S114 (NIH3T3 fibroblast cell line genetically engineered for cMet and HGF expressions from NCl), U-87MG (human malignant glioma, ATCC HTB 14) and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%-10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90-95% air and 5-10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hind flank of the mice (8-10 mice per group, $2-10 \times 10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50-100 µL excipient (DMSO, or VPD:D5W) can be delivered by IP injection at different concentrations generally starting at day one after implantation.

Met Phosphorylation—Cellular Assay

Materials and Reagents:
1. Falcon 10 cm culture dishes.
2. A549 lung carcinoma cells.
3. F12K growth medium (with 2% FBS+2 mM glutamine.
4. F12K assay medium (with 0.1% BSA).
5. Fisher cell scrapers.
6. Lysis buffer (HNTG, 1 mM sodium orthovanidate, 1 mM PMSF and 2 mM sodium fluoride).
7. 1.5 mL Eppendorf tubes.
8. Eppendorf microcentrifuge.
9. BCA assay reagents A and B (#23223 and 23224, Pierce).
10. Sample tube rotator.
11. Gel blot container rotator.
12. 5× sample buffer.
13. Novex pre-cast tris-glycine 8% acrylamide gels.
14. Bio-Rad electrophoresis chamber.
15. SDS-PAGE buffer.
16. TBS (pH 7.6)+0.1% Triton X-100 (TBST), with and without 5% milk.
17. Western blot transfer buffer.
18. Osmonics nitrocellulose paper.
19. Bio-Rad Transblot paper.
20. Gel transfer apparatus.
21. Anti-phosphotyrosine (mouse monoclonal).
22. Bio-Rad Kaleidoscope Prestained Standards (161-0324).
23. Anti-h-met (C-28) rabbit polyclonal, conjugated and non-conjugated with agarose (#sc-161 AC and sc-161, Santa Cruz Biotechnology, Inc.).
24. Donkey and anti-rabbit Ig-HRP (NA 934, Amersham).
25. Sheet anti-mouseIg-HRP (NA 931, Amersham).
26. SuperSignal West Pico Chemiluminescent Substrate (#34080, Pierce).
27. Saran Wrap.
28. Kodak BioMax exposure cassette.
29. Fuji X-ray film.
30. Kodak film developer.

Procedure:
1. Plate cells in 10 cm dishes with growth medium with 2% FBS+2 mM glutamine. Grow to near confluency.
2. Serum starve cells overnight in assay medium with 0.1% BSA.
3. Add drug to the plates, one dose per plate, usually in a 2-flod titration. Add assay medium (with the same DMSO concentration as the drugs) for no drug.
4. Incubate plates 4-5 hours with the drug, then add HG, 50 ng/mL for 10 minutes.
5. Wash plates once with PBS, add 400 µl lysis buffer, and scrape off the cells. Collect in 1.5 mL Eppendorf tubes.
6. After about 10-20 minutes in the lysis buffer, centrifuge lysates in a microcentrifuger at full speed (14,000 g) and collect the supernatants in a separate Eppendorf tube.
7. Determine protein concentration with the BCA assay reagents.
8. Adjust sample concentration to 0.5 mg protein in 0.4 mL using lysis buffer.
9. Add 15 µl anti-h-met AC for immunoprecipitation, rotate samples for 2 hours at 4° C.
10. Wash samples 3 times with lysis buffer and resuspend in 35 µl 5× sample buffer.
11. Boil sample at 100° C. for 10 minutes and microcentrifuge at highest setting for 30 minutes to pellet the agarose beads.

12. Load 15 μl each to 2 gels, one for anti-phosphorylation and the other for anti-h-met. Also load 10 μl of prestained standards, one lane per gel.

13. Run gel around 100-125 V, then transfer gel to nitrocellulose either overnight at 70 mAmps or 1 hour at 500 mAmps.

14. Block membranes on rotator for 1 hour in TBS+0.1% Triton X-100 (TBST)+5% PBS. All steps from this point are at room temperature unless otherwise unless otherwise noted.

15. Add 0.8 μg/mL antiphosphotyrosine and 0.25 μg/mL anti-h-met on rotator either for 2 hours or overnight.

16. Wash membranes 3 times 5 minutes each in TBST on rotator.

17. Add HRP-conjugated antibodies) sheep anti-mouse for the antiphosphotyroeins; donkey anti-rabbit for the nati-h-met) at 1:5000 for approximately 45 minutes on rotator.

18. Wash membranes 3 times for 5 minutes each in TBST on rotator.

19. Add the 2 reagents in the SuperSignal kit together in equal-volumes (3 mL+3 mL for each blot), rotate for 1-2 minutes.

20. Wrap blots in Saran Wrap and tape securely inside the exposure cassette.

21. In the darkroom with only the safety light on, place a sheet of film inside the cassette. After an allotted time, remove film and place in the developer machine for automatic processing. Experiment with the exposure time to get proper exposure.

TABLES

TABLE 1

| No. | Structure | Name | Met IC$_{50}$ (μM) | $^1$H-NMR | MS m/z (M + 1) |
|---|---|---|---|---|---|
| I(a) | (structure: 5-Bromo-3-(2,6-dichlorobenzyloxy)-pyridin-2-ylamine) | 5-Bromo-3-(2,6-dichloro-benzyloxy)-pyridin-2-ylamine | 5.3 | (400 MHz, DMSO-d$_6$) δ 7.62 (m, 1H), 7.56(m, 2H), 7.46(m, 2H), 5.80(s, 2H), 5.22(s, 2H) | 349 |
| I(b) | (structure: 3-Benzyloxy-5-bromo-pyridin-2-ylamine) | 3-Benzyloxy-5-bromo-pyridin-2-ylamine | >20 | (400 MHz, DMSO-d$_6$) δ 7.56(d, J=2Hz, 1H), 7.47(d, J=7.2 Hz, 2H), 7.38(m, 2H), 7.32(d, J=7.2 Hz, 1H), 7.26(d, J=2 Hz, 1H), 5.95(s, 2H), 5.14(s, 2H) | 280 |
| I(c) | (structure: 5-Bromo-3-(2,6-difluorobenzyloxy)-pyridin-2-ylamine) | 5-Bromo-3-(2,6-difluoro-benzyloxy)-pyridin-2-ylamine | 40% at 20 μM | (400 MHz, DMSO-d$_6$) δ 7.60(d, 1H), 7.52(m, 1H), 7.40(d, 1H), 7.18(m, 2H), 5.81(br. S. 2H), 5.12(s, 2H) | 315(M+) |
| I(d) | (structure: 5-Bromo-3-(2-bromobenzyloxy)-pyridin-2-ylamine) | 5-Bromo-3-(2-bromo-benzyloxy)-pyridin-2-ylamine | >20 | (400 MHz, DMSO-d$_6$) δ 7.65 (m, 2H), 7.60(d, 1H), 7.42(m, 2H), 7.30(d, 1H), 5.94(s 2H), 5.13(s, 2H) | 357(M+) |

TABLE 1-continued

| No. | Structure | Name | Met IC$_{50}$ (μM) | $^1$H-NMR | MS m/z (M + 1) |
|---|---|---|---|---|---|
| I(e) | 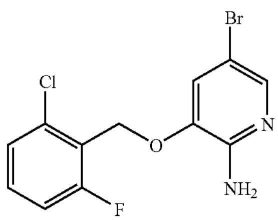 | 5-Bromo-3-(2-chloro-6-fluoro-benzyloxy)-pyridin-2-ylamine | >20 | (400 MHz, DMSO-d$_6$) δ 7.80-7.30(m, 5H), 5.80(br s, 2H), 5.15(s, 2H) | 331 |
| I(f) | 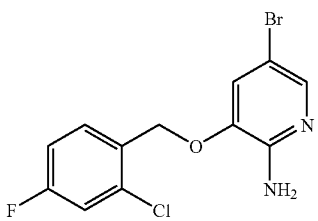 | 5-Bromo-3-(2-chloro-4-fluoro-benzyloxy)-pyridin-2-ylamine | | (400 MHz, DMSO-d$_6$) δ 7.80-7.20(m, 5H), 5.95(br s, 2H), 5.10(s, 2H) | 331 |
| I(g) | 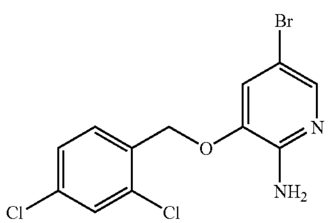 | 5-Bromo-3-(2,4-dichloro-benzyloxy)-pyridin-2-ylamine | | (400 MHz, DMSO-d$_6$) δ 7.80-7.50(m, 5H), 6.20(br s, 2H), 5.20(s, 2H) | 348 |
| I(h) | 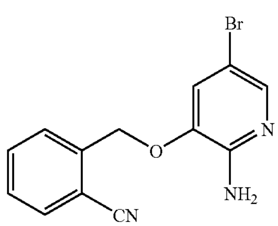 | 2-(2-Amino-5-bromo-pyridin-3-yloxymethyl)-benzonitrite | | (400 MHz, DMSO-d$_6$) δ 7.90-7.30(m, 6H), 5.90(br s, 2H), 5.20(s, 2H) | 304(M+) |
| I(i) | 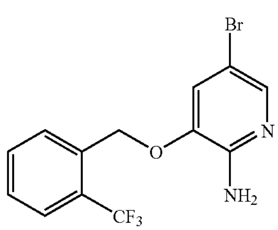 | 5-Bromo-3-(2-trifluoromethyl-benzyloxy)-pyridin-2-ylamine | | (400 MHz, DMSO-d$_6$) δ 7.80-7.30(m, 6H), 6.00(br s, 2H), 5.25(s, 2H) | 347 |
| I(j) | 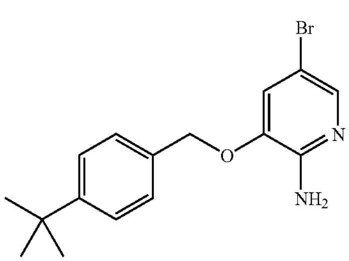 | 5-Bromo-3-(4-tert-butyl-benzyloxy)-pyridin-2-ylamine | | (400 MHz, DMSO-d$_6$) δ 7.50-7.20(m, 6H), 5.85(br s, 2H), 5.05(s, 2H), 1.25(s, 9H) | 335(M+) |

… TABLE 1-continued

| No. | Structure | Name | Met IC$_{50}$ (μM) | $^1$H-NMR | MS m/z (M + 1) |
|---|---|---|---|---|---|
| I(k) | 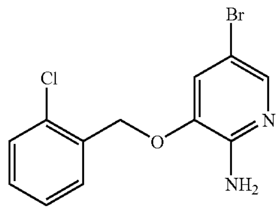 | 5-Bromo-3-(2-chloro-benzyloxy)-pyridin-2-ylamine | | (400 MHz, DMSO-d$_6$) δ 7.70-7.20(m, 6H), 5.90(br s, 2H), 5.15(s, 2H) | 313 |
| I(l) | 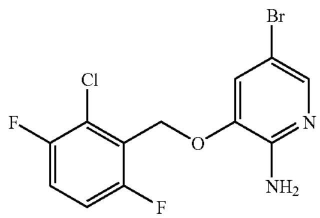 | 5-Bromo-3-(2-chloro-3,6-difluoro-benzyloxy)-pyridin-2-ylamine | 5.3 | (CDCl$_3$, 300 MHz) δ 4.7-4.8 (brs, 2H), 5.21(s, 2H), 7.03-7.10(dt, 1H, J, 4.1, 9.1), 7.17-7.25(m, 2H), 7.75-7.76(d, J, 1.86). | |
| I(m) | 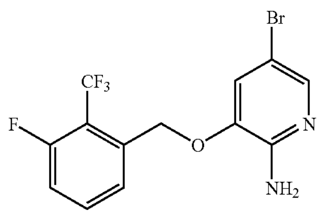 | 5-Bromo-3-(3-fluoro-2-trifluoromethyl-benzyloxy)-pyridin-2-ylamine | | | 365 |
| I(n) | 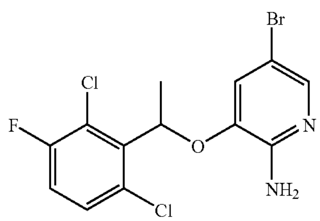 | 5-Bromo-3-[1-(2,6-dichloro-3-fluoro-phenyl)-ethoxy]-pyridin-2-ylamine | | (CDCl$_3$, 300 MHz) δ 1.85-1.95 (d, 3H), 4.7-5.0(brs, 2H), 5.9-6.01(q, 1H), 6.8-6.95(d, 1H), 7.01-7.2(t, 1H), 7.4-7.45(m, 1H), 7.8-7.85(d, 1H). | |
| I(o) | 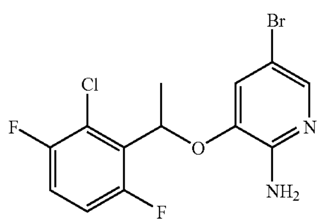 | 5-Bromo-3-[1-(2-chloro-3,6-difluoro-phenyl)-ethoxy]-pyridin-2-ylamine | | | 364 |
| II(a) | 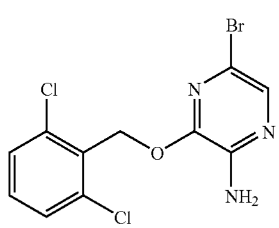 | 5-Bromo-3-(2,6-dichloro-benzyloxy)-pyrazin-2-ylamine | >20 | (400 MHz, DMSO-d$_6$) δ 5.45(s, 2H), 6.45(s, 2H), 7.50(m, 3H), 7.63(s, 1H) | 350 |
| II(b) | 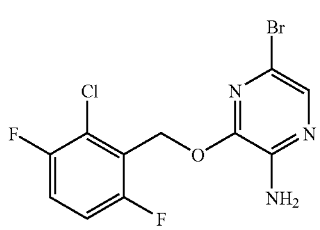 | 5-Bromo-3-(2-chloro-3,6-difluoro-benzyloxy)-pyrazin-2-ylamine | >20 | (300 MHz, CDCl$_3$) 67.7(S. 1H), 7.23-7.16(m, 1H), 7.09-7.01 (m, 1H), 5.53(s, 2H), 4.72(s, 2H) | 351 |

TABLE 1-continued

| No. | Structure | Name | Met IC$_{50}$ (μM) | $^1$H-NMR | MS m/z (M + 1) |
|---|---|---|---|---|---|
| II(c) | 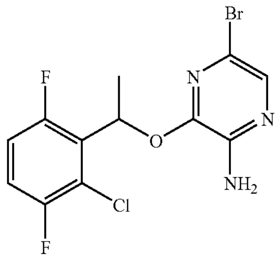 | 5-Bromo-3-[1-(2-chloro-3,6-difluoro-phenyl)-ethoxy]-pyrazin-2-ylamine | 1.81/2.67 | (400 MHz, DMSO-d$_6$) δ 1.75(d, 3H), 6.26(m, 1H), 6.46(s, 2H), 7.28(m, 1H), 7.41(m, 1H), 7.52 (s, 1H) | 365 |
| II(d) | 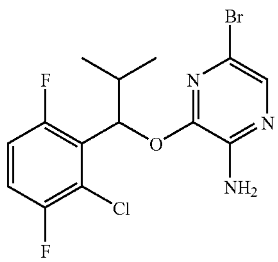 | 5-Bromo-3-[1-(2-chloro-3,6-difluoro-phenyl)-2-methyl-propoxy]-pyrazin-2-ylamine | 18.1 | (400 MHz, DMSO-d$_6$) δ 0.92(d, 3H), 1.17(m, 3H), 2.57(m, 1H), 5.75(d, 1H), 6.49(s, 2H), 7.24 (m, 1H), 7.40(m, 1H), 7.54(s, 1H) | 393 |
| II(e) | 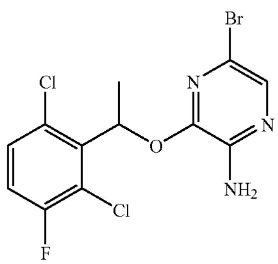 | 5-Bromo-3-[1-(2,6-dichloro-3-fluoro-phenyl)-ethoxy]-pyrazin-2-ylamine | 0.24/ 0.66/ 1.3 | (400 MHz, DMSO-d$_6$) δ 1.74(d, 3H), 6.40(m, 1H), 6.52(br s, 2H), 7.30(m, 1H), 7.48(m, 1H), 7.56(s, 1H); MS m/z 382 (M+1). | 382 |
| II(f) | 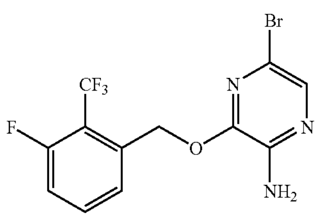 | 5-Bromo-3-(3-fluoro-2-trifluoromethyl-benzyloxy)-pyrazin-2-ylamine | | | 366 |

TABLE 2

| No. | Structure | Name | Met IC$_{50}$ (μM) |
|---|---|---|---|
| I-1 | 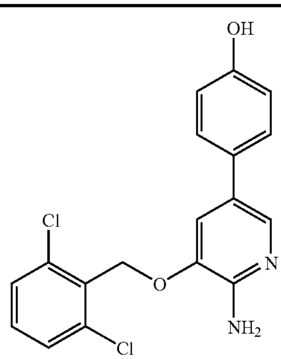 | 4-[6-Amino-5-(2,6-dichloro-benzloxy)-pyridin-3-yl]-phenol | 0.279 |

TABLE 2-continued

| | | | |
|---|---|---|---|
| I-2 | | 3-(2,6-Dichloro-benzyloxy)-5-[4-(2-morpholin-4-yl-ethoxy)-phenyl]-pyndin-2-ylamine | 0.58 |
| I-3 | | 3-(2,6-Dichloro-benzyloxy)-[3-(2-morpholin-4-yl-ethoxy)-phenyl]-pyridin-2-ylamine | 0.59 |
| I-4 | | 3-(2,6-Dichloro-benzyloxy)-5-(1H-indol-4-yl)-pyridin-2-ylamine | 1.4 |
| I-5 | | 3-(2-Chloro-6-(1H-indol-4-yl)benzyloxy]-5-(1H-indol-4-yl)-pyridine-2-ylamine | 4.71 |

TABLE 2-continued

| | | | |
|---|---|---|---|
| I-6 | | 2-[6-Amino-5-(2,6-dichloro-benzyloxy)-pyridin-3-yl]-pyrrole-1-carboxylic acid tert-butyl ester | >20 |
| I-7 | | 3-(2,6-Dichloro-benzyloxy)-5-(1H-pyrrol-2-yl)-pyridin-2-ylamine | 4.25 |
| I-8 | | 3-(2,6-Dichloro-benzyloxy)-5-(4-fluoro-phenyl)-pyridin-2-ylamime | 8.01 |
| I-9 | | 3-(2,6-Dichloro-benzyloxy)-5-phenyl-pyridin-2-ylamine | 3.9 |
| I-10 | | 3-(2,6-Dichloro-benzyloxy)-5-(2-fluoro-phenyl)-pyridin-2-ylamine | 6.09 |

TABLE 2-continued
| | | | |
|---|---|---|---|
| I-11 | 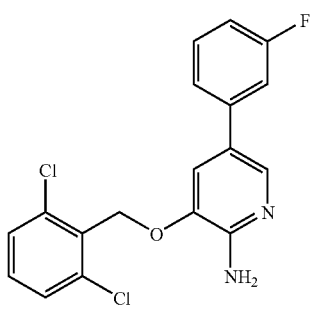 | 3-(2,6-Dichloro-benzyloxy)-5-(3-fluoro-phenyl)-pyridin-2-ylamine | 13.8 |
| I-12 | 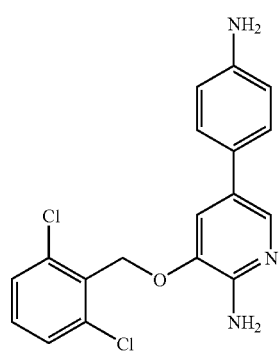 | 5-(4-Amino-phenyl)-3-(2,6-dichloro-benzyloxy)-pyridin-2-ylamine | 0.606 |
| I-13 | 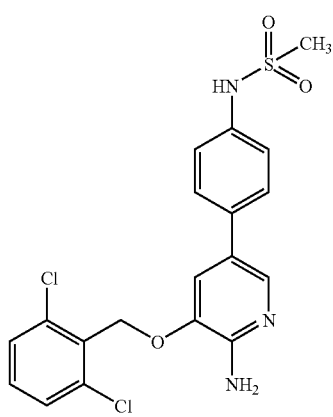 | N-{4-[6-Amino-5-(2,6-dichloro-benzyloxy)-pyridin-3-yl]-phenyl}-methanesulfonamide | 0.44 |
| I-14 | 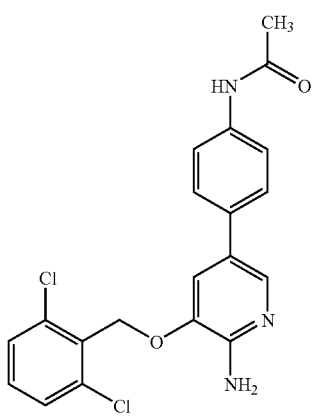 | N-{4-[6-Amino-5-(2,6-dichloro-benzyloxy)-pyridin-3-yl]-phenyl}-acetamide | >20 |

TABLE 2-continued
| | | | |
|---|---|---|---|
| I-15 | 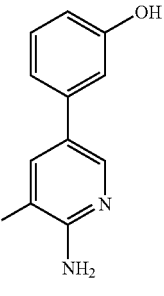 | 3-[6-Amino-5-(2,6-dichloro-benzyloxy)-pyridin-3-yl]-phenol | 1.34 |
| I-16 | 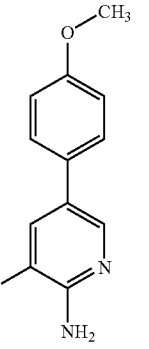 | 3-(2,6-Dichloro-benzyloxy)-5-(4-methoxy-phenyl)-pyridin-2-ylamine | 6.55 |
| I-17 | 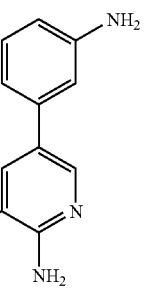 | 5-(3-Amino-phenyl)-3-(2,6-dichloro-benzyloxy)-pyridin-2-ylamine | 1.07 |
| I-18 | 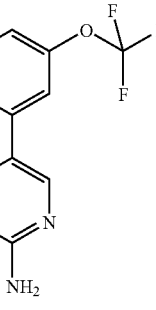 | 3-(2,6-Dichloro-benzyloxy)-5-(3-trifluoromethoxy-phenyl)-pyridin-2-ylamine | >20 |
| I-19 | 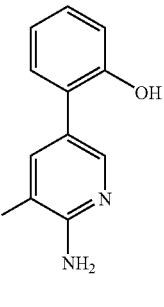 | 2-[8-Amino-5-(2,6-dichloro-benzyloxy)-pyridin-3-yl]-phenol | 2.16 |

TABLE 2-continued

| | | | |
|---|---|---|---|
| I-20 | | 3-(2,6-Dichloro-benzyloxy)-5-(2-phenoxy-phenyl}-pyridin-2-ylamine | >20 |
| I-21 | | 3-(2,6-Dichloro-benzyloxy)-5-(3,4-difluoro-phenyl)-pyridin-2-ylamine | 14.3 |
| I-22 | | 3-(2,6-Dichloro-benzyloxy)-5-(3-isopropyl-phenyl)-pyridin-2-ylamine | 15.9 |
| I-23 | | 3-(2,6-Dichloro-benzyloxy)-5-(2-trifluoromethyl-phenyl)-pyridin-2-ylamine | >20 |
| I-24 | | 3-(2,6-Dichloro-benzyloxy)-5-(2-methoxy-phenyl)-pyridin-2-ylamine | 11.5 |

TABLE 2-continued
| | | | |
|---|---|---|---|
| I-25 | 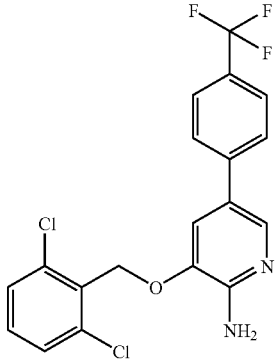 | 3-(2,6-Dichloro-benzyloxy)-5-(4-trifluoromethyl-phenyl)-pyridin-2-ylamine | >20 |
| I-26 | 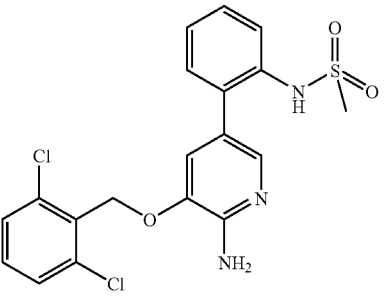 | N-(2-[6-Amino-5-(2,6-chloro-benzyloxy)-pyridin-3-yl]phenyl}-methanesulfonamide | >20 |
| I-27 | 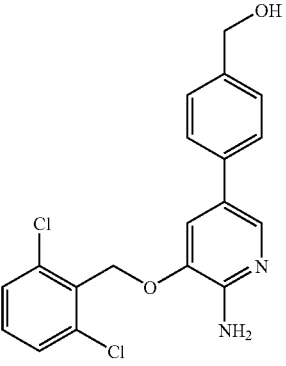 | {4-[6-Amino-5-(2,6-dichloro-benzyloxy)-pyridin-3-yl]-phenyl}-methanol | 2.5 |
| I-28 | 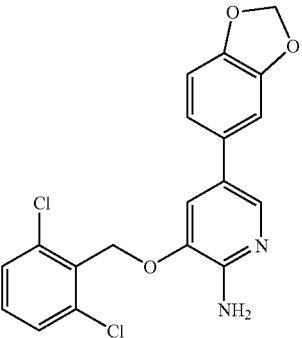 | 5-Benzo[1,3]dioxol-5-yl-3-(2,6-dichloro-benzyloxy)-pyridin-2-ylamine | 8.5 |

TABLE 2-continued
| | | | |
|---|---|---|---|
| I-29 | 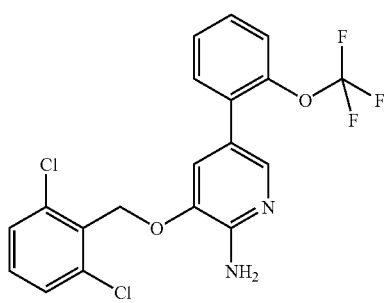 | 3-(2,6-Dichloro-benzyloxy)-5-(2-trifluoromethoxy-phenyl)-pyridin-2-ylamine | >20 |
| I-30 | 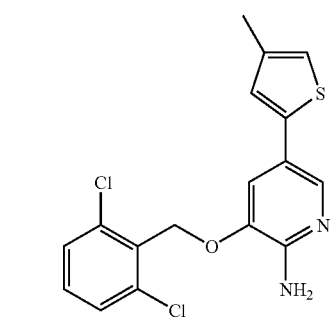 | 3-(2,6-Dichloro-benzyloxy)-5-(4-methyl-thiophen-2-yl)-pyridin-2-ylamine | 3.5 |
| I-31 | 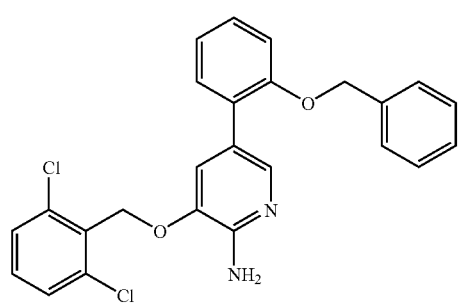 | 5-(2-Benzyloxy-phenyl)-3-(2,6-dichloro-benzyloxy)-pyridin-2-ylamine | >20 |
| I-32 | 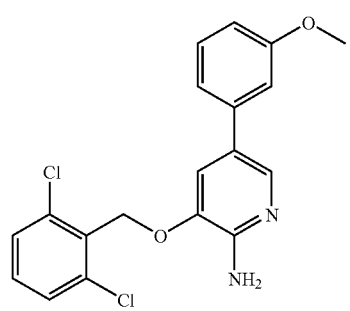 | 3-(2,6-Dichloro-benzyloxy)-5-(3-methoxy-phenyl)-pyridin-2-ylamine | 4.01 |
| I-33 | 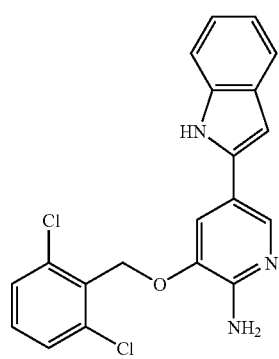 | 3-(2,6-Dichloro-benzyloxy)-5-(1H-indol-2-yl)-pyridin-2-ylamine | 7.5 |

TABLE 2-continued
| ID | Structure | Name | Value |
|---|---|---|---|
| I-34 | 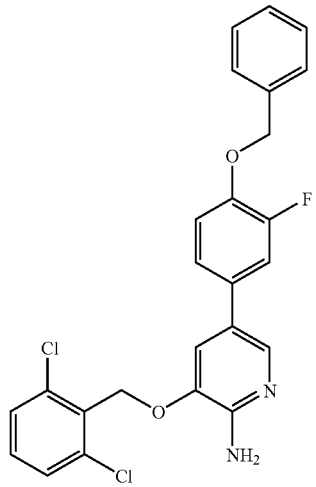 | 5-(4-Benzyloxy-3-fluoro-phenyl)-3-(2,6-dichloro-benzyloxy)-pyridin-2-ylamine | 13.5 |
| I-35 | 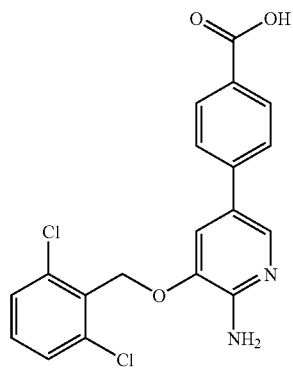 | 4-[6-Amino-5-(2,6-dichloro-benzyloxy)-pyridin-3-yl]-benzoic acid | 12.8 |
| I-36 | 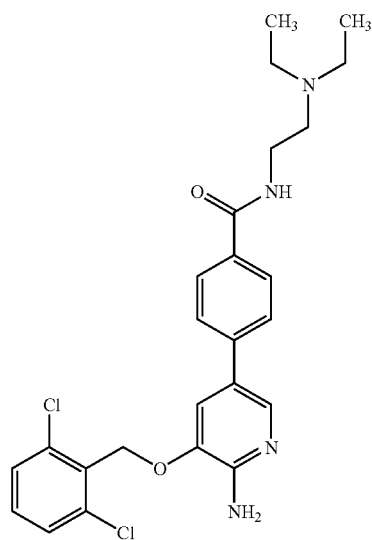 | 4-[6-Amino-5-(2,6-dichloro-benzyloxy)-pyridin-3-yl]-N-(2-diethylamino-ethyl)-benzamide | 0.99 |

TABLE 2-continued
| | | | |
|---|---|---|---|
| I-37 | 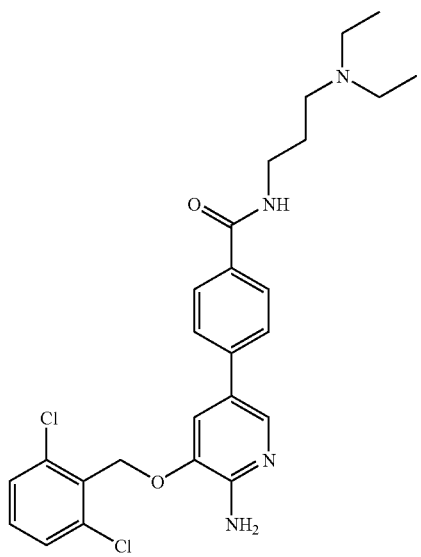 | 4-[6-Amino-5-(2,6-dichloro-benzyloxy)-pyridin-3-yl]-N-(3-diethylamino-propyl)-benzamide | 0.82 |
| I-38 | 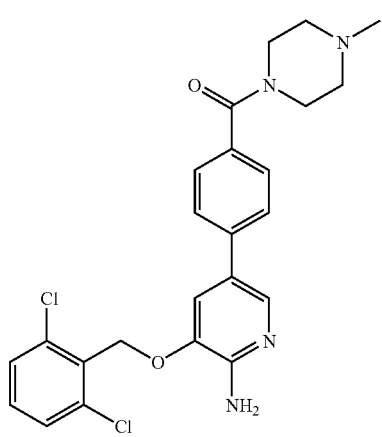 | {4-[6-Amino-5-(2,6-dichloro-benzyloxy)-pyridin-3-yl]-phenyl}-(4-methyl-piperazin-1-yl)-methanone | 1.02 |
| I-39 | 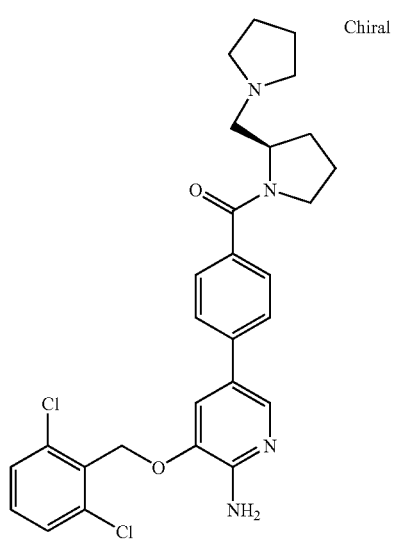 Chiral | {4-[6-Amino-5-(2,6-dichloro-benzyloxy)-pyridin-3-yl]-phenyl}-[(2R)-2-pyrrolidin-1-ylmethyl-pyrrolidin-1-yl]-methanone | 0.062/ 0.11/0.2 (Ki0.04) |

TABLE 2-continued
| | | | |
|---|---|---|---|
| I-40 | 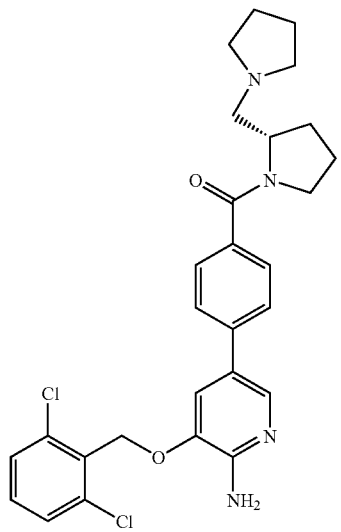 Chiral | {4-[6-Amino-5-(2,6-dichloro-benzyloxy)-pyridin-3-yl]-phenyl}-[(2S)-2-pyrrolidin-1-ylmethyl-pyrrolidin-1-yl]-methanone | 0.21 |
| I-41 | 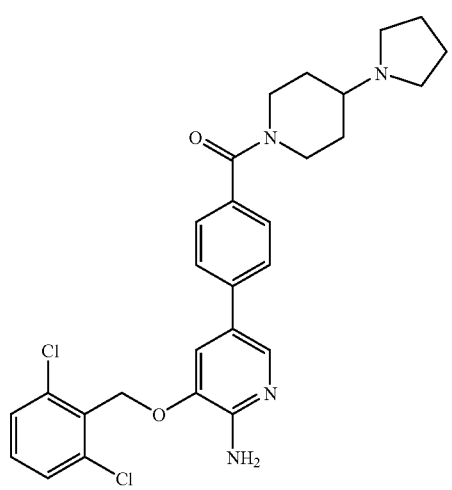 | {4-[6-Amino-5-(2,6-dichloro-benzyloxy)-pyridin-3-yl]-phenyl}-(4-pyrrolidin-1-yl-piperidin-1-yl)-methanone | 0.35 |
| I-42 | 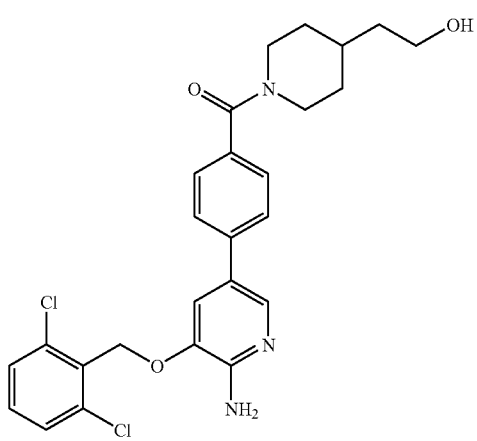 | {4-[6-Amino-5-(2,6-dichloro-benzyloxy)-pyridin-3-yl]-phenyl}-[4-(2-hydroxy-ethyl)-pipendin-1-yl]-methanone | 0.56 |

| | | | |
|---|---|---|---|
| I-43 | 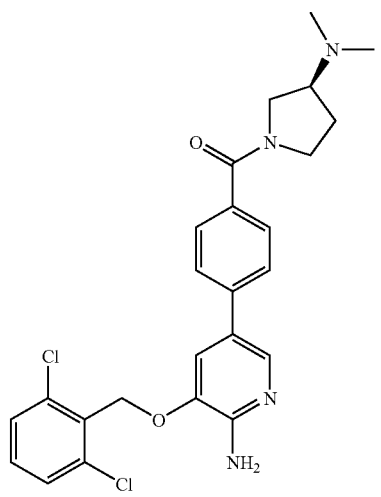 | {4-[6-Amino-5-(2,6-dichloro-benzyloxy)-pyridin-3-yl]-phenyl}-[(3S)-3-dimethylamino-pyrrolidin-1-yl]-methanone | 0.47 |
| I-44 | 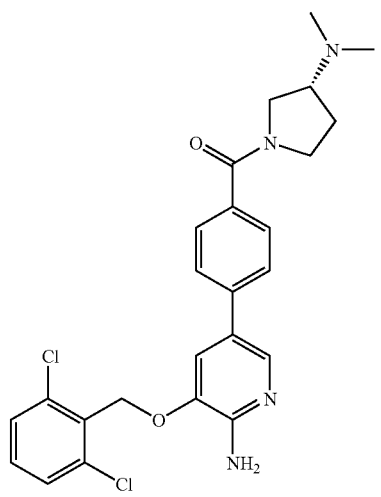 | {4-[6-Amino-5-(2,6-dichloro-benzyloxy)-pyridin-3-yl]-phenyl}-[(3R)-3-dimethylamino-pyrrolidin-1-yl]-methanone | 0.65 |
| I-45 | 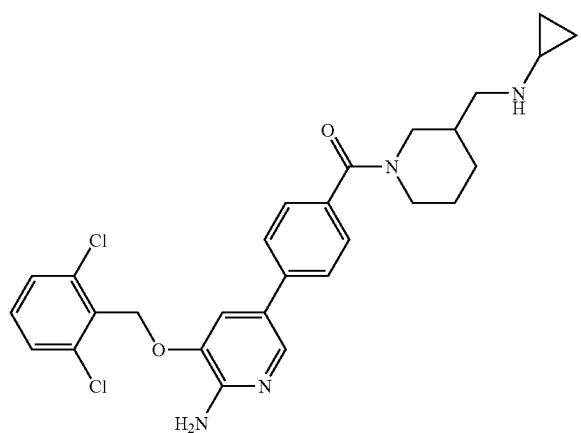 | {4-[6-Amino-5-(2,6-dichloro-benzyloxy)-pyridin-3-yl]-phenyl}-[(3S)-3-cyclopropylaminomethyl-piperidin-1-yl]-methanone | 0.77 |

TABLE 2-continued
| | | | |
|---|---|---|---|
| I-46 | 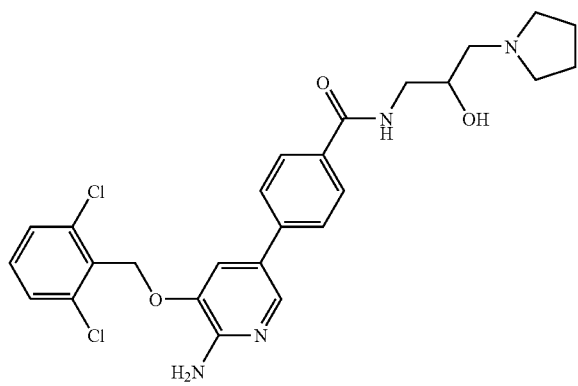 | 4-[6-Amino-5-(2,6-dichloro-benzyloxy)-pyridin-3-yl]-N-(2-hydroxy-3-pyrrolidin-1-yl-propyl)-benzamide | 0.2 |
| I-47 | 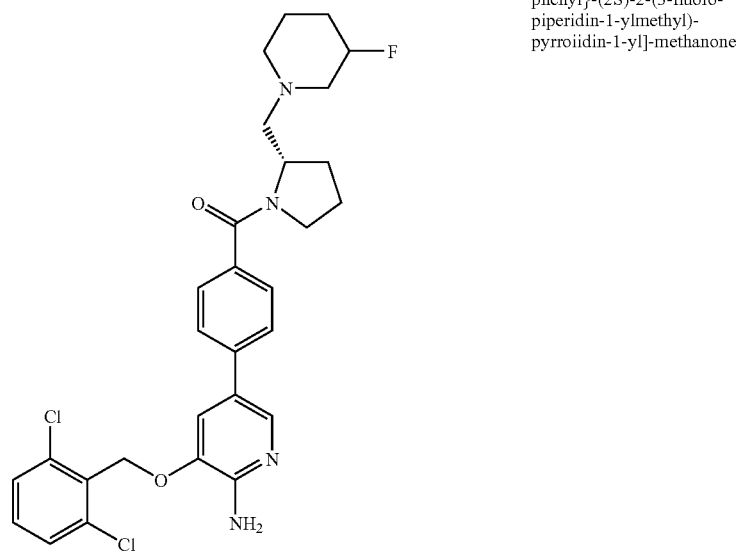 | {4-[6-Amino-5-(2,6-dichloro-benzyloxy)-pyridin-3-yl]-phenyl}-(2S)-2-(3-fluoro-piperidin-1-ylmethyl)-pyrroiidin-1-yl]-methanone | 0.42 |
| I-48 | 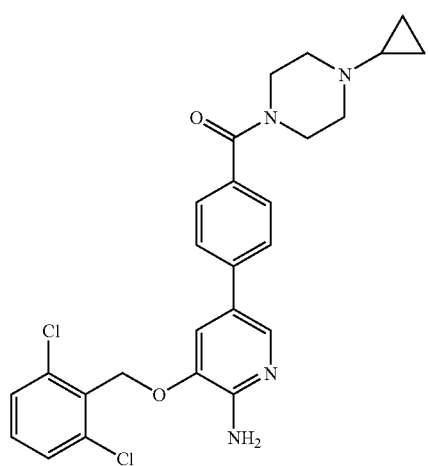 | {4-[8-Amino-5-(2,8-dichloro-benzyloxy)-pyridin-3-yl]-phenyl}-(4-cyclopropyl-piperazin-1-yl)-methanone | 1.67 |

| | | | |
|---|---|---|---|
| I-49 | 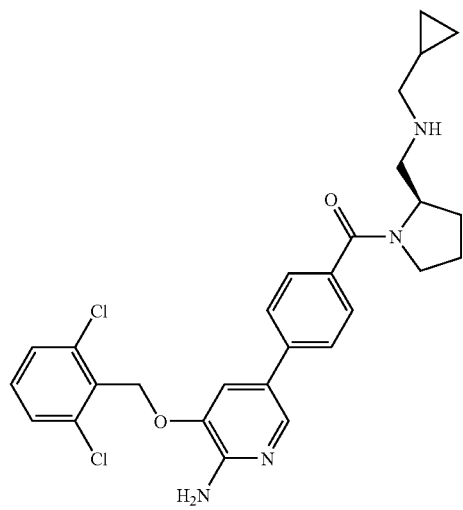 | {4-[8-Amino-5-(2,6-dichloro-benzyloxy)-pyridin-3-yl]-phenyl}-(2R)-2-[(cyclopropylmethyl-amino)-methyl]-pyrrolidin-1-yl}-methanone | 0.37 |
| I-50 | 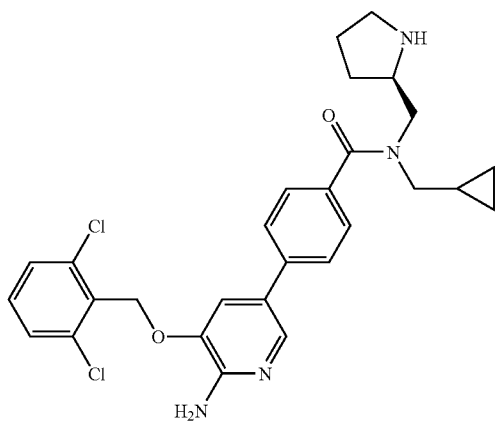 | 4-[6-Amino-5-(2,8-dichloro-benzyloxy)-pyridin-3-yl]-N-cyclopropylmethyl-N-(2R)-pyrrolidin-2-ylmethyl-benzamide | 0.29 |
| I-51 | 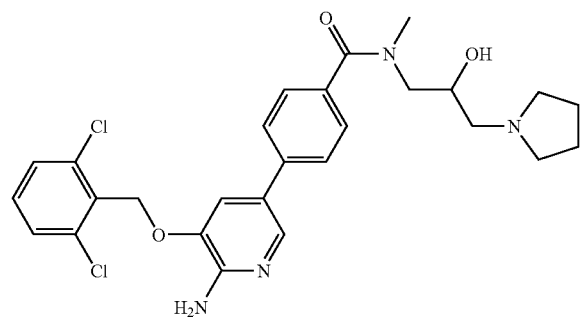 | 4-[6-Amino-5-(2,6-dichloro-benzyloxy)-pyridin-3-yl]-N-(2-hydroxy-3-pyrrolidin-1-yl-propyl)-N-methyl-benzamide | 0.71 |

TABLE 2-continued
| | | | |
|---|---|---|---|
| I-52 | 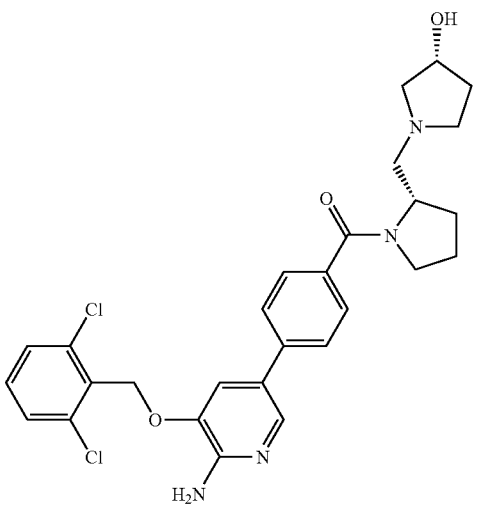 | {4-[6-Amino-5-(2,6-dichloro-benzyloxy)-pyridin-3-yl]-phenyl}-{(2S)-2-((3R)-3-hydroxy-pyrrolidin-1-ylmethyl]-pyrrolidin-1-yl}-methanone | 0.53 |
| I-53 | 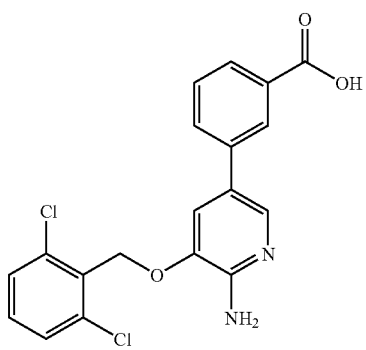 | 3-[6-Amino-5-(2,6-dichloro-benzyloxy)-pyridin-3-yl]-benzoic acid | 16 |
| I-54 | 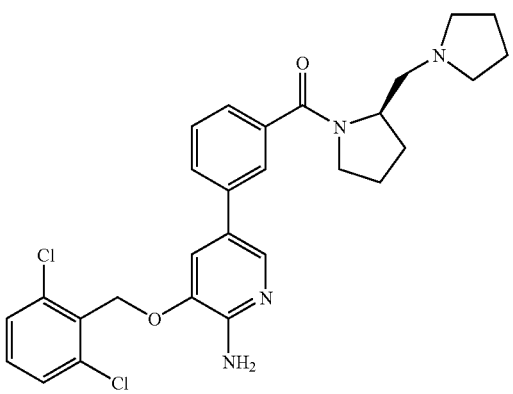 | {3-[6-Amino-5-(2,6-dichloro-benzyloxy)-pyridin-3-yl]-phenyl}-[(2R)-2-pyrrolidin-1-ylmethyl-pyrrolidin-1-yl]-methanone | 2.5 |
| I-55 | 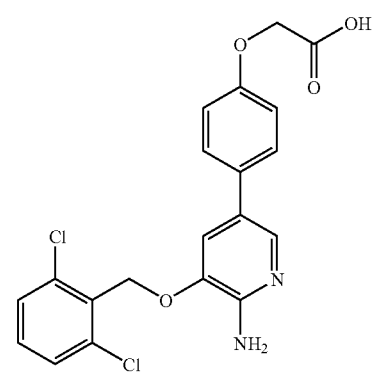 | {4-[6-Amino-5-(2,6-dichloro-benzyloxy)-pyridin-3-yl]-phenoxy}-acetic acid | 2.41 |

TABLE 2-continued
| I-56 | 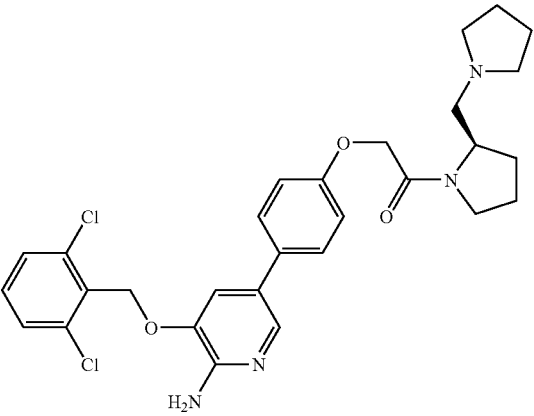 | 2-{4-[6-Amino-5-(2,6-dichloro-benzyloxy)-pyridin-yl]-phenoxy}-1-((2R)-2-pyrrolidin-1-ylmethyl-pyrrolidin-1-yl]-ethanone | 0.53 |
| --- | --- | --- | --- |
| I-57 | 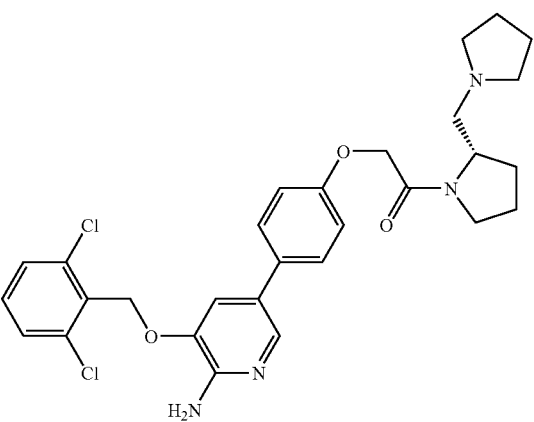 | 2-{4-[6-Amino-5-(2,6-dichloro-benzyloxy)-pyridin-3-yl]-phenoxy}-1-[(2S)-2-pyrrolidin-1-ylmethyl-pyrrolidin-1-yl]-ethanone | 0.5 |
| I-58 | 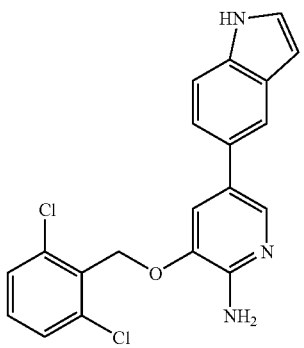 | 3-(2,6-Dichloro-benzyloxy)-5-(1H-indol-5-yl)-pyridin-2-ylamine | 4.3 |
| I-59 | 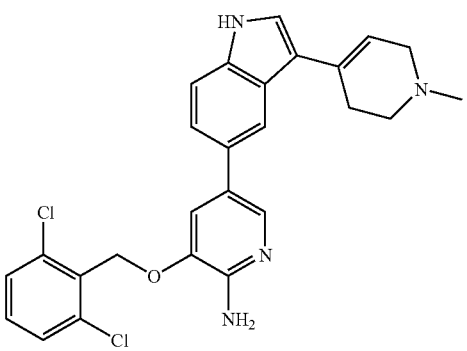 | 3-(2,6-Dichloro-benzyloxy)-5-[3-(1-methyl-1,2,3,6-tetrahydro-pyridin-4-yl)-1H-indol-5-yl]-pyridin-2-ylamine | 1.57 |

TABLE 2-continued

| | | | |
|---|---|---|---|
| I-60 | | 3-(2,6-Dichlora-benzyloxy)-5-[3-(1-methyl-pipendin-4-yl)-1H-indol-5-yl]-pyridin-2-ylamine | 3.04 |
| I-61 | | (2,8-Dichloro-benzyloxy)-(3-morpholin-4-ylmethyl-1H-indol-5-yl)-pyridin-2-ylamine | 1.19 |
| I-62 | | 3-(2,6-Dichloro-benzyloxy)-(3-piperidin-1-ylmethyl-1H-indol-5-yl)-pyridin-2-ylamine | 1.41 |
| I-63 | | 3-(2,6-Dichloro-benzyloxy)-(3-pyrrolidin-1-ylmethyl-1H-indol-5-yl)-pyridin-2-ylamine | 1.34 |

TABLE 2-continued
| | | | |
|---|---|---|---|
| I-64 | 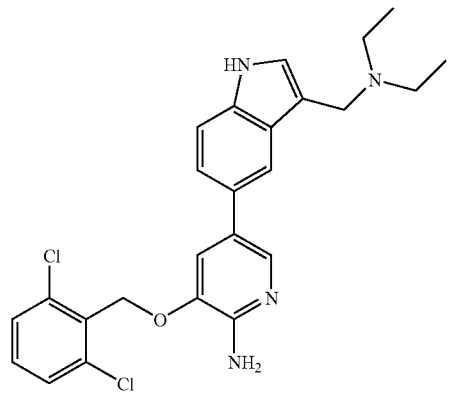 | 3-(2,6-Dichloro-benzyloxy)-5-(3-diethylaminomethyl-1H-indol-5-yl)-pyridin-2-ylamine | 3.23 |
| I-65 | 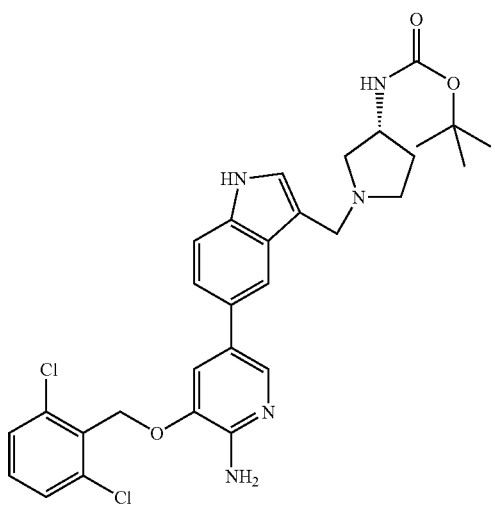 | (1-{5-[6-Amino-5-(2,6-dichloro-benzyloxy)-pyridin-3-yl]-1H-indol-3-ylmethyl}-(3R)-pyrrolidin-3-yl)-carbamic acid tert-butyl ester | 6.3 |
| I-66 | 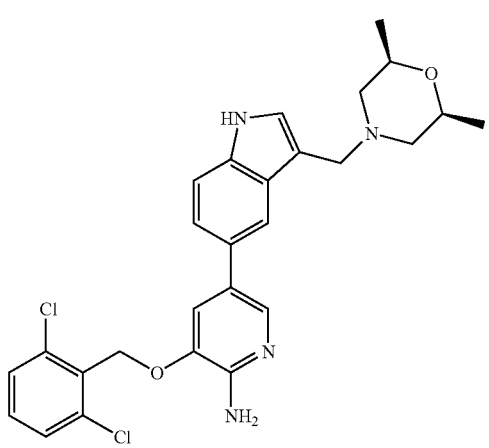 | 3-(2,6-Dichloro-benzyloxy)-5-[3-(2,6-dimethyl-morpholin-4-ylmethyl)-1H-indol-5-yl]-pyridin-2-ylamine | >20 |

| | | | |
|---|---|---|---|
| I-67 | 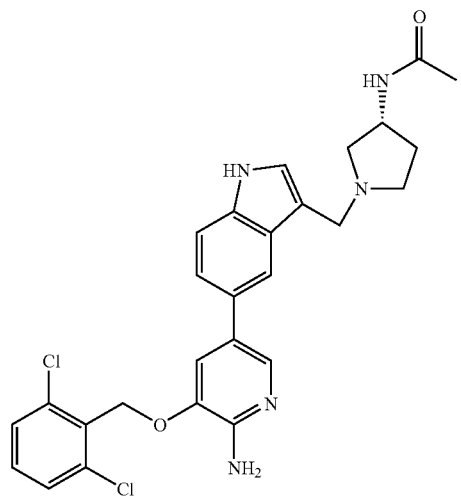 | N-(1-{5-[6-Amino-5-(2,6-dichloro-benzyloxy)-pyridin-3-yl]-1H-indol-3-ylmethyl}-(3R)-pyrrolidin-3-yl)-acetamide | 1.79 |
| I-68 | 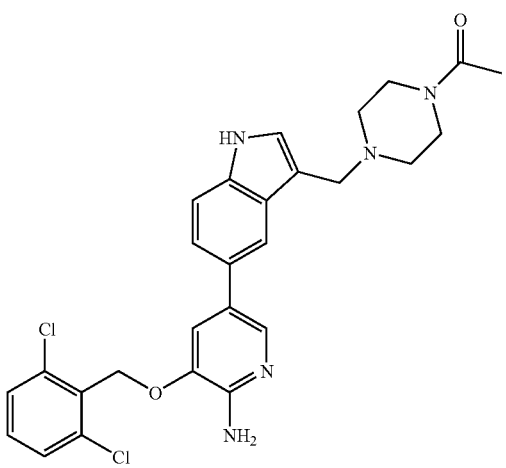 | 1-(4-{5-[6-Amino-5-(2,6-dichloro-benzyloxy)-pyridin-3-yl]-1H-indol-3-ylmethyl}-piperazin-1-yl)-ethanone | 2.18 |
| I-69 | 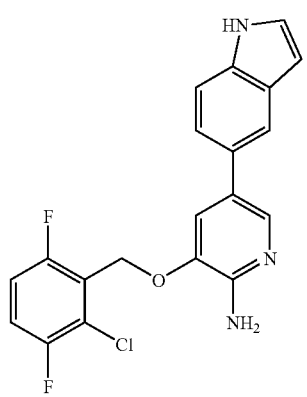 | 3-(2-Chloro-3,6-difluoro-benzyloxy)-5-(1H-indol-5-yl)-pyridin-2-ylamine | |

TABLE 2-continued
| | | | |
|---|---|---|---|
| I-70 | 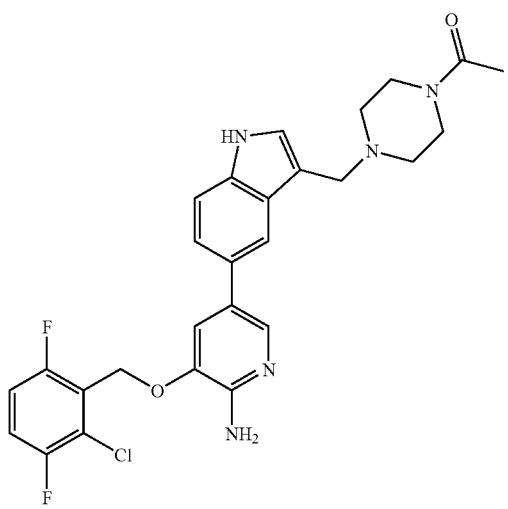 | 1-(4-{5-[6-Amino-5-(2-chloro-3,6-difluoro-benzloxy)-pyridin-3-yl]-1H-indol-3-ylmethyl}-piperazin-1-yl)-ethanone | 0.8 |
| I-71 | 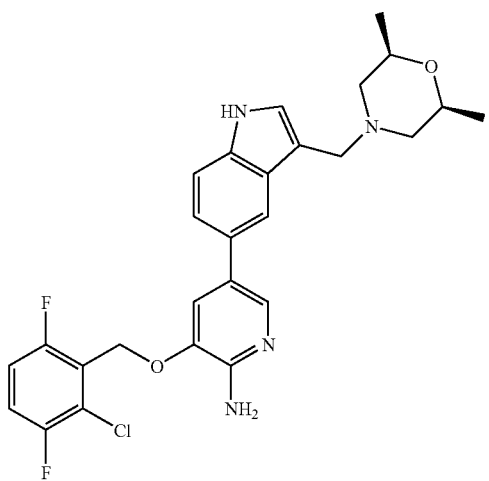 | 3-(2-Chloro-3,6-difluoro-benzyloxy)-5-[3-(2,6-dimethyl-morpholin-4-ylmethyl)-1H-indol-5-yl]-pyridin-2-ylamine | 2.71 |
| I-72 | 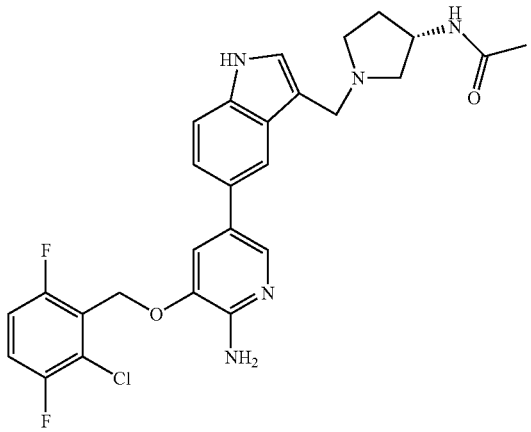 | N-(1-{5-[6-Amino-5-(2-chloro-3,6-difluoro-benzyloxy)-pyridin-3-yl]-1H-indol-3-ylmethyl}-(3S)-pyrrolidin-3-yl)-acetamide | 0.95 |

TABLE 2-continued
| | | | |
|---|---|---|---|
| I-73 | 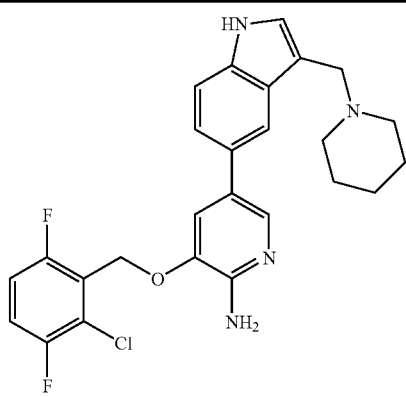 | 3-(2-Chloro-3,6-difluoro-benzyloxy)-5-(3-pipendin-1-ylmethyl-1H-indol-5-yl)-pyridin-2-ylamine | 0.74 |
| I-74 | 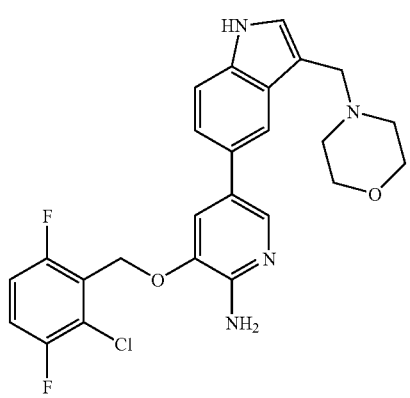 | 3-(2-Chloro-3,6-difluoro-benzyloxy)-5-(3-morpholin-4-ylmethyl-1H-indol-5-yl)-pyridin-2-ylamine | 1.4 |
| I-75 | 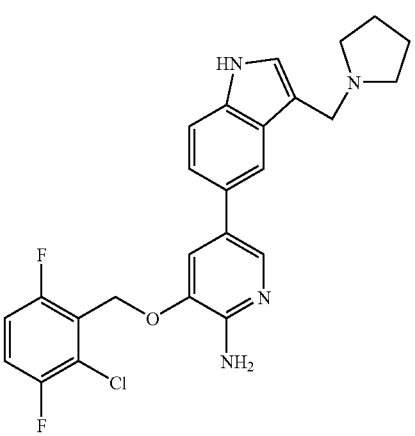 | 3-(2-Chloro-3,6-difluoro-benzyloxy)-5-(3-pyrrolidin-1-ylmethyl-1H-indol-5-yl)-pyridin-2-ylamine | 0.7 |
| I-76 | 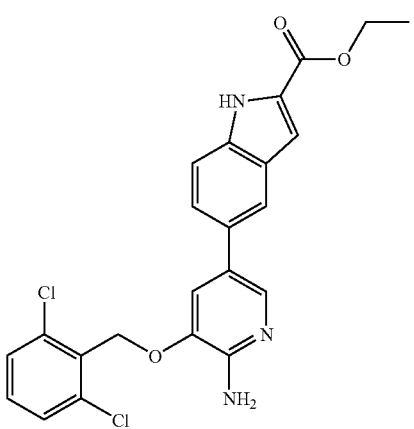 | 5-[6-Amino-5-(2,6-dichlora-benzyloxy)-pyridin-3-yl]-1H-ndole-2-carboxylic acid ethyl ester | >20 |

TABLE 2-continued
| | | | |
|---|---|---|---|
| I-77 | 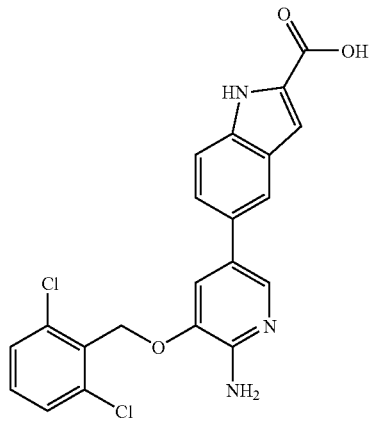 | 5-[6-Amino-5-(2,6-dichloro-benzyloxy)-pyridin-3-yl]-1H-indole-2-carboxylic acid | 1.62 |
| I-78 | 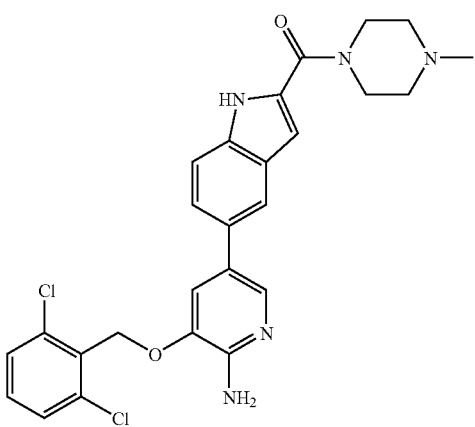 | {5-[6-Amino-5-(2,6-dichloro-benzyloxy)-pyridin-3-yl]-1H-indol-2-yl}-(4-methyl-piperazin-1-yl)-methanone | 0.18 |
| I-79 | 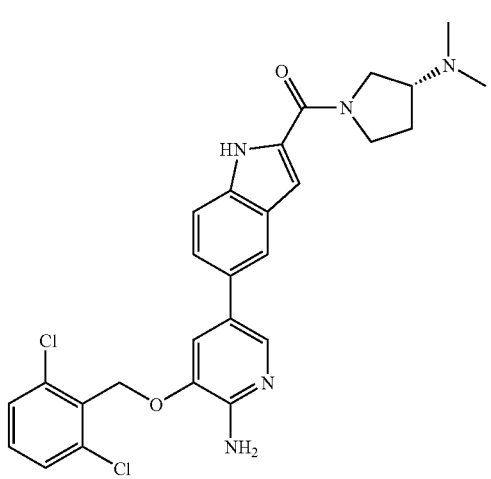 | {5-[6-Amino-5-(2,6-dichloro-benzyloxy)-pyridin-3-yl]-1H-indol-2-yl}-[(3R)-3-dimethylamino-pyrrolidin-1-yl]-methanone | 0.18 |

TABLE 2-continued
| | | | |
|---|---|---|---|
| I-80 | 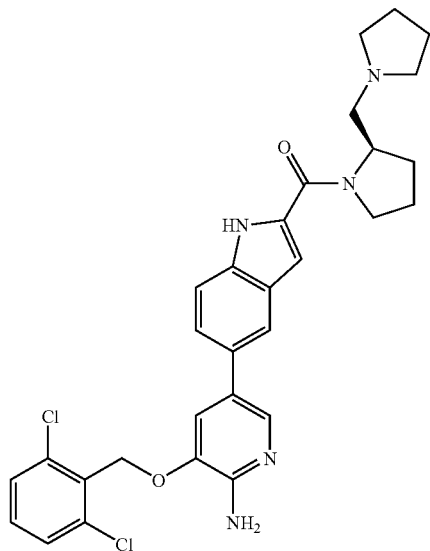 | {5-[6-Amino-5-(2,6-dichloro-benzyloxy)-pyridin-3-yl]-1H-indol-2-yl}-(2R)-2-pyrrolidin-1-ylmethyl-pyrrolidin-1-yl]-methanone | 0.079 |
| I-81 | 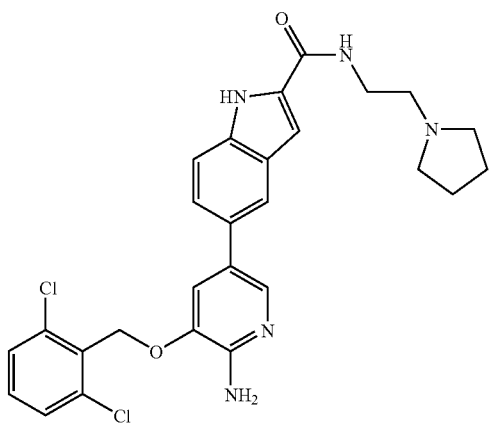 | 5-[6-Amino-5-(2,6-dichloro-benzyloxy)-pyridin-3-yl]-1H-indole-2-carboxylic acid (2-pyrrolidin-1-yl-ethyl)-amide | 1.2 |
| I-82 | 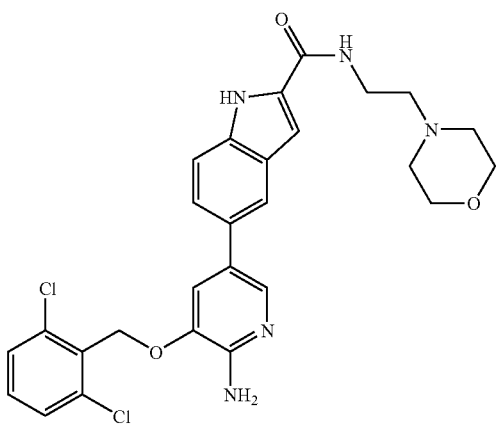 | 5-[6-Amino-5-(2,6-dichloro-benzyloxy)-pyridin-3-yl]-1H-indole-2-carboxylic acid (2-morpholin-4-yl-ethyl)-amide | 1.8 |

TABLE 2-continued
| | | | |
|---|---|---|---|
| I-83 | 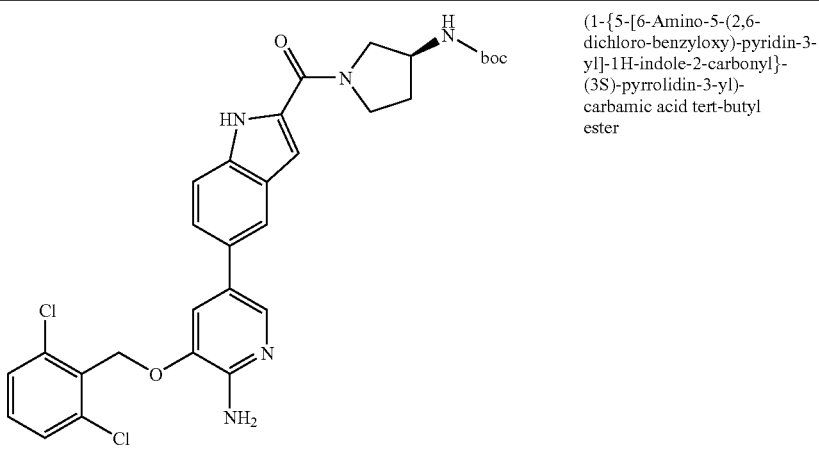 | (1-{5-[6-Amino-5-(2,6-dichloro-benzyloxy)-pyridin-3-yl]-1H-indole-2-carbonyl}-(3S)-pyrrolidin-3-yl)-carbamic acid tert-butyl ester | 5 |
| I-84 | 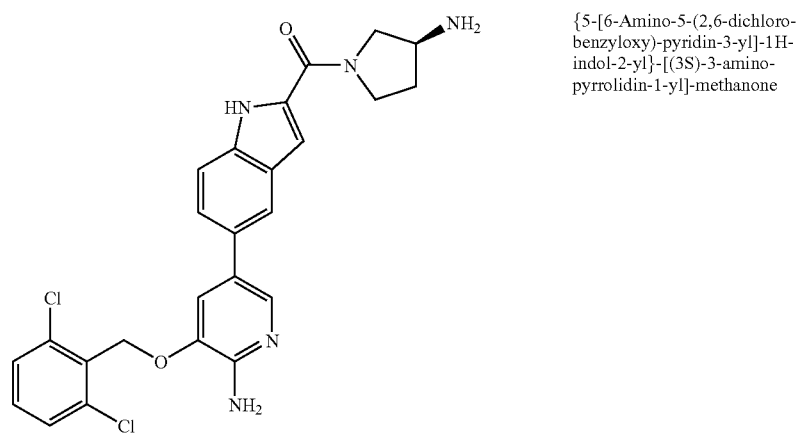 | {5-[6-Amino-5-(2,6-dichloro-benzyloxy)-pyridin-3-yl]-1H-indol-2-yl}-[(3S)-3-amino-pyrrolidin-1-yl]-methanone | 0.14 |
| I-85 | 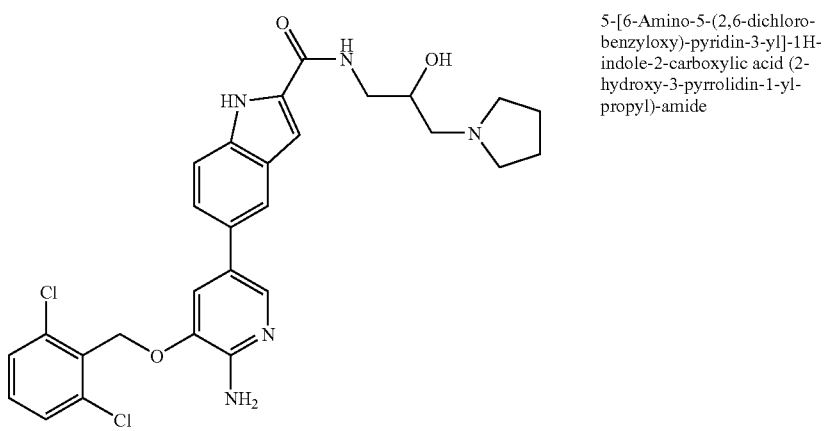 | 5-[6-Amino-5-(2,6-dichloro-benzyloxy)-pyridin-3-yl]-1H-indole-2-carboxylic acid (2-hydroxy-3-pyrrolidin-1-yl-propyl)-amide | 0.7 |
| I-86 | 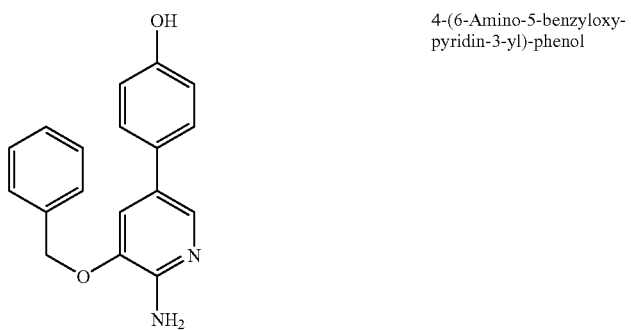 | 4-(6-Amino-5-benzyloxy-pyridin-3-yl)-phenol | 8.7 |

TABLE 2-continued
| ID | Structure | Name | Activity |
|---|---|---|---|
| I-87 | 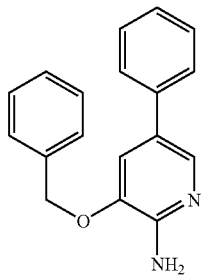 | 3-Benzyloxy-5-phenyl-pyridin-2-ylamine | |
| I-88 | 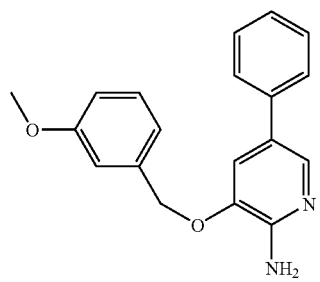 | 3-(3-Methoxy-benzloxy-5-phenyl-pyridin-2-ylamine | |
| I-89 | 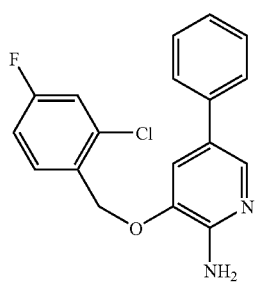 | 3-(2-Chloro-4-fluoro-benzyloxy)-5-phenyl-pyridin-2-ylamine | 17 |
| I-90 | 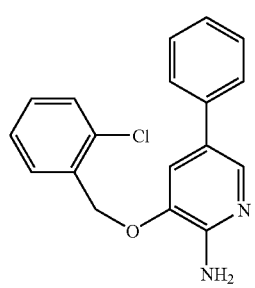 | 3-(2-Chloro-benzyloxy)-5-phenyl-pyridin-2-ylamine | 48% at 20 μM |
| I-91 | 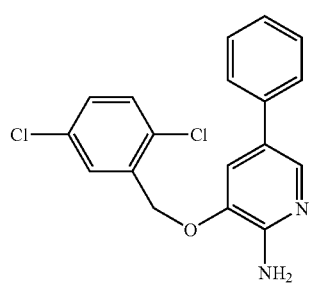 | 3-(2,5-Dichloro-benzyloxy)-5-phenyl-pyridin-2-ylamine | 48% at 20 μM |

TABLE 2-continued
| | | | |
|---|---|---|---|
| I-92 | 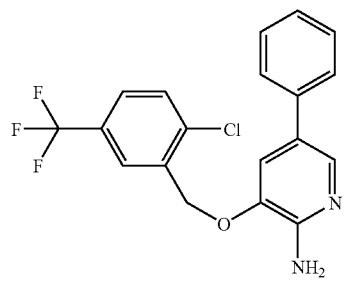 | 3-(2-Chloro-5-trifluoromethyl benzyloxy)-5-phenyl-pyridin-2-ylamine | >20 |
| I-93 | 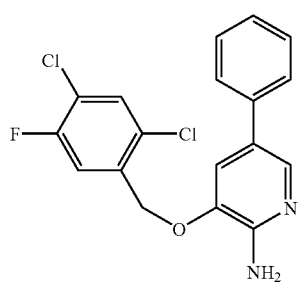 | 3-(2,4-Dichloro-5-fluoro-benzyloxy)-5-phenyl-pyridin-2-ylamine | >20 |
| I-94 | 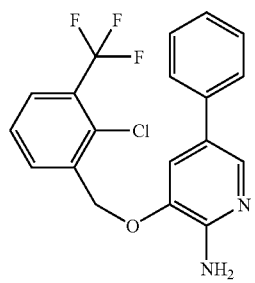 | 3-(2-Chloro-3-trifluoromethyl benzyloxy)-5-phenyl-pyridin-2-ylamine | >20 |
| I-95 | 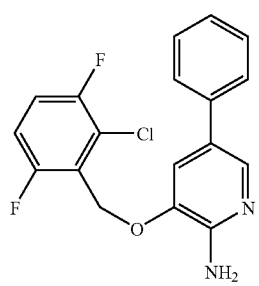 | 3-(2-Chloro-3,6-difluoro-benzyloxy)-5-phenyl-pyridin-ylamine | 0.64 |
| I-96 | 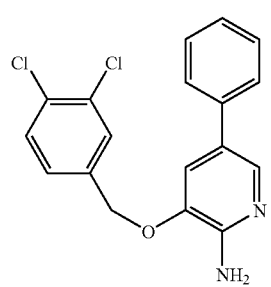 | 3-(3,4-Dichloro-benzyloxy)-5-phenyl-pyridin-2-ylamine | 16.2 |

| | | | |
|---|---|---|---|
| I-97 | 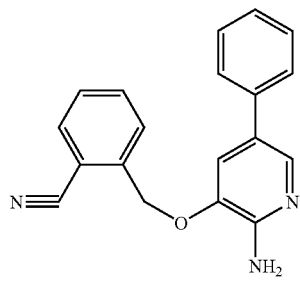 | 2-(2-Amino-5-phenyl-pyridin-3-yloxymethyl)-benzonitrile | 12.2 |
| I-98 | 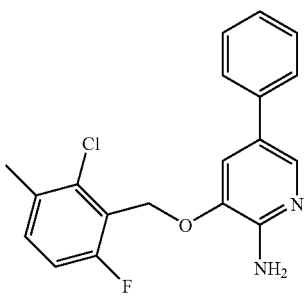 | 3-(2-Chloro-8-fluoro-3-methyl-benzyloxy)-5-phenyl-pyridin-2 ylamine | 7.6 |
| I-99 | 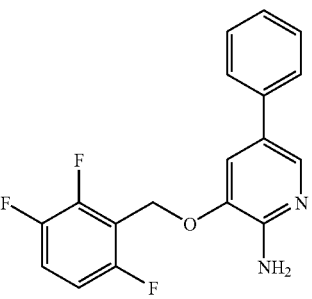 | 5-phenyl-3-(2,3,8-trifluoro-benzyloxy)-pyridin-2-ylamine | 3.9 |
| I-100 | 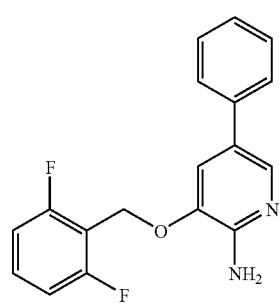 | 3-(2,6-Difluoro-benzyloxy)-5-phenyl-pyridin-2-ylamine | 9.3 |
| I-101 | 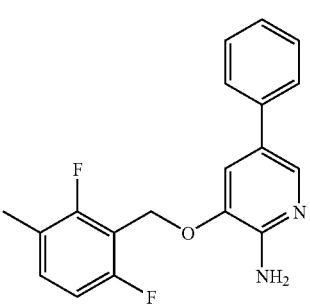 | 3-(2,6-Difluoro-3-methyl-benzyloxy)-5-phenyl-pyridin-ylamine | 12 |

TABLE 2-continued
| | | | |
|---|---|---|---|
| I-102 | 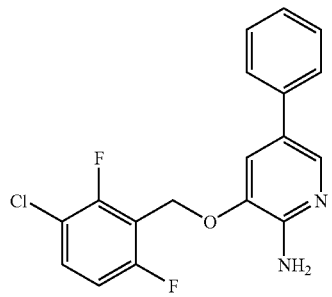 | 3-(3-Chloro-2,6-difluoro-benzyloxy)-5-phenyl-pyridin-2-ylamine | 9.6 |
| I-103 | 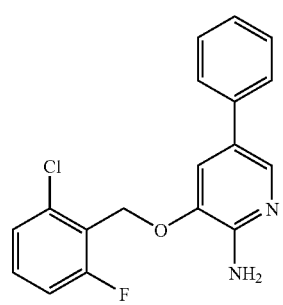 | 3-(2-Chloro-6-fluoro-benzyloxy)-5-phenyl-pyridin-2-ylamine | 7.91 |
| I-104 | 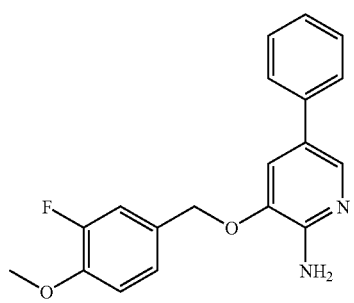 | 3-(3-Fluoro-4-methoxy-benzyloxy)-5-phenyl-pyridin-2-ylamine | 15 |
| I-105 | 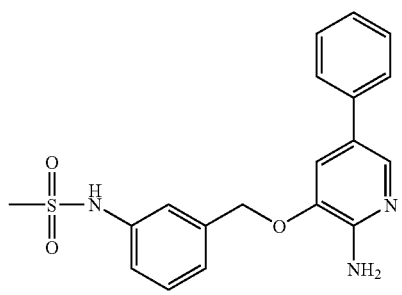 | N-[3-(2-Amino-5-phenyl-pyridin-3-yloxymethyl)-phenyl]-methanesulfonamide | >20 |

TABLE 2-continued
| | | | |
|---|---|---|---|
| I-106 | 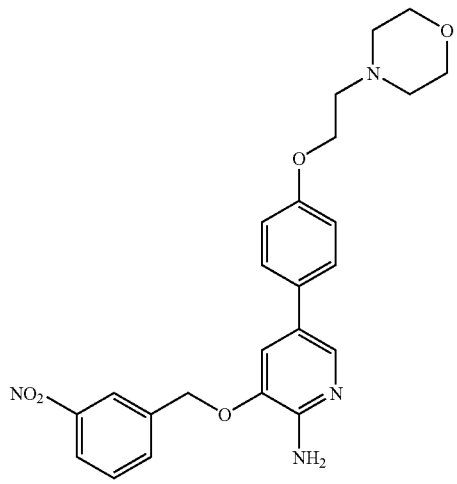 | 5-[4-(2-Morpholin-4-yl-ethoxy)-phenyl]-3-(3-nitro-benzyloxy)-pyridin-2-ylamine | 12.6 |
| I-107 | 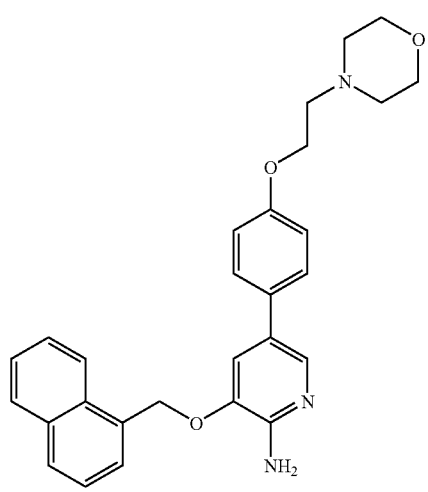 | 5-[4-(2-Morpholin-4-yl-ethoxy)-phenyl]-3-(naphthalen-1-ylmethoxy)-pyridin-2-ylamine | 7.7 |
| I-108 | 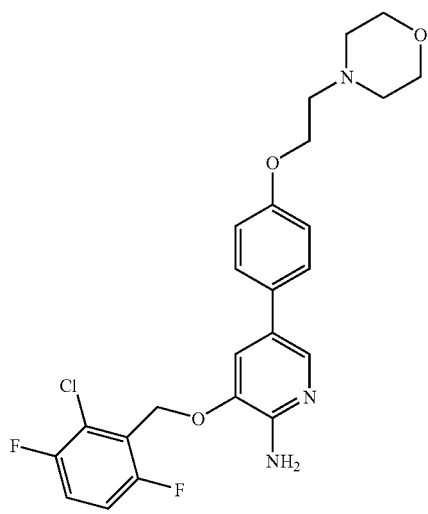 | 3-(2-Chloro-3,6-difluoro-benzyloxy)-5-[4-(2-morpholin-4-yl-ethoxy)-phenyl]-pyridin-2-ylamine | 0.21 |

TABLE 2-continued
| I-109 | 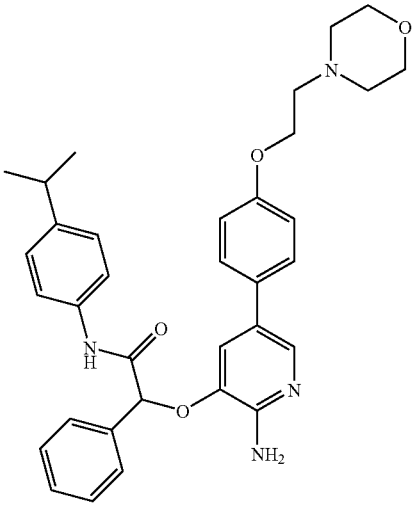 | 2-{2-Amino-5-[4-(2-morpholin-4-yl-ethoxy)-phenyl]-pylidmn-3-yloxy)-N-(4-isopropyl-phenyl)-2-phenyl-acetamide | >20 |
| I-110 | 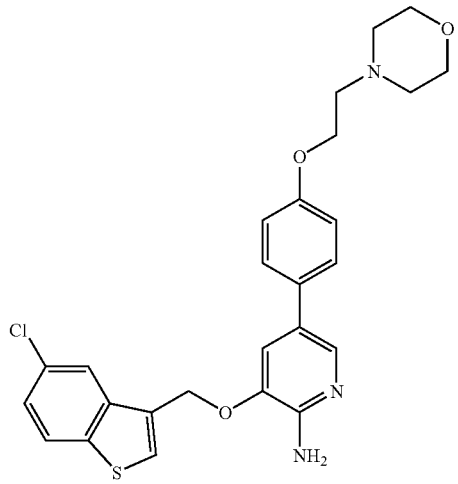 | 3-(5-Chloro-benzo[b]thiophen-3-ylmethoxy)-5-[4-(2-morpholin-4-yl-ethoxy)-phenyl]-pyridin-2-ylamine | 2.4 |
| I-111 | 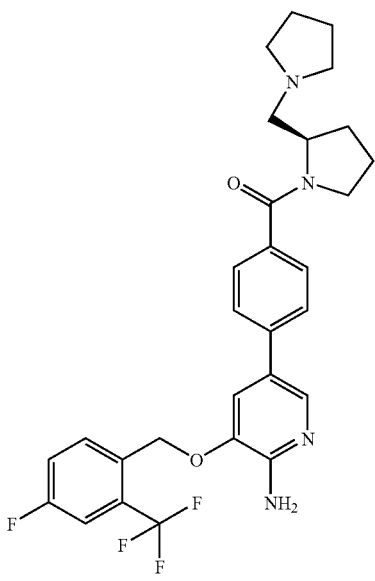 | {4-[6-Amino-5-(4-fluoro-2-trifluoromethyl-benzyloxy)-pyridin-3-yl]-phenyl}-[(2R)-2-pyrrolidin-1-ylmethyl-pyrrolidin-1-yl]-methanone | 1.51 |

TABLE 2-continued
| | | | |
|---|---|---|---|
| I-112 | 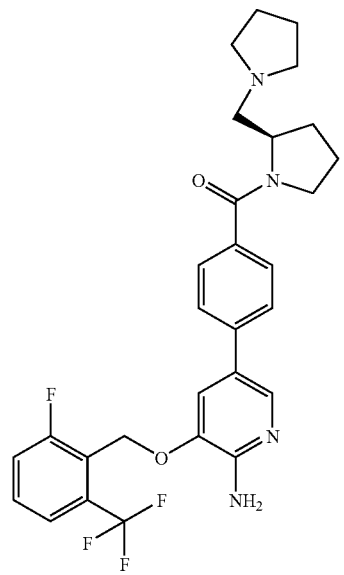 | 4-[6-Amino-5-(2-fluoro-6-trifluoromethyl-benzyloxy)-pyridin-3-yl]-phenyl}-[(2R)-2-prrolidin-1-ylmethyl-pyrrolidin-1-yl]-methanone | 0.15 |
| I-113 | 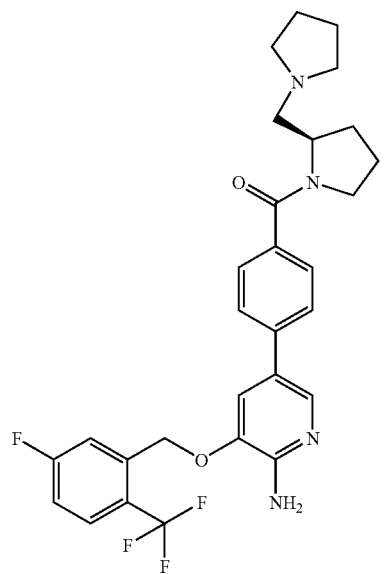 | {4-[6-Amino-5-(5-fiuoro-2-trifluoromethyl-benzyloxy)-pyridin-3-yl]-phenyl}-[(2R)-2-pyrrolidin-1-ylmethyl-pyrrolidin-1-yl]-methanone | 1.27 |

TABLE 2-continued
| I-114 | 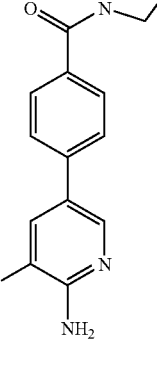 | (4-{6-Amino-5-(1-(2-trifluoromettiyl-phenyl)-ethoxy]-pyridin-3-yl}-phenyl)-[(2R)-2-pyrrolidin-1-ylmethyl-pyrrolidin-1-yl]-methanone | 0.33 |
| I-115 | 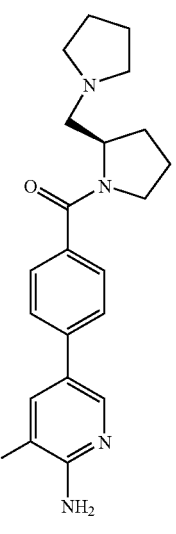 | {4-[6-Amino-5-(2-bromo-benzyloxy)-pyridin-3-yl]-phenyl}-[(2R)-2-pyrrolidin-1-ylmethyl-pyrrolidin-1-yl]-methanone | 1.75 |
| I-116 | 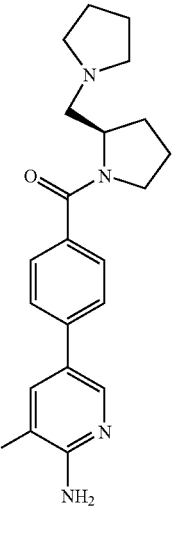 | {4-[6-Amino-5-(3-fluoro-2-trifluoromethyl-benzloxy)-pyridin-3-yl]-phenyl}-[(2R)-2-pyrrolidin-1-ylmethyl-pyrrolidin-1-yl]-methanone | 0.025 |

TABLE 2-continued
I-117
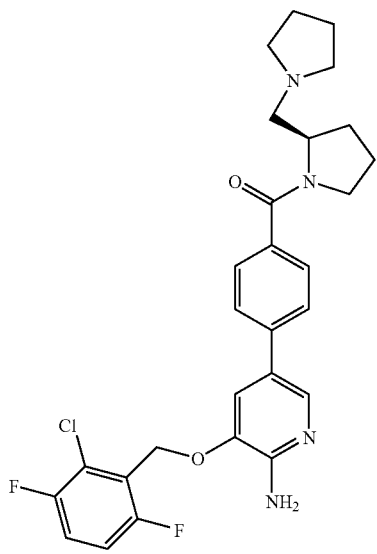
{4-[6-Amino-5-(2-chloro-3,6-difluoro-benzyloxy)-pyridin-3-yl]-phenyl)-[(2R)-2-pyrrolidin-1-ylmethyl-pyrrolidin-1-yl]-methanone    0.063
I-118
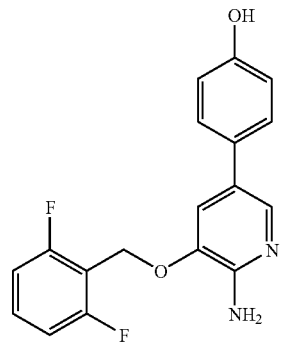
4-[6-Amino-5-(2,6-difluoro-benzyloxy)-pyridin-3-yl]-phenol    3.79
I-119
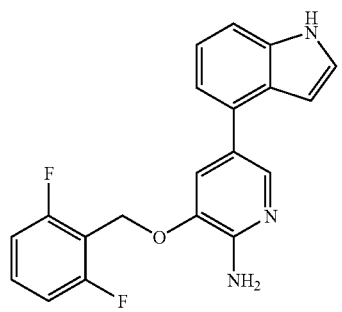
3-(2,6-Difluoro-benzyloxy)-5-(1H-indol-4-yl)-pyridin-2-ylamine    5.8

TABLE 2-continued
| I-120 | 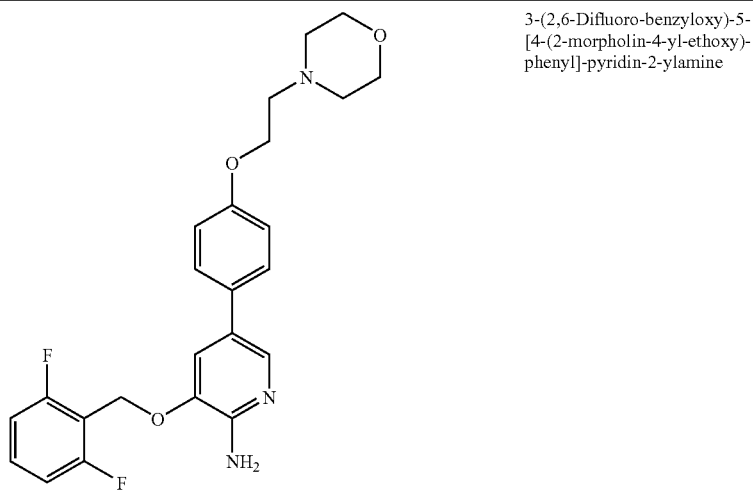 | 3-(2,6-Difluoro-benzyloxy)-5-[4-(2-morpholin-4-yl-ethoxy)-phenyl]-pyridin-2-ylamine | |
| I-121 | 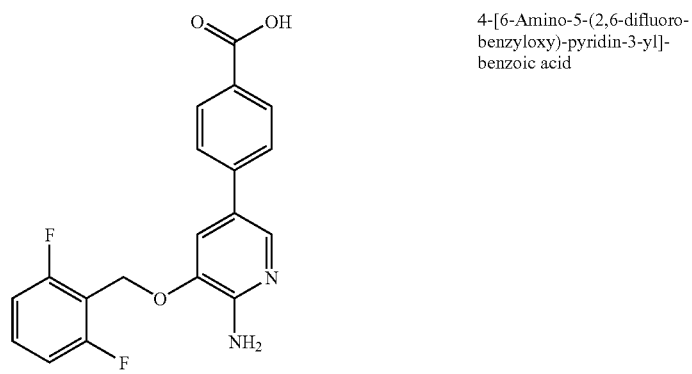 | 4-[6-Amino-5-(2,6-difluoro-benzyloxy)-pyridin-3-yl]-benzoic acid | |
| I-122 | 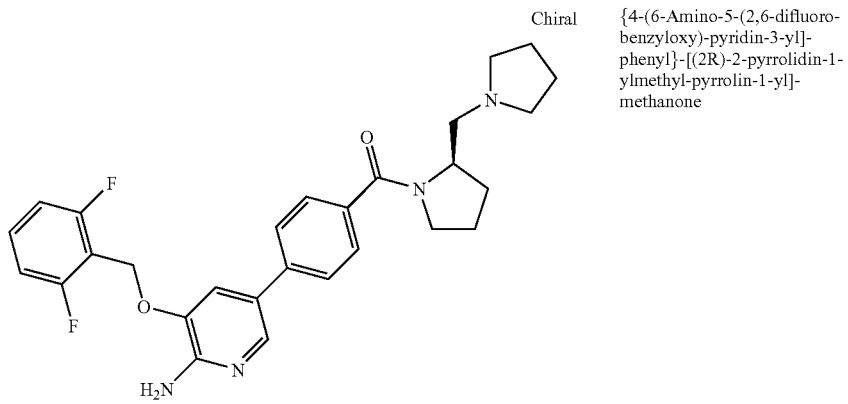 Chiral | {4-(6-Amino-5-(2,6-difluoro-benzyloxy)-pyridin-3-yl]-phenyl}-[(2R)-2-pyrrolidin-1-ylmethyl-pyrrolin-1-yl]-methanone | 1.21 |
| I-123 | 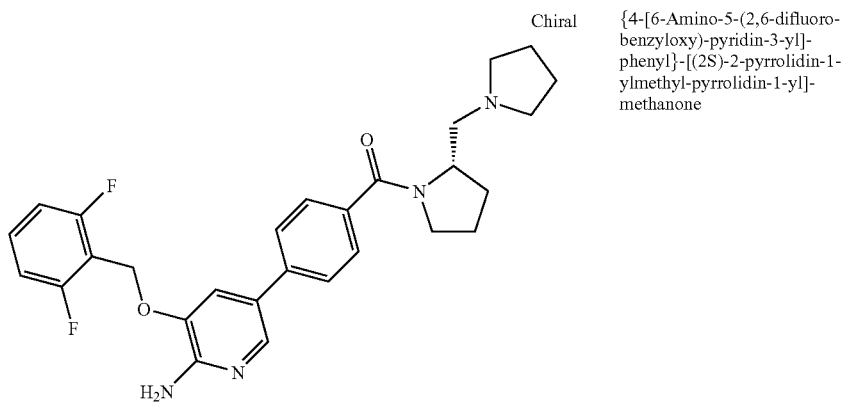 Chiral | {4-[6-Amino-5-(2,6-difluoro-benzyloxy)-pyridin-3-yl]-phenyl}-[(2S)-2-pyrrolidin-1-ylmethyl-pyrrolidin-1-yl]-methanone | 1.36 |

TABLE 2-continued
| | | | |
|---|---|---|---|
| I-124 | 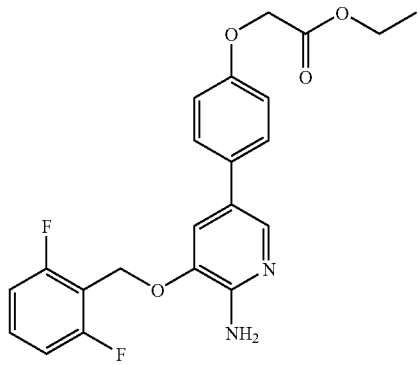 | {4-[6-Amino-5-(2,6-difluoro-benzyloxy)-pyridin-3-yl]-phenoxy}-acetic acid ethyl ester | |
| I-125 | 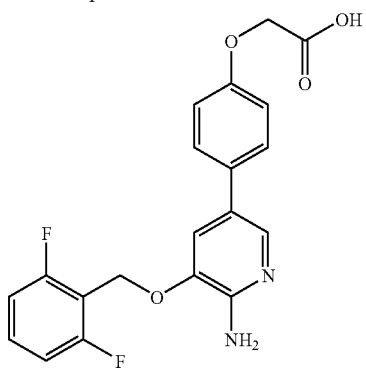 | {4-[6-Amino-5-(2,6-difluoro-benzyloxy)-pyridin-3-yl]-phenoxy}-acetic acid | 14.7 |
| I-126 | 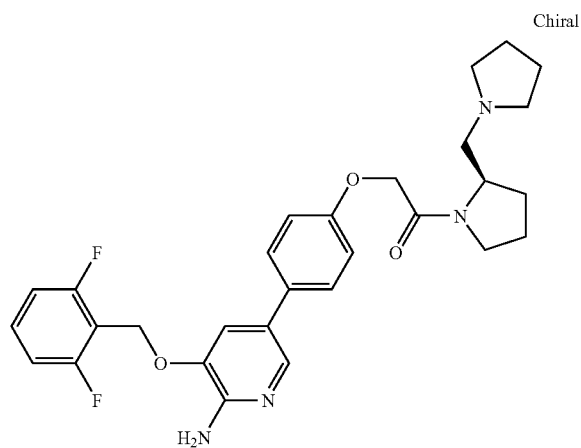 Chiral | 2-{4-[6-Amino-5-(2,6-difluoro-benzyloxy)-pyridin-3-yl]-phenoxy}-1-[(2R)-2-pyrrolidin 1-ylmethyl-pyrrolidin-1-yl]-ethanone | 3.58 |
| I-127 | 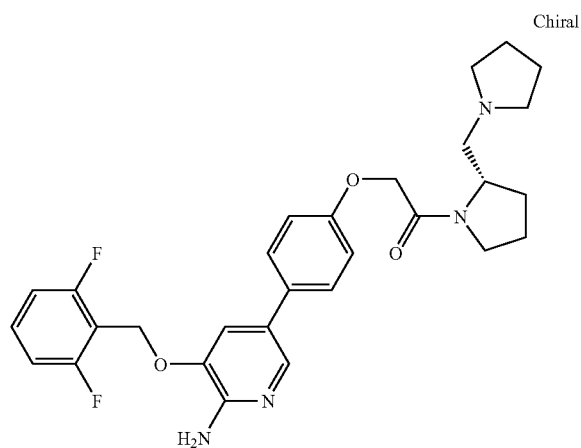 Chiral | 2-{4-[6-Amino-5-(2,6-difluoro-benzyloxy)-pyridin-3-yl]-phenoxy}-1-[(2S)-2-pyrrolidin-1-ylmethyl-pyrrolidin-1-yl]-ethanone | 5.43 |

| | | | |
|---|---|---|---|
| I-128 | 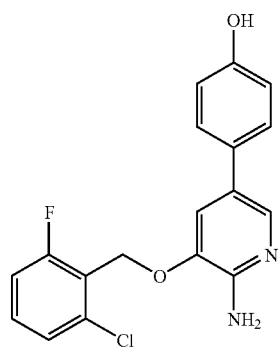 | 4-[6-Amino-5-(2-chloro-6-fluoro-benzyloxy)-pyridin-3-yl]-phenol | 3.99 |
| I-129 | 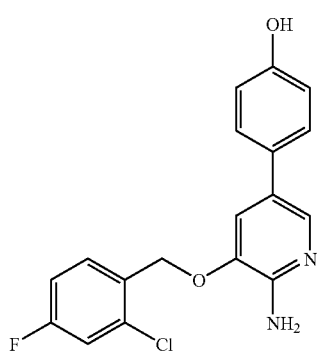 | 4-[6-Amino-5-(2-chloro-4-fluoro-benzyloxy)-pyridin-yl]-phenol | 19 |
| I-130 | 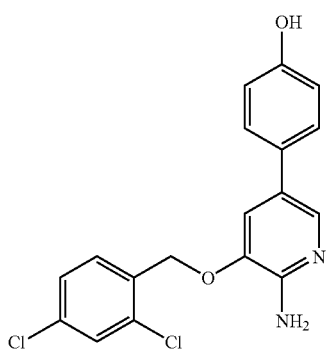 | 4-[6-Amino-5-(2,4-dichloro-benzyloxy)-pyridin-3-yl]-phenol | 9/>20 |
| I-131 | 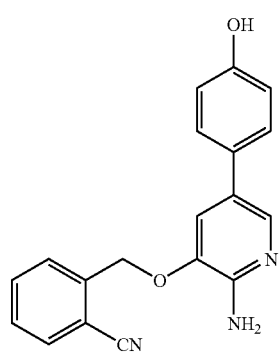 | 2-[2-Amino-5-(4-hydroxy-phenyl)-pyridin-3-yloxymethyl]-benzonitrile | 19 |

| | | | |
|---|---|---|---|
| I-132 | 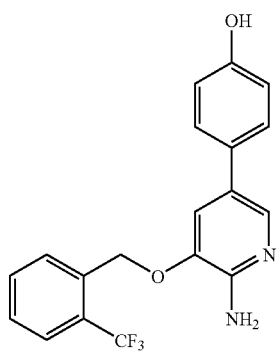 | 4-[6-Amino-5-(2-trifluoromethyl-benzyloxy)-pyridin-3-yl]-phenol | 3.67 |
| I-133 | 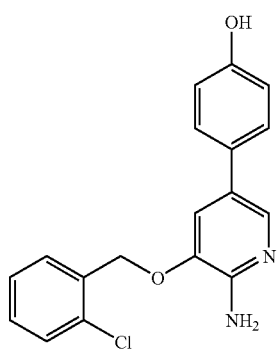 | 4-[6-Amino-5-(2-chloro-benzyloxy)-pyridin-3-yl]-phenol | 13.8 |
| I-134 | 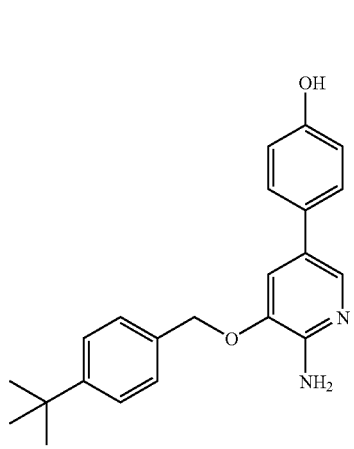 | 4-[6-Amino-5-(4-tert-butyl-benzyloxy)-pyridin-3-yl]-phenol | 4 |
| I-135 | 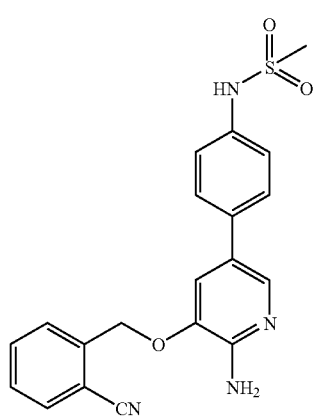 | N-{4-[6-Amino-5-(2-cyano-benzyloxy)-pyridin-3-yl]-phenyl}methanesulfonamide | 4.18 |

| | | | |
|---|---|---|---|
| I-136 | 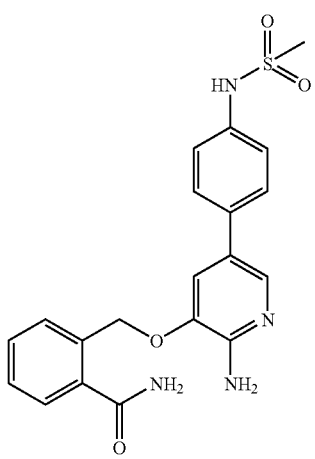 | 2-[2-Amino-5-(4-methanesulfonylamino-phenyl)-pyridin-3-yloxymethyl]-benzamide | >20 |
| I-137 | 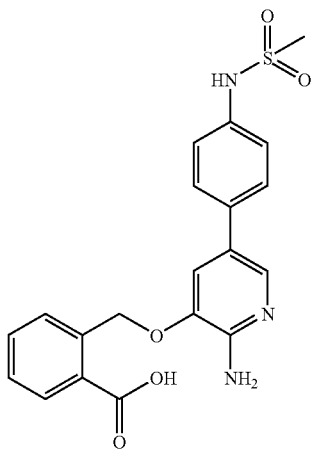 | 2-[2-Amino-5-(4-methanesulfonylamino-phenyl)-pyridin-3-yloxymethyl]-benzoic acid | >20 |
| I-138 | 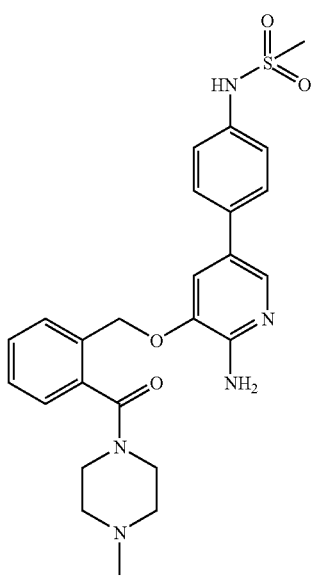 | N-(4-{6-Amino-5-[2-(4-methyl-piperazine-1-carbonyl)-benzyloxy]-pyridin-3-yl}-phenyl)-methanesulfonamide | >20 |

| | | | |
|---|---|---|---|
| I-139 | 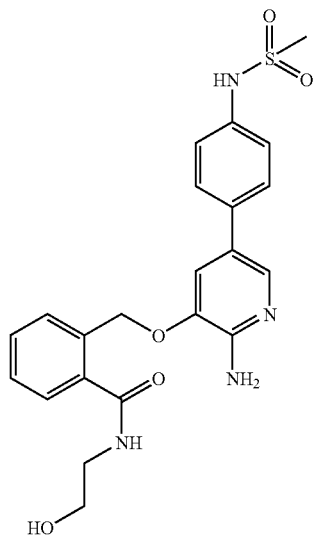 | 2-[2-Amino-5-(4-methanesulfonylamino-phenyl)-pyridin-3-yloxymethyl]-N-(2-hydroxy-ethyl)-benzamide | >20 |
| I-140 | 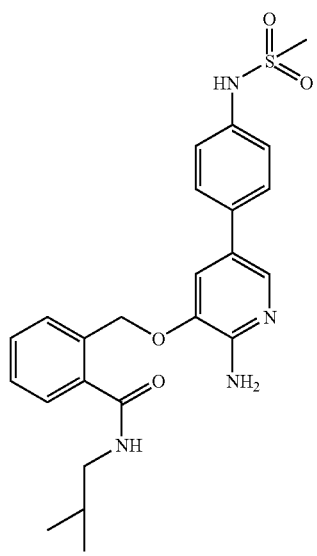 | 2-[2-Amino-5-(4-methanesulfonylamino-phenyl)-pyridin-3-yloxymethyl]-N-isobutyl-benzamide | >20 |
| I-141 | 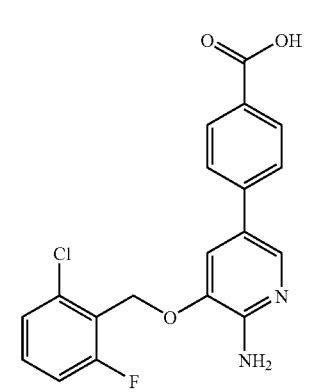 | 4-[6-Amino-5-(2-chloro-6-fluoro-benzyloxy)-pyridin-3-yl]-benzoic acid | |

TABLE 2-continued
| I-142 | 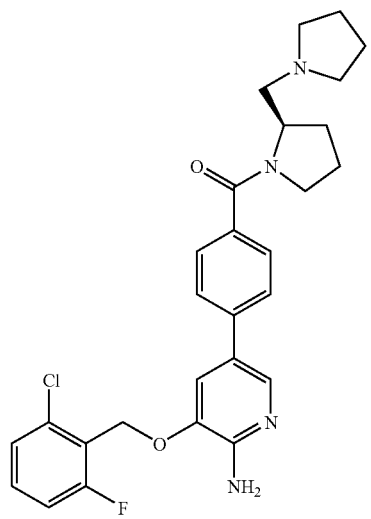 | {4-[6-Amino-5-(2-chloro-8-fluoro-benzyloxy)-pyridin-3-yl]-phenyl}-[(2R)-2-pyrrolidin-1-ylmethyl-pyrrolidin-1-yl]-methanone | 0.53 |
| I-143 | 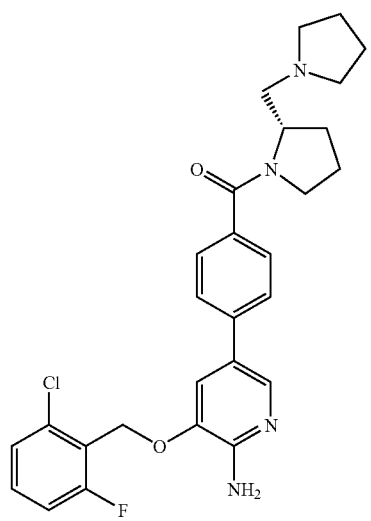 | {4-[6-Amino-5-(2-chloro-6-fluoro-benzyloxy)-pyridin-3-yl]-phenyl}-[(2S)-2-pyrrolidin-1-ylmethyl-pyrrolidin-1-yl]-methanone | 13 |
| I-144 | 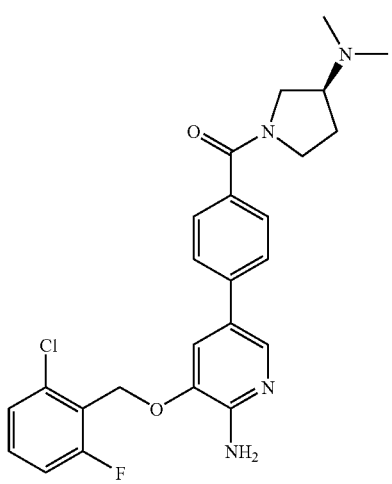 | {4-[6-Amino-5-(2-chloro-6-fluoro-benzyloxy)-pyridin-3-yl]-phenyl}-[(3S)-3-dimethylamino-pyrrolidin-1-yl]-methanone | 1.7 |

TABLE 2-continued
| I-145 | 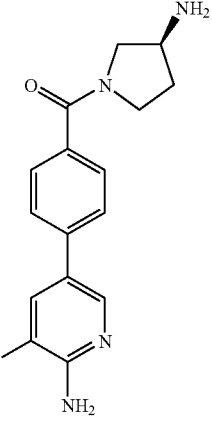 | {4-[6-Amino-5-(2-chloro-6-fluoro-benzyloxy)-pyridin-3-yl]-phenyl}-[(3S)-3-amino-pyrrolidin-1-yl]-methanone | 0.63 |
| --- | --- | --- | --- |
| I-146 | 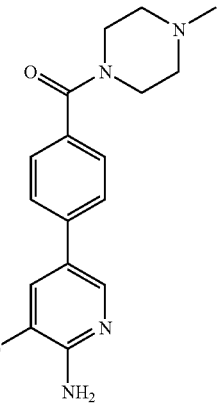 | {4-[6-Amino-5-(2-chloro-6-fluoro-benzyloxy)-pyridin-3-yl]-phenyl}-4-methyl-piperazin-1-yl)-methanone | 1.94 |
| I-147 | 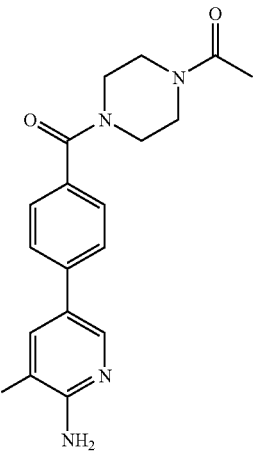 | 1-(4-{4-[6-Amino-5-(2-chloro-6-fluoro-benzloxy)-pyridin-yl]-benzoyl}-piperazin-1-yl)-ethanone | 1.45 |

TABLE 2-continued
| | | | |
|---|---|---|---|
| I-148 | 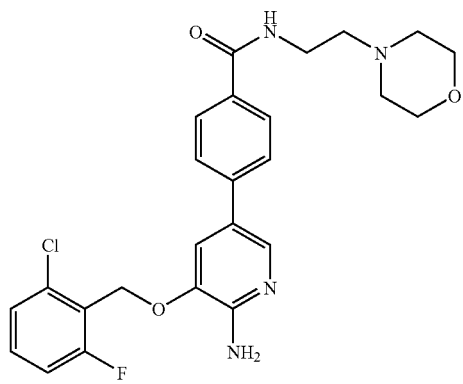 | 4-[6-Amino-5-(2-chloro-8-fluoro-benzyloxy)-pyridin-3-yl]-N-(2-morpholin-4-yl-ethyl)-benzamide | 6.4 |
| I-149 | 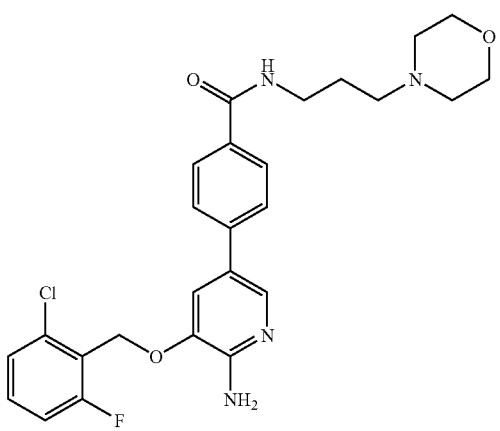 | 4-[6-Amino-5-(2-chloro-8-fluoro-benzyloxy)-pyridin-3-yl]-N-(3-morpholin-4-yl-propyl)-benzamide | 5.6 |
| I-150 | 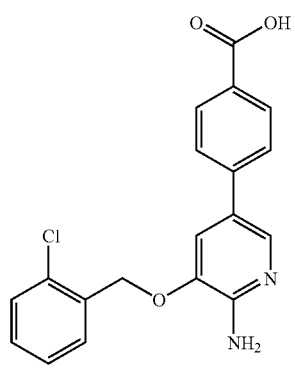 | 4-[6-Amino-5-(2-chloro-benzyloxy)-pyridin-3-yl]-benzoic acid | |

TABLE 2-continued
| I-151 | 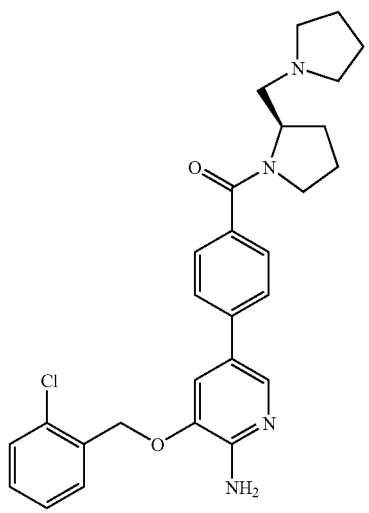 | {4-[6-Amino-5-(2-chloro-benzyloxy)-pyridin-3-yl]-phenyl}-[(2R)-2-pyrrolidin-1-ylmethyl-pyrrolidin-1-yl]-methanone | 0.87 |
| I-152 | 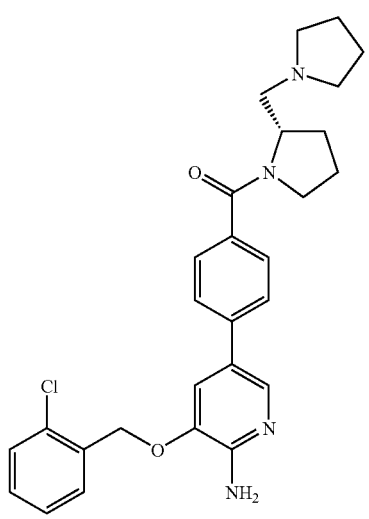 | {4-[6-Amino-5-(2-chloro-benzyloxy)-pyridin-3-yl]-phenyl}-[(2S)-2-pyrrolidin-1-ylmethyl-pyrrolidin-1-yl]-methanone | 2.3 |
| I-153 | 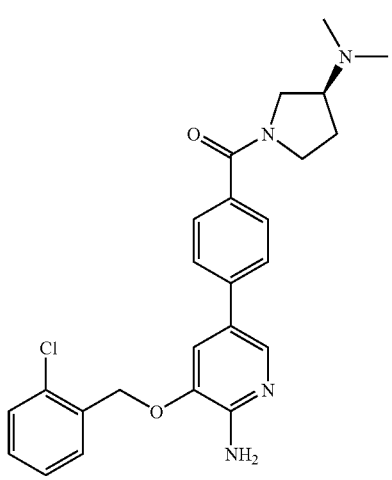 | {4-[6-Amino-5-(2-chloro-benzyloxy)-pyridin-3-yl]-phenyl}-[(3S)-3-dimethylamino-pyrrolidin-1-yl]-methanone | 12.7 |

| | | | |
|---|---|---|---|
| I-154 | 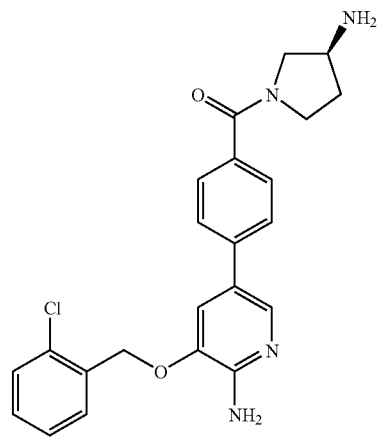 | {4-[6-Amino-5-(2-chloro-benzyloxy)-pyridin-3-yl]-phenyl}-[(3S)-3-amino-pyrrolidin-1-yl]-methanone | 1.44 |
| I-155 | 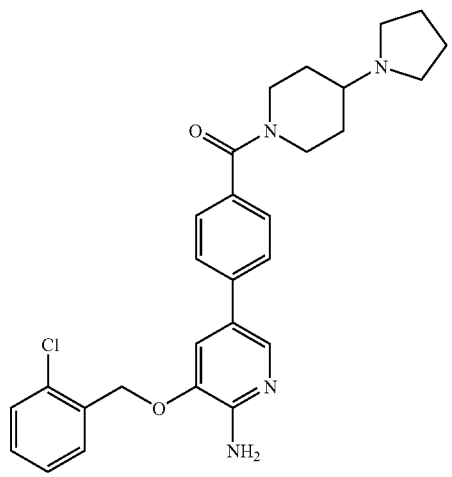 | {4-[6-Amino-5-(2-chloro-benzyloxy)-pyridin-3-yl]-phenyl}-(4-pyrrolidin-1-yl-piperidin-1-yl)-methanone | 1.5 |
| I-156 | 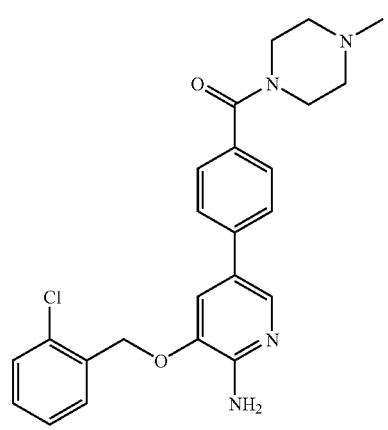 | {4-[6-Amino-5-(2-chloro-benzyloxy)-pyridin-3-yl]-phenyl}-(4-methyl-piperazin-1-yl)-methanone | 2.1 |

TABLE 2-continued
| I-157 | 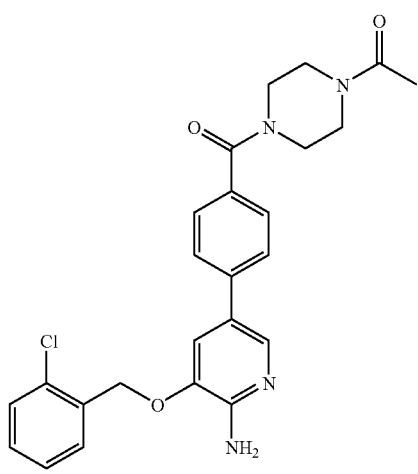 | 1-(4-{4-[6-Amino-5-(2-chloro-benzyloxy)-pyridin-3-yl]-benzoyl}-piperazin-1-yl)-ethanone | 3.8 |
| I-158 | 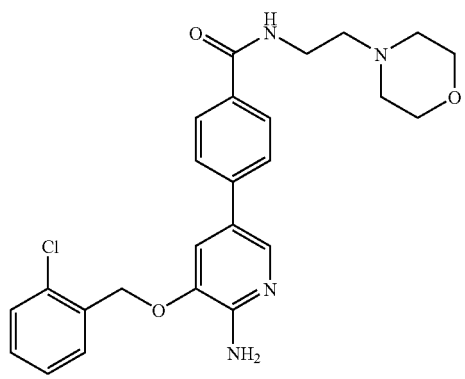 | 4-[6-Amino-5-(2-chloro-benzyloxy)-pyridin-3-yl]-N-(2-morpholin-4-yl-ethyl)-benzamide | 8.9 |
| I-159 | 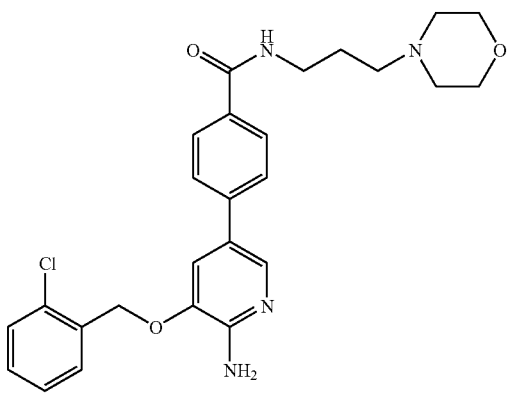 | 4-[6-Amino-5-(2-chloro-benzyloxy)-pyridin-3-yl]-N-(3-morpholin-4-yl-propyl)-benzamide | 4.5 |
| I-160 | 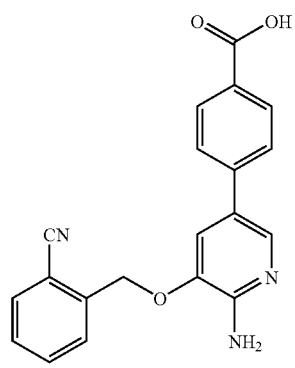 | 4-[6-Amino-5-(2-cyano-benzyloxy)-pyridin-3-yl]-benzoic acid | |

TABLE 2-continued
| I-161 | 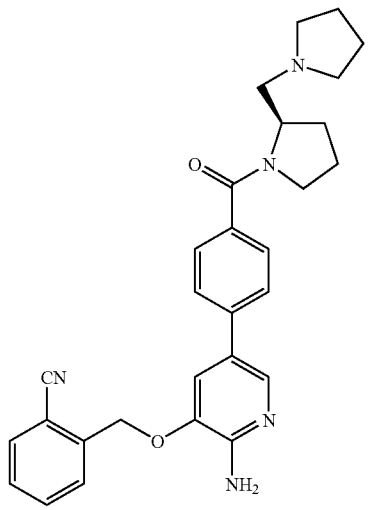 | 2-{2-Amino-5-(4-((2R)-2-pyrrolidin-1-ylmethyl-pyrrolidine-1-carbonyl)-phenyl]-pyridin-3-yloxymethyl}-benzonitrile | 1.2 |
| I-162 | 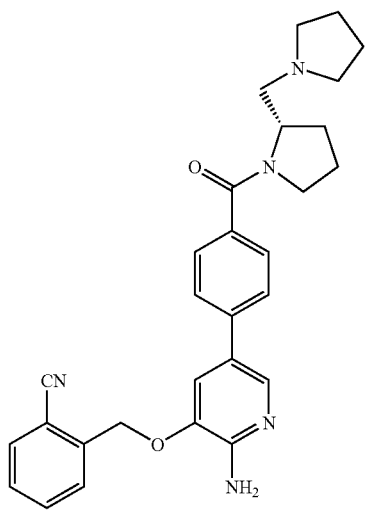 | 2-{2-Amino-5-(4-((2S)-2-pyrrolidin-1-ylmethyl-pyrrolidine-1-carbonyl)-phenyl]-pyridin-3-yloxymethyl)-benzonitrile | 2 |
| I-163 | 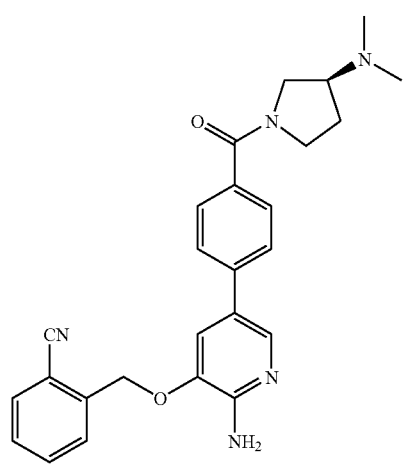 | 2-{2-Amino-5-[4-((3S)-3-dimethylamino-pyrrolidine-1-carbonyl)-phenyl]-pyridin-3-yloxymethyl}-benzonitrile | >20 |

TABLE 2-continued
| I-164 | 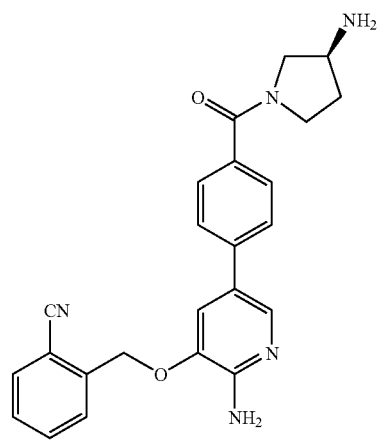 | 2-{2-Amino-5-[4-((3S)-3-amino-pyrrolidine-1-carbonyl)-phenyl]-pyridin-3-yloxymethyl}-benzonitrile | 2.05 |
| I-165 | 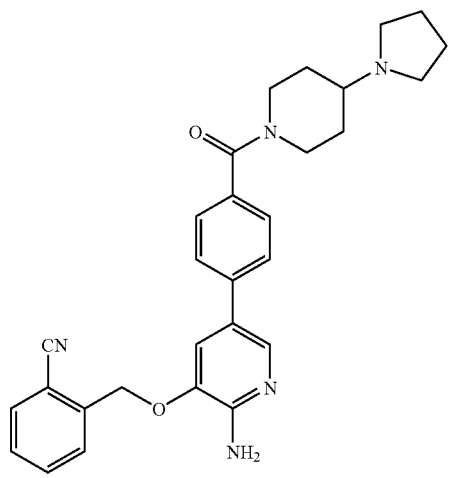 | 2-(2-Amino-5-[4-(4-pyrrolidin-1-yl-pipendine-1-carbonyl)-phenyl]-pyridin-3-yloxymethyl}-benzonitrile | 3.9 |
| I-166 | 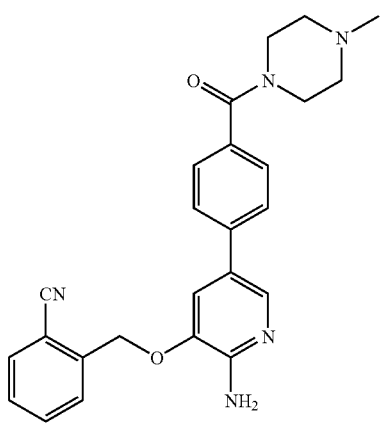 | 2-{2-Amino-5-[4-(4-methyl-piperazine-1-carbonyl)-phenyl]-pyridin-3-yloxymethyl}-benzonitrile | 3.2 |

| | | | |
|---|---|---|---|
| I-167 | 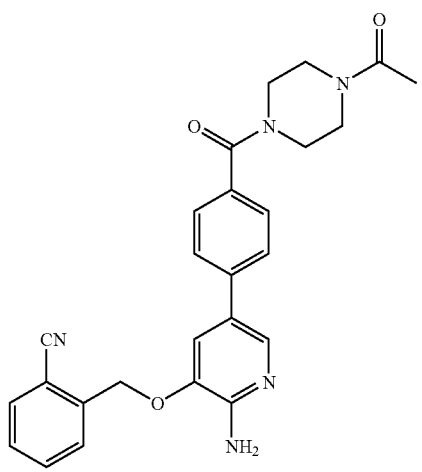 | 2-{5-(4-(4-Acetyl-piperazine-1-carbonyl)-phenyl]-2-amino-pyridin-3-yloxymethyl}-benzonitrile | 5.7 |
| I-168 | 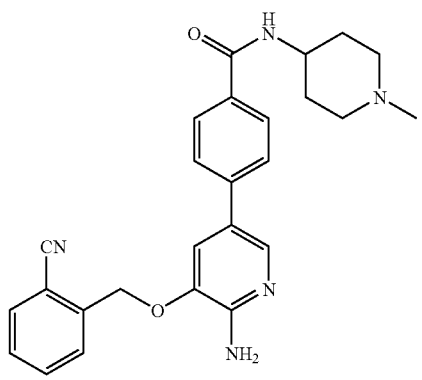 | 4-[6-Amino-5-(2-cyano-benzyloxy)-pyridin-3-yl]-N-methyl-pipendin-4-yl)-benzamide | 10.8 |
| I-169 | 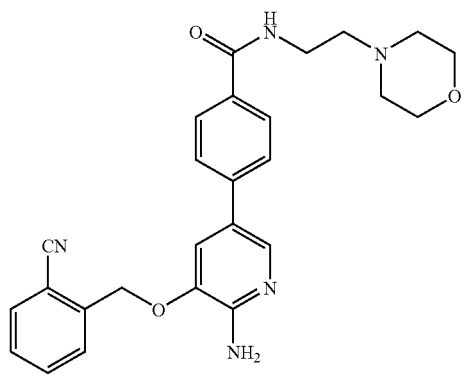 | 4-[6-Amino-5-(2-cyano-benzyloxy)-pyridin-3-yl]-N-(2-morpholin-4-yl-ethyl)-benzamide | 8.6 |
| I-170 | 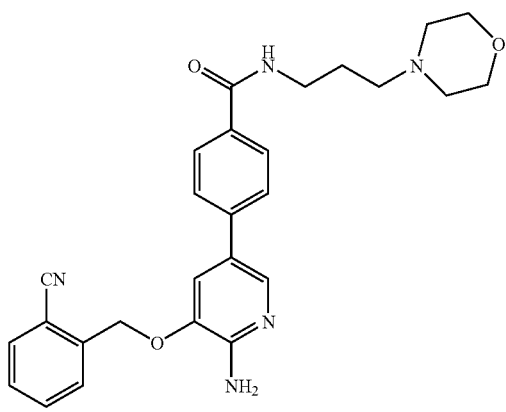 | 4-[6-Amino-5-(2-cyano-benzyloxy)-pyridin-3-yl]-N-(3-morpholin-4-yl-propyl)-benzamide | 17.3 |

TABLE 2-continued
I-171
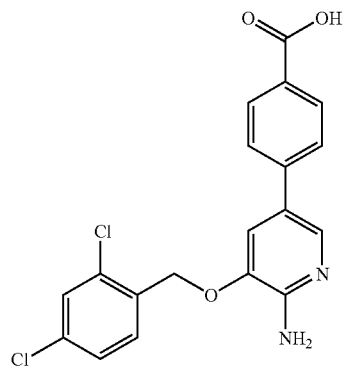
4-[6-Amino-5-(2,4-dichloro-benzyloxy)-pyridin-3-yl]-benzoic acid
I-172
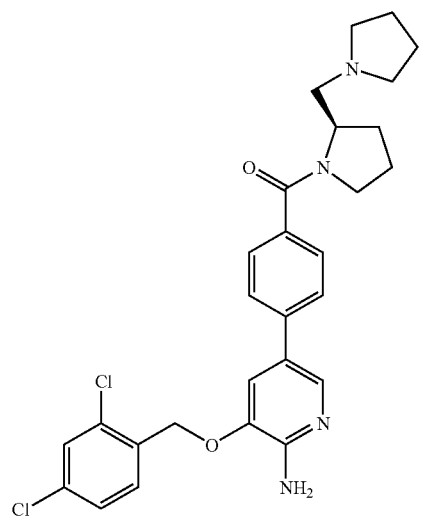
{4-[6-Amino-5-(2,4-dichloro-benzyloxy)-pyridin-3-yl]-phenyl}-[(2R)-2-pyrrolidin-1-ylmethyl-pyrrolidin-1-yl]-methanone
0.61
I-173
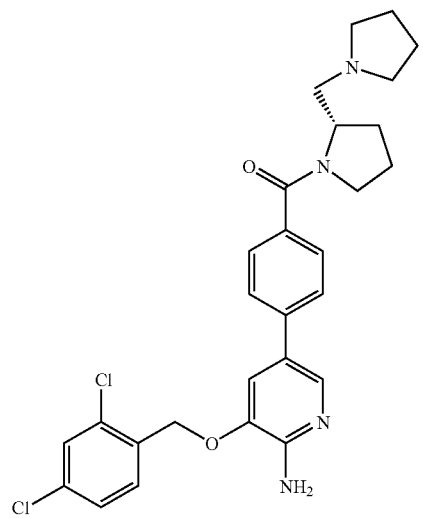
{4-[6-Amino-5-(2,4-dichloro-benzyloxy)-pyridin-3-yl]-phenyl}-[(2S)-2-pyrrolidin-1-ylmethyl-pyrrolidin-1-yl]-methanone
0.66

TABLE 2-continued
| ID | Structure | Name | Value |
|---|---|---|---|
| I-174 | 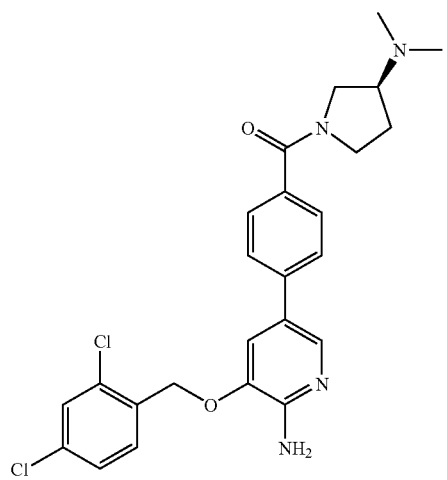 | {4-[6-Amino-5-(2,4-dichloro-benzyloxy)-pyridin-3-yl]-phenyl}-[(3S)-3-dimethylamino-pyrrolidin-1-yl]-methanone | 0.8 |
| I-175 | 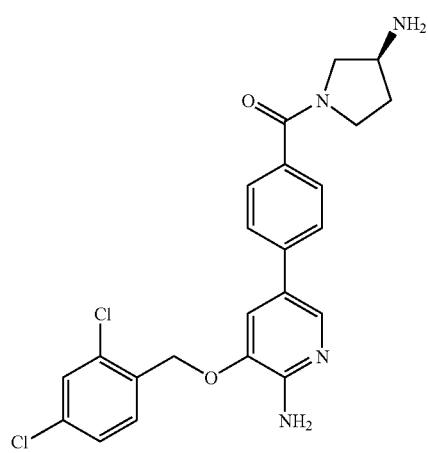 | {4-[6-Amino-5-(2,4-dichloro-benzyloxy)-pyridin-3-yl]-phenyl}-[(3S)-3-amino-pyrrolidin-1-yl]-methanone | 1.2 |
| I-176 | 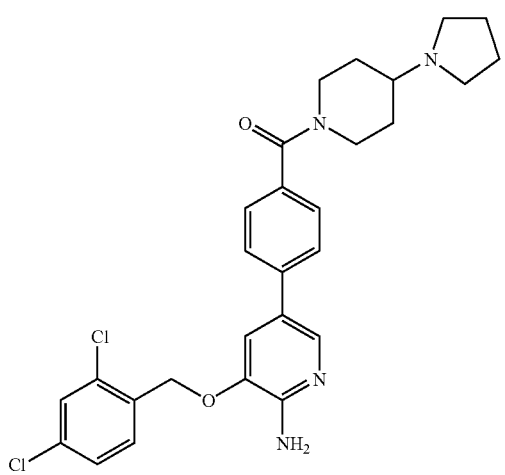 | {4-[6-Amino-5-(2,4-dichloro-benzyloxy)-pyridin-3-yl]-phenyl)-(4-pyrrolidin-1-yl-pipendin-1-yl}-methanone | 0.85 |

TABLE 2-continued
| I-177 | 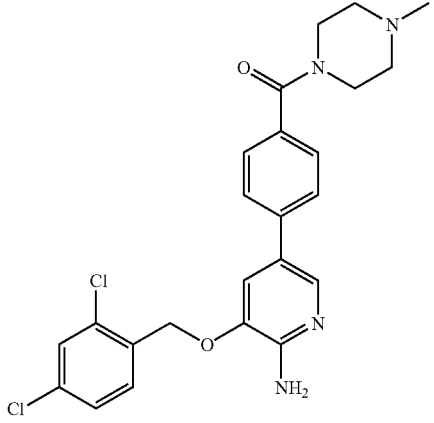 | {4-[6-Amino-5-(2,4-dichloro-benzyloxy)-pyridin-3-yl]-phenyl)-(4-methyl-piperazin-1-yl) methanone | 0.79 |
| I-178 | 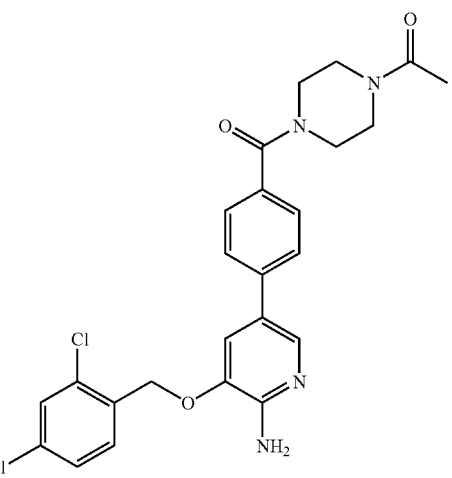 | 1-(4-{4-[(6-Amino-5-(2,4-dichloro-benzyloxy)-pyridin-3-yl]benzoyl}-piperazin-1-yl)-ethanone | 1.67 |
| I-179 | 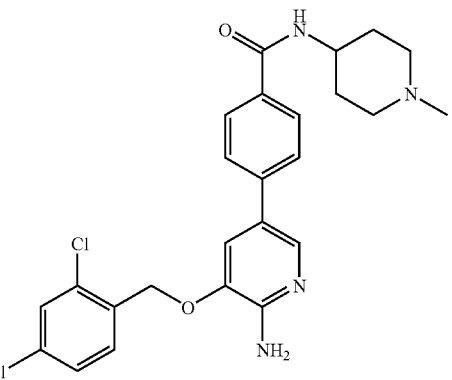 | 4-[6-Amino-5-(2,4-dichloro-benzyloxy)-pyridin-3-yl]-N-(1-methyl piperidin-4-yl)-benzamide | 1.12 |

TABLE 2-continued
| I-180 | 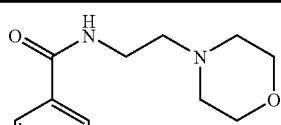 | 4-[6-Amino-5-(2,4-dichloro-benzyloxy)-pyridin-3-yl]-N-(2-morpholin-4-yl-ethyl)-benzamide | 3.8 |
| --- | --- | --- | --- |
| I-181 | 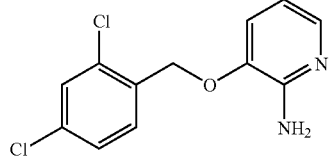 | 4-[6-Amino-5-(2,4-dichloro-benzyloxy)-pyridin-3-yl]-N-(3-morpholin-4-yl-propyl)-benzamide | 2 |
| I-182 | 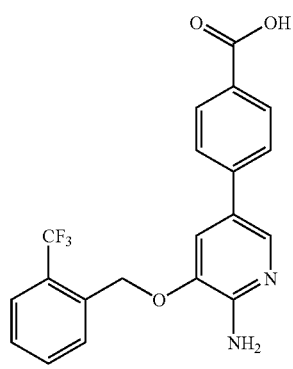 | 4-[6-Amino-5-(2-trifluoromethyl-benzyloxy)-pyridin-3-yl]-benzoic acid | |
| I-183 | 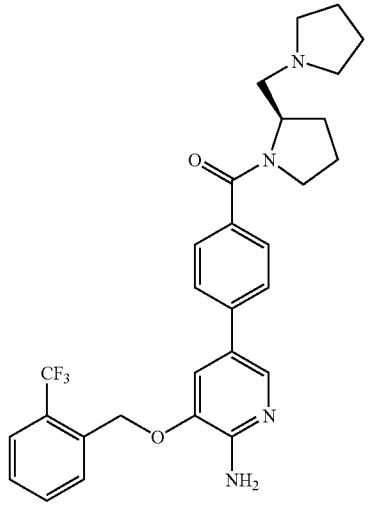 | {4-[6-Amino-5-(2-trifluoromethyl-benzyloxy)-pyridin-3-yl]-phenyl}-[(2R)-2-pyrrolidin-1-ylmethyl-pyrrolidin-1-yl]-methanone | 0.75 |

TABLE 2-continued
| | | | |
|---|---|---|---|
| I-184 | 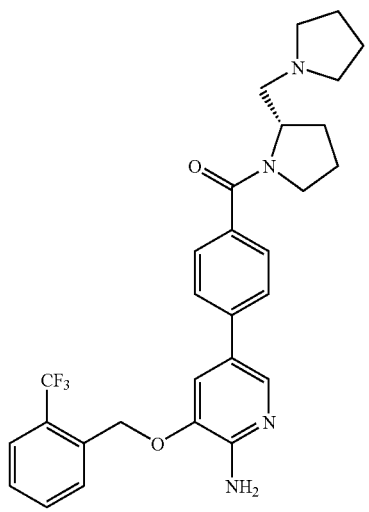 | {4-[6-Amino-5-(2-trifluoromethyl-benzyloxy)-pyridin-3-yl]-phenyl}-[(2S)-2-pyrrolidin-1-ylmethyl-pyrrolidin-1-yl]-methanone | >20 |
| I-185 | 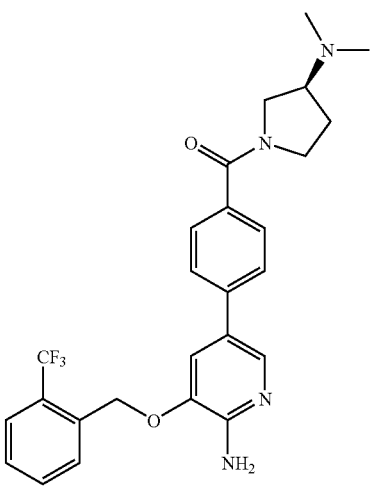 | {4-[6-Amino-5-(2-trifluoromethyl-benzyloxy)-pyridin-3-yl]-phenyl}-[(3S)-3-dimetriylamino-pyrrolidin-1-yl]-methanone | 1.39 |
| I-186 | 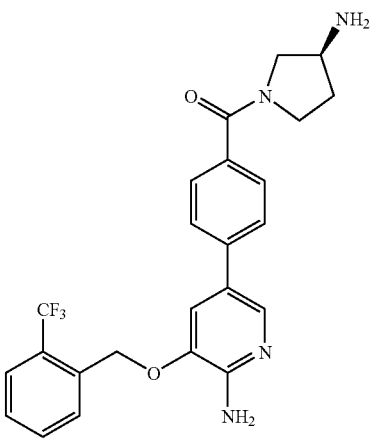 | [(3S)-3-Amino-pyrrolidin-1-yl]-{4-[6-amino-5-(2-trifluoromethyl-benzyloxy)-pyridin-3-yl]-phenyl}-methanone | 0.79 |

TABLE 2-continued
I-187 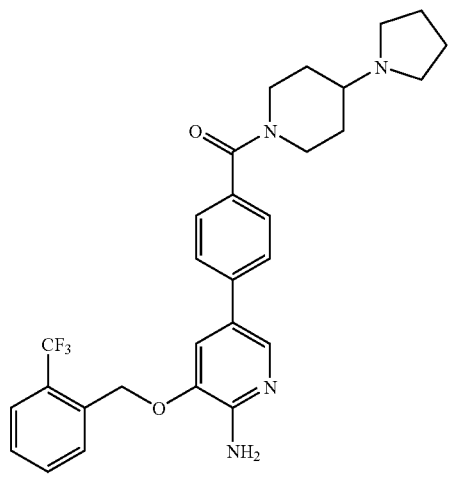 {4-[6-Amino-5-(2-trifluoromethyl-benzyloxy)-pyridin-3-yl]-phenyl}-(4-pyrrolidin-1-yl-pipendin-1-yl)-methanone 1.01
I-188 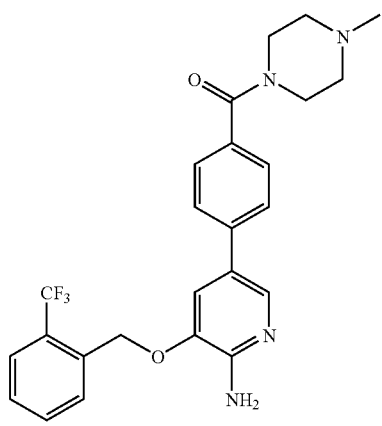 {4-(6-Amino-5-(2-trifluoromethyl-benzyloxy)-pyridin-3-yl]-phenyl}-(4-methyl-piperazin-1-yl)-methanone 1.64
I-189 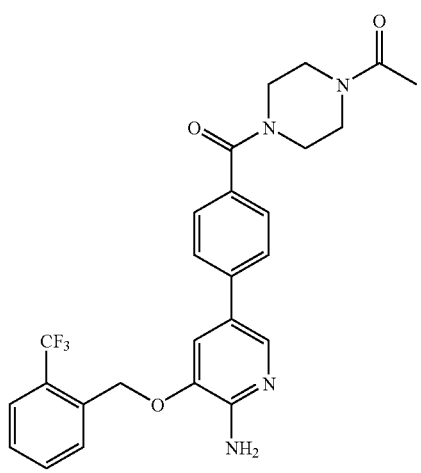 1-(4-{4-[6-Amino-5-(2-trifluoromethyl-benzyloxy)-pyridin-3-yl]-benzoyl}-piperazin-1-yl)-ethanone 6.7

TABLE 2-continued
| | | | |
|---|---|---|---|
| I-190 | 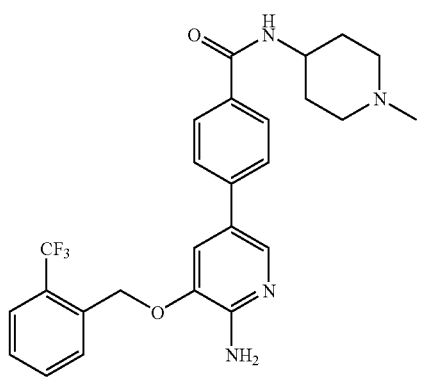 | 4-[6-Amino-5-(2-trifluoromethyl-benzyloxy)-pyridin-3-yl]-N-(1-methyl-piperidin-4-yl)-benzamide | 3.8 |
| I-191 | 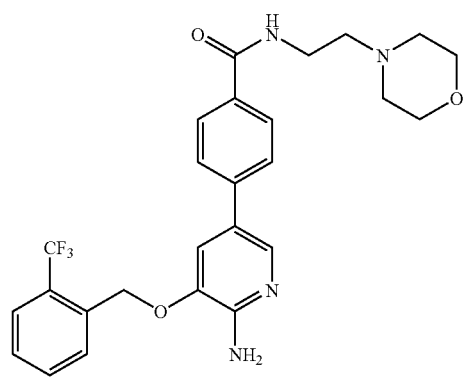 | 4-[6-Amino-5-(2-trifluoromethyl-benzyloxy)-pyridin-3-yl]-N-(2-morpholin-4-yl-ethyl)-benzamide | 5.2 |
| I-192 | 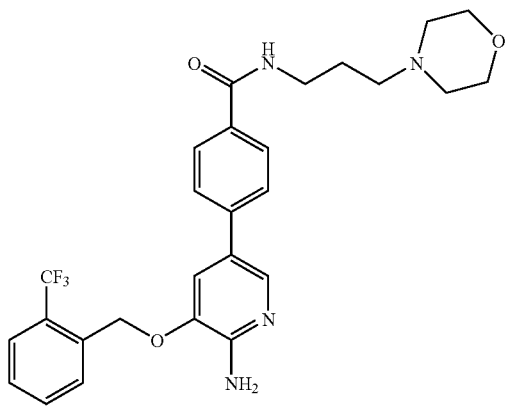 | 4-[6-Amino-5-(2-trifluoromethyl-benzyloxy)-pyridin-3-yl]-N-(3-morpholin-4-yl-propyl)-benzamide | 3.8 |
| I-193 | 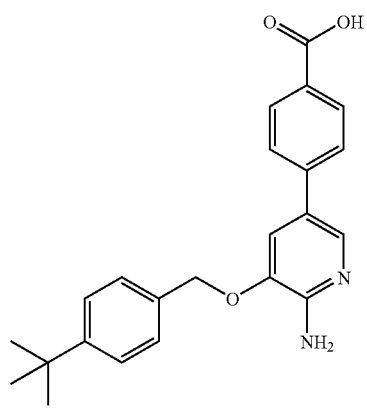 | 4-[6-Amino-5-(4-#tert-butyl-benzyloxy)-pyridin-3-yl]-benzoic acid | |

TABLE 2-continued
| I-194 | 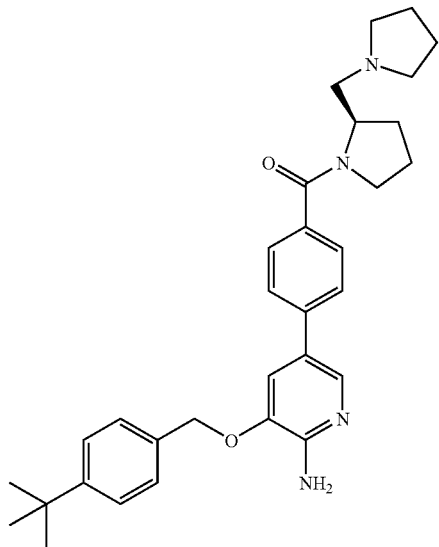 | {4-[8-Amino-5-(4-tert-butyl-benzyloxy)-pyridin-3-yl]-phenyl}-[(2R)-2-pyrrolidin-1-ylmethyl-pyrrolidin-1-yl]-methanone | 1.89 |
| I-195 | 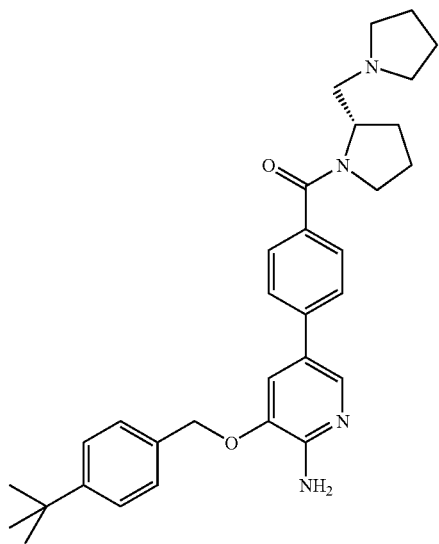 | {4-[6-Amino-5-(4-tert-butyl-benzyloxy)-pyridin-3-yl]-phenyl}-[(2S)-2-pyrrolidin-1-ylmethyl-pyrrolidin-1-yl]-methanone | 3.27 |
| I-196 | 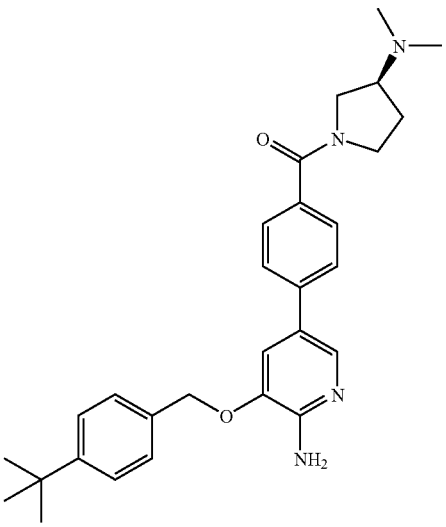 | {4-[6-Amino-5-(4-tert-butyl-benzyloxy)-pyridin-3-yl]-phenyl}-[(3R)-3-dimethylamino-pyrrolidin-1-yl]-methanone | 4.29 |

| | | | |
|---|---|---|---|
| I-197 | 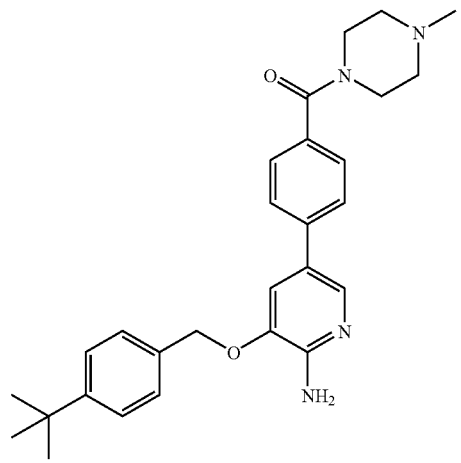 | {4-[6-Amino-5-(4-tert-butyl-benzyloxyl-pyridin-3-yl]-phenyl}-(4-methyl-piperazin-1-yl)-methanone | 3.8 |
| I-198 | 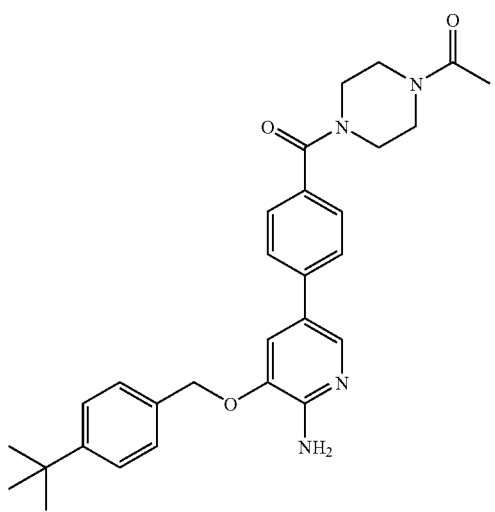 | 1-(4-{4-[6-Amino-5-(4-tert-butyl-benzyloxy)-pyridin-3-yl]benzoyl}-piperazin-1-yl)-ethanone | 3 |
| I-199 | 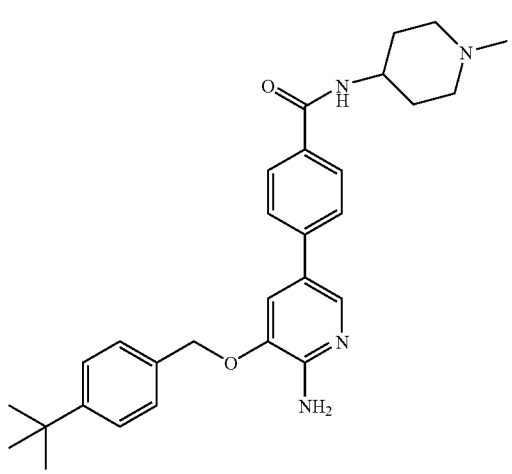 | 4-[6-Amino-5-(4-tert-butyl-benzyloxy)-pyridin-3-yl]-N-(1-methyl-pipendin-4-yl)-benzamide | 2.92 |

TABLE 2-continued
| I-200 | 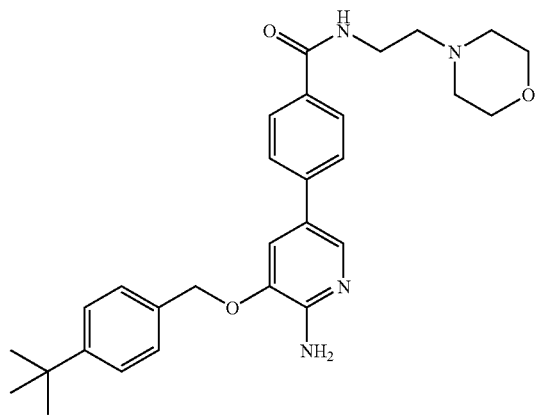 | 4-[6-Amino-5-(4-tert-butyl-benzyloxy)-pyridin-3-yl]N-(2-morpholin-4-yl-ethyl)-benzamide | 6.88 |
| --- | --- | --- | --- |
| I-201 | 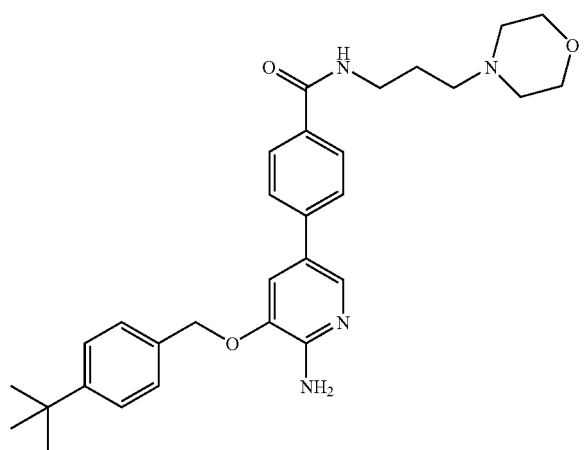 | 4-[6-Amino-5-(4-tert-butyl-benzyloxy)-pyridin-3-yl]-N-(3-morpholin-4-yl-propyl)-benzamide | 6.3 |
| I-202 | 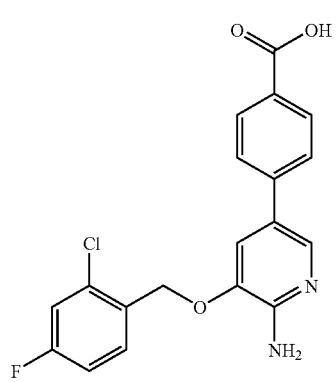 | 4-[8-Amino-5-(2-chloro-4-fluoro-benzyloxy)-pyridin-3-yl]-benzoic acid | |

TABLE 2-continued
| | | | |
|---|---|---|---|
| I-203 | 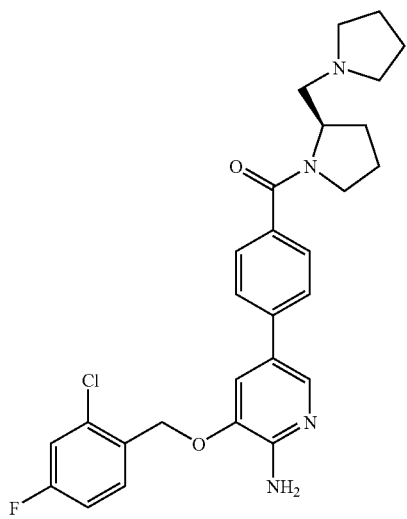 | {4-[6-Amino-5-(2-chloro-4-fluoro-benzyloxy)-pyridin-3-yl]-phenyl}-[(2R)-2-pyrrolidin-1-ylmethyl-pyrrolidin-1-yl]-methanone | 1.48 |
| I-204 | 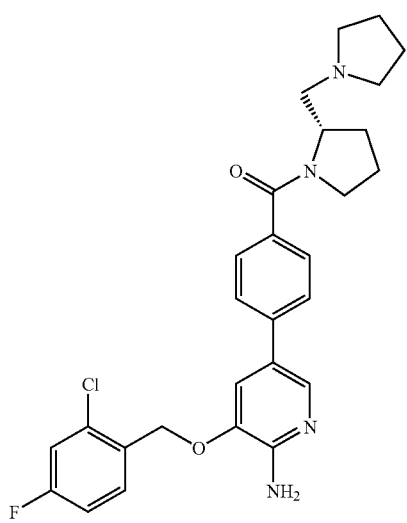 | {4-[8-Amino-5-(2-chloro-4-fluoro-benzyloxy)-pyridin-3-yl]-phenyl}-[(2S)-2-pyrrolidin-1-ylmethyl-pyrrolidin-1-yl]-methanone | 2.5 |
| I-205 | 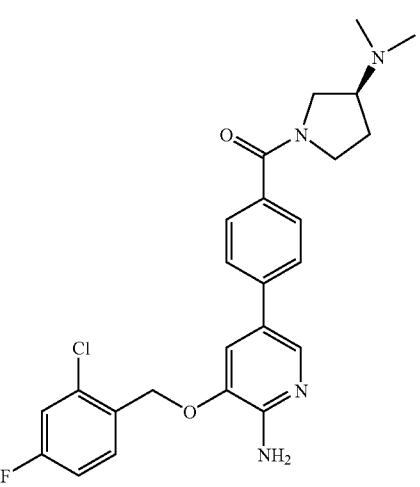 | {4-[8-Amino-5-(2-chloro-4-fluoro-benzyloxy)-pyridin-3-yl]-phen-[(3S-3-dimethylamino-pyrrolidin-1-yl]-methanone | 8.1 |

TABLE 2-continued
| | | |
|---|---|---|
| I-206 | 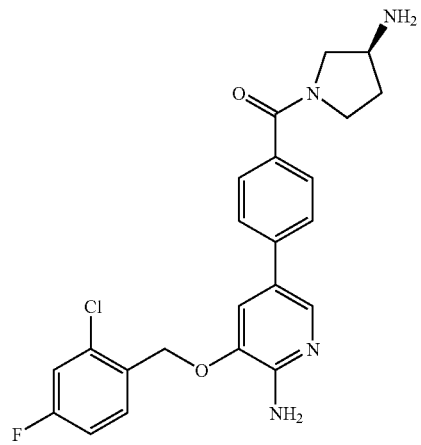 {4-[6-Amino-5-(2-chloro-4-fluoro-benzyloxy)-pyridin-3-yl]-phenyl}-[(3S)-3-amino-pyrrolidin-1-yl]-methanone | 1.83 |
| I-207 | 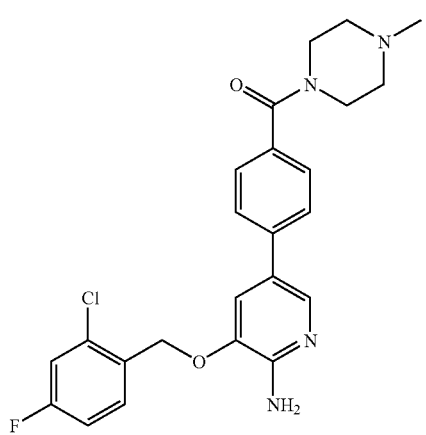 {4-[6-Amino-5-(2-chloro-4-fluoro-benzyloxy)-pyridin-3-yl]-phenyl}-(4-methyl-piperazin-1-yl)-methanone | 5 |
| I-208 | 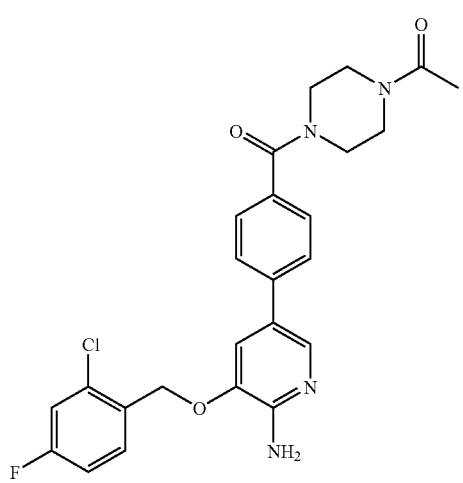 1-(4-{4-[6-Amino-5-(2-chloro-4-fluoro-benzyloxy)-pyridin-3-yl]-benzoyl}-piperazin-1-yl)-ethanone | 5.3 |

TABLE 2-continued
| | | | |
|---|---|---|---|
| I-209 | 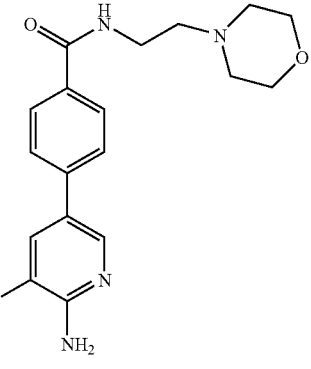 | 4-[6-Amino-5-(2-chloro-4-fluoro-benzyloxy)-pyridin-3-yl]-N-(2-morpholin-4-yl-ethyl)-benzamide | 11 |
| I-210 | 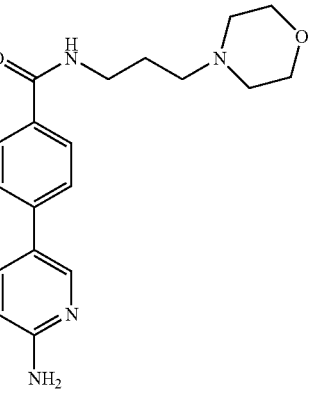 | 4-[6-Amino-5-(2-chloro-4-fluoro-benzyloxy)-pyridin-3-yl]-N-(3-morpholin-4-yl-propyl)-benzamide | 5.8 |
| I-211 | 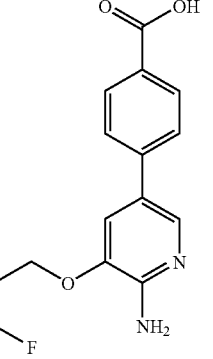 | 4-[6-Amino-5-(2-chloro-3,6-difluoro benzyloxy)-pyridin-3-yl]benzoic acid | 0.35 |
| I-212 | 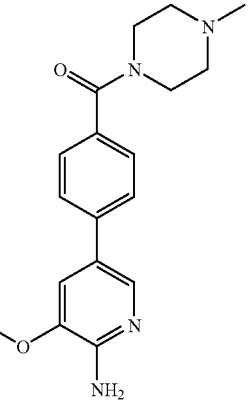 | {4-[6-Amino-5-(2-chloro-3,6-difluoro-benzyloxy)-pyridin-3-yl]-phenyl}-(4-methyl-piperazin-1-yl)-methanone | 0.063 |

TABLE 2-continued
| I-213 | 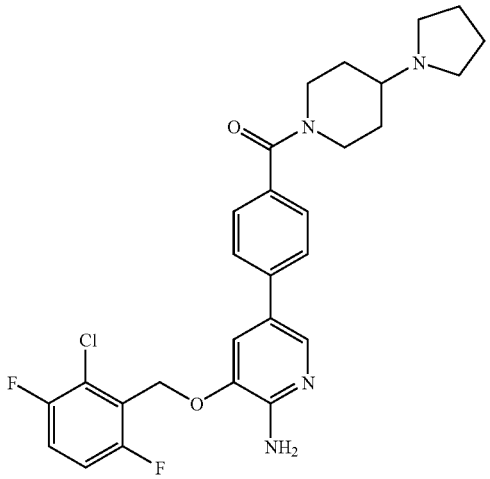 | {4-[6-Amino-5-(2-chloro-3,6-difluoro-benzyloxy)-pyridin-3-yl]-phenyl}-(4-pyrrolidin-1-yl-pipendin-1-yl)-methanone | 0.049 |
| I-214 | 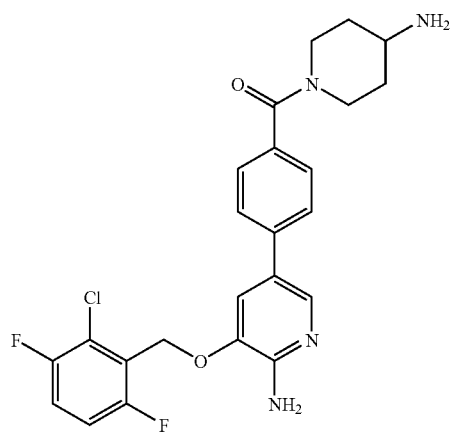 | {4-[6-Amino-5-(2-chlora-3,6-difluoro-benzyloxy)-pyridin-3-yl]-phenyl}-(4-amino-pipendin-1-yl)-methanone | 0.1 |
| I-215 | 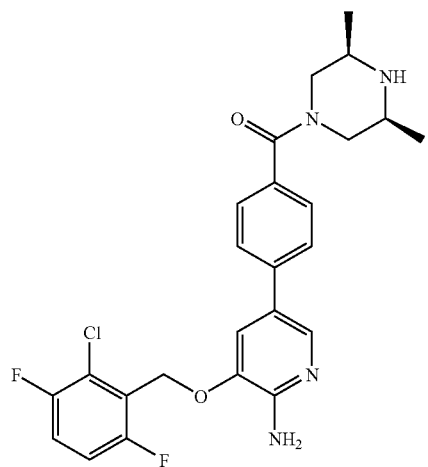 | {4-[6-Amino-5(2-chloro-difluoro-benzyloxy)-pyridin-3-yl]-phenyl}-(3,5-dimethyl-piperazin-1-yl)-methanone | 0.1 |

TABLE 2-continued
| | | | |
|---|---|---|---|
| I-216 | 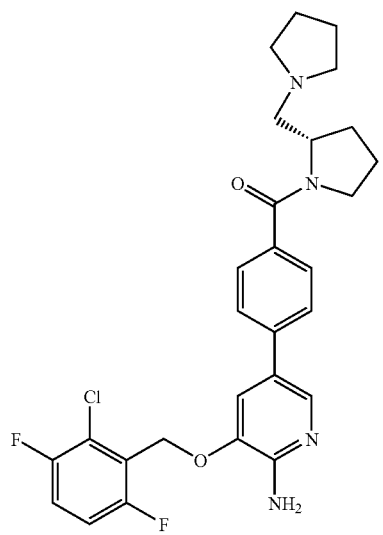 | {4-[6-Amino-5-(2-chloro-3,6-difluoro-benzyloxy)-pyridin-3-yl]-phenyl}-[(2S)-2-pyrrolidin-1-ylmethyl-pyrrolidin-1-yl]-methanone | 0.1 |
| I-217 | 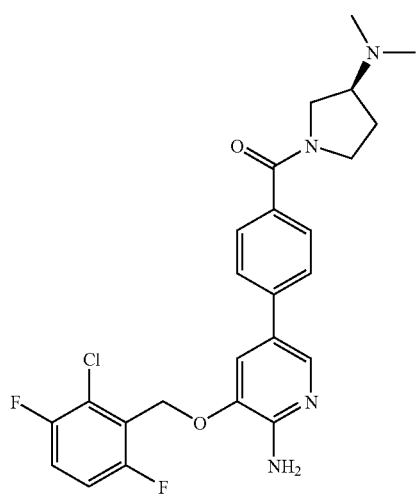 | {4-[6-Amino-5-(2-chloro-3,6-difluoro-benzyloxy)-pyridin-3-yl]-phenyl}-[(3S)-3-dimethylamino-pyrrolidin-1-yl]-methanone | 0.12 |
| I-218 | 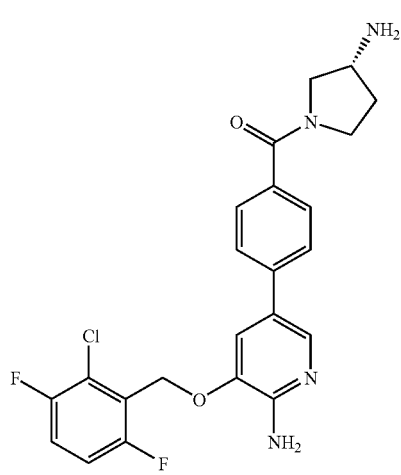 | {4-[6-Amino-5-(2-chloro-3,6-difluoro-benzyloxy)-pyridin-3-yl]-phenyl)-[(3R)-3-amino-pyrrolidin-1-yl]-methanone | 0.053 |

| | | | |
|---|---|---|---|
| I-219 | | {4-[6-Amino-5-(2-chloro-3,6-d fluoro-benzyloxy)-pyridin-3-yl]phenyl)-((3S)-3-amino-pyrrolidin-1-yl]-methanone | 0.095 |
| I-220 | | 4-[6-Amino-5-(2-chloro-3,6-difluoro-benzyloxy)-pyridin-3-yl]-N-(1-methyl-piperidin-4-yl)-benzamide | 0.11 |
| I-221 | | 4-[6-Amino-5-(2-chloro-3,6-difluoro-benzyloxy)-pyridin-3-yl]-N-(2-pyrrolidin-1-yl-ethyl)-benzamide | 0.18 |
| I-222 | | 4-[6-Amino-5-(2-chloro-3,6-difluoro-benloxy)-pyridin-3-yl]-N-(3-pyrrolidin-1-yl-propyl)-benzamide | 0.19 |

| | | | |
|---|---|---|---|
| I-223 | 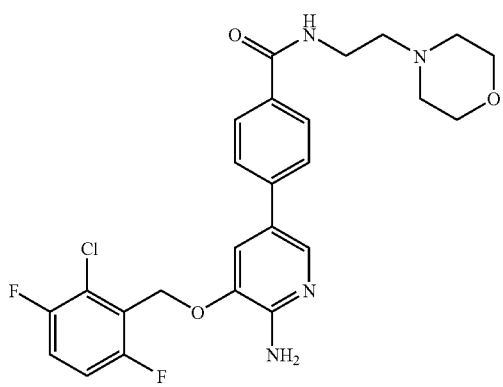 | 4-[6-Amino-5-(2-chloro-3,6-difluoro-benzyloxy)-pyridin-3-yl]-N-(2-morpholin-4-yl-ethyl)-benzamide | 0.165 |
| I-224 | 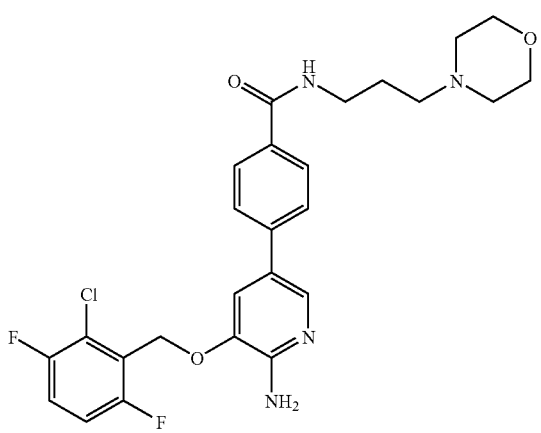 | 4-[6-Amino-5-(2-chloro-3,6-difluoro-benzyloxy)-pyridin-3-yl]-N-(3-morpholin-4-yl-propyl)-benzamide | 0.28 |
| I-225 | 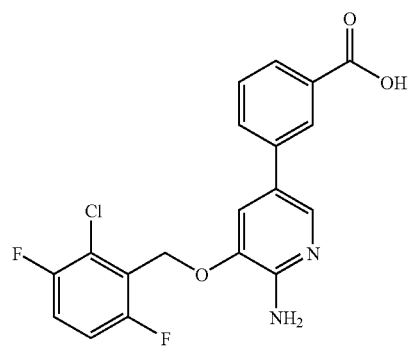 | 3-[6-Amino-5-(2-chloro-3,6-difluoro-benzyloxy)-pyridin-3-yl]-benzoic acid | 3.7/0.6 |
| I-226 | 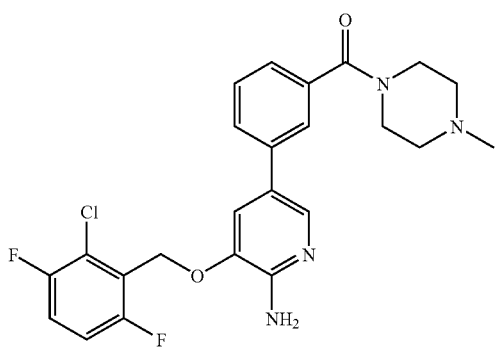 | {3-[6-Amino-5-(2-chloro-3,6-difluoro-benzyloxy)-pyridin-3-yl]-phenyl}-(4-methyl-piperazin-1-yl)-methanone | 0.068 |

TABLE 2-continued

| | | | |
|---|---|---|---|
| I-227 | | {3-[6-Amino-5-(2-chloro-3,6-difluoro-benzyloxy)-pyridin-3-yl]-phenyl}-(4-pyrrolidin-1-yl-pipendin-1-yl)-methanone | 0.05 |
| I-228 | | {3-[6-Amino-5-(2-chloro-3,6-difluoro-benzyloxy)-pyridin-3-yl]-phenyl)-(4-amino-pipendin-1-yl)-methanone | 0.23 |
| I-229 | | {3-[6-Amino-5-(2-chloro-3,6-difluoro-benzyloxy)-pyridin-3-yl]-phenyl}-(3,5-dimethyl-piperazin-1-yl)-methanone | 0.066/0.18 |
| I-230 | | {3-[6-Amino-5-(2-chloro-3,6-difluoro-benzyloxy)-pyridin-3-yl]-phenyl}-[(2S)-2-pyrrolidin-1-ylmethyl-pyrrolidin-1-yl]-methanone | 0.19 |

| | | | |
|---|---|---|---|
| I-231 | 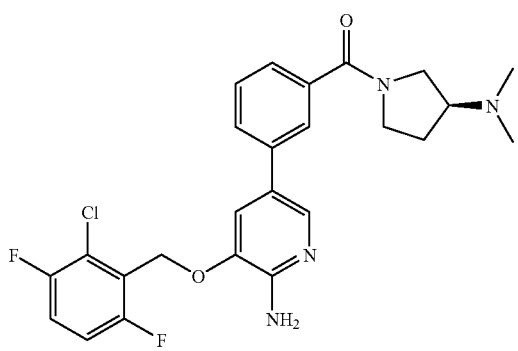 | {3-[6-Amino-5-(2-chloro-3,6-difluoro-benzyloxy)-pyridin-3-yl]-phenyl}-[(3S)-3-dimethylamino-pyrrolidin-1-yl]-methanone | 0.128 |
| I-232 | 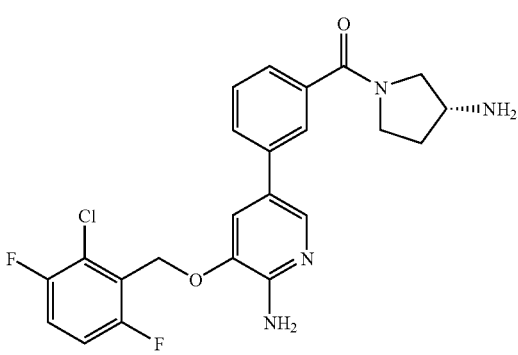 | {3-[6-Amino-5-(2-chloro-3,6-difluoro-benzyloxy)-pyridin-3-yl]-phenyl}-[(3R)-3-amino-pyrrolidin-1-yl]-methanone | 0.12 |
| I-233 | 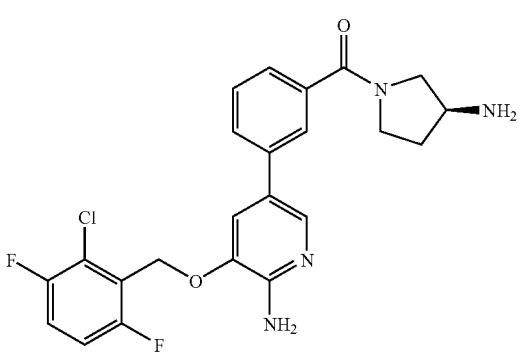 | {3-[6-Amino-5-(2-chloro-3,6-difluoro-benzyloxy)-pyridin-3-yl]-phenyl}-[(3S)-amino-pyrrolidin-1-yl]-methanone | 0.12 |
| I-234 | 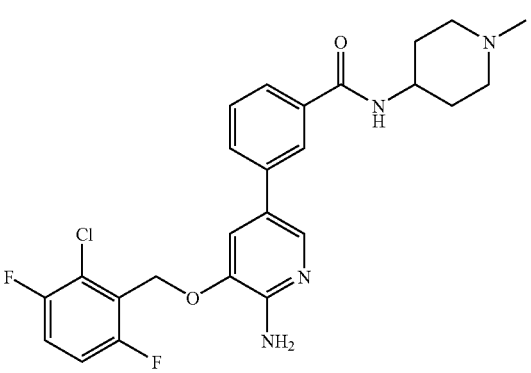 | 3-[6-Amino-5-(2-chloro-3,6-dtfluoro-benzyloxy)-pyridin-3-yl]-N-(1-methyl-pipendin-4-yl)-benzamide | 0.23 |

TABLE 2-continued
| | | | |
|---|---|---|---|
| I-235 | 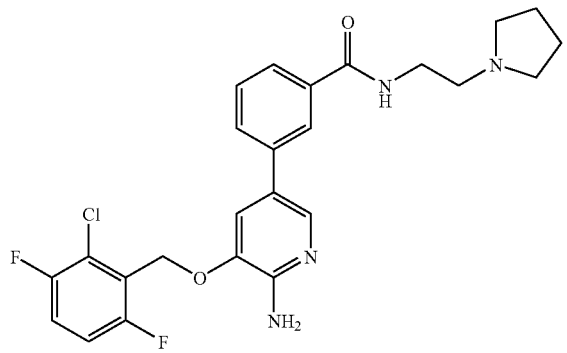 | 3-[6-Amino-5-(2-chloro-3,6-difluoro-benzyloxy)-pyridin-3-yl]-N-(2-pyrrolidin-1-yl-ethyl)-benzamide | 0.26 |
| I-236 | 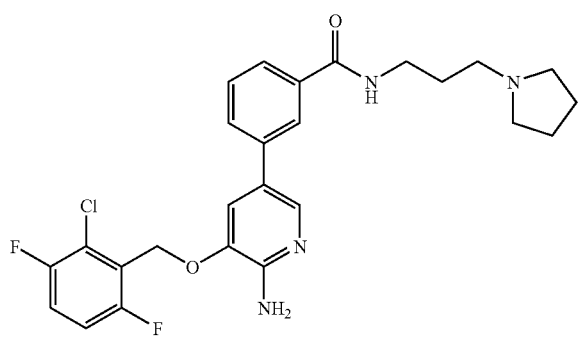 | 3-[6-Amino-5-(2-chloro-3,6-difluoro-benzyloxy)-pyridin-3-yl]-N-(3-pyrrolidin-1-yl-propyl)-benzamide | 0.28 |
| I-237 | 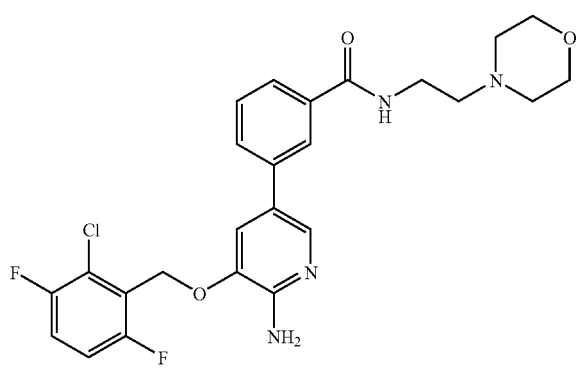 | 3-[6-Amino-5-(2-chloro-3,6-difluoro-benzyloxy)-pyridin-3-yl]N-(2-morpholin-4-yl-ethyl)-benzamide | 0.35 |
| I-238 | 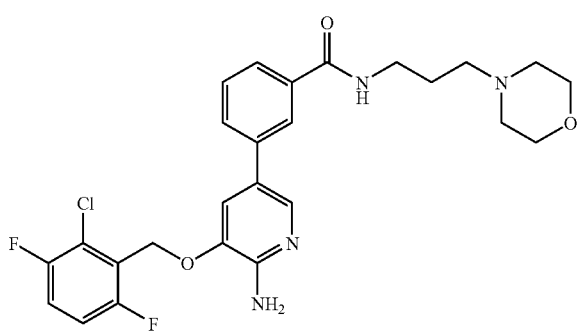 | 3-[6-Amino-5-(2-chloro-3,6-difluoro-benzyloxy)-pyridin-3-yl]-N-(3-morpholin-4-yl-propyl)-benzamide | 0.35 |

TABLE 2-continued
| I-240 | | 3-(2-Chloro-3,6-difluoro-benzyloxy)-5-[4-(1,1-dioxo-1λ⁶-isothiazolidin-2-yl)-phenyl]-pyridin-2-ylamine | 0.1 |
I-239
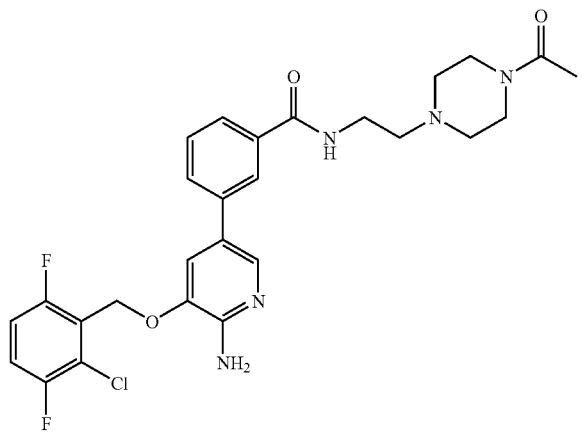
N-[2-(4-Acetyl-piperazin-1-yl)-ethyl]-3-[6-amino-5-(2-chloro-3,6-difluoro-benzyloxy)-pyridin-3-yl]-benzamide
0.1
I-240
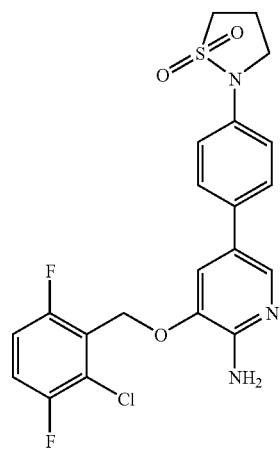
3-(2-Chloro-3,6-difluoro-benzyloxy)-5-[4-(1,1-dioxo-1λ⁶-isothiazolidin-2-yl)-phenyl]-pyridin-2-ylamine
0.1
I-241
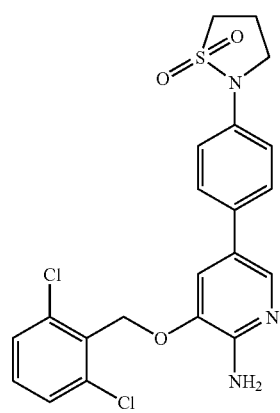
3-(2,6-Dichloro-benzyloxy)-5-[4-(1,1-dioxo-1λ⁶-isothiazolidin-2-yl)-phenyl]-pyridin-2-ylamine
0.067

TABLE 2-continued
| | | | |
|---|---|---|---|
| I-242 | 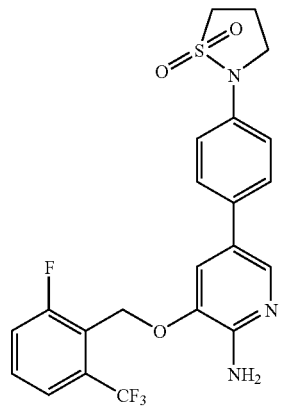 | 5-[4-(1,1-Dioxo-1λ⁶-isothiazolidin-2-yl)-phenyl]-3-(2-fluoro-8-trifluoromethyl-benzyloxy)-pyridin-2-ylamine | 0.14 |
| I-243 | 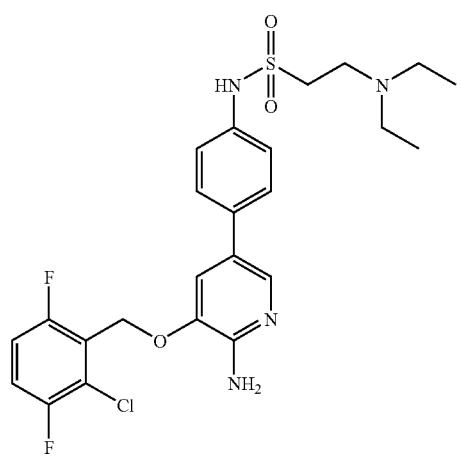 | 2-Diethylamino-ethanesulfonic acid {4-[6-amino-5-(2-chloro-3,6-difluoro-benzyloxy)-pyridin-3-yl]phenyl}-amide | 0.043 |
| I-244 | 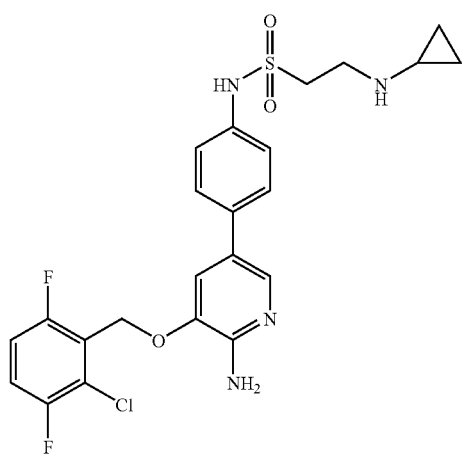 | 2-Cyclopropylamino-ethanesulfonic acid {4-[6-amino-5-(2-chloro-3,6-difluoro-benzyloxy)-pyridin-3-yl]-phenyl}-amide | 0.081 |

TABLE 2-continued
| | | | |
|---|---|---|---|
| I-245 | 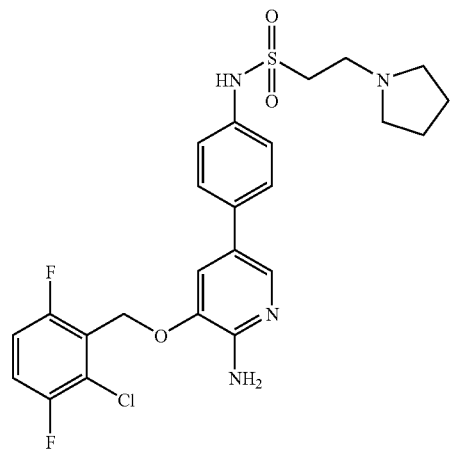 | 2-Pyrrolidin-1-yl-ethanesulfonic acid {4-[6-amino-5-(2-chloro-3,6-difluoro-benzyloxy)-pyridin-3-yl]-phenyl}-amide | 0.082 |
| I-246 | 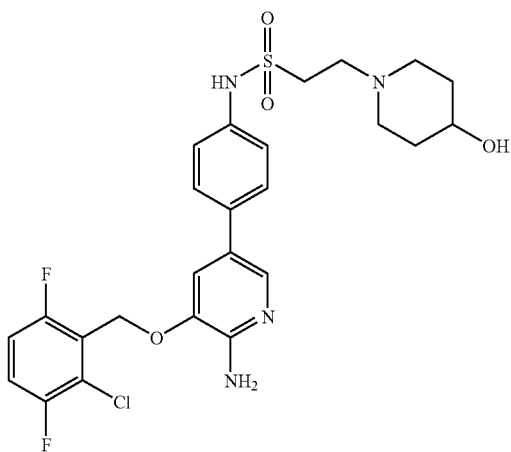 | 2-(4-Hydroxy-pipendin-1-yl)-ethanesulfonic acid {4-[6-amino-5-(2-chloro-3,6-difluoro-benzyloxy)-pyridin-3-yl]-phenyl}-amide | 0.135 |
| I-247 | 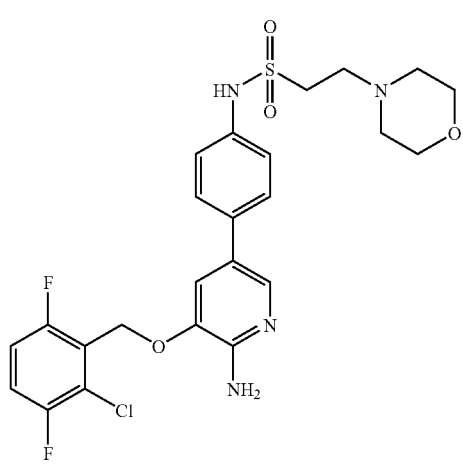 | 2-Morpholin-4-yl-ethanesulfonic acid {4-[6-amino-5-(2-chloro-3,6-difluoro-benzyloxy)-pyridin-3-yl]phenyl}-amide | 0.31 |

TABLE 2-continued
| | | | |
|---|---|---|---|
| I-248 | 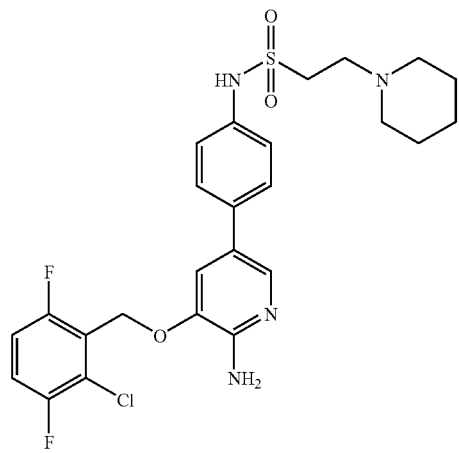 | 2-Piperidin-1-yl-ethanesulfonic acid {4-[6-amino-5-(2-chloro-3,6-difluoro-benzyloxy)-pyridin-3-yl]phenyl}-amide | 0.114 |
| I-249 | 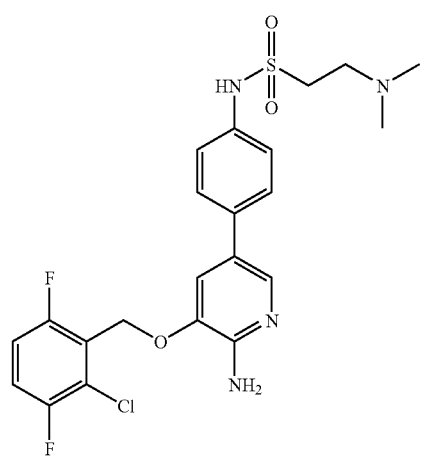 | 2-Dimethylamino-ethanesulfonic acid {4-[6-amino-5-(2-chloro-3,6-difluoro-benzyloxy)-pyridin-3-yl]-phenyl)-amide | 0.098 |
| I-250 | 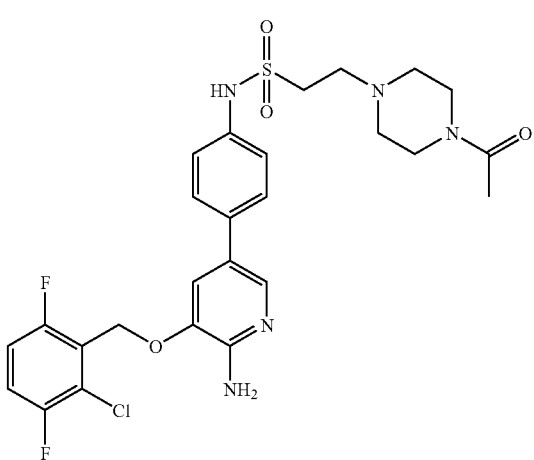 | 2-(4-Acetyl-piperazin-1-yl)-ethanesulfonic acid {4-[6-amino-5-(2-chloro-3,6-difluoro-benzyloxy)-pyridin-3-yl]-phenyl}-amide | 0.42 |

TABLE 2-continued
| I-251 | 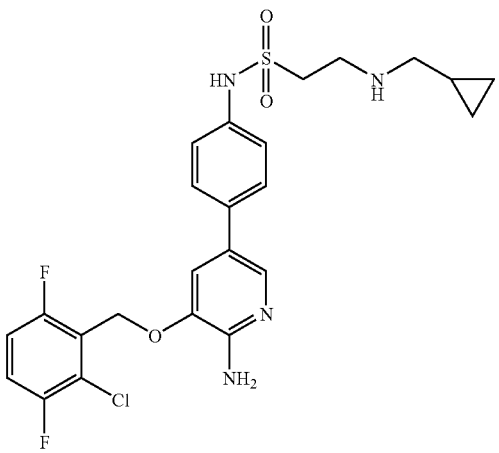 | 2-(Cyclopropylmethyl-amino)-ethanesulfonic acid {4-[6-amino-5-(2-chlaro-3,6-difluoro-benzyloxyl)-pyridin-3-yl)-phenyl)-amide | 0.075 |
| --- | --- | --- | --- |
| I-252 | 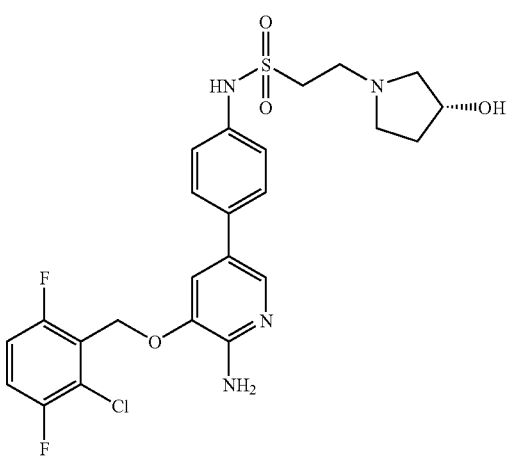 | 2-[(3R)-3-Hydroxy-pyrrolidin-1-yl]-ethanesulfonic acid {4-[6-amino-5-(2-chloro-3,6-difluoro-benzyloxy)-pyridin-3-yl]-phenyl}-amide | 0.125 |
| I-253 | 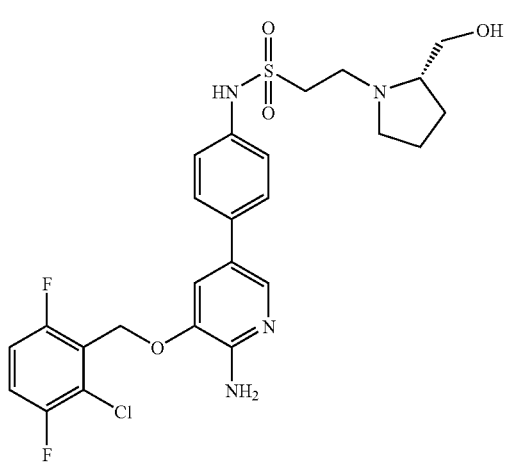 | 2-[(2S)-2-Hydroxymethyl-pyrrolidin-1-yl]-ethanesulfonic acid {4-[6-amino-5-(2-chloro-3,6-difluoro-benzyloxy)-pyridin-3-yl]-phenyl)-amide | 0.097 |

TABLE 2-continued

| I-254 | 2-[4-(2-Hydroxy-acetyl)-piperazin-1-yl]-ethanesulfonic acid {4-[6-amino-5-(2-chloro-3,6-difluoro-benzyloxy)-pyridin-3-yl]-phenyl}-amide | 0.18 |
| I-255 | 2-(4-Acety-piperazin-1-yl)-ethanesulfonic acid {3[6-amino-5-(2-chloro-3,6-difluoro-benzyloxyl)-pyridin-3-yl]-phenyl}-amide | 0.68 |
| I-256 | 2-Pyrrolidin-1-yl-ethanesulfonic acid {3-[6-amino-5-(2-chloro-3,6-difluoro-benzyloxy)-pyridin-3-yl]-phenyl}-amide | 0.23 |
| I-257 | 2-Morpholin-4-yl-ethanesulfonic acid {3-[6-amino-5-(2-chloro-3,6-difluoro-benzloxy)-pyridin-3-yl]-phenyl}-amide | 1.64 |

TABLE 2-continued

| I-258 | 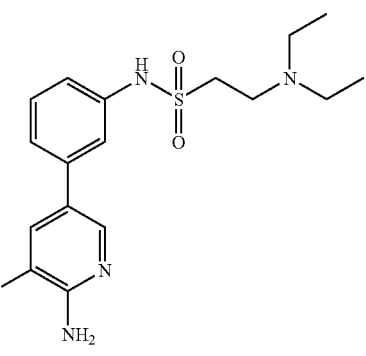 | 2-Diethylamino-ethanesulfonic acid {3-[6-amino-5-(2-chloro-3,6-difluoro-benzyloxy)-pyridin-3-yl]-phenyl}-amide | 1.67 |
| I-259 | 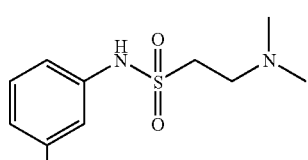 | 2-Dimethylamino-ethanesulfonic acid {3-[6-amino-5-(2-chloro-3,6-difluoro-benzyloxy)-pyridin-3-yl]-phenyl}-amide | 1.5 |
| I-260 | 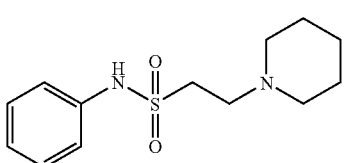 | 2-Pipendin-1-yl-ethanesulfonic acid {3-[6-amino-5-(2-chloro-3,6-difluoro-benzyloxy)-pyridin-3-yl]-phenyl}-amide | 1.63 |
| I-261 | 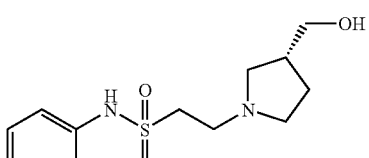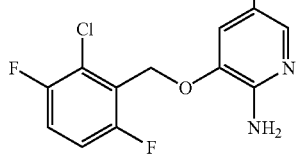 | 2-[(3R)-3-Hydroxymethyl-pyrrolldin-1-yl]-ethanesulfonic acid {3-[6-amino-5-(2-chloro-3,6-difluoro-benzyloxy)-pyridin-3-yl]-phenyl}-amide | 1.7 |

TABLE 2-continued

| I-262 | 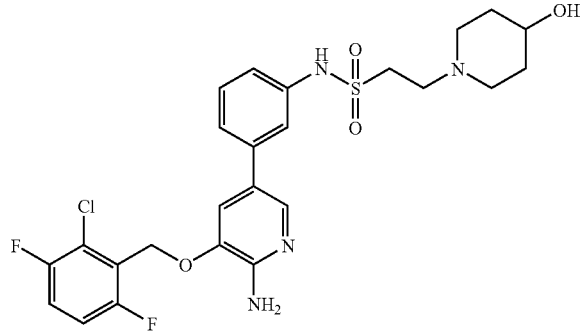 | 2-(4-Hydroxy-pipendin-1-yl)-ethanesulfonic acid {3-[6-amino-5-(2-chloro-3,6-difluoro-benzyloxy)-pyridin-3-yl]-phenyl}-amide | 1.5 |
| --- | --- | --- | --- |
| I-263 | 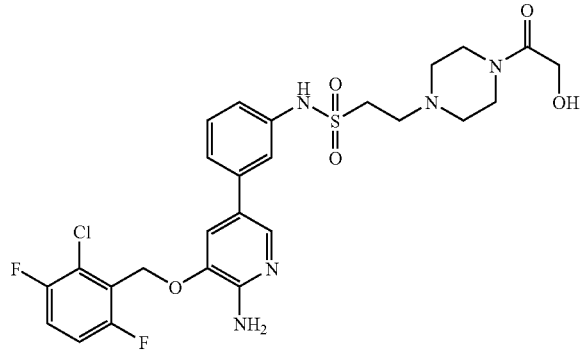 | 2-[4-(2-Hydroxy-acetyl)-piperazin-1-yl]ethanesulfonic acid {3-[6-amino-5-(2-chloro-3,6-difluoro-benzyloxy)-pyridin-3-yl]-phenyl)-amide | 1.14 |
| I-264 | 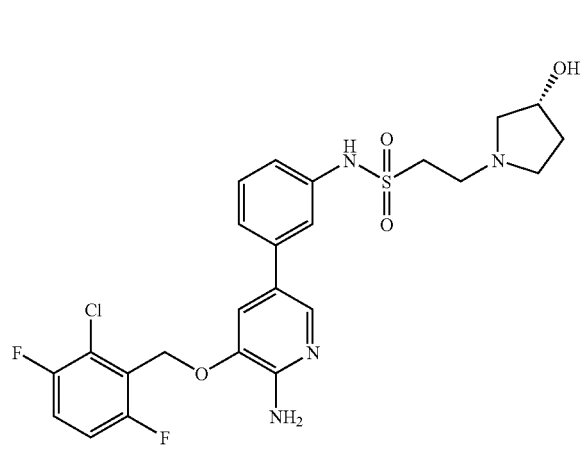 | 2-[(3R)-3-Hydroxy-pyrrolidin-1-yl]-ethanesulfonic acid {3-[6-amino-5-(2-chloro-3,6-difluoro-benzyloxy)-pyridin-3-yl]-phenyl}-amide | 1.097 |
| I-265 | 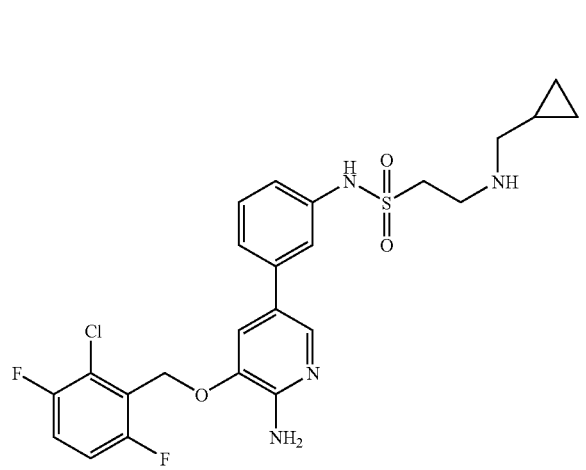 | 2-(Cyclopropylmethyl-amino)-ethanesulfonic acid {3-[6-amino-5-(2-chloro-3,6-difluoro-benzyloxy)-pyridin-3-yl]-phenyl}-amide | 1 |

TABLE 2-continued

| | | | |
|---|---|---|---|
| I-266 | 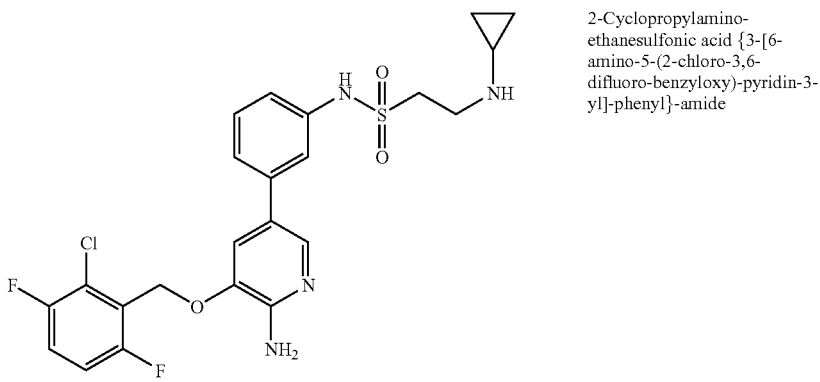 | 2-Cyclopropylamino-ethanesulfonic acid {3-[6-amino-5-(2-chloro-3,6-difluoro-benzyloxy)-pyridin-3-yl]-phenyl}-amide | 0.9 |
| I-267 | 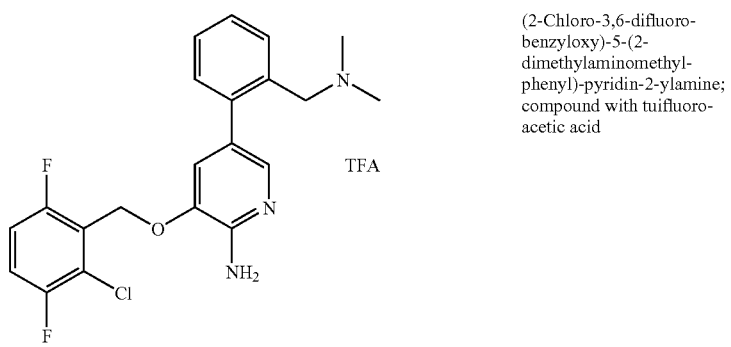 | (2-Chloro-3,6-difluoro-benzyloxy)-5-(2-dimethylaminomethyl-phenyl)-pyridin-2-ylamine; compound with trifluoro-acetic acid | |
| I-268 | 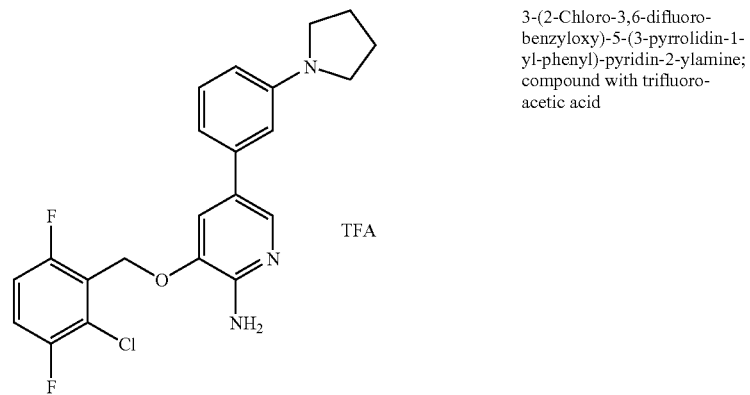 | 3-(2-Chloro-3,6-difluoro-benzyloxy)-5-(3-pyrrolidin-1-yl-phenyl)-pyridin-2-ylamine; compound with trifluoro-acetic acid | 4 |
| I-269 | 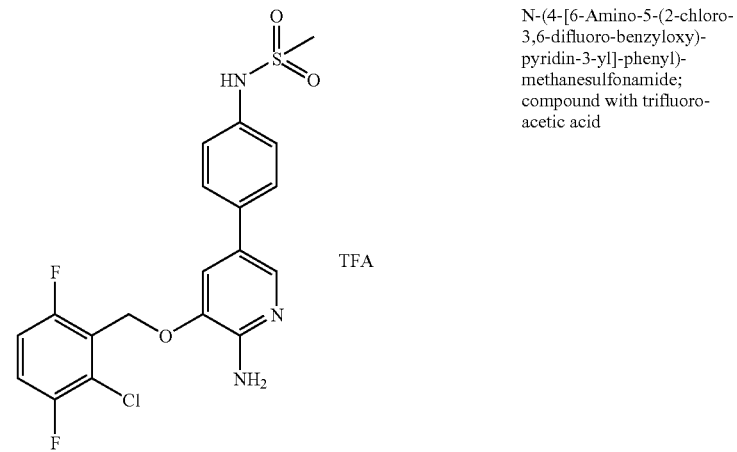 | N-(4-[6-Amino-5-(2-chloro-3,6-difluoro-benzyloxy)-pyridin-3-yl]-phenyl)-methanesulfonamide; compound with trifluoro-acetic acid | |

TABLE 2-continued
I-270
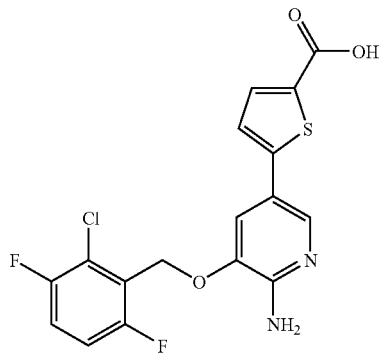
5-[6-Amino-5-(2-chloro-3,6-difluoro-benzyloxy)-pyridin-3-yl]-thiophene-2-carboxylic acid
I-271
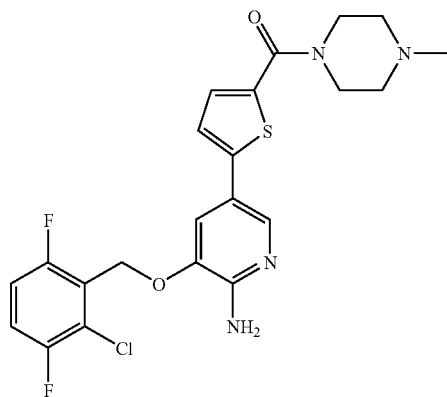
{5-[6-Amino-5-(2-chloro-3,6-difluoro-benzyloxy)-pyridin-3-yl]-thiophen-2-yl}-(4-methyl-piperazin-1-yl)-methanone
I-272
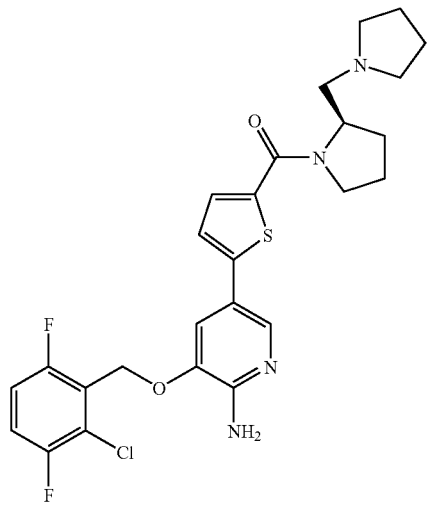
{5-[6-Amino-5-(2-chloro-3,6-difluoro-benzyloxy)-pyridin-3-yl]-thiophen-2-yl}-[(2R)-2-pyrrolidin-1-ylmethyl-pyrrolidin-1-yl]-methanone

| | | |
|---|---|---|
| I-273 | 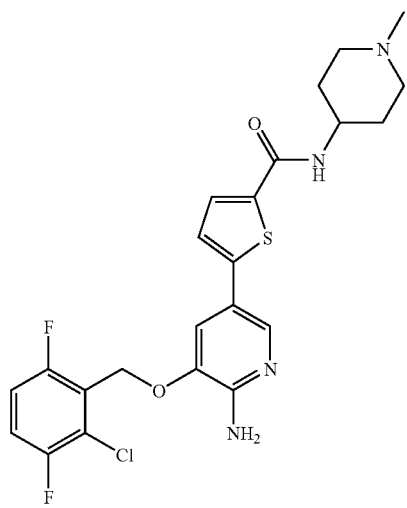 | 5-[6-Amino-5-(2-chloro-3,6-difluoro-benzyloxy)-pyridin-3-yl]-thiophene-2-carboxylic acid (1-methyl-piperidin-4-yl)-amide |
| I-274 | 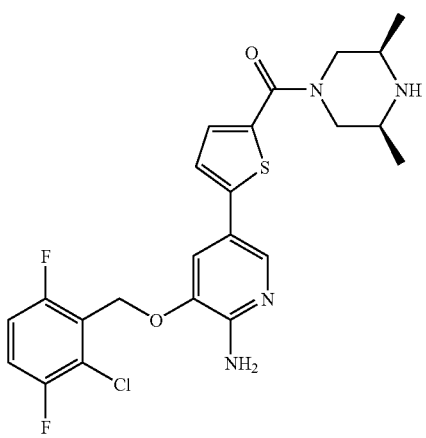 | {5-[6-Amino-5-(2-chloro-3,6-difluoro-benzyloxy)-pyridin-3-yl]-thiophen-2-yl}-(3,5-dimethyl-piperazin-1-yl)-methanone |
| I-275 | 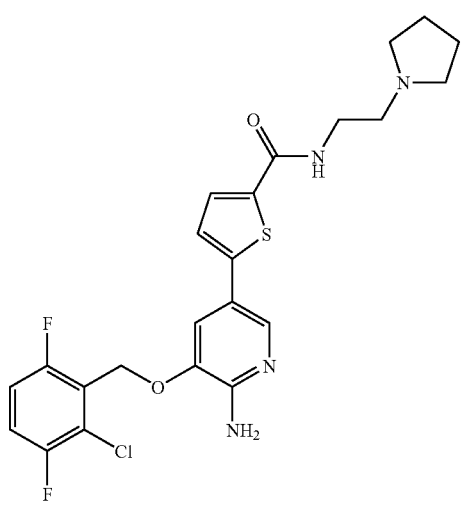 | 5-[6-Amino-5-(2-chloro-3,6-difluoro-benzyloxy)-pyridin-3-yl]-thiophene-2-carborylic acid (2-pyrrolidin-1-yl-ethyl)-amide |

| | |
|---|---|
| I-276 | {5-[6-Amino-5-(2-chloro-3,6-difluoro-benzyloxy)-pyridin-3-yl]-thiophen-2-yl}-(4-pyrrolidin-1-yl-piperidin-1-yl)-methanone |
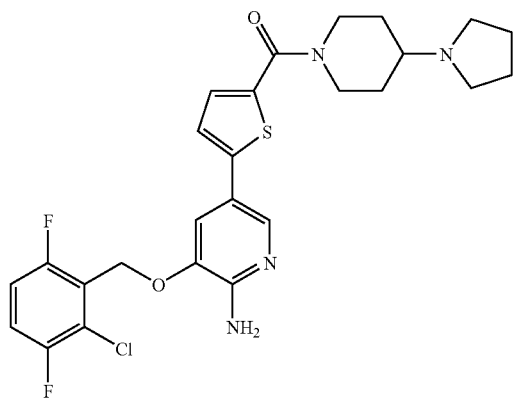
| | |
|---|---|
| I-277 | 4-[6-Amino-5-(3-fluoro-2-trifluoromethyl-benzyloxy)-pyridin-3-yl]benzoc acid |
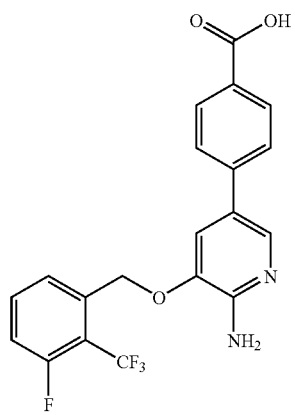
| | |
|---|---|
| I-278 | {4-[6-Amino-5-(3-fluoro-2-trifluoromethyl-benzyloxy)-pyridin-3-yl]-phenyl}-(4-pyrrolidin-1-yl-pipendin-1-yl)-methanone |
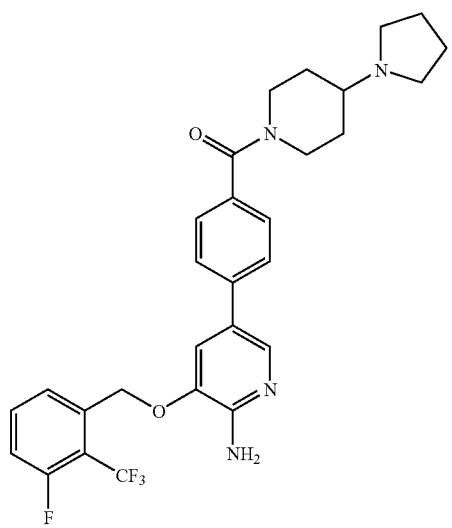

TABLE 2-continued
I-279
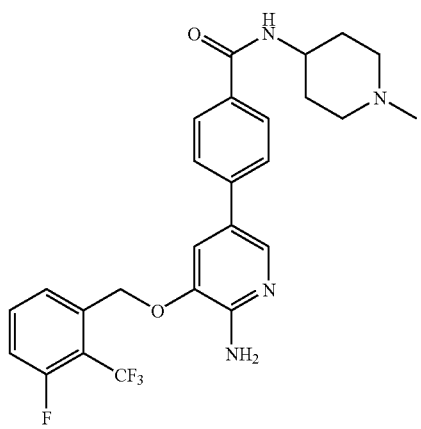
4-[6-Amino-5-(3-fluoro-2-trifluoromethyl-benzyloxy)-pyridin-3-yl]-N-(1-methyl-piperidin-4-yl)-benzamide
I-280
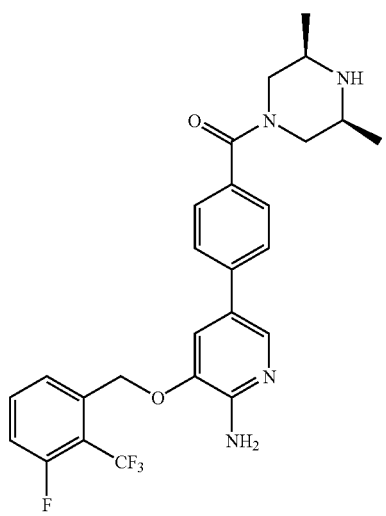
4-[6-Amino-5-(3-fluoro-2-trifluoromethyl-benzyloxy)-pyridin-3-yl]-phenyl}-(3,5-dimethyl-piperazin-1-yl-methanone
I-281
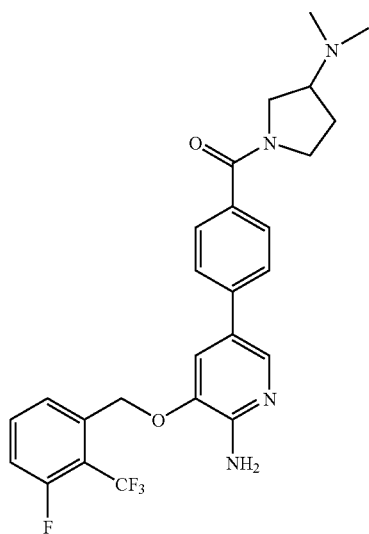
{4-[8-Amino-5-(3-fluoro-2-trifluoromethyl-benzyloxy)-pyridin-3-yl]-phenyl}-(3-dimethylamino-pyrrolidin-1-yl)-methanone

TABLE 2-continued
I-282
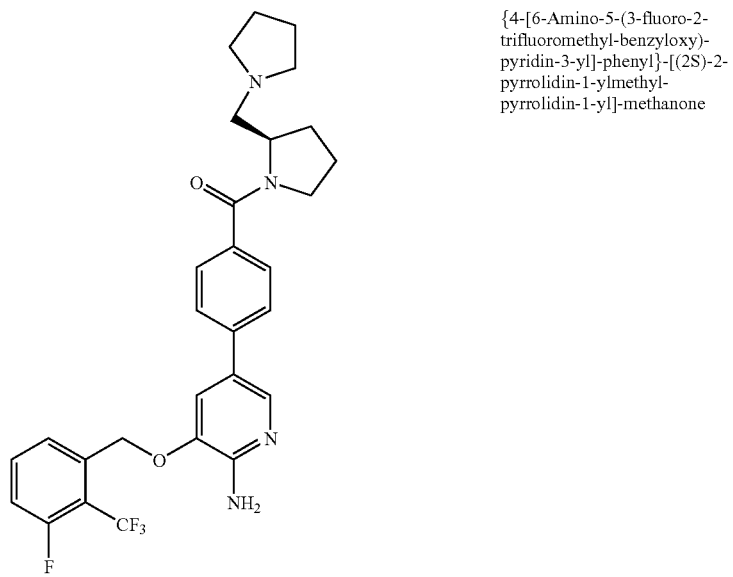
{4-[6-Amino-5-(3-fluoro-2-trifluoromethyl-benzyloxy)-pyridin-3-yl]-phenyl}-[(2S)-2-pyrrolidin-1-ylmethyl-pyrrolidin-1-yl]-methanone
I-283
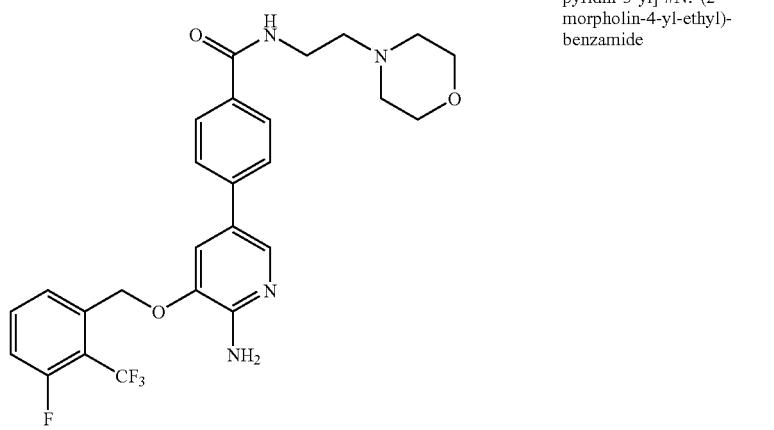
4-[6-Amino-5-(3-fluoro-2-trifluoromethyl-benzyloxy)-pyridin-3-yl]-#N!-(2-morpholin-4-yl-ethyl)-benzamide
I-284
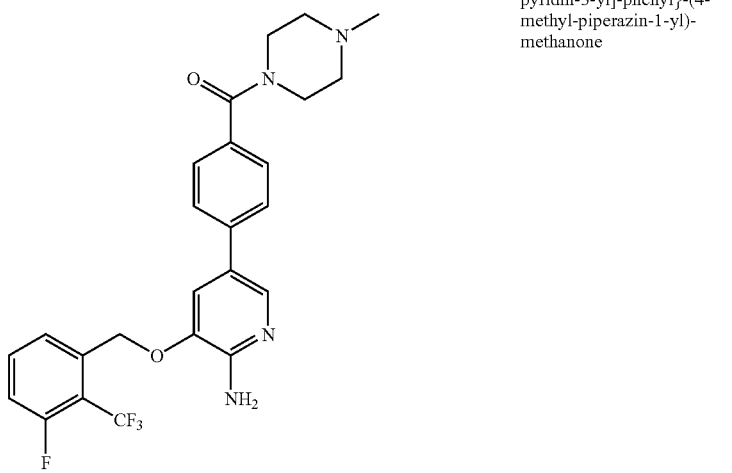
{4-[6-Amino-5-(3-fluoro-2-trifluoromethyl-benzyloxy)-pyridin-3-yl]-phenyl}-(4-methyl-piperazin-1-yl)-methanone

| | | | |
|---|---|---|---|
| I-285 | 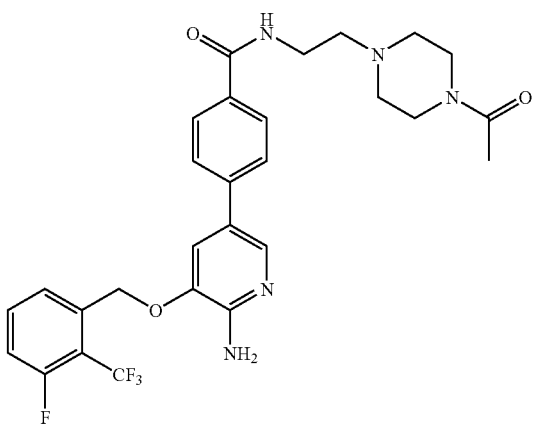 | N-[2-(4-Acetyl-piperazin-1-ethyl]-4-[6-amino-5-(3-fluoro-2-trifluoromethyl-benzyloxy)-pyridin-3-yl]-benzamide | |
| I-286 | 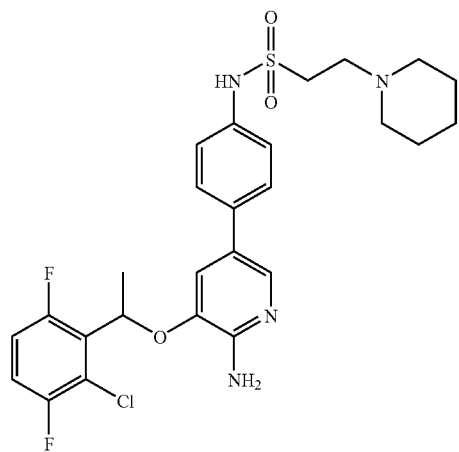 | 2-Pipendin-1-yl-ethanesulfonic acid (4-{6-amino-5-[1-(2-chloro-36-difluoro-phenyl)-ethoxy]-pyridin-3-yl}-phenyl)-amide | 0.18 |
| I-287 | 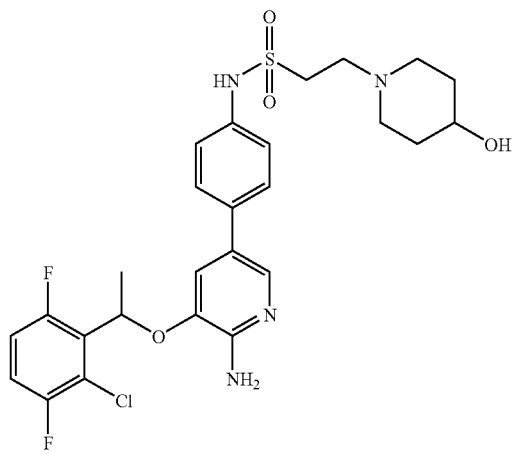 | 2-(4-Hydroxy-pipendin-1-yl)-ethanesulfonic acid (4-{6-amino-5-[1-(2-chloro-3,6-difluoro-phenyl)-ethoxy]-pyridin-3-yl}-phenyl)-amide | 0.14 |

TABLE 2-continued
| | | | |
|---|---|---|---|
| I-288 | 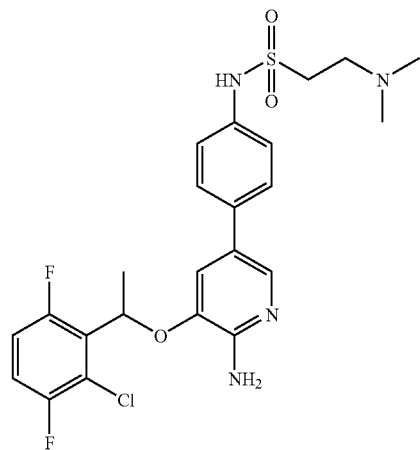 | 2-Dimethylamino-ethanesulfonic acid (4-{6-amino-5-[1-(2-chloro-3,6-difluoro-phenyl)-ethoxy]-pyridin-3-yl}-phenyl)-amide | 0.15 |
| I-289 | 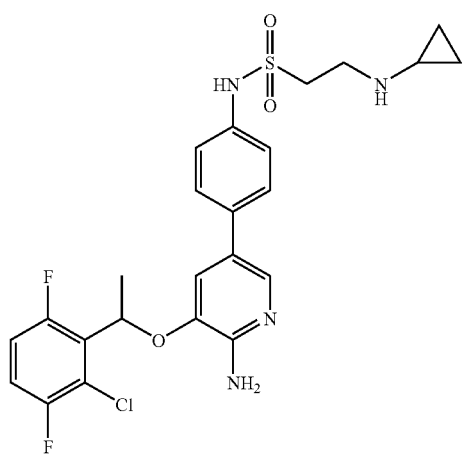 | 2-Cyclopropylamino-ethanesulfonic acid (4-{6-amino-5-[1-(2-chloro-3,6-difluoro-phenyl)-ethoxy]-pyridin-3-yl}-phenyl)-amide | 0.16 |
| I-290 | 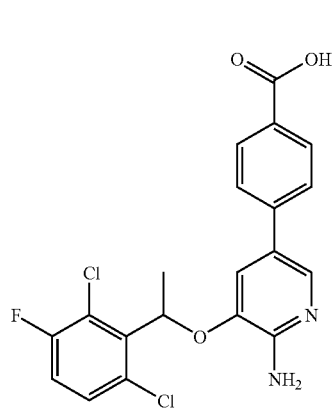 | 4-{6-Amino-5-[1-(2,6-dichloro-3-fluoro-phenyl)-ethoxy]-pyridin-3-yl}-benzoic acid | |

TABLE 2-continued
| | | | |
|---|---|---|---|
| I-291 | 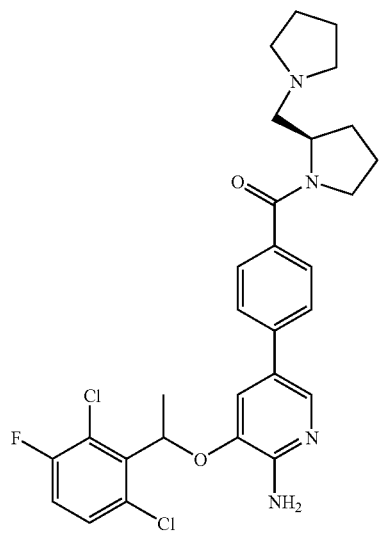 | (4-{6-Amino-5-[1-2,6-dichloro-3-fluoro-phenyl)-ethoxy]-pyridin-3-yl}-phenyl)-[(2R)-2-pyrrolidin-1-ylmethyl-pyrrolidin-1-yl)-methanone | 0.063 |
| I-292 | 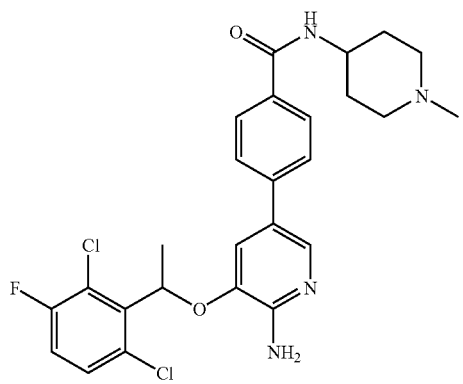 | 4-{6-Amino-5-[1-(2,6-dichloro-3-fluoro-phenyl)-ethoxy]-pyridin-3-yl}-N-(1-methyl-pipendin-4-yl)-benzamide | 0.069 |
| I-293 | 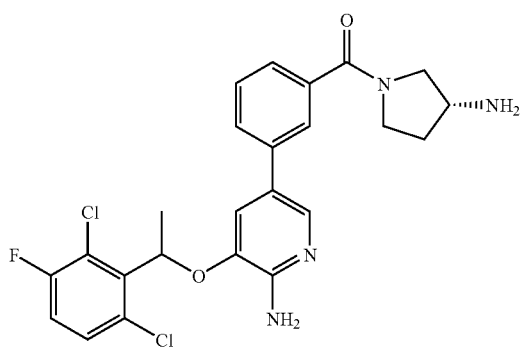 | (3-{6-Amino-5-[1-(2,6-dichloro-3-fluoro-phenyl)-ethoxy]-pyridin-3-yl}-phenyl)-[(3R)-3-amino-pyrrolidin-1-yl)]-methanone | 0.051 |

TABLE 2-continued
| | | | |
|---|---|---|---|
| I-294 | 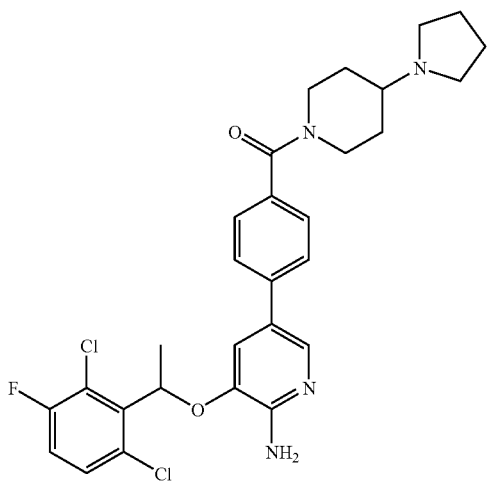 | (4-{6-Amino-5-[1-(2,6-dichloro-3-fluoro-phenyl)-ethoxy]-pyridin-3-yl}-phenyl)-(4-pyrrolidin-1-yl-piperidin-1-yl)-methanone | 0.062 |
| I-295 | 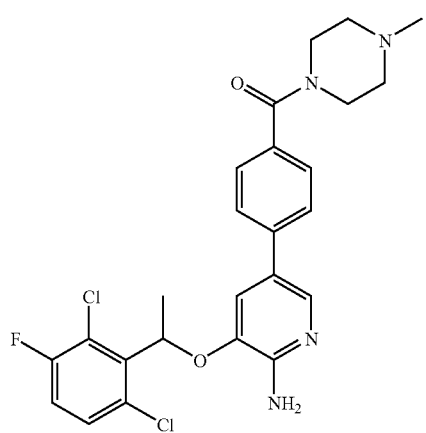 | (4-{6-Amino-5-[1-(2,6-dichloro-3-fluoro-phenyl)-ethoxy]-pyridin-3-yl}-phenyl)-(4-methyl-piperazin-1-yl)-methanone | 0.079 |
| I-296 | 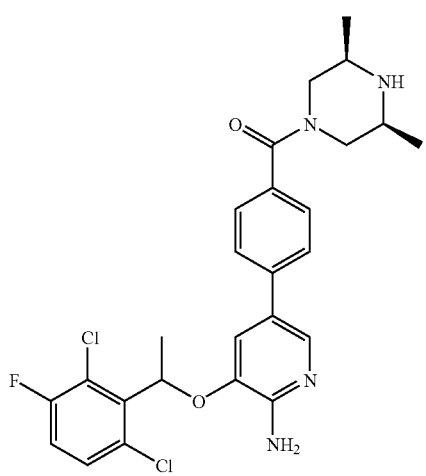 | (4-{6-Amino-5-(1-(2,6-dichloro-3-fluoro-phenyl)-ethoxy]-pyridin-3-yl}-phenyl)-(3,5-dimethyl-piperazin-1-yl)-methanone | 0.054 |

| | | | |
|---|---|---|---|
| I-297 | | 2-Cyclopropylamino-ethanesulfonic acid (4-{6-amino-5-[1-(2,6-dichloro-3-fluoro-phenyl)-ethoxy]-pyridin-3-yl}-phenyl)-amide | 0.164 |
| I-298 | | 2-Dimethylamino-ethanesulfonic acid (4-{6-amino-5-[1-(2,6-dichloro-3-fluoro-phenyl)-ethoxy]-pyridin-3-yl}-phenyl)-amide | 0.059 |
| I-299 | | 2-[(3R)-3-Hydroxy-pyrrolidin-1-yl)]-ethanesulfonic acid (4-{6-amino-5-(1-(2,6-dichloro-3-fluoro-phenyl)-ethoxy]-pyridin-3-yl}-phenyl)-amide | 0.062 |
| I-300 | | N-[2-(4-Acetyl-piperazin-1-yl)-ethyl]-4-{6-amino-5-[1-(2,6-dichloro-3-fluoro-phenyl)-ethoxy]-pyridin-3-yl}-benzamide | 0.059 |

TABLE 2-continued
| | | | |
|---|---|---|---|
| I-301 | 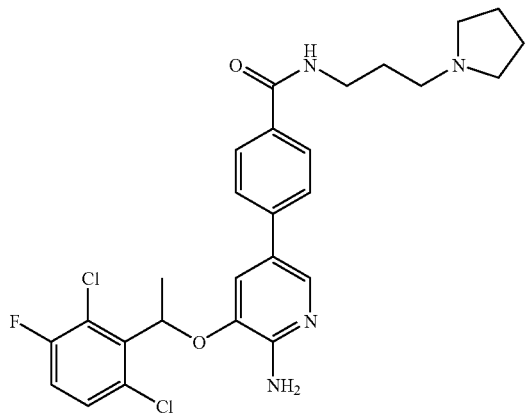 | 4-{6-Amino-5-[1-(2,6-dichloro-3-fluoro-phenyl)-ethoxy]-pyridin-3-yl}-N-(3-pyrrolidin-1-yl-propyl)-benzamide | 0.064 |
| I-302 | 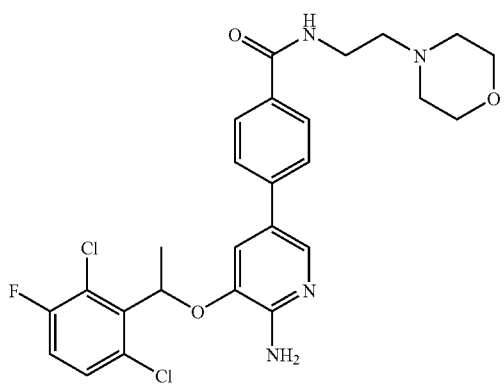 | 4-{6-Amino-5-(1-(2,6-dichloro-3-fluoro-phenyl)-ethoxy]-pyridin-3-yl}-N-(2-morpholin-4-yl-ethyl)-benzamide | 0.071 |
| I-303 | 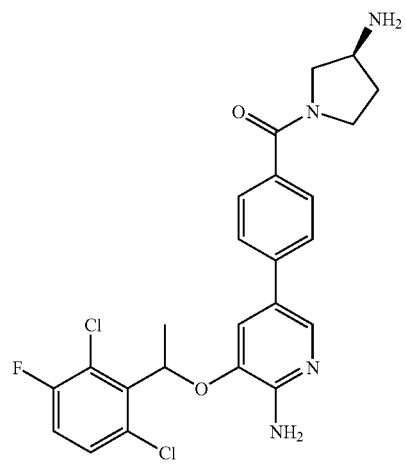 | (4-{6-Amino-5-[1-(2,6-dichloro-3-fluoro-phenyl)-ethoxy]-pyridin-3-yl}-phenyl)-((S)-3-amino-Pyrrolidin-1-yl)-methanone | 0.059 |

TABLE 2-continued
| I-304 | 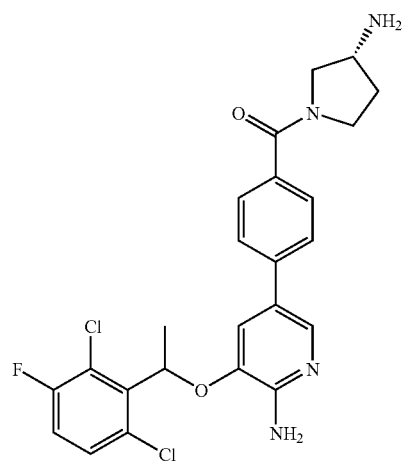 | (4-{6-Amino-5-[1-(2,6-dichloro-3-fluoro-phenyl)-ethoxy]-pyridin-3-yl}-phenyl)-((R)-3-amino-pyrrolidin-1-yl)-methanone | 0.072 |
| I-305 | 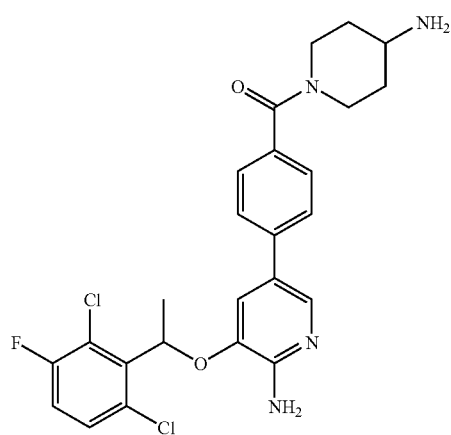 | (4-{6-Amino-5-[1-(2,6-dichloro-3-fluoro-phenyl)-ethoxy]-pyridin-3-yl}-phenyl)-(4-amino-pipendin-1-yl)-methanone | 0.018 |
| I-306 | 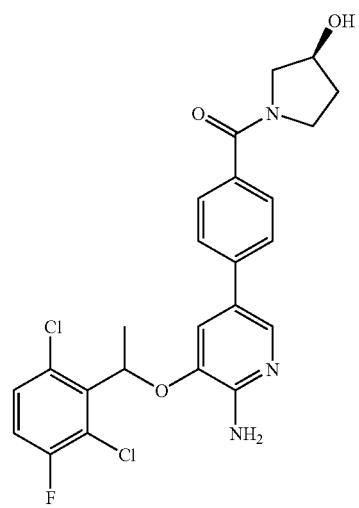 | (4-{6-Amino-5-[1-(2,6-dichloro-3-fluoro-phenyl)-ethoxy]-pyridin-3-yl}-phenyl)-((S)-3-hydroxy-pyrrolidin-1-yl)-methanone | 0.024 |

TABLE 2-continued
| | | | |
|---|---|---|---|
| I-307 | 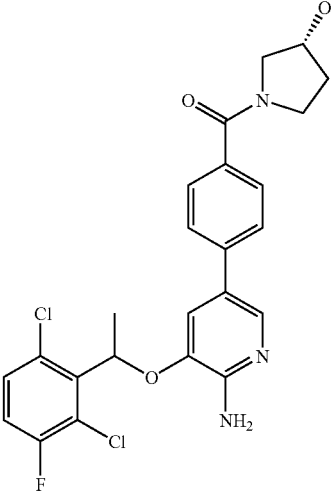 | (4-{6-Amino-5-[1-(2,6-dichloro-3-fluoro-phenyl)-ethoxy]-pyridin-3-yl}-phenyl)-((R)-3-hydroxy-pyrrolidin-1-yl)-methanone | 0.022 |
| I-308 | 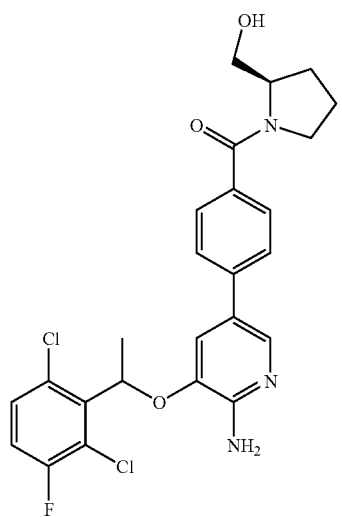 | (4-{6-Amino-5-[1-(2,6-dichloro-3-fluoro-phenyl)-ethoxy]-pyridin-3-yl}-phenyl)-((R)-2-hydroxymethyl-pyrrolidin-1-yl)-methanone | 0.033 |
| I-309 | 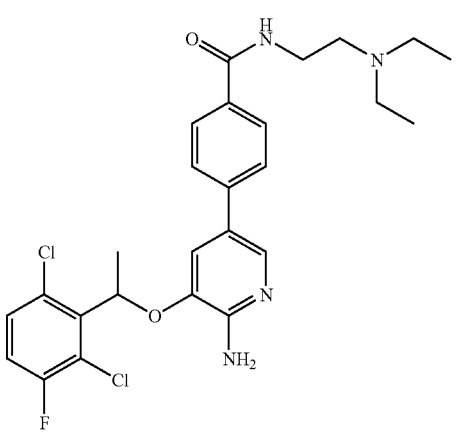 | 4-{6-Amino-5-[1-(2,6-dichloro-3-fluoro-phenyl)-ethoxy]-pyridin-3-yl}-N-(2-diethylamino-ethyl)-benzamide | 0.04 |

TABLE 2-continued

| | | | |
|---|---|---|---|
| I-310 | | 4-{6-Amino-5-[1-(2,6-dichloro-3-fluoro-phenyl)-ethoxy]-pyridin-3-yl}-N-(2-pyrrolidin-1-yl-ethyl)-benzamide | 0.12 |
| I-311 | | 3-{6-Amino-5-[1-(2,6-dichloro-3-fluoro-phenyl)-ehoxy]-pyridin-3-yl}-benzoic acid | |
| I-312 | | (3-{6-Amino-5-[1-(2,6-dichloro-3-fluoro-phenyl)-ethoxy]-pyridin-3-yl}-phenyl)-(4-methyl-piperazin-1-yl)-methanone | 0.062 |
| I-313 | | 3-{6-Amino-5-(1-(2,6-dichloro-3-fluoro-phenyl)-ethoxy]-pyridin-3-yl}-N-(1-methyl-piperidin-4-yl)-benzamide | 0.069 |

| | | | |
|---|---|---|---|
| I-314 | 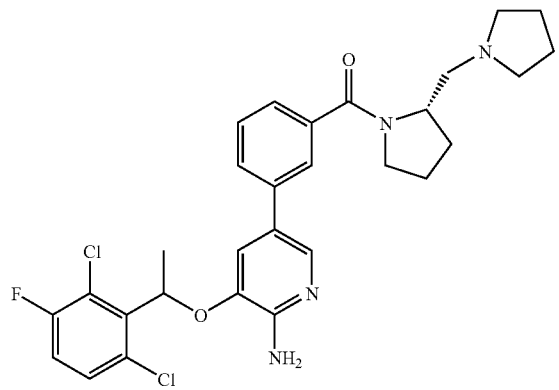 | (3-{6-Amino-5-[1-(2,6-dichloro-3-fluoro-phenyl)-ethoxy]-pyridin-3-yl}-phenyl)-((S)-2-pyrrolidin-1-ylmethyl-pyrrolidin-1-yl)-methanone | 0.06 |
| I-315 | 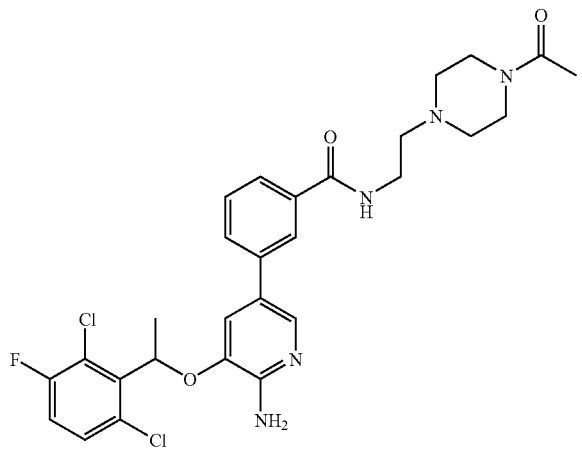 | N-[2-(4-Acetyl-piperazin-1-yl)-ethyl]-3-{6-amino-5-[1-(2,6-dichloro-3-fluoro-phenyl)-ethoxy]-pyridin-3-yl}-benzamide | 0.069 |
| I-316 | 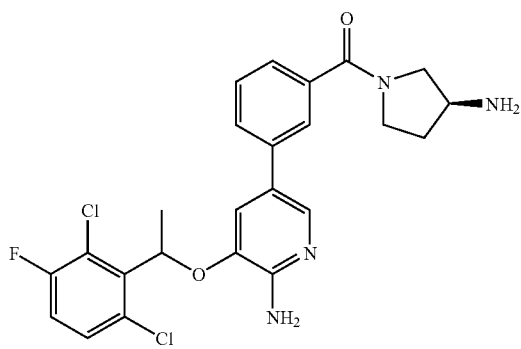 | (3-{6-Amino-5-[1-(2,6-dichloro-3-fluoro-phenyl)-ethoxy)-pyridin-3-yl}-phenyl)-((S)-3-amino-pyrrolidin-1-yl)-methanone | 0.048 |

TABLE 2-continued
| | | | |
|---|---|---|---|
| I-317 | | 3-{6-Amino-5-[1-(2,6-dichloro-3-fluoro-phenyl)-ethoxy]-pyridin-3-yl}-N-3-morpholin-4-yl-propyl)-benzamide | 0.059 |
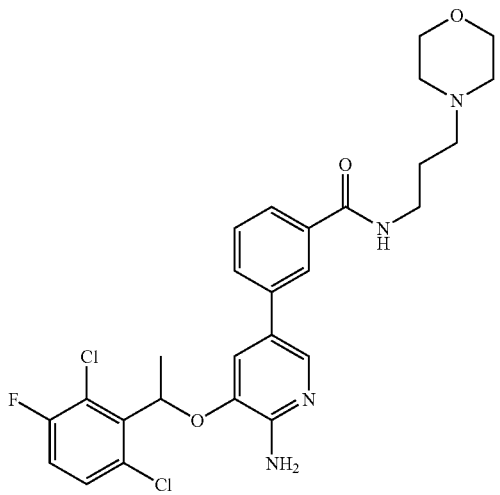
| | | | |
|---|---|---|---|
| I-318 | | (3-{6-Amino-5-[1-(2,6-dichloro-3-fluoro-phenyl)-ethoxy]-pyridin-3-yl}-phenyl)-((R)-2-pyrrolidin-1-ylmethyl-pyrrolidin-1-yl)-methanone | 0.13 |
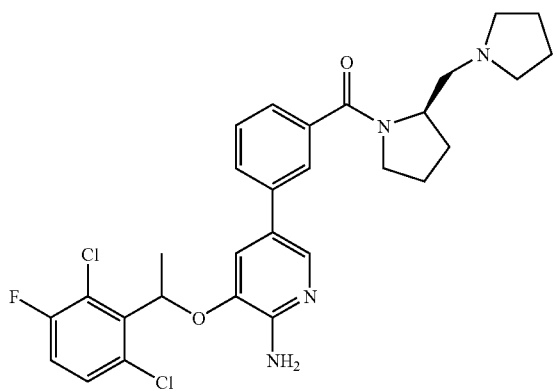
| | | | |
|---|---|---|---|
| I-319 | | 3-{6-Amino-5-[1-(2,6-dichloro-3-fluoro-phenyl)-ethoxy]-pyridin-3-yl}-N-(2-pyrrolidin-1-yl-ethyl)-benzamide | 0.1 |
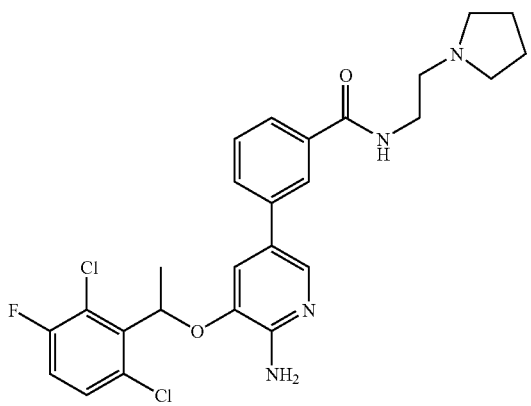

| | | | |
|---|---|---|---|
| I-320 | | 3-{6-Amino-5-[1-(2,6-dichloro-3-fluoro-phenyl)-ethoxy]-pyridin-3-yl}-N-(3-pyrrolidin-1-yl-propyl)-benzamide | 0.13 |
| I-321 | | 3-{6-Amino-5-[1-(2,6-dichloro-3-fluoro-phenyl)-ethoxy]-pyridin-3-yl}-N-(2-morpholin-4-yl-ethyl)-benzamide | 0.18 |
| I-322 | | (3-{6-Amino-5-[1-(2,6-dichloro-3-fluoro-phenyl)-ethoxy]-pyridin-3-yl}-phenyl)-(4-pyrrolidin-1-yl-pipendin-1-yl)-methanone | 0.071 |
| I-323 | | 2-Diethylamino-ethanesulfonic acid (4-{6-amino-5-[1-(2,6-dichloro-3-fluoro-phenyl)-ethoxy]-pyridin-3-yl}-phenyl)-amide | 0.08 |

TABLE 2-continued
I-324
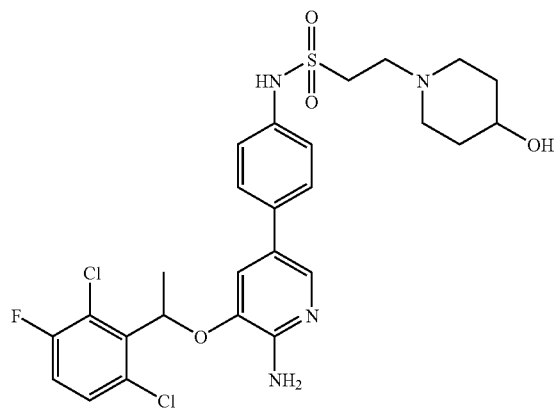
2-(4-Hydroxy-piperidin-1-yl)-ethanesulfonic acid (4-{6-amino-5-[1-(2,6-dichloro-3-fluoro-phenyl)-ethoyl]-pyridin-3-yl}-phenyl)-amide
0.059
I-325
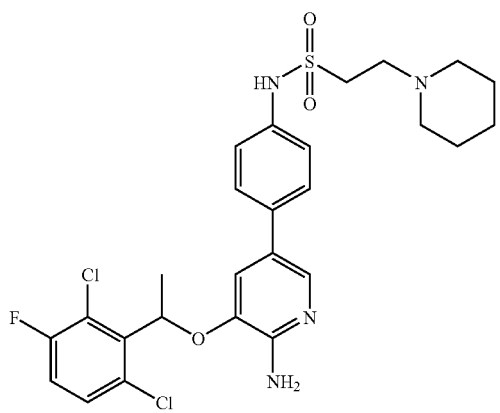
2-Pipendin-1-yl-ethanesulfonic acid (4-{6-amino-5-[1-(2,6-dichloro-3-fluoro-phenyl)-ethoxy]-pyridin-3-yl}-phenyl)-amide
0.089
I-326
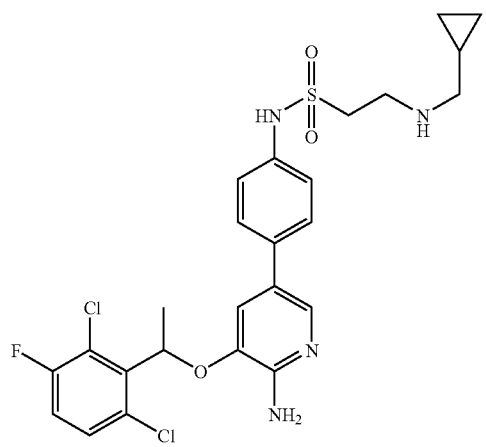
2-(Cyclopropylmethyl-amino)ethanesulfonic acid (4-{6-amino-5-[1-(2,8-dichloro-3-fluorophenyl)-ethoxy]-pyridin-3-yl}-phenyl)-amide
0.075

| | | | |
|---|---|---|---|
| I-327 | 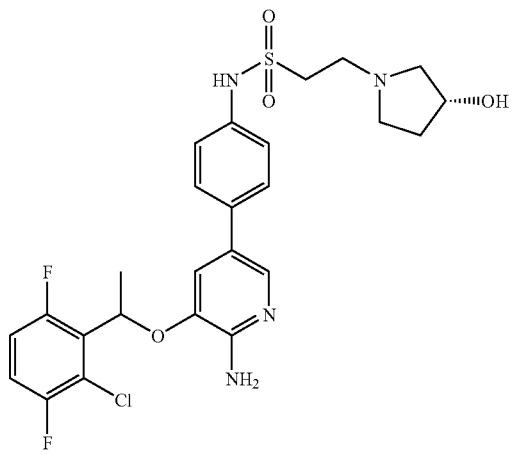 | 2-((R)-3-Hydroxy-pyrrolidin-1-yl)-ethanesulfonic acid (4-{6-amino-5-[1-(2-chloro-3,6-difluoro-phenyl)-ethoxy]-pyridin-3-yl}-phenyl)-amide | 0.093 |
| I-328 | 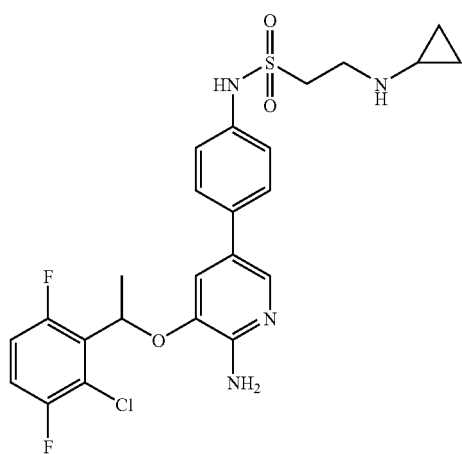 | 2-Cyclopropylamino-ethanesulfonic acid (4-{6-amino-5-[1-(2-chloro-3,6-difluoro-phenyl)-ethoxy]-pyridin-3-yl}-phenyl)-amide | 0.16 |
| I-329 | 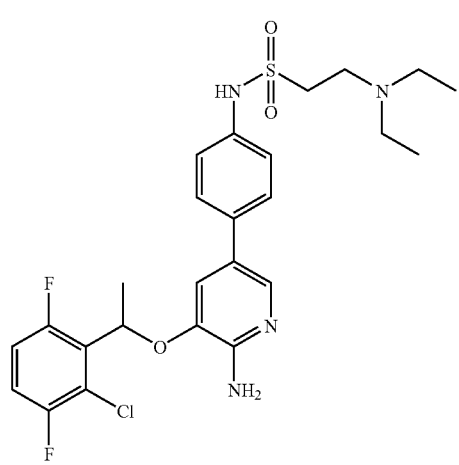 | 2-Diethylamino-ethanesulfonic acid (4-{6-amino-5-[1-(2-chloro-3,6-difluoro-phenyl)-ethoxy]-pyridin-3-yl}-phenyl)-amide | 0.095 |

TABLE 2-continued
I-330
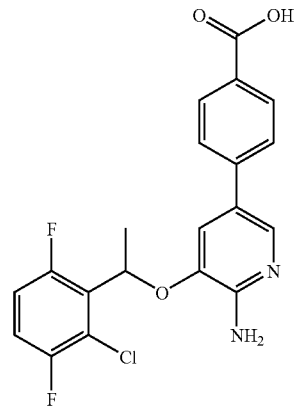
4-{6-Amino-5-[1-(2-chloro-6-difluoro-phenyl)-ethoxy]-pyridin-3-yl}-benzoic acid
I-331
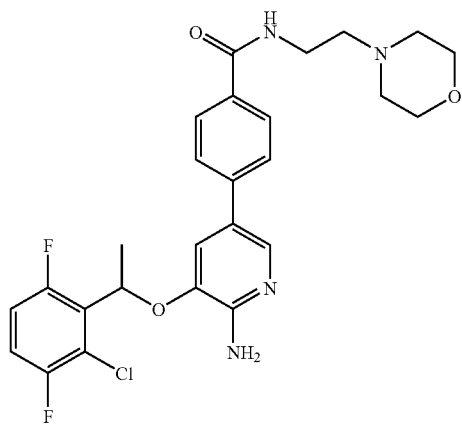
4-{6-Amino-5-[1-(2-chloro-3,6-difluoro-phenyl)-ethoxy]-pyridin-3-yl}-N-(2-morpholin-4-yl-ethyl)-benzamide
0.13
I-332
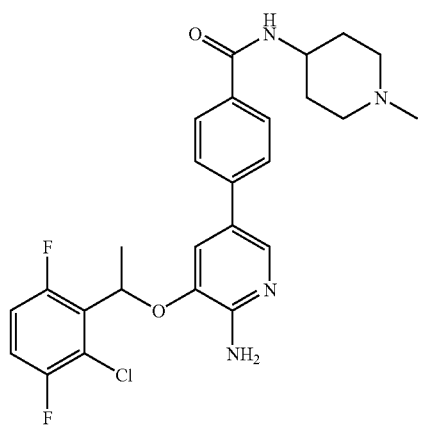
4-{6-Amino-5-(1-(2-chloro-3,6-difluorophenyl)-ethoxy]-pyridin-3-yl}-N-(1-methyl-pipendin-4-yl)-benzamide
0.079

| | | | |
|---|---|---|---|
| I-333 | 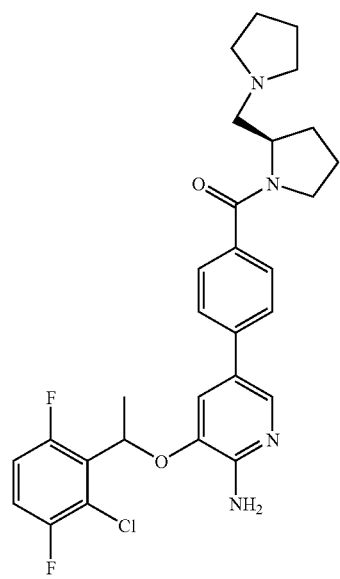 | (4-{6-Amino-5-[1-(2-chloro-3,6-difluoro-phenyl)-ethoxy]-pyridin-3-yl}-phenyl)-((R)-2-pyrrolidin-1-ylmethyl-pyrrolidin-1-yl)-methanone | 0.067 |
| I-334 | 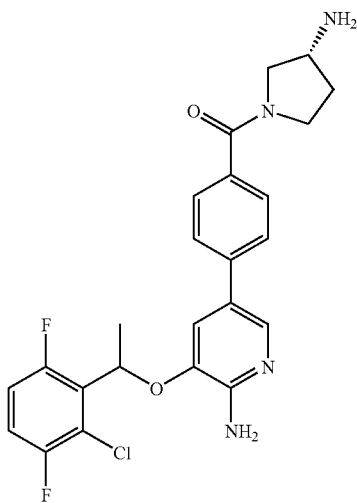 | (4-{6-Amino-5-[1-(2-chloro-3,6-difluoro-phenyl)-ethoxy]-pyridin-3-yl}-phenyl)-((R)-3-amino-pyrrolidin-1-yl)-methanone | 0.089 |
| I-335 | 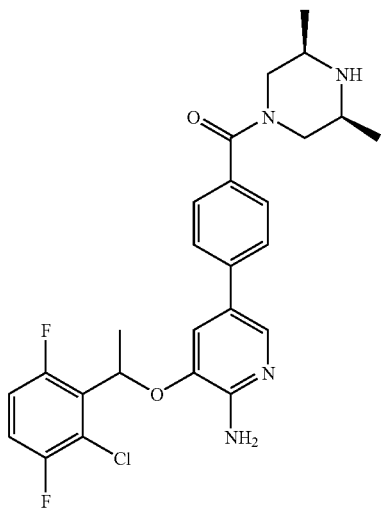 | (4-{6-Amino-5-[1-(2-chloro-3,6-difluoro-phenyl)-ethoxy]-pyridin-3-yl}-phenyl)-((3R,5S)-3,5-dimethyl-piperazin-1-yl)-methanone | 0.09 |

TABLE 2-continued
| | | | |
|---|---|---|---|
| I-336 | 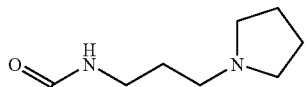 | 4-{6-Amino-5-[1-(2-chloro-3,6-difluoro-phenyl)-ethoxy]-pyridin-3-yl}-N-(3-pyrrolidin-1-yl-propyl)-benzamide | 0.09 |
| I-337 | 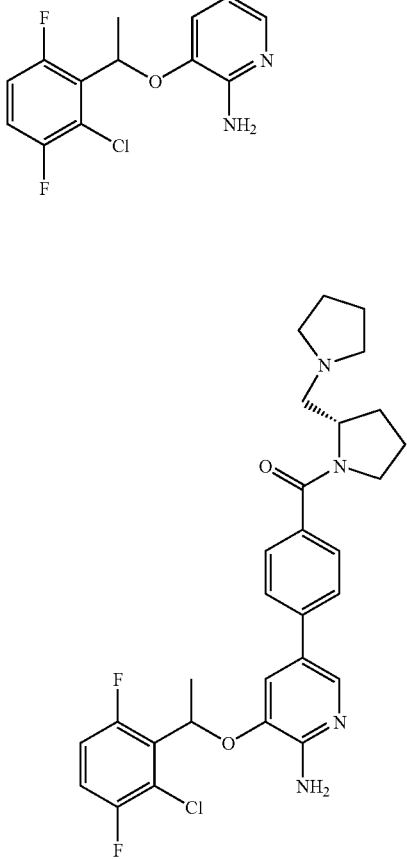 | (4-{6-Amino-5-[1-(2-chloro-3,6-difluoro-phenyl)-ethoxy]-pyridin-3-yl}-phenyl)-((S)-2-pyrrolidin-1-ylmethyl-pyrrolidin-1-yl)-methanone | 0.09 |
| I-338 | 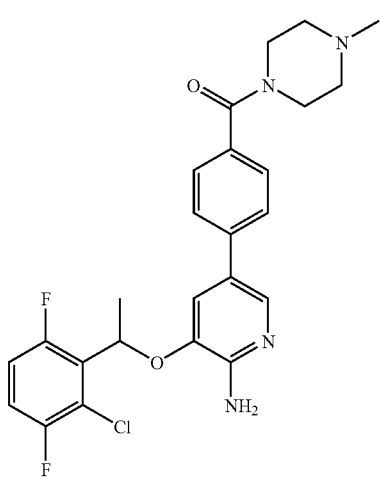 | (4-{6-Amino-5-[1-(2-chloro-3,6-difluoro-phenyl)-ethoxy]-pyridin-3-yl}-phenyl)-(4-methyl-piperazin-1-yl)-methanone | 0.077 |

| | | | |
|---|---|---|---|
| I-339 | 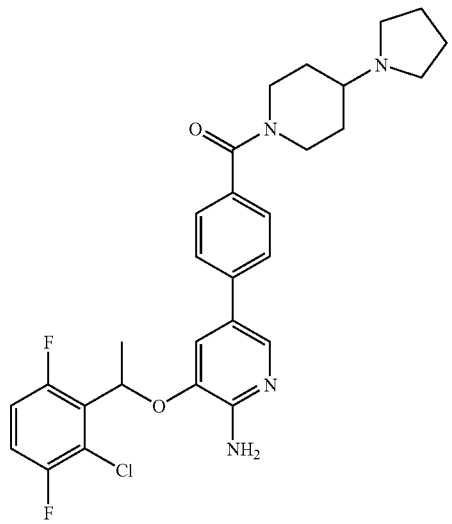 | (4-{6-Amino-5-[1-(2-chloro-3,6-difluoro-phenyl)-ethoxy]-pyridin-3-yl}-phenyl)-(4-pyrrolidin-1-yl-piperidin-1-yl)-methanone | 0.062 |
| I-340 | 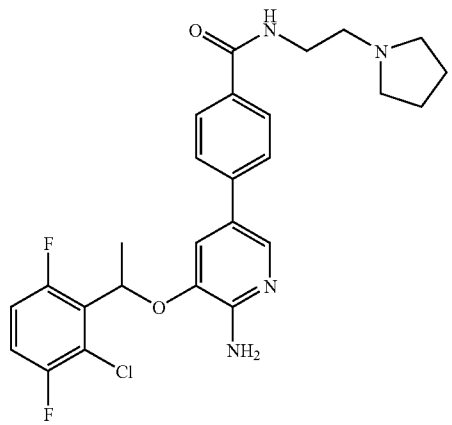 | Amino-5-[1-(2-chloro-3,6-difluoro-phenyl)-ethoxy]-pyridin-3-yl}-N-(2-pyrrolidin-1-yl-ethyl)-benzamide | 0.086 |
| I-341 | 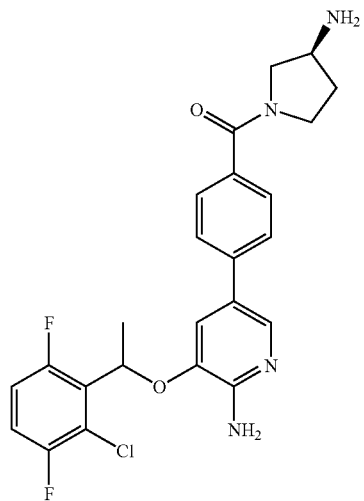 | (4-{6-Amino-5-[1-(2-chloro-3,6-difluoro-phenyl)-ethoxy]-pyridin-3-yl}-phenyl)-((S)-3-amino-pyrrolidin-1-yl)-methanone | 0.075 |

TABLE 2-continued
| I-342 | 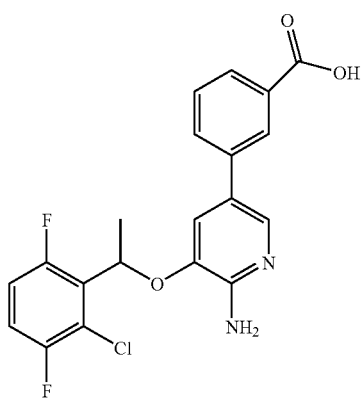 | 3-[6-Amino-5-[1-(2-chloro-3,6-difluoro-phenyl)-ethoxy]-pyridin-3-yl}-benzoic acid | as in Example 211 |
| I-343 | 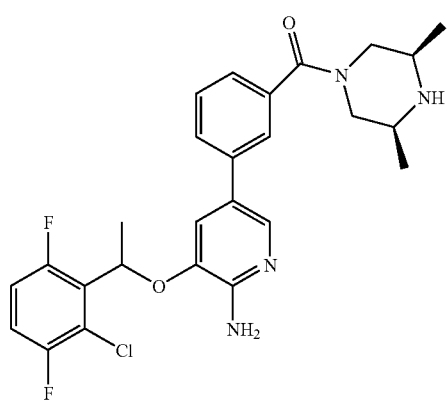 | (3-{6-Amino-5-[1-(2-chloro-3,6-difluoro-phenyl)-ethoxy]-pyridin-3-yl}-phenyl)-((3R,5S)-3,5-dimethyl-piperazin-1-yl)-methanone | 0.16 |
| I-344 | 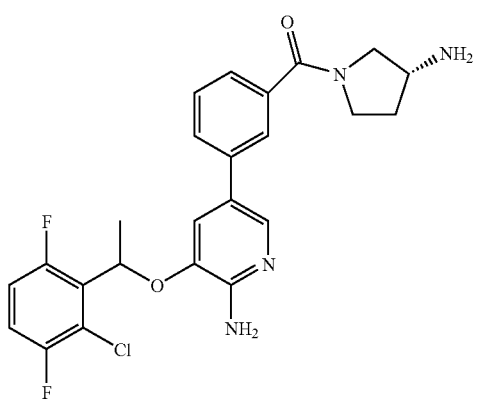 | (3-{6-Amino-5-[1-(2-chloro-3,6-difluoro-phenyl)-ethoxy]-pyridin-3-yl}-phenyl)-((R)-3-amino-pyrrolidin-1-yl)-methanone | 0.12 |
| I-345 | 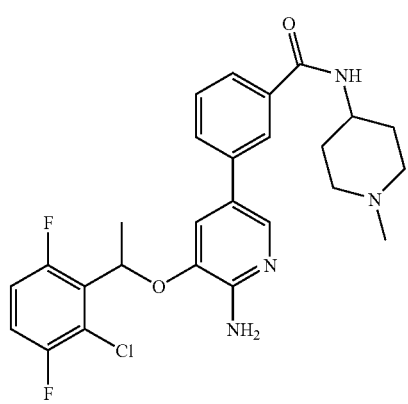 | 3-{6-Amino-5-[1-(2-chloro-3,6-difluoro-phenyl)-ethoxy]-pyridin-3-yl}-N-(1-methyl-pipendin-4-yl)-benzamide | 0.2 |

| | | | |
|---|---|---|---|
| I-346 | 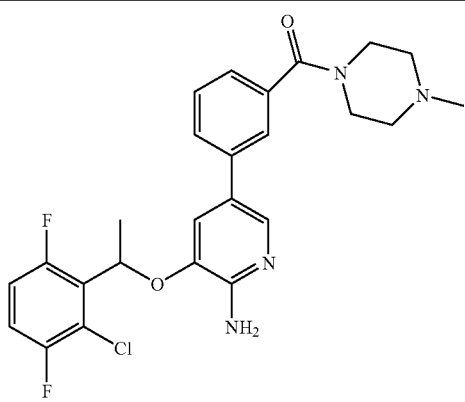 | (3-{6-Amino-5-[1-(2-chloro-3,6-difluoro-phenyl)-ethoxy]-pyridin-3-yl}-phenyl)-(4-methyl-piperazin-1-yl)-methanone | 0.19 |
| I-347 | 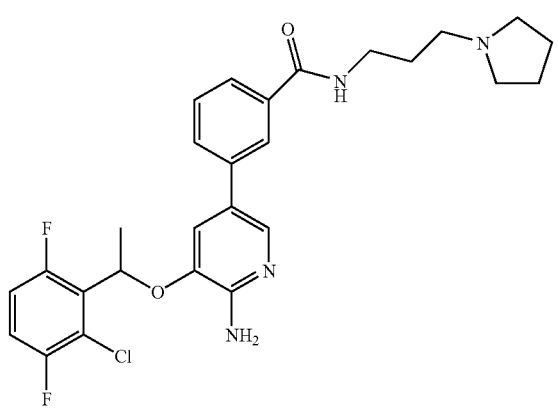 | 3-{6-Amino-5-[1-(2-chloro-3,6-difluoro-phenyl)-ethoxy]-pyridin-3-yl}-N-(3-pyrrolidin-1-yl-propyl)-benzamide | 0.21 |
| I-348 | 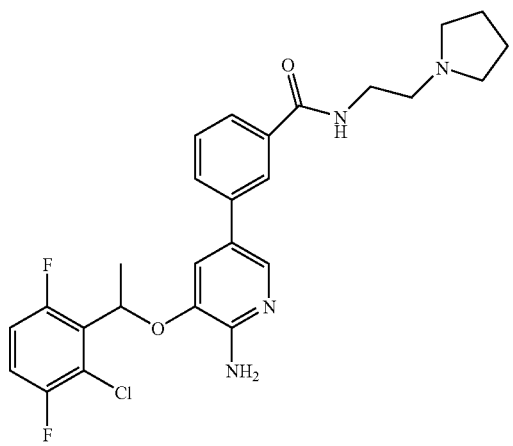 | 3-{6-Amino-5-[1-(2-chloro-3,6-difluoro-phenyl)-ethoxy]-pyridin-3-yl}-N-(2-pyrrolidin-1-yl-ethyl)-benzamide | 0.2 |
| I-349 | 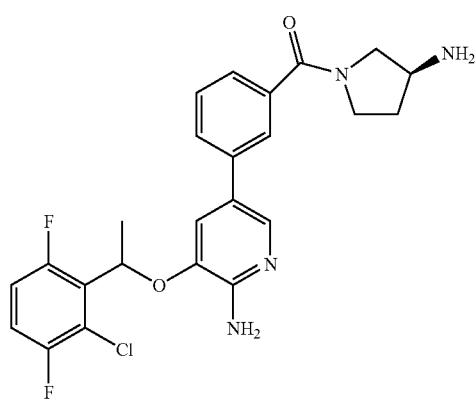 | (3-{6-Amino-5-[1-(2-chloro-3,6-difluoro-phenyl)-ethoxy]-pyridin-3-yl}-phenyl)-((S)-3-amino-pyrrolidin-1-yl)-methanone | 0.13 |

TABLE 2-continued
| | | | |
|---|---|---|---|
| I-350 | 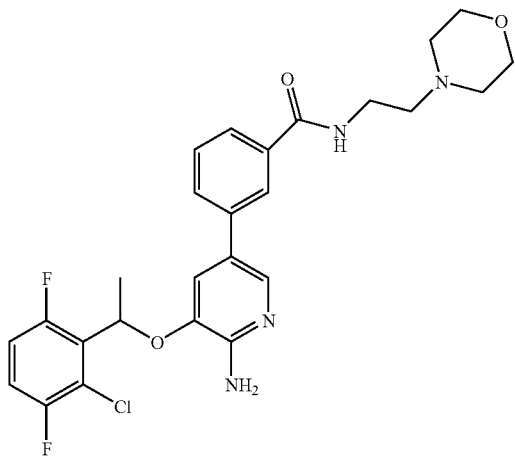 | 3-{6-Amino-5-[1-(2-chloro-3,6-difluoro-phenyl)-ethoxy]-pyridin-3-yl}-N-(2-momholin-4-yl-ethyl)-benzamide | 0.39 |
| I-351 | 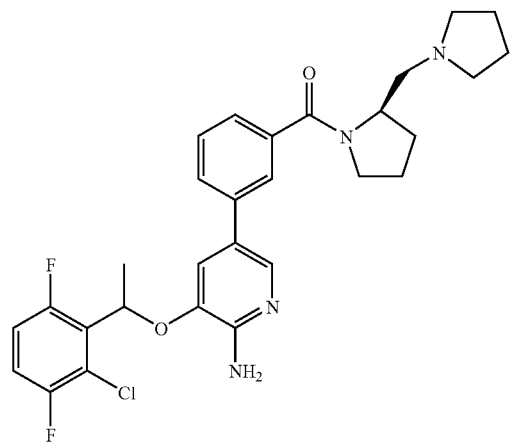 | (3-{6-Amino-5-[1-(2-chloro-3,6-difluoro-phenyl)-ethoxy]-pyridin-3-yl}-phenyl)-((R)-2-pyrrolidin-1-ylmethyl-pyrrolidin-1-yl)-methanone | 0.23 |
| I-352 | 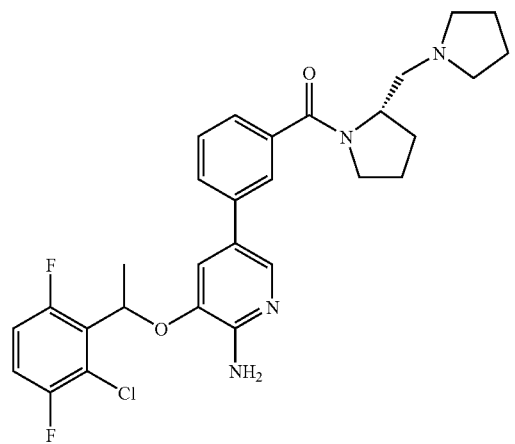 | (3-{6-Amino-5-[1-(2-chloro-3,6-difluoro-phenyl)-ethoxy]-pyridin-3-yl}-phenyl)-((S)-2-pyrrolidin-1-ylmethyl-pyrrolidin-1-yl)-methanone | 0.15 |

TABLE 2-continued

| | | | |
|---|---|---|---|
| I-353 | | 3-[1-(2-Chloro-3,6-difluoro-phenyl)-ethoxy]-5-[4-(2-morpholin-4-yl-ethoxy)-phenyl]-pyridin-2-ylamine | 0.23 |
| I-354 | | 3-[1-(2-Chloro-3,6-difluoro-phenyl)-ethoxy]-5-[3-(2-morpholin-4-yl-ethoxy)-phenyl]-pyridin-2-ylamine | 0.22 |
| I-355 | | 3-[1-(2,6-Dichlaro-3-fluoro-phenyl)-ethoxy]-5-[4-(2-pyrrolidin-1-yl-ethoxy)-phenyl]-pyridin-2-ylamine | 0.68 |

TABLE 2-continued
| | | | |
|---|---|---|---|
| I-356 | 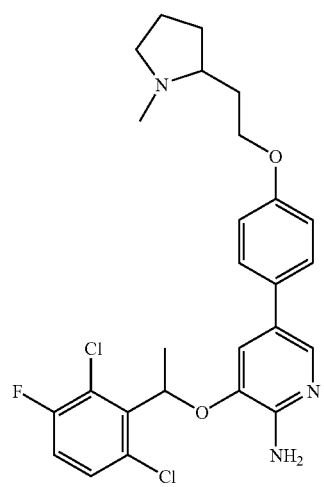 | 3-[1-(2,6-Dichloro-3-fluoro-phenyl)-ethoxy]-5-{4-(2-[1-methyl-pyrrolidin-2-yl)-ethoxy]-phenyl)-pyridin-2-ylamine | 0.79 |
| I-357 | 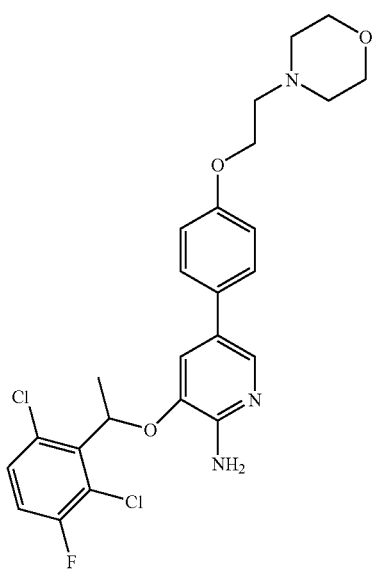 | 3-[1-(2,6-Dichloro-3-fluoro-phenyl)-ethoxy]-5-[4-(2-morpholin-4-yl-ethoxy)-phenyl]-pyridin-2-ylamine | 0.13 |
| I-358 | 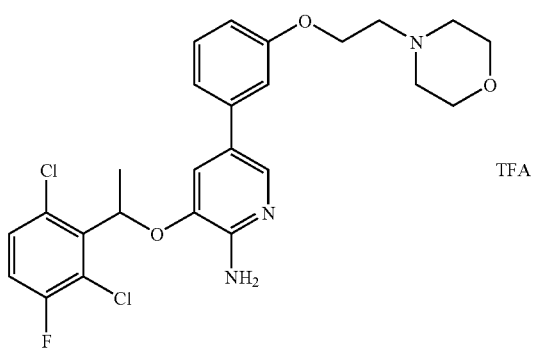 TFA | 3-[1-(2,6-Dichloro-3-fluoro-phenyl)-ethoxy]-5-[3-(2-morpholin-4-yl-ethoxy)-phenyl]-pyridin-2-ylamine | 0.22 |

TABLE 2-continued

| | | | |
|---|---|---|---|
| I-359 | | 1-(4-{6-Amino-5-[1-(2,6-dichloro-3-fluoro-phenyl)-ethoxy]-pyridin-3-yl}-phenoxy)-3-morpholin-4-yl-propan-2-ol | 0.045 |
| I-360 | | 3-[1-(2,6-Dichloro-3-fluoro-phenyl)-ethoxy]-5-[4-(2-diethylamino-ethoxy)-phenyl]-pyridin-2-ylamine | 0.033 |
| I-361 | | 3-[1-(2,6-Dichloro-3-fluoro-phenyl)-ethoxy]-5-[4-[1-methyl-pipendin-3-ylmethoxy)-phenyl]-pyridin-2-ylamine | 0.043 |
| I-362 | | 3-[1-(2,6-Dlchloro-3-fluoro-phenyl)-ethoxy]-5-[4-(2-diisopropylamino-ethoxy)-phenyl]-pyridin-2-ylamine | 0.052 |

TABLE 2-continued
I-363
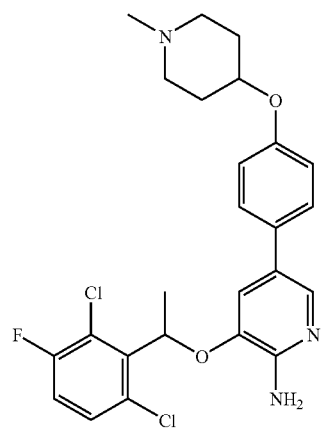
3-[1-(2,6-Dichloro-3-fluoro-phenyl)-ethoxy]-5-[4-[1-methyl-piperidin-4-yloxy)-phenyl]-pyridin-2-ylamine
0.052
I-364
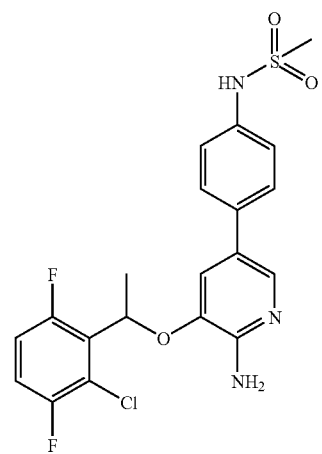
N-(4-{6-Amino-5-[1-(2-chloro-3,6-difluoro-phenyl)-ethoxy]-pyridin-3-yl}-phenyl)-methanesulfonamide
0.1
I-365
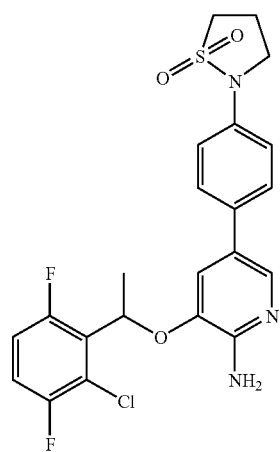
3-[1-(2-Chloro-3,8-difluoro-phenyl)-ethoxy]-5-[4-(1,1-dioxo-1lambda*6*-isothiazolidin-2-yl)-phenyl]-pyridin-2-ylamine
0.14

TABLE 2-continued

| ID | Structure | Name | Value |
|---|---|---|---|
| I-366 | 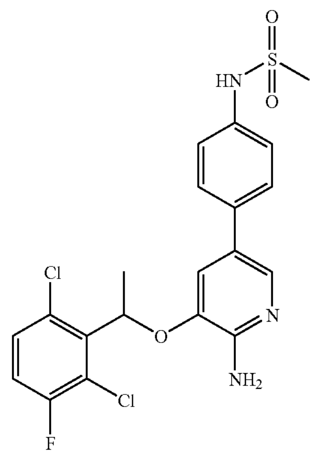 | N-(4-{6-Amino-5-[1-(2,6-dichloro-3-fluoro-phenyl)-ethoxy]-pyridin-3-yl}-phenyl)-methanesulfonamide | 0.076 |
| I-367 | 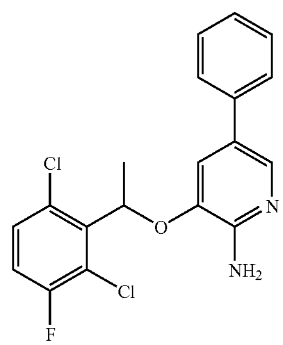 | 3-[1-(2,6-Dichloro-3-fluoro-phenyl)-ethoxy]-5-phenyl-pyridin-2-ylamine | 0.5 |
| I-368 | 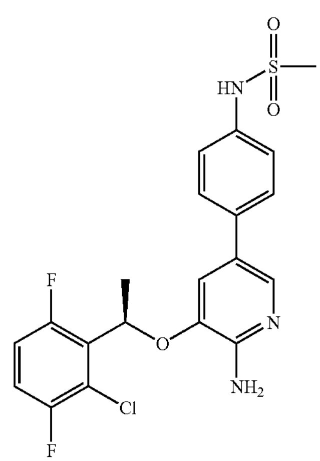 | N-(4-{6-Amino-5[(R)-1-(2-chloro-3,6-difluoro-phenyl)-ethoxy]pyridin-3-yl}-phenyl)-methanesulfonamide | 0.066 |
| I-369 | 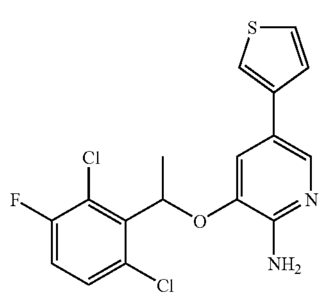 | 3-[1-(2,6-Dichloro-3-fluoro-phenyl)-ethoxy]-5-thiophen-3-yl-pyridin-2-ylamine | 0.0553 |

TABLE 2-continued
| | | | |
|---|---|---|---|
| I-370 | 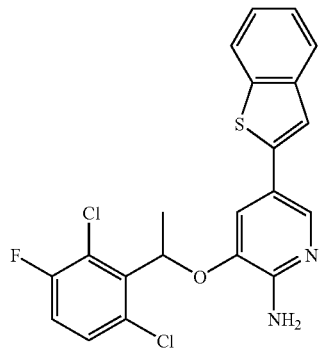 | 5-Benzo[b]thiophen-2-yl-3-[1-(2,6-dichloro-3-fluoro-phenyl)-ethoxy]-pyridin-2-ylamine | 1.95 |
| I-371 | 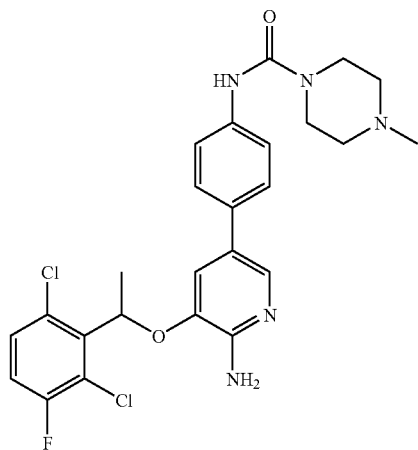 | 4-Methyl-piperazine-1-carboxylic acid (4-{6-amino-5-[1-(2,6-dichloro-3-fluoro-phenyl)-ethoxy]-pyridin-3-yl}-phenyl)-amide | 0.057 |
| I-372 | 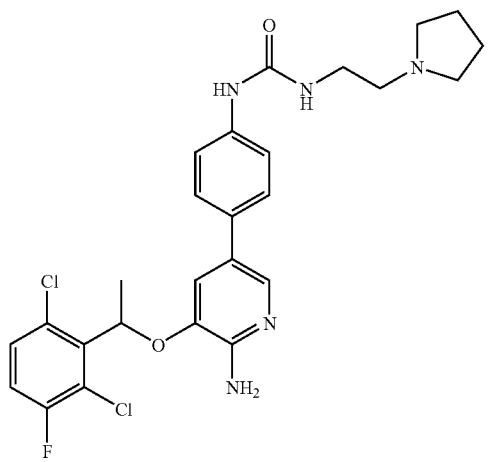 | 1-(4-{6-Amino-5-[1-(2,6-dichloro-3-fluoro-phenyl)-ethoxy]-pyridin-3-yl}-phenyl)-3-{2-pyrrolidin-1-yl-ethyl)-urea | 0.21 |

| | | | |
|---|---|---|---|
| I-373 | 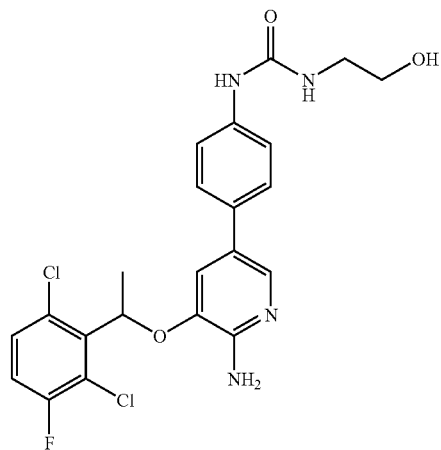 | 1-(4-{6-Amino-5-[1-(2,6-dichloro-3-fluoro-phenyl)-ethoxy]-pyridin-3-yl}-phenyl)-3-(2-hydroxy-ethyl)-urea | 0.064 |
| I-374 | 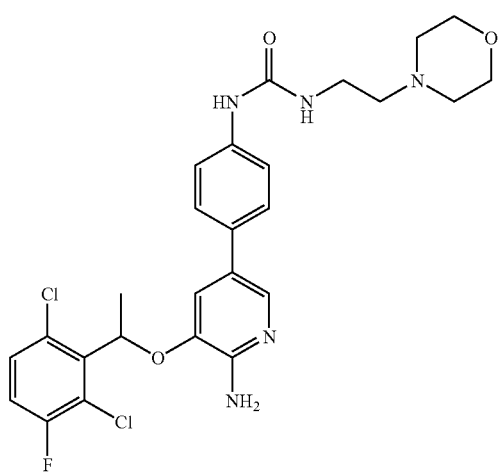 | 1-(4-{6-Amino-5-[1-(2,6-dichloro-3-fluoro-phenyl)-ethoxy]-pyridin-3-yl}-phenyl)-3-(2-morpholin-4-yl-ethyl)-urea | 0.062 |
| I-375 | 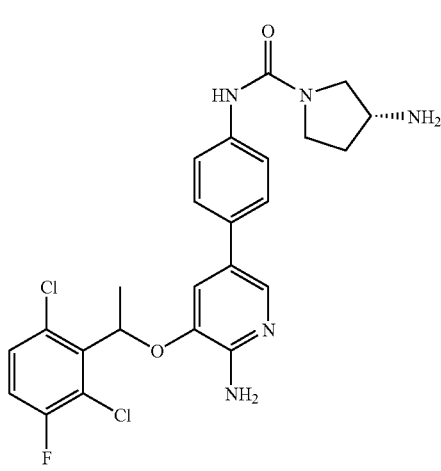 | (R)-3-Amino-pyrrolidine-1-carboxylic acid (4-{6-amino-5-[1-(2,6-dichloro-3-fluoro-phenyl)-ethoxy]-pyridin-3-yl}-phenyl)-amide | 0.053 |

TABLE 2-continued
| I-376 | 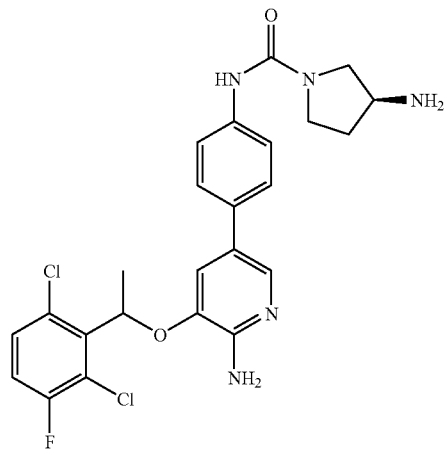 | (S)-3-Amino-pyrrolidine-1-carboxylic acid (4-{6-amino-5-[1-(2,6-dichloro-3-fluoro-phenyl)-ethoxy]-pyridin-3-yl}-phenyl)-amide | 0.052 |
| I-377 | 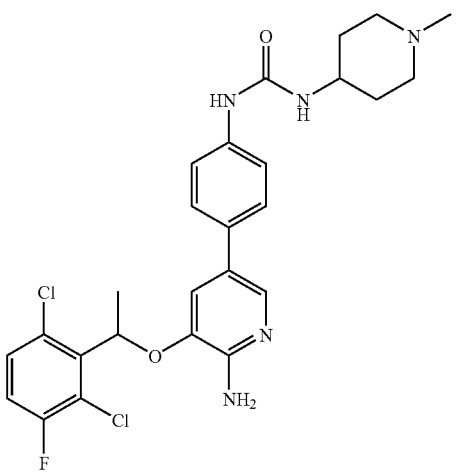 | 1-(4-{6-Amino-5-{1-(2,6-dichloro-3-lluoro-phenyl)-ethoxy]-pyridin-3-yl}-phenyl)-3-[1-methyl-pipendin-4-yl)-urea | 0.04 |
| I-378 | 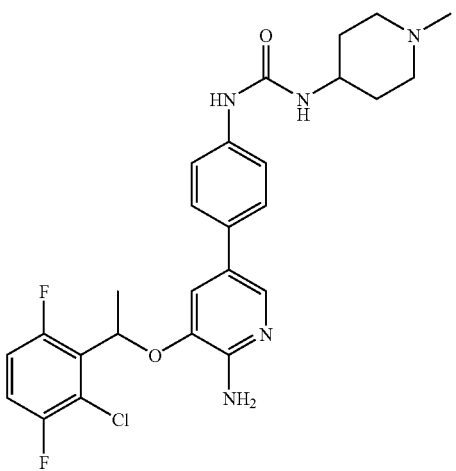 | 1-(4-{6-Amino-5-[1-(2-Chloro-3,6-difluoro-phenyl)-ethoxy]-pyridin-3-yl}-phenyl)-3-[1-methyl-pipendin-4-yl)-urea | 0.038 |

| | | | |
|---|---|---|---|
| I-379 | 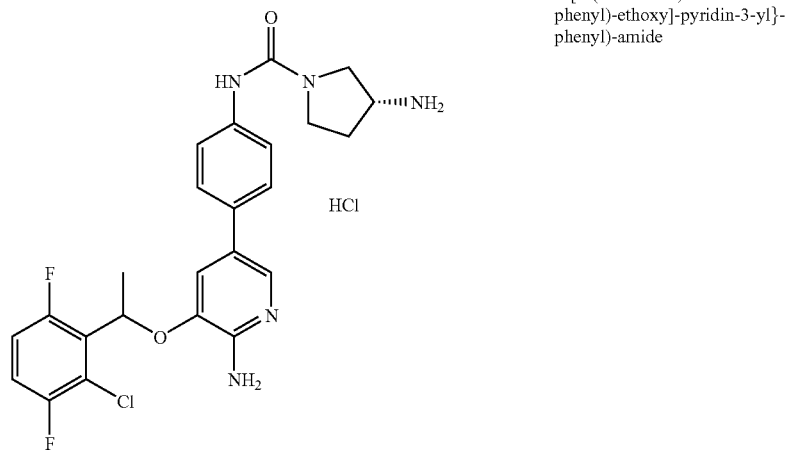 | (S)-3-Amino-pyrrolidine-1-carboxylic acid (4-{6-amino-5-[1-(2-chloro-3,6-difluoro-phenyl)-ethoxy]-pyridin-3-yl}-phenyl)-amide | 0.069 |
| I-380 | 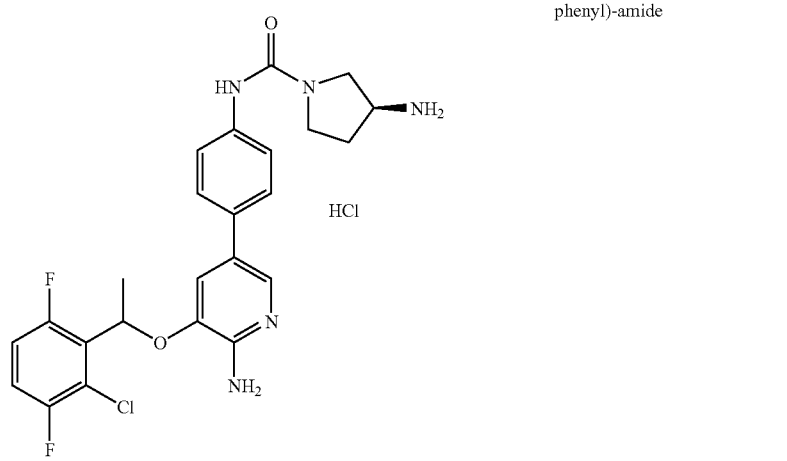 | (S)-3-Amino-pyrrolidine-1-carboxylic acid (4-(8-amino-5-[1-(2-chloro-3,6-difluoro-phenyl)-ethoxy]-pyridin-3-yl}-phenyl)-amide | 0.075 |
| I-381 | 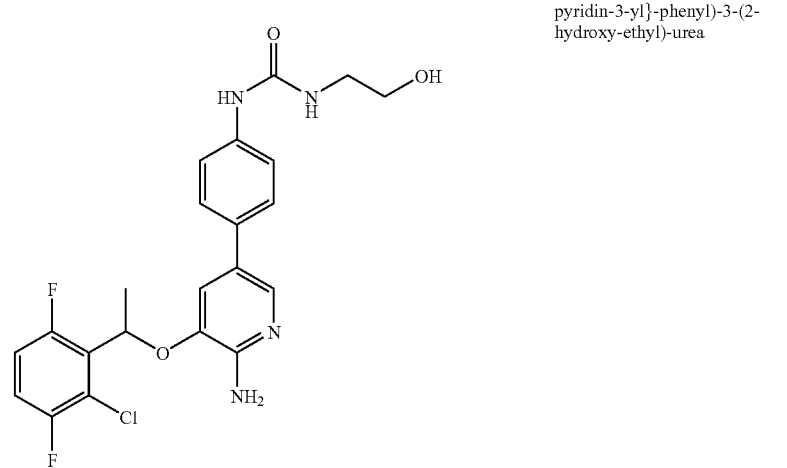 | 1-(4-{6-Amino-5-[1-(2-chloro-3,6-difluoro-phenyl)-ethoxy]-pyridin-3-yl}-phenyl)-3-(2-hydroxy-ethyl)-urea | 0.11 |

TABLE 2-continued
| | | | |
|---|---|---|---|
| I-382 | 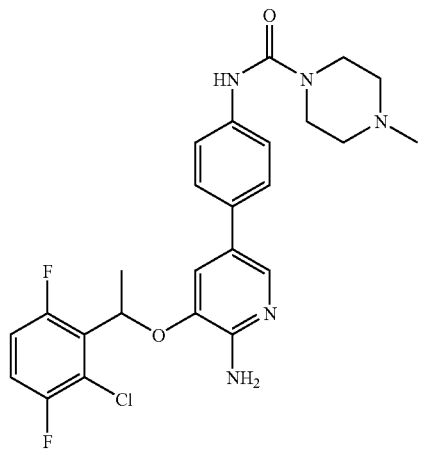 | 4-Methyl-piperazine-1-carboxylicacid (4-{6-amino-5-[1-(2-chloro-3,6-difluoro-phenyl)-ethoxy]-pyridin-3-yl}-phenyl)-amide | 0.082 |
| I-383 | 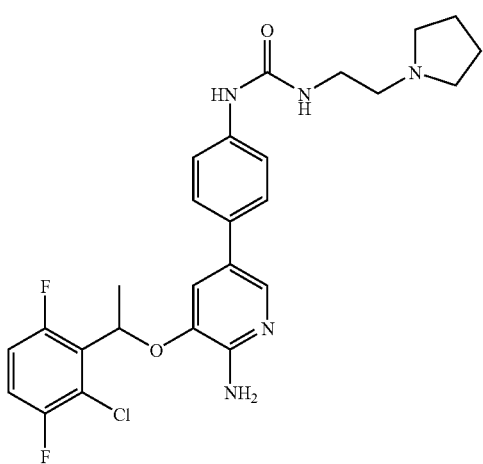 | 1-(4-{6-Amino-5-[1-(2-chloro-3,6-difluoro-phenyl)-ethoxy]-pyridin-2-yl}-phenyl)-3-(2-pyrrolidin-1-yl-ethyl)-urea | 0.11 |
| I-384 | 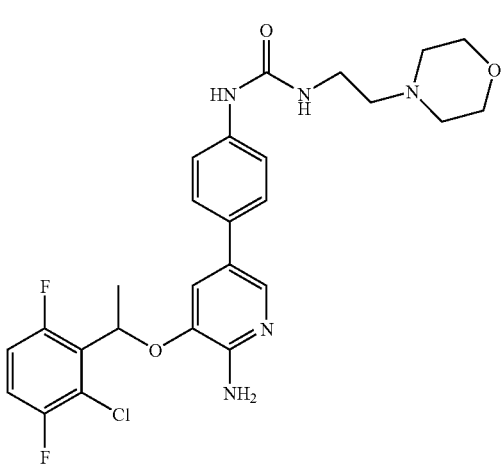 | 1-(4-{6-Amino-5-[1-(2-chloro-3,6-difluoro-phenyl)-ethoxy]-pyridin-3-yl}-phenyl)-3-(2-morpholin-4-yl-ethyl)-urea | 0.13 |

TABLE 2-continued

| | | | |
|---|---|---|---|
| I-385 | 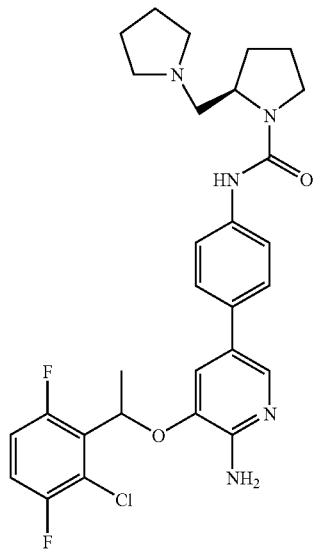 | (R)-2-Pyrrolidin-1-ylmethyl-pyrrolidine-1-carboxylic acid (4-{6-amino-5-[1-(2-chloro-3,6-difluoro-phenyl)-ethoxy]-pyridin-3-yl}-phenyl)-amide | 0.13 |
| I-386 | 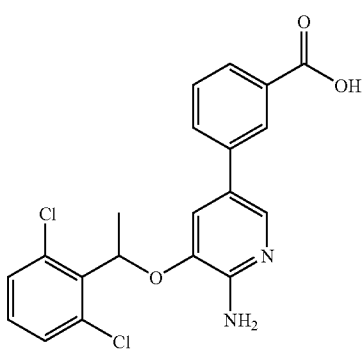 | 3-{6-Amino-5-[1-(2,6-dichloro-phenyl)-ethoxy]-pyridin-3-yl}-benzoic acid | |
| I-387 | 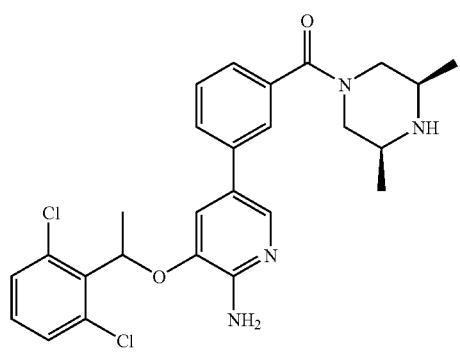 | (3-{6-Amino-5-[1-(2,6-dichloro-phenyl)-ethoxy]-pyridin-3-yl}-phenyl)-((3R,5S)-3,5-dimethyl-piperazin-1-yl)-methanone | 0.16 |
| I-388 | 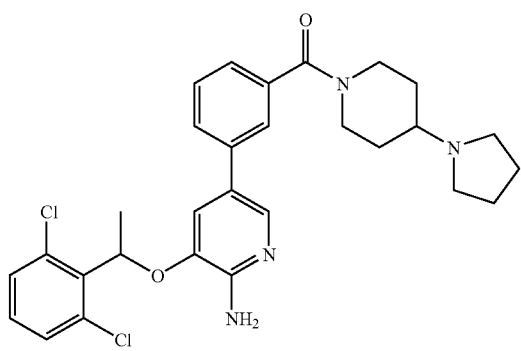 | (3-{6-Amino-5-[1-(2,6-dichloro-phenyl)-ethoxy]-pyridin-3-yl}-phenyl)-(4-pyrrolidin-1-yl-piperidin-1-yl)-methanone | 0.1 |

TABLE 2-continued
| I-389 | 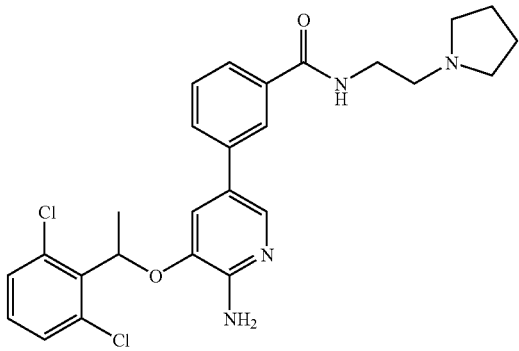 | 3-{6-Amino-5-[1-(2,6-dichloro-phenyl)-ethoxy]-pyridin-3-yl}-N-(2-pyrrolidin-1-yl-ethyl)-benzamide | 0.13 |
| I-390 | 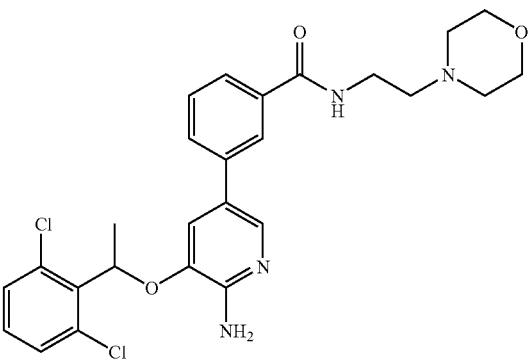 | 3-{6-Amino-5-[1-(2,6-dichloro-phenyl)-ethoxy]-pyridin-3-yl}-N-(2-morpholin-yl-ethyl)-benzamide | 0.12 |
| I-391 | 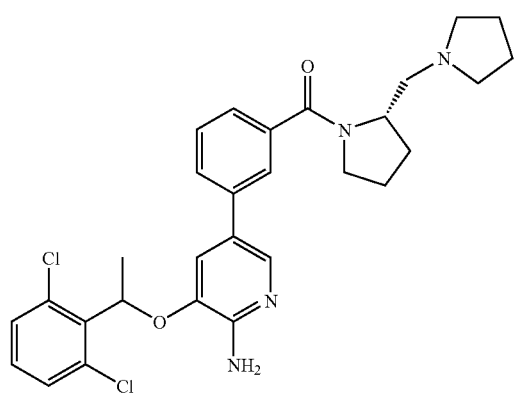 | (3-{6-Amino-5-[1-(2,6-dichloro-phenyl)-ethoxy]-pyridin-3-yl}-phenyl)-((S)-2-pyrrolidin-1-ylmethyl-pyrrolidin-1-yl)-methanone | 0.098 |
| I-392 | 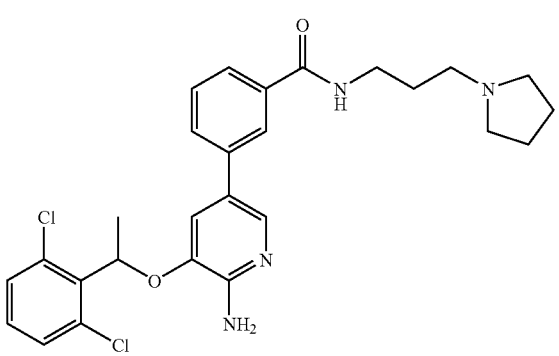 | 3-{6-Amino-5-[1-(2,6-dichloro-phenyl)-ethoxy]-pyridin-3-yl}-N-(3-pyrrolidin-yl-propyl)-benzamide | 0.072 |

TABLE 2-continued
| | | | |
|---|---|---|---|
| I-393 | 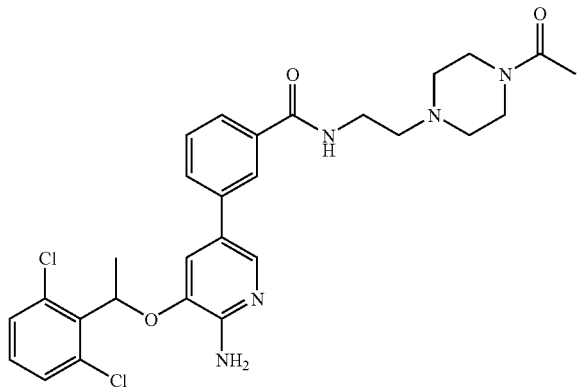 | N-[2-(4-Acetyl-piperazin-1-yl)ethyl]-3-{6-amino-5-[1-(2,6-dichloro-phenl)-ethoxy]-pyridin-3-yl}-benzamide | 0.079 |
| I-394 | 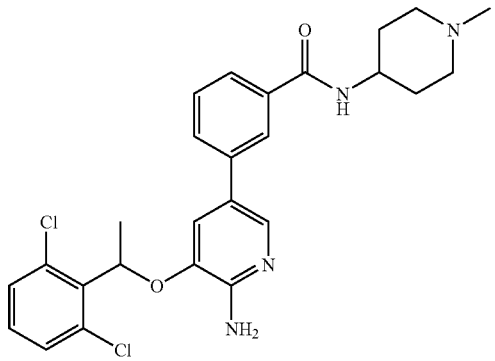 | 3-{6-Amino-5-[1-(2,6-dichloro-phenyl)-ethoxy]-pyridin-3-yl}-N-(methyl-pipendin-4-yl)-benzamide | 0.061 |
| I-395 | 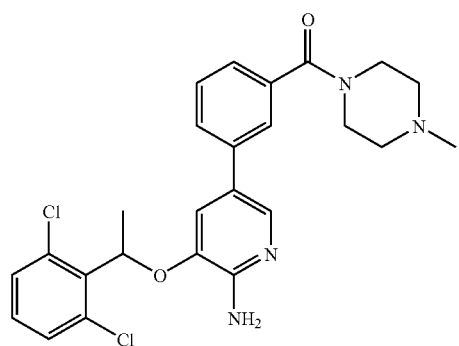 | (3-{6-Amino-5-[1-(2,6-dichloro-phenyl)-ethoxy]-pyridin-3-yl}-phenyl)-(4-methyl-piperazin-1-yl)-methanone | 0.058 |
| I-396 | 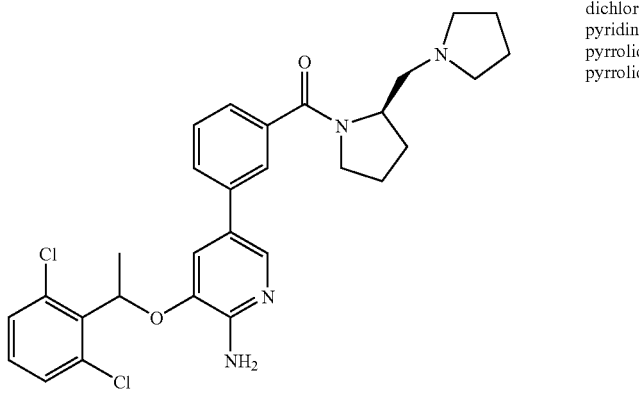 | (3-{6-Amino-5-[1-(2,6-dichloro-phenyl)-ethoxy]-pyridin-3-yl}-phenyl)-((R)-2-pyrrolidin-1-ylmethyl-pyrrolidin-1-yl)-methanone | 0.18 |

TABLE 2-continued
| | | | |
|---|---|---|---|
| I-397 | 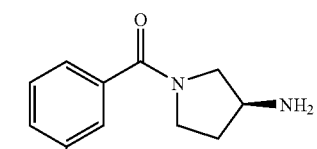 | (3-{6-Amino-5-[1-(2,6-dichloro-phenyl)-ethoxy]-pyridin-3-yl}-phenyl)-((S)-3-amino-pyrrolidin-1-yl)-methanone | 0.055 |
| I-398 | 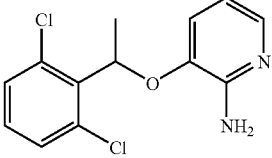 | (3-{6-Amino-5-[1-(2,6-dichloro-phenyl)-ethoxy]-pyridin-3-yl}-phenyl)-((R)-3-amino-pyrrolidin-1-yl)-methanone | 0.072 |
| I-399 | 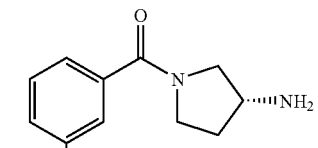 | 4-{6 Amino-5-[1-(2,6-dichloro-pheny)-ethoxy]-pyridin-3-yl}-benzoic acid | |
| I-400 | 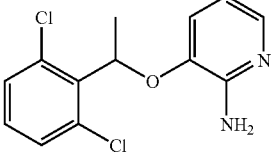 | 4-{6-Amino-5-[1-(2,6-dichloro-phenyl)-ethoxy]-pyridin-3-yl}-N-(2-pyrrolidin-yl-ethyl)-benzamide | 0.059 |

TABLE 2-continued
| | | | |
|---|---|---|---|
| I-401 | 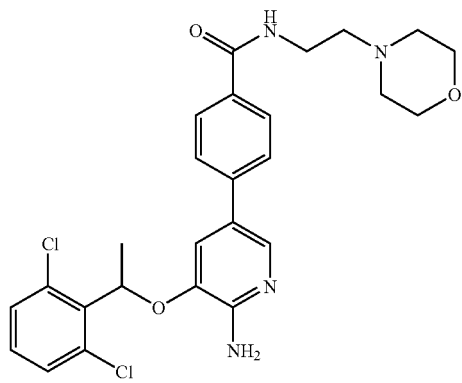 | 4-{6-Amino-5-[1-(2,6-dichloro-phenyl)-ethoxy]-pyridin-3-yl}-N-(2-morpholin-4-yl-ethyl)-benzamide | 0.073 |
| I-402 | 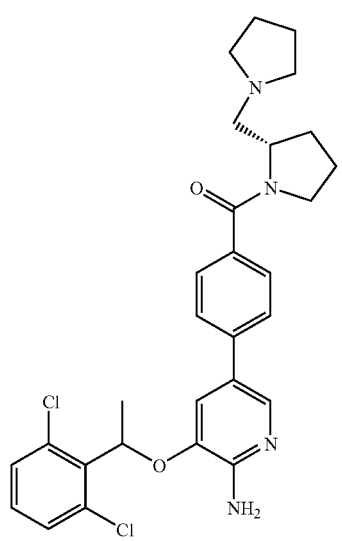 | (4-{6-Amino-5-[1-(2,6-dichloro-phenyl)-ethoxy]-pyridin-3-yl}-phenyl)-((S)-2-pyrrolidin-1-ylmethyl-pyrrolidin-1-yl)-methanone | 0.068 |
| I-403 | 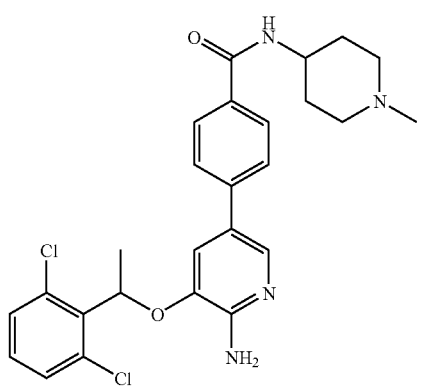 | 4-{6-Amino-5-[1-(2,6-dichloro-phenyl)-ethoxy]-pyridin-3-yl}-N-[1-methyl-piperidin-4-yl)-benzamide | 0.062 |

TABLE 2-continued
| | | | |
|---|---|---|---|
| I-404 | 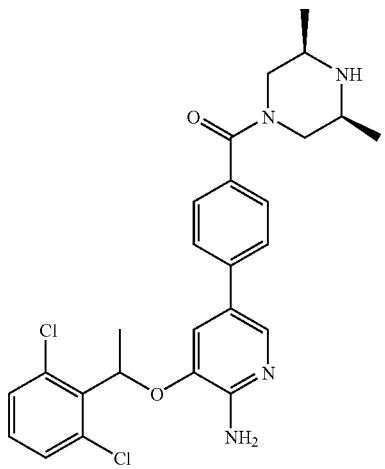 | (4-{6-Amino-5-[1-(2,6-dichloro-phenyl)-ethoxy]-pyridin-3-yl}-phenyl)-((3R,5S)-3,5-dimethyl-piperazin-1-yl)-methanone | 0.052 |
| I-405 | 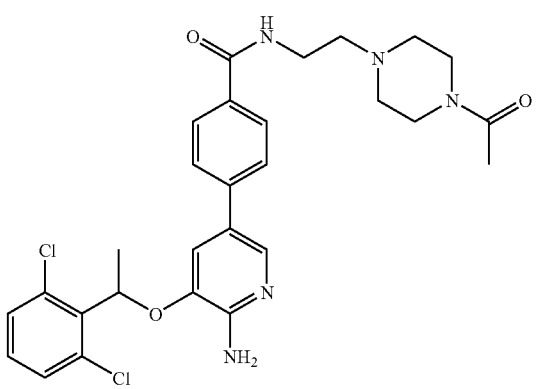 | N-[2-(4-Acetyl-piperazin-1-yl)-ethyl]-4-{6-amino-5-[1-(2,6-dichloro-phenyl)-ethoxy}-pyridin-3-yl)-benzamide | 0.062 |
| I-406 | 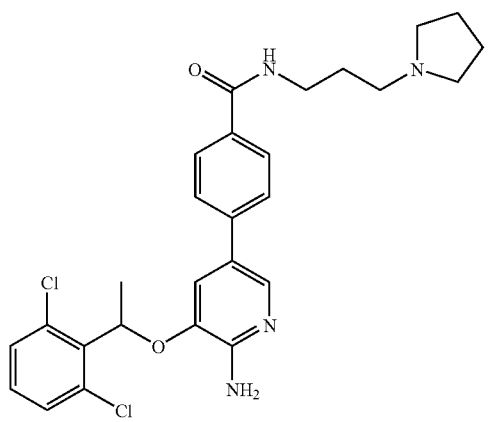 | 4-{6-Amino-5-[1-(2,6-dichloro-phenyl)-ethoxy]-pyridin-3-yl}-N-(3-pyrrolidin-1-yl-propyl)-benzamide | 0.061 |

TABLE 2-continued
| | | | |
|---|---|---|---|
| I-407 | 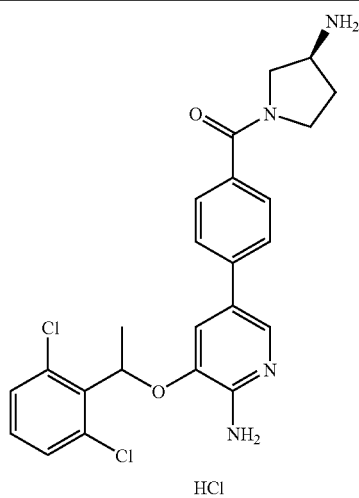 | (4-{6-Amino-5-[1-(2,6-dichloro-phenyl)-ethoxy]-pyridin-3-yl}-phenyl)-((S)-3-aminopyrrolidin-1-yl)-methanone | 0.05 |
| I-408 | 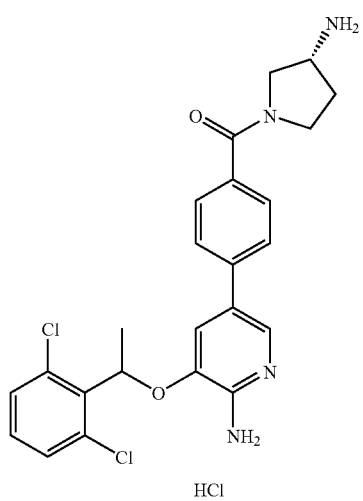 | (4-{6-Amino-5-[1-(2,6-dichloro-phenyl)-ethoxy]-pyridin-3-yl]-phenyl)-((R)-3-amino-pyrrolidin-1-yl)-methanone | 0.049 |
| I-409 | 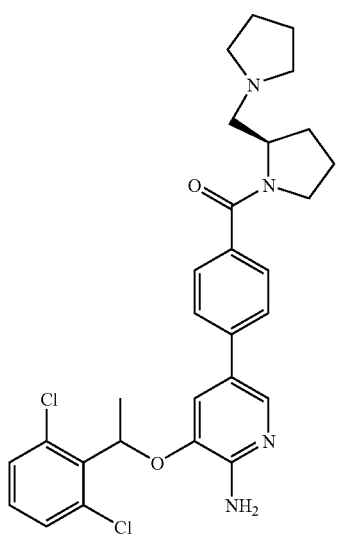 | (4-{6-Amino-5-[1-(2,6-dichloro-phenyl)-ethoxy]-pyridin-3-yl]-phenyl)-((R)-2-pyrrolidin-1-ylmethyl-pyrrolidin-1-yl)-methanone | 0.081 |

TABLE 2-continued
| | | | |
|---|---|---|---|
| I-410 | 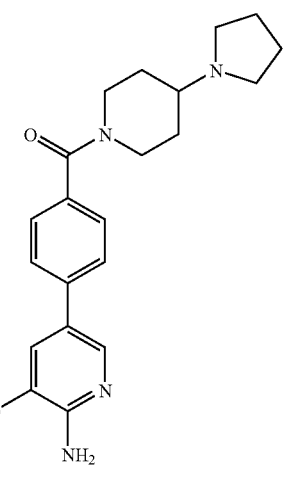 | (4-{6-Amino-5-[1-(2,6-dichloro-phenyl)-ethoxy]-pyridin-3-yl}-phenyl)-(4-pyrrolidin-1-yl-piperidin-1-yl)-methanone | 0.055 |
| I-411 | 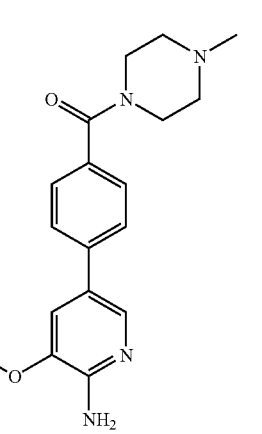 | (4-{6-Amino-5-[1-{2,6-dichloro-phenyl)-ethoxy]-pyridin-3-yl}-phenyl)-(4-methyl-piperazin-1-yl)-methanone | 0.053 |
| I-412 | 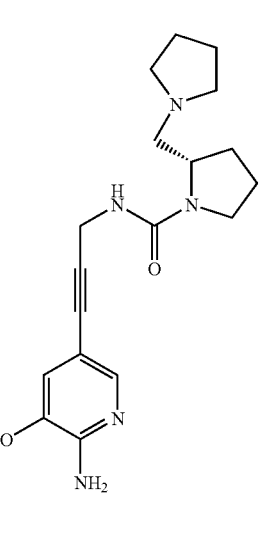 | (S)-2-Pyrrolidin-1-ylmethyl-pyrrolidine-1-carboxylic acid (3-{6-amino-5-[1-(2,6-dichloro-3-ttuoro-phenyl)-ethoxy]-pyridin-3-yl}-prop-2-ynyl)-amide | 0.067 |

| | | | |
|---|---|---|---|
| I-413 | 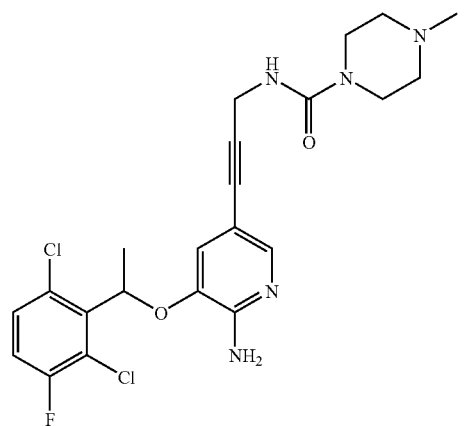 | 4-Methyl-piperazine-1-carboxylic acid (3-{6-amino-5-[1-(2,6-dichloro-3-fluoro-phenyl)-ethoxy]-pyridin-3-yl}-prop-2-ynyl)-amide | 0.056 |
| I-414 | 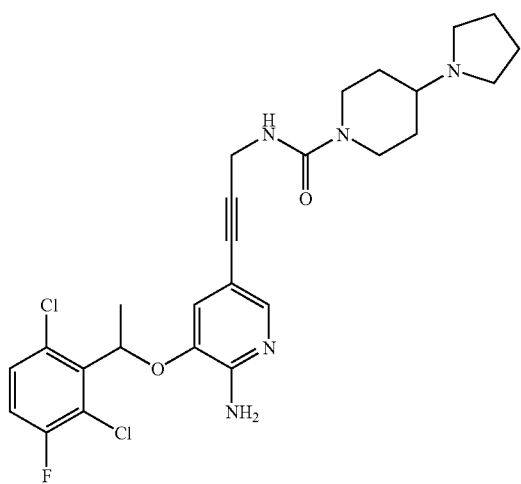 | 4-Pyyrolidin-1-yl-piperidine-1-carboxylic acid (3-{6-amino-5-[1-(2,6-dichloro-3-fluoro-phenyl)-ethoxyl-pyridin-3-yl}-prop-2-ynyl)-amide | 0.058 |
| I-415 | 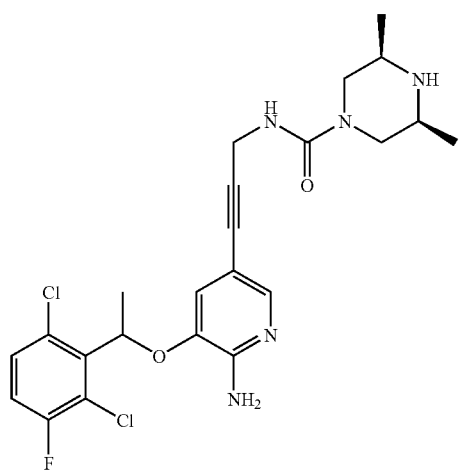 | (3R,5S)-3,5-Dimethyl-piperazine-1-carboxylic acid (3-{6-amino-5-[1-(2,6-dichloro-3-fluoro-phenyl)-ethoxy]pyridin-3-yl}-prop-2-ynyl)-amide | 0.063 |

TABLE 2-continued

| | | | |
|---|---|---|---|
| I-416 | | 1-(3-{6-Amino-5-[1-(2,6-dichloro-3-fluoro-phenyl)-ethoxy]-pyridin-3-yl}-prop-2-ynyl)-3-(1-methyl-piperidin-4-yl)-urea | 0.051 |
| I-417 | | 1-(3-{6-Amino-5-[1-(2,6-dichloro-3-fluoro-phenyl)-ethoxy]-pyridin-3-yl}-prop-2-ynyl)-3-(3-pyrrolidin-1-yl-propyl)-urea | 0.062 |
| I-418 | | 1-(3-{6-Amino-5-[1-(2,6-dichloro-3-fluoro-phenyl)-ethoxy]-pyridin-3-yl}-prop-2-ynyl)-3-(2-pyrrolidin-1-yl-ethyl)-urea | 0.052 |
| I-419 | | 1-(3-{6-Amino-5-[1-(2,6-dichloro-3-fluoro-phenyl)-ethoxy]-pyridin-3-yl}-prop-2-ynyl)-3-(2-morpholin-4-yl-ethyl)-urea | 0.055 |

| | | | |
|---|---|---|---|
| I-420 | 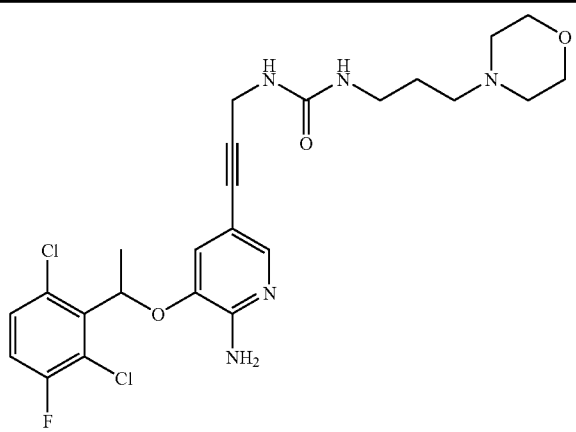 | 1-(3-{6-Amino-5-[1-(2,6-dichloro-3-fluoro-phenyl)-ethoxy]-pyridin-3-yl}-prop-2-ynyl)-3-(2-morpholin-4-yl-propyl)-urea | 0.064 |
| I-421 | 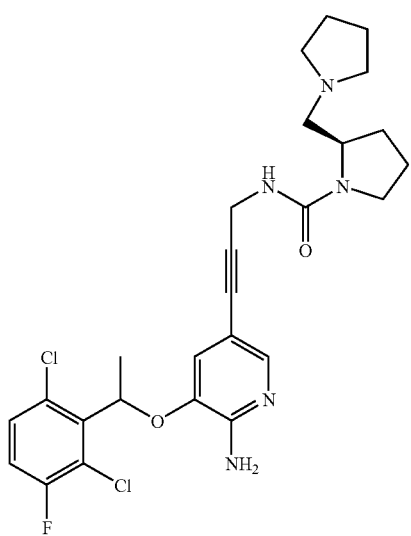 | (R)-2-Pyrrolidin-1-ylmethyl-pyrrolidine-1-carboxylic acid (3-{6-ammno-5-[1-(2,6-dichloro-3-fluoro-phenyl)-ethoxy]-pyridin-3-yl)-prop-2-ynyl) amide | 0.071 |
| I-422 | 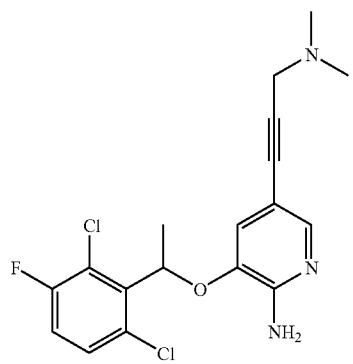 | 3-[1-(2,6-Dichloro-3-fluoro-phenyl)-ethoxy]-5-(3-dimethylamino-prop-1-ynyl)-pyridin-2-ylamine | 0.071 |
| I-423 | 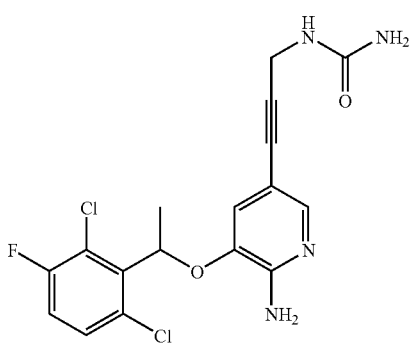 | (3-{6-Amino-5-[1-(2,6-dichloro-3-fluoro-phenyl)-ethoxy]-pyridin-3-yl}-prop-2-ynyl)-urea | 0.062 |

TABLE 2-continued

| I-424 |  | N-(3-{6-Amino-5-[1-(2,6-dichloro-3-fluoro-phenyl)-ethoxy]-pyridin-3-yl}-prop-2-ynyl)-2-piperidin-1-yl-acetamide | 0.016 |
|---|---|---|---|
| I-425 |  | N-(3-{6-Amino-5-[1-(2,6-dichloro-3-fluoro-phenyl)-ynyl)-2-morpholin-4-yl-ethoxy]-pyridin-3-yl}-prop-2-ynyl)-2-morpholin-4-yl-acetamide | 0.027 |
| I-426 | 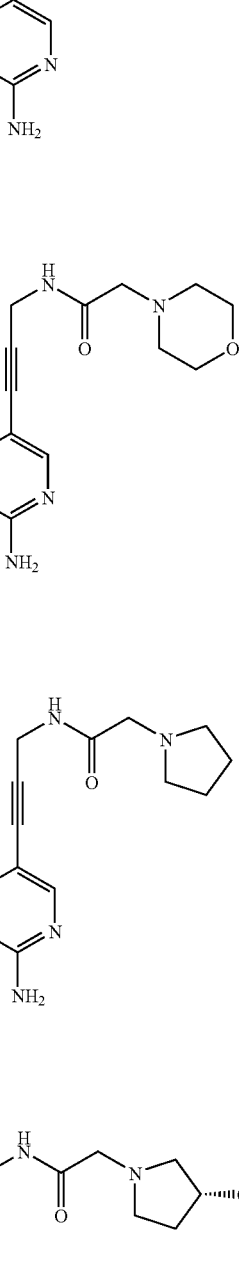 | N-(3-{6-Amino-5-[1-(2,6-dichloro-3-fluoro-phenyl)-ynyl)-2-pridin-1-y-ehoxy]-pyridin-3-yf}-prop-2-acetamide | <0.0091 |
| I-427 | 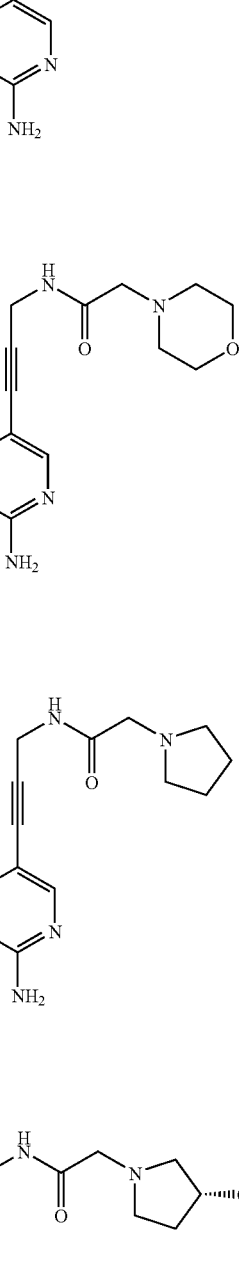 | N-(3-{6-Amino-5-[1-(2,6-dichloro-3-fluoro-phenyl)-ethoxy]-pyridin-3-yl}-prop-2-ynyl)-2-((R)-3-hydroxy-pyrrolidin-1-yl)-acetamide | 0.011 |

TABLE 2-continued

| I-428 | 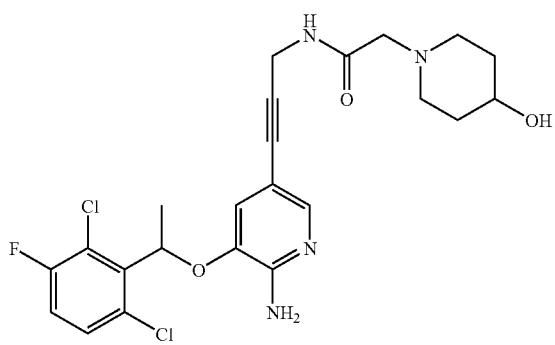 | N-(3-{6-Amino-5-[1-(2,6-dichloro-3-fluoro-phenyl)-ethoxy]-pyridin-3-yl}-prop-2-ynyl)-2-(4-hydroxy-piperidin-1-yl)-acetamide | 0.012 |
| --- | --- | --- | --- |
| I-429 | 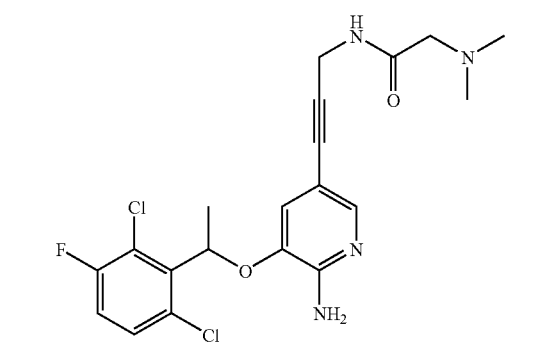 | N-(3-{6-Amino-5-[1-(2,6-dichloro-3-fluoro-phenyl)-ethoxy]-pyridin-3-yl}-prop-2-ynyl)-2-dimethylamino-acetamide | 0.022 |
| I-430 | 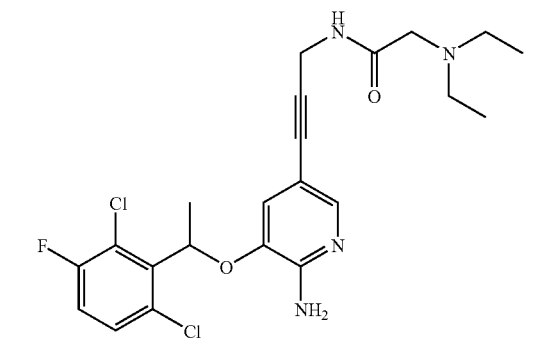 | N-(3-{6-Amino-5-[1-(2,6-dichloro-3-fluoro-phenyl)-ehoxy]-pyridin-3-yl}-prop-2-ynyl)-2-diethylamino-acetamide | 0.013 |
| I-431 | 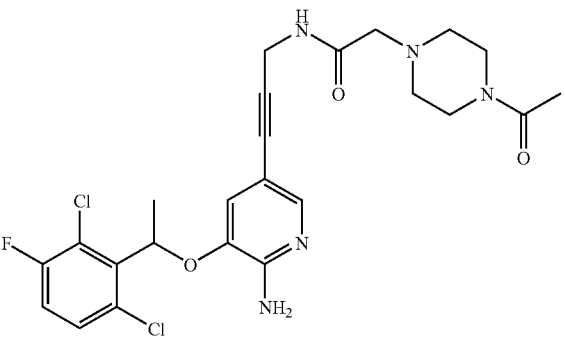 | 2-(4-Acetyl-piperazin-1-yl)-N-(3-{8-amino-5-[1-(2,6-dichloro-3-fluoro-phenyl)-ethoxy]pyridin-3-yl}-prop-2-ynyl)-acetamide | 0.027 |

TABLE 2-continued

| | | | |
|---|---|---|---|
| I-432 | 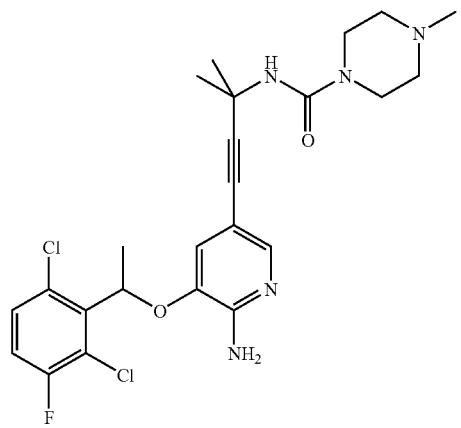 | 4-Methy-piperazine-1-carboxylic acid (3-{6-amino-5-[1-(2,6-dichloro-3-fluoro-phenyl)-ethoxy]-pyridin-3-yl}-1,1-dimethyl-prop-2-ynyl)-amide | Ki 0.61 |
| I-433 | 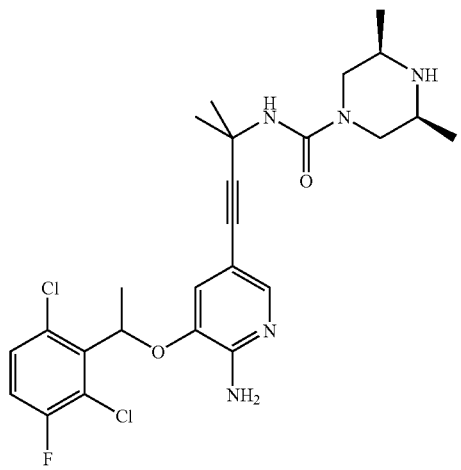 | (3R,5S)-3,5-Dimethyl-piperazine-1-carboxylic acid (3-{6-amino-5-[1-(2,6-dichloro-3-fluoro-phenyl)-ethoxy]-pyridin-3-yl}-1,1-dimethyl-prop-2-ynyl)-amide | Ki 1.5 |
| I-434 | 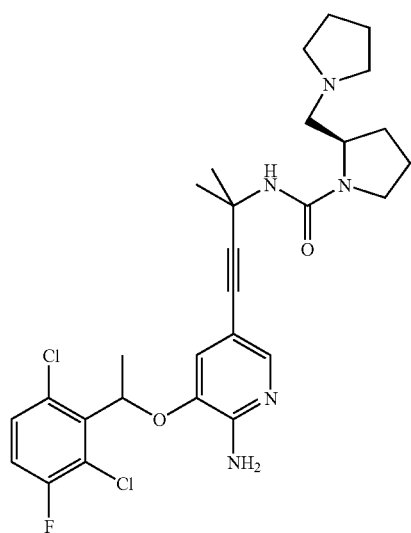 | (R)-2-Pyrrolidin-1-ylmethyl-pyrrolidine-1-carboxylic acid (3-{8-amino-5-[1-(2,8-dichloro-3-fluoro-phenyl)-ethoxy]-pyridin-3-yl}-1,1-dimethyl-prop-2-ynyl)-amide | Ki 1.22 |

TABLE 2-continued
I-435 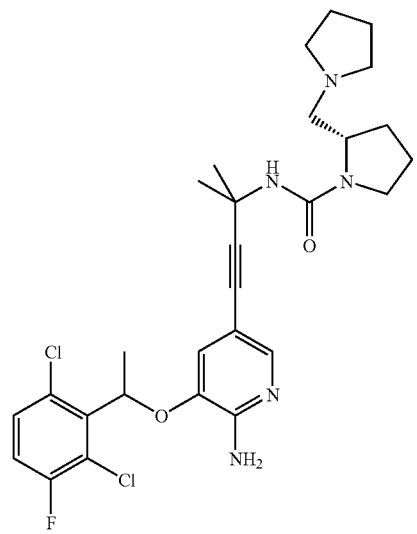 (S)-2-Pyrrolidin-1-ylmethyl-pyrrolidine-1-carboxylic acid (3-{6-amino-5-[1-(2,8-dichloro-3-fluoro-phenyl)-ethoxy]-pyridin-3-yl}-1,1-dimethyl-prop-2-ynyl)-amide    Ki 1.58
I-436 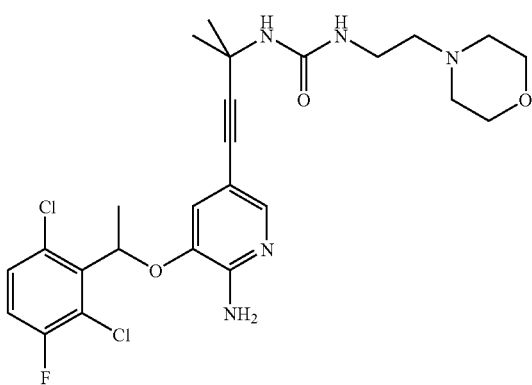 1-(3-(8-Amino-5-[1-(2,6-dichloro-3-fluoro-phenyl)-ethoxy]-pyridin-3-yl)-1,1-dimethyl-prop-2-ynyl)-3-(2-morpholin-4-yl-ethyl)-urea    Ki 1.11
I-437 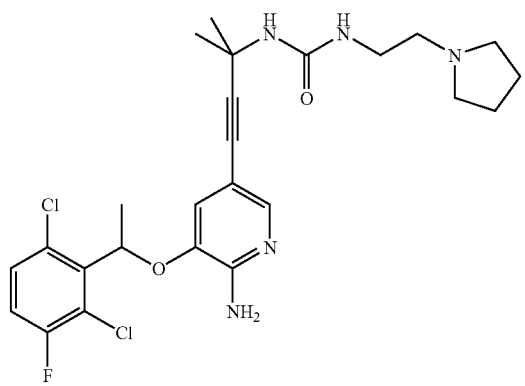 1-(3-{8-Amino-5-[1-(2,8-dichloro-3-fluoro-phenyl)-ethoxy]-pyridin-3-yl]-1,1-dimethyl-prop-2-ynyl)-3-(2-pyrrolidin-1-yl-ethyl)-urea    Ki 0.61

TABLE 2-continued

| | | | |
|---|---|---|---|
| I-438 | 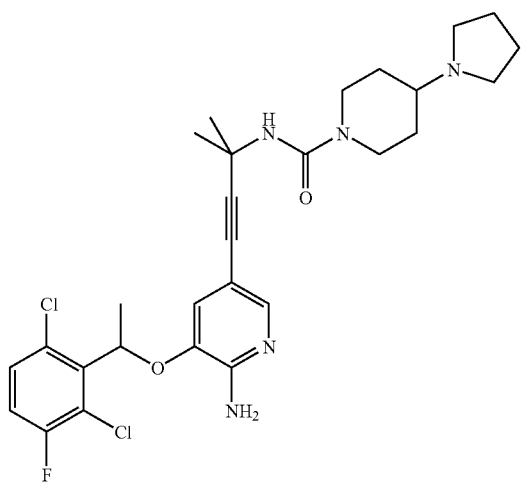 | 4-Pyrrolidin-1-yl-piperidine-1-carboxylic acid (3-{8-amino-5-[1-(2,8-dichloro-3-fluoro-phenyl)-ethoxy]-pyridin-3-yl}-1,1-dimethyl-prop-2-ynyl)-amide | Ki 0.72 |
| I-439 | 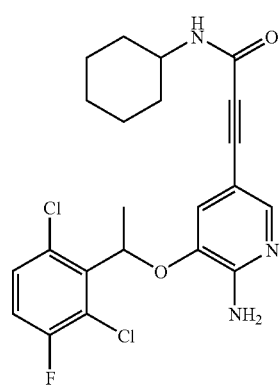 | 3-{8-Amino-5-[1-(2,6-dichloro-3-fluoro-phenyl)-ethoxy]-pyridin-3-yl}-propynoic acid cyclohexylamide | Ki 0.46 |
| I-440 | 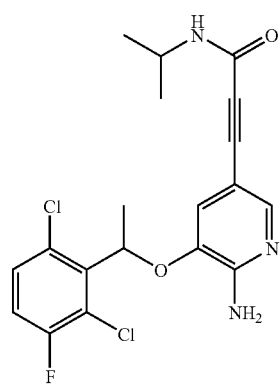 | 3-{6-Amino-5-[1-(2,6-dichloro-3-fluora-phenyl)-ethoxy]-pyridin-3-yl}-propynoic acid isopropylamide | Ki 0.43 |
| I-441 | 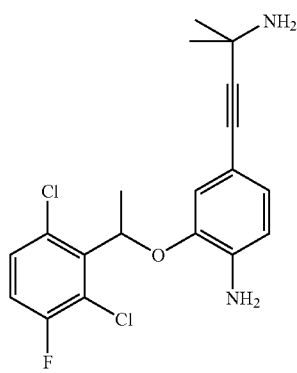 | 4-(3-Amino-3-methyl-but-1-ynyl)-2-[1-(2,8-dichloro-3-fluoro-phenyl)-ethoxy]-phenylamine | Ki 1.06 |

| | | | |
|---|---|---|---|
| I-442 | 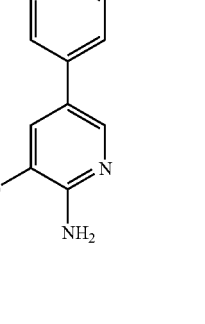 | (4-{6-Amino-5-[1-(3-fluoro-2-trifluoromethyl-phenyl)-ethoxy]-pyridin-3-yl}-phenyl)-(4-methyl-piperazin-1-yl)-methanone | 16% at 1 μM |
| I-443 | 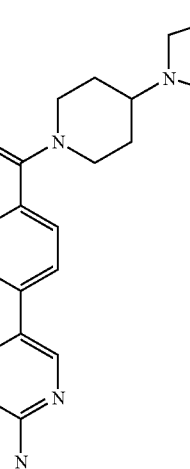 | (4-{6-Amino-5-[1-(3-fluoro-2-trifluoromethyl-phenyl)-ethoxy]-pyridin-3-yl}-phenyl)-(4-pyrrolidin-1-yl-piperidin-1yl)-methanone | 13% at 1 μM |
| I-444 | 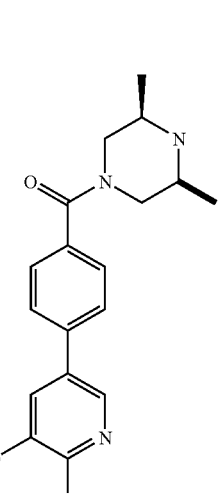 | (4-{6-Amino-5-[1-(3-fluoro-2-trinuommethyl-phenyl)-ethoxy]-pyridin-3-yl}-phenyl)-((3R,5S)-3,5-dimethyl-piperazin-1-yl)-methanone | 10% at 1 μM |

TABLE 2-continued
I-445 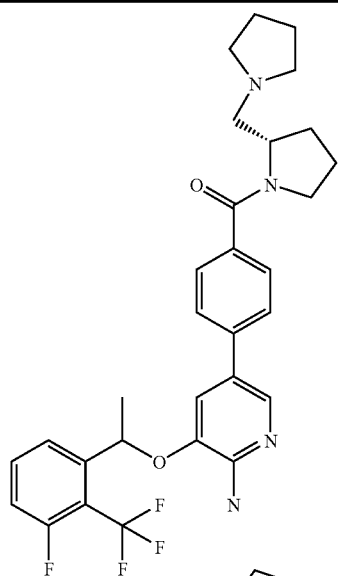 (4-{6-Amino-5-[1-(3-fluoro-2-trifluoromethyl-phenyl)-ethoxy]-pyuidin-3-yl}-phenyl)-((S)-2-pyrrolidin-1-ylmethyl-pyrrolidin-1-yl)-methanone | 15% at 1 µM
I-446 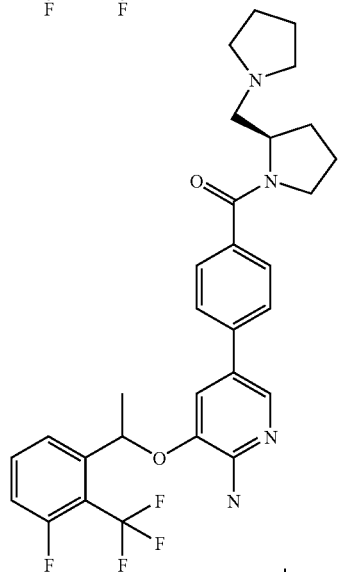 (4-{6 Amino-5-[1-(3-fluoro-2-trifluoromethyl-phenyl)-ethoxy]pyridin-3-yl}-phenyl)-((R) 2 pyrrolidin-1-ylmethyl-pyrrolidin-1-yl)-methanone | 12% at 1 µM
I-449 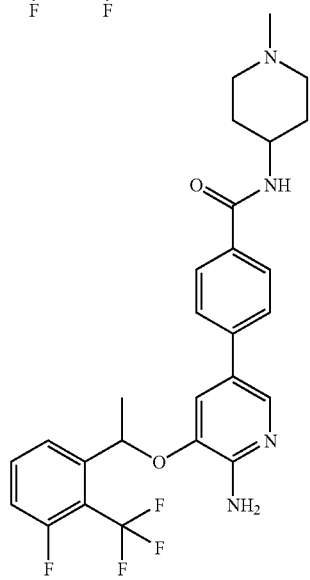 4-{6-Amino-5-[1-(3-fluoro-2-trifluoromethyl-phenyl)-ethoxy]pyridin-3-yl}-N-[1-methyl piperidin-4-yl)-benzamide | 12% at 1 µM

TABLE 2-continued
| ID | Structure | Name | Activity |
|---|---|---|---|
| I-450 | 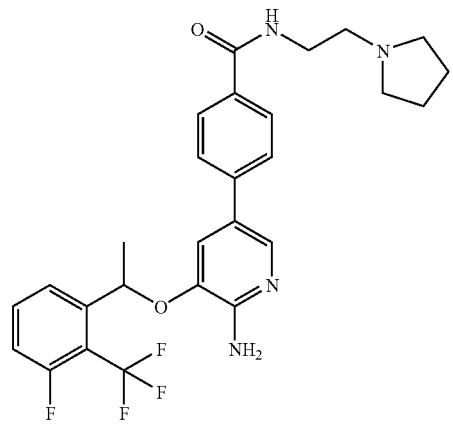 | 4-{6-Amino-5-[1-(3-fluoro-2-trifluoromethyl-phenyl)-ethoxy]-pyridin-3-yl}-N-(2-pyrrolidin-1-yl-ethyl)-benzamide | 7% at 1 μM |
| I-451 | 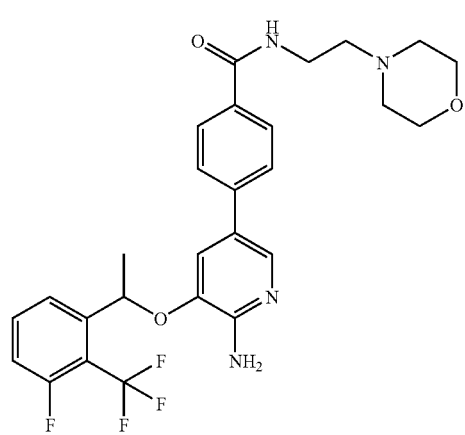 | 4-{6-Amino-5-[1-(3-fluoro-2-trifluoromethyl-phenyl)-ethoxy]-pyridin-3-yl}-N-(2-morpholin-4-yl-ethyl)-benzamide | 12% at 1 μM |
| I-452 | 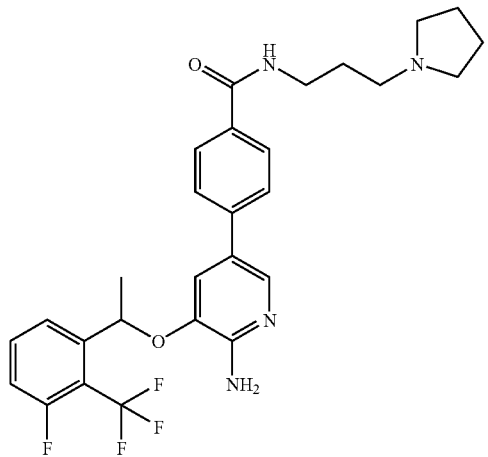 | 4-{6-Amino-5-[1-(3-fluoro-2-trifluoromethyl-phenyl)-ethoxy]-pyridin-3-yl}-N-(3-pyrrolidin-1-yl-propyl)-benzamide | 3% at 1 μM |

TABLE 2-continued
| | | | |
|---|---|---|---|
| I-453 | 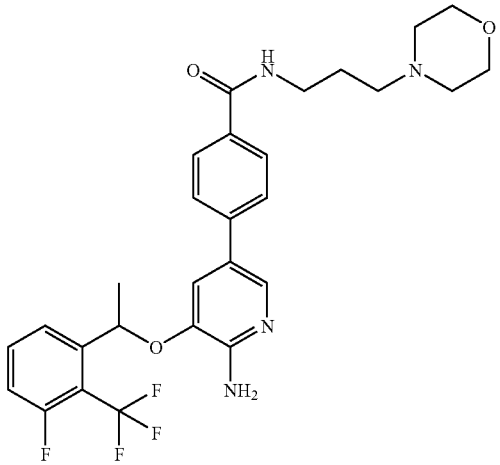 | 4-{6-Amino-5-[1-(3-fluoro-2-trifluoromethyl-phenyl)-ethoxy]-pyridin-3-yl}-N-(3-morpholin-4-yl-propyl)-benzamide | 10% at 1 μM |
| I-454 | 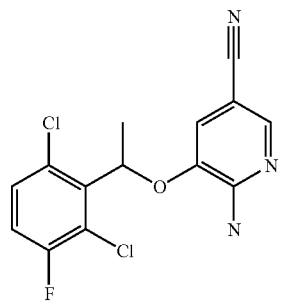 | 6-Amino-5-[1-(2,6-dichloro-fluoro-phenyl)-ethoxy]-nicotinonitrile | 7% at 1 μM |
| I-455 | 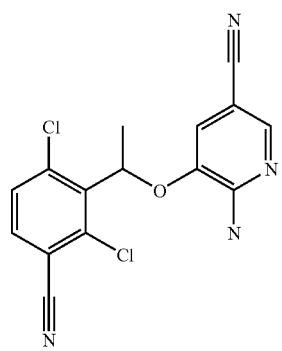 | 6-Amino-5-[1-(2,6-dichloro-3-cyano-phenyl)-ethoxy]-nicotinonitrile | 8% at 1 μM |
| I-456 | 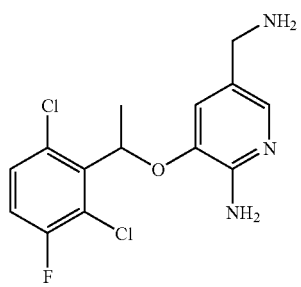 | 5-Aminomethyl-3-[1-(2,6-dichloro-3-fluoro-phenyl)-ethoxy]-pyridin-2-ylamine | 0% at 1 μM |

TABLE 2-continued

I-457 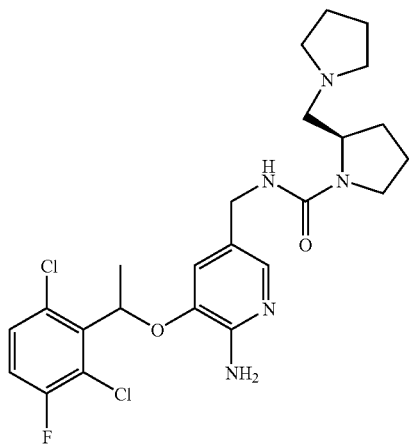 (R)-2-Pyrrolidin-1-ylmethyl-pyrrolidine-1-carboxylic acid {6-amino-5-[1-(2,6-dichloro-3-fluoro-phenyl)-ethoxy]-pyridin-3-ylmethyl}-amide | 1% at 1 µM I-458 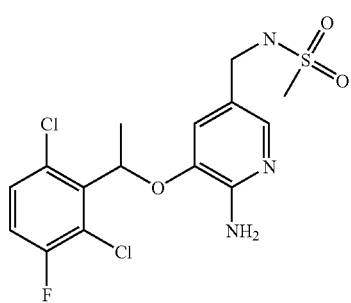 N-{6-Amino-5-[1-(2,6-dichloro-3-fluorophenyl)-ethoxy]-pyridin-3-ylmethyl}-methanesulfonamide | 0% at 1 µM I-459 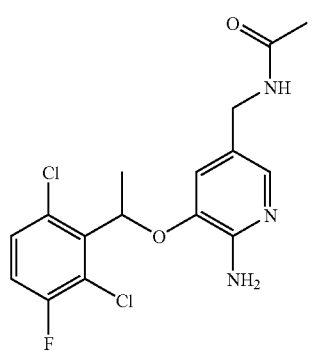 N-{6-Amino-5-[1-(2,6-dichloro-3-fluoro-phenyl)-ethoxy]-pyridin-3-ylmethyl}-acetamide | 2% at 1 µM I-460 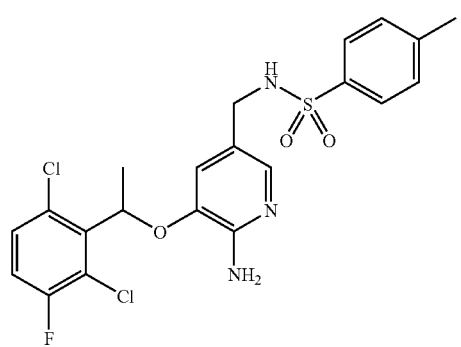 N-{6-Amino-5-[1-(2,6-dichloro-3-fluoro-phenyl)-ethoxy]-pyridin-3-ylmethyl}-4-methyl-benzenesulfonamide | 9% at 1 µM

| | | | |
|---|---|---|---|
| I-461 | 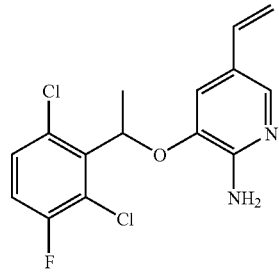 | 3-[1-(2,6-Dichloro-3-fluoro-phenyl)-ethoxy]-5-vinyl-pyridin-2-ylamine | Ki 0.68 |
| I-462 | 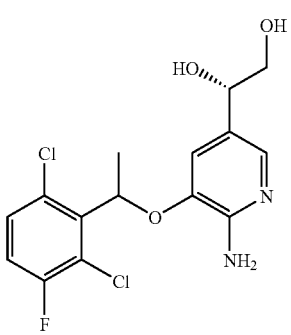 | (S)-1-{6 Amino-5-[1-(2,6-dichloro-3-fluoro-phenyl)-ethoxy]-pyridin-3-yl}-ethane-1,2-diol | 2% at 1 μM |
| I-463 | 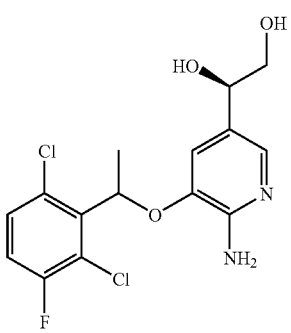 | (R)-1-{6-Amino-5-[1-(2,6-dichloro-3-fluoro-phenyl)-ethoxy]-pyridin-3-yl}-ethane-1,2-diol | 2% at 1 μM |
| I-464 | 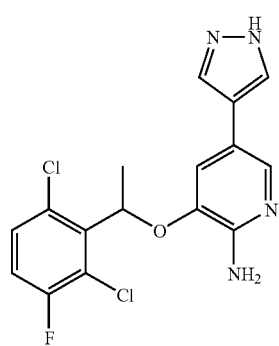 | 3-[1-(2,6-Dichloro-3-fluoro-phenyl)-ethoxy]-5-(1H-pyrazol-4-yl)-pyridin-2-ylamine | Ki 0.10 |

TABLE 2-continued
| I-465 | 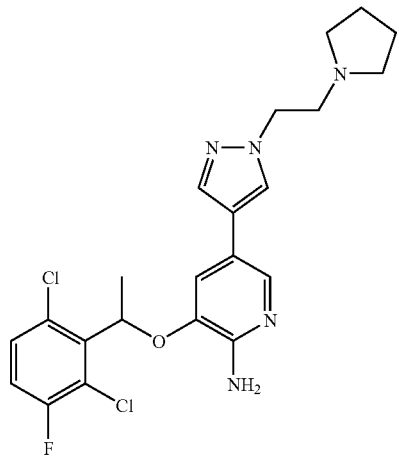 | 3-[1-(2,6-Dichloro-3-fluoro-phenyl)-ethoxy]-5-[1-(2-pyrrolidin-1-yl-ethyl)-1H-pyrazol-4-yl]-pyridin-2-ylamine | Ki 0.34 |
| I-466 | 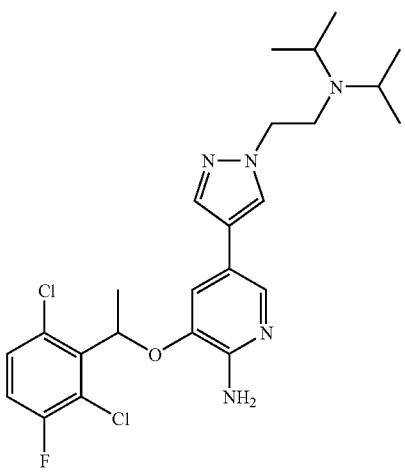 | 3-[1-(2,6-Dichloro-3-fluoro-phenyl)-ethoxy]-5-[1-(2-duisopropylamino-ethyl)-1H-pyrazol-4-yl]-pyridin-2-yl amine | Ki 0.47 |
| I-467 | 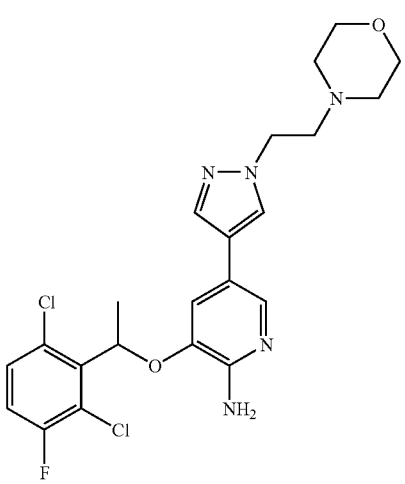 | 3-[1-(2,6-Dichloro-3-fluoro-phenyl)-ethoxy]-5-[1-(2-morpholin-4-yl-ethyl)-1H-pyrazol-4-yl]-pyridin-2-ylamine | Ki 0.083 |

TABLE 2-continued
| ID | Structure | Name | Activity |
|---|---|---|---|
| I-468 | 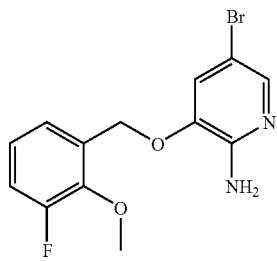 | 5-Bromo-3-(3-fluoro-2-methoxy-benzyloxy)-pyridin-2-ylamine | 8% at 1 µM |
| I-469 | 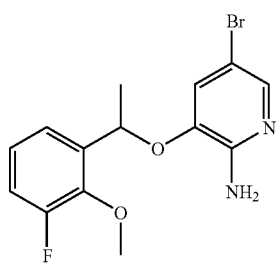 | 5-Bromo-3-[1-(3-fluoro-2-methoxy-phenyl)-ethoxy]-pyridin-2-ylamine | 7% at 1 µM |
| I-470 | 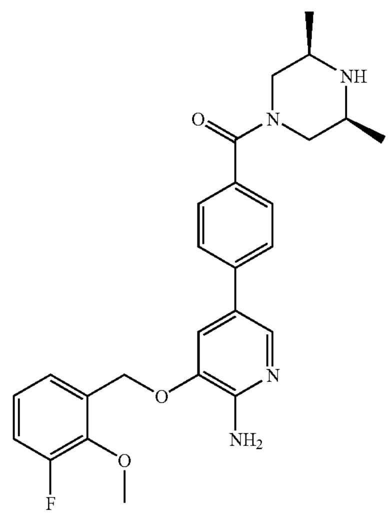 | (4-{6-Amino-5-(3-fluoro-2-methoxy-benzyloxy)-pyridin-3-yl]-phenyl}-((3R,5S)-3,5-dimethyl-piperazin-1-yl)-methanone | 3% at 1 µM |
| I-471 | 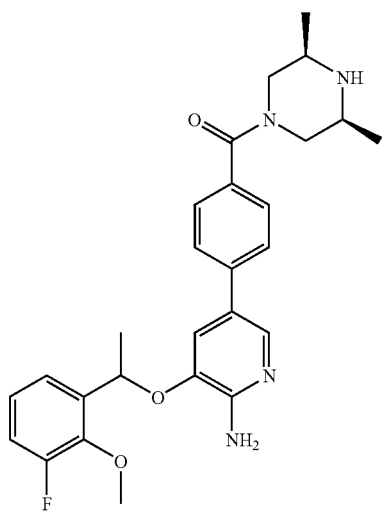 | (4-{6-Amino-5-[1-(3-fluoro-2-methoxy-phenyl)-ethoxy]-pyridin-3-yl}-phenyl)-((3R,5S)-3,5-dimethyl-pyridin-1-yl)-methanone | 1% at 1 µM |

| | | | |
|---|---|---|---|
| I-472 | 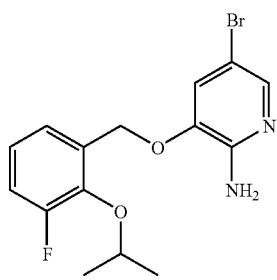 | 5-Bromo-3-(3-fluoro-2-isopropoxy-benzyloxy)-pyridin-2-ylamine | Ki 12.1 |
| I-473 | 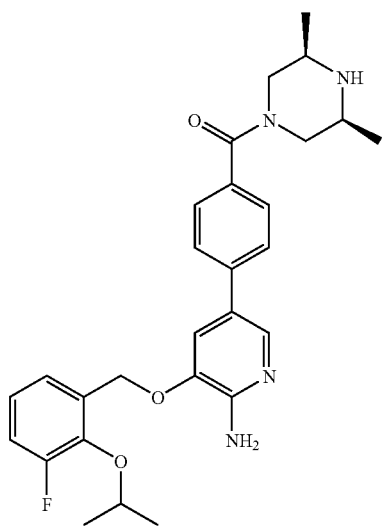 | {4-[6-Amino-5-(3-fluoro-2-isopropoxy-benzyloxy)-pyridin-3-yl]-phenyl}-((3R,5S)-3,5-dimethyl-piperazin-1-yl)-methanone | Ki 12.7 |
| I-474 | 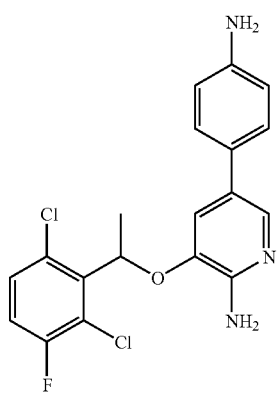 | 5-(4-Amino-phenyl)-3-[1-(2,6-dichloro-3-fluoro-phenyl)-ethoxy]-pyridin-2-ylamine | |
| I-475 | 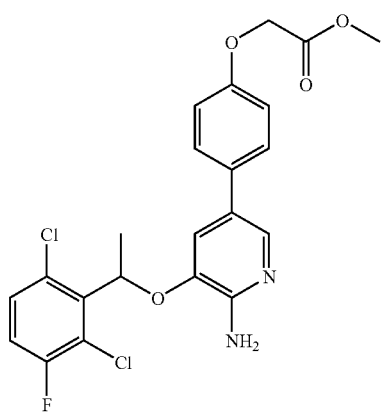 | (4-{6-Amino-5-[1-(2,6-dichloro-3-fluoro-phenyl)-ethoxy]-pyridin-3-yl}-phenoxy)-acetic acid methyl ester | Ki 0.20 |

| | | | |
|---|---|---|---|
| I-476 | 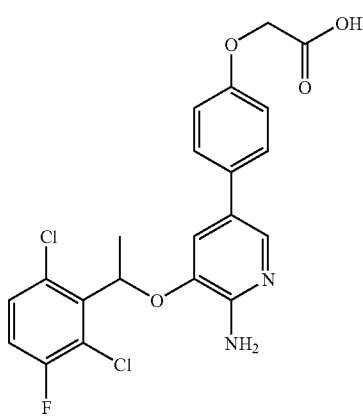 | (4-{6-Amino-5-[1-(2,6-dichloro-3-fluoro-phenyl)-ethoxy]-pyridin-3-yl}-phenoxy)-acetic acid | Ki 0.20 |
| I-477 | 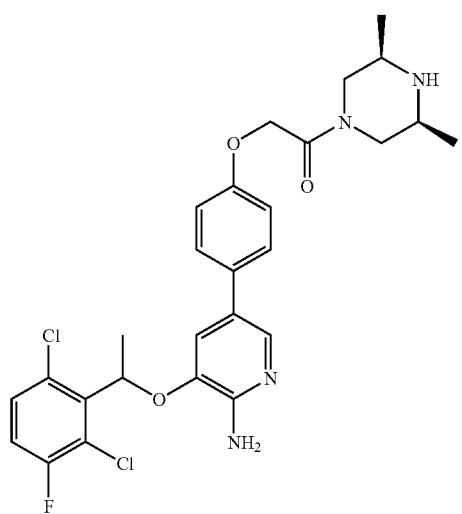 | 2-(4-{6-Amino-5-[1-(2,6-dichloro-3-fluoro-phenyl)-ethoxy]-pyridin-3-yl}-phenoxy)-1-((3R,5S)-3,5-dimethyl-piperazin-1-yl)-ethanone | Ki 0.027 |
| I-478 | 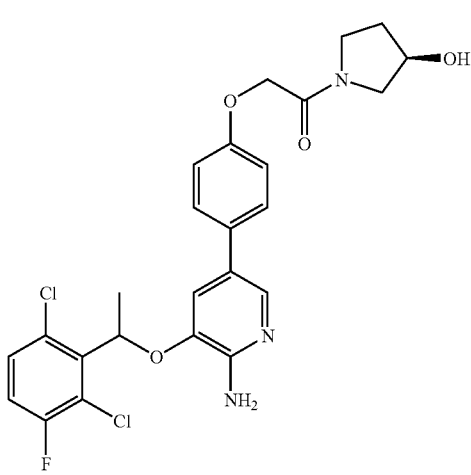 | 2-(4-{6-Amino-5-[1-(2,6-dichloro-3-fluoro-phenyl)-ethoxy]-pyridin-3-yl}-phenoxy)-1-((R)-3-hydroxy-pyrrolidin-1-yl)-ethanone | Ki 0.041 |

TABLE 2-continued
I-479 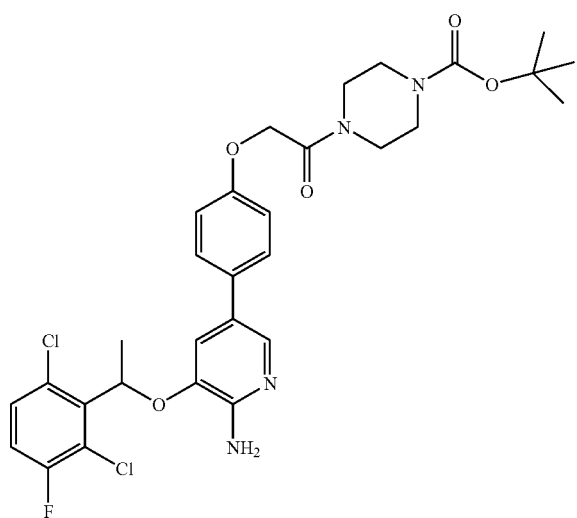 4-[2-(4-{8-Amino-5-[1-(2,6-dichloro-3-fluoro-phenyl)-ethoxy]-pyridin-3-yl}-phenoxy)-acetyl]-piperazine-1-carboxylic acid tert-butyl ester  Ki 0.016
I-480 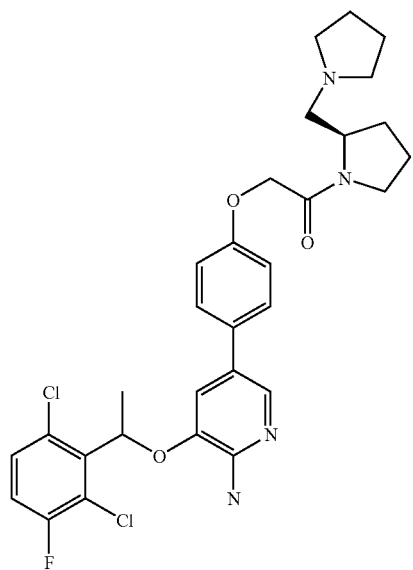 2-(4-{6-Amino-5-[1-(2,6-dichloro-3-fluoro-phenyl)-ethoxy]-pyridin-3-yl}-phenoxy)-1-((R)-2-pyrrolidin-1-ylmethyl-pyrrolidin-1-yl)-ethanone
I-481 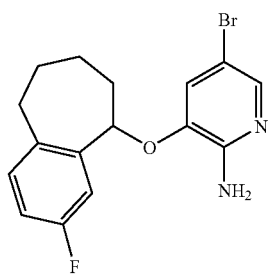 5-Bromo-3-(3-fluoro-8,7,8,9-tetrahydro-5H-benzocyclohepten-5-yloxy)-pyridin-2-ylamine TABLE 2-continued
I-482 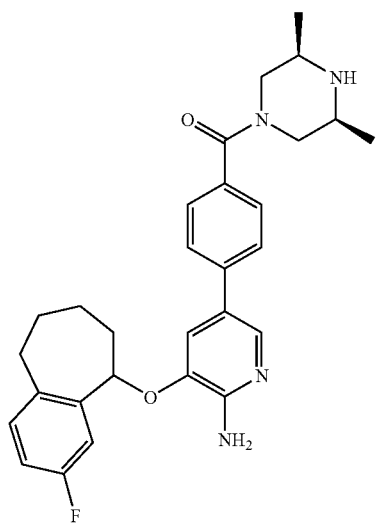 {4-{6-Amino-5-(3-fluoro-6,7,8,9-tetrahydro-5H-benzocyclohepten-5-yloxy)-pyridin-3-yl]-phenyl}-((3R,5S)-3,5-dimethyl-piperazin-1-yl)-methanone
I-483 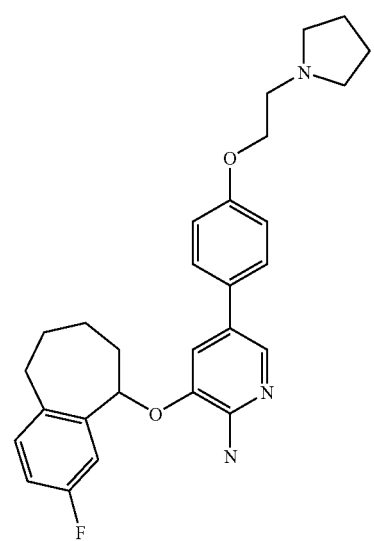 3-(3-Fluoro-6,7,8,9-tetrahydro-5H-benzocyclohepten-5-yloxy)-5-[4-(2-pyrrolidin-1-yl-ethoxy)-phenyl]-pyridin-2-ylamine
I-484 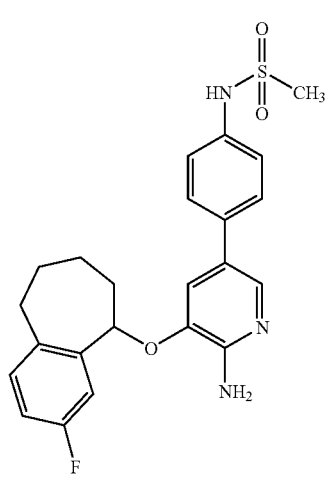 N-{4-{6-Amino-5-(3-fluoro-6,7,8,9-tetrahydro-5H-benzocyclohepten-5-yloxy)-pyridin-3-yl]-phenyl}-methanesulfonamide TABLE 2-continued
I-485 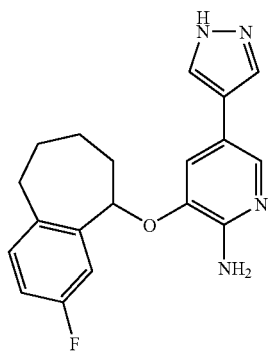 3-(3-Fluoro-6,7,8,9-tetrahydro-5H-benzocyclohepten-5-yloxy)-(1H-pyrazol-4-yl)-pyridin-2-ylamine
I-486 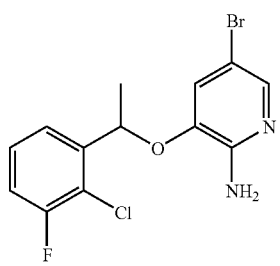 Bromo-3-[1-(2-chloro-3-fluoro-phenyl)-ethoxy]-pyridin-2-ylamine | 0% at 1 μM
I-487 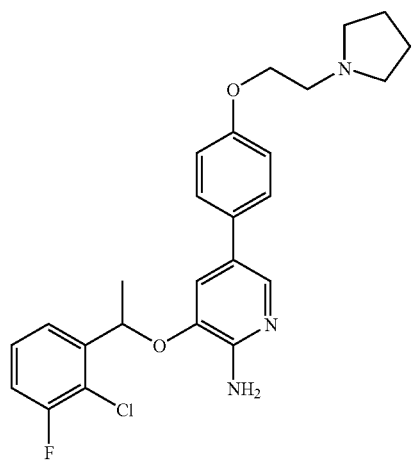 3-[1-(2-Chloro-3-fluoro-phenyl)-ethoxy]-5-[4-(2-pyrrolidin-1-yl-ethoxy)-phenyl]-pyridin-2-ylamine | Ki 3.30
I-488 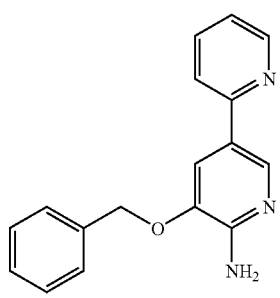 5'-Benzyloxy-[2,3']bipyridinyl-6'-ylamine | >20

TABLE 2-continued

| | | | |
|---|---|---|---|
| I-489 | | 5-Benzyloxy-[3,3']bipyridinyl-6-ylamine | >20 |
| I-490 | | Benzyloxy-5-pyrimidin-5-yl-pyridin-2-ylamine | >20 |
| I-491 | | 5-Benzyloxy-[3,3']bipyridinyl-6,6'-diamine | >20 |
| I-492 | | 5-(2-Chloro-benzyloxy)-[2,3']bipyridinyl-6'-ylamine | 8.24 |
| I-493 | | 5-(2-Chloro-benzyloxy)-[3,3']bipyridinyl-6-ylamine | 4.6 |

TABLE 2-continued

| | | | |
|---|---|---|---|
| I-494 | | 3-(2-Chloro-benzyloxy)-5-pyrimidin-5-yl-pyridin-2-ylamine | 19.3 |
| I-495 | | 5-(2-Chloro-benzyloxy)-[3,3']bipyridinyl-6,6'-diamine | 4.31 |
| I-496 | | 5'-(4-Chloro-benzyloxy)-[2,3']bipyridinyl-6'-ylamine | 14 |
| I-497 | | 5'-(4-Chloro-benzyloxy)-[3,3']bipyridinyl-6-ylamine | 14 |
| I-498 | | 3-(4-Chloro-benzyloxy)-5-pyrimidin-5-yl-pyridin-2-ylamine | >20 |

TABLE 2-continued

| ID | Structure | Name | Value |
|---|---|---|---|
| I-499 | 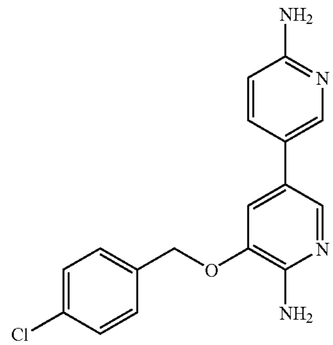 | 5-(4-Chloro-benzyloxy)-[3,3']bipyridinyl-6,6'-diamine | >20 |
| I-500 | 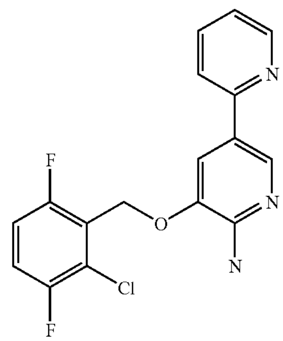 | 5-(2-Chloro-3,6-difluoro-benzyloxy)-[2,3']bipyridinyl-6'-ylamine | 1.8 |
| I-501 | 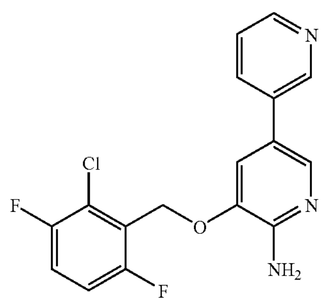 | 5-(2-Chloro-3,6-difluoro-benzyloxy)-[3,3']bipyridinyl-6-ylamine | 0.282 |
| I-502 | 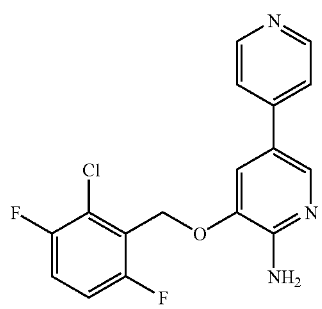 | 5-(2-Chloro-3,6-difluoro-benzyloxy)-[3,4' bipyridinyl-6-ylamine | 0.211 |
| I-503 | 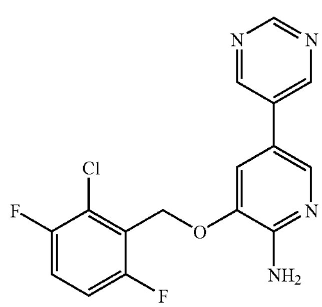 | 3-(2-Chloro-3,6-difluoro-benzyloxy)-5-pyrimidin-5-yl-pyridin-2-ylamine | 2.15 |

TABLE 2-continued

| ID | Name | Value |
|---|---|---|
| I-504 | 5-(2-Chloro-3,6-difluoro-benzyloxy)-(3,3']bipyridinyl-6,6'-diamine | 0.209 |
| I-505 | 5'-(2,6-Dichloro-benzyloxy)-[2,3']bipyridinyl-6-ylamine | 2.84 |
| I-506 | 5-(2,6-Dichloro-benzyloxy)-[3,3']bipyridinyl-8-ylamine | 2.71 |
| I-507 | 5-(2,6-Dichloro-benzyloxy)-[3,4']bipyridinyl-6-ylamine | 1.3 |
| I-508 | 3-(2,6-Dichloro-benzyloxy)-pyrimidin-5-yl-pyridin-2-ylamine | 10.3 |

| | | | |
|---|---|---|---|
| I-509 | 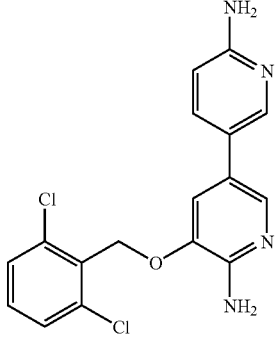 | 5-(2,6-Dichloro-benzyloxy)-[3,3']bipyridinyl-6,6'-diamine | 0.578 |
| I-510 | 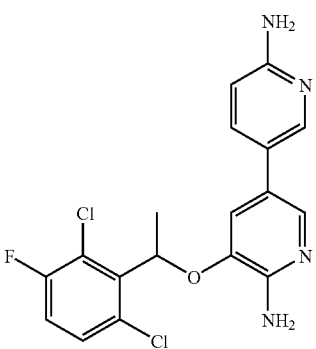 | 5-[1-(2,6-Dichloro-3-fluoro-phenyl)-ethoxy]-[3,3']bipyridinyl-6,6'-diamine | 0.0167 |
| I-511 | 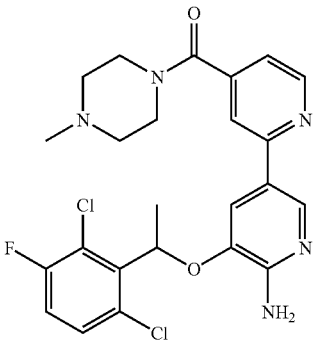 | {6'-Amino-5-[1-(2,6-dichloro-3-fluoro-phenyl)-ethoxy]-[2,3']bipyridinyl-4-yl}-(4-methyl-piperazin-1-yl)-methanone | 0.0742 |
| I-512 | 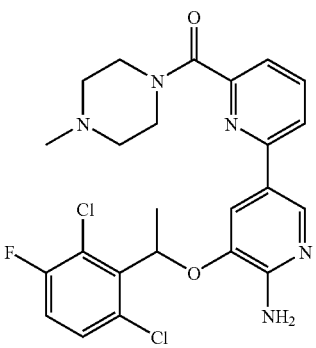 | {6'-Amino-5'-[1-(2,6-dichloro-3-fluoro-phenyl)-ethoxy]-[2,3']bipyridinyl-6-yl}-(4-methyl-piperazin-1-yl)-methanone | 0.0629 |

| | | | |
|---|---|---|---|
| I-513 | 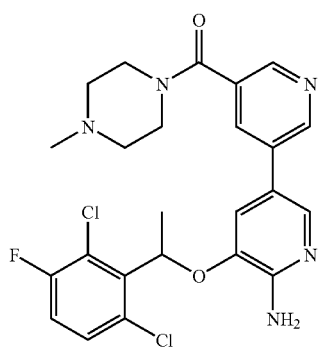 | {6'-Amino-5'-[1-(2,6-dichloro-3-fluoro-phenyl)-ethoxy]-[3,3']bipyridinyl-5-yl}-(4-methyl-piperazin-1-yl)-methanone | 0.034 |
| I-514 | 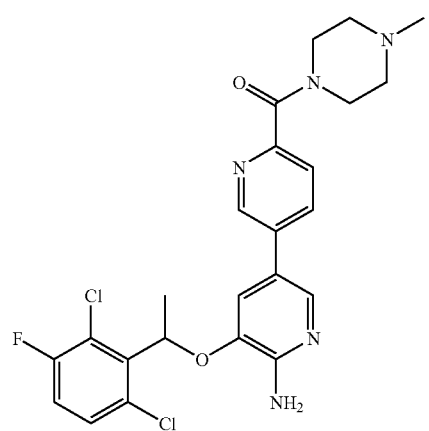 | {6'-Amino-5'-[1-(2,6-dichloro-3-fluoro-phenyl)-ethoxy]-[3,3']bipyridinyl-6-yl}-(4-methyl-piperazin-1-yl)-methanone | 0.0213 |
| I-515 | 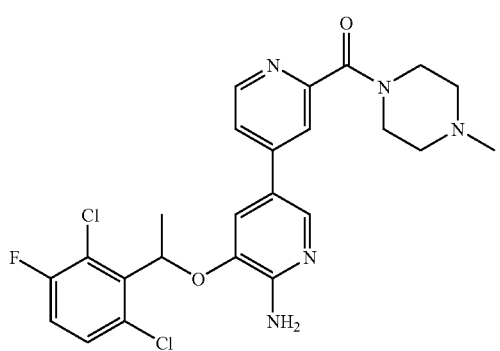 | {6-Amino-5-[1-(2,6-dichloro-3-fluoro-phenyl)-ethoxy]-[3,4]bipyridinyl-2'-yl}-(4-methyl-piperazin-1-yl)-methanone | 0.0387 |
| I-516 | 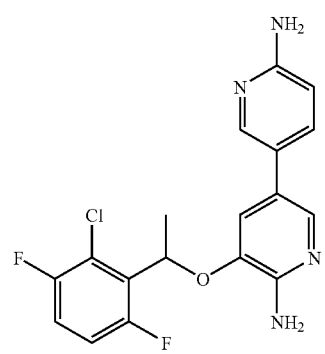 | 5-[1-(2-Chloro-3,6-difluoro-phenyl)-ethoxy]-[3,3']bipyridinyl-6,6'-diamine | 0.0393 |

| | | | |
|---|---|---|---|
| I-517 | 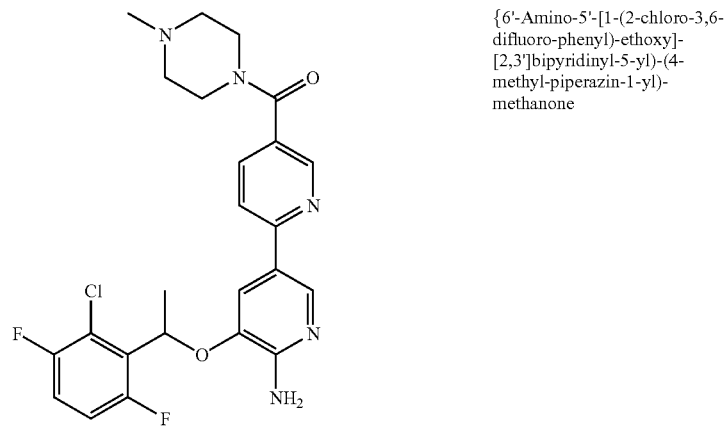 | {6'-Amino-5'-[1-(2-chloro-3,6-difluoro-phenyl)-ethoxy]-[2,3']bipyridinyl-5-yl)-(4-methyl-piperazin-1-yl)-methanone | 0.131 |
| I-518 | 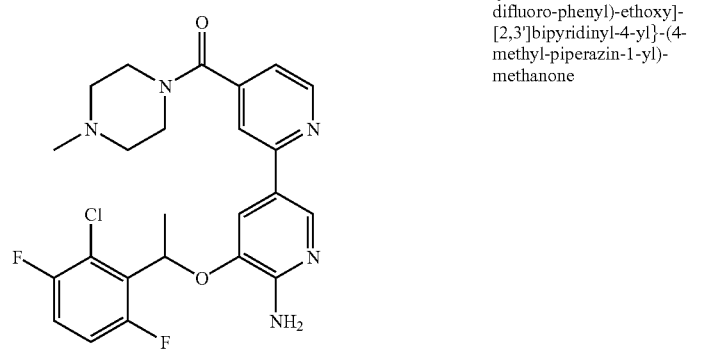 | {6'-Amino-5-[1-(2-chloro-3,6-difluoro-phenyl)-ethoxy]-[2,3']bipyridinyl-4-yl}-(4-methyl-piperazin-1-yl)-methanone | 0.209 |
| I-519 | 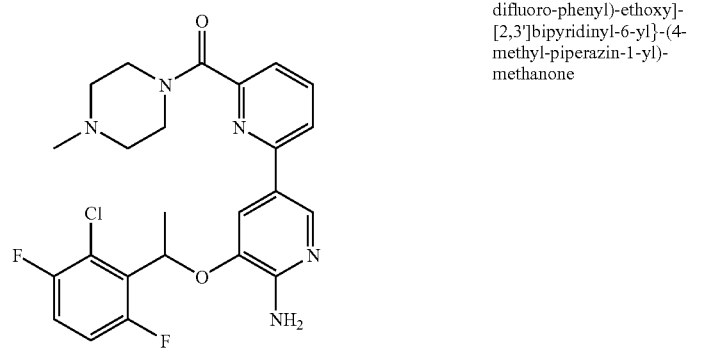 | {6'-Amino-5'-[1-(2-chloro-3,6-difluoro-phenyl)-ethoxy]-[2,3']bipyridinyl-6-yl}-(4-methyl-piperazin-1-yl)-methanone | 0.466 |
| I-520 | 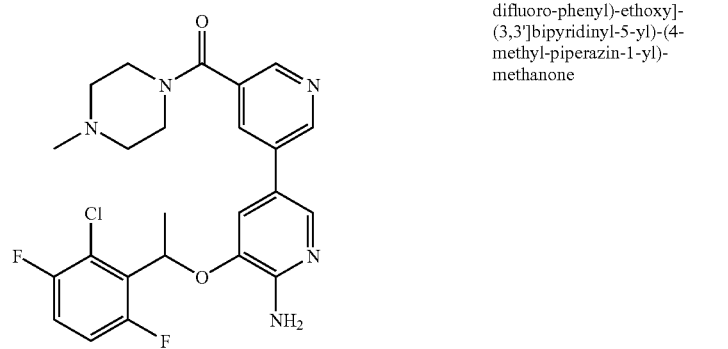 | {6-Amino-5'-[1-(2-chloro-3,6-difluoro-phenyl)-ethoxy]-(3,3']bipyridinyl-5-yl)-(4-methyl-piperazin-1-yl)-methanone | 0.134 |

| | | | |
|---|---|---|---|
| I-521 | 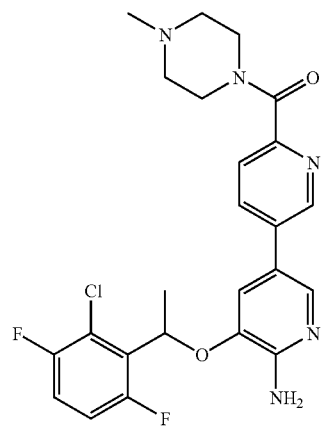 | {6'-Amino-5'-[1-(2-chloro-3,6-difluoro-phenyl)-ethoxy]-[3,3']bipyridinyl-6-yl}-(4-methyl-piperazin-1-yl)-methanone | 0.0716 |
| I-522 | 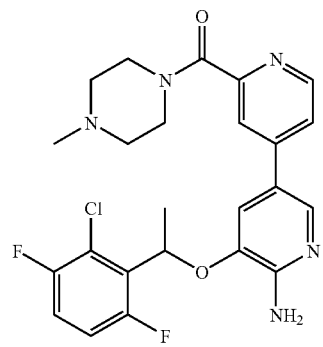 | {6-Amino-5-[1-(2-chloro-3,6-difluoro-phenyl)-ethoxy]-[3,4']bipyridinyl-2-yl}-(4-methyl-piperazin-1-yl)-methanone | 0.0626 |
| I-523 | 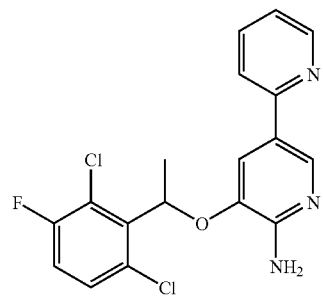 | 5'-[1-(2,6-Dichloro-3-fluoro-phenyl)-ethoxy]-[2,3']bipyridinyl-6'-ylamine | 0.0677 |
| I-524 | 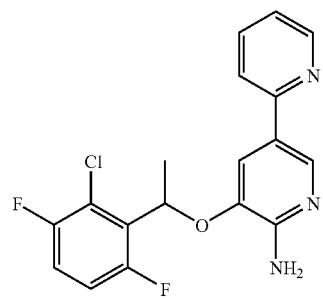 | 5'-[1-(2-Chloro-3,6-difluoro-phenyl)-ethoxy]-[2,3']bipyridinyl-6'-ylamine | 0.612 |

TABLE 2-continued
| | | | |
|---|---|---|---|
| I-525 | 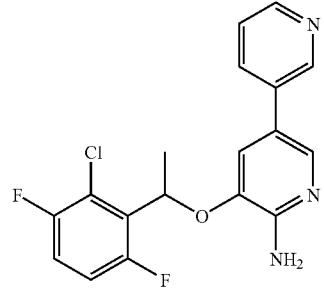 | 5-[1-(2-Chloro-3,6-difluoro-phenyl)-ethoxy]-[3,3']bipyridinyl-6'-ylamine | 0.0777 |
| I-526 | 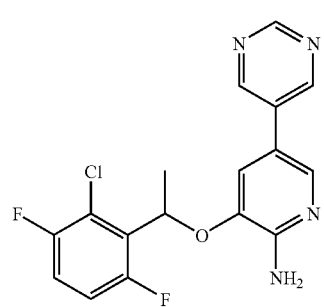 | 3-[1-(2-Chloro-3,6-difluoro-phenyl)-ethoxy]-5-pyrimidin-5-yl-pyridin-2-ylamine | 0.552 |
| I-527 | 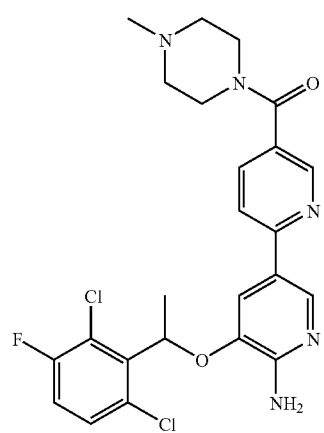 | {6'-Amino-5'-[1-(2,6-dichloro-3-fluoro-phenyl)-ethoxy]-[2,3']bipyridinyl-5-yl}-(4-methyl-piperazin-1-yl)-methanone | 0.0385 |
| I-528 | 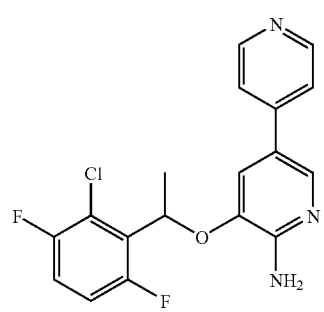 | 5-[1-(2-Chloro-3,6-difluoro-phenyl)-ethoxy]-[3,4']bipyridinyl-6-ylamine | 0.0659 |

TABLE 2-continued
I-529
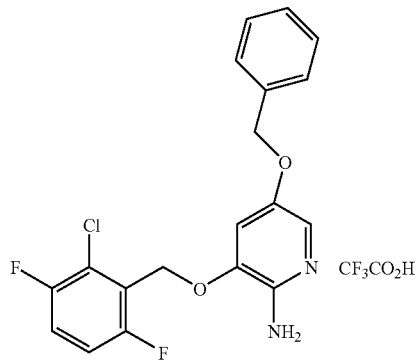
5-Benzyloxy-3-[1-(2-chloro-3,6-difluoro-phenyl)-ethoxy]-pyridin-2-ylamine
2.58
I-530
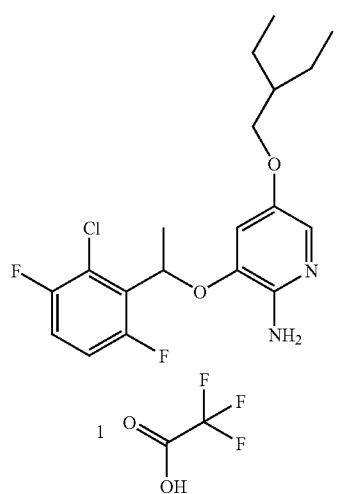
3-[1-(2-Choro-3,6-difluoro-phenyl)-ethoxy]-5-(2-ethyl-butoxy)-pyridin-2-ylamine
4.08
I-531
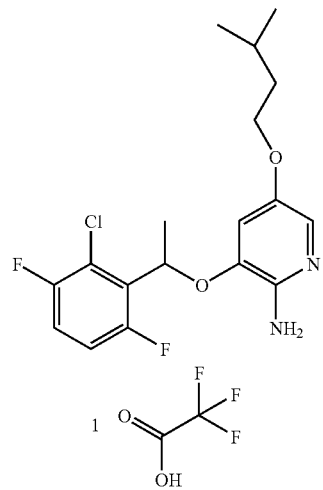
3-[1-(2-Chloro-3,6-difluoro-phenyl)-ethoxy]-5-(3-methyl-butoxy)-pyridin-2-ylamine
2.4

TABLE 2-continued
| | | | |
|---|---|---|---|
| I-532 | 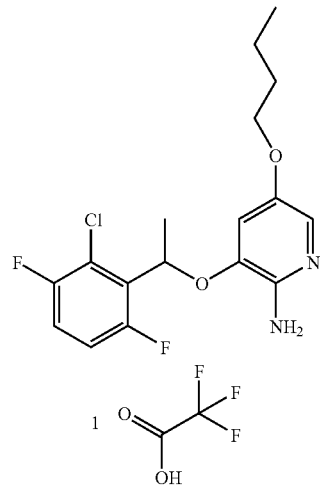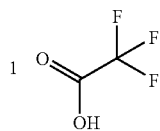 | 3-[1-(2-Chloro-3,6-difluoro-phenyl)-ethoxy]-5-butoxy-pyridin-2-ylamine | 1.94 |
| I-533 | 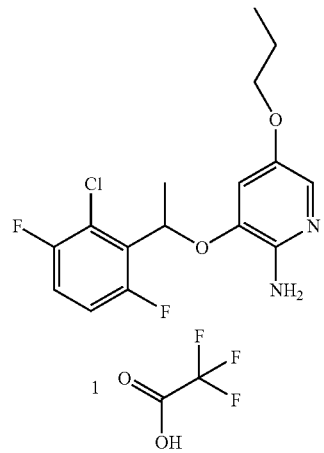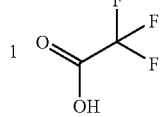 | 3-[1-(2-Chloro-3,6-difluoro-phenyl)-ethoxy]-5-propoxy-pyridin-2-ylamine | 0.672 |
| I-534 | 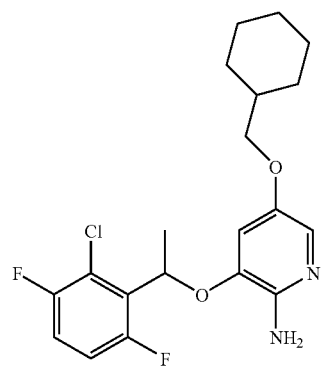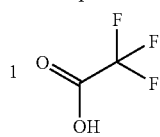 | 3-[1-(2-Chloro-3,6-difluoro-phenyl)-ethoxy]-5-cyclohexylmethoxy-pyridin-2-ylamine | 5.97 |

| | | | |
|---|---|---|---|
| I-535 | 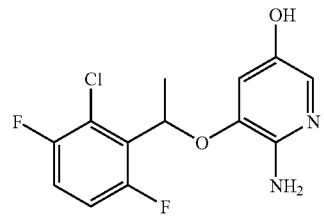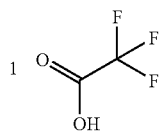 | 6-Amino-5-[1-(2-chloro-3,6-difluoro-phenyl)-ethoxy]-pyridin-3-ol | 0.54 |
| I-536 | 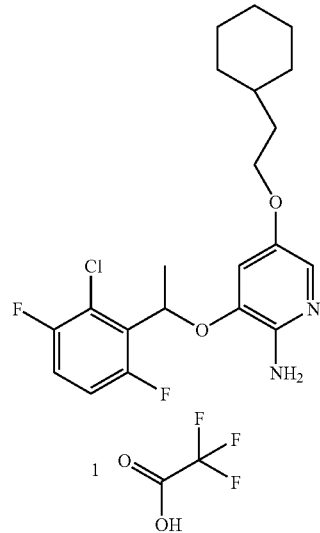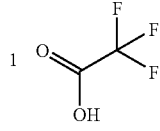 | 3-[1-(2-Chloro-3,6-difluoro-phenyl)-ethoxy]-5-(2-cyclohexyl-ethoxy)-pyridin-2-ylamine | 7.5 |
| I-537 | 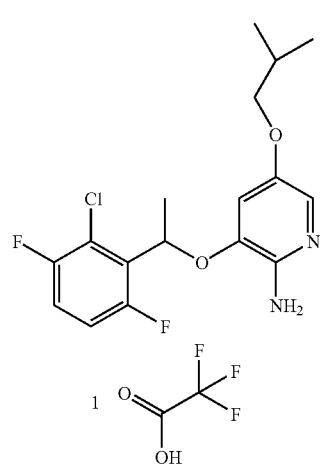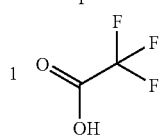 | 3-[1-(2-Chloro-3,6-difluoro-phenyl)-ethoxy]-5-isobutoxy-pyridin-2-ylamine | 1.2 |

TABLE 2-continued
| | | | |
|---|---|---|---|
| I-538 | 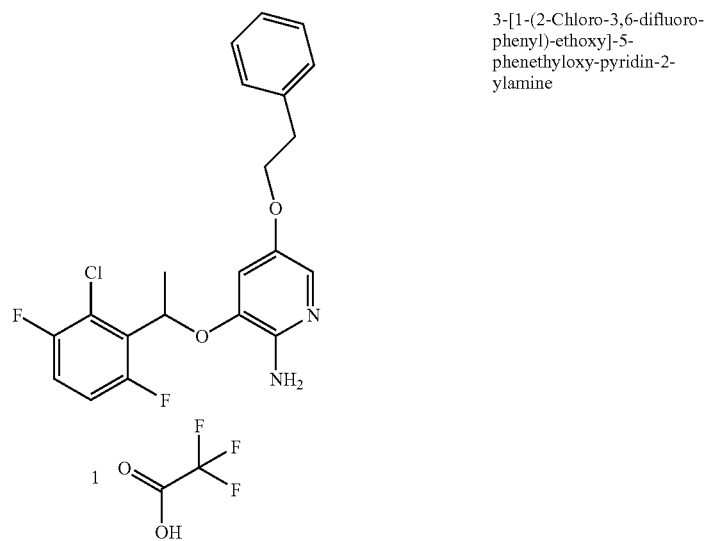 | 3-[1-(2-Chloro-3,6-difluoro-phenyl)-ethoxy]-5-phenethyloxy-pyridin-2-ylamine | 2.8 |
| I-539 | 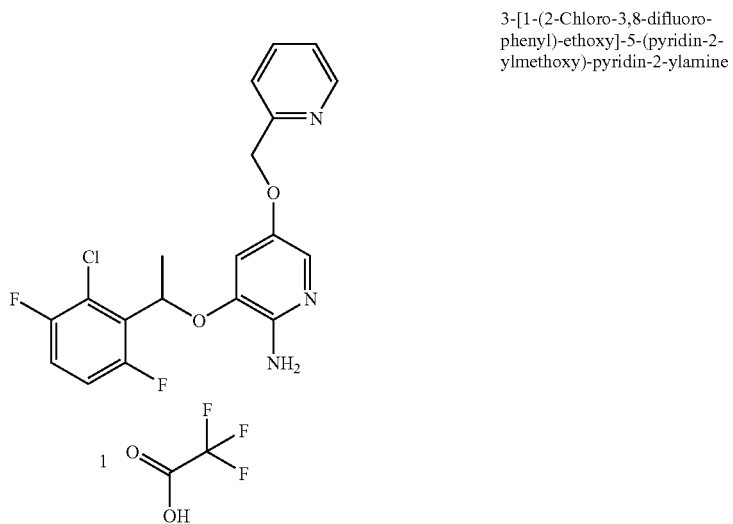 | 3-[1-(2-Chloro-3,8-difluoro-phenyl)-ethoxy]-5-(pyridin-2-ylmethoxy)-pyridin-2-ylamine | 3.2 |
| I-540 | 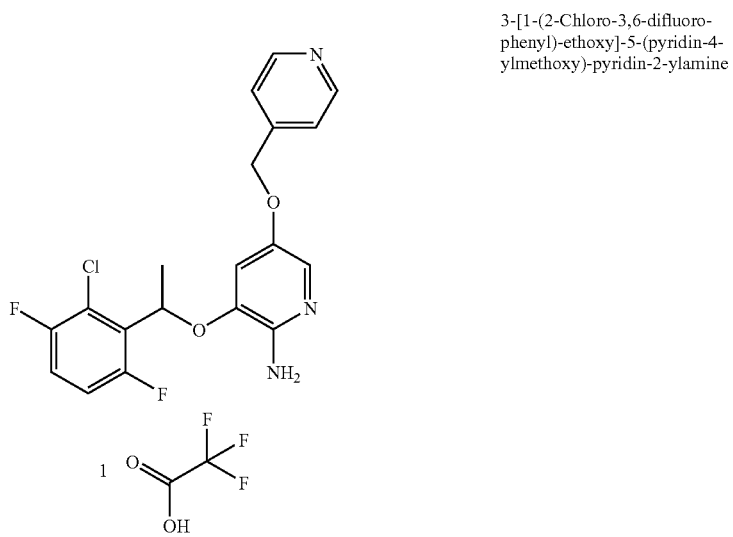 | 3-[1-(2-Chloro-3,6-difluoro-phenyl)-ethoxy]-5-(pyridin-4-ylmethoxy)-pyridin-2-ylamine | 0.8 |

TABLE 2-continued

| I-541 | 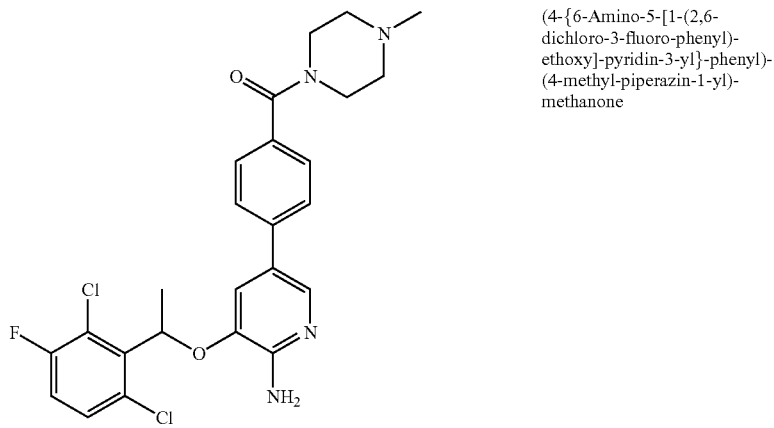 | (4-{6-Amino-5-[1-(2,6-dichloro-3-fluoro-phenyl)-ethoxy]-pyridin-3-yl}-phenyl)-(4-methyl-piperazin-1-yl)-methanone | 0.079 |
|---|---|---|---|

| No. | Procedure | $^1$H-NMR | MS m/z (M + 1) |
|---|---|---|---|
| I-1 | see examples | (400 MHz, DMSO-$d_6$) δ 9.36(s, 1H, OH), 7.77(s, 1H), 7.54(d, J=5.2 Hz, 2H), 7.43(m, 4H), 6.78 (d, J=5.2 Hz, 2H), 5.49(br, s, 2H, NH$_2$), 5.30 (s, 2H, CH$_2$). | 362 |
| I-2 | see examples | (400 MHz, DMSO-$d_6$) δ 7.81(d, J=1.2 Hz, 1H), 7.53(m, 3H), 7.48(m, 3H), 6.97(d, 2H), 5.53(br, s, 2H, NH$_2$), 5.31(s, 2H, CH$_2$), 4.08(t, 2H), 3.55 (t, 4H), 2.68(t, 2H), 2.46(t, 4H). | 374 |
| I-3 | see examples | (400 MHz, DMSO-$d_6$) δ 7.89(d, J=1.2 Hz, 1H), 7.54(d, J=5.2 Hz, 2H), 7.51(d, J=1.2 Hz, 1H), 7.44(dd, 1H), 7.28(dd, 1H), 7.18(m, 2H), 6.83 (dd, 1H), 5.65(br, s, 2H), 5.33(s, 2H), 4.12(t, 2H), 3.55(t, 6H), 2.68(t, 2H), 2.46(t, 4H) | 475 |
| I-4 | see examples | (400 MHz, DMSO-$d_6$) δ 11.18(s, 1H, NH), 7.87 (d, 1H), 7.5(d, 2H), 7.46(d, 2H), 7.36(m, 1H), 7.33(m, 1H), 7.12(t, 1H), 7.03(d, 1H), 6.49(d, 1H), 5.61(br, s, 2H, NH$_2$), 5.31(s, 2H, CH$_2$). | 384 |
| I-5 | see examples | | 465 |
| I-6 | see examples | | 435 |
| I-7 | see examples | (400 MHz, DMSO-$d_6$) δ 11.05(s, 1H), 7.85(s, 1H), 7.58(5, 1H), 7.55(s, 1H), 7.50(m, 2H), 6.75 (s, 1H), 6.35(s, 1H), 6.05(s, 1H), 5.50(br, s, 2H), 5.30(s, 2H). | 335 |
| I-8 | see examples | (400 MHz, DMSO-$d_6$) δ 7.69(s, 1H), 7.69(m, 2H), 7.58(m, 3H), 7.48(m, 1H), 7.23(m, 2H), 5.70(br, s, 2H), 5.35(s, 2H). | 364 |
| I-9 | see examples | (400 MHz, DMSO-$d_6$) δ 7.89(d, J=2 Hz, 1H), 7.63(d, J=6.8 Hz, 2H), 7.57(d, J=2 Hz, 1H), 7.54(m, 2H), 7.43(m, 1H), 7.40(m, 2H), 7.26 (m, 1H), 5.68(br, s, 2H), 5.34(s, 2H). | 345 |
| I-10 | see examples | (400 MHz, DMSO-$d_6$) δ 7.76(d, 1H), 7.55(m, 2H), 7.54(m 1H), 7.46(m, 2H), 7.32(m, 1H), 7.25(m, 2H), 5.78(br, s, 2H), 5.28(s, 2H). | 364 |
| I-11 | see examples | (400 MHz, DMSO-$d_6$) δ 7.95(d, 1H), 7.58-7.44 (m, 7H), 7.17(m 1H), 5.78(br, s, 2H), 5.35(s, 2H). | 364 |
| I-12 | see examples | (400 MHz, DMSO-$d_6$) δ 7.75(d, 1H), 7.54(dd, 4H), 7.47(m, 1H), 7.40(d, 1H), 7.29(dd, 2H), 6.60(dd, 2H), 5.44(br, s, 2H), 5.31(s, 2H), 5.15 (br s, 2H). | 360 |
| I-13 | see examples | (400 MHz, DMSO-$d_6$) δ 9.70(s, 1H), 7.86(d, 1H), 7.59(m, 1H), 7.56(m, 2H), 7.55(m, 1H), 7.45 (m, 2H), 7.22(dd, 2H), 5.63(br, s, 2H), 5.33(s, 2H), 2.95(s, 3H). | 439 |
| I-14 | see examples | (400 MHz, DMSO-$d_6$) δ 9.94(s, 1H), 7.86(d, 1H), 7.59(m, 1H), 7.57(m, 2H), 7.54(m, 2H), 7.48 (m, 2H), 5.61(br, s, 2H), 5.33(s, 2H), 2.04(s, 3H). | 402 |
| I-15 | see examples | (400 MHz, DMSO-$d_6$) δ 7.83(s, 1H), 7.55(dd, 2H), 7.46(m 2H), 7.19(m, 1H), 7.10(m, 1H), 7.04(m, 1H), 6.98(m, 1H), 6.69(m, 1H), 5.67 (br, s, 2H), 5.33(s, 2H). | 360 |

TABLE 2-continued

| | | | |
|---|---|---|---|
| I-16 | see examples | (400 MHz, DMSO-d$_6$) δ 7.83(s, 1H), 7.62-7.54 (m, 4H), 6.97(dd, 2H), 6.66(dd, 2H), 5.58(br, s, 2H), 5.33(s, 2H), 3.77(s, 3H). | 357 |
| I-17 | see examples | (300 MHz, CDCl$_3$) δ 7.64(d, 1H), 7.68(m, 1H), 7.45(m, 1H), 7.36(t, 1H), 7.28(d, 1H), 7.22(m, 1H), 6.93(d, 1H), 6.86(d, 1H), 6.64(dd, 1H), 5.34(s, 2H), 4.73(br s, 2H), 4.12(br s, 2H). | 360 |
| I-18 | see examples | (300 MHz, CDCl$_3$) δ 7.95(d, 1H), 7.49-7.24(m, 7H), 7.17(m, 1H), 5.39(s, 2H), 4.81(br s, 2H). | 429 |
| I-19 | see examples | (300 MHz, CDCl$_3$) δ 7.81(d, 1H), 7.66(m, 2H), 2.16 7.52(m, 1H), 7.37(d, 1H), 7.26(m, 3H), 6.99 (m, 2H), 5.32(s, 2H), 4.77(br s, 2H) | 361 |
| I-20 | see examples | (300 MHz, CDCl$_3$) δ 7.88(d, 1H), 7.66(m, 2H), 1745(m, 3H), 7.34(m, 2H), 7.28(m, 3H), 7.07 (m, 2H), 6.93(, 2H), 5.18(s, 2H), 4.66(br s, 2H). | 437 |
| I-21 | see examples | (300 MHz, CDCl$_3$) δ 7.89(d, 1H) 7.40(d, 2H) 7.26(m, 5H), 5.37(s, 2H), 4.80(br s, 2H). | 381 |
| I-22 | see examples | (300 MHz, CDCl$_3$) δ 7.96(d, 1H), 7.40-7.15(m, 8H), 5.36(s, 2H), 4.73(br s, 2H), 2.98(m, 1H), 1.31(d, 6H). | 387 |
| I-23 | see examples | (300 MHz, CDCl$_3$) δ 7.76(d, J=8.7 Hz, 1H), 7.69(s, 1H);7.58(t, J=7.3 Hz, 1H), 7.47(t, J= 7.4 Hz, 1H), 7.38(d, J=7.4 Hz, 2H), 7.27(m, 2H), 7.17(s, 1H), 5.29(s, 2H), 4.78(br s, 2H). | 413 |
| I-24 | see examples | (300 MHz, CDCl$_3$) δ 7.89(s, 1H), 7.41-7.24(m, 6H), 7.02(m, 2H), 5.32(s, 2H), 4.69(br s, 2H), 3.84(s, 3H). | 375 |
| I-25 | see examples | (300 MHz, CDCl$_3$) δ 7.98(d, J=1.8 Hz, 1H), 7.66(m, 3H), 7.36(m, 3H), 7.29(m, 2H), 7.89(s, 1H), 5.38(s, 2H), 4.93(br s, 2H) | 413 |
| I-26 | see examples | (300 MHz, CDCl$_3$) δ 8.75(br s, 1H), 7.70-7.14 (m, 9H), 5.31(s, 2H), 5.16(br s, 2H), 3.16(s, 3H) | 438 |
| I-27 | see examples | (300 MHz, CDCl$_3$) δ 7.84(d, J=1.8 Hz,1H), 7.66 (m, 2H), 7.63-7.18(m, 6H), 5.36(s, 2H), 4.75(d, 2H), 4.73(br s 2H), 2.5(br, 1H) | 375 |
| I-28 | see examples | (300 MHz, CDCl$_3$) δ 7.88(d, J=1.5 Hz, 1H), 7.37 (m, 2H), 7.29(m, 2H), 6.99(d, 2H), 6.87(d, 1H), 5.99(s, 2H), 5.36(s, 2H), 4.74(br s, 2H) | 389 |
| I-29 | see examples | (300 MHz, CDCl$_3$) δ 7.82(s,1H), 7.47-7.25(m, 8H), 5.33(s, 2H), 4.82(br s, 2H) | 429 |
| I-30 | see examples | (300 MHz, CDCl$_3$) δ 7.96(d, J=1.9 Hz, 1H), 7.37 d, J=8.5 Hz, 2H), 7.29(m, 2H), 7.00(d, J= 1.1Hz, 1H), 6.80(s, 1H), 5.34(s, 2H), 4.80(br s, 2H), 2.28(s, 3H) | 365 |
| I-31 | see examples | (300 MHz, CDCl$_3$) δ 7.90(d, J=1.7 Hz, 1H), 7.49(d, J=1.7 Hz, 1H), 7.31(m, 10H), 7.06(m, 2H), 5.06(s, 2H), 4.77(br s, 2H). | 451 |
| I-32 | see examples | (300 MHz, CDCl$_3$) δ 7.96 Cd, ,J=1.7 Hz, 1H), 7.39-7.11(m, 4H), 7.13(d, J=7.7 Hz, 2H), 7.07 (t, J=2.1 Hz, 1H), 6.88(dd, J=8.2 Hz, 2.1 Hz, 1H), 5.36(s, 2H), 4.78(br s, 2H), 3.87(s, 3H). | 375 |
| I-33 | see examples | (300 MHz, CDCl$_3$) δ 8.47(br s,1H), 8.04(s, 1H), 7.70(d, J=5.5 Hz, 1H), 7.62-7.11(m, 6H), 6.71 (d, J=1.3 Hz, 1H), 6.66(dd, J=7.7 Hz, 2.1 Hz, 1H), 5.29(s, 2H), 4.73(br s, 2H). | 384 |
| I-34 | see examples | (400 MHz, DMSO-d$_6$) δ 5.20(s, 2H), 5.32(s, 2H), 5.65(s, 2H), 7.25(t, 1H), 7.33(m, 1H), 7.39(m, 3H), 7.46(m, 3H), 7.51(m, 4H), 7.88(s, 1H) | 469 |
| I-35 | see examples | (400 MHz, DMSO-d$_6$) δ 7.98(s, 1H), 7.92(d, J= 5.6 Hz, 2H); 7.75(d, J=4.8 Hz, 2H), 7.55(d, J= 5.2 Hz, 1H), 7.54(dd, 2H), 7.45(m, 1H), 5.8(br. s, 2H), 5.34(s, 2H). | 390 |
| I-36 | see examples | (400 MHz, DMSOd$_6$) δ 8.45(s, 1H), 7.97(d, J= 1.2 Hz, 1H), 7.86(d, J=5.6 Hz, 2H), 7.73(d, J= 5.6 Hz, 2H), 7.60(d, J=1.2 Hz, 1H), 7.54(d, J=5.2 Hz, 2H), 7.44(dd, 1H), 5.77(br, s, 2H), 5.34(s, 2H), 3.3(m, 4H), 2.6(m, 4H), 0.99(t, 6H) | 487 |
| I-37 | see examples | (400 MHz, DMSO-d$_6$) δ 8.60(s, 1H), 7.95(d, J= 1.2 Hz, 1H), 7.85(d, J=5.6 Hz, 1H), 7.75(d, J= 5.6 Hz, 1H), 7.70(d, J=1.2 Hz, 1H), 7.60(m, 1H), 7.55(m, 2H), 7.45(m, 2H), 5.70(br, s, 2H), 5.35(s, 2H), 3.3(m, 4H), 2.6(m, 4H), 1.7(m, 2H), 1.0(t, 6H) | 501 |
| I-38 | see examples | (400 MHz, DMSO-d$_6$) δ 7.95(d, J=2 Hz, 1H), 7.72(dd, J=6, 1.6 Hz, 2H), 7.59(d, J=1.6 Hz, 1H), 7.57(d, J=1.2 Hz, 1H), 7.55(s, 1H), (dd, J=6, 1.2 Hz, 1H), 7.40(dd, J=6, 1.6 Hz, 2H), 5.76(br, s, 2H), 5.35(s, 2H), 3.6(m, 4H), 2.3(m, 4H), 2.2(s, 3H). | 471 |

TABLE 2-continued

| | | | |
|---|---|---|---|
| I-39 | see examples | (400 MHz, DMSO-d$_6$) δ 7.96(d, 1H), 7.72(dd, 2H), 7.59(m, 2H), 7.54(m, 2H), 7.47(m, 2H), 5.76(br, s, 2H), 5.36(s, 2H), 4.35(m, 1H), 3.5 (d, 2H), 3.0(m, 4H), 1.7-2.0(m, 10H). | 525 |
| I-40 | see examples | (400 MHz, DMSO-d$_6$) δ 7.93(d, 1H), 7.68(dd, 2H), 7.57(d, 1H), 7.54(dd, 2H), 7.47(m, 2H), 7.44(m, 1H), 5.74(br, s, 2H), 5.34(s,2H), 3.45 (m, 1H), 3.3(m, 4H), 2.46(m, 2H), 1.95(m, 2H), 1.84(m, 4H), 1.63(m, 4H). | 526 |
| I-41 | see examples | (400 MHz, DMSO-d$_6$) δ 7.95(d, 1H), 7.70(dd, 2H), 7.55(d, 1H), 7.48(dd, 2H), 7.41(m, 1H), 7.39(m, 2H), 5.76(br, s, 2H), 5.35(s, 2H), 3.0 (m, 4H), 2.6(m, 4H), 2.25(s, 1H), 1.89(m, 4H), 1.66(m, 4H) | 525 |
| I-42 | see examples | (400 MHz, DMSO-d$_6$) δ 7.94(d, 1H), 7.71(dd, 2H), 7.70(d, 1H), 7.59(dd, 2H), 7.55(m, 1H), 7.45(m, 2H), 5.76(br, s, 2H), 5.35(s, 2H), 4.35 (t, 2H), 3.60(m, 1H), 3.4.4(m, 2H), 3.0(m, 2H), 1.68(m, 2H), 1.40(m, 2H), 1.37(m, 2H) | 500 |
| I-43 | see examples | (400 MHz, DMSO-d$_6$) δ 7.95(d, 1H), 7.75(dd, 2H), 7.57(d, 1H), 7.55(dd, 2H), 7.48(m, 1H), 7.46(m, 2H), 5.76(br, s, 2H), 5.35(s, 2H), 3.60 (m, 1H), 3.0(m, 2H), 2.2(s, 3H), 2.1(s, 3H), 1.15 (m, 2H) | 485 |
| I-44 | see examples | (400 MHz, DMSO-d$_6$) δ 7.95(m, 1H), 7.72(m, 2H), 7.60(m, 1H), 7.55(m, 2H), 7.46(m, 3H), 5.76(br, s, 2H), 5.35(s, 2H), 3.50(m, 3H), 3.0 (m, 2H), 2.1(s, 3H), 2.05(s, 3H), 1.1(m, 2H) | 485 |
| I-45 | see examples | (400 MHz, DMSO-d$_6$) δ 7.94(d, 1H), 7.77(m, 2H), 7.57(m, 2H), 7.55(m, 1H), 7.46(dd, 1H), 7 39(m, 2H), 5.79(s, 2H), 5.35(s, 2H), 4.4(m, 1H),3.6(m, 1H), 2.6-3.0(m, 4H), 1.4-1.8(m, 8H), 0.8(m, 2H). | 526 |
| I-46 | see examples | (400 MHz, DMSO-d$_6$) δ 8.48(m, 1H), 7.99(d, 2H), 7.88(m, 2H), 7.75(m, 2H), 7.61(d, 1H), 7.57(m, 2H), 7.48(dd, 1H), 5.79(s, 2H), 5.38(s, 2H), 4.8(m, 1H), 3.75(m, 1H), 3.44(m, 1H), 3.18 (m, 1H), 2.53(m, 4H), 2.40(m, 1H), 1.87(m, 4H) | 515 |
| I-47 | see examples | | 557 |
| I-48 | see examples | | 497 |
| I-49 | see examples | (400 MHz, DMSO-d$_6$) δ 7.92(d, 1H), 7.67(m, 2H), 7.54(m, 2H), 7.49(m, 2H), 7.43(m, 2H), 5.73(s, 2H), 5.32(s, 2H), 4.2(m, 1H), 3.5(m, 1H), 3.28(m, 4H), 2.0-1.7(m, 6H), 1.18(m, 4H) | 525 |
| I-50 | see examples | (400 MHz, DMSO-d$_6$)δ8.16(d, 1H), 7.81(d, 1H), 7.38(m, 2H), 7.23-7.18(m, 4H), 7.09(m, 1H), 5.44(s, 2H), 4.98(s, 2H), 4.05(m, 1H), 3.2 (m, 1H), 3.1(m, 1H), 2.93(m, 8H), 2.78(m, 2H), 2.10(m, 4H) | 525 |
| I-51 | see examples | (400 MHz, DMSO-d$_6$) δ 7.90(m, 1H), 7.76(m, 1H), 7.83(m, 2H), 7.52(d, 2H), 7.50(m, 2H), 740(m, 1H), 5.69(s, 2H), 5.30(s, 2H), 3.70(m, 1H), 2.96(s, 3H), 2.44(m, 4H), 2.34(m, 4H), 1.75(m, 4H). | 529 |
| I-52 | see examples | (400 MHz, DMSO-d$_6$) δ 7.96(d, 1H), 7.70(m, 2H), 7.60(m, 1H), 7.57(m, 1H), 7.55(m, 3H), 7.46(m, 1H), 5.78(s, 2H), 5.37(s, 2H), 4.3(m, 3.6(m, 4H), 3.2(m, 4H), 1.9(m, 4H), 1.24 (m, 4H). | 541 |
| I-53 | see examples | (400MHz, DMSO-d$_6$) δ 8.13(m, 1H), 7.91(d, 1H) 7.98(m, 2H), 7.56(dd, 2H), 7.54(m, 2H), 7.47(m, 1H),5.76(s, 2H), 5.36(s, 2H) | 389 |
| I-54 | see examples | (400MHz, DMSO-d$_6$) δ 7.93(d, 1H), 7.74(m, 2H), 7.56(m, 3H), 7.46(m, 2H), 7.36(m, 1H), 5.74(s, 2H), 5.35(s,2H), 4.40(m, 1H), 3.40(d, 2H), 3.0(m, 4H), 1.7-2.0(m, 10H) | 525 |
| I-55 | see examples | (400 MHz, DMSO-dd$_6$) δ 7.81(d, 1H), 7.56(m, 2H), 7.48(m, 4H), 6.87(m, 2H), 5.53(s, 2H), 5.32(s, 2H), 4.33(s, 2H) | 419 |
| I-56 | see examples | (400 MHz, DMSO-d$_6$) δ 7.77(d, 1H), 7.52(d, 1H), 7.47(m, 3H), 7.41(m, 2H), 6.88(m, 2H), 0.53 5.51(s, 2H), 5.28(s, 2H), 4.67(s, 2H), 4.20(m, 1H), 3.42(m, 2H), 1.82(m, 4H), 1.96(m, 10H). | 555 |
| I-57 | see examples | (400 MHz, DMSO-d$_6$) δ 7.82(d, 1H), 7.57(d, 1H), 7.52(m, 3H), 7.45(m, 2H), 6.93(m, 2H), (s, 2H), 5.33(s, 2H), 4.72(s, 2H), 4.20(m, 1H), 3.5(m, 2H), 2.52(m, 6H), 1.85(m, 4H), 1.66 (m, 4H) | 555 |

TABLE 2-continued

| | | | |
|---|---|---|---|
| I-58 | see examples | (400 MHz, DMSO-d$_6$) δ 11.05(s, 1H, NH), 7.87 (d, 1H), 7.76(m, 1H), 7.57(m, 3H), 7.40-7.48(m, 2H), 7.34(m, 1H), 6.44(m, 1H), 5.49(br, s, 2H, NH$_2$), 536(s, 2H, CH$_2$) | 384 |
| I-59 | see examples | (400 MHz, DMSO-d$_6$) δ 11.35(d, 1H, NH), 7.95 (s, 1H), 7.89(d, 1H), 7.55(m, 4H), 7.45(m, 2H), 7.39(dd, 1H), 6.25(m, 1H), 5.54(br, s, 2H, NH$_2$), 5.37(s, 2H, CH$_2$), 3.77(m, 2H), 3.32(m, 2H), 2.82(m, 2H), 2.80(s, 3H). | 480 |
| I-60 | see examples | (400 MHz, DMSO-d$_6$) δ 10.9(d, 1H, NH), 7.90(d, 1H), 7.80(s, 1H), 7.55(m, 4H), 7.46(m, 2H), (dd, 1H), 5.50(br, s, 2H, NH$_2$), 5.38(s, 2H, CH$_2$), 3.32(m, 2H), 3.02(m, 2H), 2.90(m, 1H), 2.67(s, 3H), 2.10(m, 2H), 1.98(m, 2H). | 481 |
| I-61 | see examples | (400 MHz, DMSO-d$_6$) δ 2.31(m, 4H), 3.55(m, 4H), 3.66(s, 2H), 5.26(s, 2H), 5.45(s, 2H), 7.22 (s, 1H), 7.34(m, 2H), 7.48(m, 2H), 7.57(m, 2H), 7.80(s, 1H), 7.85(s, 1H), 10.92(br s, 1H) | 483 |
| I-62 | see examples | (300 MHz, CDCl$_3$) δ 1.43(m, 2H), 1.60(m, 4H), 2.50(m, 4H), 3.76(s, 2H), 4.65(br s, 2H), 5.40 1.41(s, 2H), 7.19(s, 1H), 7.27(m, 1H), 7.38(m, 5H), 7.87(s, 1H), 8.01(d, J=1.7 Hz, 1H), 8.17(br s, 1H) | 481 |
| I-63 | see examples | (300 MHz, CDCl$_3$) δ 1.79(m, 4H), 2.62(m, 4H), 3.88(s, 2H), 4.64(br s, 2H), 5.40(s, 2H), 7.21(d, J=2.3 Hz, 1H), 7.26(m, 1H), 7.38(m, 5H), 7.84 (s, 1H), 8.01(d, J=1.8 Hz, 1H), 8.10(br s, 1H) | 467 |
| I-64 | see examples | (300 MHz, CDCl$_3$) δ 1.13(1, 6H), 2.64(q, 4H), 3.88(s, 2H), 4.66(br s, 2H), 5.37(s, 2H), 7.19(d, J=1.7 Hz, 1H), 7.26(m, 1H), 7.37(m, 5H), 7.86 (s, 1H), 8.00(d, J=1.7 Hz, 1H), 8.44(br s, 1H) | 469 |
| I-65 | see examples | (300 MHz, CDCl$_3$) δ 1.39(s, 9H), 2.22(m, 1H), 2.40(m, 1H), 2.58(m, 1H), 2.68(m, 1H), 2.99 (m, 1H), 3.82(d, 1H), 3.88(d, 1H), 4.16(m, 1H), (br s, 2H), 4.81(m, 1H), 5.41(s, 2H), 7.17 (d, J=2.1Hz, 1H), 7.26(m, 1H), 7.38(m, 5H), 7.81(s, 1H), 8.00(d, J=1.8 Hz, 1H), 8.09(br s, 1H) | 582 |
| I-66 | see examples | (300 MHz, CDCl$_3$) δ 1.13(d, J 1.80(t, J=10.7 Hz, 2H), 1.94(br s, 1H), 2.84(d, J=10.5 Hz, 2H), 3.72(m, 4H), 4.68(br s, 2H), 5.39(s, 2H), 7.16(d, J=2.2 Hz, 1H), 7.26(m, 1H), 7.38(m, 5H), 7.89(s, 1H), 8.10(d, J=1.7 Hz, 1H), 8.32(br s, 1H) | 511 |
| I-67 | see examples | (300 MHz, CDCl$_3$) δ 1.86(s, 3H), 2.31(m, 2H), 2.59(m, 1H), 2.70(m, 1H), 2.99(m, 1H), 3.82(d, 1H), 3.90(d, 1H), 4.42(m, 1H), 4.68(br s, 2H), 5.40(s,2H), 5.91(m, 1H), 7.15(d, J=2.2 Hz, 1H), 7.26(m, 2H), 7.38(m, 5H), 7.82(s, 1H), 8.00(d, J=1.8 Hz, 1H), 8.33(br s, 1H) | 524 |
| I-68 | see examples | (300 MHz, CDCl$_3$) 62.07(s, 3H), 2,51(m, 4H), 3 44(~ 2H), 3.63(m, 2H), 3.78(s, 2H), 4.68(br 2H), 5.40(s, 2H), 7.17(d, J=2.2 Hz, 1H), 7.26(m, 1H), 7.38(m, 5H), 7.88(s, 1H), 8.00(d, J=1.8 Hz, 1H), 8.34(br s, 1H) | 524 |
| I-69 | see examples | | 386 |
| I-70 | see examples | (300 MHz, CDCl$_3$) δ 2.08(s, 3H), 2.49(m, 4H), 3.48(m, 2H), 3.61(m, 2H), 3.80(s, 2H), 4.68(s, 0.8 2H), 5.30(s, 2H), 7.02(m, 1H), 7.20(m, 2H), 7.41 (m, 3H), 7.89(s, 1H), 8.06(s, 1H), 8.63(s, 1H) | 526 |
| I-71 | see examples | (300 MHz, CDCl$_3$) δ 1.37(d, 6H), 1.92(m, 2H), 2.95(m, 2H), 3.87(m, 4H), 4.68(s, 2H), 5.34(s, 2H), 7.08(m, 1H), 7.27(m, 2H), 7.48(m, 3H), 7.89(s, 1H), 7.98(s, 1H), 8.21(br s, 1H) | 513 |
| I-72 | see examples | (300 MHz, CDCl$_3$) δ 1.71(m, 1H), 1.81(s, 3H), 2.31(m, 2H), 2.48(m, 1H), 2.79(m, 2H), 3.11(m, 1H), 3.98(m, 2H), 4.68(s, 2H), 5.31(s, 2H), 7.06 (m, 1H), 7.20(m, 2H), 7.45(m, 4H), 7.86(s, 1H), 7.98(s, 1H), 8.38(s, 1H) | 526 |
| I-73 | see examples | (300 MHz, CDCl$_3$) δ 1.84(m, 2H), 1.64(m, 4H), 2.56(m, 4H), 3.80(s, 2H), 4.68(s, 2H), 5.30(s, 2H), 7.08(m, 1H), 7.20(m, 2H), 7.45(m, 3H), 7.86(s, 1H), 7.89(s, 1H), 8.49(br s, 1H) | 483 |
| I-74 | see examples | (300 MHz, CDCl$_3$) δ 2.72(m, 4H), 3.80(m, 6H), 4.70(s, 2H), 5.33(d, 2H), 7.07(m, 1H), 7.20(m, 1H), 7.35-7.55(m, 4H), 7.86(s, 1H), 8.00(d, 1H), 8.23(s, 1H) | 485 |

TABLE 2-continued

| | | | |
|---|---|---|---|
| I-75 | see examples | (300 MHz, CDCl₃) δ 1.86(m, 4H), 2.79(m, 4H), 4.01(s, 2H), 4.63(s, 2H), 5.30(d, 2H), 7.05(m, 1H), 7.18(m, 1H), 7.30-7.60(m, 4H), 7.80(s, 1H), 8.00(d, 1H), 8.64(a, 1H) | 469 |
| I-76 | see examples | (400 MHz, DMSO-d₆) δ 1.34(t, 3H), 4.34(m, 2H), 5.34(s, 2H), 5.58(s, 2H), 7.16(s, 1H), 7.52(m, 6H), 7.84(d, 2H), 11.84(s, 1H) | 456 |
| I-77 | see examples | (400 MHz, DMSO-d₆) δ 5.46(a, 2H), 5.53(a, 2H), 6.66(s, 1H), 7.33(d, 1H), 7.44(m, 2H), 7.54(m, 3H), 7.72(s, 1H), 7.86(s, 1H), 11.12(s, 1H) | 428 |
| I-78 | see examples | (400 MHz, DMSO-d₆) δ 2.21(s, 3H), 2.36(m, 4H), 3.74(m, 4H), 5.35(s, 2H), 5.53(s, 2H), 6.78(s, 1H), 7.50(m, 6H), 7.81(s, 1H), 7.88(s, 1H), 11.56(s, 1H) | 510 |
| I-79 | see examples | (400 MHz, DMSO-d₆) δ 1.80(m, 1H), 2.12(m, 1H), 2.21(s, 6H), 2.74(m, 1H), 3.25(m, 1H), 0.18353(m, 1H), 3.78(m, 1H), 4.02(m, 1H), 5.36(s, 2H), 5.54(s, 2H), 6.98(a, 1H), 7.46(m, 3H), 7.56(m, 3H), 7.86(m, 2H),11.53(s, 1H) | 524 |
| I-80 | see examples | (400 MHz, DMSO-d₆) δ 1.80(m, 1H), 2.12(m, 1H), 2.21(s, 6H), 2.74(m, 1H), 3.25(m, 1H), 3.53(m, 1H), 3.78(m, 1H), 4.02(m, 1H), 5.38(s, 2H), 5.54(s, 2H), 8.98(s, 1H), 7.48(m, 3H), 758 (m, 3H), 7.86(m, 2H)11.53(s, 1H) (s, 1H) | 524 |
| I-81 | see examples | (400 MHz, DMSO-d₆) 61.66(m,4H), 2.51(m, (m, 2H), 7.55(m, 3H), 7.60(m, 1H), 7.82(s, 1H), 7.88(s, 1H), 8.45(t, 1H), 11.56(s, 1H) | 524 |
| I-82 | see examples | (400 MHz, DMSO-d₆) δ 2.41(m, 6H), 3.39(m, 2H), 3.58(m, 4H), 7.11(s, 1H), 7.45(m, 2H), 7.55(m, 4H), 7.82(s, 1H), 7.88(s, 1H), 8.42(t, 1H), 11.52(s, 1H) | 540 |
| I-83 | see examples | (400 MHz, DMSO-d₆) δ 1.38(s, 9H), 1.64(m, 1H), 1.98(m, 2H), 3.18(m, 2H), 3.78(m, 2H), 5.37(s, 2H), 5.53(s 2H), 6.92(m, 1H), 7.26(m, 1H), 7.48(m, 2H), 7.56(m, 3H), 7.61(m, 1H), 7.86(m, 2H), 11.52(s, 1H) | 596 |
| I-84 | see examples | (400 MHz, DMSO-d₆) δ 2.20(m, 2H), 2.68(m, 1H), 3.84(m, 4H), 5.56(s, 2H), 7.52(m, 6H), 7.94(m, 5H), 8.62(m, 2H) | 496 |
| I-85 | see examples | (400 MHz, DMSO-d₆) δ 1.67(m, 4H), 2.37(m, 1H), 2.52(m, 1H), 3.31(m, 1H), 3.62(m, 4H), (m, 1H), 3.76(m, 1H), 5.38(s, 2H), 5.52(s, 2H), 7.14(s, 1H), 7.46(m, 2H), 7.56(m, 4H), 7.86(m, 2H), 8.48(t, 1H), 11.58(s, 1H) | 554 |
| I-86 | see examples | (400 MHz, DMSO-d₆) δ 9.4(s, 1H), 7.74(d, J=2 8.7 Hz, 1H), 7.52(d, J=7.2 Hz, 2H), 7.38(m, 4H), 7.32(m, 2H), 6.8(d, J=7.2 Hz, 2H), 5.69(s, 2H), 5.22(s, 2H) | 293 |
| I-87 | see examples | (400 MHz, DMSO-d₆) 7.84(d, 1H), 7.56(d, 2H), 7.51(d, 2H), 7.38(m, 5H), 7.31(t, 1H), 7.25(t, 1H), 5.83(br s, 2H), 5.24(s, 2H) | 277 |
| I-88 | see examples | (400 MHz, DMSO-d₆) 7.85(d, 1H), 7.56(m, 2H), 7.38(m, 3H), 7.28(m, 2H), 7.08(m, 2H), 6.86 (m, 1H), 5.84(br s, 2H), 5.21(s, 2H), 3.75(s, 3H) | 307 |
| I-89 | see examples | (400 MHz, DMSO-d₆) δ 7.88(s, 1H), 7.79(m, 1H), 7.59(m, 2H), 7.51(dd, 1H), 7.40(m, 3H), 329 7.27(m, 2H), 5.84(s, 2H), 5.24(s,2H) | |
| I-90 | see examples | (400 MHz, DMSO-d₆) δ 7.88(d, 1H), 7.73(m, 1H), 7.68(m, 2H), 7.50(m, 1H), 7.38(m, 5H), 7.26(m, 1H), 5.57(s, 2H), 5.30(s, 2H) | 311 |
| I-91 | see examples | (400 MHz, DMSO-d₆) δ 7.89(d, 1H), 7.85(d, 1H), 7.59(m, 2H), 7.53(d, 1H), 7.46(d, 1H), 7.39 20 uM (m, 3H), 7.26(m, 1H), 5.95(s, 2H), 5.30(s, 2H) | 345 |
| I-92 | see examples | (400 MHz, DMSO-d₆) δ 8.15(s, 1H), 7.89(d, 1H), (d, 2H), 7.59(m, 2H), 7.48(d, 1H), 7.39(m, 2H), 7.26(m, 1H), 5.90(s, 2H); 5.36(s, 2H) | 379 |
| I-93 | see examples | (400 MHz, DMSO-d₆) δ 7.95(d, 1H), 7.88(m, 2H), 7.60(m, 2H), 7.44(d, 1H), 7.39(m, 2H), 7.26(m, 1H), 6.01(s, 2H), 5.24(s, 2H) | 364 |
| I-94 | see examples | (400 MHz, DMSO-d₆) δ 8.10(d, 1H), 7.89(d, 1H), (m, 1H), 7.60(m, 3H), 7.45(d, 1H), 7.39(m, 2H), 7.26(m, 1H), 5.93(s, 2H), 5.37(s, 2H) | 379 |
| I-95 | see examples | (400 MHz, DMSO-d₆) δ 7.89(d, 1H), 7.57(m, 4H), 7.40(m, 3H), 7.26(m, 1H), 5.72(s, 2H), 5.28(s, 2H) | 347 |

TABLE 2-continued

| | | | |
|---|---|---|---|
| I-96 | see examples | (400 MHz, DMSO-d$_6$) δ 7.86(d, 1H), 7.84(d, 1H), 7.65(m, 1H), 7.67(m, 3H), 7.39(m, 3H) 7.26 (m, 1H), 5.96(s, 2H), 5.24(s, 2H); MS m/z 345 [M + 1] | 345 |
| I-97 | see examples | (400 MHz, DMSO-d$_6$) δ 7.90(dd, 2H), 7.82(d, 1H), 7.75(m, 1H), 7.56(m, 3H), 7.48(d, 1H), 7.40(m, 2H), 7.26(m, 1H), 5.85(s, 2H), 5.39 (s, 2H) | 302 |
| I-98 | see examples | (400 MHz, DMSO-d$_6$) δ 7.88(d, 1H), 7.81(m, 2H), 7.53(d, 1H), 7.43(m, 3H), 7.25(m, 2H), 5.65(s, 2H), 5.27(s, 2H), 2.34(s, 3H) | 342 |
| I-99 | see examples | (400 MHz, DMSO-d$_6$) δ 7.89(d, 1H), 7.61(m, 3H), 7.52(d, 1H), 7.40(m, 2H), 7.25(m, 2H), 5.75(s, 2H), 5.26(s, 2H) | 331 |
| I-100 | see examples | (400 MHz, DMSO-d$_6$) δ 7.88(d, 1H), 7.61(m, 2H), 7.51(m, 2H), 7.40(m, 2H), 7.26(m, 1H), 7.18(m, 2H), 5.69(s, 2H), 5.23(s, 2H) | 314 |
| I-101 | see examples | (400 MHz, DMSO-d$_6$) δ 7.86(d, 1H), 7.60(m, 2H), 7.51(d, 1H), 7.40(m, 3H), 7.27(m, 1H), 7.07 (m, 1H), 5.68(s, 2H), 5.21(s, 2H) | 328 |
| I-102 | see examples | (400 MHz, DMSO-d$_6$) δ 7.88(d, 1H), 7.74(m, 1H),7.61(m, 2H),7.51(d, 1H), 7.40(m, 2H), 7.27 2H) | 347 |
| I-103 | see examples | (400 MHz, DMSO-d$_6$) δ 7.88(d, 1H), 7.61(m, 2H), 7.52(d, 1H), 7.49(m, 1H), 7.40(m, 3H), 7.30 (m, 2H), 5.67(s, 2H), 5.27(s, 2H) | 329 |
| I-104 | see examples | (400 MHz, DMSO-d$_6$) δ 7.84(d, 1H), 7.56(m, 1H), 7.43(d,A H), 7.38(m,3H), 7.26(m, 2H), 7.10 (m, 2H), 5.58(s, 2H), 5.15(s, 2H) | 325 |
| I-105 | see examples | (400 MHz, DMSO-d$_6$) δ 9.76(s, 1H), 7.85(d, J= 1.8 Hz, 1H), 7.57(d, 2H), 7.38(m, 5H), 7.28(m, 2H), 7.15(d, 1H), 5.85(br s, 2H), 5.22(s, 2H), 2.96(s, 3H) | 370 |
| I-106 | see examples | (DMSO-d$_6$) δ 2.50(m, 4H), 2.69(m, 2H), 3.57(t, 4H), 4.09(t, 2H), 5.37(s, 2H), 5.85(s, 2H),6.96 (d 2H), 7.38(d, 1H), 7.48(d, 2H), 7.69(t, 1H), 7.81(d, 1H), 8.01(m, 1H), 8.17(m, 1H), 8.36(m, 1H) | 451 |
| I-107 | see examples | (DMSO-d$_6$) δ 2.50(m, 4H), 2.69(t, 2H), 3.57(t, 4H), 4.10(t, 2H), 5.66(s, 2H), 5.67(s, 2H), 6.97 (d, 2H), 7.49-7.61(m, 5H), 7.78-7.82(m, 2H), 7.88-7.98(m, 2H), 8.20(dd, 1H) | 456 |
| I-108 | see examples | (400 MHz, CDCl$_3$) δ 2.60(m, 4H), 2.83(t, 2H), 3.74(t, 4H), 4.16(t, 2H), 4.63(s, 2H), 5.27(d, 2H), 6.98(d, 2H), 7.02-7.10(m, 1H), 7.16-7.22 (m, 1H), 7.30(2, 2H), 7.4.4(d, 2H), 7.91(d, 1H) | 476 |
| I-109 | see examples | (400 MHz, DMSO-d$_6$) δ 1.15(d, 6H), 2.50(m, 4H), 2.68(m, 2H), 2.77-2.89(m, 1H), 3.57(t, 6H), 4.08(t, 2H), 6.15(s, 1H), 6.20(s, 2H), 6.93 (d, 2H), 7.17(d, 1H), 7.30-7.44(m, 3H), 7.48(d, 2H), 7.68(d, 2H), 7.79(d, 1H) | 568 |
| I-110 | see examples | (400 MHz, DMSO-d$_6$) δ 2.50(m, 4H), 2.70(m, 2H), 3.58(t, 4H), 4.11(t, 2H), 5.46(s, 2H), 5.82 (s, 2H), 6.98(d, 2H), 7.43(dd, 1H), 7.50-7.56(m, 3H), 7.80(d, 1H), 8.05(d, 1H), 8.11(d, 1H), 8.16 (s, 1H) | 496.5 |
| I-111 | see examples | (400 MHz, DMSO-d$_6$) δ 7.94(s, 2H), 7.71(m, 4H), 7.44(m, 3H), 5.92(s, 2H), 5.36(s, 2H), 4.21 (m, 1H), 3.52(m, 2H), 2.69(m, 5H), 1.96(m, 2H), 1.84(m, 3H), 1.68(m, 4H) | 543 |
| I-112 | see examples | (400 MHz, DMSO-d$_6$) δ 7.94(s, 1H), 7.69(m, 5H), 7.59(s, 1H), 7.50(m, 2H), 5.72(s, 2H), 5.26 (s, 2H), 4.16(m, 1H), 3.47(m, 2H), 2.63(m, 5H), 1.96(m, 2H), 1.86(m, 3H), 1.68(m, 4H) | 543 |
| I-113 | see examples | (400 MHz, DMSO-d$_6$) δ 7.95(s, 1H), 7.85(m, 2H), 7.63(m, 2H), 7.48(m, 2H), 7.42(m, 2H), 6.04(s, 2H), 5.36(s, 2H), 4.16(m, 1H), 3.44(m, 2H), 2.62(m, 5H), 1.96(m, 2H), 1.85(m, 3H), 1.66(m, 4H) | 543 |
| I-114 | see examples | (400 MHz, DMSO-d$_6$) δ 7.85(d, 1H), 7.81(s, 1H), 7.76(m, 2H), 7.41(m, 5H), 7.03(s, 1H), 6.16(s, 2H), 5.81(m, 1H), 4.10(m, 1H), 3.41(m, 2H), 2.59(m, 5H), 1.94(m, 2H), 1.82(m, 3H), 1.64(d, 3H), 1.48(m, 4H) | 539 |
| I-115 | see examples | (400 MHz, DMSO.d$_6$) δ 7.74(s, 1H), 7.68(m, 3H), 7.45(m, 5H), 7.31(m, 1H), 5.92(s, 2H), 5.25(s, 2H), 4.16(m, 1H), 3.43(m, 2H), 2.62(m, 5H), 1.94(m, 2H), 1.82(m, 3H), 1.65(m, 4H) | 537 |

TABLE 2-continued

| | | | |
|---|---|---|---|
| I-116 | see examples | (400 MHz, DMSO-d$_6$) δ 7.92(s, 1H), 7.66(m, 4H), 7.46(m, 4H), 5.89(s, 2H), 5.39(s, 2H), 4.19 (m, 1H), 3.50(m, 2H), 2.54(m, 5H), 1.95(m, 2H), 1.83(m, 3H), 1.64(m, 4H) | 543 |
| I-117 | see examples | (400 MHz, DMSO-d$_6$) δ 7.95(d, 1H), 7.69(d, 2H), 7.58(m, 2H), 7.50(d, 2H), 7.40(m, 1H), 5.81 0.063 2H), 5.29(s, 2H), 4.35(m, 1H), 3.5(d, 2H), 2.87 (d, 2H), 2.71(d, 2H), 1.7-2.0(m, 10H) | 527 |
| I-118 | see examples | (400 MHz, DMSO-d$_6$) δ 9.38(s, 1H), 7.77(d, J= 2 Hz 1H), 7.52(m, 2H), 7.40(m, 3H), 7.17(m, 6.79(m, 2H), 5.53(br, s, 2H), 5.20(s, 2H) | 329 |
| I-119 | see examples | (400 MHz, DMSO-d$_6$) δ 7.81(d, J=2 Hz, 1H), 7.51(m, 3H), 7.45(d, J=2 Hz, 1H), 7.17(m, 2H), 6.98(m, 2H), 5.58(s, 2H), 5.21(s, 2H), 4.10 (t, 2H), 3.57(t, 4H), 2.69(t, 2H), 2.48(t, 4H) | 442 |
| I-120 | see examples | (400 MHz, DMSO-d$_6$) δ 11.18(s, 1H), 7.86(d, J= 2 Hz, 1H), 7.52(m, 1H), 7.44(d, J=2 Hz, 1H), 7.36(dd, 1H), 7.34(m, 1H), 7.18(m, 2H), 7.13 (dd, 1H), 7.02(dd, 1H), 6.49(m, 1H), 5.66(s, 2H), 5.22(s, 2H) | 352 |
| I-121 | see examples | (400 MHz, DMSO-d$_6$) δ 12.85(s, 1H), 7.94(d, J= 2 Hz, 1H), 7.89(dd, 2H), 7.71(dd, 2H), 7.55(d, J=2Hz, 1H), 7.47(m, 1H), 7.13(m, 2H), 5.83(s, 2H), 5.19(s, 2H) | 357 |
| I-122 | see examples | (400 MHz, DMSO-d$_6$) δ 7.94(d, 1H), 7.68(dd, 2H), 7.56(m, 1H), 7.51(m, 3H), 7.18(m, 2H), 5.79(s, 2H), 5.29(s, 2H), 3.48(m, 1H), 2.65(m, 4H), 2.48(d, 2H), 1.86(m, 10H) | 493 |
| I-123 | see examples | (400 MHz, DMSO-d$_6$) δ 7.94(d, 1H), 7.68(dd, 2H), 7.58(m, 1H), 7.51(m, 3H), 7.18(m, 2H), 5.78(s, 2H), 5.24(s, 2H), 4.8(m, 1H), 3.5(m, 2H), 2.52(d, 4H), 1.86(m, 10H) | 493 |
| I-124 | see examples | (400 MHz, DMSO-d$_6$) δ 7.81(d, J=2 Hz, 1H), 7.52(m, 3H), 7.18(m, 1H), 6.96(m, 2H), 5.70 (br, s, 2H), 5.23(s, 2H), 4.79(s, 2H), 2.68(q, 4H), 1.21(t, 3H) | 415 |
| I-125 | see examples | (400 MHz, DMSO-d$_6$) δ 7.79(d, 1H), 7.51(m, 1H), 7.47(m, 1H), 7.44(m, 2H), 7.17(m, 2H), 7.05(m, 2H), 5.55(br, s, 2H), 5.21(s, 2H), 4.25 (s, 2H) | 387 |
| I-126 | see examples | (400 MHz, DMSO-d$_6$) δ 7.81(d, 1H), 7.51(m, 3H), 7.45(d, 1H), 7.18(m, 2H), 6.80(m, 2H), 3.58 5.65(s, 2H), 5.22(s, 2H), 4.80(dd, 2H), 4.29(m, 1H), 3.53(m, 2H), 3.20(m, 4H), 1.93(m, 10H) | 523 |
| I-127 | see examples | (400 MHz, DMSO-d$_6$) δ 7.81(d, 1H), 7.52(m, 3H), 7.46(d, 1H), 7.18(m, 2H), 7.00(m, 2H), 5.68(s, 2H), 5.22(s, 2H), 4.80(dd, 2H), 4.60(m, 1H), 3.53(m, 2H), 3.19(m, 4H), 1.96(m, 10H) | 523 |
| I-128 | see examples | (400 MHz, DMSO-d$_6$) δ 9.38(s, 1H), 7.77(d, 1H), 750(m, 1H), 7.42(m, 4H), 7.39(m, 1H), 6.80 (m, 2H), 5.50(s, 2H), 5.24(s, 2H) | 345 |
| I-129 | see examples | (DMSO-d$_6$) δ 5.21(s, 2H), 5.67(s, 2H), 6.80(d, 2H), 7.26(t, 1H), 7.34(s, 1H), 7.41(d, 2H), 7.50 (d, 1H), 7.79(m, 2H), 9.38(s, 1H) | 345 |
| I-130 | see examples | (DMSO-d$_6$) δ 5.21(s, 2H), 5.71(s, 2H), 6.81(d, 2H), 7.40(m, 5H), 7.74(m, 2H), 9.38(s, 1H) | 361 |
| I-131 | see examples | (DMSO-d$_6$) δ 5.35(s, 2H), 5.68(a, 2H), 6.77(d, 2H), 7.41(m, 3H), 7.54(t, 1H), 7.78(m, 3H), 7.92 (d, 1H), 9.38(s, 1H) | 318 |
| I-132 | see examples | (400 MHz, DMSO-d$_6$) δ 5.32(s, 2H), 5.68(s, 2H), 6.78(d, 2H), 7.26(s, 1H), 7.36(d, 2H), 7.57(t, 1H), 7.72(t, 1H), 7.78(m, 2H), 7.86(m, 1H), 9.38 (s, 1H) | 361 |
| I-133 | see examples | (DMSO-d$_6$) δ 5.25(s, 2H), 5.69(s, 2H), 6.78(d, 13.8 2H), 7.38(m, 5H), 7.50(m, 1H), 7.71(m, 1H), 7.76(s, 1H), 9.38(s, 1H) | 326 |
| I-134 | see examples | (DMSO-d$_6$) δ 1.26(s, 9H), 5.16(s, 2H), 5.63(s, 2H), 6.78(d, 2H), 7.40(m, 7H), 7.72(s, 1H), 9.36 (s, 1H) | 349 |
| I-135 | see examples | (DMSO-d$_6$) δ 2.98(s, 3H), 5.36(s, 2H), 5.82(s, 2H), 7.24(d, 2H), 7.42(s, 1H), 7.58(m, 3H), 7.75 (t, 1H), 7.89(m, 3H), 9.70(s, 1H) | 393 |
| I-136 | see examples | (DMSO-d$_6$) δ 2.88(s, 3H), 5.37(s, 2H), 5.75(s, 2H), 7.15(d, 7.15(d, 2H), 7.30(s, 1H), 7.48(m, 6H), 7.20 1H), 7.80(s, 1H), 7.90(s, 1H) | 413 |
| I-137 | see examples | (DMSO-d$_6$) δ 3.00(s, 3H), 5.65(s, 2H), 7.26(d, 2H), 7.47(m, 3H), 7.60(m, 4H), 7.72(m, 1H), 7.82(s, 1H), 7.94(d, 1H), 9.84(s, 1H) | 414 |

TABLE 2-continued

| | | | |
|---|---|---|---|
| I-138 | see examples | (DMSO-d$_6$) δ 2.08(s, 3H), 2.26(m, 2H), 2.96(s, 3H), 3.15(m, 2H), 3.36(m, 2H), 3.59(m, 2H), 5.17(br s, 2H), 5.78(s, 2H), 7.23(d, 2H), 7.28(m, 1H), 7.36(s, 1H), 7.43(m, 2H), 7.57(m, 4H), 7.84(s, 1H) | 496 |
| I-139 | see examples | (DMSO-d$_6$) δ 2.96(s, 3H), 3.28(m, 2H), 3.46(m, 2H), 4.70(s, 1H), 5.30(s, 2H), 5.78(s, 2H), 7.23(d, 2H), 7.32(s, 1H), 7.39(m, 1H), 7.47(m, 2H), 7.53(m, 2H), 7.62(d, 1H), 7.83(s, 1H), 8.37(t, 1H), 9.72(br s, 1H) | 457 |
| I-140 | see examples | (DMSO-d$_6$) δ 0.84(d, 6H), 1.78(m, 1H), 2.82(s, 3H), 3.03(t, 2H), 5.28(s, 2H), 5.72(s, 2H), 7.12(d, 2H), 7.24(s, 1H), 7.42(m, 5H), 7.62(d, 1H), 7.79(s, 1H), 8.41(t, 1H), 9.68(s, 1H) | 469 |
| I-141 | see examples | (400 MHz, DMSO-d$_6$) δ 5.25(s, 2H, CH$_2$), 5.82(br s, 2H, NH$_2$), 6.30-8.00(multiplets, 9H, aromatic) | 373 |
| I-142 | see examples | (300 MHz, CDCl$_3$) δ 7.96(d, 1H), 7.57(m, 4H), 7.10(m, 3H), 7.04(t, 1H), 5.30(s, 2H), 4.83(s, 2H), 4.45(m, 1H), 3.40(m, 2H), 2.90(m, 4H), 2.2 1.5(m, 10H) | 509 |
| I-143 | see examples | (300 MHz, CDCl$_3$) δ 7.96(d, 1H), 7.57(m, 4H), 7.10(m, 3H), 7.04(t, 1H), 5.30(s, 2H), 4.83(s, 2H), 4.45(m, 1H), 3.40(m, 2H), 2.90(m, 4H), 2.2 1.5(m, 10H) | 509 |
| I-144 | see examples | (300 MHz, CDCl$_3$) δ 7.94(s, 1H), 7.58(m, 4H), 7.36(m, 3H), 7.05(t, 1H), 5.30(s, 2H), 5.07(s, 2H), 3.9(m, 1H), 3.6(m, 2H), 3.4(m, 1H), 3.0(m, 1H), 2.37(s, 3H), 2.27(s, 3H), 1.8(m, 2H) | 470 |
| I-145 | see examples | | 441 |
| I-146 | see examples | (300 MHz, CDCl$_3$) δ 7.93(d, J=1.7 Hz, 1H), 7.56(d, J=8.1Hz, 2H), 7.48(d, J=8.1Hz, 2H), 7.28(m, 3H), 7.07(t, J=8.8 Hz, 2H), 5.30(s, 2H), 5.05(br s, 2H), 3.75(m, 4H), 2.48(m, 4H), 2.34(s, 3H) | 455 |
| I-147 | see examples | (300 MHz, CDCl$_3$) δ 7.91(d, J=1.7 Hz, 1H), 7.58(d, J=8.2 Hz, 2H), 7.50(d, J=8.2 Hz, 2H), 7.35(m, 3H), 7.08(t, J=8.2 Hz), 5.42(br s, 2H), 5.32(s, 2H), 3.60(m, 8H), 2.14(s, 3H) | 484 |
| I-148 | see examples | (300 MHz, CDCl$_3$) δ 7.96(d, J=1.7 Hz, 1H), 7.85(d, J=8.2 Hz, 2H), 7.85(d, J=8.2 Hz, 2H), 7.30(m, 2H), 7.24(d, J=1.7 Hz, 1H), 7.08(m, 1H), 6.95(br t, 1H), 5.32(s, 2H), 5.06(br s, 2H), 3.82(m, 4H), 3.64(m, 2H), 2.76(m, 2H), 2.65(m, 4H) | 485 |
| I-149 | see examples | (300 MHz, CDCl$_3$) δ 8.02(br t, 1H), 7.95(d, J=1.7 Hz, 1H), 7.90(d, J=8.3 Hz, 2H), 7.59(d, J=8.3 Hz, 2H), 7.39(d, J=1.7 Hz, 1H), 7.30(m, 2H), 7.08(m, 1H), 6:95(br t, 1H), 5.32(s, 2H), 5.10(br s, 2H), 3.78(m, 4H), 3.62(m, 2H), 2.84(m, 6H), 1.87(m, 2H) | 499 |
| I-150 | see examples | (400 MHz, DMSO-d$_6$) δ 5.30(s, 2H, CH$_2$), 5.95(br s, 2H, NH$_2$), 7.35-7.95(multiplets, 10H, aromatic). | 353 (M − 1) |
| I-151 | see examples | (300 MHz, CDCl$_3$) δ 7.96(d, J=1.6 Hz, 1H), 7.52(m, 6H), 7.25(m, 2H), 7.21(d, J=1.6 Hz, 1H), 5.26(s, 2H), 4.88(br s, 2H), 4.32(m, 1H), 3.52(m, 2H), 2.89(m, 4H), 2.2-1.5(m, 10H). | 491 |
| I-152 | see examples | (300 MHz, CDCl$_3$) δ 7.96(d, J=1.6 Hz, 1H), 7.52(m, 6H), 7.25(m, 2H), 7.21(d, J=1.6 Hz, 1H), 5.26(s, 2H), 4.88 Clx s, 2H), 4.32(m. 1H), 3.52(m, 2H), 2.89(m, 4H), 2.2-1.5(m, 10H), MS m/z 491 [M + 1]. | 491 |
| I-153 | see examples | (300 MHz, CDCl$_3$) δ 7.95(s, 1H), 7.53(m, 6H), 7.33(m, 2H), 7.27(s, 1H), 5.26(s, 2H), 4.94(br s, 2H), 3.90(m, 1H), 3.60(m, 2H), 3.45(m, 1H), 2.85(m, 1H), 2.32(s, 3H), 2.23(s, 3H), 1.89(m, 2H) | 451 |
| I-154 | see examples | | 423 |
| I-155 | see examples | (300 MHz, CDCl$_3$) δ 7.96(d, J=1.8 Hz, 1H), 7.47(m, 6H), 7.32(m, 2H), 7.21(d, J=1.8 Hz, 1H), 5.26(s, 2H), 4.86(br s, 2H), 3.95(m, 4H), 2.55(m, 4H), 2.30(m, 1H), 1.95(m, 2H), 1.76(m 4H), 1.52(m, 2H). | 491 |
| I-156 | see examples | (300 MHz, CDCl$_3$) δ 7.94(d, J=1.8 Hz, 1H), 7.49(m, 6H), 7.32(m, 2H), 7.21(d, J=1:8 Hz, 1H), 5.27(s, 2H), 4.00(br s, 2H), 3.80(m, 4H), 2.50(m, 4H), 2.35(s, 3H) | 437 |

| | | | | |
|---|---|---|---|---|
| I-157 | see examples | (300 MHz, CDCl₃) δ 7.95(d, J=1.8 Hz, 1H), 7.51(m, 6H), 7.33(m, 2H), 7.21(d, J=1.8 Hz, 1H), 5.27(s, 2H), 4.94(br s, 2H), 3.65(m, 8H), 2.14(s, 3H) | | 465 |
| I-158 | see examples | (300 MHz, CDCl₃) δ 7.95(d, J=1.8 Hz, 1H), 7.84(d, J=8.3 Hz, 2H), 7.55(d, J=8.3 Hz, 2H), 8.9 7.51(m, 1H), 7.43(m, 1H), 7.34(m, 2H), 7.24(d, J=1.8 Hz, 1H), 7.01(br t, 1H), 5.27(s, 2H), 5.18 (br s, 2H), 3.77(m, 4H), 3.61(m, 2H), 3.25(m, 2H), 2.70(m, 2H), 2.60(m, 4H) | | 467 |
| I-159 | see examples | (300 MHz, CDCl₃) δ 7.95(d, J=1.8 Hz, 1H), 7.84(d, J=8.3 Hz, 2H), 7.55(d, J=8.3 Hz, 2H), 7.51(m, 2H), 7.43(m, 1H), 7.34(m, 2H), 7.24(d, J=1.8 Hz, 1H), 5.27(s, 2H), 4.97(br s, 2H), 3.75(m, 4H), 3.59(m, 2H), 3.25(m, 2H), 2.57 (m, 4H), 1.83(m, 2H). | | 481 |
| I-160 | see examples | (400 MHz, DMSO-d₆) δ 5.35(s, 2H, CH₂), 5.95 (br s, 2H, NH₂), 7.50-8.00(multiplets, 10H, aromatic) | | 346 |
| I-161 | see examples | (300 MHz, CDCl₃) δ 7.99(d, J=1.6 Hz, 1H), 7.76(d, J=7.5 Hz, 2H), 7.50(m, 6H), 7.24(d, J= 1.6 Hz, 1H), 5.35(s, 2H), 4.88(br s. 2H), 4.46 (m, 1H), 3.52(m, 2H), 3.24(m, 4H), 2.2-1.5(m, 10H) | | 482 |
| I-162 | see examples | ¹H NMR(300 MHz, CDCl₃) δ 7.99(d, J=1.6 1H), 7.76(d, J=7.5 Hz, 2H), 7.50(m, 6H), 7.24(d, J=1.6 Hz, 1H), 5.35(s, 2H), 4.88(br s, 2H), 4.46(m, 1H), 3.52(m, 2H), 3.24(m, 4H), 2.2 1.5(m, 10H). | | 482 |
| I-163 | see examples | (300 MHz, CDCl₃) δ 7.98(s, 1H); 7.78(d, J=7.6 2H), 7.50(m, 6H), 7.26(s, 1H), 5.36(s, 2H), 4.99(br s, 2H), 3.90(m, 1H), 3.60(m, 2H), 3.45 (m, 1H), 2.85(m, 1H), 2.32(s, 3H), 2.23(s, 3H), 1.89(m, 2H) | | 442 |
| I-164 | see examples | (300 MHz, CDCl₃) δ 7.98(d, J=1.4 Hz,, 1H), 7.76(d, J=7.5 Hz, 2H), 7.50(m, 6H), 7.24(d, J= 1.4 Hz, 1H), 5.35(s, 2H), 4.91(br s, 2H), 3.70 (m, 4H), 2.15(m, 1H), 2.23(a, 2H), 1.25(m, 1H), 1.05(m, 1H) | | 414 |
| I-165 | see examples | (300 MHz, CDCl₃) δ 7.97(d, J=1.7 Hz,, 1H), 7.76(d, J=7.5 Hz, 2H), 7.66(m, 2H), 7.51(m, 2H), 7.46(m, 2H), 7.23(d, J=1.4 Hz, 1H), 5.35 (s, 2H), 4.88(br s, 2H), 3.95(m, 4H), 2.55(m, 4H), 2.30(m, 1H), 1.95(m, 2H), 1.76(m, 4H), 1.52(m, 2H) | | 482 |
| I-166 | see examples | (300 MHz, CDCl₃) δ 7.96(d, J=1.8 Hz, 1H), 7.76(d, J=7.5 Hz, 2H), 7.66(m, 2H), 7.51(m, 2H), 7.48(m, 2H), 7.24(d, J=1.4 Hz, 1H), 5.35 (s, 2H), 5.01(br s, 2H), 3.65(m, 4H), 2.45(m, 4H), 2.36(s, 3H) | | 428 |
| I-167 | see examples | (300 MHz, CDCl₃) δ 7.95(d, J=1.7 Hz, 1H), 7.76(d, J=7.5 Hz, 2H), 7.66(m, 2H), 7.54(m, 2H), 7.50(m, 2H), 7.26(d, J=1.4 Hz, 1H), 5.36 (s, 2H), 5.27(br s, 2H), 3.65(m, 8H), 2.14(s, 3H) | | 456 |
| I-168 | see examples | (300 MHz, CDCl₃) δ 7.99(d, J=1.8 Hz, 1H), 7.82(d, J=8.3 Hz, 2H), 7.74(m, 1H), 7.66(m, 2H), 7.55(m, 3H), 7.25(d, J=1.8 Hz, 1H), 6.18 (d, J=8.0 Hz, 1H), 5.35(s, 2H), 4.88(br s, 2H), 4.05(m, 1H), 2.96(m, 1H), 2.46(s, 3H), 2.40(m, 1H), 2.05(m, 1H), 1.79(m, 1H), 1.65(m, 2H), 0.95(m, 2H) | | 442 |
| I-169 | see examples | (300 MHz, CDCl₃) δ 7.98(d, J=1.8 Hz, 1H), 7.85(d, J=8.4 Hz, 2H), 7.76(d, J=7.4 Hz, 1H), 7.66(m, 2H), 7.57(m, 3H), 7.27(d, J=1.8 Hz, 1H), 7.06(m, 1H), 5.36(s, 2H), 5.14(br s, 2H), 3.78(m, 4H), 3.63(m, 2H), 2.73(m, 2H), 2.63 (m, 4H) | | 458 |
| I-170 | see examples | (300 MHz, CDCl₃) δ 8.01(d, J=1.7 Hz, 1H), 7.87(d, J=8.4 Hz, 2H), 7.76(d, J=7.5 Hz, 1H), 17.3 7.67(m, 1H), 7.56(d, , J=8.4 Hz, 2H), 7.45(m, (br s, 2H), 3.74(m, 4H), 3.60(m, 2H), 2.57 3H), 7.27(d, J=1.8 Hz, 1H), 5.36(s, 2H), 4.89 6H), 1.82(m, 2H) | | 472 |
| I-171 | see examples | (400 MHz, DMSO-d₆) δ 5.35(s, 2H, CH₂), 5.90 (br s, 2H, NH₂), 7.30-8.00(multiplets, 9H, aromatic) | | 389 |

TABLE 2-continued

| | | | |
|---|---|---|---|
| I-172 | see examples | (300 MHz, CDCl₃) δ 7.97(d, J=1.7 Hz, 1H), 7.47(m, 6H), 7.30(dd, J=2.0 Hz, J=8.3 Hz, 1H), 7.18(d, 4 =1.7 Hz, 1H), 5.21(s, 2H), 4.85 (br s, 2H), 4.42(m, 1H), 3.50(m, 2H), 2.84(m, 4H), 2.2-1.5(m, 10H) | 527 |
| I-173 | see examples | (300 MHz, CDCl₃) 67.97(d, J=1.7 Hz, 1H), 7.47(m, 6H), 7.30(dd, 4 =2.0 Hz, 4 =8.3 Hz, 1H), 7.18(d, 4 =1.7 Hz, 1H), 5.21(s, 2H), 4.85 (br s, 2H), 4.42(m, 1H), 3.50(m, 2H), 2.84(m, 4H), 2.2-1.5(m, 10H) | 527 |
| I-174 | see examples | (300 MHz, CDCl₃) 67.95(s, 1H), 7.50(m, 6H), 7.30(dd, 4 =1.9 Hz, 4 =8.3 Hz, 1H), 7.20(s, 1H), 5.21(s, 2H), 5.07(br s, 2H), 3.90(m, 1H), 3.62(m, 2H), 3.45(m, 1H), 2.85(m, 1H), 2.32(s, 3H), 2.23(s, 3H), 1.89(m, 2H) | 486 |
| I-175 | see examples | | 458 |
| I-176 | see examples | (300 MHz, CDCl₃)67.96(d, 4 =1.8 Hz, 1H), 7.71(d, J=3.5 Hz, 1H), 7.50(m, 5H), 7.30(dd, J=2.0 Hz, J=8.3 Hz, 1H), 7.18(d, J=1.8 Hz, 1H), 5.22(s, 2H), 4.83(br s, 2H), 4.23(m, 2H), 2.78(m, 2H), 1.95(m, 2H), 1.76(m, 3H), 1.25 (m, 4H), 0.85(m, 4H) | 525 |
| I-177 | see examples | (300 MHz, CDCl₃) δ 7.95(s, 1H), 7.50(m, 6H), 7.30(dd, J=1.9 Hz, J=8.3 Hz, 1H), 7.20(s, 1H), 5.21(s, 2H), 5.07(br s, 2H), 3.65(m, 4H), 2.45(m, 4H), 2.36(s, 3H) | 473 |
| I-178 | see examples | (300 MHz, CDCl₃) δ 7.97(d, J=1.8 Hz, 1H), 7.50(m, 6H), 7.30(dd, J=2.0 Hz, J=8.3 Hz, 1H), 7.18(d, J=1.8 Hz, 1H), 5.22(s, 2H), 4.87 (br s, 2H), 3.64(m, 4H), 3.53(m, 4H), 2.14(s, 3H) | 501 |
| I-179 | see examples | (300 MHz, CDCl₃) δ 7.98(d, J=1.8Hz, 1H), 7.81(d, J=8.3 Hz, 2H), 7.55(d, J=8.3 Hz, 2H), 7.46(m, 2H), 7.30(dd, J=2.0 Hz, J=8.3 Hz, 1H), 7.18(d, J=1.8 Hz, 1H), 6.09(br d, 1H), 5.22 (s, 2H), 4.83(br s, 2H), 4.05(m, 1H), 3.06(m, 1H), 2.46(s, 3H), 2.32(m, 1H), 2.12(m, 1H), 1.83(m, 1H), 1.26(m, 2H), 0.88(m, 2H) | 486 |
| I-180 | see examples | (300 MHz, CDCl₃) δ 7.98(d, J=1.8 Hz, 1H), 7.84(d, J=8.3 Hz, 2H), 7.56(d, J=8.3 Hz, 2H), 7.46(m, 2H), 7.30(dd, J=2.0 Hz, J=8.3 Hz, 1H), 7.20(d, J=1.8 Hz, 1H), 6.90(br t, 1H), 5.22 (s, 2H), 4.91(br s, 2H), 3.75(m, 4H), 3.59(m, 2H), 2.65(m, 2H), 2.55(m, 4H) | 502 |
| I-181 | see examples | (300 MHz, CDCl₃) δ 7.99(d, J=1.7 Hz, 1H), 7.87(d, J=8.3 Hz, 2H), 7.71(m, 1H), 7.55(d, J= 8.3 Hz, 2H), 7.47(m, 2H), 7.30(dd, J=2.0 Hz, J=8.3 Hz, 1H), 7.21(d, J=1.7 Hz, 1H), 5.23(s, 2H), 4.91(br s, 2H), 3.75(m, 4H), 3.59(m, 2H), 2.60(m, 6H), 1.83(m, 2H) | 516 |
| I-182 | see examples | (400 MHz, DMSO-d₆) δ 5.35(s, 2H, OH₂), 5.95 (br s, 2H, NH₂), 7.40-8.00(multiplets, 10H, aromatic) | 388 (M+) |
| I-183 | see examples | ¹H NMR(300 MHz, CDCl₃) δ 7.96(d, J=1.7 Hz, 1H), 7.74(d, J=7.8 Hz, 1H), 7.68(d, J=7.7 Hz, 1H), 7.53(m, 6H), 7.15(d, J=1.7 Hz, 1H), 5.35(s, 2H), 4.82(br s, 2H), 4.42(m, 1H), 3.50 (m, 2H), 2.65(m, 4H), 2.2-1.5(m, 10H) | 525 |
| I-184 | see examples | (300 MHz, CDCl₃) δ 7.96(d, J=1.7 Hz, 1H), (d, J=7.8 Hz, 1H), 7.68(d, J=7.7 Hz, 1H), 7.53(m, 6H), 7.15(d, J=1.7 Hz, 1H), 5.35(s, 2H), 4.82(br s, 2H), 4.42(m, 1H), 3.50(m, 2H), 2.65(m, 4H), 2.2-1.5(m, 10H) | 525 |
| I-185 | see examples | (300 MHz, CDCl₃) δ 7.97(d, J=2.1 Hz, 1H), 7.74(d, J=7.8 Hz, 1H), 7.88(d, J=7.7 Hz, 1H), 7.51(m, 6H), 7.16(d, J=2.1Hz, 1H), 5.35(s, 2H), 4.88(br s, 2H), 3.89(m, 1H), 3.65(m, 2H), 3.45(m, 1H), 2.75(m, 1H), 2.31(s, 3H), 2.22(s, 3H), 2.11(m, 1H), 1.89(m, 1H). | 485 |
| I-186 | see examples | (300 MHz, CDCl₃) δ 7.93(d, J=1.4Hz, 1H), 7.74(d, J=7.7 Hz, 1H), 7.67(d, J=7.4 Hz, 1H), 7.55(m, 3H), 7.45(m, 3H), 7.15(d, J=1.4 Hz, 1H), 5.35(s, 2H), 5.01(br s, 2H), 3.65(m, .4H), 2.03(m, 3H), 1.75(m, 1H), 0.85(m, 1H) | 525 |

TABLE 2-continued

| | | | |
|---|---|---|---|
| I-187 | see examples | (300 MHz, CDCl₃) δ 7.96(d, J=1.8 Hz, 1H), 7.74(d, J=7.9 Hz, 1H), 7.66(m, 1H), 7.60(m, 1H), 7.47(m, 5H), 7.14(d, J=1.8 Hz, 1H), 5.35 (s, 2H), 4.81(br s, 2H), 4.60(m, 1H), 3.74(m, 1H), 2.98(m, 2H), 2.65(m, 2H), 2.22(m, 1H), 1.85(m, 2H), 1.55(m, 4H), 1.25(m, 2H), 0.95 (m, 2H) | 525 |
| I-188 | see examples | (300 MHz, CDCl₃) δ 7.95(d, J=1.8 Hz, 1H), 7.74(d, J=7.7 Hz, 1H), 7.68(d, J=7.7 Hz, 1H), 7.60(t, J=7.7 Hz, 1H), 7.48(m, 5H), 7.14(d, J= 1.8 Hz, 1H), 5.35(s, 2H), 4.89(br s, 2H), 3.80 (m, 2H), 3.51(m, 2H), 2.40(m, 4H), 2.32(s, 3H) | 471 |
| I-189 | see examples | (300 MHz, CDCl₃) δ 7.96(d, J=1.8 Hz, 1H), 7.74(d, J=7.7 Hz, 1H), 7.68(d, J=7.7 Hz, 1H), 60(t, J=7.7 Hz, 1H), 7.48(m, 5H), 7.14(d, J= Hz, 1H), 5.36(s, 2H), 4.87(br s, 2H), 3.64 4H), 3.53(m, 4H), 2.14(s, 3H) | 499 |
| I-190 | see examples | (300 MHz, CDCl₃) 67.98(d, J=1.8 Hz, 1H), 7.79(d, J=8.3 Hz, 2H), 7.74(d, J=7.8 Hz, 1H), 767(d, J=7.6 Hz, 1H), 7.60(m, 1H), 7.52(m, 3H), 7.14(d, J=1.8 Hz, 1H), 5.98(m, 1H), 5.36 (s, 2H), 4.85(br s, 2H), ), 4.05(m, 1H), 2.90(m, 12H), 2.32(s, 3H), 2.18(m, 2H), 2.01(m, 2H), 1.62(m, 2H) | 485 |
| I-191 | see examples | (300 MHz, CDCl₃) δ 7.98(d, J=1.8 Hz, 1H), 7.82(d, J=8.4 Hz, 2H), 7.74(d, J=7.8 Hz, 1H), 7.68(d, J=7.7Hz, 1H), 7.60(t, J=7.7 Hz, 1H), 7.53(m, 3H), 7.17(d, J=1.8 Hz, 1H), 6.83 (m, 1H), 5.36(s, 2H), 4.89(br s, 2H), 3.74(m, 4H), 3.57(m, 2H), 2.62(m, 2H), 2.52(m, 4H) | 501 |
| I-192 | see examples | (300 MHz, CDCl₃) δ 7.98(d, J=1.8 Hz, 1H), 7.95(m, 1H), 7.86(d, J=8.4 Hz, 2H), 7.74(d, J= 7.7 Hz, 1H), 7.68(d, J=7.7 Hz, 1H), 7.80(t, J=7.7 Hz, 1H), 7.53(m, 3H), 7.17(d, J=1.8 Hz, 1H), 5.38(s, 2H), 4.94(br s, 2H), 3.75(m, 4H), 3.59(m, 2H), 2.59(m, 6H), 1.83(m, 2H) | 515 |
| I-193 | see examples | (400 MHz, DMSO-d₆) δ 1.25(s, 9H, t-butyl), 5.20 (s, 2H, CH₂), 5.95(br s, 2H, NH₂), 7.35-8.00 (multiplets, 10H, aromatic) | 376 (M+) |
| I-194 | see examples | (300 MHz, CDCl₃) δ 7.94(d, J=1.7 Hz, 1H), 7.49(m, 8H), 7.21(d, J=1.7 Hz, 1H), 5.11(s, 2H), 4.80(br s, 2H), 4.48(m, 1H), 3.48(m, 2H), 2.82(m, 4H), 2.2-1.5(m, 10H), 1.34(s, 9H) | 513 |
| I-195 | see examples | (300 MHz, CDCl₃) δ 7.94(d, J=1.7 Hz, 1H), 7.49(m, 8H), 7.21(d, J=1.7 Hz, 1H), 5.11(s, 2H), 4.80(br s, 2H), 4.48(m, 1H), 3.48(m, 2H), 2.62(m, 4H), 2.2-1.5(m, 10H), 1.34(s, 9H) | 513 |
| I-196 | see examples | (300 MHz, CDCl₃) δ 7.94(d, J=2.1Hz, 1H), 7.54(m, 4H), 7.45(d, J=8.3 Hz, 2H), 7.38(d, J= 8.3 Hz, 2H), 7.21(d, J=1.7 Hz, 1H), 5.11(s, 2H), 4.84(br s, 2H), 3.89(m, 1H), 3.64(m, 2H), 3.42(m, 1H), 2.70(m, 1H), 2.31(s, 3H), 2.22(s, 3H), 2.05(m, 1H), 1.89(m, 1H), 1.34(s, 9H) | 473 |
| I-197 | see examples | (300 MHz, CDCl₃) δ 7.93(d, J=1.7 Hz, 1H), 7.48(m, 4H), 7.41(m, 4H), 7.21(d, J=1.7 Hz, 1H), 5.11(s, 2H), 4.85(br s, 2H), 3.80(m, 2H), 3.52(m, 2H), 2.41(m, 4H), 2.33(s, 3H), 1.34(s, 9H) | 459 |
| I-198 | see examples | (300 MHz, CDCl₃) δ 7.94(d, J=1.8 Hz, 1H), 7.50(m, 8H), 7.21(d, J=1.7 Hz, 1H), 5.11(s, 2H), 4.90(br s, 2H), 3.64(m, 4H), 3.53(m, 4H), 2.14(s, 3H), 1.34(s, 9H) | 487 |
| I-199 | see examples | (300 MHz, CDCl₃) δ 7.95(d, J=1.8 Hz, 1H), 7.80(d. J=8.3 Hz, 2H), 7.54(d, J=8.3 Hz, 2H), 7.44(d, J=7.7 Hz, 2H), 7.38(d, J=7.7 Hz, 2H), 7.21(d, J=1.8 Hz, 1H), 6.05(m, 1H), 5.11(s, 2H), 4.80(br s, 2H), 4.01(m, 1H), 2.84(m, 2H), 2.33(s, 3H) 2.20(m, 2H), 2.10(m, 2H), 1.62(m, 2H), 1.34(s, 9H) | 487 |
| I-200 | see examples | (300 MHz, CDCl₃) δ 7.95(d, J=1.8 Hz, 1H), 7.44(d, J=8.4 Hz, 2H), 7.38(d, J=8.4 Hz, 2H), 6.88 7.82(d, J=8.3 Hz, 2H), 7.54(d, J=8.3 Hz, 2H), 7.22(d, J=1.8 Hz, 1H), 8.91(t, J=4.6 Hz, 1H), 5.10(s, 2H), 4.90(br s, 2H), 3.74(m, 4H), 3.57 (m, 2H), 2.82(m, 2H), 2.51(m, 4H), 1.34(s, 9H) | 489 |

TABLE 2-continued

| | | | |
|---|---|---|---|
| I-201 | see examples | (300 MHz, CDCl$_3$) δ 8.01(t, J=4.5 Hz, 1H), 7.98 (d, J=1.8 Hz, 1H), 7.88(d, J=8.3 Hz, 2H), 7.54 (d, J=8.3 Hz, 2H), 7.44(d, J=8.4 Hz, 2H), 7.38 (d, J=8.4 Hz, 2H), 7.24(d, J=1.8 Hz, 1H), 5.12 (s, 2H), 4.89(br s, 2H), 3.74(m, 4H), 3.59(m, 2H), 2.55(m, 6H), 1.82(m, 2H), 1.34(s, 9H) | 503 |
| I-202 | see examples | (400 MHz, DMSO-d$_6$) δ 5.25(s, 2H, CH$_2$), 5.80 (br s, 2H, NH$_2$), 7.20-8.00(multiplets, 9H, aromatic) | 374 |
| I-203 | see examples | (300 MHz, CDCl$_3$) 67.97(d, J=1.7 Hz, 1H), 7.52(m, 8H), 7.20(m, 1H), 7.05(m, 1H), 5.21(s, 2H), 4.80(br s, 2H), 4.45(m, 1H), 3.52(m, 2H), 2.76(m, 4H), 2.2-1.5(m, 10H) | 509 |
| I-204 | see examples | (300 MHz, CDCl$_3$) δ 7.97(d, J=1.7 Hz, 1H), 7.52(m, 6H), 7.20(m, 1H), 7.05(m, 1H), 5.21(s, 2.5 2H), 4.80(br s, 2H), 4.45(m, 1H), 3.52(m, 2H), 2.76(m, 4H), 2.2-1.5(m, 10H) | 509 |
| I-205 | see examples | (300 MHz, CDCl$_3$) δ 7.97(s, 1H), 7.52(m, OH), 7.20(m, 1H), 7.04(m, 1H), 5.21(s, 2H), 4.95(br s, 2H), 3.90(m, 1H), 3.61(m, 2H), 3.33(m, 1H), 2.75(m, 1H), 2.32(s, 3H), 2.23(s, 3H), 2.10(m, 1H), 1.89(m, 1H) | 469 |
| I-206 | see examples | (300 MHz, CDCl$_3$) 67.97(d, J=1.8 Hz, 1H), 1.83 7.52(m, 6H), 7.20(m, 1H), 7.04(m, 1H), 5.21(s, 2H), 4.84(br s, 2H), 3.84(m, 4H), 2.15(m, 1H), 1.76(m, 2H), 1.56(m, 2H) | 441 |
| I-207 | see examples | (300 MHz, CDCl$_3$) δ 7.96(s, 1H), 7.52(m, 6H), 7.20(m, 1H), 7.04(m, 1H), 5.21(s, 2H), 4.89(br s, 2H), 3.80(m, 2H), 3.65(m, 2H), 2.43(m, 4H), 2.33(s, 3H) | 456 |
| I-208 | see examples | (300 MHz, CDCl$_3$) δ 7.96(s, 1H), 7.52(m, 6H), 7.20(m, 1H), 7.04(m, 1H), 5.21(s, 2H), 4.90(br s, 2H), 3.67(m, 4H), 3.53(m, 4H), 2.22(s, 3H) | 483 |
| I-209 | see examples | (300 MHz, CDCl$_3$) δ 7.99(d, J=1.6 Hz, 1H), 7.84(d, J=8.3 Hz, 2H), 7.57(d, J=8.3 Hz, 2H), 7.49(dd, J=6.0 Hz, 8.5 Hz, 1H), 7.20(m, 2H), 7.04(m, 1H), 6.82(m, 1H), 5.22(s, 2H), 4.85(br s, 2H), 3.74(m, 4H), 3.58(m, 2H), 2.63(m, 2H), 2.53(m, 4H) | 485 |
| I-210 | see examples | (300 MHz, CDCl$_3$) δ 8.06(m, 1H), 7.00(d, J=1.6 Hz, 1H), 7.89(d, J=8.3 Hz, 2H), 7.55(d, J=8.3 Hz, 2H), 7.49(dd, J=6.0 Hz, 8.5 Hz, 1H), 7.20(m, 2H), 7.04(m, 1H), 5.22(s, 2H), 4.85(br s, 2H), 3.75(m, 4H), 3.60(m, 2H), 2.55(m, 6H), 1.83(m, 2H) | 499 |
| I-211 | see examples | (300 MHz, DMSO-d$_6$) δ 5.21(s, 2H), 5.71(s, 2H), 7.31-7.46(m, 1H), 7.5-7.62(m, 4H), 7.91-7.94(m, 3H). | |
| I-212 | see examples | (300 MHz, CDCl$_3$) δ 7.97(d, J=1.6 Hz, 1H), 7.56(d, J=8.2 Hz, 2H), 7.48(d, J=8.2 Hz, 2H), 7.35(d, J=1.6 Hz, 1H), 7.20(m, 1H), 7.06(m, 1H), 5.29(s, 2H), 4.81(br s, 2H), 3.79(m, 2H), 3.54(m, 2H), 2.44(m, 4H), 2.33(s, 3H) | 473 |
| I-213 | see examples | (300 MHz, CDCl$_3$) δ 7.97(d, J=1.7 Hz, 1H), 7.55(d, J=8.2 Hz, 2H), 7.45(d, J=8.2 Hz, 2H), 7.35(d, J=1.6 Hz, 1H), 7.20(m, 1H), 7.06(m, 1H), 5.29(s, 2H), 4.79(br s, 2H), 4.60(m, 1H), 3.85(m, 1H), 3.02(m, 2H), 2.65(m, 4H), 2.35 (m, 1H), 2.05(m, 4H), 1.65(m, 4H). | 527 |
| I-214 | see examples | (400 MHz, DMSO-d$_6$) δ 7.92(s, 1H), 7.66(m, 4H), 7.46(m, 4H), 5.89(s, 2H), 5.39(s, 2H), 4.19 (m, 1H), 3.50(m, 2H), 2.54(m, 5H), 1.95(m, 2H), 1.83(m, 3H), 1.64(m, 4H) | MS(ES+) m/z 543 (MH+). MS m/z 473 (M + 1] |
| I-215 | see examples | (400 MHz, DMSO-d$_6$) δ 7.98(s, 1H), 7.58(d, 2H), 7.41(d, 2H), 7.31(s, 1H), 7.19(m, 1H), 7.08(m, 1H), 5.31(s, 2H), 4.81(m, 2H), 4.88(m, 1H), 3.69(m, 1H), 2.89(m, 2H), 2.69(m, 1H), 2.40 (m, 1H), 1.74(m, 1H), 1.18(d, 6H) | 487 |
| I-216 | see examples | (400 MHz, DMSO-d$_6$) δ 7.95(d, 1H), 7.69(d, 2H), 7.58(m, 2H), 7.50(d, 2H), 7.40(m, 1H), 5.81(s, 2H), 5.29(s, 2H), 4.35(m, 1H), 3.5(d, 2H), 2.87 (d, 2H), 2.71(d, 2H), 1.7-2.0(m, 10H) | 527 |
| I-217 | see examples | (400 MHz, DMSO-d$_6$) δ 7.97(s, 1H), 7.60(m, 4H), 7.32(s, 1H), 7.18(m, 1H), 7.04(m, 1H), 5.31(s, 2H), 4.78(m, 2H), 3.90(m, 1H), 3.68(m, 2H), 3.41(m, 1H), 2.78(m, 1H), 2.31(s, 3H), 2.24(s, 3H), 2.08(m, 1H), 1.84(m, 1H) | 487 |

TABLE 2-continued

| | | | |
|---|---|---|---|
| I-218 | see examples | (400 MHz, DMSO-d$_6$) δ 7.84(s, 1H), 7.62(m, 5H), 7.35(m, 1H), 7.20(m, 1H), 5.38(s, 2H), 0.053 3.78(m, 3H), 3.55(m, 1H), 3.41(m, 1H), 2.18(m, 1H), 1.82(m, 1H) | 459 |
| I-219 | see examples | 400 MHz, DMSO-d$_6$) δ 7.84(s, 1H), 7.62(m, 5H), 7.35(m, 1H), 7.20(m, 1H), 5.38(s, 2H), 3.78(m, 3H), 3.55(m, 1H), 3.41(m, 1H), 2.18(m, 1H), 1.82(m, 1H) | |
| I-220 | see examples | (400 MHz, DMSO-d$_6$) δ 7.97(s, 1H), 7.80(d, 2H), 7.58(d, 2H), 7.36(s, 1H), 7.18(m, 1H), 7.04(m, 1H), 6.01(d, 1H), 5.28(s, 2H), 4.78(s, 2H), 3.98(m, 1H), 2.85(m, 2H), 2.31(s, 3H), 2.18(t, 2H), 2.10(m, 2H), 1.65(m, 2H) | 487 |
| I-221 | see examples | (400 MHz, DMSO-d$_6$) δ 7.98(s, 1H), 7.89(d, 2H), 7.56(d, 2H), 7.45(m, 1H), 7.31(s, 1H), 7.17(m, 1H), 7.01(m, 1H), 5.28(s, 2H), 4.85(s, 2H), 3.65(m, 2H), 2.89(t, 2H), 2.76(m, 4H), 1.89(m, 4H) | 487 |
| I-222 | see examples | (400 MHz, DMSO-d$_6$) δ 8.72(m, 1H), 7.95(m, 3H), 7.57(d, 2H), 7.35(s, 1H), 7.18(m, 1H), 7.02(m, 1H), 5.31(s, 2H), 4.79(s, 2H), 3.68(m, 2H), 2.89(m, 8H), 1.97(m, 6H) | 501 |
| I-223 | see examples | (400 MHz, DMSO-d$_6$) δ 7.97(s, 1H), 7.82(d, 2H), 7.62(d, 2H), 7.36(s, 1H), 7.18(m, 1H), 7.05(m, 0.165 1H), 6.81(m, 1H), 5.28(s, 2H), 4.79(s, 2H), 3.78 (m, 4H), 3.58(m, 2H), 2.83(t, 2H), 2.51(m, 4H) | 503 |
| I-224 | see examples | (400 MHz, DMSO-d$_6$) δ 8.04(m, 1H), 7.96(s, 1H), 7.89(d, 2H), 7.58(d, 2H), 7.38(s, 1H), 7.18(m, 1H), 7.08(m, 1H), 7.29(s, 2H), 4.81(s, 2H), 3.76(m, 4H), 3.61(m, 2H), 2.59(t, 2H), 2.54(m, 4H), 1.79(m, 2H) | 517 |
| I-225 | see examples | (300 MHz, CDCl$_3$) δ 8.15(s, 1H), 7.92(s, 1H), 7.84(d, J=7.4 Hz, 1H), 7.60(m, 2H), 7.55(s, 1H), 7.40(m, 2H), 5.75(s, 2H), 5.31(br s, 2H) | 391 |
| I-226 | see examples | (300 MHz, CDCl$_3$) δ 7.96(d, J=1.7 Hz, 1H), 7.58(dd, J=1.1Hz, 6.8 Hz, 1H), 7.46(m, 1H), 7.35(m, 3H), 7.20(m, 1H), 7.06(m, 1H), 5.27(s, 4.81(br s, 2H), 3.83(m, 2H), 3.50(m, 2H), 2.49(m, 2H), 2.39(m, 2H), 2.33(s, 3H) | 391 |
| I-227 | see examples | (300 MHz, CDCl$_3$) δ 7.96(d, J=1.8 Hz, 1H), 7.57(dd, J=1.2 Hz, 8.0 Hz, 1H), 7.45(t, J=7.6 Hz, 1H), 7.34(m, 3H), 7.20(m, 1H), 7.06(m, 1H), 5.27(s, 2H), 4.77(br s, 2H), 4.60(m, 1H), 3.80(m, 1H), 3.02(m, 2H), 2.60(m, 2H), 2.30(m, 1H), 1.95(m, 2H), 1.85(m, 4H), 1.65(m, 4H) | 527 |
| I-228 | see examples | (300 MHz, CD$_3$OD) δ 8.01(s, 1H), 7.89(s, 1H), 7.75(m, 2H), 7.59(s, 1H), 7.48(t, 1H), 7.31(m, 1H), 7.18(m, 1H), 5.38(s, 2H), 4.01(m, 1H), 3.09(m, 2H), 2.68(t, 2H), 1.97(m, 2H), 1.58(m, | 473 |
| I-229 | see examples | (300 MHz, CDCl$_3$) δ 7.96(d, J=1.7 Hz, 1H), 7.56(m, 1H), 7.47(t, J=7.6 Hz, 1H), 7.36(m, 3H), 7.20(m, 1H), 7.06(m, 1H), 5.27(s, 2H), 4.82(br s, 2H), 4.68(m, 1H), 3.65(m, 1H), 3.90(m, 2H), 2.70(m, 1H), 2.40(m, 1H), 1.97(m, 1H), 1.15(d, 3H), 0.99(d, 3H) | 487 |
| I-230 | see examples | (300 MHz, CDCl$_3$) 67.96(d, J=1.7 Hz, 1H), 7.66(s, 1H), 7.57(d, J+32,6-8 Hz, 1H), 7.45(m, 2H), 7.36(d, J=1.7 Hz, 1H), 7.20(m, 1H), 7.06(m, 1H), 5.27(s, 2H), 4.78(br s, 2H), 4.42(m, 1H), 3.45(m, 2H), 2.68(m, 4H), 2.2-1.5(m, 10H) | 527 |
| I-231 | see examples | (300 MHz, CDCl$_3$) δ 7.96(s, 1H) 7.68(d, J=7.4 Hz, 1H), 7.59(m, 1H), 7.44(m, 2H), 7.36(s, 1H), 7.20(m, 1H), 7.06(m, 1H), 5.27(s, 2H), 4.80(br 5, 2H), 3.90(m, 1H), 3.61(m, 2H), 3.41(m, 1H), 2.77(m, 1H), 2.32(s, 3H), 2.22(s, 3H), 2.10(m, 1H), 1.82(m, 1H) | 487 |
| I-232 | see examples | (300 MHz, CD$_3$OD) δ 7.86(s, 1H), 7.75(m, 2H), 7.58(m, 3H), 7.38(m, 1H), 7.22(m, 1H), 5.38(s, 2H), 4.00-3.56(m, 5H), 2.40(m, 1H), 2.12(m, 1H) | 459 |
| I-233 | see examples | (300 MHz, CD$_3$OD) δ 7.88(s, 1H), 7.75(m, 2H), 7.58(m, 3H), 7.38(m, 1H), 7.22(m, 1H), 5.38(s, 2H), 4.00-3.58(m, 5H), 2.40(m, 1H), 2.12(m, 1H). | 459 |
| I-234 | see examples | (300 MHz, CDCl$_3$) δ 7.98(d, J=1.7 Hz, 1H), 7.94(s, 1H), 7.64(m, 2H), 7.47(t, J=7.7 Hz, 1H), 7.37(d, J=1.7 Hz, 1H), 7.20(m, 1H), 7.06(m, 1H), 6.25(m, 1H), 5.27(s, 2H), 4.81(br s, 2H), 3.99(m, 1H), 2.84(m, 2H), 2.30(s, 3H), 2.16(m, 2H), 2.04(m, 2H), 1.64(m, 2H) | 487 |

TABLE 2-continued

| | | | |
|---|---|---|---|
| I-235 | see examples | (300 MHz, CDCl₃) δ 8.02(s, 1H), 7.96(d, J=1.7 Hz, 1H), 7.72(d, J=7.7 Hz, 1H), 7.64(d, J=7.8 Hz, 1H), 7.47(t, J=7.7 Hz, 1H), 7.40(d, J=1.7 Hz, 1H), 7.20(m, 2H), 7.06(m, 1H), 5.27(s, 2H), 4.83(br s, 2H), 3.61(m, 2H), 2.77(m, 2H), 2.62(m, 4H), 1.81(m, 4H) | 487 |
| I-236 | see examples | (300 MHz, CDCl₃) δ 8.78(m, 1H), 8.04(d, J=1.6 Hz, 1H), 7.98(d, J=1.6 Hz, 1H), 7.68(d, J=7.7 Hz, 1H), 7.63(d, J=7.9 Hz, 1H), 7.45(t, J=7.7 Hz, 1H), 7.43(d, J=1.6 Hz, 1H), 7.20(m, 1H), 7.06(m, 1H), 5.29(s, 2H), 4.77(br s, 2H), 3.61(m, 2H), 2.77(m, 2H), 2.66(m, 4H), 1.87(m, 2H), 1.80(m, 4H) | 501 |
| I-237 | see examples | (300 MHz, CDCl₃) δ 7.99(t, J=1.5 Hz, 1H), 7.97(d, J=1.8 Hz, 1H), 7.66(m, 2H), 7.49(t, J=7.7 Hz, 1H), 7.38(d, J=1.8 Hz, 1H), 7.20(m, 1H), 7.06(m, 2H), 5.27(s, 2H), 4.85(br s, 2H), 3.72(m, 4H), 3.59(m, 2H), 2.63(m, 2H), 2.52(m, 4H) | 503 |
| I-238 | see examples | (300 MHz, CDCl₃) δ 8.02(m, 2H), 7.97(d, J=1.8 Hz, 1H), 7.68(d, J=7.8 Hz, 1H), 7.65(d, J=8.3 Hz, 1H), 7.48(t, J=7.7 Hz, 1H), 7.38(d, J=1.8 Hz, 1H), 7.19(m, 1H), 7.08(m, 1H), 5.27(s, 2H), 4.81(br s, 2H), 3.66(m, 4H), 3.59(m, 2H) 2.55(m, 2H), 2.49(m, 4H), 1.81(m, 2H) | 517 |
| I-239 | see examples | (300 MHz, CDCl₃) δ 8.00(m, 1H), 7.86(d, 1H), 1H), 7.08(m, 1H), 6.02(br s, 2H), 5.39(s, 2H), 3.75(m, 4H), 3.60(m, 2H), 2.79(m, 2H), 2.60(m, 4H), 2.11(s, 3H) | 544 |
| I-240 | see examples | (400 MHz, DMSO-d₆) δ 7.88(s, 1H), 7.62(d, 2H), 7.56(m, 1H), 7.51(s, 1H), 7.40(m, 1H), 7.23(d, 2H), 5.70(s, 2H), 5.28(s, 2H), 3.76(t, 2H), 3.49(t, 2H), 2.41(t, 2H) | 466 |
| I-241 | see examples | | 464 |
| I-242 | see examples | | 482 |
| I-243 | see examples | (300 MHz, CDCl₃) δ 7.92(d, J=1.8 Hz, 1H), 7.48(d, J=8.4 Hz, 2H), 7.31(d, J=1.8 Hz, 1H), 7.24(m, 3H), 7.20(m, 1H), 7.07(m, 1H), 5.28(s, 2H), 4.70(br s, 2H), 3.22(t, J=6.1 Hz, 2H), 3.04(t, J=6.1 Hz, 2H), 2.65(q, J=7.1Hz, 4H), 1.10(t, J=7.1 Hz, 6H) | 525 |
| I-244 | see examples | (300 MHz, CDCl₃) δ 7.92(d, J=1.8 Hz, 1H), 7.48(d, J=8.4 Hz, 2H), 7.31(d, J=1.8 Hz, 1H), 7.24(m, 3H), 7.20(m, 1H), 7.07(m, 1H), 5.28(s, 2H), 4.75(br s, 2H), 3.25(s, 4H), 2.17(m, 1H), 0.9(m, 1H), 0.50(m, 2H), 0.40(m, 2H) | 509 |
| I-245 | see examples | (300 MHz, CDCl₃) δ 7.92(d, J=1.8 Hz, 1H), 7.48(d, J=8.5 Hz, 2H), 7.31(d, J=1.8 Hz, 1H), 7.24(m, 3H), 7.20(m, 1H), 7.07(m, 1H), 5.28(s, 2H), 4.72(br s, 2H), 3.27(m, 2H), 3.06(m, 2H), 2.59(m, 4H), 1.88(m, 4H) | 523 |
| I-246 | see examples | (300 MHz, CDCl₃) δ 7.92(d, J=1.8 Hz, 1H), 7.48(d, J=8.5 Hz, 2H), 7.32(m, 2H), 7.24(m, 2H), 7.20(m, 1H), 7.07(m, 1H), 5.28(s, 2H), 4.74(br s, 2H), 3.81(m, 1H), 3.31(t, 2H), 2.98(t, 2H), 2.85(m, 2H), 2.32(m, 2H), 1.98(m, 2H), 1.68(m, 3H) | 553 |
| I-247 | see examples | (300 MHz, DMSO-d₆) δ 9.80(br s, 1H), 7.89(d, J=1.6 Hz, 1H), 7.59(m, 3H), 7.52(d, J=1.6 Hz, 1H), 7.26(d, J=8.6 Hz, 2H), 5.72(br s, 2H), 5.28(s, 2H), 3.49(m, 4H), 3.28(t, 2H), 2.69(t, 2H), 2.31(m, 4H) | 539 |
| I-248 | see examples | (300 MHz, CDCl₃) δ 7.93(d, J=1.8 Hz, 1H), 7.48(d, J=8.5 Hz, 2H), 7.30(m, 2H), 7.24(m, 2H), 7.20(m, 1H), 7.07(m, 1H), 5.28(s, 2H), 4.70(br s, 2H), 3.25(t, 2H), 2.92(t, 2H), 2.52(m, 4H), 1.85(m, 4H), 1.63(m, 2H) | 537 |
| I-249 | see examples | (300 MHz, CDCl₃) δ 7.92(d, J=1.8 Hz, 1H), 7.48(d, J=8.5 Hz, 2H), 7.30(m, 2H), 7.24(m, 2H), 7.20(m, 1H), 7.07(m, 1H), 5.28(s, 2H), 4.71(br s, 2H), 3.20(t, 2H), 2.88(t, 2H), 2.32(s, 6H) | 497 |
| I-250 | see examples | (300 MHz, CDCl₃) δ 7.92(d, J=1.8 Hz, 1H), 7.48(d, J=8.5 Hz, 2H), 7.30(m, 2H), 7.24(m, 1H), 7.20(m, 1H), 7.07(m, 2H), 5.28(s, 2H), 4.80(br s, 2H), 3.65(m, 2H), 3.48(m, 2H), 3.32(t, 2H), 2.94(t, 2H), 2.50(m, 2H), 2.46(m, 2H), 2.10(s, 3H) | 580 |

TABLE 2-continued

| | | | |
|---|---|---|---|
| I-251 | see examples | (300 MHz, CDCl$_3$) δ 7.94(s, 1H), 7.48(m, 2H), 7.31(m, 3H), 7.21(m, 1H), 7.18(m, 1H), 5.28(s, 0.075 2H), 4.75(s, 2H), 3.23(m, 4H), 2.58(m, 2H), 1.00(m, 1H), 0.56(m, 2H), 0.18(m, 2H) | 523 |
| I-252 | see examples | (300 MHz, CDCl$_3$) δ 7.92(s, 1H), 7.43(m, 2H), 7.31(m, 3H), 7.19(m, 1H), 7.05(m, 1H), 5.28 2H), 4.75(s, 2H), 4.45(m, 1H), 3.29(m, 2H), 3.10(m, 3H), 2.88(m, 1H), 2.61(m, 1H), 2.30 (m, 2H), 1.89(m, 2H) | 539 |
| I-253 | see examples | (300 MHz, CDCl$_3$) δ 7.89(s, 1H), 7.45(m, 2H), 7.30(m, 3H), 7.21(m, 1H), 7.08(m, 1H), 5.31(s, 2H), 4.78(s, 2H), 3.55(m, 2H), 3.36(t, 1H), 3.11 (m, 2H), 2.69(m, 2H), 2.21(m, 1H), 1.89(m, 6H) | 553 |
| I-254 | see examples | (300 MHz, DMSO-d$_6$) δ 9.81(s, 1H), 7.89(s, 1H), 7.58(d, 2H), 7.50(s, 1H), 7.39(m, 2H), 7.24(d, 2H), 5.75(s, 2H), 5.28(s, 2H), 4.54(t, 1H), 4.01 (d, 2H), 3.29(m, 6H), 2.79(t, 2H), 2.36(m, 4H) | 596 |
| I-255 | see examples | (300 MHz, CDCl$_3$) δ 2.02(s, 3H), 2.30(m, 4H), 2.95(m, 4H), 3.35(m, 4H), 3.55(m, 2H), 5.30(d, 2H), 5.42(s, 2H), 7.05(m, 1H), 7.20(m, 1H), 7.35(m, 5H), 8.00(d, 1H), 10.17(s, 1H) | 580 |
| I-256 | see examples | (300 MHz, CDCl$_3$) δ 1.60-1.80(m, 4H), 2.40-2.55 Hz, 2H), 5.08(s, 2H), 5.29(d, J=1.3 Hz, 2H), 4H), 3.02(t, J=6.6 Hz, 2H), 3.29(t, J=6.6 6.95-7.05(m, 1H), 7.10-7.20(m, 1H), 7.25-7.45 (m, 5H), 7.97(d, J=1.7 Hz, 1H) | 524 |
| I-257 | see examples | (300 MHz, CDCl$_3$) δ 2.42(t, J=4.6 Hz, 4H), 2.90 (t, J=6.9 Hz, 2H), 3.31(t, J=6.9 Hz, 2H), 3.62 (t, J=4.6 Hz, 4H), 5.24(s, 2H), 5.30(d, J=1.3 Hz, 2H), 6.95-7.05(m, 1H), 7.10-7.20(m, 1H), 7.30-7.45(m, 5H), 7.99(d, J=1.6 Hz, 1H), 9.38 (s, 1H) | 540 |
| I-258 | see examples | (300 MHz, CDCl$_3$) δ 1.00(t, 6H), 2.52(q, 4H), 3.02(t, 2H), 3.25(t, 2H), 5.19(s, 2H), 5.29(d, 2H), 7.05(m, 1H), 7.20(m, 1H), 7.35(m, 5H), 7.98(d, 1H) | 526 |
| I-259 | see examples | (300 MHz, CDCl$_3$) δ 2.24(s, 6H), 2.85(t, 2H), 3.24(t, 2H), 5.11(s, 2H), 5.29(d, 2H), 7.07(m, 7.15(m, 1H), 7.35(m, 5H), 7.98(d, 1H) | 498 |
| I-260 | see examples | (300 MHz, CDCl$_3$) δ 1.30.1.60(m, 8H), 2.30-2.45 (m, 4H), 2.89(t, J=6.7 Hz, 2H), 3.28(t, J=6.7 Hz 2H), 5.13(s, 2H), 5.29(d, J=1.4 Hz, 2H), 6.95-7.05(m, 1H), 7.15-7.45(m, 6H), 7.98(d, J= 1.6 Hz, 1H) | 538 |
| I-261 | see examples | (300 MHz, CDCl$_3$) δ 1.60-1.8(m, 4H), 2.05-2.15 (m, 1H), 2.55-2.75(m, 2H), 2.95-3.15(m, 2H), 3.25-3.55(m, 3H), 3.82(dd, J=3.0, 11.2 Hz, 1H), 4.97(s, 2H), 5.28(d, J=1.6 Hz, 2H), 6.98-7.08(m, 1H), 7.10-7.20(m, 1H), 7.25-7.45(m, 5H), 7.98(d, J=1.8 Hz, 1H) | 554 |
| I-262 | see examples | (300 MHz, DMSO-d$_6$) δ 1.15-1.30(m, 2H), 1.45-1.55(m, 2H), 1.90-2.02(m, 2H), 2.50-2.70(m, 4H), 4.49(br s, 1H), 5.28(s, 2H), 5.82(s, 2H), 7.05-7.10(m, 1H), 7.20-7.40(m, 5H), 7.45-7.60 (m, 1H), 7.83(d, J=1.6 Hz, 1H) | 554 |
| I-263 | see examples | (300 MHz, CDCl$_3$) δ 2.36(m, 4H), 2.92(t, 2H), 3.14(m, 2H), 3.32(t, 2H), 3.54(m, 2H), 3.60(br s, 1H) 4.07(s, 2H), 5.30(s, 2H), 5.40(br s, 2H), 7.06(m, 1H), 7.24(m, 2H), 7.34(m, 2H), 7.44(m, 2H), 7.99(d, J=1.6 Hz, 1H), 9.88(br s, 1H) | 596 |
| I-264 | see examples | (300 MHz, CDCl$_3$) δ 1.65(m, 1H), 2.08(m, 1H), 2.22(m, 1H), 2.46(m, 1H), 2.76(m, 1H), 2.87 (m, 1H), 3.02(m, 2H), 3.32(m, 2H), 4.28(m, 1H), 5.28(br s, 2H) 5.29(s, 2H), 7.06(m, 1H), 7.24(m, 2H), 7.44(m, 5H), 8.00(d, J=1.7 Hz, 1H) | 539 |
| I-265 | see examples | (300 MHz, CDCl$_3$) δ 0.02(m, 2H), 0.39(m, 2H), 0.84(m, 1H), 2.40(d, 2H), 3.14(t, 2H), 3.32(t, 2H), 5.28(s, 2H), 5.38(br s, 2H), 7.06(m, 1H), 7.24(m, 2H), 7.44(m, 5H), 8.00(d, J=1.7 Hz, 1H) | 523 |
| I-266 | see examples | (300 MHz, CDCl$_3$) δ 0.28(m, 2H), 0.37(m, 2H), 2.06(m, 1H), 3.15-3.40(m, 4H), 5.30(d, 2H), 5.39(s, 2H), 7.07(m, 1H), 7.19(m, 1H), 7.30-7.55(m, 5H), 8.01(d, 1H) | 509 |
| I-267 | see examples | | 404 |

TABLE 2-continued

| | | | |
|---|---|---|---|
| I-268 | see examples | (400 MHz, DMSO-$d_6$) δ 1.94(t, 4H), 3.31(t, 4H), 5.44(s, 2H), 6.56(d, 1H), 6.74(s, 1H), 6.88(d, 1H), 7.24(t, 1H), 7.43(m, 1H), 7.58(m, 3H), 7.83(m, 2H) | 416 |
| I-269 | see examples | (400 MHz, DMSO-$d_6$) δ 2.99(s, 3H), 5.35(s, 2H), 8.72(br s, 2H), 7.27(d, 2H), 7.42(m, 1H), 7.59(m, 1H), 7.65(d, 2H), 7.73(s, 1H), 7.84(s, 1H), 9.79(s, 1H) | 440 |
| I-270 | see examples | | 397 |
| I-271 | see examples | (300 MHz, $CDCl_3$) δ 8.00(d, J=1.8 Hz, 1H), 7.30(d, J=1.8 Hz, 1H), 7.25(d, J=1.5 Hz, 1H), 7.20(m, 1H), 7.10(d, J=3.8 Hz, 1H), 7.07(m, H), 5.27(d, J=1.7Hz, 2H), 4.82(br s, 2H), 3.81(m, 4H), 2.47(m, 4H), 2.34(s, 3H) | 479 |
| I-272 | see examples | (300 MHz, $CDCl_3$) δ 8.02(d, J=1.8 Hz, 1H), 7.52(m, 1H), 7.32(d, J=1.8 Hz, 1H), 7.21(m, 1H), 7.14(d, J=3.9 Hz, 1H), 7.07(m, 1H), 5.27(d, J=1.5Hz, 2H), 4.80(br s, 2H), 4.50(m, 1H), 3.81(m, 2H), 2.74(m, 4H), 2.25-1.82(m, 10H). | 533 |
| I-273 | see examples | (300 MHz, $CDCl_3$) δ 8.02(d, J=1.8 Hz, 1H), 7.42(d, J=3.9 Hz, 1H), 7.29(d, J=1.8 Hz, 1H), 7.21(m, 1H), 7.15(d, J=3.9 Hz, 1H), 7.07(m, 1H), 5.89(brd, 1H), 5.29(d, J=1.5 Hz, 2H), 4.82(br s, 2H), 4.05(m, 1H), 3.05(m, 2H), 2.50(s, 3H), 2.40(m, 2H), 1.85(m, 2H), 1.62(m, 2H) | 493 |
| I-274 | see examples | (300 MHz, $CDCl_3$) δ 8.00(d, J=1.8 Hz, 1H), 7.30(d, J=1.8 Hz, 1H), 7.24(d, J=3.8 Hz, 1H), 7.21(m, 1H), 7.10(d, J=3.8 Hz, 1H), 7.07(m, 1H), 5.28(d, J=1.5 Hz, 2H), 4.82(br s, 2H), 4.38(m, 2H), 2.98(m, 2H), 2.65(m, 2H), 1.68(br s, 1H), 1.11(d, J=6.2 Hz, 6H) | 493 |
| I-275 | see examples | (300 MHz, $CDCl_3$) δ 8.00(d, J=1.8 Hz, 1H), 7.82(br m, 1H), 7.66(d, J=3.9 Hz, 1H), 7.29(d, J=1.8 Hz, 1H), 7.21(m, 1H), 7.11(d, J=3.9 Hz, 1H), 7.07(m, 1H), 5.26(d, J=1.5 Hz, 2H), 4.81(br s, 2H), 3.71(m, 2H), 3.02(m, 2H), 2.95(m, 2H), 2.01(m, 4H), 1.97(m, 2H), 1.11(d, J=6.2 Hz, 6H) | 493 |
| I-276 | see examples | (300 MHz, $CDCl_3$) δ 8.00(d, J=1.8 Hz, 1H), 7.29(d, J=1.8 Hz, 1H), 7.24(d, J=3.8 Hz, 1H), 7.20(m, 1H), 7.09(d, J=3.8 Hz, 1H), 7.07(m, 1H), 5.27(d, Hz, 2H), 4.80(br s, 2H), 4.43(m, 2H), 3.10(m, 2H), 2.63(m, 4H), 2.34(m, 1H), 1.99(m, 2H), 1.83(m, 4H), 1.63(m, 2H). | 533 |
| I-277 | see examples | | 407 |
| I-278 | see examples | (300 MHz, $CDCl_3$) δ 7.97(d, J=1.8 Hz, 1H), 7.61-7.42(m, 6H), 7.21(d, J=8.7 Hz, 1H), 7.12(d, J=1.8 Hz, 1H), 5.33(s, 2H), 4.81(br s, 2H), 4.82(m, 1H), 3.84(m, 1H), 2.98(m, 2H), 2.65(m, 4H), 2.32(m, 1H), 1.97(m, 2H), 1.84(m, 4H), 1.60(m, 2H) | 543 |
| I-279 | see examples | (300 MHz, $CDCl_3$) δ 7.99(d, J=1.8 Hz, 1H), 7.80(d, J=8.3 Hz, 2H), 7.55(m, 1H), 7.52(d, J=8.3 Hz, 2H), 7.44(d, J=7.8 Hz, 1H), 7.22(t, J=8.7 Hz, 1H), 7.12(d, J=1.8 Hz, 1H), 5.99(br d, 1H), 5.34(s, 2H), 4.83(br s, 2H), 4.04(m, 1H), 2.87(m, 2H), 2.34(s, 3H), 2.20(m, 2H), 2.05(m, 2H), 1.63(m, 2H) | 503 |
| I-280 | see examples | (300 MHz, $CDCl_3$) δ 7.98(s, 1H:,7.61-7.43(m, 6H), 7.22(t, J=8.7 Hz, 1H), 7.13(d, J=1.6 Hz, 1H), 5.33(s, 2H), 4.82(br s, 2H), 4.85(m, 1H), 3.65(m, 1H), 2.90(m, 2H), 2.68(m, 1H), 2.42(m, 1H), 1.60(m, 1H), 1.12(d, 3H), 1.00(d, 3H) | 503 |
| I-281 | see examples | (300 MHz, $CDCl_3$) δ 7.98(d, J=2.4 Hz, 1H), 7.81-7.43(m, 6H), 7.21(t, J=8.8 Hz, 1H), 7.14(d, J=2.4 Hz, 1H), 5.33(s, 2H), 4.87(br s, 2H), 3.89(m, 1H), 3.65(m, 2H), 3.42(m, 1H), 2.70(m, 1H), 2.32(s, 3H), 2.23(s, 3H), 2.14(m, 1H), 1.82(m, 1H) | 503 |
| I-282 | see examples | (300 MHz, $CDCl_3$) δ 7.98(d, J=1.4 Hz, 1H), 7.58-7.43(m, 6H), 7.20(t, J=8.8 Hz, 1H), 7.13(d, J=1.4 Hz, 1H), 5.34(s, 2H), 4.81(br s, 2H), 4.46(m, 1H), 3.50(m, 2H), 2.77(m, 4H), 2.30-1.50(m, 10H) | 543 |
| I-283 | see examples | (300 MHz, $CDCl_3$) δ 8.00(d, J=1.2 Hz, 1H), 7.83(d, J=8.2 Hz, 2H), 7.58(m, 1H), 7.55(d, J=8.2 Hz, 2H), 7.45(d, 1H), 7.20(t, J=8.8 Hz, | 519 |

TABLE 2-continued

| | | | |
|---|---|---|---|
| | | 1H), 7.13(d, J=1.4 Hz, 1H), 6.76(m, 1H), 5.34 (s, 2H), 4.85(br s, 2H), 3.74(m, 4H), 3.55(m, 2H), 2.62(m, 2H), 2.52(m, 4H) | |
| I-284 | see examples | (300 MHz, CDCl$_3$) δ 7.97(d, J=1.8 Hz, 1H), 758-7.43(m, 6H), 7.20(t, J=8.8 Hz, 1H), 7.12 (d J=1.8 Hz, 1H), 5.34(s, 2H), 4.93(br s, 2H), 3.80(m, 2H), 3.56(m, 2H), 2.44(m, 4H), 2.33(s, 3H) | 489 |
| I-285 | see examples | (300 MHz, CDCl$_3$) δ 8.00(d, J=1.2 Hz, 1H), 7.82(d, J=8.2 Hz, 2H), 7.58(m, 1H), 7.55(d, J= 8.2 Hz, 2H), 7.44(d J=7.8 Hz, 1H), 7.22(t, J= 8.8Hz, 1H), 7.14(d, J=1.4 Hz, 1H), 6.72(m, 1H), 5.34(s, 2H), 4.85(br s, 2H), 3.65(m, 2H), 3.60(m, 2H), 3.50(m, 2H), 2.65(m, 2H), 2.51 (m, 4H), 2.10(s, 3H) | 560 |
| I-286 | see examples | (300 MHz, CDCl$_3$) δ 7.84(d, 1H), 7.26(d, 2H), 7.20(d, 2H), 7.06(m, 3H), 7.59(s, 1H), 4.86(s, 2H), 3.25(m, 2H), 2.89(m, 2H), 2.49(m, 4H), 1.83(d, 3H), 1.62(m, 4H), 1.48(m, 2H) | 551 |
| I-287 | see examples | (300 MHz, CDCl$_3$) δ 7.84(d, 1H), 7.26(d, 2H), 7.20(d, 2H), 7.06(m, 3H), 7.59(s, 1H), 4.86(s, 2H), 3.76(m, 1H), 3.25(m, 2H), 2.89(m, 2H), 2.78(m, 2H), 2.26(m, 2H), 1.83(m, 5H), 1.62 (m, 2H) | 567 |
| I-288 | see examples | (300 MHz, CDCl$_3$) δ 7.84(d, 1H), 7.26(d, 2H), 7.20(d, 2H), 7.06(m, 3H), 7.59(s, 1H), 4.86(s, 2H), 3.21(m, 2H), 2.88(m, 2H), 2.30(s, 6H), 2.26(m, 2H), 1.82(d, 3H) | 511 |
| I-289 | see examples | (300 MHz, CDCl$_3$) δ 7.89(s, 1H), 7.38(d, 2H), 7.26(d, 2H), 7.18(m, 3H), 5.95(m, 1H), 4.89(s, 2H), 3.22(m, 4H), 2.14(m, 1H), 1.85(d, 3H), 0.50(m, 2H), 0.38(m, 2H) | 523 |
| I-290 | see examples | | 422 |
| I-291 | see examples | (300 MHz, CDCl$_3$) δ 7.84(d, 1H) 7.52(d, 2H), 7.31(d, 2H), 7.08(m, 3H), 6.13(m, 1H), 4.86(s, 2H), 4.30(m, 1H), 3.40(m, 2H), 2.60(m, 4H), 1.82(d, 3H), 1.70-2.0(m, 10H) | 557 |
| I-292 | see examples | (300 MHz, CDCl$_3$) δ 7.84(d, 1H), 7.78(d, 2H), 7.35(d, 2H), 7.31(m, 3H), 6.16(tert, 1H), 5.90 (d, 1H), 4.86(s, 2H), 4.05(m, 1H), 2.85(d, 1H), 2.35(s, 3H), 2.05(d, 1H), 2.25(t, 1H), 1.82(d, 3H), 1.60(m, 1H), 1.29(m, 2H), 0.86(m, 2H) | 559 |
| I-293 | see examples | (300 MHz, CDCl$_3$) δ 7.84(d, 1H), 7.51(s, 1H), 7.38(m, 3H), 7.30(m, 1H), 7.15(m, 1H), 6.97(s, 1H), 6.15(m, 1H), 4.94(s, 2H), 3.45-3.89(m, 4H), 3.20(m, 1H), 2.25(m, 1H), 2.15(m, 1H), 1.82(d, 3H), 1.34(m, 2H) | 489 |
| I-294 | see examples | (300 MHz, CDCl$_3$) δ 7.84(d, 1H), 7.70(m, 1H), 7.45(m, 1H), 7.30(s, 2H), 7.08(t, 1H), 6.92(d, 2H), 6.13(m, 1H), 4.86(s, 2H), 4.30(t, 1H), 2.80 (m, 4H), 1.82(d, 3H), 1.80(m, 4H), 1.35(m. 4H), 0.89(m, 4H) | 559 |
| I-295 | see examples | (300 MHz, CDCl$_3$) δ 7.89(s, 1H), 7.71(m, 2H), 7.49(d, 2H), 7.40(s, 1H), 7.35(m, 1H), 7.08(m, 1H), 6.17(m, 1H), 4.98(s, 2H), 4.28(t, 2H), 3.68 (m, 4H), 2.38(m, 2H), 2.31(s, 3H), 1.88(d, 3H) | 503 |
| I-296 | see examples | | |
| I-297 | see examples | (300 MHz, CDCl$_3$) δ 7.79(s, 1H), 7.30(m, 3H), 7.24(m, 3H), 7.08(t, 1H), 6.95(s, 1H), 8.09(m, 1H), 4.89(s, 2H), 3.21(m, 4H), 2.12(m, 1H), 1.84(d, 3H), 0.87(m, 1H), 0.50(m, 2H), 0.36(m, 2H) | 539 |
| I-298 | see examples | (300 MHz, CDCl$_3$) δ 7.81(s, 1H), 7.26(m, 6H), 7.04(t, 1H), 6.94(s, 1H), 6.12(m, 1H), 4.95(s, 2H), 3.21(t, 2H), 2.85(t, 2H), 2.31(s, 6H), 1.85 (d, 3H) | 527 |
| I-299 | see examples | (300 MHz, CDCl$_3$) δ 7.84(d, 1H), 7.30(m, 5H), 7.10(t, 1H), 8.89(s, 1H), 6.10(tert, 1H), 4.86(s, 2H), 4.40(s, 1H), 3.21(m, 2H), 2.88(m, 3H), 2.67(d, 1H), 2.46(m, 1H), 2.20(m, 2H), 2.05(s, 1H), 1.85(d, 3H), 1.25(s, 1H) | 570 |
| I-300 | 4 as in Example I-291 | (300 MHz, CDCl$_3$) δ 7.85(s, 1H), 7.79(d, 2H), 7.42(d, 2H), 7.30(dd, 1H), 7.07(t, 1H), 7.02(d, 1H), 6.81(bm, 1H), 6.13(q, 1H), 5.42(s, 2H), 3.80(m, 2H), 3.62(m, 2H), 3.53(m, 2H), 2.68 (m, 2H), 2.52(m, 4H), 2.10(s, 3H), 1.87(d, 3H). | 575 [M + 1] |
| I-301 | 4 as in Example I- | (300 MHz, CDCl$_3$) δ 6.71(bm, 1H), 7.92(m, 3H), 742(d, 2H), 7.31(dd, 1H), 7.06(t, H), 7.01(s, | 533 [M + 1] |

TABLE 2-continued

| | | | |
|---|---|---|---|
| | | 291 | 1H), 6.12(q, 1H), 4.97(s, 2H), 3.65(m, 2H), 3.00 (m, 6H), 2.00(m. 6H), 1.87(d, 3H). | |
| I-302 | 4 as in Example I-291 | (300 MHz, CDCl$_3$) δ 7.90(d, 1H), 7.79(d, 2H), 7.44(d, 2H), 7.31(dd, 1H), 7.06(t, 1H), 7.01(d, 1H), 6.83(bm, 1H), 6.12(q, 1H), 5.05(s, 2H), 3.74(m, 4H), 3.58(m, 2H), 2.63(m, 2H), 2.53 (m, 4H), 1.87(d, 3H). | 491 [M + 1] |
| I-303 | 4 as in Example I-291 | (300 MHz, CD$_3$OD) δ 7.76(s, 1H),7.54(m, 1H), 7.42(m, 4H), 7.24(t, 1H), 7.04(s, 1H), 6.22(q, 1H), 4.82(s, 2H), 3.76(m, 1H), 3.68(m, 2H), 3.52(m, 1H), 2.28(m, 1H), 1.92(m, 3H), 1.75 (m, 1H), 1.42(m, 1H). | 491 [M + 1] |
| I-304 | 4 as in Example I-291 | (300 MHz, CD$_3$OD) δ 7.76(s, 1H),7.54(m, 1H), 7.42(m, 4H), 7.24(t, 1H), 7.04(s, 1H), 6.22(q, 1H), 4.82(s, 2H), 3.76(m, 1H), 3.68(m, 2H), 3.52(m, 1H), 2.28(m, 1H), 1.92(m, 3H), 1.75 (m, 1H), 1.42(m, 1H). | 491 [M + 1] |
| I-305 | 4 as in Example I-291 | | 504 [M + 1] |
| I-306 | 4 as in Example I-291 | (300 MHz, CD$_3$OD) δ 7.78(d, 1H), 7.47(m, 3H), 7.37(m, 3H), 6.92(d, 1H), 6.07(q. 1H), 5.88(s, 2H), 4.82(dd, 1H), 4.15(d, 1H), 3.53(m, 2H), 3.42(m, 1H), 3.15(m, 1H), 2.43(m, 1H), 1.85 (m, 1H), 1.75(d, 3H). | 491 [M + 1] |
| I-307 | 4 as in Example I-291 | (300 MHz, CD$_3$OD) δ 7.80(d, 1H), 7.47(m, 3H), 7.37(m, 3H), 6.92(d, 1H), 6.07(q, 1H), 5.89(s, 2H), 4.82(dd, 1H), 4.15(d, 1H), 3.53(m. 2H), 3.42(m, 1H), 3.15(m. 1H), 2.43(m, 1H), 1.85 (m, 1H), 1.75(d, 3H). | 491 [M + 1] |
| I-308 | 4 as in Example I-291 | (300 MHz, CD$_3$OD) δ 7.80(d, 1H), 7.47(m, 3H), 7.37(m, 3H) 6.92(d, 1H), 6.07(q, 1H), 5.89(s, 2H), 4.70(m, 1H), 4.05(m, 1H), 3.5(m, 2H), 3.32 (m, 1H), 2.43(m, 1H), 1.85(m, 3H), 1.75(d, 3H), 1.1 5(m, 1H). | 505 [M + 1] |
| I-309 | 4 as in Example I-291 | (300 MHz, CDCl$_3$) δ 9.55(bm, 1H), 8.80(t, 1H), 7.95(s, 1H), 7.58(d, 2H), 7.55(m, 3H), 7.45(t, 1H), 7.09(d, 1H), 6.23(q, 1H), 3.60(q, 2H), (m, 5H), 3.09(m, 1H), 1.85(d, 3H), 1.22(dd, 6H). | 519 [M + 1] |
| I-310 | 4 as in Example I-291 | (300 MHz, CDCl$_3$) δ 8.25(bm, 1H), 7.90(d, 1H), 7.82(s, 2H), 7.34(d, 2H), 7.25(m, 1H), 7.04(t, 1H), 8.98(s, 1H), 6.09(q, 1H), 4.97(s, 2H), 3.82 (m, 2H), 3.15(m, 6H), 2.00(m, 4H), 1.85(d, 3H). | 518 [M + 1] |
| I-311 | 3 as in Example 211 | | 420 [M + 1] |
| I-312 | 4 | (300 MHz, CDCl$_3$) δ 7.86(s, 1H), 7.41(m, 3H), 7.30(m, 3H), 7.07(t, 1H), 6.99(s, 1H); 6.12(q, 1H), 4.99(s, 2H), 3.89(m, 2H), 3.50(m, 2H), 2.54(m, 2H), 2.40(m, 2H), 2.35(s, 3H), 1.87(d, 3H). | 503 [M + 1] |
| I-313 | 4 as in Example I-312 | (300 MHz, CDCl$_3$) δ 7.89(s, 1H), 7.76(s, 1H), 7.67(d, 1H), 7.49(d, 1H), 7.42(t, 1H), 7.31(dd, 1H), 7.05(t, 1H), 7.01(s, 1H), 6.28(bd, 1H), 6.12 1H), 4.99(s, 2H), 4.08(m, 1H), 3.04(m, 2H), 2.42(s, 3H), 2.32(m, 2H), 2.10(m, 2H), 1.87(d, 3H), 1.80(m, 2H). | 517 [M + 1] |
| I-314 | 4 as in Example I-312 | (300 MHz, CDCl$_3$) δ 7.87(s, 1H), 7.40(m, 4H), 7.29(dd, 1H), 7.05(t, 1H), 7.00(s, 1H), 6.12(q, 1H), 4.92(s, 2H), 3.50(m, 2H), 3.74(m, 4H). 1.88(d, 3H), 1.57-2.18(m, 11H). | 559 [M + 1] |
| I-315 | 4 as in Example I-312 | (300 MHz, CDCl$_3$) δ 7.88(s, 1H), 7.83(s, 1H). 7.65(d, 1H), 7.46(m, 2H), 7.32(dd, 1H), 7.06(t, 1H), 7.03(s, 1H), 6.95(bt, 1H), 6.12(q, 1H), (s, 2H), 3.66(m, 4H), 3.50(m, 2H), 2.73(m, 2H), 2.52(m, 4H), 2.09(s, 3H), 1.87(d, 3H). | 576 [M + 1] |
| I-316 | 4 as in Example I-312 | (300 MHz, CDCl$_3$) δ 7.87(s, 1H), 7.38(m, 4H), 7.28(m, 1H), 7.06(t, 1H), 6.98(s, 1H), 6.12(q, H), 5.05(s, 2H), 3.82(m, 2H), 3.72(m, 2H), 2.10(m, 1H), 1.86(d, 3H), 1.84(m, 2H). | 491 [M + 1] |
| I-317 | 4 as in Example I-312 | (300 MHz, CDCl$_3$) δ 7.91(s, 1H), 7.87(s, 1H), 7.85(d, 1H), 7.50(m, 2H), 7.31(dd, 1H), 7.04(m 2H), 6.13(q, 1H), 4.93(s, 2H), 3.64(m, 6H), 2.50(m, 6H), 1.87(d, 3H), 1.81(m, 2H). | 549 [M + 1] |
| I-318 | 4 as in Example I-312 | (300 MHz, CDCl$_3$) δ 7.87(s, 1H), 7.40(m, 4H), 7.29(dd, 1H), 7.05(t, 1H), 7.00(s, 1H), 6.12(q, 1H), 4.92(s, 2H), 3.50(m, 2H), 3.74(m, 4H), 1.88(d, 3H), 1.57-2.18(m, 11H). | 558 [M + 1] |

TABLE 2-continued

| | | | |
|---|---|---|---|
| I-319 | 4 as in Example I-312 | (300 MHz, CDCl$_3$) δ 7.86(s, 1H), 7.82(s, 1H), 7.73(d, 1H), 7.46(m, 4H), 7.22(t, 1H), 7.04(s, 1H), 8.95(bt, 1H), 6.22(q, 1H), 4.82(s, 2H), (m, 2H), 2.82(m, 2H), 2.70(m, 4H), 1.87(d, 3H), 1.82(m, 2H). | 518 [M + 1] |
| I-320 | 4 as in Example I-312 | (300 MHz, CDCl$_3$) δ 8.68(bt, 1H), 7.90(s, 1H), 7.85(s, 1H), 7.61(d, 1H), 7.42(m, 2H), 7.31 (dd, 1H), 7.05(m, 2H), 6.14(q, 1H), 4.88(s, 2H), 3.65(m, 2H), 2.71(m, 2H), 2.56(m, 4H), 1.87(d, 3H), 1.80(m, 2H), 1.71(m, 4H). | 531 [M + 1] |
| I-321 | 4 as in Example I-312 | (300 MHz, CDCl$_3$) δ 7.90(s, 1H), 7.84(s, 1H), 7.66(d, 1H), 7.46(m, 2H), 7.32(dd, 1H), 7.05 (m, 2H), 6.88(bt, 1H), 6.14(q, 1H), 5.04(s, 2H), 3.82(m, 4H), 3.66(m, 2H), 2.72(t, 2H), 2.60(m, 4H), 1.88(d, 3H). | 535 [M + 1] |
| I-322 | 4 as in Example I-312 | (300 MHz, CDCl$_3$) δ 7.86(s, 1H), 7.41(m, 3H), 7.30(m, 3H), 7.07(t, 1H), 6.99(s, 1H), 6.12(q, 1H), 4.95(s, 2H), 4.70(m, 1H), 3.82(m, 1H), 3.06(m, 1H), 2.98(m, 1H), 2.65(m, 4H), 2.28 (m, 1H), 1.02(m, 1H), 1.81(m, 5H), 1.55(m, 2H). | 559 [M + 1] |
| I-323 | 9 | (300 MHz, CDCl$_3$) δ 7.83(s, 1H), 7.32(m, 4H), 7.21(d, 2H), 7.06(t, 1H), 6.96(s, 1H), 5.96(q, 1H), 4.81(s, 2H), 3.22(m, 2H), 3.02(m, 2H), 2.62(m, 4H), 1.84(d, 3H), 1.08(t, 6H). | 571 [M + 1] |
| I-324 | 9 as in Example I-297 | (300 MHz, CDCl$_3$) δ 7.81(s, 1H), 7.31(m, 3H), 7.25(m, 3H), 7.07(t, 1H), 6.96(s, 1H), 8.11(q, 4.95(s, 2H), 3.76(m, 1H), 3.25(t, 2H), 2.92 (t, 2H), 2.79(m, 2H), 2.25(m, 2H), 1.93(m, 2H). 1.88(d, 3H), 1.62(m, 2H). | 583 [M + 1] |
| I-325 | 9 as in Example I-297 | (300 MHz, CDCl$_3$) δ 7.84(s, 1H), 7.32(m, 4H), 7.21(d, 2H), 7.06(dd, 1H), 6.96(s, 1H), 6.11(q, 1H), 4.88(s, 2H), 3.24(t, 2H), 2.89(t, 2H), 2.48 297(m, 4H), 1.86(d, 3H), 1.62(m, 4H), 1.49(m, 2H). | 558 [M + 1] |
| I-326 | 9 as in Example I-297 | (300 MHz, CDCl$_3$) δ 7.83(s, 1H), 7.28(m, 6H) (dd, 1H), 6.96(s, 1H), 6.11(q, 1H), 4.91(s, 2H), 3.22(m, 4H), 2.50(d, 2H), 1.86(d, 3H), 0.84 297(m, 2H), 0.52(m, 2H), 0.15(m, 1H). | 517 [M + 1] |
| I-327 | 9 as in Example I-286 | (300 MHz, CDCl$_3$) δ 7.83(s, 1H), 7.32(m, 5H), 7.05(m, 3H), 5.95(q, 1H), 4.84(s, 2H), 4.43(m, 1H), 3.25(m, 2H), 3.02(m, 3H), 2.84(m, 1H), 2.53(m, 1H), 2.30(m, 1H), 2.22(m, 1H), 1.84(d, 3H), 1.81(m, 1H). | 553 [M + 1] |
| I-328 | 9 as in Example I-286 | (300 MHz, CDCl$_3$) δ 7.89(s, 1H), 7.38(d, 2H), 7.24(m, 2H), 7.18(m, 3H), 5.95(q, 1H), 4.89(s, 2H), 3.22(m, 4H), 2.14(m, 1H), 1.85(d, 3H), 0.50(m, 2H), 0.38(m, 2H). | 523 [M + 1] |
| I-329 | 9 as in Example I-286 | (300 MHz, CDCl$_3$) δ 7.84(s, 1H), 7.34(d, 2H). 7.23(m, 3H), 7.02(m, 3H), 5.96(q, 1H), 4.81(s, 2H), 3.22(m, 2H), 3.02(m, 2H), 2.62(m, 4H), 1.84(d, 3H), 1.08(t, 6H). | 539 [M + 1] |
| I-330 | 3 as in Example I-211 | | 405 [M + 1] |
| I-331 | 4 | (300 MHz, CDCl$_3$) δ 7.91(s, 1H), 7.80(d, 2H), 7.46(d, 2H), 7.05(m, 3H), 6.87(m, 1H), 5.97(q, 1H), 4.97(s, 2H), 3.75(m, 4H), 3.58(m, 2H), 2.60(m, 6H), 1.84(m, 3H). | 517 [M + 1] |
| I-332 | 4 as in Example I-331 | (300 MHz, CDCl$_3$) δ 7.90(s, 1H), 7.78(d, 2H), 7.45(d, 2H), 7.05(m, 4H), 5.98(q, 1H), 4.90(s, 2H), 4.00(m, 1H), 2.88(m, 2H), 2.32(s, 3H), 2.18(m, 2H), 2.08(m, 2H), 1.84(d, 3H), 1.57(m, 2H). | 501 [M + 1] |
| I-333 | 4 as in Example I-331 | (300 MHz, CDCl$_3$) δ 7.90(s, 1H), 7.54(m, 2H), 7.42(d, 2H), 7.05(m, 3H), 5.98(q, 1H), 4.86(s, 2H), 3.50(m, 2H), 3.74(m, 4H), 1.84(d, 3H), 1.57-2.18(m, 11H) | 541 [M + 1] |
| I-334 | 4 as in Example I-331 | (300 MHz, CDCl$_3$) δ 7.68(m, 5H), 7.25(m, 3H), 6.27(m, 1H), 4.88(s, 2H), 3.75(m, 5H), 3.31(m, 2H), 2.44(m, 1H), 2.17(m, 1H), 1.93(m, 3H). | 473 [M + 1] |
| I-335 | 4 as in Example I-331 | (300 MHz, CDCl$_3$) δ 7.90(s, 1H), 7.42(m, 4H), 7.05(m, 3H), 5.97(q, 1H), 4.86(s, 2H), 4.62(m, 1H), 3.65(m, 1H), 2.88(m, 2H), 2.68(m, 1H), 2.41(m, 1H), 1.84(d, 3H), 1.64(m, 1H), 1.05(m, 6H). | 501 [M + 1] |
| I-336 | 4 as in Example I-331 | (300 MHz, CDCl$_3$) δ 9.00(s, 1H), 7.92(s, 1H). 7.83(d, 2H), 7.42(d, 2H), 7.09(m, 2H), 7.01(m, 1H), 5.96(q, 1H), 4.89(s, 2H), 3.60(m, 2H), 2.75 (m, 2H), 2.62(m, 4H), 1.85(m, 7H). | 515 [M + 1] |

TABLE 2-continued

| | | | |
|---|---|---|---|
| I-337 | 4 as in Example I-331 | (300 MHz, CDCl$_3$) δ 7.90(s, 1H), 7.53(m, 2H), (d, 2H), 7.05(m, 3H), 5.98(q, 1H), 4.86(s, 2H), 4.45(m, 1H), 3.58(m, 2H), 3.00(m, 4H), 1.84(d, 3H), 1.70-2.18(m, 10H) | 541 [M + 1] |
| I-338 | 4 as in Example I-331 | (300 MHz, CDCl$_3$) δ 7.90(s, 1H), 7.44(m, 4H), 7.07(m, 3H), 5.95(q, 1H), 4.87(s, 2H), 3.60 (m, 4H), 2.43(m, 4H), 2.33(s, 3H), 1.84(d, 3H). | 587 [M + 1] |
| I-339 | 4 as in Example I-331 | (300 MHz, CDCl$_3$) δ 7.90(s, 1H), 7.42(m, 4H), 7.02(m, 3H), 6.00(q, 1H), 4.87(s, 2H), 4.64(m, 1H), 3.85(m, 1H), 2.99(m, 2H), 2.67(m, 4H), 2.38(m, 1H), 1.90(m, 9H), 1.62(m, 2H). | 541 [M + 1] |
| I-340 | 4 as in Example I-331 | (300 MHz, CDCl$_3$) δ 7.91(s, 1H), 7.86(d, 2H), 7.45(d, 2H), 7.10(m, 3H), 7.01(m, 1H), 5.98(q, H), 4.90(s, 2H), 3.60(m, 2H), 2.80(m, 2H), 2.68(m, 4H), 1.85(m, 7H). | 501 [M + 1] |
| I-341 | 4 as in Example I-331 | (300 MHz, CDCl$_3$) δ 7.76(s, 1H), 7.67(m, 2H), 7.59(d, 2H), 7.42(s, 1H), 7.32(m, 1H), 7.20(m, 1H), 6.27(m, 1H), 4.86(s, 2H), 3.75(m, 5H), 3.31(m, 2H), 2.44(m, 1H), 2.14(m, 1H), 1.95 (m, 3H). | 473 [M + 1] |
| I-342 | as in Example 211 | | 405 [M + 1] |
| I-343 | 4 | (300 MHz, CDCl$_3$) δ 7.88(s, 1H), 7.43(m, 2H), 7.30(m, 2H), 7.10(m, 2H), 6.95(m, 1H), 5.97(q, 0.164 1H), 4.87(s, 2H), 4.65(m, 1H), 3.60(m, 1H), 2.72(m, 3H), 2.41(m, 1H), 2.01(s, 1H), 1.84(d, 3H), 1.17(m, 3H), 0.98(m, 3H). | 501 [M + 1] |
| I-344 | 4 as in Example 343 | (300 MHz, CDCl$_3$) δ 7.65(m, 5H), 7.42(s, 1H), 7.32(m, 1H), 7.20(m, 1H), 6.27(m, 1H), 4.85(s, 2H), 3.75(m, 5H), 3.31(m, 2H), 2.44(m, 1H), 2.16(m, 1H), 1.93(m, 3H). | 473 [M + 1] |
| I-345 | 4 as in Example 343 | (300 MHz, CDCl$_3$) δ 7.90(s, 1H), 7.78(s, 1H), 7.67(d, 1H), 7.45(m, 2H), 7.00(m, 3H), 6.15 (bd, 1H), 5.98(q, 1H), 4.08(m, 1H), 2.97(m, 2H), 2.38(s, 3H), 2.27(m, 2H), 2.10(m, 2H), 1.84(d, 3H), 1.74(m, 2H). | 501 [M + 1] |
| I-346 | 4 as in Example 343 | (300 MHz, CDCl$_3$) δ 7.88(s, 1H), 7.42(m, 3H), 7.30(m, 2H), 7.09(m, 2H), 7.00(m, 1H), 5.95 1H), 4.87(s, 2H), 3.83(m, 2H), 3.47(m, 2H), 2.51(m, 2H), 2.33(m, 5H), 1.84(d, 3H). | 487 [M + 1] |
| I-347 | 4 as in Example 343 | (300 MHz, CDCl$_3$) δ 8.69(s, 1H), 7.91(m, 2H), 7.65(d, 1H), 7.42(m, 2H), 7.00(m, 3H), 5.99(q, 1H), 4.85(s, 2H), 3.60(m, 2H), 2.76(m, 2H), 2.63(m, 4H), 1.84(d, 3H), 1.77(m, 6H). | 515 [M + 1] |
| I-348 | 4 as in Example 343 | (300 MHz, CDCl$_3$) δ 7.91(s, 1H), 7.86(s, 1H), 7.70(d, 1H), 7.50(m, 2H), 7.00(m, 4H), 5.99(q, 1H), 4.86(s, 2H), 3.60(m, 2H), 2.78(m, 2H), 2.63(m, 4H), 1.85(m, 7H). | 501 [M + 1] |
| I-349 | 4 as in Example 343 | (300 MHz, CDCl$_3$) δ 7.70(m, 5H), 7.42(s, 1H), 7.28(m, 1H), 7.20(m, 1H), 6.27(m, 1H), 4.85(s, 2H), 3.75(m, 5H), 3.31(m, 2H), 2.66(m, 1H), 2.44(m, 1H), 1.93(m, 3H). | 473 [M + 1] |
| I-350 | 4 as in Example 343 | (300 MHz, CDCl$_3$) δ 7.91(s, 1H), 7.84(s, 1H), 7.65(d, 1H), 7.46(m, 2H), 7.05(m, 3H), 6.83 (bs, 1H), 5.97(q, 1H), 4.91(s, 2H), 3.74(m, 4H), 3.58(m, 2H), 2.63(m, 2H), 2.52(m, 4H), 1.84 (m, 3H). | 517 [M + 1] |
| I-351 | 4 as in Example 343 | (300 MHz, CDCl$_3$) δ 7.88(s, 1H), 7.45(m, 4H), 7.05(m, 3H), 5.98(q, 1H), 4.86(s, 2H), 4.45(m, 1H), 3.64(m, 2H), 3.44(m, 4H), 2.64(d, 4H), 1.83(d, 3H), 1.70-2.18(m, 10H) | 541 [M + 1] |
| I-352 | 4 as in Example 343 | (300 MHz, CDCl$_3$) δ 7.88(s, 1H), 7.45(m, 4H), 7.05(m, 3H), 5.98(q, 1H), 4.86(s, 2H), 4.45(m, 1H), 3.45(m, 2H), 2.75(m, 4H), 1.84(d, 3H), 1.70-2.18(m, 10H) | 541 [M + 1] |
| I-353 | 3 as in Example I-2 | | |
| I-354 | 3 as in Example I-2 | | |
| I-355 | 3 as in Example I-2 | (400 MHz, DMSO-d$_6$): δ 7.74(d, J=2.0 Hz, 1H), 7.53(m, 1H), 7.44(m, 2H), 7.32(d, J=9.0 Hz, 2H), 7.00(d, J=8.6 Hz, 2H), 6.88(d, J=1.6 Hz 1H), 6.11(m, 1H), 5.79(s, 2H), 4.30(m, 2H), 3.5 (m, 6H), 1.90(m, 4H), 1.807(d, J=6.7 Hz, 3H). | 491 [M + 1] |
| I-356 | 3 as in Example I-2 | (400 MHz, DMSO-d$_6$): δ 7.73(s, 1H), 7.54(m, 1H), 7.44(m, 2H), 7.284(d, J=8.2 Hz, 2H), 6.95 (d, J=8.6 Hz, 2H), 6.88(s, 1H, pyridine-H), 6.10 | 504 [M + 1] |

TABLE 2-continued

| | | | |
|---|---|---|---|
| | | (m 1H), 5.78(s, 2H), 4.7(m, 1H), 3.3(m, 2H), 3.1(m, 2H), 2.77(s, 3H), 2.3(m, 6H), 1.81(d, J= 6.2 Hz, 3H). | |
| I-357 | 3 as in Example I-2 | (400 MHz, DMSO-d$_6$): δ 7.72(d, 1H), 7.53(m, 1H), 7.44(m, 1H), 7.33(m, 2H), 7.03(m, 3H), 6.23(q, 1H), 4.35(m, 2H), 3.95(m, 1H), 3.0-3.8 (m, 9H), 1.851(d, 3H). | 506 [M + 1] |
| I-358 | 3 as in Example I-2 | (400 MHz, DMSO-d$_6$): δ 7.82(d, 1H), 7.53(q, 1H), 7.46(t, 1H), 7.33(t, 1H), 7.03(m, 3H), 6.95 (dd, 1H), 6.24(q, 1H), 4.38(m, 2H), 3.95(m, 2H) 3.75(m, 2H), 3.61(m, 2H), 3.5(m, 2H), 3.25(m, 2H), 1.851(d, 3H). | 506 [M + 1] |
| I-359 | 3 as in Example I-2 | (400 MHz, DMSO-d$_6$): δ 7.73(d, J=1.6 Hz, 1H), 7.56(m, 1H), 7.44(t, J=8.8 Hz, 1H), 7.28(d, J= 6.7 Hz, 2H), 6.94(d, J=8.6 Hz, 2H), 6.88(d, J= 2.0 Hz, 1H), 6.11(m, 1H), 5.75(s, 2H), 4.88(d, J=2.0 Hz, 1H), 3.96(m, 3H), 3.57(t, J=4.3 Hz, 4H), 2.42 (m, 6H), 1.81(d, J=6.7 Hz, 3H). | 536 [M + 1] |
| I-360 | 3 as in Example I-2 | (400 MHz, DMSO-d$_6$): δ 7.73(d, J=1.6 Hz, 1H), 7.56(m, 1H), 7.44(t, J=8.6 Hz, 1H), 7.28(d, J= 8.6 Hz, 2H), 6.92(d, J=8.6 Hz, 2H), 6.88(d, J= 1.6 Hz, 1H), 6.11(m, 1H), 5.75(s, 2H), 4.02(t, J= 6.2 Hz, 2H), 2.756(m, 2H), 2.55(m, 4H), 1.81 (d, J=6.7 Hz, 3H), 0.99(t, J=7.0 Hz, 6H). | 494 [M + 1] |
| I-361 | 3 as in Example I-2 | (400 MHz, DMSO-d$_6$): δ 7.73(d, J=2.0 Hz, 1H), 7.53(m, 1H), 7.44(t, J=8.6 Hz, 1H), 7.27(d, J= 6.7 Hz, 2H), 6.92(d, J=8.6 Hz, 2H), 6.87(d, J= 1.6 Hz, 1H), 6.10(m, 1H), 5.75(s, 2H), 3.831(m, 2H), 2.81(m, 1H), 2.62(s, 1H), 2.153(s, 3H), 1.95(m, 3H), 1.81(d, J=6.7 Hz, 3H), 1.72 (m, 4H). | 504 [M + 1] |
| I-362 | 3 as in Example I-2 | (400 MHz, DMSO-d$_6$): δ 7.73(d, J=2.0 Hz, 1H), 7.53(m, 1H), 7.44(t, J=8.6 Hz, 1H), 7.27(m, 2H), 6.91(m, 2H), 6.88(d, J=2.0Hz, 1H), 6.11 (m, 1H), 5.74(s, 2H), 3.88(t, J=6.7 Hz, 2H), 3.02(m, 2H), 2.76(t, J=6.7 Hz, 2H), 1.81(d, J= 6.7 Hz, 3H), 0.986(m, 12H). | 520 [M + 1] |
| I-363 | 3 | (400 MHz, DMSO-d$_6$): δ 7.66(d, J=1.6 Hz, 1H), 7.49(m, 1H), 7.377(t, J=8.2 Hz, 1H), 7.20(m, 2H), 6.87(m, 2H), 6.81(d, J=1.6 Hz, 1H), 6.04 (m, 1H), 5.68(s, 2H), 4.30(m, 1H), 2.55(m, 2H), 2.12(m, 5H), 1.84(m, 2H), 1.74(d, J=6.7 Hz, 3H), 1.57(m, 2H). | 490 [M + 1] |
| I-364 | 3 as in Example I-135 | | 454 [M + 1] |
| I-365 | 3 as in Example I-240 | | 476 [M + 1] |
| I-366 | 3 as in Example I-135 | (300 MHz, CDCl$_3$) δ 9.75(s, 1H), 7.88(d, 1H), (q, 1H), 7.45(t, 1H), 7.35(d, 2H), 7.18(d, 2H), 8.9(d, 1H), 8.10(q, 1H), 5.85(s, 2H), 2.99(s, 3H),1.80(d, 3H). | 470 [M + 1] |
| I-367 | 3 | (300 MHz, CDCl$_3$) δ 7.80(d, 1H), 7.55(q, 1H), 7.45(t, 1H), 7.35(dd, 4H), 7.25(m, 1H), 6.95(d, 1H), 6.12(q, 1H), 5.85(s, 2H), 1.80(d, 3H). | 377 [M + 1] |
| I-368 | 3 as in Example I-135 | (300 MHz, CDCl$_3$) δ 9.80(s, 1H), 7.70(d, 1H), 7.43(m, 3H), 7.30(ddd, 1H), 7.25(d, 1H), 7.18 (m, 2H), 6.10(q, 1H), 2.95(s, 3H),1.75(d, 3H). | 454 [M + 1] |
| I-369 | 3 | | 383 [M + 1] |
| I-370 | 3 | | 433 [M + 1] |
| I-371 | 3 | (300 MHz, CDCl$_3$) δ 7.71(s, 1H), 7.40(d, 2H), 7.32-7.23(m, 3H), 7.06(t, 1H), 6.99(s, 1H), 6.77 (bs, 1H), 6.11(q, 1H), 5.62(s, 2H), 3.60(m, 4H), 2.57(m, 4H), 2.40(s, 3H), 1.87(d, 3H). | 518 [M + 1] |
| I-372 | 10 as in Example I-371 | | 532 [M + 1] |
| I-373 | 10 as in Example I-371 | (300 MHz, CDCl$_3$) δ 7.88(s, 2H), 7.48(m, 2H), 7.38(d 2H), 7.25(m, 2H), 6.95(s, 2H), 6.55(q, 1H), 4.86(s, 2H), 3.63(t, 2H), 3.31(m, 3H), 1.87 (d, 3H). | 479 [M + 1] |
| I-374 | 10 as in Example I-371 | (300 MHz, CDCl$_3$) δ 7.88(s, 1H), 7.55(m, 3H), 7.35(d, 2H), 7.23(m, 3H), 6.95(s, 1H), 6.55(q, 1H), 4.86(s, 2H), 3.71(t, 2H), 3.31(m, 6H), 2.51 (m, 4H), 1.86(d, 3H). | 548.2 [M + 1] |
| I-375 | 10 as in Example I- | (300 MHz, CDCl$_3$) δ 7.65(m, 4H), 7.31(m, 3H), 7.19(m, 2H), 6.37(m, 1H), 4.87(s, 2H), 3.95(m, | 503.8 [M + 1] |

TABLE 2-continued

| | | | |
|---|---|---|---|
| | 371 | 1H), 3.80(m, 1H), 3.60(m, 2H), 3.31(m, 2H), 2.45(m, 1H), 2.18(m, 1H), 1.95(d, 3H). | |
| I-376 | 10 as in Example I-371 | (300 MHz, CDCl$_3$) δ 7.65(m, 4H), 7.31(m, 3H), 7.19(m, 2H), 6.37(m, 1H), 4.87(s, 2H), 3.95(m, 1H), 3.80(m, 1H), 3.60(m, 2H), 3.31(m, 2H), 2.45(m, 1H), 2.18(m, 1H), 1.95(d, 3H). | 504.1 [M + 1] |
| I-377 | 10 as in Example I-371 | | 534 [M + 1] |
| I-378 | 10 as in Example I-371 | | 518 [M + 1] |
| I-379 | 10 as in Example I-371 | | 488 [M + 1] |
| I-380 | 10 as in Example I-371 | | 488 [M + 1] |
| I-381 | 10 as in Example I-371 | (300 MHz, CDCl$_3$) δ 7.69(d, 2H), 7.37(d, 2H), 7.25(d, 2H), 7.15(m, 2H), 7.09(d, 2H), 6.00(q 1H), 4.86(s, 2H), 3.63(t, 2H), 3.32(m, 3H), 1.83 (d, 3H). | 463 [M + 1] |
| I-382 | 10 as in Example I-371 | (300 MHz, CDCl$_3$) δ 7.78(s, 1H), 7.41(d, 2H), 7.29(d, 2H) 7.09(s, 1H), 7.05(m, 1H), 6.95(m, 1H), 6.56(bs, 1H), 6.00(q, 1H), 5.25(s, 2H), 3.58(m, 4H), 2.53(m, 4H), 2.38(s, 3H), 1.84(d, 3H). | 503 [M + 1] |
| I-383 | 10 as in Example I-371 | | 516 [M + 1] |
| I-384 | 10 as in Example I-371 | (300 MHz, CDCl$_3$) δ 7.83(d, 1H), 7.29(m, 5H), 7.00(m, 4H), 5.94(q, 1H), 4.87(bs, 2H), 3.67 (m, 4H), 3.38(m, 2H), 2.52(m, 4H), 1.86(d, 3H). | 533.7 [M + 1] |
| I-385 | 10 as in Example I-371 | (300 MHz, CDCl$_3$) δ 7.93(s, 1H), 7.67(d, 2H), 7.27(d, 2H), 6.95(m, 4H), 6.70(q, 1H), 4.84(s, 2H), 3.85(m, 1H), 3.75(m, 1H), 3.40(m, 1H), 2.90(m, 4H), 2.65(m, 4H), 2.10(m, 3H), 1.85(d, 3H), 1.9-1.7(m, 3H). | 555.8 [M + 1] |
| I-386 | 3 as in Example I-211 | | 403 [M + 1] |
| I-387 | 4 | (300 MHz, CDCl$_3$) δ 7.86(s, 1H), 7.39(m, 4H), 7.31(d, 2H), 7.15(t, 1H), 7.02(s, 1H), 6.15(m, 1H), 4.93(s, 2H), 4.65(m, 1H), 3.56(m, 1H), 2.95(m, 1H), 2.79(m, 1H), 2.71(m, 1H), 2.44 (m, 1H), 1.84(d, 3H), 1.95(m, 1H), 1.25(d, 3H), 1.17(d, 3H). | 501 [M + 1] |
| I-388 | 4 as in Example I-387 | (300 MHz, CDCl$_3$) δ 7.85(s, 1H), 7.39(m, 4H), 7.32(d, 2H), 7.15(t, 1H), 7.02(s, 1H), 6.15(m, 1H), 4.90(s, 2H), 4.65(m, 1H), 3.65(m, 1H), 3.05(m, 2H), 2.80(m, 1H), 2.65(m, 4H), 2.30 (m, 1H), 2.05(m, 1H), 1.86(d, 3H), 1.81(m, 3H), 1.52(m, 4H). | 539 [M + 1] |
| I-389 | 4 as in Example I-387 | (300 MHz, CDCl$_3$) δ 7.88(s, 1H), 7.82(s, 1H), 7.69(d, 1H), 7.45(m, 3H), 7.32(d, 2H), 7.15(t, 1H), 7.08(s, 1H), 6.99(bm, 1H), 8.16(q, 1H), 4.93(s, 2H), 3.61(m, 2H), 2.78(m, 2H), 2.63(m, 4H), 1.87(d, 3H), 1.82(m, 4H). | 501 [M + 1] |
| I-390 | 4 as in Example I-387 | (300 MHz, CDCl$_3$) δ 7.89(s, 1H), 7.82(s, 1H), 7.65(d, 1H), 7.48(m, 3H), 7.32(d, 2H), 7.15(t, 1H), 7.06(s, 1H), 6.78(bm, 1H), 6.16(q, 1H), 4.95(s, 2H), 3.73(m, 4H), 3.59(m, 2H), 2.62(m, 2H), 2.51(m, 4H), 1.87(d, 3H). | 517 [M + 1] |
| I-391 | 4 as in Example I-387 | (300 MHz, CDCl$_3$) δ 7.86(d, 1H), 7.37(m, 4H), 7.30(d, 2H), 7.15(t, 1H), 7.02(s, 1H), 6.15(m, 1H), 4.91(s, 2H), 4.45(m, 1H), 3.41(m, 2H), 2.70(m, 4H), 1.84(d, 3H), 1.70-2.0(m, 10H) | 541 [M + 1] |
| I-392 | 4 as in Example I-387 | (300 MHz, CDCl$_3$) δ 8.60(bm, 1H), 7.89(s, 1H), 7.65(d, 1H), 7.45(m, 3H), 7.32(d, 2H), 7.15(t, 1H), 7.04(s, 1H), 6.17(q, 1H), 4.89(s, 2H), 3.62 (m, 2H), 2.78(m, 2H), 2.66(m, 4H), 1.86(d, 3H), 1.83(m, 2H), 1.79(m, 4H). | 513 [M + 1] |
| I-393 | 4 as in Example I-387 | (300 MHz, CDCl$_3$) δ 7.88(s, 1H), 7.81(s, 1H), 7.63(d, 1H), 7.48(m, 3H), 7.32(d, 2H), 7.15(t, 1H), 7.06(s, 1H), 6.69(bm, 1H), 6.16(q, 1H), 4.94(s, 2H), 3.65(m,4H), 3.50(m, 2H), 2.62(m, 2H), 2.52(m, 4H), 2.09(s, 3H), 1.87(d, 3H). | 556 [M + 1] |
| I-394 | 4 as in Example I- | (300 MHz, CDCl$_3$) δ 7.89(s, 1H), 7.73(s, 1H), 7.65(d, 1H), 7.50(d, 1H), 7.43(t, 1H), 7.32(d, | 499 [M + 1] |

TABLE 2-continued

| | | | |
|---|---|---|---|
| | | 387 | 2H), 7.16(t, 1H), 7.04(s, 1H), 6.15(m, 1H), 6.05 1H), 4.92(s, 2H), 4.03(m, 1H), 2.94(m, 2H), 2.38(s, 3H), 2.26(m, 2H), 2.09(m, 2H), 1.86(d, 3H), 1.70(m, 2H). | |
| I-395 | 4 as in Example I-387 | (300 MHz, CDCl$_3$) δ 7.85(s, 1H), 7.40(m, 4H), 7.30(d, 2H), 7.16(t, 1H), 7.02(s, 1H), 6.15(m, 1H), 4.93(s, 2H), 3.82(m, 2H), 3.45(m, 2H), 2.52(m, 2H), 2.38(m, 2H), 2.33(s, 3H), 1.86(d, 2H). | 487 [M + 1] |
| I-396 | 4 as in Example I-387 | (300 MHz, CDCl$_3$) δ 7.86(d, 1H), 7.37(m, 4H), 7.30(d, 2H), 7.15(t, 1H), 7.02(s, 1H), 6.15(m, 1H), 4.91(s, 2H), 4.45(m, 1H), 3.41(m, 2H), 2.70(m, 4H), 1.84(d, 3H), 1.70-2.0(m, 10H) | 541 [M + 1] |
| I-397 | 4 as in Example I-387 | (300 MHz, CD$_3$OD) δ 7.74(s, 1H), 7.69-7.43(m, 6H), 7.32(t, 1H), 7.22(s, 1H), 6.42(m, 1H), 4.05-3.60(m, 4H), 3.50(m, 1H), 2.50(m, 1H), 2.18 (m, 1H), 1.90(d, 3H). | 471 [M + 1] |
| I-398 | 4 as in Example I-387 | (300 MHz, CD$_3$OD) δ 7.74(s, 1H), 7.69-7.43(m, 6H), 7.32(t, 1H), 7.22(s, 1H), 6.42(m, 1H), 4.05-3.60(m, 4H), 3.50(m, 1H), 2.50(m, 1H), 2.18 (m, 1H), 1.90(d, 3H). | 471 [M + 1] |
| I-399 | 3 as in Example I-211 | | 403 [M + 1] |
| I-400 | 4 | (300 MHz, CDCl$_3$) δ 7.89(s, 1H), 7.79(d, 2H), 7.43(d, 2H), 7.32(d, 2H), 7.15(t, 1H), 7.02(s, 1H), 6.87(bm, 1H), 6.15(q, 1H), 4.93(s, 2H), 3.58(m, 2H), 2.72(m, 2H), 2.58(m, 4H), 1.87(d, 3H), 1.80(m, 4H). | 501 [M + 1] |
| I-401 | 4 as in Example I-400 | (300 MHz, CDCl$_3$) δ 7.90(s, 1H), 7.79(d, 2H), 7.44(d, 2H), 7.32(d, 2H), 7.15(t, 1H), 7.03(s, 1H), 6.77(bm, 1H), 6.15(q, 1H), 4.95(s, 2H), 3.74(m, 4H), 3.57(m, 2H), 2.61(m, 2H), 2.52 (m, 4H), 1.87(d, 3H). | 515 [M + 1] |
| I-402 | 4 as in Example I-400 | (300 MHz, CDCl$_3$) δ 7.87(s, 1H), 7.52(m, 2H), 7.39(d, 2H), 7.31(d, 2H), 7.15(t, 1H), 7.01(s, 1H), 6.15(q, 1H), 4.91(s, 2H), 4.45(m, 1H), 3.41 (m, 2H), 2.70(m, 4H), 1.86(d,3H), 1.70-2.0(m, 10H) | 539 [M + 1] |
| I-403 | 4 as in Example I-400 | (300 MHz, CDCl$_3$) δ 7.89(s, 1H), 7.76(d, 2H), 7.42(d, 2H), 7.31(d, 2H), 7.15(t, 1H), 7.02(s, 1H), 6.15(q, 1H), 5.97(bd, 1H), 4.94(s, 2H), 4.03(m, 1H), 2.85(m, 2H), 2.32(s, 3H), 2.18(m, 2H), 2.06(m, 2H), 1.86(d, 3H), 1.60(m, 2H). | 501 [M + 1] |
| I-404 | 4 as in Example I-400 | (300 MHz, CDCl$_3$) δ 7.88(s, 1H), 7.41(m, 4H), 7.32(d, 2H), 7.15(t, 1H); 7.02(s, 1H), 6.15(q, 1H), 4.92(s, 2H), 4.62(m, 1H), 3.66(m, 1H), 2.82(m, 2H), 2.68(m, 1H), 2.40(m, 1H), 1.87(d, 3H), 1.65(m, 1H), 1.15(d, 3H), 0.98(d, 3H). | 499 [M + 1] |
| I-405 | 4 as in Example I-400 | (300 MHz, CDCl$_3$) δ 7.90(s, 1H), 7.78(d, 2H), 7.44(d, 2H), 7.32(d, 2H), 7.15(t, 1H), 7.03(s, 1H), 6.69(bm, 1H), 6.15(q, 1H), 4.96(s, 2H), 3.66(m, 2H), 3.61(m, 2H), 3.50(m, 2H), 2.62 (m, 2H), 2.52(m, 4H), 2.10(s, 3H), 1.87(d, 3H). | 556 [M + 1] |
| I-406 | 4 as in Example I-400 | (300 MHz, CDCl$_3$) δ 8.80(bm, 1H), 7.90(s, 1H), 7.79(d, 2H), 7.40(d, 2H), 7.31(d, 2H), 7.15(t, 1H), 7.02(s, 1H), 6.15(q, 1H), 4.91(s, 2H), 3.62 (m, 2H), 2.78(m, 2H), 2.66(m, 4H), 1.87(d, 3H), 1.85(m, 4H), 1.25(m, 2H). | 513 [M + 1] |
| I-407 | 4 as in Example I-400 | (300 MHz, CD$_3$OD) δ 7.74.7.24(m, 9H), 6.39(m, 1H), 4.05-3.60(m, 4H), 3.50(m, 1H), 2.50(m, 1H), 2.18(m, 1H), 1.90(d, 3H). | 471 [M + 1] |
| I-408 | 4 as in Example I-400 | (300 MHz, CD$_3$OD) δ 7.74-7.24(m, 9H), 6.39(m, 1H), 4.05-3.60(m, 4H), 3.50(m, 1H), 2.50(m, 1H), 2.18(m, 1H), 1.90(d, 3H). | 471 [M + 1] |
| I-409 | 4 as in Example I-400 | (300 MHz, CDCl$_3$) δ 7.87(s, 1H), 7.52(m, 2H), 7.39(d, 2H), 7.31(d, 2H), 7.15(t, 1H), 7.01(s, 1H), 6.15(q, 1H), 4.91(s, 2H), 4.45(m, 1H), 3.41 (m, 2H), 2.70(m, 4H), 1.86(d, 3H), 1.70-2.0(m, 10H) | 539 [M + 1] |
| I-410 | 4 as in Example I-400 | (300 MHz, CDCl$_3$) δ 7.87(s, 1H), 7.39(m, 4H), 7.32(d, 2H), 7.17(t, 1H), 7.01(s, 1H), 6.15(q, 1H),4.91(s, 2H), 4.60(m, 1H), 3.76(m, 1H), 3.00(m, 2H), 2.60(m, 4H), 2.28(m, 1H), 1.95 (m, 2H), 1.86(d, 3H), 1.81(m, 4H), 1.56(m, 2H). | 541 [M + 1] |
| I-411 | 4 as in Example I-400 | (300 MHz, CDCl$_3$) δ 7.87(s, 1H), 7.40(m, 4H), 7.31(d, 2H), 7.15(t, 1H), 7.01(s, 1H), 6.15(q, 4.92(s, 2H), 3.78(m, 2H), 3.52(m, 2H), 2.41(m, 4H), 2.34(s, 3H), 1.86(d, 3H). | 487 [M + 1] |

TABLE 2-continued

| | | | |
|---|---|---|---|
| I-412 | 11 | (300 MHz, CDCl₃) δ 9.05(br, 1H), 7.70(s, 1H), 7.05(t, 1H), 6.70(s, 1H), 6.02(q, 1H), 5.01(s, 2H), 4.15(dd, 2H), 3.75(m, 2H), 3.25(m, 1H), 2.75(m, 3H), 2.45(m, 3H), 2.05(m, 1H), 1.78(d, 3H), 1.65(br, 7H). | 534 [M + 1] |
| I-413 | 11 | (300 MHz, CDCl₃) δ 7.75(s, 1H), 7.30(m, 2H), 7.05(t, 1H), 6.75(s, 1H), 6.02(q, 1H), 5.01(s, 2H), 4.20(d, 2H), 3.45(m, 4H), 2.45(m, 4H), 2.25(s, 3H), 1.81(d, 3H). | 480 [M + 1] |
| I-414 | 11 | (300 MHz, CDCl₃) δ 7.75(s, 1H), 7.30(m, 2H), 7.10(t, 1H), 6.70(s, 1H), 6.02(q, 1H), 5.01(s, 2H), 4.20(d, 2H), 3.89(d, 1H) 2.89(t, 2H), 2.55 (s, 4H), 2.21(m, 2H), .1.90(d, 2H),1.81(d, 3H), 1.45(m, 2H), 1.25(m, 2H). | 534 [M + 1] |
| I-415 | 11 | (300 MHz, CDCl₃) δ 7.75(s, 1H), 7.30(m, 2H), 7.05(t, 1H), 6.75(s, 1H), 6.02(q, 1H), 5.01(s, 2H), 4.78(s, 1H), 4.20(d, 2H), 3.85(d, 1H), 2.85(m, 4H), 2.45(t, 1H), 1.89(s, 3H), 1.01(d, 6H). | 494 [M + 1] |
| I-416 | 11 | (300 MHz, CDCl₃) δ 7.75(s, 1H), 7.30(m, 2H), 7.05(t, 1H), 6.70(s, 1H), 6.00(q, 1H), 5.25(m, 1H), 5.05(s, 2H), 4.80(d, 1H), 4.15(d, 2H), 2.75 (d, 2H), 2.20(s, 3H), 2.10(t, 2H), 1.95(d, 2H), 1.75(d, 3H), 1.45(d, 2H). | 494 [M + 1] |
| I-417 | 11 | (300 MHz, CDCl₃) δ 7.70(s, 1H), 7.30(m, 2H), 7.05(t, 1H), 6.70(s, 1H), 6.00(q, 1H), 5.30(m, 1H), 5.01(s, 2H), 4.15(d, 2H), 3.25(m, 2H), 2.50(m, 6H), 1.80(d, 3H), 1.82(m, 4H), 1.60(m, 2H). | 508 [M + 1] |
| I-418 | 11 | (300 MHz, CDCl₃) δ 7.70(s, 1H), 7.30(m, 2H), 7.05(t, 1H), 6.70(s, 1H), 6.00(q, 1H), 5.45(s, 1H), 5.15(s, 2H), 4.15(d, 2H), 3.25(m, 2H), 2.60(t, 2H), 2.50(m, 4H), 1.80(d, 3H), 1.70(s, 4H). | 496 [M + 1] |
| I-419 | 11 | (300 MHz, CDCl₃) δ 7.73(s, 1H), 7.28(m, 2H), 7.05(t, 1H), 6.70(s, 1H), 6.00(q. 1H), 5.25(s, 1H), 5.15(s, 2H), 4.15(d, 2H), 3.65(m, 4H), 3.25(m, 2H), 2.45(m, 6H), 1 .60(d, 3H). | 510 [M + 1] |
| I-420 | 11 | (300 MHz, CDCl₃) δ 7.70(s, 1H), 7.30(m, 2H), 6.00(q, 1H), 5.10(s, 6H), 3.20(s, 2H), | 524 [M + 1] |
| I-421 | 11 | (300 MHz, CDCl₃) δ 9.05(br, 1H), 7.70(s, 1H), 7.05(t, 1H), 6.70(s, 1H), 6.02(q. 1H), 5.01(s, 2H), 4.15(dd, 2H), 3.75(m, 2H), 3.25(m, 1H), 2.75(m, 3H), 2.45(m, 3H), 2.05(m, 1H), 1.78(d, 3H), 1.65(br, 7H). | 534 [M + 1] |
| I-422 | 11 | | 382 [M + 1] |
| I-423 | 11 | | 397 [M + 1] |
| I-424 | 12 | (300 MHz, CDCl₃) δ 7.74(s, 1H), 7.45(bm, 1H), 77.31(dd, 1H), 7.07(t, 1H), 6.73(s, 1H), 6.00(q, 21H), 4.99(s, 2H), 4.26(d, 2H), 2.98(s, 2H), 2.46 2(m, 4H), 1.81(d, 3H), 1.59(m, 4H), 1.45(m, 2H). | 579 [M + 1] |
| I-425 | 12 | (300 MHz, CDCl₃) δ 7.74(s, 1H), 7.45(bm, 1H), 7.31(m, 2H), 7.08(t, 1H), 6.71(s, 1H), 6.00(q, 1H), 5.02(s, 2H), 4.27(d, 2H), 3.73(m, 4H), 3.05(s 2H), 2.54(m 4H), 1.81(d, 3H). | 481 [M + 1] |
| I-426 | 12 | (300 MHz, CDCl₃) δ 7.74(s, 1H), 7.37(bm, 1H), 7.31(dd, 1H), 7.08(t, 1H), 6.72(s, 1H), 6.00(q, 1H), 5.01(s, 2H), 4.27(d, 2H), 3.18(s, 2H), 2.63 (m, 4H), 2.01(m, 2H), 1.81(d, 3H), 1.80(m, 2H). | 465 [M + 1] |
| I-427 | 12 | (300 MHz, CDCl₃) δ 7.71(s, 1H), 7.45(bm, 1H), 1H), 5.06(s, 2H), 4.42(m, 1H), 4.25(m, 2H), 3.21(s, 2H), 3.00(m, 1H), 2.80(m, 1H), 2.71(m, 1H), 2.45(m, 1H), 2.22(m, 1H), 1.79(d, 3H), 1.78(m, 2H). | 481 [M + 1] |
| I-428 | 12 | (300 MHz, CDCl₃) δ 7.73(d, 1H), 7.38(bm, 1H), 7.31(dd, 1H), 7.08(dd, 1H), 6.72(d, 1H), 6.00 (q, 1H), 5.03(s, 2H), 4.26(d, 2H), 3.74(m, 1H) 3.02(s, 2H), 2.78(m, 2H), 2.32(m, 2H), 1.92(m, 4H), 1.80(d, 3H). | 495 [M + 1] |
| I-429 | 12 | (300 MHz, CDCl₃) δ 7.73(d, 1H), 7.38(bm, 1H), 7.31(dd, 1H), 7.08(dd, 1H), 6.72(d, 1H), 6.00 (q, 1H), 4.99(s, 2H), 4.26(d, 2H), 2.98(s, 2H), 2.31(s, 6H), 1.80(d, 3H). | 439 [M + 1] |
| I-430 | 12 | (300 MHz, CDCl₃) δ 7.73(d, 1H), 7.59(bm, 1H), 7.30(dd, 1H), 7.07(dd, 1H), 6.72(d, 1H), 6.00 (q, 1H), 4.98(s, 2H), 4.25(d, 2H), 3.05(s, 2H), 2.57(dd, 4H), 1.80(d, 3H), 1.03(t, 6H). | 467 [M + 1] |

TABLE 2-continued

| | | | |
|---|---|---|---|
| I-431 | 12 | (300 MHz, CDCl₃) δ 7.73(d, 1H), 7.31(dd, 1H), 7.25(bm, 1H), 7.08(dd, 1H), 6.71(d, 1H), 6.00 (q, 1H), 5.04(s, 2H), , 4.27(d, 2H), 3.66(m, 2H) 3.52(m, 2H), 3.08(s, 2H), 2.78(m, 2H), 2.32(m, 2H), 2.53(m, 4H), 2.10(s, 3H), 1.81(d, 3H). | 522 [M + 1] |
| I-432 | 13 as in Example 1-412 | (300 MHz, CDCl₃) δ 7.73(d, 1H), 7.30(dd, 1H), 7.07(1, 1H); 6.78(d, 1H), 6.01(q, 1H), 5.01(s, 2H), 4.64(s, 1H), 3.38(m, 4H), 2.42(m, 4H), 2.31(s, 3H), 1.79(d, 3H), 1.70(s, 6H). | 508 [M + 1] |
| I-433 | 11 | (300 MHz, CDCl₃) δ 7.74(s, 1H), 7.30(dd, 1H), 7.07(t, 1H), 8.79(s, 1H), 6.01(q, 1H), 4.93(s, 2H), 4.59(s, 1H), 3.75(m, 2H), 2.82(m, 2H), 2.35(m, 2H), 1.80(d, 3H), 1.71(s, 8H), 1.09(d, 6H). | 522 [M + 1] |
| I-434 | 11 | (300 MHz, CDCl₃) δ 8.44 Cbs, 1H), 7.72(d, 1H), 7.30(dd, 1H), 7.07(t, 1H), 8.79(s, 1H), 6.01(q, 1H), 4.87(s, 2H), 3.75(m, 1H), 3.25(m, 1H), 2.88(m, 2H), 2.58(m, 2H), 2.40(m, 1H), 2.05 (m 1H), 1.82-1.88(m, 17H), 1.58(m, 1H). | 562 [M + 1] |
| I-435 | 11 | (300 MHz, CDCl₃) δ 8.44(bs, 1H), 7.72(s, 1H), 7.30(dd, 1H), 7.07(t, 1H), 6.79(s, 1H), 6.01(q, 1H), 4.87(s, 2H), 3.75(m, 1H), 3.25(m, 1H), 2.88(m, 2H), 2.58(m, 2H), 2.40(m, 1H), 2.05 (m, 1H), 1.82-1.88(m, 17H), 1.58(m, 1H). | 562 [M + 1] |
| I-436 | 11 | (300 MHz, CDCl₃) δ 7.72(s, 1H), 7.31(dd, 1H), 7.08(t, 1H), 6.75(s, 1H), 8.01(q, 1H), 5.53(bm, 1H), 5.00(s, 2H), 4.68(bs, 1H), 3.56(m, 4H), 3.32(m, 2H), 2.45(m, 2H), 2.35(m, 4H), 1.81(d, 3H), 1.84(s, 6H). | 538 [M + 1] |
| I-437 | 11 | (300 MHz, CDCl₃) δ 7.72(s, 1H), 7.31(dd, 1H), 7.08(t, 1H), 6.77(s, 1H), 6.01(q, 1H), 5.68(bm, 1H), 5.14 Cbs, 1H), 5.01(s, 2H), 3.30(m, 2H), 2.85(m, 2H), 2.50(m, 4H), 1.81(d, 3H), 1.68(m, 4H), 1.63(s, 8H). | 522 [M + 1] |
| I-438 | 11 | (300 MHz, CDCl₃) δ 7.73(s, 1H), 7.31(dd, 1H), 7.07(t, 1H), 8.79(s, 1H), 6.01(q, 1H), 5.88(bm, 1H), 4.95(s, 2H), 4.68 Cbs, 1H), 3.88(m, 2H), 2.82(m, 2H), 2.58(m, 4H), 2.28(m, 1H), 1.92 (m, 2H), 1.81(d, 3H), 1.80(m, 4H), 1.70(s, 6H), 1.50(m, 2H). | 562 [M + 1] |
| I-439 | 11 | (300 MHz, CDCl₃) δ 7.85(d, 1H), 7.31(dd, 1H), 1H), 5.14(s, 2H), 4.12(m, 1H), 1.81(d, 3H), 1.20 7.09(t, 1H), 6.78(d, 1H), 6.00(q, 1H), 5.89(bd, (d, 8H). | 410 [M + 1] |
| I-440 | 11 | (300 MHz, CDCl₃) δ 7.88(s, 1H), 7.31(dd, 1H). 7.09(t, 1H), 8.79(s, 1H), 8.00(q, 1H), 5.72(bd, 1H), 5.14(s, 2H), 3.82(m, 1H), 1.95(m, 2H), 1.80(d, 3H), 1.72(m, 2H), 1.85(m, 2H), 1.38(m, 2H), 1.20(m, 2H). | 450 [M + 1] |
| I-441 | 11 | (300 MHz, CD₃OD) δ 7.60(d, 1H), 7.45(dd, 1H), 7.25(t, 1H), 8.88(d, 1H), 8.06(q, 1H), 1.84(d, 3H), 1.88(s, 6H). | 382 [M + 1] |
| I-442 | 13 | (300 MHz, CDCl₃) δ 7.90(s, 1H), 7.51(m, 1H), 7.40(m, 5H), 7.10(m, 1H), 6.90(s, 1H), 5.80(q, 1H), 4.94(s, 2H), 3.58(m, 4H), 2.53(m, 4H), 2.32(s, 3H), 1.84(d, 3H). | 503 [M + 1] |
| I-443 | 13 | (300 MHz, CDCl₃)6 7.89(s, 1H), 7.54(m, 1H), 7.32(d, 5H), 7.17(m, 1H), 8.90(d, 1H), 5.79(q, 1H), 4.93(s, 2H), 4.60(m, 1H), 3.80(m, 1H), 2.95(m, 2H), 2.64(m, 4H), 2.34(m, 1H), 1.95 (m, 2H), 1.81(m, 4H), 1.73(d, 3H), 1.56(m, 2H). | 557 [M + 1] |
| I-444 | 13 | (300 MHz, CDCl₃) δ 7.9(d, 1H), 7.50(m, 1H), 7.36(m, 5H), 7.11(m, 1H), 6.90(s, 1H), 5.81(q, 1H), 4.93(s, 2H), 4.62(m, 1H), 3.66(m, 1H), 2.85(m, 2H), 2.65(m, 1H), 2.40(m, 1H), 1.73(d, 3H), 1.10(m, 7H). | 517 [M + 1] |
| I-445 | 13 | (300 MHz, CDCl₃) δ 7.90(s, 1H), 7.73(m, 1H). 7.53(m, 3H), 7.34(d, 2H), 7.13(m, 1H), 6.90(s, 1H), 5.80(q, 1H), 4.93(s, 2H), 4.45(m, 1H), 3.50 (m, 2H), 2.70(m, 4H), 1.73(d, 3H), 1.20-2.0(m, 10H). | 557 [M + 1] |
| I-446 | 13 | (300 MHz, CDCl₃) δ 7.90(s, 1H), 7.73(m, 1H), 7.53(m, 3H), 7.34(d, 2H), 7.13(m, 1H), 6.90(s, 1H), 5.80(q, 1H), 4.93(s, 2H), 4.45(m, 1H), 3.50 (m, 2H), 2.70(m, 4H), 1.73(d, 3H), 1.20-2.0(m, 10H). | 557 [M + 1] |
| I-449 | 13 | (300 MHz, CDCl₃) δ 7.90(d, 1H), 7.75(d, 2H), 7.72(m, 1H), 7.52(m, 1H), 7.48(d, 2H), 7.10(m, | 517 [M + 1] |

TABLE 2-continued

| | | | |
|---|---|---|---|
| | | 1H), 6.89(d, 1H), 6.00(bd, 1H), 5.60(q, 1H), 4.93 (s, 2H), 4.02(m, 1H), 2.85(m, 2H), 2.31(s, 3H), 2.16(m, 2H), 2.05(m, 2H), 1.73(d, 3H), 1.62(m, 2H). | |
| I-450 | 13 | (300 MHz, CDCl₃) δ 7.90(d, 1H), 7.79(d, 2H), 7.55(m, 2H), 7.48(d, 2H), 7.13(m, 1H), 7.08 (bs, 1H), 8.90(s, 1H), 5.80(q, 1H), 4.94(s, 2H), 3.58(m, 2H), 2.78(m, 2H), 2.62(m, 4H), 1.81 (m, 4H), 1.72(d, 3H). | 517 [M + 1] |
| I-451 | 13 | (300 MHz, CDCl₃) δ 7.91(d, 1H), 7.78(d, 2H), 7.51(m, 2H), 7.39(d, 2H), 7.10(m, 1H), 6.91(d, 1H), 8.78(bs, 1H), 5.82(q, 1H), 4.97(s, 2H), 3.72(m, 4H), 3.57(m, 2H), 2.62(m, 2H), 2.52 (m, 4H), 1.73(d, 3H). | 533 [M + 1] |
| I-452 | 13 | (300 MHz, CDCl₃) δ 8.81(s, 1H), 7.92(s, 1H), 7.78(d, 2H), 7.53(m, 1H), 7.48(d, 2H), 7.13(m, 1H), 6.90(s, 1H), 5.80(q, 1H), 4.90(s, 2H), 3.80 (m, 2H), 2.78(m, 2H), 2.66(m, 4H), 1.85(m, 6H), 1.73(d, 3H). | 531 [M + 1] |
| I-453 | 13 | (300 MHz, CDCl₃) δ 7.93(s, 1H), 7.80(d, 2H), 7.53(m, 3H), 7.38(d, 2H), 7.10(m, 1H), 6.91(d, 1H), 5.82(q, 1H), 4.95(s, 2H), 3.70(m, 4H), 3.57 (m, 2H), 2.54(m, 6H), 1.81(m, 2H), 1.73(d, 3H). | 547 [M + 1] |
| I-454 | Example I-454 | (400 MHz, DMSO-d₆) δ 7.93(s, 1H), 7.56(m, 1H), 7.46(t, 1H), 6.88(br, 2H), 6.76(s, 1H), 6.02 (q, 1H), 1.77(d, 3H). | 325 [M + 1] |
| I-455 | Example I-455 | (400 MHz, DMSO-d₆) δ 8.00(s, 1H), 7.81(d, 1H), 7.07(t, 2H), 5.78(d, 1H), 1.74(d, 3H). | 332 [M + 1] |
| I-456 | Example I-456 | (400 MHz, DMSO-d₆) δ 7.53(m, 1H), 7.43(m, 2H), 6.76(s, 1H), 5.98(q, 1H), 5.47(br, 2H), 1.74(d, 3H) | 331 [M + 1] |
| I-457 | Example I-457 | (400 MHz, DMSO-d₆) δ 9.58(s, 1H), 7.93(s, 1H), 7.55(m, 1H), 7.40(s, 1H), 6.59(dd, 1H), 6.80 (d, 1H), 6.06(t, 1H), 4.19(dd, 1H), 4.10(dd, 1H), 3.94(dd, 1H), 3.85(dd, 1H), 3.21(m, 2H). 3.15(m, 2H), 3.01(m, 2H), 1.98(m, 2H), 1.90(m, 2H), 1.84(m, 2H), 1.78(d, 3H), 1.72(br, 1H). | 511 [M + 1] |
| I-458 | as in Example I-13 | (400 MHz, DMSO-d₆) δ 7.51(m, 1H), 7.43(t, 2H), 7.28(m, 1H), 6.70(s, 1H), 5.96(q, 1H), 5.68(s, 2H), 3.84(d, 2H), 2.68(s, 3H), 1.76(d, 3H) | 409 [M + 1] |
| I-459 | as in Example I-14 | (400 MHz, CDCl₃): δ 7.49(s, 1H), 7.29(m. 1H), 7.06(t, 1H), 6.71(s, 1H), 6.03(q, 1H), 5.49(bs, 1H), 4.82(bs, 2H), 4.29(dd, 1H), 4.12(dd, 1H), 1.96(s, 3H), 1.83(d, J=8.0 Hz, 3H). | 372 [M + 1] |
| I-460 | as in Example I-14 | (400 MHz, CDCl₃): δ 7.69(d, 2H), 7.29(m, 4H), 7.06(t, 1H), 6.69(s, 1H), 5.98(q, 1H), 4.84(bs, 2H), 4.51(m, 1H), 3.86(dt, 2H), 2.43(s, 3H), 1.83(d, J=8.0 Hz, 3H). | 485 [M + 1] |
| I-461 | 3 | (400 MHz, CDCl₃): δ 7.56(s, 1H), 7.29(m, 1H), 7.05(t, 1H), 6.91(s, 1H), 6.19(dd, 1H), 6.07(q, 1H), 5.40(d, J=16Hz, 1H), 5.02(d, J=12 Hz, 1H), 4.85(bs, 2H), 1.85(d, J=8.0 Hz, 3H). | 327 [M + 1] |
| I-462 | Example I-462 | (400 MHz, CDCl₃): δ 7.55(s, 1H), 7.29(m, 1H), 7.05(t, 1H), 6.82(s, 1H), 6.05(q, 1H), 4.82(bs, 2H), 4.63(m, 1H), 3.54(m, 4H), 1.83(d, J=8.0 Hz, 3H). | 362 [M + 1] |
| I-463 | as in Example I-462 | (400 MHz, CDCl₃): δ 7.55(s, 1H), 7.29(m, 1H), 7.05(t, 1H), 6.82(s, 1H), 6.05(q, 1H), 4.82(bs, 2H), 4.63(m, 1H), 3.54(m, 4H), 1.83(d, J=8.0 Hz, 3H). | 362 [M + 1] |
| I-464 | 3 | (400 MHz, CDCl₃): δ 7.65(s, 2H), 7.52(s, 1H), 7.37(m, 1H), 7.13(m, 1H), 7.04(s, 1H), 6.17(q, J=8.0 Hz, 1H), 1.93(d, J=8.0 Hz, 3H) | 367 [M + 1] |
| I-465 | 14 | (400 MHz, CDCl₃): δ 7.71(s, 1H), 7.55(s, 2H), 737(m, 1H), 7.06(m, 1H), 6.87(s, 1H), 6.09(m, 1H), 4.26(t, J=8.0 Hz, 2H), 2.96(t, J=8.0 Hz, 2H), 2.55(m, 4H), 1.87(d, J=8.0 Hz, 3H), 1.26(m, 4H) | 465 [M + 1] |
| I-466 | 14 | (400 MHz, CDCl₃): δ 7.76(s, 1H), 7.54(s, 1H), 7.46(s, 1H), 7.28(m, 1H), 7.04(m, 1H), 6.86(m, 1H), 6.08(m, 1H), 4.05(t, J=8.0 Hz, 2H), 2.83(t, 2H), 1.86(d, J=4.0 Hz, 3H), 0.96(d, J=8.0 Hz, 12H). | 495 [M + 1] |
| I-467 | 14 | (400 MHz, CDCl₃): δ 7.72(s, 1H), 7.60(s, 1H), 7.50(s, 1H), 7.38(m, 1H), 7.13(m, 1H), 7.05(s, 1H), 6.19(m, 1H), 4.61(m, 2H), 3.89(m, 4H), 3.53(m, 2H),3.02(m, 4H), 1.93(d, J=8.0 Hz, 3H). | 481 [M + 1] |

TABLE 2-continued

| | | | |
|---|---|---|---|
| I-468 | 15 | (400 MHz, DMSO-$d_6$) δ 7.67(s, 1H), 7.43(d, 1H), 7.40(d, 1H), 7.33(t, 1H), 7.20(m, 1H), 6.00(s, 2H), 5.19(s, 2H), 3.96(s, 3H) | 328 [M + 1] |
| I-469 | 15 | (400 MHz, DMSO-$d_6$) δ 7.51(s, 1H), 7.25(d, 1H), 7.18(m, 1H), 7.09(m, 1H), 6.94(s, 1H), 6.02(s, 2H), 5.72(q, 1H), 3.93(s, 3H), 1.57(d, 3H) | 342 [M + 1] |
| I-470 | 3 | (400 MHz, DMSO-$d_6$) δ 9.24(s, 1H), 8.61(d, 1H), 7.96(d, 1H), 7.81(d, 2H), 7.57(d, 1H), 7.43(d, 2H), 7.32(t, 1H), 7.18(m, 1H), 5.34(s, 2H), 3.91(s, | 465 [M + 1] |
| I-471 | 3 | (400 MHz, DMSO-$d_6$) δ 9.25(d, 1H), 8.64(d, 1H), 7.88(s, 1H), 7.61(d, 2H), 7.53(d, 2H), 7.46(s, 1H), 7.35(d, 1H), 7.21(t, 1H), 7.13(m, 1H), 6.03(m, 1H), 3.93(s, 3H), 3.38(m, 2H), 2.49(m, 4H), 1.67(d, 3H), 1.20(m, 6H) | 479 [M + 1] |
| I-472 | 15 | (400 MHz, DMSO-$d_6$) δ 7.59(s, 1H), 7.36(d, 1H), 7.31(d, 1H), 7.25(t, 1H), 7.12(m, 1H), 5.90(s, 2H), 5.10(s, 2H), 4.43(m, 1H),1.26(d, 6H) | 356 |
| I-473 | 3 | (400 MHz, DMSO-$d_6$) δ 9.45(d, 1H), 8.79(q, 1H), 7.99(s, 1H), 7.88(s, 1H), 7.80(d, 2H), 7.58(d, 2H), 7.41(d, 1H), 7.32(t, 1H), 7.17(m, 1H), 5.37(s, 2H), 4.45(m, 1H), 3.40(m, 2H), 2.49(m, 4H), 1.28(d, 8H), 1.20(m, 6H) | 493 |
| I-474 | 3 | (400 MHz, DMSO-$d_6$) δ 7.66(d, 1H), 7.55(q, 1H), 1H), 7.02(d, 2H), 6.81(s, 1H), 6.56(d, 2H), 6.08(q, 1H), 5.60(s, 2H), 5.08(s, 2H), 1.78(d, 3H) | 393 |
| I-475 | as in Example I-55 | (400 MHz, CDCl$_3$): δ 7.82(s, 1H), 7.30(m, 3H), 7.06(m, 1H), 6.95(m, 3H), 6.12(q, 1H), 4.80(m, 2H 4.66(s, 2H), 3.82(s, 3H), 1.66(d, J=8.0 Hz, 3H). | 467 |
| I-476 | as in Example I-55 | (400 MHz, CDCl$_3$): δ 7.70(s, 1H), 7.50(m, 2H), 7.45(m, 2H), 7.20(m, 2H), 6.85(m, 2H), 6.05(q, 1H), 5.72(s, 2H), 4.49(s, 2H), 3.82(s, 3H), 1.75 (d, J=8.0 Hz, 3H). | 453 |
| I-477 | 4 | (400 MHz, CDCl$_3$): δ 7.48(s, 1H), 7.35(m, 1H), 7.20(m, 2H), 7.12(m, 2H), 7.01(m, 2H), 6.20(q, 1H), 4.73(m, 3H), 4.10(m, 1H), 3.36(m, 1H), 3.13(m, 2H), 2.84(m, 1H), 1.94(d, J=8.0 Hz, 3H), 1.34(m, 6H). | 548 |
| I-478 | 4 | (400 MHz, CDCl$_3$): δ 7.48(s, 1H), 7.36(m, 1H), 7.21(d, 2H), 7.19(m, 2H), 7.10(m, 2H), 7.01(m, 2H), 6.20(q, 1H), 4.65(m, 2H), 4.55(m, 1H). 3.69(m, 3H), 3.48(m, 1H), 2.10(m, 3H), 1.92 (m, 5H). | 521 |
| I-479 | 4 | (400 MHz, CDCl$_3$): δ 7.50(s, 1H), 7.36(m, 1H), 7.22(d, 2H), 7.19(m, 2H), 7.15(m, 2H), 7.00(m, 2H), 6.20(q, 1H), 4.75(s, 2H), 3.57(m, 4H), 3.45 (m, 4H), 1.93(d, J=8.0 Hz, 3H), 1.47(s, 9H). | 620 |
| I-480 | 4 | (400 MHz, CDCl$_3$): δ 7.48(s, 1H), 7.36(m, 1H), 7.20(d, 2H), 7.15(m, 2H), 7.00(d, 2H), 6.20(q, 1H), 4.68(s, 2H), 4.46(m, 1H), 4.04(m, 1H), 3.93(m, 1H), 3.60(m, 1H), 3.52(m, 1H), 3.50 (m, 1H), 3.12(m, 1H), 3.09(m, 1H), 283(m, 1H), 1.93(d, J=8.0 Hz, 3H), 2.16-1.66(m, 10H). | 588 |
| I-481 | 15 | (400 MHz, DMSO-$d_6$) δ 7.57(d, 1H), 7.16(m, 3H), 6.95(dt, 1H), 6.07(d, 2H), 5.63(d, 1H), 2.10(m. 2H), 2.16(m, 2H), 1.86(m, 1H),1.77(m, 2H), 1.34(m, 1H). | 352 |
| I-482 | 3 | | 493 |
| I-483 | 3 | | 462 |
| I-484 | 3 | | 442 |
| I-485 | 3 | | 337 [M + 1] |
| I-486 | 15 | (400 MHz, CDCl$_3$), δ 7.68(s, 1H), 7.24(m, 3H), 6.69(s, 1H), 5.64(q, 1H), 4.78(ba, 2H), 1.68(d, J=8.0 Hz, 3H). | 347 |
| I-487 | 15 | (400 MHz, CDCl$_3$): δ 7.50(s, 1H), 7.30(m, 2H), 7.20(m, 3H), 7.00(s, 1H), 6.95(m, 2H), 5.90(q, 1H), 4.36(m, 2H), 3.85(m, 2H), 3.55(m, 2H), 2.95(m, 2H), 2.10(m, 4H), 1.82(d, J=8.0 Hz, 3H). | 456 |
| I-488 | 16 | (CDCl$_3$) δ 5.15(br s, 2H), 5.19(s, 2H), 7.17(m, 1H), 7.34-7.46(m, 5H), 7.64(d, J=8 Hz, 1H), 7.70(td, J=7.8, 1.9 Hz, 1H), 7.86(d, J=1.6 Hz, 1H), 8.22(d, J=2 Hz, 1H), 8.83(d, J=4 Hz, 1H). | 278 |

TABLE 2-continued

| | | | |
|---|---|---|---|
| I-489 | 16 | (CDCl₃) δ 5.17(s, 2H), 5.27(br s, 2H), 7.19(d, J= 2 Hz, 1H), 7.33(dd, J=7.8, 4.6 Hz, 1H), 7.35-7.44(m, 5H), 7.70(dt, J=2, 8 Hz, 1H), 7.85(d, J= 2 Hz, 1H), 8.56(dd, J=1.8, 4.8 Hz, 1H), 8.71 (d, J=2 Hz, 1H). | 278 |
| I-490 | 16 | (CDCl₃) δ 5.22(s, 2H), 8.15(br s, 2H), 7.21(s, 1H), 7.43(m, 5H), 7.77(s, 1H), 8.81(s, 2H), 9.20 (s, 1H). | 279 |
| I-491 | 16 | (CDCl₃) δ 4.40(br s, 2H), 4.94(br s, 2H), 5.13 (s, 2H), 6.58(d, J=8.4 Hz, 1H), 7.09(d, J=1.6 Hz, 1H), 7.35-7.44(m, 5H), 7.56(dd, J=2.4, 8.4 Hz, 1H), 7.77(d, J=1.6 Hz, 1H), 8.13(d, J=2 Hz, 1H). | 293 |
| I-492 | 16 | (CDCl₃) δ 5.33(s, 2H), 5.99(ba, 2H), 7.22-7.26 (m, 1H), 7.29-7.37(m, 2H), 7.42-7.51(m, 2H), 7.63(d, 1H), 7.72(dt 1H), 7.99(d, 1H), 8.13(d, 1H), 8.65(dd, 1H). | 312 |
| I-493 | 16 | | 312 |
| I-494 | 16 | | 313 |
| I-495 | 16 | | 317 |
| I-496 | 16 | (CDCl₃) δ 5.18(s, 2H), 5.48(bs, 2H), 7.1 9-7.22 (m, 1H), 7.38(s, 4H), 7.63-7.65(m, 1H), 7.73(dt, 1H), 7.89(d, 1H), 8.17(d, 1H), 8.63(d, 1H). | 312 |
| I-497 | 16 | | 312 |
| I-498 | 16 | | 313 |
| I-499 | 16 | | 317 |
| I-500 | 16 | (CDCl₃) 8 5.39(s, 2H), 6.19(bs, 2H), 7.08(dt, 1H), 7.21-7.28(m, 2H), 7.65(d, 1H), 7.77(dt, 1H), 8.13(d, 1H), 8.67(dd, 1H) | 348 |
| I-501 | 16 | | 348 |
| I-502 | 16 | | 348 |
| I-503 | 16 | | 349 |
| I-504 | 16 | | 363 |
| I-505 | 16 | (CDCl₃) δ 5.47(s, 2H), 5.76(bs, 2H), 7.21-7.25 (m, 1H), 7.27-7.32(m, 1H), 7.37-7.41(m, 2H), 7.66(d, 1H), 7.75(dt, 1H), 8.06(d, 1H), 8.17(d, 1H), 8.66(dd, 1H). | 346 |
| I-506 | 16 | | 346 |
| I-507 | 16 | | 346 |
| I-508 | 16 | | 347 |
| I-509 | 16 | | 361 |
| I-510 | 16 | (CDCl₃) δ 1.87(d, J=6.6 Hz, 3H), 4.60(br s, 2H), 4.96(br s, 2H), 6.11(q, J=6.6 Hz, 1H), 6.56(d, J=8.4 Hz, 1H), 6.91(s, 1H), 7.06(t, J= 8.5 Hz, 1H), 7.31(dd, J=4.8, 8.7 Hz, 1H), 7.48 (dd, J=1.8, 8.4 Hz, 1H), 7.75(s, 1H), 8.05(s, 1H). | 393 |
| I-511 | 16 | (CDCl₃) δ 1.87(d, J=6.6 Hz, 3H), 2.37(s, 3H), 2.39(br s, 2H), 2.56(br s, 2H), 3.43(br s, 2H), 3.86(br s, 2H), 5.13(br s, 2H), 6.21(q, J=6.7 Hz, 1H), 7.04(dd, J=8.1, 8.7 Hz, 1H), 7.10(dd, J=1.2, 5.1Hz, 1H), 7.29(dd, J=5.1, 9.3 Hz, 1H), 7.48(s, 1H), 7.57(d, J=1.5 Hz, 1H), 8.24 (d, J=1.8 Hz, 1H), 8.65(dd, 0.6,4.8Hz, 1H). | 504 |
| I-512 | 16 | (CDCl₃) δ 1.87(d, J=6.6 Hz, 3H), 2.36(s, 3H), 2.46(m, 2H), 2.58(m, 2H), 3.66(m, 2H), 3.89 (m, 2H), 5.08(br s, 2H), 6.17(q, J=6.6 Hz, 1H), 7.05(dd, J=8.1, 8.8 Hz, 1H), 7.31(dd, J=5.0, 8.9 Hz, 1H), 7.46(dd, J=0.8, 7.7 Hz, 1H), 7.51 (d, J=1.8 Hz, 1H), 7.55(dd, J=0.8, 8.0 Hz, 1H), 7.76(t, J=7.5 Hz, 1H), 8.27(d, J=1.2 Hz, 1H). | 504 |
| I-513 | 16 | (CDCl₃) δ 1.88(d, J=6.6 Hz, 3H), 238(s, 3H), 2.44(m, 2H), 2.56(m, 2H), 3.52(m, 2H), 3.87 (m, 2H), 5.05(br s, 2H), 6.12(q, J=6.7 Hz, 1H), 6.97(d, J=1.8 Hz, 1H), 7.08(dd, J=8.1, 8.7 Hz, 1H), 7.33(dd, J=5.0, 8.9 Hz, 1H), 7.72(t, J= 2.1Hz, 1H), 7.86(d, J=2.1Hz, 1H), 8.54(d, J= 1.8 Hz, 1H), 8.65(d, J=2.4 Hz, 1H). | 504 |
| I-514 | 16 | (CDCl₃) δ 1.88(d, J=6.9 Hz, 3H), 2.39(s, 3H), 2.52(br s, 2H), 2.61(br s, 2H), 3.74(br s, 2H), 3.89(br s, 2H), 5.02(br s, 2H), 6.12(q, J=6.7 Hz, 1H), 6.97(d, J=1.2 Hz, 1H), 7.08(t, J=8.4 Hz, 1H), 7.33(dd, J=4.8, 8.7 Hz, 1H), 7.68(d, J= 9 Hz, 1H), 7.76(dd, J=1.8, 8.4 Hz, 1H), 7.89 (d, J=1.5 Hz, 1H), 8.59(d, J=1.5 Hz, 1H). | 504 |
| I-515 | 16 | (CDCl₃) δ 1.88(d, J=6.9 Hz, 3H), 2.39(s, 3H), 2.51(m, 2H), 2.61(m, 2H), 3.67(m, 2H), 3.90 (m, 2H), 5.08(br s, 2H), 6.14(q, J=6.7 Hz, 1H), 7.05(s, 1H), 7.06(dd, J=7.8,9 Hz, 1H), 7.32(d, J=5.1Hz, 1H), 7.34(dd, J=5.0,7.7 Hz, 1H), | 504 |

TABLE 2-continued

| | | | |
|---|---|---|---|
| | | 7.66(d, J=1.2 Hz, 1H), 8.00(d, J=1.8 Hz, 1H), 8.53(d, J=5.1Hz, 1H). | |
| I-516 | 16 | (CDCl$_3$) δ 1.83(d, J=6.6 Hz, 3H), 4.55(br s, 2H), 4.87(br s, 2H), 5.95(q, J=6.5 Hz, 1H), 6.55(d, J=8.4 Hz, 1H), 6.93-7.12(m, 3H), 7.48 (dd, J=1.8, 8.4 Hz, 1H), 7.76(s, 1H), 8.09(s, 1H). | 377 |
| I-517 | 16 | (CDCl$_3$) δ 1.84(d, J=6.6 Hz, 3H), 2.39(s, 3H), 2.53(br s, 4H), 3.63(br 8, 2H), 3.82(br s, 2H), 5.09(br s, 2H), 6.06(q, J=6.5 Hz, 1H), 6.93-7.10(m, 2H), 7.60(d, J=7.8 Hz, 1H), 7.69(d, J=7.8 Hz, 1H), 7.76(dd, J=2.1, 8.4 Hz, 1H), 8.28 (d, J=1.5 Hz, 1H), 8.66(d, J=1.5 Hz, 1H). | 488 |
| I-518 | 16 | (CDCl$_3$) δ 1.84(d, J=6.6 Hz, 3H), 2.40(s, 3H), 2.45(br s, 2H), 2.61(br s, 2H), 3.48(br s, 2H), 3.89(br s, 2H), 5.13(br s, 2H), 6.06(q, J=6.6 Hz, 1H), 6.93-7.10(m, 2H), 7.12(dd, J=1.2, 5.1 Hz, 1H), 7.52(s, 1H), 7.68(d, J=1.2 Hz, 1H), 8.24(d, J=1.8 Hz, 1H), 8.67(d, J=4.8 Hz, 1H). | 488 |
| I-519 | 16 | (CDCl$_3$) δ 1.84(d, J=6.6 Hz, 3H), 2.38(s, 3H), 2.49(m, 2H), 2.60(m, 2H), 3.70(m, 2H), 3.91 (m, 2H), 5.01(br s, 2H), 6.02(q, J=6.6 Hz, 1H), 6.93-7.12(m, 2H), 7.49(dd, J=0.8, 7.7 Hz, 1H), 7.58(dd, J=0.9, 8.1Hz, 1H), 7.62(d, J=1.8 Hz, 1H), 7.78(t, J=7.8 Hz, 1H), 8.29(d, J=1.8 Hz, 1H). | 488 |
| I-520 | 16 | (CDCl$_3$) δ 1.85(d, J=6.6 Hz, 3H), 2.44(s, 3H), 2.57(m, 4H), 3.59(m, 2H), 3.91(m, 2H), 5.02(br s, 2H), 5.97(q, J=6.4 Hz, 1H), 6.96-7.14(m, 3H), 7.74(s, 1H), 7.87(br s, 1H), 8.57(br s, 1H), 8.71(br s, 1H). | 488 |
| I-521 | 16 | (CDCl$_3$) δ 1.86(d, J=6.6 Hz, 3H), 2.45(s, 3H), 2.62(br s, 2H), 2.69(br s, 2H), 3.82(br s, 2H), 3.95(br s, 2H), 4.97(br s, 2H), 5.98(q, J=6.5 Hz, 1H), 6.96-7.14(m, 3H), 7.71(d, J=8.1 Hz, 1H), 7.79(dd, J=2.3, 8.3 Hz, 1H), 7.90(d, J=2.1Hz, 1H), 8.62(d, J=1.5 Hz, 1H). | 488 |
| I-522 | 16 | (CDCl$_3$) δ 1.86(d, J=6.6 Hz, 3H), 2.45(s, 3H), 2.62(br s, 2H), 2.70(br s, 2H), 3.77(br s, 2H), 3.96(br s, 2H), 5.03(br s, 2H), 5.99(q, J=6.7 Hz, 1H), 6.96-7.14(m, 2H), 7.16(d, J=1.8 Hz, 1H), 7.36(dd, J=2.0, 5.3 Hz, 1H), 7.71(d, J=1.2 Hz, 1H), 8.01(d, J=1.8 Hz, 1H), 8.45(d, J=4.8 Hz, 1H). | 488 |
| I-523 | 16 | (CDCl$_3$) δ 1.87(d, J=6.6 Hz, 3H), 5.20(br s, 2H), 6.23(q, J=6.7 Hz, 1H), 7.04(t, J=8.4 Hz, 1H), 7.15(dd, J=4.8, 6.6 Hz, 1H), 7.29(dd, J=5.1, 9.3 Hz, 1H), 7.51(d, J=8.1Hz, 1H), 7.59(d, J=1.2 Hz, 1H), 7.67(td, J=7.8, 1.8 Hz, 1H), 8.24(d, J=1.5 Hz, 1H), 8.60(d, J=3.9 Hz, 1H). | 378 |
| I-524 | 16 | (CDCl$_3$) δ 1.84(d, J=6.9 Hz, 3H), 5.14(br s, 2H), 6.08(q, J=6.5 Hz, 1H),6.93-7.10(m, 2H), 7.16(dd, J=5.1, 6.6 Hz, 1H), 7.54(d, J=8.1 Hz, 1H), 7.65-7.70(m, 2H), 8.24(s, 1H), 8.62(d, J=4.2 Hz, 1H) | 362 |
| I-525 | 16 | (Cl$_3$) δ 1.87(d, J=6.6 Hz, 3H), 5.37(br s, 2H), 6.00(q, J=6.5 Hz, 1H), 6.97-7.15(m, 3H). 7.34(dd, J=4.7, 7.7 Hz, 1H), 7.69(d, J=7.8 Hz, 1H), 7.82(s, 1H), 8.56(d, J=3.9 Hz, 1H), 8.65 1H). | 362 |
| I-526 | 16 | (CDCl$_3$) δ 1.87(d, J=6.6 Hz, 3H), 5.16(br s, 2H), 5.98(q, J=6.5 Hz, 1H), 6.96-7.14(m, 3H), 7.86(s, 1H), 8.77(s, 2H), 9.14(s, 1H). | 363 |
| I-527 | 16 | (CDCl$_3$) δ 1.87(d, J=6.6 Hz, 3H), 2.38(s, 3H), 2.51(br s, 4H), 3.62(br s, 2H), 3.81(br s, 2H), 5.13(br s, 2H), 6.21(q, J=6.7 Hz, 1H), 7.04(t, J=8.4 Hz, 1H), 7.30(dd, J=4.8. 8.7 Hz, 1H), 7.75 (dd, J=1.9, 8.2 Hz, 1H), 8.28(s, 1H), 8.64(s, 1H). | 504 |
| I-528 | 16 | (CDCl$_3$) δ 1.84(d, J=6Hz, 3H), 5.13(br s, 2H), 5.97(q, J=6.5 Hz, 1H), 6.95-7.10(m, 2H), 7.12 (d, J=1.6 Hz, 1H), 7.30(d, J=6 Hz, 2H), 7.95 (d, J=2Hz, 1H), 8.58(d, J=5.6 Hz, 2H). | 363 |
| I-529 | 17 | (CDCl$_3$) δ 1.84(d, 3H), 4.88(s, 2H), 5.89(q, 1H), 6.79(d, 1H), 6.+1(d, 1H), 7.01(dt, 1H), 7.11 7.17(m, 1H), 7.28-7.40(m, 5H). | 391 |
| I-530 | 17 | | 385 |
| I-531 | 17 | | 371 |
| I-532 | 17 | | 357 |
| I-533 | 17 | | 343 |

TABLE 2-continued

| No. | | | |
|---|---|---|---|
| I-534 | 17 | | 397 |
| I-535 | 17 | | 301 |
| I-536 | 17 | | 411 |
| I-537 | 17 | | 357 |
| I-538 | 17 | | 405 |
| I-539 | 17 | | 392 |
| I-540 | 17 | | 392 |
| I-541 | 4 as in Example I-291 | (300 MHz, CDCl$_3$) δ 7.89(s, 1H), 7.40(m, 4H), 7.35(dd, 1H), 7.08(t, 1H), 7.02(s, 1H), 6.17(q, 1H), 4.98(s, 2H), 3.82(m, 2H), 3.82(m, 2H), 2.52(m, 4H), 1.88(d, 3H). | 567 |

TABLE 3

| No. | Structure | Name |
|---|---|---|
| I-542 | 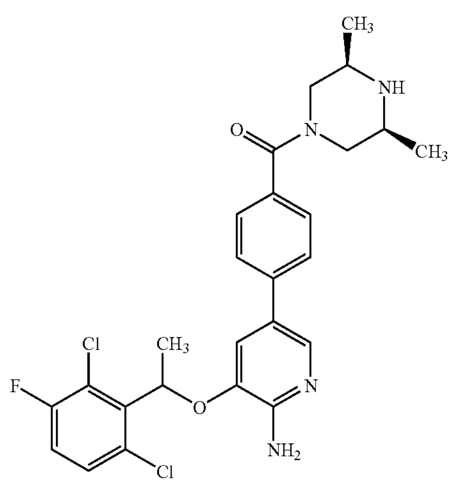 | (4-{6-Amino-5-[1-(2,6-dichloro-3-fluoro-phenyl)-ethoxy]-pyridin-3-yl}-phenyl)-((3R,5S)-3,5-dimethyl-piperazin-1-yl)-methanone |
| I-543 | 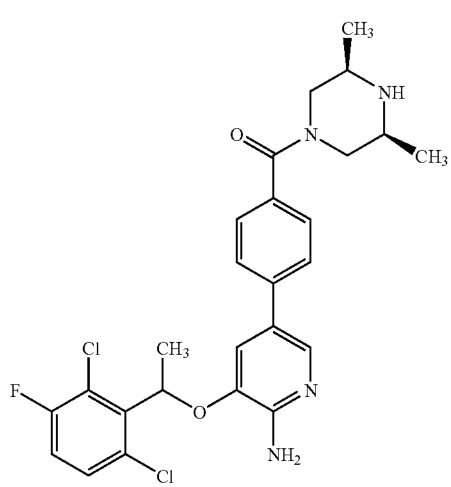 | (4-{6-Amino-5-[1-(2,6-dichloro-3-fluoro-phenyl)-ethoxy]-pyridin-3-yl}-phenyl)-((3R,5S)-3,5-dimethyl-piperazin-1-yl)-methanone |

TABLE 3-continued
| | | |
|---|---|---|
| I-544 | 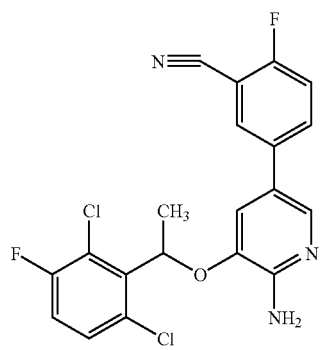 | 5-{6-Amino-5-[1-(2,6-dichloro-3-fluoro-phenyl)-ethoxy]-pyridin-3-yl}-2-fluoro-benzonitrile |
| I-545 | 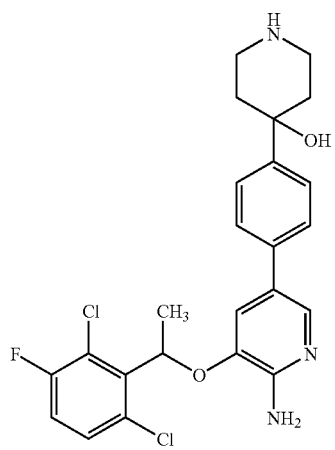 | 4-(4-{6-Amino-5-[1-(2,6-dichloro-3-fluoro-phenyl)-ethoxy]-pyridin-3-yl}-phenyl)-piperidin-4-ol |
| I-546 | 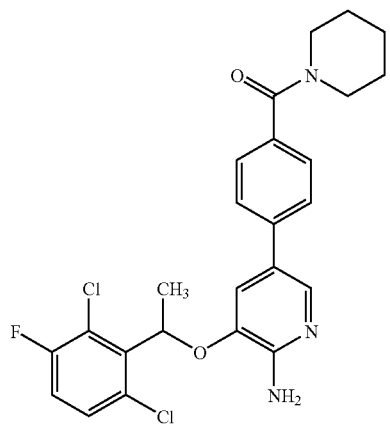 | (4-{6-Amino-5-[1-(2,6-dichloro-3-fluoro-phenyl)-ethoxy]-pyridin-3-yl}-phenyl)-piperidin-1-yl-methanone |
| I-547 | 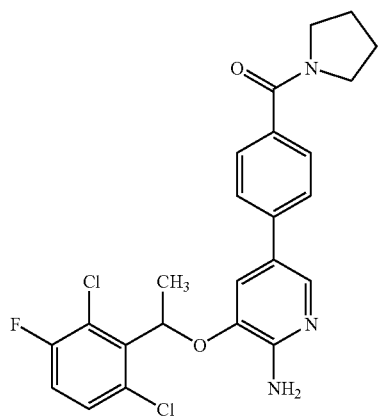 | (4-{6-Amino-5-[1-(2,6-dichloro-3-fluoro-phenyl)-ethoxy]-pyridin-3-yl}-phenyl)-pyrolidin-1-yl-methanone |

TABLE 3-continued
I-548 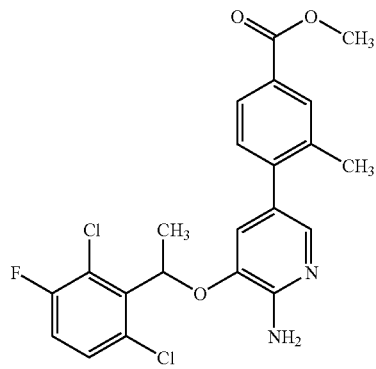
4-{6-Amino-5-[1-(2,6-dichloro-3-fluoro-phenyl)-ethoxy]-Pyridin-3-yl}-3-methyl-benzoic acid methyl ester
I-549 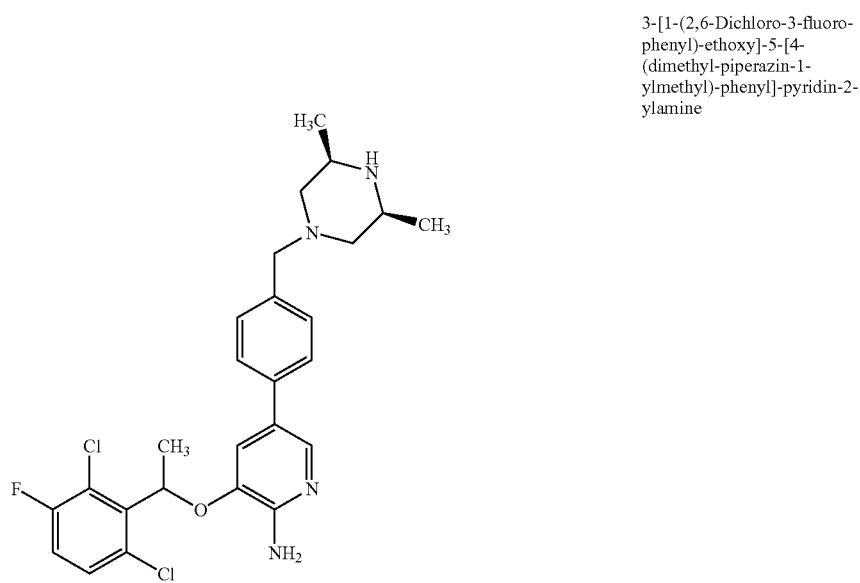
3-[1-(2,6-Dichloro-3-fluoro-phenyl)-ethoxy]-5-[4-(dimethyl-piperazin-1-ylmethyl)-phenyl]-pyridin-2-ylamine
I-550 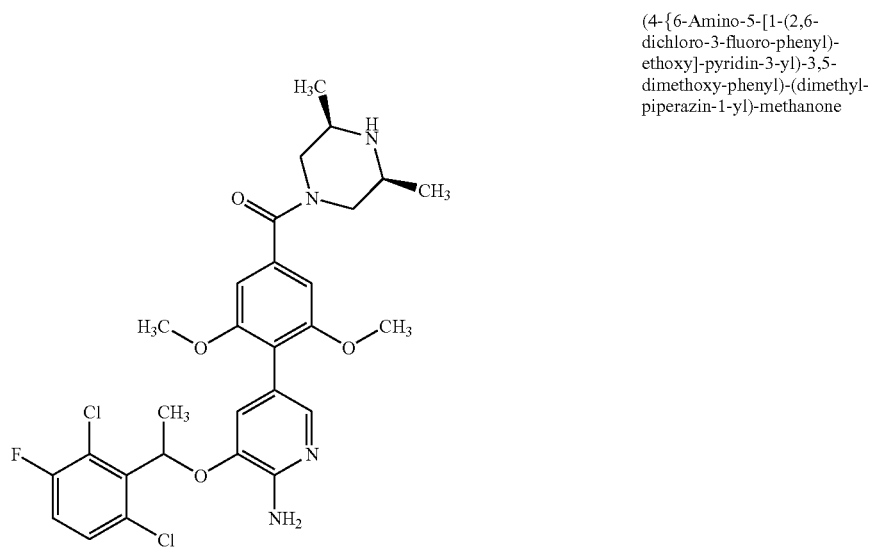
(4-{6-Amino-5-[1-(2,6-dichloro-3-fluoro-phenyl)-ethoxy]-pyridin-3-yl}-3,5-dimethoxy-phenyl)-(dimethyl-piperazin-1-yl)-methanone TABLE 3-continued
I-551 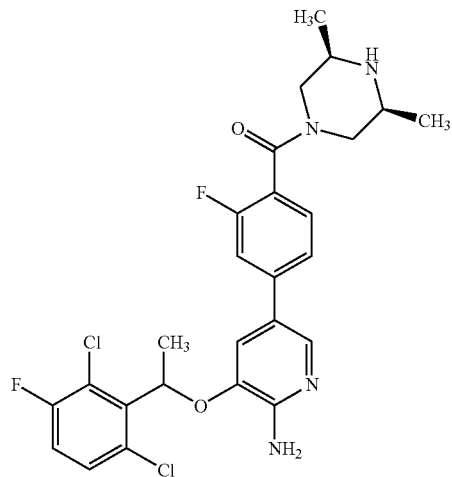
(4-{6-Amino-5-[1-(2,6-dichloro-3-fluoro-phenyl)-ethoxy]-pyridin-3-yl}-2-fluoro-phenyl)-(dimethyl-piperazin-1-yl)-methanone
I-552 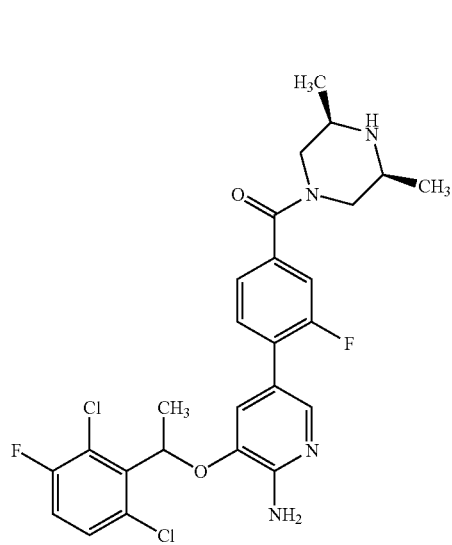
(4-{6-Amino-5-[1-(2,6-dichloro-3-fluoro-phenyl)-ethoxy]-pyridin-3-yl)-3-fluoro-phenyl)-(dimethyl-piperazin-1-yl)-methanone
I-553 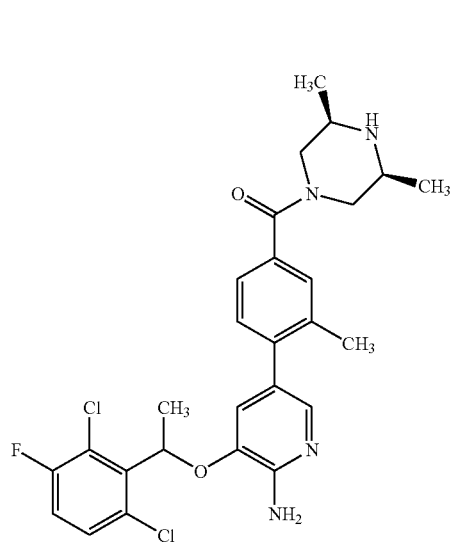
(4-{6-Amino-5-[1-(2,6-dichloro-3-fluoro-phenyl)-ethoxy]-pyridin-3-yl}-3-methyl-phenyl)-(dimethyl-piperazin-1-yl)-methanone

| | | |
|---|---|---|
| I-554 | 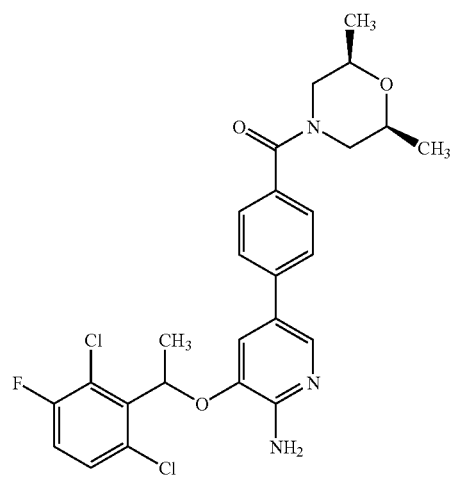 | (4-{6-Amino-5-[1-(2,6-dichloro-3-fluoro-phenyl)-ethoxy]-pyridin-3-yl}-phenyl)-((2R,6S)-2,6-dimethyl-morpholin-4-yl)-methanone |
| I-555 | 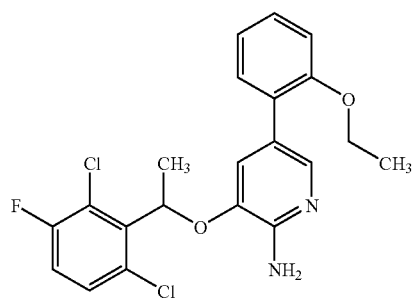 | 3-[1-(2,6-Dichloro-3-fluoro-phenyl)-ethoxy]-5-(2-ethoxy-phenyl)-pyridin-2-ylamine |
| I-556 | 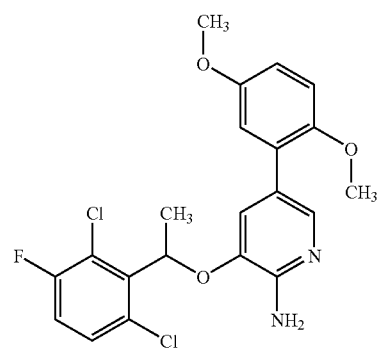 | 3-[1-(2,6-Dichloro-3-fluoro-phenyl)-ethoxy]-5-(2,5-dimethoxy-phenyl)-pyridin-2-ylamine |
| I-557 | 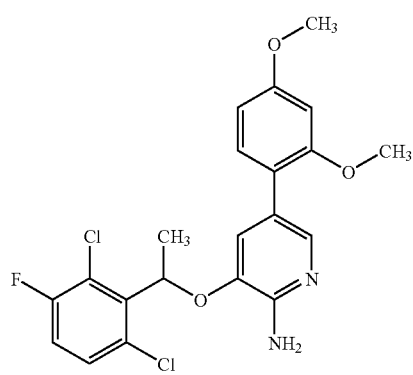 | 3-[1-(2,6-Dichloro-3-fluoro-phenyl)-ethoxy]-5-(2,4-dimethoxy-phenyl)-pyridin-2-ylamine |

TABLE 3-continued

I-558 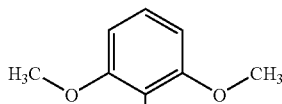 3-[1-(2,6-Dichloro-3-fluoro-phenyl)-ethoxy]-5-(2,6-dimethoxy-phenyl)-pyridin-2-ylamine I-559 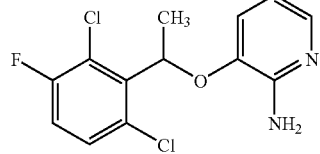 3-[1-(2,6-Dichloro-3-fluoro-phenyl)-ethoxy]-5-(2-trifluoromethyl-phenyl)-pyridin-2-ylamine I-560 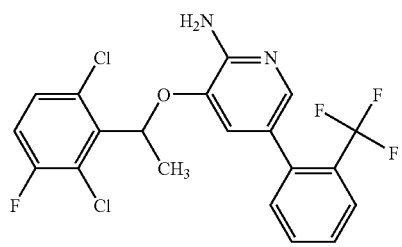 5-(2-Chloro-phenyl)-3-[1-(2,6-dichloro-3-fluoro-phenyl)-ethoxy]-pyridin-2-ylamine I-561 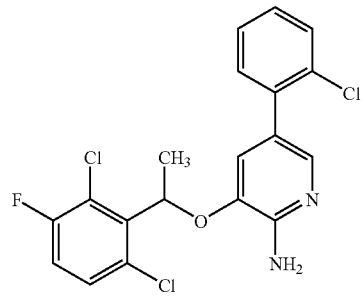 3-[1-(2,6-Diclloro-3-fluoro-phenyl)-ethoxy]-5-(2-trifluoromethoxy-phenyl)-pyridin-2-ylamine I-562 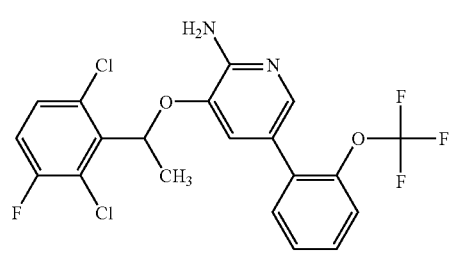 1-(2-{6-Amino-5-[1-(2,6-dichloro-3-fluoro-phenyl)-ethoxy]-pyridin-3-yl}-phenyl)-ethanone

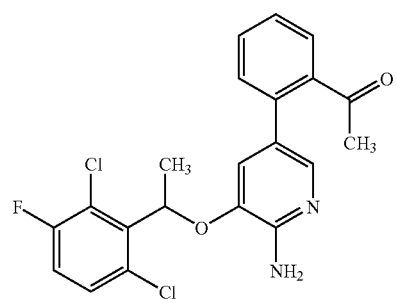

TABLE 3-continued
I-563 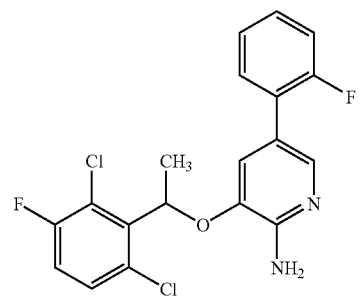 3-[1-(2,6-Dichloro-3-fluoro-phenyl)-ethoxy]-5-(2-fluoro-phenyl)-pyridin-2-ylamine
I-564 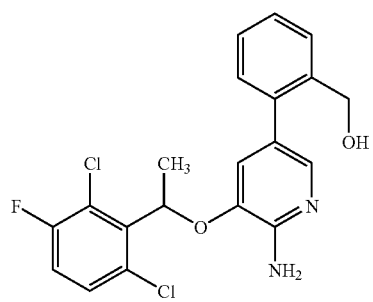 (2-{6-Amino-5-[1-(2,6-dichloro-3 fluoro-phenyl)-ethoxy]pyridin-3-yl}-phenyl)-methanol
I-565 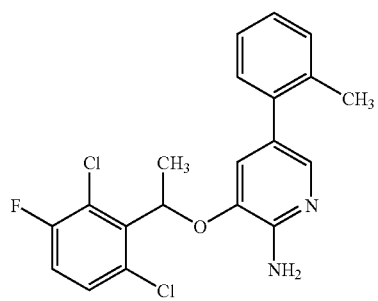 3-[1-(2,6-Dichloro-3-fluoro-phenyl)-ethoxy]-5-o-tolyl-pyridin-2-ylamine
I-566 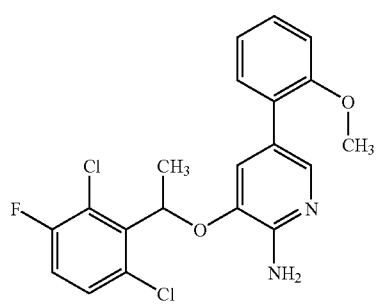 3-[1-(2,6-Dichloro-3-fluoro-phenyl)-ethoxy]-5-(2-methoxy-phenyl)-pyridin-2-ylamine
I-567 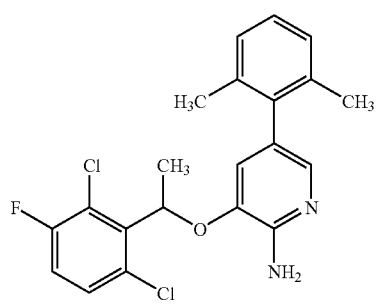 3-[1-(2,6-Dichloro-fluoro-pheny)-ethoxy]-5-(2,6-dimethyl phenyl)-pyridin-2-ylamine TABLE 3-continued
I-568
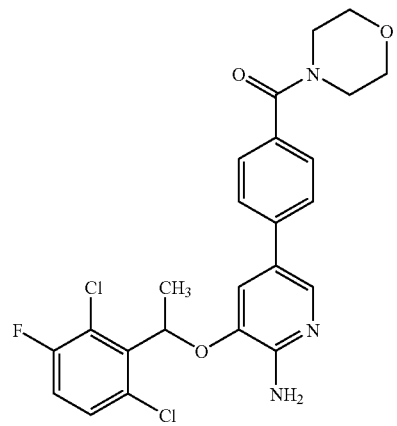
(4-{6-Amino-5-[1-(2,6-dichloro-3-fluoro-phenyl)-ethoxy]-pyridin-3-yl}-phenyl)-morpholin-4-yl-methanone
I-569
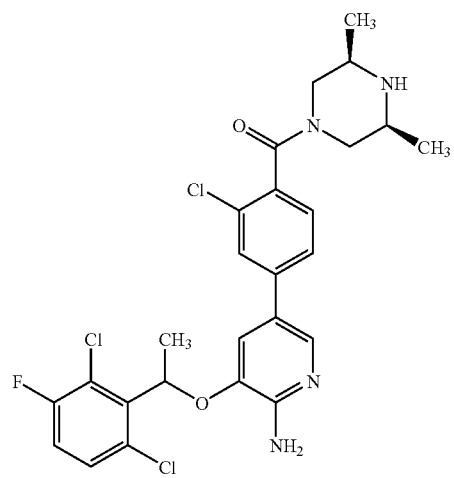
(4-{6-Amino-5-[1-(2,6-dichloro-3-fluoro-phenyl)-ethoxy]-pyridin-3-yl}-2-chloro-phenyl)-((3R,5S)-dimethyl-piperazin-1-yl)-methanone
I-570
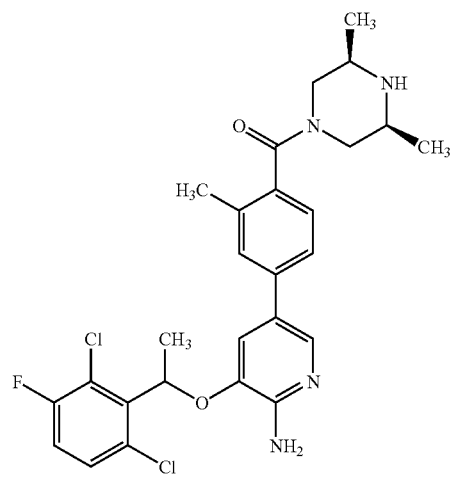
Amino-5-[1-(2,6-dichloro-3-fluoro-phenyl)-ethoxy]-pyridin-3-yl)-2-methyl-phenyl)-((3R,5S)-dimethyl-piperazin-1-methanone TABLE 3-continued
I-571 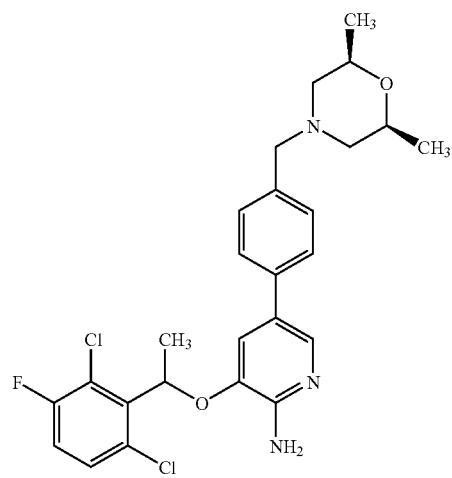 3-[1-(2,6-Dichloro-3-fluoro-phenyl)-ethoxy]-5-(4-((2R,6S)-2,6-dimethyl-morpholin-4-ylmethyl)-phenyl]-pyridin-2-ylamine
I-572 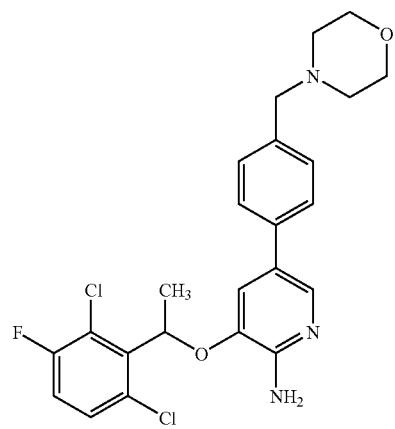 3-[1-(2,6-Dichloro-3-fluoro-phenyl)-ethoxy]-(4-morpholin-4-ylmethyl-phenyl)-pyridin-2-ylamine
I-573 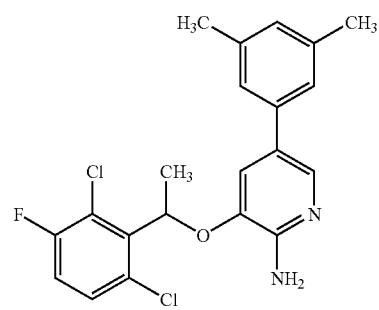 3-[1-(2,6-Dichloro-3-fluoro-phenyl)-ethoxyl-5-(3,5-dimethyl-phenyl)-pyridin-2-ylamine
I-574 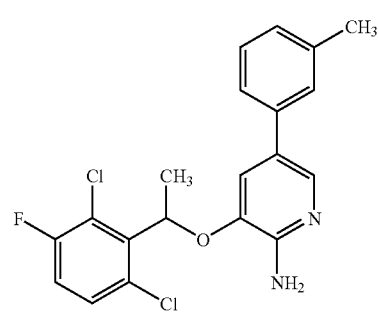 3-[1-(2,6-Dichloro-3-fluoro-phenyl)-ethoxy]-5-m-tolyl-pyridin-2-ylamine TABLE 3-continued
I-575 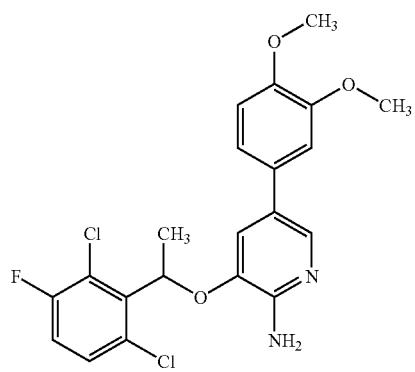
3-[1-(2,6-Dichlora-3-fluoro-phenyl)-ethoxy]-5-(3,4-ylamine
I-576 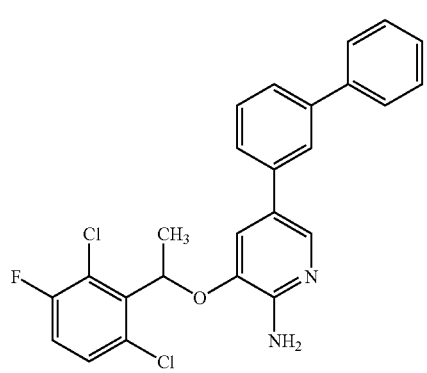
5-Biphenyl-3-yl-3-[1-(2,6-dichloro-3-fluoro-phenyl)-ethoxy]-pyridin-2-ylamine
I-577 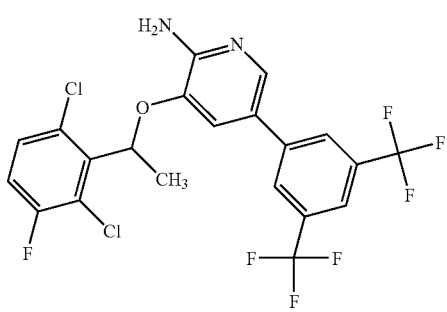
5-(3,5-Bis-trifluoromethyl-phenyl)-3-[1-(2,6-dichloro-3-fluoro-phenyl)-ethoxy]-pyridin-2-ylamine
I-578 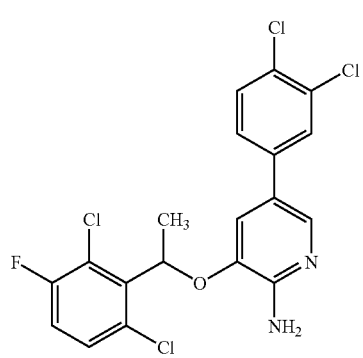
3-[1-(2,6-Dichloro-3-fluoro-phenyl)-ethoxy]-5-(3,4-dichloro-phenyl)-pyridin-2-ylamine

| | | |
|---|---|---|
| I-579 | 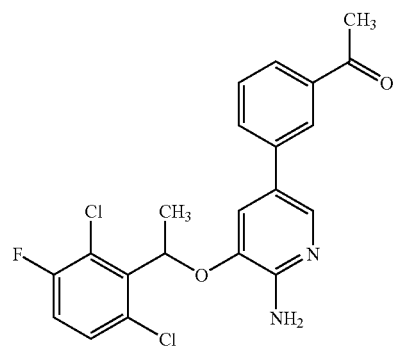 | 1-(3-{6-Amino-5-[1-(2,6-dichloro-3-fluoro-phenyl)-ethoxy]-pyridin-3-yl}-phenyl)-ethanone |
| I-580 | 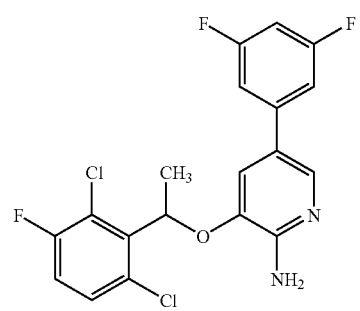 | 3-[1-(2,6-Dichloro-3-fluoro-phenyl)-ethoxy]-5-(3,5-difluoro-phenyl)-pyridin-2-ylamine |
| I-581 | 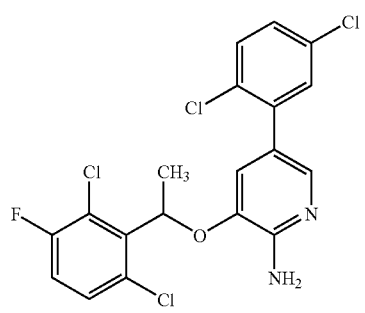 | 3-[1-(2,6-Dichloro-3-fluoro-phenyl)-ethoxy]-5-(2,5-dichloro-phenyl)-pyridin-2-ylamine |
| I-582 | 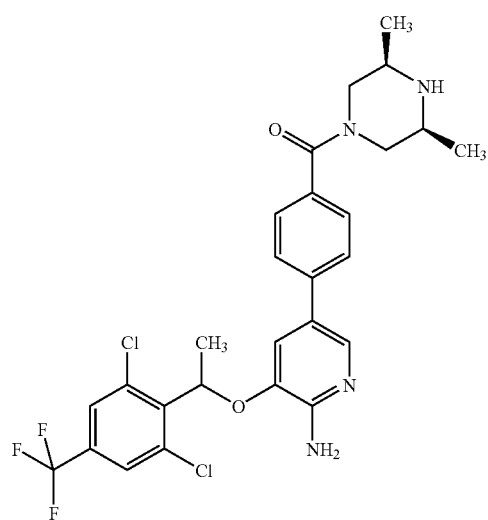 | (4-{6-Amino-5-[1-(2,6-dichloro-4-trifluoromethyl-phenyl)-ethoxy]-pyridin-3-yl}-phenyl)-((3R,5S)-3,5-dimethyl-piperazin-1-yl}-methanone |

TABLE 3-continued

| | | |
|---|---|---|
| I-583 | 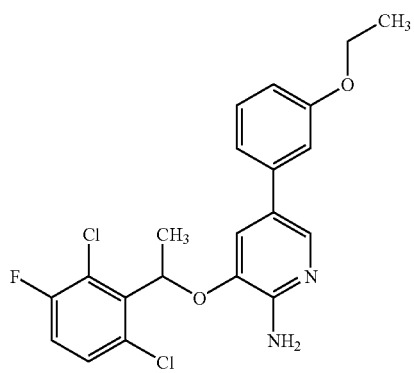 | 3-[1-(2,6-Dichloro-3-fluoro-phenyl)-ethoxy]-5-{3-ethoxy-phenyl)-pyridin-2-ylamine |
| I-584 | 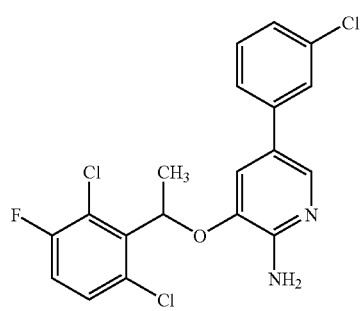 | 5-(3-Chloro-phenyl)-3-[1-(2,6-dichloro-3-fluoro-phenyl)-ethoxy]-pyridin-2-ylamine |
| I-585 | 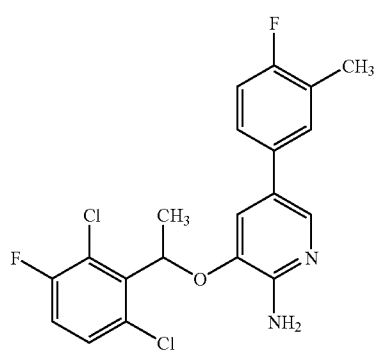 | 3-[1-(2,6-Dichloro-3-fluoro-phenyl)-ethoxy]-5-(4-fluoro-3-methyl-phenyl)-pyridin-2-ylamine |
| I-586 | 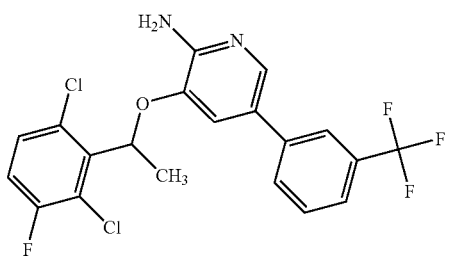 | 3-[1-(2,6-Dichloro-3-fluoro-phenyl)-ethoxy]-5-(4-fluoro-3-trifluoromethyl-phenyl)-pyridin-2-ylamine |
| I-587 | 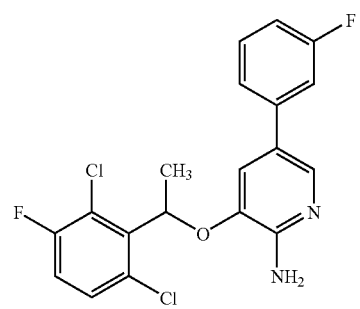 | 3-[1-(2,6-Dichloro-3-fluoro-phenyl)-ethoxy]-5-(3-fluoro-phenyl)-pyridin-2-ylamine |

TABLE 3-continued
| | | |
|---|---|---|
| I-588 | 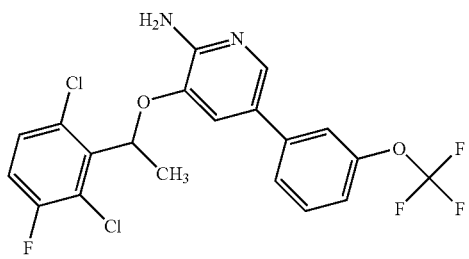 | 3-[1-(2,6-Dichloro-3-fluoro-phenyl)-ethoxy]-5-(3-trifluoromethoxy-phenyl)-pyridin-2-ylamine |
| I-589 | 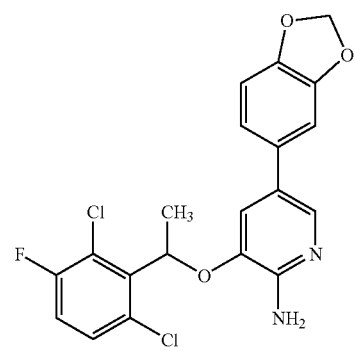 | 5-Benzo[1,3]dioxol-5-yl-3-[1-(2,6-dichloro-3-fluoro-phenyl)-ethoxy]-pyridin-2-ylamine |
| I-590 | 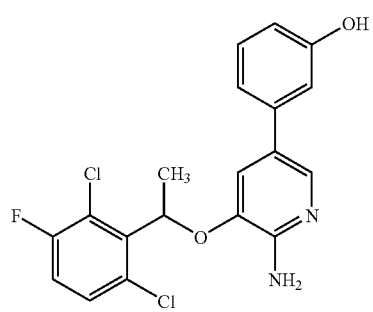 | 3-{6-Amino-5-[1-(2,6-dichloro-3-fluoro-phenyl)-ethoxy]-pyridin-3-yl}-phenol |
| I-591 | 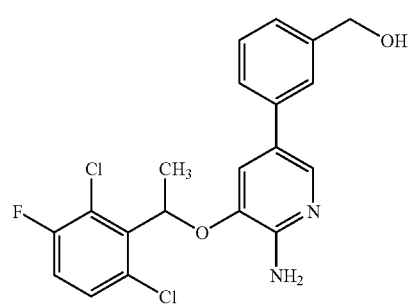 | (3-{6-Amino-5-[1-(2,6-dichloro-3-tfuoro-phenyl)-ethoxy]-pyridin-3-yl}-phenyl)-methanol |
| I-592 | 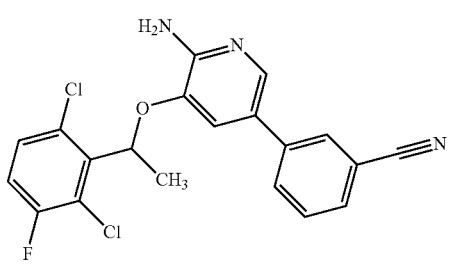 | 3-{6-Amino-5-[1-(2,6-dichloro-3-fluoro-phenyl)-ethoxy]-pyridin-3-yl}-benzonitrile |

TABLE 3-continued
| | | |
|---|---|---|
| I-593 | 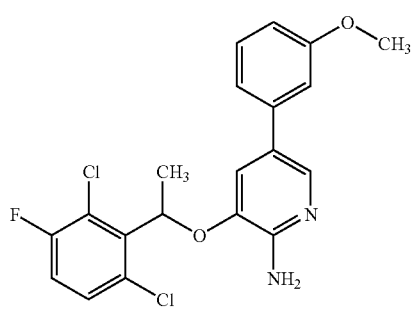 | 3-[1-(2,6-Dichloro-3-fluoro-phenyl)-ethoxy]-5-(3-methoxy-phenyl)-pyridin-2-ylamine |
| I-594 | 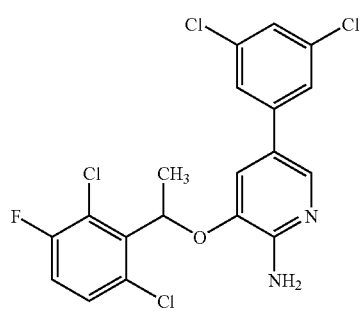 | 3-[1-(2,6-Dichloro-3-fluoro-phenyl)-ethoxy]-5-(3,5-dichloro-phenyl)-pyridin-2-ylamine |
| I-595 | 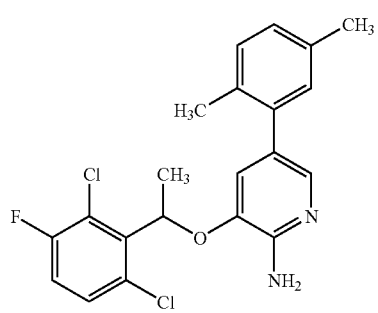 | 3-[1-(2,6-Dichloro-3-fluoro-phenyl)-ethoxy]-5-(2,5-dimethyl-phenyl)-pyridin-2-ylamine |
| I-596 | 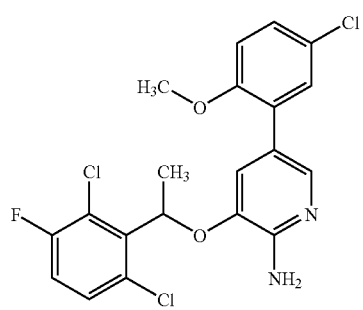 | 5-(5-Chloro-2-methoxy-phenyl)-3-[1-(2,6-dichloro-3-fluoro-phenyl)-ethoxy]-pyridin-2-ylamine |
| I-597 | 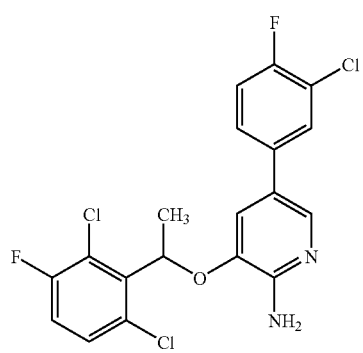 | 5-(3-Chloro-4-fluoro-phenyl)-3-[1-(2,6-dichloro-3-fluoro-phenyl)-ethoxy]-pyridin-2-ylamine |

TABLE 3-continued

I-598 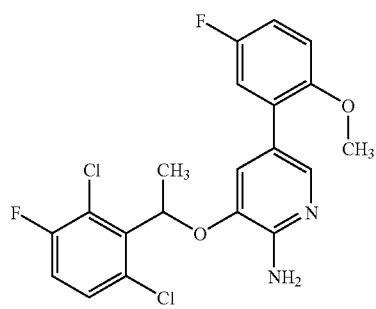 3-[1-(2,6-Dichloro-3-fluoro-phenyl)-ethoxy]-5-(5-fluoro-2-methoxy-phenyl)-pyridin-2-ylamine I-599 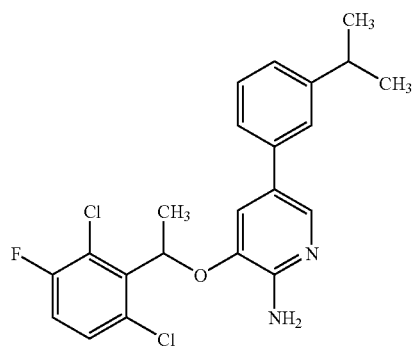 3-[1-(2,6-Dichloro-3-fluoro-phenyl)-ethoxy]-5-(3-sopropyl-phenyl)-pyridin-2-ylamine I-600 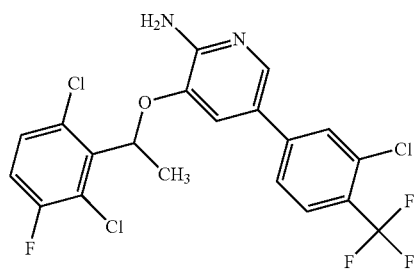 5-(3-Chloro-4-trifluoromethyl-phenyl)-3-[1-(2,6-dichloro-3-fluoro-phenyl)-ethoxy]-pyridin-2-ylamine I-601 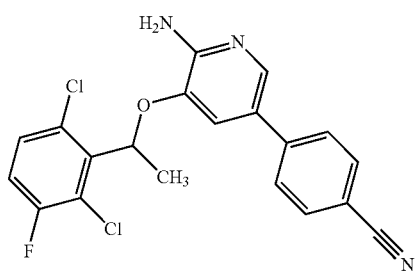 4-{6-Amino-5-[1-(2,6-dichloro-3-fluoro-phenyl)-ethoxy]-pyridin-yl}-benzonitrile I-602 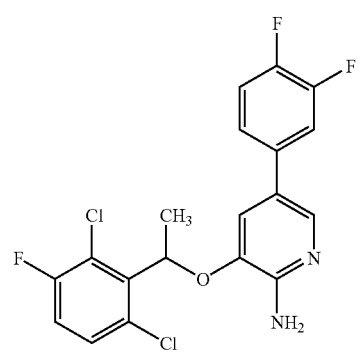 3-[1-(2,6-Dichloro-3-fluoro-phenyl)-ethoxy]-5-(3,4-difluoro-phenyl)-pyridin-2-ylamine TABLE 3-continued
| | | |
|---|---|---|
| I-603 | 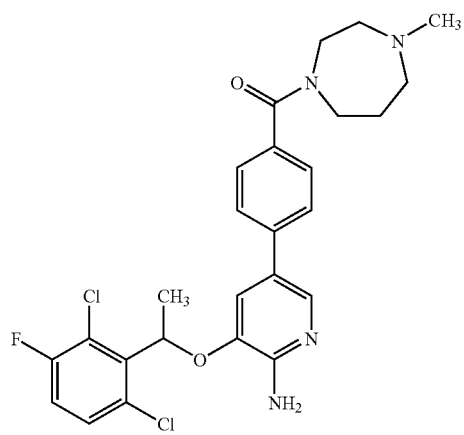 | (4-{6-Amino-5-[1-(2,6-dichloro-3-fluoro-phenyl)-ethoxy]-pyridin-3-yl}-phenyl)-(4-methyl-[1,4]diazepan-1-yl)-methanone |
| I-604 | 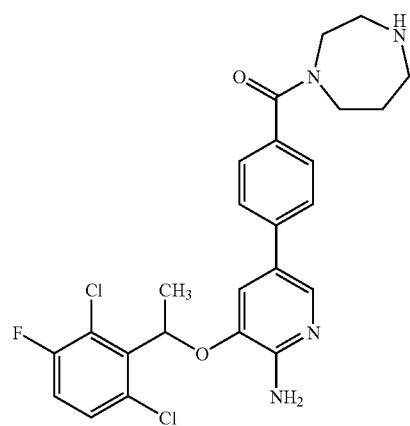 | (4-{6-Amino-5-[1-(2,6-dichloro-3-fluoro-phenyl)-ethoxy]-pyridin-3-yl}-phenyl)-[1,4]diazepan-1-yl-methanone |
| I-605 | 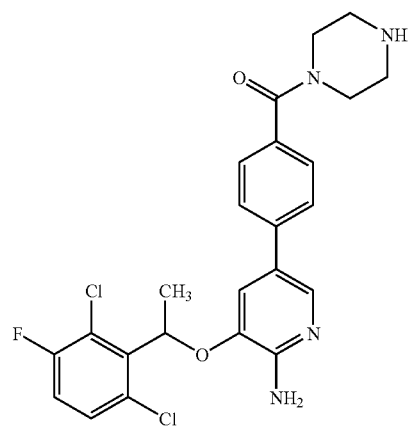 | (4-{6-Amino-5-[1-(2,6-dichloro-3-fluoro-phenyl)-ethoxy]-pyridin-3-yl}-phenyl)-piperazin-1-yl-methanone |
| I-606 | 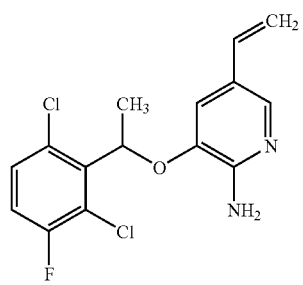 | 3-[1-(2,6-Dichloro-3-fluoro-phenyl)-ethoxy]-5-vinyl-pyridin-2-ylamine |

TABLE 3-continued
| | | |
|---|---|---|
| I-607 | 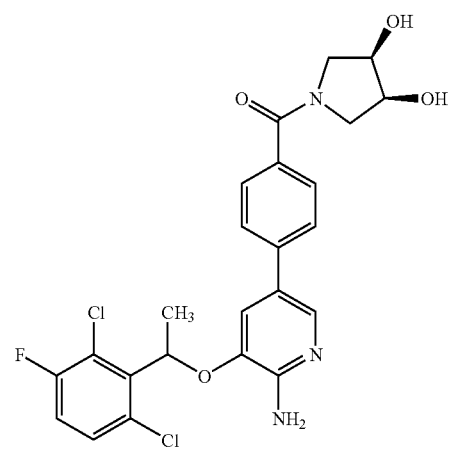 | (4-{6-Amino-5-[1-(2,6-dichloro-3-fluoro-phenyl)-ethoxy]-pyridin-3-yl}-phenyl)-((3R,4S)-3,4-dihydroxy-pyrrolidin-1-yl)-methanone |
| I-608 | 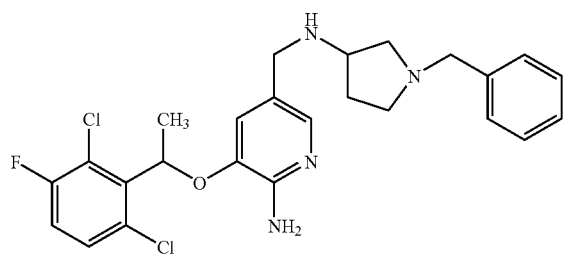 | 5-[(1-Benzyl-pyrrolidin-3-ylamino)-methyl]-3-[1-(2,6-dichloro-3-fluoro-phenyl)-ethoxy]-pyridin-2-ylamine |
| I-609 | 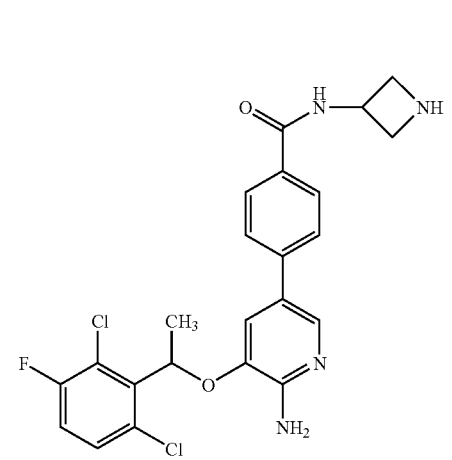 | 4-{6-Amino-5-[1-(2,6-dichloro-3-fluoro-phenyl)-ethoxy]-pyridin-3-yl}-azetidin-3-yl-benzamide |
| I-610 | 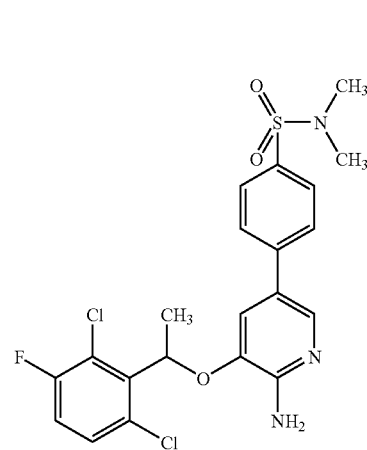 | 4-{6-Amino-5-[1-(2,6-dichloro-3-fluoro-phenyl)-ethoxy]-pyridin-3-yl}-N,N-dimethyl-benzenesulfonamide |

| | | |
|---|---|---|
| I-611 | 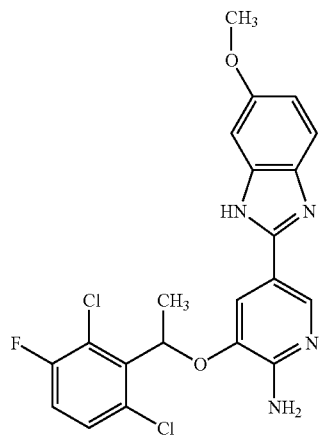 | 3-[2,6-Dichloro-3-fluoro-phenyl)-ethoxy]-5-{6-methoxy-1H-benzoimidazol-2-yl}-pyridin-2-ylamine |
| I-612 | 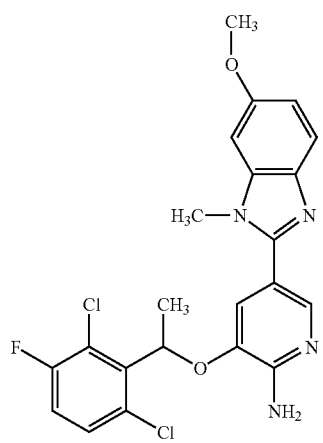 | 3-[1-(2,6-Dichloro-3-fluoro-phenyl)-ethoxyl-5-{6-methoxy-1-methyl-1H-benzoimidazol-2-yl}-pyridin-2-ylamine |
| I-613 | 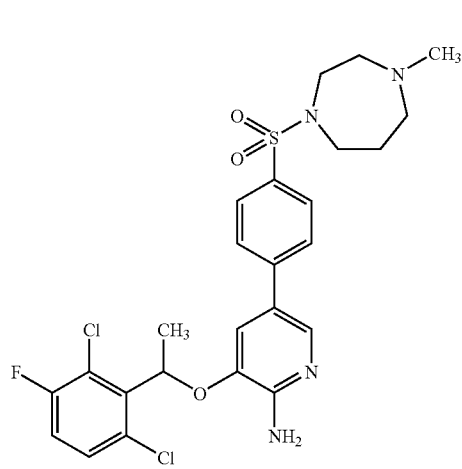 | 3-[1-(2,6-Dichlora-3-fluoro-phenyl)-ethoxy]-5-[4-(4-methyl-[1,4]diazepane-1-sulfonyl)-phenyl]-pyridin-2-ylamine |

TABLE 3-continued
I-614 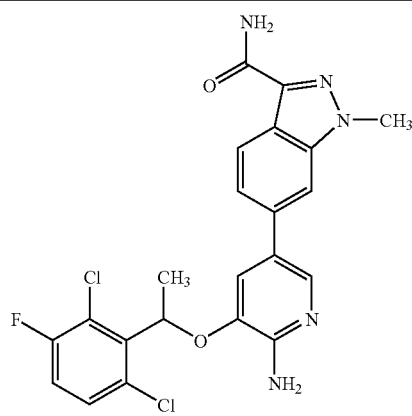 6-{6-Amino-5-[1-(2,6-dichloro-3-fluoro-phenyl)-ethoxy]-pyridin-3-yl}-1-methyl-1H-indazole-3-carboxylic acid amide
I-615 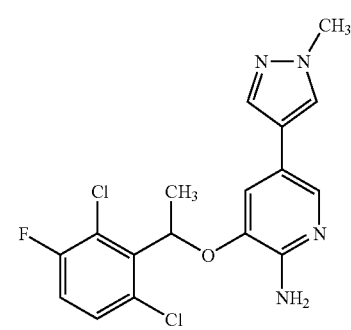 3-[1-(2,6-Dichloro-3-fluoro-phenyl)-ethoxy]-5-[1-methyl-1H-pyrazol-4-yl)-pyridin-2-ylamine
I-616 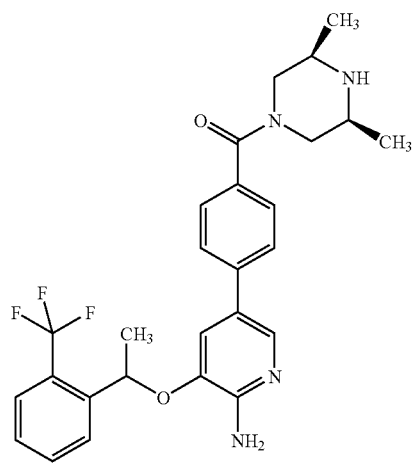 (4-{6-Amino-5-[1-(2-trifluoromethyl-phenyl)-ethoxy]-pyridin-3-yl}-phenyl)-(3,5-dimethyl-piperazin-1-yl-methanone
I-617 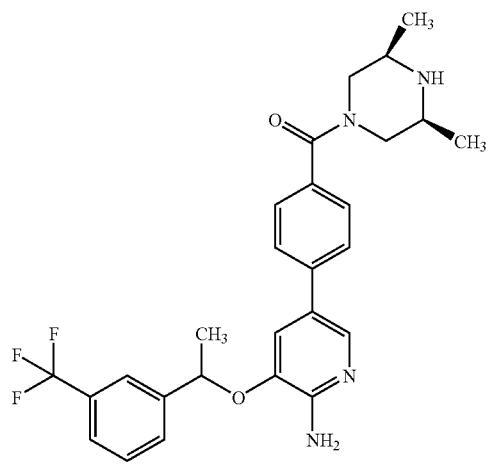 (4-{6-Amino-5-[1-(3-trifluoromethyl-phenyl)-ethoxy]-pyridin-3-yl]-phenyl)-(3,5-dimethyl-piperazin-1-yl)-methanone

TABLE 3-continued
I-618 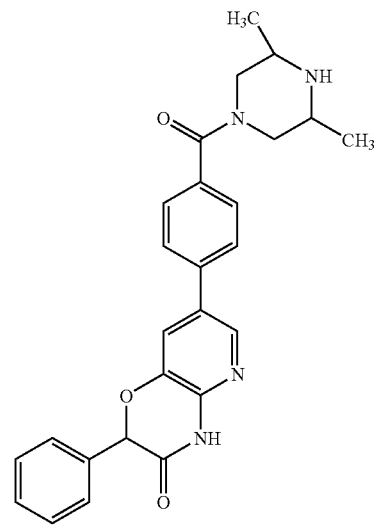 7-(4-(3,5-Dimethyl-piperazine-1-carbonyl)-phenyl]-2-phenyl-4H-pyrido[3,2-b](1,4]oxazin-3-one
I-619 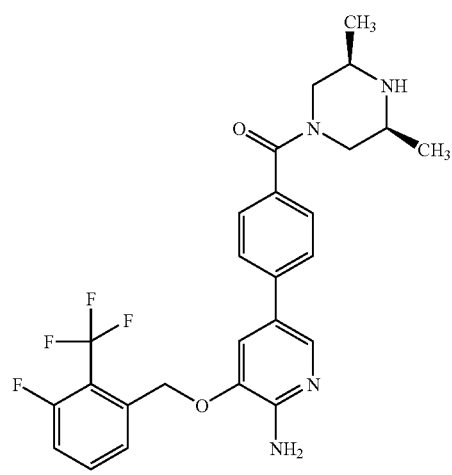 {4-[6-Amino-5-(3-fluoro-2-trifluoromethyl-benzyloxy)-pyridin-3-yl]-phenyl}-(3,5-dimethyl-piperazin-1-yl)-methanone
I-620 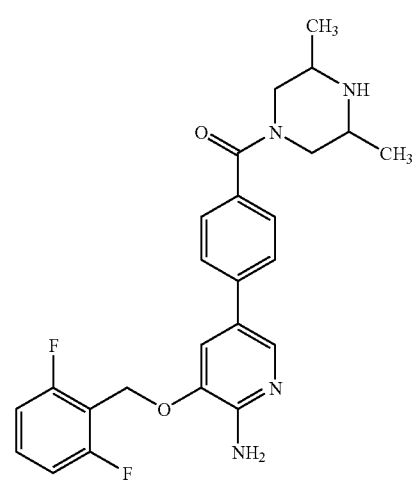 {4-[6-Amino-5-(2,6-difluoro-benzyloxy)-pyridin-3-yl]-phenyl}-(3,5-dimethyl-piperazin-1-yl)-methanone TABLE 3-continued
I-621 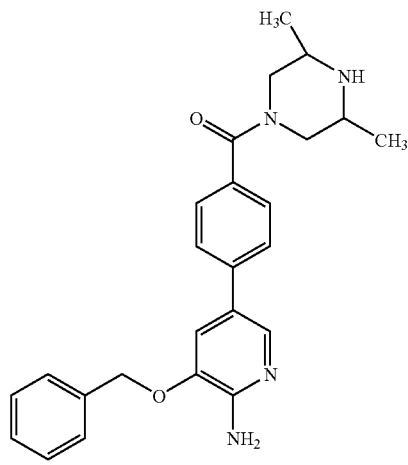
{4-(6-Amino-5-benzyloxy-pyridin-3-yl)-phenyl]-(3,5-dimethyl-piperazin-1-yl)-methanone
I-622 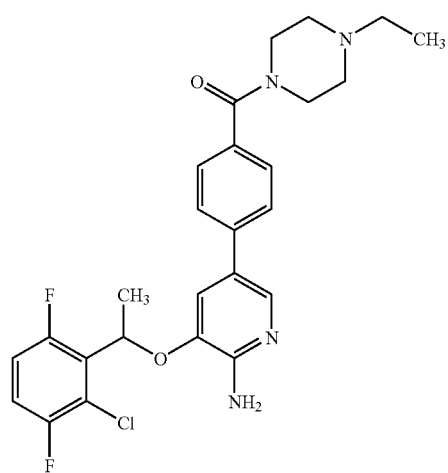
(4-{6-Amino-5-[1-(2-chloro-3,6-difluoro-phenyl)-ethoxy]-pyridin-3-yl}-phenyl)-(4-ethyl-piperazin-1-yl)-methanone
I-623 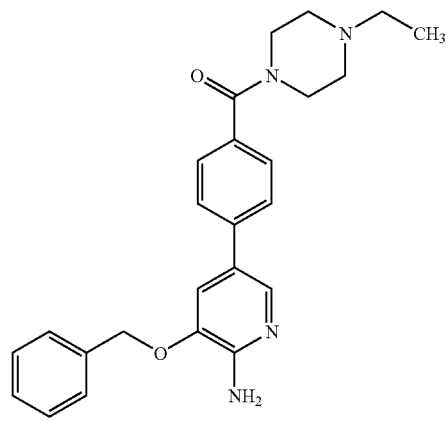
[4-(6-Amino-5-benzyloxy-pyridin-3-yl)-phenyl]-(4-ethyl-piperazin-1-yl)-methanone TABLE 3-continued
I-624 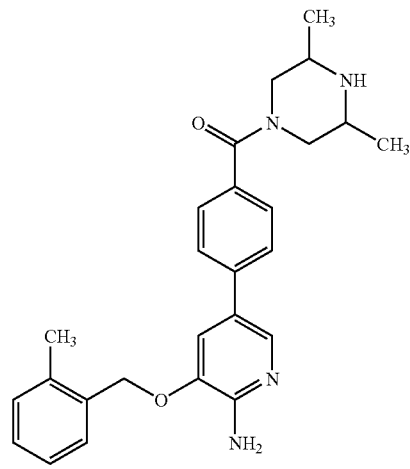 {4-[6-Amino-5-(2-methyl-benzyloxy)-pyridin-3-yl]-phenyl}-(3,5-dimethyl-piperazin-1-yl)-methanone
I-625 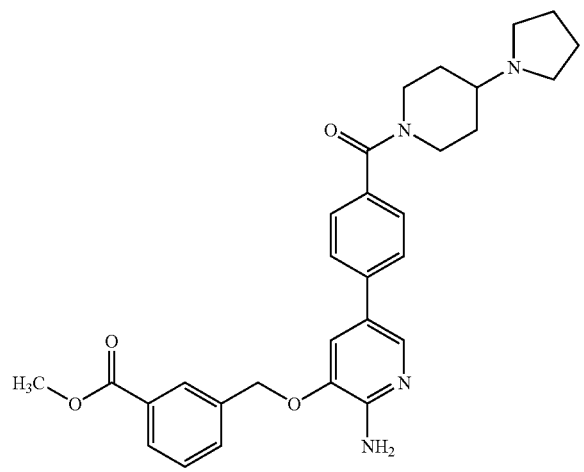 3-{2-Amino-5-[4-(4-pyrrolidin-1-yl-piperidzne-1-carbonyl)-phenyl]-pyridin-3-yloxymethyl)-benzoic acid methyl ester
I-626 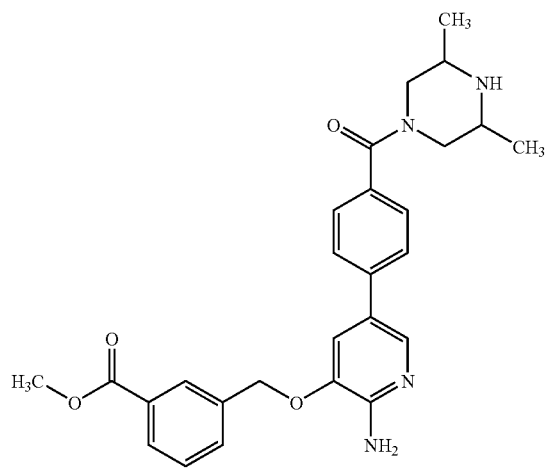 3-{2-Amino-5-[4-(3,5-dimethyl-piperazine-1-carbonyl)-phenyl]-pyridin-3-yloxymethyl}-benzoic acid methyl ester TABLE 3-continued
I-627 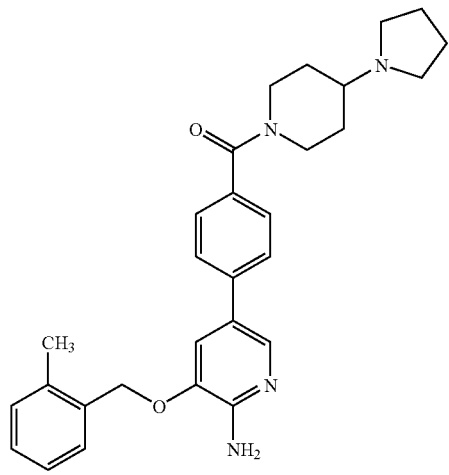 {4-[6-Amino-5-(2-methyl-benzxloxy)-pyridin-3-yl]-phenyl}-(4-pyrrolidin-1-yl-piperidin-1-yl)-methanone
I-628 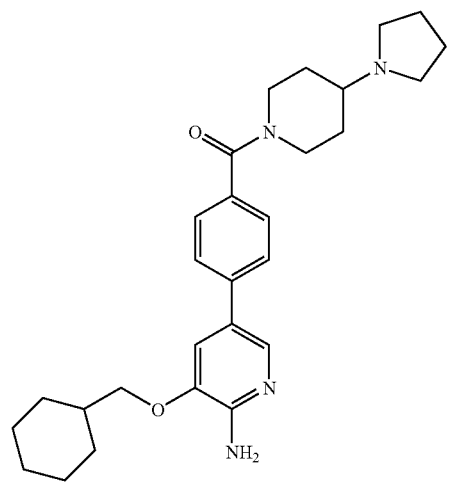 [4-(6-Amino-5-cyclohexylmethoxy-pyridin-3-yl)-phenyl]-(4-pyrrolidin-1-yl-piperidin-1-yl)-methanone
I-629 4-(1-{2-Amino-5-[4-(4-pyrrolidin-1-yl-piperidine-1-carbonyl)-phenyl]-pyridin-3-yloxy}-ethyl)-[2-(3-hydroxy-phenyl)-ethyl]-benzamide
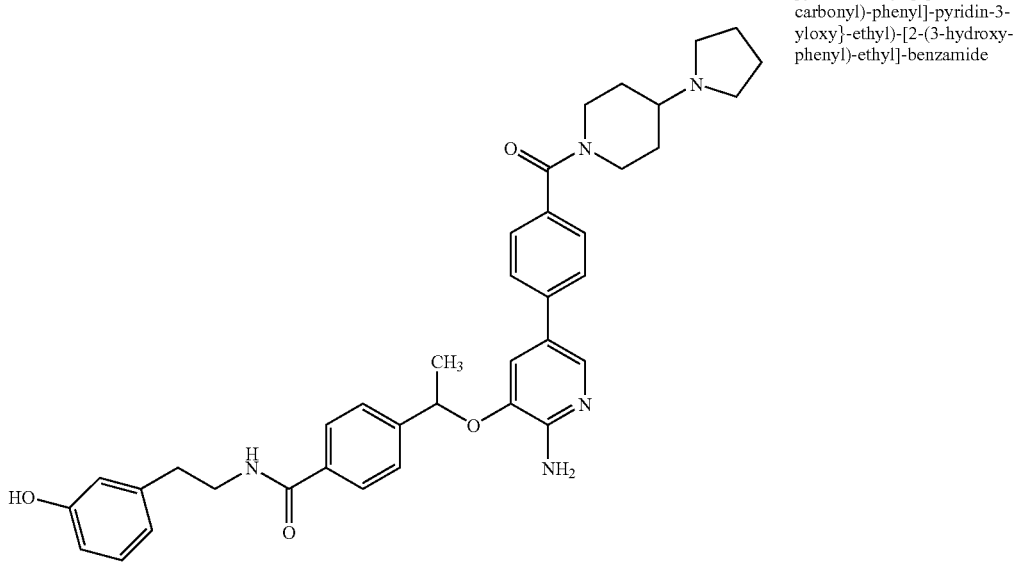

TABLE 3-continued
I-630
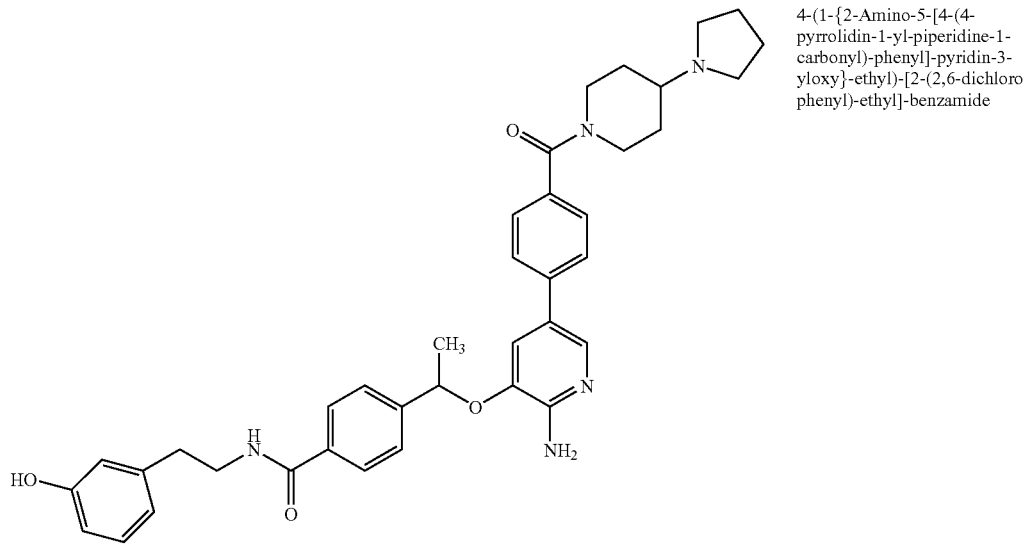
4-(1-{2-Amino-5-[4-(4-pyrrolidin-1-yl-piperidine-1-carbonyl)-phenyl]-pyridin-3-yloxy}-ethyl)-[2-(2,6-dichloro-phenyl)-ethyl]-benzamide
I-631
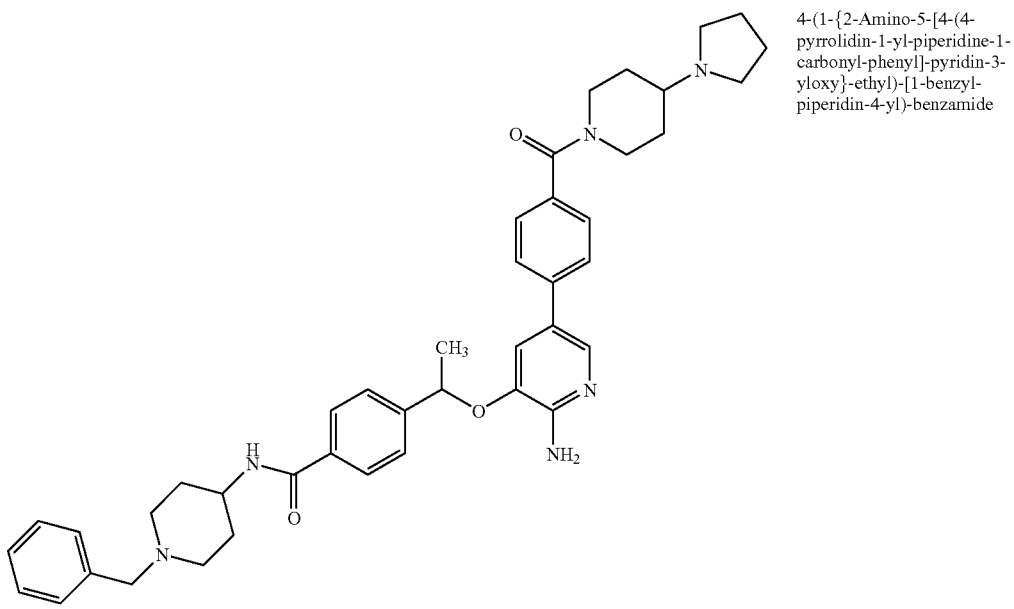
4-(1-{2-Amino-5-[4-(4-pyrrolidin-1-yl-piperidine-1-carbonyl)-phenyl]-pyridin-3-yloxy}-ethyl)-[1-benzyl-piperidin-4-yl)-benzamide
I-632
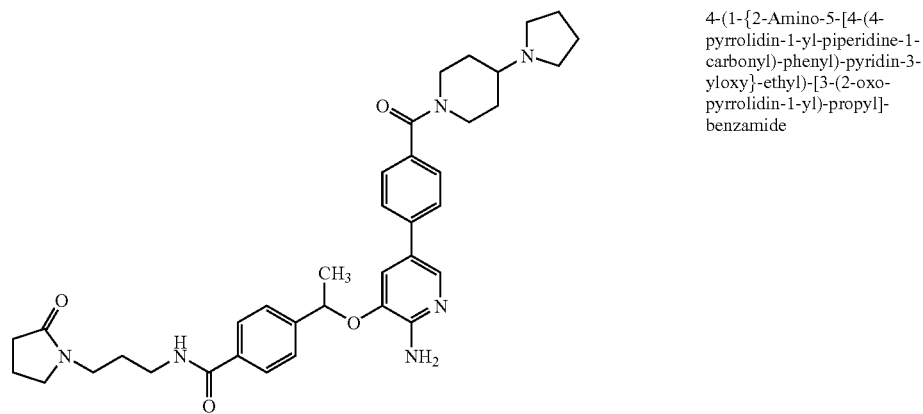
4-(1-{2-Amino-5-[4-(4-pyrrolidin-1-yl-piperidine-1-carbonyl)-phenyl)-pyridin-3-yloxy}-ethyl)-[3-(2-oxo-pyrrolidin-1-yl)-propyl]-benzamide TABLE 3-continued
I-633 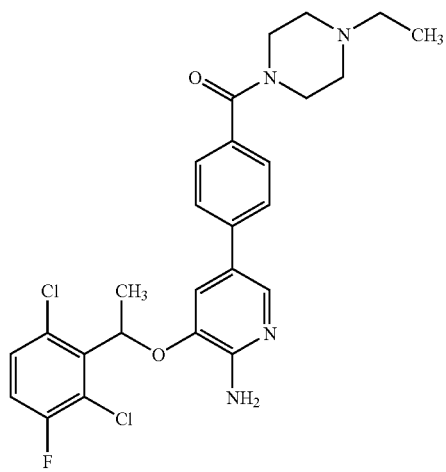
(4-{6-Amino-5-[1-(2,6-dichloro-3-fluoro-phenyl)-ethoxy]-pyridin-3-yl}-phenyl)-(4-ethyl-piperazin-1-yl)-methanone
I-634 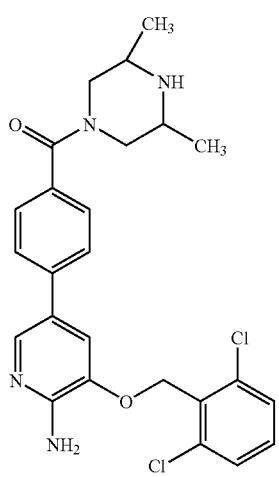
{4-[6-Amino-5-(2,6-dichloro-benzyloxy)-pyridin-3-yl]-phenyl}-(3,5-dimethyl-piperazin-1-yl)-methanone
I-635 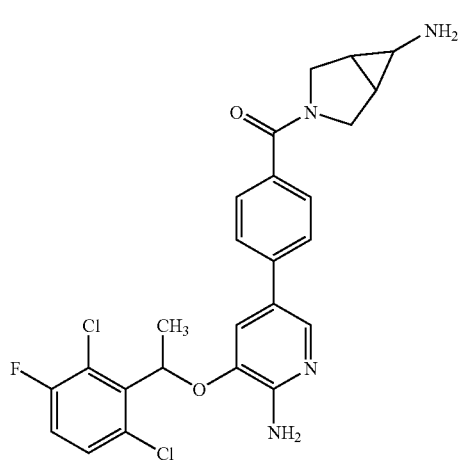
{6-Amino-3-aza-bicyclo[3.1.0]hex-3-yl)-(4-{6-amino-5-[1-(2,6-dichloro-3-fluoro-phenyl)-ethoxy]-pyridin-3-yl}-phenyl)-methanone TABLE 3-continued
I-636 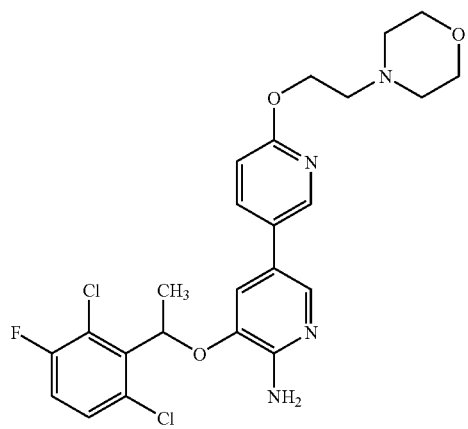 5-[1-(2,6-Dichloro-3-fluoro-phenyl)-ethoxy]-6'-(2-morpholin-4-yl-ethoxy)-[3,3']bipyridinyl-6-ylamine
I-637 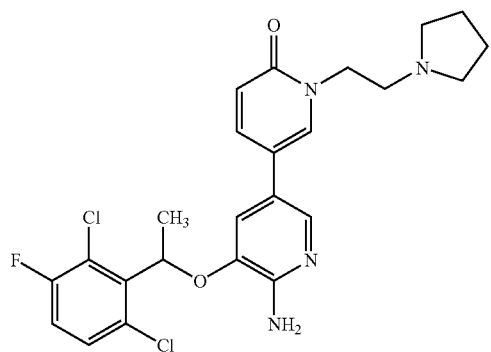 6'-Amino-5'-[1-(2,6-dichloro-3-fluoro-phenyl)-ethoxy]-1-(2-pyrrolidin-1-yl-ethyl)-1H-[3,3']bipyridinyl-6-one
I-638 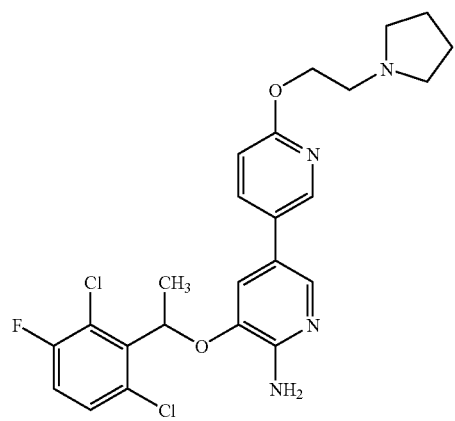 5-[1-(2,6-Dichloro-3-fluoro-phenyl)-ethoxy]-6'-(2-pyrrolidin-1-yl-ethoxy)-[3,3']bipyridinyl-6-ylamine
I-639 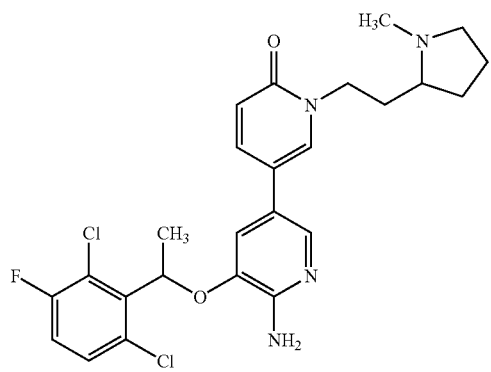 6'-Amino-5'-[1-(2,6-dichloro-3-fluoro-phenyl)-ethoxy]-1-[2-(1-methyl-pyrrolidin-2-yl)-ethyl]-1H-[3,3']bipylidinyl-6-one TABLE 3-continued
I-640 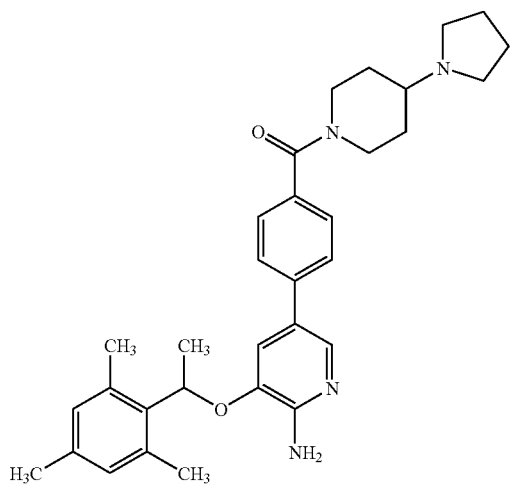 (4-{6-Amino-5-[1-(2,4,6-trimethyl-phenyl)-ethoxy]-pyridin-3-yl}-phenyl)-(4-pyrrolidin-1-yl-piperidin-1-yl)-methanone
I-641 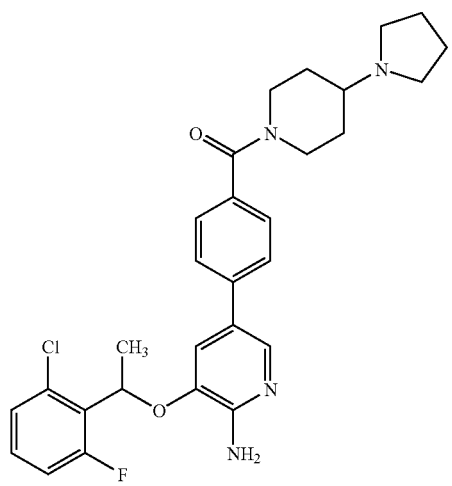 (4-{6-Amino-5-[1-(2-chloro-6-fluoro-phenyl)-ethoxy]-pyridin-3-yl}-phenyl)-(4-pyrrolidin-1-yl-piperidin-1-yl)-methanone
I-642 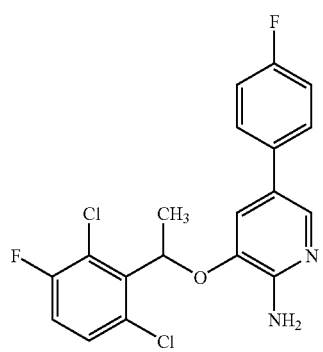 3-[1-(2,6-Dichloro-3-fluoro-phenyl)-ethoxy]-5-(4-fluoro-phenyl)-pyridin-2-ylamine
I-643 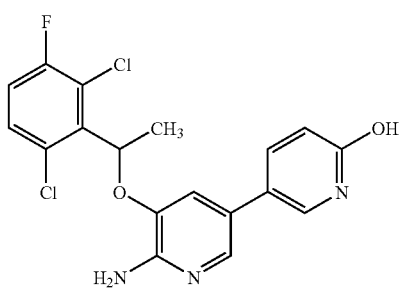 6'-Amino-5'-[1-(2,6-dichloro-3-fluoro-phenyl)-ethoxy]-1H-[3,3']bipyridinyl-6-one TABLE 3-continued
I-644 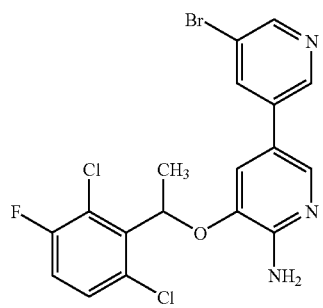 5'-Bromo-5-[1-(2,6-dichloro-3-fluoro-phenyl)-ethoxy]-[3,3']bipyridinyl-6-ylamine
I-645 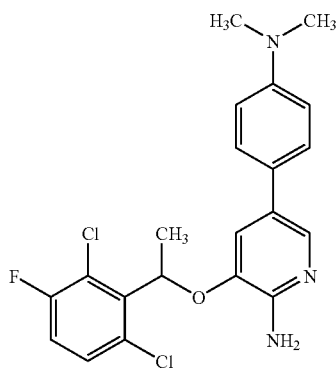 3-[1-(2,6-Dichloro-3-fluoro-phenyl)-ethoxy]-5-(4-dimethylamino-phenyl)-pyridin-2-ylamine
I-646 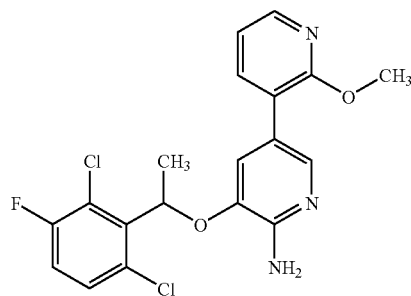 5-[1-(2,6-Dichloro-3-fluoro-phenyl)-ethoxy]-2-methoxy-[3,3]bipyridinyl-6-ylamine
I-647 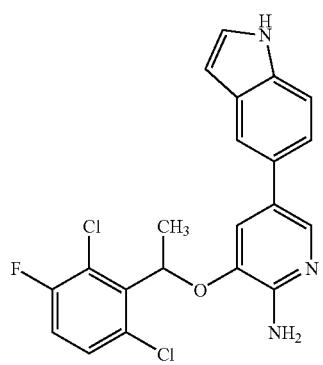 3-[1-(2,6-Didchloro-3-fluoro-phenyl)-ethoxy]-5-(1H-indol-5-yl)-pyridin-2-ylamine TABLE 3-continued
I-648
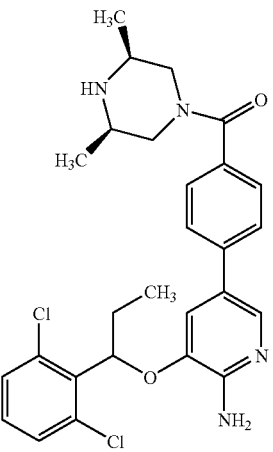
(4-{6-Amino-5-[1-(2,6-dichloro-phenyl)-propoxy]-pyridin-3-yl}-phenyl)-(3,5-dimethyl-piperazin-1-yl}-methanone
I-649
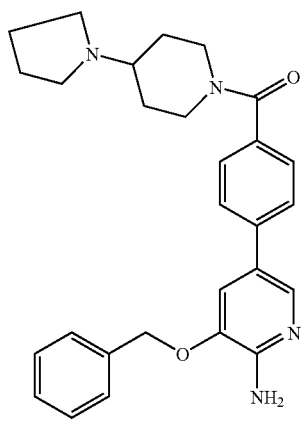
[4-(6-Amino-5-benzyloxy-pyridin-3-yl)-phenyl]-(4-pyrrolidin-1-yl-piperidin-1-yl)-methanone
I-650
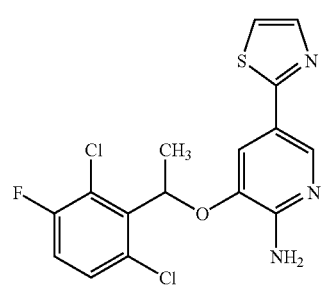
3-(2,6-Dichloro-3-fluoro-benzyloxy)-5-thiazol-2-yl-pyridin-2-ylamine

| | | |
|---|---|---|
| I-651 | 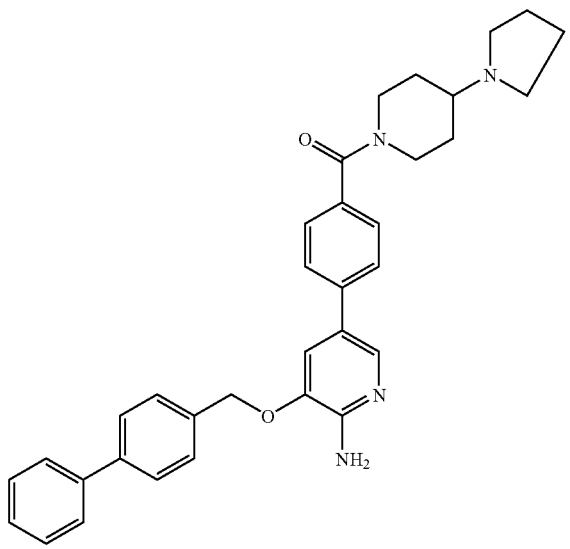 | (4-{6-Amino-5-[1-(2-fluoro-6-trifluoromethyl-phenyl)-ethoxy]-pyridin-3-yl}-phenyl)-(4-pyrrolidin-1-yl-piperidin-1-yl)-methenone |
| I-652 | 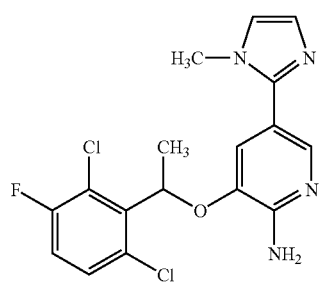 | 3-(2,6-Dichloro-3-fluoro-benzyloxy)-5-(1-methyl-1H-imidazol-2-yl)-pyridin-2-ylamine |
| I-653 | 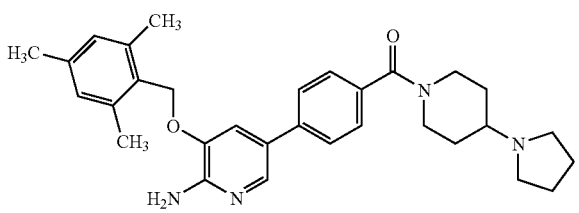 | {4-[6-Amino-5-(2,4,6-trimethyl-benzyloxy)-pyridin-3-yl]-phenyl}-(4-pyrrolidin-1-yl-piperidin-1-yl)-methanone |
| I-654 | 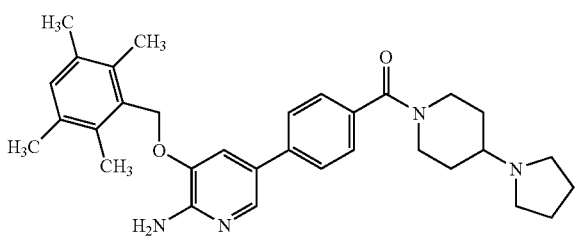 | {4-[6-Amino-5-(2,3,5,6-tetramethyl-benzyloxy)-pyridin-3-yl]-phenyl}-(4-pyrrolidin-1-yl-piperidin-1-yl)-methanone |
| I-655 | 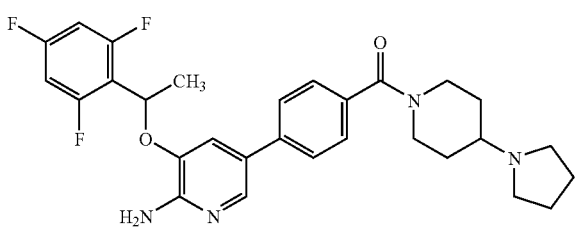 | {4-[6-Amino-5-(2,4,6-trifluoro-benzyloxy)-pyridin-3-yl]-phenyl}-(4-pyrrolidin-1-yl-piperidin-1-yl)-methanone |

TABLE 3-continued
I-656 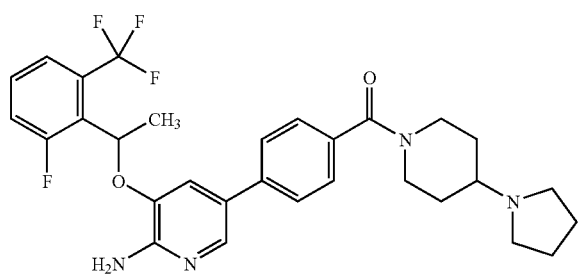
(4-{6-Amino-5-[1-(2-fluoro-6-trifluoromethyl-phenyl)-ethoxy]-pyridin-3-yl}-phenyl-(4-pyrrolidin-1-yl-piperidin-1-yl-methanone
I-657 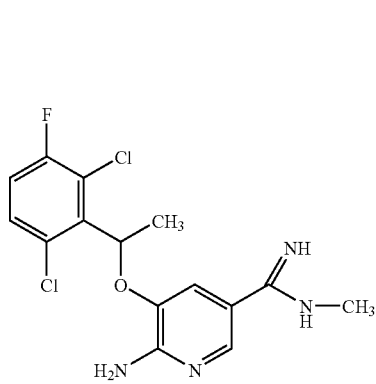
6-Amino-5-[1-(2,6-dichloro3-fluoro-phenyl)-ethoxy]-N-methyl-nicotinamidine
I-658 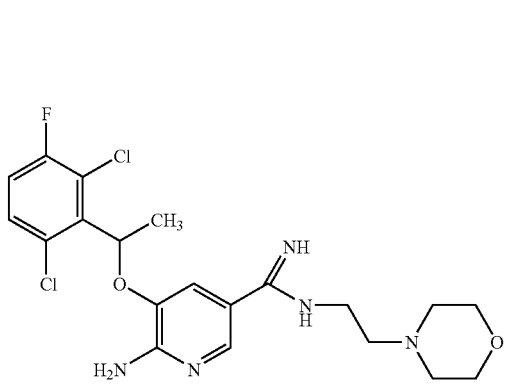
6-Amino-5-[1-(2,6-dichloro-3-fluoro-phenyl)-ethoxy]-N-(2-morpholin-4-yl-ethyl)-nicotinamidine
I-659 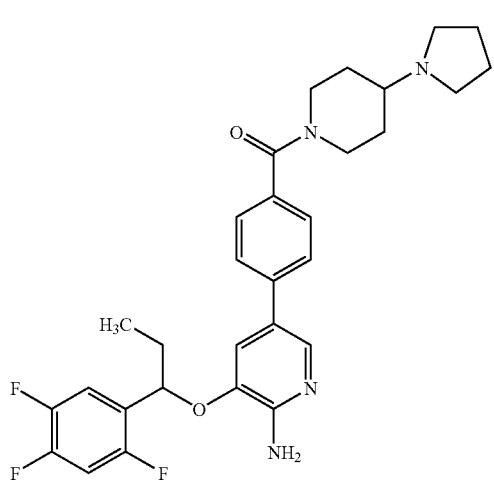
(4-{6-Amino-5-[1-(2,4,5-trifluoro-phenyl)-propoxy]-pyridin-3-yl}-phenyl)-(4-pyrrolidin-1-yl-piperidin-1-yl-methanone

TABLE 3-continued

I-670

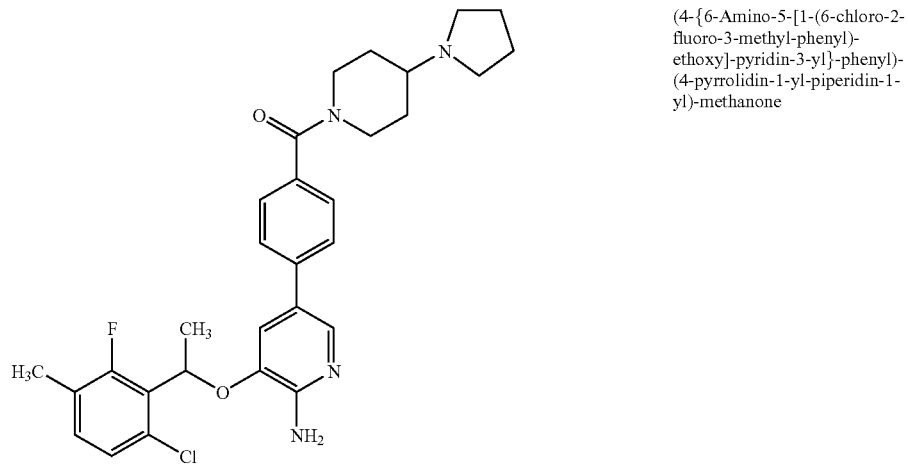

(4-{6-Amino-5-[1-(6-chloro-2-fluoro-3-methyl-phenyl)-ethoxy]-pyridin-3-yl}-phenyl)-(4-pyrrolidin-1-yl-piperidin-1-yl)-methanone

I-671

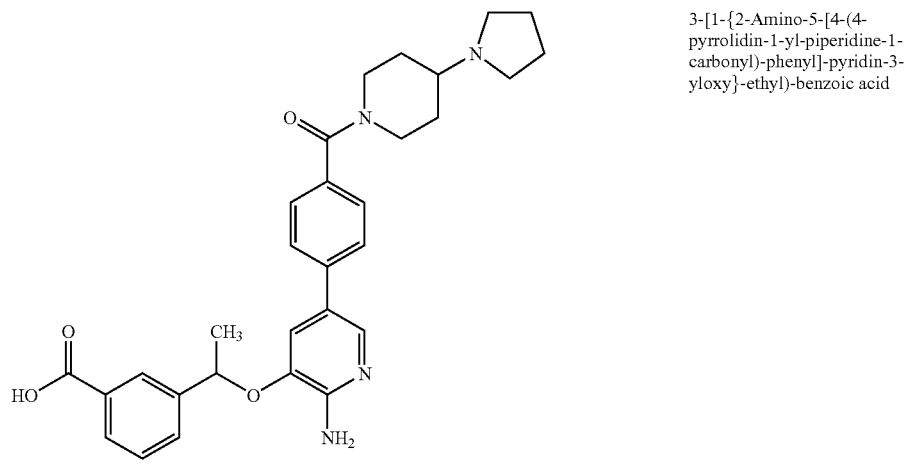

3-[1-{2-Amino-5-[4-(4-pyrrolidin-1-yl-piperidine-1-carbonyl)-phenyl]-pyridin-3-yloxy}-ethyl)-benzoic acid

| No. | Ki(μM) or I(%) | $^1$H-NMR | MS m/z (M + H) | Procedure |
|---|---|---|---|---|
| I-542 | 0.0023 | (400 MHz, DMSO-D6) d ppm 0.84(s, 3H) 0.93-1.10(m, 3H) 1.80(d, J=6.57 Hz, 3H) 2.30(s, 2 H) 2.55-2.74(m, 2H) 3.38-3.49(m, 1H) 4.32 (s, 1H) 5.96(s, 2H) 6.14(q, J=6.57 Hz, 1H) 7.00(d, J=1.77 Hz, 1H) 7.36(m, 2H) 7.45(m, 3H) 7.56(dd, J=8.97, 4.93 Hz, 1H) 7.88(d, J=1.77 Hz, 1H) | 517 | 18/19/20/31 |
| I-543 | 1.5 | (400 MHz, DMSO-D6) d ppm 0.84(s, 3H) 0.93-1.10(m, 3H) 1.80(d, J=6.57 Hz, 3H) 2.30(s, 2 H) 2.55-2.74(m, 2H) 3.38-3.49(m, 1H) 4.32 (s, 1H) 5.96(s, 2H) 6.14(q, J=6.57 Hz, 1H) 7.00(d, J=1.77 Hz, 1H) 7.36(m, 2H) 7.45(m, 3 H) 7.56(dd, J=8.97, 4.93 Hz, 1H) 7.88(d, J=1.77 Hz, 1H) | 517 | 18/19/20/31 |
| I-544 | | (400 MHz, DMSO-D6) d ppm 1.80(d, J=6.82 Hz, 3H) 6.01(s, 2H) 6.17(q. J=6.57 Hz, 1H) 7.05 (d, J=1.77 Hz, 1H) 7.44(t, J=8.72 Hz, 1H) 7.55 (m, 2H) 7.79(m, 1H) 7.89(d, J=1.77 Hz, 1H) 7.97(dd, J=6.06, 2.27 Hz, 1H) | 420 | 27 |
| I-545 | | (400 MHz, DMSO-D6) d ppm 1.49-1.65(m, 2H) 1.75-1.86(m, 3H) 1.86-1.98(m, 3H) 2.53(s, 1H) 2.88(s, 2H) 2.99(s, 2H) 5.84(s, 2H) 6.11 (d, J=6.57 Hz, 1H) 6.93(s, 1H) 7.28 -7.38(m, J=8.08 Hz, 2H) 7.39-7.50(m, J=8.21, 8.21 Hz, 3H) 7.57(dd, J=8.72, 4.93 Hz, 1H) 7.81(s, 1H) | 477 | 27 |
| I-546 | 0.057 | (400 MHz, DMSO-D6) d ppm 1.43-1.56(m, 4H) 1.61(d, J=3.79 Hz, 4H) 1.81(d, J=6.57 Hz, 3H) 3.51(s, 2H) 5.94(s, 2H) 6.15(d, J=6.82 Hz, 1 H) 7.00(d, J=1.77 Hz, 1H) 7.28-7.41(m, 2H) 7.40-7.50(m, 3H) 7.57(dd, J=9.09, 5.05 Hz, 1 H) 7.87(d, J=2.02 Hz, 1H) | 488 | 20 |

TABLE 3-continued

| | | | | |
|---|---|---|---|---|
| I-547 | 0.067 | (400 MHz, DMSO-D6) d ppm 1.73-1.93(m, 7H) 3.39-3.52(m, 4H) 5.96(s, 2H) 6.07-6.20(m, J=6.82 Hz, 1H) 6.99(d, J=1.77 Hz, 1H) 7.39-7.47 en, 3H) 7.52(d, 2H) 7.56(dd, J=9.09, 5.05 Hz, 1H) 7.82-7.92(m, J=1.77 Hz, 1H) | 474 | 20 |
| I-548 | 17% | (400 MHz, CHLOROFORM-D) d ppm 1.77-1.88 (m, 3H) 2.11(s, 3H) 3.91(s, 3H) 4.90(s, 2H) 6.02(d, J=6.82 Hz, 1H) 6.69(d, J=1.77 Hz, 1H) 7.00-7.09(m, 1H) 7.14(d, J=7.83 Hz, 1H) 7.26-7.31(m, 1H) 7.59(d, J=1.77 Hz, 1H) 7.83(dd, J=7.96, 1.39 Hz, 1H) 7.88(s, 1H) | 450 | 19 |
| I-549 | 0.095 | (400 MHz, DMSO-D6) d ppm 0.84-0.96(m, 6H) 1.44-1.61(m, 2H) 1.72-1.83(m, 3H) 2.58-2.70(m, 2H) 2.71-2.84(m, 4H) 5.76-5.92(m, 2H) 6.02-6.18(m, 1H) 6.88-7.01(m,H) 7.25(d, 2H) 7.32(d, 2H) 7.38-7.49(m, 1H) 7.50-7.84(m, 2H) 7.76-7.88(m, 1H) | 503 | 28 |
| I-550 | 15% | (400 MHz, DMSO-D6) d ppm 0.77 -0.91(m, 3H) 1.00(s, 3H) 1.75(d, J=6.82 Hz, 3H) 2.16-2.30 (m, J=12.63 Hz, 3H) 2.64-2.76(m, 3H) 3.54(s, 6H) 4.25-4.40(m, 1H) 5.69(s, 2H) 5.91(q, J=8.74 Hz, 1H) 6.54-6.67(m, 3H) 7.37-7.43 (m, 1H) 7.43-7.51(m, 1H) 7.51-7.60(m, 1H) | 577 | 19/20 |
| I-551 | 0.091 | (400 MHz, DMSO-D6) d ppm 0.80-0.96(m, 3H) 1.06(s, 3H) 1.80(d, J=6.57 Hz, 3H) 2.26-2.42 (m, J=1.52 Hz, 2H) 2.61-2.85(m, J=1.77 Hz, 3 H) 4.35-4.47(m, J=6.32 Hz, 1H) 6.06(s, 2H) 6.16(q, J=6.57 Hz, 1H) 7.02(s, 1H) 7.27-7.40 (m, 3H) 7.40-7.49(m, J=8.72, 8.72 Hz, 2H) 7.51-7.62(m,.38.84, 5.05 Hz, 1H) 7.93(s, 1H) | 535 | 19/20 |
| I-552 | 0.2237 | (400 MHz, DMSO-06) d ppm 0.83-1.00(m, 3H) 1.02-1.17(m, 3H) 1.78(d, 3H) 2.70-2.98(m, 6H) 4.38-4.50(m, 1H) 6.01-6.10(m, 2H) 6.10-6.22(m, 1H) 6.96-7.04(m, 1H) 7.06-7.15(m, 1H) 7.16-7.23(m, 1H) 7.30-7.39(m, 1H) 7.40-7.49(m, 1H) 7.50-7.59(m, 1H) 7.86-7.98(m, 1H) | 535 | 19/20 |
| I-553 | 0.2593 | (400 MHz, DMSO-D6) d ppm 0.88(s, 3H) 1.01 (s, 3H) 1.77(d, J=6.57 Hz, 3H) 1.96(s, 3H) 2.31(s, 1H) 2.73(s, 3H) 3.50(s, 2H) 4.35(s, 1 H) 5.89(s, 2H) 6.00(q, J=6.57 Hz, 1H) 6.60(s, 1H) 7.01-7.12(m, JH7.83 Hz, 1H) 7.12-7.28 (m, 2H) 7.37-7.63(m, 3H) | 531 | 19/20 |
| I-554 | 0.1407 | (400 MHz, DMSO-D6) d ppm 1.00-1.31(m, 4 H), 1.87(d, J=6.82 Hz, 3H) 3.37-3.40(m, 6H) 3.55-3.65(m, 2H) 6.01-6.05(m, 2H) 6.21(q, J=6.57 Hz, 1H) 7.07(d, J=1.77 Hz, 1H) 7.45-7.55(m, 5H) 7.63(dd, J=8.84, 5.05 Hz, 1H) 7.92-7.98(m, 1H) | 518 | 19 |
| I-555 | 22% | (400 MHz, DMSO-D6) d ppm 1.36(t, J=6.82 Hz, 3H) 1.95(d, J=6.57 Hz, 3H) 4.08-4.16(m, 2H) 5.91-5.95(m, 2H) 6.16(q, J6.57 Hz, 1H) 7.08-7.13(m, 2H) 7.19(d, J=7.83 Hz, 1H) 7.27(dd, J=7.58, 1.77 Hz, 1H) 7.40(t, J=8.59 Hz, 1H) 7.62(t, J=8.59 Hz, 1H) 7.73(dd, J=9.09, 5.05 Hz, 1H) 7.84(d, J=1.77 Hz, 1H) | 421 | 19 |
| I-556 | 0.5746 | (400 MHz, DMSO-D6) d ppm 1.82(d, J=6.57 Hz, 3H) 3.57-3.58(m, 3H) 3.74-3.75(m, 3H) 5.82-5.86(m, 2H) 6.03(q, J=6.57 Hz, 1H) 6.72 H) 6.89(d, J=1.77 Hz, 1H) 6.98(d, J=9.09 Hz, 1 (d, J=3.28 Hz, 1H) 6.84(dd, J=8.84, 3.03 Hz, 1 H) 7.50(t, J=8.59 Hz, 1H) 7.61(dd, J=8.84, 4.60 Hz, 1H) 7.66(d, J=1.77 Hz, 1H) | 437 | 19 |
| I-557 | 0.2172 | (400 MHz, DMSO-D6) d ppm 1.83(d, J=6.82 Hz, 3H) 3.64-3.67(m, 3H) 3.81-3.84(m, 3H) 5.74-5.78(m, 2H) 6.03(q, J=6.57 Hz, 1H) 6.59 0.2172(dd, J=8.34, 2.27 Hz, 1H) 6.64(d, J=2.53 Hz, 1 H) 6.88(d, J=1.77 Hz, 1H) 7.10(d, J=8.34 Hz, 1 H) 7.53(t, J=8.59 Hz, 1H) 7.58(d, J=1.77 Hz, 1 H) 7.63(dd, J=8.84, 5.05 Hz, 1H) | 437 | 19 |
| I-558 | 2% | (400 MHz, DMSO-D6) d ppm 1.81(d, J=6.82 Hz, 3H) 3.58-3.59(m, 6H) 5.68-5.69(m, 2H) 5.96(q, J=6.82 Hz, 1H) 6.63(d, J=1.77 Hz, 1H) 6.71(d, J=8.34 Hz, 2H) 7.26(t, J=8.34 Hz, 1H) 7.42(d, J=1.52 Hz, 1H) 7.52(t, J=8.59 Hz, 1H) 7.61(dd, J=8.84, 5.05 Hz, 1H) | 437 | 19 |
| I-559 | 4% | (400 MHz, DMSO-D6) d ppm 1.78(d, J=6.57 Hz, 3H) 5.91-5.99(m, 3H) 6.59-6.60(m, 1H) | 445 | 19 |

TABLE 3-continued

| | | | | |
|---|---|---|---|---|
| | | 7.26(d, J=7.58 Hz, 1H) 7.42-7.48(m, 2H) 7.50-7.58(m, 2H) 7.65(t, J=7.33 Hz, 1H) 7.75(d, J=7.83 Hz, 1H) | | |
| I-560 | 24% | (400 MHz, DMSO-06) d ppm 1.79(d, J=6.82 Hz, 3H) 5.96-6.03(m, 3H) 6.75(d, J=1.77 Hz, 1H) 7.27-7.38(m 3H), 7.42-7.49(m 2H) 7.52-7.57(m, 2H) | 411 | 19 |
| I-561 | 14% | (400 MHz, DMSO-06) d ppm 1.74(d, J=6.82 Hz, 3H) 5.92-5.98(m, 3H) 6.74(d, J=1.77 Hz, 1H) 7.29-7.43(m, 5H) 7.50(dd, J=9.09, 5.05 Hz, 1 H) 7.56(d, J=1.77 Hz, 1H) | 461 | 19 |
| I-562 | 8% | (400 MHz, DMSO-06) d ppm 1.83(d, J=6.82 Hz, 3H) 1.92-1.93(m, 3H) 6.01-6.07(m, 3H) 6.59(d, J=2.02 Hz, 1H) 7.26(d, J=7.83 Hz, 1H) 7.45(t, J=7.33 Hz, 1H) 7.48-7.51(m, 1H) 7.52-7.58(m, 3H) 7,61(dd, J=8.84, 5.05 Hz, 1H) | 419 | 19 |
| I-563 | 0.4332 | (400 MHz, DMSO-D6) d ppm 1.71(d, J=8.57 Hz, 3H) 5.88.5.90(m, 2H) 5.96(q, J=6.82 Hz, 1H) 6.76-6.78(m, 1H) 7.10-7.16(m, 2H) 7.19-7.28(m, 2H) 7.36(t, J=8.59 Hz, 1H) 7.47(dd, J=8.84, 4.80 Hz, 1H) 7.60-7.63(m, 1H) | 395 | 19 |
| I-564 | 21% | (400 MHz, DMSO-D6) d ppm 1.79(d, J=6.57 Hz, 3H) 4.20(t, J=5.05 Hz, 2H) 5.03(t, J=5.56 Hz, 1 H) 5.82-5.83(m, 2H) 6.02(q, J=6.57 Hz, 1H) Hz, 1H) 7.25(dt, J=7.58, 1.52 Hz, 1H) 7.31(dt, 6.68(d, J=1.77 Hz, 1H) 7.01(dd, J=7.58, 1.52 J=7.33, 1.26 Hz, 1H) 7.46(t, J=8.59 Hz, 1H) 7.49-7.53(m, 2H) 7.56(dd, J=8.84, 5.05 Hz, 1 H) | 407 | 19 |
| I-565 | 25% | (400 MHz, DMSO-D6) d ppm 1.65(d, J=6.57 Hz, 3H) 1.80-1.80(m, 3H) 5.67-5.69(m, 2H) 5.86(q, J=6.57 Hz, 1H) 6.45(d, J=1.77 Hz, 1H) 6.86-6.90(m, 1H) 7.00-7.09(m, 3H) 7.29-7.35(m, 2H) 7.42(dd, J=8.84. 5.05 Hz, 1H) | 391 | 19 |
| I-566 | 0.2779 | (400 MHz, DMSO-D6) d ppm 1.84(d, J=6.57 Hz, 3H) 3.65-3.66(m, 3H) 5.83-5.84(m, 2H) 6.04(q, J=6.57 Hz, 1H) 6.93(d, J=1.77 Hz, 1H) 7.00(dt, J=7.33, 1.01 Hz, 1H) 7.08(d, J=7.83 Hz, 1H) 7.19(dd, J=7.58, 1.77 Hz, 1H) 7.28-7.34(m, 1H) 7.53(t, J=8.84 Hz, 1H) 7.61-7.66 (m, 2H) | 407 | 19 |
| I-567 | 0% | (400 MHz, DMSO-D6) d ppm 1.57-1.58(m, 3 H) 1.79(d, J=6.82 Hz, 3H) 1.97-1.98(m, 3H) 5.73-5.75(m, 2H) 5.98(q, J=6.57 Hz, 1H) 6.41 (d, J=1.77 Hz, 1H) 6.99-7.11(m, 3H) 7.25(d, J=1.77 Hz, 1H) 7.44(t, J=8.59 Hz, 1H) 7.54(dd, J=8.84, 5.05 Hz, 1H) | 405 | 19 |
| I-568 | 0.0525 | Anal. Calcd for C24 H22 Cl2 F N3 O3: C, 58.79; H, 4.52; N, 8.57. Found: C, 58.39; H, 4.72; N, 8.24. | 490 | 20 |
| I-569 | 0.0478 | Anal. Calcd for C26 H26 Cl3 F N4 O2: C, 56.59; H. 4.75; N, 10.15. Found: C, 52.83;H, 5.16; N, 8.79. 1.1 eq of H2O; 1.3 eq AcOH | 551 | 19/20 |
| I-570 | 0.225 | Anal. Calcd for C27 H29 Cl2 F N4 O2: C, 61.02; H, 5.50; N, 10.54. Found: C, 55.99;H, 5.79; N, 9.01. 1.2 eq of H20; 1 Seq of AcOH | 531 | 19/20 |
| I-571 | 0.2704 | (400 MHz, CHLOROFORM-D) d ppm 1.09(d, J=6.32 Hz, 6H) 1.80(d, J=6.82 Hz, 3H) 1.88-1.98(m, 2H) 2.78-2.90(m, 2H) 3.59-3.70(m, 2H) 3.86-3.95(m, 2H) 5.12-5.16(m, 2H) 6.06(q, J=6.57 Hz, 1H) 6.94-7.04(m, 2H) 7.25 (dd, J=8.84, 4.80 Hz, 1H) 7.28-7.34(m, 1H) 7.36-7.44(m, 2H) 7.77(d, J=1.52 Hz, 1H) | 504 | 28 |
| I-572 | 0.554 | (400 MHz, CHLOROFORM-D) d ppm 1.80(d, J=6.57 Hz, 3H) 2.51-2.58(m, 4H) 3.58-3.60 (m, 2H) 3.75(t, J=4.55 Hz, 4H) 5.27-5.31(m, 2 H) 6.06(9, J=6.57 Hz, 1H) 6.95(d, J=1.52 Hz, 1 H) 7.00(t, J=8.08 Hz, 1H) 7.22-7.29(m, 3H) 7.33-7.37(m, 2H) 7.74(d, J=1.77 Hz, 1H) | 476 | 28 |
| I-573 | | (400 MHz, DMSO-D6) d ppm 1.64(d, J=6.57 Hz, 3H) 2.08-2.10(m, 6H) 5.65-5.68(m, 2H) 6.78(m, 2H) 7.28(t, J=8.59 Hz, 1H) 7.40(dd, 5.93(q, J=6.57 Hz, 1H) 6.69-6.71(m, 2H) 6.75 J=9.09, 4.80 Hz, 1H) 7.62(d, J=1.77 Hz, 1H) | 405 | 19 |
| I-574 | | (400 MHz, DMSO-D6) d ppm 1.78(d, 1=6.57 Hz, 3H) 2.27-2.28(m, 3H) 5.80-5.84(m, 2H) 6.08(q, J=6.57 Hz, 1H) 6.88(d, J=1.77 Hz, 1H) 7.02(d, J=7.33 Hz, 1H) 7.09-7.15(m, 2H) 7.21 | 391 | 19 |

TABLE 3-continued

| | | | |
|---|---|---|---|
| | (t, J=7.58 Hz, 1H) 7.41(t, J=8.59 Hz, 1H) 7.54 (dd, J=9.09, 5.05 Hz, 1H) 7.77(d, 11.77 Hz, 1H) | | |
| I-575 | (400 MHz, DMSO-D6) d ppm 1.60(d, J=6.57 Hz, 3H) 3.55(d, J=14.91 Hz, 6H) 5.57-5.60(m, 2H) 5.90(q, J=6.57 Hz, 1H) 6.63(d, J=2.02 Hz, 1H) 6.65(d, J=1.77 Hz, 1H) 6.68-6.76(m, 2H) 7.23(t, J=8.59 Hz, 1H) 7.36(dd, J=4.80, 4.04 Hz, 1H) 7.58(d, J=1.77 Hz, 1H) | 437 | 19 |
| I-576 | (400 MHz, DMSO-D6) d ppm 1.83(d, J=6.57 Hz, 3H) 5.92-5.95(m, 2H) 6.16(q, J=6.57 Hz, 1H) 453 19 7.01(d, J=1.52 Hz, 1H) 7.38-7.59(m, 9H) 7.69 (d, J=7.33 Hz, 2H) 7.93(d, J=1.52 Hz, 1H) | 453 | 19 |
| I-577 | (400 MHz, DMSO-D6) d ppm 1.84(d, J=6.57 Hz, 3H) 6.16-6.24(m, 3H) 7.03(d, J=1.77 Hz, 1H) 7.45(t, J=8.59 Hz, 1H) 7.54(dd, J=9.09, 5.05 Hz, 1H) 7.92-7.95(m, 1H) 8.00-8.02(m, 2H) 8.08(d, 12.02 Hz, 1H) | 513 | 19 |
| I-578 | (400 MHz, DMSO-D6) d ppm 1.87(d, J=6.57 Hz, 3H) 6.09-6.12(m, 2H) 6.22(q, J=6.57 Hz, 1H) 7.04(d, J=1.77 Hz, 1H) 7.46-7.53(m, 2H) 7.62 (dd, J=9.09, 5.05 Hz, 1H) 7.66-7.70(m, 2H) 7.96(d, J=2.02 Hz, 1H) | 446 | 19 |
| I-579 | (400 MHz, DMSO-D6) d ppm 1.76(d, J=6.57 Hz, 3H) 2.54-2.55(m, 3H) 5.90-5.94(m, 2H) 6.10(q, J=6.57 Hz, 1H) 6.93(d, J=1.77 Hz, 1H) 7.39(t, J=8.59 Hz, 1H) 7.46(t, J=7.83 Hz, 1H) 7.51(dd, J=9.09, 5.05 Hz, 1H) 7.63(d, J=8.34 Hz, 1H) 7.76(d, J=7.83 Hz, 1H) 7.81-7.83(m, 1H) 7.85(d, J=2.02 Hz, 1H) | 419 | 19 |
| I-580 | (400 MHz, DM50-OS) d ppm 1.82(d, J=6.57 Hz, 3H) 6.06-6.10(m, 2H) 6.18(q, J=6.57 Hz, 1H) 7.01(d, J=1.77 Hz, 1H)7.06-7.19(m,3H)7.45 (t, J=6.84 Hz, 1H) 7.58(dd, J=9.09, 5.05 Hz, 1H) 7.95(d, J=2.02 Hz, 1H) | 413 | 19 |
| I-581 | (400 MHz, DMSO-D6) d ppm 1.90(d, J=6.82 Hz, 3H) 6.10(q, J=6.57 Hz, 1H) 6.17-6.19(m, 2H) 6.84(d, J=1.77 Hz, 1H) 7.44-7.51(m, 2H) 7.56 (t, J=8.59 Hz, 1H) 7.59-7.70(m, 3H) | 446 | 19 |
| I-582 | Passed CHN 1.0 eq AcOH | 567 | 18/20 |
| I-583 | (400 MHz, DMSO-D6) d ppm 1.35(t, J=6.82 Hz, 3H) 1.82(d, J=6.57 Hz, 3H) 3.99-4.09(m, 2H) 5.88-5.91(m, 2H) 6.13(q, J=6.57 Hz, 1H) 6.80 (dd, J=8.08, 2.27 Hz, 1H) 6.84(t, J=2.02 Hz, 1H) 6.92(d J=1.77 Hz, 1H) 6.96(d, J=7.58 Hz, 1H) 7.26(t, J=7.83 Hz, 1H) 7.46(t, J=8.59 Hz, 1H) 7.57(dd, J=8.84, 5.05 Hz, 1H) 7.83(d, J=1.77 Hz, 1H) | 421 | 19 |
| I-584 | (400 MHz, DMSO-D6) d ppm 1.87(d, J=6.57 Hz, 7.02(d, J=2.02 Hz, 1H) 7.35(td, J=6.82, 1.77 3H) 6.03-6.06(m, 2H) 6.18-6.24(m, 1H) Hz, 1H) 7.41-7.53(m, 4H) 7.62(dd, J=8.84, 5.05 Hz, 1H) 7.93(d, J=2.02 Hz, 1H) | 411 | 19 |
| I-585 | (400 MHz, DMSO-D6) d ppm 1.58(d, J=6.57 Hz, 3H) 2.01-2.02(m, 3H) 5.62-5.64(m, 2H) 5.89(q, J=6.82 Hz, 1H) 6.68(d, J=1.77 Hz, 1H) 6.90(t, J=8.84 Hz, 1H) 6.96-7.04(m, 2H) 7.22 (t J=8.59 Hz, 1H) 7.34(dd, J=9.09, 5.05 Hz, 1H) 7.56(d, J=1.77 Hz, 1H) | 409 | 19 |
| I-586 | (400 MHz, DMSO-D6) d ppm 1.64(d, J=6.57 Hz, 3H) 6.05-6.07(m, 2H) 6.14-6.21(m, 1H) 6.99(d, J=1.77 Hz, 1H) 7.46(t, J=8.59 Hz, 1H) 7.56(dd, J=6.84, 5.05 Hz, 1H) 7.59-7.65(m, 3H) 7.76-7.80(m, 1H) 7.95(d, J=1.77 Hz, 1H) | 445 | 19 |
| I-587 | (400 MHz, DMSO-D6) d ppm 1.82(d, J=6.57 Hz, 3H) 5.98-6.00(m, 2H) 6.13-6.20(m, 1H) 6.99(d, J=1.77 Hz, 1H) 7.05-7.11(m, 1H) 7.21 7.27(m, 2H) 7.39-7.49(m, 2H) 7.59(dd, J=9.09, 5.05 Hz, 1H) 7.90(d, J=2.02 Hz, 1H) | 395 | 19 |
| I-588 | (400 MHz, DMSO-D6) d ppm 1.60(d, J=6.57 Hz, 3H) 5.80-5.84(m, 2H) 5.90-5.98(m, 1H) 6.73(d, J=2.02 Hz, 1H) 7.00-7.07(m, 2H) 7.20-7.30(m, 3H) 7.34(dd, J=8.84, 4.80 Hz, 1H) 7.68(d, J=1.77 Hz, 1H) | 461 | 19 |
| I-589 | (400 MHz, DMSO-D6) d ppm 1.82(d, J=6.57 Hz, 3H) 5.81.5.83(m, 2H) 6.03-6.04(m, 2H) 6.10-6.17(m, 1H) 6.83-6.96(m, 4H) 7.46(t, J=8.64 Hz, 1H) 7.58(dd, J=9.09, 5.05 Hz, 1H) 7.76(d, J=2.02 Hz, 1H) | 421 | 19 |

TABLE 3-continued

| | | | |
|---|---|---|---|
| I-590 | (400 MHz, DMSO-D6) d ppm 1.95(d, J=6.82 Hz, 3H) 5.98-6.00(m, 2H) 6.22-6.28(m, 1H) 6.78-6.81(m, 1H) 6.89-6.93(m, 2H) 7.04(d, J=1.77 Hz, 1H) 7.29(t J=8.08 Hz, 1H) 7.58(t, J=9.09, 8.59 Hz, 1H) 7.71(dd, J=8.84, 4.80 Hz, 1H) 7.89(d, J=1.77 Hz, 1H) 9.55-9.57(m, 1H) | 393 | 19 |
| I-591 | (400 MHz, DMSO-D6) d ppm 1.63(d, J=6.57 Hz, 3H) 4.52(d, J=5.31 Hz, 2H) 5.16-5.22(m, 1H) 5.88-5.90(m, 2H) 6.11-6.17(m, 1H) 6.96(d, J=1.52 Hz, 1H) 7.20-7.28(m, 2H) 7.31-7.36 (m, 2H) 7.46(t, J=8.84 Hz, 1H) 7.58(dd, J=9.09, 5.05 Hz, 1H) 7.63(d, J=1.77 Hz, 1H) | 407 | 19 |
| I-592 | (400 MHz, DMSO-D6) d ppm 1.88(d, J=6.57 Hz, 3H) 6.10-6.12(m, 2H) 6.24 Cq, J=6.57 Hz, 1H) 7.12(d, J=1.77 Hz, 1H) 7.51(t J=8.59 Hz, 1H) 7.60-7.68(m, 2H) 7.77(d, J=7.83 Hz, 1H) 7.81 (d, J=8.08 Hz, 1H) 7.94-7.96(m, 1H) 8.00(d, J=1.77 Hz, 1H) | 402 | 19 |
| I-593 | (400 MHz, DMSO-D6) d ppm 1.83(d, J=6.57 Hz, 3H)3.79-3.80(m, 3H)5.91-5.92(m, 2H) 6.11-6.18(m, 1H) 6.81-6.64(m, 1H) 6.86-6.89(m, 1H) 6.93(d, J=1.52 Hz, 1H) 6.97-7.01 (m, 1H) 7.29(t, J=8.34, 7.83 Hz, 1H) 7.46(t J=8.64 Hz, 1H) 7.59(dd, J=9.09, 5.05 Hz, 1H) 7.85(d, J=1.77 Hz, 1H) | 407 | 19 |
| I-594 | (400 MHz, DMSO-D6) d ppm 1.83(d, J=6.57 Hz, 1H) 6.10-6.12(m, 2H) 6.16-6.22(m, 1H) 7.00(d, J=1.77 Hz, 1H) 7.44-7.49(m, 4H) 7.58 (dd,.J=9.09, 5.31 Hz, 1H) 7.95(d, J=2.02 Hz, 1 H) | 446 | 19 |
| I-595 | (400 MHz, DMSO-D6) d ppm 1.80(d, J=6.82 Hz, 3H) 1.90-1.93(m, 3H) 2.24-217(m, 3H) 5.81-5.83(m, 2H) 6.00(q, J=8.82, 6.32 Hz, 1 H) 6.57(d, J=1.77 Hz, 1H) 6.79-6.82(m, 1H) 6.98-7.03(m, 1H) 7,10(d, J=7.83 Hz, 1H) 7.45-7.52(m, 2H) 7.58(dd, J=8.84, 5.05 Hz, 1H) | 405 | 19 |
| I-596 | (400 MHz, DMSO-D6) d ppm 1.79(d, J=6.57 Hz, 3H) 3.61-3.63(m, 3H) 5.89-5.91(m, 2H) 5.97-6.03(m, 1H) 6.86(d, J~1.77 Hz, 1H) 7.06 (d, J=8.84 Hz, 1H) 7.15(d, 42.78 Hz, 1H) 7.29 (dd, J=8.84, 2.53 Hz, 1H) 7.49(t, 48.59 Hz, 1 H) 7.59(dd, J=9.09, 5.31 Hz, 1H) 7.63(d, J=1.77 Hz, 1H) | 441 | 19 |
| I-597 | (400 MHz, DMSO-D6) d ppm 1.83(d, 46.57 Hz, 3H) 5.98-6.00(m, 2H) 6.14-6.20(m, 1H) 6.98(d, J=1.77 Hz, 1H) 7.42-7.45(m, 2H) 7.47 (d, J=8.59 Hz, 1H) 7.55-7.60(m, 2H) 7.87(d, J=2.02 Hz, 1H) | 429 | 19 |
| I-598 | (400 MHz, DMSO-D6) d ppm 1.79(d, J=6.57 Hz, 3H) 3.59-3.60(m, 3H) 5.88.5.91(m, 2H) 6.00(q, J=6.82 Hz, 1H) 6.90(d, J=1.77 Hz, 1H) 6.99-7.10(m, 3H) 7.48(t, J=8.84 Hz, 1H) 7.59 (dd, J=9.09, 5.31 Hz, 1H) 7.64(d, 42.02 Hz, 1 H) | 425 | 19 |
| I-599 | (400 MHz, DMSO-D6) d ppm 1.20-1.25(m, 6 H) 1.83(d, J=6.57 Hz, 3H) 2.86-2.94(m, 1H) 5.88-5.91(m, 2H) 6.13(q, J=6.32 Hz, 1H) 6.89 (d, J=1.77 Hz, 1H) 7.11-7.15(m, 2H) 7.23-7.31(m, 2H) 7.47(t, J=8.59 Hz, 1H) 7.58(dd, J=8.84, 4.80 Hz, 1H) 7.83(d, J=2.02 Hz, 1H) | 419 | 19 |
| I-600 | (400 MHz, DMSO-D6) d ppm 1.83(d, J=6.57 Hz, 3H) 6.11-6.13(m, 2H) 6.17(q, J=6.57 Hz, 1H) 6.99(d, J=1.77 Hz, 1H) 7.46(t, J=8.84 Hz, 1H) 7.56(dd, J=9.09, 5.05 Hz, 1H) 7.68(d, J=1.77 Hz, 1H) 7.72(d, J=8.59 Hz, 1H) 7.80(dd, J=8.34, 1.77 Hz, 1H) 7.95(d, J=2.02 Hz, 1H) | 478.90 | 19 |
| I-601 | (400 MHz, DMSO-D6) d ppm 1.83(d, J=6.57 Hz, 3H) 6.13-6.22(m, 3H) 7.06(d, J=1.77 Hz, 1H) 7.45(t, J=8.59 Hz, 1H) 7.57(dd, J=9.09, 5.05 Hz, 1H) 7.63(d, J=8.59 Hz, 2H) 7.84(d, J=8.59 Hz, 2H) 7.97(d, J=1.77 Hz, 1H) | 402 | 19 |
| I-602 | (400 MHz, DMSO-D6) d ppm 1.82(d, J=6.62 Hz, 3H) 5.96-6.00(m, 2H) 6.17(q, J=6.57 Hz, 1H) 6.99(d, J=1.77 Hz, 1H) 7.22-7.27(m, 1H) 7.41-7.52(m, 3H) 7.58(dd, J=9.09, 5.05 Hz, 1H) 7.87(d, J=2.02 Hz, 1H) | 413 | 19 |
| I-603 | (400 MHz, DMSO-D6) d ppm 1.73(m, 1H) 1.80 (d, J=6.82 Hz, 3H) 1.84(m, 1H) 2.26(d, J=21.98 Hz, 2H) 2.53(m, 2H) 2.63(m, 2H) 3.40 (m, 2H) 3.60(m, 2H) 5.95(s, 2H) 6.14(d, | 517 | 20 |

TABLE 3-continued

| | | J=6.57 Hz, 1H) 6.99(s, 1H) 7.36(d, J=7.58 Hz, 2H) 7.44(m, 3H) 7.57(dd, J=8.97, 4.93 Hz, 1 H) 7.86(d, J=1.77 Hz, 1H) | | |
|---|---|---|---|---|
| I-604 | | (400 MHz, DMSO-D6) d ppm 1.61(t, J=6.19 Hz, 3H) 1.90(m, 2H) 2.96(m, 2H) 3.10(d, J=36.88 0.031 Hz, 2H) 3.45(m, 2H) 3.7(m, 2H) 5.96(s, 2H) 6.14(q, J=6.82 Hz, 1H) 6.99(d, J=1.52 Hz, 1H) 7.44(m, 5H) 7.56(dd, J=8.97, 4.93 Hz, 1H) 7.87(d, J=1.77 Hz, 1H) | 503 | 20/21 |
| I-605 | | (400 MHz, DMSO-D6) d ppm 1.80(d, J=6.57 Hz, 3H) 2.72(m, 4H) 3.36(m, 2H) 3.52(m, 2H) 5.96(s, 2H) 6.14(q, J=6.74 Hz, 1H) 6.99(d, J=1.77 Hz, 1H) 7.37(m, 2H) 7.44(m, 3H) 7.57(dd, J=8.97, 4.93 Hz, 1H) 7.87(d, J=1.77 Hz, 1 H) | 489 | 20/21 |
| I-606 | | (400 MHz, CHLOROFORM-D) d ppm 1.83(d, J=6.57 Hz, 3H) 4.84(s, 2H) 5.03(d, J=11.12 Hz, 1H) 5.38(d, J=17.43 Hz, 1H) 6.06(q, J=6.82 Hz, 1H) 6.49(dd, J=17.68, 10.86 Hz, 1 H) 6.90(d, J=1.77 Hz, 1H) 7.04(dd, J=8.84, 7.83 Hz, 1H) 7.29(dd, J=8.84, 4.80 Hz, 1H) 7.55(d, J=1.77 Hz, 1H) | 327 | 19 |
| I-607 | 0.058 | (400 MHz, DMSO-D6) d ppm 1.81(d, J=6.82 Hz, 3H) 3.28(m, 2H) 3.54(m, 2H) 3.97(d, J=4.04 Hz, 2H) 4.08(d, J=4.29 Hz, 2H) 5.10(br, 2H) 5.98(d, 2H) 7.00(d, J=1.77 Hz, 1H) 7.45(m, 3H) 7.48(m, 2H) 7.57(dd, J=8.97, 4.93 Hz, 1H) 7.88(d, J=1.77 Hz, 1H) | 506 | 20/21 |
| I-608 | 0% | (400 MHz, DMSO-D6) d ppm 1.34(m, 1H) 1.74 (d, J=5.94 Hz, 3H) 1.78(m, 1H) 2.08(m, 1H) 2.40(m, 2H) 2.54(m, 1H) 2.89(m, 1H) 3.33(s, 2H) 3.49(s, 2H) 5.52(s, 2H) 5.94(q, J=6.57 Hz, 1H) 6.68(s, 1H) 7.27(m, 5H) 7.36(m, 1H) 7.39(m, 1H) 7.48(m, 1H) | 489 | 23 |
| I-609 | 0.045 | (400 MHz, DMSO-D6) d ppm 1.80(d, J=6.57 Hz, 3H) 2.87(m, 1H) 3.43(m, 1H) 3.81(m, 2H) 0.045 4.74(m, 1H) 6.00(s, 2H) 6.13(q, J=6.48 Hz, 1 NH) 6.96(dd, J=6.57, 1.77 Hz, 1H) 7.45(m, 3H) 7.54(dd, J=8.97, 4.93 Hz, 1H) 7.87(m, 3H) | 475 | 20/21 |
| I-610 | 0.069 | (400 MHz, CHLOROFORM-D) d ppm 1.67(d, J=6.82 Hz, 3H) 2.72(s, 6H) 4.99(s, 2H) 6.12 (q, J=6.57 Hz, 1H) 6.99(d, J=1.77 Hz, 1H) 7.07 (m, 1H) 7.32(dd, J=8.84, 4.80 Hz, 1H) 7.50(m, 2H) 7.76(d, J=8.59 Hz, 2H) 7.91(d, J=1.77 Hz, 1H) | 484 | 29 |
| I-611 | | (400 MHz, MeOD) d ppm 1.72(d, J=6.57 Hz, 3 H) 3.69(s, 3H) 4.78(s, 2H) 6.13(q, J=6.57 Hz, 1H) 6.71(dd, J=8.84, 2.27 Hz, 1H) 6.88(d, J=2.02 Hz, 1H) 7.04(m, 1H) 7.26(m, 2H) 7.40 (d, J=1.77 Hz, 1H) 8.03(d, J=2.02 Hz, 1H) | 447 | 24 |
| I-612 | | (400 MHz, MeOD) d ppm 1.78(d, J=6.57 Hz, 3 H) 3.51(s, 3H) 3.75(s, 3H) 6.10(q, J=6.32 Hz, 1H) 6.90(m, 1H) 6.92(m, 1H) 7.13(m, 1H) 7.35(m, 2H) 7.60(d, J=7.33 Hz, 1H) | 461 | 24 |
| I-613 | | (400 MHz, MeOD) d ppm 1.63(m, 2H) 1.87(d, J=6.57 Hz, 3H) 2.66(m, 4H) 3.35(m, 2H) 3.40 (m, 2H) 6.20(q, J=6.65 Hz, 1H) 7.02(d, J=1.77 Hz, 1H) 7.20(t, J=8.59 Hz, 1H) 7.43(dd, J=8.97, 4.93 Hz, 1H) 7.54(d, J=8.34 Hz, 2H) 7.77(d, J=8.59 Hz, 2H) 7.81(d, J=1.26 Hz, 1H) | 553 | 29 |
| I-614 | | (400 MHz, DMSO-D6) d ppm 1.82(d, J=6.57 Hz, 3H) 3.92(s, 3H) 5.96(s, 2H) 6.17(q, J=6.48 Hz, 1H) 7.03(d, J=1.77 Hz, 1H) 7.35(dd, J=8.59, 1.26 Hz, 1H) 7.44(t, J=8.72 Hz, 1H) 7.56(m, 2H) 7.91(d, J=2.02 Hz, 1H) 8.03(d, J=8.59 Hz, 1H) | 475 | 26 |
| I-615 | | (400 MHz, CHLOROFORM-D) d ppm 1.84(d, J=6.82 Hz, 3H) 3.89(s, 3H) 4.76(s, 2H) 6.05 (q, J=6.57 Hz, 1H) 6.84(d, J=1.77 Hz, 1H) 7.03 (m, 1H) 7.28(dd, J=8.97, 4.93 Hz, 1H) 7.40(s, 1H) 7.53(s, 1H) 7.74(d, J=1.77 Hz, 1H) | 381 | 19 |
| I-616 | 3% | (400 MHz, DMSO-D6) d ppm 9.29(d, J=9.60 Hz, 1H) 8.63(d, J=10.86 Hz, 1H) 7.84-7.94(m, 2 H) 7.72(~ J=7.96 Hz, 3H) 7.47-7.57(m, 6H) (s, 1H) 5.97-6.05H) 337(s, 2H) 1.69(d, J=6.06 Hz, 3H) 1.15(s, 5H) 1.06(s, 1 H) | 500 | 33 |
| I-617 | 2% | (400 MHz, DMSO-D6) d ppm 9.26(s, 2H) 8.84 (s, 2H) 7.93(s, 2H) 7.84(d, J=1.52 Hz, 2H) 7.81(d, J=7.58 Hz, 2H) 7.66(s, 2H) 7.60(d, | 500 | 32 |

TABLE 3-continued

| | | | | |
|---|---|---|---|---|
| | | J=8.34 Hz, 5H) 7.53-7.59(m, 2H) 7.46(d, J=8.34 Hz, 4H) 6.01(q, J=6.32 Hz, 2H) 3.32(s, 4H) 3.03(s, 1H) 2.75(s, 1H) 1.61(d, J=6.32 Hz, 5H) 1.13(s, 7H) | | |
| I-618 | 0% | (400 MHz, DMSO-D6) d ppm 8.53(s, 2H) 8.33 (d, J=2.02 Hz, 2H) 7.84(d, J=2.02 Hz, 2H) 7.80 (d, J=8.34 Hz, 5H) 7.36-7.42(m, 12H) 5.93(s, 2H) 4.55(s, 1H) 3.73(s, 3H) 3.40(s, 6H) 1.19 (s, 10H) | 444 | 32 |
| I-619 | 16% | (400 MHz, DMSO-D8) d ppm 7.97(d, J=1.77 Hz, 1H) 7.79(s, 1H) 7.66-7.74(m, 3H) 7.48(d, J=1.77 Hz, 2H) 7.41(d, J=8.34 Hz, 2H) 7.24(s, 1H) 5.91(s, 1H) 5.40(s, 2H) 3.61(s, 1H) 2.61-2.70(m, 3H) 2.33(s, 1H) 2.17(s, 1H) 1.95-2.06(m, 1H) 1.47(s, 1H) 1.23(s, 7H) 1.00(s, 3 H) 0.80-0.92(m, 6H) | 504 | 32 |
| I-620 | 5% | (400 MHz, DMSO.D6) d ppm 8.02(s, 1H) 7.96 (s, 1H) 7.85(d, J=8.34 Hz, 2H) 7.51-7.62(m, 3 H) 7.23(t, J=8.08 Hz, 2H) 5.43(s, 2H) 4.09(s, 1 H) 3.37(s, 1H) 1.40(s, 9H) 1.14(d, J=2.27 Hz, 3H) 1.08(d, J=16.42 Hz, 3H) | 454 | 34 |
| I-621 | 6% | (400 MHz, DMSO-D6) d ppm 9.35(s, 1H) 8.70 (s, 1H) 7.96(s, 2H) 7.78(d, J=8.59 Hz, 4H) 7.55(d, J=8.08 Hz, 5H) 7.42(t, J=7.20 Hz, 2H) 7.35(t, J=7.33 Hz, 1H) 5.40(s, 2H) 3.39(s, 2H) 3.16(s, 1H) 1.20(s, 4H) | 418 | 34 |
| I-622 | 0.375 | (400 MHz, DMSO-D6) d ppm 7.95(d, J=1.77 Hz, 1H) 7.57(d, J=8.34 Hz, 2H) 7.52(s, 1H) 7.45 (d, J=8.08 Hz, 3H) 7.25(d, J=1.77 Hz, 1H) 6.11 (s, 1H) 5.95(s, 2H) 3.62(s, 1H) 3.49(s, 1H) 2.44(s, 2H) 2.41(d, J=7.07 Hz, 4H) 1.85(d, J=6.32 Hz, 3H) 1.06(t, J=7.20 Hz, 3H) | 502 | 4 |
| I-623 | 7% | (400 MHz, DMSO-D6) d ppm 7.91(d, J=2.02 Hz, 1H) 7.65(d, J=8.34 Hz, 2H) 7.53(d, J=7.33 Hz, 2H) 7.44(d, Jol.77 Hz, 1H) 7.37-7.42(m, 3H) 7.32(t, J=7.33 Hz, 1H) 5.94(s, 2H) 5.25(s, 2H) 3.60(s, 1H) 3.38(s, 1H) 2.30-2.41(m, 5H) 0.99(t, J=7.20 Hz, 3H) | 418 | 34 |
| I-624 | 0% | (400 MHz, DMSO-D6) d ppm 9.40(s, 1H) 8.77 (s, 1H) 7.98(d, J=1.52 Hz, 1H) 7.77-7.88(m, 4 H) 7.57(d, J=8.34 Hz, 2H) 7.53(d, J=7.33 Hz, 1 H) 7.21-7.31(m, 3H) 5.37(s, 2H) 3.39(s, 2H) 2.37(s, 3H) 1.20(s, 4H) | 432 | 34 |
| I-625 | 6% | (400 MHz, DMSO-D6) d ppm 9.78(s, 1H) 8.12 (s, 1H) 7.92-7.98(m, 2H) 7.88(d, J=7.58 Hz, 1 H) 7.74-7.83(m, 3H) 7.59(t, J=7.71 Hz, 2H) 7.48(d, J=8.34 Hz, 2H) 5.47(s, 2H) 3.86(s, 3 H) 3.50(s, 2H) 3.41(s, 1H) 3.10(s, 2H) 2.00 (s, 3H) 1.85(s, 2H) 1.53(s, 2H) | 516 | 6 |
| I-626 | 0% | (400 MHz, DMSO-D6) d ppm 9.31(s, 2H) 8.67 (s, 2H) 8.12(s, 2H) 7.92-7.99(m, 4H) 7.88(d, J=7.83 Hz, 2H) 7.75-7.84(m, 6H) 7.53-7.63 (m, 6H) 5.48(s, 4H) 3.81-3.91(m, 6H) 3.39 (s,4H) 3.13(s, 1H) 1.20(s, 7H) | 476 | 34 |
| I-627 | 6% | (400 MHz, DMSO-D6) d ppm 9.91(s, 1H) 7.95 (d, J=1.52 Hz, 1H) 7.85(s, 1H) 7.80(d, J=8.34 Hz, 2H) 7.53(d, J=7.07 Hz, 1H) 7.49(d, J=8.34 Hz, 2H) 7.21-7.31(m, 3H) 5.36(s, 2H) 4.56 (s, 1H) 3.68(s, 1H) 3.51(s, 2H) 3.41(s, 1H) 3.10(s, 3H) 2.82(s, 1H) 2.37(s, 3H) 1.99(s, 3 H) 1.79-1.90(m, 2H) 1.56(s, 2H) | 472 | 6 |
| I-628 | 7% | (400 MHz, DMSO-D6) d ppm 7.90(d, J=1.52 Hz, 1H) 7.79(d, J=8.34 Hz,3H)7.66CS, 1H)7.44-7.55(m, 2H) 4.03(d, J=6.06 Hz, 2H) 3.83(s, 1 H) 3.67(s, 1H) 3.51(s, 2H) 3.39(s, 1H) 3.09 (s, 2H) 2.62(s, 1H) 2.14(s, 2H) 1.99(s, 3H) 1.79-1.91(m, 5H) 1.84-1.76(m, 3H) 1.54(s, 2H) 1.20-1.30(m, 2H) 1.07(d, J=11.62 Hz, 2 H) | 464 | 6 |
| I-629 | 7% | (400 MHz, DMSO-D6) d ppm 9.76(s, 1H) 8.51 (t, J=5.56 Hz, 1H) 7.86(d, J=1.52 Hz, 2H) 7.79 (d, J=8.34 Hz, 2H) 7.63(dd, J=14.40, 8.34 Hz, 5 H) 7.45(d, J=8.34 Hz, 2H) 7.04(t, J.7.96 Hz, 1 H) 6.55-6.65(m, 3H) 6.00(d, J=6.32 Hz, 1H) 3.49(s, 2H) 3.34-3.45(m, 3H) 3.09(s, 3H) 2.75(s, 1H) 2.65-2.74(m, 2H) 2.13(s, 1H) 1.99(s, 3H) 1.78-1.89(m, 2H) 1.65(d, J=6.32 Hz, 3H) 1.52(s, 2H) | 635 | 6 |
| I-630 | 3% | (400 MHz, DMSO-D6) d ppm 9.80(s, 1H) 8.62 (1, J=5.81 Hz, 1H) 7.85(d, J=1.26 Hz, 1H) 7.78 | 688 | 6 |

| | | | | |
|---|---|---|---|---|
| | | | (d, J=8.34 Hz, 3H) 7.62(dd, J=12.63, 8.34 Hz, 5 H) 7.39-7.49(m, 4H) 7.21-7.30(m, 1H) 5.98 (d, J=6.32 Hz, 1H) 3.65(s, 1H) 3.40-3.51(m, J=6.63, 6.63, 6.63, 6.63 Hz, 4H) 3.03-3.15(m, 5H) 2.82(s, 1H) 2.13(s, 1H) 1.98(s, 3H) 1.78-1.89(m, 2H) 1.65(d, J=6.06 Hz, 3H) 1.53(s, 2 H) | | |
| I-631 | 3% | (400 MHz, DMSO-D6) d ppm 7.75-7.82(m, 2H) 7.56-7.67(m, 4H) 7.39-7.49(m, 6H) 4.27(d, J=4.80 Hz, 2H) 3.92(s, 1H) 3.49(s, 2H) 3.37 (s, 2H) 3.07(s, 3H) 2.12(s, 1H) 1.92-2.04(m, 4H) 1.79-1.91(m, 2H) 1.71(d, J=11.87 Hz, 1 H) 1.59-1.68(m, 3H) 1.51(s, 2H) | 688 | 4 |
| I-632 | 0% | (400 MHz, DMSO-D6) d ppm 8.39(s, 1H) 7.77-7.85(m, 3H) 7.61(t, J=8.08 Hz, 6H) 7.43(d, J=8.34 Hz, 2H) 5.96(s, 1H) 3.69(s, 2H) 3.49 (s, 3H) 3.39(s;2H) 3.30(t, J=6.95 Hz, 3H) 3.14-3.22(m, 4H) 3.09(s, 3H) 2.18(t, J=8.08 Hz, 2 H) 2.00(s, 3H) 1.86(ddd, J=15.28, 7.58, 7.45 Hz, 4H) 1.65(t, J=6.06 Hz, 5H) 1.52(s, 2H) | 640 | 6 |
| I-633 | 0.0472 | (400 MHz, DMSO-D6) d ppm 9.65(s, 1H) 7.91 (d, J=1.77 Hz, 1H) 7.58(dd, J=8.97, 4.93 Hz, 1 H) 7.50-7.55(m, 4H) 7.44-7.50(m, 1H) 7.13 (d, J=1.52 Hz, 1H) 6.27(q, J=6.57 Hz, 1H) 3.48 (s, 2H) 3.15(q, J=7.07 Hz, 3H) 3.06(s, 2H) 1.84(d, J=6.57 Hz, 3H) 1.22(t, J=37.33 Hz, 3H) | 518 | 6 |
| I-634 | 10% | (400 MHz, DMSO-D6) d ppm 9.29(s, 2H) 8.66 (s, 2H) 7.91-8.00(m, 5H) 7.85(d, J=6.82 Hz, 5 H) 7.54-7.61(m, 10H) 7.48-7.53(m, 3H) 5.48 (s, 5H) 4.61(s, 1H) 1.21(d, J=4.55 Hz, 9H) 1.15(s, 8H) | 466 | 34 |
| I-635 | 0.0554 | (400 MHz, DMSO-D6) d ppm 8.14(d, J=3.54 Hz, 3H) 7.87(s, 1H) 7.58(dd, J=8.97, 4.93 Hz, 1H) 7.44-7.53(m, 8H) 7.12(s, 1H) 6.25(s, 1H) 3.95(d, J=11.87 Hz, 1H) 3.69(s, 2H) 1.96(d, J=13.39 Hz, 2H) 1.84(s,J=6.57 Hz, 3H) | 502 | 35 |
| I-636 | 0.109 | (400 MHz, DMSO-D6) d ppm 8.20(s, J=2.27 Hz, 1H) 7.83(d, J=1.77 Hz, 1H) 7.79(ss, J=8.59, 2.53 Hz, 1H) 7.61(ss, J=8.97, 4.93 Hz, 1H) 0.109 7.49(1J=8.84 Hz, 1H) 6.98(s, J=1.77 Hz, 1H) 6.88(d, J=8.59 Hz, 1H) 6.18(q, J=8.82 Hz, 1H) 5.92(s, 2H) 4.41(t, J=5.81 Hz, 2H) 3.61(m, 4 H) 2.72(t, J=5.81 Hz, 2H) 2.47-2.52(m, 4H) 1.85(s, J=6.57 Hz, 3H) | 507 | 36 |
| I-637 | 0.692 | (400 MHz, DMSO-D6) d ppm 7.42-7.52(m, 2H) 7.25-7.35(m, 2H) 7.22(1. J=8.72 Hz, 1H) 6.64 (d, J=1.52 Hz, 1H) 6.19(s, J=9.35 Hz, 1H) 5.89 (q, J=6.74 Hz, 1H) 5.58(s, 2H) 3.72-3.84(m, 2 H) 2.42-2.53(m, 2H) 1.57(s, J=6.57 Hz, 3H) 1.39-1.50(m, 4H) | 491 | 35 |
| I-638 | 0.094 | (400 MHz, DMSO-D6) d ppm 7.98{6, J=2.53 Hz, 1H) 7.62{6. J=2.02 Hz, 1H) 7.57{66, J=8.59, 2.53 Hz, 1H) 7.40(dd, J=8.97, 4.93 Hz, 1H) 7.27(t, J=8.72 Hz, 1H) 6.77(d, J=1.77 Hz, 1H) 6.66(d, J=8.59 Hz, 1H) 5.97(q, J=6.57 Hz, 1H) 5.70(s, 2H) 4.17(t, J=5.81 Hz, 2H) 2.56-2.65 (m, 2H) 1.63{6, J=6.82 Hz, 3H) 1.46-1.54(m, 4H) 0.97-1.09(m, 1H) | 491 | 35 |
| I-639 | 0.513 | (400 MHz, DMSO-D6) d ppm 7.71(dd, J=9.60, 1.77 Hz, 2H) 7.46-7.56(m, 2H) 7.42(t, J=8.72 Hz, 1H) 6.84(s, 1H) 6.39(d, J=9.35 Hz, 1H) 6.10(q, J=6.57 Hz, 1H) 5.79(s, 2H) 3.98-4.08 (m, 4H) 3.81-3.92(m, 2H) 2.65-2.92(m, 2H) 2.14-2.18(m, 7H) 1.93-2.05(m, 5H) 1.84-1.89(m, 2H) 1.76-1.82(m, 4H) 1.52-1.63(m, 6H) 1.26-1.38(m, 2H) 1.08-1.18(m, 6H) | 505 | 3 |
| I-640 | | (400 MHz, MeOD) d ppm 7.62(d; J=1.52 Hz, 1 H) 7.25-7.31(m, 2H) 7.19-7.25(m, 2H) 6.73 (s, 2H) 6.65(d, J=1.77 Hz, 1H) 5.65(q, J=6.57 Hz, 1H) 4.46-4.57(m, 1H) 3.61-3.73(m, 1H) 2.96-3.07(m, 1H) 2.73-2.84(m, 1H) 2.50-2.59(m, 4H) 2.23-2.31(m, 7H) 2.10(s, 3H) 1.92-2.04(m, 1H) 1.77-1.88(m, 1H)1.69-1.76(m, 4H) 1.66{6, J=6.82 Hz, 3H) 1.29-1.40 (m, 2H) | 513 | 6 |
| I-641 | | (400 MHz, MeOD) d ppm 7.66{6, J=2.02 Hz, 1 H) 7.28-7.39(m, 4H) 7.12-7.23(m, 2H) 7.07 (d, J=1.77 Hz, 1H) 6.92-7.02(m, 1H) 5.97(q, J=6.06 Hz, 1H) 4.44-4.56(m, 1H) 3.62-3.74 (m, 1H) 2.96-3.08(m, 1H) 2.72-2.84(m, 1H) | 523 | 6 |

TABLE 3-continued

| | | | | |
|---|---|---|---|---|
| | | 2.48-2.59(m, 4H) 2.20-2.31(m, 1H) 1.91-2.02(m, 1H) 1.78-1.69(m, 1H) 1.66-1.77(m, 8H) 1.28-1.40(m, 2H) | | |
| I-642 | | (400 MHz, DMSO-D6) d ppm 7.61(d, J=1.77 Hz, 1H) 7.38{66, J=8.97, 4.93 Hz, 1H) 7.20-7.29 (m, 3H) 6.99-7.07(m, 2H) 6.76(d, J=1.77 Hz, 1H) 5.95(q, J=6.65 Hz, 1H) 5.70(s, 2H) 1.62 (d, J=6.57 Hz, 3H) | 395 | 1 |
| I-643 | 0.0432 | (500 MHz, DMSO-D6) d ppm 7.73(s, 1H) 7.73-7.46(m, 5H) 7.09(d, J=1.55 Hz, 1H) 6.42(d, J=9.5 Hz, 1H) 6.29(q, J=6.65 Hz, 1H) 1.84(d, J=6.60 Hz, 3H) | 394 | 3 |
| I-644 | 0.1958 | (300 MHz, CDCl3-D1) d ppm 8.54(d, 2H) 7.80 (m, 2H) 7.33(m, 1H) 7.08(m, 1H) 6.93(s, 1H) 6.12(q, J=6.7 Hz, 1H) 5.041(br s, 2H) 1.88 (d, J=6.7 Hz, 3H) | 458 [M + 2] | 3 |
| I-645 | 0.1572 | (300 MHz, CDCl3-D1) d ppm 7.83(d, J=1.87 Hz, 1H) 7.28(m, 4H) 7.04(m, 1H) 6.98(d, J= 1.76 Hz, 1H) 6.75(m, 2H) 8.11(q, J=6.7 Hz, 1 H) 4.76(br. s, 2H) 2.97(s, 6H) 1.85(d, J=6.7 Hz, 3H) | 420 | 3 |
| I-646 | 0.099 | (300 MHz, CDCl3-D1) d ppm 8.10(s, 1H) 7.77 (s, 1H) 7.50(m, 1H) 7.30(m, 1H) 7.09(m, 2H) 6.92(m, 1H) 6.06(q, J=6.7 Hz, 1H) 4.91(br, s, 2H) 3.87(s, 3H) 1.83(d, J=6.7 Hz, 3H) | MS 408 m/z | 3 |
| I-647 | 0.1664 | (300 MHz, CDCl3-D1) d ppm 8.21(s, 1H) 7.93 (m, 1H) 7.64(m, 1H) 7.43(m, 1H) 7.32-7.21 (m, 3H) 7.09-7.024(m, 2H) 6.58(m, 1H) 6.16 (m, 1H) 4.80(s, 2H) 3.50(s, 2H) 1.87(d, J=6.69 Hz, 3H) | 416 | 3 |
| I-648 | 0.5533 | (300 MHz, CDCl3-D1) d ppm 7.87(s, 1H) 7.42 (m, 4H) 7.30(m, 3H) 7.16(m, 1H) 7.05(s, 1H) 5.92(m, 1H) 4.97(s, 2H) 4.61(br, s, 2H) 3.65 (br, s, 2H) 2.85(br, s, 3H) 2.49(br, s, 1H) 2.41 (m, 3H) 2.19(m, 1H) 1.08(m, 6H) | 513 | 1 |
| I-649 | 29% | (400 MHz, DMSO-D6) d ppm 7.92(d, S1.77 Hz, 1H) 7.68(d, J=8.34 Hz, 2H) 7.53(d, J=7.07 Hz, 2H) 7.37-7.46(m, 5H) 7.33(m, 1H) 5.96(s, 2 H) 5.25(s, 2H) 3.49(s, 2H) 3.09(s, 2H) 2.00 (s, 2H)1.84(s, 2H)1.56(s, 1H) | 457 | 1 |
| I-650 | 0.3627 | (300 MHz, CDCl3-D1) d ppm 8.25(d, J=1.79 Hz, 1H) 7.76(d, J=3.30 Hz) 7.36-7.26(m, 3H) 7.20(m, 1H) 7.05(m, 1H) 6.17(q, J=6.7 Hz, 1 H) 5.09(br, s, 2H) 1.86(d, J=6.7 Hz, 3H) | 384 | 37 |
| I-651 | 1.5258 | (400 MHz, DMSO-D6) d ppm 7.93(d, J=1.52 Hz, 1H) 7.74-7.82(m, 3H) 7.71 m, 3H) 7.62-7.67 (m, 3H) 7.47(m, 4H) 7.38(m, 1H) 5.43(s, 2H) 3.67(br, s, 2H) 3.51(br, s, 3H) 3.40(br, s, 1H) 3.09(br, s, 2H) 2.00(br, s, 3H) 1.83(br, s, 2H) 1.53(br, s, 2H) | 533 | 6 |
| I-652 | 11% | (300 MHz, CDCl3-D1) d ppm 7.90(d, J=1.67 Hz, 1H) 7.30(m, 2H) 7.05(m, 3H) 6.91(d, J= 0.98 Hz, 1H) 6.10(q, J=6.7 Hz, 1H) 4.99(br, s, 2H) 3.57(s, 3H) 1.83(d, J=6.7 Hz, 3H) | 381 | 38 |
| I-653 | 2% | (400 MHz, DMSO-D6) d ppm 7.92(s, 1H) 7.90 (s, 1H).7.84(d, J=8.34 Hz, 2H) 7.50(d, J=8.34 Hz, 2H) 6.92(s, 2H) 5.27(s, 2H) 3.51(br, s, 8 H) 3.09(br, s, 3H) 2.32(s, 6H) 2.25(s, 3H) 1.99(br, s, 2H) 1.84(br, s, 2H) 1.55(br, s, 2H) | 499 | 6 |
| I-654 | 9% | (400 MHz, DMSO-D6) d ppm 9.75(s, 1H) 7.88 (s, 2H) 7.79(d, J=6.34 Hz, 2H) 7.45(d, J=8.08 Hz, 3H) 6.97(s, 1H) 5.28(s, 2H) 3.64(s, 1H) 3.45(s, 2H) 3.34(s, 1H) 3.04(s, 3H) 2.15(s, 12H) 1.94(s, 3H) 1.79(s, 2H) 1.50(s, 2H) | 513 | 6 |
| I-655 | | (400 MHz, DMSO-D6) d ppm 7.83(d, J=2.02 Hz, 1H) 7.48(d, J=8.34 Hz, 3H) 7.33(d, J=8.34 Hz, 3H) 7.24(d, J=1.77 Hz, 1H) 7.12-7.22(m, 2H) 5.86(m, 1H) 5.76(s, 2H) 4.19(br, s, 1H) 3.55 (br, s, 1H) 2.96(br, s, 2H) 2.16(br, s, 1H) 1.83 (br, s, 2H) 1.69(br, s, 5H) 1.60(d, J=5.67 Hz, 5 H) 1.30(br, s, 2H) | 525 | 6 |
| I-656 | | (400 MHz, DMSO-D6) d ppm 7.89(d, J=1.77 Hz, 1H) 7.57-7.66(m, 3H) 7.41-7.49(m, 2H) 7.36(d, J=8.08 Hz, 2H) 7.19(d, J=1.77 Hz, 1H) 5.85(s, 2H) 5.80(s, 1H) 4.21(s, 1H) 3.57(br. s, 1H) 3.02(s, 2H) 2.22(s, 1H) 1.80(br, s, 2H) 1.78(d, J=6.3 Hz, 3H) 1.66(s, 4H) 1.34(s, 2H) | 557 | 6 |

TABLE 3-continued

| | | | | |
|---|---|---|---|---|
| | I-657 | (400 MHz, DMSO-D6) d ppm 8.82(br, s, 1H) 7.97(d, J=1.77 Hz, 1H) 7.52-7.57(m, 1H) 7.46(t, J=8.72 Hz, 1H) 7.05(d, J=1.26 Hz, 1H) 6.73(br, s, 1H) 6.06(quart, J=6.57 Hz, 1H) 2.91(s, 3H) 1.78(d, J=6.57 Hz, 3H) | 357 | 39 |
| | I-658 | (400 MHz, DMSO-D6) d ppm 9.07(br, s, 1H) 7.94(d, J=1.52 Hz, 1H) 7.53(m, 1H) 7.47(m, 1 H) 6.97(s, 1H) 6.77(br. s, 1H) 6.06(s, 1H) 3.55(quart, J=4.29 Hz, 2H) 3.54(m, 2H) 3.47 (m, 2H) 2.54(t, J=6.06 Hz, 2H) 2.42(s, 3H) 1.78(d, J=6.82 Hz, 3H) | 456 | 39 |
| | I-659 | (400 MHz, DMSO-D6) d ppm 9.84(s, 1H) 7.91 (d, J=1.52 Hz, 1H) 7.78-7.88(m, 1H) 7.65-7.75(m, 3H) 7.57(dd, J=10.23, 3.66 Hz, 1H) 7.46(d, J=8.34 Hz, 2H) 5.91-5.98(m, 1H) 3.50 (s, 2H) 3.40(s, 1H) 3.09(s, 2H) 2.09(dt, J=14.08, 6.98 Hz, 2H) 1.99(s, 2H) 1.92(dt, J=13.90, 6.95 Hz, 2H) 1.83(s, 2H) 1.55(s, 2H) 0.92(1, J=7.33 Hz, 3H) | 540 | 6 |
| | I-660 | NMR(400 MHz, DMSO-D6) d ppm 9.84(s, 1H) 7.95(s, 2H) 7.65(d, J=8.34 Hz, 2H) 7.53-7.60 (m, 2H) 7.48(s, 1H) 7.32-7.42(m, 2H) 6.25 (q, J=6.48 Hz, 1H) 3.58(s, 2H) 3.49(s, 1H) 3.18(d, J=5.05 Hz, 3H) 2.27(d, J=1.52 Hz, 5H) 2.01-2.13(m, 4H) 1.89(d, J=6.57 Hz, 5H) 1.64 (s, 2H) | 539 | 6 |
| | I-661 | (400 MHz, DMSO-D6) d ppm 10.14(s, 1H) 8.12 (s, 1H) 7.93(s, 1H) 7.76-7.87(m, 4H) 7.72(s, 1H) 7.65(d, J=8.34 Hz, 2H) 7.53(ddd, J=15.92, 7.83, 7.58 Hz, 2H) 7.40-7.47(m, 3H) 6.03-6.10(m, 1H) 4.55(s, 1H) 3.64(s, 1H) 3.47(s, 2 H) 3.38(s, 1H) 3.07(s, 3H) 2.13(s, 1H) 1.98 (s, 3H) 1.78-1.89(m, 3H) 1.65(t, J=5.68 Hz, 3 H) 1.56(s, 2H) 1.31(d, J=6.57 Hz, 2H) | 516 | 6 |

TABLE 4

| No. | Structure | (μM) | Met IC$_{50}$ Procedure | $^1$H-NMR (M + 1) | MS m/z |
|---|---|---|---|---|---|
| II-1 | 4-[5-Amino-6-(2,6-dichloro-benzyloxy)-pyrazin-2-yl]-phenol | 1.35 | see examples | (400 MHz, DMSO-d$_6$) δ 5.61 (s, 2H), 6.09 (s, 2H), 6.79 (d, 2H), 7.45 (t, 1H), 2.56 (d, 2H), 7.76 (d, 2H), 7.99 (s, 1H), 9.46 (s, 1H) | 362 |
| II-2 | 3-(2,6-Dichloro-benzyloxy)-5-[4-(1,1-dioxo-1λ$^6$-isothiazolidin-2-yl)-phenyl]-pyrazin-2-ylamine | 0.825 | see examples | (400 MHz, DMSO-d$_6$) δ 2.41 (m, 2H), 3.51 (m, 2H), 3.76 (m, 2H), 5.62 (s, 2H), 6.28 (s, 2H), 7.22 (m, 2H), 7.48 (m, 1H), 7.56 (m, 2H), 7.94 (m, 2H), 6.14 (s, 1H) | 465 |

TABLE 4-continued

| No. | Structure | (μM) | Met IC$_{50}$ Procedure | $^1$H-NMR (M + 1) | MS m/z |
|---|---|---|---|---|---|
| II-3 | 3-(2,6-Dichloro-benzyloxy)-5-[3-(2-morpholin-4-yl-ethoxy)-phenyl]-pyrazin-2-ylamine | 0.74 | see examples | (400 MHz, DMSO-d$_6$) δ 2.45 (m, 4H), 2.71 (t, 2H), 3.56 (t, 4H), 4.15 (t, 2H), 5.61 (s, 2H), 6.32 (s, 2H), 6.86 (d, 1H), 7.29 (t, 1H), 7.46 (m, 2H), 7.52 (m, 1H), 7.55 (s, 1H), 7.57 (d, 1H), 8.16 (s, 1H) | 475 |
| II-4 | 3-(2,6-Dichloro-benzyloxy)-5-[4-(2-morpholin-4-yl-ethoxy)-phenyl]-pyrazin-2-ylamine | 1.25 | see examples | (400 MHz, DMSO-d$_6$) δ 2.45 (m, 4H), 2.71 (m, 2H), 3.59 (t, 4H), 4.11 (t, 2H), 5.64 (s, 2H), 6.18 (s, 2H), 6.97 (d, 2H), 7.46 (t, 1H), 7.56 (d, 2H), 7.86 (d, 2H), 6.06 (s, 1H) | 475 |

TABLE 4-continued

| No. | Structure | (µM) | Met IC₅₀ Procedure | ¹H-NMR | (M + 1) | MS m/z |
|---|---|---|---|---|---|---|
| II-5 | 5-(4-Amino-phenyl)-3-(2,6-dichloro-benzyloxy)-pyrazin-2-ylamine | 0.94 | see examples | (400 MHz, DMSO-d₆) δ 5.19 (s, 2H), 5.59 (s, 2H), 5.96 (s, 2H), 6.60 (d, 2H), 7.45 (t, 1H), 7.56 (d, 2H0, 7.62 (d, 2H), 7.91 (s, 1H) | | 361 |
| II-6 | 4-[5-Amino-6-(2,6-dichloro-benzyloxy-pyrazin-2-yl]-benzoic acid | 1.75 | see examples | (400 MHz, DMSO-d₆) δ 5.64 (s, 2H), 6.52 (s, 2H), 7.46 (m, 1H), 7.56 (m, 2H), 7.96 (d, 2H), 8.07 (d, 2H), 8.27 (s, 1H) | | 390 |

TABLE 4-continued

| No. | Structure | (µM) | Met IC₅₀ Procedure | ¹H-NMR | MS m/z (M + 1) |
|---|---|---|---|---|---|
| II-7 | {4-[5-Amino-6-(2,6-dichloro-benzyloxy)-pyrazin-2-yl]-phenyl}-[(2R)-2-pyrrolidin-1-ylmethyl-pyrrolidin-1-yl]-methanone | 0.24 | see examples | (400 MHz, DMSO-d₆) δ 1.79 (m, 10H), 2.64 (m, 4H), 3.45 (m, 3H), 5.64 (s, 2H), 6.42 (s, 2H), 7.49 (m, 3H), 7.58 (m, 2H), 7.98 (d, 2H), 8.00 (s, 1H) | 526 |
| II-8 | {4-[5-Amino-6-(2,6-dichloro-benzyloxy)-pyrazin-2-yl]-phenyl}-(4-pyrrolin-1-yl-piperidin-1-yl)-methanone | 0.56 | see examples | (400 MHz, DMSO-d₆) δ 1.37 (m, 2H), 1.66 (m, 4H), 1.85 (m, 2H), 2.32 (m, 2H), 2.52 (m, 4H), 3.04 (m, 2H), 3.92 (m, 1H), 5.62 (s, 2H), 6.42 (s, 2H), 7.40 (d, 2H), 7.46 (t, 1H), 7.58 (m, 2H), 8.00 (d, 2H), 8.21 (s, 1H) | 526 |

TABLE 4-continued

| No. | Structure | (μM) | Met IC50 Procedure | 1H-NMR | MS m/z (M + 1) |
|---|---|---|---|---|---|
| II-9 | 2-Morpholin-4-yl-ethanesulfonic acid {4-[5-amino-6-(2-chloro-3,6-difluoro-benzyloxy)-pyrazin-2-yl]-phenyl}-amide | 1.26 | see examples | (300 MHz, CDCl₃) δ 2.50 (t, 4H), 2.92 (t, 2H), 3.29 (t, 2H), 3.72 (t, 2H), 4.81 (s, 2H), 5.67 (d, 2H), 7.05 (m, 1H), 7.20 (m, 1H), 7.28 (d, 2H), 7.90 (d, 2H), 8.04 (s, 1H) | 540 |
| II-10 | 2-Piperidin-1-yl-ethanesulfonic acid {4-[5-amino-6-(2-chloro-3,6-difluoro-benzyloxy)-pyrazin-2-yl]-phenyl}-amide | 1.2 | see examples | (300 MHz, CDCl₃) δ 1.60 (m, 2H), 1.63 (m, 4H), 2.49 (m, 4H), 2.90 (t, 2H), 3.26 (t, 2H), 4.85 (s, 2H), 5.67 (d, 2H), 7.05 (m, 1H), 7.20 (m, 1H), 7.29 (d, 2H), 7.89 (d, 2H), 8.04 (s, 1H) | 538 |

TABLE 4-continued

| No. | Structure | (µM) | Met IC$_{50}$ Procedure | $^1$H-NMR | MS m/z (M + 1) |
|---|---|---|---|---|---|
| II-11 | 2-(4-Hydroxy-piperidin-1-yl)-ethanesulfonic acid {4-[5-amino-6-(2-chloro-3,6-difluoro-benzyloxy)-pyrazin-2-yl]-phenyl}-amide | 0.65 | see examples | (300 MHz, CDCl$_3$) δ 1.63 (m, 2H), 1.90 (m, 2H), 2.27 (t, 2H), 2.80 (m, 2H), 2.92 (t, 2H), 4.86 (s, 2H), 5.67 (d, 2H), 7.05 (m, 1H), 7.20 (m, 1H), 7.28 (d, 2H), 7.90 (d, 2H), 8.04 (s, 1H) | 554 |
| II-12 | 2-Pyrrolidin-1-yl-ethanesulfonic acid {4-[5-amino-6-(2-chloro-3,6-difluoro-benzyloxy)-pyrazin-2-yl]-phenyl}-amide | 0.58 | see examples | (300 MHz, CDCl$_3$) δ 1.83 (m, 4H), 2.56 (m, 4H), 3.04 (t, 2H), 3.28 (q, 2H), 4.91 (s, 2H), 5.67 (d, 2H), 7.05 (m, 1H), 7.20 (m, 1H), 7.27 (d, 2H), 7.88 (d, 2H), 8.03 (s, 1H) | 524 |

TABLE 4-continued

| No. | Structure | (μM) Met IC$_{50}$ Procedure | $^1$H-NMR | MS m/z (M + 1) |
|---|---|---|---|---|
| II-13 | 2-[(3R)-3-Hydroxy-pyrrolidin-1-yl]-ethanesulfonic acid {4-[5-amino-6-(2-chloro-3,6-difluoro-benzyloxy)-pyrazin-2-yl]-phenyl}-amide | 1.59 see examples | (300 MHz, CDCl$_3$) δ 1.85 (m, 1H), 2.25 (m, 2H), 2.55 (m, 1H), 2.84 (d, 1H), 3.02 (m, 3H), 3.26 (m, 2H), 4.43 (m, 1H), 4.82 (s, 2H), 5.67 (d, 2H), 7.05 (m, 1H), 7.20 (m, 1H), 7.35 (d, 2H), 7.88 (d, 2H), 8.04 (s, 1H) | 540 |
| II-14 | 2-[(2S)-2-Hydroxymethyl-pyrrolidin-1-yl]-ethanesulfonic acid {4-[5-amino-6-(2-chloro-3,6-difluoro-benzyloxy)-pyrazin-2-yl]-phenyl}-amide | 1.78 see examples | (300 MHz, CDCl$_3$) δ 1.85 (m, 4H), 2.20 (m, 1H), 2.70 (m, 2H), 3.05 (m, 2H), 3.30–3.70m, 3H), 3.95 (m, 1H), 4.79 (s, 2H), 5.67 (d, 2H), 7.05 (m, 1H), 7.20 (m, 1H), 7.32 (d, 2H), 7.88 (d, 2H), 6.05 (s, 1H) | 554 |

TABLE 4-continued

| No. | Structure | (µM) | Met IC$_{50}$ Procedure | $^1$H-NMR | $^1$H-NMR (M + 1) | MS m/z |
|---|---|---|---|---|---|---|
| II-15 | 2-(Cyclopropylmethyl-amino)-ethanesulfonic acid {4-[5-amino-6-(2-chloro-3,6-difluoro-benzyloxy)-pyrazin-2-yl]-phenyl}-amide | 1.28 | see examples | | $^1$H NMR (300 MHz, CDCl$_3$) δ 0.14 (m, 2H), 0.52 (m, 2H), 0.95 (m, 1H), 2.50 (d, 2H), 3.21(m, 4H), 4.86 (s, 2H), 5.67 (d, 2H), 7.05 (m, 1H), 7.20 (m, 1H), 7.30 (d, 2H), 7.89 (d, 2H), 8.04 (s, 1H) | 524 |
| II-16 | 2-Dimethylamino-ethanesulfonic acid {4-[5-amino-6-(2-chloro-3,6-difluoro-benzyloxy)-pyrazin-2-yl]-phenyl}-amide | 0.91 | see examples | | (300 MHz, CDCl$_3$) δ 2.30 (s, 6H), 2.86 (t, 2H), 3.21 (t, 2H), 4.83 (s, 2H), 5.67 (d, 2H), 7.05 (m, 1H), 7.18 (m, 1H), 7.28 (d, 2H), 7.88 (d, 2H), 8.05 (s, 1H) | 498 |

TABLE 4-continued

| No. | Structure | (μM) Met IC$_{50}$ Procedure | $^1$H-NMR | MS m/z (M + 1) |
|---|---|---|---|---|
| II-17 | 2-Diethylamino-ethanesulfonic acid {4-[5-amino-6-(2-chloro-3,6-difluoro-benzyloxy)-pyrazin-2-yl]-phenyl}-amide 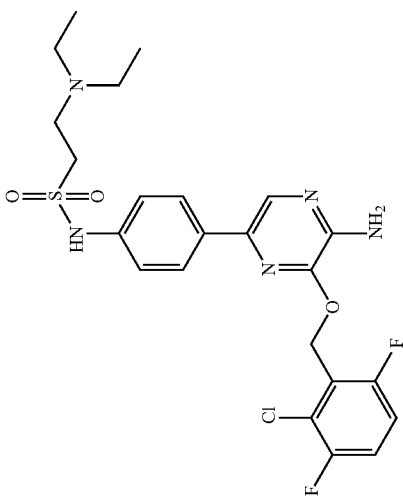 | 0.46 see examples | (300 MHz, CDCl$_3$) δ 1.08 (t, 6H), 2.61 (q, 4H), 3.03 (t, 2H), 3.23 (t, 2H), 4.80 (s, 2H), 5.67 (d, 2H), 7.05 (m, 1H), 7.19 (m, 1H), 7.27 (d, 2H), 7.88 (d, 2H), 8.04 (s, 1H) | 526 |
| II-18 | 2-(4-Acetyl-piperazin-1-yl)-ethanesulfonic acid {4-[5-amino-6-(2-chloro-3,6-difluoro-benzyloxy)-pyrazin-2-yl]-phenyl}-amide 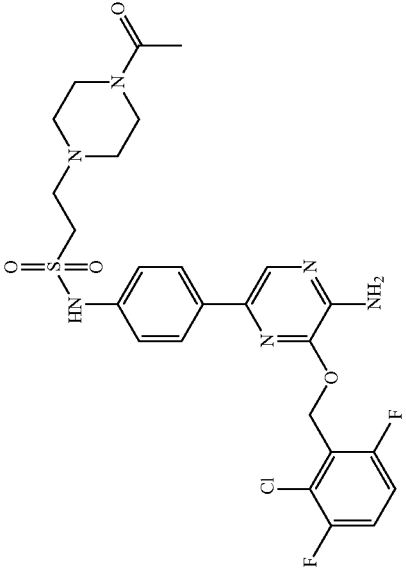 | 1.5 see examples | (300 MHz, CDCl$_3$) δ 2.08 (s, 3H), 2.46 (m, 4H), 2.93 (t, 2H), 3.30 (t, 2H), 3.47 (t, 2H), 3.62 (t, 2H), 4.82 (s, 2H), 5.67 (s, 2H), 7.05 (m, 1H), 7.20 (m, 1H), 7.28 (d, 2H), 7.91 (d, 2H), 8.05 (s, 1H) | 581 |

TABLE 4-continued

| No. | Structure | (µM) | Met IC$_{50}$ Procedure | $^1$H-NMR | MS m/z (M + 1) |
|---|---|---|---|---|---|
| II-19 | 2-[4-(2-Hydroxy-acetyl)-piperazin-1-yl]-ethanesulfonic acid {4-[5-amino-6-(2-chloro-3,6-difluoro-benzyloxy)-pyrazin-2-yl]-phenyl}-amide | 0.45 | see examples | (300 MHz, CDCl$_3$) δ 2.48 (t, 4H), 2.93 (t, 2H), 3.30 (m, 4H), 3.55 (brs, 1H), 3.67(t, 2H), 4.14 (s, 2H), 4.84 (s, 2H), 5.67 (s, 2H), 7.05 (m, 1H), 7.20 (m, 1H), 7.27 (d, 2H), 7.92 (d, 2H), 8.05 (s, 1H) | 597 |
| II-20 | 2-Cyclopropylamino-ethanesulfonic acid {4-[5-amino-6-(2-chloro-3,6-difluoro-benzyloxy)-pyrazin-2-yl]-phenyl}-amide | 1.20 | see examples | (300 MHz, CDCl$_3$) δ 0.37 (m, 2H), 0.49 (m, 2H), 2.14 (m, 1H), 3.24 (m, 4H), 4.93 (s, 2H), 5.67 (d, 2H), 7.05 (m, 1H), 7.20 (m, 1H), 7.28 (d, 2H), 7.90 (d, 2H); 8.03 (s, 1H) | 510 |

TABLE 4-continued

| No. | Structure | (μM) | Met IC$_{50}$ Procedure | $^1$H-NMR | MS m/z (M + 1) |
|---|---|---|---|---|---|
| II-21 | 2-[(3R)-2-Hydroxymethyl-pyrrolidin-1-yl]-ethanesulfonic acid {3-[5-amino-6-(2-chloro-3,6-difluoro-benzyloxy)-pyrazin-2-yl]-phenyl}-amide | 1.38 | see examples | (300 MHz, CDCl$_3$) δ 1.60–2.0 (m, 5H), 2.15 (m, 1H), 2.55–2.70 (m, 2H), 2.90–3.15 (m, 2H), 3.3–3.62 (m, 2H), 3.89 (dd, J=3.0, 11.3 Hz, 1H), 4.92 (s, 2H), 5.66 (s, 2H), 6.95–7.60 (m, 5H), 7.55–7.70 (m, 2H), 7.77 (s, 1H), 8.10 (s, 1H) | 554 |
| II-22 | 2-(4-Hydroxy-piperidin-1-yl)-ethanesulfonic acid {3-[5-amino-6-(2-chloro-3,6-difluoro-benzyloxy)-pyrazin-2-yl]-phenyl}-amide | 0.7 | see examples | (300 MHz, CDCl$_3$) δ 1.40–1.60 (m, 2H), 1.75–1.88 (m, 2H), 2.21 (t, J=9.0 Hz, 2H), 2.65–2.75 (m, 2H), 2.85–2.95 (m, 2H), 3.20–3.35 (m, 2H), 3.69 (m, 1H), 5.17 (s, 2H), 5.68 (s, 2H), 6.92–7.02 (m, 1H), 7.08–7.20 (m, 1H), 7.30–7.45 (m, 2H), 7.69 (s, 1H), 7.76 (d, J=7.5 Hz, 1H), 8.14 (s, 1H) | 555 |

TABLE 4-continued

| No. | Structure (µM) | Met IC$_{50}$ Procedure | $^1$H-NMR (M + 1) | MS m/z |
|---|---|---|---|---|
| II-23 | 2-(4-Acetyl-piperazin-1-yl)-ethanesulfonic acid {3-[5-amino-6-(2-chloro-3,6-difluoro-benzyloxy)-pyrazin-2-yl]-phenyl}-amide | 2.79 | see examples | (300 MHz, CDCl$_3$) δ 2.03 (s, 3H), 2.30–2.40 (m, 2H), 2.75–2.85 (m, 2H), 3.20–3.40 (m, 4H), 3.45–3.55 (m, 2H), 5.35 (s, 2H), 5.68 (s, 2H), 6.95–7.02 (m, 1H), 7.05–7.20 (m, 1H), 7.30–7.45 (m, 2H), 7.64 (s, 1H), 7.76 (d, J=7.3 Hz, 1H), 8.13 (s, 1H), 8.52 (s, 1H) | 582 |
| II-24 | 2-Piperidin-1-yl-ethanesulfonic acid {3-[5-amino-6-(2-chloro-3,6-difluoro-benzyloxy)-pyrazin-2-yl]-phenyl}-amide | 3.5 | see examples | (300 MHz, CDCl$_3$) δ 1.30–1.60 (m, 6H), 2.30–2.45 (m, 4H), 2.75–2.90 (m, 2H), 3.15–3.30 (m, 2H), 5.10 (s, 2H), 5.66 (s, 2H), 6.95–7.05 (m, 1H), 7.10–7.20 (m, 1H), 7.25–7.40 (m, 2H), 7.60–7.75 (m, 2H), 8.10 (s, 1H) | 539 |

TABLE 4-continued

| No. | Structure | (µM) | Met IC$_{50}$ Procedure | $^1$H-NMR | MS m/z (M + 1) |
|---|---|---|---|---|---|
| II-25 | 2-Diethylamino-ethanesulfonic acid {3-[5-amino-6-(2-chloro-3,6-difluoro-benzyloxy)-pyrazin-2-yl]-phenyl}-amide 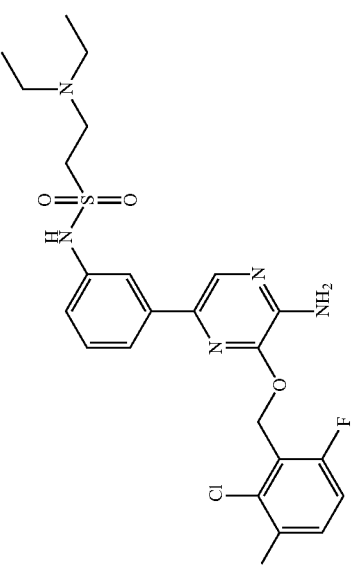 | 3.7 | see examples | (300 MHz, CDCl$_3$) δ 0.95–1.05 (m, 6H), 2.45–2.55 (m, 4H), 2.95–3.10 (m, 2H), 3.15–3.25 (m, 2H), 5.11 (s, 2H), 5.67 (s, 2H), 6.90–7.15 (m, 2H), 7.20–7.40 (m, 2H), 7.55–7.70 (m, 2H), 8.10 (s, 1H) | 527 |
| II-26 | 2-Morpholin-4-yl-ethanesulfonic acid {3-[5-amino-6-(2-chloro-3,6-difluoro-benzyloxy)-pyrazin-2-yl]-phenyl}-amide 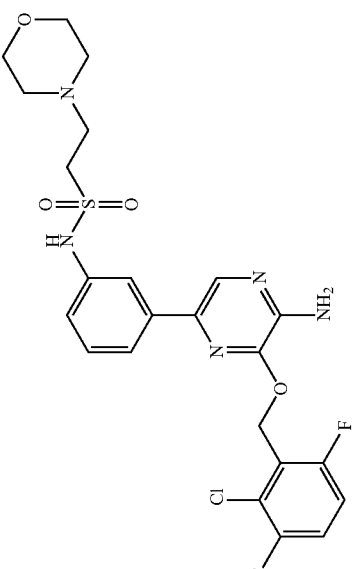 | 3.3 | see examples | (300 MHz, CDCl$_3$) δ 2.30–2.50 (m, 2H), 2.80–3.00 (m, 2H), 3.20–3.40 (m, 2H), 3.50–3.75 (m, 4H), 5.21 (s, 2H), 5.67 (s, 2H), 6.95–7.08 (m, 1H), 7.10–7.20 (m, 1H), 7.30–7.50 (m, 2H), 7.67 (s, 1H), 7.74 (d, J=7.5 Hz, 1H), 8.12 (s, 1H) | 541 |

TABLE 4-continued

| No. | Structure | (µM) | Met IC$_{50}$ Procedure | $^1$H-NMR | MS m/z (M + 1) |
|---|---|---|---|---|---|
| II-27 | 2-Pyrrolidin-1-yl-ethanesulfonic acid {3-[5-amino-6-(2-chloro-3,6-difluoro-benzyloxy)-pyrazin-2-yl]-phenyl}-amide  | 1.8 | see examples | (300 MHz, CDCl$_3$) δ 1.62–1.82 (m, 4H), 2.40–2.55 (m, 4H), 2.92–3.00 (m, 2H), 3.25–3.35 (m, 2H), 5.24 (s, 2H), 5.67 (s, 2H), 6.95–7.08 (m, 1H), 7.10–7.20 (m, 1H), 7.25–7.40 (m, 2H), 7.63 (s, 1H), 7.73 (d, J=7.1 Hz, 1H), 8.12 (s, 1H) | 525 |
| II-28 | 2-Dimethylamino-pyrrolidin-1-yl]-ethanesulfonic acid {3-[5-amino-6-(2-chloro-3,6-difluoro-benzyloxy)-pyrazin-2-yl]-phenyl}-amide 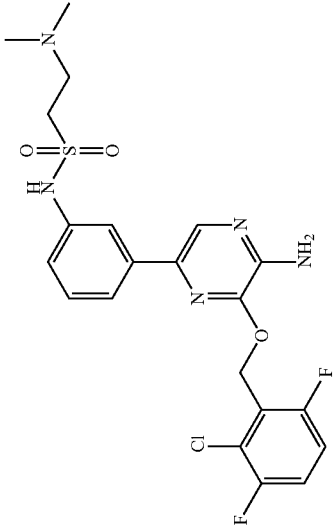 | 2.28 | see examples | (300 MHz, CDCl$_3$) δ 2.27 (s, 6H), 2.86 (t, J=6.4 Hz, 2H), 3.23 (t, J=6.4 Hz, 2H), 5.08 (s, 2H), 5.67 (s, 2H), 7.00–7.45 (m, 4H), 7.65–7.75 (m, 2H), 8.11 (s, 1H) | 499 |

TABLE 4-continued

| No. | (μM) | Met IC$_{50}$ Procedure | $^1$H-NMR | (M + 1) | MS m/z |
|---|---|---|---|---|---|
| II-29 | 2-[4-(2-Hydroxy-acetyl)-pyrrolidin-1-yl]-ethanesulfonic acid {3-[5-amino-6-(2-chloro-3,6-difluoro-benzyloxy)-pyrazin-2-yl]-phenyl}-amide | 1.82 | see examples | (300 MHz, CDCl$_3$) δ 2.43 (t, 4H), 2.92 (t, 2H), 3.20 (t, 2H), 3.33 (t, 2H), 3.54 (brs, 1H), 3.61 (t, 2H), 4.08 (s, 2H), 5.18 (brs, 2H), 5.67 (s, 2H), 7.00–7.45 (m, 4H), 7.65–7.75 (m, 2H), 8.11(s, 1H) | 597 |
| II-30 | 2-(Cyclopropylmethyl-amino)-ethanesulfonic acid {3-[5-amino-6-(2-chloro-3,6-difluoro-benzyloxy)-pyrazin-2-yl]-phenyl}-amide | 1.84 | see examples | (300 MHz, CDCl$_3$) δ 0.07 (m, 2H), 0.44 (m, 2H), 0.89 (m, 1H), 2.45 (d, 2H), 3.16 (t, 2H), 3.29 (t, 2H), 5.27 (brs, 2H), 5.67 (s, 2H), 7.07 (m, 1H), 7.20 (m, 1H), 7.41 (m, 2H), 7.65 (s, 1H), 7.77 (m, 1H), 8.12 (s, 1H) | 524 |

TABLE 4-continued

| No. | Structure (µM) | Met IC$_{50}$ Procedure | $^1$H-NMR | MS m/z (M + 1) |
|---|---|---|---|---|
| II-31 | 2-[(3R)-3-Hydroxy-pyrrolidin-1-yl]-ethanesulfonic acid {3-[5-amino-6-(2-chloro-3,6-difluoro-benzyloxy)-pyrazin-2-yl]-phenyl}-amide | 2.16 | see examples | 540 |
| | (300 MHz, CDCl$_3$) δ 1.80 (m, 1H), 2.20 (m, 2H), 2.50 (m, 1H), 2.70–3.20 (m, 5H), 3.32 (m, 2H), 4.35 (m, 1H), 5.12 (s, 2H), 5.68 (s, 2H), 7.05 (m, 1H), 7.20 (m, 1H), 7.40 (m, 2H), 7.73 (m, 2H), 8.15 (s, 1H) | | | |
| II-32 | 2-Cyclopropylamino-ethanesulfonic acid {3-[5-amino-6-(2-chloro-3,6-difluoro-benzyloxy)-pyrazin-2-yl]-phenyl}-amide | 2.13 | see examples | 510 |
| | (300 MHz, CDCl$_3$) δ 0.25–0.50 (m, 4H), 2.09 (m, 1H), 3.15–3.40 (m, 4H), 5.37 (s, 2H), 5.68 (s, 2H), 7.07 (m, 1H), 7.18 (m, 1H), 7.42 (m, 2H), 7.62 (m, 1H), 7.77 (m, 1H), 8.13 (s, 1H) | | | |

TABLE 4-continued

| No. | Structure | (μM) | Met IC$_{50}$ Procedure | ¹H-NMR | MS m/z (M + 1) |
|---|---|---|---|---|---|
| II-33 | 4-[5-Amino-6-(2-chloro-3,6-difluoro-benzyloxy)-pyrazin-2-yl]-benzoic acid | | see examples | | 392 |
| II-34 | {4-[5-Amino-6-(2-chloro-3,6-difluoro-benzyloxy)-pyrazin-2-yl]-phenyl}-[(2R)-2-pyrrolidin-1-ylmethyl-pyrrolidin-1-yl]-methanone | 0.15 | see examples | (300 MHz, CDCl$_3$) δ 1.5–2.2 (m, 10H), 2.65 (m, 4H), 3.50 (m, 2H), 4.42 (m, 1H), 4.86 (br s, 2H), 5.68 (d, J=1.3 Hz, 2H), 7.05 (m, 1H), 7.19 (m, 1H), 7.57 (m, 2H), 7.96 (d, 2H), 8.12 (s, 1H) | 528 |

TABLE 4-continued

| No. | Structure (μM) | Met IC$_{50}$ Procedure | $^1$H-NMR (M + 1) | MS m/z |
|---|---|---|---|---|
| II-35 | 4-[5-Amino-6-(2-chloro-3,6-difluoro-benzyloxy)-pyrazin-2-yl]-N-(2-pyrrolidin-1-yl-ethyl)-benzamide | 0.13 | see examples | (300 MHz CDCl$_3$) δ 1.87 (m, 4H), 2.73 (m, 4H), 2.85 (t, 2H), 3.64 (m, 2H), 4.91 (s, 2H), 5.68 (d, 2H), 7.05 (m, 1H), 7.20 (m, 1H), 7.89 (d, 2H), 7.99 (d, 2H), 8.13 (s, 1H) | 489 |
| II-36 | {4-[5-Amino-6-(2-chloro-3,6-difluoro-benzyloxy)-pyrazin-2-yl]-phenyl}-[(3S)-3-amino-pyrrolidin-1-yl]-methanone | 0.37 | see examples | (300 MHz, CD$_3$OD) δ 1.80–2.40 (m, 2H), 2.24 (s, 3H), 3.30–3.90 (m, 5H), 5.71 (s, 2H), 7.25 (m, 1H), 7.35 (m, 1H), 7.60 (m, 2H), 8.03 (d, 2H), 8.10 (s, 1H) | 461 |

TABLE 4-continued

| No. | (μM) Structure | Met IC$_{50}$ Procedure | $^1$H-NMR (M + 1) | MS m/z |
|---|---|---|---|---|
| II-37 | N-[2-(4-Acetyl-piperazin-1-yl)-ethyl]-4-[5-amino-6-(2-chloro-3,6-difluoro-benzyloxy)-pyrazin-2-yl]-benzamide | 1.35 | see examples | 545 |
| | (300 MHz, CDCl$_3$) δ 2.10 (s, 3H), 2.52 (m, 4H), 2.66 (t, 2H), 3.40–3.80 (m, 6H), 4.94 (s, 2H), 5.68 (s, 2H), 6.75 (brs, 1H), 7.05 (m, 1H), 7.20 (m, 1H), 7.84 (d, 2H), 8.00 (d, 2H), 8.14 (s, 1H) | | | |
| II-38 | 4-[5-Amino-6-(2-chloro-3,6-difluoro-benzyloxy)-pyrazin-2-yl]-N-(3-pyrrolidin-1-yl-propyl)-benzamide | 0.58 | see examples | 503 |
| | (300 MHz, CDCl$_3$) δ 1.91 (m, 6H), 2.72 (m, 4H), 2.82 (t, 2H), 3.61 (m, 2H), 4.93 (s, 2H), 5.69 (d, 2H), 7.05 (m, 1H), 7.20 (m, 1H), 7.89 (d, 2H), 7.97 (d, 2H), 8.12 (s, 1H), 8.73 (s, 1H) | | | |

TABLE 4-continued
| No. | Structure | (µM) | Met IC₅₀ Procedure | ¹H-NMR | MS m/z (M+1) |
|---|---|---|---|---|---|
| II-39 | 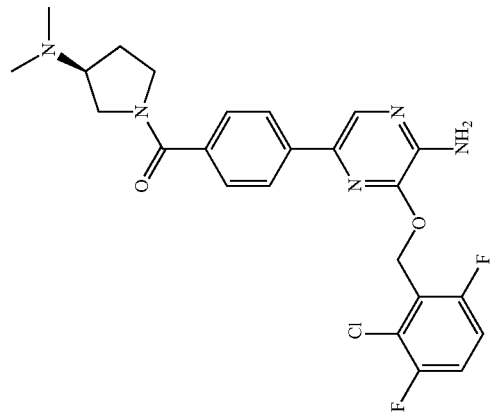 {4-[5-Amino-6-(2-chloro-3,6-difluorobenzyloxy)-pyrazin-2-yl]-phenyl}-[(3S)-3-dimethylamino-pyrrolidin-1-yl]-methanone | 0.67 | see examples | (300 MHz, CDCl₃) δ 1.70–2.10 (m, 1H), 2.24 (s, 3H), 2.34 (s, 3H), 2.60–2.90 (m, 1H), 3.30–4.00 (m, 4H), 4.90 (s, 2H), 5.68 (d, 2H), 7.10 (m, 1H), 7.20 (m, 1H), 7.60 (m, 2H), 7.97 (d, 2H), 8.13 (s, 1H) | 489 |
| II-40 | 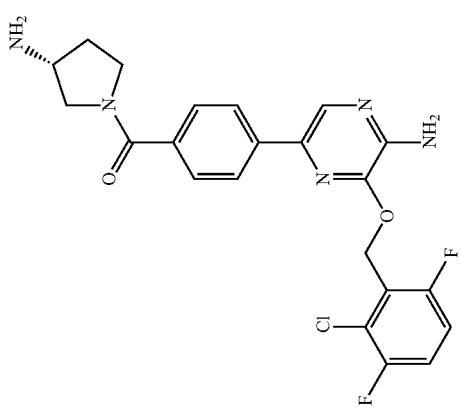 {4-(5-Amino-6-(2-chloro-3,6-difluoro-benzyloxy)-pyrazin-2-yl]-phenyl}-[(3R)-3-amino-pyrrolidin-1-yl]-methanone | 0.46 | see examples | (300 MHz, CD₃OD) δ 1.80–2.40 (m, 2H), 2.24 (s, 3H), 3.30–3.90 (m, 5H), 5.71 (s, 2H), 7.25 (m, 1H), 7.35 (m, 1H), 7.60 (m, 2H), 6.03 (d, 2H), 8.10 (s, 1H) | 461 |

TABLE 4-continued
| No. | Structure | (μM) Met IC₅₀ Procedure | ¹H-NMR | (M + 1) | MS m/z |
|---|---|---|---|---|---|
| II-41 | 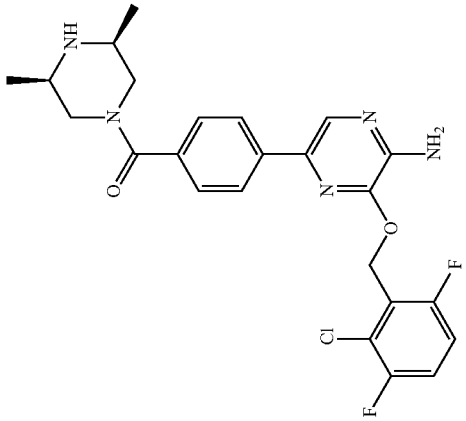 {4-[5-Amino-6-(2-chloro-3,6-difluoro-benzyloxy)-pyrazin-2-yl]-phenyl}-(3,5-dimethyl-piperazin-1-yl)-methanone | 0.48 see examples | (300 MHz, COCl₃) δ 0.9–1.2 (m, 6H), 2.2–3.2 (m, 6H), 4.91 (s, 2H), 5.68 (s, 2H), 7.10 (m, 1H), 7.20 (m, 1H), 7.48 (d, 2H), 7.97 (d, 2H), 8.12 (s, 1H) | | 489 |
| II-42 | 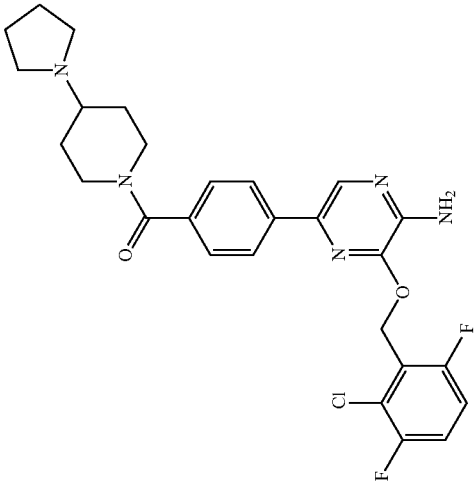 {4-[5-Amino-6-(2-chloro-3,6-difluoro-benzyloxy)-pyrazin-2-yl]-phenyl}-(4-pyrrolidin-1-yl-piperadin-1-yl)-methanone | 0.33 see examples | (300 MHz, CDCl₃) δ 1.60–3.40 (m, 17H), 4.89 (s, 2H), 5.68 (d, 2H), 7.10 (m, 1H), 7.20 (m, 1H), 7.47 (d, 2H), 7.96 (d, 2H), 8.11 (s, 1H) | | 528 |

TABLE 4-continued

| No. | Structure | (μM) | Met IC$_{50}$ Procedure | $^1$H-NMR | MS m/z (M + 1) |
|---|---|---|---|---|---|
| II-43 | 4-[5-Amino-6-(2-chloro-3,6-difluoro-benzyloxy)-pyrazin-2-yl]-N-(3-morpholin-4-yl-propyl)-benzamide | 0.59 | see examples | (300 MHz, CDCl$_3$) δ 1.83 (m, 2H), 2.60 (m, 6H), 3.61 (m, 2H), 3.76 (m, 4H), 4.93 (s, 2H), 5.70 (d, 2H), 7.05 (m, 1H), 7.20 (m, 1H), 7.88 (d, 2H), 8.00 (d, 2H), 8.14 (s, 1H) | 518 |
| II-44 | 4-[5-Amino-6-(2-chloro-3,6-difluoro-benzyloxy)-pyrazin-2-yl]-N-(1-methyl-piperadin-4-yl)-benzamide | 0.5 | see examples | (300 MHz, CDCl$_3$) δ 1.80 (m, 2H), 2.07 (m, 2H), 2.22 (m, 2H), 2.34 (s, 3H), 2.88 (m, 2H), 4.04 (m, 2H), 4.92 (s, 2H), 5.69 (d, 2H), 6.03 (d, 1H), 7.05 (m, 1H), 7.20 (m, 1H), 7.82 (d, 2H), 7.98 (d, 2H), 8.13 (s, 1H) | 489 |

| No. | Structure | (μM) | Met IC$_{50}$ Procedure | $^1$H-NMR (M+1) | MS m/z |
|---|---|---|---|---|---|
| II-45 | 4-[5-Amino-6-(2-chloro-3,6-difluoro-benzyloxy)-pyrazin-2-yl]-N-(2-morpholin-4-yl-ethyl)-benzamide | 1.11 | see examples | (300 MHz, CD$_3$OD) δ 2.68 (m, 6H), 3.60 (m, 2H), 3.75 (m, 4H), 5.72 (s, 2H), 7.25 (m, 1H), 7.35 (m, 1H), 7.88 (d, 2H), 8.05 (d, 2H), 8.12 (s, 1H) | 504 |
| II-46 | {4-(5-Amino-6-(2-chloro-3,6-difluoro-benzyloxy)-pyrazin-2-yl]-phenyl}-(4-methyl-piperazin-1-yl)-methanone | 0.68 | see examples | (300 MHz, CDCl$_3$) δ 2.39 (s, 3H), 2.48 (m, 4H), 3.69 (m, 4H), 4.89 (s, 2H), 5.69 (s, 2H), 7.08 (m, 1H), 7.20 (m, 1H), 7.52 (d, 2H), 7.95 (d, 2H), 8.08 (s, 1H) | 474 |

TABLE 4-continued

| No. | Structure | (μM) | Met IC$_{50}$ Procedure | $^1$H-NMR | MS m/z (M + 1) |
|---|---|---|---|---|---|
| II-47 | 3-[5-Amino-6-(2-chloro-3,6-difluoro-benzyloxy)-pyrazin-2-yl]-benzoic acid | | see examples | | 392 |
| II-48 | {3-[5-Amino-6-(2-chloro-3,6-difluoro-benzyloxy)-pyrazin-2-yl]-phenyl}-(4-methyl-piperazin-1-yl)-methanone | 2.85 | see examples | (300 MHz, CDCl$_3$) δ 2.33 (s, 3H), 2.46 (m, 4H), 3.68 (m, 4H), 4.86 (br s, 2H), 5.67 (s, 2H), 7.08 (m, 1H), 7.20 (m, 1H), 7.35 (d, 1H), 7.47 (t, 1H), 7.95 (m, 2H), 8.10 (s, 1H) | 474 |
| II-49 | {3-(5-Amino-6-(2-chloro-3,6-difluoro-benzyloxy)-pyrazin-2-yl]-phenyl}-[(3R)-3-amino-pyrrolidin-1-yl]-methanone | 1.02 | see examples | (300 MHz, CD$_3$OD) δ 2.12 (m, 1H), 2.44 (m, 1H), 3.52-4.05 (m, 5H), 5.77 (s, 2H), 7.24 (m, 1H), 7.38 (m, 1H), 7.54 (m, 2H), 8.02 (s, 1H), 8.12 (m, 2H) | 460 |

TABLE 4-continued

| No. | Structure | (μM) | Met IC$_{50}$ Procedure $^1$H-NMR | (M + 1) | MS m/z |
|---|---|---|---|---|---|
| II-50 | {3-[5-Amino-6-(2-chloro-3,6-difluoro-benzyloxy)-pyrazin-2-yl]-phenyl}-[(3S)-3-amino-pyrrolidin-1-yl]-methanone | 0.91 | see examples | (300 MHz, CD$_3$OD) δ 2.12 (m, 1H), 2.44 (m, 1H), 3.52–4.05 (m, 5H), 5.77 (s, 2H), 7.24 (m, 1H), 7.38 (m, 1H), 7.54 (m, 2H), 8.02 (s, 1H), 8.12 (m, 2H) | 460 |
| II-51 | {3-[5-Amino-6-(2-chloro-3,6-difluoro-benzyloxy)-pyrazin-2-yl]-phenyl}-(3,5-dimethyl-piperazin-1-yl)-methanone | 2.56 | see examples | (300 MHz, CDCl$_3$) δ 0.99 (br d, 3H), 1.15 (br d, 3H), 2.42 (m, 1H), 2.70 (m, 1H), 2.84 (m, 1H), 2.93 (m, 1H), 3.66 (m, 1H), 4.67 (m, 1H), 4.92 (br s, 2H), 5.66 (s, 2H), 7.05 (m, 1H), 7.20 (m, 1H), 7.35 (m, 1H), 7.47 (t, 1H), 7.97(m, 2H), 8.10 (s, 1H) | 488 |
| II-52 | 3-[5-Amino-6-(2-chloro-3,6-difluoro-benzyloxy)-pyrazin-2-yl]-N-(3-morpholin-4-yl-propyl)-benzamide | 4.2 | see examples | (300 MHz, CDCl$_3$) δ 1.82 (m, 2H), 2.50 (m, 4H), 2.56 (m, 2H), 3.67 (m, 6H), 4.88 (br s 2H), 5.68 (s, 2H), 7.05 (m, 1H), 7.19 (m, 1H), 7.48 (t, 1H), 7.70 (d, 1H), 7.90 (m, 1H), 8.06 (d, 1H), 8.14 (s, 1H), 8.38 (t, J=1.6 Hz, 1H) | 519 |

TABLE 4-continued

| No. | Structure (μM) | Met IC$_{50}$ Procedure | $^1$H-NMR (M + 1) | MS m/z |
|---|---|---|---|---|
| II-53 | {3-[5-Amino-5-(2-chloro-3,6-difluoro-benzyloxy)-pyrazin-2-yl]-phenyl}-(4-pyrrolidin-1-yl-piperadin-1-yl)-methanone | 0.83 see examples | (300 MHz, CDCl$_3$) δ 1.60 (m, 2H), 1.80 (m, 4H), 1.86 (m, 2H), 2.00 (m, 2H), 2.32 (m, 1H), 2.61 (m, 4H), 2.56 (m, 2H), 3.00 (m, 2H), 3.82(m, 1H), 4.66 (m, 1H), 4.93 (br s, 2H), 5.66 (s, 2H), 7.06 (m, 1H), 7.18 (m, 1H), 7.32 (dt, 1H), 7.46 (t, 1H), 7.70 (d, 1H), 7.97 (m, 2H), 8.09 (d, J=3.6 Hz, 1H) | 528 |
| II-54 | {3-[5-Amino-6-(2-chloro-3,6-difluoro-benzyloxy)-pyrazin-2-yl]-phenyl}-[(3S)-3-dimethylamino-pyrrolidin-1-yl]-methanone | 1.45 see examples | (300 MHz, CDCl$_3$) δ 1.85 (m, 1H), 2.10 (m, 1H), 2.21 (s, 3H), 2.31 (s, 3H), 2.75 (m, 1H), 3.42 (m, 1H), 3.64 (m, 2H), 3.92 (m, 1H), 4.93 (br s, 2H), 5.67 (s, 2H), 7.06 (m, 1H), 7.18 (m, 1H), 7.46 (m, 2H), 7.97 (m, 1H), 8.09 (m, 2H) | 488 |

TABLE 4-continued

| No. | (μM) | Structure | Met IC$_{50}$ Procedure | $^1$H-NMR | MS m/z (M+1) |
|---|---|---|---|---|---|
| II-55 | 3-[5-Amino-6-(2-chloro-3,6-difluoro-benzyloxy)-pyrazin-2-yl]-N-(2-pyrrolidin-1-yl-ethyl)-benzamide | 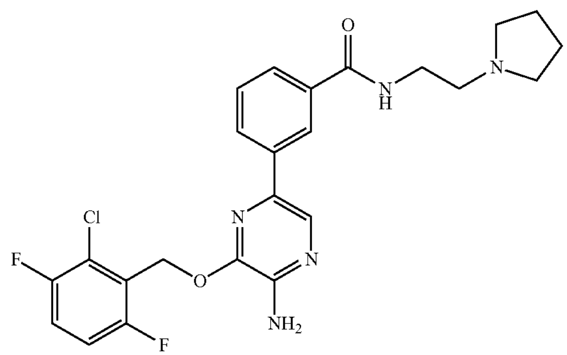 | 1.6 | see examples (300 MHz, CDCl$_3$) δ 1.82 (m, 4H), 2.69 (m, 4H), 2.84 (m, 2H), 3.65 (m, 2H), 4.93 (br s, 2H), 5.68 (s, 2H), 7.06 (m, 1H), 7.16 (m, 1H), 7.22 (m, 1H), 7.49 (t, J=7.7 Hz, 1H), 7.77 (d, J=7.8 Hz, 1H), 8.04 (dt, J=7.9 Hz, 1.5 Hz, 1H), 8.13 (s, 1H), 8.38 (t, J=1.5 Hz, 1H) | 488 |
| II-56 | 3-[5-Amino-6-(2-chloro-3,6-difluoro-benzyloxy)-pyrazin-2-yl]-N-(1-methyl-piperadin-4-yl)-benzamide | 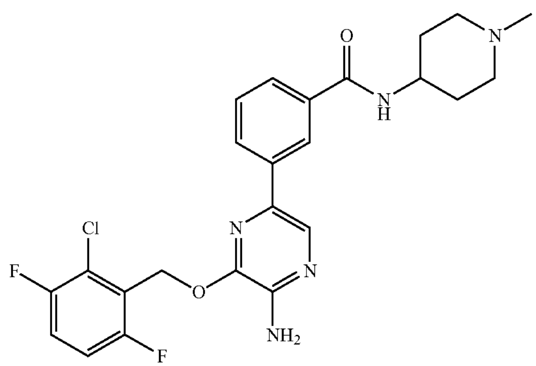 | 0.9 | see examples (300 MHz, CDCl$_3$) δ 1.71 (m, 2H), 2.11 (m, 2H), 2.28 (t, 2H), 2.95 (m, 2H), 4.11 (m, 1H), 4.89 (s, 2H), 5.69 (s, 2H), 6.28 (m, 1H), 7.06 (m, 1H), 7.18 (m, 1H), 7.45 (t, 1H), 7.68 (d, 1H), 8.06 (d, 1H), 8.11 (s, 1H), 8.35 (s, 1H) | 488 |

TABLE 4-continued

| No. | Structure (µM) | Met IC$_{50}$ Procedure | $^1$H-NMR (M + 1) | MS m/z |
|---|---|---|---|---|
| II-57 | {3-[5-Amino-6-(2-chloro-3,6-difluoro-benzyloxy)-pyrazin-2-yl]-phenyl}-[(2S)-pyrrolidin-1-ylmethyl-pyrrolidin-1-yl]-methanone | 0.63 | see examples | (300 MHz, CDCl$_3$) δ 2.02 (m, 10H), 2.75 (m, 4H), 3.49 (m, 2H), 4.51 (m, 1H), 4.69 (s, 2H), 5.69 (s, 2H), 7.08 (m, 1H), 7.20 (m, 1H), 7.46 (m, 2H), 7.98 (m, 1H), 8.07 (m, 1H), 6.11 (s, 1H) | 528 |
| II-58 | 3-[5-Amino-6-(2-chloro-3,6-difluoro-benzyloxy)-pyrazin-2-yl]-N-(2-morpholin-4-yl-ethyl)-benzamide | 2.5 | see examples | (300 MHz, CD$_3$OD) δ 2.51 (m, 4H), 2.65 (t, 2H), 3.58 (t, 2H), 3.69 (m, 4H), 5.72 (s, 2H), 7.20 (m, 1H), 7.35 (m, 1H), 7.52 (t, 1H), 7.76 (d, 1H), 8.12 (m, 2H), 6.41 (s, 1H) | 504 |

TABLE 4-continued

| No. | Structure (µM) | Met IC$_{50}$ Procedure | $^1$H-NMR (M + 1) | MS m/z |
|---|---|---|---|---|
| II-59 | N-[2-(4-Acetyl-piperazin-1-yl)-ethyl]-3-[5-amino-6-(2-chloro-3,6-difluoro-benzyloxy)-pyrazin-2-yl]-benzamide | 2.77 | see examples | (300 MHz, CD$_3$OD) δ 2.08 (s, 3H), 2.59 (m, 6H), 3.57 (m, 6H), 5.71 (s, 2H), 7.21 (m, 1H), 7.37 (m, 1H), 7.50 (t, 1H), 7.75 (d, 1H), 8.08 (m, 2H), 8.39 (s, 1H) | 545 |
| II-60 | 3-[5-Amino-6-(2-chloro-3,6-difluoro-benzyloxy)-pyrazin-2-yl]-N-(3-pyrrolidin-1-yl-propyl)-benzamide | 1.48 | see examples | (300 MHz, CDCl$_3$) δ 1.79 (m, 4H), 1.88 (t, 2H), 2.65 (m, 4H), 2.78 (t, 2H), 3.65 (m, 2H), 4.86 (s, 2H), 5.69 (s, 2H), 7.06 (m, 1H), 7.21 (m, 1H), 7.45 (t, 1H), 7.68 (d, 1H), 8.06 (d, 1H), 8.16 (s, 1H), 8.40 (s, 1H), 8.69 (m, 1H) | 502 |

TABLE 4-continued
| No. | Structure | (μM) | Met IC$_{50}$ Procedure | $^1$H-NMR | MS m/z (M + 1) |
|---|---|---|---|---|---|
| II-61 | 3-(2-Chloro-3,6-difluoro-benzyloxy)-5-(1H-indol-5-yl)-pyrazin-2-ylamine 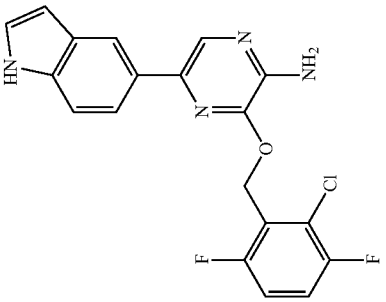 | | see examples | | 387 |
| II-62 | 3-(2-Chloro-3,6-difluoro-benzyloxy)-5-(3-pyrrolidin-1-ylmethyl-1H-indol-5-yl)-pyrazin-2-ylamine 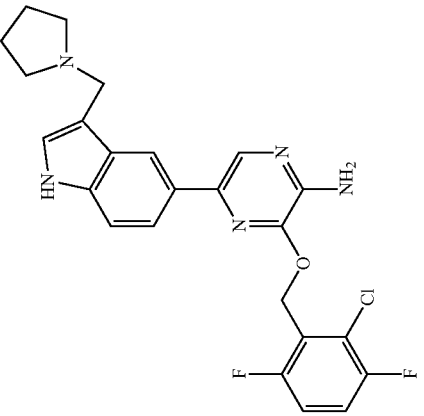 | 0.35 | see examples | (300 MHz, CDCl$_3$) δ 1.78 (m, 4H), 2.66 (m, 4H), 3.89 (s, 2H), 4.89 (s, 2H), 5.69(s, 2H), 7.08 (m, 1H), 7.18 (m, 2H), 7.39 (d, 1H), 7.79 (d, 1H), 8.08 (s, 1H), 8.18 (s, 1H), 8.79 (s, 1H) | 470 |

TABLE 4-continued

| No. | Structure | (µM) | Met IC$_{50}$ Procedure | $^1$H-NMR | MS m/z (M + 1) |
|---|---|---|---|---|---|
| II-63 | 3-(2-Chloro-3,6-difluoro-benzyloxy)-5-(3-diethylaminomethyl-1H-indol-5-yl)-pyrazin-2-ylamine | 0.73 | see examples | (300 MHz CDCl$_3$) δ 1.11 (m, 6H), 2.69 (m, 4H), 3.80 (s, 2H), 4.69(s, 2H), 5.77 (s, 2H), 7.02 (m, 1H), 7.21 (m, 2H), 7.45 (d, 1H), 7.89 (d, 1H), 8.22 (m, 3H) | 472 |
| II-64 | 1-(4-{5-[5-Amino-6-(2-chloro-3,6-difluoro-benzyloxy)-pyrazin-2-yl]-1H-indol-3-ylmethyl}-piperazin-1-yl)-ethanone | 1.5 | see examples | (300 MHz CDCl$_3$) δ2.08 (s, 3H), 2.55 (m, 4H), 3.45 (m, 2H), 3.64 (m, 2H), 3.81 (s, 2H), 4.78 (s, 2H), 5.71 (s, 2H), 7.08 (m, 1H), 7.18 (m, 2H), 7.31 (d, 1H), 7.79 (d, 1H), 8.04 (s, 1H), 8.22 (s, 1H), 8.49 (s, 1H) | 527 |

TABLE 4-continued

| No. | Structure | (µM) Met IC₅₀ Procedure | ¹H-NMR | MS m/z (M + 1) |
|---|---|---|---|---|
| II-65 | 3-(2-Chloro-3,6-difluoro-benzyloxy)-5-[3-(2,6-dimethyl-morpholin-4-ylmethyl)-1H-indol-5-yl]-pyrazin-2-ylamine 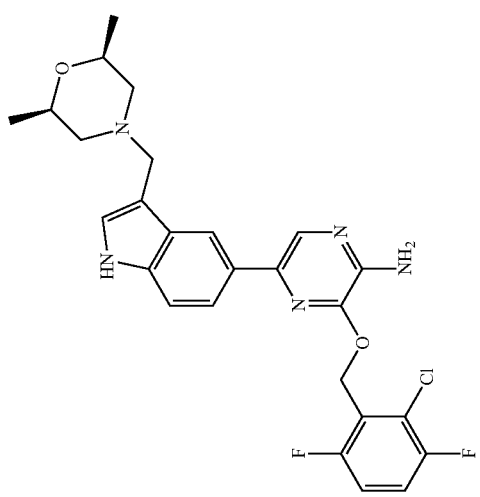 | 2.4 see examples | (300 MHz, CDCl₃) δ 1.11 (d, 6H), 1.98 (m, 2H), 2.98 (m, 2H), 3.87 (m, 4H), 4.75 (s, 2H), 5.78 (s, 2H), 7.08 (m, 1H), 7.27 (m, 2H), 7.48 (d, 1H), 7.89 (d, 1H), 8.19 (s, 1H), 8.28 (s, 2H) | 514 |
| II-66 | N-(1-{5-[5-Amino-6-(2-chloro-3,6-difluoro-benzyloxy)-pyrazin-2-yl]-1H-indol-3-ylmethyl}-(3S)-pyrrolidin-3-yl)-acetamide 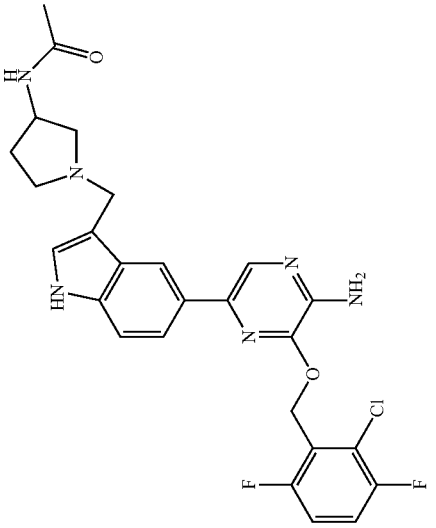 | 0.55 see examples | (300 MHz, CDCl₃) δ 1.69 (m, 1H), 1.88 (s, 3H), 2.39 (m, 2H), 2.75 (m, 2H), 3.08 (m, 1H), 3.95 (m, 2H), 4.50 (m, 1H), 4.79 (s, 2H), 5.78 (s, 2H), 6.01 (m, 1H), 7.05 (m, 1H), 7.18 (m, 2H), 7.42 (d, 1H), 7.79 (d, 1H), 8.12 (s, 1H), 8.21 (s, 1H), 8.28 (s, 1H) | 527 |

TABLE 4-continued

| No. | Structure | (μM) | Met IC₅₀ Procedure | ¹H-NMR (M + 1) | MS m/z |
|---|---|---|---|---|---|
| II-67 | | 3-(2-Chloro-3,6-difluoro-benzyloxy)-5-(3-piperidin-1-ylmethyl-1H-indol-5-yl)-pyrazin-2-ylamine | 0.51 | see examples | (300 MHz, CDCl₃) δ 1.49 (m, 2H), 1.71 (m, 4H), 2.66 (m, 4H), 3.89 (s, 2H), 4.79 (s, 2H), 5.69 (s, 2H), 7.08 (m, 1H), 7.18 (m, 1H), 7.31 (s, 1H), 7.42 (d, 1H), 7.78 (d, 1H), 8.08 (s, 1H), 8.18 (s, 1H), 8.69 (br s, 1H) | 484 |
| II-68 | | 3-(2-Chloro-3,6-difluoro-benzyloxy)-5-(3-morpholin-4-ylmethyl-1H-indol-5-yl)-pyrazin-2-ylamine | 1.15 | see examples | (300 MHz, CDCl₃) δ 2.72 (m, 4H), 3.80 (m, 6H), 4.73 (s, 2H), 5.73 (s, 2H), 7.06 (m, 1H), 7.20 (m, 1H), 7.46 (d, 1H), 7.80 (dd, 1H), 8.12 (s, 1H), 8.25 (s, 1H) | 486 |

TABLE 4-continued

| No. | Structure | (μM) | Met IC$_{50}$ Procedure | $^1$H-NMR | MS m/z (M + 1) |
|---|---|---|---|---|---|
| II-69 | 3-[1-(2-Chloro-3,6-difluoro-phenyl)-2-methyl-propoxy]-5-[4-(2-morpholin-4-yl-ethoxy)-phenyl]-pyrazin-2-ylamine | 10.58 | see examples | (400 MHz, DMSO-d$_6$) δ 0.89 (d, 3H), 1.19 (d, 3H), 2.47 (m, 4H), 2.56 (m, 1H), 2.68 (t, 2H), 3.56 (t, 4H), 4.07 (t, 2H), 5.96 (d, 1H), 6.28 (s, 2H), 6.89 (d, 2H), 7.26 (m, 1H), 7.38 (m, 1H), 7.63 (d, 2H), 7.95 (s, 1H) | 519 |
| II-70 | 3-[1-(2-Chloro-3,6-difluoro-phenyl)-ethoxy]-5-{4-(2-morpholin-4-yl-ethoxy)-phenyl]-pyrazin-2-ylamine; compound with trifluoro-acetic acid | 0.51 | see examples | (400 MHz, DMSO-d$_6$) δ 1.78 (d, 3H), 3.21 (m, 2H), 3.51 (m, 2H), 3.54 (m, 2H), 3.74 (m, 2H), 3.98 (m, 2H), 4.38 (t, 2H), 6.34 (br s, 2H), 6.42 (m, 1H), 6.97 (d, 2H), 7.25 (m, 1H), 7.38 (m, 1H), 7.66 (d, 2H), 7.86 (s, 1H) | 491 |

TABLE 4-continued

| No. | Structure | (μM) | Met IC₅₀ Procedure | ¹H-NMR (M + 1) | MS m/z |
|---|---|---|---|---|---|
| II-71 | 3-[1-(2,6-Dichloro-3-fluoro-phenyl)-ethoxy]-5-[4-(2-morpholin-4-yl-ethoxy)-phenyl]-pyrazin-2-ylamine; compound with trifluoro-acetic acid | 0.3 | see examples | (400 MHz, DMSO-d₆) δ 1.79 (d, 3H), 3.21 (m, 3H), 3.46 (m, 2H), 3.57 (m, 2H), 3.74 (m, 2H), 3.95 (m, 2H), 4.36 (t, 2H), 6.34 (br s, 2H), 6.49 (m, 1H), 6.94 Cd, 2H), 7.37 (t, 1H), 7.48 (m, 1H), 7.66 (d, 2H), 7.98 (s, 1H) | 491 |
| II-72 | N-(4-{5-Amino-6-[1-(2-chloro-3,6-difluoro-phenyl)-ethoxy]-pyrazin-2-yl}-phenyl)-methanesulfonamide | | see examples | (400 MHz, DMSO-d₆) δ 1.78 (d, 3H), 2.96 (s, 3H), 6.41 (m, 3H), 7.15 (d, 2H), 7.26 (m, 1H), 7.37 (m, 1H), 7.64 (d, 2H), 8.00 (s, 1H), 9.72 (s, 1H) | 455 |

TABLE 4-continued

| No. | Structure | (μM) | Met IC$_{50}$ Procedure | $^1$H-NMR (M + 1) | MS m/z |
|---|---|---|---|---|---|
| II-73 | 2-Pyrrolidin-1-yl-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl$_3$) δ 1.84 (m, 7H), 2.56 (m, 4H), 3.04 (m, 2H), 3.25 (m, 2H), 4.94 (br s, 2H), 6.71 (q, 1H), 6.95 (m, 2H), 7.21 (d, 2H), 7.72 (d, 2H), 7.96 (s, 1H) | 538 |
| II-74 | 2-(4-Hydroxy-piperidin-1-yl)-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl$_3$) δ 1.60 (m, 2H), 1.82 (m, 5H), 2.23 (m, 2H), 2.77 (m, 2H), 2.89 (t, 2H), 3.26 (t, 2H), 3.74 (m, 1H), 5.07 (br s, 2H), 6.70 (q, 1H), 7.00 (m, 2H), 7.24 (d, 2H), 7.73 (d, 2H), 7.94 (s, 1H) | 568 |

TABLE 4-continued

| No. | Structure | (μM) | Met IC$_{50}$ Procedure | $^1$H-NMR | MS m/z (M + 1) |
|---|---|---|---|---|---|
| II-75 | 2-Piperidin-1-yl-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl$_3$) δ 1.49 (m, 2H), 1.61 (m, 4H), 1.83 (d, 3H), 2.50 (m, 4H), 2.86 (m, 2H), 3.20 (m, 2H), 4.95 (brs, 2H), 6.70 (q, 1H), 7.00 (m, 2H), 7.24 (d, 2H), 7.74 (d, 2H), 7.96 (s, 1H) | 552 |
| II-76 | 2-(Cyclopropylmethyl-amino)-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl$_3$) δ 0.14 (m, 2H), 0.50 (m, 2H), 0.95 (m, 1H), 1.82 (d, 3H), 2.49 (m, 2H), 3.20 (m, 4H), 4.73 (bra, 1H), 5.02 (br s, 2H), 6.71 (q, 1H), 7.00 (m, 2H), 7.25 (d, 2H), 7.74 Cd, 2H), 7.96 (s, 1H) | 538 |

TABLE 4-continued

| No. | Structure | (μM) | Met IC50 Procedure | 1H-NMR | MS m/z (M+1) |
|---|---|---|---|---|---|
| II-77 | 2-[(3R)-3-Hydroxy-pyrrolidin-1-yl]-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl₃) δ 1.79 (m, 1H), 1.82 (d, 3H), 2.26 (m, 2H), 2.54 (m, 1H), 2.82 (m, 1H), 2.98 (m, 2H), 3.08 (m, 1H), 3.26 (m, 2H), 4.44 (m, 1H), 4.94 (br s, 1H), 6.70 (q, 1H), 7.00 (m, 2H), 7.29 (d, 2H), 7.73 (d, 2H), 7.96 (s, 1H) | 554 |
| II-78 | 2-[(2S)-2-Hydroxymethyl-pyrrolidin-1-yl]-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl₃) δ 1.79 (m, 4H), 1.82 (d, 3H), 2.15 (m, 1H), 2.66 (m, 2H), 2.98 (m, 2H), 3.35 (m, 1H), 3.48 (m, 1H), 3.54 (m, 1H), 3.92 (m, 1H), 4.97 (br s, 1H), 6.70 (q, 1H), 7.00 (m, 2H), 7.28 (d, 2H), 7.71 (d, 2H), 7.95 (s, 1H) | 568 |

| No. | Structure | (μM) | Met IC50 Procedure | 1H-NMR | MS m/z (M+1) |
|---|---|---|---|---|---|
| II-79 |  2-Dimethylamino-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl₃) δ 1.82 (d, 3H), 2.29 (s, 6H), 2.85 (t, 2H), 3.21 (t, 2H), 5.00 (br s, 2H), 6.71 (q, 1H), 7.00 (m, 2H), 7.23 (d, 2H), 7.74 (d, 2H), 7.96 (s, 1H) | 512 |
| II-80 | 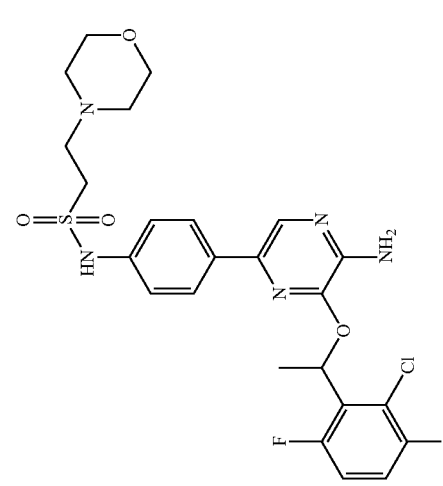 2-Morpholin-4-yl-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl₃) δ 1.82 (d, 3H), 2.48 (m, 4H), 2.90 (m, 2H), 3.27 (m, 2H), 3.71 (m, 4H), 4.92 (br s, 2H), 6.71 (q, 1H), 7.00 (m, 2H), 7.24 (d, 2H), 7.74 (d, 2H), 7.97 (s, 1H) | 554 |

| No. | Structure | (μM) | Met IC$_{50}$ Procedure | $^1$H-NMR | MS m/z (M + 1) |
|---|---|---|---|---|---|
| II-81 | 2-Diethylamino-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl$_3$) δ 1.07 (t, 6H), 1.82 (d, 3H), 2.60 (q, 4H), 3.02 (t, 2H), 3.22 (t, 2H), 4.95 (br s, 2H), 6.71 (q, 1H), 7.00 (m, 2H), 7.22 (d, 2H), 7.74 (d, 2H), 7.96 (s, 1H) | 540 |
| II-82 | 2-Cyclopropylamino-ethanesulfonic acid (4-{5-amino-6-[1-(2-chloro-3,6-difluoro-phenyl)-ethoxy]-pyrazin-2-yl}-phenyl)-amide | | see examples | (300 MHz, CDCl$_3$) δ 0.38 (m, 2H), 0.50 (m, 2H), 1.82 (d, 3H), 2.15 (m, 1H), 3.24 (m, 4H), 4.93 (br s, 2H), 6.71 (q, 1H), 7.00 (m, 2H), 7.21 (d, 2H), 7.74 (d, 2H), 7.97 (s, 1H) | 540 |

TABLE 4-continued

| No. | Structure | (μM) | Met IC$_{50}$ Procedure | $^1$H-NMR | MS m/z (M + 1) |
|---|---|---|---|---|---|
| II-83 | 3-{5-Amino-6-[1-(2,6-dichloro-3-fluoro-phenyl)-ethoxy]-pyrazin-2-yl}-benzoic acid | 1.36 | see examples | | 423 |
| II-84 | (3-{5-Amino-6-[1-(2,6-dichloro-3-fluoro-phenyl)-ethoxy]-pyrazin-2-yl}-phenyl)-[(3S)-3-amino-pyrrolidin-1-yl]-m-ethanone | 0.069 | see examples | (300 MHz, MeOD) δ 7.84 (d, 1H), 7.71 (m, 2H), 7.38 (m, 3H), 7.10 (m, 1H), 6.60 (m, 1H), 4.86 (s, 2H), 4.20 (m, 1H), 3.45–3.89 (m, 4H), 1.82 (d, 3H), 1.34 (m, 1H), 0.89 (m, 1H) | 492 |
| II-85 | (3-{5-Amino-6-[1-(2,6-dichloro-3-fluoro-phenyl)-ethoxy]-pyrazin-2-yl}-phenyl)-[(3R)-3-amino-pyrrolidin-1-yl]-m-ethanone | 0.11 | see examples | (300 MHz, MeOD) δ 7.84 (d, 1H), 7.71 (m, 2H), 7.38 (m, 3H), 7.10 (m, 1H), 6.60 (m, 1H), 4.86 (s, 2H), 4.20 (t, 1H), 3.45–3.89 (m, 4H), 1.82 (d, 3H), 1.34 (m, 1H), 0.69 (m, 1H) | 492 |

TABLE 4-continued

| No. | Structure | (μM) | Met IC$_{50}$ Procedure | $^1$H-NMR | MS m/z (M + 1) |
|---|---|---|---|---|---|
| II-86 | (3-{5-Amino-6-[1-(2,6-dichloro-3-fluoro-phenyl)-ethoxy]-pyrazin-2-yl}-phenyl)-[(2R)-2-pyrrolidin-1-ylmethyl-pyrrolidin-1-yl]-methanone | 0.15 | see examples | (300 MHz, CDCl$_3$) δ 8.04 (d, 1H), 7.84 (d, 2H), 7.30 (d, 2H), 7.15 (tert, 1H), 6.99 (t, 1H), 5.89 (m, 1H), 4.89 (s, 2H), 4.44 (s, 1H), 3.89 (m, 1H), 3.65 (m, 1H), 3.30 (m, 2H), 2.85 (m, 3H), 1.82 (d, 3H), 0.89–2.20 (m, 9H) | 558 |
| II-87 | N-[2-(4-Acetyl-piperazin-1-yl)-ethyl]-3-(5-amino-6-{1-(2,6-dichloro-3-fluoro-phenyl)-ethoxy]-pyrazin-2-yl}-benzamide | 0.186 | see examples | (300 MHz, CDCl$_3$) δ 8.04 (d, 1H), 7.99 (s, 1H), 7.78 (d, 1H), 7.60 (d, 1H), 7.34 (m, 2H), 7.15 (t, 1H), 6.72 (tert, 1H), 4.89 (s, 2H), 4.56 (m, 6H), 3.21 (d, 3H), 2.60 (t, 1H), 2.55 (dd, 1H), 2.09 (s, 3H), 1.80 (d, 4H) | 575 |

TABLE 4-continued

| No. | Structure | (µM) | Met IC₅₀ Procedure | ¹H-NMR (M + 1) | MS m/z |
|---|---|---|---|---|---|
| II-88 | (3-{5-Amino-6-[1-(2,6-dichloro-3-fluoro-phenyl)-ethoxy]-pyrazin-2-yl}-[(2S)-2-pyrrolidin-1-ylmethyl-pyrrolidin-1-yl)-methanone | 0.17 | see examples | (300 MHz, MeOD) δ 8.04 (d, 1H), 7.84 (d, 2H), 7.35 (m, 3H), 7.20 (m, 1H), 6.60 (m, 1H), 4.89 (s, 2H), 4.44 (s, 1H), 3.59 (m, 1H), 3.30 (m, 1H), 3.25 (s, 2H), 3.16 (m, 3H), 1.82 (d, 3H), 0.89–2.32 (m, 9H) | 559 |
| II-89 | 3-{5-Amino-6-[1-(2-chloro-3,6-difluoro-phenyl)-ethoxy]-pyrazin-2-yl}-benzoic acid | | see examples | | 406 |

TABLE 4-continued

| No. | Structure | (μM) | Met IC$_{50}$ Procedure | $^1$H-NMR | MS m/z (M + 1) |
|---|---|---|---|---|---|
| II-90 | 3-{5-Amino-6-[1-(2,6-dichloro-3-fluoro-phenyl)-ethoxy]-pyrazin-2-yl}-N-(1-methyl-piperidin-4-yl)-benzamide | 0.21 | see examples | (300 MHz, CDCl$_3$) δ 8.20 (s, 1H), 8.08 (s, 1H), 7.89 (d, 1H), 7.75 (d, 1H), 7.44 (t, 1H), 7.01 (m, 2H), 6.78 (m, 1H), 6.20 (s, 1H), 4.98 (s, 2H), 4.09 (m, 1H), 2.97 (m, 2H), 2.39 (s, 3H), 2.29 (t, 2H), 2.12 (m, 2H), 1.90 (d, 3H), 1.79 (m, 2H) | 502 |
| II-91 | 3-{5-Amino-6-[1-(2,6-dichloro-3-fluoro-phenyl)-ethoxy]-pyrazin-2-yl}-N-(3-pyrrolidin-1-yl-propyl)-benzamide | 0.15 | see examples | (300 MHz, CD$_3$OD) δ 8.15 (s, 1H), 7.98 (s, 1H), 7.80 (d, 1H), 7.61 (d, 1H), 7.35 (m, 2H), 7.09 (t, 1H), 6.69 (m, 1H), 3.44 (t, 2H), 2.55 (m, 6H), 1.88 (d, 3H), 1.80 (m, 6H) | 532 |

TABLE 4-continued

| No. | Structure (μM) | Met IC$_{50}$ Procedure | $^1$H-NMR (M + 1) | MS m/z |
|---|---|---|---|---|
| II-92 | (3-{5-Amino-6-[1-(2,6-dichloro-3-fluoro-phenyl)-ethoxy]-pyrazin-2-yl]-phenyl}-(4-pyrrolidin-1-yl-piperidin-1-yl)-methanone | 0.15 | see examples | (300 MHz CD$_3$OD) δ 7.96 (s, 1H), 7.76 (d, 1H), 7.65 (m, 1H), 7.41 (m, 2H), 7.21 (d, 1H), 7.12 (t, 1H), 6.61 (m, 1H), 4.68 (m, 2H), 3.62 (m, 1H), 3.05 (m, 2H), 2.69 (m, 6H), 2.45 (m, 2H), 2.12 (m, 2H), 1.86 (d, 3H), 1.48 (m, 2H) | 556 |
| II-93 | 4-[5-Amino-6-(3-fluoro-2-trifluoromethyl-benzyloxy)-pyrazin-2-yl]-benzoic acid | | see examples | | 408 |

TABLE 4-continued
| No. | Structure | (μM) | Met IC₅₀ Procedure | ¹H-NMR | MS m/z (M + 1) |
|---|---|---|---|---|---|
| II-94 | 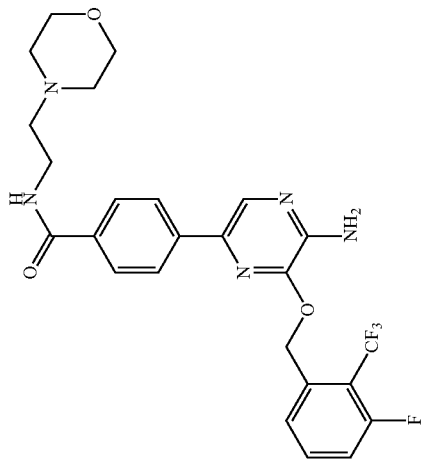 4-[5-Amino-6-(3-fluoro-2-trifluoromethyl-benzyloxy)-pyrazin-2-yl]-N-(2-morpholin-4-yl-ethyl)-benzamide | 0.22 | see examples | (300 MHz, CDCl₃) δ 8.14 (s, 1H), 7.92 (d, 2H), 7.84 (d, 2H), 7.50 (m, 1H), 7.42 (m, 1H), 7.20 (m, 1H), 6.75 (s, 1H), 5.70 (s, 2H), 4.97 (s, 2H), 3.74 (m, 4H), 3.58 (m, 2H), 2.62 (m, 2H), 2.52 (s, 4H) | 520 |
| II-95 | 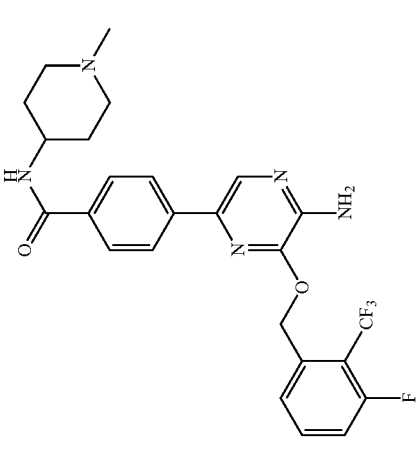 4-[5-Amino-6-(3-fluoro-2-trifluoromethyl-benzyloxy)-pyrazin-2-yl]-N-(1-methyl-piperidin-4-yl)-benzamide | 0.081 | see examples | (300 MHz, CDCl₃) δ 8.14 (s, 1H), 7.92 (d, 2H), 7.84 (d, 2H), 7.50 (m, 1H), 7.42 (m, 1H), 7.20 (m, 1H), 6.04 (d, 1H), 5.75 (s, 2H), 5.01 (s, 2H), 4.0 (m, 1H), 2.85 (d, 2H), 2.30 (s, 3H), 2.20 (t, 2H), 2.12 (d, 2H), 1.59 (m, 2H) | 504 |

TABLE 4-continued

| No. | Structure | (μM) | Met IC$_{50}$ Procedure | $^1$H-NMR (M + 1) | MS m/z |
|---|---|---|---|---|---|
| II-96 | 3-{5-Amino-6-[1-(2,6-dichloro-3-fluoro-phenyl)-ethoxy]-pyrazin-2-yl}-N-(3-pyrrolidin-1-yl-propyl)-benzamide | 0.15 | 4 as in Example II-84 | (300 MHZ, CD$_3$OD) δ 8.18 (s, 1H), 7.98 (s, 1H), 7.80 (d, 1H), 7.61 (d, 1H), 7.35 (m, 2H), 7.12 (t, 1H), 6.75 (q, 1H), 3.44 (t, 2H), 2.55 (m, 6H), 1.88 (d, 3H), 1.80 (m, 6H). | 532 |
| II-97 | 3-{Amino-6-[1-(2-chloro-3,6-difluoro-phenyl)-ethoxy]-pyrazin-2-yl]-N-(3-pyrrolidin-1-yl-propyl)-benzamide | 0.35 | 4 as in Example II-90 | (300 MHZ, CDCl$_3$) δ 8.38 (s, 1H), 8.18 (s, 2H), 7.92 (m, 2H), 7.48 (t, 1H), 7.02 (m, 2H), 6.78 (q, 1H), 4.96 (s, 2H), 3.72 (m, 2H), 3.18 (m, 2H), 2.83 (m, 2H), 2.22 (m, 2H), 2.08 (m, 4H), 1.83 (d, 3H), 1.70 (m, 2H). | 516 |

TABLE 4-continued
| No. | Structure | (μM) | Met IC₅₀ Procedure | ¹H-NMR | (M + 1) MS m/z |
|---|---|---|---|---|---|
| II-98 | 3-{5-Amino-6-[1-(2-chloro-3,6-difluoro-phenyl)-ethoxy]-pyrazin-2-yl}-N-(1-methyl-piperidin-4-yl)-benzamide 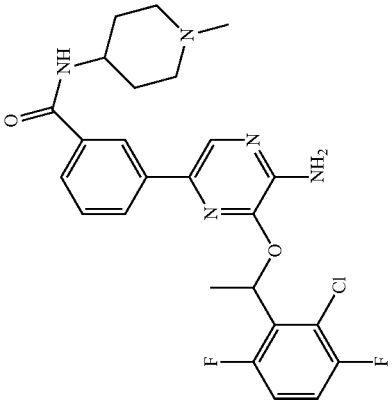 | 0.21 | 4 as in Example II-90 | (300 MHZ, CDCl₃) δ 8.20 (s, 1H), 8.08 (s, 1H), 7.89 (d, 1H), 7.75 (d, 1H), 7.44 (t, 1H), 7.01 (m, 2H), 6.78 (q, 1H), 6.20 (bd, 1H), 4.98 (s, 2H), 4.09 (m, 1H), 2.97 (m, 2H), 2.39 (s, 3H), 2.29 (m, 2H), 2.12 (m, 2H), 1.90 (d, 3H), 1.79 (m, 2H). | 502 |
| II-99 | 3-{5-Amino-6-[1-(2-chloro-3,6-difluoro-phenyl)-ethoxy]-pyrazin-2-yl}-N-(2-pyrrolidin-1-yl-ethyl)-benzamide 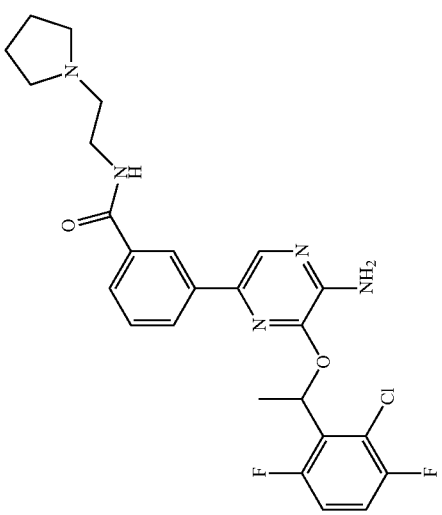 | 0.18 | 4 as in Example II-90 | (300 MHZ, CDCl₃) δ 8.19 (s, 1H), 8.09 (s, 1H), 7.88 (d, 1H), 7.78 (d, 1H), 7.48 (t, 1H), 7.06 (bm, 1H), 6.96 (m, 2H), 6.75 (q, 1H), 5.08 (s, 2H), 3.68 (m, 2H), 2.88 (m, 2H), 2.68 (m, 4H), 1.86 (m, 7H). | 502 |

TABLE 4-continued

| No. | Structure (μM) | Met IC$_{50}$ Procedure | $^1$H-NMR (M + 1) | MS m/z |
|---|---|---|---|---|
| II-100 | 3-{5-Amino-6-[1-(2-chloro-3,6-difluoro-phenyl)-ethoxy]-pyrazin-2-yl}-N-(2-morpholin-4-yl-ethyl)-benzamide | 0.31 | 4 as in Example II-90 | (300 MHZ, CDCl3) δ 8.17 (s, 1H), 8.08 (s, 1H), 7.88 (d, 1H), 7.68 (d, 1H), 7.48 (t, 1H), 6.98 (m, 2H), 6.80 (bt, 1H), 6.74 (q, 1H), 5.02 (s, 2H), 3.76 (m, 4H), 3.68 (m, 2H), 2.68 (m, 2H), 2.58 (m, 4H), 1.85 (d, 3H), | 518 |
| II-101 | N-[2-(4-Acetyl-piperazin-1-yl)-ethyl]-3-{5-amino-6-[1-(2-chloro-3,6-difluoro-phenyl)-ethoxy]-pyrazin-2-yl}-benzamide | 0.64 | 4 as in Example II-90 | (300 MHZ, CDCl3) δ 8.16 (s, 1H), 8.03 (s, 1H), 7.86 (d, 1H), 7.68 (d, 1H), 7.40 (t, 1H), 6.98 (m, 3H), 6.71 (q, 1H), 5.13 (s, 2H), 3.69 (m, 4H), 3.51 (m, 2H), 2.80 (m, 2H), 2.66 (m, 4H), 2.08 (s, 3H), 1.83 (d, 3H). | 559 |

TABLE 4-continued

| No. | Structure | (μM) | Met IC$_{50}$ Procedure | $^1$H-NMR | MS m/z (M + 1) |
|---|---|---|---|---|---|
| II-102 | 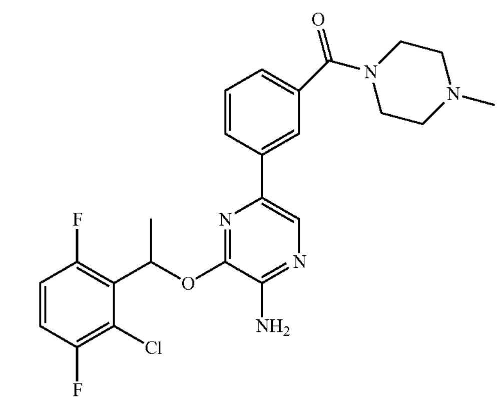 | (3-{5-Amino-6-[1-(2-chloro-3,6-difluoro-phenyl)-ethoxy]-pyrazin-2-yl}-phenyl)-(4-methyl-piperazin-1-yl)-methanone | 4 as in Example II-90 | (300 MHZ, CDCl3) δ 8.02 (s, 1H), 7.82 (m, 2H), 7.41 (t, 1H), 7.28 (m, 1H), 6.95 (m, 2H), 6.71 (q, 1H), 5.00 (s, 2H), 3.85 (m, 2H), 3.46 (m, 2H), 2.36 (m, 4H), 2.33 (s, 3H), 1.83 (d, 3H). | 488 |
| II-103 | 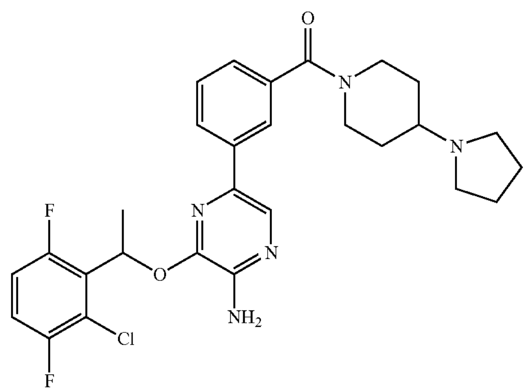 | (3-{5-Amino-6-[1-(2-chloro-3,6-difluoro-phenyl)-ethoxy]-pyrazin-2-yl}-phenyl)-(4-pyrrolidin-1-yl-piperidin-1-yl)-methanone | 4 as in Example II-90 | (300 MHZ, CDCl3) δ 8.02 (s, 1H), 7.80 (m, 2H), 7.41 (t, 1H), 7.29 (m, 1H), 6.95 (m, 2H), 6.69 (q, 1H), 4.97 (s, 2H), 4.72 (m, 1H), 3.83 (m, 1H), 2.81 (m, 7H), 1.83 (d, 3H), 2.10-1.70 (m, 8H). | 542 |

TABLE 4-continued

| No. | Structure | (μM) | Met IC₅₀ Procedure | ¹H-NMR | MS m/z (M + 1) |
|---|---|---|---|---|---|
| II-104 | (3-{5-Amino-6-[1-(2-chloro-3,6-difluoro-phenyl)-ethoxy]-pyrazin-2-yl}-phenyl)-((3R,5S)-3,5-dimethyl-piperazin-1-yl)-methanone | | 4 as in Example II-90 | (300 MHZ, CDCl3) δ 8.03 (s, 1H), 7.80 (m, 2H), 7.41 (t, 1H), 7.29 (m, 1H), 6.95 (m, 2H), 6.70 (q, 1H), 5.00 (s, 2H), 4.68 (m, 1H), 3.56 (m, 1H), 2.75 (m, 3H), 2.42 (m, 1H), 1.83 (d, 3H), 1.57 (m, 1H), 1.15 (m, 3H), 0.96 (m, 3H). | 502 |
| II-105 | (3-{5-Amino-6-[1-(2-chloro-3,6-difluoro-phenyl)-ethoxy]-pyrazin-2-yl}-phenyl)-((S)-2-pyrrolidin-1-ylmethyl-pyrrolidin-1-yl)-methanone | | 4 as in Example II-90 | (300 MHZ, CDCl3) δ 8.04 (s, 1H), 7.83 (m, 2H), 7.39 (m, 2H), 6.98 (m, 2H), 6.70 (q, 1H), 5.00 (s, 2H), 4.47 (m, 1H), 3.50 (m, 2H), 3.00 (m, 5H), 2.30 (m, 3H), 2.00 (m, 5H), 1.83 (d, 3H), 1.53 (m, 1H). | 542 |

TABLE 4-continued

| No. | Structure | (μM) | Met IC$_{50}$ Procedure | $^1$H-NMR (M + 1) | MS m/z |
|---|---|---|---|---|---|
| II-106 | 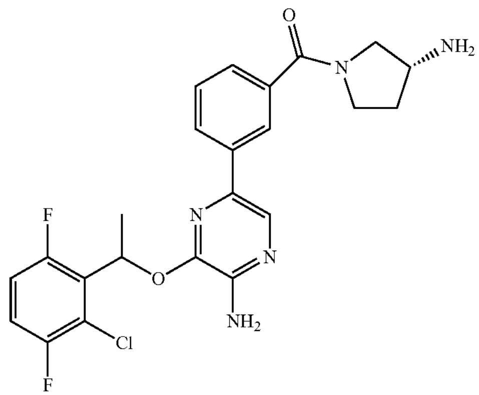 | (3-{5-Amino-6-[1-(2-chloro-3,6-difluoro-phenyl)-ethoxy]-pyrazin-2-yl}-phenyl)-((R)-3-amino-pyrrolidin-1-yl)-methanone | 4 as in Example II-90 | (300 MHZ, CDCl3) δ 8.02 (s, 1H), 7.83 (m, 2H), 7.40 (m, 2H), 6.98 (m, 2H), 6.70 (d, 1H), 4.98 (s, 2H), 3.75 (m, 4H), 3.61–3.15 (m, 1H), 2.15 (m, 1H), 1.85 (d, 3H), 1.95–1.75 (m, 3H). | 300 |
| II-107 | 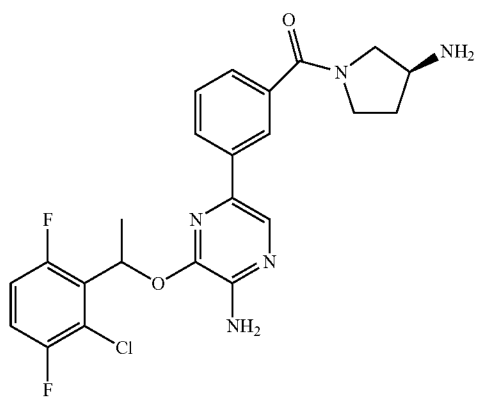 | (3-{5-Amino-6-[1-(2-chloro-3,6-difluoro-phenyl)-ethoxy]-pyrazin-2-yl}-phenyl)-((S)-3-amino-pyrrolidin-1-yl)-methanone | 4 as in Example II-90 | (300 MHZ, CDCl3) δ 8.02 (s, 1H), 7.83 (m, 2H), 7.40 (m, 2H), 6.98 (m, 2H), 6.70 (d, 1H), 4.98 (s, 2H), 3.75 (m, 4H), 3.61–3.15 (m, 1H), 2.15 (m, 1H), 1.85 (d, 3H), 1.95–1.75 (m, 3H). | 300 |

TABLE 4-continued

| No. | Structure | (μM) | Met IC$_{50}$ Procedure | $^1$H-NMR | MS m/z (M + 1) |
|---|---|---|---|---|---|
| II-108 | 4-{5-Amino-6-[1-(2-chloro-3,6-difluoro-phenyl)-ethoxy]-pyrazin-2-yl}-benzoic acid | | 3 as in Example I-211 | | 406 |
| II-109 | 4-{5-Amino-6-[1-(2-chloro-3,6-difluoro-phenyl)-ethoxy]-pyrazin-2-yl}-N-(3-pyrrolidin-1-yl-propyl)-benzamide | 0.1 | 4 as in Example II-109 | (300 MHZ, CDCl3) δ 8.28 (bm, 1H), 8.04 (m, 3H), 7.84 (d, 2H), 6.95 (m, 2H), 6.71 (d, 1H), 5.03 (s, 2H), 3.85 (m, 2H), 3.72 (m, 2H), 3.18 (m, 2H), 2.82 (m, 2H), 2.25 (m, 4H), 2.08 (m, 2H), 1.87 (d, 3H). | 516 |

TABLE 4-continued

| No. | Structure | (μM) | Met IC$_{50}$ Procedure | $^1$H-NMR | MS m/z (M+1) |
|---|---|---|---|---|---|
| II-110 | (4-{5-Amino-6-[1-(2-chloro-3,6-difluoro-phenyl)-ethoxy]-pyrazin-2-yl}-phenyl)-(4-methyl-piperazin-1-yl)-methanone | 0.16 | 4 as in Example II-109 | (300 MHZ, CDCl3) δ 7.99 (s, 1H), 7.78 (d, 2H), 7.43 (d, 2H), 7.29 (m, 1H), 6.85 (t, 1H), 6.94 (q, 1H0, 5.07 (s, 2H), 3.75 (m, 2H), 3.50 (m, 2H), 2.43 (m, 4H), 2.33 (s, 3H), 1.84 (d, 3H). | 488 |
| II-111 | (4-{5-Amino-6-[1-(2-chloro-3,6-difluoro-phenyl)-ethoxy]-pyrazin-2-yl}-phenyl)-(4-pyrrolidin-1-yl-piperidin-1-yl)-methanone | 0.17 | 4 as in Example II-109 | (300 MHZ, CDCl3) δ 8.02 (s, 1H), 7.81 (d, 2H), 7.40 (d, 2H), 6.99 (m, 2H), 6.71 (q, 1H), 5.02 (s, 2H), 4.64 (m, 1H), 3.65 (m, 1H), 2.99 (m, 2H), 2.67 (m, 4H), 2.38 (m, 1H), 1.90 (m, 9H), 1.62 (m, 2H). | 542 |

TABLE 4-continued

| No. | Structure | (µM) | Met IC$_{50}$ Procedure | $^1$H-NMR | (M + 1) | MS m/z |
|---|---|---|---|---|---|---|
| II-112 | 4-{5-Amino-6-[1-(2-chloro-3,6-difluoro-phenyl)-ethoxy]-pyrazin-2-yl}-phenyl)-[(3R,5S)-3,5-dimethyl-piperazin-1-yl]-methanone | 0.19 | 4 as in Example II-109 | (300 MHZ, CDCl3) δ 8.02 (s, 1H), 7.81 (d, 2H), 7.38 (d, 2H), 6.99 (m, 2H), 6.71 (q, 1H), 4.99 (s, 2H), 4.65 (m, 1H), 3.65 (m, 1H), 2.88 (m, 2H), 2.68 (m, 1H), 2.41 (m, 1H), 1.84 (d, 3H), 1.64 (m, 1H), 1.18 (s, 3H), 1.06 (s, 3H). | | 502 |
| II-113 | (4-{5-Amino-6-[1-(2-chloro-3,6-difluoro-phenyl)-ethoxy]-pyrazin-2-yl}-phenyl)-((S)-2-pyrrolidin-1-ylmethyl-pyrrolidin-1-yl)-methanone | 0.18 | 4 as in Example II-109 | (300 MHZ, CDCl3) δ 8.07 (s, 1H), 7.81 (d, 2H), 7.53 (d, 2H), 6.95 (m, 2H), 6.69 (q, 1H), 4.99 (s, 2H), 4.45 (m, 1H), 3.55 (m, 2H), 2.95 (m, 4H), 1.90–2.3 (m, 9H),1.82 (d, 3H), 1.65 (m, 1H). | | 542 |

TABLE 4-continued

| No. | Structure | (μM) | Met IC$_{50}$ Procedure | $^1$H-NMR | (M+1) | MS m/z |
|---|---|---|---|---|---|---|
| II-114 | (4-{5-Amino-6-[1-(2-chloro-3,6-difluoro-phenyl)-ethoxy]-pyrazin-2-yl}-phenyl)-((R)-2-pyrrolidin-1-ylmethyl-pyrrolidin-1-yl)-methanone | 0.13 | 4 as in Example II-109 | (300 MHZ, CDCl3) δ 8.02 (s, 1H), 7.81 (d, 2H), 7.53 (d, 2H), 6.95 (m, 2H), 6.69 (d, 1H), 4.99 (s, 2H), 4.45 (m, 1H), 3.55 (m, 2H), 2.95 (m, 4H), 2.21 (m, 3H), 1.92 (m, 6H), 1.82 (d, 3H), 1.59 (m, 1H). | | 542 |
| II-115 | (4-{5-Amino-6-[1-(2-chloro-3,6-difluoro-phenyl)-ethoxy]-pyrazin-2-yl}-phenyl)-((R)-3-amino-pyrrolidin-1-yl)-methanone | 0.078 | 4 as in Example II-109 | (300 MHZ, CD$_3$OD) δ 8.02 (s, 1H), 7.81 (d, 2H), 7.53 (d, 2H), 7.01 (m, 2H), 6.69 (q, 1H), 4.91 (s, 2H), 3.85 (m, 1H), 3.71 (m, 2H), 3.55 (m, 1H), 2.18 (m, 1H), 1.85 (d, 3H), 1.75 (m, 1H), 1.42 (m, 3H). | | 574 |

TABLE 4-continued
| No. | Structure | (μM) | Met IC₅₀ Procedure | ¹H-NMR | MS m/z (M + 1) |
|---|---|---|---|---|---|
| II-116 | 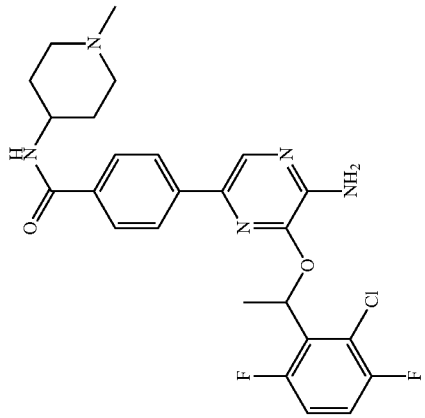4-{5-Amino-6-[1-(2-chloro-3,6-difluoro-phenyl)-ethoxy]-pyrazin-2-yl}-N-(1-methyl-piperidin-4-yl)-benzamide | 0.19 | 4 as in Example II-109 | (300 MHZ, CDCl3) δ 8.06 (s, 1H), 7.82 (m, 4H), 7.00 (m, 2H), 6.72 (m, 2H), 5.04 (s, 2H), 4.09 (m, 1H), 2.97 (m, 2H), 2.39 (s, 3H), 2.29 (m, 2H), 2.12 (m, 2H), 1.90 (d, 3H), 1.79 (m, 2H). | 502 |
| II-117 | 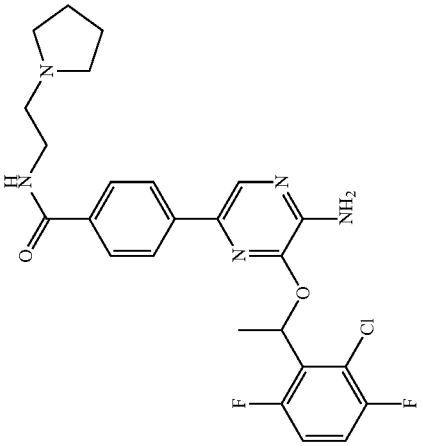4-{5-Amino-6-[1-(2-chloro-3,6-difluoro-phenyl)-ethoxy]-pyrazin-2-yl}-N-(2-pyrrolidin-1-yl-ethyl)-benzamide | 0.11 | 4 as in Example II-109 | (300 MHZ, CDCl3) δ 8.06 (s, 1H), 7.82 (m, 4H), 7.00 (m, 2H), 6.72 (m, 2H), 5.04 (s, 2H), 3.68 (m, 2H), 2.88 (m, 2H), 2.68 (m, 4H), 1.86 (m, 7H). | 502 |

TABLE 4-continued

| No. | Structure (µM) | Met IC$_{50}$ Procedure | $^1$H-NMR | MS m/z (M + 1) |
|---|---|---|---|---|
| II-118 | 4-{5-Amino-6-[1-(2-chloro-3,6-difluoro-phenyl)-ethoxy]-pyrazin-2-yl}-N-(2-morpholin-4-yl-ethyl)-benzamide | 0.26 | 4 as in Example II-109 | (300 MHZ, CDCl3) δ 8.06 (s, 1H), 7.82 (m, 4H), 7.00 (m, 2H), 6.72 (m, 2H), 5.04 (s, 2H), 3.75 (m, 4H), 3.56 (m, 2H), 2.62 (t, 2H), 2.52 (m, 4H), 1.83 (d, 3H). | 518 |
| II-119 | N-[2-(4-Acetyl-piperazin-1-yl)-ethyl]-4-(5-amino-6-[1-(2-chloro-3,6-difluoro-phenyl)-ethoxy]-pyrazin-2-yl}-benzamide | 0.48 | 4 as in Example II-109 | (300 MHZ, CDCl3) δ 8.06 (s, 1H), 7.82 (m, 4H), 7.00 (m, 2H), 6.70 (m, 2H), 5.03 (s, 2H), 3.62 (m, 4H), 3.50 (m, 2H), 2.65 (t, 2H), 2.52 (m, 4H), 2.10 (s, 3H), 1.83 (d, 3H). | 559 |

TABLE 4-continued

| No. | Structure (μM) | Met IC₅₀ Procedure | ¹H-NMR | (M + 1) | MS m/z |
|---|---|---|---|---|---|
| II-120 | 2-[4-(2-Hydroxy-acetyl)-piperazin-1-yl]-ethanesulfonic acid (4-{5-amino-6-[1-(2-chloro-3,6-difluoro-phenyl)-ethoxy]-pyrazin-2-yl}-phenyl)-amide | 0.19 | 3 as in Example I-243 | (300 MHZ, CDCl3) δ 7.96 (s, 1H), 7.75 (d, 2H), 7.24 (m, 3H), 7.08 (m, 1H), 6.95 (m, 1H), 6.70 (q, 1H), 5.02 (s, 2H), 4.14 (s, 2H), 3.64 (m, 3H), 3.25 (m, 4H), 2.91 (m, 2H), 2.44 (m, 4H), 1.83 (d, 3H). | 611 |
| II-121 | 3-[5-Amino-6-(3-fluoro-2-trifluoromethyl-benzyloxy)-pyrazin-2-yl]-benzoic acid | | 3 as in Example I-211 | | 408 |

TABLE 4-continued

| No. | Structure | (μM) | Met IC$_{50}$ Procedure | $^1$H-NMR | MS m/z (M + 1) |
|---|---|---|---|---|---|
| II-122 | {3-[5-Amino-6-(3-fluoro-2-trifluoromethyl-benzyloxy)-pyrazin-2-yl]-phenyl}-(4-pyrrolidin-1-yl-piperidin-1-yl)-methanone 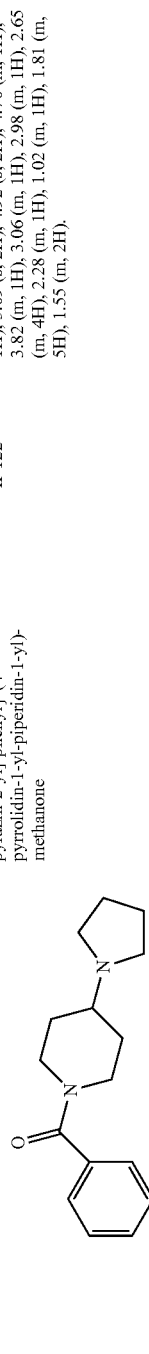 | 0.19 | 4 as in Example II-122 | (300 MHZ, CDCl3) δ 8.09 (s, 1H), 7.88 (m, 2H), 7.56 (m, 1H), 7.44 (t, 1H), 7.34 (d, 1H), 7.21 (t, 1H), 5.69 (s, 2H), 4.92 (s, 2H), 4.70 (m, 1H), 3.82 (m, 1H), 3.06 (m, 1H), 2.98 (m, 1H), 2.65 (m, 4H), 2.28 (m, 1H), 1.02 (m, 1H), 1.81 (m, 5H), 1.55 (m, 2H). | 544 |
| II-123 | 3-[5-Amino-6-(3-fluoro-2-trifluoromethyl-benzyloxy)-pyrazin-2-yl]-N-{2-[ethyl-(2-methoxy-ethyl)-amino]-ethyl}-benzamide  | 0.45 | 4 as in Example II-122 | (300 MHZ, CDCl3) δ 8.34 (s, 1H), 8.14 (s, 1H), 8.01 (d, 1H), 7.68 (d, 1H), 7.53 (m, 1H), 7.50 (t, 1H), 7.45 (d, 1H), 7.21 (t, 1H), 6.79 (bm, 1H), 5.72 (s, 2H), 4.92 (s, 2H), 3.72 (m, 4H), 3.61 (m, 2H), 2.65 (m, 2H), 2.55 (m, 4H). | 520 |

TABLE 4-continued
| No. | Structure | (μM) | Met IC50 Procedure | 1H-NMR | MS m/z (M + 1) |
|---|---|---|---|---|---|
| II-124 | {3-[5-Amino-6-(3-fluoro-2-trifluoromethyl-benzyloxy)-pyrazin-2-yl]-phenyl}-(4-methyl-piperazin-1-yl)-methanone 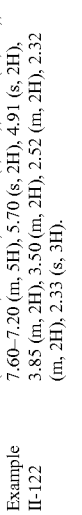 | 0.23 | 4 as in Example II-122 | (300 MHZ, CDCl3) δ 8.10 (s, 1H), 7.90 (m, 2H), 7.60–7.20 (m, 5H), 5.70 (s, 2H), 4.91 (s, 2H), 3.85 (m, 2H), 3.50 (m, 2H), 2.52 (m, 2H), 2.32 (m, 2H), 2.33 (s, 3H). | 490 |
| II-125 | 3-[5-Amino-6-(3-fluoro-2-trifluoromethyl-benzyloxy)-pyrazin-2-yl]-N-(3-pyrrolidin-1-yl-propyl)-benzamide 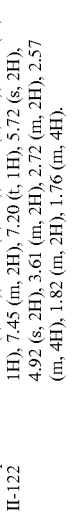 | 0.22 | 4 as in Example II-122 | (300 MHZ, CDCl3) δ 8.85 (bm, 1H), 8.34 (s, 1H), 8.13 (s, 1H), 7.95 (d, 1H), 7.80 (d, 1H), 7.56 (m, 1H), 7.45 (m, 2H), 7.20 (t, 1H), 5.72 (s, 2H), 4.92 (s, 2H), 3.61 (m, 2H), 2.72 (m, 2H), 2.57 (m, 4H), 1.82 (m, 2H), 1.76 (m, 4H). | 518 |

| No. | Structure | (μM) | Met IC$_{50}$ Procedure | $^1$H-NMR | MS m/z (M+1) |
|---|---|---|---|---|---|
| II-126 | N-[2-(4-Acetyl-piperazin-1-yl)-ethyl]-5-[5-amino-6-(3-fluoro-2-trifluoromethyl-benzyloxy)-pyrazin-2-yl]-benzamide | 0.65 | 4 as in Example II-122 | (300 MHZ, CDCl3) δ 8.28 (s, 1H), 8.14 (s, 1H), 7.99 (d, 1H), 7.67 (d, 1H), 7.58 (m, 1H), 7.52 (t, 1H), 7.42 (d, 1H), 7.22 (t, 1H), 6.75 (bm, 1H), 5.72 (s, 2H), 4.95 (s, 2H), 3.62 (m, 4H), 3.47 (m, 2H), 2.63 (m, 2H), 2.52 (m, 4H), 2.08 (s, 3H). | 561 |
| II-127 | {4-[5-Amino-6-(3-fluoro-2-trifluoromethyl-benzyloxy)-pyrazin-2-yl]-phenyl}-(4-pyrrolidin-1-yl-piperidin-1-yl)-methanone | 0.047 | 4 as in Example II-94 | (300 MHZ, CDCl3) δ 8.10 (s, 1H), 7.88 (d, 2H), 7.52 (m, 1H), 7.44 (d, 2H), 7.42 (m, 1H), 7.20 (t, 1H), 5.71 (s, 2H), 5.05 (s, 2H), 4.62 (m, 1H), 3.82 (m, 1H), 3.06 (m, 1H), 2.98 (m, 1H), 2.65 (m, 4H), 2.28 (m, 1H), 1.02 (m, 1H), 1.81 (m, 5H), 1.55 (m, 2H). | 544 |

TABLE 4-continued

| No. | Structure | (μM) | Met IC50 Procedure | 1H-NMR | (M + 1) | MS m/z |
|---|---|---|---|---|---|---|
| II-128 | {4-[5-Amino-6-(3-fluoro-2-trifluoromethyl-benzyloxy)-pyrazin-2-yl]-phenyl}-(4-methyl-piperazin-1-yl)-methanone | 0.15 | 4 as in Example II-94 | (300 MHZ, CDCl3) δ 8.08 (s, 1H), 7.88 (d, 2H), 7.55–7.40 (m, 4H), 7.21 (t, 1H), 5.72 (s, 2H), 5.01 (s, 2H), 3.82 (m, 2H), 3.50 (m, 2H), 2.50 (m, 2H), 2.32 (m, 2H), 2.33 (s, 3H). | | 490 |
| II-129 | {4-[5-Amino-6-(3-fluoro-2-trifluoromethyl-benzyloxy)-pyrazin-2-yl]-phenyl}-((S)-2-pyrrolidin-1-ylmethyl-pyrrolidin-1-yl)-methanone | 0.052 | 4 as in Example II-94 | (300 MHZ, CDCl3) δ 8.11 (s, 1H), 7.88 (d, 2H), 7.68 (m, 3H), 7.42 (d, 1H), 7.22 (t, 1H), 5.72 (s, 2H), 4.92 (s, 2H), 3.50 (m, 2H), 3.74 (m, 4H), 1.84 (d, 3H), 1.57-2.18 (m, 11H). | | 544 |

TABLE 4-continued

| No. | Structure | (μM) | Met IC$_{50}$ Procedure | $^1$H-NMR | MS m/z (M + 1) |
|---|---|---|---|---|---|
| II-130 | (3-{5-Amino-6-[1-(2,6-dichloro-3-fluoro-phenyl)-ethoxy]-pyrazin-2-yl}-phenyl)-(4-methyl-piperazin-1-yl)-methanone | 0.17 | 4 as in Example II-84 | (300 MHZ, CDCl3) δ 8.02 (s, 1H), 7.79 (m, 2H), 7.40 (t, 1H), 7.29 (m, 1H), 7.01 (t, 1H), 6.81 (q, 1H), 5.06 (s, 2H), 3.85 (m, 2H), 3.46 (m, 2H), 2.51 (m, 2H), 2.35 (m, 2H), 2.33 (s, 3H), 1.84 (d, 3H). | 506 |
| II-131 | (3-{5-Amino-6-[1-(2,6-dichloro-3-fluoro-phenyl)-ethoxy]-pyrazin-2-yl}-phenyl)-((3R,5S)-3,5-dimethyl-piperazin-1-yl)-methanone | 0.12 | 4 as in Example II-84 | (300 MHZ, CDCl3) δ 8.02 (s, 1H), 7.78 (m, 2H), 7.39 (t, 1H), 7.24 (m, 1H), 7.01 (t, 1H), 6.81 (q, 1H), 5.07 (s, 2H), 4.71 (m, 1H), 3.58 (m, 1H), 2.96 (m, 1H), 2.82 (m, 1H), 2.66 (m, 1H), 2.42 (m, 1H), 1.84 (d, 3H), 1.74 (m, 1H), 1.22 (d, 3H), 1.00 (d, 3H). | 518 |

TABLE 4-continued

| No. | Structure | (μM) | Met IC₅₀ Procedure | ¹H-NMR | MS m/z (M+1) |
|---|---|---|---|---|---|
| II-132 | 3-{5-Amino-6-[1-(2,6-dichloro-3-fluoro-phenyl)-ethoxy]-pyrazin-2-yl}-N-(1-methyl-piperidin-4-yl)-benzamide | 0.13 | 4 as in Example II-84 | (300 MHZ, CD₃OD) δ 8.16 (s, 1H), 7.99 (s, 1H), 7.82 (d, 1H), 7.66 (d, 1H), 7.42 (m, 2H), 7.15 (t, 1H), 6.74 (q, 1H), 3.95 (m, 1H), 2.98 (m, 2H), 2.34 (s, 3H), 2.25 (m, 2H), 2.01 (m, 2H), 1.84 (d, 3H), 1.73 (m, 2H). | 520 |
| II-133 | 3-{5-Amino-6-[1-(2,6-dichloro-3-fluoro-phenyl)-ethoxy]-pyrazin-2-yl}-N-(2-pyrrolidin-1-yl-ethyl)-benzamide | 0.17 | 4 as in Example II-84 | (300 MHZ, CD₃OD) δ 8.17 (s, 1H), 7.99 (s, 1H), 7.82 (d, 1H), 7.66 (d, 1H), 7.38 (m, 2H), 7.12 (t, 1H), 6.72 (q, 1H), 3.64 (m, 2H), 2.86 (m, 2H), 2.75 (m, 4H), 2.25 (m, 2H), 2.01 (m, 2H), 1.84 (m, 7H). | 520 |

TABLE 4-continued

| No. | Structure | (μM) | Met IC$_{50}$ Procedure | $^1$H-NMR | MS m/z (M + 1) |
|---|---|---|---|---|---|
| II-134 | 3-{5-Amino-6-[1-(2,6-dichloro-3-fluoro-phenyl)-ethoxy]-pyrazin-2-yl}-N-(2-morpholin-4-yl-ethyl)-benzamide | 0.21 | 4 as in Example II-84 | (300 MHZ, CDCl3) δ 8.13 (s, 1H), 8.03 (s, 1H), 7.85 (d, 1H), 7.67 (d, 1H), 7.42 (t, 1H), 7.28 (dd, 1H), 7.00 (t, 1H), 6.86 (q, 1H), 6.84 (bm, 1H), 5.11 (s, 2H), 3.72 (m, 4H), 3.61 (m, 2H), 2.63 (m, 2H), 2.53 (m, 4H), 1.84 (d, 3H). | 534 |
| II-135 | 3-{5-Amino-6-[1-(2,6-dichloro-3-fluoro-phenyl)-ethoxy]-pyrazin-2-yl}-N-(3-morpholin-4-yl-propyl)-benzamide | 0.26 | 4 as in Example II-84 | (300 MHZ, CDCl3) δ 8.19 (s, 1H), 8.06 (s, 1H), 7.87 (d, 1H), 7.70 (bm, 1H), 7.67 (d, 1H), 7.42 (t, 1H), 7.28 (dd, 1H), 7.01 (t, 1H), 6.86 (q, 1H), 5.11 (s, 2H), 3.64 (m, 6H), 2.54 (m, 2H), 2.48 (m, 4H), 1.84 (m, 5H). | 548 |

TABLE 4-continued

| No. | Structure (μM) | Met IC50 Procedure | 1H-NMR | MS m/z (M + 1) |
|---|---|---|---|---|
| II-136 | (3-{5-Amino-6-[1-(2,6-dichloro-3-fluoro-phenyl)-ethoxy]-pyrazin-2-yl}-phenyl)-(4-cyclopropylamino-piperidin-1-yl)-methanone | 0.15 | 4 as in Example II-84 | 544 |
| II-137 | 3-{5-Amino-6-[1-(2,6-dichloro-3-fluoro-phenyl)-ethoxy]-pyrazin-2-yl}-N-((S)-2-hydroxy-3-morpholin-4-yl-propyl)-benzamide | 0.3 | 4 as in Example II-84 | 564 |

TABLE 4-continued

| No. | Structure | (μM) | Met IC$_{50}$ Procedure | $^1$H-NMR (M + 1) | MS m/z |
|---|---|---|---|---|---|
| II-138 | 3-{5-Amino-6-[1-(2,6-dichloro-3-fluoro-phenyl)-ethoxy]-pyrazin-2-yl}-N-((R)-2-hydroxy-3-pyrrolidin-1-yl-propyl)-benzamide | 0.13 | 4 as in Example II-84 | | 548 |
| II-139 | (3-{6-Amino-5-[1-(2,6-dichloro-3-fluoro-phenyl)-ethoxy]-pyridin-3-yl}-phenyl)-(4-pyrrolidin-1-yl-piperidin-1-yl)-methanone | 0.071 | 4 as in Example II-84 | (300 MHZ, CDCl3) δ 7.86 (s, 1H), 7.41 (m, 3H), 7.30 (m, 3H), 7.07 (t, 1H), 6.99 (s, 1H), 6.12 (q, 1H), 4.95 (s, 2H), 4.70 (m, 1H), 3.82 (m, 1H), 3.06 (m, 1H), 2.98 (m, 1H), 2.65 (m, 4H), 2.28 (m, 1H), 1.02 (m, 1H), 1.81 (m, 5H), 1.55 (m, 2H). | 559 |

TABLE 4-continued

| No. | Structure (μM) | Met IC$_{50}$ Procedure | $^1$H-NMR (M + 1) | MS m/z |
|---|---|---|---|---|
| II-140 | 2-Diethylamino-ethanesulfonic acid (4-{5-amino-6-[1-(2,6-dichloro-3-fluoro-phenyl)-ethoxy]-pyrazin-2-yl}-phenyl)-amide | 0.35 | 3 as in Example I-243 | (300 MHZ, CDCl3) δ 7.89 (s, 1H), 7.70 (d, 2H), 7.28 (m, 2H), 7.21 (d, 2H), 7.01 (t, 1H), 6.82 (q, 1H), 5.05 (s, 2H), 3.22 (m, 2H), 3.00 (m, 2H), 2.55 (m, 4H), 1.83 (d, 3H), 1.60 (d, 6H). | 556 |
| II-141 | 2-(4-Hydroxy-piperidin-1-yl)-ethanesulfonic acid (4-{5-amino-6-[1-(2,6-dichloro-3-fluoro-phenyl)-ethoxy]-pyrazin-2-yl}-phenyl)-amide | 0.21 | 3 as in Example I-243 | (300 MHZ, CDCl3) δ 7.95 (s, 1H), 7.71 (d, 2H), 7.28 (m, 2H), 7.21 (d, 2H), 7.01 (t, 1H), 6.82 (q, 1H), 5.00 (s, 2H), 3.78 (m, 1H), 3.25 (t, 2H), 2.90 (t, 2H), 2.82 (m, 2H), 2.25 (m, 2H), 1.90 (m, 2H), 1.84 (d, 3H), 1.60 (m, 2H). | 584 |

TABLE 4-continued

| No. | Structure | (μM) | Met IC$_{50}$ Procedure | $^1$H-NMR (M + 1) | MS m/z |
|---|---|---|---|---|---|
| II-142 | 2-Dimethylamino-ethanesulfonic acid (4-(5-amino-6-[1-(2,6-dichloro-3-fluoro-phenyl)-ethoxy]-pyrazin-2-yl}-phenyl)-amide | 0.22 | 3 as in Example I-243 | (300 MHZ, CDCl3) δ 7.89 (s, 1H), 7.70 (d, 2H), 7.28 (m, 2H), 7.21 (d, 2H), 7.01 (t, 1H), 6.82 (q, 1H), 5.05 (s, 2H), 3.20 (m, 2H), 2.85 (m, 2H), 2.28 (s, 3H), 1.83 (d, 3H). | 528 |
| II-143 | 2-((R)-3-Hydroxy-pyrrolidin-1-yl)-ethanesulfonic acid (4-{5-amino-6-[1-(2,6-dichloro-3-fluoro-phenyl)-ethoxy]-pyrazin-2-yl}-phenyl)-amide | 0.19 | 3 as in Example I-243 | (300 MHZ, CDCl3) δ 7.93 (s, 1H), 7.69 (d, 2H), 7.27 (m, 4H), 7.00 (t, 1H), 6.84 (q, 1H), 5.03 (s, 2H), 4.43 (m, 1H), 3.25 (m, 2H), 3.02 (m, 3H), 2.84 (m, 1H), 2.53 (m, 1H), 2.30 (m, 1H), 2.22 (m, 1H), 1.84 (d, 3H), 1.81 (m, 1H), | 570 |

| No. | (µM) | Met IC$_{50}$ Procedure | $^1$H-NMR | MS m/z (M + 1) |
|---|---|---|---|---|
| II-144 | 2-Pyrrolidin-1-ylethanesulfonic acid (4-{5-amino-6-[1-(2,6-dichloro-3-fluoro-phenyl)-ethoxy]-pyrazin-2-yl}-phenyl)-amide | 0.36 | 3 as in Example I-243 | (300 MHZ, CDCl3) δ 7.94 (s, 1H), 7.69 (d, 2H), 7.27 (m, 2H), 7.19 (d, 2H), 7.04 (t, 1H), 6.82 (q, 1H), 5.01 (s, 2H), 3.28 (m, 2H), 3.08 (m, 2H), 2.60 (m, 4H), 1.88 (m, 7H). | 554 |
| II-145 | 4-{5-Amino-6-[1-(2,6-dichloro-3-fluoro-phenyl)-ethoxy]-pyrazin-2-yl}-benzoic acid | 1.56 | 3 as in Example I-211 | | 422 |

TABLE 4-continued
| No. | Structure (µM) | Met IC$_{50}$ Procedure | $^1$H-NMR | MS m/z (M + 1) |
|---|---|---|---|---|
| II-146 | 4-{5-Amino-6-[1-(2,6-dichloro-3-fluoro-phenyl)-ethoxy]-pyrazin-2-yl}-N-((R)-2-hydroxy-3-pyrrolidin-1-yl-propyl)-benzamide  TFA | 0.15 | 4 as in Example II-146 | 548 |
| II-147 | (4-{5-Amino-6-[1-(2,6-dichloro-3-fluoro-phenyl)-ethoxy]-pyrazin-2-yl}-phenyl)-(4-cyclopropylamino-piperidin-1-yl)-methanone 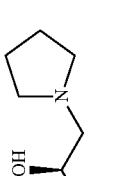 | 0.13 | 4 as in Example II-146 | 544 |

TABLE 4-continued
| No. | Structure | (μM) | Met IC$_{50}$ Procedure | $^1$H-NMR | MS m/z (M + 1) |
|---|---|---|---|---|---|
| II-148 | 4-{5-Amino-6-[1-(2,6-dichloro-3-fluoro-phenyl)-ethoxy]-pyrazin-2-yl}-N-((S)-2-hydroxy-3-pyrrolidin-1-yl-propyl)-benzamide  TFA | 0.12 | 4 as in Example II-146 | | 548 |
| II-149 | 4-{5-Amino-6-[1-(2,6-dichloro-3-fluoro-phenyl)-ethoxy]-pyrazin-2-yl}-N-((R)-2-hydroxy-3-morpholin-4-yl-propyl)-benzamide  | 0.13 | 4 as in Example II-146 | | 564 |

TABLE 4-continued

| No. | Structure (μM) | Met IC$_{50}$ Procedure | $^1$H-NMR (M+1) | MS m/z |
|---|---|---|---|---|
| II-150 | 4-{5-Amino-6-[1-(2,6-dichloro-3-fluoro-phenyl)-ethoxy]-pyrazin-2-yl}-N-(1-methyl-piperidin-4-yl)-benzamide | 0.068 | 4 as in Example II-146 | (300 MHZ, CDCl3) δ 8.01 (s, 1H), 7.78 (m, 4H), 7.28 (m, 1H), 6.95 (t, 1H), 6.80 (q, 1H), 5.95 (bd, 1H), 5.07 (s, 2H), 4.05 (m, 1H), 2.85 (m, 2H), 2.32 (s, 3H), 2.21 (m, 2H), 2.08 (m, 2H), 1.85 (d, 3H), 1.68 (m, 2H). | 518 |
| II-151 | (4-{5-Amino-6-[1-(2,6-dichloro-3-fluoro-phenyl)-ethoxy]-pyrazin-2-yl}-phenyl)-((S)-2-pyrrolidin-1-ylmethyl-pyrrolidin-1-yl)-methanone | 0.18 | 4 as in Example II-146 | (300 MHZ, CDCl3) δ 8.00 (d, 1H), 7.75 (d, 2H), 7.51 (d, 2H), 7.28 (m, 1H), 7.00 (t, 1H), 6.90 (q, 1H), 5.05 (s, 2H), 4.45 (m, 2H), 3.41 (m, 2H), 2.70 (m, 4H), 1.84 (d, 3H), 1.70–2.0 (m, 10H) | 558 |

| No. | Structure | (μM) | Met IC₅₀ Procedure | ¹H-NMR (M + 1) | MS m/z |
|---|---|---|---|---|---|
| II-152 | (4-{5-Amino-6-[1-(2,6-dichloro-3-fluoro-phenyl)-ethoxy]pyrazin-2-yl}-phenyl)-(4-pyrrolidin-1-yl-piperidin-1-yl)-methanone | 0.11 | 4 as in Example II-146 | (300 MHZ, CDCl3) δ 7.00 (s, 1H), 7.75 (d, 2H), 7.40 (d, 2H), 7.28 (m, 1H), 6.99 (t, 1H), 6.76 (q, 1H), 5.04 (s, 2H), 4.64 (m, 1H), 3.84 (m, 1H), 3.02 (m, 2H), 2.60 (m, 4H), 2.30 (m, 1H), 1.92 (m, 1H), 1.81 (m, 6H), 1.69 (m, 2H), 1.62 (m, 2H). | 558 |
| II-153 | 4-{5-Amino-6-[1-(2,6-dichloro-3-fluoro-phenyl)-ethoxy]-pyrazin-2-yl}-N-(2-morpholin-4-yl-ethyl)-benzamide | 0.102 | 4 as in Example II-146 | (300 MHZ, CDCl3) δ 8.05 (s, 1H), 7.79 (m, 5H), 7.25 (m, 1H), 6.95 (t, 1H), 6.83 (q, 1H), 5.10 (s, 2H), 3.74 (m, 4H), 3.49 (m, 2H), 2.63 (m, 2H), 2.52 (m, 4H), 1.85 (d, 3H). | 536 |

TABLE 4-continued

| No. | Structure | (μM) | Met IC$_{50}$ Procedure | $^1$H-NMR | MS m/z (M + 1) |
|---|---|---|---|---|---|
| II-154 | (4-{5-Amino-6-[1-(2,6-dichloro-3-fluoro-phenyl)-ethoxy]-pyrazin-2-yl}-phenyl)-(4-methyl-piperazin-1-yl)-methanone | 0.16 | 4 as in Example II-146 | (300 MHZ, CDCl3) δ 7.99 (s, 1H), 7.78 (d, 2H), 7.43 (d, 2H), 7.29 (m, 1H), 6.85 (t, 1H), 6.94 (q, 1H), 5.07 (s, 2H), 3.75 (m, 2H), 3.50 (m, 2H), 2.43 (m, 4H), 2.33 (s, 3H), 1.84 (d, 3H). | 506 |
| II-155 | (4-{5-Amino-6-[1-(2,6-dichloro-3-fluoro-phenyl)-((3R,5S)-3,5-dimethyl-piperazin-1-yl)-methanone | 0.095 | 4 as in Example II-146 | (300 MHZ, CDCl3) δ 8.02 (s, 1H), 7.79 (d, 2H), 7.40 (d, 2H), 7.28 (m, 1H), 6.98 (t, 1H), 6.84 (q, 1H), 5.04 (s, 2H), 4.65 (m, 1H), 3.56 (m, 1H), 2.85 (m, 2H), 2.70 (m, 1H), 2.44 (m, 1H), 1.84 (d, 3H), 1.65 (m, 1H), 1.13 (m, 3H), 1.00 (m, 3H). | 518 |

TABLE 4-continued

| No. | Structure | (μM) | Met IC$_{50}$ Procedure | $^1$H-NMR | MS m/z (M + 1) |
|---|---|---|---|---|---|
| II-156 | 4-{5-Amino-6-[1-(2,6-dichloro-phenyl)-ethoxy]-pyrazin-2-yl}-benzoic acid | | 3 | as in Example I-211 | 404 |
| II-157 | (4-{5-Amino-6-[1-(2,6-dichloro-phenyl)-ethoxy]-pyrazin-2-yl}-phenyl)-(4-pyrrolidin-1-yl-piperidin-1-yl)-methanone | 0.16 | 4 | as in Example II-157 | (300 MHZ, CDCl3) δ 8.05 (s, 1H), 7.82 (d, 2H), 7.50 (d, 2H), 7.31 (d, 2H), 7.15 (t, 1H), 6.90 (q, 1H), 5.05 (s, 2H), 2.98 (br, 2H), 2.60 (s, 4H), 2.25 (br, 2H), 1.89 (d, 3H), 1.2–1.98 (br, 8H). | 540 |

TABLE 4-continued

| No. | Structure | (μM) | Met IC$_{50}$ Procedure | $^1$H-NMR (M + 1) | MS m/z |
|---|---|---|---|---|---|
| II-158 | 4-{5-Amino-6-[1-(2,6-dichloro-phenyl)-ethoxy]-pyrazin-2-yl}-N-(2-morpholin-4-yl-ethyl)-benzamide | 0.32 | 4 as in Example II-157 | (300 MHZ, CDCl3) δ 8.16 (s, 1H), 7.89 (d, 2H), 7.75 (d, 2H), 7.32 (m, 2H), 7.15 (t, 1H), 6.91 (q, 1H), 6.78 (m, 1H), 5.10 (s, 2H), 3.74 (m, 4H), 3.63 (m, 2H), 2.65 (m, 2H), 2.54 (m, 4H), 1.85 (d, 3H). | 516 |
| II-159 | (4-{5-Amino-6-[1-(2,6-dichloro-phenyl)-ethoxy]-pyrazin-2-yl}-phenyl)-((3R,5S)-3,5-dimethyl-piperazin-1-yl)-methanone | 0.14 | 4 as in Example II-157 | (300 MHZ, CDCl3) δ 8.05 (s, 1H), 7.82 (d, 2H), 7.50 (d, 2H), 7.31 (d, 2H), 7.15 (t, 1H), 6.90 (q, 1H), 2.70 (m, 4H), 1.89 (d, 3H), 0.8–1.2 (br, 6H). | 500 |

TABLE 4-continued

| No. | Structure | (µM) | Met IC$_{50}$ Procedure | $^1$H-NMR | MS m/z (M+1) |
|---|---|---|---|---|---|
| II-160 | | 4-{5-Amino-6-[1-(2,6-dichloro-phenyl)-ethoxy]-pyrazin-2-yl}-N-(1-methyl-piperidin-4-yl)-benzamide | 0.12 | 4 as in Example II-157 | (300 MHZ, CDCl3) δ 8.16 (s, 1H), 7.90 (d, 2H), 7.83 (d, 2H), 7.32 (t, 2H), 7.16 (t, 1H), 6.84 (q, 1H), 6.00 (d, 1H), 5.08 (s, 2H), 4.05 (m, 1H), 2.81 (m, 2H), 2.35 (s, 3H), 2.21 (m, 2H), 2.08 (m, 2H), 1.84 (d, 3H), 1.60 (m, 2H). | 500 |
| II-161 | | (4-{5-Amino-6-[1-(2,6-dichloro-phenyl)-ethoxy]-pyrazin-2-yl}-phenyl)-((R)-2-pyrrolidin-1-ylmethyl-pyrrolidin-1-yl)-methanone | 0.16 | 4 as in Example II-157 | (300 MHZ, CDCl3) δ 8.05 (s, 1H), 7.62 (d, 2H), 7.50 (d, 2H), 7.26 (d, 2H), 7.15 (t, 1H), 6.90 (q, 1H), 5.05 (s, 2H), 4.30 (t, 1H), 3.50 (m, 2H), 2.65 (m, 4H), 1.86 (d, 3H), 1.70–2.0 (m, 10H). | 542 |

TABLE 4-continued

| No. | Structure | (μM) | Met IC$_{50}$ Procedure | $^1$H-NMR | (M + 1) | MS m/z |
|---|---|---|---|---|---|---|
| II-162 | (4-{5-Amino-6-[1-(2,6-dichloro-phenyl)-ethoxy]-pyrazin-2-yl}-phenyl)-((S)-2-pyrrolidin-1-ylmethyl-pyrrolidin-1-yl)-methanone | 0.14 | 4 as in Example II-157 | (300 MHZ, CDCl3) δ 8.05 (s, 1H), 7.82 (d, 2H), 7.50 (d, 2H), 7.31 (d, 2H), 7.15 (t, 1H), 6.90 (q, 1H), 5.05 (s, 2H), 4.45 (m, 1H), 3.41 (m, 2H), 2.70 (m, 4H), 1.86 (d, 3H), 1.70–2.0 (m, 10H) | | 542 |
| II-163 | (4-{5-Amino-6-[1-(2,6-dichloro-phenyl)-ethoxy]-pyrazin-2-yl}-phenyl)-(4-methyl-piperazin-1-yl)-methanone | 0.15 | 4 as in Example II-157 | (300 MHZ, CDCl3) δ 8.05 (s, 1H), 7.82 (d, 2H), 7.50 (d, 2H), 7.31 (d, 2H), 7.15 (t, 1H), 6.90 (q, 1H), 5.05 (s, 2H), 3.60 (m, 4H), 2.45 (m, 4H), 2.31 (s, 3H), 1.89 (d, 3H) | | 486 |

TABLE 4-continued
| No. | Structure | (μM) | Met IC50 Procedure | 1H-NMR | (M + 1) MS m/z |
|---|---|---|---|---|---|
| II-164 | 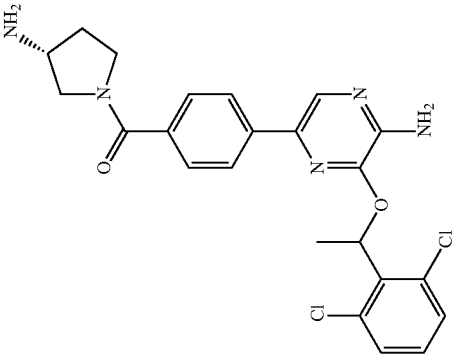 (4-{5-Amino-6-[1-(2,6-dichloro-phenyl)-ethoxy]-pyrazin-2-yl}-phenyl)-((R)-3-aminopyrrolidin-1-yl)-methanone | 0.15 | 4 as in Example II-157 | (300 MHZ, CD3OD) δ 7.89 (m, 3H), 7.60 (m, 2H), 7.40 (m, 2H), 7.25 (m, 1H), 6.74 (m, 1H), 4.90 (s, 2H), 4.05–3.60 (m, 4H), 3.50 (m, 2H), 2.50 (m, 1H), 2.18 (m, 1H), 1.90 (d, 3H). | 472 |
| II-165 | 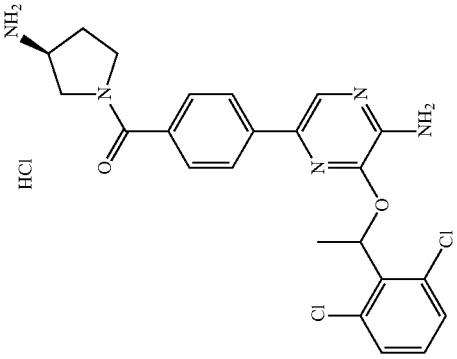 (4-{5-Amino-6-[1-(2,6-dichloro-phenyl)-ethoxy]-pyrazin-2-yl}-phenyl)-((S)-3-aminopyrrolidin-1-yl)-methanone hydrogen chloride | 0.1 | 4 as in Example II-157 | (300 MHZ, CD3OD) δ 7.89 (m, 3H), 7.60 (m, 2H), 7.40 (m, 2H), 7.25 (m, 1H), 6.74 (m, 1H), 4.90 (s, 2H), 4.05–3.60 (m, 4H), 3.50 (m, 2H), 2.50 (m, 1H), 2.18 (m, 1H), 1.90 (d, 3H). | 472 |

TABLE 4-continued

| No. | Structure | (μM) | Met IC$_{50}$ Procedure | $^1$H-NMR | MS m/z (M + 1) |
|---|---|---|---|---|---|
| II-166 | 4-{5-Amino-6-[1-(2,6-dichloro-phenyl)-ethoxy]-pyrazin-2-yl}-N-(2-pyrrolidin-1-yl-ethyl)-benzamide | 0.11 | 4 as in Example II-157 | (300 MHZ, CDCl3) δ 8.01 (s, 1H), 7.80 (m, 4H), 7.31 (dt, 2H), 7.16 (t, 1H), 6.84 (m, 2H), 5.04 (s, 2H), 3.55 (m, 2H), 2.71 (m, 2H), 2.57 (m, 4H), 1.84 (d, 3H), 1.83 (m, 4H). | 502 |
| II-167 | 4-{5-Amino-6-[1-(2,6-dichloro-phenyl)-ethoxy]-pyrazin-2-yl}-N-(3-pyrrolidin-1-yl-propyl)-benzamide | 0.22 | 4 as in Example II-157 | (300 MHZ, CDCl3) δ 8.80 (s, 1H), 8.10 (s, 1H), 7.80 (m, 4H), 7.21 (d, 2H), 7.16 (t, 1H), 6.84 (q, 1H), 5.04 (s, 2H), 3.55 (m, 2H), 2.71 (m, 2H), 2.57 (m, 4H), 1.84 (m, 4H), 1.83 (d, 3H), 1.81 (m, 2H). | 514 |

TABLE 4-continued

| No. | Structure | (μM) | Met IC₅₀ Procedure | ¹H-NMR | MS m/z (M + 1) |
|---|---|---|---|---|---|
| II-168 | 3-{5-Amino-6-[1-(2,6-dichloro-phenyl)-ethoxy]-pyrazin-2-yl}-benzoic acid | | 3 as in Example I-211 | | 404 |
| II-169 | 3-{5-Amino-6-[1-(2,6-dichloro-phenyl)-ethoxy]-pyrazin-2-yl]-N-(1-methyl-piperidin-4-yl)-benzamide | 0.18 | 4 as in Example II-169 | (300 MHZ, CDCl3) δ 8.16 (s, 1H), 8.03 (s, 1H), 7.88 (d, 1H), 7.70 (d, 1H), 7.42 (t, 1H), 7.28 (d, 2H), 7.10 (1, 1H), 6.94 (q, 1H), 6.15 (bd, 1H), 5.08 (s, 2H), 4.05 (m, 1H), 2.91 (m, 2H), 2.35 (s, 3H), 2.21 (m, 2H), 2.08 (m, 2H), 1.84 (d, 3H), 1.68 (m, 2H). | 502 |

TABLE 4-continued

| No. | Structure | (μM) | Met IC$_{50}$ Procedure | $^1$H-NMR | MS m/z (M+1) |
|---|---|---|---|---|---|
| II-170 | 3-{5-Amino-6-[1-(2,6-dichloro-phenyl)-ethoxy]-pyrazin-2-yl}-N-(2-pyrrolidin-1-yl-ethyl)-benzamide | 0.33 | 4 as in Example II-169 | (300 MHZ, CDCl3) δ 8.15 (s, 1H), 8.02 (s, 1H), 7.85 (d, 1H), 7.71 (d, 1H), 7.40 (t, 1H), 7.28 (d, 2H), 7.10 (m, 2H), 6.90 (q, 1H), 5.10 (s, 2H), 3.64 (m, 2H), 2.80 (m, 2H), 2.64 (m, 4H), 1.85 (m, 7H). | 500 |
| II-171 | (3-{5-Amino-6-[1-(2,6-dichloro-phenyl)-ethoxy]-pyrazin-2-yl}-phenyl)-((3R,5S)-3,5-dimethyl-piperazin-1-yl)-methanone | 0.36 | 4 as in Example II-169 | (300 MHZ, CDCl3) δ 8.04 (s, 1H), 7.79 (m, 2H), 7.40 (t, 1H), 7.28 (m, 3H), 7.11 (t, 1H), 6.86 (q, 1H), 5.05 (s, 2H), 4.69 (m, 1H), 2.95 (m, 1H), 2.79 (m, 1H), 2.71 (m, 1H), 2.44 (m, 1H), 1.84 (d, 3H), 1.25 (d, 3H), 1.17 (d, 3H). | 500 |

TABLE 4-continued

| No. | Structure (µM) | Met IC$_{50}$ Procedure | $^1$H-NMR (M + 1) | MS m/z |
|---|---|---|---|---|
| II-172 | 3-{5-Amino-6-[1-(2,6-dichloro-phenyl)-ethoxy]-pyrazin-2-yl}-N-(2-morpholin-4-yl-ethyl)-benzamide | 0.48 | 4 as in Example II-169 | (300 MHZ, CDCl3) δ 8.16 (s, 1H), 8.03 (s, 1H), 7.89 (d, 1H), 7.69 (d, 1H), 7.43 (t, 1H), 7.28 (d, 2H), 7.10 (t, 1H), 6.91 (q, 1H), 6.88 (m, 1H), 5.10 (s, 2H), 3.74 (m, 4H), 3.63 (m, 2H), 2.65 (m, 2H), 2.54 (m, 4H), 1.85 (d, 3H). | 516 |
| II-173 | (3-{5-Amino-6-[1-(2,6-dichloro-phenyl)-ethoxy]-pyrazin-2-yl}-phenyl)-((S)-2-pyrrolidin-1-ylmethyl-pyrrolidin-1-yl)-methanone | 0.18 | 4 as in Example II-169 | (300 MHZ, CDCl3) δ 8.01 (d, 1H), 7.87 (m, 2H), 7.37 (m, 2H), 7.28 (m, 2H), 7.11 (t, 1H), 6.90 (m, 1H), 5.05 (s, 2H), 4.45 (m, 1H), 3.41 (m, 2H), 2.70 (m, 4H), 1.84 (d, 3H), 1.70–2.0 (m, 10H) | 540 |

TABLE 4-continued

| No. | Structure | (µM) | Met IC$_{50}$ Procedure | $^1$H-NMR | (M + 1) | MS m/z |
|---|---|---|---|---|---|---|
| II-174 | (3-[5-Amino-6-[1-(2,6-dichloro-phenyl)-ethoxy]-pyrazin-2-yl]-phenyl)-(4-pyrrolidin-1-yl-piperidin-1-yl)-methanone | 0.17 | 4 as in Example II-169 | (300 MHZ, CDCl3) δ 7.99 (s, 1H), 7.78 (m, 2H), 7.39 (t, 1H), 7.28 (m, 3H), 7.08 (t, 1H), 6.87 (q, 1H), 5.04 (s, 2H), 4.64 (m, 1H), 3.84 (m, 1H), 3.02 (m, 2H), 2.60 (m, 4H), 2.30 (m, 1H), 1.92 (m, 1H), 1.81 (m, 6H), 1.69 (m, 2H), 1.62 (m, 2H). | | 540 |
| II-175 | N-[2-(4-Acetyl-piperazin-1-yl)-ethyl]-4-[5-amino-6-[1-(2,6-dichloro-phenyl)-ethoxy]-pyrazin-2-yl]-benzamide | 0.28 | 4 as in Example II-169 | (300 MHZ, CDCl3) δ 8.06 (s, 1H), 7.89 (d, 2H), 7.75 (d, 2H), 7.31 (dt, 2H), 7.11 (t, 1H), 6.91 (q, 1H), 6.78 (m, 1H), 5.12 (s, 2H), 4.25 (t, 1H), 3.60 (m, 3H), 3.45 (m, 1H), 2.65 (t, 2H), 2.50 (m, 3H), 2.05 (s, 2H), 1.85 (d, 3H). | | 559 |

TABLE 4-continued

| No. | (µM) Structure | Met IC$_{50}$ Procedure | $^1$H-NMR | MS m/z (M + 1) |
|---|---|---|---|---|
| II-176 | N-[2-(4-Acetyl-piperazin-1-yl)-ethyl]-3-{5-amino-6-[1-(2,6-dichloro-phenyl)-ethoxy]-pyrazin-2-yl}-benzamide | 0.35 | 4 as in Example II-169 | (300 MHZ, CDCl3) δ 8.16 (s, 1H), 8.03 (s, 1H), 7.99 (d, 1H), 7.69 (d, 1H), 7.43 (t, 1H), 7.28 (d, 2H), 7.11 (t, 1H), 6.91 (q, 1H), 6.78 (m, 1H), 5.12 (s, 2H), 3.65 (m, 4H), 3.49 (m, 2H), 2.68 (m, 2H), 2.54 (m, 4H), 2.09 (s, 5H), 1.85 (d, 3H). | 559 |
| II-177 | (3-{5-Amino-6-[1-(2,6-dichloro-phenyl)-ethoxy]-pyrazin-2-yl}-phenyl)-(R)-2-pyrrolidin-1-ylmethyl-pyrrolidin-1-yl)-methanone | 0.33 | 4 as in Example II-169 | (300 MHZ, CDCl3) δ 8.01 (d, 1H), 7.87 (m, 2H), 7.37 (m, 2H), 7.28 (m, 2H), 7.11 (t, 1H), 6.90 (m, 1H), 5.05 (s, 2H), 4.45 (m, 1H), 3.41 (m, 2H), 2.70 (m, 4H), 1.64 (d, 3H), 1.70–2.0 (m, 10H) | 540 |

| No. | Structure | (μM) | Met IC$_{50}$ Procedure | $^1$H-NMR | MS m/z (M + 1) |
|---|---|---|---|---|---|
| II-178 | 3-{5-Amino-6-[1-(2,6-dichloro-phenyl)-ethoxy]-pyrazin-2-yl}-N-(3-pyrrolidin-1-yl-propyl)-benzamide | 0.34 | 4 as in Example II-169 | (300 MHZ, CDCl3) δ 8.48 (m, 1H), 8.22 (t, 1H), 8.05 (s, 1H), 7.91 (dt, 1H), 7.66 (d, 1H), 7.40 (t, 1H), 7.28 (d, 2H), 7.10 (t, 1H), 6.94 (q, 1H), 5.04 (s, 2H), 3.62 (m, 2H), 2.71 (m, 2H), 2.57 (m, 4H), 1.84 (d, 3H), 1.83 (m, 2H), 1.81 (m, 4H). | 514 |
| II-179 | (3-{5-Amino-6-[1-(2,6-dichloro-phenyl)-ethoxy]-pyrazin-2-yl}-phenyl)-((S)-3-amino-pyrrolidin-1-yl)-methanone | 0.11 | 4 as in Example II-169 | (300 MHZ, CD$_3$OD) δ 7.83 (m, 2H), 7.48 (m, 3H), 7.37 (m, 2H), 7.23 (m, 1H), 6.74 (m, 1H), 4.05–3.60 (m, 4H), 3.50 (m, 1H), 2.50 (m, 1H), 2.18 (m, 1H), 1.90 (d, 3H). | 472 |

TABLE 4-continued

| No. | Structure | (μM) | Met IC$_{50}$ Procedure | $^1$H-NMR | MS m/z (M + 1) |
|---|---|---|---|---|---|
| II-180 | (3-{5-Amino-6-[1-(2,6-dichloro-phenyl)-ethoxy]-pyrazin-2-yl}-phenyl-((R)-3-amino-pyrrolidin-1-yl)-methanone hydrochloride salt | 0.18 | 4 as in Example II-169 | (300 MHZ, CD$_3$OD) δ 7.83 (m, 3H), 7.48 (m, 2H), 7.37 (m, 2H), 7.23 (m, 1H), 6.74 (m, 1H), 4.05–3.60 (m, 4H), 3.50 (m, 1H), 2.50 (m, 1H), 2.18 (m, 1H), 1.90 (d, 3H). | 472 |
| II-181 | (3-{5-Amino-6-[1-(2,6-dichloro-phenyl)-ethoxy]-pyrazin-2-yl}-phenyl)(4-methyl-piperazin-1-yl)-methanone | 0.25 | 4 as in Example II-169 | (300 MHZ, CDCl3) δ 8.00 (s, 1H), 7.80 (m, 2H), 7.40 (t, 1H), 7.28 (m, 3H), 7.11 (t, 1H), 6.87 (q, 1H), 5.05 (s, 2H), 4.64 (m, 1H), 3.87 (m, 2H), 3.45 (m, 2H), 2.53 (m, 2H), 2.36 (m, 1H), 2.34 (s, 3H), 1.84 (d, 3H). | 486 |

TABLE 4-continued

| No. | Structure | (μM) | Met IC50 Procedure | 1H-NMR | (M + 1) | MS m/z |
|---|---|---|---|---|---|---|
| II-182 |  1-(4-{5-Amino-6-[1-(2-chloro-3,6-difluoro-phenyl)-ethoxy]-pyrazin-2-yl}-phenyl)-3-(2-morpholin-4-yl-ethyl)-urea | 0.18 | 10 as in Example I-371 | (300 MHZ, CDCl3) δ 7.93 (s, 1H), 7.68 (d, 2H), 7.38 (s, 2H), 6.95 (m, 4H), 6.70 (q, 1H), 4.94 (s, 2H), 3.75 (m, 4H), 3.46 (m, 2H), 2.69 (m, 4H), 2.25 (m, 2H), 1.85 (d, 3H). | | 534 |
| II-183 | 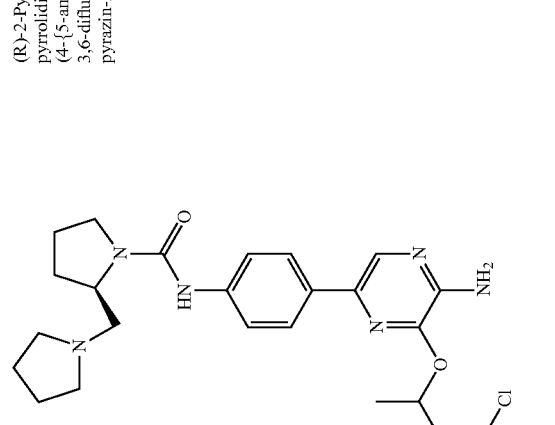 (R)-2-Pyrrolidin-1-ylmethyl-pyrrolidine-1-carboxylic acid (4-{5-amino-6-[1-(2-chloro-3,6-difluoro-phenyl)-ethoxy]-pyrazin-2-yl}-phenyl)-amide | 0.21 | 10 as in Example I-371 | (300 MHZ, CDCl3) δ 7.83 (s, 1H), 7.40 (d, 2H), 7.27 (d, 2H), 6.95 (m, 3H), 5.95 (q, 1H), 4.85 (s, 2H), 3.85 (m, 1H), 3.75 (m, 1H), 3.40 (m, 1H), 2.90 (m, 4H), 2.65 (m, 4H), 2.10 (m, 3H), 1.85 (d, 3H), 1.9–1.7 (m, 3H). | | 557 |

TABLE 4-continued

| No. | Structure | (µM) | Met IC$_{50}$ Procedure | $^1$H-NMR | MS m/z (M + 1) |
|---|---|---|---|---|---|
| II-184 | 1-(4-{5-Amino-6-[1-(2-chloro-3,6-difluoro-phenyl)-ethoxy]-pyrazin-2-yl}-phenyl)-3-(2-pyrrolidin-1-yl-ethyl)-urea | 0.18 | 10 as in Example I-371 | (300 MHZ, CDCl3) δ 7.91 (s, 1H), 7.80 (bs, 1H), 7.69 (d, 2H), 7.46 (d, 2H), 7.35 (bm, 1H), 7.05 (m, 2H), 6.72 (q, 1H), 4.86 (s, 2H), 3.58 (m, 2H), 3.19 (m, 4H), 3.12 (m, 2H), 2.16 (m, 4H), 2.51 (s, 3H), 1.81 (d, 3H). | 517 |
| II-185 | 4-Methyl-piperazine-1-carboxylic acid (4-{5-amino-6-[1-(2-chloro-3,6-difluoro-phenyl)-ethoxy]-pyrazin-2-yl}-phenyl)-amide | 0.1 | 10 as in Example I-371 | (300 MHZ, CDCl3) δ 7.95 (s, 1H), 7.69 (d, 2H), 7.39 (d, 2H), 7.01–8.91 (m, 2H), 6.70 (m, 2H), 4.90 (s, 2H), 3.61 (m, 4H), 2.58 (m, 4H), 2.41 (s, 3H), 1.81 (d, 3H). | 503 |

TABLE 4-continued

| No. | Structure | (µM) | Met IC$_{50}$ Procedure | $^1$H-NMR | (M + 1) | MS m/z |
|---|---|---|---|---|---|---|
| II-186 | 1-(4-{5-Amino-6-[1-(2-chloro-3,6-difluoro-phenyl)-ethoxy]-pyrazin-2-yl}-phenyl)-3-(2-hydroxy-ethyl)-urea | 0.21 | 10 as in Example I-371 | (300 MHZ, CDCl3) δ 7.78 (s, 1H), 7.60 (d, 2H), 7.35 (d, 2H), 7.15 (m, 4H), 6.55 (q, 1H), 4.86 (s, 2H), 3.64 (t, 2H), 3.31 (t, 3H), 1.82 (d, 3H). | 464 |
| II-187 | (S)-3-Amino-pyrrolidine-1-carboxylic acid (4-{5-amino-6-[1-(2-chloro-3,6-difluoro-phenyl)-ethoxy]-pyrazin-2-yl}-phenyl)-amide | 0.082 | 10 as in Example I-371 | (300 MHZ, CDCl3) δ 7.71 (s, 1H), 7.65 (d, 2H), 7.53 (d, 2H), 7.15 (m, 3H), 6.77 (m, 1H), 4.87 (s, 2H), 3.95 (m, 1H), 3.80 (m, 1H), 3.65 (m, 2H), 3.31 (m, 2H), 2.57 (m, 1H), 2.20 (m, 1H), 1.95 (d, 3H). | 489 |

TABLE 4-continued

| No. | Structure | (μM) | Met IC$_{50}$ Procedure | $^1$H-NMR (M + 1) | MS m/z |
|---|---|---|---|---|---|
| II-188 | 1-(4-{5-Amino-6-[1-(2-chloro-3,6-difluoro-phenyl)-ethoxy]-pyrazin-2-yl}-phenyl)-3-(1-methyl-piperidin-4-yl}-urea | 0.054 | 10 as in Example I-371 | | 517 |
| II-189 | 4-Methyl-piperazine-1-carboxylic acid (4-{5-amino-6-[1-(2,6-dichloro-3-fluoro-phenyl)-ethoxy]-pyrazin-2-yl}-phenyl)-amide | 0.074 | 10 as in Example I-371 | (300 MHZ, CDCl3) δ 7.94 (s, 1H), 7.66 (d, 2H), 7.37 (d, 2H), 7.24 (m, 1H), 6.95 (t, 1H), 6.81 (m, 2H), 4.95 (s, 2H), 3.68 (m, 4H), 2.73 (m, 4H), 2.51 (s, 3H), 1.83 (d, 3H). | 519 |

TABLE 4-continued

| No. | Structure | (μM) | Met IC$_{50}$ Procedure | $^1$H-NMR | (M + 1) | MS m/z |
|---|---|---|---|---|---|---|
| II-190 | 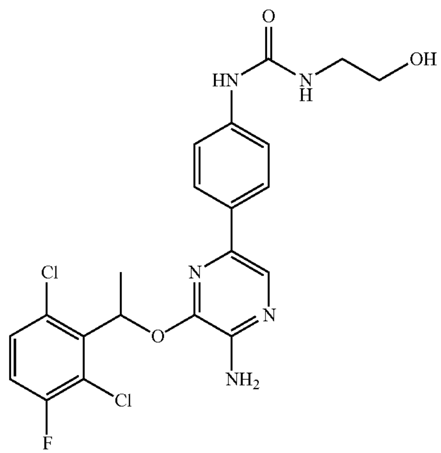 | 1-(4-{5-Amino-6-[1-(2,6-dichloro-3-fluoro-phenyl)-ethoxy]-pyrazin-2-yl}-phenyl)-3-(2-hydroxy-ethyl)-urea | 0.28 | 10 as in Example I-371 | (300 MHZ, CDCl3) δ 7.84 (s, 1H), 7.60 (m, 4H), 7.33 (m, 3H), 7.15 (m, 1H), 6.70 (q, 1H), 4.86 (s, 2H), 3.64 (t, 2H), 3.31 (m, 3H), 1.82 (d, 3H). | 480 |
| II-191 | 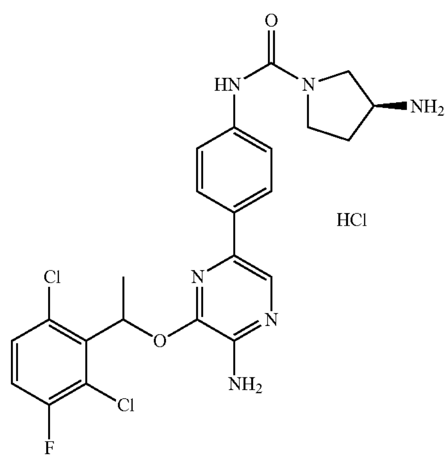 | (S)-3-Amino-pyrrolidine-1-carboxylic acid (4-{5-amino-6-[1-(2,6-dichloro-3-fluoro-phenyl)-ethoxy]-pyrazin-2-yl}-phenyl)-amide | 3 | 10 as in Example I-371 | | 502 |

TABLE 4-continued

| No. | Structure | (μM) | Met IC$_{50}$ Procedure | $^1$H-NMR | (M + 1) | MS m/z |
|---|---|---|---|---|---|---|
| II-192 | 1-(4-{5-Amino-6-[1-(2,6-dichloro-3-fluoro-phenyl)-ethoxy]-pyrazin-2-yl}-phenyl)-3-(1-methyl-piperidin-4-yl)-urea | 0.052 | | 10 as in Example I-371 | | 535 |
| II-193 | 5-{5-Amino-6-(2-chloro-3,6-difluoro-benzyloxy)-pyrazin-2-yl}-thiophene-2-carboxylic acid | | | 3 as in Example I-270 | | 398 |

TABLE 4-continued

| No. | Structure (µM) | Met IC$_{50}$ Procedure | $^1$H-NMR (M + 1) | MS m/z |
|---|---|---|---|---|
| II-194 | {5-[5-Amino-6-(2-chloro-3,6-difluoro-benzyloxy)-pyrazin-2-yl]-thiophene-2-yl}-(4-methyl-piperazin-1-yl)-methanone | 0.62 | 4 as in Example II-194 | (300 MHZ, CDCl3) δ 8.01 (s, 1H), 7.35 (s, 1H), 7.27 (s, 1H), 7.15 (m, 1H), 6.98 (m, 1H), 5.63 (s, 1H), 4.87 (m, 1H), 3.80 (m, 4H), 2.48 (m, 4H), 2.34 (s, 3H). | 480 |
| II-195 | {5-[5-Amino-6-(2-chloro-3,6-difluoro-benzyloxy)-pyrazin-2-yl]-thiophen-2-yl}-(4-pyrrolidin-1-yl-piperidin-1-yl)-methanone | 0.51 | 4 as in Example II-194 | (300 MHZ, CDCl3) δ 8.01 (s, 1H), 7.35 (d, 1H), 7.24 (d, 1H), 7.15 (m, 1H), 6.98 (m, 1H), 5.63 (s, 2H), 4.88 (m, 2H), 4.42 (m, 4H), 3.05 (t, 4H), 2.63 (m, 2H), 2.35 (m, 1H), 2.00 (m, 2H), 1.82 (m, 2H), 1.60 (m, 2H). | 534 |

TABLE 4-continued

| No. | Structure | (μM) | Met IC$_{50}$ Procedure | $^1$H-NMR | MS m/z (M + 1) |
|---|---|---|---|---|---|
| II-196 | (5-{5-Amino-6-(2-chloro-3,6-difluoro-benzyloxy)-pyrazin-2-yl]-thiophen-2-yl}-((3R,5S)-3,5-dimethyl-piperazin-1-yl)-methanone | 0.55 | 4 as in Example II-194 | (300 MHZ, CDCl3) δ 8.01 (s, 1H), 7.35 (d, 1H), 7.24 (d, 1H), 7.07 (m, 1H), 7.01 (m, 1H), 5.63 (s, 2H), 4.88 (m, 2H), 4.35 (m, 2H), 2.93 (m, 2H), 2.60 (m, 2H), 1.10 (d, 6H). | 494 |
| II-197 | (5-{5-Amino-6-(2-chloro-3,6-difluoro-benzyloxy)-pyrazin-2-yl]-thiophen-2-yl)-((R)-2-pyrrolidin-1-ylmethyl-pyrrolidin-1-yl)-methanone | 0.8 | 4 as in Example II-194 | (300 MHZ, CDCl3) δ 8.03 (s, 1H), 7.52 (d, 1H), 7.38 (d, 1H), 7.07 (m, 1H), 7.01 (m, 1H), 5.63 (s, 2H), 4.88 (m, 2H), 4.5–0.80 (m, 17H). | 534 |

TABLE 4-continued

| No. | Structure | (μM) | Met IC$_{50}$ Procedure | $^1$H-NMR (M + 1) | MS m/z |
|---|---|---|---|---|---|
| II-198 | S-{5-Amino-6-[2-chloro-3,6-difluoro-benzyloxy)-pyrazin-2-yl]-thiophene-2-carboxylic acid (2-morpholin-4-yl-ethyl)-amide | 0.7 | 4 as in Example II-194 | (300 MHZ, CDCl3) δ 8.03 (s, 1H), 7.45 (d, 1H), 7.38 (d, 1H), 7.20 (m, 1H), 7.05 (m, 1H), 6.58 (m, 1H), 5.65 (s, 2H), 4.89 (m, 2H), 3.75 (m, 4H), 3.55 (m, 2H), 2.61 (m, 2H), 2.50 (m, 4H) | 510 |
| II-199 | 3-[1-(2,6-dichloro-3-fluorophenyl)ethoxy]-5-{5-[(4-methylpiperazin-1-yl)carbonyl]pyridin-2-yl}pyrazin-2-amine trifluoroacetate | 0.15 | 4 as in Example II-194 | (DMSO-d$_6$ + TFA/300 MHZ) δ 6.64 (s, 1H), 8.29 (s, 1H), 7.96 (d, 1H), 7.81 (d, 1H), 7.51 (m, 1H), 7.35 (m, 1H), 6.63 (q, 1H), 4.69–4.25 (m, 1H), 4.08–3.69 (m, 1H), 3.58–3.01 (m, 6H), 2.82 (s, 3H), 1.84 (d, 3H). | 505 |

TABLE 4-continued

| No. | Structure | (μM) | Met IC$_{50}$ Procedure | $^1$H-NMR (M+1) | MS m/z |
|---|---|---|---|---|---|
| II-200 | 3-[1-(2,6-Dichloro-3-fluoro-phenyl)-ethoxy]-5-pyridin-4-yl-pyrazin-2-ylamine | 0.045 | 3 | | 379 |
| II-201 | 3-[1-(2,6-Dichloro-3-fluoro-phenyl)-ethoxy]-5-(1H-pyrrol-2-yl)-pyrazin-2-ylamine | 0.22 | 3 | | 367 |

TABLE 4-continued
| No. | Structure | (μM) | Met IC50 Procedure | 1H-NMR | MS m/z (M + 1) |
|---|---|---|---|---|---|
| II-202 | (6-{5-Amino-6-[1-(2,6-dichloro-3-fluoro-phenyl)-ethoxy]-pyrazin-2-yl}-pyridin-3-yl)-(4-methyl-piperazin-1-yl)-methanone 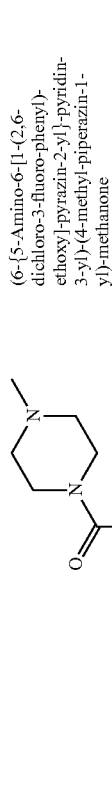 | 0.15 | 16 as in Example I-488 | | 505 |
| II-203 | (2-{5-Amino-6-[1-(2,6-dichloro-3-fluoro-phenyl)-ethoxy]-pyrazin-2-yl}-pyridin-4-yl)-(4-methyl-piperazin-1-yl)-methanone 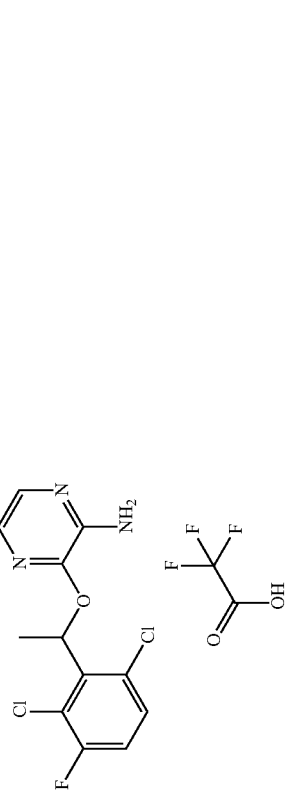 | 0.18 | 16 as in Example I-488 | (DMSO-d6 + TFA/300 MHZ) δ 8.68 (d, 1H), 8.34 (s, 1H), 7.62 (s, 1H), 7.52–7.27 (m, 3H), 6.57 (q, 1H), 4.66 (m, 1H), 3.70–2.91 (m, 7H), 2.86 (s, 3H), 1.82 (d, 3H). | 505 |

TABLE 4-continued

| No. | Structure (μM) | Met IC$_{50}$ Procedure | $^1$H-NMR (M + 1) | MS m/z |
|---|---|---|---|---|
| II-204 | (6-{5-Amino-6-[1-(2,6-dichloro-3-fluoro-phenyl)-ethoxy]-pyrazin-2-yl}-pyridin-2-yl)-(4-methyl-piperazin-1-yl)-methanone | 0.22 | 16 as in Example I-488 | (DMSO-d$_6$ + TFA/300 MHZ) δ 8.24 (s, 1H), 7.96 (dd, 1H), 7.79 (d, 1H), 7.53 (m, 2H), 7.35 (dd, 1H), 6.61 (q, 1H), 4.60 (br, 1H), 4.12 (br, 1H), 3.61–3.30 (m, 3H), 3.24–3.04 (m, 3H), 2.83 (s, 3H), 1.84 (d, 3H). | 505 |
| II-205 | (5-{5-Amino-6-[1-(2,6-dichloro-3-fluoro-phenyl)-ethoxy]-pyrazin-2-yl}-pyridin-3-yl)-(4-methyl-piperazin-1-yl)-methanone | 0.1 | 16 as in Example I-488 | (DMSO-d$_6$ + TFA/300 MHZ) δ 9.07 (s, 1H), 8.77 (s, 1H), 8.44 (s, 1H), 8.31 (s, 1H), 7.53 (br, 1H), 7.44 (m, 1H), 7.32 (m, 1H), 6.58 (q, 1H), 4.63 (br, 1H), 3.74 (br, 1H), 3.61–3.15 (m, 4H), 3.06 (m, 2H), 2.83 (s, 3H), 1.81 (d, 3H). | 505 |

TABLE 4-continued

| No. | Structure | (μM) | Met IC$_{50}$ Procedure | $^1$H-NMR | (M + 1) | MS m/z |
|---|---|---|---|---|---|---|
| II-206 | (4-{5-Amino-6-[1-(2,6-dichloro-3-fluoro-phenyl)-ethoxy]-pyrazin-2-yl}-pyridin-2-yl)-(4-methyl-piperazin-1-yl)-methanone | 0.1 | 16 as in Example I-488 | (DMSO-d$_6$ + TFA/300 MHZ) δ 8.63 (d, 1H), 8.39 (s, 1H), 8.01 (s, 1H), 7.93 (d, 1H), 7.43 (m, 1H), 7.28 (dd, 1H), 6.58 (q, 1H), 4.63 (m, 1H), 3.92 (m, 1H), 3.64–3.13 (m, 4H), 3.11–2.96 (m, 2H), 2.84 (s, 3H), 1.81 (d, 3H). | | 505 |
| II-207 | 6-{5-Amino-6-[1-(2,6-dichloro-3-fluoro-phenyl)-ethoxy]-pyrazin-2-yl}-N-(2-morpholin-4-yl-ethyl)-nicotinamide | | 16 as in Example I-488 | (DMSO-d$_6$ + TFA/300 MHZ) δ 9.76 (br, 1H), 8.96 (m, 2H), 8.37 (s, 1H), 8.26 (d, 1H), 7.80 (d, 1H), 7.51 (m, 1H), 7.37 (dd, 1H), 6.61 (q, 1H), 4.00 (d, 2H), 3.74–3.50 (m, 6H), 3.34 (m, 2H), 3.16 (m, 2H), 1.83 (d, 3H). | | 535 |

TABLE 4-continued

| No. | Structure (μM) | Met IC$_{50}$ Procedure | $^1$H-NMR (M + 1) | MS m/z |
|---|---|---|---|---|
| II-208 | 5-{5-Amino-6-[1-(2,6-dichloro-3-fluoro-phenyl)-ethoxy]-pyrazin-2-yl}-N-(2-morpholin-4-yl-ethyl)-nicotinamide | 0.038 | 16 as in Example I-488 | (DMSO-d$_6$ + TFA/300 MHZ) δ 9.16 (m, 1H), 9.09 (s, 1H), 9.03 (s, 1H), 8.83 (s, 1H), 8.28 (s, 1H), 7.47 (m, 1H), 7.32 (dd, 1H), 6.66 (q, 1H), 4.00 (d, 2H), 3.77–3.50 (m, 6H), 3.35 (m, 2H), 3.16 (m, 2H), 1.83 (d, 3H). | 535 |
| II-209 | 6-{5-Amino-6-[1-(2,6-dichloro-3-fluoro-phenyl)-ethoxy]-pyrazin-2-yl}-N-(3-morpholin-4-yl-propyl)-nicotinamide | | 16 as in Example I-488 | (DMSO-d$_6$ + TFA/300 MHZ) δ 9.74 (br, 1H), 8.97 (s, 1H), 8.84 (m, 1H), 8.36 (s, 1H), 8.26 (d, 1H), 7.79 (d, 1H), 7.50 (m, 1H), 7.37 (dd, 1H), 6.61 (q, 1H), 3.97 (d, 2H), 3.64 (t, 2H), 3.50–3.30 (m, 4H), 3.23–2.98 (m, 4H), 1.92 (m, 2H), 1.83 (d, 3H). | 549 |

TABLE 4-continued

| No. | Structure | (μM) Met IC50 | Procedure | 1H-NMR (M + 1) | MS m/z |
|---|---|---|---|---|---|
| II-210 | 5-{5-Amino-6-[1-(2,6-dichloro-3-fluoro-phenyl)-ethoxy]-pyrazin-2-yl}-N-(3-morpholin-4-yl-propyl)-nicotinamide  | 0.022 | 16 as in Example I-488 | (DMSO-$d_6$ + TFA/300 MHZ) δ 9.88 (br, 1H), 8.86 (s, 1H), 8.30 (s, 1H), 7.68–7.40 (m, 2H), 7.32 (m, 1H), 6.67 (q, 1H), 3.97 (d, 2H), 3.66 (t, 2H), 3.43 (m, 4H), 3.25–2.97 (m, 4H), 1.96 (br, 2H), 1.83 (d, 3H). | 549 |
| II-211 | (6-{5-Amino-6-[1-(2,6-dichloro-3-fluoro-phenyl)-ethoxy]-pyrazin-2-yl}-pyridin-3-yl)-(4-isopropyl-piperazin-1-yl)-methanone 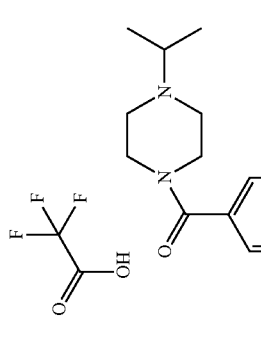 | | 16 as in Example I-488 | (DMSO-$d_6$ + TFA/300 MHZ) δ 9.70 (br, 1H), 8.65 (s, 1H), 8.38 (s, 1H), 7.95 (d, 1H), 7.80 (d, 1H), 7.53 (m, 1H) 7.39 (dd, 1H), 6.62 (q, 1H), 4.57 (br, 1H), 3.85 (br, 1H), 3.60–3.05 (m, 7H), 1.83 (d, 3H), 1.26 (d, 6H). | 533 |

TABLE 5
Section A: Examples L-1 to L-16
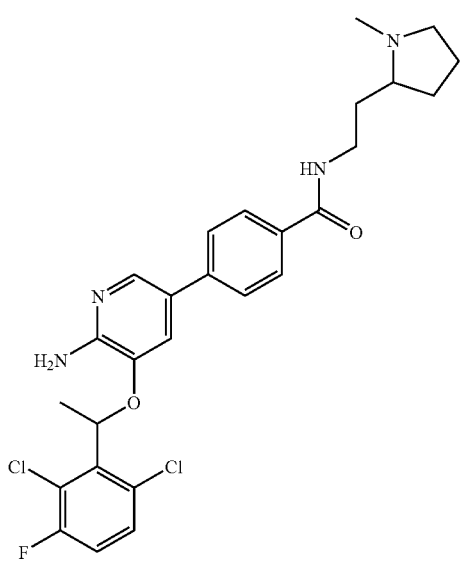
% inhibition = 58
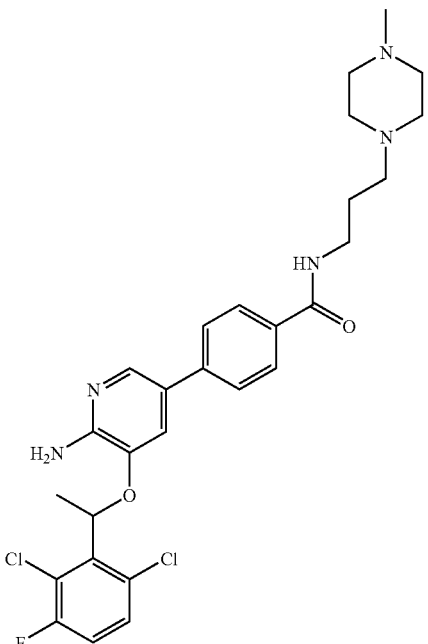
% inhibition = 63
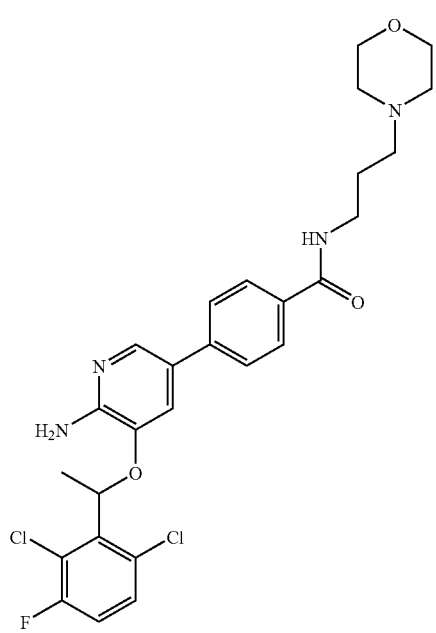
% inhibition = 59
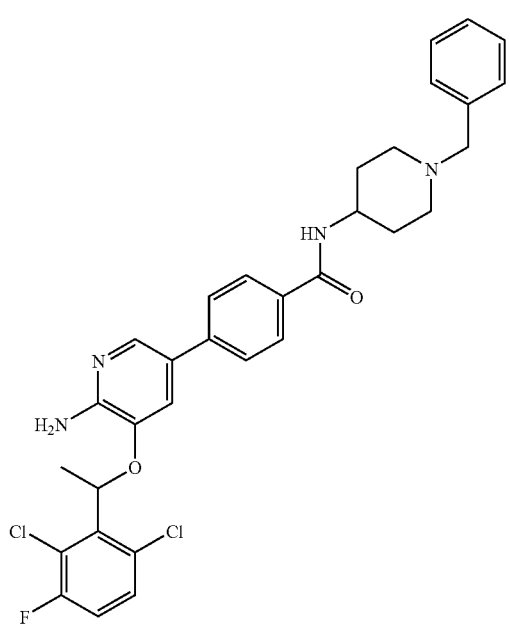
% inhibition = 47

TABLE 5-continued
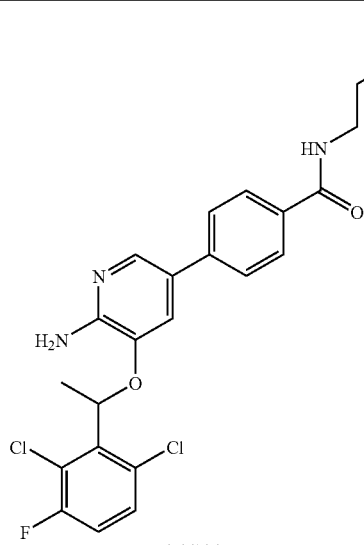
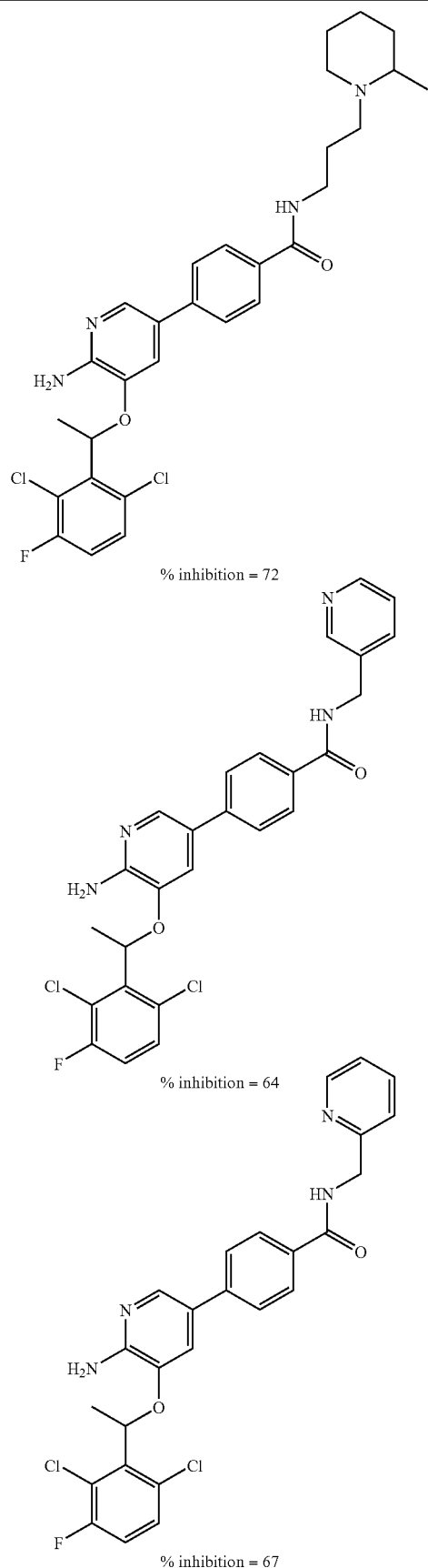

TABLE 5-continued
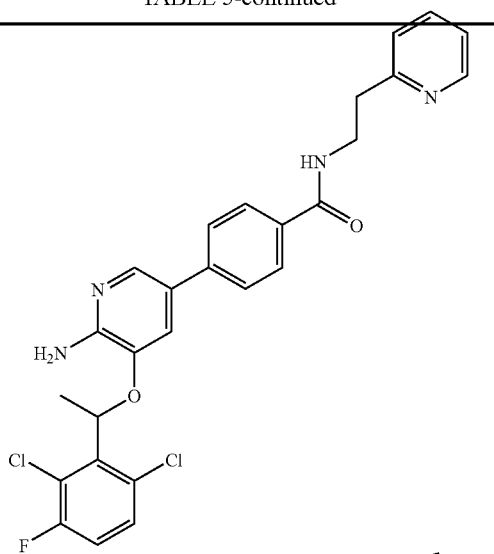
% inhibition = 67
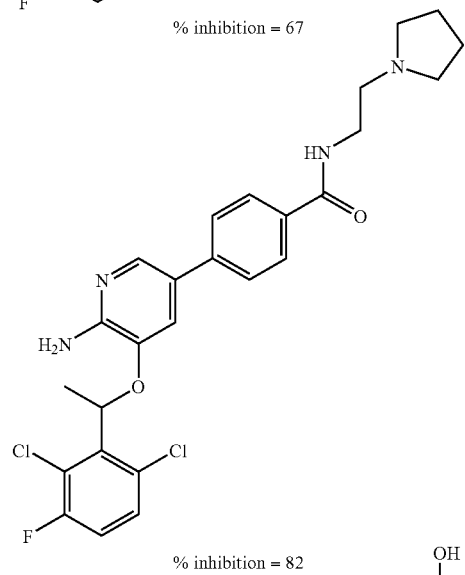
% inhibition = 82
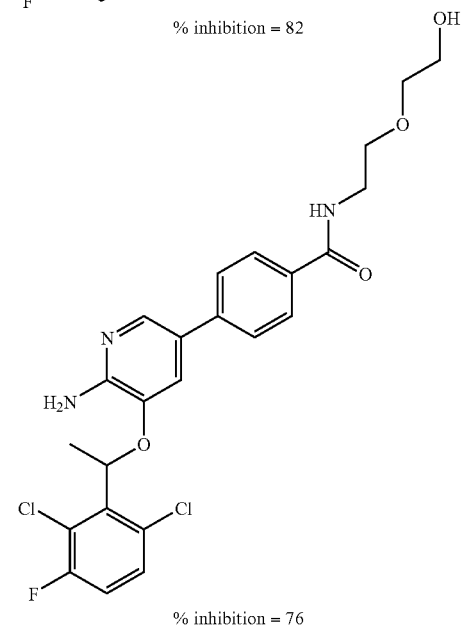
% inhibition = 76
TABLE 5-continued
% inhibition = 72
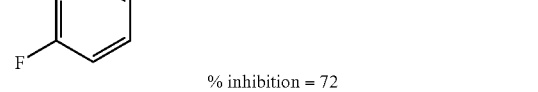
% inhibition = 67
% inhibition = 83

TABLE 5-continued
Section B: Examples L-17 to L-32
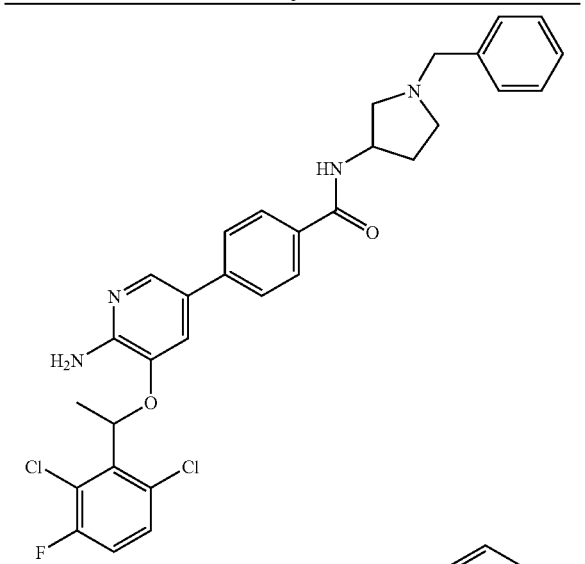
% inhibition = 76
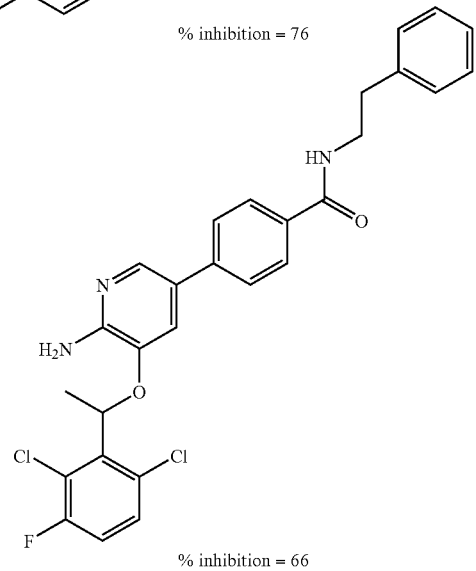
% inhibition = 66
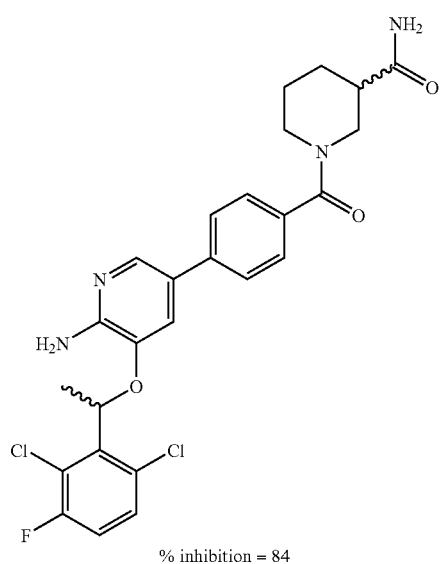
% inhibition = 84
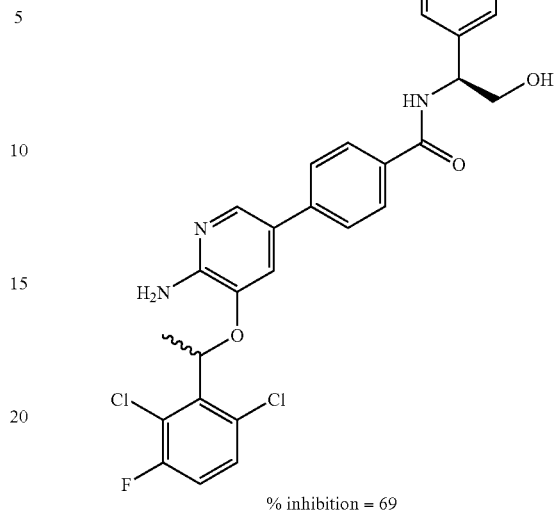
% inhibition = 69
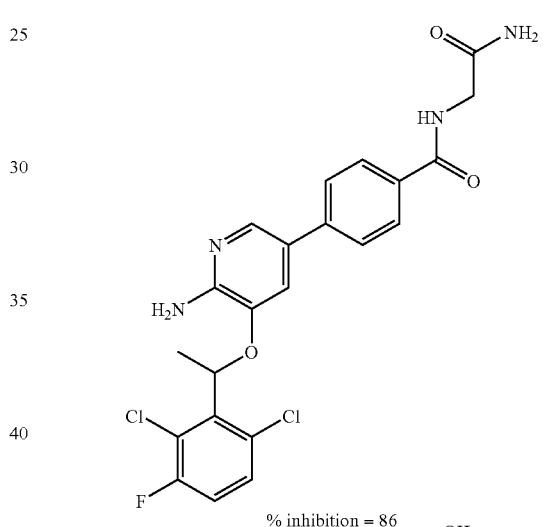
% inhibition = 86
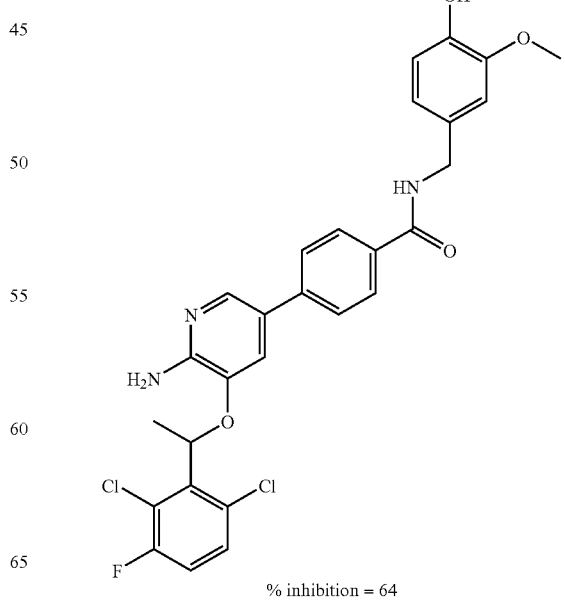
% inhibition = 64

TABLE 5-continued
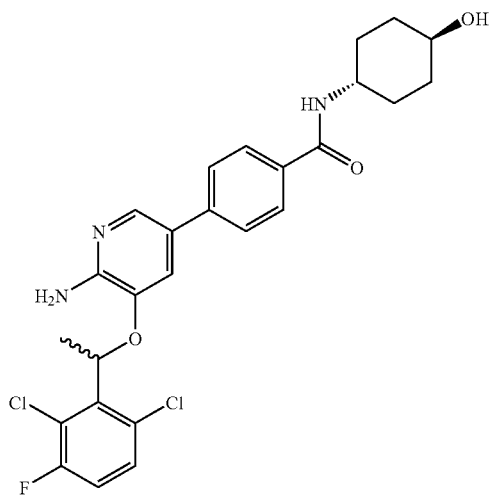
% inhibition = 72
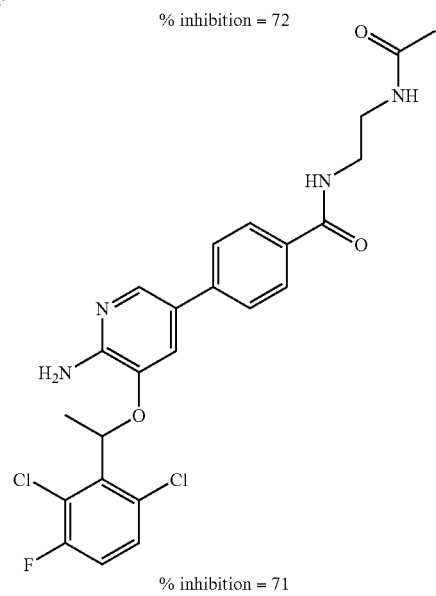
% inhibition = 71
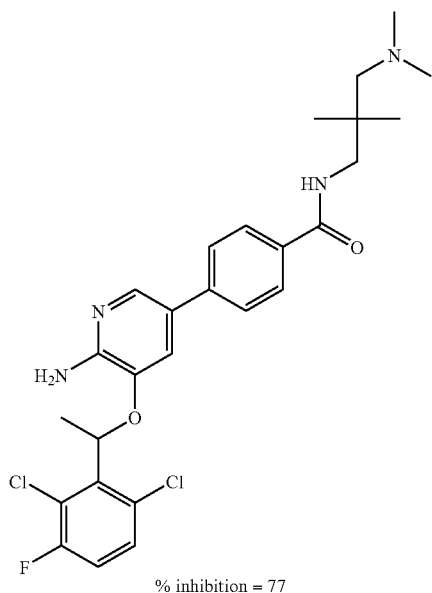
% inhibition = 77
TABLE 5-continued
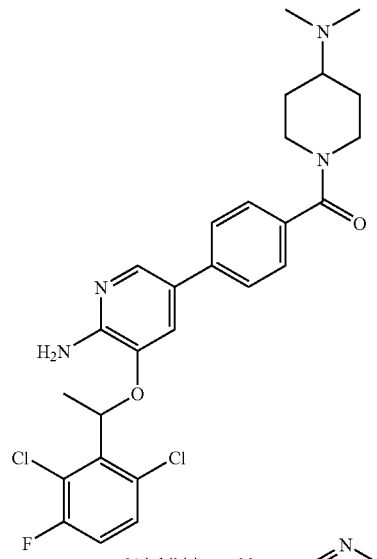
% inhibition = 92
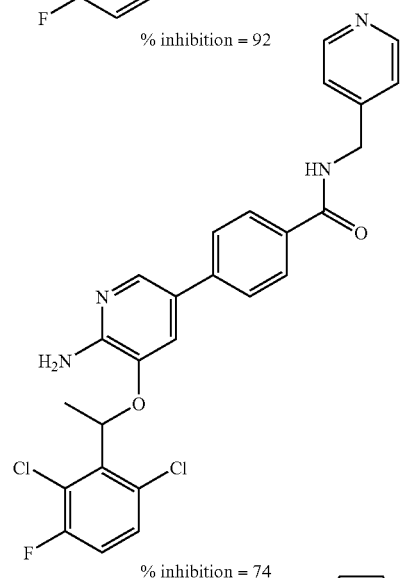
% inhibition = 74
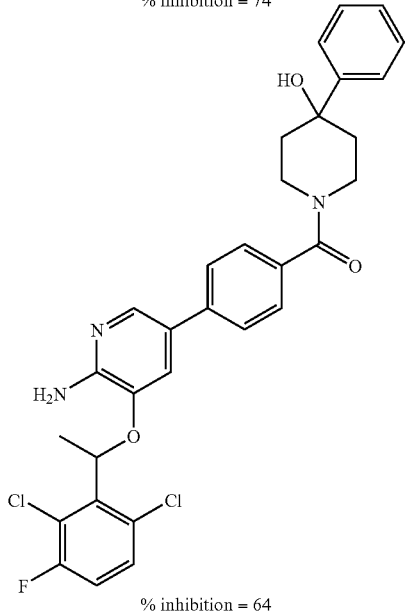
% inhibition = 64

TABLE 5-continued
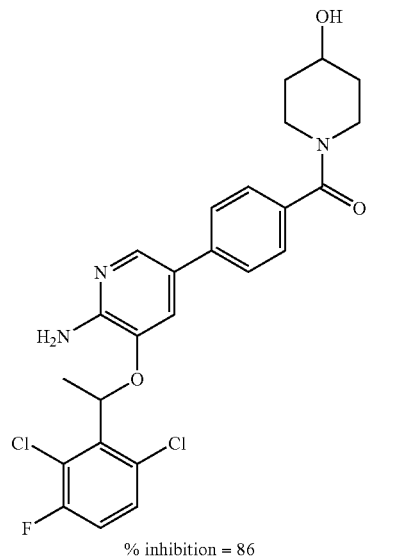
% inhibition = 86
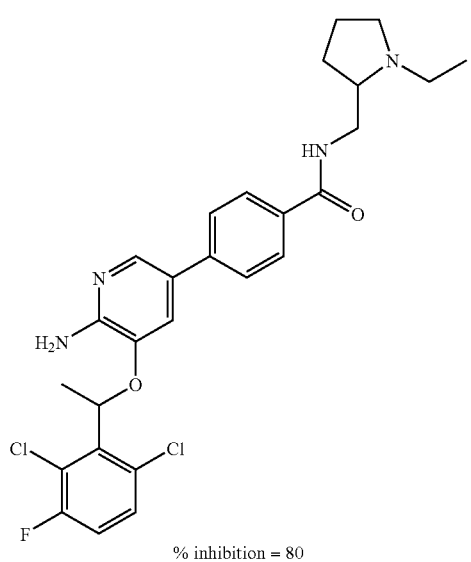
% inhibition = 80
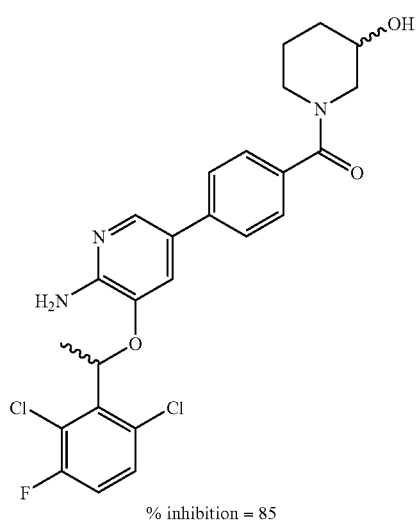
% inhibition = 85
TABLE 5-continued
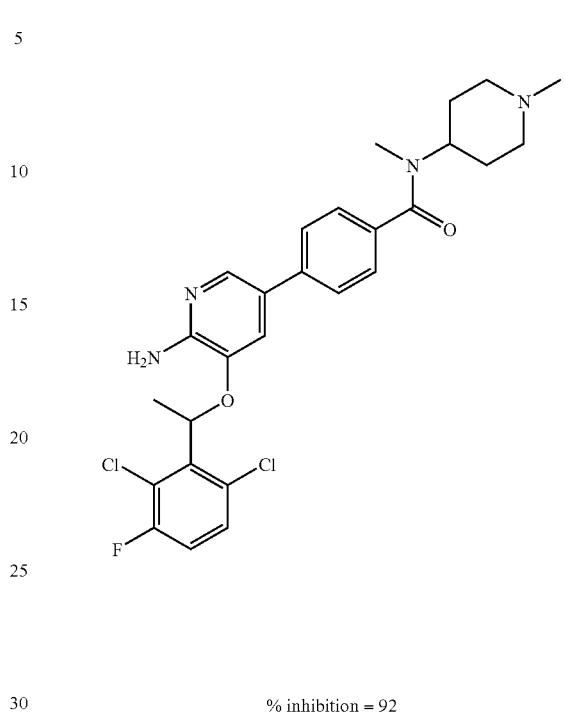
% inhibition = 92
Section C: Examples L-33 to L-48
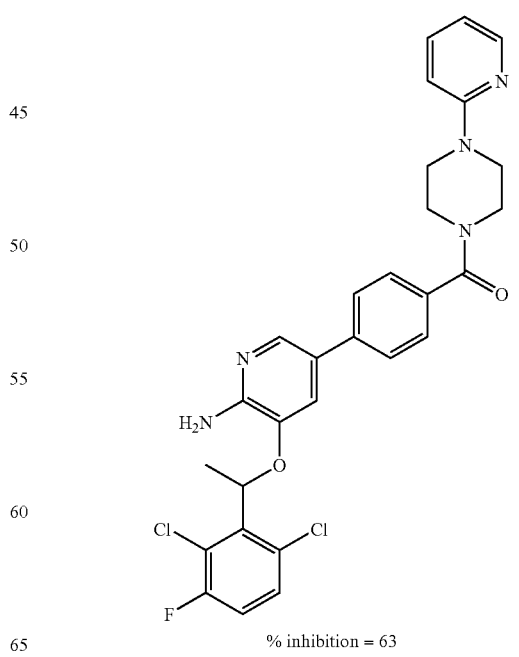
% inhibition = 63

TABLE 5-continued
833
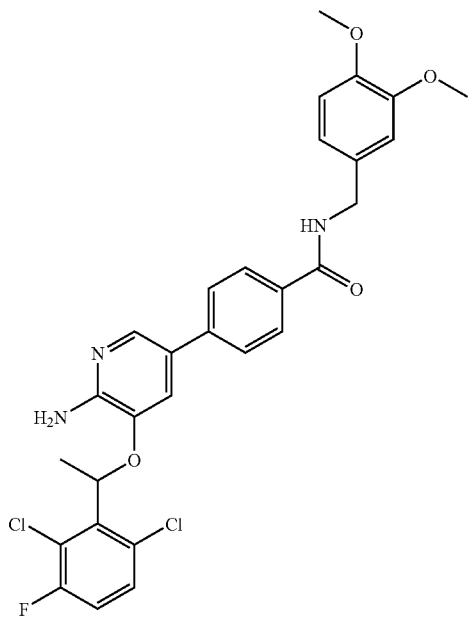
% inhibition = 62
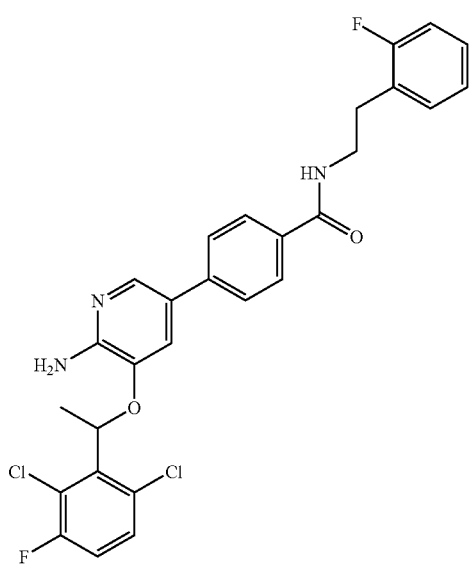
% inhibition = 55
TABLE 5-continued
834
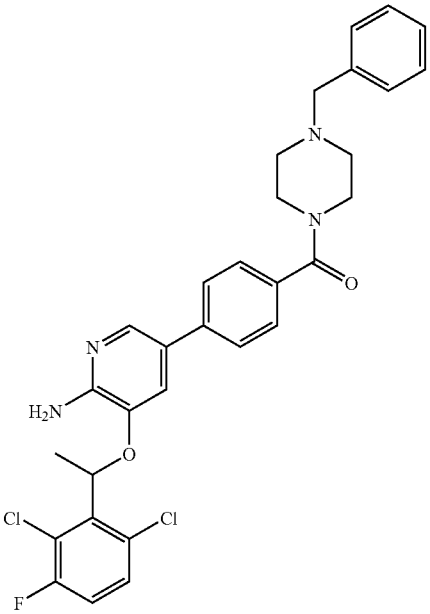
% inhibition = 62
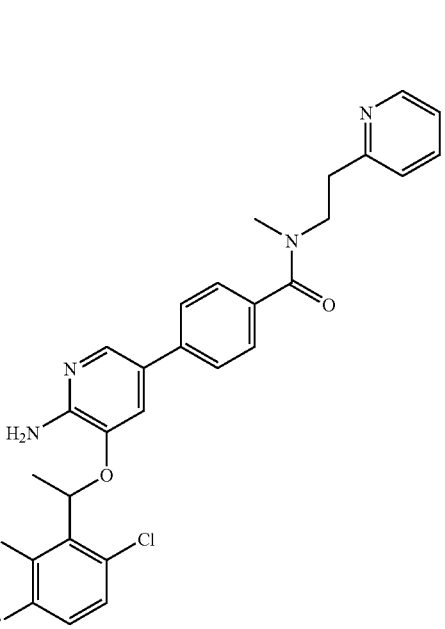
% inhibition = 75

TABLE 5-continued
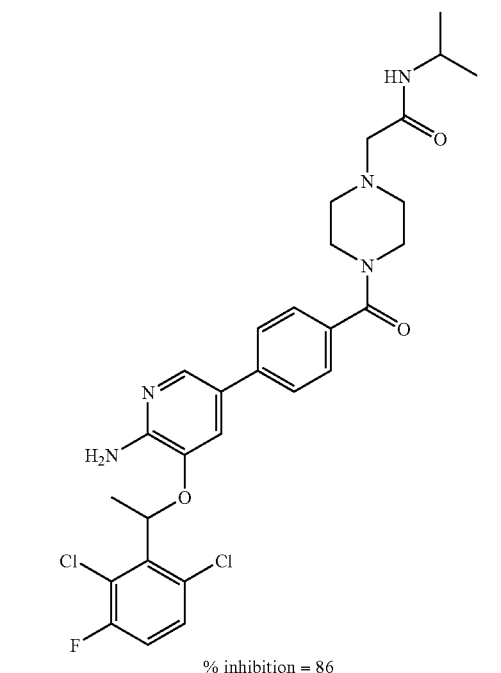
% inhibition = 86
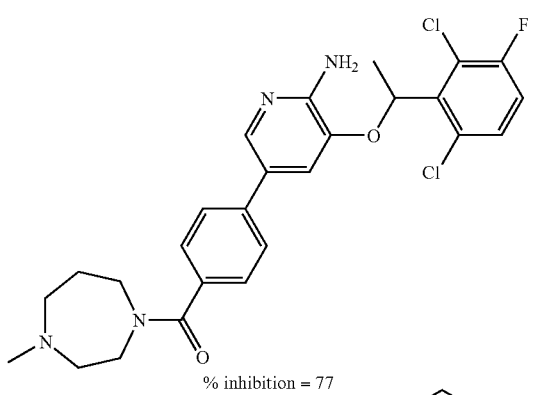
% inhibition = 77
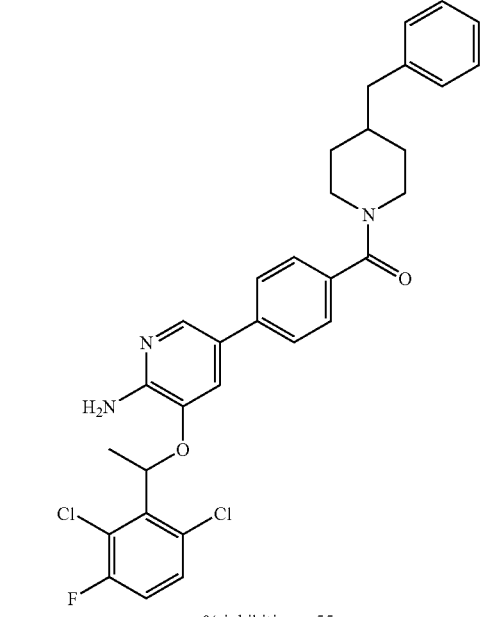
% inhibition = 55
TABLE 5-continued
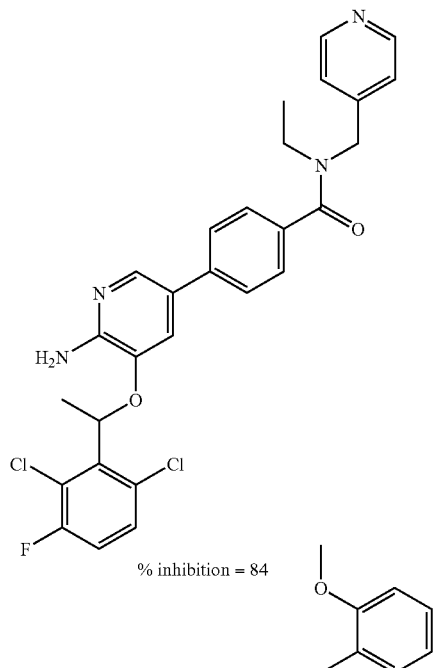
% inhibition = 84
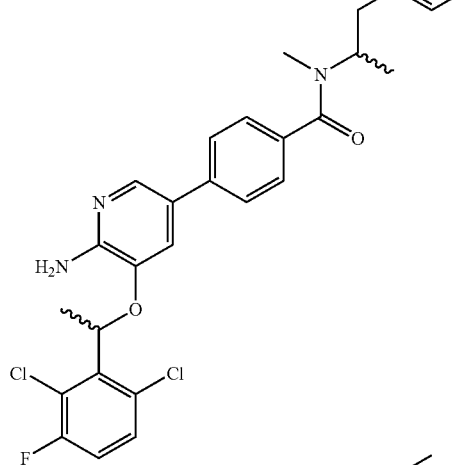
% inhibition = 55
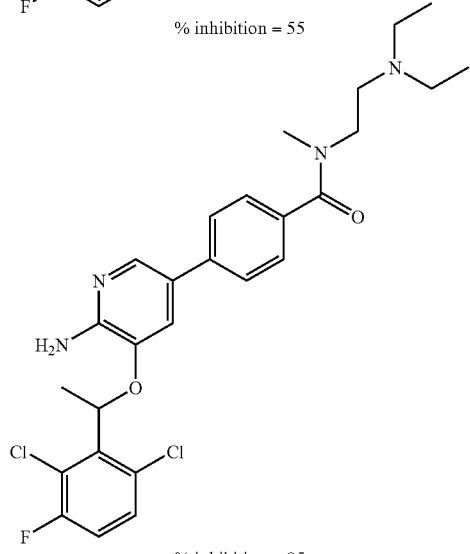
% inhibition = 85

TABLE 5-continued
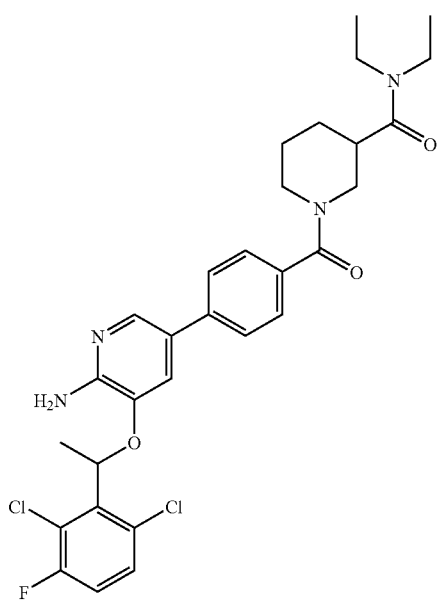
% inhibition = 55
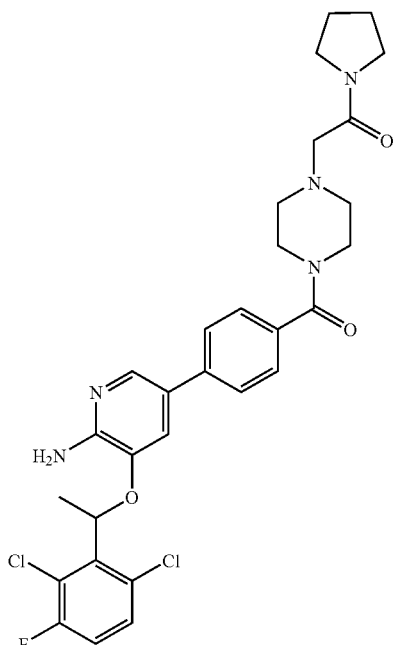
% inhibition = 78
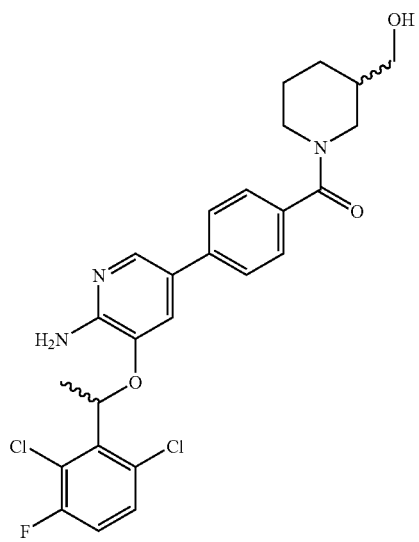
% inhibition = 84
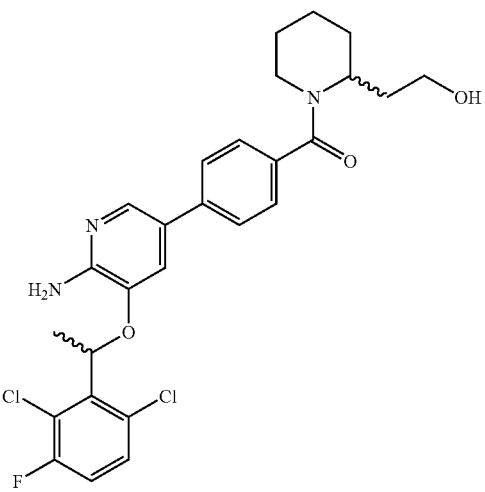
% inhibition = 63

TABLE 5-continued
Section D: Examples L-49 to L-64
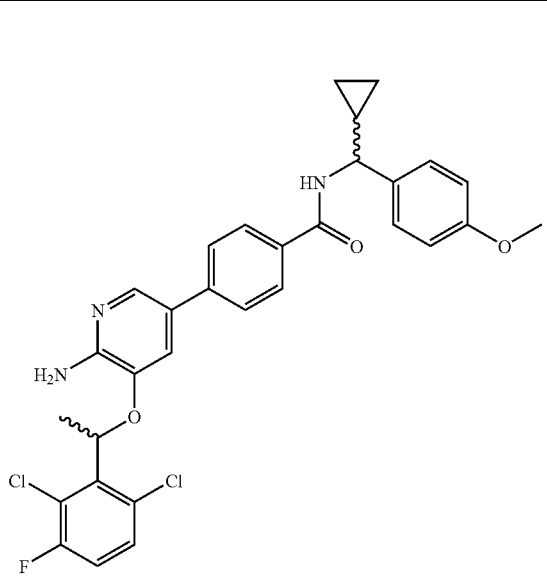
% inhibition = 67
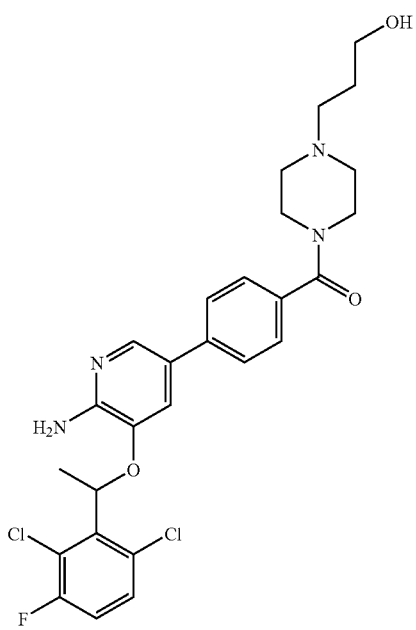
% inhibition = 74
TABLE 5-continued
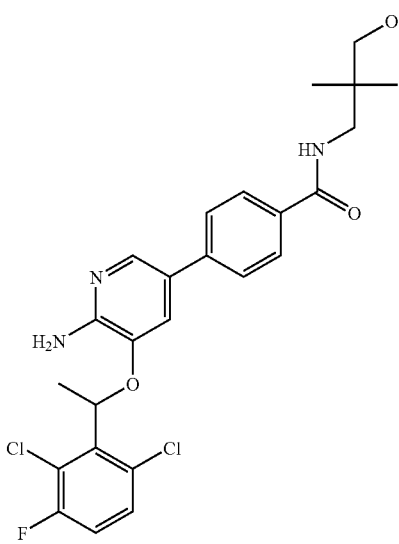
% inhibition = 73
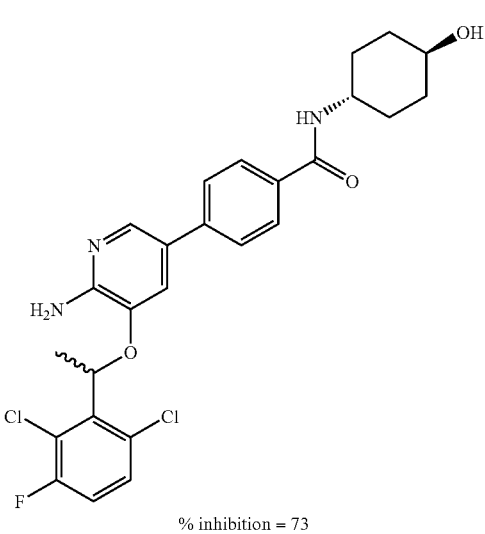
% inhibition = 73
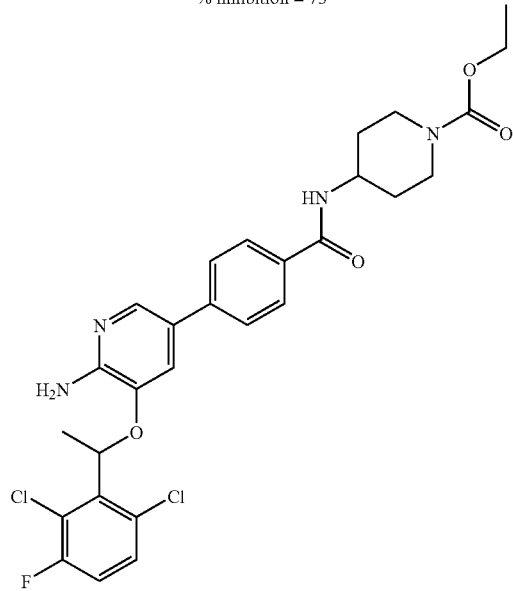
% inhibition = 66

TABLE 5-continued
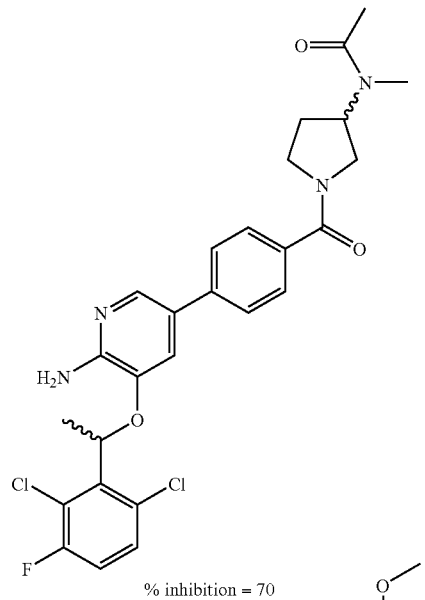
% inhibition = 70
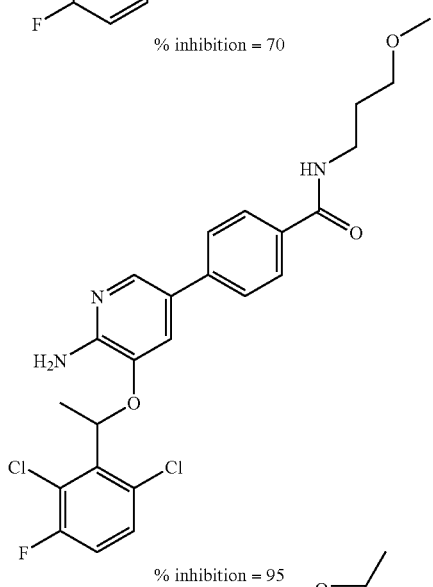
% inhibition = 95
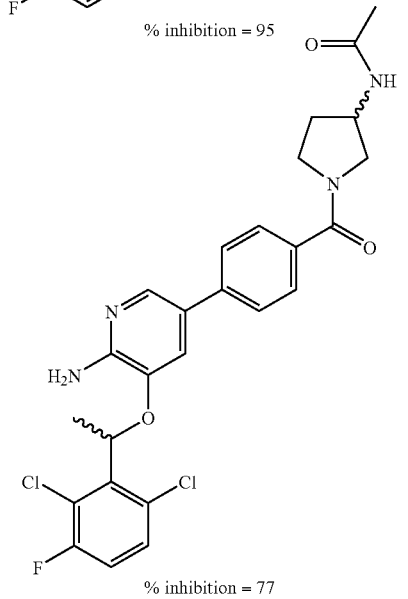
% inhibition = 77
TABLE 5-continued
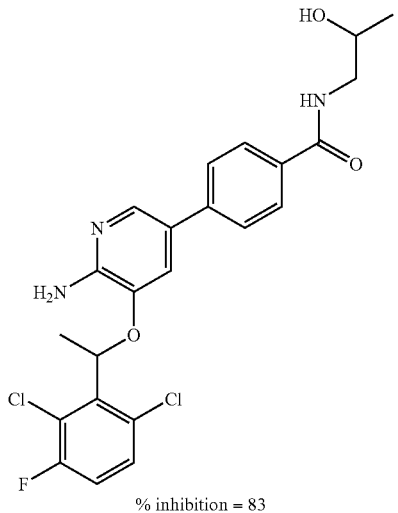
% inhibition = 83
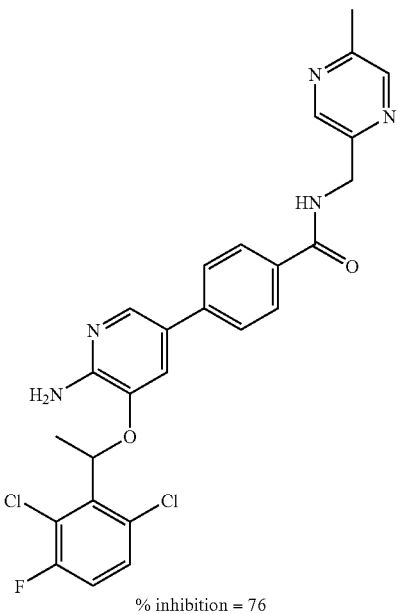
% inhibition = 76
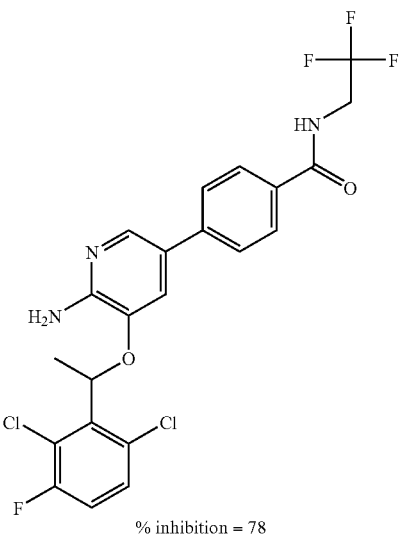
% inhibition = 78

TABLE 5-continued
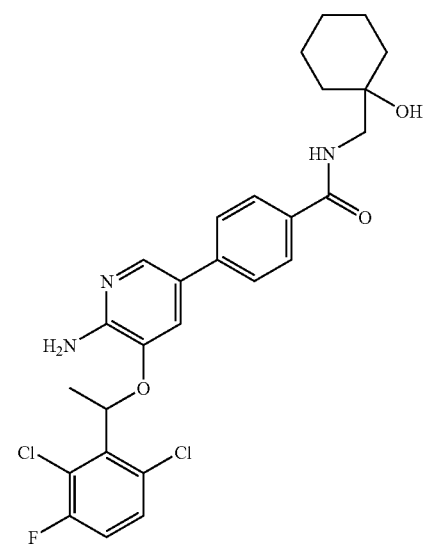
% inhibition = 81
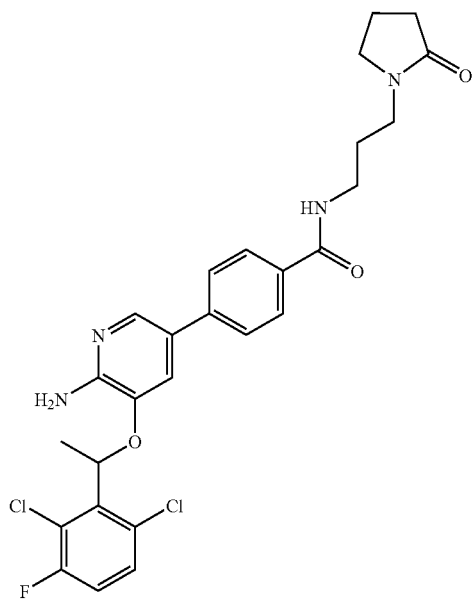
% inhibition = 83
TABLE 5-continued
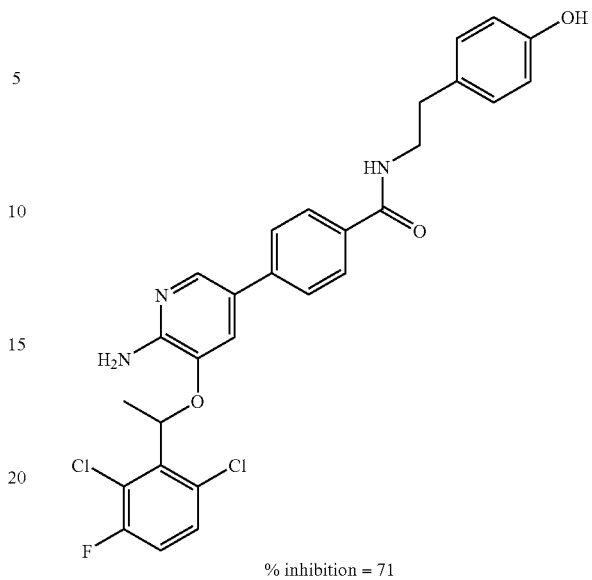
% inhibition = 71
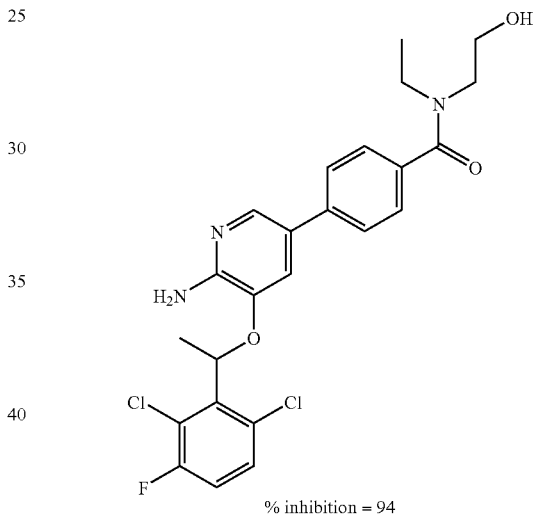
% inhibition = 94
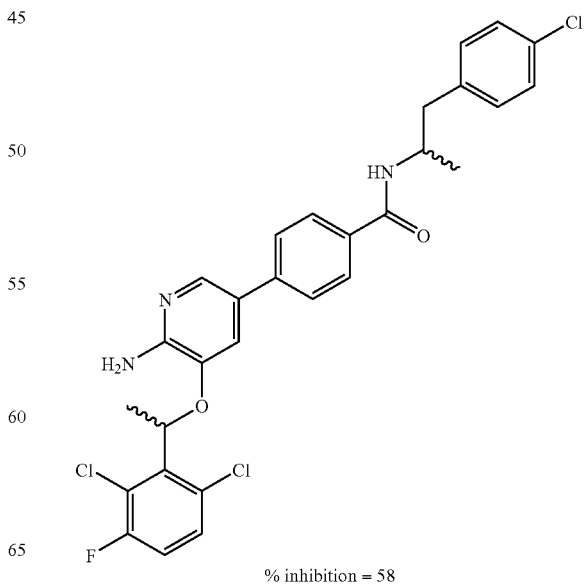
% inhibition = 58

TABLE 5-continued
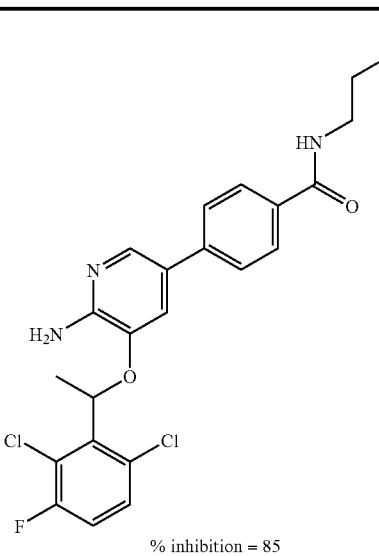
% inhibition = 85
Section E: Examples L-65 to L-80
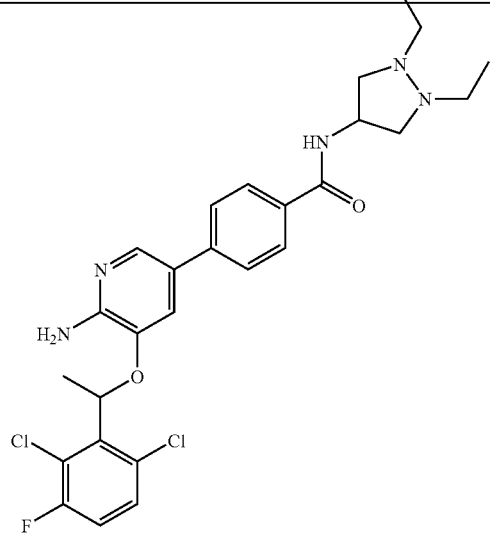
% inhibition = 79
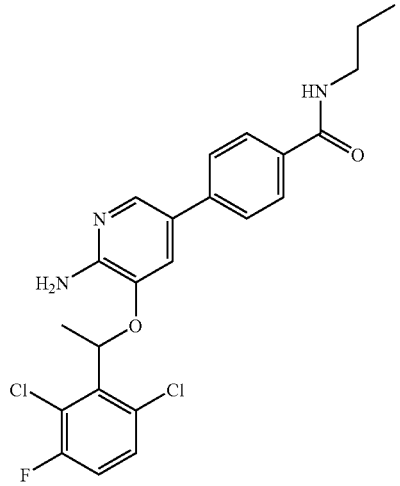
% inhibition = 73
TABLE 5-continued
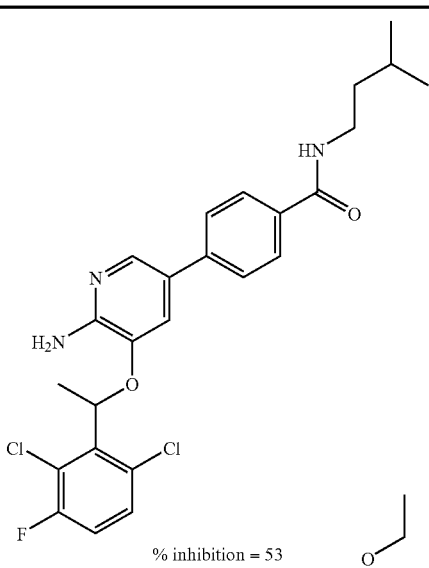
% inhibition = 53
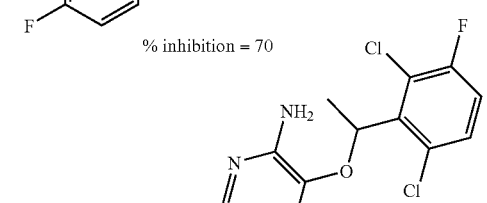
% inhibition = 70
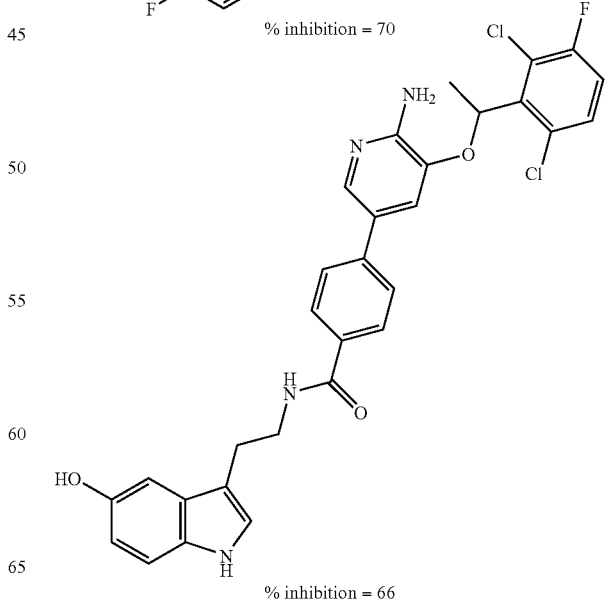
% inhibition = 66

TABLE 5-continued
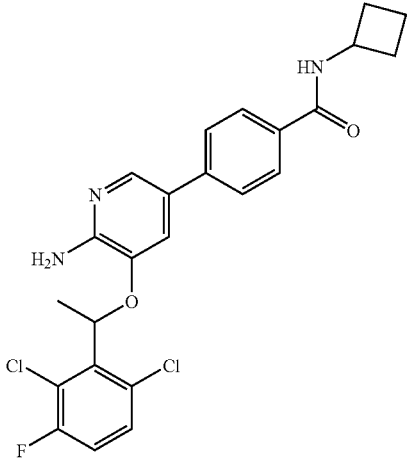
% inhibition = 71
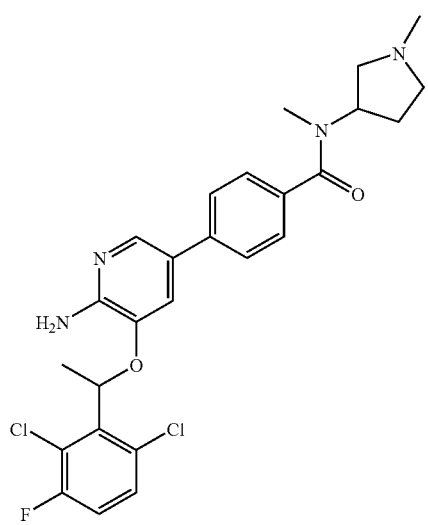
% inhibition = 92
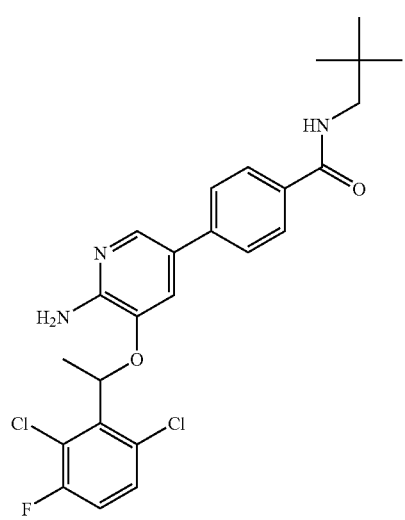
% inhibition = 62
TABLE 5-continued
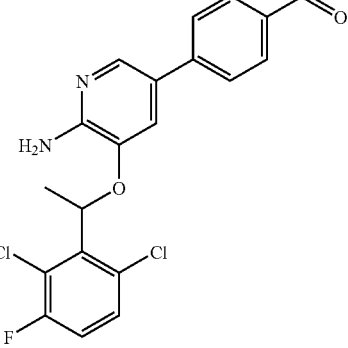
% inhibition = 90
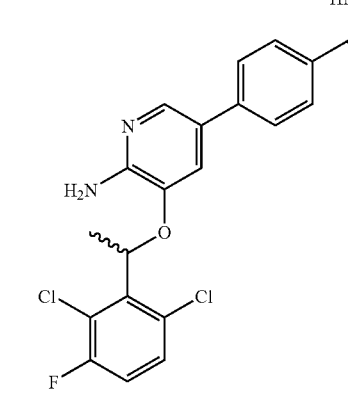
% inhibition = 65
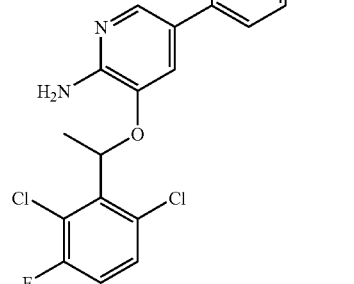
% inhibition = 53

TABLE 5-continued
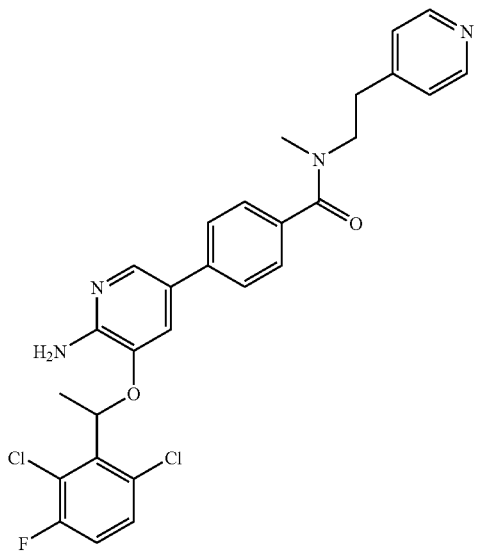
% inhibition = 73
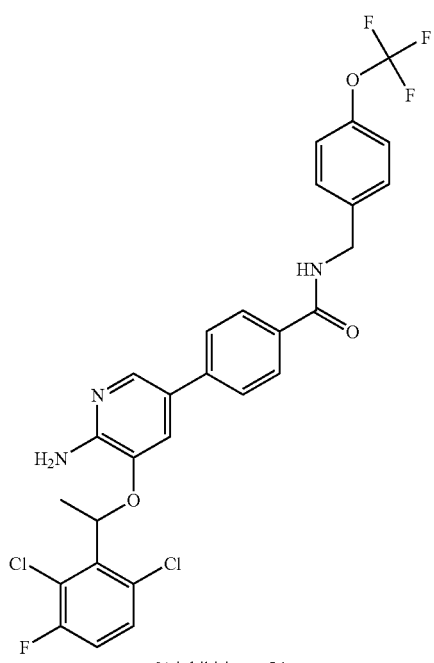
% inhibition = 54
TABLE 5-continued
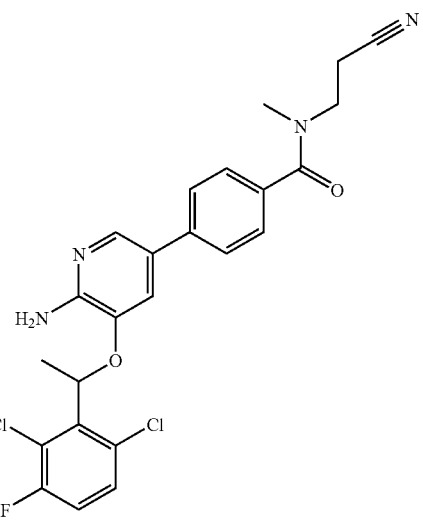
% inhibition = 68
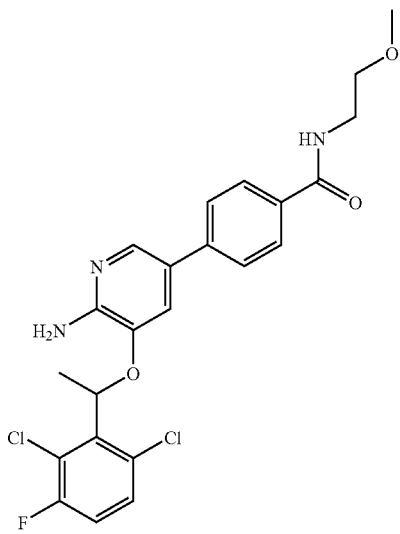
% inhibition = 73
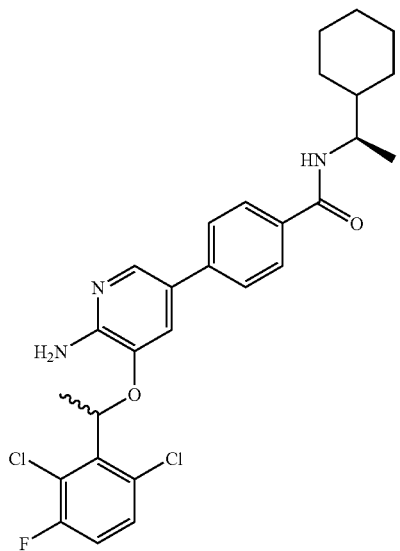
% inhibition = 60

TABLE 5-continued
Section F: Examples L-81 to L-96
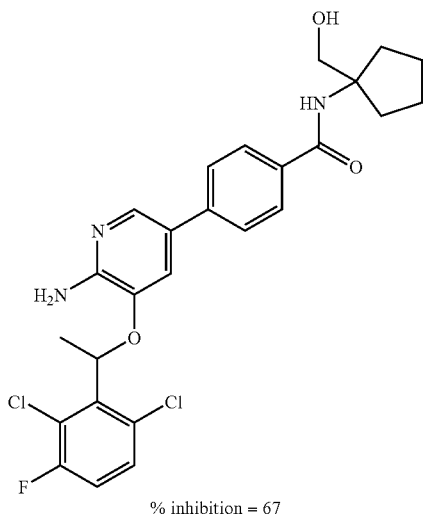
% inhibition = 67
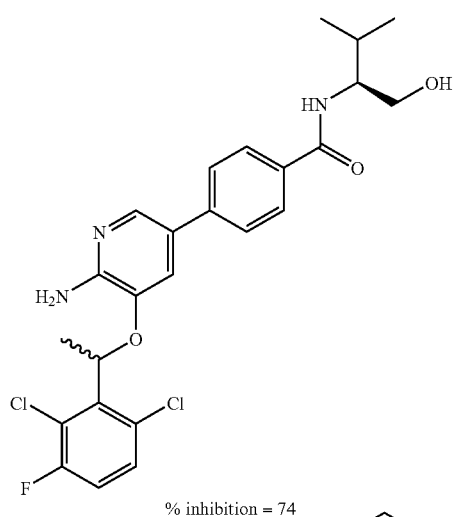
% inhibition = 74
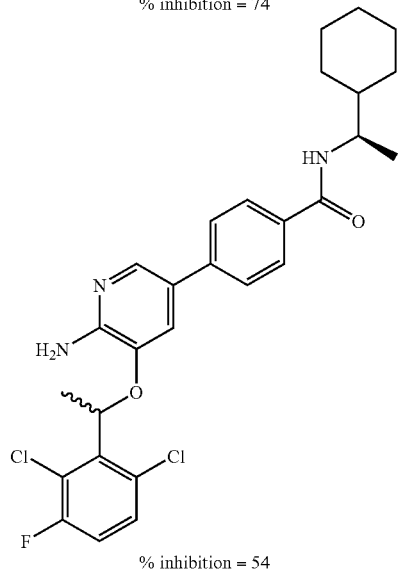
% inhibition = 54
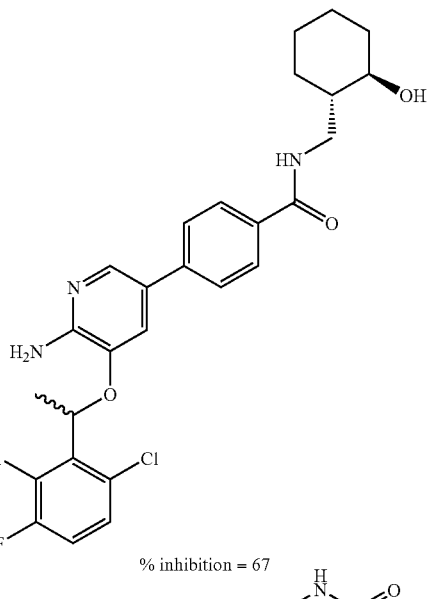
% inhibition = 67
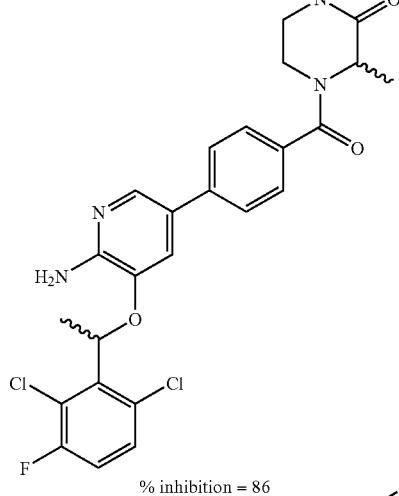
% inhibition = 86
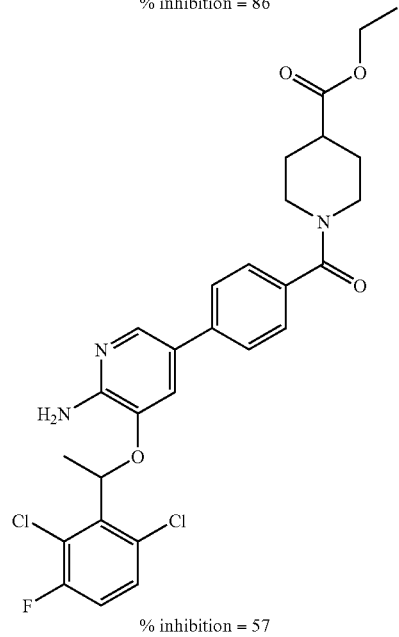
% inhibition = 57

TABLE 5-continued
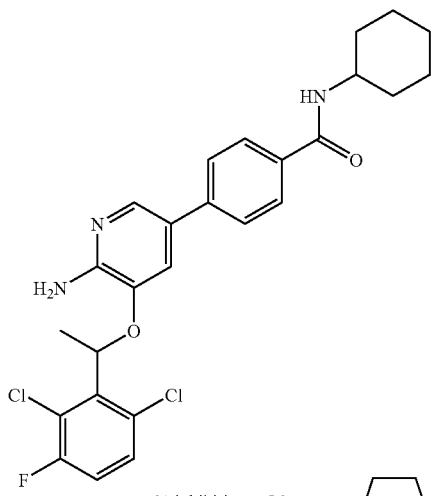
% inhibition = 56
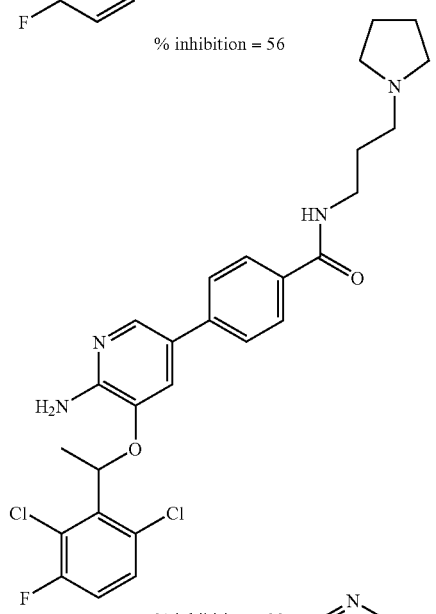
% inhibition = 90
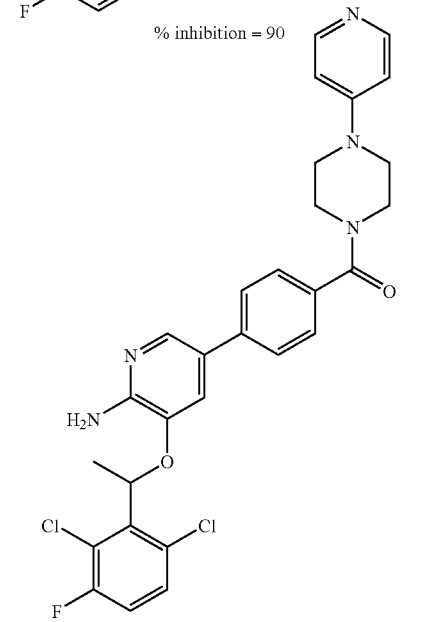
% inhibition = 96
TABLE 5-continued
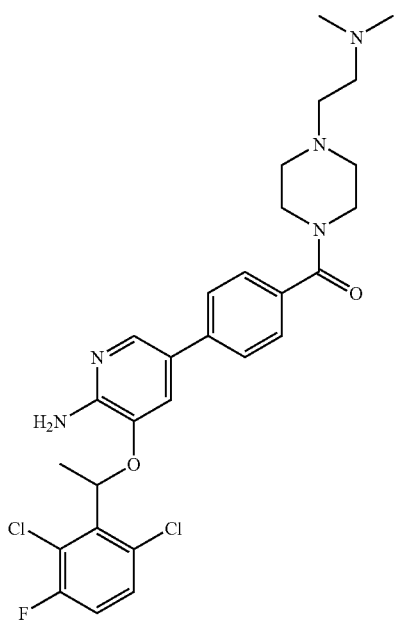
% inhibition = 85
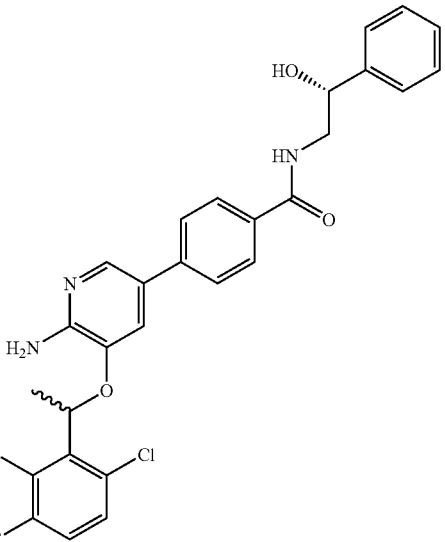
% inhibition = 69

TABLE 5-continued
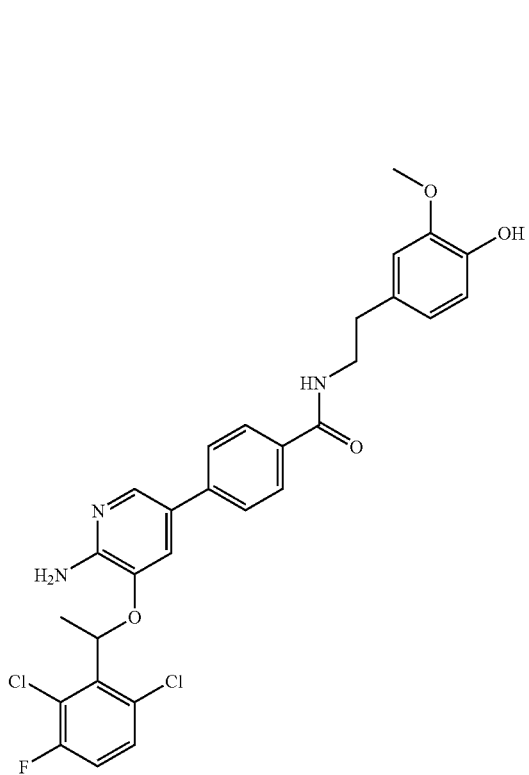
% inhibition = 64
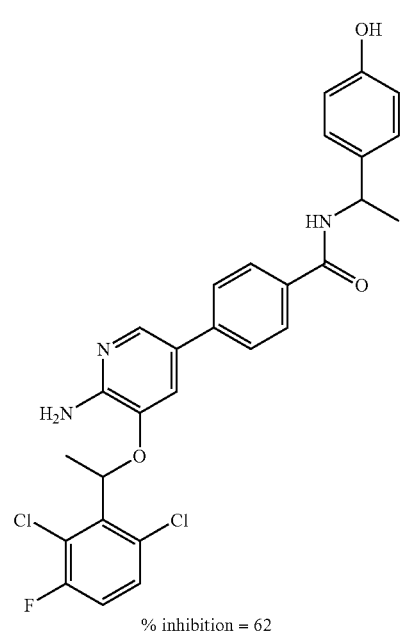
% inhibition = 62
TABLE 5-continued
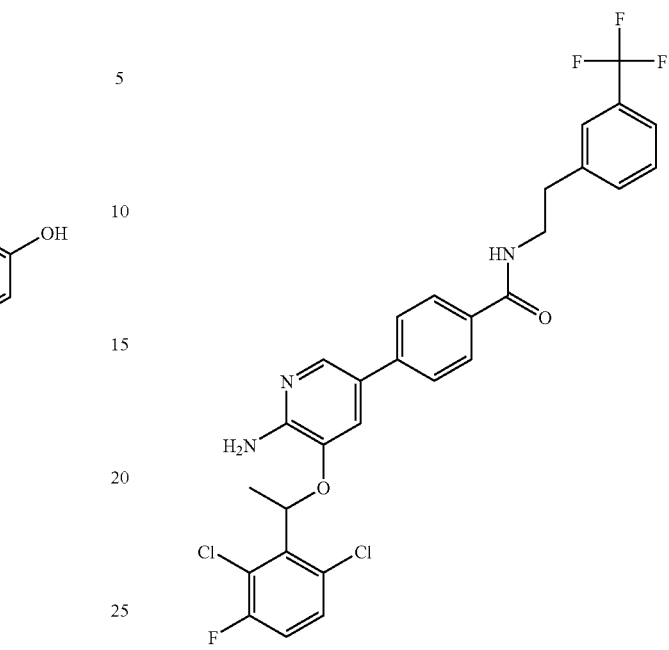
% inhibition = 51
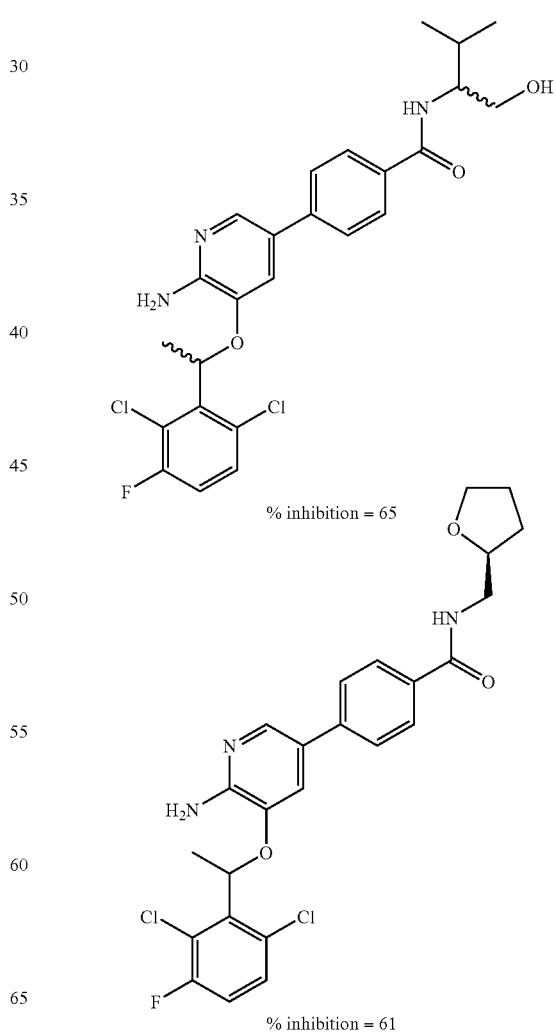
% inhibition = 65
% inhibition = 61

TABLE 5-continued

Section G: Examples L-97 to L-112

% inhibition = 60

% inhibition = 77

% inhibition = 73

% inhibition = 79

% inhibition = 83

% inhibition = 82

TABLE 5-continued
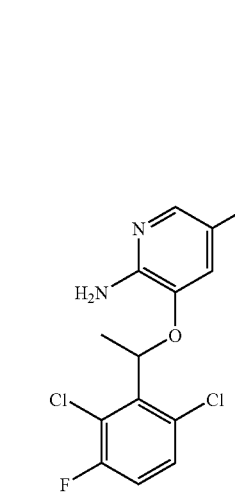
% inhibition = 91
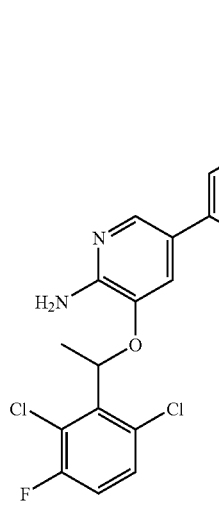
% inhibition = 69
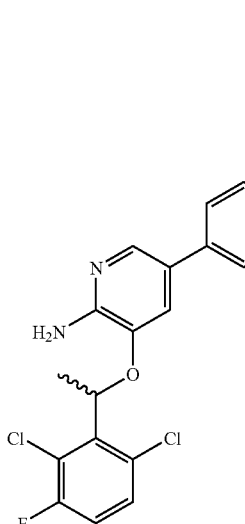
% inhibition = 81
TABLE 5-continued
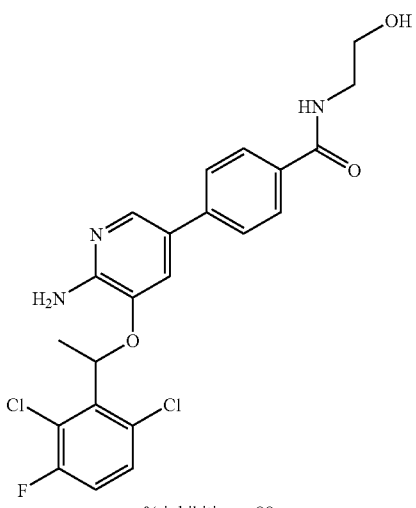
% inhibition = 89
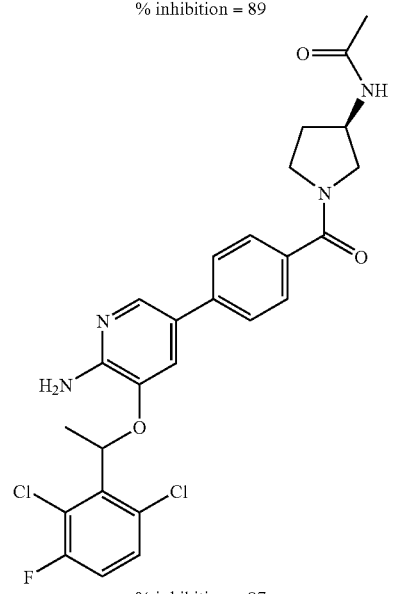
% inhibition = 87
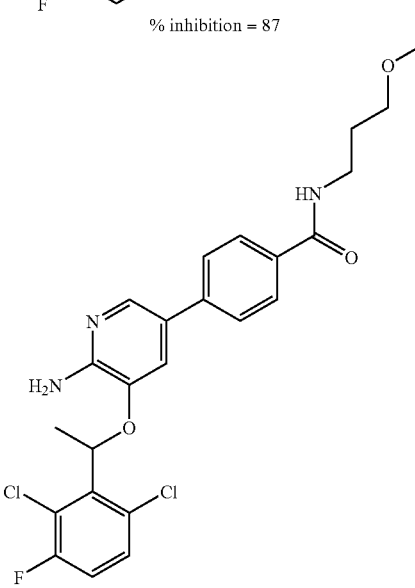
% inhibition = 70

TABLE 5-continued
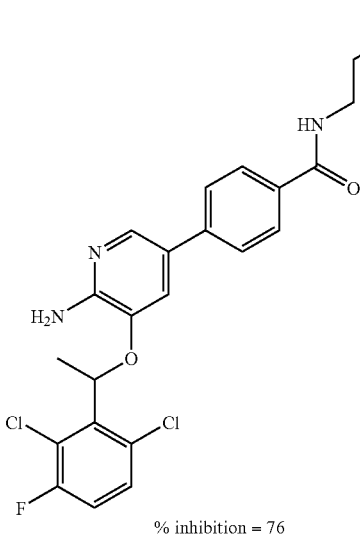
% inhibition = 76
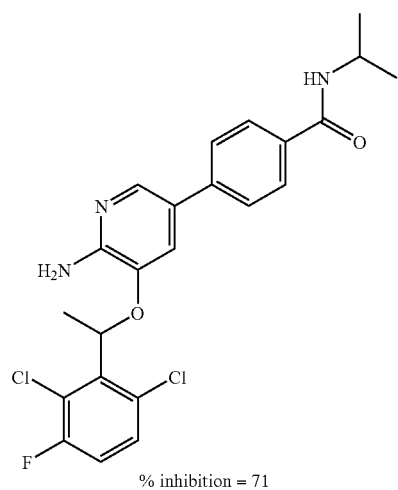
% inhibition = 71
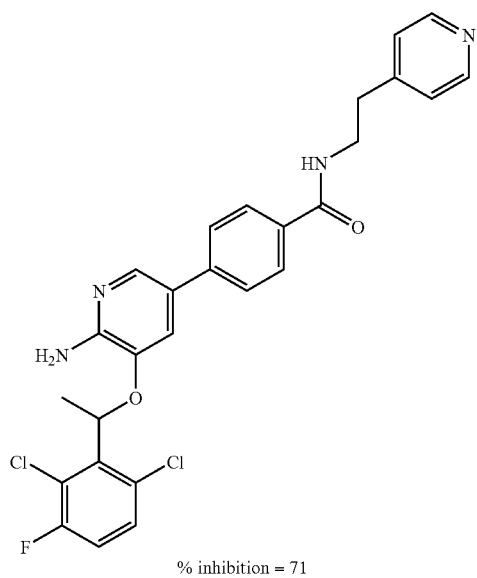
% inhibition = 71
TABLE 5-continued
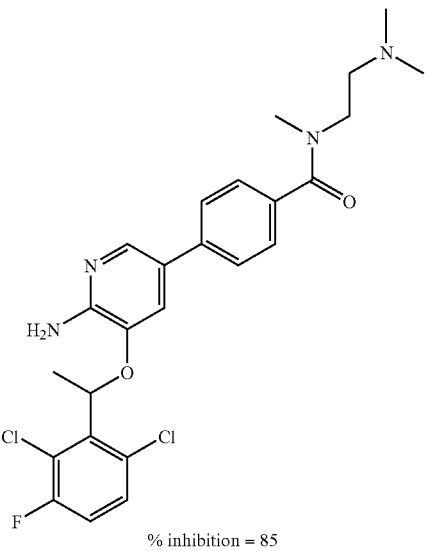
% inhibition = 85
Section H: Examples L-113 to L-128
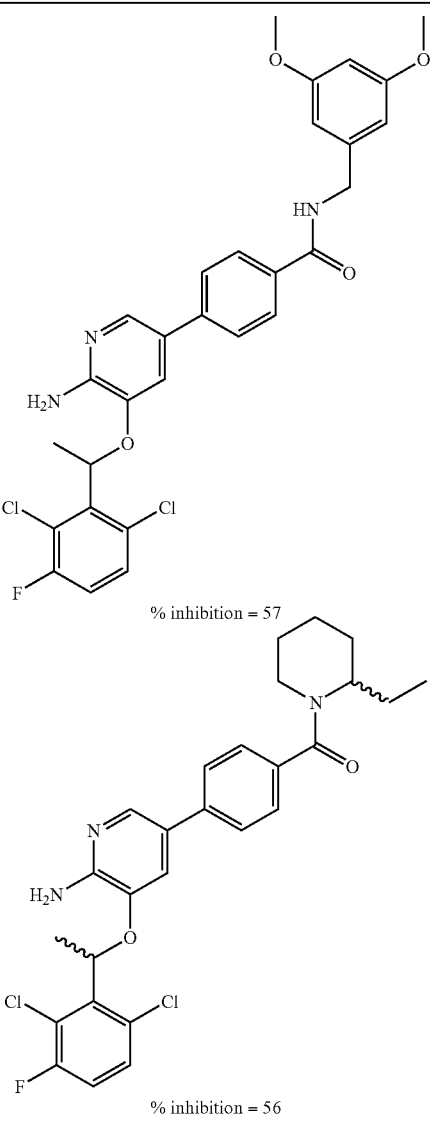
% inhibition = 57
% inhibition = 56

TABLE 5-continued
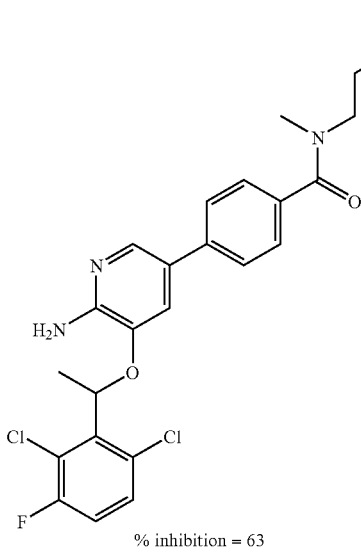
% inhibition = 63
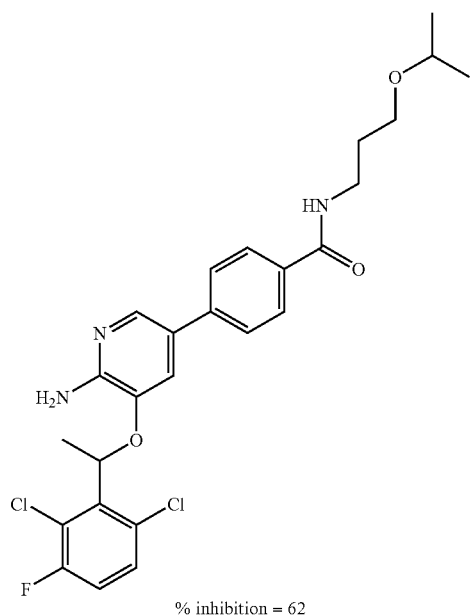
% inhibition = 62
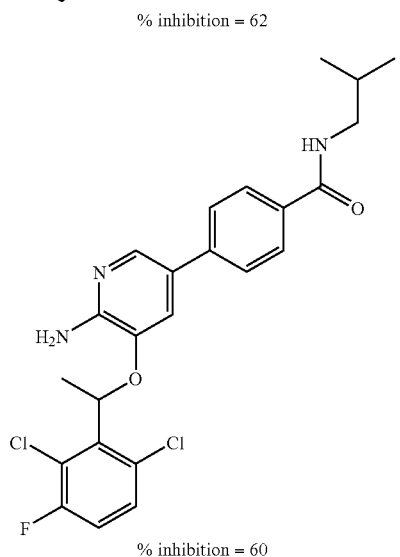
% inhibition = 60
TABLE 5-continued
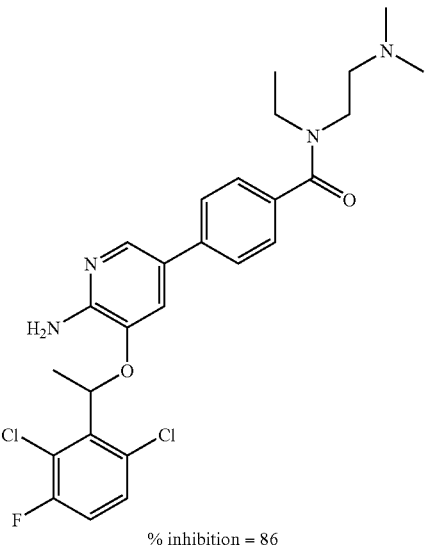
% inhibition = 86
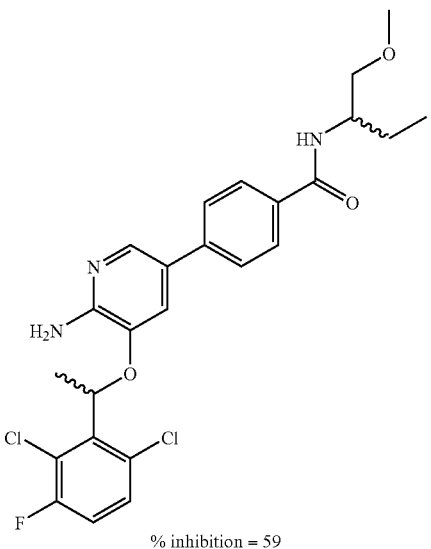
% inhibition = 59
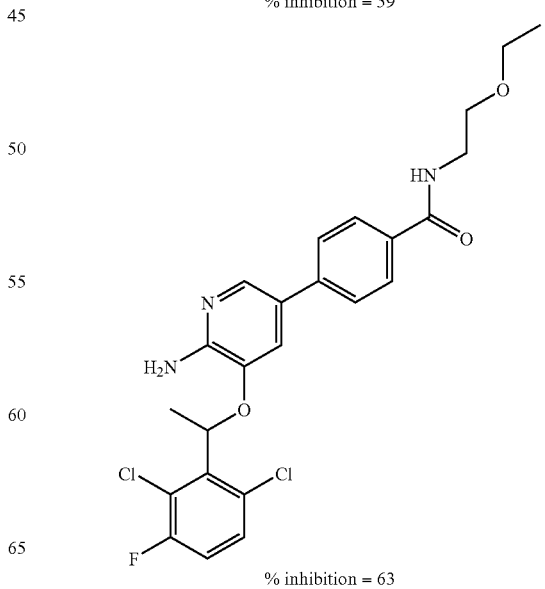
% inhibition = 63

TABLE 5-continued
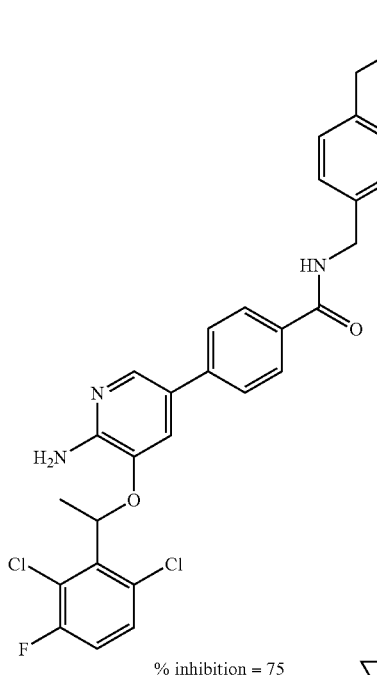
% inhibition = 75
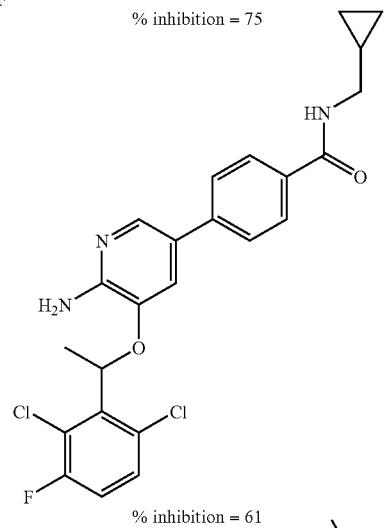
% inhibition = 61
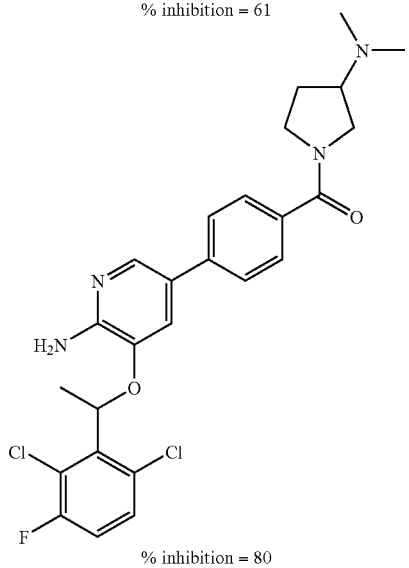
% inhibition = 80
TABLE 5-continued
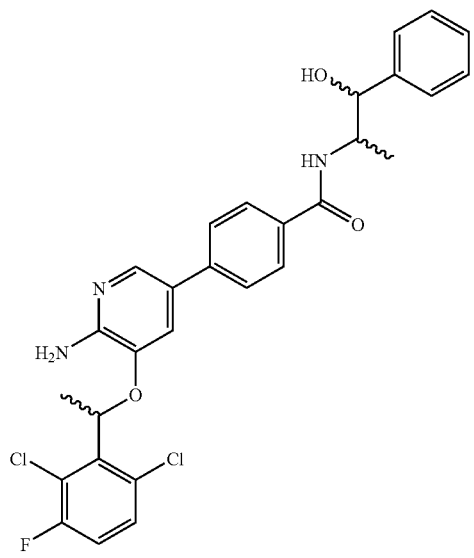
% inhibition = 69
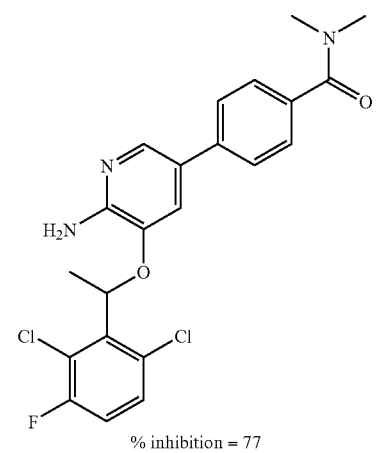
% inhibition = 77
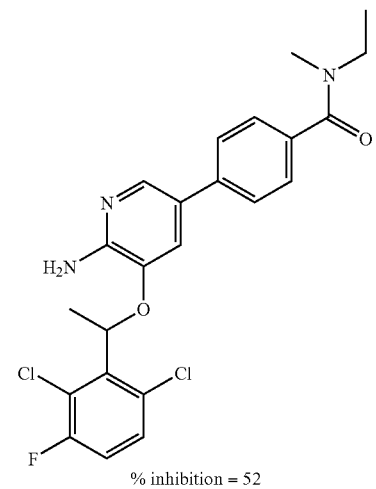
% inhibition = 52

TABLE 5-continued
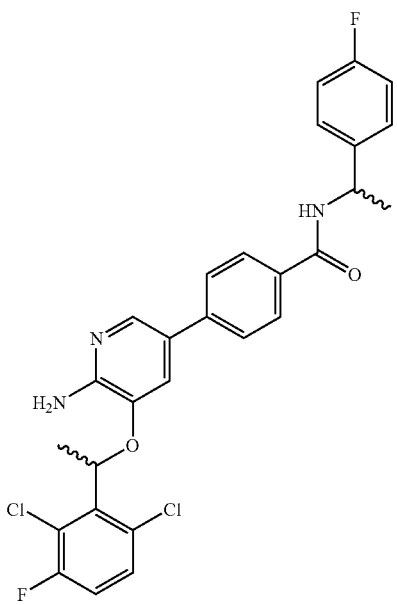
% inhibition = 56
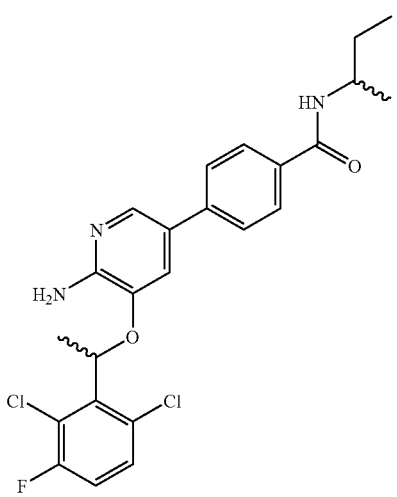
% inhibition = 64
TABLE 5-continued
Section I: Examples L-129 to L-144
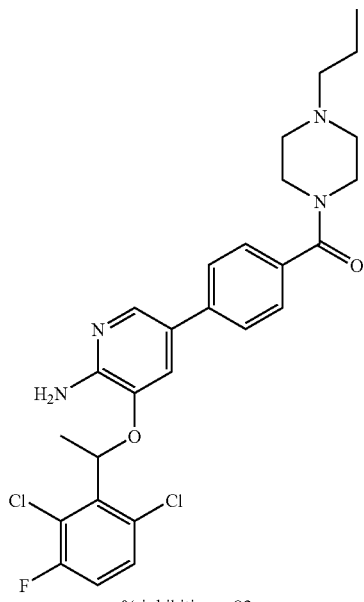
% inhibition = 82
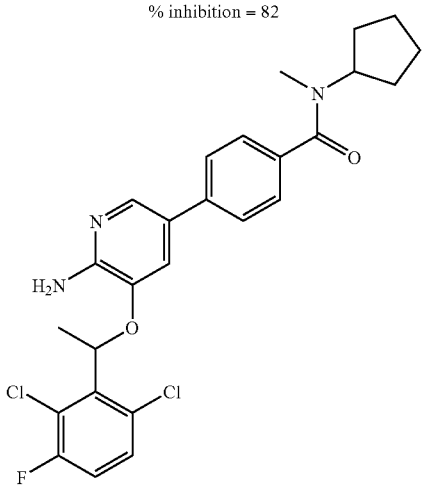
% inhibition = 60
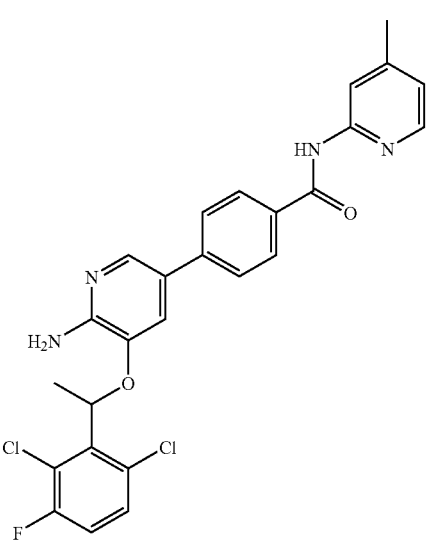
% inhibition = 61

TABLE 5-continued
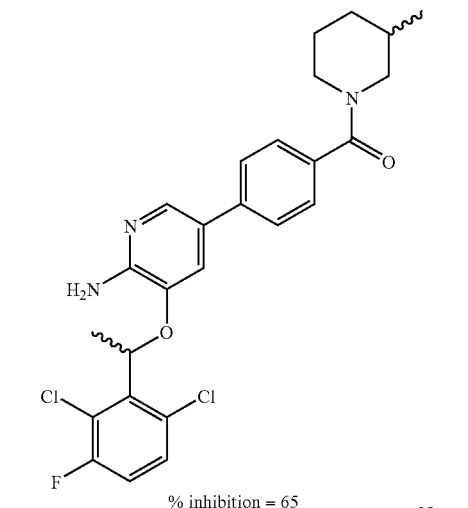
% inhibition = 65
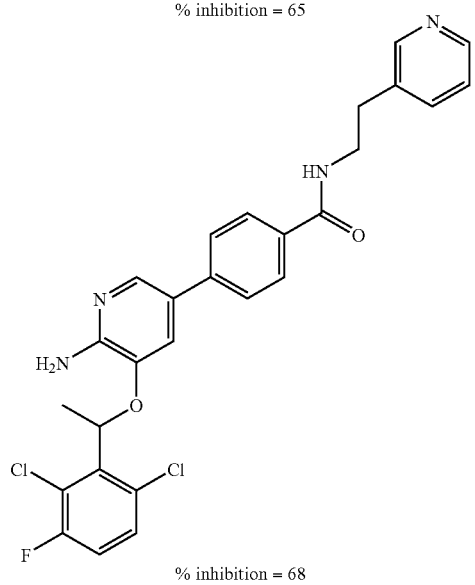
% inhibition = 68
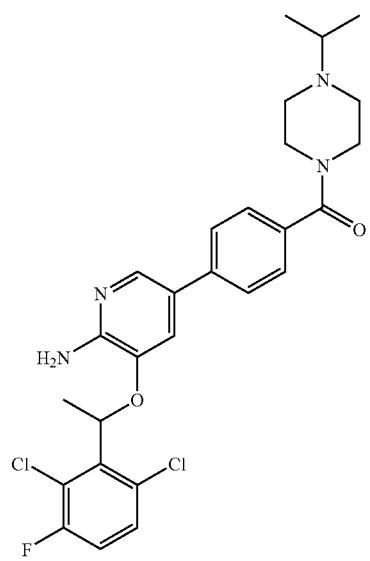
% inhibition = 76
TABLE 5-continued
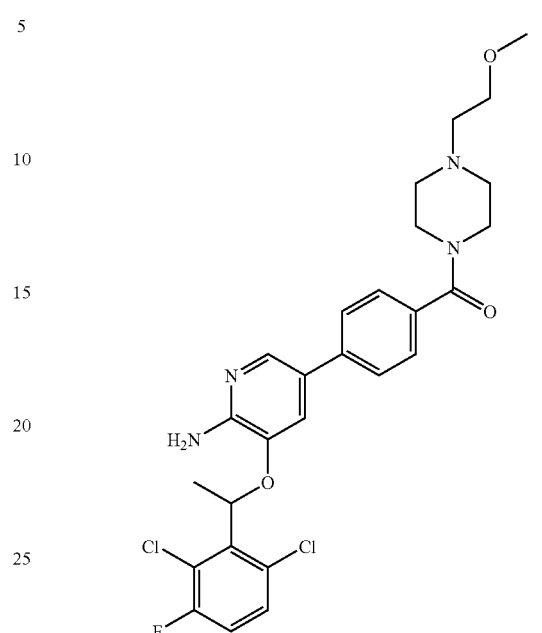
% inhibition = 76
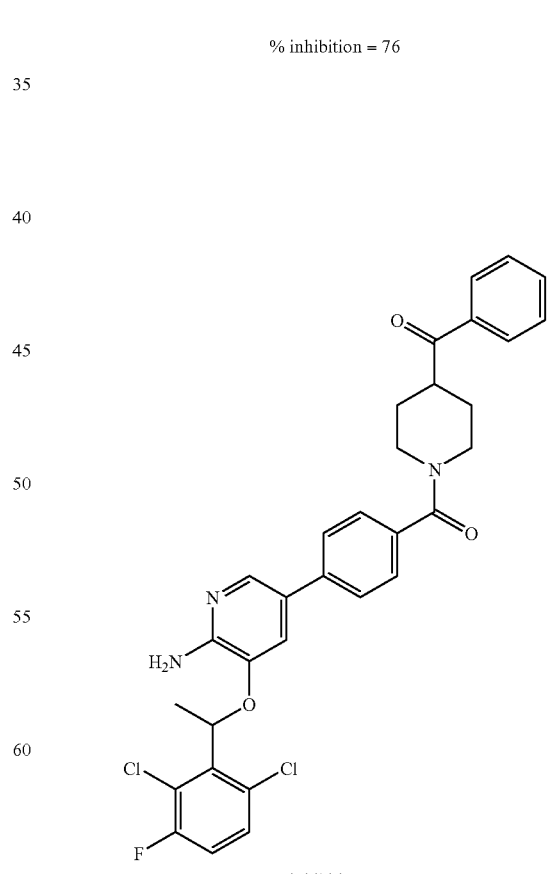
% inhibition = 61

TABLE 5-continued
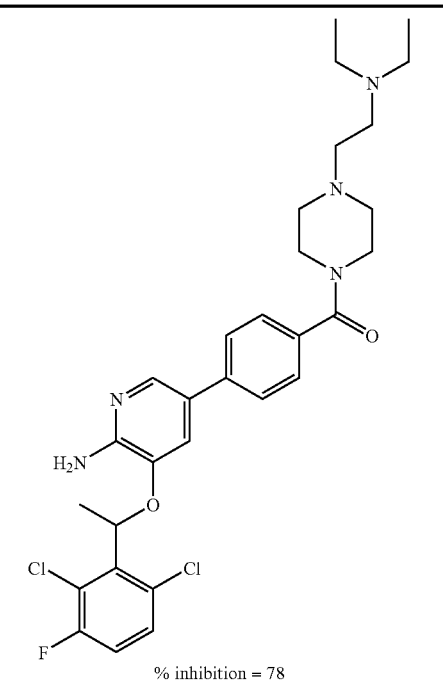
% inhibition = 78
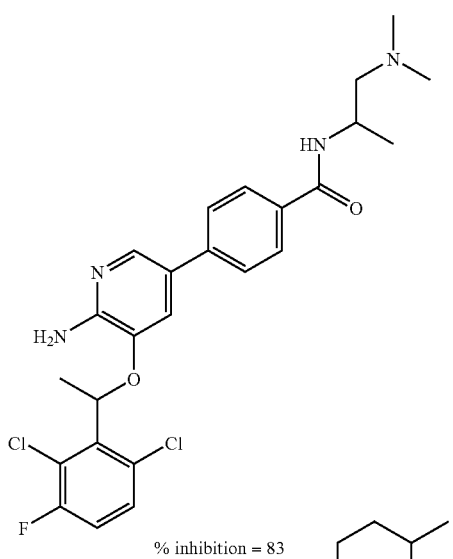
% inhibition = 83
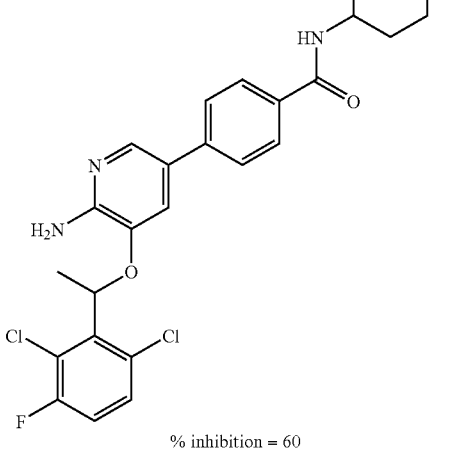
% inhibition = 60
TABLE 5-continued
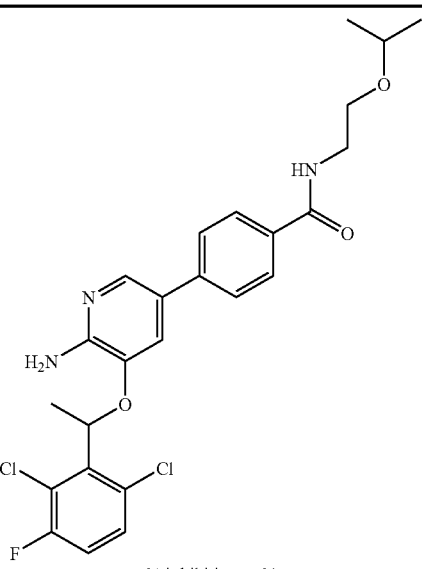
% inhibition = 64
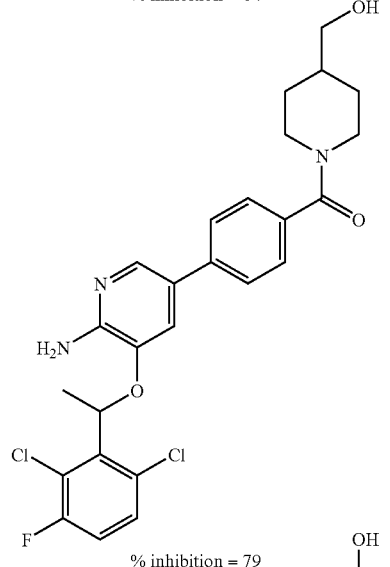
% inhibition = 79
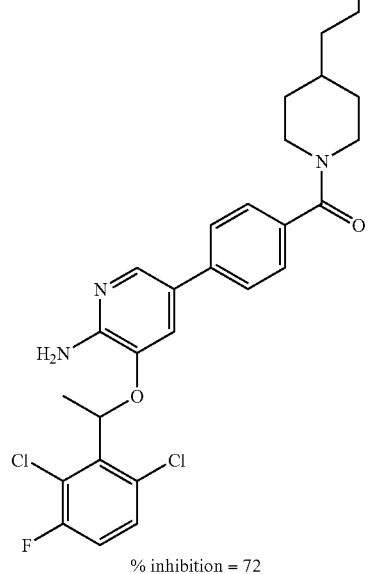
% inhibition = 72

TABLE 5-continued
Section J: Examples L-145 to L-160
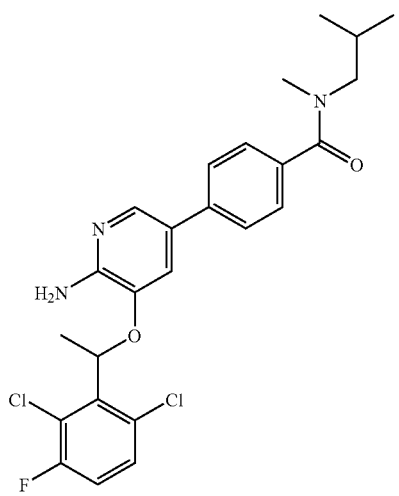
% inhibition = 59
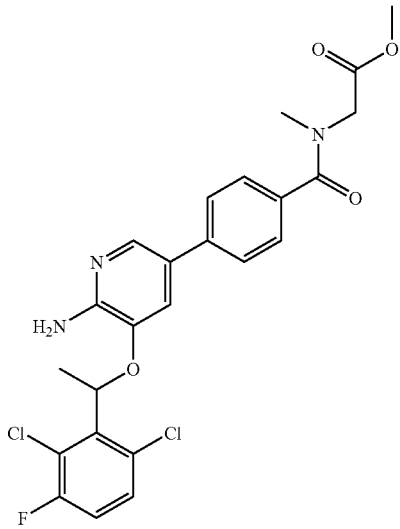
% inhibition = 77
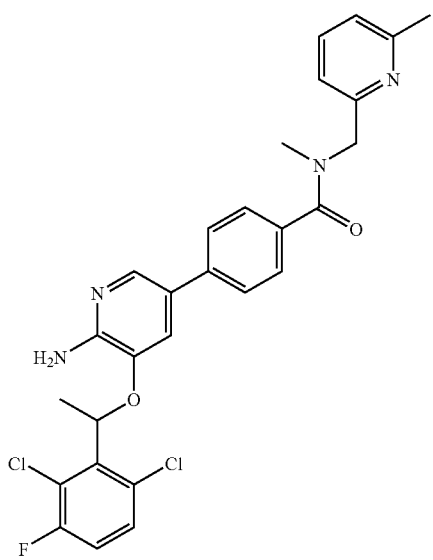
% inhibition = 71
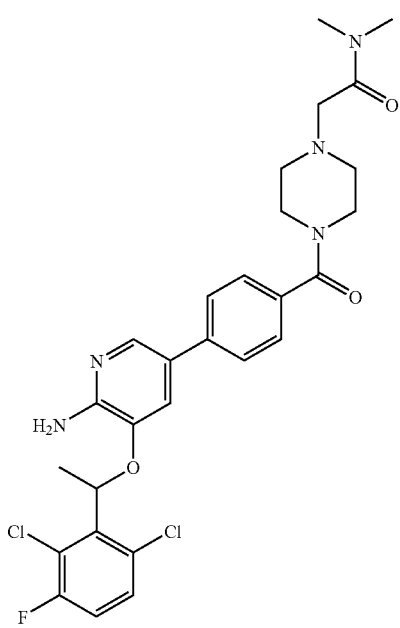
% inhibition = 89

TABLE 5-continued
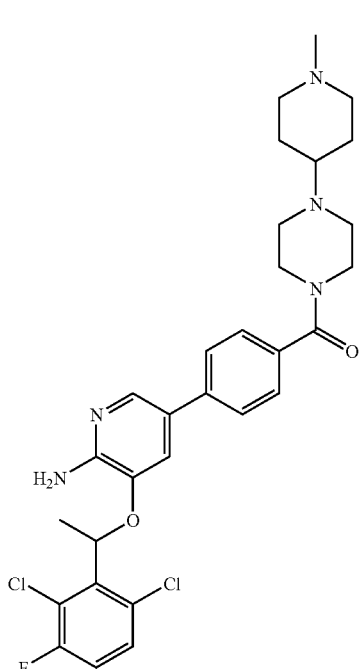
% inhibition = 96
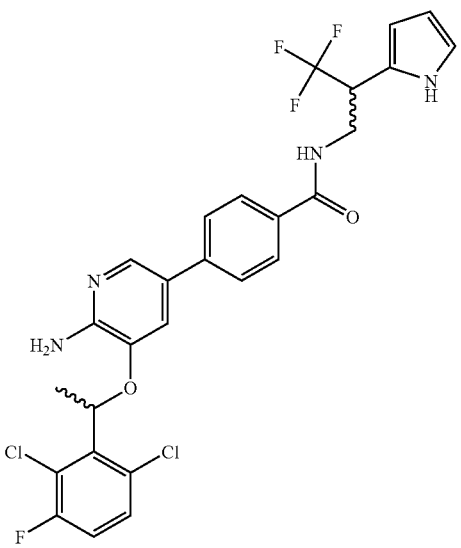
% inhibition = 70
TABLE 5-continued
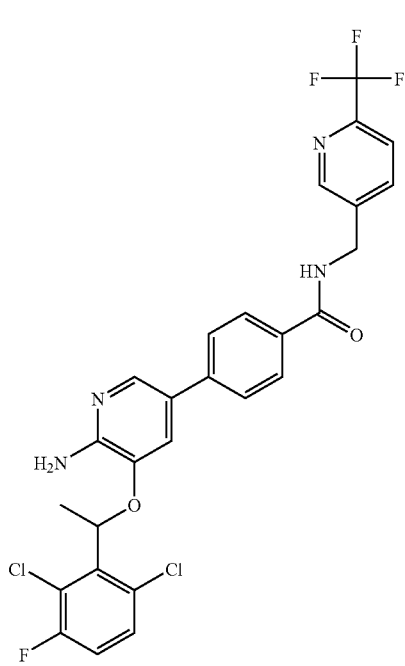
% inhibition = 62
% inhibition = 81

TABLE 5-continued
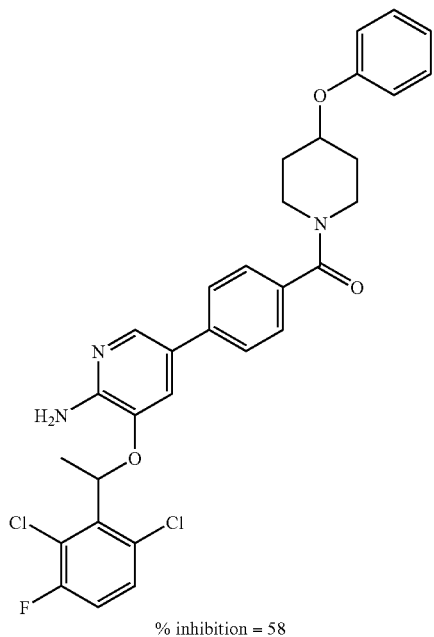
% inhibition = 58
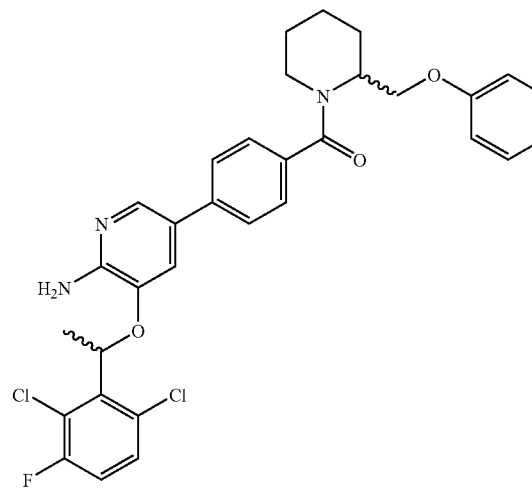
% inhibition = 53
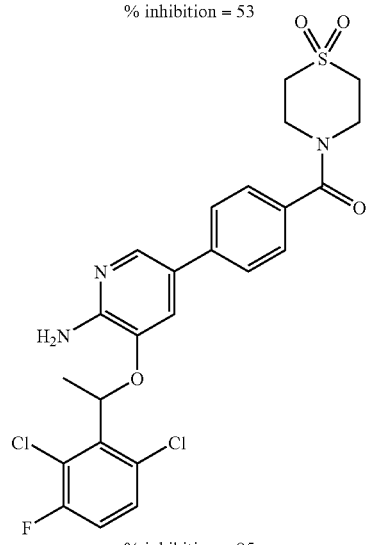
% inhibition = 95
TABLE 5-continued
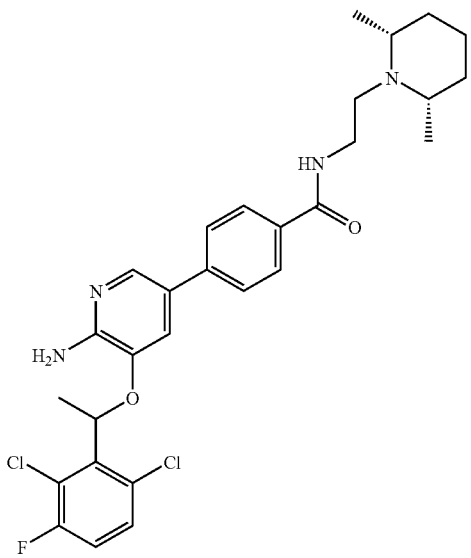
% inhibition = 77
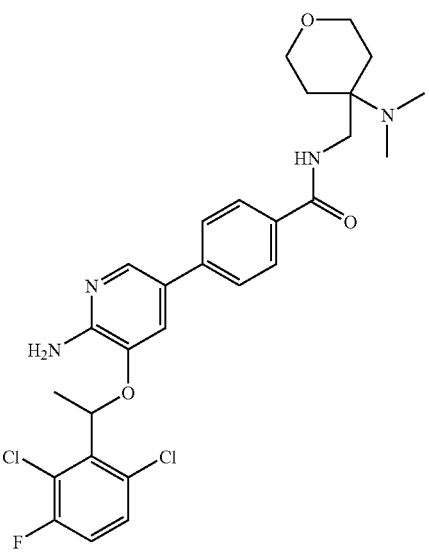
% inhibition = 66
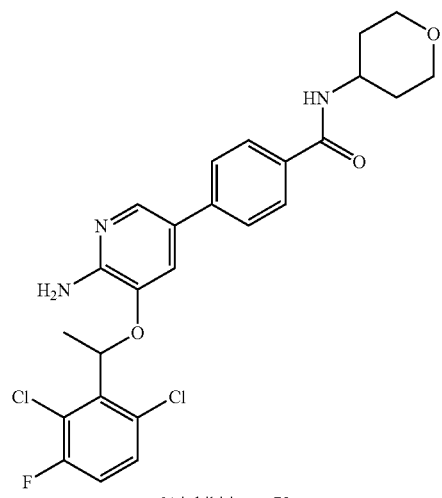
% inhibition = 73

TABLE 5-continued
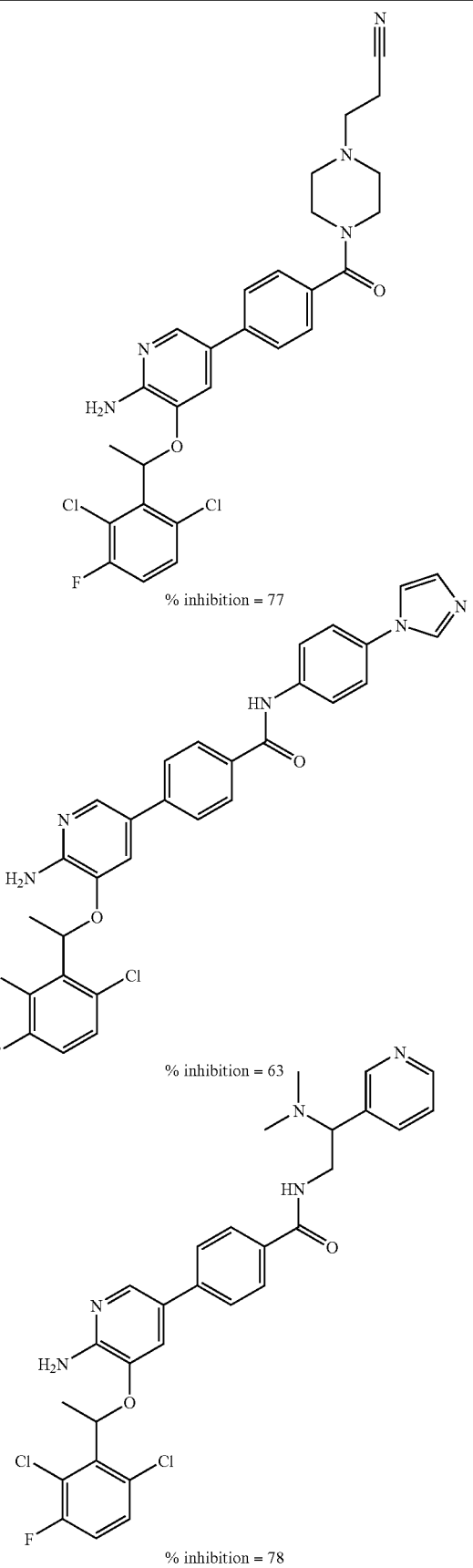
TABLE 5-continued
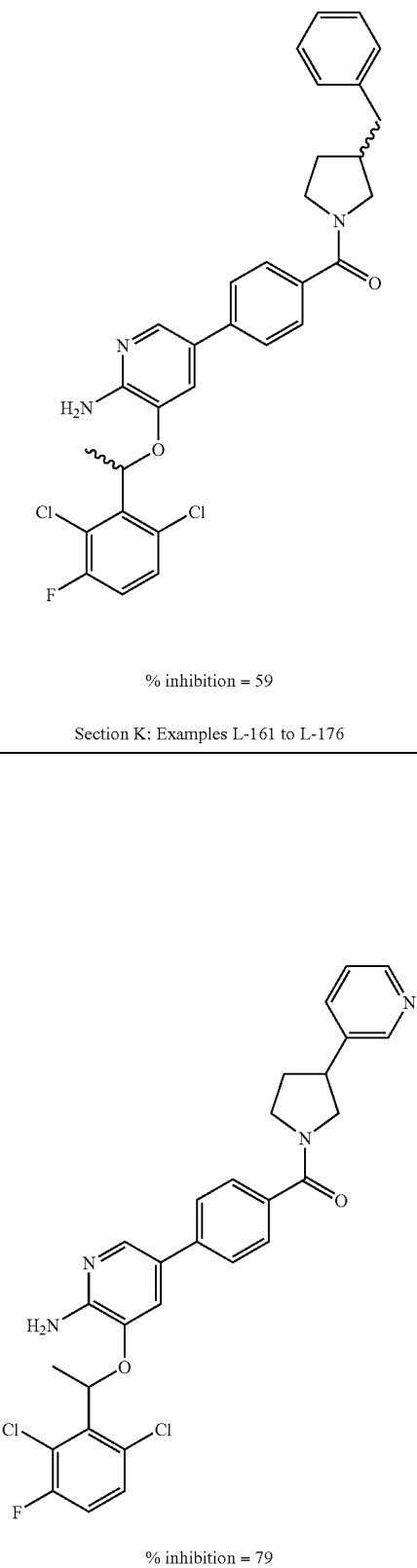
Section K: Examples L-161 to L-176

881
TABLE 5-continued
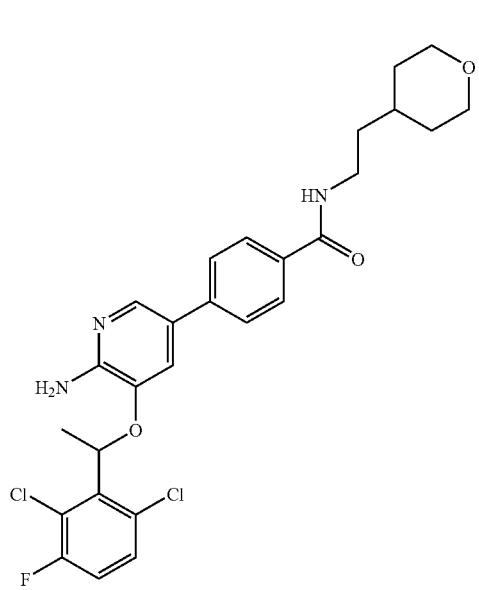
% inhibition = 66
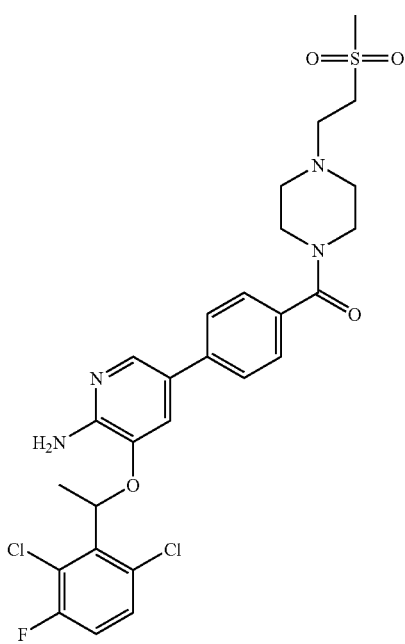
% inhibition = 83
882
TABLE 5-continued
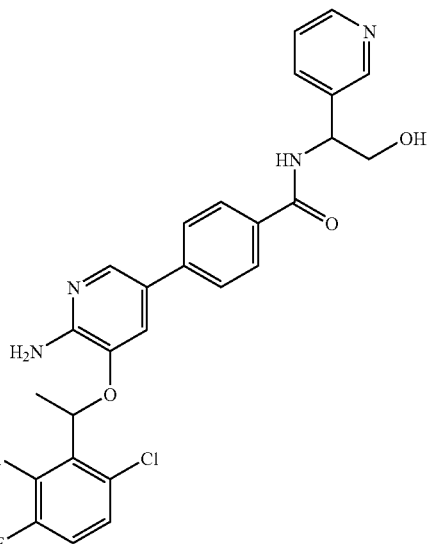
% inhibition = 61
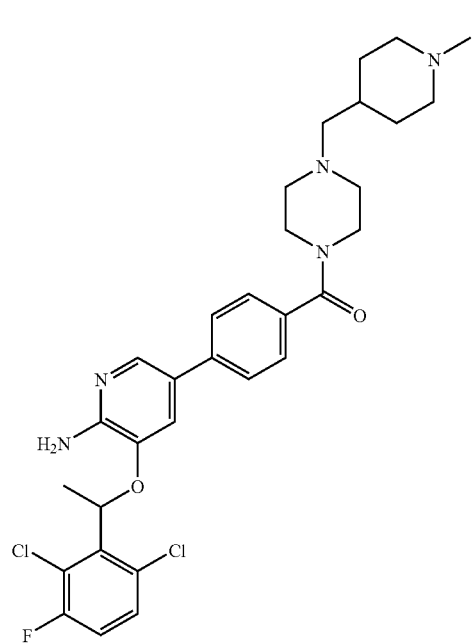
% inhibition = 88

883
TABLE 5-continued
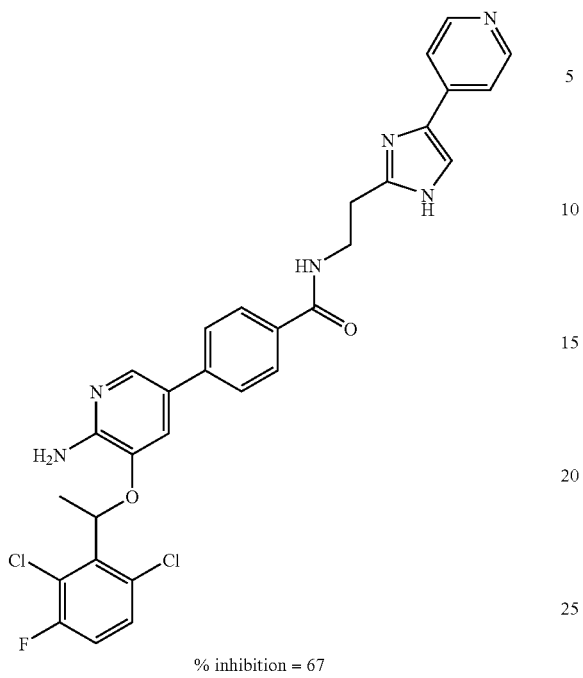
% inhibition = 67
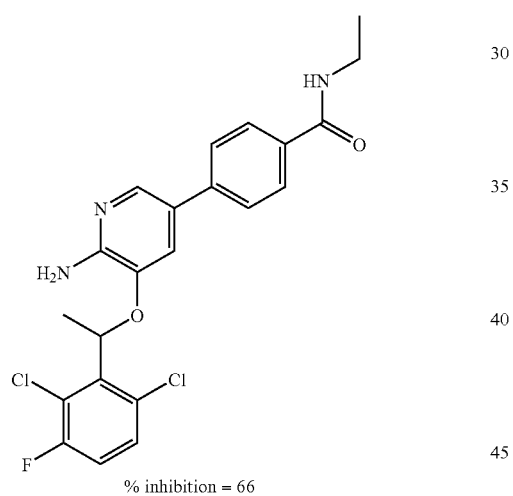
% inhibition = 66
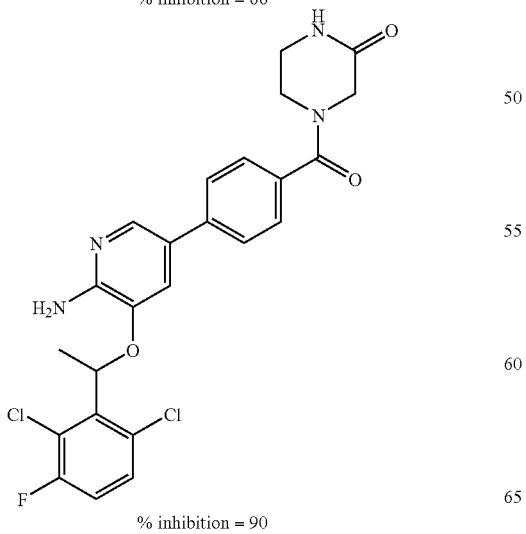
% inhibition = 90
884
TABLE 5-continued
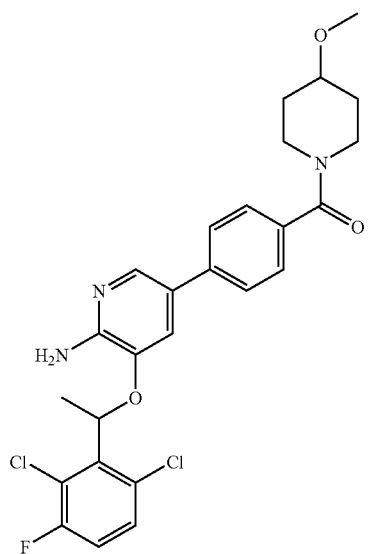
% inhibition = 79
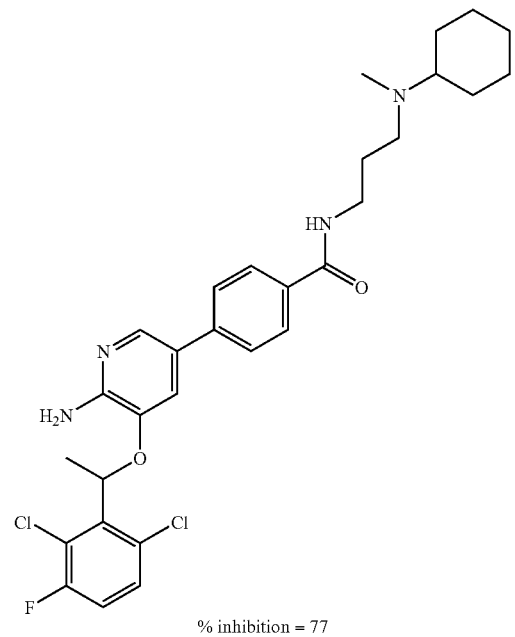
% inhibition = 77

TABLE 5-continued
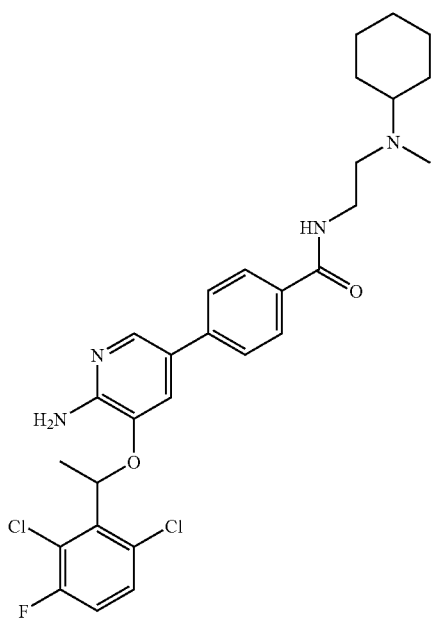
% inhibition = 69
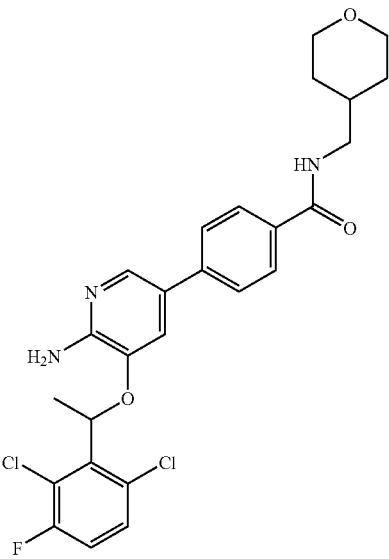
% inhibition = 63
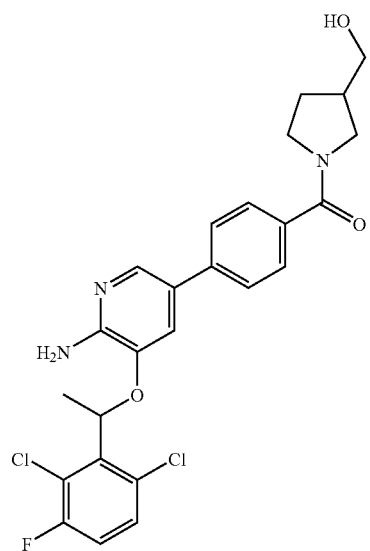
% inhibition = 79
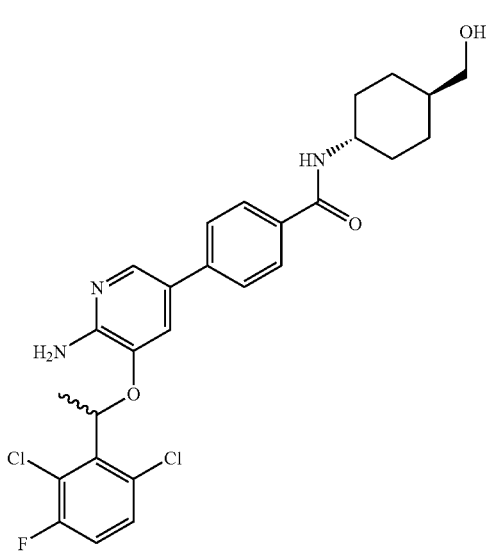
% inhibition = 68

TABLE 5-continued
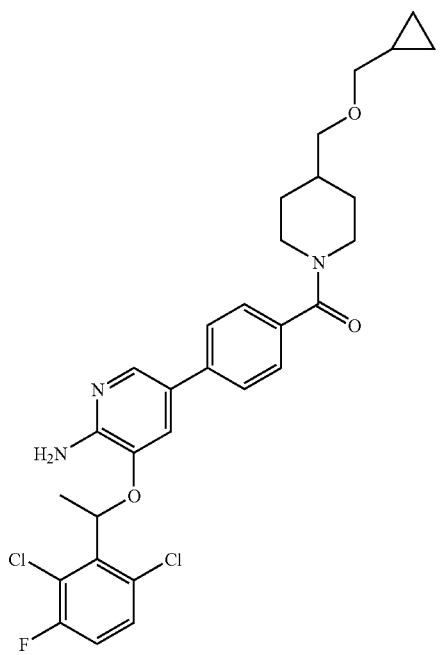
% inhibition = 60
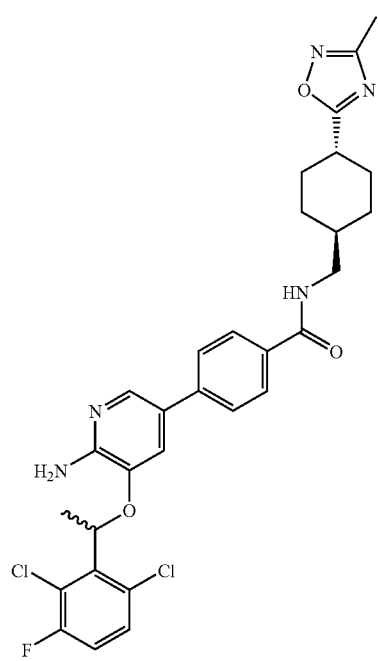
% inhibition = 51
TABLE 6
Section A: Examples L-177 to L-192
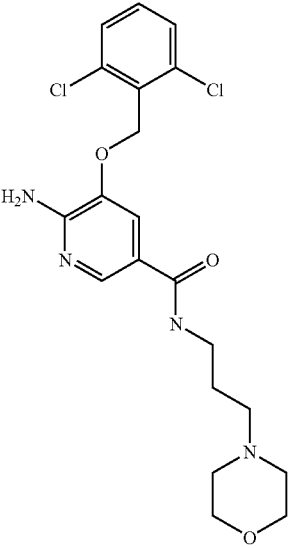
% inhibition = 26
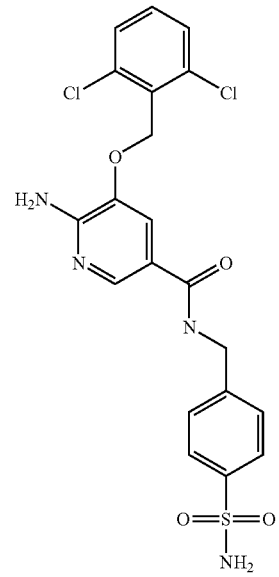
% inhibition = 30

TABLE 6-continued
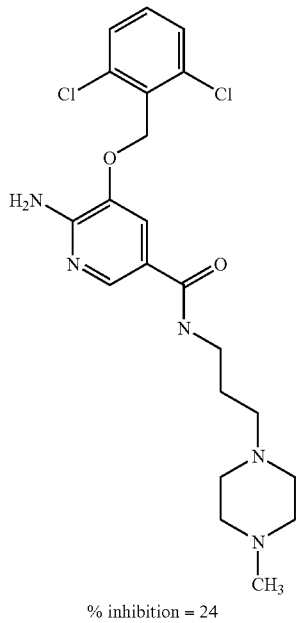
% inhibition = 24
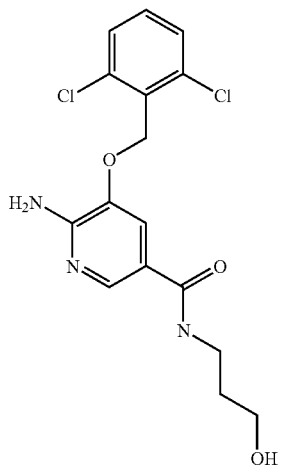
% inhibition = 26
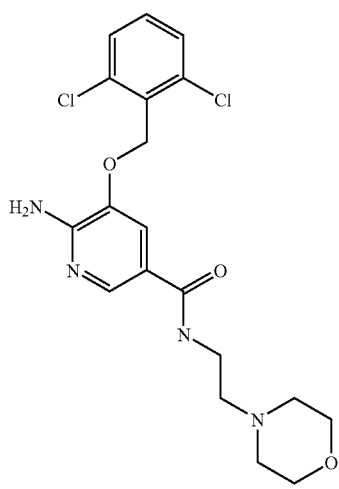
% inhibition = 31
TABLE 6-continued
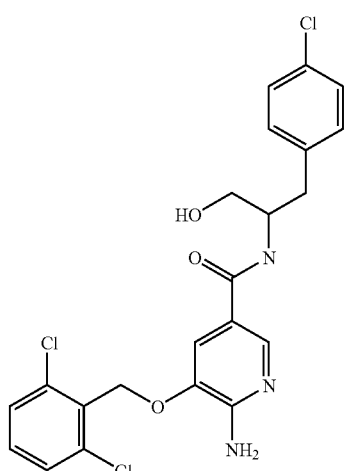
% inhibition = 27
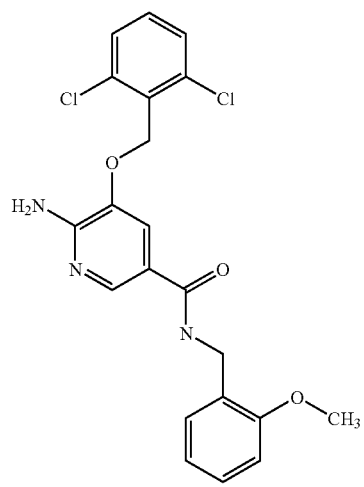
% inhibition = 32
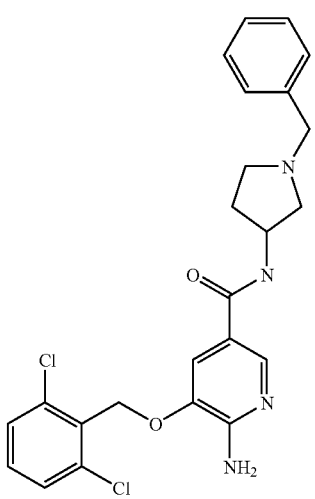
% inhibition = 27

TABLE 6-continued
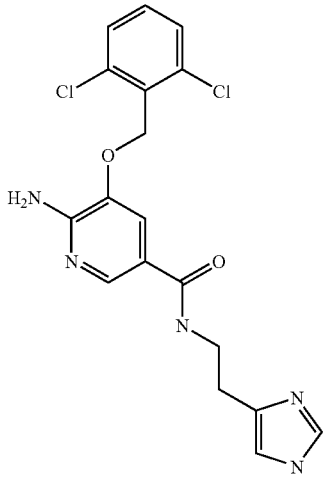
% inhibition = 29
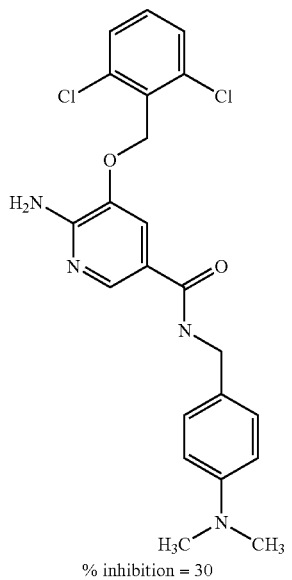
% inhibition = 30
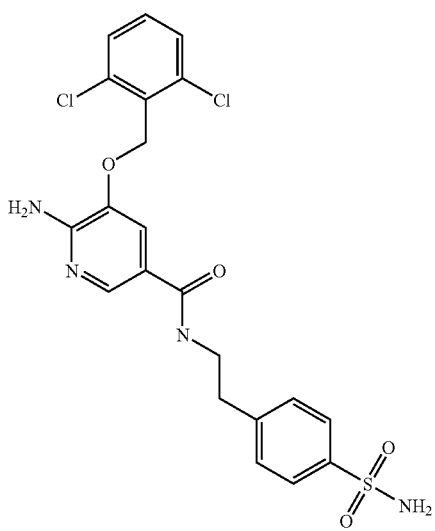
% inhibition = 30
TABLE 6-continued
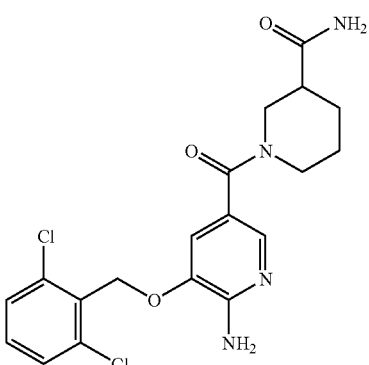
% inhibition = 39
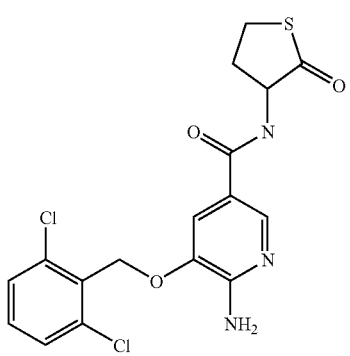
% inhibition = 35
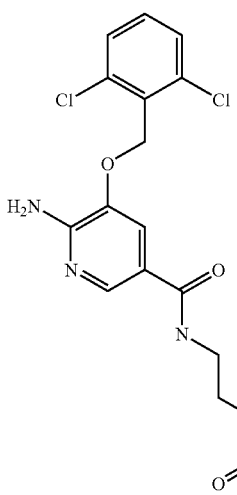
% inhibition = 35

TABLE 6-continued
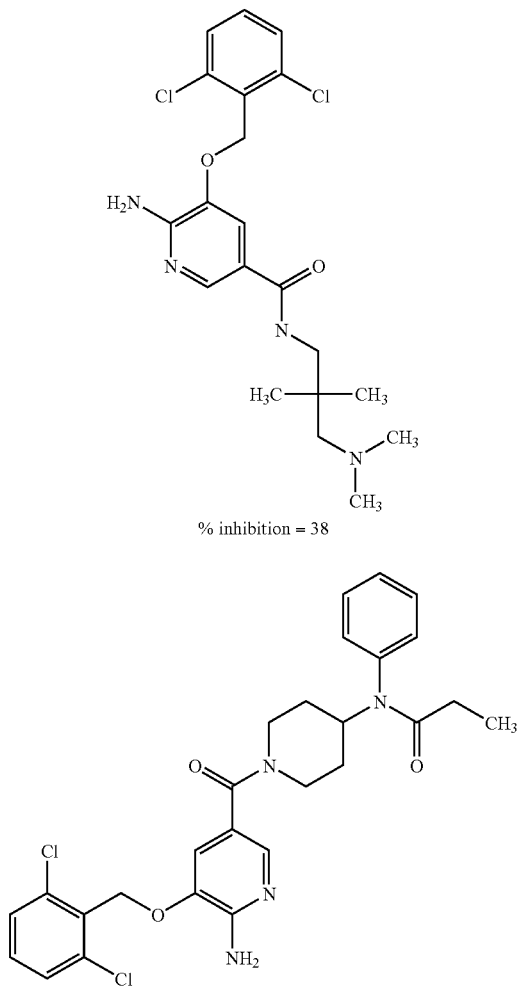
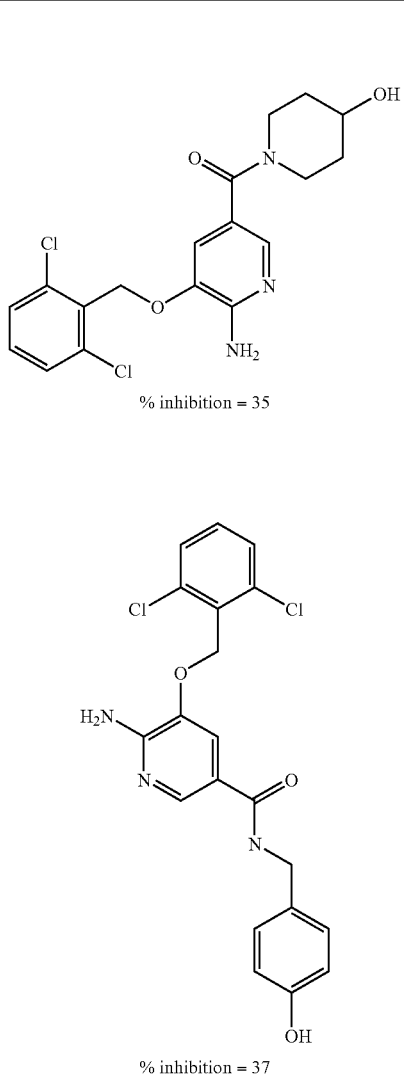
Section B: Examples L-193 to L-208
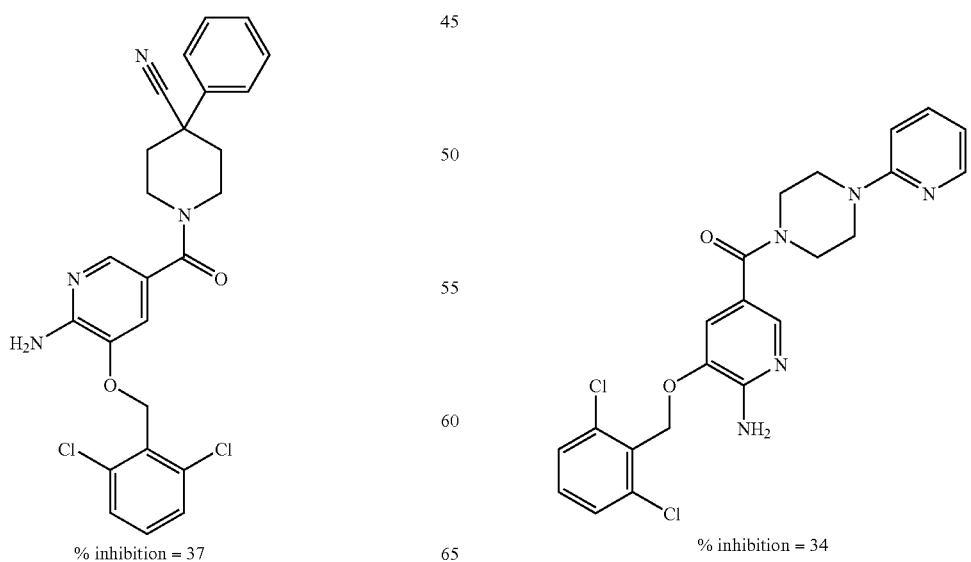

TABLE 6-continued
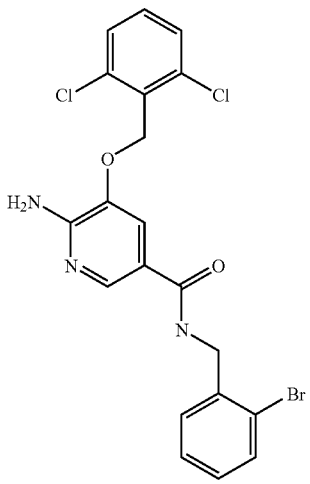
% inhibition = 36
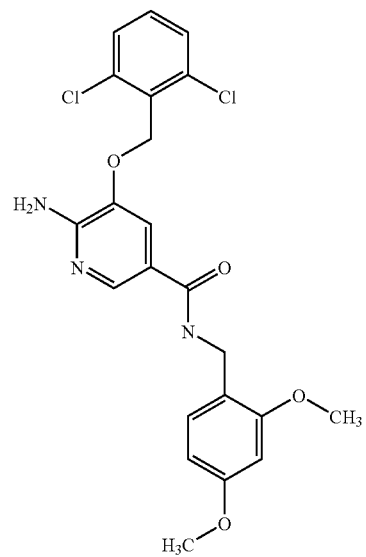
% inhibition = 59
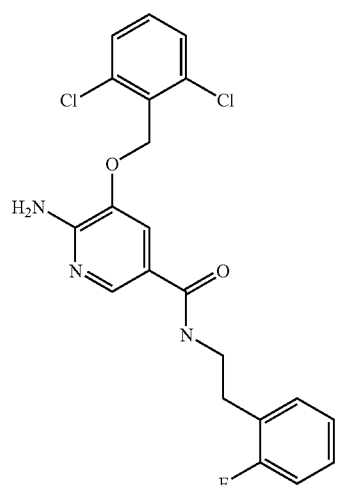
% inhibition = 33
TABLE 6-continued
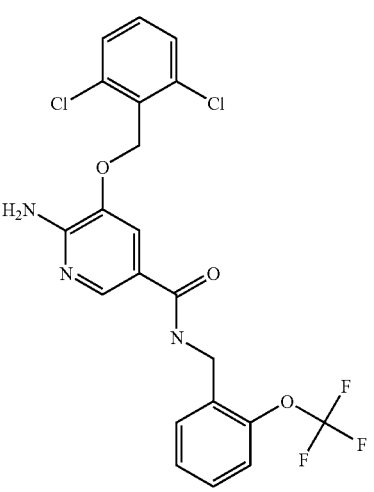
% inhibition = 31
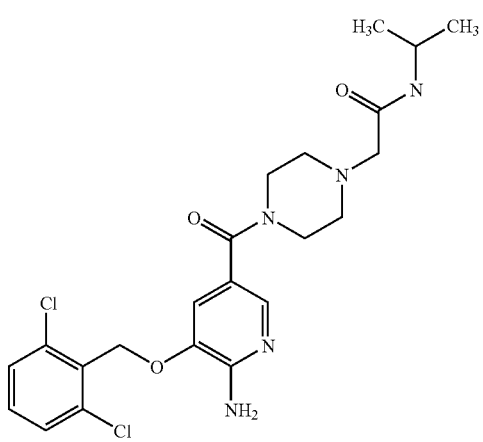
% inhibition = 30
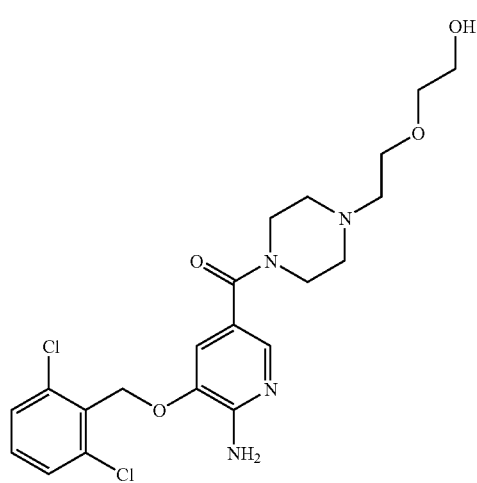
% inhibition = 33

TABLE 6-continued
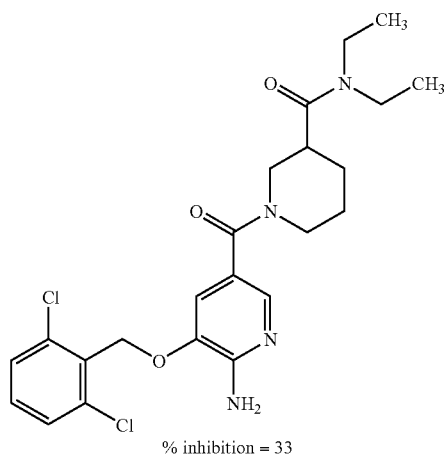
% inhibition = 33
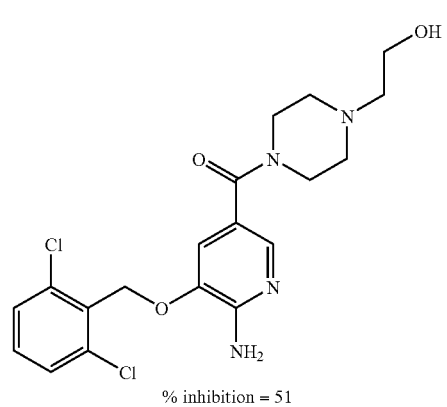
% inhibition = 51
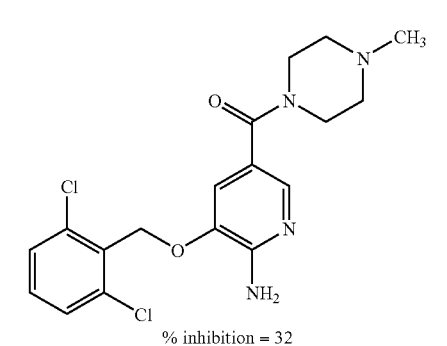
% inhibition = 32
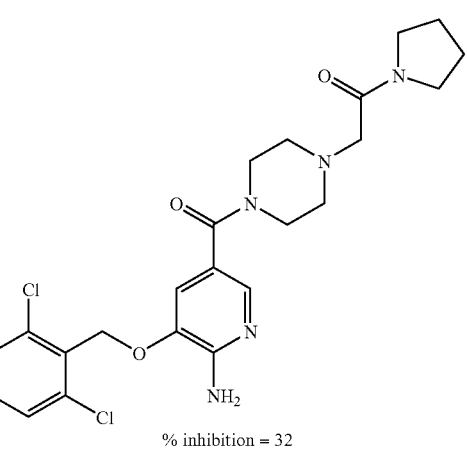
% inhibition = 32
TABLE 6-continued
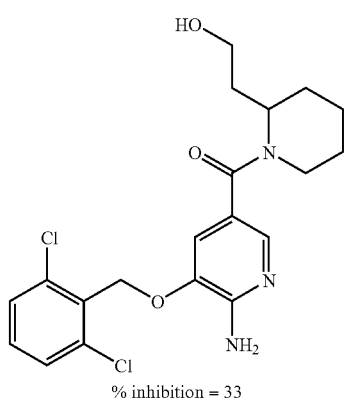
% inhibition = 33
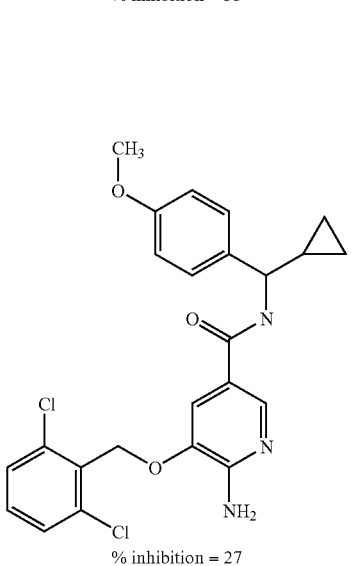
% inhibition = 27
Section C: Examples L-209 to L-224
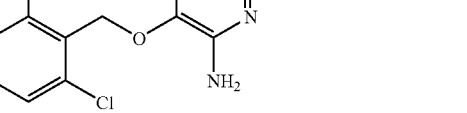
% inhibition = 31

TABLE 6-continued
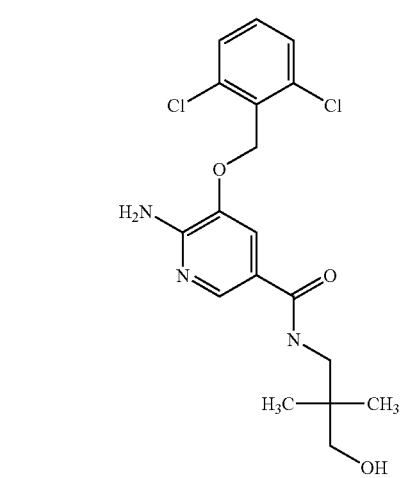
% inhibition = 39
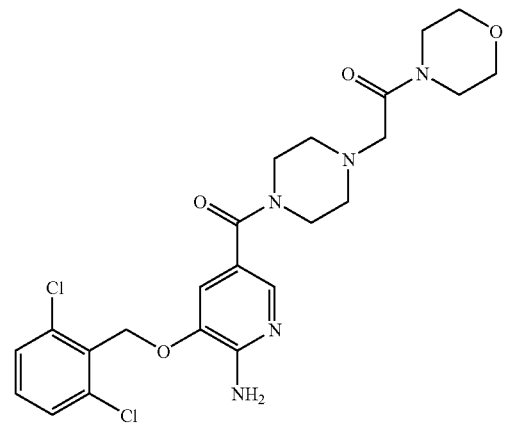
% inhibition = 31
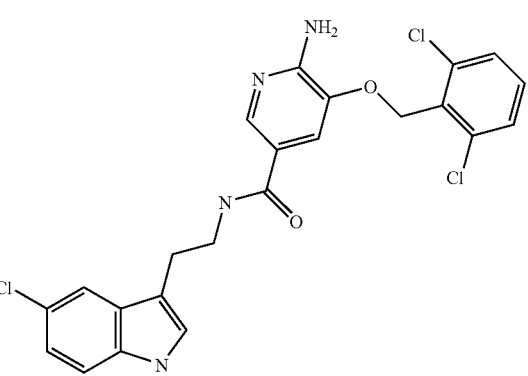
% inhibition = 36
TABLE 6-continued
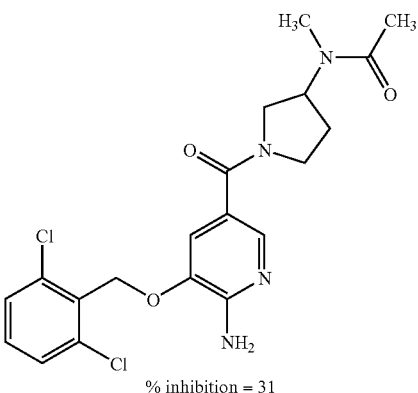
% inhibition = 31
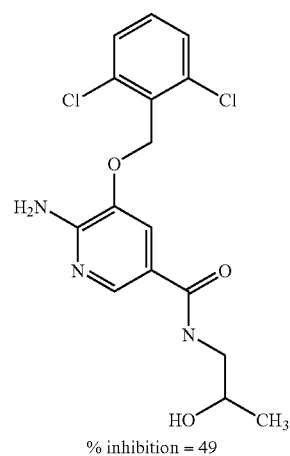
% inhibition = 49
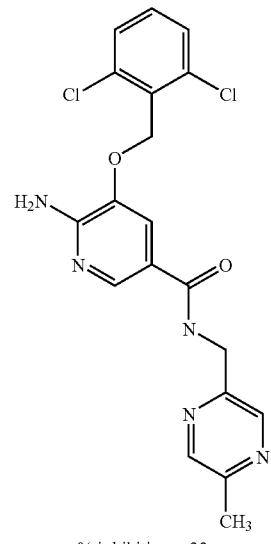
% inhibition = 33

TABLE 6-continued
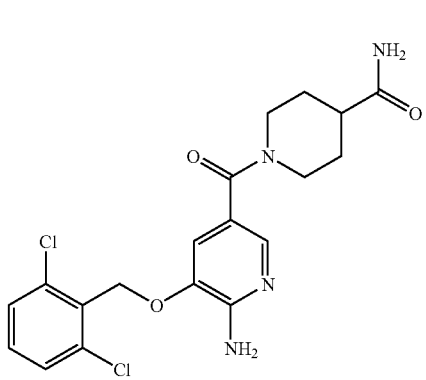
% inhibition = 29
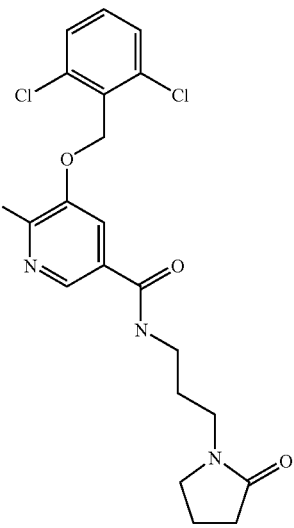
% inhibition = 34
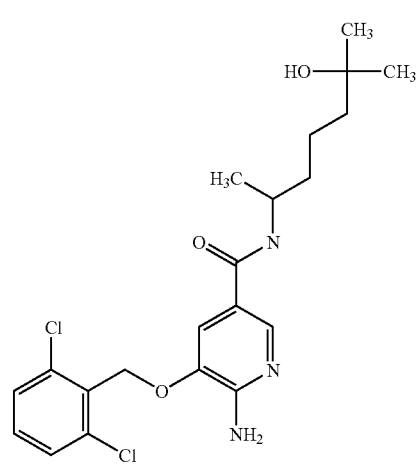
% inhibition = 35
TABLE 6-continued
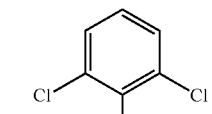
% inhibition = 34
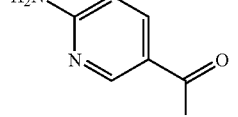
% inhibition = 32
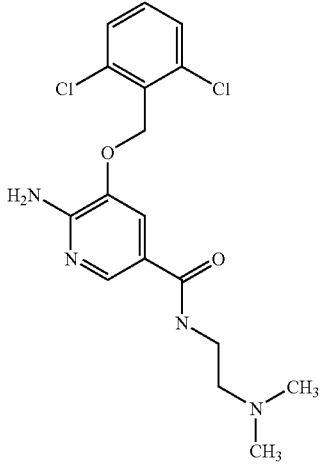
% inhibition = 29

TABLE 6-continued
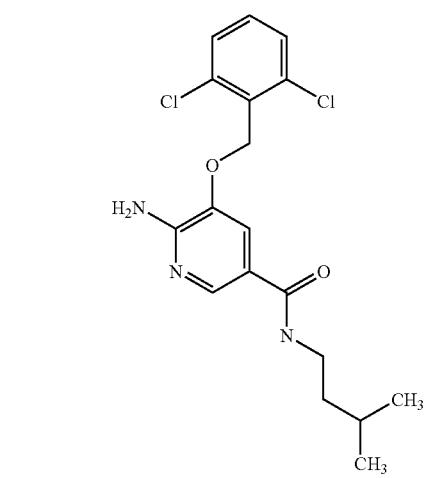
% inhibition = 26
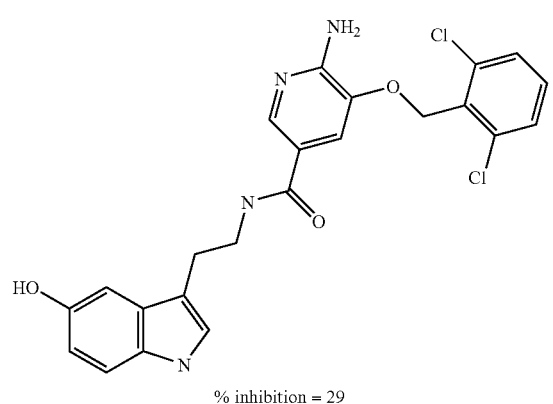
% inhibition = 29
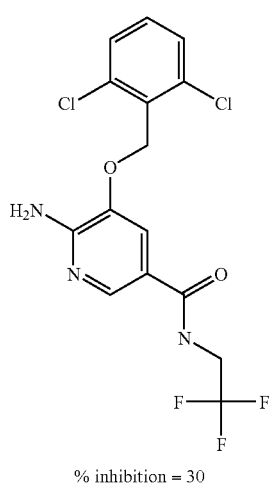
% inhibition = 30
TABLE 6-continued
Section D: Examples L-225 to L-240
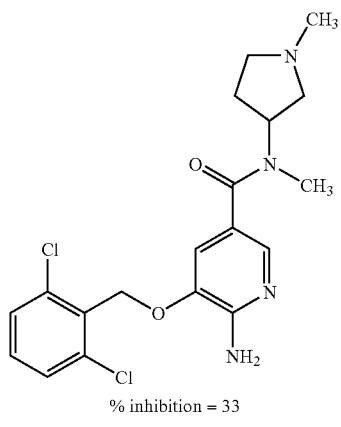
% inhibition = 33
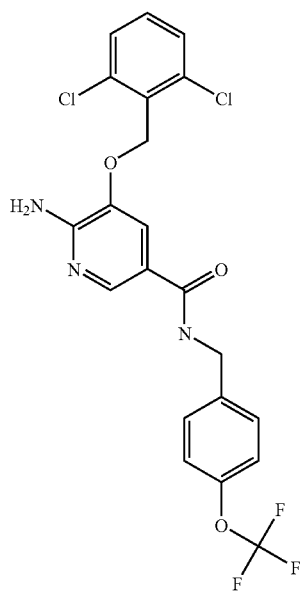
% inhibition = 24
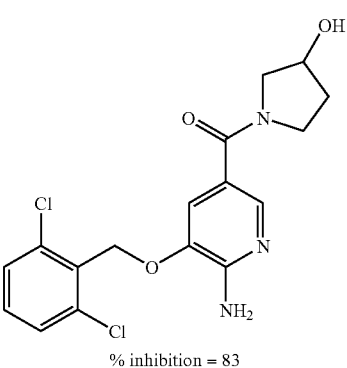
% inhibition = 83

TABLE 6-continued
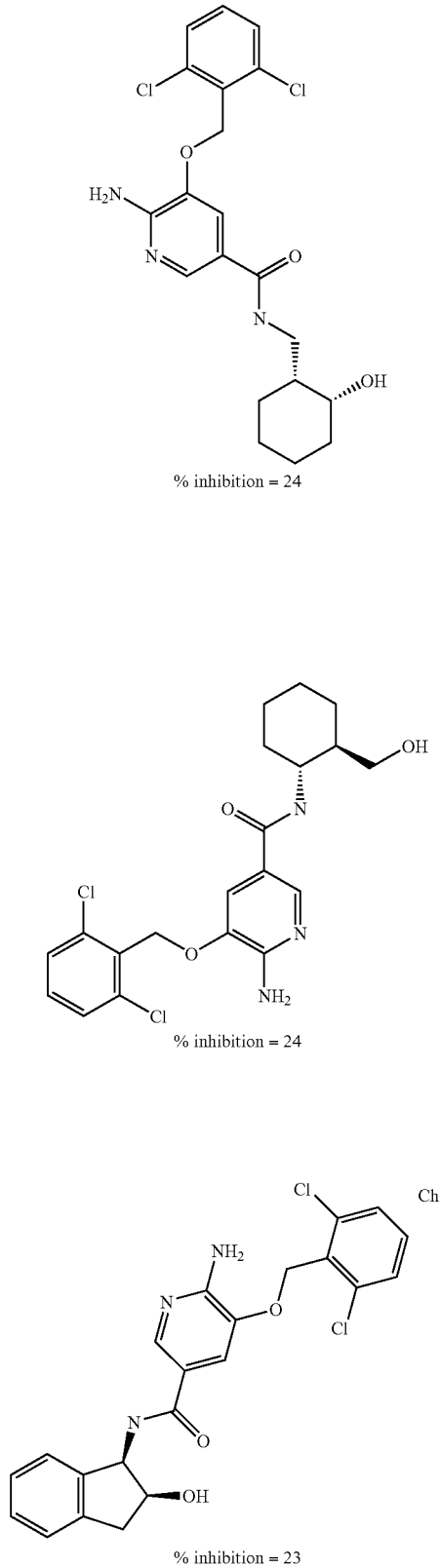

TABLE 6-continued
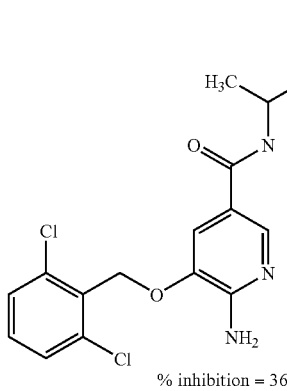
% inhibition = 36
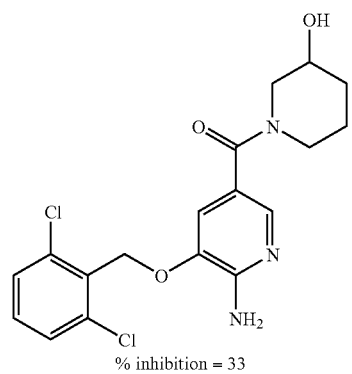
% inhibition = 33
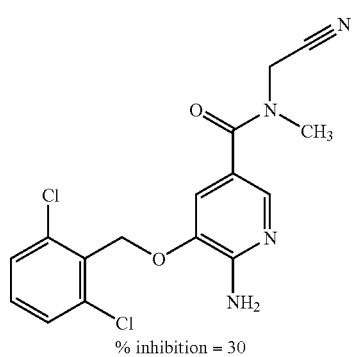
% inhibition = 30
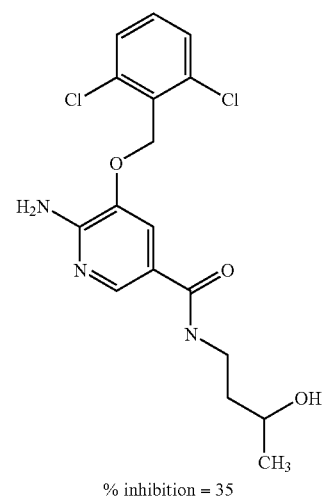
% inhibition = 35
TABLE 6-continued
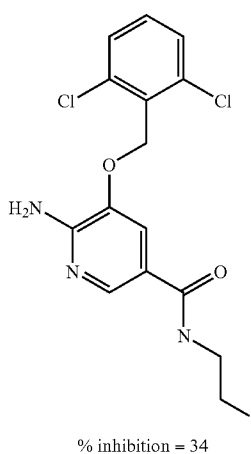
% inhibition = 34
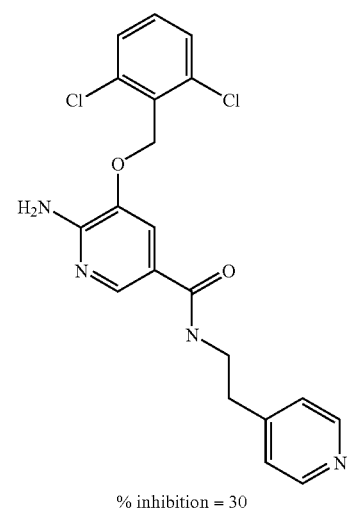
% inhibition = 30
Section E: Examples L-241 to L-256
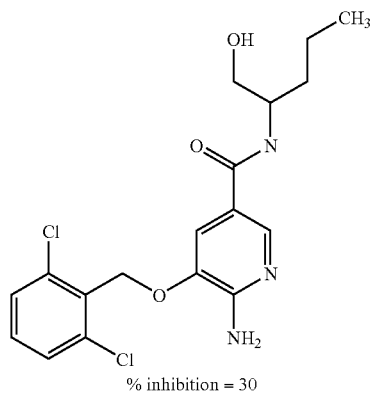
% inhibition = 30

TABLE 6-continued
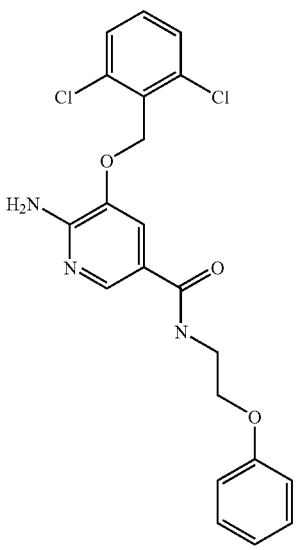
% inhibition = 66
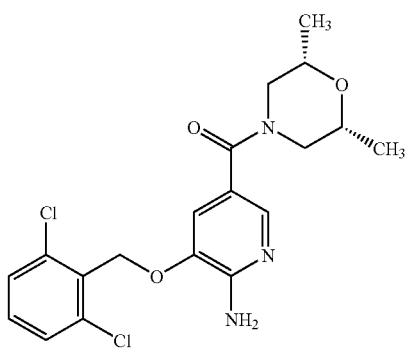
% inhibition = 32
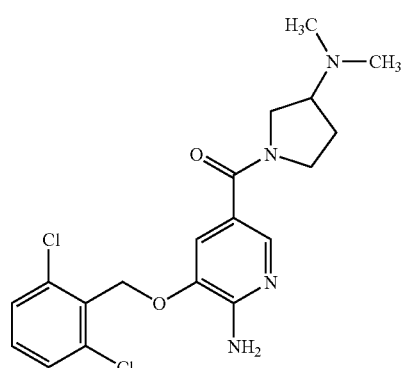
% inhibition = 33
TABLE 6-continued
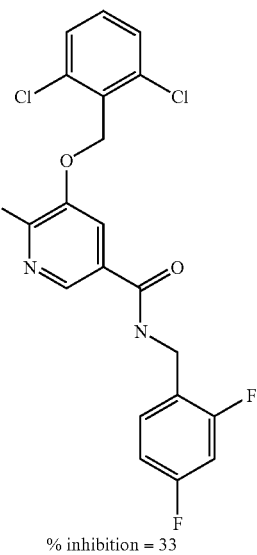
% inhibition = 33
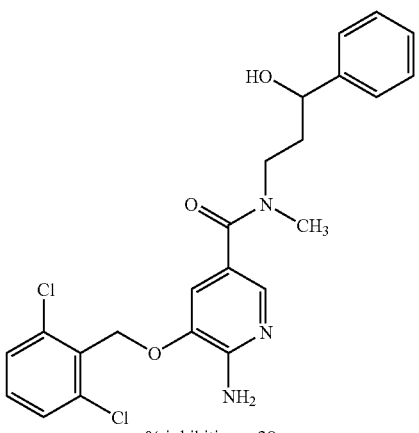
% inhibition = 28
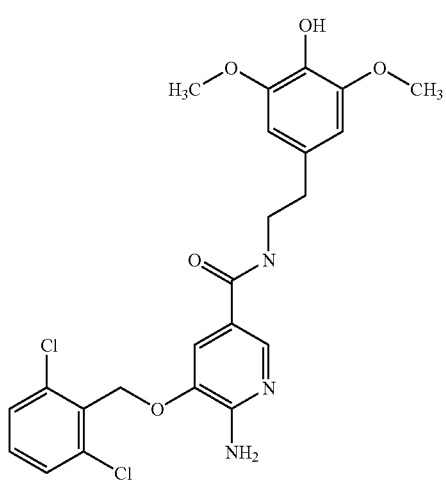
% inhibition = 25

TABLE 6-continued
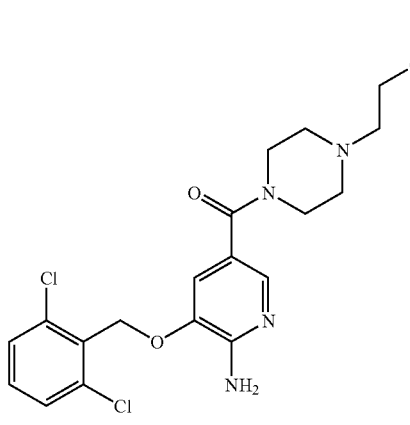
% inhibition = 27
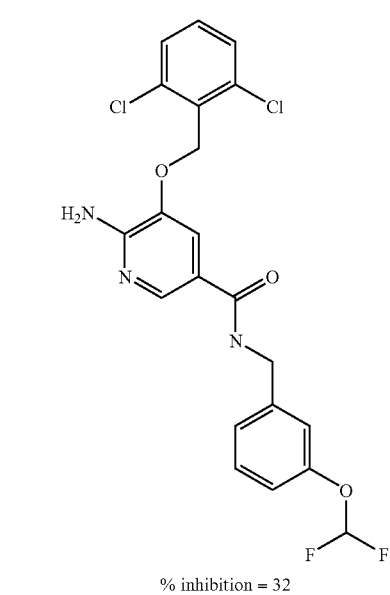
% inhibition = 32
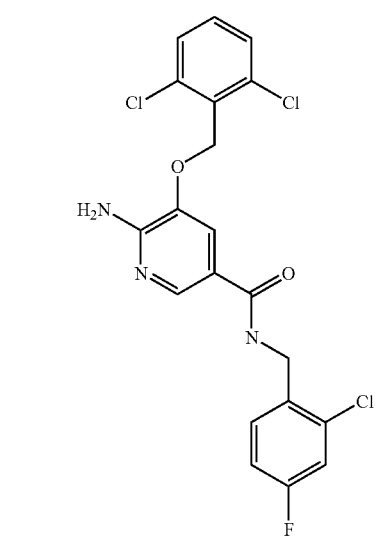
% inhibition = 37
TABLE 6-continued
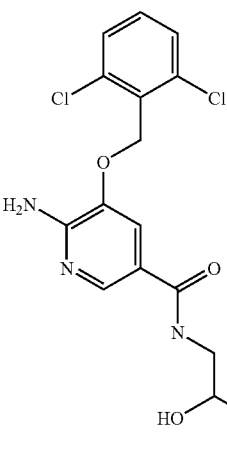
% inhibition = 29
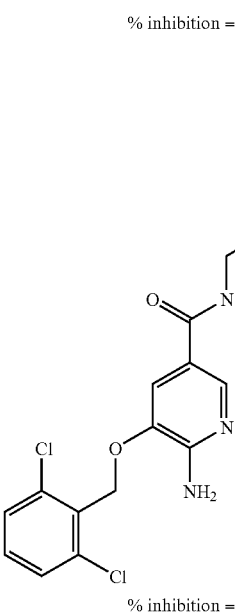
% inhibition = 32
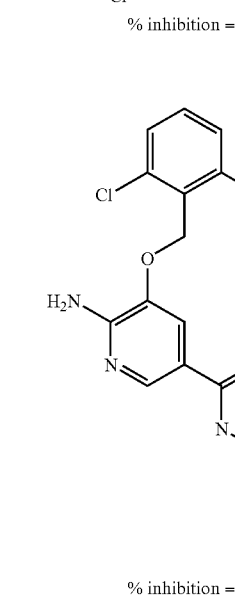
% inhibition = 28

TABLE 6-continued
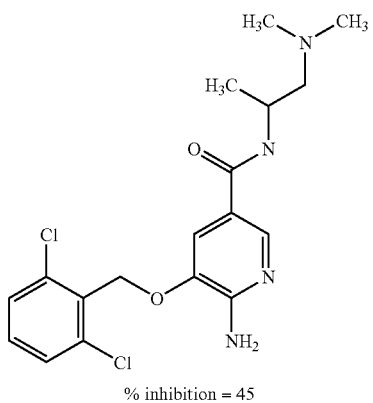
% inhibition = 45
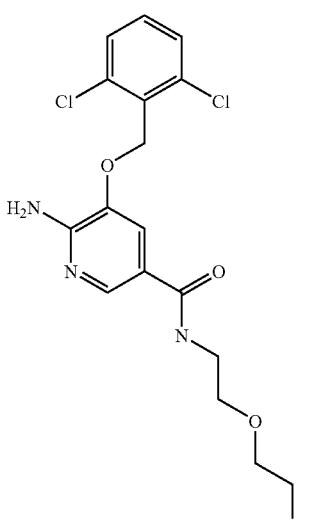
% inhibition = 45
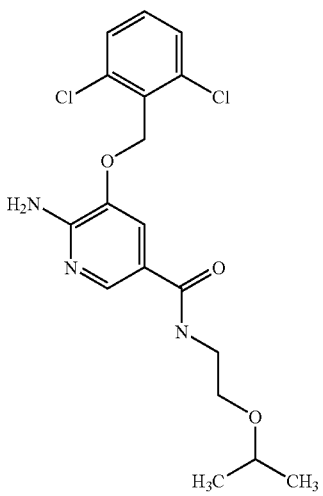
% inhibition = 46
TABLE 6-continued
Section F: Examples L-257 to L-272
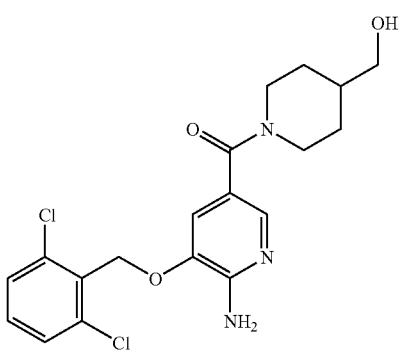
% inhibition = 43
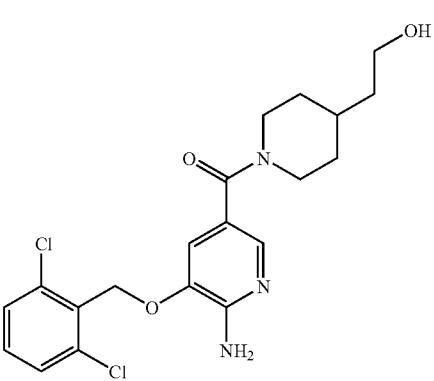
% inhibition = 45
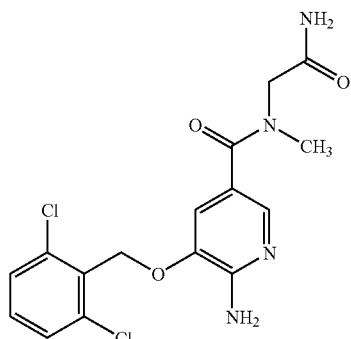
% inhibition = 39
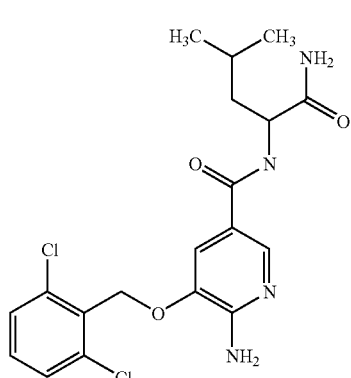
% inhibition = 40

TABLE 6-continued
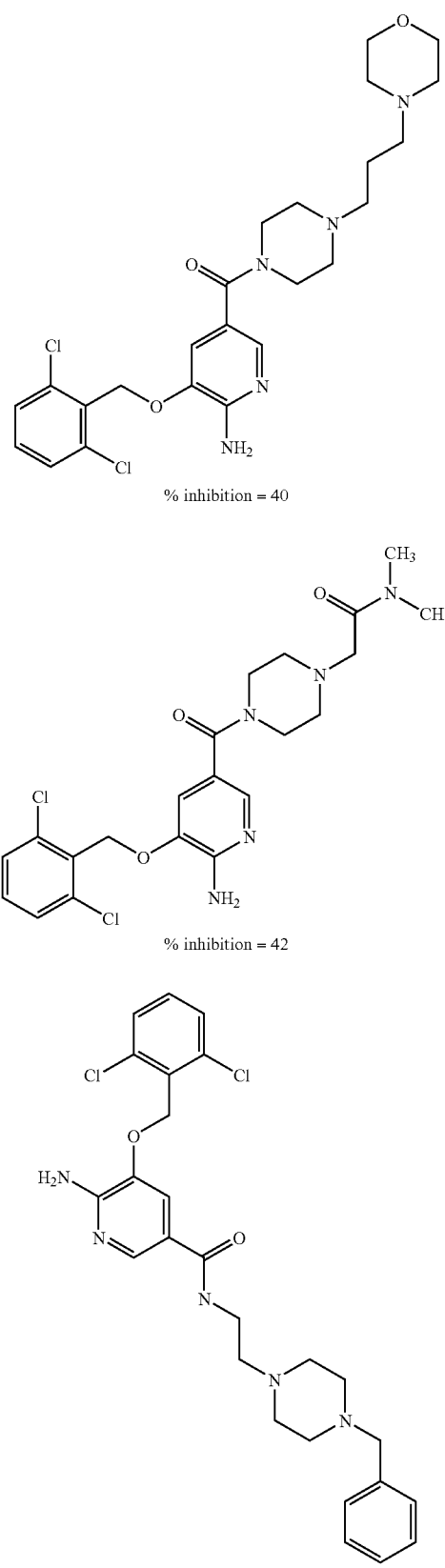
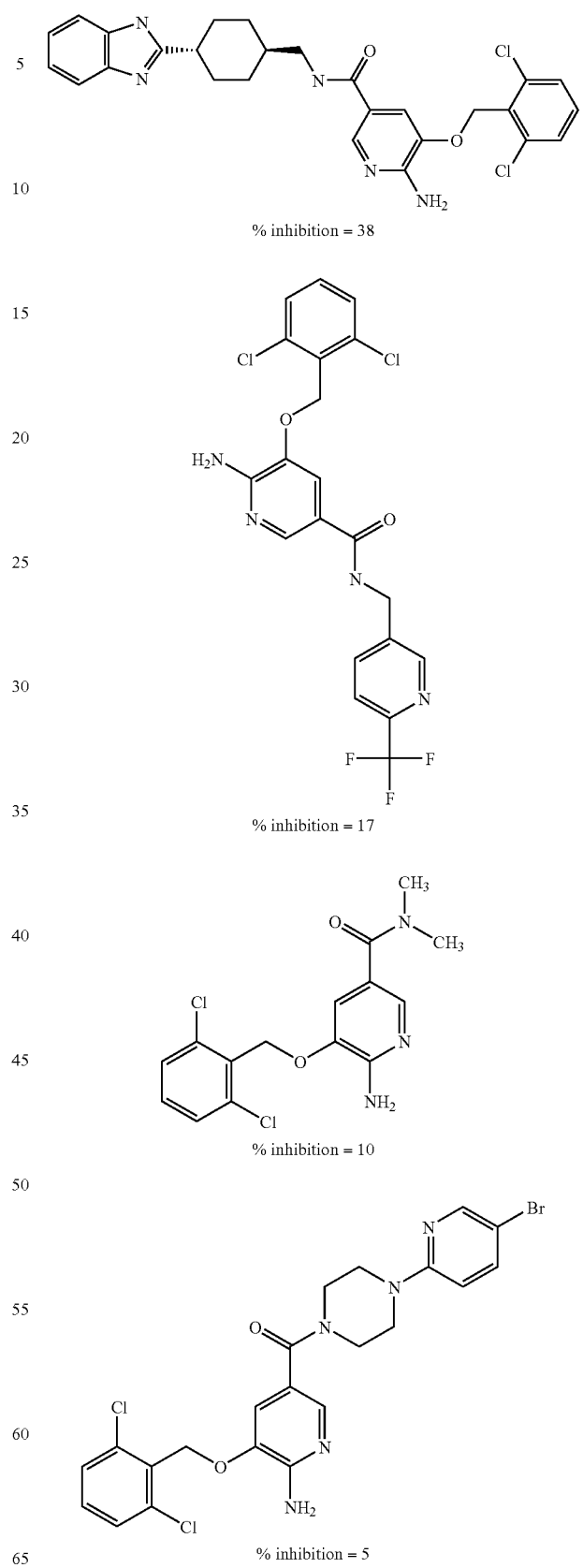

TABLE 6-continued
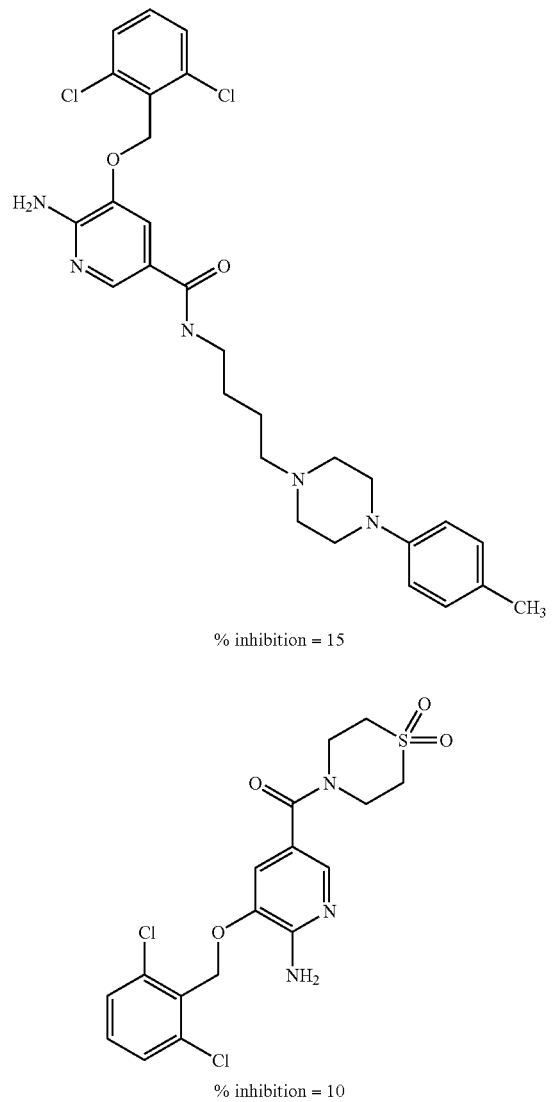
% inhibition = 15
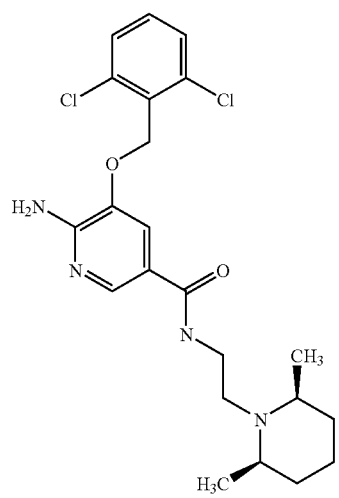
% inhibition = 10
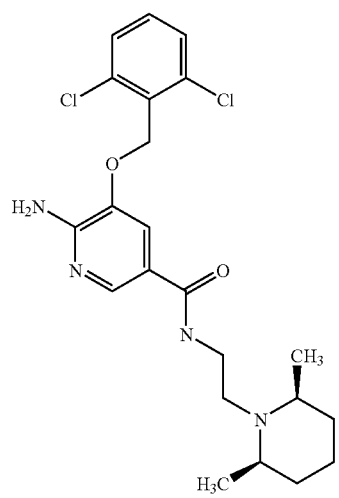
% inhibition = 2
TABLE 6-continued
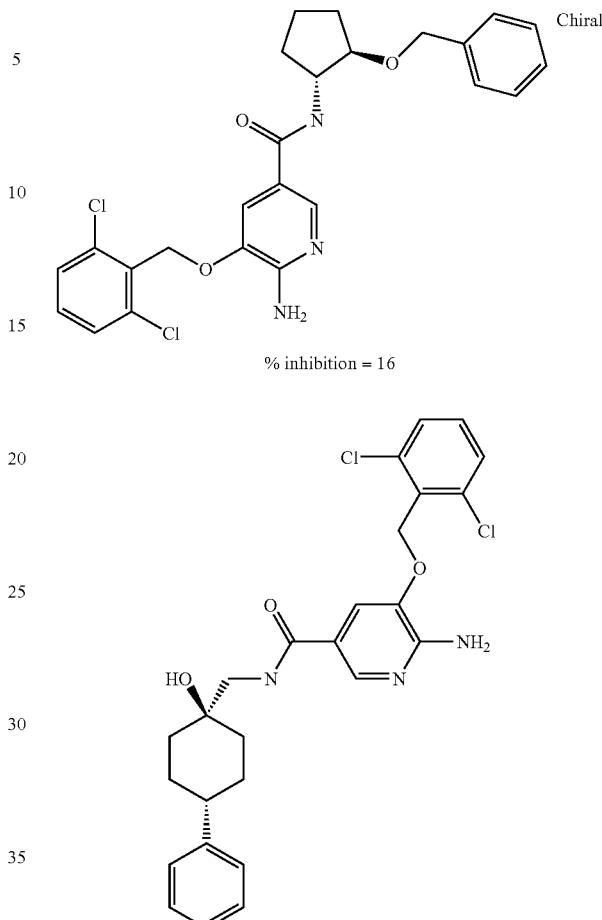
% inhibition = 16
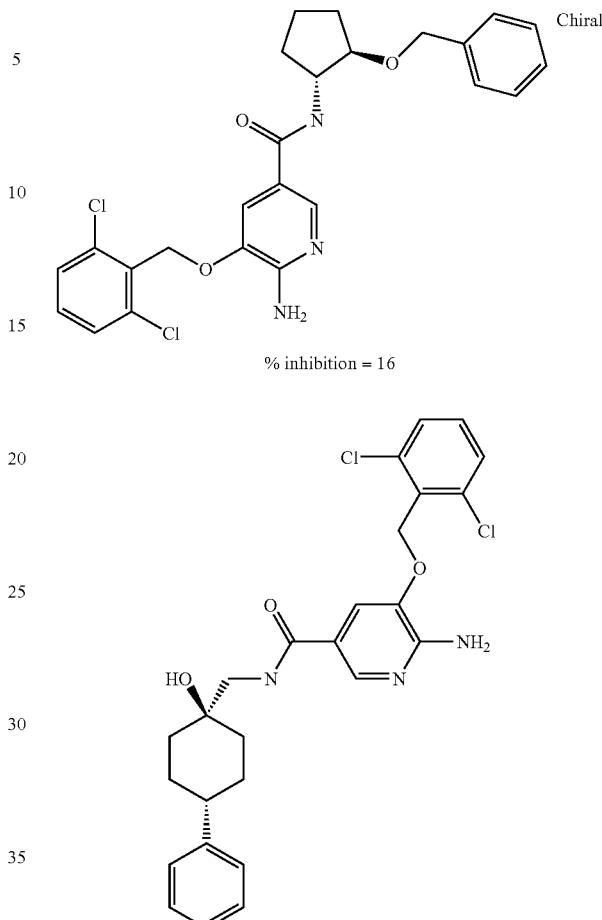
% inhibition = 15
Section G: Examples L-273 to L-288
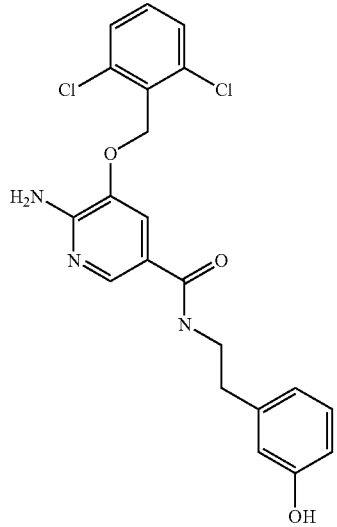
% inhibition = 17

TABLE 6-continued
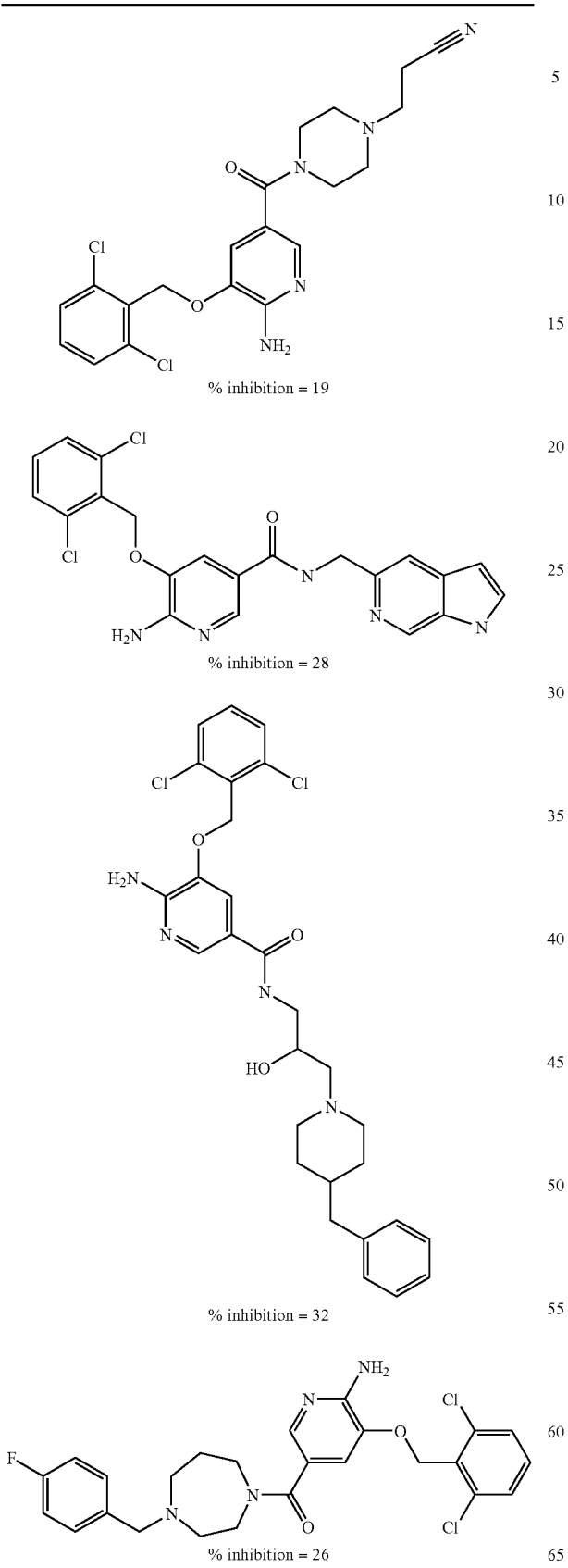
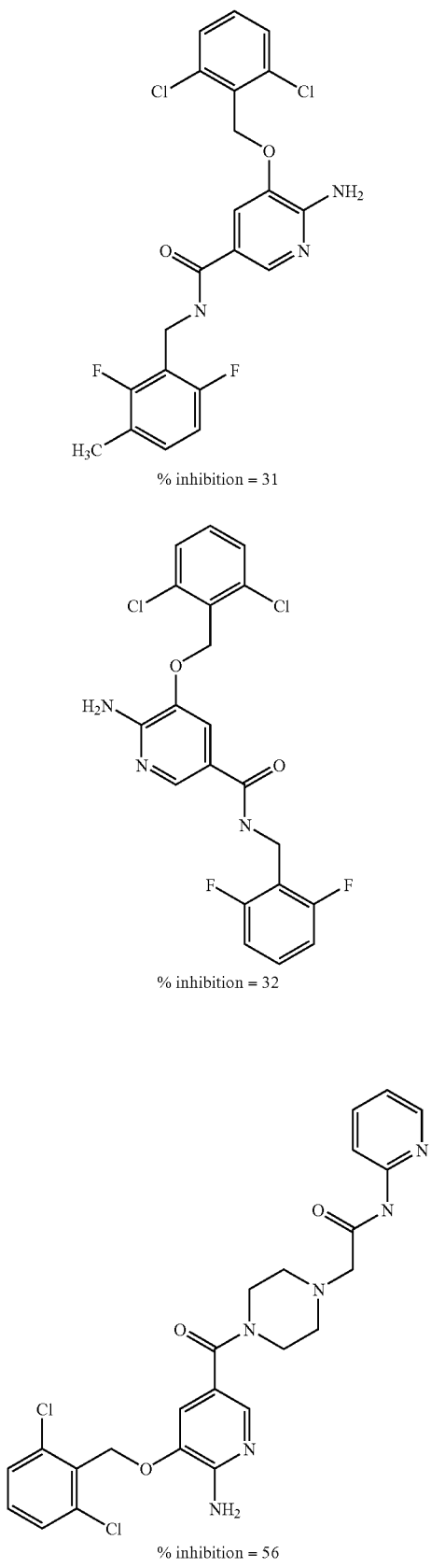

TABLE 6-continued
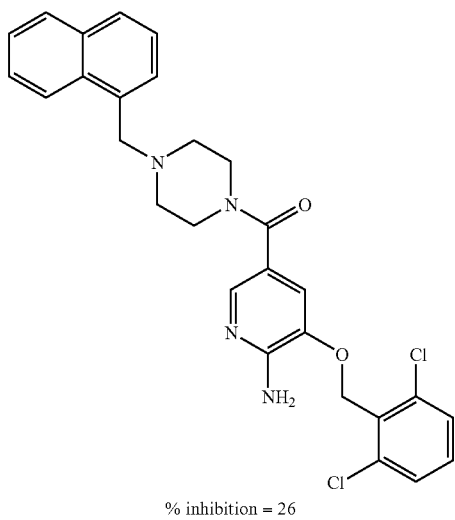
% inhibition = 26
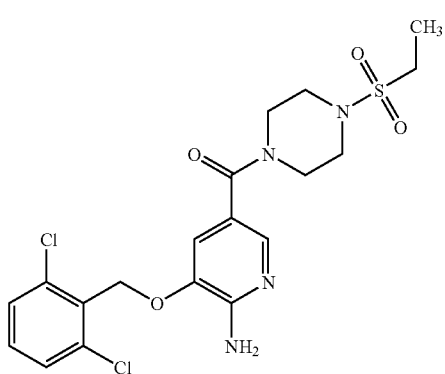
% inhibition = 22
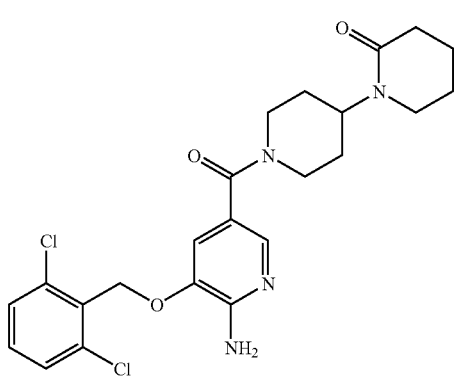
% inhibition = 26
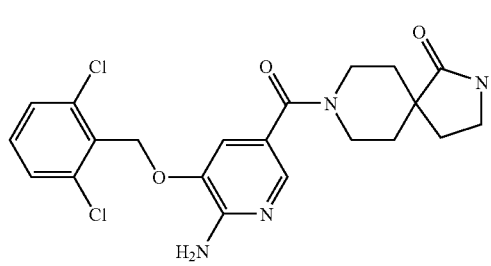
% inhibition = 27
TABLE 6-continued
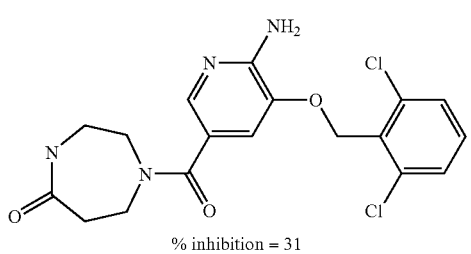
% inhibition = 31
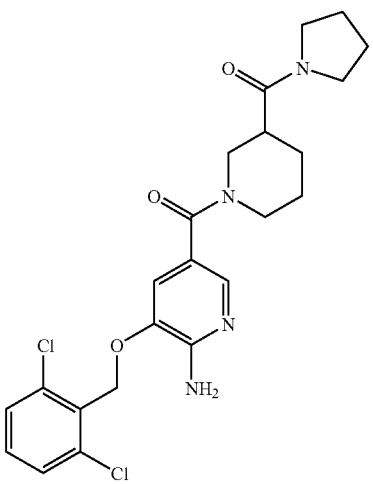
% inhibition = 47
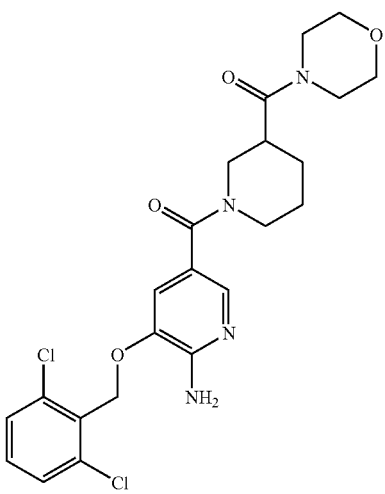
% inhibition = 21

TABLE 6-continued
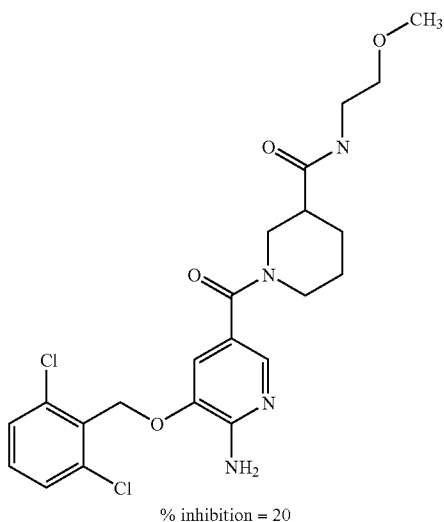
% inhibition = 20
Section G: Examples L-289 to L-304
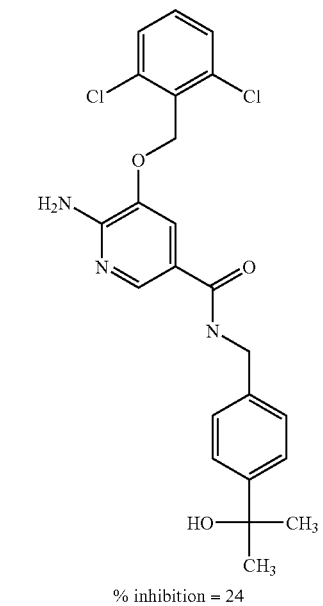
% inhibition = 24
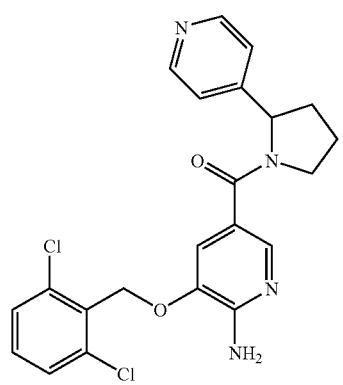
% inhibition = 19
TABLE 6-continued
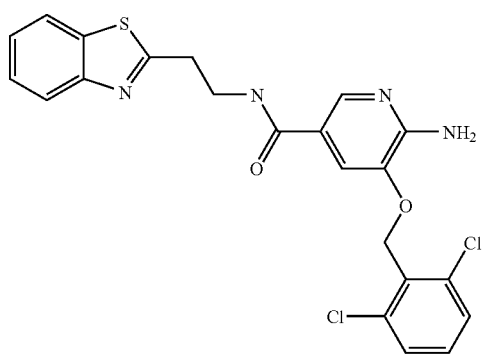
% inhibition = 26
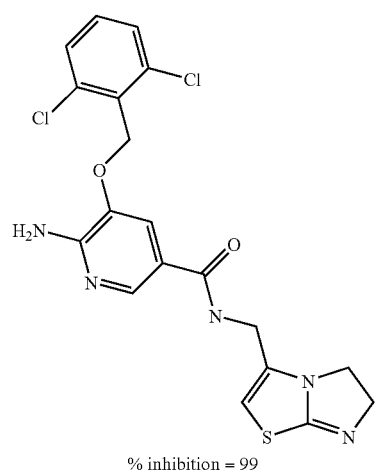
% inhibition = 99
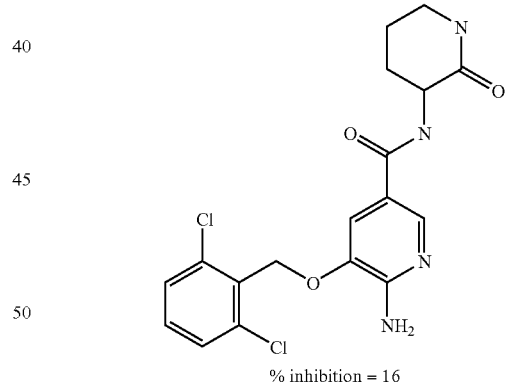
% inhibition = 16
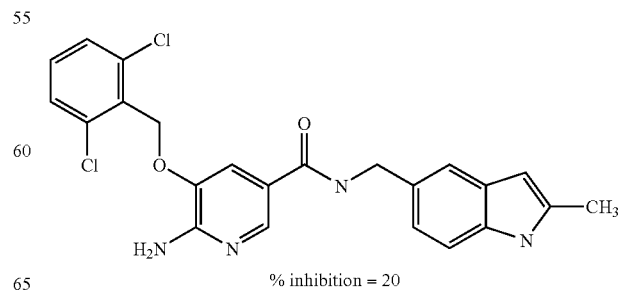
% inhibition = 20

TABLE 6-continued
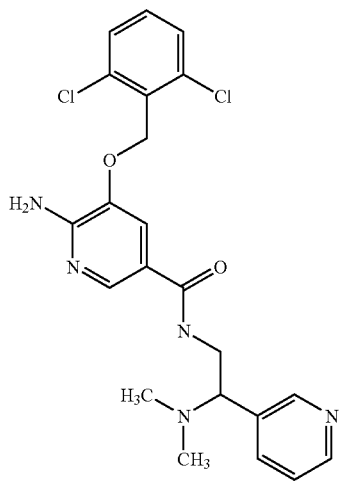
% inhibition = 18
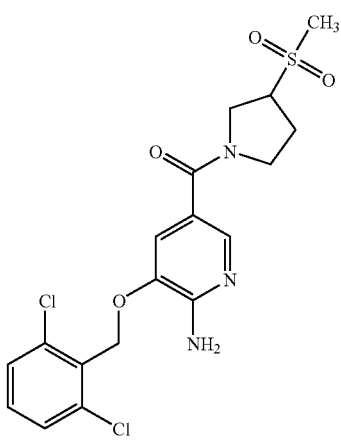
% inhibition = 23
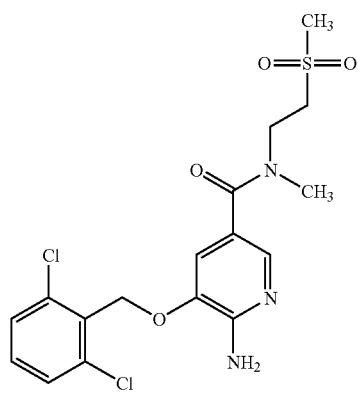
% inhibition = 26
TABLE 6-continued
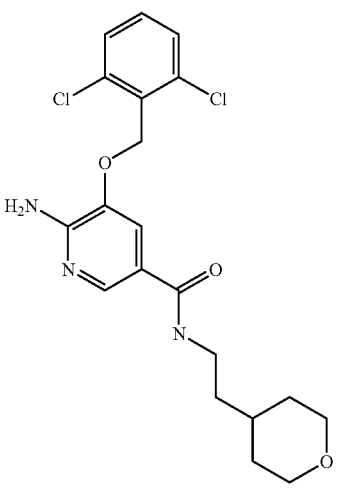
% inhibition = 31
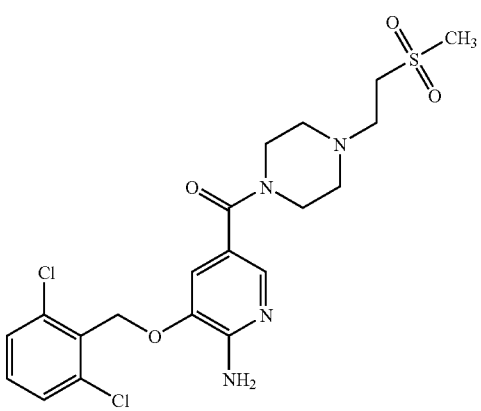
% inhibition = 25
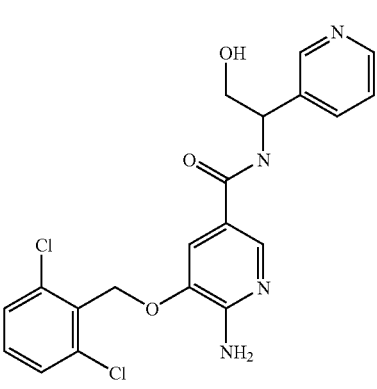
% inhibition = 22

TABLE 6-continued
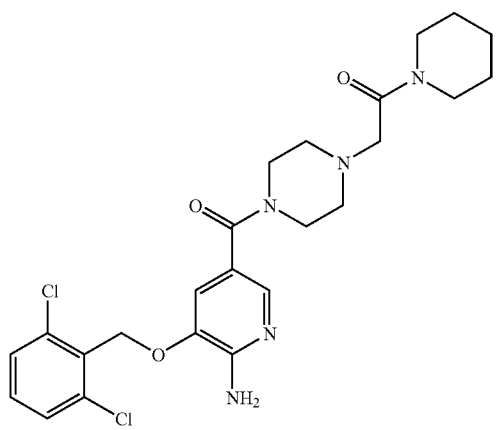
% inhibition = 24
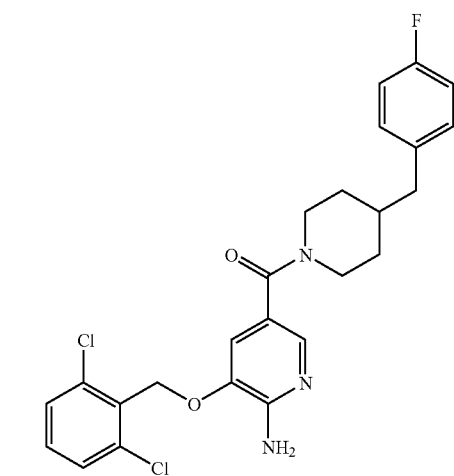
% inhibition = 41
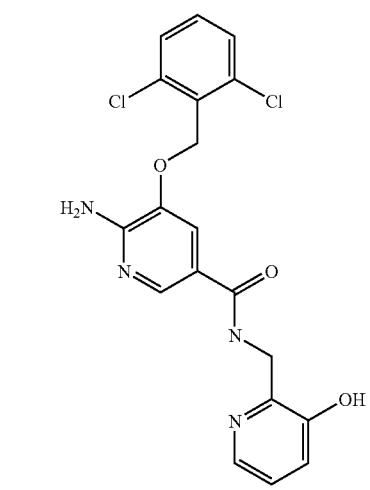
% inhibition = 24
TABLE 6-continued
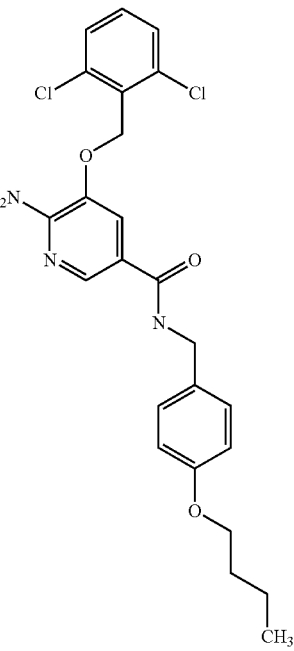
% inhibition = 18
Section I: Examples L-305 to L-320
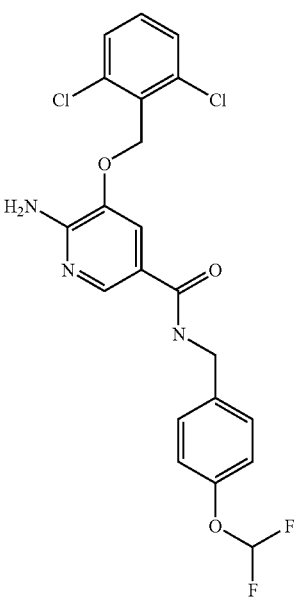
% inhibition = 26

TABLE 6-continued
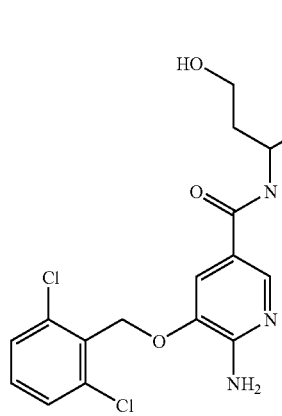
% inhibition = 22
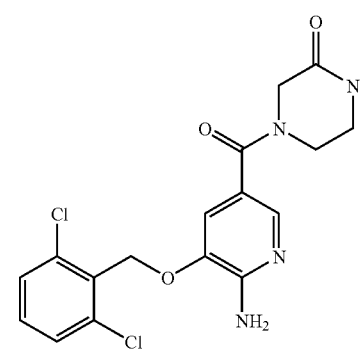
% inhibition = 22
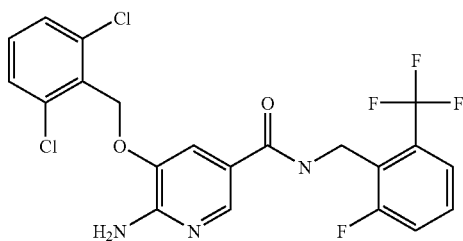
% inhibition = 33
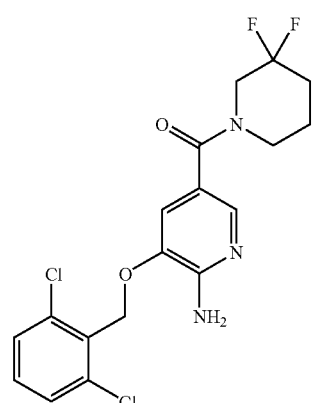
% inhibition = 16
TABLE 6-continued
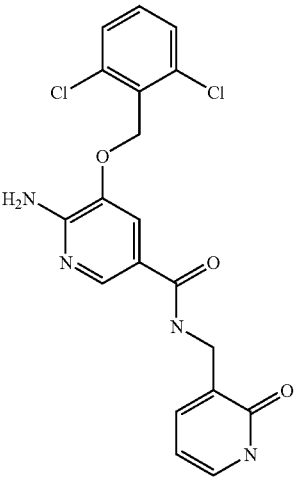
% inhibition = 16
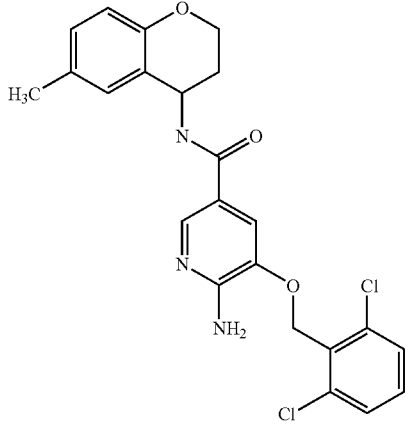
% inhibition = 17
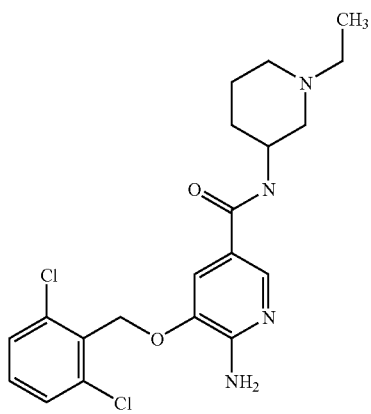
% inhibition = 19

TABLE 6-continued
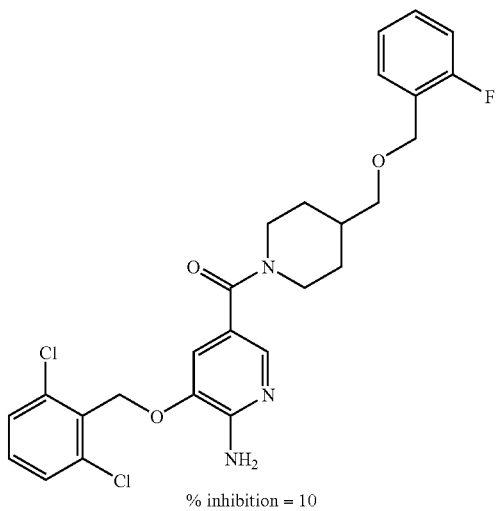
% inhibition = 10
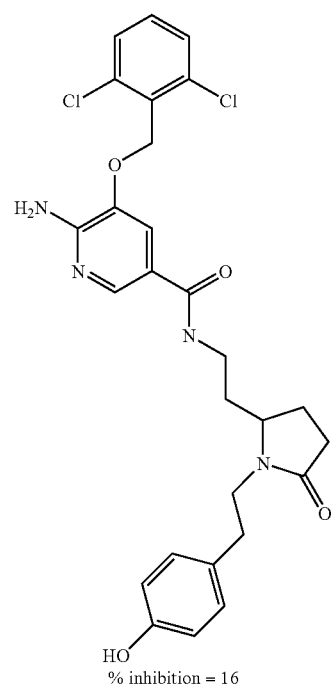
% inhibition = 16
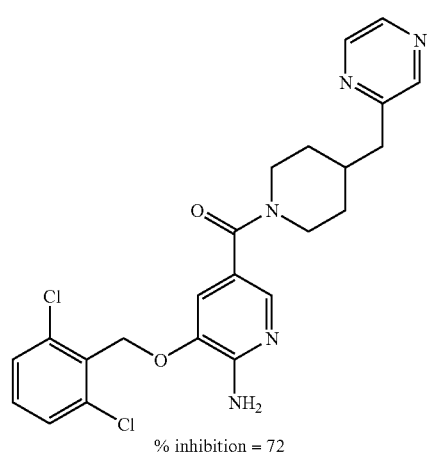
% inhibition = 72
TABLE 6-continued
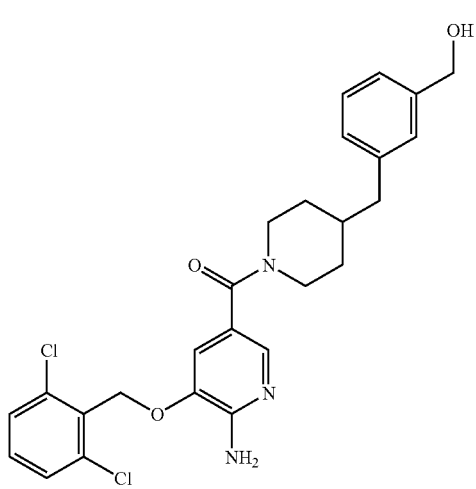
% inhibition = 11
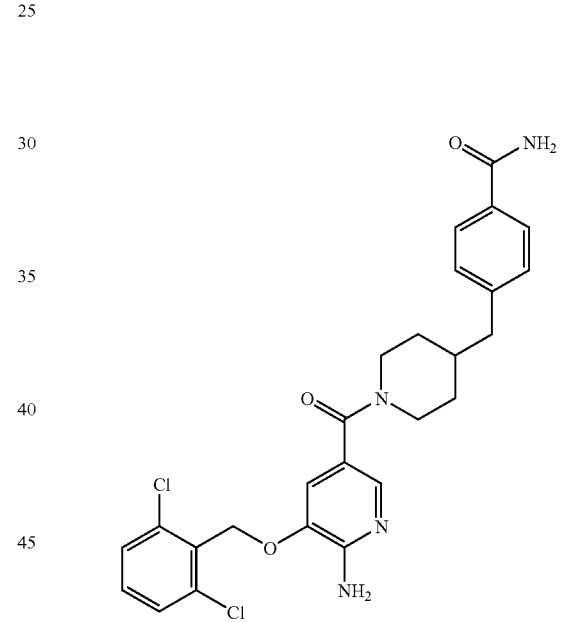
% inhibition = 12
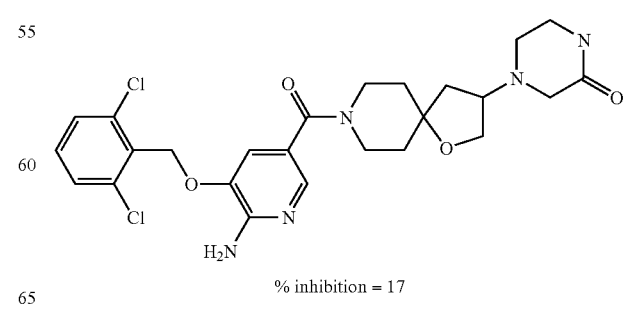
% inhibition = 17

TABLE 6-continued
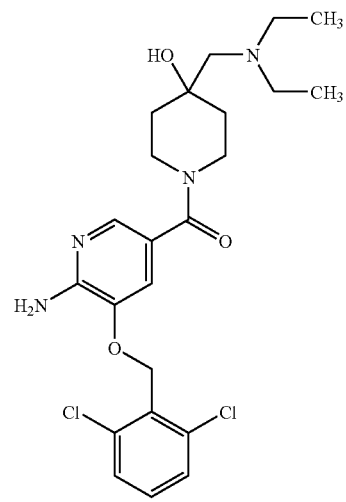
% inhibition = 71
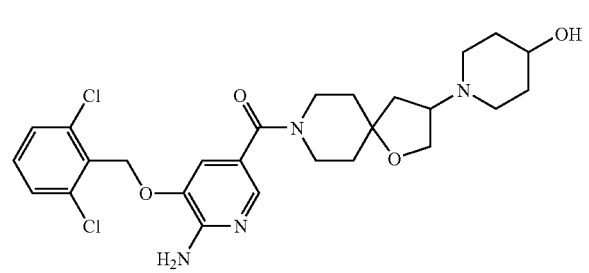
% inhibition = 28
Section J: Examples L-321 to L-336
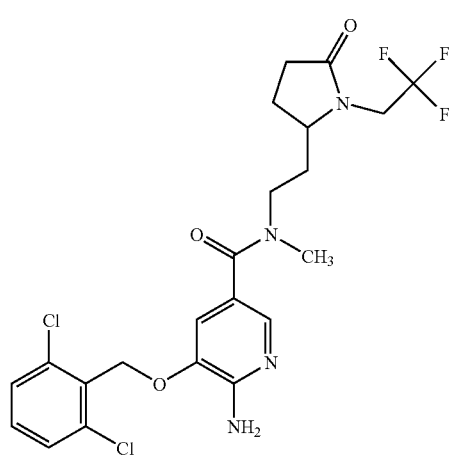
% inhibition = 25
TABLE 6-continued
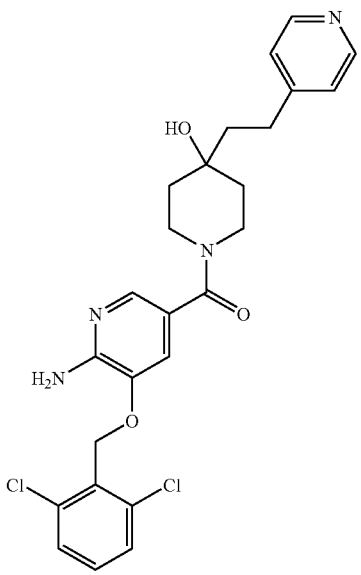
% inhibition = 25
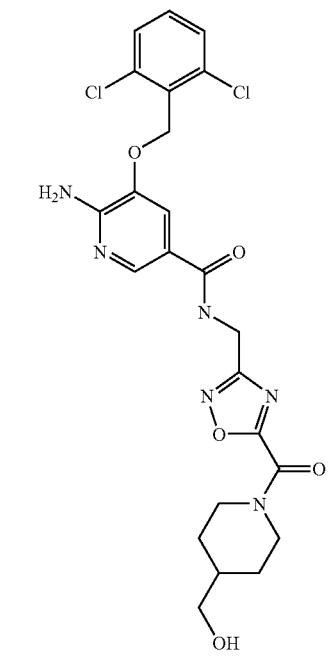
% inhibition = 26

TABLE 6-continued
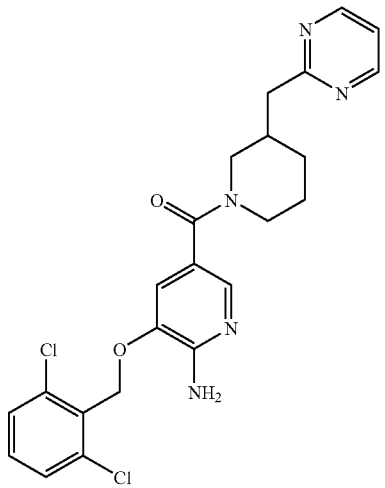
% inhibition = 25
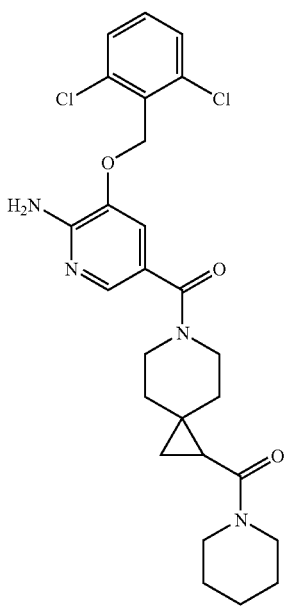
% inhibition = 26
TABLE 6-continued
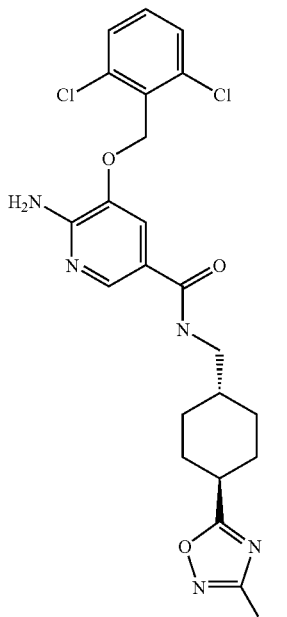
% inhibition = 3
Chiral
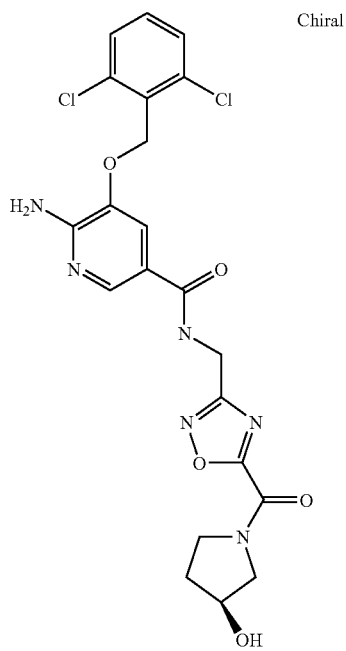
% inhibition = 26

US 8,106,197 B2
937
TABLE 6-continued
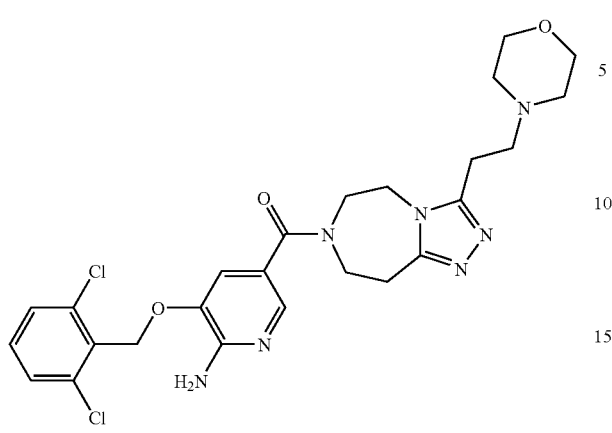
% inhibition = 27
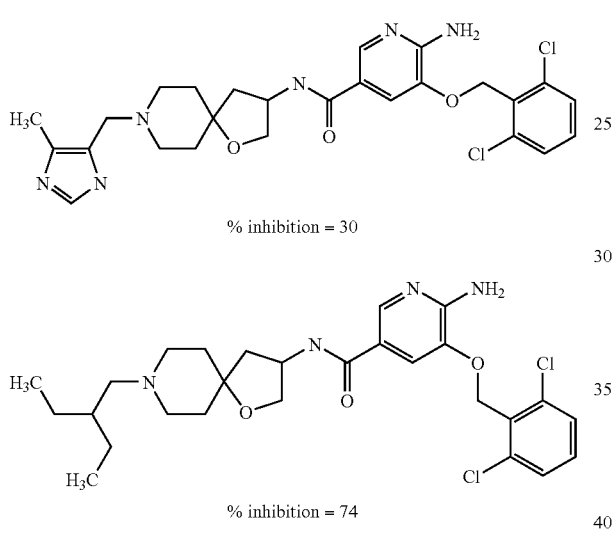
% inhibition = 30
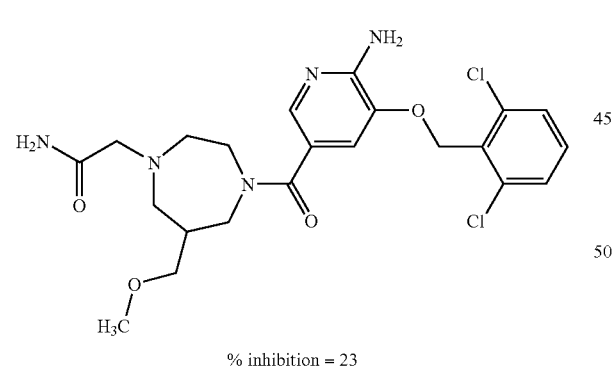
% inhibition = 74
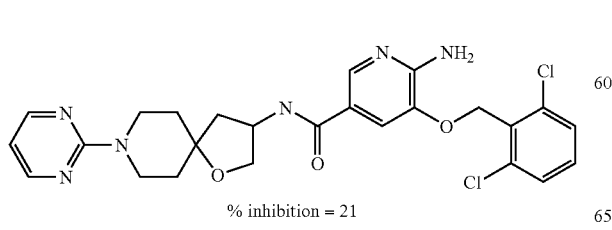
% inhibition = 23
938
TABLE 6-continued
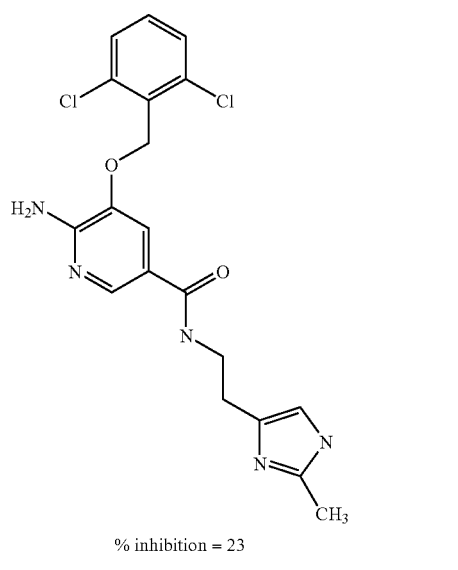
% inhibition = 23
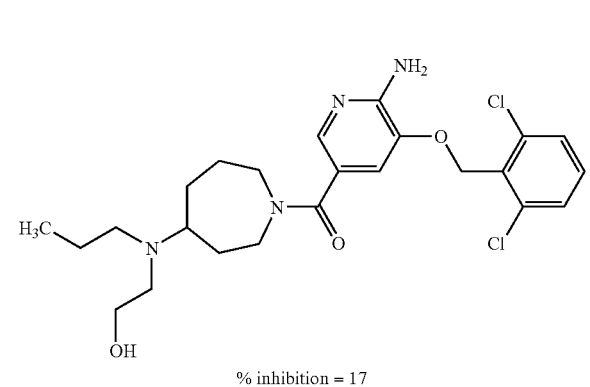
% inhibition = 17
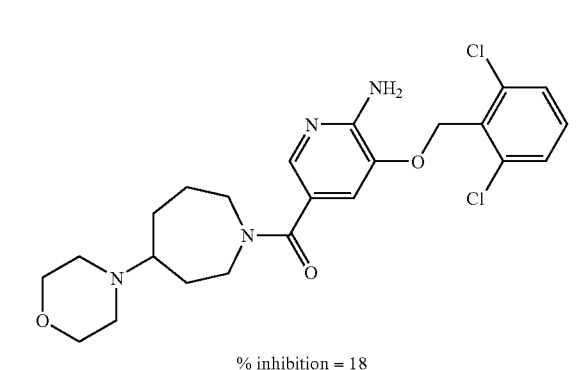
% inhibition = 18
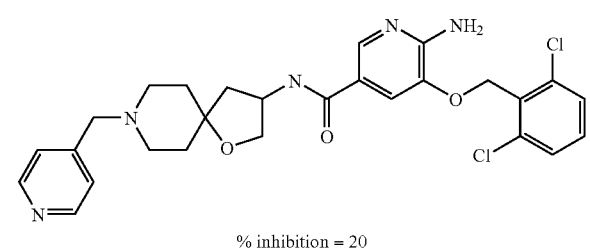
% inhibition = 20
% inhibition = 21

TABLE 6-continued
Section K: Examples L-337 to L-352
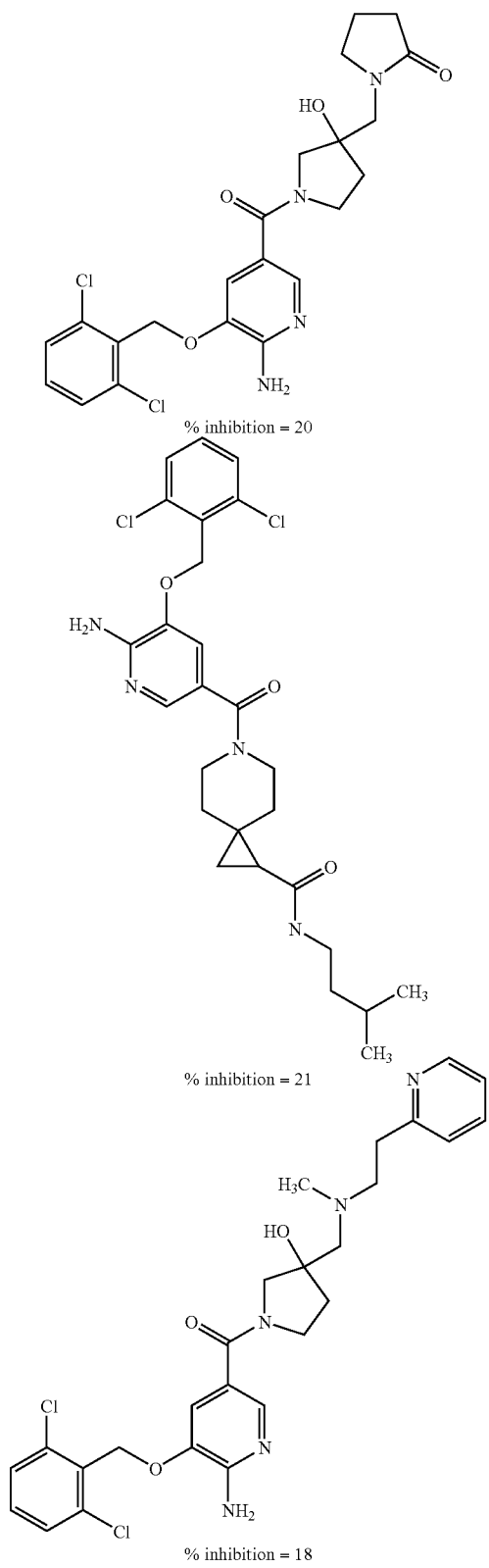
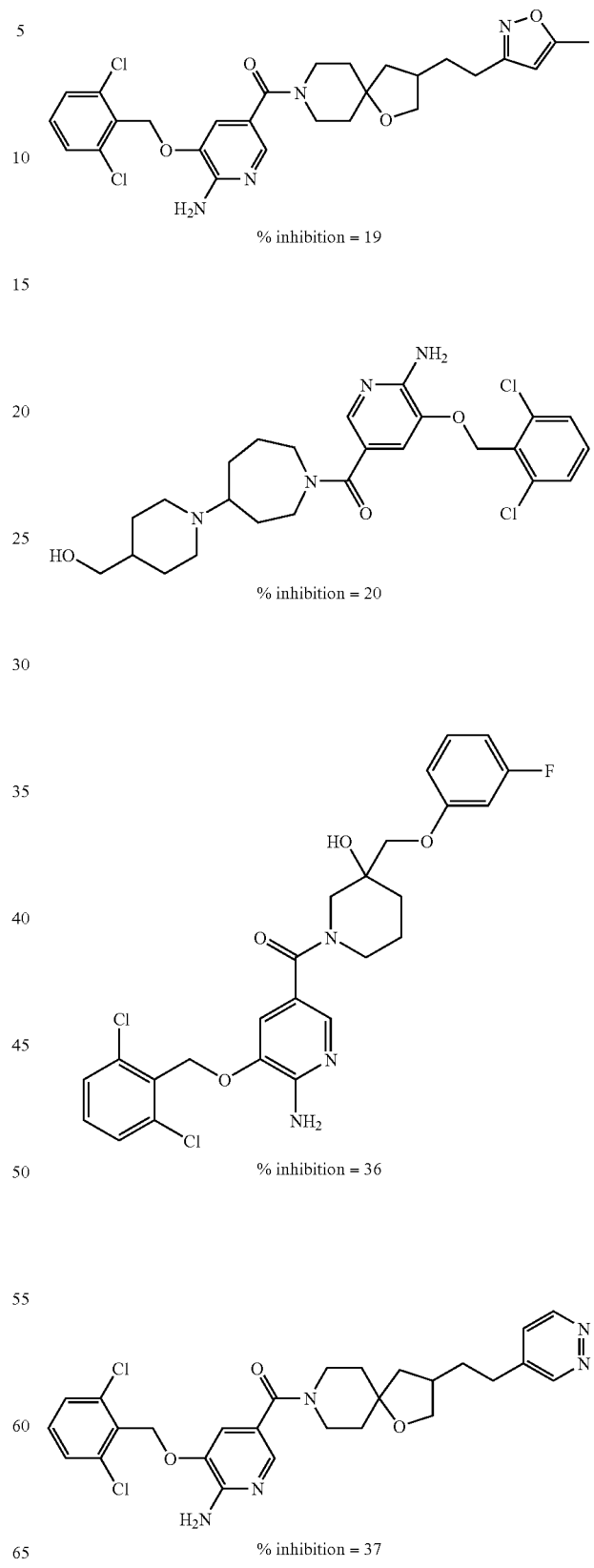

TABLE 6-continued
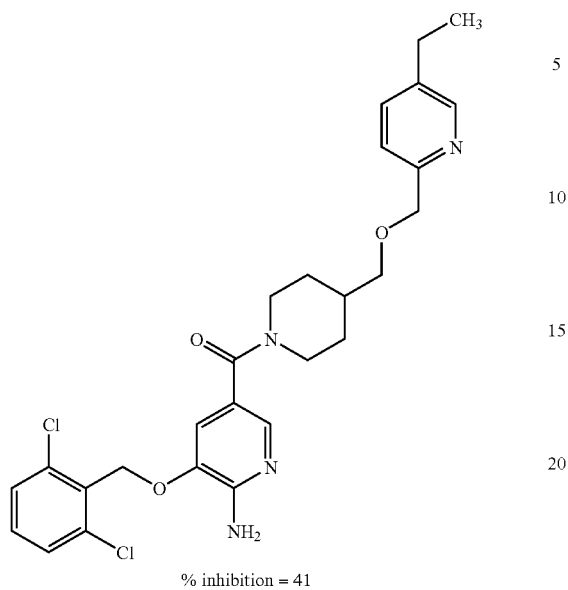
% inhibition = 41
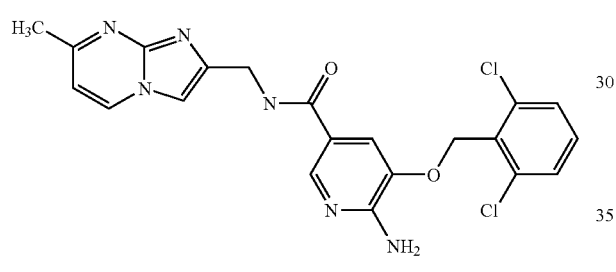
% inhibition = 45
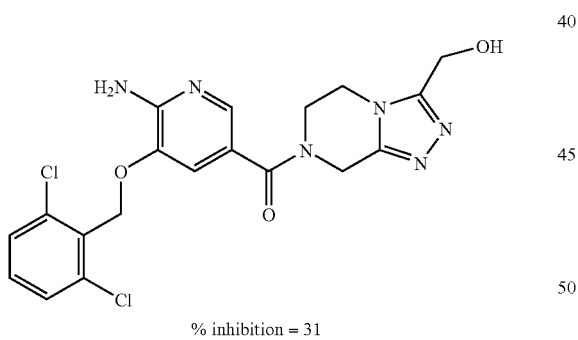
% inhibition = 31
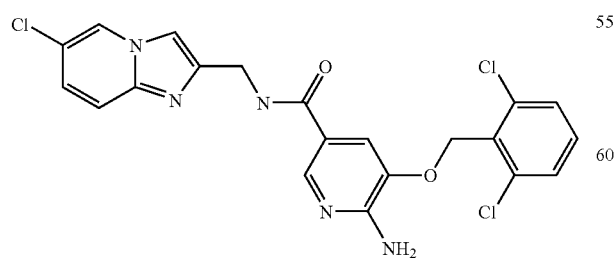
% inhibition = 38
TABLE 6-continued
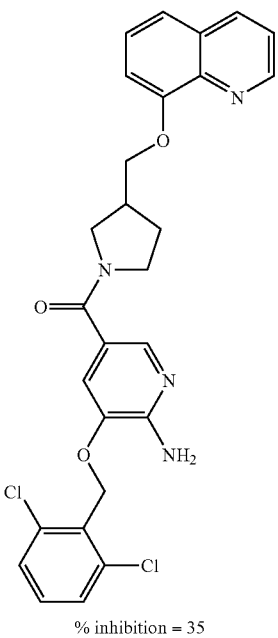
% inhibition = 35
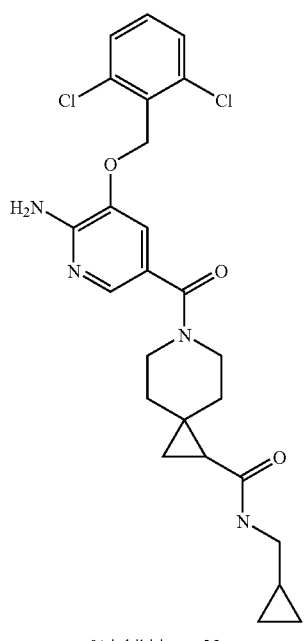
% inhibition = 32

TABLE 6-continued
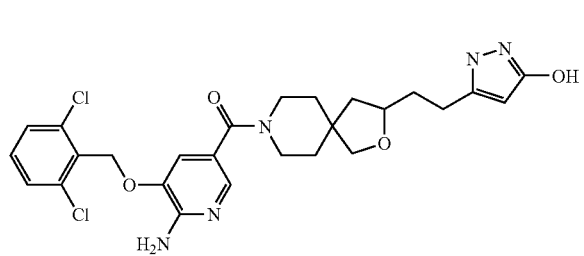
% inhibition = 34
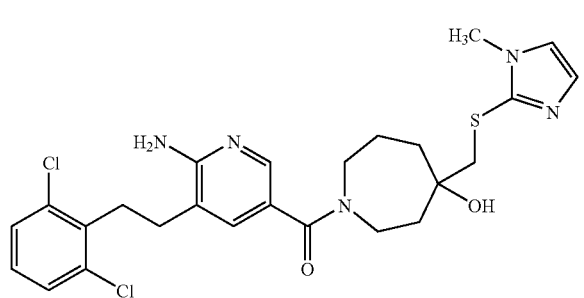
TABLE 6-continued
% inhibition = 35
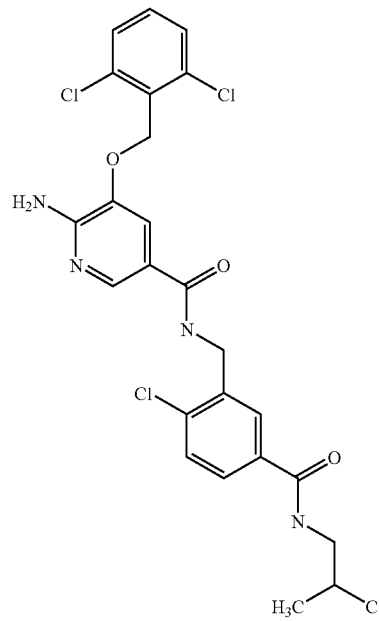
% inhibition = 47
TABLE 7
Section A: Examples L-353 to L-368
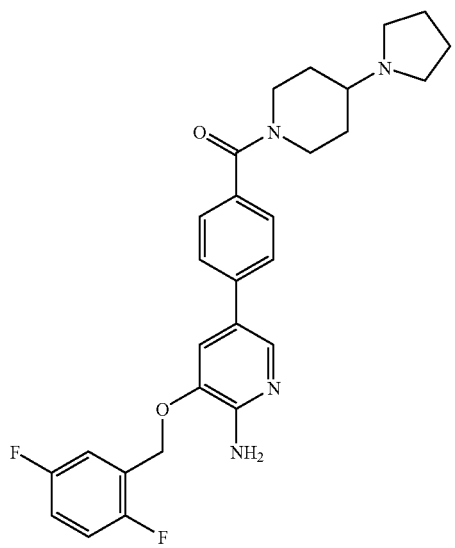
% inhibition = 24
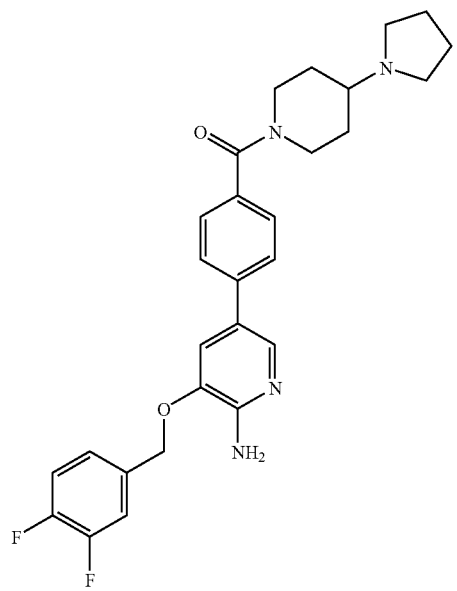
% inhibition = 19

TABLE 7-continued
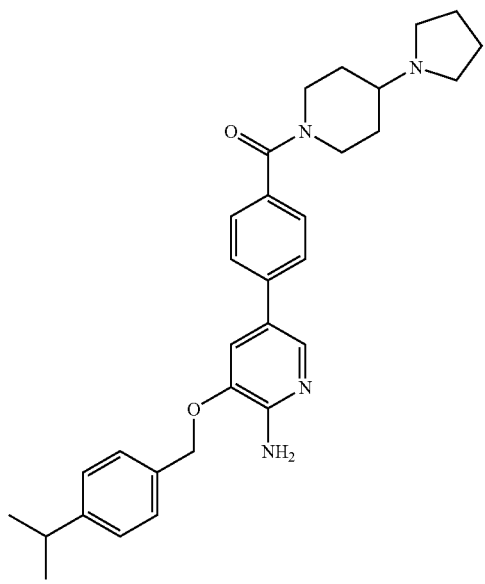
% inhibition = 32
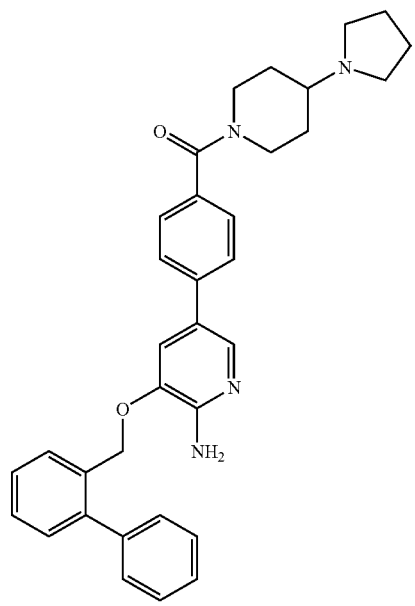
% inhibition = 22
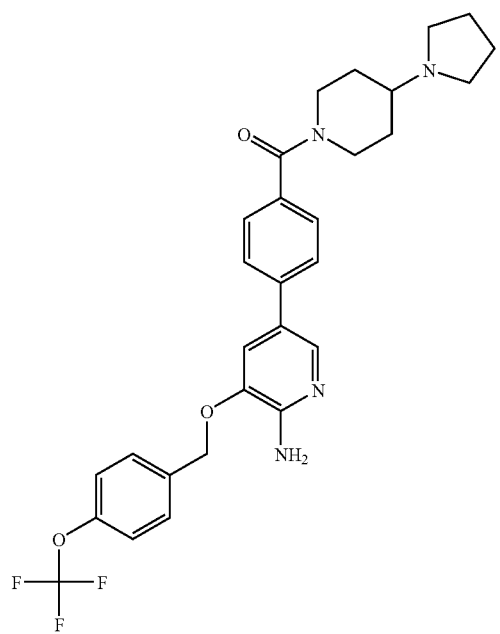
% inhibition = 20
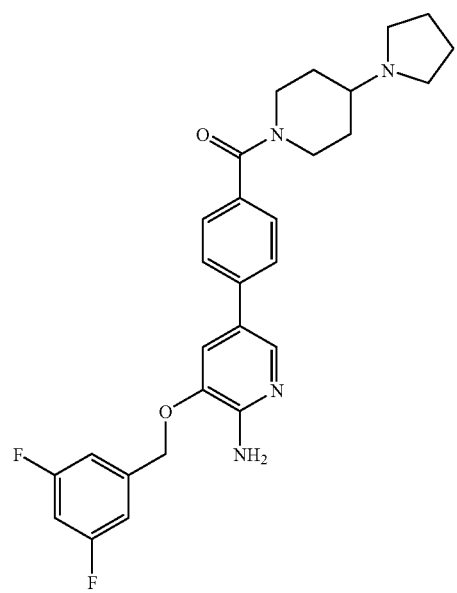
% inhibition = 14

TABLE 7-continued
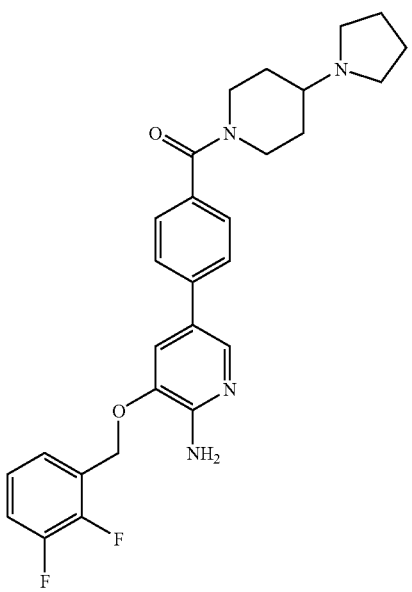
% inhibition = 24
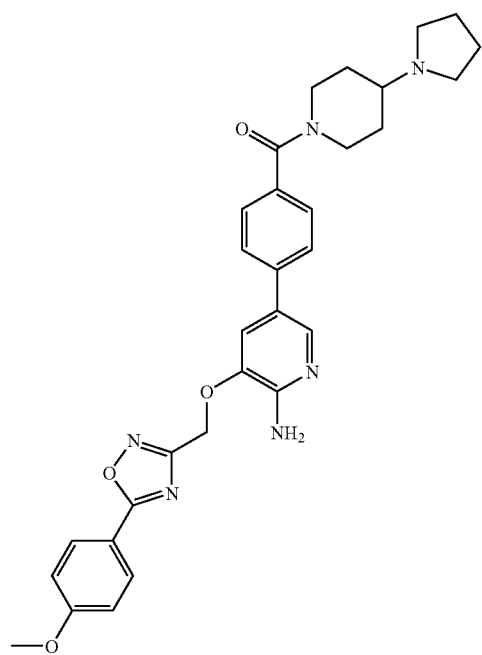
% inhibition = 10
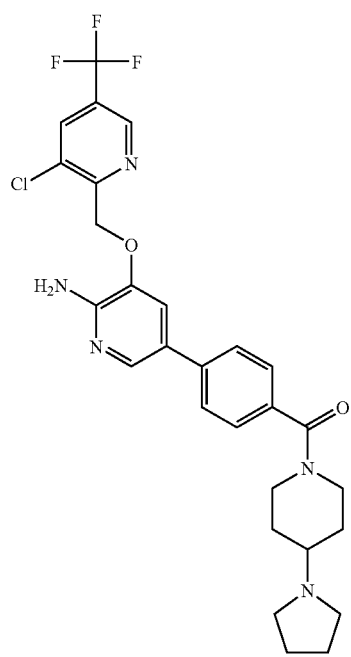
% inhibition = 8
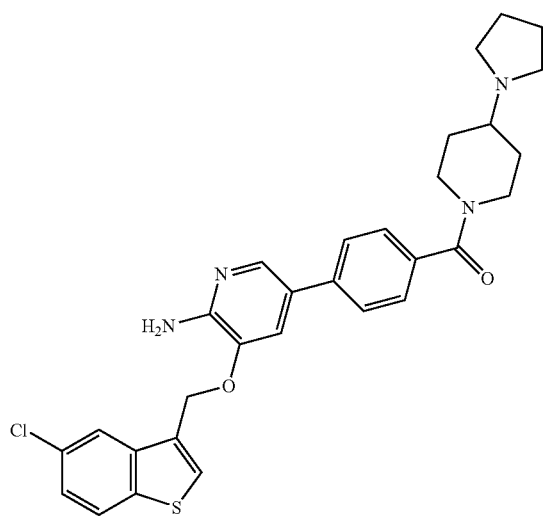
% inhibition = 37

TABLE 7-continued
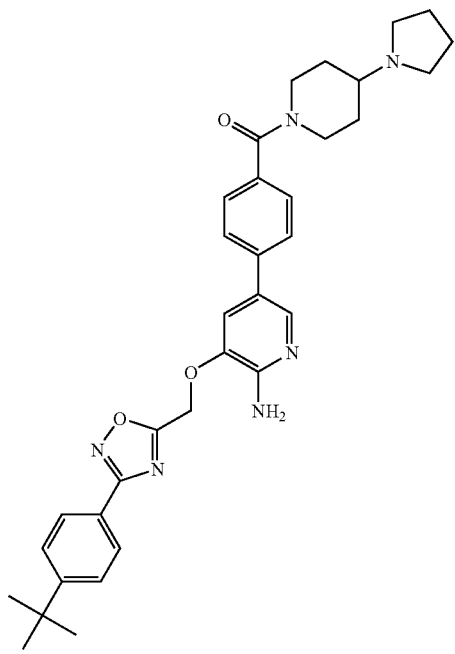
% inhibition = 36
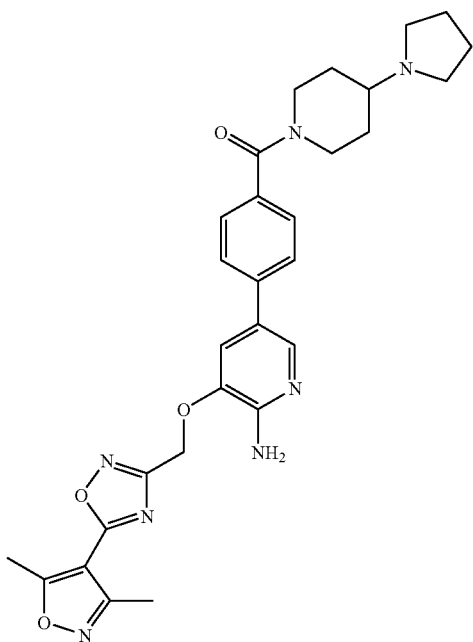
% inhibition = 6
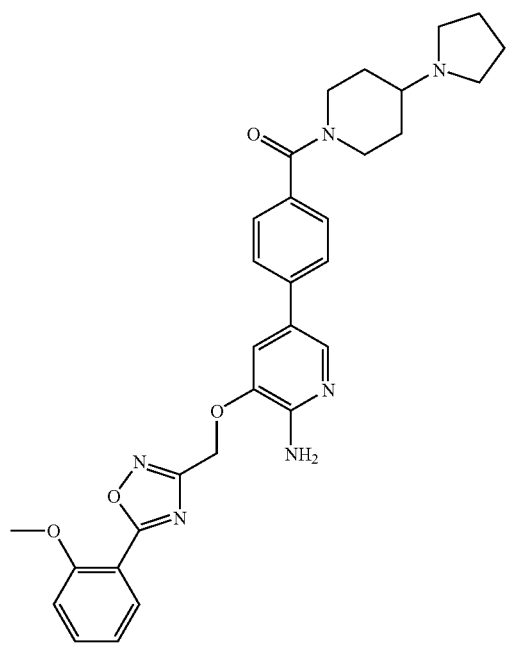
% inhibition = 8
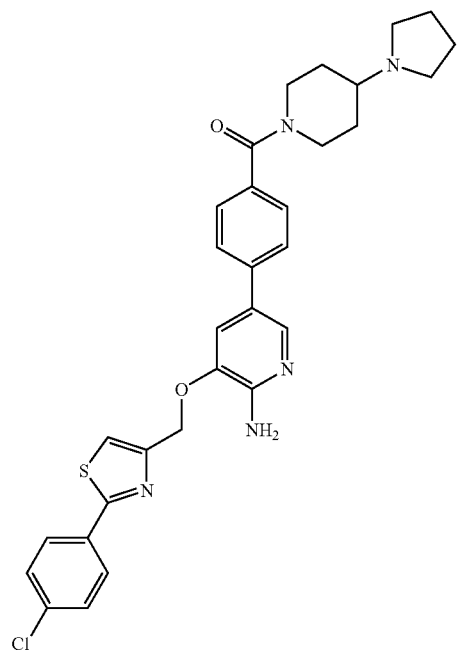
% inhibition = 9

TABLE 7-continued
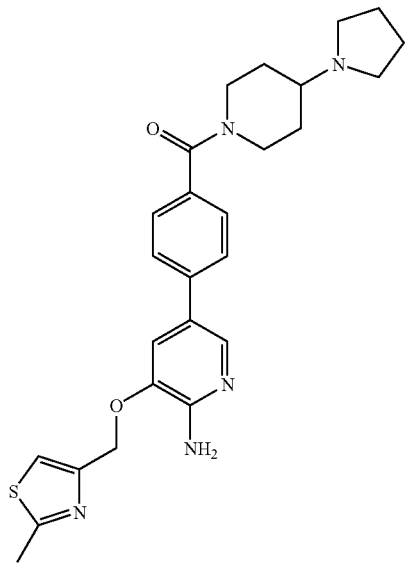
% inhibition = 6
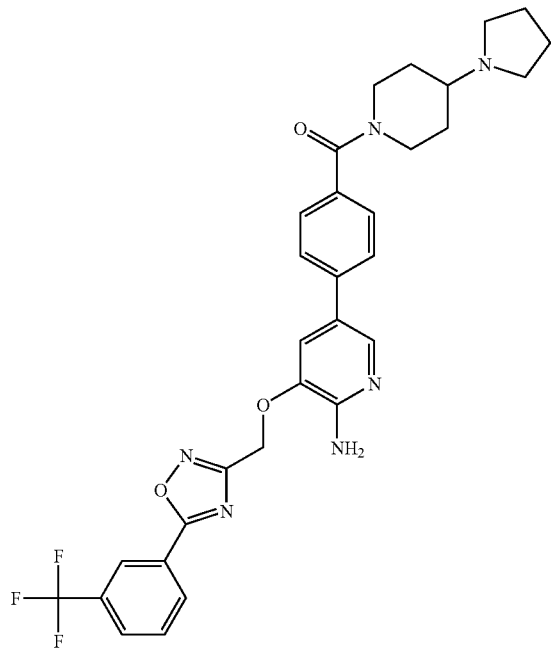
% inhibition = 27
Section B: Examples L-369 to L-384
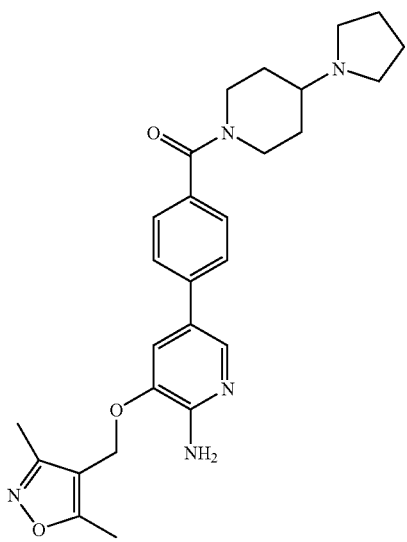
% inhibition = 10
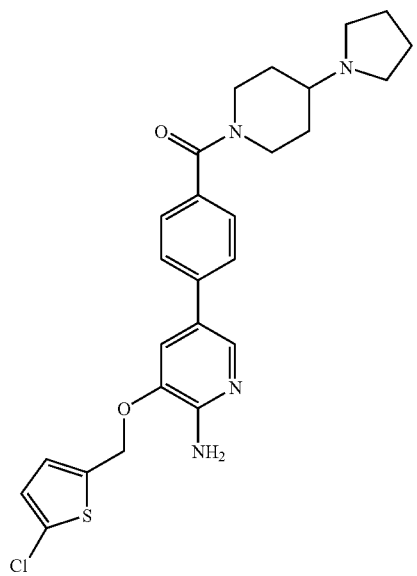
% inhibition = 19

TABLE 7-continued
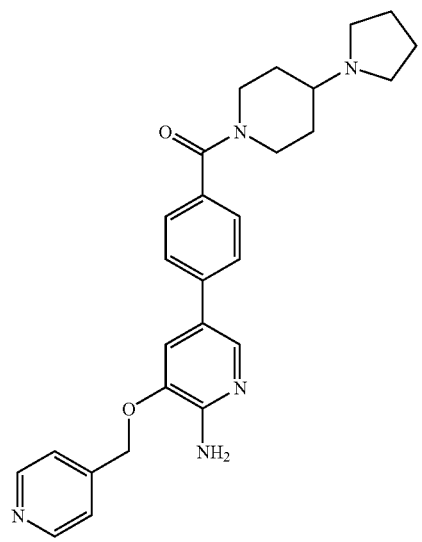
% inhibition = 10
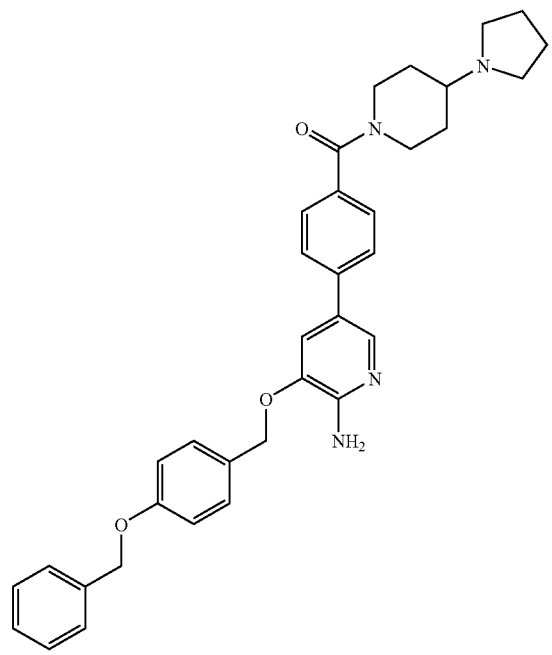
% inhibition = 49
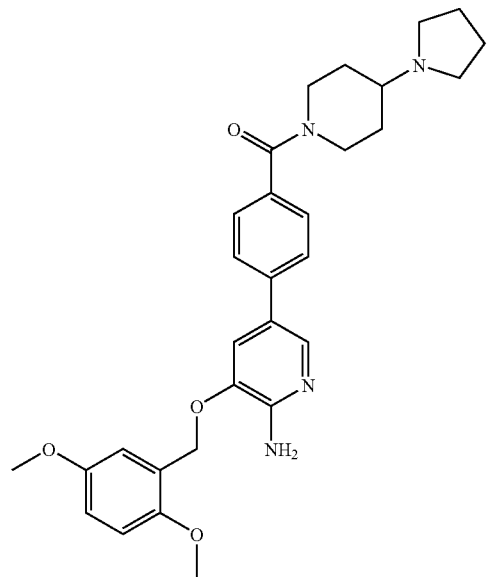
% inhibition = 19
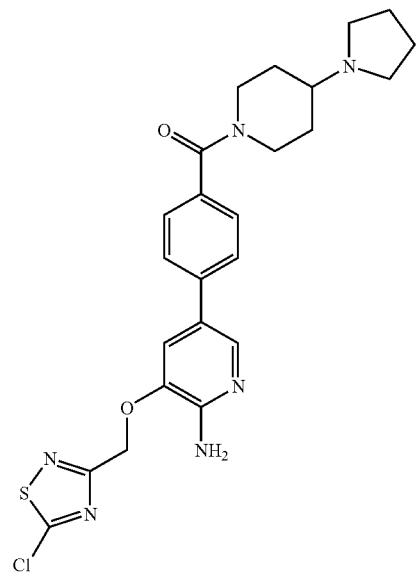
% inhibition = 5

TABLE 7-continued
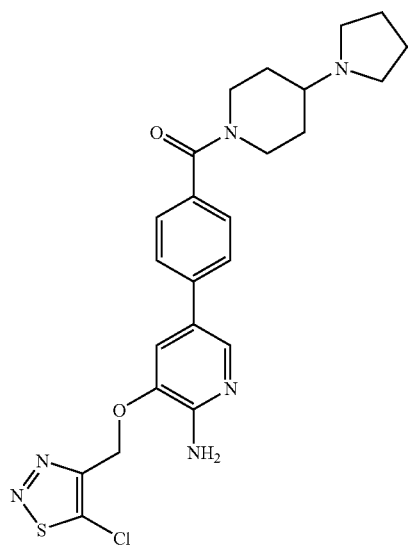
% inhibition = 10
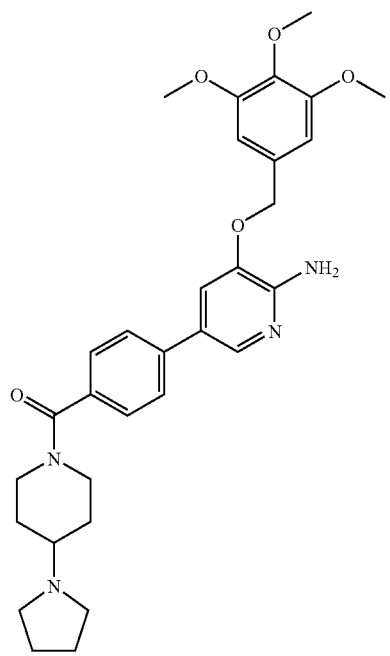
% inhibition = 10
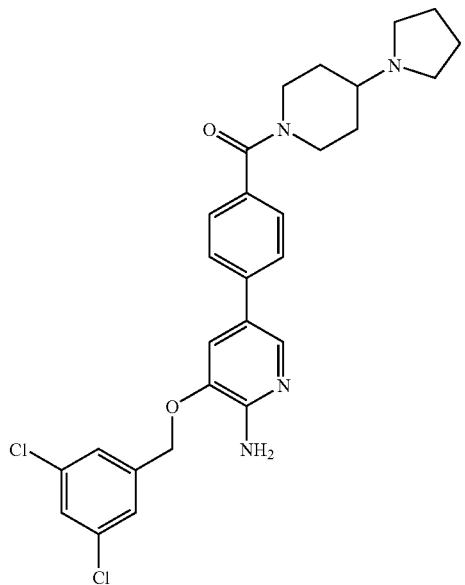
% inhibition = 19
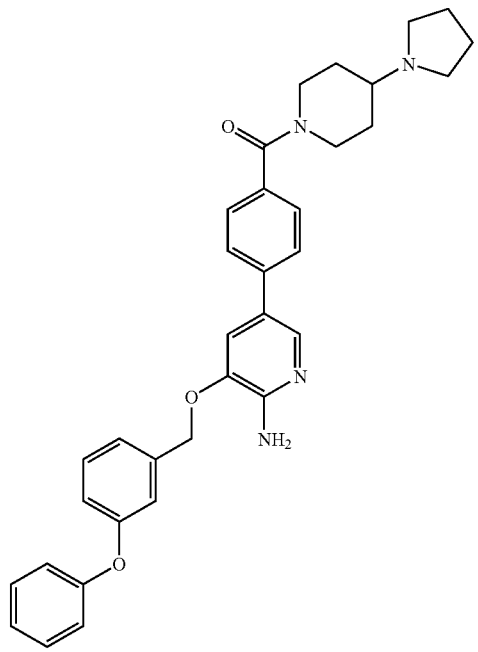
% inhibition = 34

TABLE 7-continued
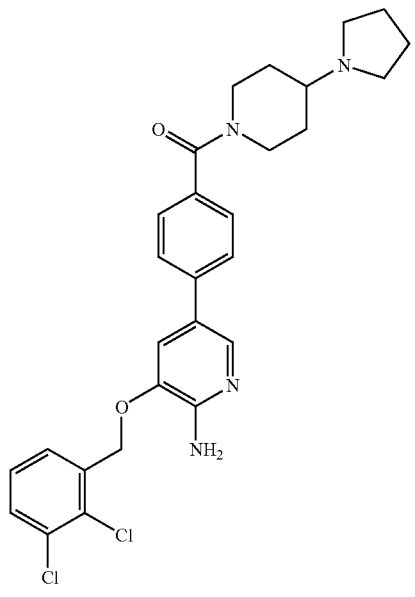
% inhibition = 40
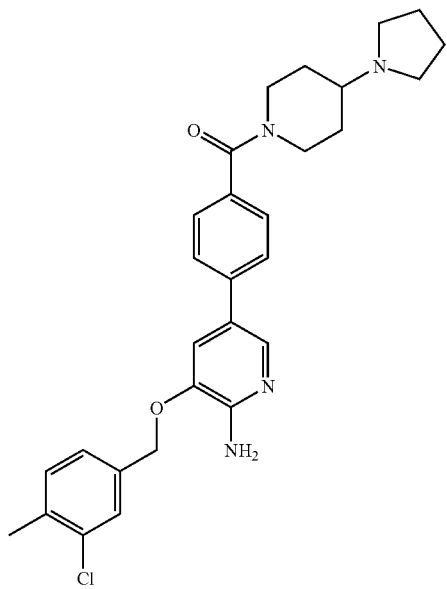
% inhibition = 26
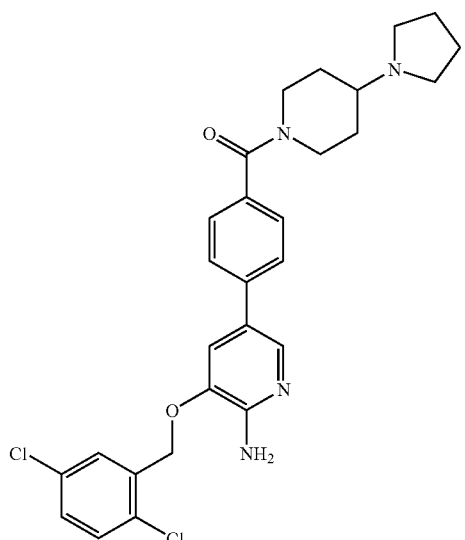
% inhibition = 26
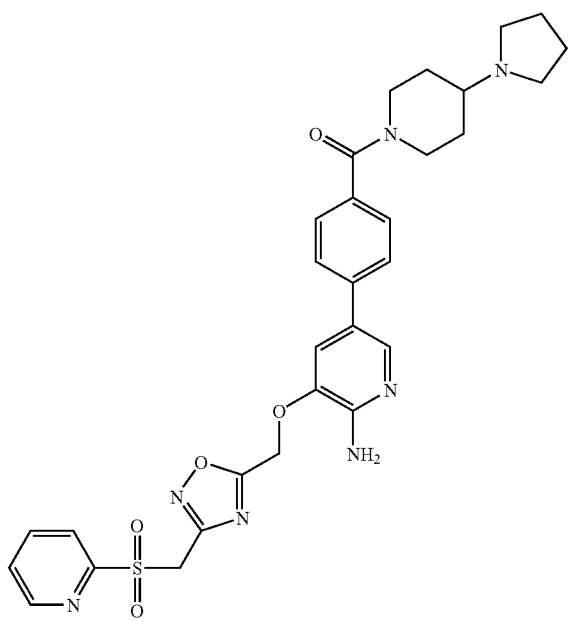
% inhibition = 9

TABLE 7-continued
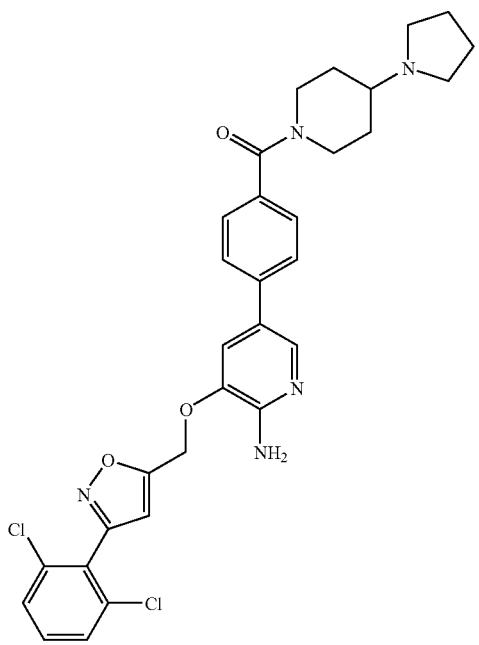
% inhibition = 14
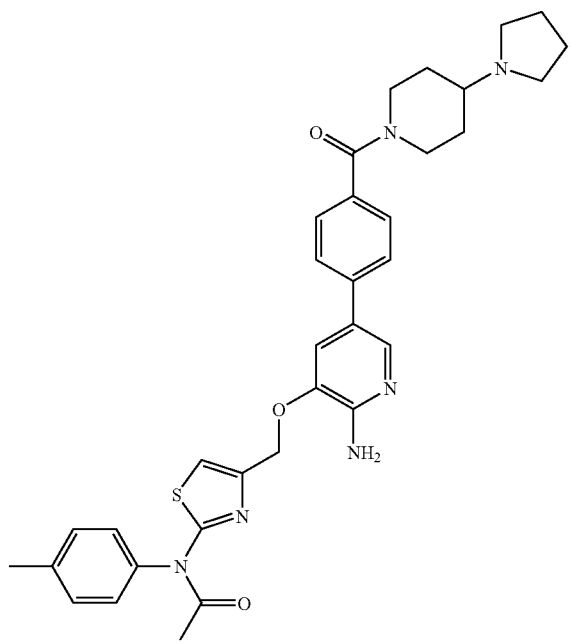
% inhibition = 9
Section C: Examples L-385 to L-400
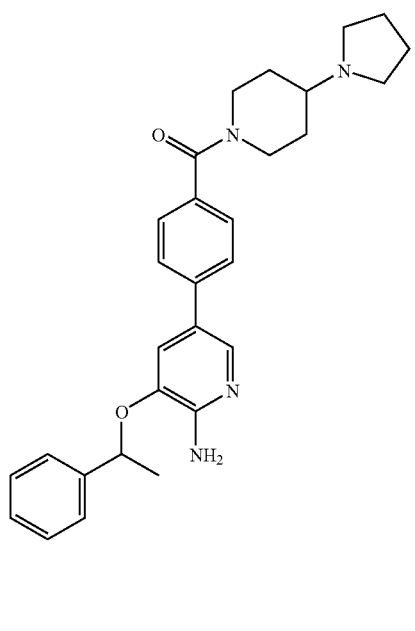
% inhibition = 10
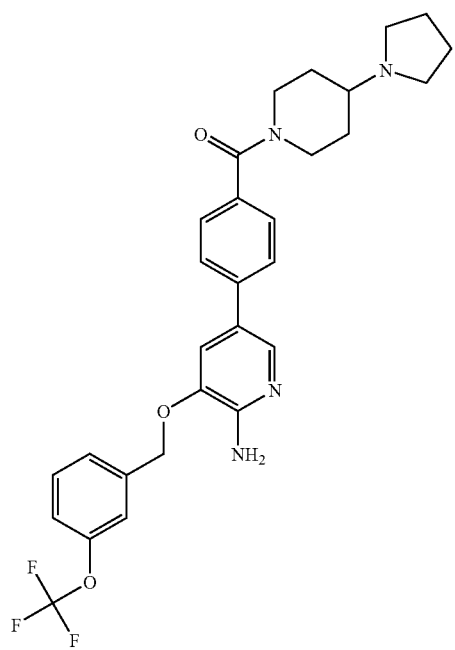
% inhibition = 13

TABLE 7-continued
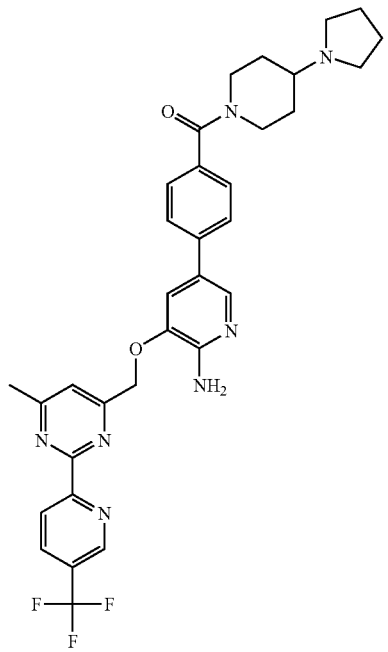
% inhibition = 8
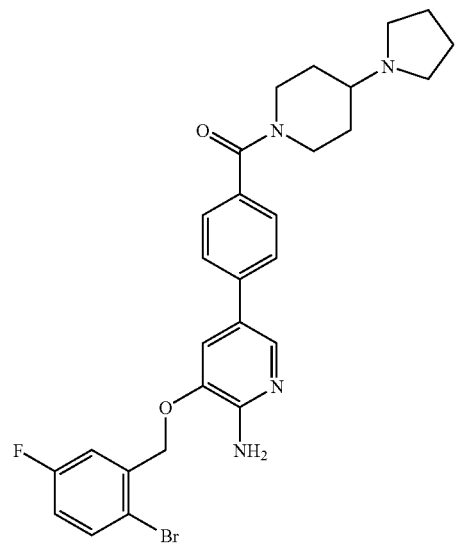
% inhibition = 24
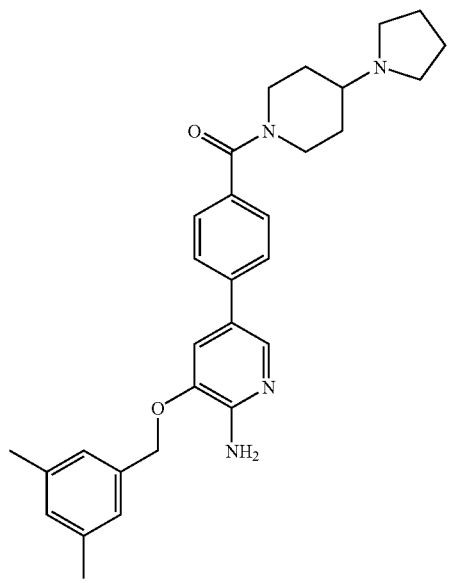
% inhibition = 14
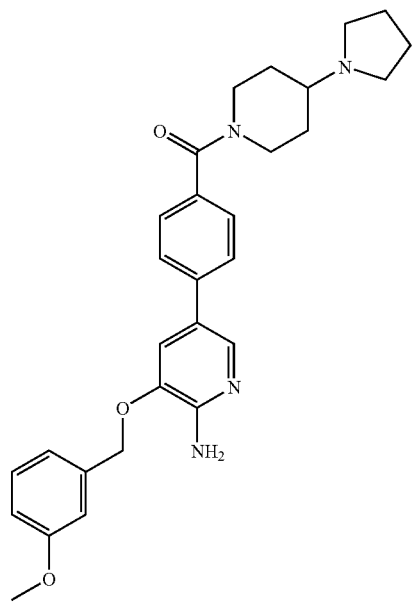
% inhibition = 15

TABLE 7-continued
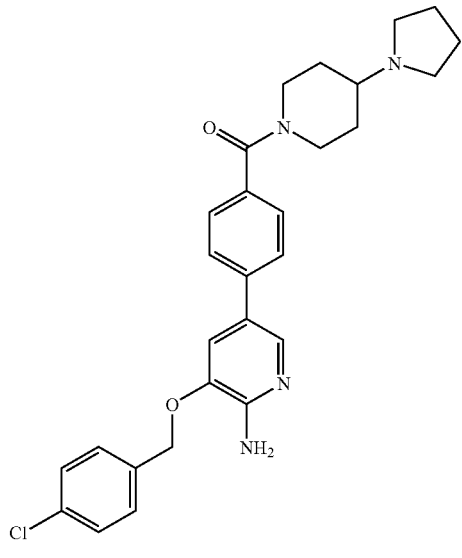
% inhibition = 15
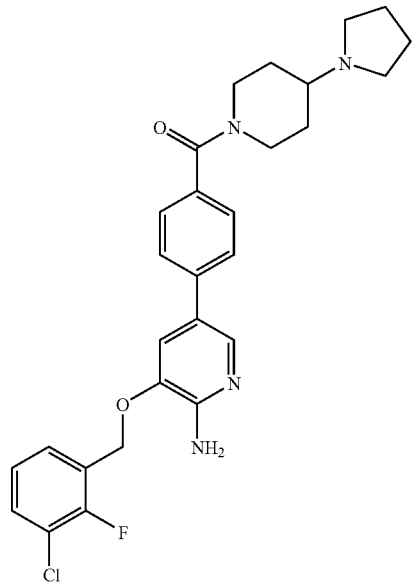
% inhibition = 28
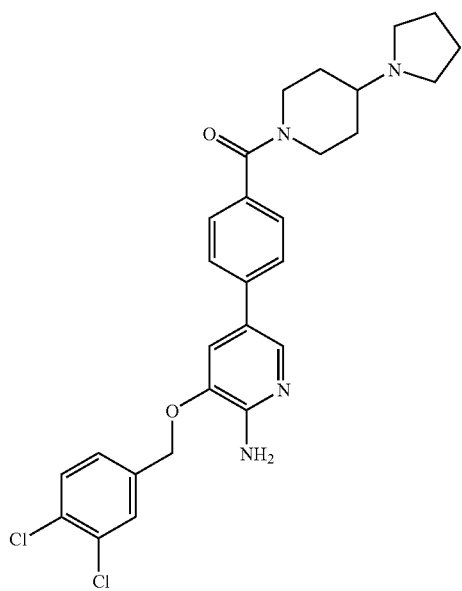
% inhibition = 26
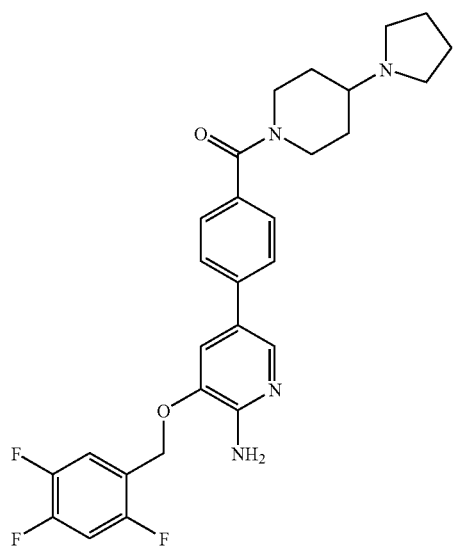
% inhibition = 12

TABLE 7-continued
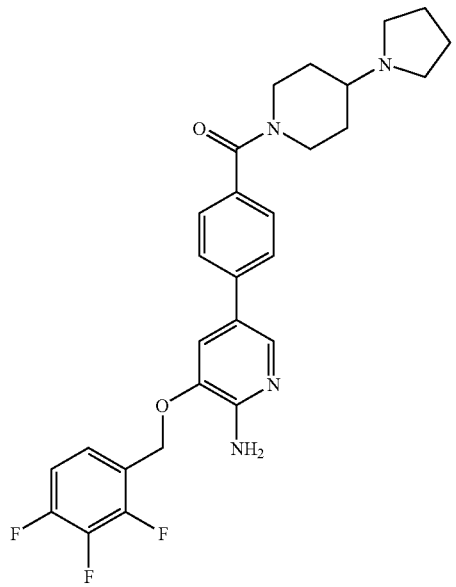
% inhibition = 19
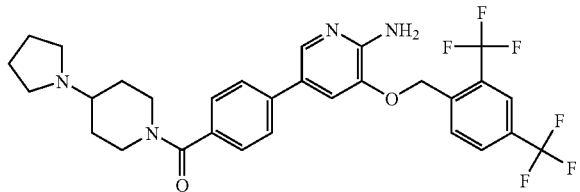
% inhibition = 12
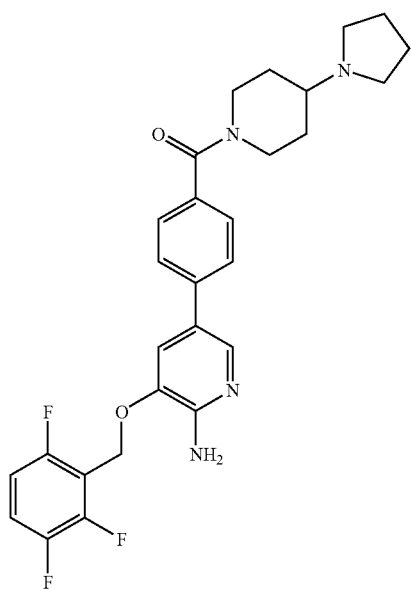
% inhibition = 30
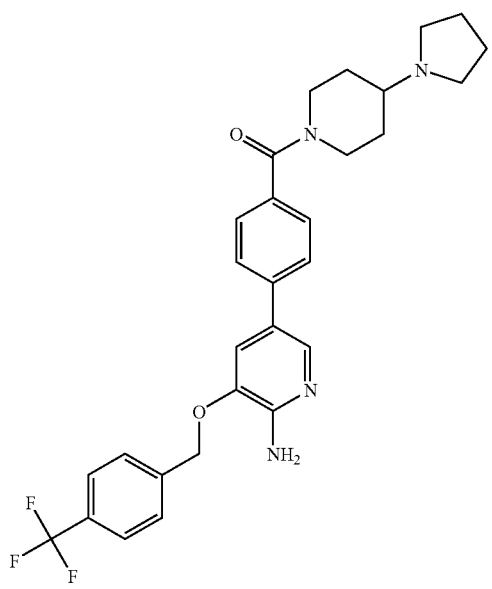
% inhibition = 10

TABLE 7-continued
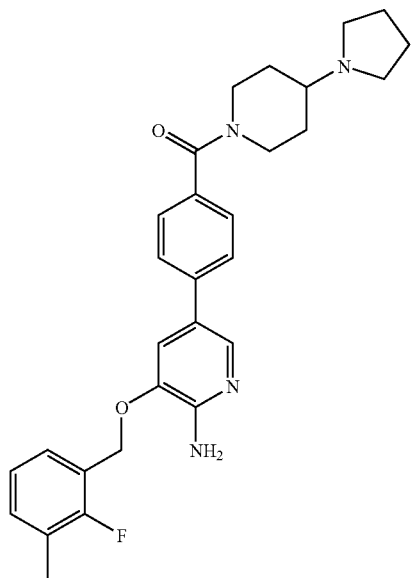
% inhibition = 28
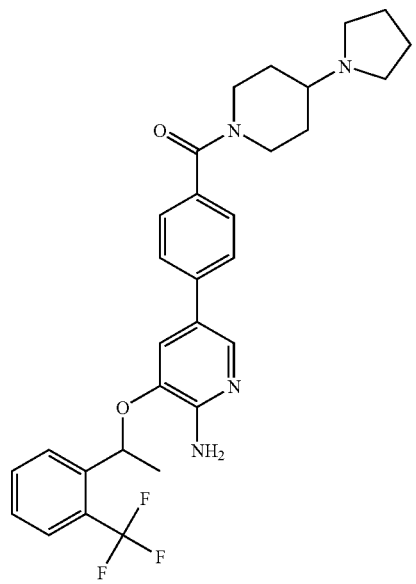
% inhibition = 21
Section D: Examples L-401 to L-416
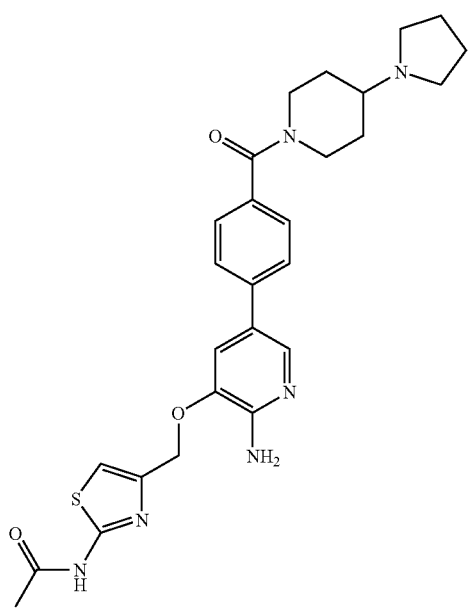
% inhibition = 9
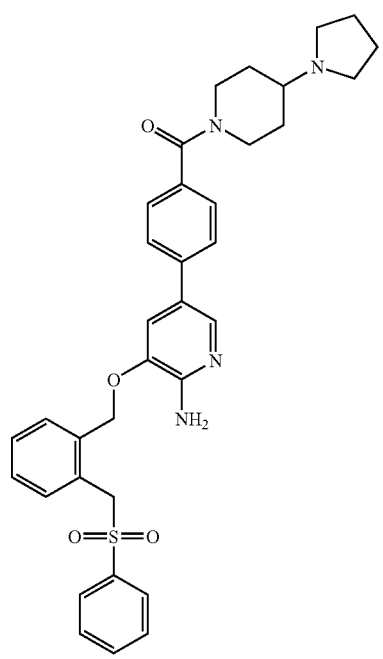
% inhibition = 11

TABLE 7-continued
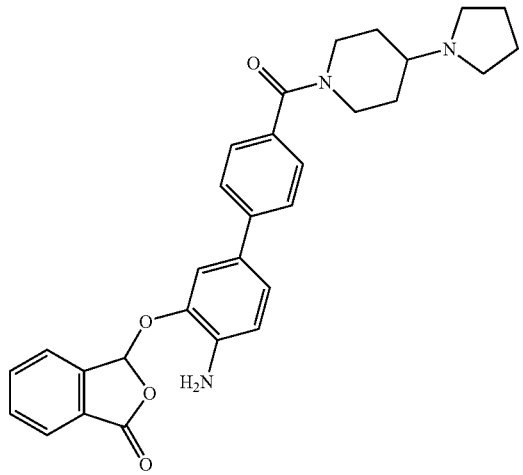
% inhibition = 4
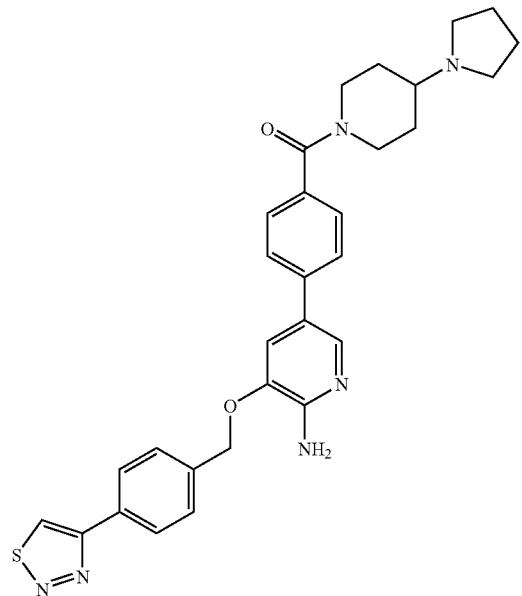
% inhibition = 41
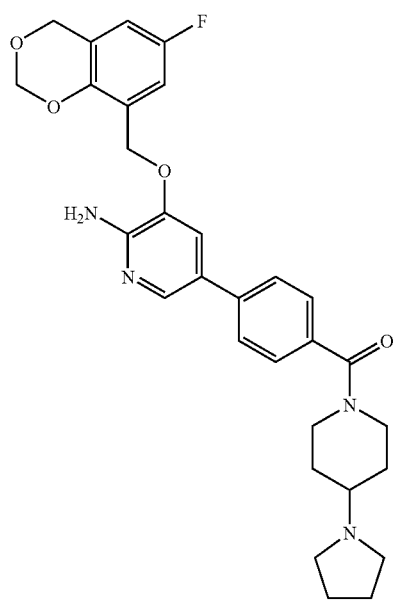
% inhibition = 21
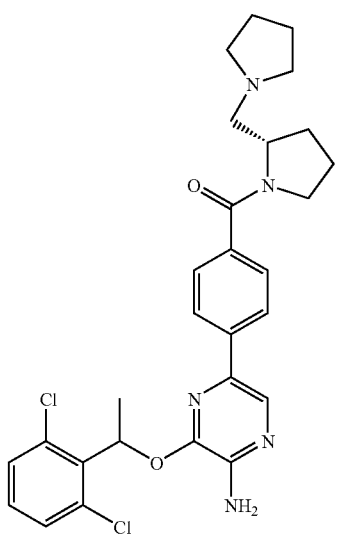
% inhibition = 14

TABLE 7-continued
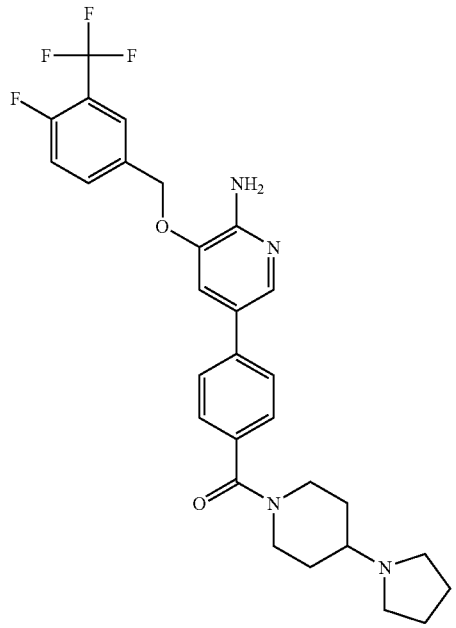
% inhibition = 13
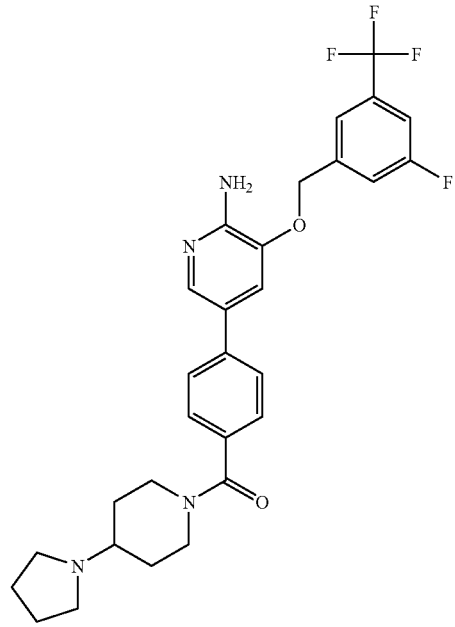
% inhibition = 12
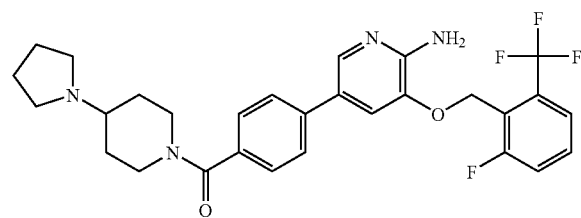
% inhibition = 31
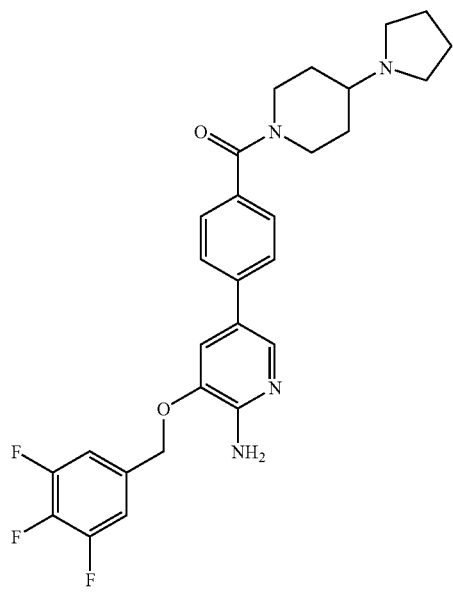
% inhibition = 19

TABLE 7-continued
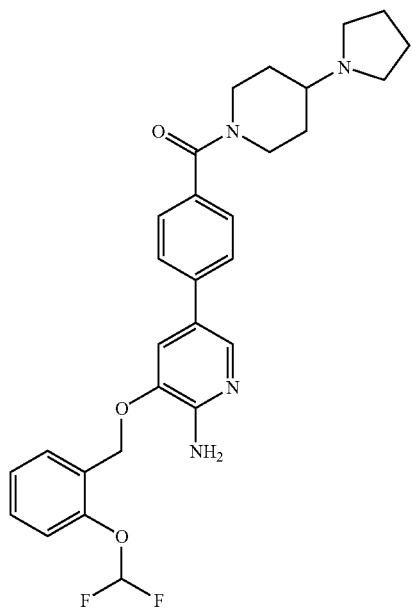
% inhibition = 27
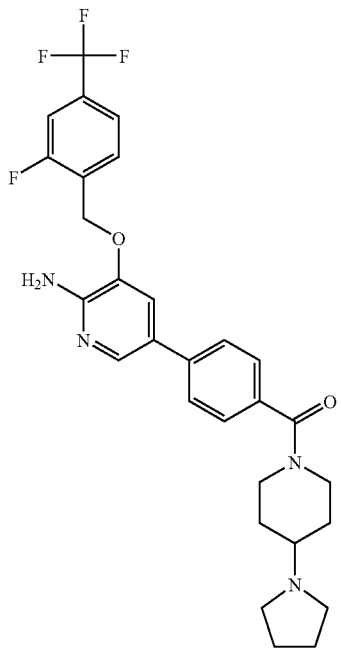
% inhibition = 25
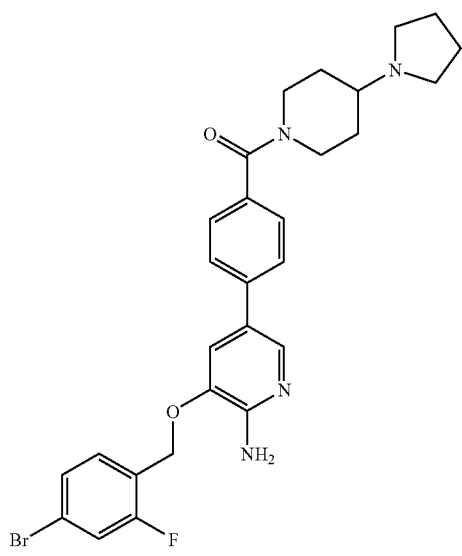
% inhibition = 31
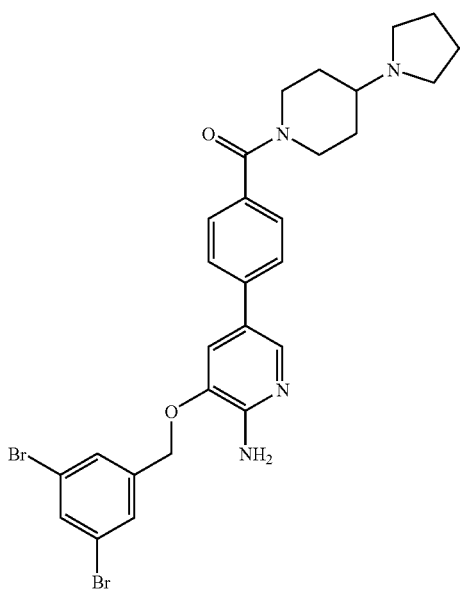
% inhibition = 45

TABLE 7-continued
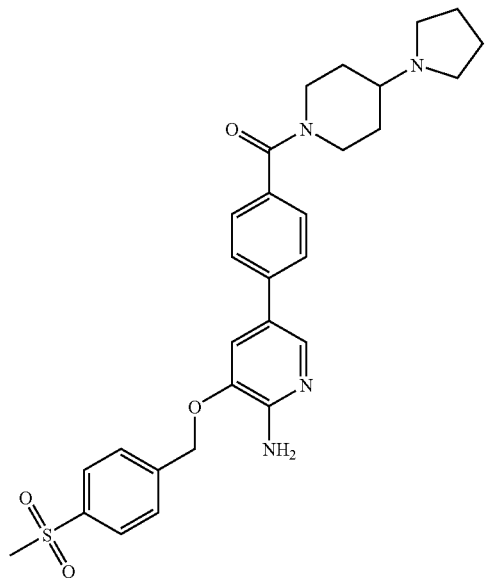
% inhibition = 11
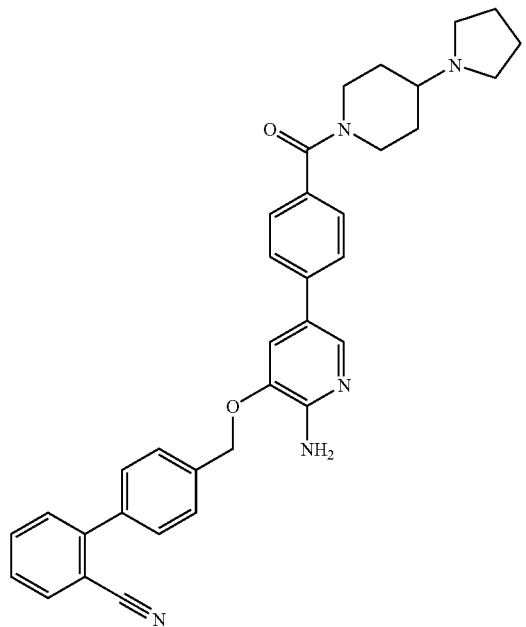
% inhibition = 77
Section E: Examples L-417 to L-432
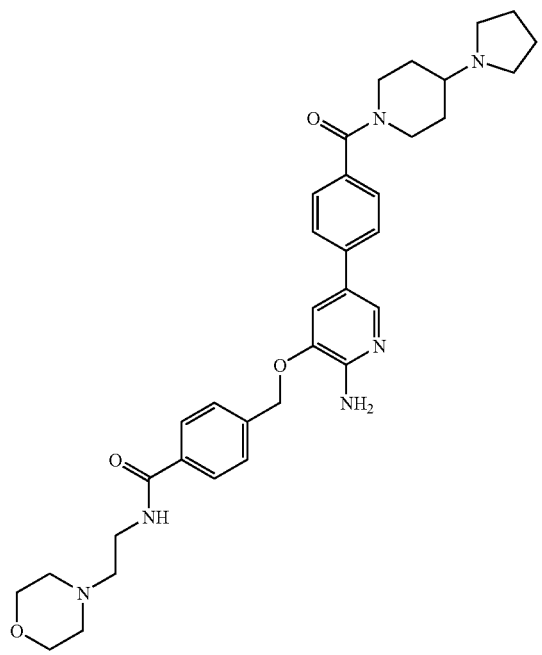
% inhibition = 11
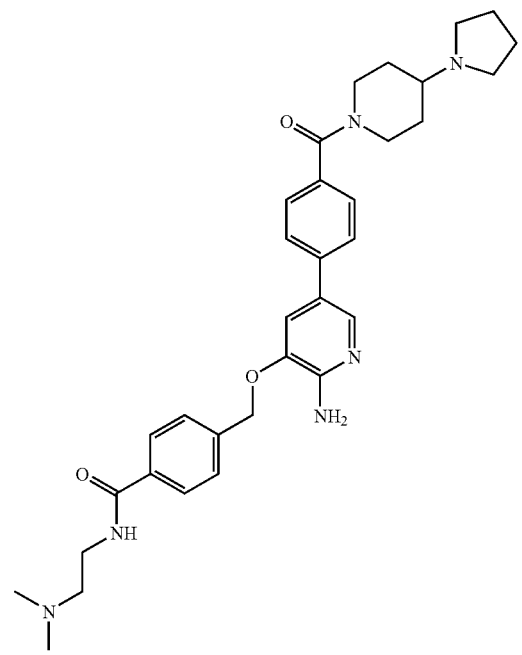
% inhibition = 9

TABLE 7-continued
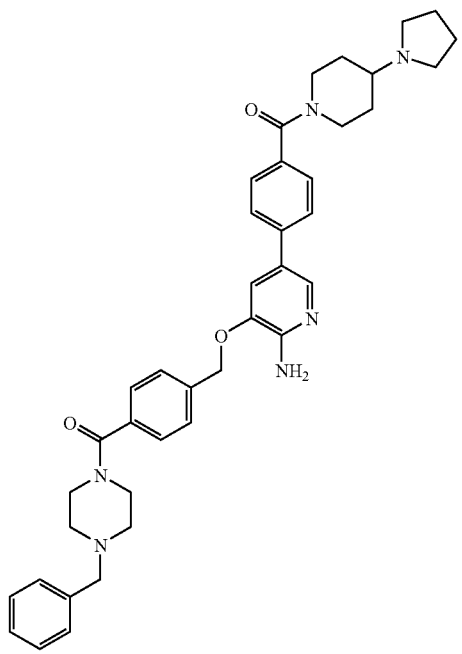
% inhibition = 12
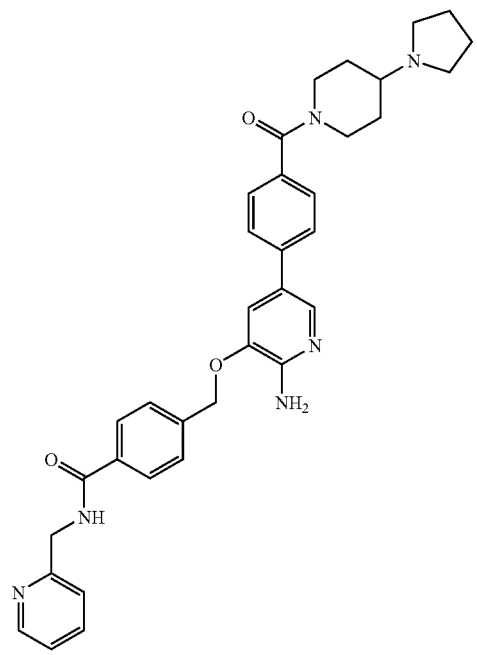
% inhibition = 7
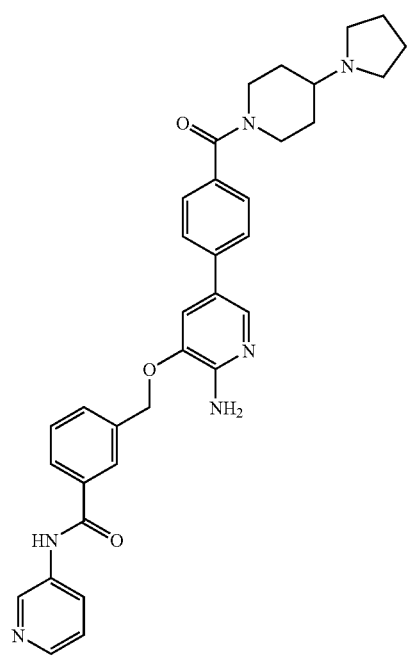
% inhibition = 10
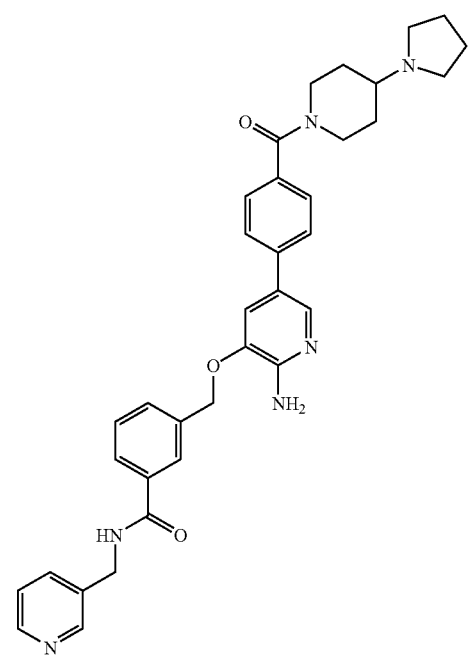
% inhibition = 14

TABLE 7-continued
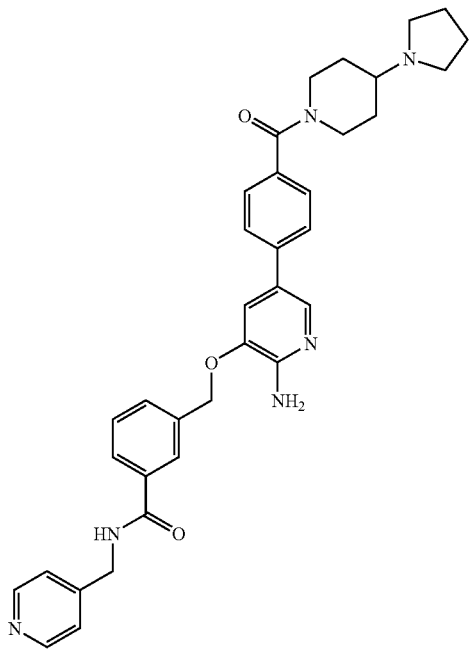
% inhibition = 10
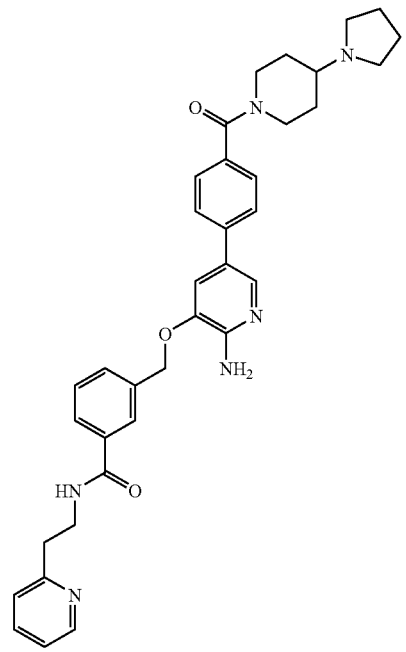
% inhibition = 12
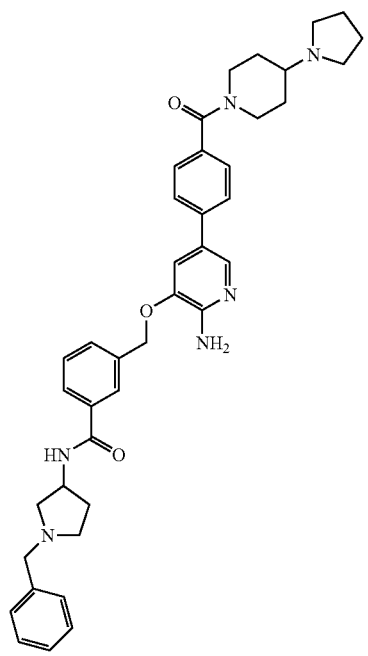
% inhibition = 13
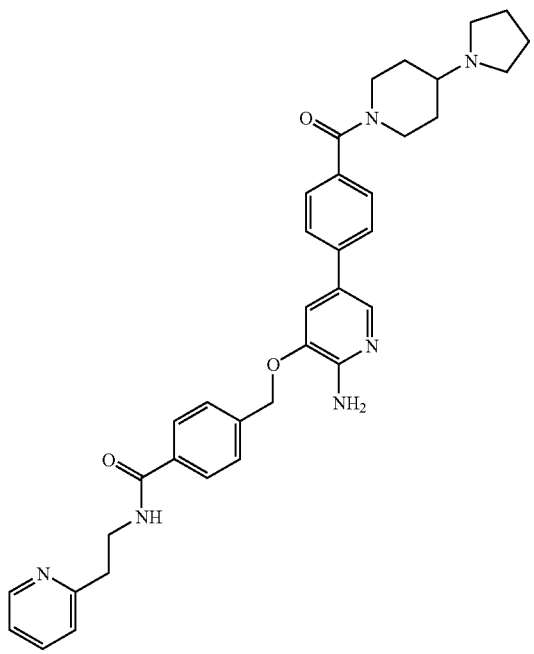
% inhibition = 11

TABLE 7-continued
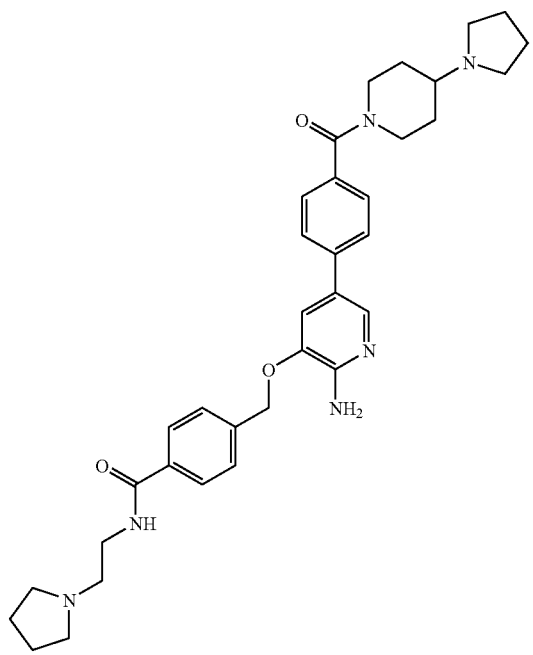
% inhibition = 10
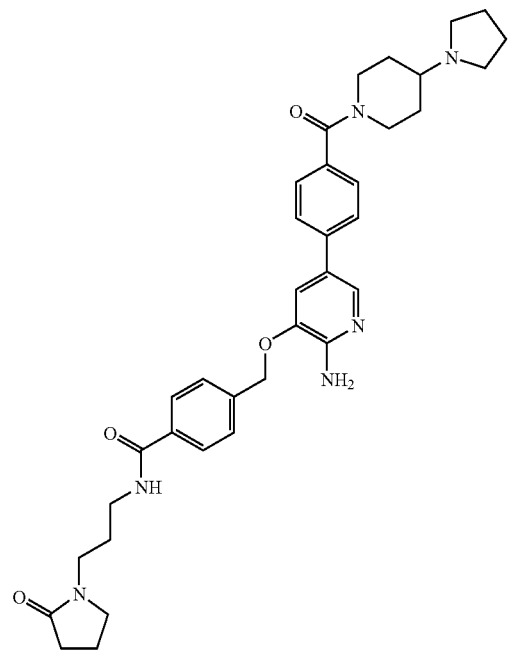
% inhibition = 11
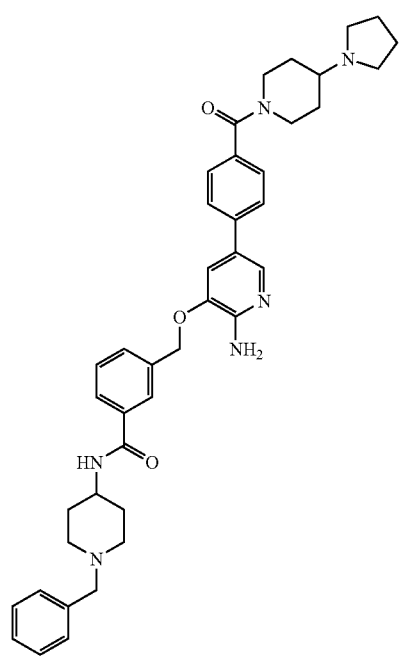
% inhibition = 13
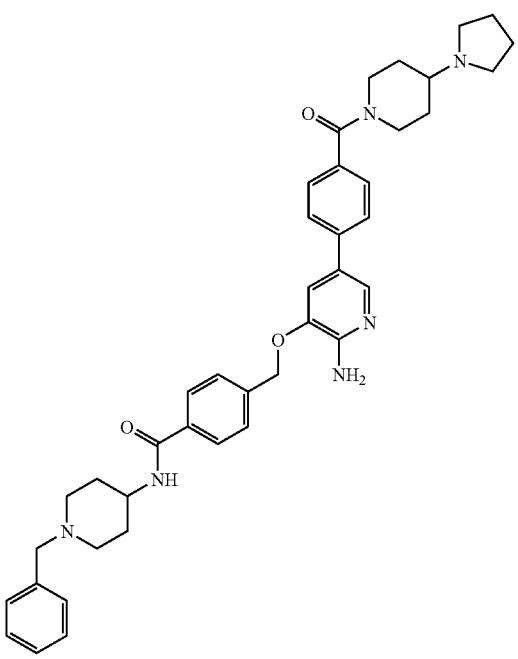
% inhibition = 11

TABLE 7-continued
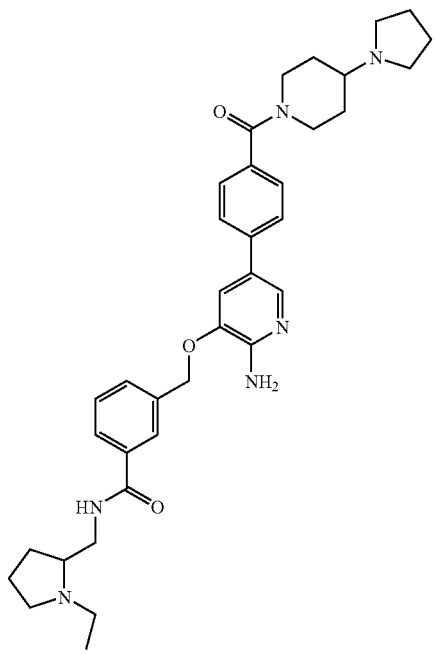
% inhibition = 10
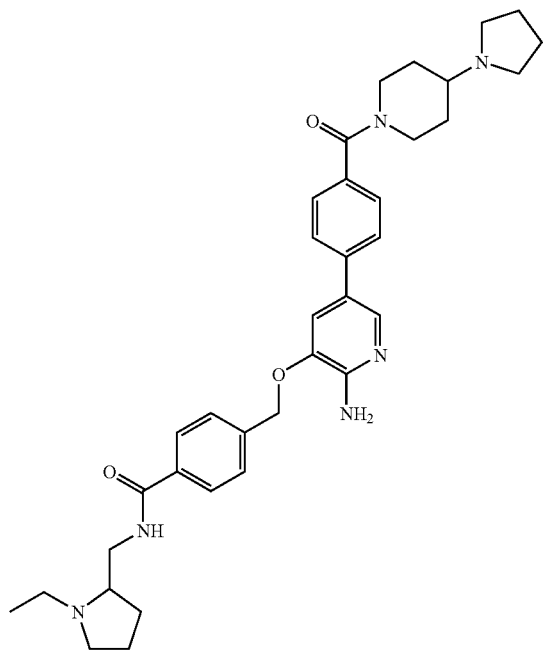
% inhibition = 18
Section F: Examples L-433 to L-448
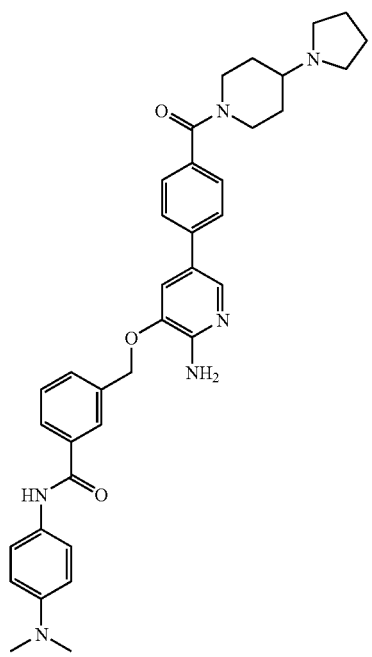
% inhibition = 23
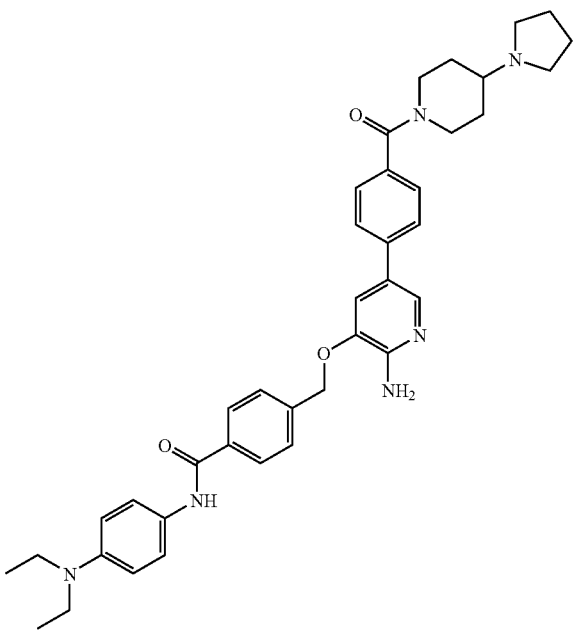
% inhibition = 47

TABLE 7-continued
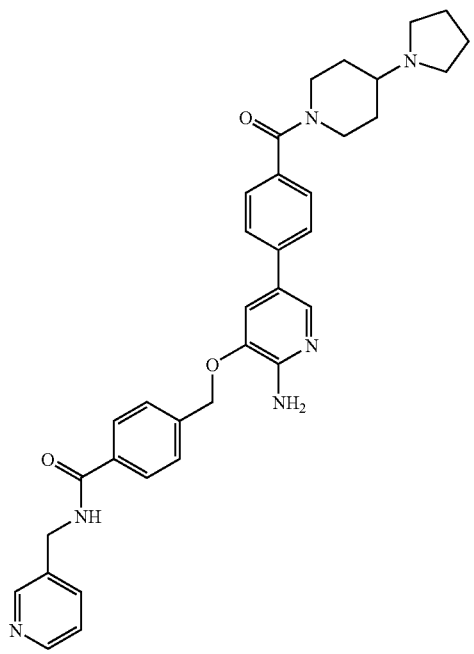
% inhibition = 15
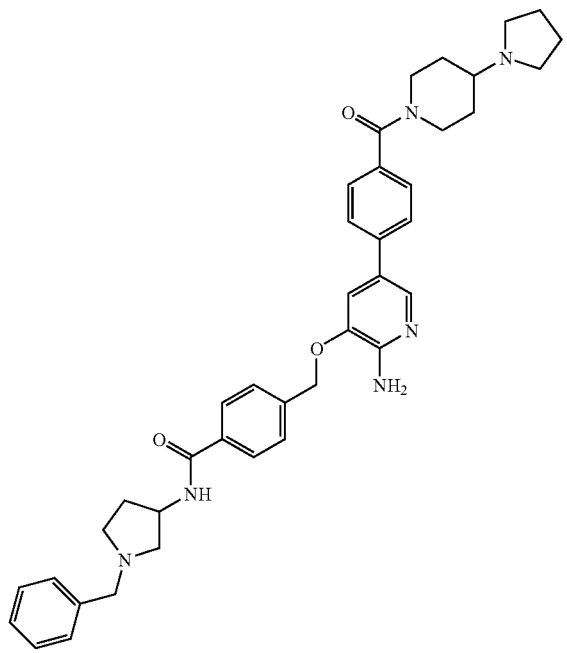
% inhibition = 24
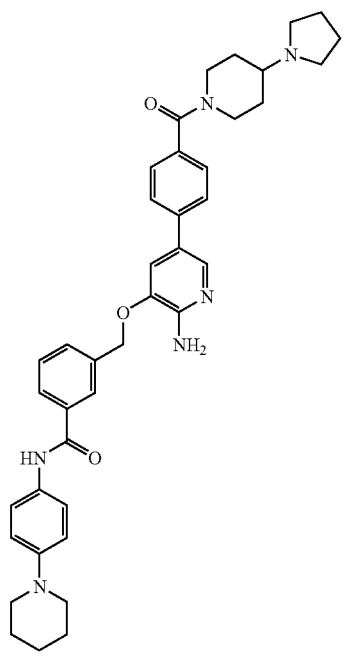
% inhibition = 32
% inhibition = 19

TABLE 7-continued
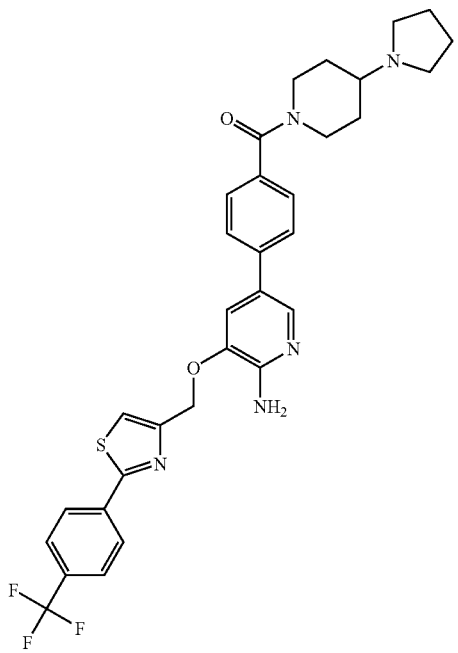
% inhibition = 21
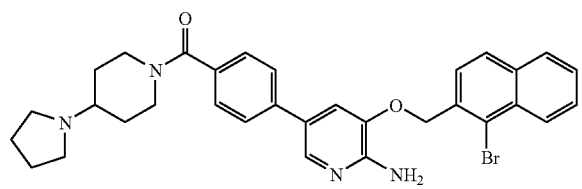
% inhibition = 59
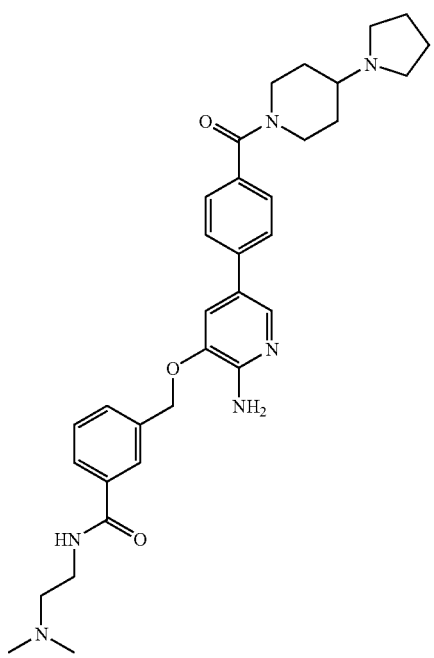
% inhibition = 20
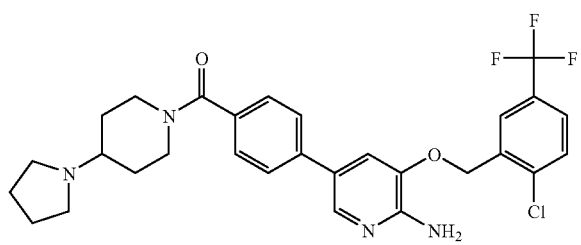
% inhibition = 26

TABLE 7-continued
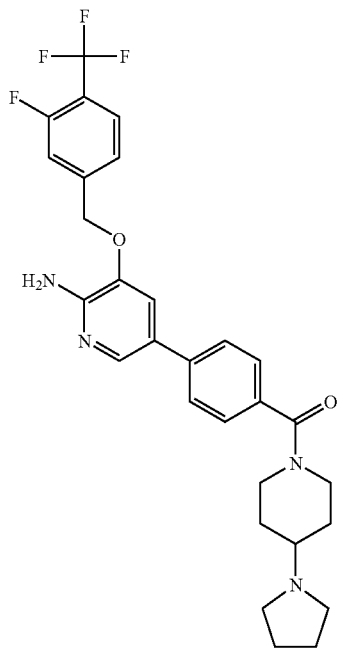
% inhibition = 24
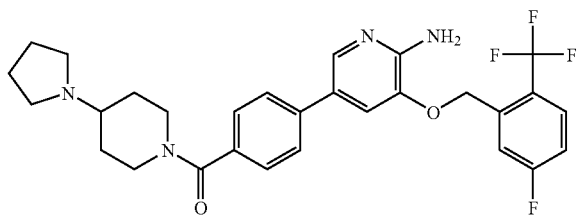
% inhibition = 26
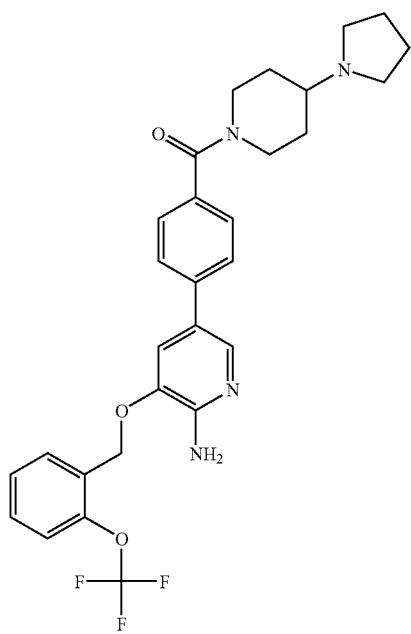
% inhibition = 21
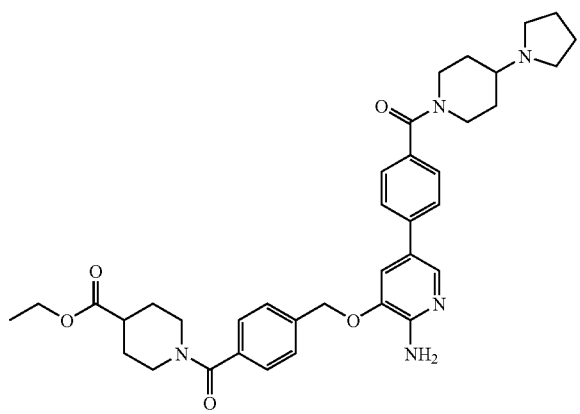
% inhibition = 16

TABLE 7-continued
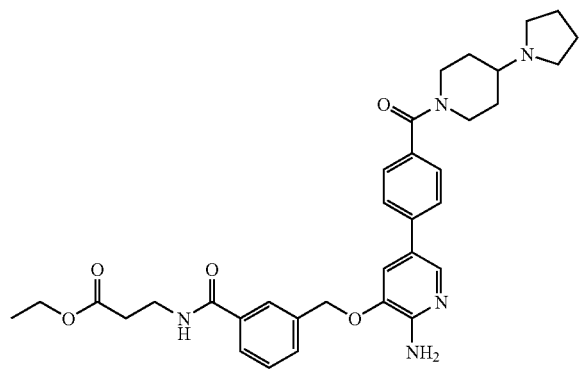
% inhibition = 14
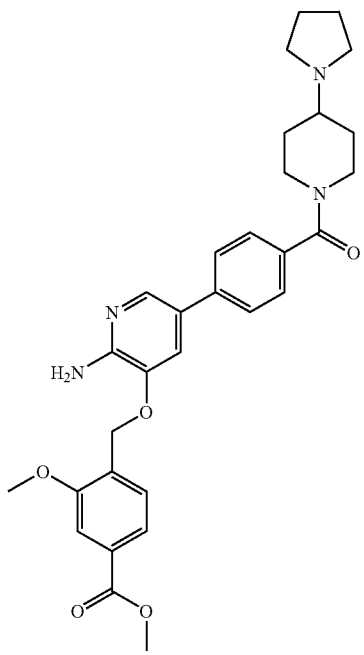
% inhibition = 15
Section G: Examples L-449 to L-464
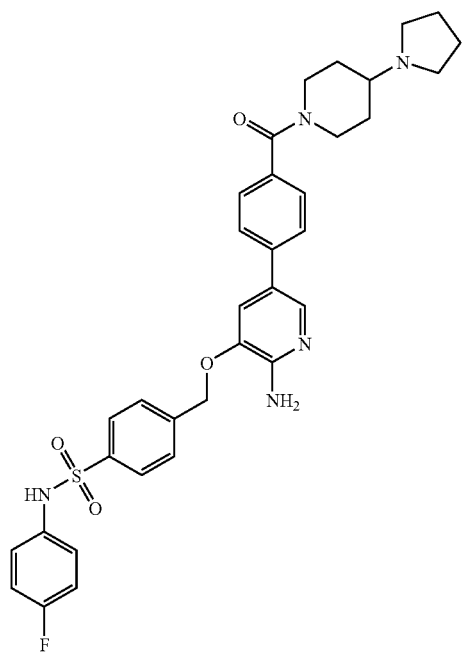
% inhibition = 15
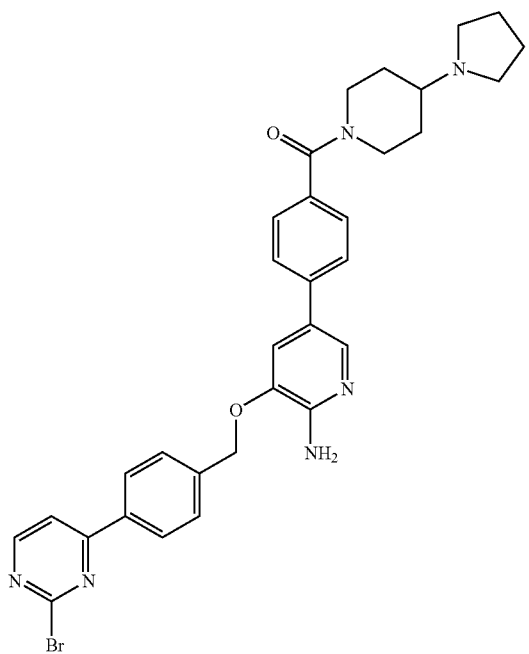
% inhibition = 17

TABLE 7-continued
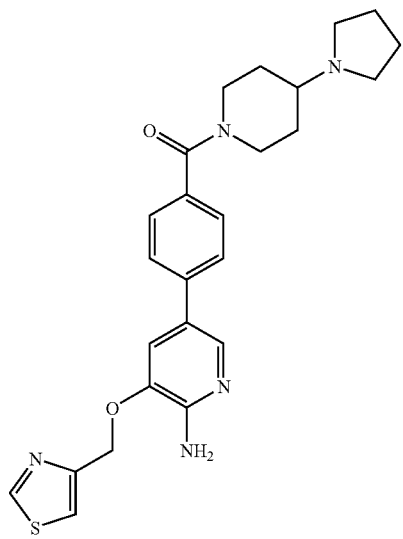
% inhibition = 12
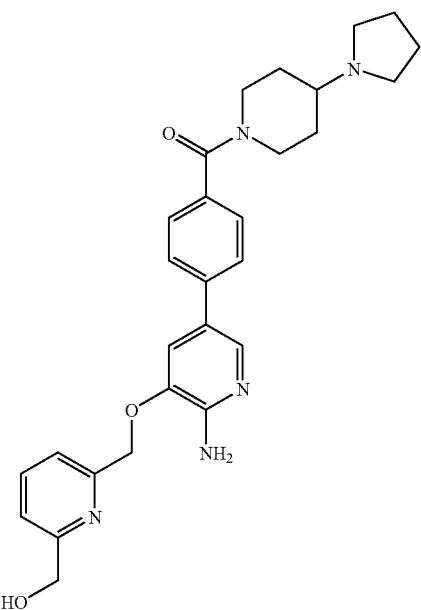
% inhibition = 15
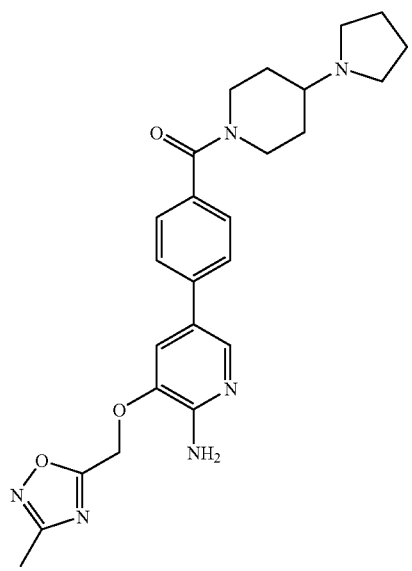
% inhibition = 11
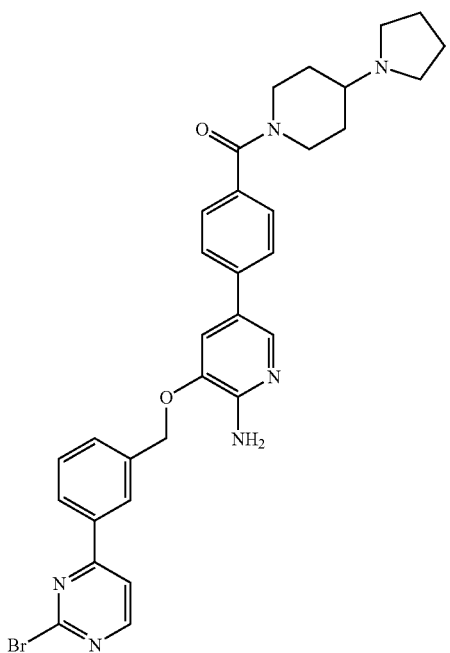
% inhibition = 13

TABLE 7-continued
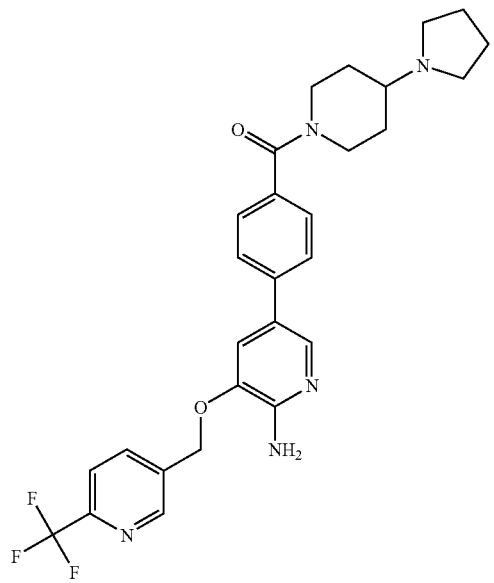
% inhibition = 13
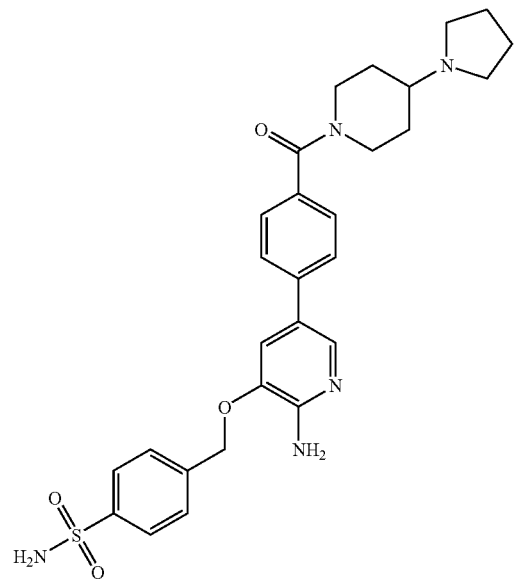
% inhibition = 17
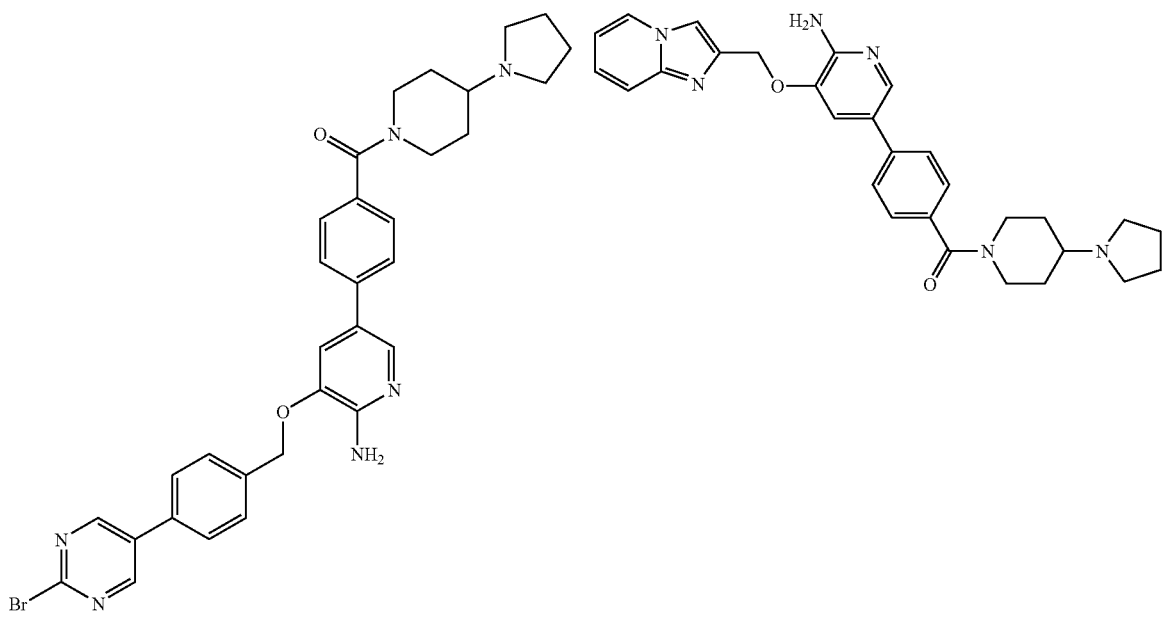
% inhibition = 33
% inhibition = 11

TABLE 7-continued
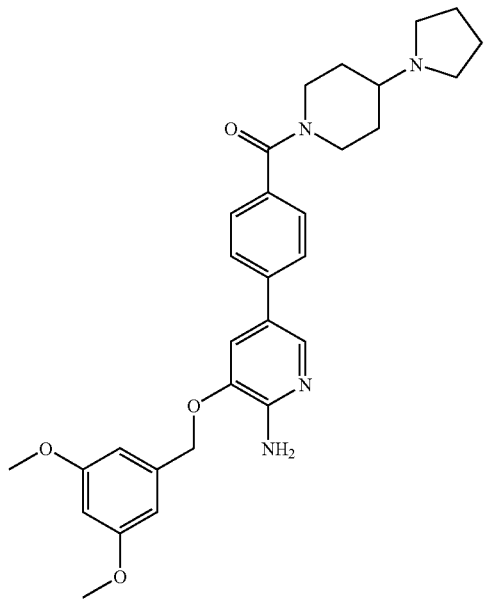
% inhibition = 17
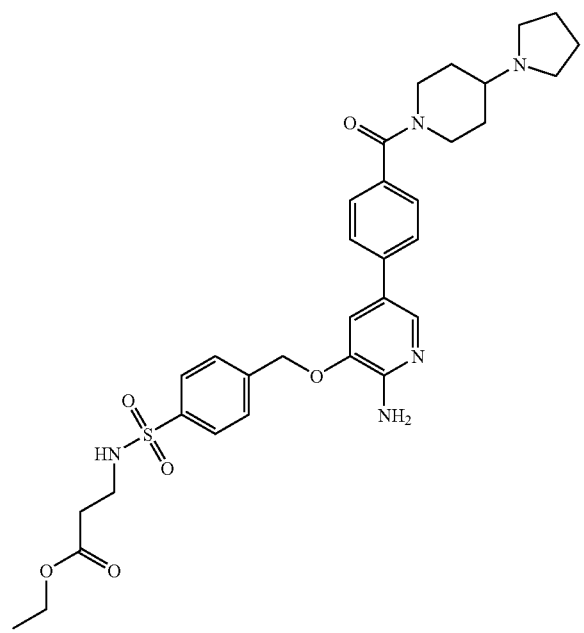
% inhibition = 15
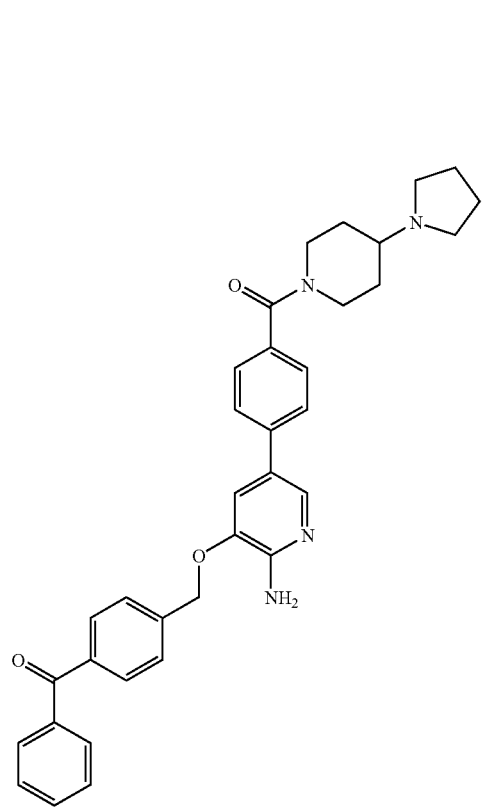
% inhibition = 31
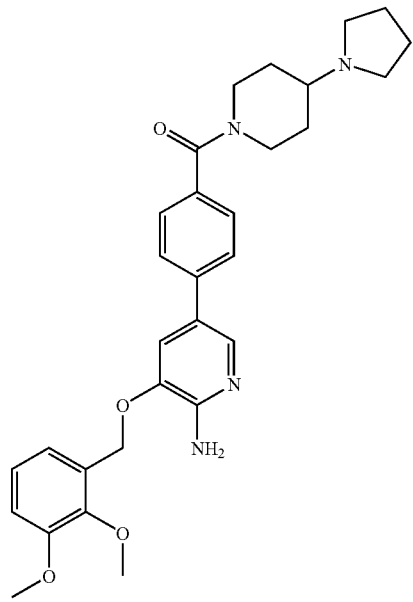
% inhibition = 23

TABLE 7-continued
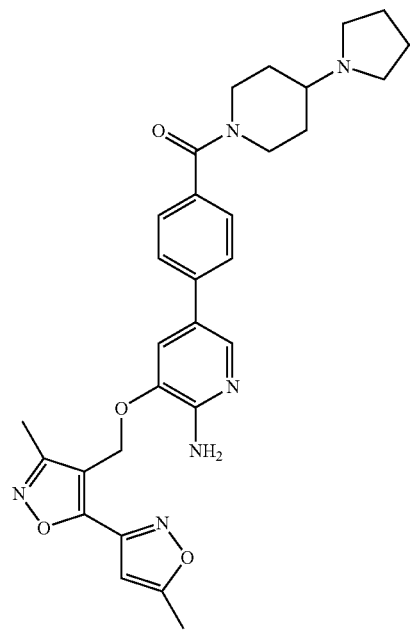
% inhibition = 22
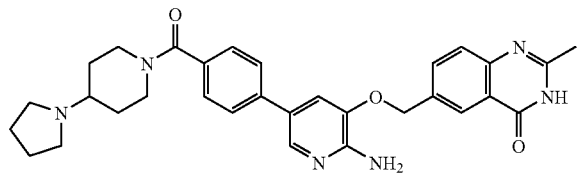
% inhibition = 12
Section H: Examples L-465 to L-480
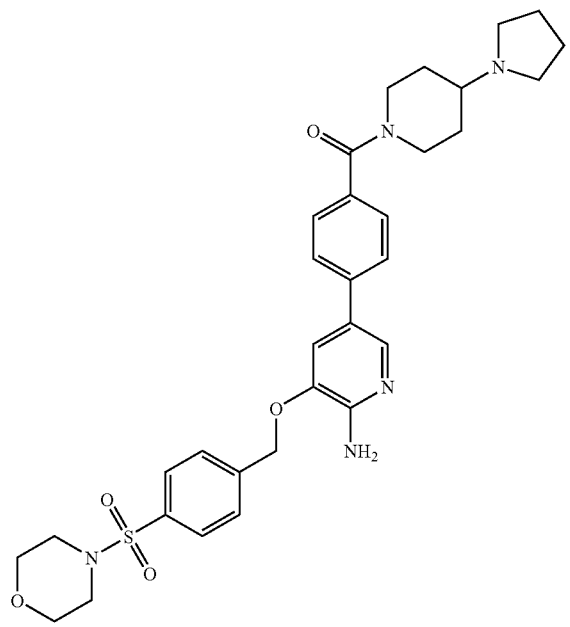
% inhibition = 14
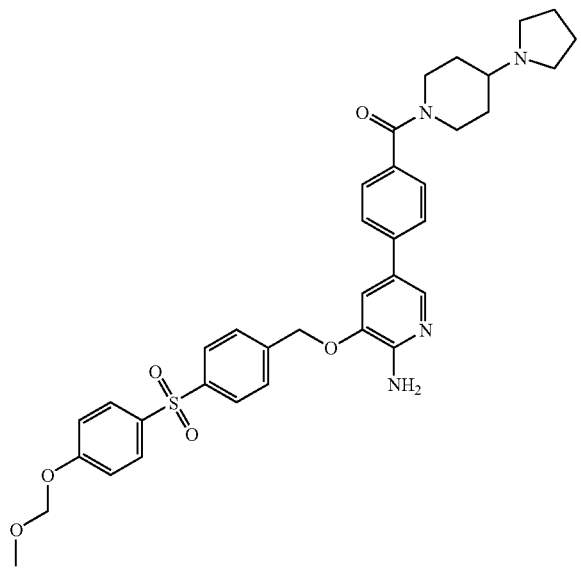
% inhibition = 18

TABLE 7-continued
| 1001 | 1002 |
|---|---|
| 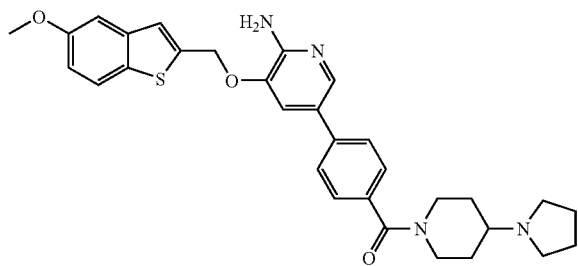 | 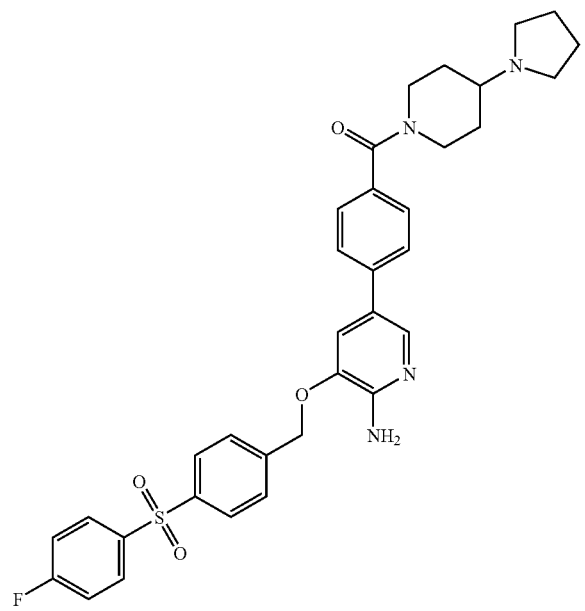 |
| % inhibition = 13 | % inhibition = 13 |
| 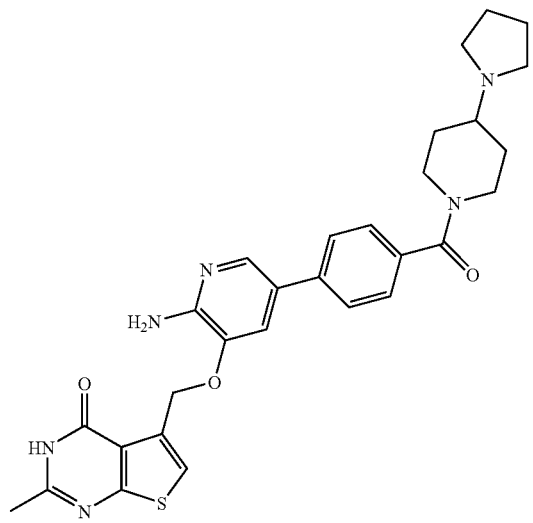 | 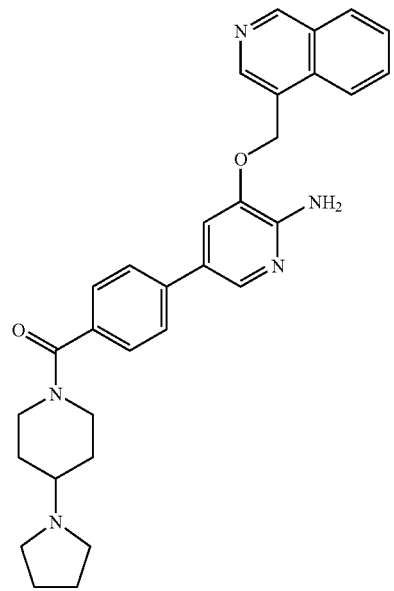 |
| % inhibition = 10 | % inhibition = 9 |

TABLE 7-continued
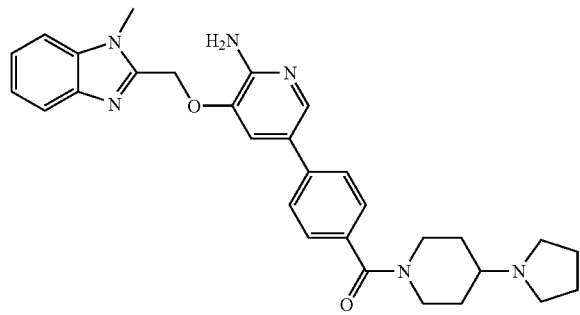
% inhibition = 10
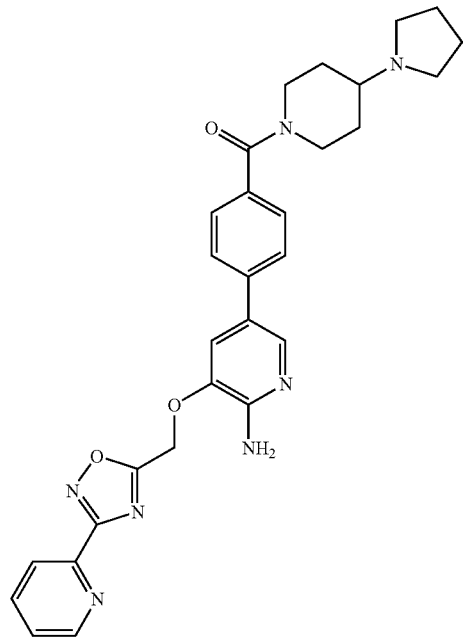
% inhibition = 9
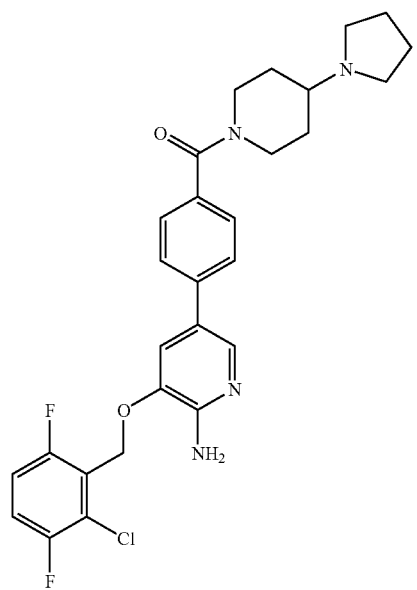
% inhibition = 50
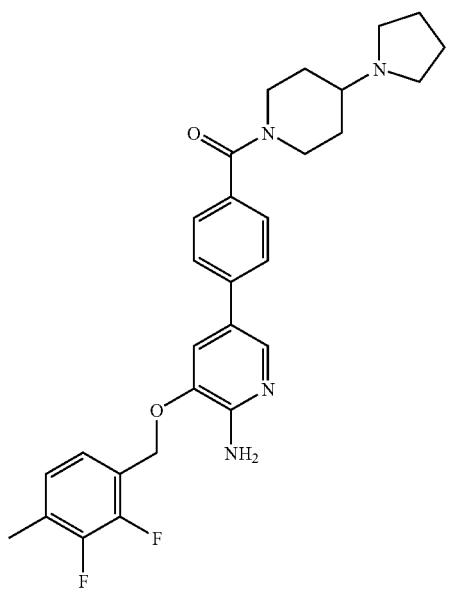
% inhibition = 39

TABLE 7-continued
| 1005 | 1006 |
|---|---|
| 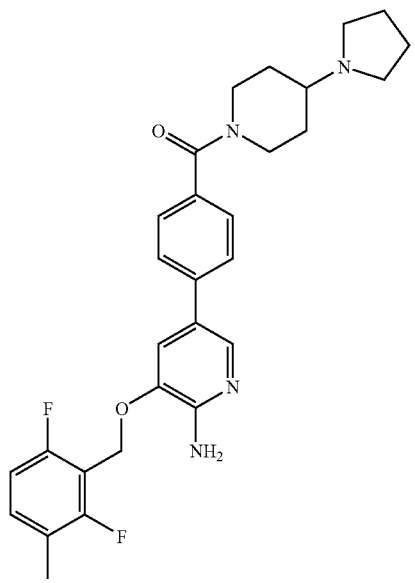 % inhibition = 51 | 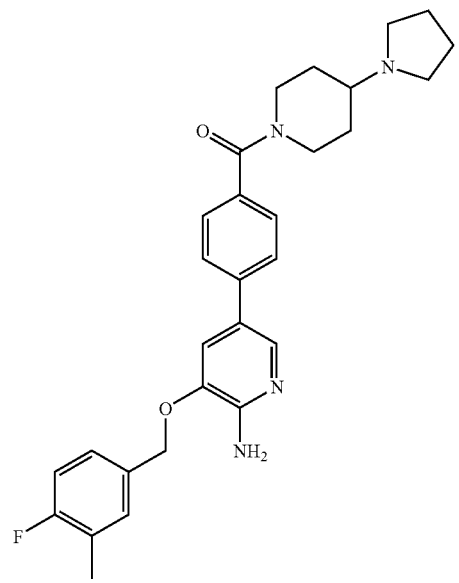 % inhibition = 27 |
| 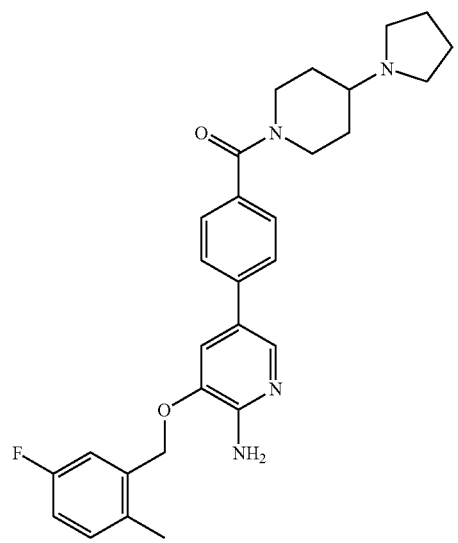 % inhibition = 29 | 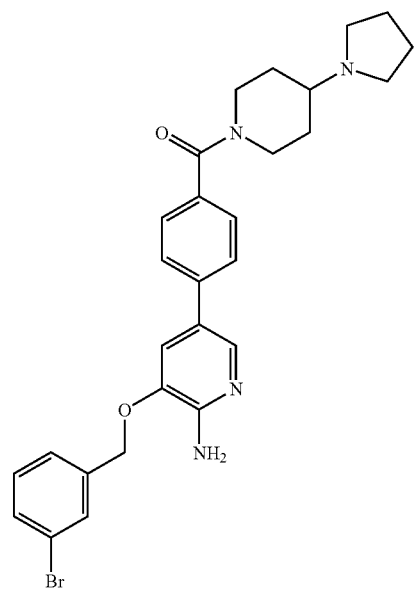 % inhibition = 24 |

TABLE 7-continued
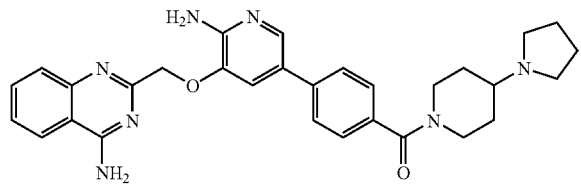
% inhibition = 15
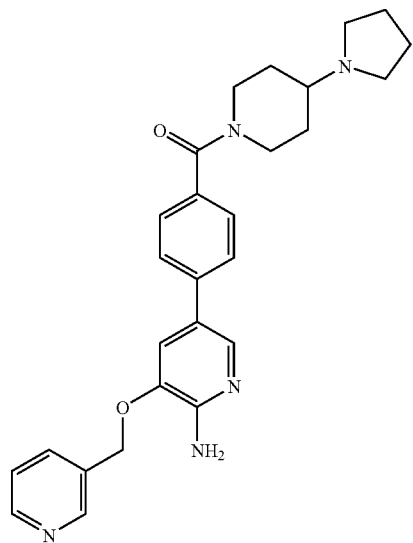
% inhibition = 17
Section I: Examples L-481 to L-496
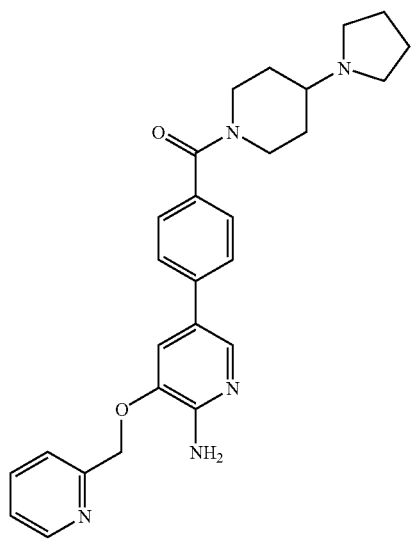
% inhibition = 16
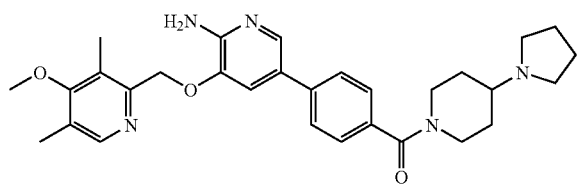
% inhibition = 20

TABLE 7-continued
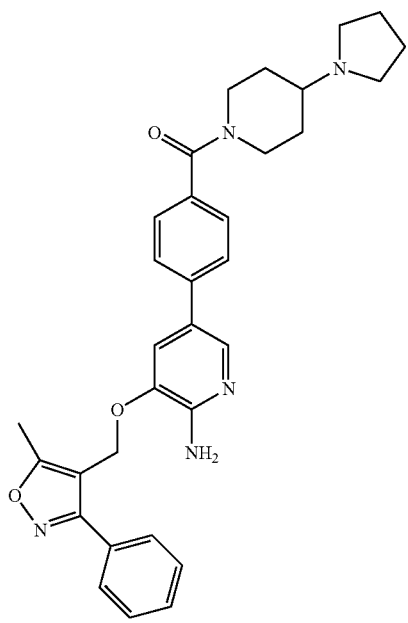
% inhibition = 19
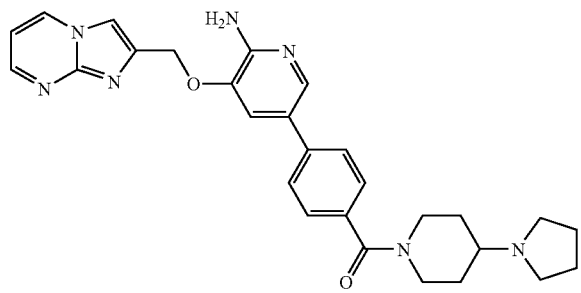
% inhibition = 16
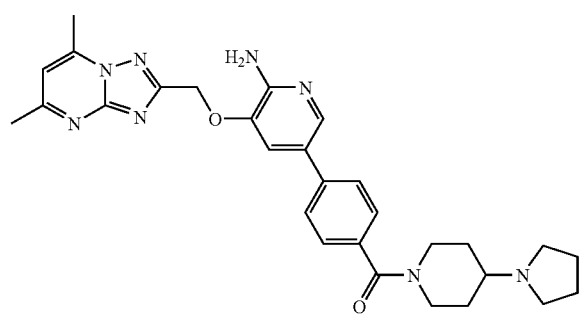
% inhibition = 18
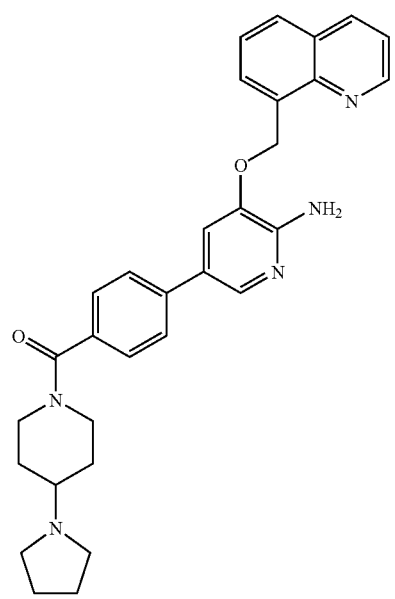
% inhibition = 22

TABLE 7-continued
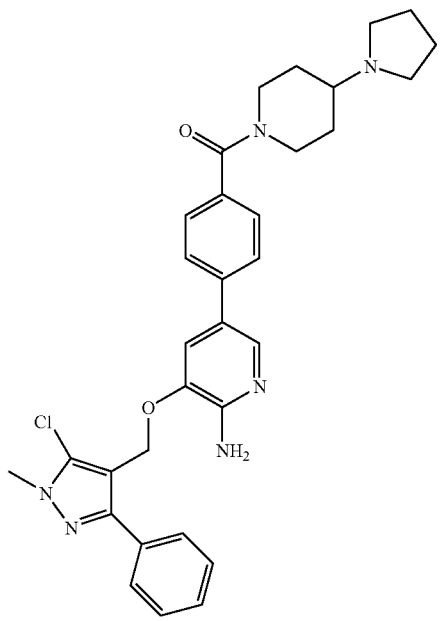
% inhibition = 63
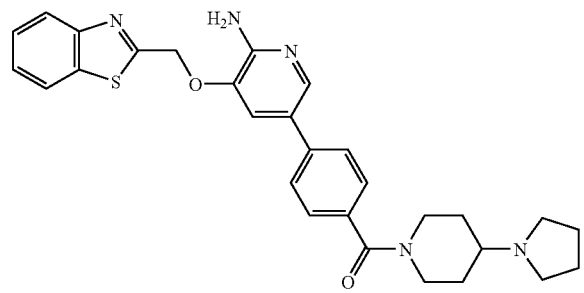
% inhibition = 17
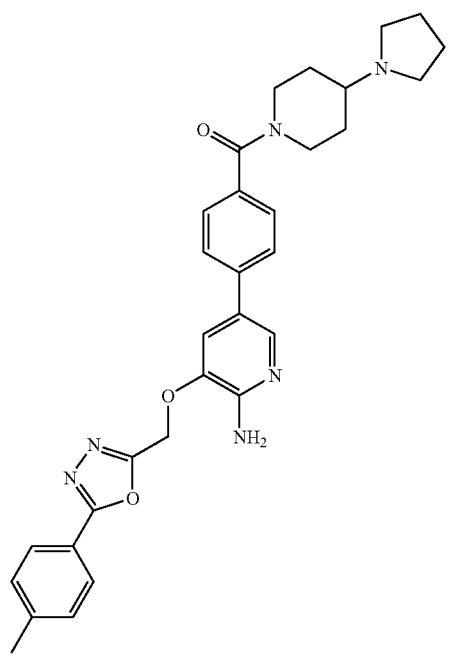
% inhibition = 18
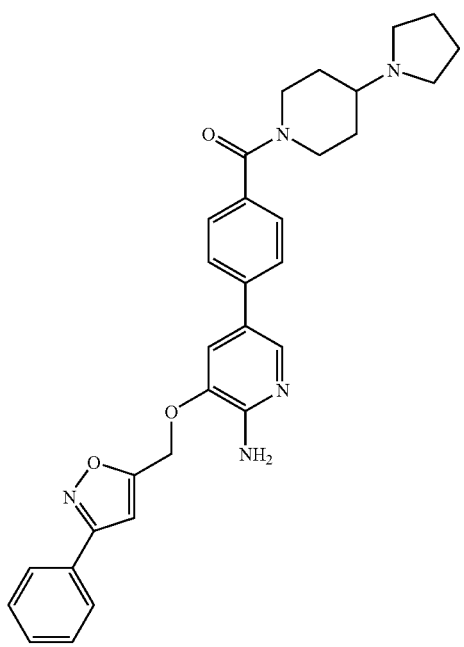
% inhibition = 23

TABLE 7-continued
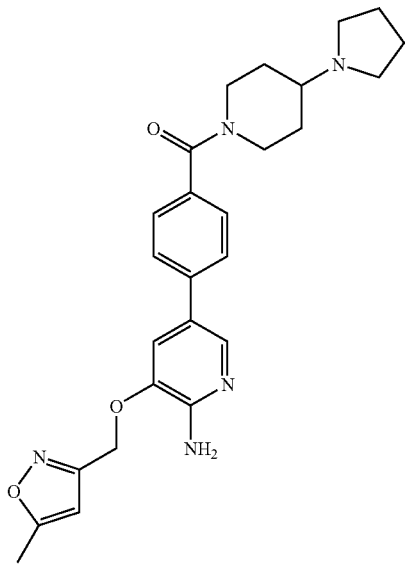
% inhibition = 16
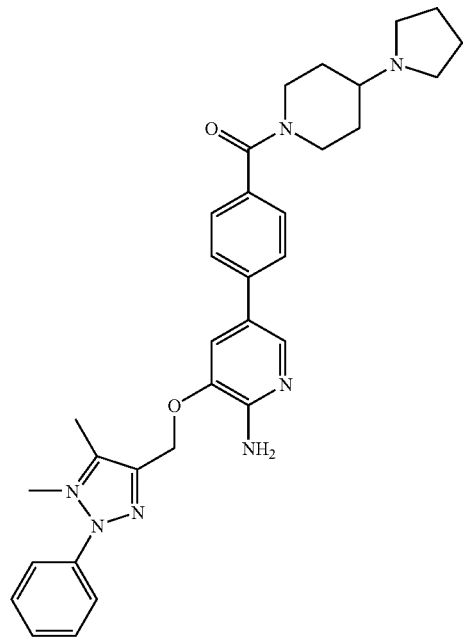
% inhibition = 22
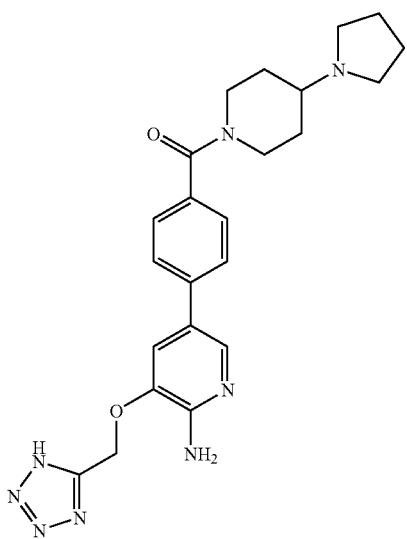
% inhibition = 14
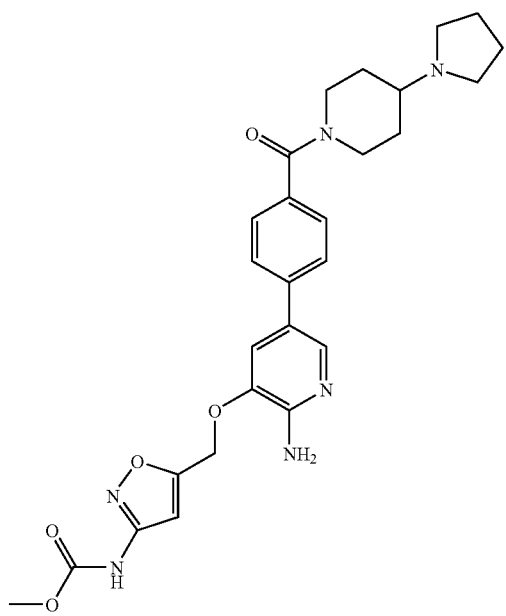
% inhibition = 18

TABLE 7-continued
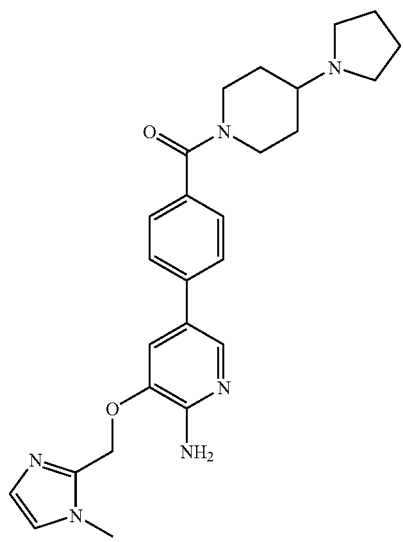
% inhibition = 14
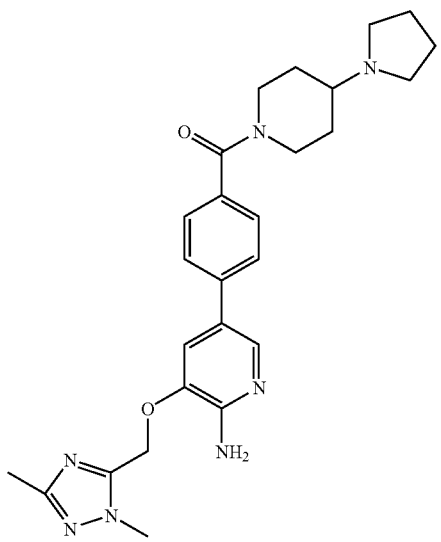
% inhibition = 14
Section J: Examples L-497 to L-512
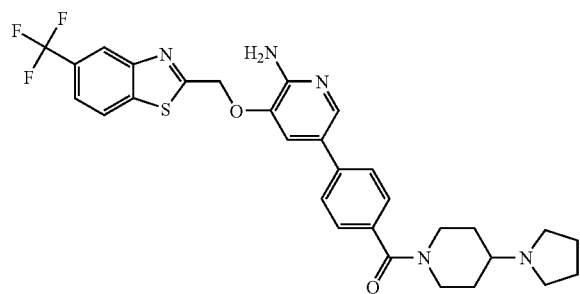
% inhibition = 34
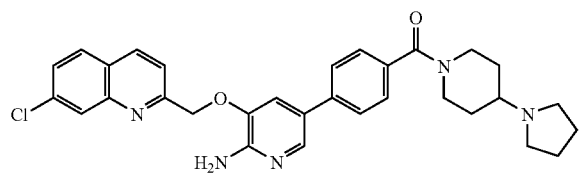
% inhibition = 24
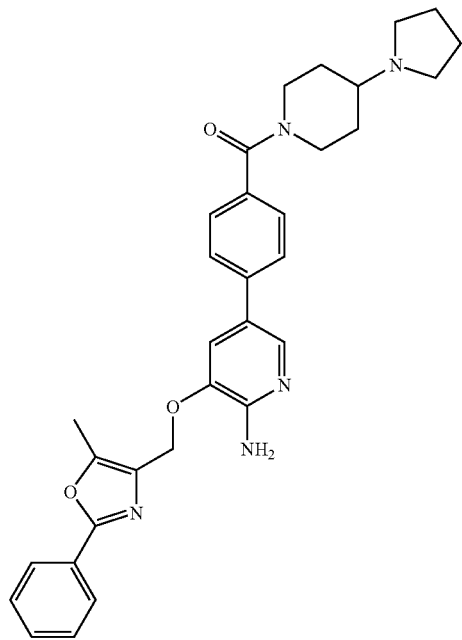
% inhibition = 19
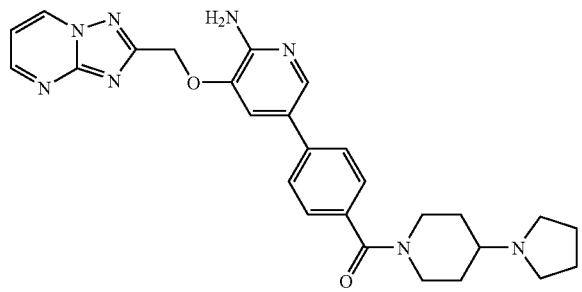
% inhibition = 19

TABLE 7-continued
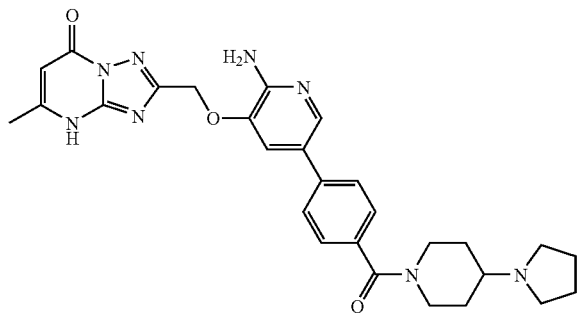
% inhibition = 18
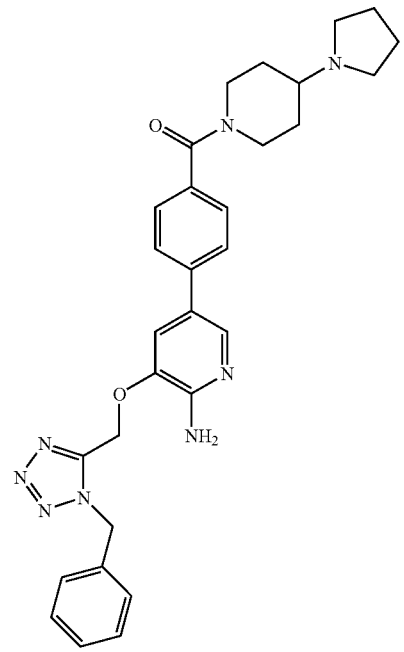
% inhibition = 19
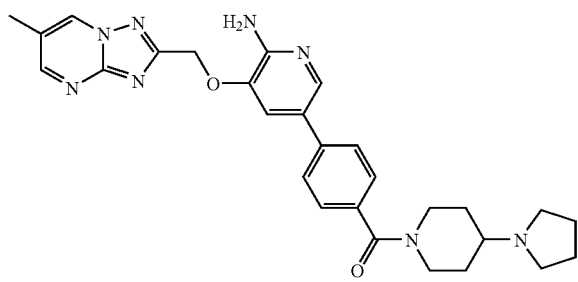
% inhibition = 17
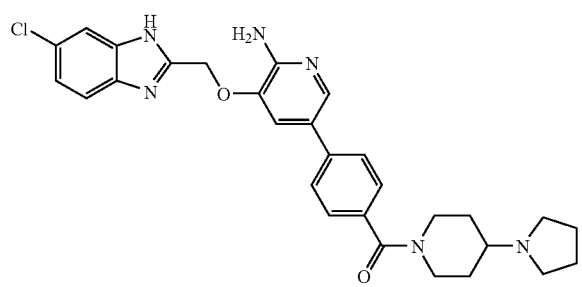
% inhibition = 16
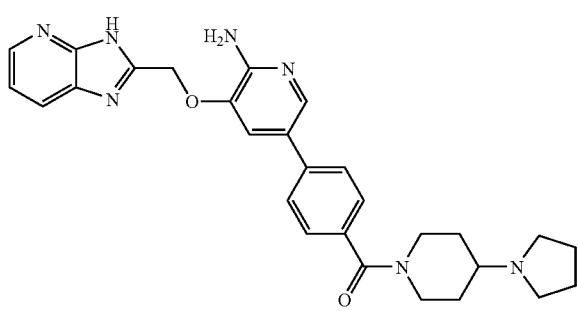
% inhibition = 17
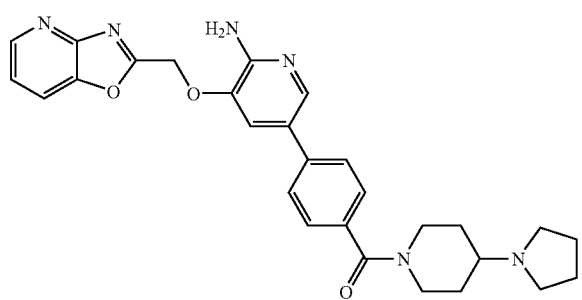
% inhibition = 17

TABLE 7-continued
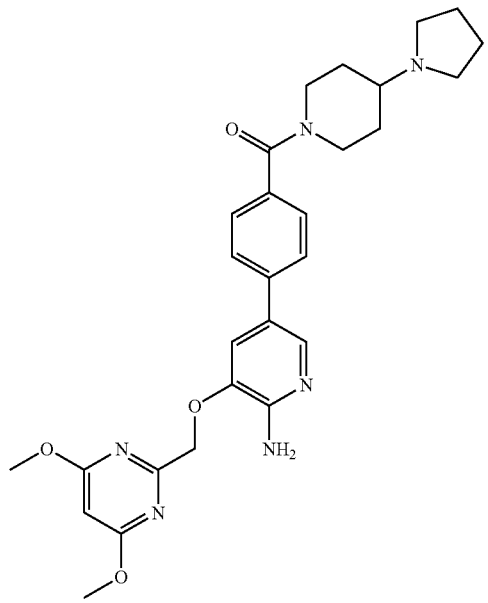
% inhibition = 20
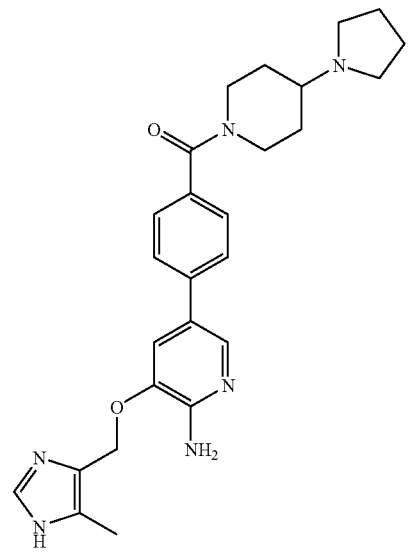
% inhibition = 12
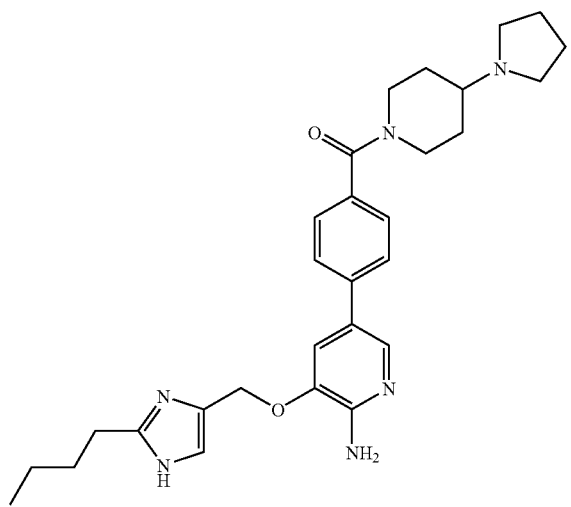
% inhibition = 16
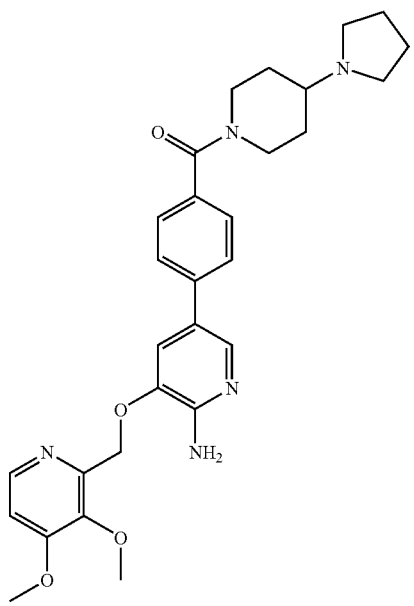
% inhibition = 23

TABLE 7-continued
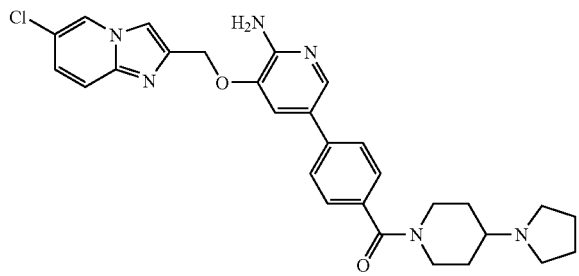
% inhibition = 16
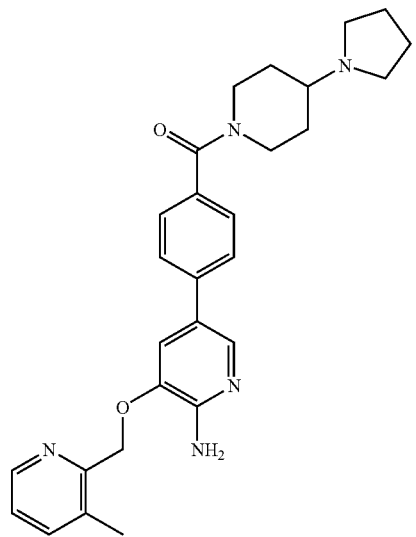
% inhibition = 16
Section H: Examples L-513 to L-528
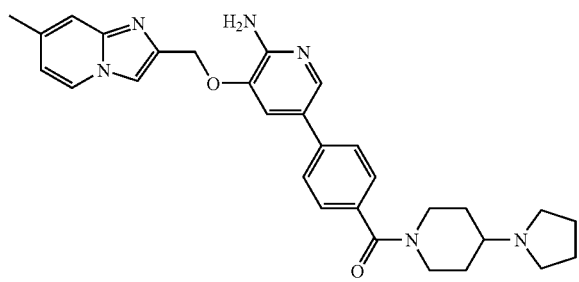
% inhibition = 18
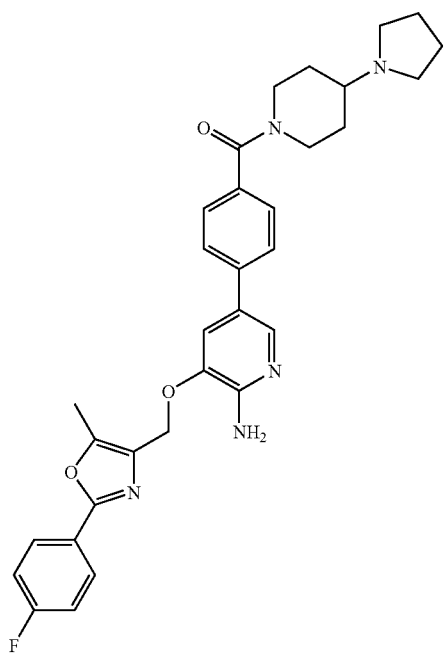
% inhibition = 17

TABLE 7-continued
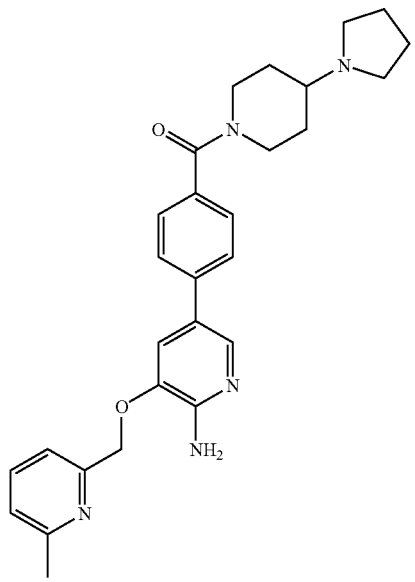
% inhibition = 17
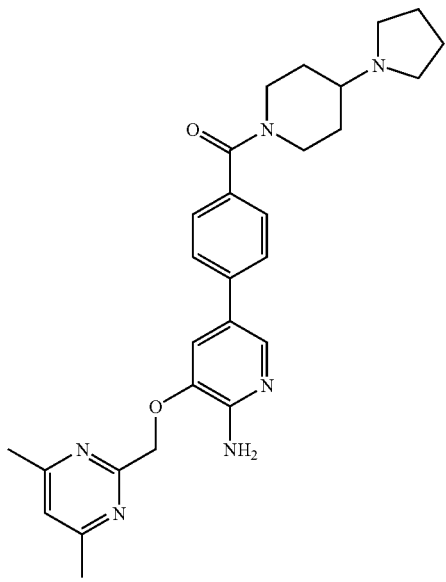
% inhibition = 16
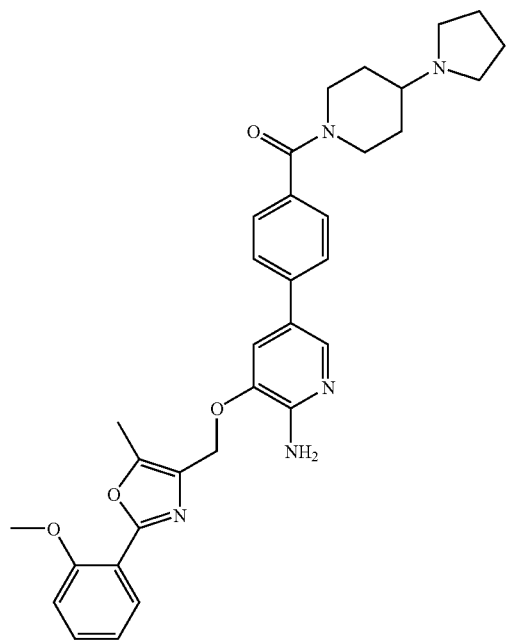
% inhibition = 19
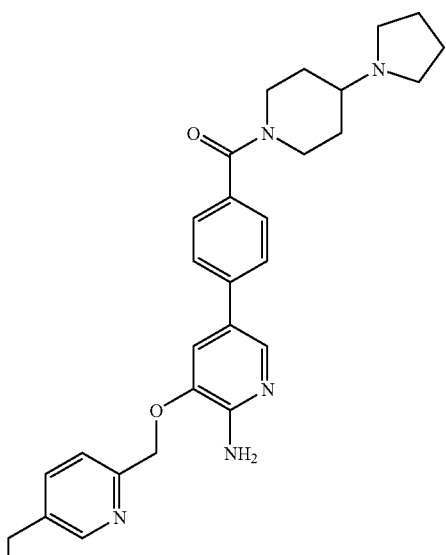
% inhibition = 15

TABLE 7-continued
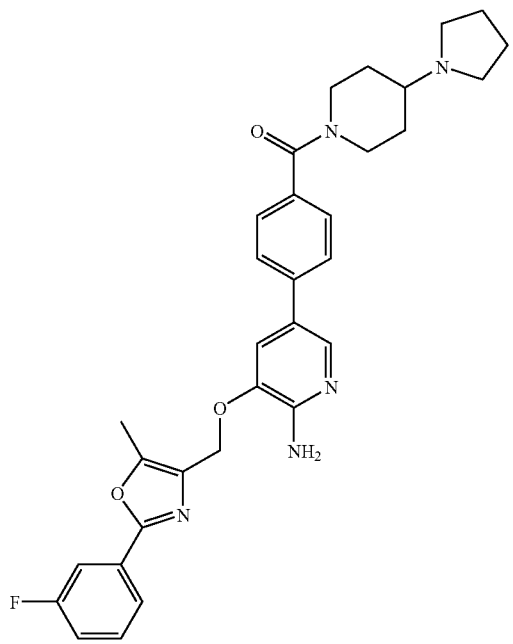
% inhibition = 8
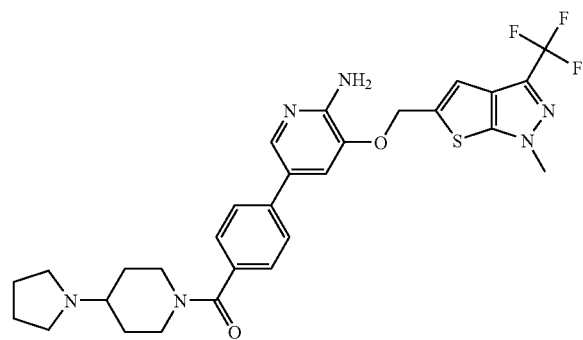
% inhibition = 14
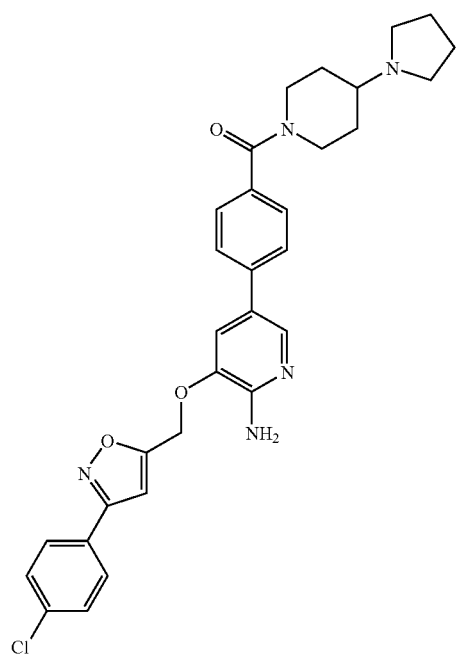
% inhibition = 23
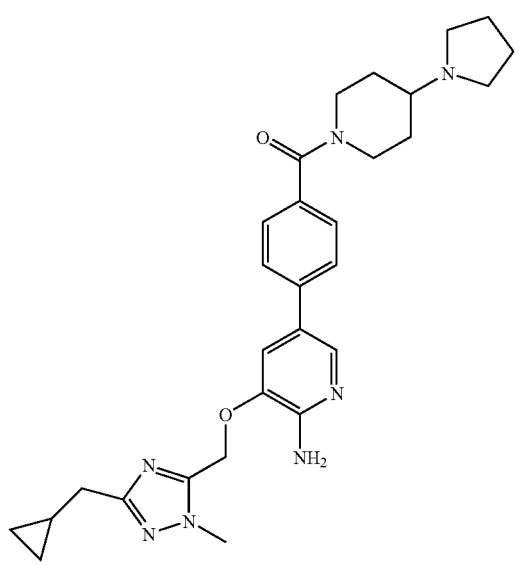
% inhibition = 7

TABLE 7-continued
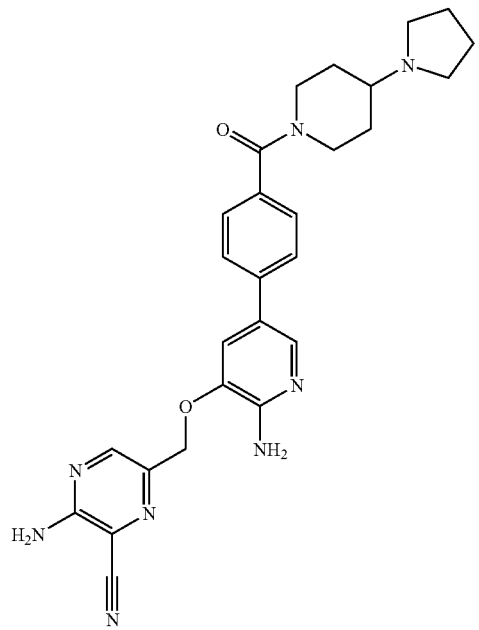
% inhibition = 9
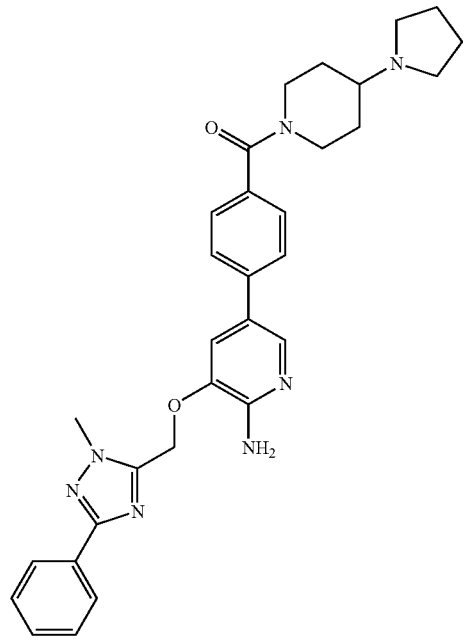
% inhibition = 5
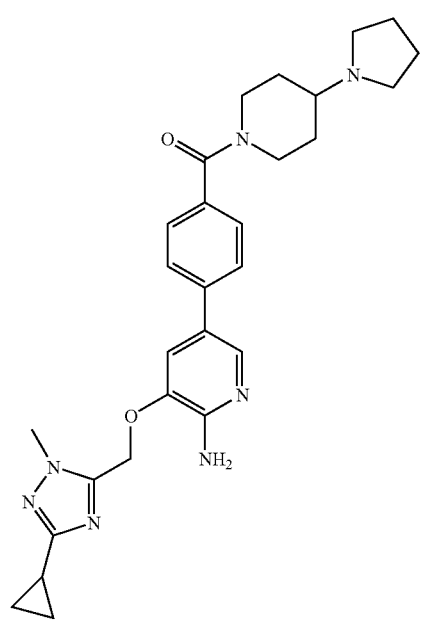
% inhibition = 5
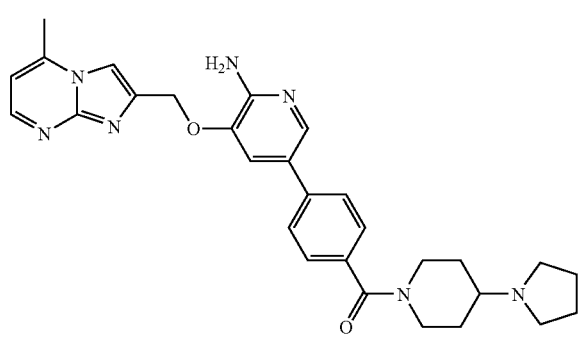
% inhibition = 10

TABLE 7-continued
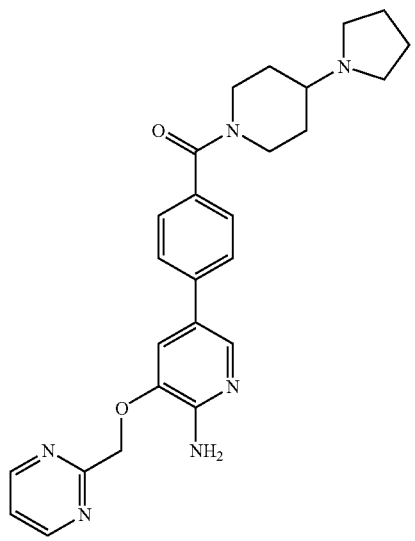
% inhibition = 9
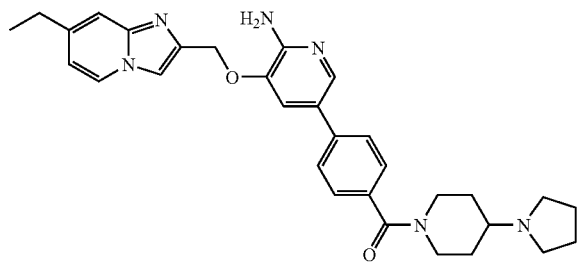
% inhibition = 9
Section L: Examples L-529 to L-548
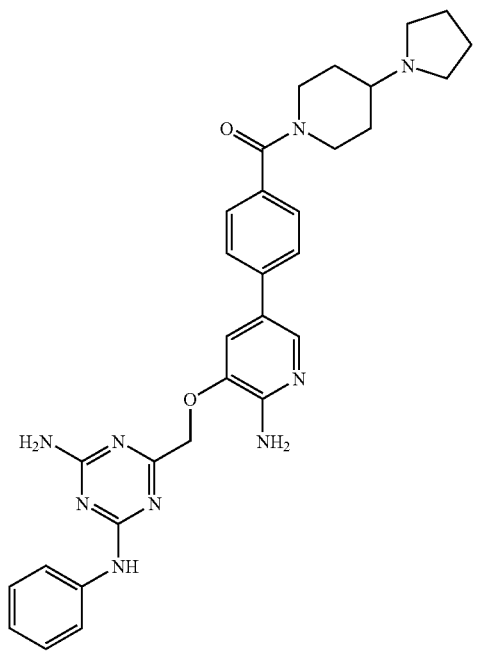
% inhibition = 9
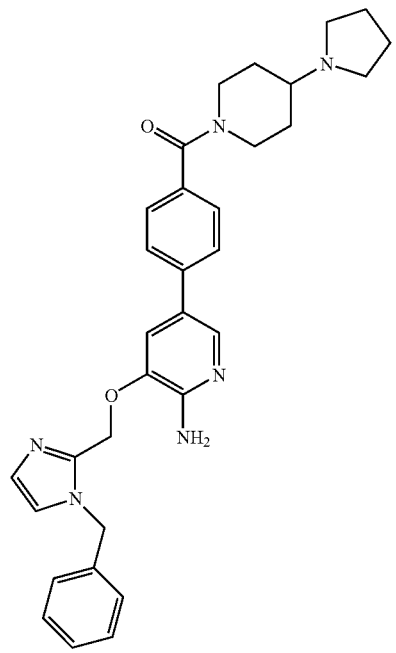
% inhibition = 8

TABLE 7-continued
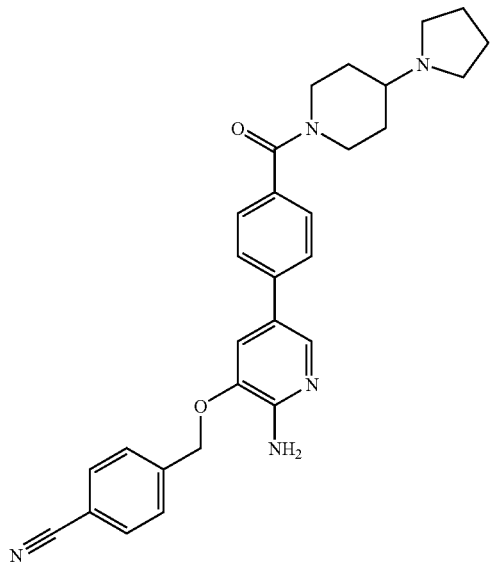
% inhibition = 8
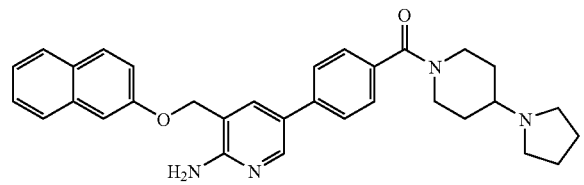
% inhibition = 27
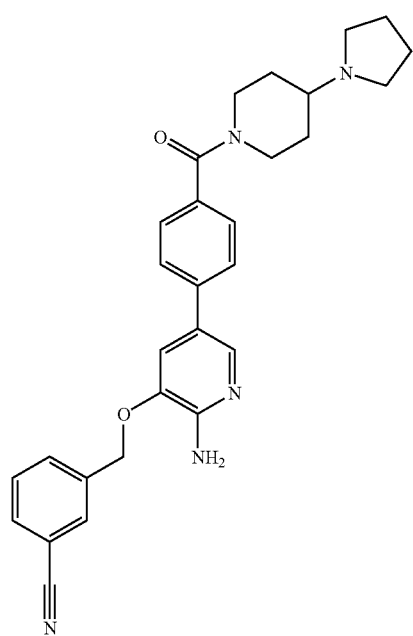
% inhibition = 12
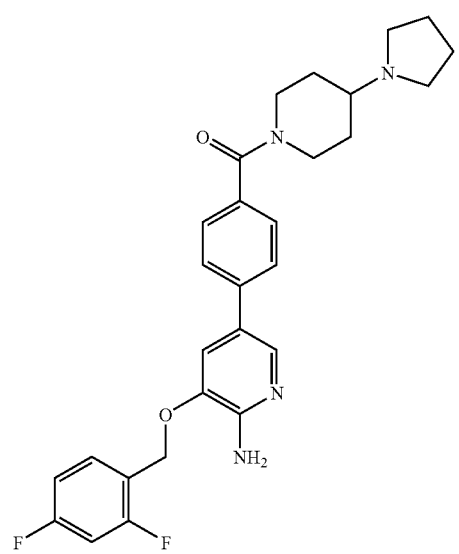
% inhibition = 18

TABLE 7-continued
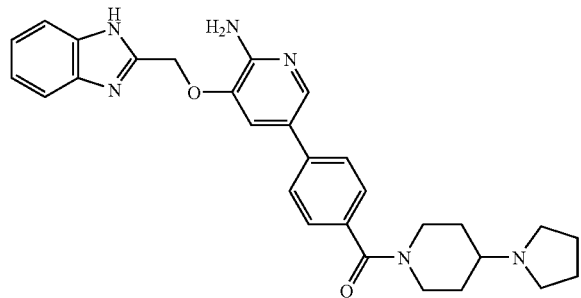
% inhibition = 4
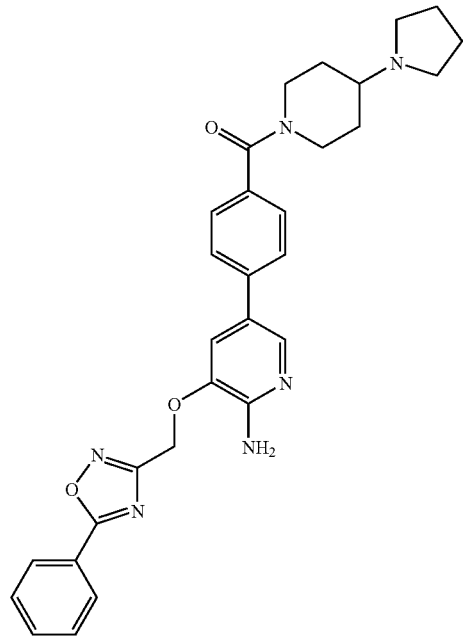
% inhibition = 16
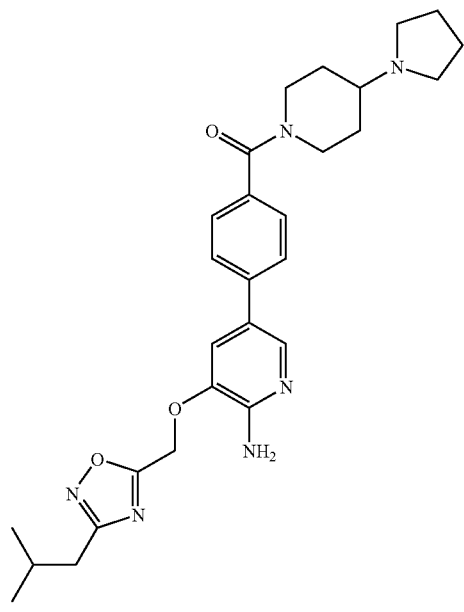
% inhibition = 12
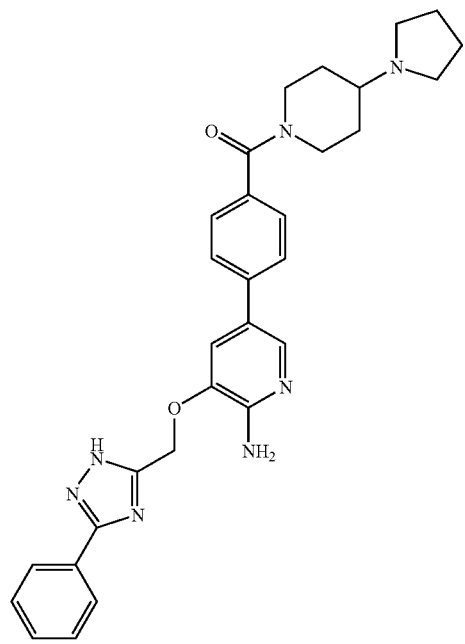
% inhibition = 2

TABLE 7-continued
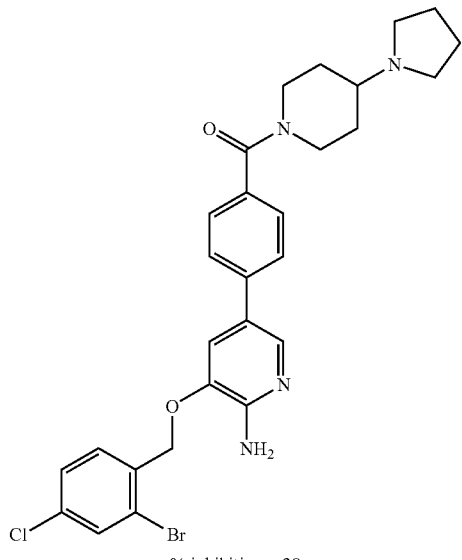
% inhibition = 28
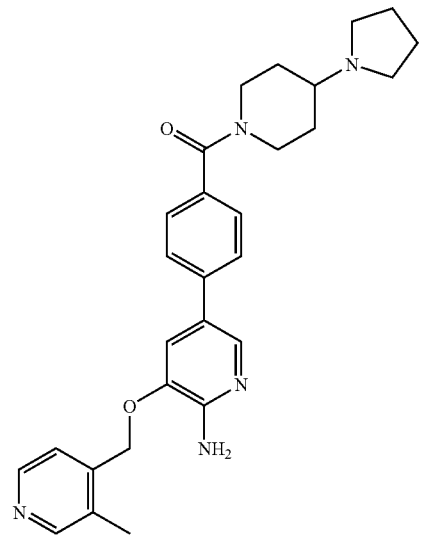
% inhibition = 11
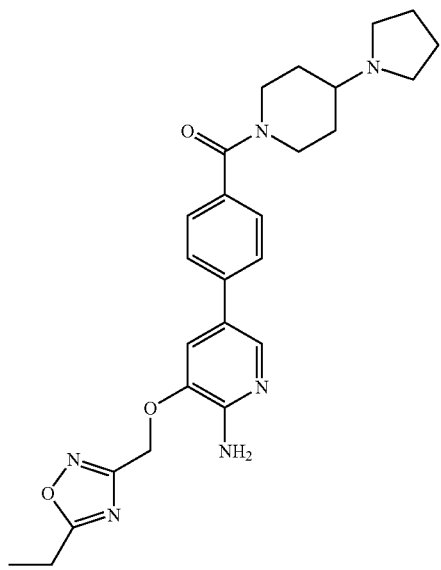
% inhibition = 5
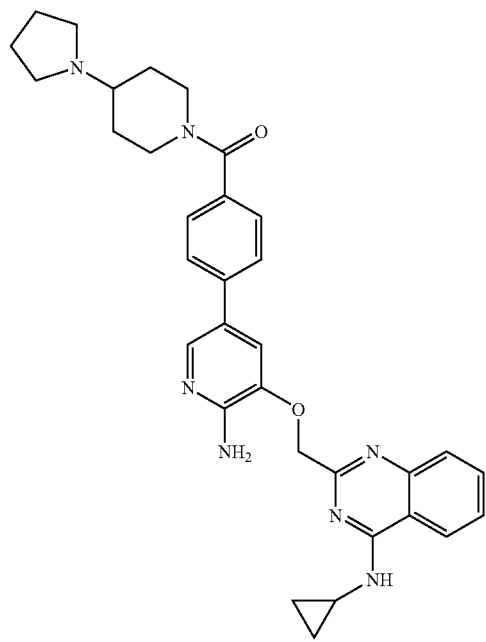
% inhibition = 6

TABLE 7-continued
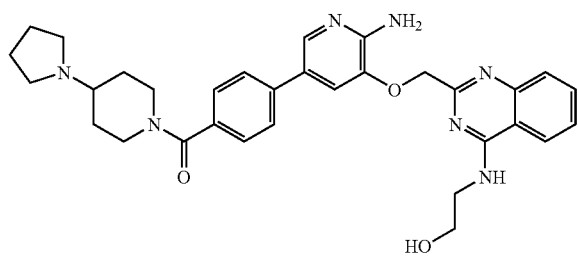
% inhibition = 7
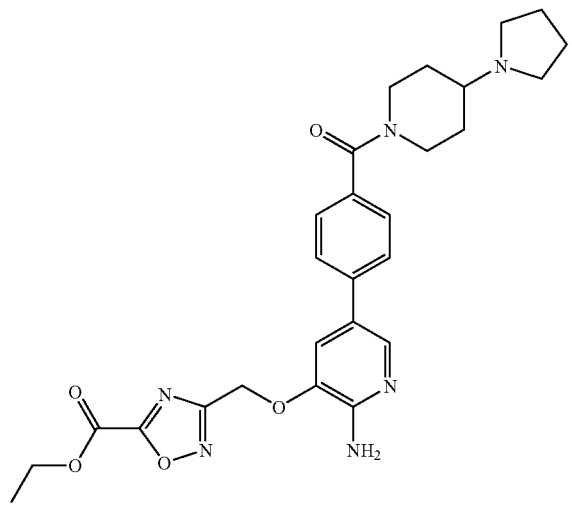
% inhibition = 8
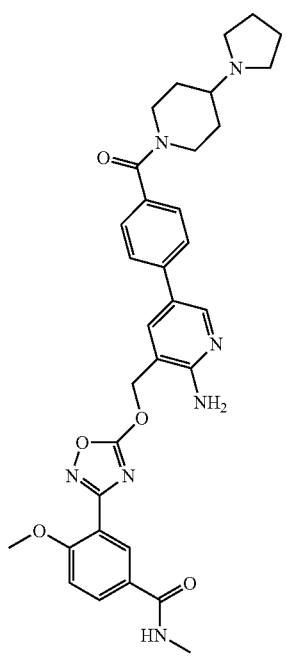
% inhibition = 11
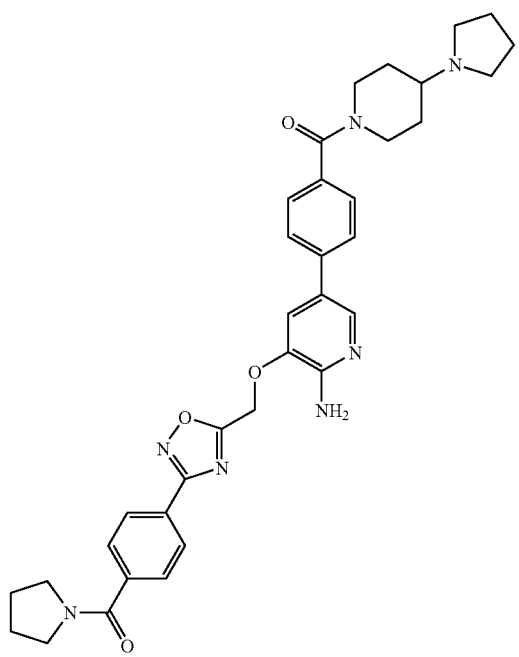
% inhibition = 11

TABLE 7-continued
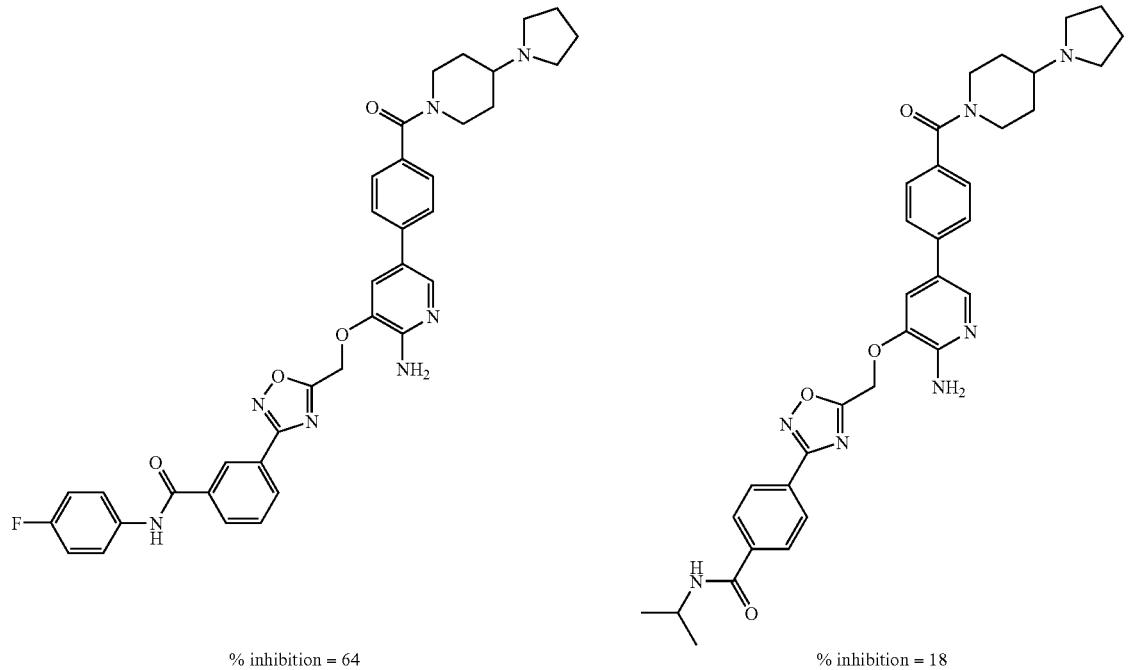
TABLE 8
Section A: Examples L-549 to L-561
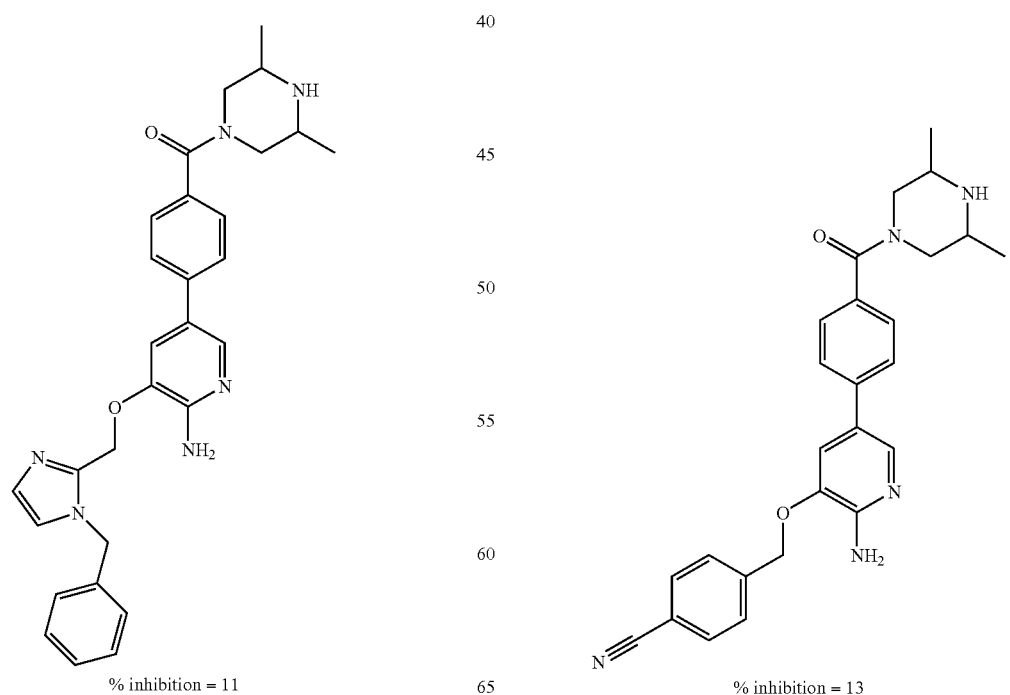

TABLE 8-continued
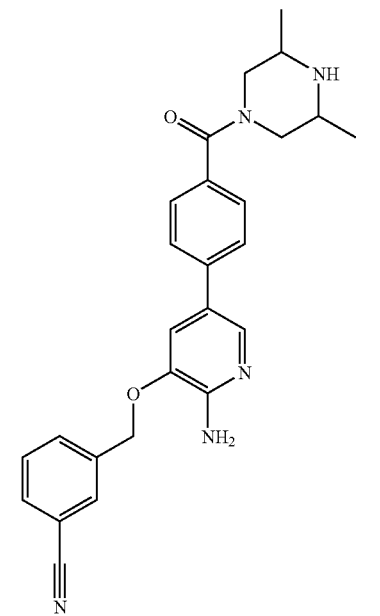
% inhibition = 11
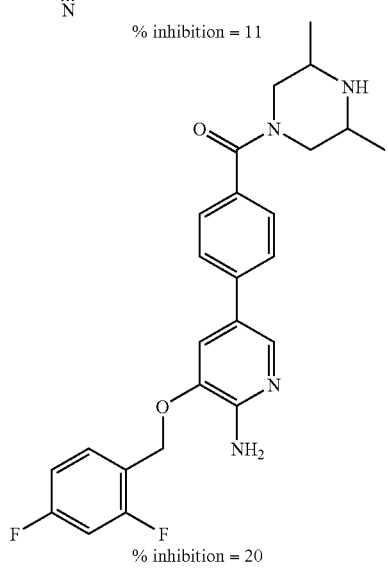
% inhibition = 20
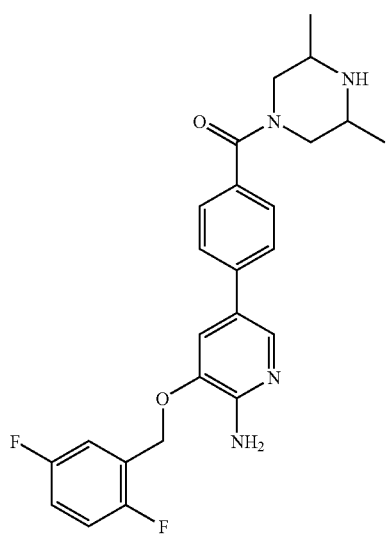
% inhibition = 25
TABLE 8-continued
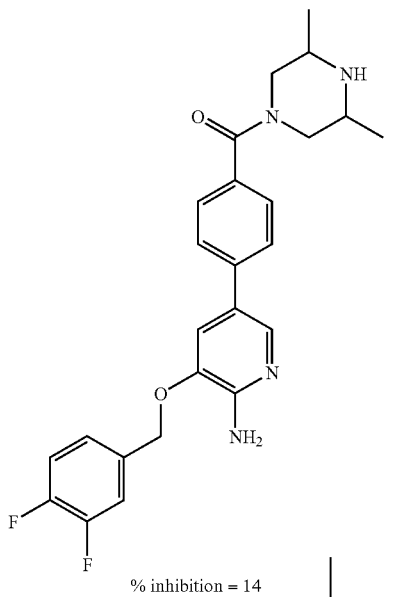
% inhibition = 14
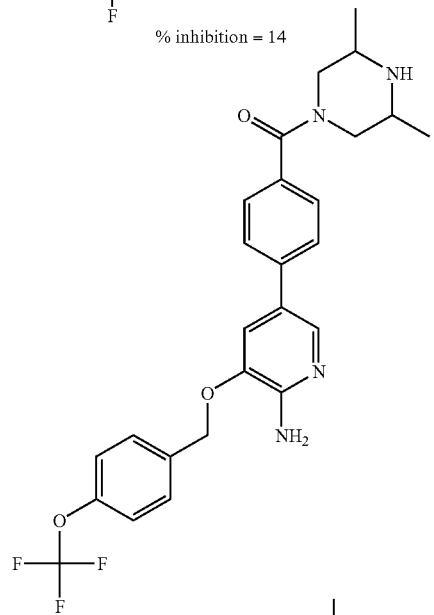
% inhibition = 21
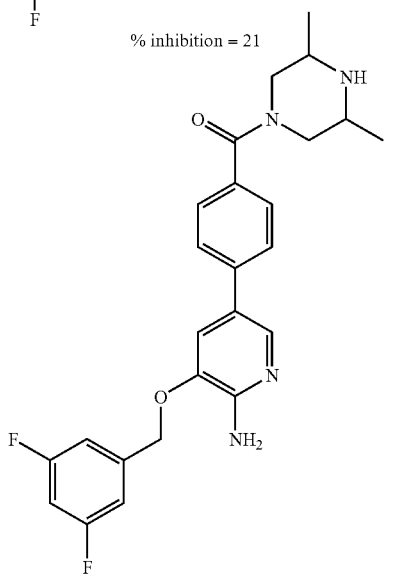
% inhibition = 12

TABLE 8-continued
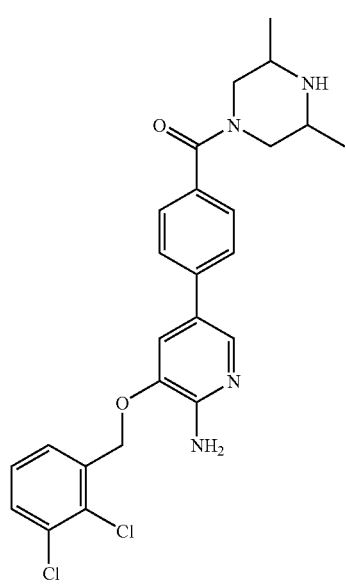
% inhibition = 40
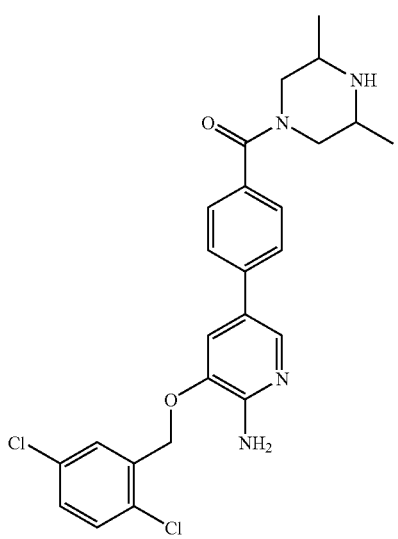
% inhibition = 32
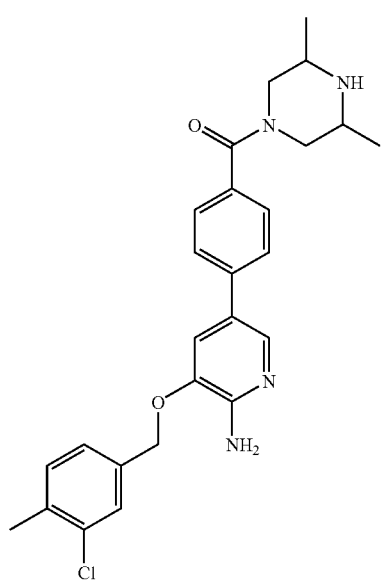
% inhibition = 27
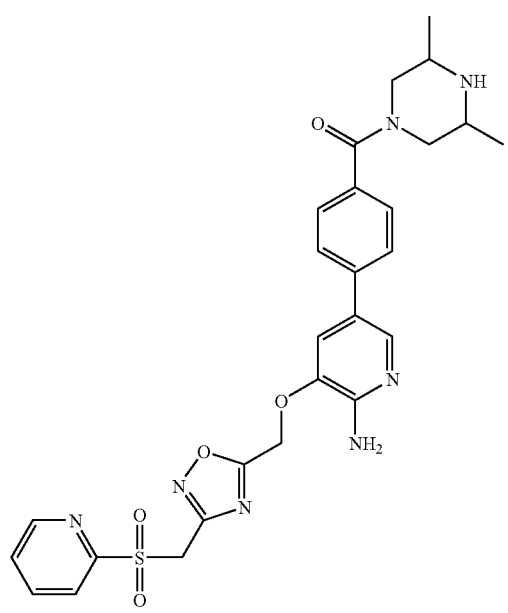
% inhibition = 16

TABLE 8-continued
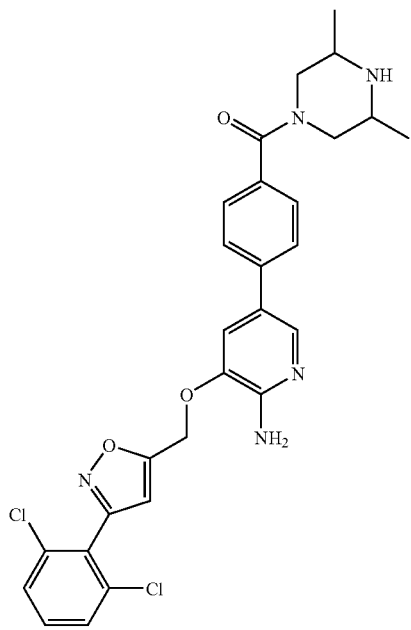
% inhibition = 16
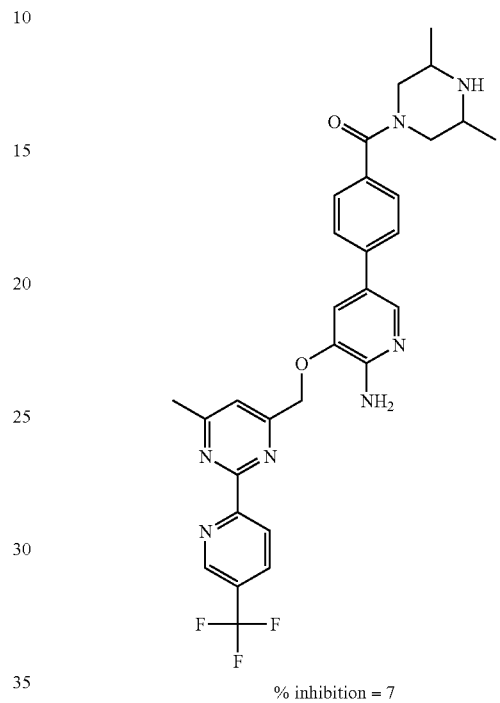
% inhibition = 7
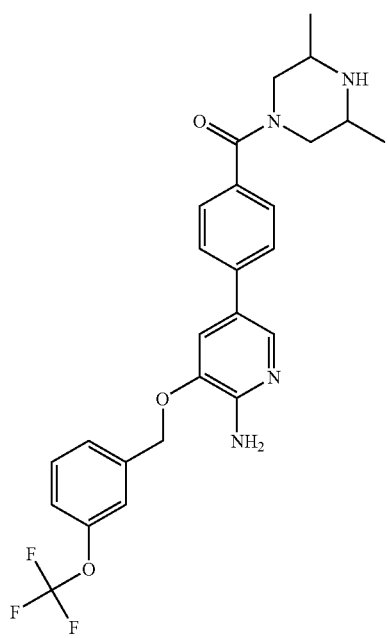
% inhibition = 17
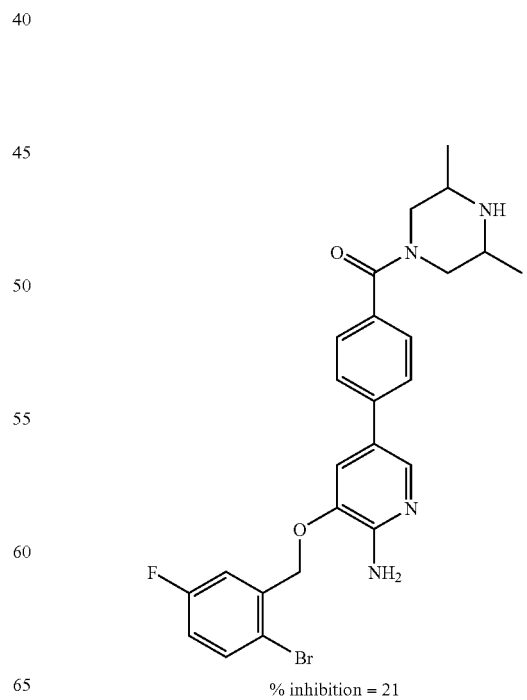
% inhibition = 21

TABLE 8-continued
Section B: Examples L-565 to L-580
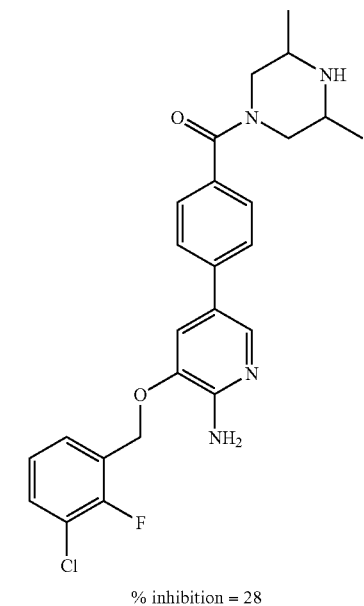
% inhibition = 28
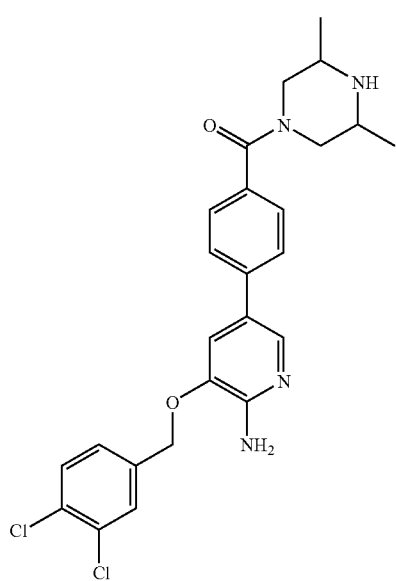
% inhibition = 29
TABLE 8-continued
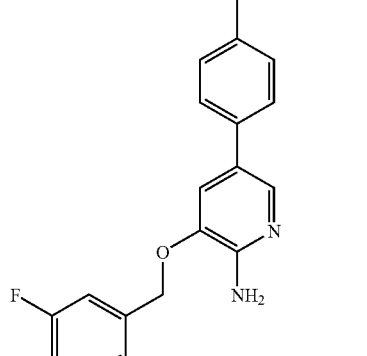
% inhibition = 20
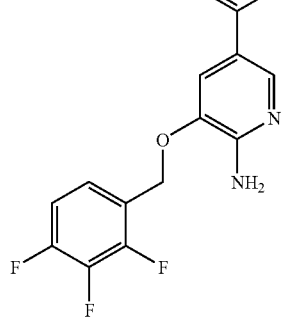
% inhibition = 25
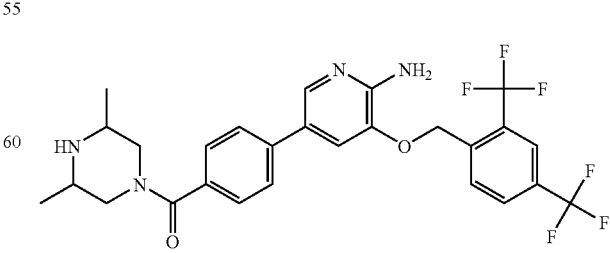
% inhibition = 22

TABLE 8-continued
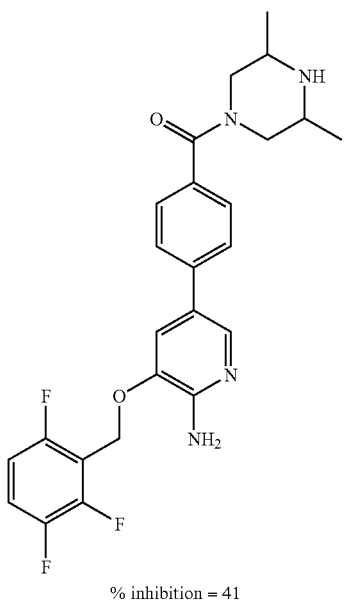
% inhibition = 41
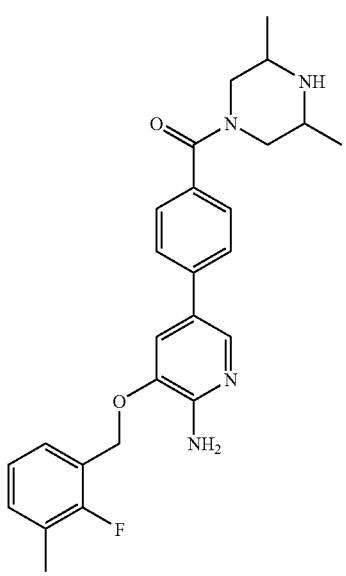
% inhibition = 28
TABLE 8-continued
% inhibition = 17
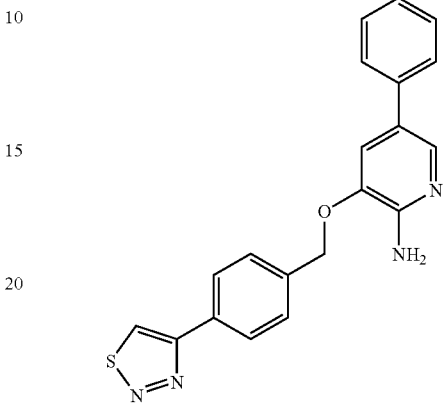
% inhibition = 19
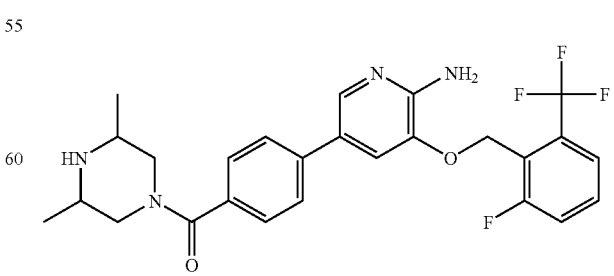
% inhibition = 33

TABLE 8-continued
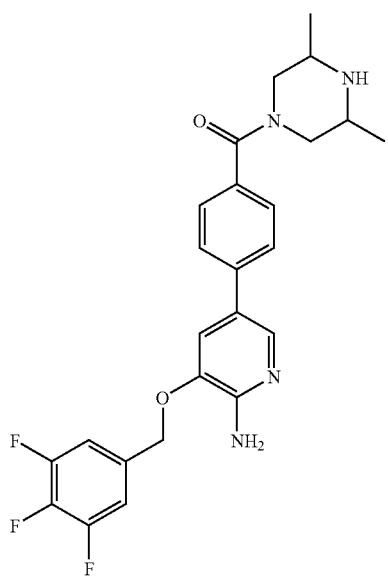
% inhibition = 11
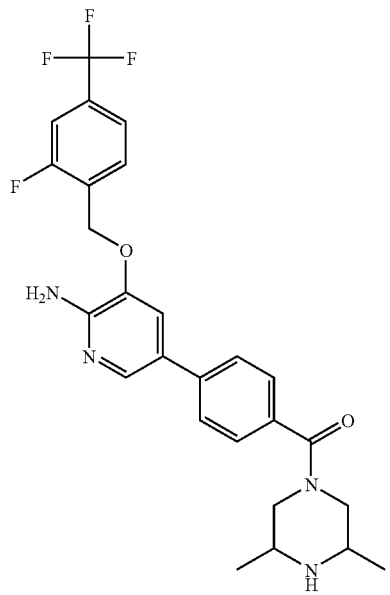
% inhibition = 24
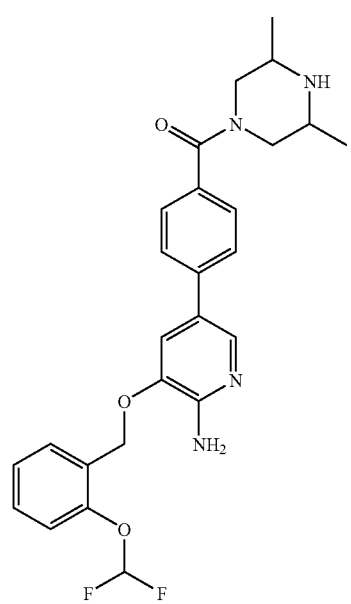
% inhibition = 24
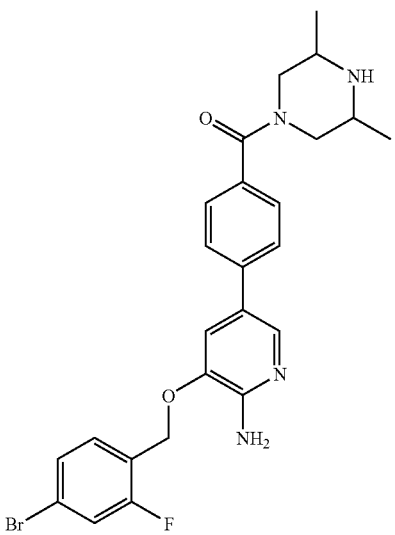
% inhibition = 29

TABLE 8-continued
TABLE 8-continued
Section C: Examples L-581 to L-596
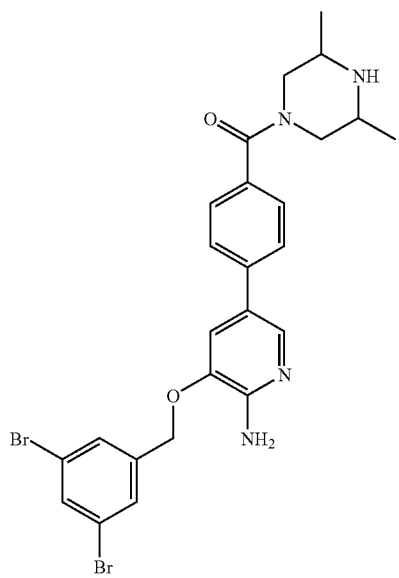
% inhibition = 42
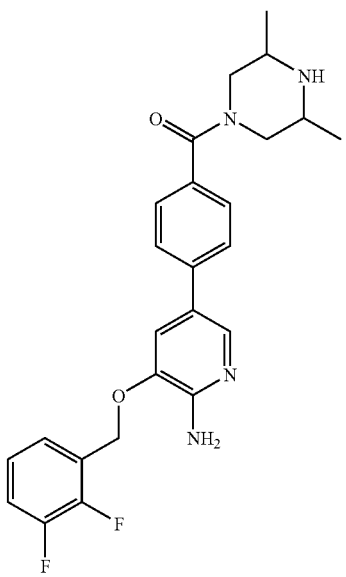
% inhibition = 19
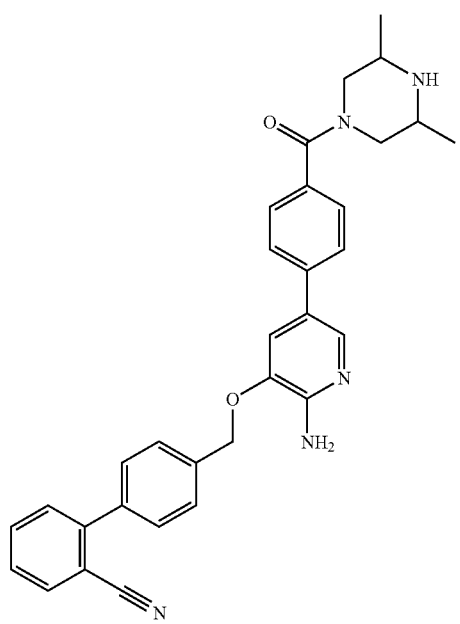
% inhibition = 73
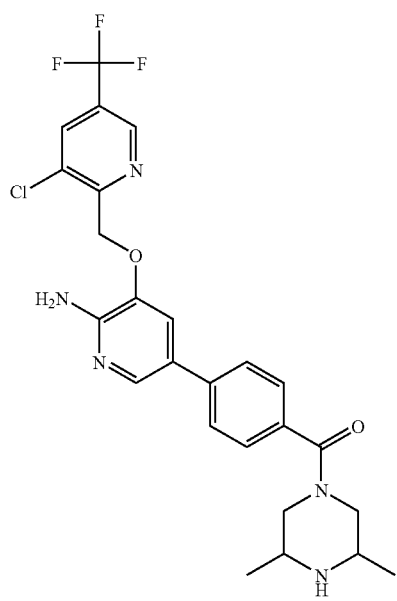
% inhibition = 17

TABLE 8-continued
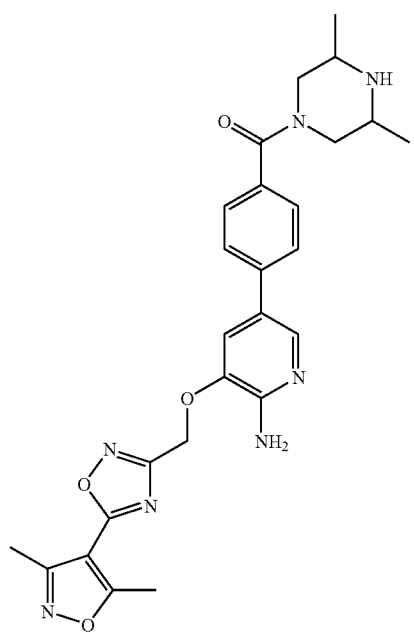
% inhibition = 14
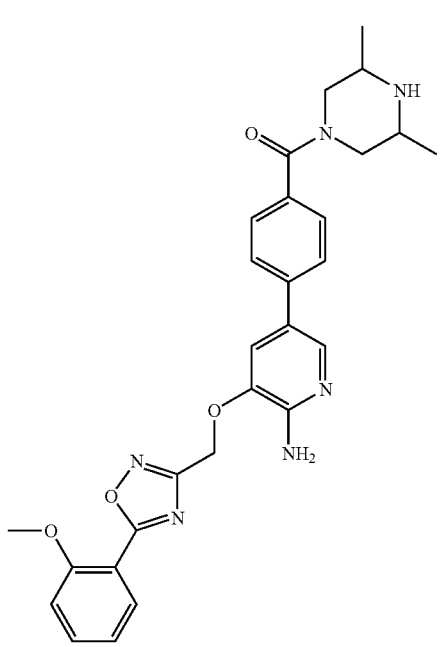
% inhibition = 9
TABLE 8-continued
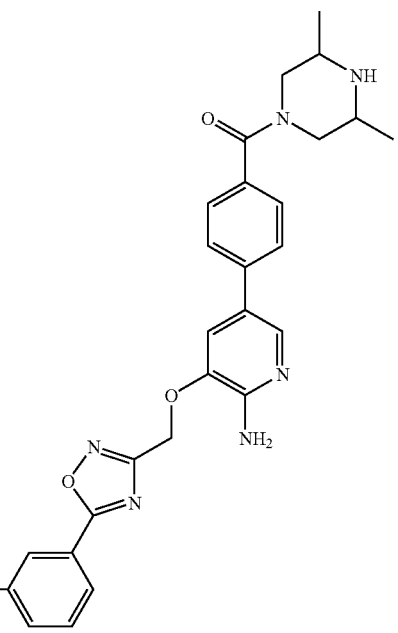
% inhibition = 30
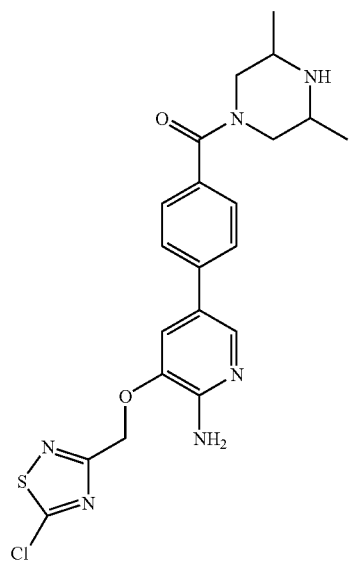
% inhibition = 6

TABLE 8-continued
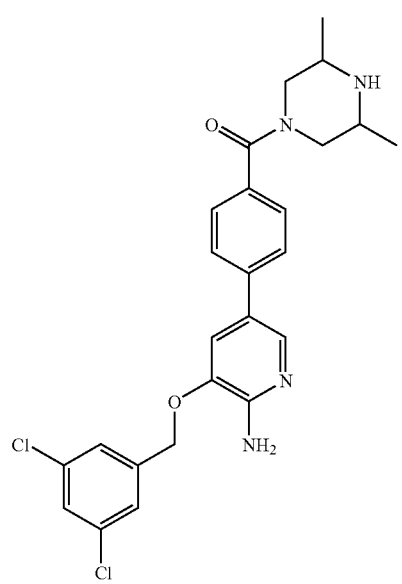
% inhibition = 26
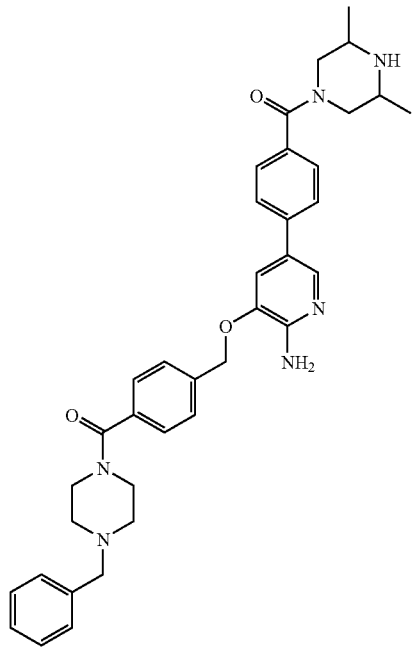
% inhibition = 15
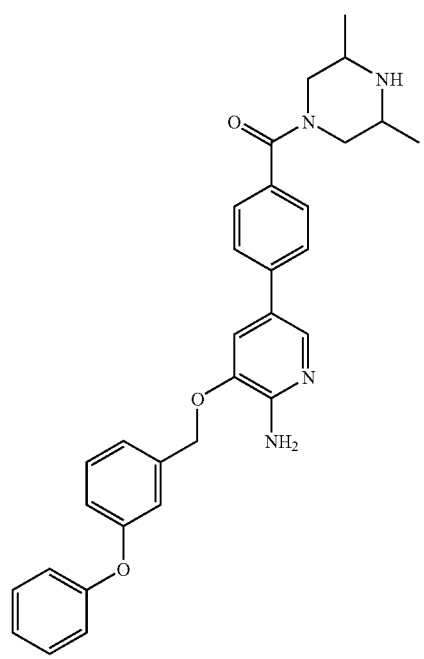
% inhibition = 32
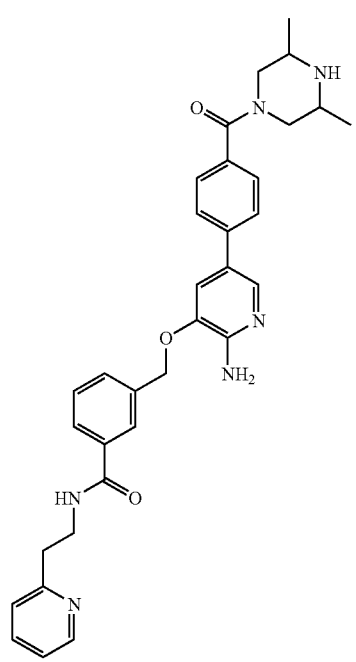
% inhibition = 18

TABLE 8-continued
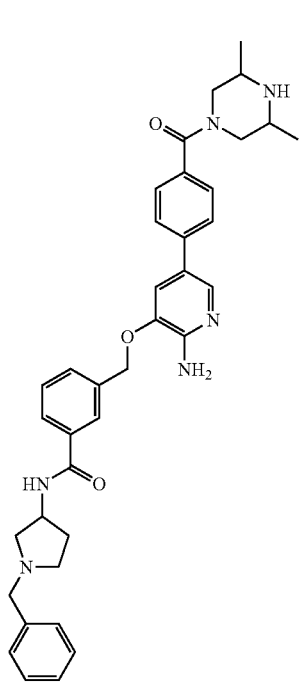
% inhibition = 18
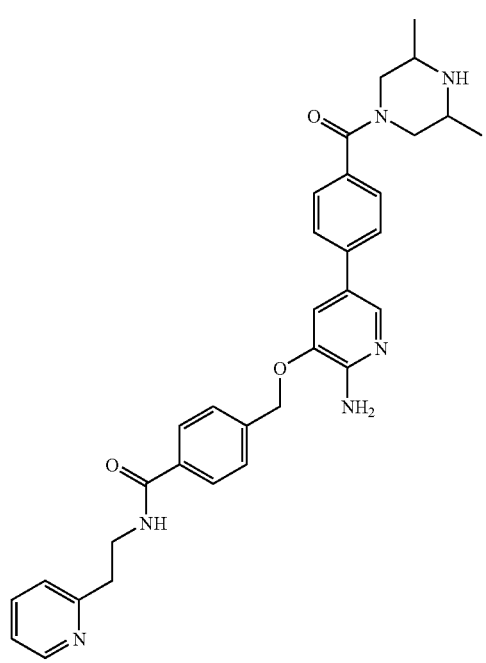
% inhibition = 19
TABLE 8-continued
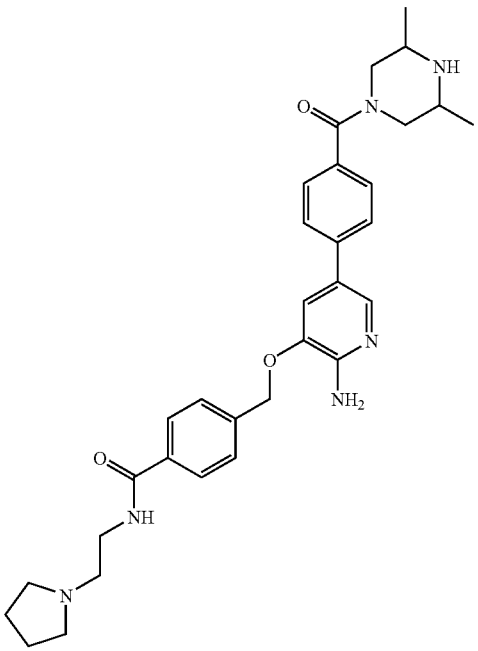
% inhibition = 12
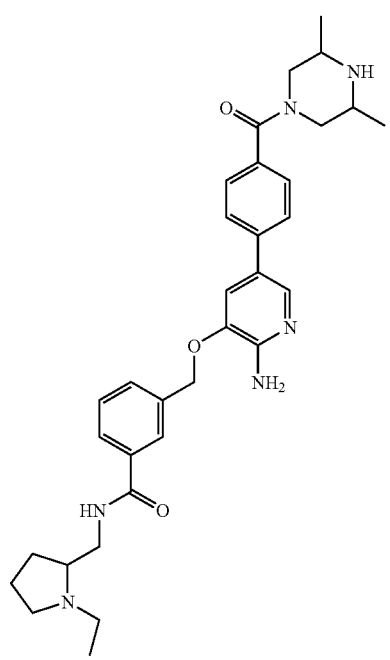
% inhibition = 10

TABLE 8-continued
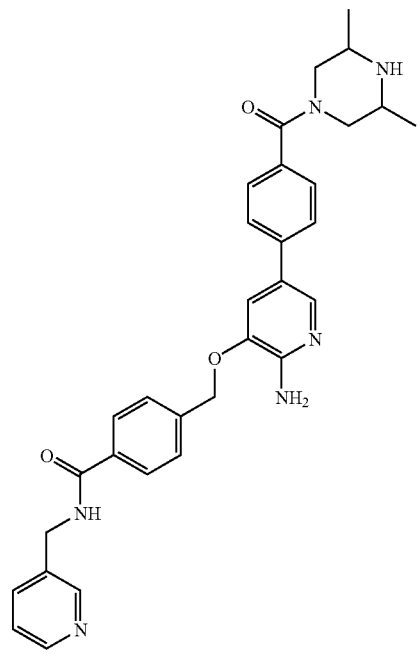
% inhibition = 8
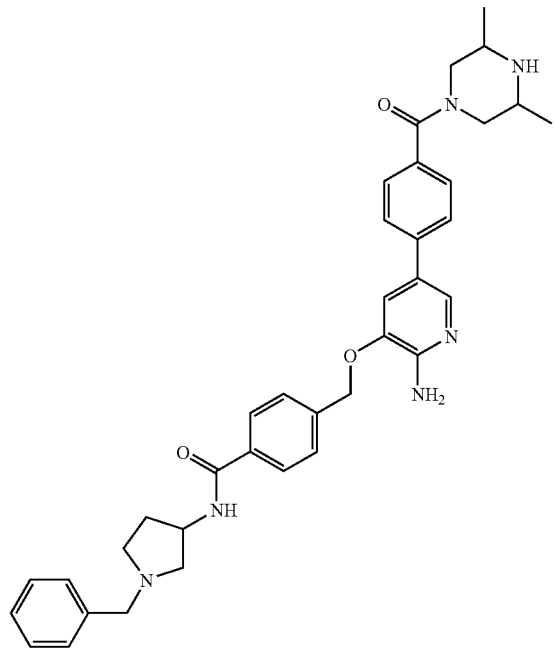
% inhibition = 19
TABLE 8-continued
Section D: Examples L-597 to L-612
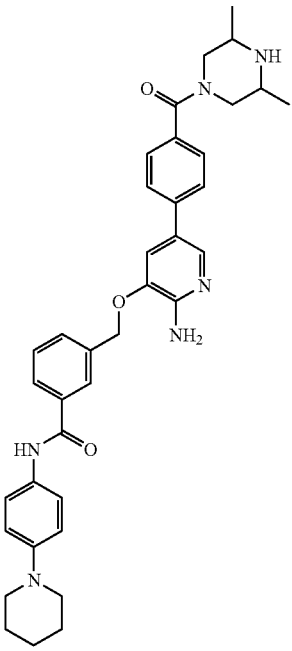
% inhibition = 28
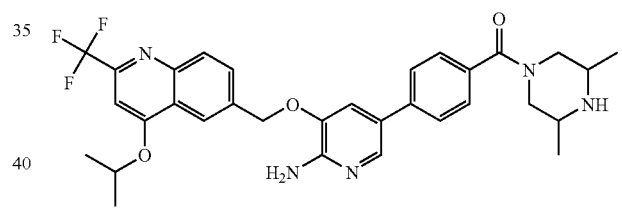
% inhibition = 17
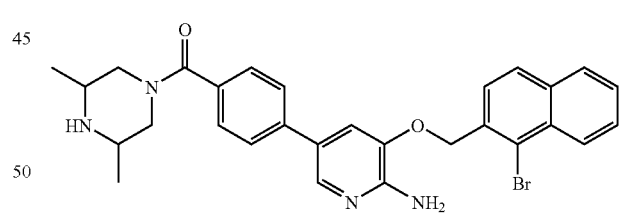
% inhibition = 58
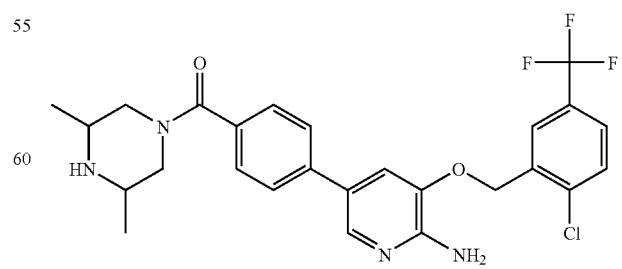
% inhibition = 25

TABLE 8-continued
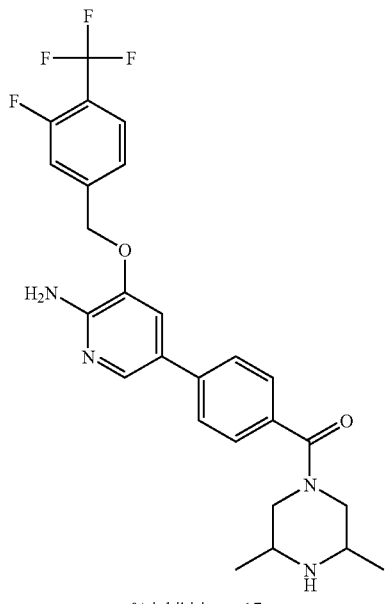
% inhibition = 17
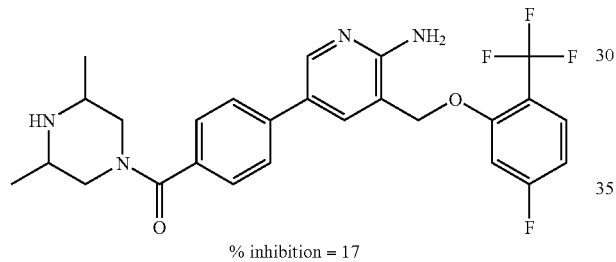
% inhibition = 17
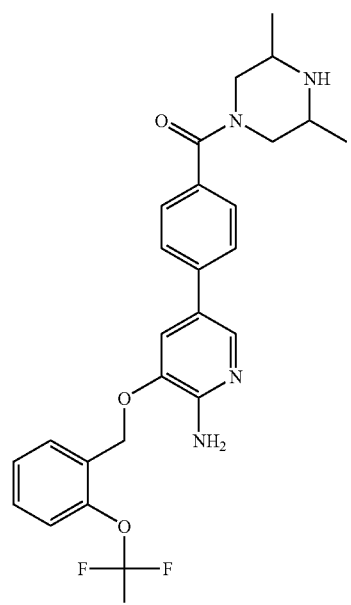
% inhibition = 20
TABLE 8-continued
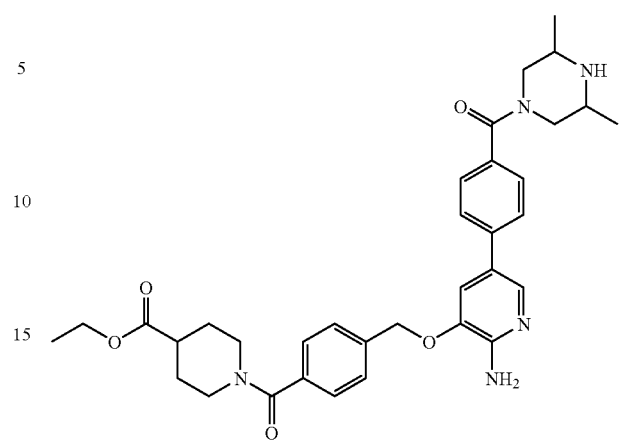
% inhibition = 12
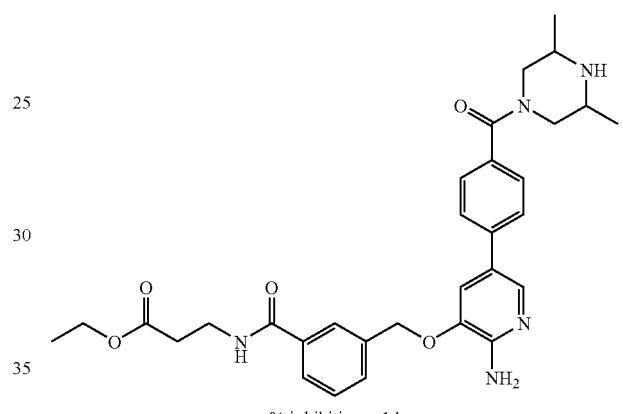
% inhibition = 14
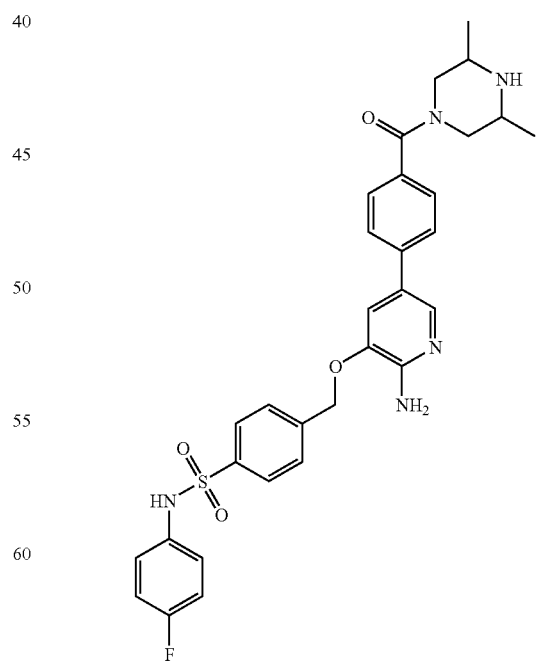
% inhibition = 14

TABLE 8-continued
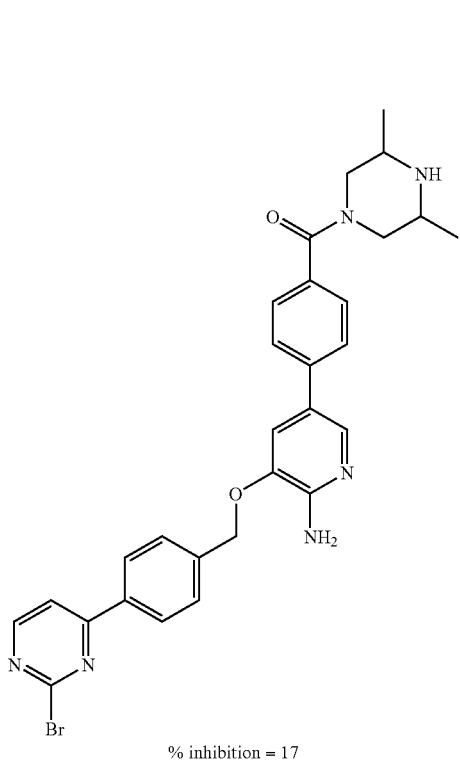
% inhibition = 17
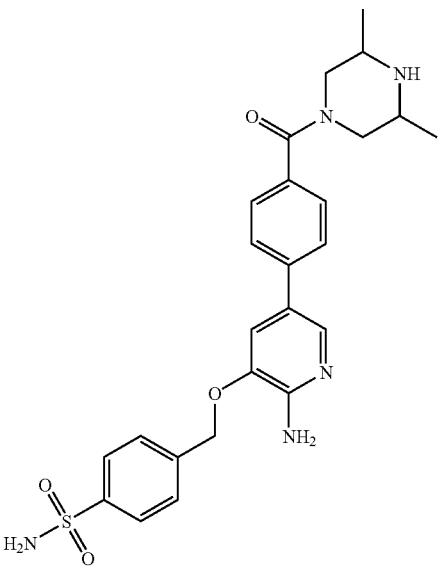
% inhibition = 16
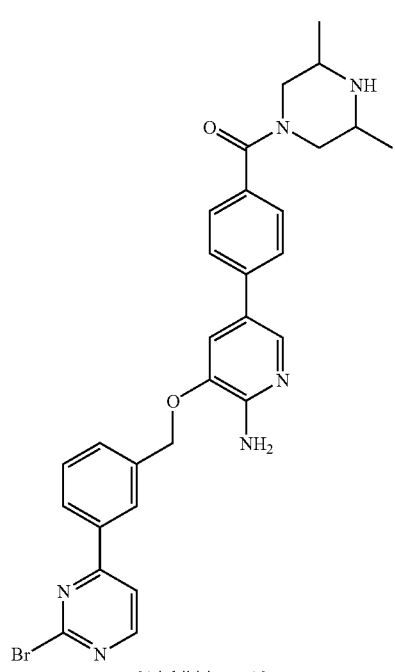
% inhibition = 19
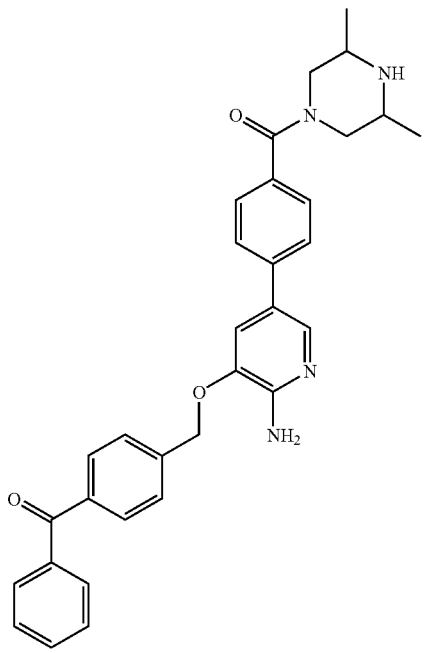
% inhibition = 35

TABLE 8-continued
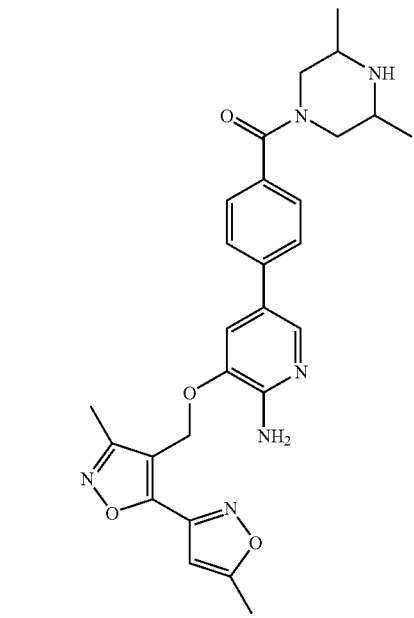
% inhibition = 25
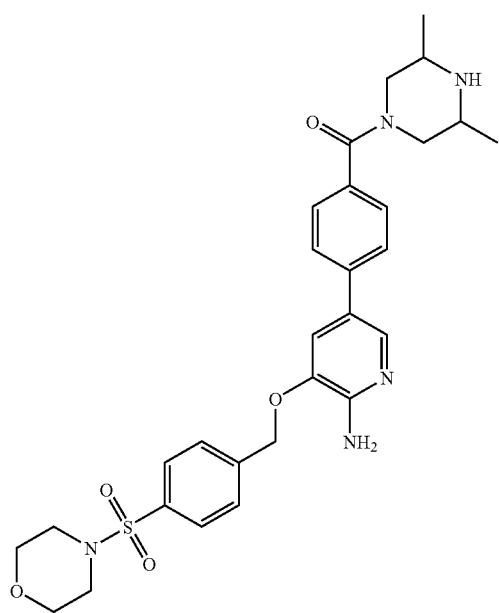
% inhibition = 13
TABLE 8-continued
Section E: Examples L-613 to L-628
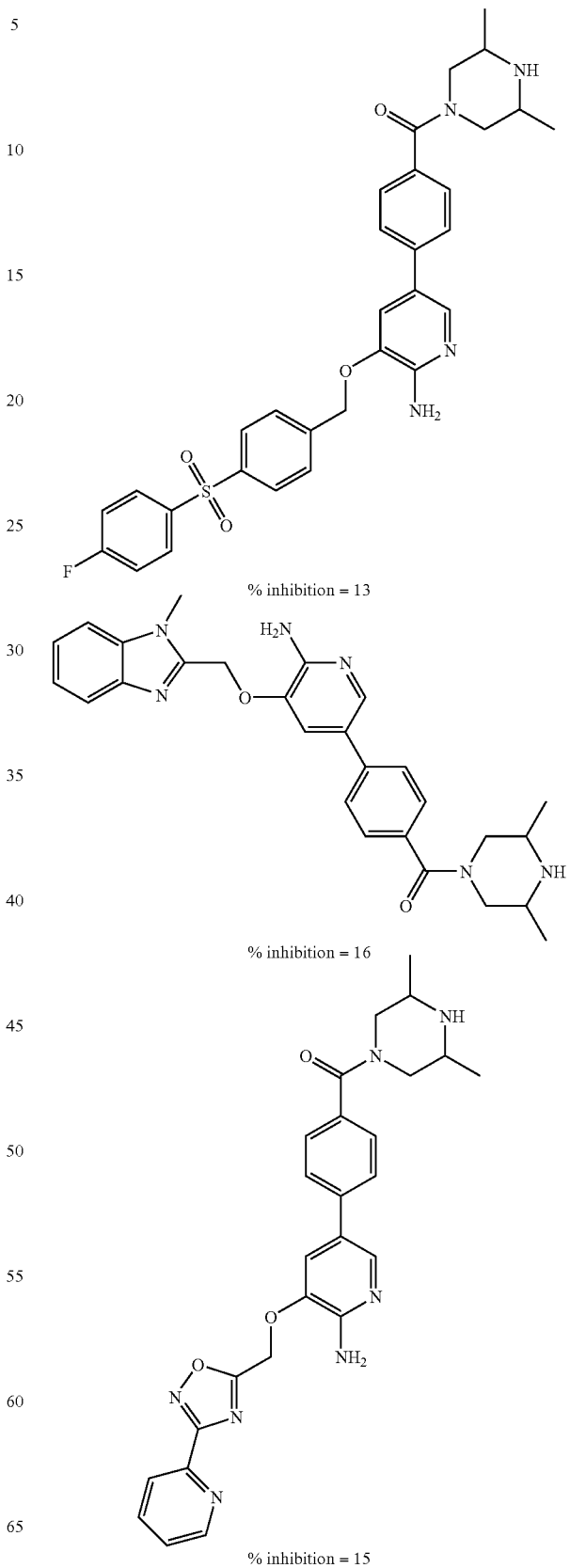
% inhibition = 13
% inhibition = 16
% inhibition = 15

TABLE 8-continued
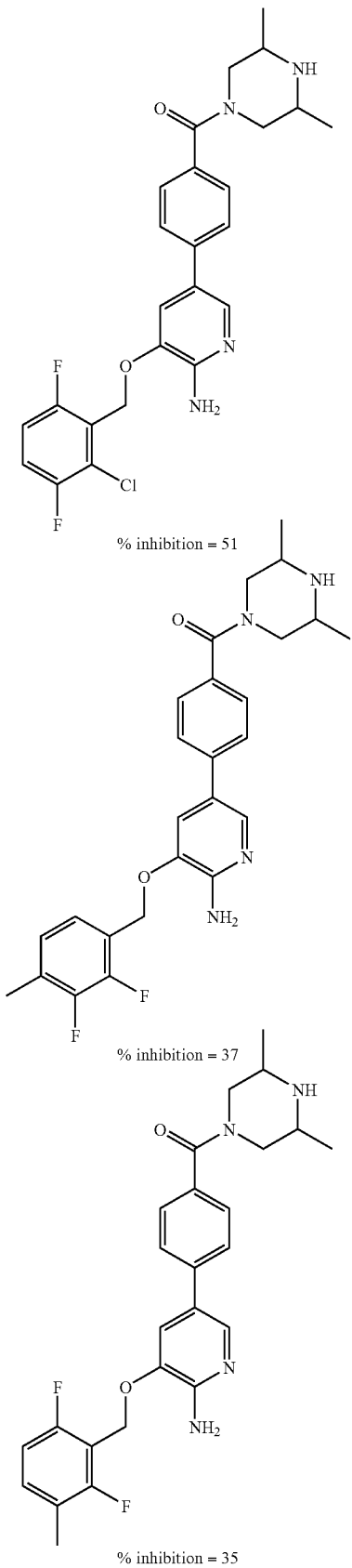
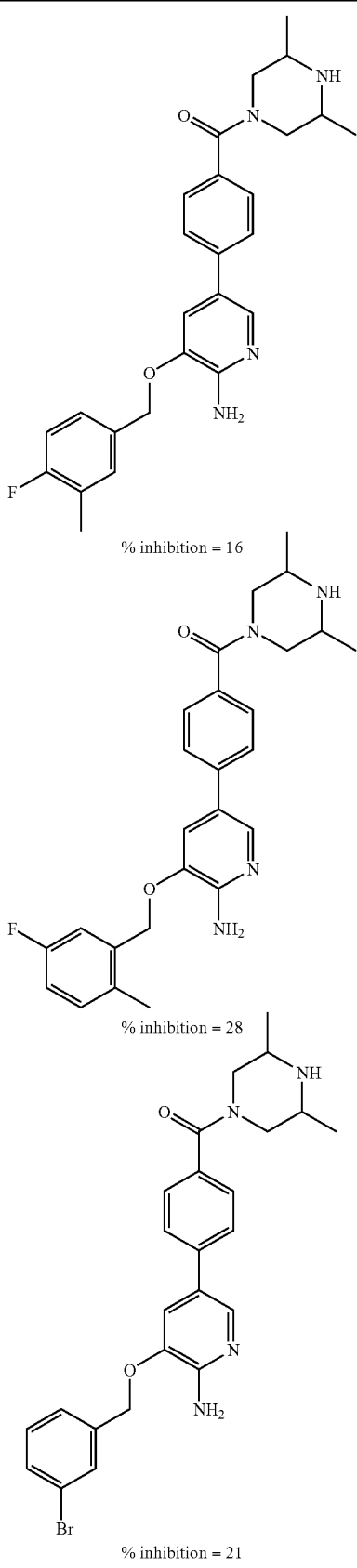

TABLE 8-continued
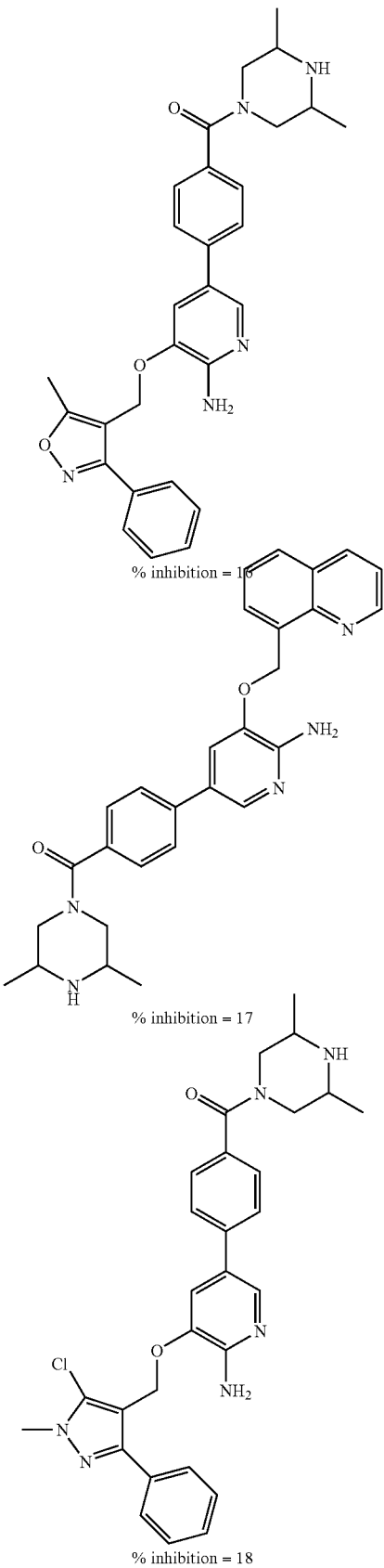
% inhibition = 16
% inhibition = 17
% inhibition = 18
TABLE 8-continued
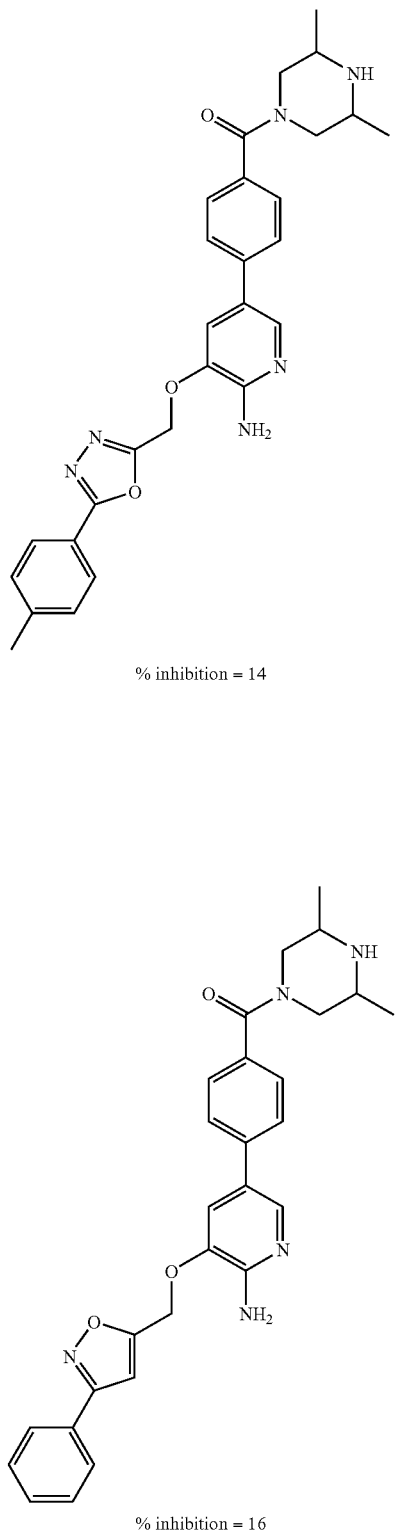
% inhibition = 14
% inhibition = 16

TABLE 8-continued
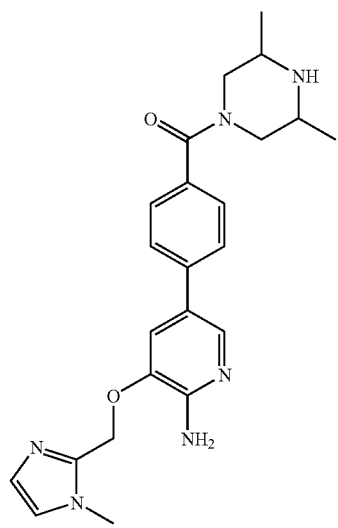
% inhibition = 12
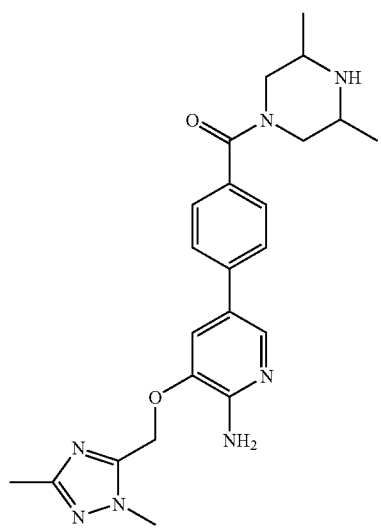
% inhibition = 13
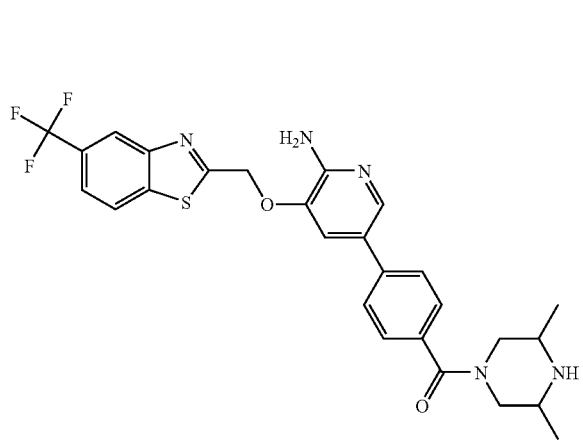
% inhibition = 27
TABLE 8-continued
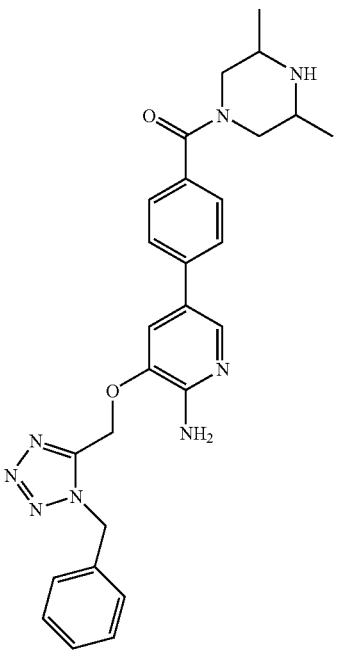
% inhibition = 15
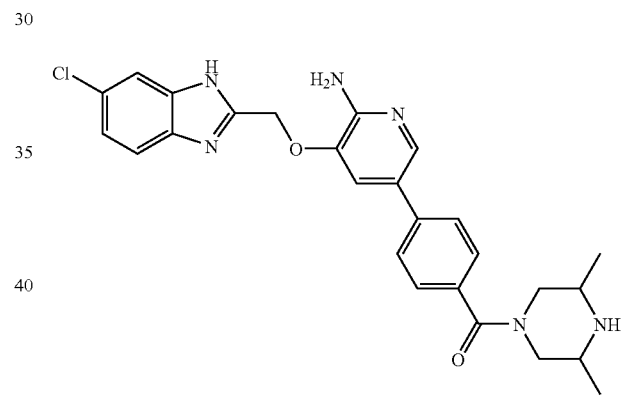
% inhibition = 10
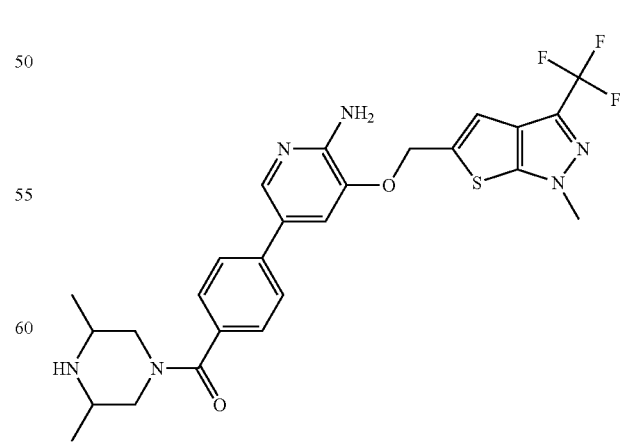
% inhibition = 13

TABLE 8-continued

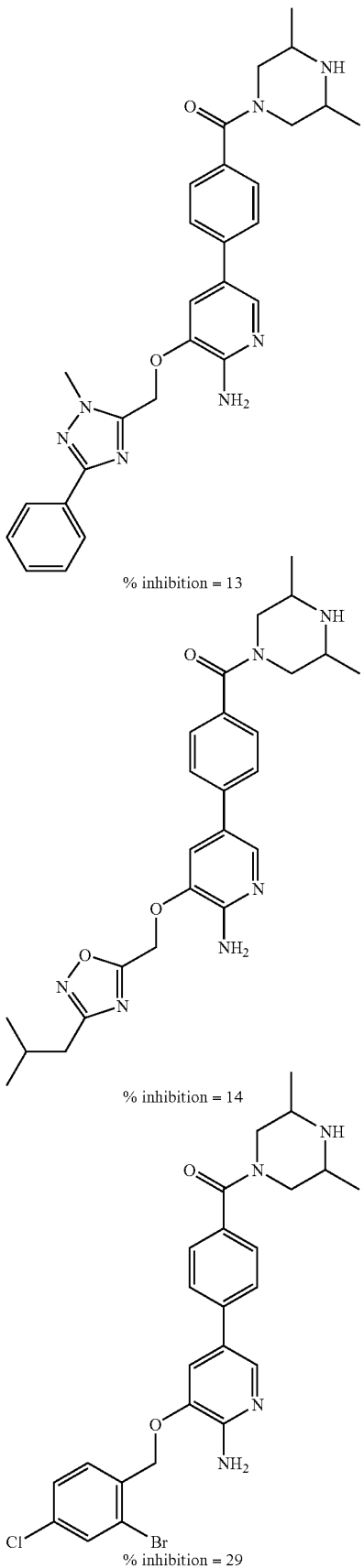

% inhibition = 13

% inhibition = 14

% inhibition = 29

TABLE 8-continued

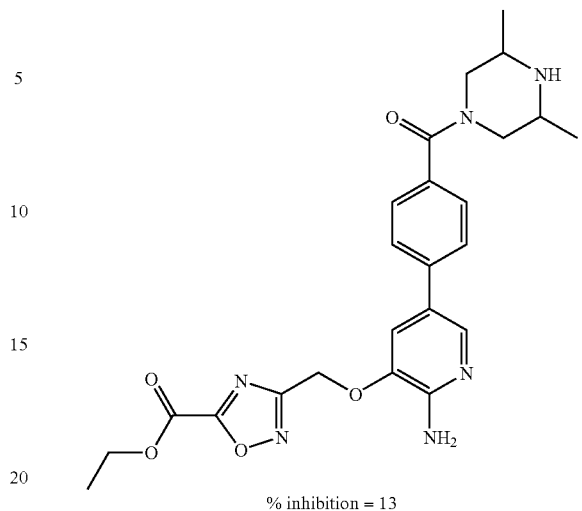

% inhibition = 13

The present invention is not to be limited in scope by the exemplified aspects which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

The disclosure of U.S. Provisional Application Ser. No. 60/449,588, filed Feb. 26, 2003, and U.S. Provisional Application Ser. No. 60/540,229, filed Jan. 29, 2004, are hereby incorporated by reference in their entireties.

All references cited herein are hereby incorporated by reference in their entireties.

We claim:

1. A compound of formula

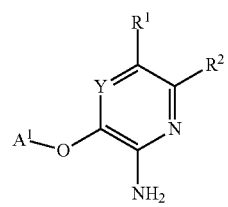

wherein:

Y is N;

$R^1$ is selected from $C_{6-12}$ aryl, 5-12 membered heteroaryl, $C_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —C(=NR$^6$)NR$^4$R$^5$, $C_{1-8}$ alkyl, $C_{2-8}$ alkenyl, and $C_{2-8}$ alkynyl; and each hydrogen in $R^1$ is optionally substituted by one or more $R^3$ groups;

$R^2$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —C(=NR$^6$)NR$^4$R$^5$, —NR$^4$C(O)NR$^5$R$^6$, —NR$^4$S $(O)_pR^5$ or —C(O)NR$^4$R$^5$, and each hydrogen in R$^2$ is optionally substituted by one or more R$^8$ groups;

each R$^3$ is independently selected from the group consisting of halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —(CR$^6$R$^7$)$_n$C(O)OR$^4$, —C(=NR$^6$)NR$^4$R$^5$, —NR$^4$C(O)NR$^5$R$^6$, and —NR$^4$S(O)$_p$R$^5$, each hydrogen in R$^3$ is optionally substituted by one or more R$^8$ groups, and R$^3$ groups on adjacent atoms may combine to form a C$_{6-12}$ aryl, 5-12 membered heteroaryl, C$_{3-12}$ cycloalkyl or 3-12 membered heteroalicyclic group;

each R$^4$, R$^5$, R$^6$ and R$^7$ is independently hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl; or any two of R$^4$, R$^5$, R$^6$ and R$^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of R$^4$, R$^5$, R$^6$ and R$^7$ bound to the same carbon atom may be combined to form a C$_{3-12}$ cycloalkyl, C$_{6-12}$ aryl, 3-12 membered heteroalicyclic or 5-12 membered heteroaryl group; and each hydrogen in R$^4$, R$^5$, R$^6$ and R$^7$ is optionally substituted by one or more R$^8$ groups;

each R$^8$ is independently halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —CN, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic) or —O—(CH$_2$)$_n$(5-12 membered heteroaryl); and each hydrogen in R$^8$ is optionally substituted by one or more R$^{11}$ groups;

A$^1$ is —(CR$^9$R$^{10}$)$_n$-A$^2$ except that:
 (i) when Y is N and R$^1$ is substituted or unsubstituted aryl or substituted or unsubstituted heteroaryl, A$^1$ is —(CR$^9$R$^{10}$)$_n$-A$^2$ and n is not zero; and
 (ii) when Y is N and R$^2$ is H and A$^1$ is m-chlorobenzyl, R$^1$ is not unsubstituted piperazine;

each R$^9$ and R$^{10}$ is independently hydrogen, halogen, C$_{1-12}$ alkyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —NR$^4$C(O)R$^5$, —(CR$^6$R$^7$)$_n$C(O)OR$^4$, —NR$^4$C(O)NR$^5$R$^6$, —NR$^4$S(O)$_p$R$^5$ or —C(O)NR$^4$R$^5$; R$^9$ and R$^{10}$ combine to form a C$_{3-12}$ cycloalkyl, or 3-12 membered heteroalicyclic, ring; and each hydrogen in R$^9$ and R$^{10}$ is optionally substituted by one or more R$^3$ groups;

A$^2$ is C$_{6-12}$ aryl, 5-12 membered heteroaryl, C$_{3-12}$ cycloalkyl or 3-12 membered heteroalicyclic, and A$^2$ is optionally substituted by one or more R$^3$ groups;

each R$^{11}$ is independently halogen, C$_{1-12}$ alkyl, C$_{1-12}$ alkoxy, C$_{3-12}$ cycloalkyl, C$_{6-12}$ aryl, 3-12 membered heteroalicyclic, 5-12 membered heteroaryl, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic), —O—(CH$_2$)$_n$(5-12 membered heteroaryl) or —CN, and each hydrogen in R$^{11}$ is optionally substituted by one or more groups selected from halogen, —OH, —CN, —C$_{1-12}$ alkyl which may be partially or fully halogenated, —O—C$_{1-12}$ alkyl which may be partially or fully halogenated, —CO, —SO and —SO$_2$;

m is 0, 1 or 2;

n is 0, 1, 2, 3 or 4; and p is 1 or 2;

wherein 3-12 membered heteroalicyclic group is selected from pyrroline, pyrrolidine, dioxolane, imidazoline, imidazolidine, pyrazoline, pyrazolidine, pyran, piperidine, dioxane, morpholine, dithiane, thiomorpholine, piperazine and trithiane and 5-12 membered heteroaryl group is selected from furan, thiophene, pyrrole, oxazole, thiazole, imidazole, pyrazole, isoxazole, isothiazole, oxadiazole, triazole, thiadiazole, pyridine, pyridazine, pyrimidine, pyrazine and triazine;

or a pharmaceutically acceptable salt thereof.

2. The compound of claim 1, wherein the compound has formula

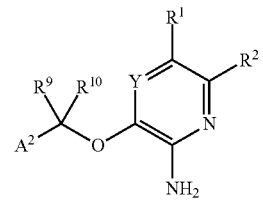

wherein A$^2$ is C$_{6-12}$ aryl or 5-12 membered heteroaryl optionally substituted by one or more R$^3$ groups.

3. The compound of claim 2, wherein R$^1$ is selected from C$_{6-12}$ aryl and 5-12 membered heteroaryl, and each hydrogen in R$^1$ is optionally substituted by one or more R$^3$ groups.

4. The compound of claim 2, wherein R$^1$ is selected from C$_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —C(=NR$^6$)NR$^4$R$^5$, C$_{1-8}$ alkyl, C$_{2-8}$ alkenyl, and C$_{2-8}$ alkynyl; and each hydrogen in R$^1$ is optionally substituted by one or more R$^3$ groups.

5. The compound of claim 2, wherein A$^2$ is substituted by at least one halogen atom.

6. The compound of claim 2, wherein R$^2$ is hydrogen, R$^9$ and R$^{10}$ are independently C$_{1-4}$ alkyl, and A$^2$ is phenyl substituted by at least one halogen atom.

7. The compound of claim 1, wherein R$^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane or phenyl group, and each hydrogen in R$^1$ is optionally substituted by one or more R$^3$ groups.

8. The compound of claim 1, wherein R$^1$ is a fused ring heteroaryl group, and each hydrogen in R$^1$ is optionally substituted by one or more R$^3$ groups.

9. The compound of claim 1, wherein R$^1$ is a —SO$_2$NR$^4$R$^5$ group.

10. A compound of formula

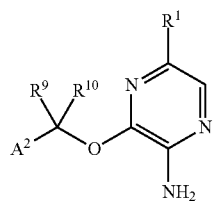

wherein:
R$^1$ is selected from C$_{6-12}$ aryl, 5-12 membered heteroaryl, C$_{3-12}$ cycloalkyl, 3-12 membered heteroalicyclic, —O(CR$^6$R$^7$)$_n$R$^4$, —C(O)R$^4$, —C(O)OR$^4$, —CN, —NO$_2$, —S(O)$_m$R$^4$, —SO$_2$NR$^4$R$^5$, —C(O)NR$^4$R$^5$, —C(=NR$^6$)NR$^4$R$^5$, C$_{1-8}$ alkyl, C$_{2-8}$ alkenyl, and C$_{2-8}$ alkynyl; and each hydrogen in R$^1$ is optionally substituted by one or more R$^3$ groups;

R$^3$ is independently selected from the group consisting of halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —(CR$^6$R$^7$)$_n$C(O)OR$^4$, —C(=NR$^6$)NR$^4$R$^5$, —NR$^4$C(O)NR$^5$R$^6$, and —NR$^4$S(O)$_p$R$^5$, each hydrogen in R$^3$ is optionally substituted by one or more R$^8$ groups, and R$^3$ groups on adjacent atoms may combine to form a C$_{6-12}$ aryl, 5-12 membered heteroaryl, C$_{3-12}$ cycloalkyl or 3-12 membered heteroalicyclic group;

each R$^4$, R$^5$, R$^6$ and R$^7$ is independently hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl; or any two of R$^4$, R$^5$, R$^6$ and R$^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of R$^4$, R$^5$, R$^6$ and R$^7$ bound to the same carbon atom may be combined to form a C$_{3-12}$ cycloalkyl, C$_{6-12}$ aryl, 3-12 membered heteroalicyclic or 5-12 membered heteroaryl group; and each hydrogen in R$^4$, R$^5$, R$^6$ and R$^7$ is optionally substituted by one or more R$^8$ groups;

each R$^8$ is independently halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl, —CN, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic) or —O—(CH$_2$)$_n$(5-12 membered heteroaryl); and each hydrogen in R$^8$ is optionally substituted by one or more R$^{11}$ groups;

each R$^9$ and R$^{10}$ is independently hydrogen, halogen, C$_{1-12}$ alkyl, C$_{3-12}$ cycloalkyl, C$_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —NR$^4$C(O)R$^5$, —(CR$^6$R$^7$)$_n$C(O)OR$^4$, —NR$^4$C(O)NR$^5$R$^6$, —NR$^4$S(O)$_p$R$^5$ or —C(O)NR$^4$R$^5$; R$^9$ and R$^{10}$ combine to form a C3-12 cycloalkyl, or 3-12 membered heteroalicyclic, ring; and each hydrogen in R$^9$ and R$^{10}$ is optionally substituted by one or more R$^3$ groups;

A$^2$ is C$_{6-12}$ aryl, 5-12 membered heteroaryl, C$_{3-12}$ cycloalkyl or 3-12 membered heteroalicyclic, and A$^2$ is optionally substituted by one or more R$^3$ groups; except that when R$^2$, R$^9$ and R$^{10}$ are all H and A$^2$ is m-chlorophenyl, R$^1$ is not unsubstituted piperazine;

each R$^{11}$ is independently halogen, C$_{1-12}$ alkyl, C$_{1-12}$ alkoxy, C$_{3-12}$ cycloalkyl, C$_{6-12}$ aryl, 3-12 membered heteroalicyclic, 5-12 membered heteroaryl, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic), —O—(CH$_2$)$_n$(5-12 membered heteroaryl) or —CN, and each hydrogen in R$^{11}$ is optionally substituted by one or more groups selected from halogen, —OH, —CN, —C$_{1-12}$ alkyl which may be partially or fully halogenated, —O—C$_{1-12}$ alkyl which may be partially or fully halogenated, —CO, —SO and —SO$_2$;

m is 0, 1 or 2;

n is 0, 1, 2, 3 or 4; and p is 1 or 2;

or a pharmaceutically acceptable salt thereof.

11. The compound of claim 10, wherein A$^2$ is C$_{6-12}$ aryl or 5-12 membered heteroaryl optionally substituted by one or more R$^3$ groups.

* * * * *